US012291709B2

(12) United States Patent
Prakash et al.

(10) Patent No.: US 12,291,709 B2
(45) Date of Patent: May 6, 2025

(54) COMPOSITIONS AND METHODS FOR MODULATING APOLIPOPROTEIN (a) EXPRESSION

(71) Applicant: Ionis Pharmaceuticals, Inc., Carlsbad, CA (US)

(72) Inventors: Thazha P. Prakash, Carlsbad, CA (US); Punit P. Seth, Carlsbad, CA (US); Eric E. Swayze, Encinitas, CA (US); Mark J. Graham, San Clemente, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/501,779

(22) Filed: Nov. 3, 2023

(65) Prior Publication Data

US 2024/0352455 A1  Oct. 24, 2024

Related U.S. Application Data

(63) Continuation of application No. 17/060,440, filed on Oct. 1, 2020, now Pat. No. 11,851,655, which is a continuation of application No. 15/891,156, filed on Feb. 7, 2018, now Pat. No. 10,883,104, which is a continuation of application No. 14/839,580, filed on Aug. 28, 2015, now Pat. No. 9,957,504, which is a continuation of application No. 14/588,061, filed on Dec. 31, 2014, now Pat. No. 9,181,550, which is a continuation of application No. PCT/US2014/036460, filed on May 1, 2014.

(60) Provisional application No. 61/986,867, filed on Apr. 30, 2014, provisional application No. 61/976,991, filed on Apr. 8, 2014, provisional application No. 61/880,790, filed on Sep. 20, 2013, provisional application No. 61/871,673, filed on Aug. 29, 2013, provisional application No. 61/843,887, filed on Jul. 8, 2013, provisional application No. 61/823,826, filed on May 15, 2013, provisional application No. 61/818,442, filed on May 1, 2013.

(51) Int. Cl.
| | |
|---|---|
| *C07H 21/04* | (2006.01) |
| *A61K 31/7088* | (2006.01) |
| *A61K 31/713* | (2006.01) |
| *A61K 47/54* | (2017.01) |
| *C12N 15/11* | (2006.01) |
| *C12N 15/113* | (2010.01) |

(52) U.S. Cl.
CPC ........ *C12N 15/113* (2013.01); *A61K 31/7088* (2013.01); *A61K 31/713* (2013.01); *A61K 47/549* (2017.08); *C07H 21/04* (2013.01); *C12N 15/111* (2013.01); *C12N 2310/11* (2013.01); *C12N 2310/113* (2013.01); *C12N 2310/17* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2310/3511* (2013.01); *C12N 2310/3513* (2013.01); *C12N 2310/3515* (2013.01); *C12N 2310/3525* (2013.01); *C12N 2310/353* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts et al. |
| 4,751,219 A | 6/1988 | Kempen |
| 4,845,205 A | 7/1989 | Huynh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |

(Continued)

FOREIGN PATENT DOCUMENTS

| | | |
|---|---|---|
| CA | 2450022 A1 | 12/2002 |
| CN | 102753186 A | 10/2012 |

(Continued)

OTHER PUBLICATIONS

Duell, et al., Long-term mipomersen treatment is associated with a reduction in cardiovascular events in patients with familial hypercholesterolemia, Journal of Clinical Lipidology, 10(4), 1011-1021, Aug. 2016.

(Continued)

*Primary Examiner* — Traviss C McIntosh, III
(74) *Attorney, Agent, or Firm* — Timothy P. O'Dea

(57) ABSTRACT

Provided herein are oligomeric compounds with conjugate groups targeting apoplipoprotein (a) [apo(a)]. In certain embodiments, the apo(a) targeting oligomeric compounds are conjugated to N-Acetylgalactosamine. Also disclosed herein are conjugated oligomeric compounds targeting apo (a) for use in decreasing apo(a) to treat, prevent, or ameliorate diseases, disorders or conditions related to apo(a) and/or Lp(a). Certain diseases, disorders or conditions related to apo(a) and/or Lp(a) include inflammatory, cardiovascular and/or metabolic diseases, disorders or conditions. The conjugated oligomeric compounds disclosed herein can be used to treat such diseases, disorders or conditions in an individual in need thereof.

16 Claims, No Drawings
Specification includes a Sequence Listing.

(56) References Cited

U.S. PATENT DOCUMENTS

| | | |
|---|---|---|
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,198 A | 1/1993 | Spielvogel et al. |
| 5,185,444 A | 2/1993 | Summerton et al. |
| 5,223,618 A | 6/1993 | Cook et al. |
| 5,256,775 A | 10/1993 | Froehler |
| 5,264,562 A | 11/1993 | Matteucci |
| 5,264,564 A | 11/1993 | Matteucci |
| 5,319,080 A | 6/1994 | Leumann |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,432,272 A | 7/1995 | Benner |
| 5,434,257 A | 7/1995 | Matteucci et al. |
| 5,446,137 A | 8/1995 | Maag et al. |
| 5,457,187 A | 10/1995 | Gmeiner et al. |
| 5,459,255 A | 10/1995 | Cook et al. |
| 5,466,786 A | 11/1995 | Buhr et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Haralambidis |
| 5,567,811 A | 10/1996 | Misiura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,602,240 A | 2/1997 | Mesmaeker et al. |
| 5,610,289 A | 3/1997 | Cook et al. |
| 5,610,300 A | 3/1997 | Altmann et al. |
| 5,614,617 A | 3/1997 | Cook et al. |
| 5,625,050 A | 4/1997 | Beaton et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | Mcgee |
| 5,670,633 A | 9/1997 | Cook et al. |
| 5,681,941 A | 10/1997 | Cook et al. |
| 5,698,685 A | 12/1997 | Summerton et al. |
| 5,700,920 A | 12/1997 | Altmann et al. |
| 5,750,692 A | 5/1998 | Cook et al. |
| 5,763,588 A | 6/1998 | Matteucci et al. |
| 5,792,847 A | 8/1998 | Buhr et al. |
| 5,801,154 A | 9/1998 | Baracchini et al. |
| 5,830,653 A | 11/1998 | Froehler et al. |
| 5,994,517 A | 11/1999 | Ts et al. |
| 5,998,203 A | 12/1999 | Matulic-Adamic et al. |
| 6,005,096 A | 12/1999 | Matteucci et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,525,031 B2 | 2/2003 | Manoharan |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan |
| 6,670,461 B1 | 12/2003 | Wengel et al. |
| 6,727,064 B2 | 4/2004 | Karras |
| 6,770,748 B2 | 8/2004 | Imanishi et al. |
| 6,794,499 B2 | 9/2004 | Wengel et al. |
| 6,906,182 B2 | 6/2005 | Ts et al. |
| 6,908,903 B1 | 6/2005 | Theodore et al. |
| 7,034,133 B2 | 4/2006 | Wengel et al. |
| 7,053,207 B2 | 5/2006 | Wengel |
| 7,259,150 B2 * | 8/2007 | Crooke ............... A61P 9/00 536/23.1 |
| 7,262,177 B2 | 8/2007 | Ts et al. |
| 7,267,819 B2 | 9/2007 | Ferrara et al. |
| 7,399,845 B2 | 7/2008 | Seth et al. |
| 7,399,853 B2 | 7/2008 | Freier et al. |
| 7,425,544 B2 | 9/2008 | Dobie et al. |
| 7,427,672 B2 | 9/2008 | Imanishi et al. |
| 7,439,043 B2 | 10/2008 | Defrees et al. |
| 7,482,117 B2 | 1/2009 | Cargill et al. |
| 7,491,805 B2 | 2/2009 | Vargeese et al. |
| 7,563,884 B2 | 7/2009 | Cowsert et al. |
| 7,569,686 B1 | 8/2009 | Bhat et al. |
| 7,582,744 B2 | 9/2009 | Manoharan et al. |
| 7,598,227 B2 | 10/2009 | Crooke et al. |
| 7,696,344 B2 | 4/2010 | Khvorova et al. |
| 7,723,509 B2 | 5/2010 | Manoharan et al. |
| 7,741,457 B2 | 6/2010 | Seth et al. |
| 7,750,141 B2 | 7/2010 | Crooke et al. |
| 7,750,142 B2 | 7/2010 | Freier |
| 7,851,615 B2 | 12/2010 | Manoharan et al. |
| 7,935,796 B2 | 5/2011 | Lee et al. |
| 7,989,612 B2 | 8/2011 | Mcswiggen et al. |
| 8,084,437 B2 | 12/2011 | Freier et al. |
| 8,093,222 B2 | 1/2012 | Freier et al. |
| 8,101,743 B2 | 1/2012 | Brown-driver et al. |
| 8,106,022 B2 | 1/2012 | Manoharan et al. |
| 8,137,695 B2 | 3/2012 | Rozema et al. |
| 8,143,230 B2 | 3/2012 | Bhanot et al. |
| 8,158,601 B2 | 4/2012 | Chen et al. |
| 8,216,786 B2 | 7/2012 | Shiffman et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,376 B2 | 9/2013 | Ferrara et al. |
| 8,541,548 B2 | 9/2013 | Rozema |
| 8,546,556 B2 | 10/2013 | Seth et al. |
| 8,552,163 B2 | 10/2013 | Lee et al. |
| 8,642,752 B2 | 2/2014 | Swayze et al. |
| 8,653,047 B2 | 2/2014 | Crooke et al. |
| 8,664,190 B2 | 3/2014 | Freier et al. |
| 8,673,632 B2 | 3/2014 | Crooke et al. |
| 8,697,860 B1 | 4/2014 | Monia et al. |
| 8,742,075 B2 | 6/2014 | Lee et al. |
| 9,127,276 B2 | 9/2015 | Prakash et al. |
| 9,133,461 B2 | 9/2015 | Bettencourt et al. |
| 9,145,558 B2 | 9/2015 | Prakash et al. |
| 9,163,239 B2 | 10/2015 | Prakash et al. |
| 9,181,549 B2 | 11/2015 | Prakash et al. |
| 9,181,550 B2 | 11/2015 | Prakash et al. |
| 9,322,018 B2 | 4/2016 | Bettencourt et al. |
| 9,550,988 B2 | 1/2017 | Swayze |
| 9,884,045 B2 | 2/2018 | Takahashi |
| 9,957,292 B2 | 5/2018 | Prakash et al. |
| 9,957,504 B2 | 5/2018 | Prakash et al. |
| 9,957,505 B2 | 5/2018 | Hauser |
| 9,994,855 B2 | 6/2018 | Prakash et al. |
| 10,023,861 B2 | 7/2018 | Prakash et al. |
| 10,280,423 B2 | 5/2019 | Prakash et al. |
| 10,294,477 B2 | 5/2019 | Swayze |
| 10,883,104 B2 * | 1/2021 | Prakash ............. C12N 15/113 |
| 11,851,655 B2 | 12/2023 | Prakash et al. |
| 2001/0053519 A1 | 12/2001 | Fodor et al. |
| 2002/0082227 A1 | 6/2002 | Henry |
| 2003/0017488 A1 | 1/2003 | Koishi et al. |
| 2003/0077829 A1 | 4/2003 | Maclachlan |
| 2003/0119724 A1 | 6/2003 | Ts et al. |
| 2003/0170249 A1 | 9/2003 | Hakomori et al. |
| 2003/0228597 A1 | 12/2003 | Cowsert et al. |
| 2004/0038274 A1 | 2/2004 | Cook et al. |
| 2004/0171564 A1 | 9/2004 | Honkanen et al. |

(56) References Cited

U.S. PATENT DOCUMENTS

| | | |
|---|---|---|
| 2004/0171570 A1 | 9/2004 | Allerson et al. |
| 2004/0203145 A1 | 10/2004 | Zamore et al. |
| 2004/0208856 A1 | 10/2004 | Crooke et al. |
| 2004/0242516 A1 | 12/2004 | Crooke et al. |
| 2004/0259086 A1 | 12/2004 | Schlegel et al. |
| 2005/0009088 A1 | 1/2005 | Crooke et al. |
| 2005/0112118 A1 | 5/2005 | Cimbora et al. |
| 2005/0130923 A1 | 6/2005 | Bhat et al. |
| 2005/0153337 A1 | 7/2005 | Manoharan |
| 2005/0164235 A1 | 7/2005 | Manoharan et al. |
| 2005/0244869 A1 | 11/2005 | Brown-driver et al. |
| 2005/0255487 A1 | 11/2005 | Khvorova et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2007/0054856 A1 | 3/2007 | Gerber et al. |
| 2007/0088154 A1 | 4/2007 | Khvorova et al. |
| 2007/0287831 A1 | 12/2007 | Seth et al. |
| 2008/0039618 A1 | 2/2008 | Allerson et al. |
| 2008/0108801 A1 | 5/2008 | Manoharan et al. |
| 2008/0113351 A1 | 5/2008 | Naito et al. |
| 2008/0177045 A1 | 7/2008 | Lee et al. |
| 2008/0206869 A1 | 8/2008 | Smith et al. |
| 2008/0255030 A1 | 10/2008 | Yu et al. |
| 2008/0281041 A1 | 11/2008 | Rozema et al. |
| 2008/0281044 A1 | 11/2008 | Monahan et al. |
| 2009/0012281 A1 | 1/2009 | Swayze et al. |
| 2009/0203132 A1 | 8/2009 | Swayze et al. |
| 2009/0203135 A1 | 8/2009 | Forst et al. |
| 2009/0239814 A1 | 9/2009 | Manoharan et al. |
| 2009/0286973 A1 | 11/2009 | Manoharan et al. |
| 2009/0306180 A1 | 12/2009 | Bhanot et al. |
| 2009/0318536 A1 | 12/2009 | Freier et al. |
| 2009/0326040 A1 | 12/2009 | Geary et al. |
| 2010/0093085 A1 | 4/2010 | Yamada et al. |
| 2010/0240730 A1 | 9/2010 | Beigelman et al. |
| 2010/0331390 A1 | 12/2010 | Crooke et al. |
| 2011/0039910 A1 | 2/2011 | Crooke et al. |
| 2011/0077386 A1 | 3/2011 | Lee et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0124853 A1 | 5/2011 | Chen et al. |
| 2011/0201798 A1 | 8/2011 | Manoharan |
| 2011/0207799 A1 | 8/2011 | Rozema et al. |
| 2011/0243948 A1 | 10/2011 | Lee et al. |
| 2011/0269814 A1 | 11/2011 | Manoharan et al. |
| 2011/0294868 A1 | 12/2011 | Monia et al. |
| 2012/0035115 A1 | 2/2012 | Manoharan et al. |
| 2012/0071641 A1 | 3/2012 | Manoharan et al. |
| 2012/0095075 A1 | 4/2012 | Manoharan et al. |
| 2012/0101148 A1 | 4/2012 | Aking et al. |
| 2012/0122958 A1 | 5/2012 | Dawson et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2012/0225927 A1 | 9/2012 | Sah et al. |
| 2012/0230938 A1 | 9/2012 | Rozema et al. |
| 2013/0004427 A1 | 1/2013 | El-sayed et al. |
| 2013/0017250 A1 | 1/2013 | Ginsberg et al. |
| 2013/0023579 A1 | 1/2013 | Crooke et al. |
| 2013/0035366 A1 | 2/2013 | Swayze et al. |
| 2013/0053431 A1 | 2/2013 | Tachas et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0236968 A1 | 9/2013 | Manoharan et al. |
| 2013/0317085 A1 | 11/2013 | Crooke et al. |
| 2014/0107184 A1 | 4/2014 | Swayze et al. |
| 2014/0256797 A1 | 9/2014 | Monia et al. |
| 2014/0343123 A1 | 11/2014 | Prakash et al. |
| 2014/0357701 A1 | 12/2014 | Swayze et al. |
| 2015/0057329 A1 | 2/2015 | Bhanot et al. |
| 2015/0126720 A1 | 5/2015 | Prakash et al. |
| 2016/0046939 A1 | 2/2016 | Prakash et al. |
| 2016/0222389 A1 | 8/2016 | Grossman et al. |
| 2018/0256629 A1 | 9/2018 | Crooke et al. |
| 2021/0087566 A1 | 3/2021 | Prakash et al. |

FOREIGN PATENT DOCUMENTS

| | | |
|---|---|---|
| JP | 2005520489 A | 7/2005 |
| JP | 2009524431 A | 7/2009 |
| RU | 1834904 A3 | 8/1993 |
| RU | 2145964 C1 | 2/2000 |
| RU | 2249458 C2 | 4/2005 |
| RU | 2249463 C2 | 4/2005 |
| RU | 2392966 C2 | 6/2010 |
| WO | 9402499 A1 | 2/1994 |
| WO | 9417093 A1 | 8/1994 |
| WO | 9519433 A2 | 7/1995 |
| WO | 9614329 A1 | 5/1996 |
| WO | 9720563 A1 | 6/1997 |
| WO | 9746098 A1 | 12/1997 |
| WO | 9813381 A1 | 4/1998 |
| WO | 9839352 A1 | 9/1998 |
| WO | 9914226 A2 | 3/1999 |
| WO | 0010599 A2 | 3/2000 |
| WO | 0014048 A1 | 3/2000 |
| WO | 0063364 A2 | 10/2000 |
| WO | 0076554 A1 | 12/2000 |
| WO | 0105825 A2 | 1/2001 |
| WO | 0107602 A2 | 2/2001 |
| WO | 0153528 A1 | 7/2001 |
| WO | 0243771 A2 | 6/2002 |
| WO | 0149687 A2 | 7/2002 |
| WO | 02092772 A2 | 11/2002 |
| WO | 03004602 A2 | 1/2003 |
| WO | 03010284 A2 | 2/2003 |
| WO | 03014307 A2 | 2/2003 |
| WO | 03044172 A2 | 5/2003 |
| WO | 2004024757 A2 | 3/2004 |
| WO | 2004035765 A2 | 4/2004 |
| WO | 2004044181 A2 | 5/2004 |
| WO | 2004045543 A2 | 6/2004 |
| WO | 2004063208 A1 | 7/2004 |
| WO | 2004071407 A2 | 8/2004 |
| WO | 2004072046 A2 | 8/2004 |
| WO | 2004078922 A2 | 9/2004 |
| WO | 2004093783 A2 | 11/2004 |
| WO | 2004096016 A2 | 11/2004 |
| WO | 2004096996 A2 | 11/2004 |
| WO | 2004101619 A1 | 11/2004 |
| WO | 2004106356 A1 | 12/2004 |
| WO | 2005000201 A2 | 1/2005 |
| WO | 2005005599 A2 | 1/2005 |
| WO | 2005021570 A1 | 3/2005 |
| WO | 2005028628 A2 | 3/2005 |
| WO | 2005071080 A2 | 8/2005 |
| WO | 2005083124 A1 | 9/2005 |
| WO | 2005097155 A1 | 10/2005 |
| WO | 2005121371 A2 | 12/2005 |
| WO | 2006014729 A2 | 2/2006 |
| WO | 2006031461 A2 | 3/2006 |
| WO | 2006044531 A2 | 4/2006 |
| WO | 2006047842 A2 | 5/2006 |
| WO | 2007035759 A1 | 3/2007 |
| WO | 2007035771 A2 | 3/2007 |
| WO | 2007089584 A2 | 8/2007 |
| WO | 2007090071 A2 | 8/2007 |
| WO | 2007131237 A2 | 11/2007 |
| WO | 2007134014 A2 | 11/2007 |
| WO | 2007134181 A2 | 11/2007 |
| WO | 2007136988 A2 | 11/2007 |
| WO | 2007143317 A2 | 12/2007 |
| WO | 2007146511 A2 | 12/2007 |
| WO | 2008036825 A2 | 3/2008 |
| WO | 2008066776 A2 | 6/2008 |
| WO | 2008073300 A2 | 6/2008 |
| WO | 2008098788 A2 | 8/2008 |
| WO | 2008101157 A1 | 8/2008 |
| WO | 2008150729 A2 | 12/2008 |

(56) References Cited

FOREIGN PATENT DOCUMENTS

| | | |
|---|---|---|
| WO | 2008154401 A2 | 12/2008 |
| WO | 2009003009 A1 | 12/2008 |
| WO | 2009006478 A2 | 1/2009 |
| WO | 2009029293 A2 | 3/2009 |
| WO | 2009046141 A2 | 4/2009 |
| WO | 2009061851 A2 | 5/2009 |
| WO | 2009073809 A2 | 6/2009 |
| WO | 2009082607 A2 | 7/2009 |
| WO | 2009126933 A2 | 10/2009 |
| WO | 2009134487 A2 | 11/2009 |
| WO | 2009143369 A2 | 11/2009 |
| WO | 2009148605 A2 | 12/2009 |
| WO | 2010017509 A1 | 2/2010 |
| WO | 2010036696 A1 | 4/2010 |
| WO | 2010036698 A1 | 4/2010 |
| WO | 2010045509 A2 | 4/2010 |
| WO | 2010048228 A2 | 4/2010 |
| WO | 2010048549 A2 | 4/2010 |
| WO | 2010048585 A2 | 4/2010 |
| WO | 2010054406 A1 | 5/2010 |
| WO | 2010077578 A1 | 7/2010 |
| WO | 2010083615 A1 | 7/2010 |
| WO | 2010088537 A2 | 8/2010 |
| WO | 2010101951 A1 | 9/2010 |
| WO | 2010103204 A1 | 9/2010 |
| WO | 2010121074 A1 | 10/2010 |
| WO | 2010/129709 A1 | 11/2010 |
| WO | 2010144740 A1 | 12/2010 |
| WO | 2010148013 A2 | 12/2010 |
| WO | 2011/005860 A2 | 1/2011 |
| WO | 2011/005861 A1 | 1/2011 |
| WO | 2011005786 A2 | 1/2011 |
| WO | 2011038356 A2 | 3/2011 |
| WO | 2011047312 A1 | 4/2011 |
| WO | 2011085271 A2 | 7/2011 |
| WO | 2011100131 A2 | 8/2011 |
| WO | 2011115818 A1 | 9/2011 |
| WO | 2011120053 A1 | 9/2011 |
| WO | 2011133871 A2 | 10/2011 |
| WO | 2011139702 A2 | 11/2011 |
| WO | 2011139917 A1 | 11/2011 |
| WO | 2011163121 A1 | 12/2011 |
| WO | 2012037254 A1 | 3/2012 |
| WO | 2012068187 A1 | 5/2012 |
| WO | 2012083620 A2 | 6/2012 |
| WO | 2012083185 A2 | 6/2012 |
| WO | 2012089352 A1 | 7/2012 |
| WO | 2012089602 A1 | 7/2012 |
| WO | 2012135736 A2 | 10/2012 |
| WO | 2012142458 A1 | 10/2012 |
| WO | 2012145674 A1 | 10/2012 |
| WO | 2012145697 A1 | 10/2012 |
| WO | 2012149495 A1 | 11/2012 |
| WO | 2012174154 A1 | 12/2012 |
| WO | 2012177639 A2 | 12/2012 |
| WO | 2012177784 A2 | 12/2012 |
| WO | 2012177947 A2 | 12/2012 |
| WO | 2013033230 A1 | 3/2013 |
| WO | 2013043817 A1 | 3/2013 |
| WO | 2013075035 A1 | 5/2013 |
| WO | 2013119979 A1 | 8/2013 |
| WO | 2013142514 A1 | 9/2013 |
| WO | 2013142571 A2 | 9/2013 |
| WO | 2013155204 A2 | 10/2013 |
| WO | 2013165816 A2 | 11/2013 |
| WO | 2013166121 A1 | 11/2013 |
| WO | 2013173789 A2 | 11/2013 |
| WO | 2013177468 A2 | 11/2013 |
| WO | 2013192233 A1 | 12/2013 |
| WO | 2014025805 A1 | 2/2014 |
| WO | 2014076195 A1 | 5/2014 |
| WO | 2014076196 A1 | 5/2014 |
| WO | 2014118267 A1 | 8/2014 |
| WO | 2014118272 A1 | 8/2014 |
| WO | 2014179620 A1 | 11/2014 |
| WO | 2014179625 A1 | 11/2014 |
| WO | 2014179626 A2 | 11/2014 |
| WO | 2014179627 A2 | 11/2014 |
| WO | 2014179629 A2 | 11/2014 |
| WO | 2014207232 A1 | 12/2014 |
| WO | 2015002971 A2 | 1/2015 |
| WO | 2015006740 A2 | 1/2015 |
| WO | 2015179693 A1 | 11/2015 |
| WO | 2015188194 A1 | 12/2015 |
| WO | 2017079739 A1 | 5/2017 |
| WO | 2017079745 A1 | 5/2017 |

OTHER PUBLICATIONS

Jaeger, et al., Longitudinal cohort study on the effectiveness of lipid apheresis treatment to reduce high lipoprotein (a) levels and prevent major adverse coronary events, Nature Clinical Practice Cardivascular Medicine, 6(3), 229-239, Mar. 2009.

Abifadel, et al., Mutations in PCSK9 cause autosomal dominant hypercholesterolemia, Nature Genetics, Jun. 2003, 154-156, 34(2).

Akinc, et al., Targeted Delivery of RNAi Therapeutics With Endogenous and Exogenous Ligand-Based Mechanisms, Molecular Therapy, Jul. 2010, 1357-1364, 18(7).

Albaek, et al., Analogus of a Locked Nucleic Acid with Three-Carbon 2',4'-Linkages: Synthesis by Ring-Closing Metathesis and Influence on Nucleic Acid Duplex Stability and Structure, J. Org. Chem., 2006, 7731-7740, 71(20).

Allshire, RNAi and Heterochromatin—a Hushed-Up Affair, Science, Sep. 13, 2002, 1818-1819, 297.

Altmann, et al., Second Generation Antisense Oligonucleotides-Inhibition of PKC-a and c-raf Kinase Expression by Chimeric Oligonucleotides Incorporating 6"-Substituted Carbocyclic Nucleosides and 2"-O-Ethylene Glycol Substituted Ribonucleosides, Nucleosides, Nucleotides & Nucleic Acids, 1997, 917-926, 16(7-9).

Altmann, et al., Second Generation of Antisense Oligonucleotides: From Nuclease Resistance to Biological Efficacy in Animals, Chimia, 1996, 168-176, 50(4).

Altmann, et al., Second-generation antisense oligonucleotides: structure-activity relationships and the design of improved signal-transduction inhibitors, Biochemical Society Transaction, 1996, 630-637, 24.

Ando, et al., A decreased expression of angiopoietin-like 3 is protective against atherosclerosis in apoE-deficient mice, Journal of Lipid Research, 2003, 1216-1223, 44.

Andre, et al., Determination of modulation of ligand properties of synthetic complex-type biantennary N-glycans by introduction of bisecting GlcNAc in silico, in vitro and in vivo, Eur. J. Biochem., 2004, 118-134, 271.

Angelakopoulou, et al., Comparative analysis of genome-wide association studies signals for lipids, diabetes, and coronary heart disease: Cardiovascular Biomarker Genetics Collaboration, European Heart Journal, 2012, 393-407, 33.

Asseline, Modification of the 5' Terminus of Oligonucleotides for Attachment of Reporter and Conjugate Groups, Current Protocols in Nucleic Acid Chemistry, 2000, 4.2.1-4.2.33.

Atsma, et al., Partial characterization of low density lipoprotein preparations isolated from fresh and frozen plasma after radiolabeling by seven different methods, Journal of Lipid Research, 1991, 173-181, 32.

Baker, et al., 2'-O-(2-Methoxy)ethyl-modified Anti-intercellular Adhesion Molecule 1 (ICAM-1) Oligonucleotides Selectively Increase ICAM-1 mRNA Level and Inhibit Formation of the ICAM-1 Translation Initiation Complex in Human Umbilical Vein Endothelial Cells, J Biol Chem, May 2, 1997, 11994-12000, 272(18).

Beaucage, et al., The functionalization of oligonucleotides via phosphoramidite derivatives, Tetrahedron, Mar. 5, 1993, 1925-1963, 49(10).

Bennett, Pharmacological properties of 2'-O-methoxyethyl modified oligonucleotides, Antisense Drug Technology, 2008, 273-303, chapter 10.

Bergeron, et al., Subtilase-like pro-protein convertases: from molecular specificity to therapeutic applications, Journal of Molecular Endocrinology, 2000, 1-22, 24.

(56) References Cited

OTHER PUBLICATIONS

Bhattacharjee, et al., Inhibition of Vascular Permeability by Antisense-Mediated Inhibition of Plasma Kallikrein and Coagulation Factor 12, Nucleic Acid Therapeutics, 2013, 175-187, 23(3).

Biessen, et al., Novel hepatotrophic prodrugs of the antiviral nucleoside 9-(2-phosphonylmethoxyethyl)adenine with improved pharmacokinetics and antiviral activity, FASEB Journal, 2000, 1784-1792, 14.

Biessen, et al., Synthesis of Cluster Galactosides with High Affinity for the Hepatic Asialoglycoprotein Receptor, J. Med. Chem., Apr. 1995, 1538-1546, 38.

Biessen, et al., The Cholesterol Derivative of a Triantennary Galactoside with High Affinity for the Hepatic Asialoglycoprotein Receptor: a Potent Cholesterol Lowering Agent, J. Med. Chem., May 1995, 1846-1852, 38.

Bligh, et al., A rapid method of total lipid extraction and purification, Canadian Journal of Biochemistry and Physiology, Aug. 1959, 911-917, 37(8).

Bock, et al., Glycosylation Reactions with Di-O-acetyl-2,6-dibromo-2,6-dideoxy-alpha-D-mannopyranosyl Bromide. A Simple Synthesis of Methyl 2,6-Dideoxy-D-arabino-hexopyranoside, Acta Chem Scandinavica, 1988, 640-645, B42.

Braasch, et al., Locked nucleic acid (LNA): fine-tuning the recognition of DNA and RNA, Chemistry & Biology, 2001, 1-7, 8(1).

Braasch, et al., Novel antisense and peptide nucleic acid strategies for controlling gene expression, Biochemistry, Apr. 9, 2002, 4503-4510, 41(14).

Branch, A good antisense molecule is hard to find, TIBS, Feb. 1998, 45-50, 23.

Branda, et al., Amplification of antibody production by phosphorothioate oligodeoxynucleotides, J Lab Clin Med, Sep. 1996, 329-338, 128(3).

Browning, et al., Molecular mediators of hepatic steatosis and liver injury, Journal of Clinical Investigation, Jul. 2004, 147-152, 114(2).

Brubaker, et al., Structure-function of the glucagon receptor family of G protein-coupled receptors: the glucagon, GIP, GLP-1, and GLP-2 receptors, Receptors and Channels, 2002, 179-188, 8.

Camenisch, et al., ANGPTL3 Stimulates Endothelial Cell Adhesion and Migration via Integrin avb3 and Induces Blood Vessel Formation in Vivo, Journal of Biological Chemistry, May 10, 2002, 17281-17290, 277(19).

Chen, et al., Strand-specific 59-O-methylation of siRNA duplexes controls guide strand selection and targeting specificity, RNA, 2008, 263-274, 14.

Chiang, et al., Antisense Oligonucleotides Inhibit Intercellular Adhesion Molecule 1 Expression by Two Distinct Mechanisms, Journal of Biological Chemistry, Sep. 25, 1991, 18162-18171, 266(27).

Chin, On the Preparation and Utilization of Isolated and Purified Oligonucleotides, Mar. 9, 2002.

Coltart, et al., Principles of Mucin Architecture: Structural Studies on Synthetic Glycopeptides Bearing Clustered Mono-, Di-, Tri-, and Hexasaccharide Glycodomains, J. Am. Chem. Soc., 2002, 9833-9844, 124.

Conklin, et al., Identification of a Mammalian Angiopoietin-Related Protein Expressed Specifically in Liver, Genomics, 1999, 477-482, 62.

Connolly, et al., Binding and Endocytosis of Cluster Glycosides by Rabbit Hepatocytes, Journal of Biological Chemistry, Jan. 25, 1982, 939-945, 257(2).

Costa, et al., Amyloid fibril protein related to prealbumin in familial amyloidotic polyneuropathy, PNAS, Sep. 1978, 4499-4503, 75(9).

Crew, et al., Eukaryotic initiation factor-4E in superficial and muscle invasive bladder cancer and its correlation with vascular endothelial growth factor expression and tumour progression, British Journal of Cancer, 2000, 161-166, 82(1).

Crooke, Basic Principles of Antisense Therapeutic, Antisense Research and Application, 1998, 1-50.

Crooke, et al., Pharmacokinetic Properties of Several Novel Oligonucleotide Analogs in Mice, The Journal of Pharmacology and Experimental Therapeutics, 1996, 923-937, 277(2).

Czech, et al., RNAi-based therapeutic strategies for metabolic disease, Nature Reviews Endocrinology, Aug. 2011, 473-484, 7.

Davidson, et al., Apolipoprotein B: mRNA Editing, Lipoprotein Assembly, and Presecretory Degradation, Annu. Rev. Nutr., 2000, 169-193, 20.

De Benedetti, et al., Overexpression of eukaryotic protein synthesis initiation factor 4E in HeLa cells results in aberrant growth and morphology, PNAS, Nov. 1990, 8212-8216, 87.

Dellinger, et al., Solid-Phase Chemical Synthesis of Phosphonoacetate and Thiophosphonoacetate Oligodeoxynucleotides, J. Am. Chem. Soc., 2003, 940-950, 125.

Dickson, et al., Rat Choroid Plexus Specializes in the Synthesis and the Secretion of Transthyretin (Prealbumin, Journal of Biological Chemistry, Mar. 15, 1986, 3475-3478, 261(8).

Dubuc, et al., Statins Upregulate PCSK9, the Gene Encoding the Proprotein Convertase Neural Apoptosis-Regulated Convertase-1 Implicated in Familial Hypercholesterolemia, Arterioscler Thromb Vasc Biol., Aug. 2004, 1454-1459.

Duff, et al., Intrabody Tissue-Specific Delivery of Antisense Conjugates in Animals: Ligand-Linker-Antisense Oligomer Conjugates, Methods in Enzymology, 2000, 297-321, 313.

Dupouy, et al., Watson-Crick Base-Pairing Properties of Nucleic Acid Analogues with Stereocontrolled a and b Torsion Angles (a,b-D-CNAs), Angew. Chem. Int. Ed., 2006, 3623-3627, 45.

Elayadi, et al., Application of PNA and LNA oligomers to chemotherapy, Current Opinion in Investigational Drugs, 2001, 558-561, 2(4).

Elchebly, et al., Increased Insulin Sensitivity and Obesity Resistance in Mice Lacking the Protein Tyrosine Phosphatase-1B Gene, Science, Mar. 5, 1999, 1544-1548, 283.

EMBL Accession No. BG400407.1, *Homo sapiens* cDNA clone, Mar. 17, 2001, retrieved from https://www.ebi.ac.uk/ena/browser/view/BG400407.

Encio, et al., The Genomic Structure of the Human Glucocorticoid Recepto, Journal of Biological Chemistry, Apr. 15, 1991, 7182-7188, 266(11).

Englisch, et al., Chemically Modified Oligonucleotides as Probes and Inhibitors, Angew Chem Int Ed Eng, Jun. 1991, 613-629, 30(6).

Executive Summary of the Third Report of the National Cholesterol Education Program (NCEP) Expert Panel on Detection, Evaluation, and Treatment of High Blood Cholesterol in Adults (Adult Treatment Panel III), JAMA, May 16, 2001, 2486-2497, 285(19).

Freier, et al., The ups and downs of nucleic acid duplex stability: structure-stability studies on chemically-modified DNA: RNA duplexes, Nucleic Acids Research, 1997, 4429-4443, 25(22).

Fried, et al., HBeAg and Hepatitis B Virus DNA as Outcome Predictors During Therapy with Peginterferon Alfa-2a for HBeAg-Positive Chronic Hepatitis B, Hepatology, 2008, 428-434, 47.

Frieden, et al., Expanding the design horizon of antisense oligonucleotides with alpha-L-LNA, Nucleic Acids Research, 2003, 6365-6372, 31(21).

Fujimoto, et al., Angptl3-null mice show low plasma lipid concentrations by enhanced lipoprotein lipase activity, Exp. Anim., 2006, 27-34, 55(1).

Fukada, et al., Two Signals Are Necessary for Cell Proliferation Induced by a Cytokine Receptor gp130: Involvement of STAT3 in Anti-Apoptosis, Immunity, Nov. 1996, 449-450, 5.

Ganem, et al., Hepatitis B Virus Infection—Natural History and Clinical Consequences, N Engl J Med., Mar. 11, 2004, 1118-1129, 350(11).

Gao, et al., Angiopoietin-like protein 3 regulates the motility and permeability of podocytes by altering nephrin expression in vitro, Biochemical and Biophysical Research Communications, Jul. 13, 2010, 31-36, 399.

Gautschi, et al., Activity of a Novel bcl-2/bcl-xL-Bispecific Antisense Oligonucleotide Against Tumors of Diverse Histologic Origins, Journal of the National Cancer Institute, Mar. 21, 2001, 463-471, 93(6).

Geary, et al., A Nonradioisotope Biomedical Assay for Intact Oligonucleotide and Its Chain-Shortened Metabolites Used for Determination of Exposure and Elimination Half-Life of Antisense Drugs in Tissue, Analytical Biochemistry, 1999, 241-248, 274.

(56) References Cited

OTHER PUBLICATIONS

Geary, et al., Effect of dose and plasma concentration on liver uptake and pharmacologic activity of a 20-methoxyethyl modified chimeric antisense oligonucleotide targeting PTEN, Biochemical Pharmacology, 2009, 284-291, 78.
Geary, et al., Pharmacokinetic Properties of 29-O-(2-Methoxyethyl)-Modified Oligonucleotide Analogs in Rats, Journal of Pharmacology and Experimental Therapeutics, 2001, 890-897, 296.
Gehring, et al., Assignment of the human gene for the glucocorticoid receptor to chromosome 5, PNAS, Jun. 1985, 3751-3755, 82.
GenBank accession No. NM014495.1, *Homo sapiens* angiopoietin like 3 (ANGPTL3), mRNA, retrieved from https://www.ncbi.nlm.nih.gov/nuccore/NM_014495.
Gensberg, et al., Subtilisin-related serine proteases in the mammalian constitutive secretory pathway, Cell and Developmental Biology, 1998, 11-17, 9.
Giguere, et al., Functional Domains of the Human Glucocorticoid Receptor, Cell, Aug. 29, 1986, 645-652, 46.
Gough, et al., Mitochondrial STAT3 Supports Ras-Dependent Oncogenic Transformation, Science, Jun. 26, 2009, 1713-1716, 324.
Graff, et al., Translational control and metastatic progression: Enhanced activity of the mRNA cap-binding protein eIF-4E selectively enhances translation of metastasis-related mRNAs, Clinical & Experimental Metastasis, 2003, 265-273, 20.
Graham, et al., Antisense inhibition of apolipoprotein(a) in cynomolgus monkeys significantly reduces plasma apolipoprotein(a) levels without affecting plasminogen or other major lipid classes, Circulation, 2012, Abstract A11050, 126(21).
Graham, et al., Antisense Oligonucleotide Inhibition of Apolipoprotein C-III Reduces Plasma Triglycerides in Rodents, Nonhuman Primates, and Humans, Circulation Research, May 24, 2013, 1479-1490, 112.
Graham, et al., Cardiovascular and Metabolic Effects of ANGPTL3 Antisense Oligonucleotides, N Engl J Med., Jul. 20, 2017, 222-232, 377(3).
Gu, et al., Base Pairing Properties of D- and L-Cyclohexene Nucleic Acids (CeNA), Oligonucleotides, 2003, 479-489, 13.
Gu, et al., Enzymatic resolution and base pairing properties of D- and L-cyclohexenyl nucleic acids (CeNA), Nucleosides Nucleotides Nucleic Acids, 2005, 993-998, 24(5-7).
Gu, et al., Synthesis of enantiomeric-pure cyclohexenyl nucleoside building blocks for oligonucleotide synthesis, Tetrahedron, 2004, 2111-2123, 60.
Guzaev, et al., A Conformationally Preorganized Universal Solid Support for Efficient Oligonucleotide Synthesis, J. Am. Chem. Soc., 2003, 2380-2381, 125.
Hall, et al., Establishment and Maintenance of a Heterochromatin Domain, Science, Sep. 27, 2002, 2232-2237, 297.
Hanessian, et al., Synthesis of chemically and functionally diverse scaffolds from pentaerythritol, Can. J. Chem., 1996, 1731-1737, 74.
Hansen, et al., Glucagon Receptor mRNA Distribution in Rat Tissues, Peptides, 1995, 1163-1166, 16(6).
Hatsuda, et al., Association between Plasma Angiopoietin-Like Protein 3 and Arterial Wall Thickness in Healthy Subjects, J Vasc Res, 2007, 61-66, 44.
Haydon, et al., Progression of eIF4E Gene Amplification and Overexpression in Benign and Malignant Tumors of the Head and Neck, Cancer, Jun. 15, 2000, 2803-2810, 88(12).
Henry, et al., Drug properties of second-generation antisense oligonucleotides: How do they measure up to their predecessors?, Curr Opin Investig Drugs, 2001, 1444-1449, 2.
Henry, et al., Toxicologic properties od 2'O-Methoxyethyl chimeric antisense inhibitors in animals and man, Antisense Drug Technology, 2008, 327-363, chapter 12.
Hoffmann, et al., 'Brain-type' N-glycosylation of asialo-transferrin from human cerebrospinal fluid, FEBS Letters, 1995, 164-168, 359.
Hollenberg, et al., Primary structure and expression of a functional human glucocorticoid receptor cDNA, Nature, Dec. 1985, 635-641, 318.
Hooper, et al., Recent developments in the genetics of LDL deficiency, Curr Opin Lipidol., Apr. 2013, 111-115, 24 (2).
Horn, et al., Chemical synthesis and characterization of branched oligodeoxyribonucleotides (bDNA) for use as signal amplifiers in nucleic acid quantification assays, Nucleic Acids Research, 1997, 4842-4849, 25(23).
Horton, et al., Combined analysis of oligonucleotide microarray data from transgenic and knockout mice identifies direct SREBP target genes, PNAS, Oct. 14, 2010, 12027-12032, 100(21).
Horvath, et al., Stereoselective synthesis of (-)-ara-cyclohexenyl-adenine, Tetrahedron Letters, Mar. 12, 2007, 3621-3623, 48.
Ichimura, et al., Serum Angiopoietin-like Protein 3 Levels: Possible Correlation with Progressive Skin Sclerosis, Digital Ulcers and Pulmonary Vascular Involvement in Patients with Systemic Sclerosis, Acta Derm Venereol, 2014, 157-162, 94.
Inaba, et al., Angiopoietin-like Protein 3 Mediates Hypertriglyceridemia Induced by the Liver X Receptor, Journal of Biological Chemistry, Jun. 13, 2003, 21344-21351, 278(24).
Inukai, et al., ANGPTL3 is increased in both insulin-deficient and -resistant diabetic states, Biochemical and Biophysical Research Communications, 2004, 1075-1079, 317.
Ishibashi, et al., Hypercholesterolemia in Low Density Lipoprotein Receptor Knockout Mice and its Reversal by Adenovirus-mediated Gene Delivery, Journal of Clinical Investigation, 1993, 883-893, 92(2).
Jain, et al., Repression of Stat3 activity by activation of mitogen-activated protein kinase (MAPK), Oncogene, 1998, 3157-3167, 17.
Jayaprakash, et al., Non-Nucleoside Building Blocks for Copper-Assisted and Copper-Free Click Chemistry for the Efficient Synthesis of RNA Conjugates, Organic Letters, 2010, 5410-5413, 12(23).
Jenuwein, An RNA-Guided Pathway for the Epigenome, Science, Sep. 27, 2002, 2215-2218, 297.
Jervis, et al., New CD1d agonists: Synthesis and biological activity of 600-triazole-substituted a-galactosyl ceramides, Bioorganic & Medicinal Chemistry Letters, May 9, 2012, 4348-4352, 22.
Jiang, et al., Glucagon and regulation of glucose metabolism, Am J Physiol Endocrinol Metab, 2003, 671-678, 284.
Jiang, et al., The Design and Synthesis of Highly Branched and Spherically Symmetric Fluorinated Oils and Amphiles, Tetrahedron, May 7, 2007, 3982-3988, 63(19).
Jin, et al., Use of alpha-N,N-bis[carboxymethyl]lysine-modified peroxidase in immunoassays, Analytical Biochemistry, 1995, 54-60, 229.
Jones, et al., RNA Quantitation by Fluorescence-Based Solution Assay: RiboGreen Reagent Characterization, Analytical Biochemistry, 1998, 368-374, 265.
Kabanov, et al., A new class of antivirals: antisense oligonucleotides combined with a hydrophobic substituent effectively inhibit influenza virus repproduction and synthesis of virus-specific proteins in MDCK cells, FEBS Letters, Jan. 1990, 327-330, 259(2).
Kanasty, et al., Delivery materials for siRNA therapeutics, Nature Materials, Nov. 2013, 967-977, 12.
Kaplan, et al., Regulation of the angiopoietin-like protein 3 gene by LXR, Journal of Lipid Research, 2003, 136-143, 44.
Kassim, et al., Gene therapy for dyslipidemia: a review of gene replacement and gene inhibition strategies, Clin Lipidol., Jun. 2010, 793-809, 5(6).
Kato, et al., N-acetylgalactosamine incorporation into a peptide containing consecutive threonine residues by UDP-N-acetyl-D-galactosaminide:polypeptide N-acetylgalactosaminyltransferases, Glycobiology, 2001, 821-829, 11(10).
Kerekatte, et al., The Proto-Oncogene/Translation Factor eIF4E: A Survey of Its Expression in Breast Carcinomas, Int. J. Cancer, 1995, 27-31, 64.
Khorev, et al., Trivalent, Gal/GalNAc-containing ligands designed for the asialoglycoprotein receptor, Bioorganic & Medicinal Chemistry, 2008, 5216-5231, 16.
Kim, et al., Oligomeric Glycopeptidomimetics Bearing the Cancer Related TN-Antigen, Tetrahedron Letters, 1997, 3487-3490, 38(20).
Kim, et al., Synthesis of Novel Phosphoramidite Building Blocks from Pentaerythritol, Synlett, 2003, 1838-1840, 12.

(56) References Cited

OTHER PUBLICATIONS

Klaman, et al., Increased Energy Expenditure, Decreased Adiposity, and Tissue-Specific Insulin Sensitivity in Protein-Tyrosine Phosphatase 1B-Deficient Mice, Molecular and Cellular Biology, Aug. 2000, 5479-5489, 20(15).
Koishi, et al., Angptl3 regulates lipid metabolism in mice, Nature Genetics, Feb. 2002, 151-157, 30.
Koller, et al., Mechanisms of single-stranded phosphorothioate modified antisense oligonucleotide accumulation in hepatocytes, Nucleic Acids Research, Feb. 23, 2011, 4795-4807, 39(11).
Komilova, et al., Development of a fluorescence polarization binding assay for asialoglycoprotein receptor, Analytical Biochemistry, 2012, 43-46, 425.
Korstanje, et al., Locating Ath8, a locus for murine atherosclerosis susceptibility and testing several of its candidate genes in mice and humans, Atherosclerosis, Sep. 27, 2004, 443-450, 177.
Koshkin, et al., LNA (locked nucleic acids): Synthesis of the adenine, cytosine, guanine, 5-methylcytosine, thymine and uracil bicyclonucleoside monomers, oligomerisation, and unprecedented nucleic acid recognition, Tetrahedron, 1998, 3607-3630, 54.
Koster, et al., Transgenic Angiopoietin-Like (Angptl)4 Overexpression and Targeted Disruption of Angptl4 and Angptl3: Regulation of Triglyceride Metabolism, Endocrinology, 2005, 4943-4950, 146(11).
Kroschwitz, Polynucleotides, Concise Encyclopedia of Polymer Science and Engineering, 1990, 858-859.
Kumar, et al., The first analogues of LNA (locked nucleic acids): phosphorothioate-LNA and 2'-thio-LNA, Bioorganic & Medicinal Chemistry Letters, 1998, 2219-2222, 8.
Kurosawa, et al., Selective silencing of a mutant transthyretin allele by small interfering RNAs, Biochemical and Biophysical Research Communications, 2005, 1012-1018, 337.
Lazaris-Karatzas, et al., Malignant transformation by a eukaryotic initiation factor subunit that binds to mRNA 5' cap, Nature, Jun. 7, 1990, 544-547, 345.
Lee, et al., Antisense Technology: An Emerging Platform for Cardiovascular Disease Therapeutics, J. of Cardiovasc. Trans. Res., 2013, 969-980, 6.
Lee, et al., Facile Synthesis of a High-Affinity Ligand for Mammalian Hepatic Lectin Containing Three Terminal N-Acetylgalactosamine Residues, Bioconjugate Chemistry, 1997, 762-765, 8.
Lee, et al., Identification of a New Functional Domain in Angiopoietin-like 3 (ANGPTL3) and Angiopoietin-like 4 (ANGPTL4) Involved in Binding and Inhibition of Lipoprotein Lipase (LPL), Journal of Biological Chemistry, May 15, 2009, 13735-13745, 284(20).
Lee, et al., New and more efficient multivalent glyco-ligands for asialoglycoprotein receptor of mammalian hepatocytes, Bioorganic & Medicinal Chemistry, Mar. 15, 2011, 2494-2500, 19.
Lee, et al., New Synthetic Cluster Ligands for Galactose/N-Acetylgalactosamine-Specific Lectin of Mammalian Liver1, Biochemistry, 1984, 4255-4261, 23.
Lee, et al., Preparation of Cluster Glycosides of N-Acetylgalactosamine That Have Subnanomolar Binding Constants Towards the Mammalian Hepatic Gal/GalNAc-specific Receptor, Glycoconjugate J, 1987, 317-328, 4.
Lee, et al., Protein microarrays to study carbohydrate-recognition events, Bioorganic & Medicinal Chemistry Letters, Jul. 27, 2006, 5132-5135, 16.
Lee, et al., Synthesis of Multivalent Neoglyconjugates of MUC1 by the Conjugation of Carbohydrate-Centered, Triazole-Linked Glycoclusters to MUC1 Peptides Using Click Chemistry, Journal of Organic Chemistry, Aug. 9, 2012, 7564-7571, 77.
Lee, et al., Synthesis of Peptide-Based Trivalent Scaffold for Preparation of Cluster Glycosides, Methods in Enzymology, 2003, 38-43, 362.
Lee, Synthesis of some cluster glycosides suitable for attachment to proteins or solid matrices, Carbohydrate Research, 1978, 509-514, 67.
Leeds, et al., Quantitation of phosphorothioate oligonucleotides in human plasma, Analytical Biochemistry, 1996, 36-43, 235.
Leren, Mutations in the PCSK9 gene in Norwegian subjects with autosomal dominant hypercholesterolemia, Clin Genet, 2004, 419-422, 65.
Letsinger, et al., Cholesteryl-conjugated oligonucleotides: Synthesis, properties, and activity as inhibitors of replication of human immunodeficiency virus in cell culture, Proc. Natl. Acad. Sci. USA, Sep. 1989, 6553-6556, 86.
Leumann, et al., DNA Analogues: From Supramolecular Principles to Biological Properties, Bioorganic & Medicinal Chemistry, 2002, 841-854, 10.
Liang, et al., Hepatitis B e Antigen—The Dangerous Endgame of Hepatitis B, N Engl J Med., Jul. 18, 2002, 208-210, 347(3).
Lichtenstein, et al., Modulation of plasma TG lipolysis by Angiopoietin-like proteins and GPIHBP1, Biochimica et Biophysica Acta, Jan. 6, 2010, 415-420, 1801.
Lima, et al., Single-Stranded siRNAs Activate RNAi in Animals, Cell, Aug. 31, 2012, 883-894, 150.
Link, Pharmacological regulation of hepatic glucose production, Current opinion in investigational drugs, 2003, 421-429, 4(4).
Linton, et al., Transgenic mice expressing high plasma concentrations of human apolipoprotein B100 and lipoprotein(a), Journal of Clinical Investigation, 1993, 3029-3037, 92(6).
Machida, et al., Bivalent Inhibitors for Disrupting Protein Surface-Substrate Interactions and for Dual Inhibition of Protein Prenyltransferases, J. Am. Chem. Soc., Dec. 15, 2010, 958-963, 133.
Machida, et al., Postmortem findings in a patient with cerebral amyloid angiopathy actively treated with corticosteroid, Amyloid, 2012, 47-52, 19(1).
Maher, et al., Comparative bybrid arrest by tandem antisense oligodeoxyribonucleotides or oligodeoxyribonucleoside methylphosphonates in a cell-free system, Nucleic Acids Research, 1988, 3341-3358, 16(8).
Maier, et al., Synthesis of Antisense Oligonucleotides Conjugated to a Multivalent Carbohydrate Cluster for Cellular Targeting, Bioconjugate Chemistry, 2003, 18-29, 14.
Maierhofer, et al., Probing multivalent carbohydrate-lectin interactions by an enzyme-linked lectin assay employing covalently immobilized carbohydrates, Bioorganic & Medicinal Chemistry, Sep. 6, 2007, 7661-7676, 15.
Makino, et al., Intravenous Injection With Antisense Oligodeoxynucleotides Against Angiotensinogen Decreases Blood Pressure in Spontaneously Hypertensive Rats, Hypertension, May 1998, 1166-1170, 31.
Manoharan, et al., Chemical Modifications to Improve Uptake and Bioavailability of Antisense Oligonucleotides, Ann. N.Y. Acad. Sci., Oct. 1992, 306-309.
Manoharan, et al., Cholic Acid-Oligonucleotide Conjugates for Antisense Applications, Bioorganic & Medicinal Chemistry Letters, 1994, 1053-1060, 4(8).
Manoharan, et al., Introduction of a Lipophilic Thioether Tether in the Minor Groove of Nucleic Acids for Antisense Applications, Bioorganic & Medicinal Chemistry Letters, 1993, 2765-2770, 3(12).
Manoharan, et al., Lipidic Nucleic Acids, Tetrahedron Letters, 1995, 3651, 36(21).
Manoharan, et al., N-(2-Cyanoethoxycarbonyloxy)succinimide: A New Reagent for Protection of Amino Groups in Oligonucleotides, J. Org.Chem., 1999, 6468-6472, 64.
Manoharan, et al., Oligonucleotide Conjugates Alteration of the Pharmacokinetic Properties of Antisense Agents, Nucleosides, Nucleotides & Nucleic Acids, 1995, 969-973, 14(3-5).
Manoharan, et al., Oligonucleotide Conjugates as Potential Antisense Drugs with Improved Uptake, Biodistribution, Targeted Delivery, and Mechanism of Action, Antisense and Nucleic Acid Drug Development, 2002, 103-128, 12.
Marcaurelle, et al., Synthesis of Oxime-Linked Mucin Mimics Containing the Tumor-Related TN and Sialyl TN Antigens, Organic Letters, 2001, 3691-3694, 3(23).
Martin, New acces to 2'-O-alkylated ribonucleosides and properties of 2'-O-alkylated oligoribonucleotides, Helvetica Chimica Acta, 1995, 486-504, 78.

(56) References Cited

OTHER PUBLICATIONS

Martin-Campos, et al., Identification of a novel mutation in the ANGPTL3 gene in two families diagnosed of familial hypobetalipoproteinemia without APOB mutation, Clinica Chimica Acta, 2012, 552-555, 413.
Maxwell, et al., Novel putative SREBP and LXR target genes identified by microarray analysis in liver of cholesterol-fed mice, Journal of Lipid Research, 2003, 2109-2119, 44.
Merwin, et al., Targeted Delivery of DNA Using YEE(GalNAcAH3, a Synthetic Glycopeptide Ligand for the Asialoglycoprotein Receptor, Bioconjugate Chemistry, 1994, 612-620, 5.
Minicocci, et al., Clinical characteristics and plasma lipids in subjects with familial combined hypolipidemia: a pooled analysis, Journal of Lipid Research, 2013, 3481-3490, 54.
Minicocci, et al., Mutations in the ANGPTL3 Gene and Familial Combined Hypolipidemia: A Clinical and Biochemical Characterization, J Clin Endocrinol Metab., Jul. 2012, 1266-1275, 97(7).
Mishra, et al., Improved keishmanicidal effect of phosphorotioate antisense oligonucleotides by LDL-mediated delivery, Biochimica et biophysica acta, 1995, 229-237, 1264.
Miura, et al., Fluorometric determination of total mRNA with oligo(dT) immobilized on microtiter plates, Clinical Chemistry, 1996, 1758-1764, 42(11).
Moucari, et al., Early Serum HBsAg Drop: A Strong Predictor of Sustained Virological Response to Pegylated Interferon Alfa-2a in HBeAg-Negative Patients, Hepatology, 2009, 1151-1157, 49.
Musunuru, et al., Exome Sequencing, ANGPTL3 Mutations, and Familial Combined Hypolipidemia, N Engl J Med., Dec. 2, 2010, 2220-2227, 363.
Naoumova, et al., A new drug target for treatment of dyslipidemia associated with type 2 diabetes and the metabolic syndrome?, Lancet, Jun. 29, 2002, 2215-2216, 3599.
Nauwelaerts, et al., Cyclohexenyl nucleic acids: conformationally flexible oligonucleotides, Nucleic Acids Research, 2005, 2452-2463, 33(8).
Nauwelaerts, et al., Structural Characterization and Biological Evaluation of Small Interfering RNAs Containing Cyclohexenyl Nucleosides, J. Am. Chem. Soc., 2007, 9340-9348, 129.
Neel, et al., Protein tyrosine phosphatases in signal transduction, Current Opinion in Cell Biology, 1997, 193-204, 9.
New England Biolabs Catalog 1998/99 (cover page and pp. 121-284).
Nishimura, et al., Synthetic Glycoconjugates. 4.1 Use of—(Acrylamido)alkyl Glycosides for the Preparation of Cluster Glycopolymers, Macromolecules, 1994, 4876-4880, 27.
Norata, et al., Gene silencing approaches for the management of dyslipidemia, Trends in Pharmacological Sciences, Apr. 2013, 198-205, 34(4).
Noto, et al., Prevalence of ANGPTL3 and APOB Gene Mutations in Subjects With Combined Hypolipidemia, Arterioscler Thromb Vasc Biol, Mar. 2012, 805-809, 32.
Oberhauser, et al., Effective incorporation of 2'-O-methyl-oligoribonucleotides into liposomes and enhanced cell association through modification with thiocholesterol, Nucleic Acids Research, 1992, 533-538, 20(3).
Orum, et al., Locked nucleic acids: A promising molecular family for gene-function analysis and antisense drug development, Current Opinion in Molecular Therapeutics, 2001, 239-243, 3(3).
Pal-Bhadra, et al., Heterochromatic Silencing and HP1 Localization in *Drosophila* are Dependent on the RNAi Machinery, Science, Jan. 30, 2004, 669-672, 303.
Palha, et al., Transthyretin as a Thyroid Hormone Carrier: Function Revisited, Clin Chem Lab Med, 2002, 1292-1300, 40(12).
Park, et al., The asialoglycoprotein receptor clears glycoconjugates terminating with sialic acidalpha2,6GalNAc, PNAS, Nov. 22, 2005, 17125-17129, 102(47).
Pavia, et al., Synthetic Tn glycopeptide related to human glycophorin Am, Int. J. Peptide Protein Res., 1983, 539-548, 22.
Petrova, et al., Carrier-free cellular uptake and the gene-silencing activity of the lipophilic siRNAs is strongly affected by the length of the linker between siRNA and lipophilic group, Nucleic Acids Research, 2012, 2330-2344, 40 (5).
Pisciotta, et al., Characterization of Three Kindreds With Familial Combined Hypolipidemia Caused by Loss-of-Function Mutations of ANGPTL3, Circ Cardiovasc Genet, Feb. 2012, 42-50, 5.
Prakash, et al., Identification of metabolically stable 5-phosphate analogs that support single-stranded siRNA activity, Nucleic Acids Research, Mar. 9, 2015, 2993-3011, 43(6).
Pujol, et al., A Sulfur Tripod Glycoconjugate that Releases a High-Affinity Copper Chelator in Hepatocytes, Angew. Chem. Int. Ed., 2012, 7445-7448, 51.
Quesada, et al., Physiology of the pancreatic a-cell and glucagon secretion: role in glucose homeostasis and diabetes, Journal of Endocrinology, 2008, 5-19, 199.
Rajeev, et al., Conjugation Strategies for in vivo siRNA Delivery, 8th Annual Meeting of the Oligonucleotide Therapeutics, 2012.
Rajur, et al., Covalent Protein-Oligonucleotide Conjugates for Efficient Delivery of Antisense Molecules, Bioconjugate Chemistry, 1997, 935-940, 8.
Raouane, et al., Synthesis, Characterization, and in Vivo Delivery of siRNA-Squalene Nanoparticles Targeting Fusion Oncogene in Papillary Thyroid Carcinoma, J Med Chem., 2011, 4067-4076, 54.
Rensen, et al., Design and Synthesis of Novel N-Acetylgalactosamine-Terminated Glycolipids for Targeting of Lipoproteins to the Hepatic Asialoglycoprotein Receptor, J Med Chem., 2004, 5798-5808, 47.
Rensen, et al., Determination of the Upper Size Limit for Uptake and Processing of Ligands by the Asialoglycoprotein Receptor on Hepatocytes in Vitro and in Vivo, Journal of Biological Chemistry, Oct. 5, 2001, 37577-37584, 276(40).
Rensen, et al., Stimulation of Liver-Directed Cholesterol Flux in Mice by Novel N-Acetylgalactosamine-Terminated Glycolipids With High Affinity for the Asialoglycoprotein Receptor, Arterioscler Thromb Vasc Biol., 2006, 169-175, 26.
Reynolds, et al., Rational siRNA design for RNA interference, Nature Biotechnology, Mar. 2004, 326-330, 22(3).
Robeyns, et al., Oligonucleotides with cyclohexene-nucleoside building blocks: crystallization and preliminary X-ray studies of a left-handed sequence GTGTACAC, Acta Cryst., Jun. 1, 2005, 585-586, F61.
Robeyns, et al., Structure of the Fully Modified Left-Handed Cyclohexene Nucleic Acid Sequence Gtgtacac, J. Am. Chem. Soc., 2008, 1979-1984, 130.
Romeo, et al., Rare loss-of-function mutations in ANGPTL family members contribute to plasma triglyceride levels in humans, Journal of Clinical Investigation, Jan. 2009, 70-79, 119(1).
Rosenwald, et al., Growth factor-independent expression of the gene encoding eukaryotic translation initiation factor 4E in transformed cell lines, Cancer Letters, 1995, 77-82, 98.
Rosenwald, et al., Upregulation of protein synthesis initiation factor elF-4E is an early event during colon carcinogenesis, Oncogene, 1999, 2507-2517, 18.
Rouchaud, et al., A New and Efficient Synthesis of Derivatives of Octahydro-4H-pyrrolo-[1,2-c]pyrido[1',2'-a] imidazole, Eur. J. Org. Chem., 2011, 2346-2353.
Saison-Behmoaras, et al., Short modified antisense oligonucleotides directed against Ha-ras point mutation induce selective cleavage of the mRNA and inhibit T24 cells proliferation, The EMBO Journal, 1991, 1111-1118, 10(5).
Sakaki, et al., Human Transthyretin (Prealbumin) Gene and Molecular Genetics of Familial Amyloidotic Polyneuropathy, Mol. Biol. Med., 1989, 161-168, 6.
Sanan, et al., Low density lipoprotein receptor-negative mice expressing human apolipoprotein B-100 develop complex atherosclerotic lesions on a chow diet: No accentuation by apolipoprotein(a), PNAS, Apr. 1998, 4544-4549, 95.
Sanghvi, Heterocyclic Base Modifications in Nucleic Acids and Their Applications in Antisense Oligonucleotides, Antisense Research and Applications, 1993, 273-288.
Saraiva, et al., Amyloid fibril protein in familial amyloidotic polyneuropathy, Portuguese type. Definition of molecular abnormality in transthyretin (prealbumin), Journal of Clinical Investigation, 1984, 104-119, 74(1).

(56) References Cited

OTHER PUBLICATIONS

Sato, et al., Glycoinsulins: Dendritic Sialyloligosaccharide-Displaying Insulins Showing a Prolonged Blood-Sugar-Lowering Activity, J. Am. Chem. Soc., 2004, 14013-14022, 126.

Seeger, et al., Hepatitis B Virus Biology, Microbiology and Molecular Biology Reviews, Mar. 2000, 51-68, 64(1).

Sehgal, et al., Liver as a target for oligonucleotide therapeutics, Journal of Hepatology, 2013, 1354-1359, 59.

Sehgal, et al., RNAi-mediated inhibition of natural anticoagulants for treatment of hemophilia, Alnylam, 2012.

Seth, et al., Design, synthesis and evaluation of constrained methoxyethyl (cMOE) and constrained ethyl (cEt) nucleoside analogs, Nucleic Acids Symposium Series, 2008, 553-554, 52.

Seth, et al., Synthesis and biophysical characterization of R-6'-Me—a—L—LNA modified oligonucleotides, Bioorganic & Medicinal Chemistry Letters, 2011, 1122-1125, 21.

Seth, et al., Synthesis and Biophysical Evaluation of 20,40 -Constrained 20 O-Methoxyethyl and 20,40-Constrained 20 O-Ethyl Nucleic Acid Analogues, Journal of Organic Chemistry, 2010, 1569-1581, 75.

Shchepinov, et al., Oligonucleotide dendrimers: stable nanostructures, Nucleic Acids Research, 1999, 3035-3041, 27(15).

Shchepinov, et al., Oligonucleotide dendrimers: synthesis and use as polylabelled DNA probes, Nucleic Acids Research, 1997, 4447-4454, 25(22).

Shea, et al., Synthesis, hybridization properties and antiviral activity of lipid-oligodeoxynucleotide conjugates, Nucleic Acids Research, 1990, 3777-3783, 18(13).

Shimamura, et al., Angiopoietin-like protein 3, a hepatic secretory factor, activates lipolysis in adipocytes, Biochem Biophys Res Commun, 2003, 604-609, 301.

Shimamura, et al., Angiopoietin-Like Protein3 Regulates Plasma HDL Cholesterol Through Suppression of Endothelial Lipase, Arterioscler Thromb Vasc Biol., 2007, 366-372, 27.

Shimamura, et al., Leptin and insulin down-regulate angiopoietin-like protein 3, a plasma triglyceride-increasing factor, Biochem Biophys Res Commun, 2004, 1080-1085, 322.

Shimizugawa, et al., ANGPTL3 Decreases Very Low Density Lipoprotein Triglyceride Clearance by Inhibition of Lipoprotein Lipase, Journal of Biological Chemistry, Sep. 13, 2002, 33742-33748, 277(37).

Shioji, et al., Genetic variants in PCSK9 affect the cholesterol level in Japanese, J Human Genet, 2004, 109-114, 49.

Sindelka, et al., Association of Obesity, Diabetes, Serum Lipids and Blood Pressure Regulates Insulin Action, Physiol. Res., 2002, 85-91, 51.

Singh, et al., LNA (locked nucleic acids): synthesis and high-affinity nucleic acid recognition, Chem. Commun., 1998, 455-456.

Singh, et al., Synthesis of 2'-Amino-LNA: A Novel Conformationally Restricted High-Affinity Oligonucleotide Analogue with a Handle, J. Org. Chem., 1998, 10035-10039, 63(26).

Sliedregt, et al., Design and Synthesis of Novel Amphiphilic Dendritic Galactosides for Selective Targeting of Liposomes to the Hepatic Asialoglycoprotein Receptor, J Med Chem., 1999, 609-618, 42.

Smith, et al., Comparison of Biosequences, Advanced in Applied Mathematics, 1981, 482-489, 2.

Sofia, et al., Discovery of a β-D-20-Deoxy-20 -r-fluoro-20-β-C-methyluridine Nucleotide Prodrug (PSI-7977) for the Treatment of Hepatitis C Virus, J Med Chem., 2010, 7202-7218, 53.

Sonnenburg, et al., GPIHBP1 stabilizes lipoprotein lipase and prevents its inhibition by angiopoietin-like 3 and angiopoietin-like 4, Journal of Lipid Research, 2009, 2421-2429, 50.

Sousa, et al., Neurodegeneration in familial amyloid polyneuropathy: from pathology to molecular signaling, Progress in Neurobiology, 2003, 385-400, 71.

Srivastava, et al., Five- and Six-Membered Conformationally Locked 2', 4'-Carbocyclic ribo-Thymidines: Synthesis, Structure, and Biochemical Studies, J Am Chem Soc, 2007, 8362-8379, 129(26).

Svinarchuk, et al., Inhibition of HIV proliferation in MT-4 antisense oligonucleotide conjugated to lipophilic groups, Biochimie, 1993, 49-54, 75.

Swayze, et al., The Medicinal Chemistry of Oligonucelotides, Antisense Drug Technology, 2007, 143-182, chapter 6.

Tachas, et al., A GH receptor antisense oligonucleotide inhibits hepatic GH receptor expression, IGF-I production and body weight gain in normal mice, Journal of Endocrinology, 2006, 147-154, 189.

Tanskanen, et al., Senile systemic amyloidosis affects 25% of the very aged and associates with genetic variation in alpha2-macroglobulin and tau: A population-based autopsy study, Annals of Medicine, 2008, 232-239, 40.

Taylor, et al., Curbing activation: proprotein convertases in homeostasis and pathology, FASEB Journal, 2003, 1215-1227, 17.

Timms, et al., A mutation in PCSK9 causing autosomal-dominant hypercholesterolemia in a Utah pedigree, Hum Genet, 2004, 349-353, 114.

Tober, et al., Self-Metathesis of Polyol Allyl Ethers towards Carbohydrate-Based Oligohydroxy Derivatives, Eur. J. Org. Chem., 2013, 566-577.

Tomiya, et al., Liver-targeting of primaquine-(poly-c-glutamic acid) and its degradation in rat hepatocytes, Bioorganic & Medicinal Chemistry, 2013, 5275-5281, 21.

Toyokuni, et al., Svnthelfc Vaccines: I. Svnthesis of Multfvalent Tn Antfgen Cluster-Lvsvllvsine Conjugates, Tetrahedron Letters, 1990, 2673-2676, 31(19).

Trappeniers, et al., 6'-Derivatised alpha-GalCer Analogues Capable of Inducing Strong CD1d mediated Th1-biased NKT cell responses in mice, J. Am. Chem. Soc., 2008, 16468-16469, 130.

Tsimikas, et al., Antisense therapy targeting apolipoprotein(a): a randomised, double-blind, placebo-controlled phase 1 study, Lancet, 2015, 2239-2253, 388(10057).

Valdivielso, et al., Association of moderate and severe hypertriglyceridemia with obesity, diabetes mellitus and vascular disease in the Spanish working population: Results of the ICARIA study, Atherosclerosis, May 27, 2009, 573-578, 207.

Valentijn, et al., Solid-phase Synthesis of Lysine-based Cluster Galactosides with High Affinity for the Asialoglycoprotein Receptor, Tetrahedron, 1997, 759-770, 53(2).

Van Rossenberg, et al., Stable polyplexes based on arginine-containing oligopeptides for in vivo gene delivery, Gene Therapy, 2004, 457-464, 11.

Verbeure, et al., Valdivielso et al_May 27, 2009_Atherosclerosis, Valdivielso et al_May 27, 2009_Atherosclerosis, 2001, 4941-4947, 29(24).

Verdel, et al., RNAi-Mediated Targeting of Heterochromatin by the RITS Complex, Science, Jan. 30, 2004, 672-676, 303.

Viney, et al., Antisense oligonucleotides targeting apolipoprotein(a) in people with raised lipoprotein(a): two randomised, double-blind, placebo-controlled, dose-ranging trials, Lancet, Nov. 5, 2016, 2239-2253, 388(10057).

Volpe, et al., Regulation of Heterochromatic Silencing and Histone H3 Lysine-9 Methylation by RNAi, Science, Sep. 13, 2002, 1833-1837, 297.

Wahlestedt, et al., Potent and nontoxic antisense oligonucleotides containing locked nucleic acids, Proc. Natl. Acad. Sci. USA, 2000, 5633-5638, 97.

Wang, et al., A Straightforward Stereoselective Synthesis of D- and L-5-Hydroxy-4-hydroxymethyl-2-cyclohexenylguanine, Journal of Organic Chemistry, 2001, 8478-8482, 66.

Wang, et al., Cyclohexene nucleic acids (CeNA) form stable duplexes with RNA and induce RNase H activity, Nucleosides Nucleotides Nucleic Acids, 2001, 785-788, 20(4-7).

Wang, et al., Cyclohexene Nucleic Acids (CeNA): Serum Stable Oligonucleotides that Activate RNase H and Increase Duplex Stability with Complementary RNA, J. Am. Chem. Soc., 2000, 8595-8602, 122.

Wang, et al., Expression of the Eukaryotic Translation Initiation Factors 4E and 2 in Non-Hodgkin's Lymphomas, American Journal of Pathology, Jul. 1999, 247-255, 153(1).

Wang, et al., Stereocontrolled Synthesis of Ara-Type Cyclohexenyl Nucleosides, Journal of Organic Chemistry, 2003, 4499-4505, 68.

(56) References Cited

OTHER PUBLICATIONS

Weber, et al., Design and Synthesis of P2-Pi'-Linked Macrocyclic Human Renin Inhibitors, J Med Chem., 1991, 2692-2701, 34.

Weinberger, et al., Identification of Human Glucocorticoid Receptor Complementary DNA Clones by Epitope Selection, Science, 1985, 740-742, 228.

Westerlind, et al., Ligands of the asialoglycoprotein receptor for targeted gene delivery, part 1: synthesis of and binding studies with biotinylated cluster glycosides containing N-acetylgalactosamine, Glycoconjugate J, 2004, 227-241, 21.

Willer, et al., Newly identified loci that influence lipid concentrations and risk of coronary artery disease, Nature Genetics, Feb. 2008, 161-169, 40(2).

Winkler, et al., Oligonucleotide conjugates for therapeutic applications, Ther. Deliv., 2013, 791-809, 4(7).

Woolf, et al., Specifity of antisense oligonucleotides in vivo, Proc. Natl. Acad. Sci. USA, Aug. 1992, 7305-7309, 89.

Wu, et al., A New N-Acetylgalactosamine Containing Peptide as a Targeting Vehicle for Mammalian Hepatocytes via Asialoglycoprotein Receptor Endocytosis, Current Drug Delivery, 2004, 119-127, 1.

Yadav, et al., Carbohydrate functionalized iron(III) complexes as biomimetic siderophores, Chemical Communications, 2012, 1704-1706, 48.

Yang, et al., STAT3 complements defects in an interferon-resistant cell line: Evidence for an essential role for STAT3 in interferon signaling and biological activities, PNAS, May 1998, 5568-5572, 95.

Yu, et al., Effects of ANGPTL3 antisense oligodeoxynucleotides transfection on the cell growths and invasion of human hepatocellular carcinoma cells, Hepatogastroenterology, 2011, 1742-1746, 58(110-111).

Zhang, et al., PowerBlast: A New Network Blast Application for Interactive or Automated Sequence Analysis and Annotation, Genome Research, 1997, 649-656, 7.

Zhang, et al., Spontaneous Atherosclerosis in Aged Lipoprotein Lipase-Deficient Mice With Severe Hypertriglyceridemia on a Normal Chow Diet, Circulation Research, 2008, 250-256, 102.

Zhao, et al., Synthesis and Preliminary Biochemical Studies with 5'-Deoxy-5'-methylidyne Phosphonate Linked Thymidine Oligonucleotides, Tetrahedron Letters, 1996, 6239-6242, 37(35).

Zhong, et al., Stat3 and Stat4: Members of the family of signal transducers and activators of transcription, PNAS, May 1994, 4806-4810, 91.

Zhou, et al., Fine Tuning of Electrostatics around the Internucleotidic Phosphate through Incorporation of Modified 2',4'-Carbocyclic-LNAs and -ENAs Leads to Significant Modulation of Antisense Properties, J. Org. Chem., 2009, 118-134, 74.

Zhou, et al., Proteolytic Processing in the Secretory Pathway, Journal of Biological Chemistry, Jul. 23, 1999, 20745-20748, 274(30).

Zimmerman, et al., Carbohydrate conjugation to sirna for liver-specific delivery, Hepatology, 2010, 587A, 52(1).

* cited by examiner

SEQUENCE LISTING

```
Sequence total quantity: 167
SEQ ID NO: 1            moltype = DNA   length = 6489
FEATURE                 Location/Qualifiers
source                  1..6489
                        mol_type = genomic DNA
                        organism = Homo sapiens
SEQUENCE: 1
aggtaccttt ggggctggct ttctcaagga agcccagctc cctgtgattg agaatgaagt    60
gtgcaatcgc tatgactggg attgggacac actttctggg cactgctggc cagtcccaaa   120
atggaacata aggaagtggt tcttctactt cttttatttc tgaaatcagc agcacctgag   180
caaagccatg tggtccagga ttgctaccat ggtgatggac agagttatcg aggcacgtac   240
tccaccactg tcacaggaag gacctgccaa gcttggtcat ctatgacacc acatcaacat   300
aataggacca cagaaaacta cccaaatgct ggcttgatca tgaactactg caggaatcca   360
gatgctgtgg cagctcctta ttgttatacg agggatcccg gtgtcaggtg ggagtactgc   420
aacctgacgc aatgctcaga cgcagaaggg actgccgtcg cgcctccgac tgttacccg    480
gttccaagcc tagaggctcc ttccgaacaa gcaccgactg agcaaaggcc tggggtgcag   540
gagtgctacc atggtaatgg acagagttat cgaggcacat actccaccac tgtcacagga   600
agaacctgcc aagcttggtc atctatgaca ccacactcgc atagtcggac cccagaatac   660
tacccaaatg ctggcttgat catgaactac tgcaggaatc cagatgctgt ggcagctcct   720
tattgttata cgagggatcc cggtgtcagg tgggagtact gcaacctgac gcaatgctca   780
```

-continued

```
gacgcagaag ggactgccgt cgcgcctccg actgttaccc cggttccaag cctagaggct    840
ccttccgaac aagcaccgac tgagcaaagg cctggggtgc aggagtgcta ccatggtaat    900
ggacagagtt atcgaggcac atactccacc actgtcacag gaagaacctg ccaagcttgg    960
tcatctatga caccacactc gcatagtcgg accccagaat actacccaaa tgctggcttg   1020
atcatgaact actgcaggaa tccagatgct gtggcagctc cttattgtta tacgagggat   1080
cccggtgtca ggtgggagta ctgcaacctg acgcaatgct cagacgcaga agggactgcc   1140
gtcgcgcctc cgactgttac cccggttcca agcctagagg ctccttccga caagcaccg    1200
actgagcaga ggcctggggt gcaggagtgc taccacggta atggacagag ttatcgaggc   1260
acatactcca ccactgtcac tggaagaacc tgccaagctt ggtcatctat gacaccac    1320
tcgcatagtc ggaccccaga atactaccca aatgctggct tgatcatgaa ctactgcagg   1380
aatccagatg ctgtggcagc tccttattgt tatacgaggg atcccggtgt caggtgggag   1440
tactgcaacc tgacgcaatg ctcagacgca aagggactg ccgtcgcgcc tccgactgtt    1500
accccggttc caagcctaga ggctccttcc gaacaagcac cgactgagca aaggcctggg   1560
gtgcaggagt gctaccatgg taatggacag agttatcgag gcacatactc caccactgtc   1620
acaggaagaa cctgccaagc ttggtcatct atgacaccac actcgcatag tcggacccca   1680
gaatactacc caaatgctgg cttgatcatg aactactgca ggaatccaga tgctgtggca   1740
gctccttatt gttatacgag ggatcccggt gtcaggtgga gtactgcaa cctgacgcaa    1800
tgctcagacg cagaagggac tgccgtcgcg cctccgactg ttaccccggt tccaagccta   1860
gaggctcctt ccgaacaagc accgactgag caaaggcctg gggtgcagga gtgctaccat   1920
ggtaatggac agagttatcg aggcacatac tccaccactg tcacaggaag aacctgccaa   1980
gcttggtcat ctatgacacc acactcgcat agtcggaccc cagaatacta cccaaatgct   2040
ggcttgatca tgaactactg caggaatcca gatgctgtgg cagctcctta ttgttatacg   2100
agggatcccg gtgtcaggtg ggagtactgc aacctgacgc aatgctcaga cgcagaaggg   2160
actgccgtcg cgcctccgac tgttacccg gttccaagcc tagaggctcc ttccgaacaa    2220
gcaccgactg agcaaaggcc tggggtgcag gagtgctacc atggtaatgg acagagttat   2280
cgaggcacat actccaccac tgtcacagga agaacctgcc aagcttggtc atctatgaca   2340
ccacactcgc atagtcggac cccagaatac tacccaaatg ctggcttgat catgaactac   2400
tgcaggaatc cagatgctgt ggcagctcct tattgttata cgagggatcc cggtgtcagg   2460
tgggagtact gcaacctgac gcaatgctca gacgcagaag gactgccgt cgcgcctccg    2520
actgttaccc cggttccaag cctagaggct cttccgaac aagcaccgac tgagcagagg    2580
cctggggtgc aggagtgcta ccacggtaat ggacagagtt atcgaggcac atactccacc   2640
actgtcactg gaagaacctg ccaagcttgg tcatctatga caccacactc gcatagtcgg   2700
accccagaat actacccaaa tgctggcttg atcatgaact actgcaggaa tccagatcct   2760
gtggcagccc cttattgtta tacgagggat cccagtgtca ggtgggagta ctgcaacctg   2820
acacaatgct cagacgcaga agggactgcc gtcgcgcctc caactattac cccgattcca   2880
agcctagagg ctccttctga caagcacca actgagcaaa ggcctggggt gcaggagtgc    2940
taccacggaa atggacagag ttatcaaggc acatacttca ttactgtcac aggaagaacc   3000
tgccaagctt ggtcatctat gacaccacac tcgcatagtc ggacccagc atactaccca    3060
aatgctggct tgatcaagaa ctactgccga aatccagatc ctgtggcagc cccttggtgt   3120
tatacaacag atcccagtgt caggtgggag tactgcaacc tgacacgatg ctcagatgca   3180
gaatggactg ccttcgtccc tccgaatgtt attctggctc caagcctaga ggcttttttt   3240
gaacaagcac tgactgagga aaccccggg gtacaggact gctactacca ttatggacag    3300
agttaccgag gcacatactc caccactgtc acaggaagaa cttgccaagc ttggtcatct   3360
atgacaccac accagcatag tcggacccca gaaaactacc caaatgctgg cctgaccagg   3420
aactactgca ggaatccaga tgctgagatt cgcccttggt gttacaccat ggatcccagt   3480
gtcaggtggg agtactgcaa cctgacacaa tgcctggtga cagaatcaag tgtccttgca   3540
actctcacgg tggtcccaga tccaagcaca gaggcttctt ctgaagaagc accaacggag   3600
caaagccccg gggtccagga ttgctaccat ggtgatggac agagttatcg aggctcattc   3660
tctaccactg tcacaggaag gacatgtcag tcttggtcct ctatgacacc acactggcat   3720
cagaggacaa cagaatatta tccaaatggt ggcctgacca ggaactactg caggaatcca   3780
gatgctgaga ttagtccttg gtgttatacc atggatccca atgtcagatg ggagtactgc   3840
aacctgacac aatgtccagt gacagaatca agtgtccttg cgacgtccac ggctgttttct  3900
gaacaagcac caacggagca agcccacca gtccaggact gctaccatgg tgatggacag    3960
agttatcgag gctcattctc caccactgtt acaggaagga catgtcagtc ttggtcctct   4020
atgacaccac actggcatca gagaaccaca gaatactaca caaatggtgg cctgaccagg   4080
aactactgca ggaatccaga tgctgagatt cgcccttggt gttataccat ggatcccagt   4140
gtcagatggg agtactgcaa cctgacgcaa tgtccagtga tggaatcaac tctcctcaca   4200
actcccacgt tggtcccagt tccaagcaca gagcttcctt ctgaagaagc accaactgaa   4260
aacagcactg gggtccagga ctgctaccga ggtgatggac agagttatcg aggcacactc   4320
tccaccacta tcacaggaag aacatgtcag tcttggtcgt ctatgacacc acattggcat   4380
cggaggatcc cattatacta tccaaatgct ggcctgacca ggaactactg caggaatcca   4440
gatgctgaga ttcgcccttg tgttacacc atggatccca gtgtcaggtg ggagtactgc    4500
aacctgacac gatgtccagt gacagaatcg agtgtcctca caactcccac agtggccccg   4560
gttccaagca cagaggctcc ttctgaacaa gcaccacctg agaaaagccc tgtggtccag   4620
gattgctacc atggtgatgg acggagttat cgaggcatat cctccaccac tgtcacagga   4680
aggacctgtc aatcttggtc atctatgata ccacactggc atcagaggac cccagaaaac   4740
tacccaaatg ctggcctgac cgagaactac tgcaggaatc cagattctgg gaaacaaccc   4800
tggtgttaca caaccgatcc gtgtgtgagg tgggagtact gcaatctgac acaatgctca   4860
gaaacagaat caggtgtcct agagactccc actgttgttc cagtteccaag catggaggct   4920
cattctgaag cagcaccaac tgagcaaacc cctgtggtcc ggcagtgcta ccatggtaat   4980
ggccagagtt atcgaggcac attctccacc actgtcacag gaaggacatg tcaatcttgg   5040
tcatccatga caccacaccg gcatcagagg acccagaaaa actacccaaa tgatggcctg   5100
acaatgaact actgcaggaa tccagatgcc gatacaggcc ttggtgttt taccatggac   5160
ccagcacaa ggtgggagta ctgcaacctg acgcgatgct cagacacaga agggactgcc    5220
gtcgctcctc cgactgtcat ccaggttcca agcctaggc ctccttctga caagactgt    5280
atgtttggga atgggaaagg ataccggggc aagaaggcaa ccactgttac tgggacgcca   5340
tgccaggaat gggctgccca ggagcccat agacacagca cgttcattcc agggacaaat   5400
aaatgggcag gtctggaaaa aaattactgc cgtaaccctg atggtgacat caatggtccc   5460
tggtgctaca caatgaatcc aagaaaactt tttgactact gtgatatccc tctctgtgca   5520
```

```
tcctcttcat ttgattgtgg gaagcctcaa gtggagccga agaaatgtcc tggaagcatt    5580
gtagggggt gtgtggccca cccacattcc tggccctggc aagtcagtct cagaacaagg     5640
tttggaaagc acttctgtgg aggcacctta atatccccag agtgggtgct gactgctgct    5700
cactgcttga agaagtcctc aaggccttca tcctacaagg tcatcctggg tgcacaccaa    5760
gaagtgaacc tcgaatctca tgttcaggaa atagaagtgt ctaggctgtt cttggagccc    5820
acacaagcag atattgcctt gctaaagcta agcaggcctg ccgtcatcac tgacaaagta    5880
atgccagctt gtctgccatc cccagactac atggtcaccg ccaggactga atgttacatc    5940
actggctggg gagaaaccca aggtaccttt gggactggcc ttctcaagga agcccagctc    6000
cttgttattg agaatgaagt gtgcaatcac tataagtata tttgtgctga gcatttggc     6060
agaggcactg acagttgcca gggtgacagt ggagggcctc tggtttgctt cgagaaggac    6120
aaatacattt tacaaggagt cacttcttgg ggtcttggct gtgcacgcc caataagcct      6180
ggtgtctatg ctcgtgtttc aaggtttgtt acttggattg agggaatgat gagaaataat    6240
taattggacg ggagacagag tgaagcatca acctacttag aagctgaaac gtgggtaagg    6300
atttagcatg ctggaaataa tagacagcaa tcaaacgaag acactgttcc cagctaccag    6360
ctatgccaaa ccttggcatt tttggtattt ttgtgtataa gctttttaagg tctgactgac   6420
aaattctgta ttaaggtgtc atagctatga catttgttaa aaataaactc tgcacttatt    6480
ttgatttga                                                            6489

SEQ ID NO: 2           moltype = DNA  length = 150001
FEATURE                Location/Qualifiers
source                 1..150001
                       mol_type = genomic DNA
                       organism = Homo sapiens
SEQUENCE: 2
atctttcagc ctctatatta tttttattgtg atttttaatt tccttgaatt ggattttgcc     60
attgtgctaa atcttgatga tcttcatttg tatccgtagt ctgaattata tttctgtcat    120
ttgagttagc tcagtcttgt taagaaccct tgttggaaaa ctggtgcagt tgtttggagg    180
acatatgacc ttctggccat ttgatttatt ggagttctta cgttggtct ttctcatgtc     240
tctgtgtggg tgtttcttta actgcagtgt agattgagta cagccaatag acttcttctt    300
tggaggtttt cacagggcca aggccttgta caggtcttt atttgtagct gacttcttgt     360
ctttggtttc atagtggggc atgttagcaa aatagttttg ctgttgaagt tttgggtgt      420
gatccatttt ttatttaat gattgtgtat ttccttatat cctaaaacaa gcagaaaacc     480
agtaaaggtc tttgagtctc tgaattcata actccagcat tcatattgct tcctcaggta    540
agtggggttt tcacccagcc cttaagggtg ttagattatt ttttatgtga aattagcagt    600
attgtatttc taaacatgat gtaaaacaat aatgacaaaa gttataataa actagccttc    660
ttaccaaatc cacatgtcta atgtgtgtgg gagggtgtta ggcaggggac ctgcagctaa    720
gggagaggca gacaggcccc atggccccaa atctaggata gtatttggta ttggttgatg    780
ggtgagagaa agagagggaa catctgtgca ggatgtggta tcagcacctg gactacatct    840
tagggattcc ttcttcattt ttcagtatgc cctgacaata attatatcta tcagacttac    900
ccccttgacc actggaacac taagactgtt ttgggatctc tgcctgactt tctcagaggt    960
gctggtgagg acattatgag tctgaacct agaaaagcgt tctgactctg ctgactttct   1020
cagaggtgct ggtgaggaca ttatgagtct ggagccctag aaaagcgttc tgactctgcc   1080
actagccaga cagacctgga ctaggcacgt taactctttg tatgacttga ctccaaccc    1140
tcatttgtaa aaccagcatt tcaagtggg gttttccaca tcagccttt gcataagctg     1200
tcatttgaag aaaggtttt gtttgttgt ttttgttta acaaaaaggt taaaaaccac       1260
tggtctagat aattgcaaag tttgcttcc ttttttctgtg cttttctac tatttttaaa     1320
atgtcatcct ccttggtttc ttgatccccc ttttctgcact cctgagtctg ggaacactga   1380
ggccaactaa aaggaaactt ggcaaaagag gaacaccttt gggtgtgcca ggctgctccc    1440
agtgttttgc acttataaaa atttaaatgc tgcaaacctc taagacttag atattattgt    1500
tcctatttta caagtgagga acctgaggct cagagaaggt gcaggatggc acagggagac    1560
ctgaattgga accctggttc ccacttactg gctgtcggga cttagaaaag tcatgaactc    1620
tcattgattg ttttcttata tgaaatgggg gctgcagggt tgtcggggga gaaacaataa    1680
gaatgtgcat caagtgtcga gcacgtgcta cgcactccat catggcagct cctactaata    1740
tacagaatag agttgtatct aacatgactc tttcttgcaa gtgacagaaa atccaactta    1800
agatggatta agcaaaaaag gggaattctt gttgagctga aaagtcttta ggctcacatg    1860
atggccccag ggcccaggcc ctgtccagcc atgcagtagg catcatcctt gggcacaaag    1920
gtgagattct tgtggtggca gatgctgtgg cagctcttgc tttgcagga aagactgagg     1980
aaggccactg tccccattaa gtgaacaata gttggccagg tctgagaggt tgaacttggg    2040
tcacaggcct gtccctgaac ccatcactga ttggctccaa cctgcatcag ctattacatg    2100
ctagaggtgg aggcaggacc ccactcatac ccagaagggc aaagggtgga tccctcaaca    2160
ggattatggg atgtaggggt atagactgct gggcagccag aaagcaaaca gatcctctcc    2220
aatacctcaa ctgatgaaag caccaagcta aaatcataag gatctgggtg tgaattctgg    2280
ctctaccatc ttccatgtga cattgggcag ttattttaat tcttttagcc ttggcttct      2340
tacctgtact aacatataag gtgattgtga tgagcatcat catcgtcaac atcatcatca    2400
ccatccacat tgccaccacc actcccatta tcatcttcat caacatcatc accaccgcca    2460
ccatcaccat tatcattacc accaccgcta tcactattat catcccctc aacatcatca    2520
ccatcatcac tatcatcacc accaccatca tcgttactac cactaccacc accatcatca    2580
ccacagccac caccaccatc accatcatta ctactcagca ccatcaccac cattccacca    2640
ccatcaccat cattccacca tcaccattat cattacacc accactgtca ctattatcat     2700
caccctcaac atcatcacca ccaccatcat cattactacc accaccacca ccatcaccat    2760
catcatcatt ctaccaccat caccattatc atcaccatca ccatcaccac cgctatcatc    2820
atgataatca ttatcattac caccaccatt agcattatca ttaccaccac catcactatc    2880
actatcacca tcaccacgac cactaccacc atcaccaaca ccatcattac tacccaccac    2940
caccatcatc tcattccaca caccatcaca attattacca ccaccaccac caccaccacc    3000
accaccatca ctatcatcat cagtagacat catataacca gtttgtagct ggcccagagc    3060
ctacttgctg tttcttctgc cccacaacca tccacacatt tctaaccacc atcccccact    3120
aggcttctgc ctcgcctggt ctcacctgca ggtccactga gaaaatgatt ctcagaacac    3180
taactagacc atgaggtgcc acaaaacata actcaggcct gttcatcaat tttctacatg    3240
tcaataatga catcaggtca attggcgttc tcagcctctg agagggaggt caaagttttc    3300
```

```
ctgctctccc cttcatgttt ccaggtgttc cctgacttgg atcaaatgca gagtttggag   3360
gtgttgaggc caaggggatt ttccaggtca gtcgtcatcc acaatcaatg gactgatcct   3420
gccgctggac ttaccctgct gccctctccc caaggcccca tcagggaggg cttcaatcct   3480
cttgtcacct gtggcctacc tgccctcaga gatgacatct ctatgtcggc cactggatgg   3540
cagcacctac tcgcagacca catcaacttt cctggcaact tgcggtaggt tttcaccatt   3600
atcaggatgt ttgccttgct caaatagcag attctagaga acggtgctcc ctcacacaac   3660
tatgtagtcc aggtgatgca ccctctgccc gatgcttggt agtcagaaac ttccatcatg   3720
cagctctgcc cagattgagc tgagctggcc tctggagtga ggtgctggga caaacatctt   3780
ccatgctgct catgtcaact ccagatgcag tcaggtttct gaaccaaagt caatgatcta   3840
agtgcagtca aaggctctgg gggaagaaag agagagtgcc tcatctcttg cctgtgccat   3900
gctcgcaaag caaggatttt tgcaaaattc taatgaaagc tgggcttgca aaattagaaa   3960
actggattat ttgtgagaac actgaaacat ccctgggtgt gtccatctgg aaaaacagca   4020
tttcctctgg caattttgca accgttctat ttgaatttgg caaagaaaat aaagcagttt   4080
ttcacaaaag aataaacaca accaggagaa tcttcactct cccaaattgt caaagaagta   4140
taaattagaa aatgaatcag gacaatttca acctgttaga ttagctaata tttaaaaatt   4200
gaacactcat acaagtgtgg tgaagtgatt gttttctagt gacattttac actgtcataa   4260
ccttctgaaa aataaaattgg cagtgttatt gggagacaga aatatgtcta tataatttat   4320
gggaacttag gctcagaaaa tattaaggaa taagaatgaa ctttatgaac aaagatgtgg   4380
agggttggaa gcaagagggg ggccaacgcg cacggggagg aagcatttgg gcagtgactc   4440
cgcagaccca ggctcaggtt gaactagaca acctccttac acctcagttt ccttaactgt   4500
agagcaggag tgatggaact gcctgtttca taggactgtt gtgaggatga agtgagatac   4560
accacattat aagcttgtgc ctggaaagga taatgcttaa taaatgatga ctattctttt   4620
ttattgcaat aaaaatgtaca cagcgtaaga gttactattt taaccatttt tgcagggtac   4680
caccaagtgg catttagtac attcacagtg gtgtgcaacc atcatcatat ttccagaata   4740
ttttcctcat ccccaaagga aacctcatgc tcattaatca gtagctctcc tttaaaatat   4800
tagttatgaa gatcatagca tatacaaaa ctcattatgt aatgttgagt gaaaaatca   4860
gggtgtgaaa ttttgtgata tgatgtaatt agtgaaagaa gcatacaaaa agtctgaaaa   4920
tataaaaaca atagcaattg catttctcag actctacatt taaacattat tctttatggt   4980
tttaaaagca aagaaaaagg taagaaaaca acaaccaacc gcaaagcacc atgacaaagc   5040
tcagattgtt aaatccaggt tttggaaca tagactctta tatgacgttt acactctcca   5100
gggttcagag agtctggcag cattgggagc tgccttgtgt tctacagcct cacggacaga   5160
caggaggtcc atcaccactg ctctgttctt ctggagtttc cttgtgaaca tgttgtggac   5220
gtagttacca tttctttcat cttttttaaac acaggtacct ttggggctgg ctttctcaag   5280
gaagcccagc tccctgtgat tgagaatgaa gtgtgcaact gctatgagtt tctgaatgaa   5340
agagtcaaat ccactgagct ctgtgctggg catttggctg gaggcattga cagttgcaag   5400
gtaagaaaag atcaagagac caaagttagt cttgtgctct cctgtctcag tctcagtccc   5460
ttagacttga gtcccaaagt agcgaattca agtaggattt aatcaatgga agaccccagt   5520
ctaagtgttg ctcagaaact ccctagatct gtcccaaatg tatattcaga tcatccaagg   5580
ggacttcttg gggcttgagt tccagatcag cagcaaggga gccataagtg ccataactac   5640
ctcagaccac tcaccctcct gggggtgtcc ggtggccagg gactaaagtg gtgattttc   5700
tggtagggaa ggaggtagag ggtacaggac agagactaac tgcacacaat atctgagact   5760
ggagctcaga tattgctgat gatcagagtt ggcgtgtctc cccaattgat ttacaactgg   5820
ggcttggata ctgtttaaa cgggaggagc ctcctaacca tcttgacaca accactgacg   5880
tgactacact agagatagac tctttccact taattctacc actcttgctt tacttcatga   5940
gaacgaaaat gtaagattgc accatgaatt catttgcgga aagattgata ctatgctttt   6000
attttatttt attttatttt attttatttt attttatttt attgagactc tcaccccggt   6060
tgaagtgcac tgacgtgatt ttggctcact gcaacttcca cctcctggt tcaagtgaat   6120
actccagcct cccctagtagc tgggattaca ggtgccacc accacggctg gctaatttt   6180
gtattttag tagagatggg gtttcaccac attggcctgg ctggtctcaa actcctgacc   6240
ttgtgatcca cctgtcttgg cctcccaaag tgctgggatt acagagttga gccaccgcac   6300
tcgaccctat gtttttttt taaaaatatt tatttattta tttaagccac aactactaga   6360
ataggaagga ttgatatttt attaatttta tttggtattt attattttt ttctttcct   6420
gagacattct tgctctgtca cccaggctgg agtgcagtgg cacattcttg gctcactgca   6480
acctccatct cctgtgttca agcaattcta gtgcctcagc ctacttagta gctgggatga   6540
ctggcatgtg cctccacacc cagctaattt ttgtattttt tgtagagaca gggttttgc   6600
atgttgccca ggcttgtctc aaactcctgg cctcaggtga tccatctgcc gtggcctccc   6660
aaaatgctgg gattataggc atgagccacc accccctcct ggaaggattg atatcttata   6720
acataattta taattacaga aaacatgtga gttcactagg aataaataaa ttttgaagat   6780
aataaaagat tttcacttat gttgtcattt cggcacagtt tggtatagga tgtggagatg   6840
ttaacattta tacctagctt gctcgtaaac taagacctga aagggttgtg tctatcagct   6900
gcaccctgg gtagcgacac aacctcggga aggcctcagc cccctcctcg tacagcactg   6960
cctgttggaa agcttgaggg aggctatgga tgtgcagcac ttggcagagg gtctggtcat   7020
ggaagttacc agcaaatatg agctactttt atgatttat tttatccaaa agaaagaaa   7080
tgaaagaaga ggggaggaaa caagactaat caggaaagat gaaggtctag gggtgaggga   7140
aggagtaagg agacataaag gcaatgtgga gcagctgagg ggggaaatgg ctttcaccac   7200
ttcccagcat ctattgacat tgcactctca aatattttat aagactctat attcaaggta   7260
atgtttgaac cctgctgagc cagtggcatg ggtctctgag agaatcatta acttaatttg   7320
actatctggt ttgtgggtgc gtttactctc atgtaagtca acaatgtcct gggattggga   7380
cacactttct gggcactgct ggccagtccc aaaatggaac ataaggaagt ggttcttcta   7440
cttcttttat ttctgaaatc aggtaagaca tagtttttttt aaattataag aattattttt   7500
tctcccacaa tgtagtaaaa atacatatgc catggcttta tgtcaattc atttaatttt   7560
tgattcatga aattcccagt tcaaaatctt gtatatgatt gaaaattct taaaaaata   7620
agtttaattt ccccgtgaag actgtcacgg tgctggaatg aatgggcaga aaaaataatg   7680
ttgattttt ctaatctaaa agagtgtgcc tacatgtagg ccagtctggc tgaaaaataa   7740
atagccattg tagctaacta tgcaaaggat ggctaagctc ttcgcttggt tctcagtttc   7800
attaattat atcatctctg ttcaggtgcc atgctccct cactagcaag ttgaaacaat   7860
gaaataactc tttgaatatg tttggttcct tgacctgttc atggagtggg actcagcatt   7920
tctctctttg ttatggcctg agtaaggctt tccatcggta tacatttgct tcttatccct   7980
ggagaaatta tacacatcca tttgccagat gatatacgca tataatgatt caacaaatac   8040
```

```
tcagggtatt tgttgagtgg gttaggtccc cacattttta tacatacata cacacataca   8100
caccgtgtgt gattgtgaat gtaagtgtgt gtcctttaca aatactagct tatttagctc   8160
atggtatagg tagggtagca tagtcatccc cattttataa acaaagaaat ctagacttag   8220
gaaaatcatg ttatttgtct cgtgaccaaa ttcccaaatc aaggaaataa agaaacctgg   8280
atttaagcca gatttccaag aaaaaatcta gggctcttct cactttttca tctttgttcc   8340
aacatttgaa aaaataaatc taaacacatt ccaatgtaac tgaagagcag gttaattgtt   8400
tgccacttgc agaatccaat taagaagaga gaagtctggt ataaagaaag tgatttgctt   8460
ccaaagctag cttaggggaa gaaatgcagc agtcctgccg tactacttca ctttaggagc   8520
agaaagtggc acttttaaaa ggcaacagag gaggcgagca aggattcagg ggtccatgct   8580
agcttgggca ccttatccac caggtagttg agcagttgcc tgctggtgcc tttgtgagca   8640
gggtgttgtc ccttgaggca aatctctgga gggtgagagt tttgtagtgg gcatgctttg   8700
gtttataaat cacctgtgaa ctcaggagtt ccatcttgaa gcacatacat agttagatga   8760
acttgccctg cagggagagt ctgatgaaag ggaggtagat gcttgcaatt taatctataa   8820
attaccagat aaaattttac aagttgactt taaagtcaaa cacatttgaa tttagtggaa   8880
gccattcaag aaaatatcaa agaaaataca gagcaggaga agattaagca aagagttttt   8940
tggggaaatt ggtgtctatg tctgtgtgtg tagggagtgc aggggatatg aatattctat   9000
ttcagcccat ggaaactagg atgtagatca ctgtgaactt attcagcagg ctacacccaa   9060
aggctagaac aaacttctct gccacaggat taacatatgt tttaatcgac ctgggggca   9120
cattctctga taagctcttt tggaaagcca ggctttctgt ggacgtgtta tctttccaat   9180
gtgtgctgga atgcccgggg agaggaaaaa gtttctttta cagccatgct cagtgagaag   9240
cggagaaaca tcttctattc acaaattgct aagtctttta cacatgcaaa tatgcataca   9300
cattcacaca ccacagtgag gaagaaattc tcacaccatt aataaaatac atttacttca   9360
gtagcaatat acatctacat tttgcctata atataaaagt attttttccta ttaaaagatt   9420
tgtttaatgt ttcttcacca acaaataaac cctattaaat ccccattgcc atatgagccc   9480
tggaggtgaa tcagagaaac aaaaggattg tggaaaaatc atcaggttaa aaaaagaaaa   9540
attgattctg ttttgggata tttcctagca acatgagctg gggaggggat ctcagcagtg   9600
atgctctatg aagcataata aaatgacaca gttacaggta acttagttaa agggggaat   9660
aaaatggaagt ttcctctttt tgaatatcaa ttgtagcctg ctctgctaca tttcaaaaac   9720
actcttcaaa atgtttaact gaactcactg taggaagcac cttattaatt tattgtgtgt   9780
tttgaagtca cactgtgagc tatagaattt acccaagcac aactcttcct ggaaaagaga   9840
gttcaaatga gaaacagtgc ggggtgaaga catggatatg ggcctaaaat atctatttct   9900
caatgatatt ttgatatatc tatcaagtgc ttttttagtgg attaggttca gaatgcatca   9960
gccaatgcct gttcaataat ccagttttcc agcatagagc atattaaatt gaggaaggac  10020
aaagtcacag aggtggggag caggtggact actttgcatg aaacagtgag  10080
cgtgcatcct cctccttgcc ctgccctcat ggtctgtgta ctctcaggag gtcaggacag  10140
gcctttctga gaatgagaat ctgttcatct gcctttctac tggatacttg tcatcggcat  10200
acaaacacat gttctctgca gtgtgtcatc tttcagaacc tcccctgacc ctgtattccc  10260
tagaagtctc gctgctttca gagccaggct tctctcctgc tgccaccccc actgctcttc  10320
tagtcactct ttaacccact ccatctgcat gtggccccca ccacacccct caaagtggtc  10380
aaggttgtcc tgttgcttaa ttccatggaa gcttggctat cttcattttta ttagcctctt  10440
ttggcctctc accctgtgaa aatcactaca ttttgtgcca gagatggagc tggcatctcc  10500
aggcttggaa gagggctgct gaagctcagc caggtgtcct aaggagcctc aggacagggg  10560
atgctcagta gccttgcaat gggaacacag ctgagcccca cttggccaca ctttgccaca  10620
accaggcaga aagcagcttt tgaacagatt tgttgcctca gatttgatct caaagaaaaa  10680
tcgtgggcag tattggtccc aggttctgct tttttacaat ttcctctgaa atctggatgc  10740
ctatcaacac cttggaaaaa ctgaattctc cccaactaat agtggtgtgt cactgtagta  10800
agcctagtac aaaaatggcc ttctttgtgg aggagcttca tatcctccat tttttttttg  10860
cttaattttt gcccaagatg agaacataat ttagttcact ttttatttat tcccaacatc  10920
atccatgcac caacatttt gtaactaaag gagggaccat tcagaagatg cttatcaact  10980
gtcaaagtga cagtgttaca accaatgcac atattgtaag aaatcaaaca atggcctcca  11040
aggttcattt ctacacaggg attagcagat caacatccaat cttggcaaca cagttgccaa  11100
tgatggtgtc ttattttttt tatcatgaca tggcaatcaa gagcaaacat gatttattct  11160
tatttaagat tttatggtta gactaggcag atagctagat atgagcagga ggtggaagcc  11220
cctgagagaa tggaggtctg gagaatctga accccagag attacccaag tcctgcatgc  11280
tagacatgag tggaggaggg ggaataccta ggtagaaaag aatgccccctt aagatgccca  11340
gcagtcgctc actgtgcagt taactttttca gaatgctgct agatacatgc tgatagggag  11400
ggaagagggc aaaggagaaa ttcctaagag atacacggtt gcagttagta tacatctgag  11460
tgctatacaa ccttctttgg gtggtggcaa gaagcaatgc agccattacg tagaattcat  11520
atcaaacacc tgtatcacag gtgttaaaga aacaagaaac atttgtacttc ttgtattctt  11580
aataatgatt tgcaatattg tcttttagtat cactgcaaac ctctataaat atgattttta  11640
aaaagtatttt ctttaggttg gaattacttc tacgcattga cttatcttcc tgggtttcat  11700
tagccgtacc cgttgtactt tcttccttac cactgtttat ctcaaactct tgagattaaa  11760
gtatgggctc aggagggagc gaggagcttc aggactctca cggacctcca gcacagttga  11820
gctgccttat ggaaaagtgg ccacactgtt ttctgcactg gtccctgccc ctactattca  11880
tcactgggca gagcacagcc accctggccc tgcctgaaca ttttagtcag tgttggctct  11940
gtgcttctct ggggaggaaa tccaagagac aacccacagc ccctctgcca tttcagctgc  12000
agcagtacca ccgttaatgc ccttgggctt gagaaagaag ggacctggcc acttccctga  12060
cacctccagc acacagcagg gaaagaattc cagtttctct ttcttgtgag ctttcacctg  12120
ctactcttca ccaggcaagg ctcctggctt gggcccacag tgcaggcacc tcgaactcag  12180
ttgaacattt ccactggctg cactctgtgt ttttgtgggg tgaagctccc agaggtgact  12240
gaaagtcctt ctgccactaa cactgcagtc atactgccct tgctgtactt ggactaggga  12300
aggaaaaaag atcctgagtg ctttactcac accccagtgt gccccagcca ccctatgaa   12360
aagaggccag tgtgtcatcc ctgcaagcac cctgaggccc ctgcccctgc tgcccccaag  12420
ctgtagagcc agaatataaa gctggcagaa aaatgtaaaa aggctagcct attagcct    12480
cccagcctac atcttctcc tgtgctggat ccttcctgct cttgaacatc ggactccaag  12540
ttcttcagct gtgggacttg gactgtcttc cttgctcctc agattgcagg tggcctatta  12600
tgggaccttg taatcttgtg agttaatacc acttaataag ctccccttg tgtgagtata   12660
tctatatcta tagatagata taggtatact cactatatat acacatatat acatatactc  12720
tctctctctc tctctcatat atatatatat ataatctcct attagttctg tccctctaga  12780
```

```
gaacccgac taatacagat tttcatacca gaagtggttc ttgaggaaca gaatattaag   12840
gatggaattc tttcattggt tttgggactt ctggtgttgg ctgattaata tgattagacc   12900
aaaaaatgct aaggactcta cttctaatag tatggagaac actgatagta cttggcctga   12960
attgtttaga gagttatgca aaataaatgc atttgacact actgattcat cacttatgag   13020
aggcaaggag tttagtgact ctatacataa tacctttgac tatatgtgga gaaccaagga   13080
acataatgaa gttggttgat tgctcctaag ttctctggag aaagagatga agaaaatga    13140
tgatctcagg ggatctgtct cccaccttca gaagcagata ctgagccaca aatctgctaa   13200
gattgccctg aatgagagtt ttaactcctg tagagaaaga gttgaaattg tgaaaaaaca   13260
gagacaagct gttatcatgc gagtagctga tctgcaacaa gaggtgcatg cacagccttg   13320
ccaggtgttt actgttaaag tgagggcatt gactggaaaa aaatgggacc ctggaacttg   13380
gagtggggat gtgtgggaga accctgatga agctgaggac actgagtttg tgaactctga   13440
tgaaactttt ttgccagaag aaacagtttc cccatcccca gtagtggtaa catccctcc   13500
ctgacccgtg ctgccattag cctttccacc tttgtctgag gatgtaaacc ctgcactgct   13560
tgaggcaaca gtgatggcct tccctgaggc agctgccagg caagataatg ttgattctcc   13620
tcaagaggca ccctaatgc ccctgaatgc ttctagacct ataactaggc taaattcctt    13680
gcgggcccca gaggtgaggt tcagagtgtg acccatgagg aggtgcatta tactctaaaa   13740
gaactgctta agctttctaa tttatattgg cagaaatctg gagaacaggc atgggaatgg   13800
atattaaggg taagggataa tggtggaagg gacatagagt tggatcaagc tgaatttatt   13860
ggtttggccc tactaagtag ggattctgca tttaatgttg cagctcgggg acttagaaaa   13920
ggttctgata gggccgggag cagtggctca cgcctgtaat cccagcacct gggaggcgg    13980
gggcgggcag atcacgagat caggagattg agacaattct ggctaaaatg gtgaaacccc   14040
atctctgcta aaaatacaaa aattagctgg gcatggtgat gcgtaactgt aatctcatct   14100
acttgggagg ctgaggcaag agaactgctt gaacctgtga ggcagagatt gcagtgagcc   14160
aagatcgccc cactgcattc cagcctggta acagagcaag actccatttc caaaaaaaaa   14220
aaaaaaaaag ttataatagt ttatttgctt ggttagctga aatatggatt aaaagatggt   14280
ccaatgttag tgagctggaa atgccttggt ttaatgtaga ggaagtgatc caaaggctta   14340
gggagattag gatggtggag tggattagtc actttagacc tactcatccc agctgggagg   14400
gtccagaaga tacacccttg gccgaagctt tgtgaaatag atttgtgaga gcagcacctg   14460
tattttgaa gagcccgtaa ttgctcttct ctgtatgtca gatctaacag taggaaccac    14520
agtcactcaa ctacaaaatt taaatacaat gggaataatt ggatcctgag gtgcagggg   14580
ccaagtgttg gcactgaacc atcaaaggca aggtgggcat aactaccata atagacagca   14640
gaggcaaagc agccatcaga atagtctgac tcatgtagag ctctggcatt ggctaattaa   14700
tcatggtgtt cctagaagtg aaattgatgg gaaacctact gtattcctac ttgatttata   14760
taaacaaaaa actgccaggt agaatggact aaagactaat ctgaattata aaaacagaga   14820
atcatgggcc ctcaatcaat ttccagactc gaacctgtta cagttccaga acccactgaa   14880
tgaaggggag gctggatccc cttgaggaag acaccacta ggctactgac aacttatgct    14940
gttactcttt ctcccatcct tccctaagga gacctctggc cttttaccag ggtaactgtg   15000
tgtactggag aaagggaagt aatgagacat ttcagaaagt actggacact ggctctgagc   15060
tgacgttgat tccaggtac ccaaaacgtt attgtgcttc cccagttaaa gtaggggctt    15120
atggaggtta ggtaattaat ggagttttag ctcatttctg acttacagtg gttccagtgg   15180
gtccctggac ttatcctctg gtcattttcc cagtgccaaa atgcataatt tgtatagaca   15240
tactattag ctggcagaaa tgccacattg gctccctgac tggtaggatg agggctatta    15300
tggtgggaaa ggccaaacag aagccattag agctgtctct acctagaaaa ataaaaaaat   15360
caaaaacaat atcccatccc tggagggact gaagtgatta gtgtcaccat caaggacttg   15420
aaagacgcag gggtggtgat tcccaccaca tccctgttca actctcccat ttgacctgtg   15480
cagaggacag atggatcttg gaaaatgatg gtggattatt ttaagcttaa ccaagtggtg   15540
actccaattg cagctgctct accagttgtg gttttgttgc ttgagcaaat taacacatct   15600
cctggtgcct ggtatgcagc cattggcttg gcaagtggct ttttctccat tcctgtccat   15660
aagacccacc agaagcaatt tgccttcagc tgacaaggcc agcattatac ctttaccacc   15720
ctacctcagg ggtgtatcaa ctctccagct ttgtgtcata atcttatttg gagagacctt   15780
gctcgctttt cacttccacg agatataaca ctggtccatt acattcatga cattatgatg   15840
attggataca gtgagcaaga agtagcaaac acactgaact tattggtgag acatttgtat   15900
gccagaggat gggaaataaa tccagctaaa atttagggac tttctacctc ggtaaaattt   15960
ctagggttcc agtggcatga gacctatgga gatattcctt ctaaggtgaa gcataacttg   16020
ctgcgtttgg cccctcttac aaccaagaaa gaggcacaat gcctggtggg cctatttgga   16080
ttttggaggc aacacattcc tcgtttgggt gtgttactct ggcccattta tcgagtgacc   16140
tgaaaggctg ccagatttaa gtgcagtcta gaacaaaaga aggctctgaa acaggtccag   16200
gctgctgtga aagctgctct gccatttggg ccacatgacc ccgcagatcc aatggtgctt   16260
gaggtgtcag tggcagatag ggatgctgtt tgggagcctt ggcaggccca cataggtgaa   16320
tcacagtgga gacctctagg attttggagc aaggccctgc cacttctgca gataactact   16380
ctcctttga gagacagcta ttggtctgtt attgggcttt ggtggtaact gaacgtttga    16440
ctgtgggtca taaagtcacc atgctacctg aacctgccta tcatgaactg gttgctttct   16500
gacccatcta gccatgaagt gggtcagcac agcggcattt catcatcaaa ttgaagtggt   16560
gtgtatgtga tcgggcttga gcaggtcctg aaggcacaag taagttacat aaggaagtgg   16620
ctcaaatgcc catgttctcc actcatgcca cctgccttc cctcccccag cctgcaccaa    16680
tggcctcatg gggagttccc tatgatcagt tgacagagga agggaagact aaggactggt   16740
tcatagatgt ttctgcacga tatgcaggca ccacccgaaa gtgacagct gcagcactat    16800
atccacttc taaatgcttg tgtacacttg tgctaagaaa atatctttat tttatttcct   16860
ttattttcc tttatcatgt gaccttagat ttatggactt cacatcagca tttaagcatt    16920
taagtgttgt tcatatcagc atttaaatat tgttaaccttt atgtaataac tttttggtttg   16980
gggattggtg cgtttctggt tgtatgagga tagttgtatt atattaggca taattatgac   17040
cttattattg tctttatttg aagattatgt atgatttcag gatgtgtgta tgggttcaag   17100
ttgacaagga gttggacttg tgatggtta tactgtcaac ttgattggat tgaaagatgc    17160
aaagtattaa tctcggttat gtctgtgagg gtgtggcaa aggagattaa catttgagtc     17220
agtgggctgg gaaggcagac ccaccccttaa tctgggtaca caccatctaa tcaagttcca   17280
gtgtggccaa attgtaaagc agggagaaaa atgtgaaaag actagactga attagcttcc   17340
cagcctacat ctttctcctg tgccaaatgc ttcctgctct tgaacatcgg actccaagtt   17400
cttcagcgtt gggagttgga ctggcttttct tgctcctcag cttgcagagg gcctgttgtg   17460
gaaccttgtg atccgctgag ttaatactac ttaataagat ccccttttata tacatataat   17520
```

```
atattatatt atatataata tatataataat atattatata taatatatat aatatattat 17580
atattatata taatatatat tatatattat atatataata tattatatat aatatatatt 17640
atatattata tattatatat aatatatatt atatataata tatataaaat atatatatat 17700
cctattagtt ctgtccctct agagaaccct gactaataca atttatgtca ttaatctcat 17760
ttattgattt gtatacattg aaccaacctt atatcccagg aataaaacct acttgattgt 17820
ggtggattag cttttgatg tactcttgga ttcaattgct ggtatttat tgagaatttt 17880
tgcatctgtg ttcatcaagg atattggctt gaagttttct ttttttgttg ttccatatca 17940
gaatgatgac gacctcatag aatgagttag tctgtcctct tttatctttt ggaattgttt 18000
caggaggctt gatatcagct cttctttata tgactggtat actttggcta ggaatctctt 18060
tggtccaggg gttttctgg tgtaggtttt taattactga ttcaacttca gaactcatta 18120
ctcattattg agttctaaaa ctcactttca tgtactcttc aaaagactgt cttcttctgt 18180
tgttgagcgg ggtgttctct caaggtcgtt taggtgaagg tggttgctgg tgttcttctg 18240
tatccttact gcttgtcttt ctcttttttt attgactact gaggattaat ggtgatgtgt 18300
ccaacttaa ctctagatta gtctatttct ctttagatt gtaactctgt tttatatatt 18360
ttgaagctct gttgttaggc atgtgtattt ggattgttag gtcttcttga tgatgacctt 18420
tatcattatg taatgtttct tcttatctct ggaagtattc gttgttctga agtctatttg 18480
tgctgatatg aatacagcct tcacagctct attttcacta gtatttgtat atcttttct 18540
cagcttttaa attgagatgt tcagaccatt tgcattaaag tagttgttaa taggattaaa 18600
tttaaatcta ccattaagtt ggttatttct ctttgtccca tttaaactttt gttccttttt 18660
tcatattttt ctgccttcat ttatattgag tttatctcca cgacttactt attaaattaa 18720
ttttttaatgg ttttagtatt ttccacaatg tttataaatt atactttgat ttttcacat 18780
tccaccttca aatgacaga ttatactgga tatatagaaa ttgcacttct 18840
ccttcctccc tctcaaaatg ttgtgctatt gctcttgta atagaggctt acttctatta 18900
tgttatagct ctcataatac attgacacta ttttacct gaataatcag ttgttttta 18960
aagtgattat gactacaaat attttgaata atttctttat tttaccattt ctggtgctcc 19020
ttatcttta cagtagatcc caatttccat ctggagtcac attctttctg tgaaaaacaa 19080
cctttagcat ttcttatagc acgggactgc tgttgctgtt gtctttcagc ttttctttgt 19140
ctgaagaagt ctttattttg ccttcagttt ttaaaagtga ttttgctgag tatagatact 19200
gggttgagag tttcattcct tgtatcattt taacaatgat gttccattat attccgtttt 19260
gaatagttc tgactagaaa tctgatcttt gtttctttgt attcaatagt tcctttttcc 19320
ctgactgcct ttaagatatt ctcatctttg tttttcaaca gtttgactat aatttgttta 19380
ttattaactt tttgtattta ttctgcttga ggttcctga gctccttgga tttgcagatt 19440
gttgatttt attgttttg taaaattcat agccattatc tattctactg ttttgttttt 19500
tttttcactt ctctctctct gtattcttct ttttggactg taagtattca agtttagt 19560
cattcatatt gcttcataaa cctatatgc ttcttctgct tttttttttt tgtcaggaac 19620
tcttttttg tatctgtgtt ggtttggata agttctagta gactatgttc aagtttatgg 19680
attatttgt tagttgtgtc taattgactc ctcagtgcat tcagagaatt cttcatctct 19740
gatattataa atctcttcct agcatttca tgttactcta ttctatagtt tccatctctt 19800
tgctgaaatt ctccccctat ccatgatat tgtccaccatt taccacaaga ttcttaaca 19860
tattaacata ggtatcatac aaacccaaac tgatagttc cagatggtgt cttttctgag 19920
tctgtctgtc ttgattgctt tattatttaa cagtgactta tcttccctct tcagcttttg 19980
gtgtgtcttg taattgttta atcaaacact gggtatcata aatggaggaa cagtagagat 20040
tgcagtaaat attatttatg ctttgaaatg ggcacccatc ttctgttgaa aatatgtttt 20100
gtggtcaatt gagtcaacct agtaactggt tgaactgaat ttggcatttg tgcttgttgc 20160
ttttatctta aatgcaccac aggtttaaat tcctccagtg atgggttgct gctatctttt 20220
gcttagagtg gggcctgggg tgtggaagaa ttttctcagt gttcctatct attattagat 20280
tttagcagtc actgcatgcc tgcactacag agggatatc ttcatacaca taatctaacc 20340
ccattgaaac tgctgttct tcttaatgaa tgctcaatct ttggtggaaa taaacaaatg 20400
ctgtatctcc tggagccact tcagtcttag tcaggttctg cagggctttg aagggaatgc 20460
attctcagta ttccttgtgcc ttatttggat ggaacttgaa cctgtggtgg gtttggagag 20520
aaagagtagc agacgtctgc tatgttgcaa tgcaggatgc tgggcacaag aaaatttcca 20580
gtctctcctc caaggaaata agatttgatc atctaccttat ccctgagaag tgaagggctt 20640
tgcctgcggt gctagatgca aaaccatttt tctccccccca ttgcccagaa acttaaggct 20700
ttggcttttc tgagcagtgg tctagggaat tgtgcaaggt tttcatattt gaccctgaca 20760
gcccatcacc acctacagct tgcagtgcca aatgtatctc cctctgatct ctcctgtcct 20820
gtggtcctca tgaacattaa gaagagattt ctaaaaaaga gcttgcacat gagcatagtt 20880
tctggtgaga agaattctga tatgttaact tccctctaaac ttttaaataa aatatttcta 20940
agaattaaat aaagttctag aatgatatga atctattcct ttggttttt gcacgtctgt 21000
ctgcctgcta atcaaggaaa gagaatggtc gtaattctca gagactttt cctgttttgtg 21060
tcataaatga cttccacattt ttttctgttc taagaactat tcagcttgat ttcttctgtt 21120
ttaattttag cagcacctga gcaaagccat gtggtccagg attgctacca tggtgatgga 21180
cagagttatc gaggcacgta ctccaccact gtcacaggaa ggacctgcca agcttggtca 21240
tctatgacac cacatcaaca taataggacc acagaaaact acccaaatgc gtatgtcatt 21300
aatcttacag taagcaaaac aaggtccaag taaaatttgt cttagaaaag gtgtgcgtca 21360
agctaacttc ttatgattaa atttttctca cacatagaat gcatggcaaa atgtctgaga 21420
aacattactt tgagcaaaga gtatgataga agagaaatgt taagctggct ctcttttcctg 21480
agagtttgat aaaatcagga gaatatctgg cgtggtgag gccacaataa tggaaaatca 21540
gaatgtttag acagagtcag cttcaacaac actcactaaa ggtcaatgtg atctttaccc 21600
cttgaaattc tataattcta atctccaatt cctgaagtga aggttgtgtt ggctttttct 21660
gtcttggctc acaagtaaat gatatgtgca tatctatgga aaggcgaatc tatctttttc 21720
tatatctatg tctattccaa cgggtagaaa caccctgggt cctgagcacc agtggtctga 21780
aggaatacgg gttgccagga agagagaagc aaaggcagga aggcagatga aagtaagaaa 21840
tgagacagat gctaaacaat aaaaagtgcg ggaagataga cagaagctgg ggtctgacca 21900
caccatggcc agtctttcac acataagtga ctaccaaaga caagaaaaaa tgatttccgc 21960
ttgttggaca atagatgagta gaggaccaag ggaattgcga gagagagaac aatgagatca 22020
actcaacaga tgcactggtt ttcttcctgg agacccttcc tgcactgaag ggcaggagat 22080
ggagcccaaa aaaactgta gccatcttgc tgaacagagg agggacattg gagtttggga 22140
ttattcaggt ggctaggatt ttctaggcct gctaacaatg agaacagatt tgtggaggaa 22200
aggagttcta gaaatatgca tagaaatctc ctcgagtcat tggctaaaca tgaagctgca 22260
```

```
tgtacacaga aaatagatcc acaagaaagt agggcaaaga acatctacgg aagagcagca   22320
actacaatgg aacagtgagc tcaataaaca tgcagagct  caaatagcac taagggatat   22380
tggagtttgg accacacaga ggagagagac ttcactgaac atcttgggca ttcagtagag   22440
acccaggaaa agccatactt taggagtaga attagtatat tcttagaata aaggcagctc   22500
cacacaaaca atagcaaaac tgaaaaggaa gtctccaagc atcagaatga tgtccaagtc   22560
aatgaactgc ctctgagagg aaaactcaac catctttaga ggtaaacatc aaagtcaagt   22620
ggctcagcta tgcagtatcc acagtgtgag gcctaaatat aaaacttgac tacacataga   22680
aaccttttag tgtgacccac aagcaggagg aaaatcagcc aatacaaaca gacccagaag   22740
agacagaaat gattagaatg gcataaaaat ttgcatatatc actatataat aattgagttc   22800
taggatttaa gaaaacatga atatagaatg caacagacac cttatccaga gacagtaaga   22860
gtataaagag ccaaatcgaa gaactactaa gagatatgtc ttaaatgaaa aaattactag   22920
atggcctccc catctagtta gacatttcag aagaaaatac caaatgaaaa ataattgcat   22980
agaacctaca gaaccagata cacacataca aaacacacgc atgcatacac acacactcaa   23040
acatgtataa gcttacaaac acacacacac atccacaaat gctgaaaaat gaaatcaacc   23100
gagccacaca gacataaagg aaaacataaa aagatttcct acatgtggga agcaagtcac   23160
agaaaggggg aaggagattg gaacagaaat atatactgaa agcaaggatg gctgaaaatt   23220
ttccaaatat aaagaagatt aaaaaatcac ggactcaaga agctcaatgg atcagaaaaa   23280
taatttctaa aatgacaatt ataggatgcc actgggtaca tagcagttca actgtcagag   23340
ggcaaagaca taatacacag aaaaatctcg taaggaacgg gaaaaacaaa aagctgtgtc   23400
ttgctagagg aacagtgata caagtgacta atgtgttccc atcagaaaca ctgcaacctg   23460
gacacaaaag aataacatta aagtaataaa cgtaagaaag aagagctcaa ctgagaaggc   23520
tacatccagc aataaaatgc cttgaagttc atccatgttg gaggaatgca cattgtgcac   23580
tccctaaac  aaagaaaccg gaactgtaa  gactttggaa tcagcaggct tatgtaacaa   23640
aagaggtgac cctaaggaat taggagaag  aagaatagaa caagaaggga actttctgca   23700
gcctatataa tgaagaacct agcaattggc aaatgtagat gaaaatgcta catgtttct    23760
tgatcaaacg tttatatctt tttaaatgag agttgacgag ttgaagcaaa atgataccaa   23820
tatatttaac tttaccatat gtagaagtaa aaatttgaac atgtagcata aatcatgtag   23880
ggattaattg gaagtgtacc actgtaagtt tcttacctca tgcacgatag tatgtaaatac  23940
taataaaagg ttaatgtgtg ggttcaaagg gatattgcaa atcctagagc aatcacaaag   24000
tttttaactc tgaggtttgt tgtataataa caatatttta tgtattcaaa agagggaagc   24060
caaggaagaa aaaaagtct  ttaaagagct ctggctctta gtacatccag ttgctcattg   24120
aatgagcttc ctggaatgga gggtctggga ctgagactag gccacatgtg tagagccact   24180
agagacacaa tgttggatcc ccatggccca taatacattt cccatttttct caggcagcca   24240
caggtcatga atgtgaggat actgagaggt tggagcaacg ttcttgggag gcataaggaa   24300
gagcgaatgc ttcaagatcc ccgcagccca aactcctcag ctgctttgcc tcctaattca   24360
ttgtttttg  ctcctccata gctgtccgac ctcttcagat ctcttagtct tcctgccatc   24420
ttcctttatg ccatgggacc cactgttctt tcaactcatc ccccagtcct ggagtggctg   24480
tggacagcag aggatagact gagagcagga gagaaggtcc tgcccaggaa cccattctag   24540
agatactgca ttctgcctgg gagcaagttt tccagggcag ctttgagaag tcttgcagaa   24600
acaaacctac ttgaccgaca tgatatggga atgacagaca gtaatactat ttgcacaatg   24660
cttttccatg ggaaaggtag agccttttca ctaggttttg agtacatgga gtgtgagagt   24720
tgacctggaa aggttatcct ccttgatgcc atgttttctc tgaagaacta catgttcgtt   24780
gcaactccca cattagaata tgaagtccta ccgagagaa  tacggagact agacagatac   24840
agatgcattt gcatgtgaat acacaatccc acaatacaga cgtcaaaacc cataccagtt   24900
attccagaga gatggattgg gcagaaggca gaaggagaat actctgatcg tttttcggcc   24960
acgtgtgtgt gttatctcag tgtttctaag aagcgtttgc tactttagat ttttttattta  25020
aaaaaaatag taataatcta ttaagtatga gagatgtgca gagaggatta gtgatcgaga   25080
gccatttttg ctggtggcaa tcatatggta cttttaatgg gaatattaga aaggcaccgg   25140
taatgacctt gttgcagcac aaaggagaga gtgtggggtg cccctgcatg ttgtcccacc   25200
tcttgtgacg tgtatcgttt tggaatttcc agtggcttga tcatgaacta ctgcaggaat   25260
ccagatgctg tggcagctcc ttattgttat acgagggatc ccggtgtcag gtgggagtga   25320
tgcaacctga cgcaatgctc agacgcagaa gggactgccg tcgcgcctcc gactgttacc   25380
ccggttccaa gcctagaggc tccttccgaa caagttaagg agtctgtggc cagacatcta   25440
cacgcttcga tgctgggatg aaaagccatg gaaattccca ctgatgcagc cgccttcaat   25500
ggtaaacgga tgctcgagtg ttgcctgagt tctaccatgt aggaggaagc ctccgtgcac   25560
tctctgggga agccagcgga gtgatttctg gtgcaacgtg gttgggcttt gtctttagga   25620
tgggcacaaa ccctccaggg ggatcgactt caaaattcac cttgttgtaa aacgggctac   25680
ctcagtgtcc cagccaaaat ttttattgta acatgctgtc aggtgtgtca ctctttccaa   25740
gccagtaagc ttttccgggg attttcttcaa gtagccagca ttcagagcaa tcttcagcat   25800
tgcagattct gagaaatgtg gctctgagc  ctgtcaccct cgagaaacct aagagggctg   25860
cattgattcc atgtggccct gggtctatgg agcagtacat gagctcccag tgctctaagg   25920
ctcttcagcc ctaggctttg aagggagtga tttctcagta ttcttaaacc tctttctgat   25980
gacacttgta cctgtgaggg gtctagagag aaagagtagt agactcctac tttactacaa   26040
ttcaggatgc agggcatgag aggattccct ctctcctcca ggggaagaag cttttggcgt   26100
gcacacatcc ctgagaagca aagtgtcttt gtcttcagtc agatacatag gaccgttttc   26160
tgccccatgg cccggaagcc aaaggccttg gctttcatga tcaacggtct agggaaacat   26220
gcaaatttc  catgtctgtc ccaaactctg cccccgacag ccaattacca cctgcagccc   26280
gcattgccaa atgcggtgcc gtttgcatga agattcagta gagtttccta gaaaggtgct   26340
acctcgtgag ctcactttcc aatgaggaat ctgatctgtt gtgtttctct aagatgtcag   26400
gtgaaatatt tccaagaact tactacagtt ctagaatggg aggaatctgt tgctttggtg   26460
tttgtttgtt ggtcggtttt ctcacatcca tctgcctatg gataaggaaa agagaacggt   26520
cgtaattctc atagactcct ttctggttgt gtcacaaatg gcttcacatg tttctctatg   26580
ctcagagata ctcagcttga tttcccgtgt ttttcatttca gcaccgactg agcaaaggcc   26640
tggggtgcag gagtgctacc atggtaatgg acagagttat cgaggcacat actccaccac   26700
tgtcacagga agaacctgcc aagcttggtc atctatgaca ccacactcgc atagtcggac   26760
cccagaatac tacccaaatg cgtatgtctt tgttctttac cataagagaa gaagggccca   26820
agtgaagttt ctgttacaag agatgtgtct caagctgagt tctccgaact caacttgtga   26880
cagatgcaga tggcgtagca aaatgtctca ggatgattgc cttggagcta agggtctgag   26940
agaagggaaa tgttaagctc cctctccttc ctcctagttc tattgagcag aagggaaatc   27000
```

```
tggaggtgag gagatcacat tatgaagaaa gtcagaatga caaaggacca gacacttaga   27060
ttacccttcc acaacaccaa ctaaacgtca atggagactt tccagttgga attccgttat   27120
tctggcttcc acttcctgaa gggaaggttg cgtttgcctt ttctctctgg gttcaagagg   27180
aaagaatagg tgcttattta tggacaggtg aattgatctg tttctatatc tacgtatatt   27240
ccgattgtca gaaaaacact cgttcctaag taccagtggc ctgaagggat acaggttccc   27300
agcaagagaa gatccaagga aggaaggcag atgagagtca gcacagagag ggatgctgaa   27360
aagtaaaagg gatgggtgga tggagagaag cccgggtctg accacccaat ggccaatatt   27420
ttggccacaa gcgactacca gagacatgga aaaatggttt ctacatgtgg gacaacagat   27480
ggtagaggac ctagagaatt gagagagggg caatgatggg ctccactccg cagatgcctt   27540
ggctttcttc ctggatatcc ttcctgcact gaatagcaag gagatggagc ccaagcagac   27600
tgtagccatc ttgctgaatg gaggagaggg attggagttt gggatgactg tggtagctga   27660
aatttttcta ggtctgctag aaataagaac tggtttgtgt ggaggaaaag agctctacaa   27720
atacgcatag aagtctcctc cagtcgttgg cctgacatga cgctgcctgt gcacaggaaa   27780
tggttccacg agaaagtgtg gcaaagaaca tttactgaga aacagcaagt acaagagcac   27840
aggaagctca ataaagaaga gagagatcac atagcactct gggatactgg agttcttccc   27900
agctagacca gagagtcctc acggagcaca ttgccaattc agtggagacc ccagaacagc   27960
cgtaatttaa aggtacactt agtatattac tagaataaag tcagctgcag acaacccctt   28020
gcacagctgg aaagcaagtg tccaagcatc aaatcggttt ccaatcaatg aagtgcctgt   28080
gagaggaaat ctcaactctc tttagaagta aacaacaaag tcgattgcct cagctatgcg   28140
gtatccgcag agtgagtcct aaatttaaaa tctgactaca tgtagaaaag cgtttcgtgt   28200
gacccatgac caggaaataa atcgggtaat acaaacaggc tcaggaatga gagaaatgat   28260
tagaattgcg tgaaaatttg acatatcagt atgataactg atttcaaata tttaaaaaaa   28320
caacatgcaa gaaagcagat atcatatcaa gagaaattaa cagtacagaa tagccaaatt   28380
aaattaaaga ggtagtataa aaaaagtatg tcttaattga aaaaaattac tgtatggccg   28440
gctgatcaat ttagacgttt cagaggaaaa cattacccaa cacacaattc tagagaacct   28500
acagaatgag ctacacacac acacacacac acactgaaaa cacacccata   28560
ctcacacaca cgcagaaact cacaagttct aacacacaca gacacgcgca ccccctgaaga   28620
aacagtgaaa tataaaatta agcgagcctc acagacatgt aggaaaatat gaaaagattt   28680
cctgcatgtg ggaagcaagt cacagtaaag agcaaggag tttataatag aaacaaatac   28740
cagaatcaag gatggctgat aacttttcaa ttacgaagaa cattaaaaaa aatcacagaa   28800
tcgtgaaact caagggatca tatagggaat ttcggaaaaa aaacccaacc tgtatgatgt   28860
acttttgtac atcacagttc gaaggtaaca aggcaaagat gtaataagaa gaaacctgtc   28920
acgagaaact ggaggaaaaa gagctgtgtc ttcctacaag tacactgata caaattgcca   28980
atgtgttcac ctcagaaaca ctggaagcca gataccaggg aatattgtta aaatgataat   29040
caggaacaaa aagagatcaa ccgggaatgc tgaatctgac aataaaatgc cttgaaggtc   29100
atccatgtcg gataaatgca tattgtgcac tgccccaaag aaagaaaccg gaaactgtaa   29160
gaattggaaa tcagcaggct tatgtaacaa gagaggtgac ccgaaggaat taggtagaag   29220
aagaattgaa caagaaagga actttctgca gcccacgtaa tgaagaatcc agcaattggc   29280
aaatgtagat agatgtaaat gcaaaatatt ttcttgatca aatttctata tctttgtaaa   29340
tgagagttga ctacttgaaa caaaatgata gcaagatatt taacttcagc atatgtagag   29400
gtaagaattt gaaatggtag cataaatcac gaagggatta attcgaagtg taccgttgta   29460
agtttcttta cctcatgcac gatggtgtgt catattaata aaagggtact gtgcgggttc   29520
gaagggatat tgcaaatcct agagcaatca caaaggtttg aactctgagg tttttggtat   29580
aataagaata gtccatgcat tcaaaagagg gaagccaagg aagaactaga agtctttcaa   29640
gagctcaggc tcttatacat ccagttgctc attgaaccag cttcctgaaa tggagggtct   29700
ggggttgaga ctaggccaca agtctagagt ctctagagag acagtgttgg aaccccatgg   29760
cccataatac atttcccatt ttctcaggca gccagagtgc atgaatgtga ggatactggg   29820
aggttggagc aacgttcttg ggaggcataa ggaagagcga atgcttcaag atccccgcag   29880
cccaaactac tcgcctgctt tgcccccctaa tgcattttc tctgctgctc cgtagctgtc   29940
cgacctcttc agatctctta gtccaccctg ccgtcttcct ttatgccatg ggtcccactg   30000
ttctttcaac tcatcccct ttccctcagt cccggagtag ctgcggccag cagagggtag   30060
actgagagca ggagagaagg acctgcctag gaacccttc tagagatact gcatcctgcc   30120
tgggagcaag ttttccaggg cagctttgag aagtcttgga gaaacaaacc tactaaacct   30180
gacagacagt aatactattt gcacaatgct tttctgtggg aaaggtagag ccttttcact   30240
acgtattgag tacatagagt gtgagggttg acctggaacg gctatcctcc tggatgacgt   30300
gtgttttctg aagaactaca tgttcgttgc aactcccaca ttagaatatg aagtcctacc   30360
gagagagata cggagactag acagatacag atgcatttgc atgtgaatac acaatcccac   30420
aatacagacg tcaaacccca taccagttat tccagagaga tggattgggc agaaggcaga   30480
aggagaatac tctgatcgtt tttcggccac gtgtgtgtgt tatctcagtg tttctaagaa   30540
gcgtttgcta cttttagattt tttattttaaa aaaatagtaa taatctatta agtatgagag   30600
atgtgcagag aggattagtg atcgagagcc attttttgctg gtgcaatca tatggtactt   30660
ttaatgggaa tattagaaag gcaccggtaa tgaccttgtt gcagcacaaa ggagagagtg   30720
tggggtgccc ctgcatgttg tcccacctct tgtgacgtgt atcgttttgg aatttccagt   30780
ggcttgatca tgaactactg caggaatcca gatgctgtgg cagctcctta ttgttatacg   30840
agggatcccg gtgtcaggtg ggagtactgc aacctgacgg aatgctcaga cgcagaaggg   30900
actgccgtcg cgcctccgac tgttaccccg gttccaagcc tagaggctcc ttccgaacaa   30960
ggtaaggagt ctgtggccag acatctacac gcttcgatgc tgggatgaaa agccatgaa   31020
attcccactg atgcagccgc cttcaatggt aaacggatgc tcgatgtgtg cctgagttct   31080
accatgtagg aggaagcctc cgtgcactct ctgggggagc cagcggagtg atttctggtg   31140
caacgtggtt gggctttgtc tttaggatgg gcacaaaccc tccaggggga tcgacttcaa   31200
aattcacctt gttgtaaaac gggctacctc agtgtcccag ccaaaatttt tattgtaaca   31260
tgctgtcagg tgtgtcactc tttccaagcc agtaagcttt tccggggatt tcttcaagta   31320
gccagcattc agagcaatct tcagcattgc agattctgag aaatgtggct ctggagcctg   31380
tcaccctcga gaaacctaag agggctgcat tgattccatg cccctgggt tctatggagc   31440
agtacatgag ctcccagtgc tctaaggctc ttcagcccta ggctttgaag ggagtgattt   31500
ctcagtattc ttaaacctct ttctgatgac acttgtacct gtgaggggtc tagagagaaa   31560
gagtagtaga ctcctacttt actacaattc aggatgcagg gcatgagagg attccctctc   31620
tcctccaagg gaagaagctt ttggcgtgca cacatccctg agaagcaaag tgtctttgtc   31680
ttcagtcaga tacataggac cgttttctgc cccatggccc ggaagccaaa ggccttggct   31740
```

```
ttcatgatca acggtctagg gaaacatgca aaatttccat gtctgtccca aactctgccc   31800
ccgacagcca attaccacct gcagcccgca ttgccaaatg cggtgccgtt tgcatgaaga   31860
ttcagtagag tttcctagaa aggtgctacc tcgtgagctc actttccaat gaggaatctg   31920
atctgttgtg tttctctaag gtgtcaggtg aaatatttcc aagaacttac tacagttcta   31980
gaatgggagg aatctgttgc tttggtgttt gtttgttggt cggttttctc acatccatct   32040
gcctatggat aaggaaaaga gaacggtcgt aattctcata gactcctttc tggttgtgtc   32100
acaaatggct tcacatgttt ctctatgctc agagatactc agcttgattt cccgtgtttt   32160
catttcagca ccgactgagc aaaggcctgg ggtgcaggag tgctaccatg gtaatggaca   32220
gagttatcga ggcacatact ccaccactgt cacaggaaga acctgccaag cttggtcatc   32280
tatgacacca cactcgcata gtcggacccc agaatactac ccaaatgcgt atgtctttgt   32340
tctttaccat aagagaagaa agggccaagt gaagtttctg ttacaagaga tgtgtctcaa   32400
gctgagttct ccgaactcaa cttgtgacag atgcagatgg cgtagcaaaa tgtctcagga   32460
tgattgcctt ggagctaagg gtctgagaga agggaaatgt taagctccct ctccttcctc   32520
ctagttctat tgagcagaag ggaaatctgg aggtgaggag atcacattat gaagaaagtc   32580
agaatgacaa aggaccagac acttagatta cccttccaca acaccaacta aacgtcaatg   32640
gagactttcc agttggaatt ccgttattct ggcttccact tcctgaaggg aaggttgcgt   32700
ttgcctttc tctctgggtt caagaggaaa gaataggtgc ttatttatgg acaggtgaat   32760
tgatctgttt ctatatctac gtatattccg attgtcagaa aaacactcgt tcctaagtac   32820
cagtggcctg aagggataca ggttcccagc aagagaagat ccaaggaagg aaggcagatg   32880
agagtcagca cagagaggga tgctgaaaag taaaagggat gggtggatgg agagaagccc   32940
gggtctgacc acccaatggc caatattttg gccacaagcg actaccagag acatggaaaa   33000
atggtttcta catgtgggac aacagatggt agaggaccta gagaattgag agaggggcaa   33060
tgatgggctc cactccgcag atgccttggc tttcttcctg gataccttc ctgcactgaa   33120
tagcaaggag atggagccca agcagactgt agccatcttg ctgaatggag gagagggatt   33180
ggagtttggg atgactgtgg tagctgaaat ttttctaggt ctgctagaaa taagaactgg   33240
tttgtggagg aaaagagctc tacaaatacg catagaagtc tcctccagtc gttggcctga   33300
catgacgctg cctgtgcaca ggaaatggtt ccacgagaaa gtgtggcaaa gaacatttac   33360
tgagaaacag caagtacaag agcacaggaa gctcaataaa gaagagagag atcacatagc   33420
actctgggat actggagttc ttcccagcta gaccagagag tcctcacgga gcacattgcc   33480
aattcagtgg agaccccaga acagccgtaa tttaaaggta cacttagtat attactagaa   33540
taaagtcagc tgcagacaac cccttgcaca gctggaaagc aagtgtccaa gcatcaaatc   33600
ggtttccaat caatgaagtg cctgtgagag gaaatctcaa ctctctttag aagtaaacaa   33660
caaagtcgat tgcctcagct atgcggtatc cgcagagtga gtcctaaatt taaaatctga   33720
ctacatgtag aaaagcgttt cgtgtgaccc atgacaggga aataaatcgg gtaatacaaa   33780
caggctcagg aatgagagaa atgattagaa ttgcgtgaaa atttgacata tcagtatgat   33840
aactgatttc aaatatttaa aaaaacaaca tgcaagaaag cagatatcat atcaagagaa   33900
attaacagta cagaatagcc aaattaaatt aaagagctag tataaaaaaa gtatgtctta   33960
attgaaaaaa attactgtat ggccggctga tcaatttaga cgtttcagag gaaaacatta   34020
cccaacacac aattctagag aacctacaga atgagctaca cacacacaca cacacacaca   34080
cacaaactga aaacacaccc atactcacac acacgcagaa actcacaagt tctaacacac   34140
acagacacgc gcacccctga agaaacagtg aaatataaaa ttaagcgagc ctcacagaca   34200
tgtaggaaaa tatgaaaaga tttcctgcat gtgggaagca agtcacagta aagagcaagg   34260
gagtttggaa tagaaacaaa taccggaatc aaggatggct gataacttt caattacgaa   34320
gaacattaaa aaaaatcaca gaatcgtgaa actcaaggga tcacataggg aatttcggaa   34380
aaaaaaccca acctgtatga tgtacttttg tacatcacag ttcgaaggta acaaggcaaa   34440
gatataataa gaagaaacct gtcacgagaa actggaggaa aaagagctgt gtcttcctac   34500
aagtacactg atacaaattg ccaatgtgtt cacctcagaa acactggaag ccagataccca   34560
gggaatattg ttaaaatgat aatcaggaac aaaaagagat caaccggaa tgctgaatcc   34620
agcaataaaa tgccttgaag atcatccatg tcggataaat gcatattgtg cactgcccca   34680
aagaaagaaa ccggaaactg taagaattgg aaatcagcag gcttatgtaa caagagaggt   34740
gacccgaagg aattaggtag aagaagaatt gaacaagaaa ggaacttct gcagcccacg   34800
taatgaagaa tccagcaatt ggcaaatgta gatagatgta aatgcaaaat attttcttga   34860
tcaaatttct atatctttgt aaatgagagt tgactacttg aaacaaaatg atagcaagat   34920
atttaacttc agcatatgta gaggtaagaa tttgaaatgg tagcataaat cacgaaggga   34980
ttaattcgaa gtgtaccgtt gtaagtttct ttacctcatg cacgatggtg tgtcatatta   35040
ataaaagggt actgtgcggg ttcgaaggga tattgcaaat cctagagcaa tcacaaaggt   35100
ttgaactctg aggttttttgg tataataaga atagtccatg cattcaaaag agggaagcca   35160
aggaagaact agaagtctttt caagagctca ggctcttata catccagttg ctcattgaac   35220
cagcttcctg gaatggaggg tctggggttg agactaggcc acaagtctag agtctctaga   35280
gagacagtgt tggaacccca tggcccataa tacatttccc attttctcag gcagccagag   35340
gtcatgaatg tgaggatact gggaggttgg agcaacgttc ttgggaggca taaggaagag   35400
cgaatgcttc aagatccccg cagcccaaac tactcgcctg cttttgccccc taatgcattt   35460
ttctctgctg ctccgtagct gtccgacctc ttcagatctc ttagtccacc ctgccgtctt   35520
cctttatgcc atgggtccca ctgttctttc aactcatccc ccttccctc agtcccggag   35580
tagctgcggc cagcagaggg tagactgaga gcaggagaga aggacctgcc taggaacccc   35640
ttctagagat actgcatcct gcctgggagc aagttttcca gggcagcttt gagaagtctt   35700
ggagaaacaa acctactaaa cctgacagac agtaatacta tttgcacaat gcttttctgt   35760
gggaaaggta gagccttttc actacgtatt gagtacatag agtgtgaggg ttgacctgga   35820
acggctatcc tcctggatga cgtgtgtttt ctgaagaact acatgttcgt tgcaactccc   35880
acattagaat atgaagtcct accgagagag atacggagac tagacagata cagatgcatt   35940
tgcatgtgaa tacacaatcc cacaatacag acgtcaaaac ccataccagt tattccagag   36000
agatggattg ggtaggaggc agaaggagaa tactctgatc gttttcggc cacgtgtgtg   36060
tgttatctca gtgtttctaa gaagcgtttg ctactttaga tttttttattt aaaaaaaata   36120
gtaataatct attaagtatg agagatgtgc agagaggatt agtgatcgag agcattttt   36180
gctggtggca atcatatggt acttttaatg ggaattattag aaaggcaccg gtaatgacct   36240
tgttgcagca caaaggagag agtgtggggt gccctgcat gttgtcccac ctcttgtgac   36300
gtgtatcgtt ttgaatttc cagtggcttg atcatgaact actgcaggaa tccagatgct   36360
gtggcagctc cttattgtta tacgagggat cccggtgtca ggtgggagta ctgcaacctg   36420
acgcaatgct cagacgcaga agggactgcc gtcgcgcctc cgactgttac cccggttcca   36480
```

-continued

```
agcctagagg ctccttccga acaaggtaag gagtctgtgg ccagacatct acacgcttcg   36540
atgctgggat gaaaagccat ggaaattccc actgatgcag ccgccttcaa tggtaaacgg   36600
atgctcgagt gttgccggag ttctgccatg ttgggggaag cctccgtgta ctctctgggg   36660
gagccagcgg agtgatttct ggtgcaactt gggtgggctt tgtctttaga atgggcacaa   36720
accttccagg gtgatgggct tcacaactca cctccttcta aaatgggcta tctcagtgtc   36780
ttagccaaaa tttttattgt aacgtgctgt caggtgtgtg attctttctg tcgcagtaag   36840
cttttctggg gatttcttca agtagccagc agtcagtgca atcttcagca ttgcagattt   36900
caaaaaatgt ggctctggag cctgtcatcc tcgagaaacc taacagggct gcattaattc   36960
catatggtcc tgggtctatg gagcagtata tgagctccca atgctctaag gctcttcagt   37020
cctaggcttt gaagggagtg atttctcagt gttcttaaac ctcctttctga tggcacttgt   37080
acctgtgagg ggtctagaga gaaaggttag tagacttctc ctttactgca attcaggatg   37140
cagggcatga gaagattccc tccctcctcc aagggaagaa ggttttggcg tgcacacatc   37200
cttgagaagc aaagtgtctt tgccttcagt cagatatata ggatcgtttt ctgccccatg   37260
gcctgaaagc cagaggcctt ggctttcatg atcaactgta tagggaaaca tgcaaaattt   37320
ccatgtcttt ccctcctct gccctcgaca gccaattacc acctgcatcc tgcattgcca   37380
aatgcagtgc cctttgtatg aacattcagt agagtttcat agaaaggtgc tacttcgtga   37440
gcgcactttg cagtgagaag gagtctgttc tgttctgttt ttctaaggat ttcaggtgaa   37500
atatttccta gaacttacta cagttctaga ttggtaggaa tctgtaggtt tgctgtatgt   37560
tttttggttg gttttctccc atccatctgc ctacaggtaa gggaaagata acgttcgtaa   37620
ttctcatagag ctcctttctg gttgtgtcat aaatggcttc acatatttcg ttattctcag   37680
agatactcag tttatttctt gtgtttcat ttcagcaccg actgagcaga ggcctggggt   37740
gcaggagtgc taccacggta atggacagag ttatcgagac acatactcca ccactgtcac   37800
tggaagaacc tgccaagctt ggtcatctat gacaccacac tcgcatagtc ggaccccaga   37860
atactaccca aatgcgtatg tctttgttct ttaccataag agaagaaagg gccaagtgaa   37920
gtttctgtta caagagatgt gtctcaagct gagttctccg aactcaactt gtgacagatg   37980
cagatggcgt agcaaaatgt ctcaggatga ttgccttgga gctaagggtc tgagagaagg   38040
gaaatgttaa gctccctctc cttcctccta gttctattga gcagaaggga aatctgagg    38100
tgaggagatc acattatgaa gaaagtcaga atgacaaagg accagacact tagattaccc   38160
ttccacaaca ccaactaaac gtcaatggag acttccagt tggaattccg ttattctggc    38220
ttccacttcc tgaagggaag gttgcgtttg ccttttctct ctgggttcaa gaggaaagaa   38280
taggtgctta tttatggaca ggtgaattga tctgttttcta tatctacgta tattccgatt   38340
gtcagaaaaa cactcgttcc taagtaccag tggcctgaag ggatacaggt tcccagcaag   38400
agaagatcca aggaaggaag gcagatgaga gccagcacag agagggatgc tgaaaagtaa   38460
aagggatggg tggatggaga gaagcccggg tctgaccacc caatggccaa tattttggcc   38520
acaagcgact accagagaca tggaaaaatg gtttctacat gtgggacaac agatggtaga   38580
ggacctagag aattgagaga ggggcaatga tgggctccac tccgcagatg ccttggcttt    38640
cttcctggat acccttcctg cactgaatag caaggagatg gagcccaagc agactgtagc    38700
catcttgctg aatggaggag agggattgga gtttgggatg actgtggtag ctgaaatttt    38760
tctaggtctg ctagaaataa gaactggttt gtggaggaaa agagctctac aaatacgcat    38820
agaagtctcc tccagtcgtt ggcctgacat gacgctgcct gtgcacagga aatggttcca    38880
cgagaaagtg tggcaaagaa catttactga gaaacagcaa gtacaagagc acaggaagct    38940
caataaagaa gagagagatc acatagcact ctgggatact ggagttcttc ccagctagac    39000
cagagagtcc tcacggagca cattgccaat tcagtggaga ccccagaaca gccgtaattt    39060
aaaggtacac ttagtatatt actagaataa agtcagctgc agacaacccc ttgcacagct    39120
ggaaagcaag tgtccaagca tcaaatcggt ttccaatcaa tgaagtgcct gtgggaggaa    39180
atctcaactc tctttagaag taaacaacaa agtcgattgc ctcagctatg cggtatccgc    39240
agagtgagtc ctaaatttaa aatctgacta catgtagaaa agcgttcgt tgtgacccatg    39300
accaggaaat aaatcgggta atacaaacag gctcaggaat gagagaaatg attagaattg    39360
cgtgaaaatt tgacatatca gtatgataac tgatttcaaa tatttaaaaa acaacatgc    39420
aagaaagcag atatcatatc aagagaaatt aacagtacag aatagccaaa ttaaattaaa   39480
gagctagtat aaaaaaagta tgtcttaatt gaaaaaaatt actgtatggc cggctgatca   39540
aattagacgt ttcagaggaa aacattaccc aacacacaat tctagagaac ctacagaatg   39600
agctacacac acacacacac acacacacac acactgaaa aacacaccca tactcacaca   39660
cacgcagaaa ctcacaagtt ctaacacaca cagacacgcg caccctgaa gaaacagtga    39720
aatataaaat taagcgagcc tcacagacat gtaggaaat atgaaaagat ttcctgcatg    39780
tgggaagcaa gtcacagtaa agagcaaggg agtttggaat agaaacaaat accggaatca   39840
aggatggctg ataactttc aattacgaag aacattaaaa aaaatcacag aatcgtgaaa    39900
ctcaagggat catatagga atttcggaaa aaaaacccaa cctgtatgat gtactttgt     39960
acatcacagt tcgaaggtaa caaggcaaag atataataag aagaaacctg tcacgagaaa   40020
ctggaggaaa aagagctgtg tcttcctaca agtacactga tacaaattgc caatgtgttc   40080
acctcagaaa cactcgaagc cagataccag ggaatatgt taaaatgata atcaggaaca    40140
aaaagagatc aaccgggaat gctgaatcca gcaataaaat gccttgaaga tcatccatgt   40200
cggataaatg catattgtgc actgcccaa agaaagaaac cggaaactgt cagaattgga    40260
aatcagcagg cttatgtaac aagagaggtg acccgaagga attaggtaga agaagaattg   40320
aacaagaaag gaactttctg cagcccacgt aatgaagaat ccagcaattg gcaaatgtag   40380
atagatgtaa atgcaaata ttttcttgat caaattccta tatcttttgta aatgagagtt   40440
gactacttga aacaaaatga tagcaagata ttaacttca gcatatgtag aggtaagat     40500
ttgaaatggt agcataaatc acgaagggat taattcgaag tgtaccgttg taagtttctt   40560
tacctcatgc acgatggtgt gtcatatta taaaggggta ctgtcgggt tcgaagggat     40620
attgcaaatc ctagagcaat cacaaaggtt tgaactctga ggttttggt ataatagaa     40680
tagtccatgc attcaaaga gggaagccaa ggaagaacta gaagtctttc aagagctcag    40740
gctcttatac atccagttgc tcattgaacc agcttcctgg aatggaggt ctggggttga   40800
gactaggcca caagtctaga gtctctagag acacagtgtt ggaaccccat ggcccataat   40860
acatttccca ttttctcagg cagccagagg tcatgaatgt gaggatactg ggaggttgga   40920
gcaacgttct tgggaggcat aaggaagagc gaatgcttca agatcccgc agcccaaact   40980
actcgcctgc tttgccccct aatgcatttt tctctgctgc tccgtagctg tccgacctct   41040
tcagatctct tagtccaccc tgccgtcttc ctttatgcca tgggtcccat tgttctttca   41100
actcatcccc ctttcccctca gtcccggagt agctgcggcc agcagagggt agactgagag   41160
caggagagaa ggacctgcct aggaacccct tctagagata ctgcatcctg cctggagca    41220
```

```
agttttccag ggcagctttg agaagtcttg gagaaacaaa cctactaaac ctgacagaca  41280
gtaatactat ttgcacaatg cttttctgtg ggaaaggtag agccttttca ctacgtattg  41340
agtacataga gtgtgagggt tgacctggaa cggctatcct cctggatgac gtgcgttttc  41400
tgaagaacta catgttcgtt gcaactccca cattagaata tgaagtccta ccgagagaga  41460
tacggagact agacagatac agatgcattt gcatgtgaat acacaatccc acaatacaga  41520
cgtcaaaacc cataccagtt attccagaga gatggattgg gcagaaggca gaaggagaat  41580
actctgatcg tttttcggcc acgtgtgtgt gttatctcag tgtttctaag aagcgtttgc  41640
tactttagat ttttttattta aaaaaaatag taataatcta ttaagtatga gagatgtgca  41700
gagaggatta gtgatcgaga gccattttg ctggtggcaa tcatatggta cttttaatg  41760
gaatattaga aaggcaccgg taatgacctt gttgcagcac aaaggagaga gtgtggggtg  41820
ccctgcatg ttgtcccacc tcttgtgacg tgtatcgttt tggaatttcc agtggcttga  41880
tcatgaacta ctgcaggaat ccagatgctg tggcagctcc ttattgttat acgagggatc  41940
ccggtgtcag gtgggagtac tgcaacctga cgcaatgctc agacgcagaa gggactgccg  42000
tcgcgcctcc gactgttacc ccggttccaa gcctagaggc tccttccgaa caaggtaagg  42060
agtctgtggc cagacatcta cacgcttcga tgctgggatg aaaagccatg gaaattccca  42120
ctgatgcagc cgccttcaat ggtaaacgga tgctcgagtg ttgcctgagt ctaccatgt  42180
aggaggaagc ctccgtgcac tctctggggg agccagcgga gtgatttctg gtgcaacgtg  42240
gttgggcttt gtctttagga tgggcacaaa ccctccaggg ggatcgactt caaaattcac  42300
cttgttgtaa aacgggctac ctcagtgtcc cagccaaaat ttttattgta acatgctgtc  42360
aggtgtgtca ctcttttccaa gccagtaagc ttttccgggg atttcttcaa gtagccagca  42420
ttcagagcaa tcttcagcat tgcagattct gagaaatgtg gctctggagc ctgtcaccct  42480
cgagaaaacct aagagggctg cattgattcc atgtggccgt ggctctatgg agcagtacat  42540
gagctcccag tgctctaagg ctcttcagcc ctaggctttg aagggagtga tttctcagta  42600
ttcttaaacc tcttctgat gacacttgta cctgtgaggg gtctagagag aaagagtagt  42660
agactcctac tttactacaa ttcaggatgc agggcatgag aggattccct ctctcctcca  42720
agggaagaag cttttggcgt gcacacatcc ctgagaagca aagtgtcttt gtcttcagtc  42780
agatacatag gaccgttttc tgccccatgg cccggaagcc aaaggccttg gctttcatga  42840
tcaacggtct agggaaacat gcaaaatttc catgtctgtc ccaaactctg cccccgacag  42900
ccaattacca cctgcagccc gcattgccaa atgcggtgcc gtttgcatga agattcagta  42960
gagtttccta gaaaggtgct acctcgtgag ctcacttttcc aatgaggaat ctgatctgtt  43020
gtgtttctct aaggtgtcag gtgaaatatt tccaagaact tactacagtt ctagaatggg  43080
aggaatctgt tgctttggtg tttgtttgtt ggtcggtttt ctcacatcca tctgcctatg  43140
gataaggaaa agaacggt cgtaattctc atagactcct ttctggttgt gtcacaaatg  43200
gcttcacatg tttctctatg ctcagagata cttcccgtgt tttcatttca  43260
gcaccgactg agcaaaggcc tggggtgcag gagtgcttac atggtaatgg acagagttat  43320
cgaggcacat actccaccac tgtcacagga agaacctgcc aagcttggtc atctatgaca  43380
ccacactcgc atagtcggac cccagaatac tacccaaatg cgtatgtctt tgttctttac  43440
cataagagaa gaaagggcca agtgaagttt ctgttacaag agatgtgtct caagctgagt  43500
tctccgaaact caacttgtga cagatgcaga tggcgtagca aaatgtctca ggatgattgc  43560
cttggagcta agggtctgag agaagggaaa tgttaagctc cctctccttc ctccagttc  43620
tattgagcag aagggaaatc tggaggtgag gagatcacat tatgaagaaa gtcagaatga  43680
caaaggacca gacacttaga ttaccctccc acaacaccaa ctaaacgtca atggagactt  43740
tccagttgga attccgttat tctggcttcc acttcctgga gggaaggttg cgtttgcctt  43800
ttctctctgg gttcaagagg aaagaatagg tgcttattta tggacaggtg aattgatctg  43860
tttctatatc tacgtatatt ccgattgtca gaaaaacact cgttcctaag taccagtggc  43920
ctgaagggat acaggttccc agcaagaaga gatccaagga aggaaggcag atgagagtca  43980
gcacagagag ggatgctgaa aagtaaaagg gatgggtgga tggagaacag cccgggtctg  44040
accacccaat ggccaatatt ttggccacaa gcgactacca gagacatgga aaaatgtttt  44100
ctacatgtgg gacaacagat ggtagaggac ctagagaatt gagagagggg caatgatggg  44160
ctccactccg cagatgcctt ggcttttcttc ctggatatccc ttcctgcact gaatagcaag  44220
gagatgagc ccaagcagac tgtagccatc ttgctgataa gaggagaggg attggagttt  44280
gggatgactg tggtagctga aatttttcta ggtctgctag aaataagaac tggtttgtgg  44340
aggaaaagag ctctacaaat acgcatagaa gtctcctcca gtcgttggcc tgacatgacg  44400
ctgcctgtgc acaggaaatg gttccacgag aaagtgtggc aaagaacatt tactgagaaa  44460
cagcaagtac aagagcacag gaagctcaat aaagaagaga agatcacat agcactctgg  44520
gatactggag ttcttcccag ctagaccaga gagtcctcac ggagcacatt gccaattcag  44580
tggagacccc agaacagccg taattttaaag gtacacttag tatattacta gaataaagtc  44640
agctgcagac aaccccttgc acagctgaaa agcaagtgtc caagcatcaa atcggtttcc  44700
aatcaatgaa gtgcctgtga gaggaaatct caactctctt tagaagtaaa caacaaagtc  44760
gattgcctca gctatgcggt atccgcagag tgagtcctaa atttaaaatc tgactacatg  44820
tagaaaagcg tttcgtgtga cccatgacca ggaaataaat cgggtaatac aaacaggctc  44880
aggaatgaga gaaatgatta gaattgcgtg aaaatttgaa atatcagtat gataactgat  44940
ttcaaatatt taaaaaaaca acatgcaaga aagcagatat catatcaaga gaaattaaca  45000
gtacagaata gccaaattaa attaaagagc tagtataaaa aagtatgtc ttaattgaaa  45060
aaaattactg tatggccggc tgatcaattt agacgtttca gaggaaaaca tacccaaca  45120
cacaattcta gagaacctac agaatgagct acacacacac acacacacac acacacaaac  45180
tgaaaacaca cccatactca cacacacgca gaaactcaca agttctaaca cacacagaca  45240
cgcgcacccc tgaagaaaca gtgaaatata aaattaagcg agcctcacag acatgtagga  45300
aaatatgaaa agatttcctg catgtgggaa gcaagtgca gtaaagagca agggagttg  45360
gaatagaaac aaataccaga atcaaggatg gctgataact tttcaattac gaagaacatt  45420
aaaaaaaatc acagaatcgt gaaactcaag ggatcacata gggaatttcg gaaaaaaaac  45480
ccaacctgta tgatgtactt ttgtacatca cagttcgaag gtaacaaggc aaagatataa  45540
taagaagaaa cctgtcacga gaaactggag gaaaagagc tgtgtcttcc tacaagtaca  45600
ctgatacaaa ttgccaatgt gttcacctca gaaacactgg aagccagata ccagggaata  45660
ttgttaaaat gataatcagg aacaaaaaga gatcaaccgg gaatgctgaa tccagcaata  45720
aaatgccttg aagatcatcc atgtcggata aatgcatatt gtgcactgcc ccaaagaaag  45780
aaaccggaaa ctgtaagaat tggaaatcag caggcttatg taacaagaga ggtgacccga  45840
aggaattagg tagaagaaga attgaacaag aaaggaactt tctgcagccc acgtaatgaa  45900
gaatccagca attggcaaat gtagatagat gtaaatgcaa aatattttct tgatcaaatt  45960
```

```
tctatatctt tgtaaatgag agttgactac ttgaaacaaa atgatagcaa gatatttaac    46020
ttcagcatat gtagaggtaa gaatttgaaa tggtagcata aatcacgaag ggattaattc    46080
gaagtgtacc gttgtaagtt tctttacctc atgcacgatg gtgtgtcata ttaataaaag    46140
ggtactgtgc gggttcgaag ggatattgca aatcctagag caatcacaaa ggtttgaact    46200
ctgaggtttt tggtataata agaatagtcc atgcattcaa aagagggaag caaggaaga    46260
actagaagtc tttcaagagc tcaggctctt atacatccag ttgctcattg aaccagcttc    46320
ctggaatgga gggtctgggg ttgagactag gccacaagtc tagagtctct agagagacag    46380
tgttggaacc ccatggccca taatacattt cccattttct caggcagcca gaggtcatga    46440
atgtgaggat actgggaggt tggagcaacg ttcttgggag gcataaggaa gagcgaatgc    46500
ttcaagatcc ccgcagccca aactactcgc ctgctttgcc ccctaatgca tttttctctg    46560
ctgctccgta gctgtccgac ctcttcagat ctcttagtcc accctgccgt cttcctttat    46620
gccatgggtc ccactgttct ttcaactcat cccccttttcc ctcagtcccg gagtagctgc    46680
ggccagcaga gggtagactg agagcaggag agaaggacct gcctaggaac cccttctaga    46740
gatactgcat cctgcctggg agcaagtttt ccagggcagc tttgagaagt cttggagaaa    46800
caaacctact aaacctgaca gacagtaata ctatttgcac aatgctttc tgtgggaaag    46860
gtagagcctt tcactacgt attgagtaca tagagtgtga gggttgacct ggaacggcta    46920
tcctcctgga tgacgtgtgt tttctgaaga actacatgtt cgttgcaact cccacattag    46980
aatatgaagt cctaccgaga gagatacgga gactagacag atacagatgc atttgcatgt    47040
gaatacacaa tcccacaata cagacgtcaa aacccatacc agttattcca gagagatgga    47100
ttgggcagaa ggcagaagga gaatactctg atcgttttc ggccacgtgt gtgtgttatc    47160
tcagtgtttc taagaagcgt ttgctacttt agattttta tttaaaaaaa atagtaataa    47220
tctattaagt atgagagatg tgcagagagg attagtgatc gagagccatt tttgctggtg    47280
gcaatcatat ggtacttta atgggaatat tagaaaggca ccggtaatga ccttgttgca    47340
gcacaaagga gagagtgtgg ggtgcccctg catgttgtcc cacctcttgt gacgtgtatc    47400
gttttggaat ttccagtggc ttgatcatga actactgcag gaatccagat gctgtggcag    47460
ctccttattg ttatacgagg gatcccggtg tcaggtggga gatgtgcaac ctgacgcaat    47520
gctcagacgc agaagggact gccgtcgcgc ctccgactgt taccccggtt ccaagcctag    47580
aggctcctc cgaacaaggt aaggagtctg tggccagaca tctacacgct tcgatgctgg    47640
gatgaaaagc catggaaatt cccactgatg cagccgcctt caatggtaaa cggatgctcg    47700
agtgttgcct gagttctacc atgtaggagg aagcctccag gcactctctg ggggagccag    47760
cggagtgatt tctggtgcaa cgtggttggg ctttgtcttt aggatgggca caaaccctcc    47820
aggggggatcg acttcaaaat tcaccttgtt gtaaacgggg ctacctcagt gtcccagcca    47880
aaattttttat tgtaacatgc tgtcaggtgt gtcactcttt ccaagccagt aagcttttcc    47940
gggatttct tcaagtagcc agcattcaga gcaatcttca gcattgcaga ttctgagaaa    48000
tgtggctctg gagcctgtca ccctcgagaa acctaagagg gctgcattga ttccatgtgg    48060
ccctgggtct atggagcagt acatgagctc ccagtgctct aaggctcttc agccctaggc    48120
tttgaaggga gtgatttctc agtattctta aacctctttc tgatgacact tgtacctgtg    48180
aggggtctag agagaaagag tagtagactc ctactttact acaattcagg atgcaggca    48240
tgagaggatt ccctctctcc tccaaggaa gaagcttttg gcgtgcacac atccctgaga    48300
agcaaagtgt cttttgtcttc agtcagatac ataggaccgt tttctgcccc atggcccgga    48360
agccaaaggc cttggctttc atgatcaacg gtctagggaa acatgcaaaa tttccatgtc    48420
tgtcccaaac tcttcccccg acagccaatt accacctgca gcccgcattg ccaaatgcgg    48480
tgccgtttgc atgaagattc agtagagttt cctagaaagg tgctacctcg tgagctcact    48540
ttccaatgag gaatctgatc tgttgtgttt ctctaaggtg tcaggtgaaa tatttccaag    48600
aacttactac agttctagaa tgggaggaat ctgttgcttt ggtgtttgtt tgttggtcgg    48660
ttttctcaca tccatctgcc tatggataag gaaaagagaa cggtcgtaat tctcatagac    48720
tcctttctgg ttgtgtcaca aatggcttca catgtttctc tatgctcaga gatactcagc    48780
ttgatttccc gtgttttcat ttcagccaccg actgagcaaa ggcctggggt gcaggagtgc    48840
taccatggta atggacagag ttatcgaggc acatactcca ccactgtcac aggaagaacc    48900
tgccaagctt ggtcatctat gacaccacac tcgcatagtc ggaccccaga atactaccca    48960
aatgcgtatg tcttttgttct ttaccataag agaagaaagg gccaagtgaa gttttctgtta    49020
caagagatgt gtctcaagct gagttctccg aactcaactt gtgacagatg cagatggcgt    49080
agcaaaatgt ctcaggatga ttgccttgga gctaagggtc tgagagaagg gaaatgttaa    49140
gctccctct cttcctccta gttctattga gcagaaggga aatctggagg tgagaagatc    49200
acattatgaa gaaagtcaga atgacaaagg accagacact tagattaccc ttccacaaca    49260
ccaactaaac gtcaatggag actttccagt tggaattccg ttattctggc ttccacttcc    49320
tgaagggaag gttgcgtttg ccttttctct ctgggttcaa gaggaaagaa taggtcttta    49380
tttatgcaca ggtgaattga tctgtttcta tatctacgta tattccgatt gtcagaaaaa    49440
cactcgttcc taagtaccag tggcctgaag ggatacaggt tcccagcaag agaagatcca    49500
aggaaggaag gcagatgaga gtcagcacag agagggatgc tgaaaagtaa aagggatggg    49560
tggatggaga gaagcccggg tctgaccacc caatggccaa tattttggcc acaagcgact    49620
accagagaca tggaaaaatg gtttctacat gtgggacaac agatggtaga ggacctagag    49680
aattgagaga ggggcaatga tgggctccac tccgcagatg ccttggcttt cttcctggat    49740
acccttcctg cactgaatag caaggagatg gagcccaagc agactgtagc catcttgctg    49800
aatggaggag agggattgga gtttgggatg actgtggtag ctgaaatttt tctaggtctg    49860
ctagaaataa gaactggttt gtgtggagga aagagctct acaaatacgc atagaagtct    49920
cctccagtcg ttggcctgac atgacgctgc ctgtgcacag gaaatggttc cacgagaaag    49980
tgtggcaaag aacatttact gagaaacagc aagtacaaga gcacaggaag ctcaataaag    50040
aagagagaa tcacatagca ctctgggata ctggagttct tcccagctac accagagagt    50100
cctcacggag cacattgcca attcagtgga gaccccagaa cagccgtaat ttaaaggtac    50160
acttagtata ttactagaat aaagtcagct gcagacaacc ccttgcacag ctggaaagca    50220
agtgtccaag catcaaatcg gtttccaatc aatgaagtgc ctgtgagagg aaatctcaac    50280
tctctttaga agtaaacaac aaagtcgatt gcctcagcta tgcggtatcc gcagagtgag    50340
tcctaaattt aaaatctgac tacatgtaga aaagcgtttc gtgtgaccca tgaccaggaa    50400
ataaatcggg taatacaaac aggctcagga atgagagaaa tgattagaat tgcgtggaaaa    50460
tttgacatat cagtatgata actgatttca aatatttaaa aaaacaacat gcaagaaagc    50520
agatatcata tcaagagaaa ttaacagtac agaatagcca aattaaatta aagaggtagt    50580
ataaaaaaag tatgtcttaa ttgaaaaaaa ttactgtatg gccggctgat caatttagac    50640
gtttcagagg aaaacattac ccaacacaca attctagaga acctacagaa tgagctacac    50700
```

```
acacacacac acacacacac acaaactgaa aacacaccca tactcacaca cacgcagaaa    50760
ctcacaagtt ctaacacaca cagacacgcg caccccctgaa gaaacagtga aatataaaat   50820
taagcgagcc tcacagacat gtaggaaaat atgaaaagat ttcctgcatg tgggaagcaa   50880
gtcacagtaa agagcaaggg agtttggaat agaaacaaat accggaatca aggatggctg   50940
ataactttc  aattacgaag aacattaaaa aaaatcgtgaaa aatcgtgaaa ctcaagggat  51000
cacataggga atttcggaaa aaaaacccaa cctgtatgat gtactttgt acatcacagt    51060
tcgaaggtaa caaggcaaag atataataag aagaaacctg tcacgagaaa ctggaggaaa   51120
aagagctgtg tcttcctaca agtacactga tacaaattgc caatgtgttc acctcagaaa  51180
cactggaagc cagataccag ggaatattgt taaaatgata atcaggaaca aaaagagatc  51240
aaccgggaat gctgaattcca gcaataaaat gccttgaagg tcatccatgt cggataaatgt 51300
catattgtgc actgccccaa agaaagaaac cggaaactgt aagaattgga aatcagcagg  51360
cttatgtaac aagagaggtg acccgaagga attaggtaga agaagaattg aacaagaaag  51420
gaactttctg cagcccacgt aatgaagaat ccagcaattg gcaaatgtag atagatgtaa  51480
atgcaaaata ttttcttgat caaatttcta tatctttgta aatgagagtt gactacttga  51540
aacaaaatga tagcaagata tttaactcca gcatatgtag aggtaagaat ttgaaatggt 51600
agcataaatc acgaagggat taattcgaag tgtaccgttg taagtttctt tacctcatgc  51660
acgatggtgt gtcatattaa taaagggta ctgtgcgggt tcgaagggat attgcaaatc   51720
ctagagcaat cacaaaggtt tgaactctga ggttttttgt ataataagaa tagtccatgc 51780
attcaaaaga gggaagccaa ggaagaacta gaagtcttc aagagctcag gctcttatac   51840
atccagttgc tcattgaacc agcttcctgg aatggaggt ctgggggttga gactaggcca   51900
caagtctaga gtctctagag agacagtgtt ggaaccccat ggcccataat acatttccca   51960
ttttctcagg cagccagagg tcatgaatgt gaggatactg ggaggtttga gcaacgttct  52020
tgggaggcat aaggaagagc gaatgcttca agatcccgc agcccaaact actcgctgc    52080
tttgccccct aatgcatttt tctctgctgc tccgtagctg tccgacctct tcagatctct  52140
tagtccaccc tgccgtcttc ctttatgcca tgggtcccac tgttctttca actcatccc   52200
ctttccctca gtcccggagt agctgcggcc agcagaggat agactgagag caggagagaa  52260
ggacctgcct aggaaccctt tctagagata ctgcatcctg cctgggagca agttttccag  52320
ggcagctttg agaagtcttg gagaaacaaa cctactaaac ctgacagaca gtaatactat  52380
ttgcacaatg ctttttctgtg ggaaaggtag agcctttca ctacgtattg agtacataga  52440
gtgtgagggt tgacctggaa cggctatcct cctggatgac gtgcgttttc tgaagaacta 52500
catgttcgtt gcaactccca cattagaata tgaagtccta ccgagagaga tacgagact   52560
agacagatac agatgcattt gcatgtgaat acacaatccc acaatacaga cgtcaaaacc  52620
cataccagtt attccagaga gatggattgg gcagaaggca gaaggagaat actctgatcg  52680
ttttcggcc  acgtgtgtgt gttatctcag tgtttctaag aagcgtttgc tactttagat  52740
tttttattta aaaaaaatag taataatcta ttaagtatga gagatgtgca gagaggatta 52800
gtgatcgaga gccattttg  ctggtggcaa tcatatggta cttttaatgg gaatattaga  52860
aaggcacggg taatgacctt gttgcagcac aaaggagaga gtgtgggggtg cccctgcatg  52920
ttgtcccacc tcttgtgacg tgtatcgttt tggaatttcc agtggcttga tcatgaacta  52980
ctgcaggaat ccagatgctg tggcagctcc ttattgttat acgagggatc ccggtgtcag  53040
gtgggagtac tgcaacctga cgcaatgctc agacgcagaa gggactgccg tcgcgcctcc  53100
gactgttacc ccggttccaa gcctagaggc tccttccgaa caaggtaagg agtcgtggc  53160
cagacatcta cacgcttcga tgctgggatg aaagcatg gaaattccca ctgatgcagc    53220
cgccttcaat ggtaaacgga tgtcctgagtt ttgcctgagt tctaccatgt aggaggaagc 53280
ctccgtgcac tctctggggg agccagcgga gtgattctg gtgcaacgtg ttgggcttt    53340
gtctttagga tgggcacaaa ccctccaggg ggatcgactt caaaattcac cttgttgtaa 53400
aacgggctac ctcagtgtcc cagccaaaat ttttattgta acatgctgtc aggtgtgtca  53460
ctctttccaa gccagtaagc ttttccgggg atttcttcaa gtagccagca ttcagagcaa  53520
tcttcagcat tgcagattct gagaaatgtg gctctggagc ctgtcaccct cgagaaacct 53580
aagagggctg cattgattcc atgtggccct gggtctatgg agcagtacat gagctcccag  53640
tgctctaagg ctcttcagcc ctaggctttg aaggagtga tttctcagta ttcttaaacc   53700
tcttttctgat gacacttgta cctgtgaggg gtctagagag aaagagtagt agactcctac  53760
tttactacaa ttcaggatgc agggcatgag aggattccct ctctcctcca agggaagaag  53820
cttttggcgt gcacacatcc ctgagaagca aagtgtcttt gtcttcagtc agatacatag  53880
gaccgttttc tgcccccatgg cccggaagcc aaaggccttg gctttcatga tcaacggtct 53940
agggaaacat gcaaaatttc catgtctgtc ccaaactgtc ccccgacag ccaattacca   54000
cctgcagccc gcattgccaa atgcggtgcc gtttgcatga agattcagta gagtttccta  54060
gaaaggtgct acctcgtgag ctcactttcc aatgaggaat ctgatctgtt gtgtttctct  54120
aaggtgtcag gtgaaatatt tccaagaact tactacagtt ctagaatggg aggaatctgt  54180
tgctttggtg tttgtttgtt ggtcggtttt ctcacatcca tctgcctatg gataaggaaa  54240
agagaacggt cgtaattctc atagactcct ttctggttgt gtcacaaatg gcttcatg    54300
tttctctatg ctcagagata ctcagcttga tttcccgtgt tttcatttca gcaccgactg  54360
agcaaaggcc tggggtgcag gagtgctacc atggtaatgg acagagttat cgaggcacat  54420
actccaccac tgtcacagga agaacctgcc aagcttggtc atctatgaca ccacactcgc  54480
atagtcggac cccagaatac tacccaaatg cgtatgtctt tgttctttac cataagagaa 54540
gaaagggcca agtgaagttt ctgttacaag agatgtgtct caagctgagt tctccgaact 54600
caacttgtga cagatgcaga tggcgtagca aaatgtctca ggatgattgc cttggagcta  54660
agggtctgag agaaggggaa tgttaagctc cctctccttc ctcctagttc tattgagcag  54720
aagggaaatc tggaggtgag gagatcacat atgaagaaa gacaatga caaaggacca    54780
gacacttaga ttacccttcc acaacaccaa ctaaacgtca atggagactt tccagttgga  54840
attccgttat tctggcttcc acttcctgaa gggaaggttg cgtttgcctt ttctctctgg  54900
gttcaagagg aaagaatagg tgcttattta tggacaggtg aattgatctg tttctatatc  54960
tacgtatatt ccgattgtca gaaaacact cgttcctaag taccagtggc ctgaagggat    55020
acaggttccc agcaagagaa gatccaagga aggaaggcag atgagagtca gcacagagag  55080
ggatgcctga aagtaaaagg gatgggtgga tggagaacag cccggagtca accacccaat  55140
ggccaatatt ttggcacaa gcgactacca gagacatgga aaaatggttt ctacatgtgg   55200
gacaacagat ggtagaggac ctagagaatt gagagagggg caatgatggg ctccactccg  55260
cagatgcctt ggctttcttc ctggataccc ttcctgcact gaatagcaag agatggagc   55320
ccaagcagac tgtagccatc ttgctgaatg gaggagaggg attggagttt gggatgctg   55380
tggtagctga aattttcta ggtctgctag aaataagaac tggtttgtgt ggaggaaaag    55440
```

-continued

```
agctctacaa atacgcatag aagtctcctc cagtcgttgg cctgacatga cgctgcctgt  55500
gcacaggaaa tggttccacg agaaagtgtg gcaaagaaca tttactgaga aacagcaagt  55560
acaagagcac aggaagctca ataaagaaga gagagatcac atagcactct gggatactgg  55620
agttcttccc agctagacca gagagtcctc acggagcaca ttgccaattc agtggagacc  55680
ccagaacagc cgtaatttaa aggtacactt agaatattac tagaataaag tcagctgcag  55740
acaacccctt gcacagctgg aaagcaagtg tccaagcatc aaatcggttt ccaatcaatg  55800
aagtgcctgt gagaggaaat ctcaactctc tttagaagta aacaacaaag tcgattgcct  55860
cagctatgcg gtatccgcag agtgagtcct aaatttaaaa tctgactaca tgtagaaaag  55920
cgtttcgtgt gacccatgac caggaaataa atcgggtaat acaaacaggc tcaggaatga  55980
gagaaatgat tagaattgcg tgaaaatttg acatatcagt atgataactg atttcaaata  56040
tttaaaaaaa caacatgcaa gaaagcagat atcatatcaa gagaaattaa cagtacagaa  56100
tagccaaatt aaattaaaga gctagtataa aaaaagtatg tcttaattga aaaaaattac  56160
tgtatggccg gctgatcaaa ttagacgttt cagaggaaaa cattacccaa cacacaattt  56220
tagagaacct acagaatgag ctacacacac acacacacac acacacacac acacaaactg  56280
aaaacacacc catactcaca cacacgcaga aactcacaag ttctaacaca cacagacacg  56340
cgcacccctg aagaaacagt gaaatataaa attaagcgag cctcacagac atgtaggaaa  56400
atatgaaaag atttcctgca tgtgggaagc aagtcacagt aaagagcaag ggagtttata  56460
atagaaacaa ataccagaat caaggatggc tgataacttt tcaattacga agaacattaa  56520
aaaaaatcac agaatcgtga aactcaaggg atcatatagg gaatttcgga aaaaaaaccc  56580
aacctgtatg atgtactttt gtacatcaca gttcgaaggt aacaaggcaa agatgtaata  56640
agaagaaacc tgtcacgaga aactggagga aaaagagctg tgtcttccta caagtacact  56700
gatacaaatt gccaatgtgt tcacctcaga aacactggaa gccagatacc agggaatatt  56760
gttaaaatga taatcaggaa caaaaagaga tcaaccggga atgctgaatc cagcaataaa  56820
atgccttgaa ggtcatccat gtcggataaa tgcatattgt gcactgcccc aaagaaagaa  56880
accggaaact gtaagaattg gaaatcagca ggcttatgta acaagagagg tgacccgaag  56940
gaattaggta gaagaagaat tgaacaagaa aggaactttc tgcagcccac gtaatgaaga  57000
atccagcaat tggcaaatgt agatagatgt aaatgcaaaa tattttcttg atcaaatttc  57060
tatatctttg taaatgagag ttgactactt gaaacaaaat gatagcaaga tatttaactt  57120
cagcatatgt agaggtaaga atttgaaatg gtagcataaa tcacgaaggg attaattcga  57180
agtgtaccgt tgtaagtttc tttacctcat gcacgatggt gtgtcatatt aataaaaggg  57240
tactgtgcgg gttcgaaggg atattgcaaa tcctagagca atcacaaagg tttgaactct  57300
gaggtttttg gtataataag aatagtccat gcattcaaaa gagggaagcc aaggaagaac  57360
tagaagtctt tcaagagctc aggctcttat acatccagtt gctcattgaa ccagcttcct  57420
ggaatggagg gtctggggtt gagactaggc cacaagtcta gagtctctag agagacagtg  57480
ttggaacccc atggcccata atacatttcc cattttctca ggcagccaga ggtcatgaat  57540
gtgaggatac tgggaggttg gagcaacgtt cttgggaggc ataaggaaga gcgaatgctt  57600
caagatcccc gcagcccaaa ctactcgcct gctttgcccc ctaatgcatt tttctctgct  57660
gctccgtagc tgtccgacct cttcagatct cttagtccac cctgccgtct tcctttatgc  57720
catgggtccc actgttcttt caactcatcc ccctttccct cagtcccgga gtagctgcgg  57780
ccagcagagg gtagactgag agcaggagag aaggacctgc ctaggaaccc cttctagaga  57840
tactgcatcc tgcctgggag caagttttcc agggcagctt tgagaagtct tggagaaaca  57900
aacctactaa acctgacaga cagtaatact atttgcacaa tgcttttctg tgggaaaggt  57960
agagcctttt cactacgtat tgagtacata gagtgtgagg gttgacctgg aacggctatc  58020
ctcctggatg acgtgcgttt tctgaagaac tacatgttcg ttgcaactcc cacattagaa  58080
tatgaagtcc taccgagaga gatacggaga ctagacagat acagatgcat ttgcatgtga  58140
atacacaatc ccacaataca gacgtcaaaa cccataccag ttattccaga gagatggatt  58200
gggcagaagg cagaaggaga atactctgat cgtttttcgg ccacgtgtgt gtgttatctc  58260
agtgtttcta agaagcgttt gctactttag atttttttatt taaaaaaaat agtaataatc  58320
tattaagtat gagagatgtg cagagacgat tagtgatcga gagccatttt tgctggtggc  58380
aatcatatgg tacttttaat gggaatatta gaaaggcacc ggtaatgacc ttgttgcagc  58440
acaaaggaga gagtgtgggg tgcccctgca tgttgtccca cctcttgtga cgtgtatcgt  58500
tttggaattt ccagtggctt gatcatgaac tactgcagga atccagatgc tgtggcagct  58560
ccttattgtt atacgaggga tcccggtgtc aggtgggagt actgcaacct gacgcaatgc  58620
tcagacgcag aagggactgc cgtcgcgcct ccgactgtta ccccggttcc aagcctagag  58680
gctccttccg aacaaggtaa ggagtctgtg gccagacatc tacacgcttc gatgctggga  58740
tgaaaagcca tggaaattcc cactgatgca gccgccttca atggtaaacg gatgctcgag  58800
tgttgcctga gttctaccat gtaggaggaa gcctccgtgc actctctggg ggagccagcg  58860
gagtgatttc tggtgcaacg tggttgggct ttgtctttag gatgggcaca aaccctccag  58920
ggggatcgac ttcaaaattc accttgttgt aaaacgggct acctcagtgt cccagccaaa  58980
atttttattg taacatgctg tcaggtgtgt cactctttcc aagccagtaa gcttttccgg  59040
ggatttcttc aagtagccag cattcagagc aatcttcagc attgcagatt ctgagaaatg  59100
tggctctgga gcctgtcatc ctcgagaaac ctaacagggc tgcattaatt ccatatggtc  59160
ctgggtctat ggagcagtat atgagctccc aatgctctaa ggctcttcag tcctaggctt  59220
tgaagggagt gatttctcag tgttcttaaa cctctttctg atggcacttg tacctgtgag  59280
gggtctagag agaaaggtta gtagacttct cctttactgc aattcaggat gcagggcatg  59340
agaagattcc ctccctcctc caagggaaga aggttttggc gtgcacacat ccttgagaag  59400
caaagtgtct ttgccttcag tcagatatat aggatcgttt tctgccccat ggcctggaag  59460
ccagaggcct tggctttcat gatcaacgat ctagggaaac atgcaaaatt tccatgtctt  59520
tcccctcctc tgccctcgac agccaattac cacctgcatc ctgcattgcc aaatgcagtg  59580
ccctttgtat gaacattcag tagagtttca tagaaaggtg ctacttcgtg agcgcacttt  59640
gcagtgagaa ggagtctgtt ctgttctgtt tttctaagga tttcaggtga aatatttcct  59700
agaacttact acagttctag attggtagga atctgtaggt ttgctgtatg tttttggtt  59760
ggttttctcc catccatctg cctacaggta agggaaagat aacgttcata attctcatag  59820
actcctttct ggttgtgtca taaatggctt cacatatttc gttattctca gagatactca  59880
gtttatttct tgtgttttca tttcagcacc gactgagcag aggcctgggg tgcaggagtg  59940
ctaccacggt aatggacaga gttatcgagg cacatactcc accactgtca ctggaagaac  60000
ctgccaagct tggtcatcta tgacaccaca ctcgcatagt cggaccccag aatactaccc  60060
aaatgcgtat gtctttgttc tttaccataa gagaataaag ggccaactga agtttctgtg  60120
acaagagaca tgcttcaagc tgagttctcc gaactcaact tgtgtcagat tcagatggtg  60180
```

-continued

```
tagcaaaatg tctcaggatg atttccttgg agctaagggt ctgagagaag agaaatgtta    60240
agctgcctca ccttcctcct agttttgtgg agcagaaggg aaatgaggag gcgaggagat    60300
caccttatga agaaagtcag aatgacgaac caccaaacac ttagattacc cttgcccaac    60360
acccactaag cgtcaatgaa gacttttccag ttggaattcc gttattctga cttccaattc    60420
ctgaagggaa gattgtgttt gccttttctg tctgggctca tgaggaaagt ttatgtgctt    60480
acttatggac aggtgaattg atctgttttct atttctacct gtattccaat agggagaaaa    60540
tctcttggtc ctaagtacca gtggcctgaa aggatagagg ttcccagcaa gagaagatcc    60600
aaggaaggaa ggcagatgag agtcagcaca gagagggatg ctgaaaagta aaagggatgg    60660
gtagatggat agaagccctg gtctgaccac cccatgaaca atcatttggc cataatcaac    60720
aaccaaagac atggaaaaat ggtttctaca tgtgggacaa cagatggtag aggacctaga    60780
gaattgagag agggccaatg atgagctcaa ctccatagat gccttggctt tcttcctgga    60840
tacccttcct gcactgaata gcaaggagat ggagctcaag cagcctgtag ccatctagct    60900
gagcagagga gagggattgg agtttgggat gactctggta ttttctaggt ccgctacaaa    60960
taagaactgg tttgtggagg aaaggagctc tacaaatacg catagaagtc tcctccagta    61020
gttggcctca catgacactg catgtgcaca gaaaatggtt ctacagaaag tgtggcaaag    61080
aacatttact gagaaacagc aactacaaga gaacagcaag ctcaattaag aagatagaga    61140
tcacatagca ctctgtgtta ttggagttct taccagctag atgagagagt gctcacggaa    61200
cacattgcca attcagtgga gacccccagaa cagccataat ttcaaagtac aattagtata    61260
ttactagaat aaaggcagct gcagacaacc ccttgcacag ctgaaaagca agtgtccaag    61320
catcaaatgg gtttccaatc aatgaagtgc ctgtgagagg aaatctcaac tctcttcaga    61380
agtaaacaac aaagtcaatt gcctcagcta tgcggtatcc ccagagtgag tcctaaatta    61440
aaaatttgac tacgtgtaga aaagaatttc gtgtgatcca tgaccagaaa ataaatcagg    61500
caatacaaac aggctcagaa atgacatcga taattagaat tgcatgaaaa tttgacatat    61560
cagtatgata actgatttca gatatttaaa aaaagtgcaa caaagcaggt atcatatcaa    61620
gacaaattaa tagtatagaa tagccaaatc aaattaaaga actattatac aaaaagtatg    61680
tcttaaatga agaaaattact gtatgtccgc ctgaaaaatt tatgtgtttc agaagaaaaa    61740
attaaccaaa aacaattctg cagaacctac agaatgagcc acacacacac acattcaaaa    61800
cacacccata cacacacaca tgcaaaaact cacaagttct aacacacaca caaacacaca    61860
cacacatgca catccctaaa gaaatagga aatataaaat taaccgaccc tcagagacat    61920
gcaggaaaat ataagaagat ttcctgcatg tgggaagcaa gtcacagtaa agagcaaggg    61980
agtttggagt agatacaaat accggaatca cggatggctg ataacttttc aattatgaag    62040
aacgttagaa aaatcacaga ttcatgaaac taaagggatc aaataggaaa tttcgagaaa    62100
aaaaactaca tgatgcactt ctctacatca cagttcaaag gtaacaaggc aaggatataa    62160
gaagaagaaa catctcacga gaaactggag aaaaaagagc tgtgtcttcc tagagtacag    62220
tgatacaaat tgctaatgcg ttccctcag aaacactgga agccagatac caggaaatat    62280
tattaaaatg ataatgagga acaagaagag atcaaccgag aatgctgaat ccagcaataa    62340
aatgccttga agatcatcca tgttggataa atgcatattg tgcactgccc aaaacaaaga    62400
aactggaaag tgtaagactt tggaatcagc aggcttatgt agcaacagag gtgaccccgaa    62460
agaattggat ataagaagaa tagaagaatt gcatgaaaat ttgacatatg actaagataa    62520
ctatttcaaa tatttaaaaa aagatgaata tgtaataaaa cagataaaat atcaaaagaa    62580
agtaacagta ttgactagcc aaatcaaatt aaagacttag tgtaaaaagc tatgtcttaa    62640
aagaaaaaat tactggatgg ctgcctgatc aatttagaca tttctgaata ggaaactaac    62700
caaaaatcaa ttctacagaa ccaactacac acatatatac acatacaaca caaccataca    62760
cacccacgca aaaactcaca agttcacaca cacacacaca cacacacaac cctcaagaaa    62820
tagtgaaaata gaaaaccaac cgaacctcac agacatgttg caaaatagga aaagatttcc    62880
tgcatatggg aagcaagtca cagaaaagag aacgggagat tggaaacaga aacaaatacc    62940
ggaatcaagg atggccgaaa acttttcatt gatcaagaat attaacaaaa tcgcaaaaac    63000
acgaaattca atgcatcaaa taggcgtttc gaaaaaaaga aaaaatctgg tatgatgcac    63060
ttttgtactt cacattttca cggtaagaag acaaagatat aataacaaga aacttcttat    63120
gagaaactgg ggaaaacaa gctgtttctt gctagaagaa cagtgataca aattgctaat    63180
gcattctcgt caaaaacact ggaagccaga taccgggaat gttattaatg tggtaaacag    63240
gaacaagaag agatcaacca agaatgctaa atccagcaat aaaaatgcctt gaagatcatc    63300
catgctgcat aaatgtatgt tgtgcactgc cccaaacaaa gaaaccggaa actgtaagaa    63360
tttgaatca gcaggctgat gtaacaagag aggtgaccca aaggaattag gtagaagaag    63420
aatagtacaa gaagggaact ttctgcagcc catgtaatga agaacccagc aattggcaaa    63480
tgtagatgta aatgcaaaat atttcttga ccaaatttct atatatttt aaatgagcgt    63540
tgactactgg aaacaaaatg atagcaatat atttaatttt agcatatgta gaggtaagaa    63600
tttgaacaag tagcgtaaat catgtaggga ataattagaa gtgtaccatt gtaagtttct    63660
tacctcatgc acaatggtat gtaatattaa taaaatgtta ctgtgtgggt tcaaggagat    63720
attgcaaatc ctagagcaat cacaaagttt tgaactctga tgtatattgt ataataagaa    63780
tattccatgt attcaaaaga gagagccaa ggagaaaaga aatttgtcac gagtttgggc    63840
tcttagtaca tcctgtagct cattgaacca gcttcctgga atggagggtc tgggattgac    63900
actaggccac atgtatagag tctctagaga gacagtgttt catccccatg gcccgtaata    63960
cattcccat tttctcaggc agccacaggt catgaatgtg aggatagaga gaggttggga    64020
caacgttctt gggaggcata aggaagagca aatgcttcaa gatccccgca gcccaaactc    64080
ctacctgctt tgcccctaa tgcagtgttc ctccgtagct gtccgacctc ttcagatctc    64140
ttagtctacc ctgccatctt cctttatgcc atgggtccca ctgttctttc aactcatccc    64200
ccttccctc agtgcagagt agctgcggcc agcagagggt agactgagag caggagagaa    64260
ggtcctgccc aggaacccat tctagagatg ctgcattctg cctgggagca agttttccag    64320
ggcagctttg agaagtcttg cagaaacaaa cctatttgac ccacatgata tgggaatgac    64380
agaaagtaat acaatttgca cagtgctttt ccatgggaaa agtagagcct tttcgcgagg    64440
ttttgagtac atagagagtg aaggttgacc tggaaaggtt atcctcctgg atcccatgtt    64500
tttctgaag aactacctgt tagttgcaac ttgcacatta gaatatgaag tcctaccgag    64560
agaatacgg agaactagat aaatacagat acttttgtat gattccacaa    64620
tacacacatc aaaatccata ccagttattc cagagagatg gattgggcag aaggcagaag    64680
gagaatactc tgatcgtttt ttgcccacgt gtatgtatta tctcagtgtt tctaagaagc    64740
gtttgctact ttagattttt tttttataata ataatctttt aagtatgaga aatgtgcaga    64800
caggattagt gattgagagc catttgtgct tgtggcaatc atatggtact tttatgggaa    64860
tattagaaag gcactggtaa tgaccttgtt gcagcacaaa ggagagggtg tggggtgccc    64920
```

```
ctgcatattg tcccacctct tgtgacgtgt atcgttttgg aatttccagt ggcttgatca   64980
tgaactactg caggaatcca gatcctgtgg cagcccctta ttgttatacg agggatccca   65040
gtgtcaggtg ggagtactgc aacctgacac aatgctcaga cgcagaaggg actgccgtcg   65100
cgcctccaac tattacccog attccaagcc tagaggctcc ttctgaacaa ggtaaggagc   65160
ctgtggccag aaacctacac gtttcgatgc tgggatgaaa agccatggaa attcccactg   65220
atgcagcagc ctccaatggt aaacggatgc tcgagtgttg actgagttct gtcatgtagg   65280
aggaagcctc cgtgcactct ctgggggagc cagcggattg atttctggta caacgttggg   65340
tgggctgtgt ctttagaatt ggcacaaacc ctccagggtg atcgacttca caactcacct   65400
cgttgaaaaa tgggctatct cagtgtctta gccaaaattt ttattgtaac atgctgtcag   65460
atgtgtgact cttccaagc cagtaagctt ttcctgggac ttcttcaatt agccagcatt   65520
cagtgcaatc ttcagcattg cagattcaga gaaatgtggc tctggagcct gtcacccttg   65580
agaaacaggg ctaacagggt tgcattaatt ccaaatcacc ctggttctat ggagcagtac   65640
atgaactccc aatgatctat gtttcaggac ttcctcagtc ataggtgggc tctgcagccc   65700
taggtttta agtgagtgac tgccccgtgt tctggtggca gttgtacctg tgagcggtct   65760
ggatagaaag agtcggagac ttctgtatta ttgcaactca ggatgtgggt catgagagga   65820
tttcatctct cctgcagggg agtaagctgt tcgcctccac ccatccctga taactgaagt   65880
gtctttgtct gcagtcctag acgaaggact gttgtctctc ccatggccca gaagctgaag   65940
accttgcctt ttgttatgaa acgttcattg ttttcatgtc tgtccgtttc tctgcccta   66000
acacccaatc accatgtatg gcctgtaccc caaatgcat cgtgctttgc tgtttgctgc   66060
cccatagtcc tcatgaacat tcagtagaaa ttcccataaa tgtgcttgca cgtgagcaca   66120
gtttccattg agaagccctc tcatttgtcc tttttttcta agcttttatg tgaaatattt   66180
ctaagaactt actacagttc taaagtgtta ggaatttgtt tctttggtgt tttttgtttgt   66240
tggttggttg ttgctttct caagtccatc tgcctacaaa taagaaaca agaatgttac   66300
ttgtcatatt ctcctgaggt cataattctc agagactttt ttctggtttg tgccataagt   66360
ggcttcacat gtttgtctct tcttggaaac actcagtttg atttcttttc ttttcatttc   66420
agcaccaact gagcaaaggc ctggggtgca ggagtgctac cggaaaatg gacagagtta   66480
tcaaggcaca tacttcatta ctgtcacagg aagaacctgc caagcttggt catctatgac   66540
accacactcg catagtcgga ccccagcata ctacccaaat gcgtatgtct attttctta   66600
ccataagtga aggaagggtc agtggaaatt tctgttagta gagtcatgct tcaagctgag   66660
tgttcaggac tcaagttgtc tcagatgaac agtgcatagc aaaatgtctc aggaacattg   66720
tctttgagca aagagtctaa gagaagacaa atgttaatct ggctctcctt cctcctagtt   66780
taatggagca gaaaggtatc tggaggcaag gatatcacat taagaaacaa gtcaagatga   66840
caaatgatga aactcttaga gtaccttcc acaacaccca ctaaggttca atgcagcctt   66900
ttctccttgg aattctatta aactaaactc caattcctga agtgaaggtt ctgttggggt   66960
tttctgtttt ggcttacaag gaaagtatat atgtatatct atggagaggc aaatctatct   67020
cttttctatat ctacgtctat tccaatatgt agaaacacag tcggttctga ccaccagtgg   67080
tctgaaggga tactggttgt tagagaataa aaatggcagg aaggcagatg agagtcagca   67140
aagagagaga tcctgtaaag taaaagggtg gatagatgga cagaagccca ggtctgacca   67200
gcccatggcc aggcttagg ccataagtga caccaaagac atggaaaaat ggtttctaca   67260
tgttggacaa cagacagtag tggaccaaaa gaatagtgac aggggaaca atgagatcaa   67320
ctccatagat accttggctt tcttcctgga ggcccttctt gcactgaaga gcaaggtgat   67380
ggagcccaga tggactgtag ccatcttcct gaatgcagga gagagattgg aatttgggac   67440
tactggtgta gctaggattt tataggcctg ctgagaatga gaatggattt gtggatgaaa   67500
ggagctccag gggcacgcat agtagtctcc tcgaatcttt ggctaaacat gacgttgcat   67560
gtgcccagaa aaaggttcca caagaaagta gagaaagaa tatatcctga ggaatagcaa   67620
ctgcgattga acagtgagct caataaagag gacagagccc tcatagcatt ctgggatact   67680
ggagttctga ccagctggag gagagacctc actgaaccto ttgggaatac agtagagact   67740
ccagaaaagt catactttag gagtagaatt agtaaatttc tagaaaaaaa ggcagctcta   67800
gacaaaccct ggcaaaactg aaaagcaagt ctccaagcat taaaatcatt tccaagtcaa   67860
ttaactgcct gggagaggaa aaccctcttt agaggtaaac aacaaagtca agtggctcag   67920
ctatgtggtg ttcacagtgt gagttctaaa tttaaaactt gactacacat agagaagctt   67980
ttagtatgaa ccatgaccag gtgaaaaatc agtcaataca aatagaccta gaaatgacag   68040
aaatgattag aatggcaaaa aatttgcat atcaatatgt caactgagtt ttaggtttta   68100
agaaaacatg aatacggaat gaagcagata ccatatcaag acagtaac agtatagaag   68160
agccaaatta aattaaagaa ctagtataag aaggtatgtc ttaaatgaaa aaattactag   68220
atgtattccc aatggagtga gatgtttcag aagtaaaaac taactgaaaa acaattttat   68280
accacctaca gaaccagcta cacatacaca aatgacacac acatatacac acatactcac   68340
acatgcacag gcttagaaac atgcacgcac acacacacac acacacacac acacctccac   68400
aaatactaaa aaatgaaatc cactgatcct cacagacagg cggaaaata taaaaagatt   68460
tcctgcatgt gggtaggaag tcacagaagg agaggaagga gagattgcta caggaacaaa   68520
tactggaagc aaggatagct aaaaacttt caaataagaa gaatattaaa aaccacagat   68580
tcaagaagct gaatgaatca gacagggaat ttccaaaaaa aaaaaaaaaa aaactgtatg   68640
attcacttttt gtacatcacc gttcaacagt cagaaggcaa agatataata acaagaaaca   68700
tctcatgaga aactggagca aaaagagctg tgtcttgcta gagacacagt gatacaaatt   68760
gctaatgcat tctcatcaga aacactggaa cccagttaac aggggatatc attaaaatga   68820
taaactagaa aaaaaagaga tcaaatgaga atgctacatc cagcaataaa atgccttgaa   68880
gatcatccat gttggataaa tgcatattgt gcactgcccc aaataaataa accaaaaact   68940
aataatttgg aatcagcagg cttgtgtaac aagagatgtt gcccaaagaa aattagctag   69000
aagaagaata gttcaagagg agaacttct gcagcccacg taatgagaa cccagcaaat   69060
ggcaaatgta gatgtaaatg caaaatattt tcttgatcaa atttctatat ctttttaaat   69120
gagagttgac tacttgaagc aaaatgatag caatatattt aactttagca tatgtagagg   69180
taaaaatttg aacatataga ctaaatcatg tggggaataa ttggaagtgt accattgtaa   69240
gtttcttacc ttatccacga tggtatgtaa tattaatgaa aggttgaatt tgtgggtcca   69300
aagggatatt gtaaatccta aagcaatcat aaaatttta attctgaggg atattatata   69360
ataagaattt tccatgtatc caaagagggg aagccaagga agaaaagaa gtctttcaag   69420
tactcaagct ctgagcacat ccagttctc attgaaccag cttcctgaa tgagggtct   69480
gggcttgaga ctaggtcaca tgtgtagagt ctctagagag acagtgttgg atccccatgg   69540
cccataatac atttcccgtt ttcccaggca gccacaggtc acgaatggga ggattctgag   69600
aggttggagc aatgttctta ggaggcataa ggaggagtga atgctctgag atttccccag   69660
```

```
cctgaggtcc tccatagctg cccgacctct tcagacctca tagtctgccc agctgtctcc  69720
ctttatgcca tgagtgccac tgttctttca actcatcccc cattccctca gtcccggaat  69780
tgctgtggcc agcagaggat ggactgagag caggagagga agtcctgacc aggaacccat  69840
cctagagata ctgcatcctg cctgaaagct aggtttccag ggcagctttg agaagtcttg  69900
cagaaagaaa cccacttgac ccacctgata cggtatcgac agacaggaat acttttttgtg 69960
caatggtttt acatgctgaa catagagcct tttggctaca ttttgagtac attgaatgag  70020
actgctggcc tgggaaggat atcatgctgg atgccatttt tttctctgga gaactatgtg  70080
ttagttccaa ctcgcacatt actatatgaa gtcctacaca gagagatacg gagagctaga  70140
cagatagaga tacttttgta tgtgcataac caattccaca atacacacgt caaaatccat  70200
accagttatt ccagagagat ggattgggca gaaggcagaa ggaggatatt ctgatccctt  70260
tttggccaca tgtatgtata atctcagtgt ttctaggaag tgtgtgctgc attagatttt  70320
ttttctttaa aaaagtgat aatatattaa gtatgagaaa tgtgcagaga ggattagaga  70380
ttgagagcca tttgtcattg tggcaattgt atggtatctc ttttgggaat atttcaaagg  70440
caccagtaat gaccttgttg tagcaaaata tacagtgttc ctgcatatgt acccattttt  70500
tgtgatgtgt attctttttgg aatttccagt ggcttgatca agaactactg ccgaaatcca  70560
gatcctgtgg cagcccctcg tgttataca acagatccca gtgtcaggtg ggagtactgc  70620
aacctgacac gatgctcaga tgcagaatgg actgccttcg tccctccgaa tgttattctg  70680
gctccaagcc tagaggcttt ttttgaacaa ggtaagaagt tgtgccagac atttacctgc  70740
ttggatgctg ggatgaaaag ccatggatac ccccactgac gcacaaccct tcagtgctac  70800
actggttctc gtgtgttggt tctgggtctg ccatgtggga ggaagcctta gcgcactctc  70860
tgggggagcc agaggtgtga ttttggtgc aacctgtgcg agctgtgtct ttaggatggg  70920
cggaaaccat tctgggtgct cgacttcacc actcccctca ttgtaaaagg ggctatctca  70980
ttgtcctaga caaaattctt attgtaatat gctgtcagat gtgtgtgtct ttccaagcca  71040
gtaaactttt ccagggattt cttcaagtag acagcattca gtgcaatctt cagcattgca  71100
gattccgaga aatgtggctc tagatcctgt tatccttgag aaacctaact gggttgcatt  71160
aattccatat ctccctgggt ctgtgtggta gtacatgagc tcccgaagct ctatctctca  71220
ggtcttttttc agtccgaggc aggttgtgca gttcttagct ttgaagggag tgattttttttc  71280
gtgtgctttt gcctctttct gatggaactt gtacctgcgg ggggtctgga gaaaaagagt  71340
agtagacttt tgctttattg caatgcatta tgctgggcac gagaggattc cctatcttat  71400
tgtaggtgat aagcttttgg cctccactca tccctgacaa gtgaagtgtt gttgcctaca  71460
gttttagctg caggactgtt gtctgcccca tcaccaggag tttaatgctt tcttttttga  71520
gcaatcatct agggacacat gcaaggttttt tatatgtcct tgcctcctcc ccaaaaaacc  71580
atttaatgc ttggagactt gcttttcagc tttgccaaat gcatcaccct ttcttctatg  71640
ctgttccatg tcgtcatgaa cactctgtag agattcctag aaatgagctt ccatgttagt  71700
ggagtttccg atgagaagca atctgatatt tcttttccac taagttttac atgaaatatt  71760
tctaagaact tactacagtt ctagaatggt aggcatctct tactttcgtg tttgtttgtg  71820
tgttttctca tgtccatttg cctattaata aagaatagag aatggttgta aatctcagtg  71880
actcttttttt ggtttatgtc ataaatggct tcctgtatttt ttctgttcta ggaaataata  71940
agcttgatgt cttctgttttt aatttcagca ctgactgagg aaaccccgg ggtacaggac  72000
tgctactacc attatggaca gagttaccga ggcacatact ccaccactgt cacaggaaga  72060
acttgccaag cttggtcatc tatgacacca caccagcata gtcggacccc agaaaactac  72120
ccaaatgcgt acgtctttgt tctttaccat aagcgaagga agggccaatg gaagtttctg  72180
ttagaagagt catgcttcaa ggtagctgct caggactcaa cttggctcag atgcagagga  72240
acatttcctg tgagcaaaag ttcttagaga agacttgtt tttttgagac agagtcttgc  72300
tttgttgccc aggctggagt gcagtggcat gatctcggct cactgcaagc tccgcctccc  72360
gggttcacac cattctcctg cttcagcctc tctagcagct gggactacag gcacccacca  72420
ccacacccgg ctaattttt gtattttttag tagacacgg gtttcactgt tctagccagg  72480
atggtcttgg tctcctgacc tcgtgatccg cctgcctcag cctcccaaag tgctgggatt  72540
acaggcgtga gccaccgtgc ctggctgaga agacatttttt taagctggct ctccttcctc  72600
ctagtttttat ggaagcagaa ggatatatgg agttgagaag atcttattaa taaaacagcc  72660
gggatgacaa atgaccaaag agttagagta tccttctaca acatcggctg agggttaata  72720
caacctttttc accttggaat tctatcattc taagctctag tccctgaagt gaatgttgtg  72780
ttggccttttt gcatcttggg tcacaggaa ttgatacttg cacatctatg gagaggcaaa  72840
tcttttttcta tctacttctt tttcaatggg tacaaacaca cttggtcctg agcaccagtg  72900
gtctgaagag atacggtctg cccagagag aagaacaaag gcaggaaagc agatgagagt  72960
cagcaaaggg gcgatgctga aaagtaaaag gggcgggtag atggacagaa gccatgatct  73020
ggccattcta tggccagtct ttcggccata agtgactacc aaagacacgg caaaacggtt  73080
tccacatgtt gaacaacaga tgctagagga ccaagagtat tgcaagaggg agaaaatgag  73140
atcaacccat caatgccttg gctttcttca aggagaccct tcctgcactg aagagcaagg  73200
agatggagcc caagctgact gtagccatgt tgctgaacag aggagagtga ttggactttg  73260
ggattactca ggtagttagg attttctagc catgctaaga gtaagaatgg acttgtggag  73320
gataggagct ccaggcatag aagtctcctc aagtgttagt ctaaacataa agcagcactt  73380
gcatagaaga ttttccacaa gaaaatatgg caaaaaaaca ccatatattg aggaacaaca  73440
actacaaggg aacagtgagc ttaataaagg tgacagagat cacatagtgc tctgaaatat  73500
tggagttttg accagctaga gagaagagac ctcattgaaa atcttgggca ttcagtagag  73560
acctcagaaa agtcagactt tatgagtaga cttgtgtatat tcctagaata aaggcagctc  73620
cagaaaaaac ctagcaaagc tgaaaagcaa atctccaagc attaaaatgg tgtcctagtc  73680
aattaactgc cttctagaag aaaactcaac actctcttaca ggtgaacaac aaagttaagt  73740
tgctgagcta tgcaatatcc acagtgtgag tcctaaattt ataactttac tacacataat  73800
aaagcattta gtgtgaacca taccaggaa aataatcagt caataaaaat agaaccagga  73860
atgatagaaa tgatttaaat ggcatgagaa tttgacatat tagtatcata actgcattgc  73920
tggatttaag aaaacataaa catggaacgt aacagatatc atatcaaggg aaagtaaaag  73980
gataaaagag tcaaatcaaa ttaaaggact attaaaaggt atatcttaaa tgaaaaattc  74040
actggatggt ctcccaatca ggttagttgt ttccagggaa aaattaact gaaaaataat  74100
tcaatagaat ctacagaaat agctgcacat atatacacac aatggcacac gtgcacacac  74160
ccacacccac acaggtgtga atcctagagc cacacgagca ttgaaacata gagaagtaaa  74220
aattgttcat tgaggaatat gtagcaatgc tcaatgtgtt ttaccctaat aagagctttt  74280
gtgatgtatg attgaaaaac tgacacaact gaagagagaa atagataagc ccacactctg  74340
agttagagat ttccttgatt ctctcactat ggttataaat ctttcccaaa cacaacaggc  74400
```

-continued

```
tagaacaaat atgcagaaaa ttagacatag tatctttgtt ctcaataaaa acgtcgacct 74460
atttaacatt ataccgaact accgagtaca cattaaagtg tgcatggagc attcactgag 74520
gtgtactcta cacatgacct tccagcaagt ctccatagat ttaaaagaat taaagtcata 74580
cagagtgtgt cactttattc tcccagaata aagtgagata tgaataatga gaagtttgcc 74640
agcttctcaa atatttggga gtcatacggt gcatttcaaa atactctttg ggacaaagaa 74700
aacatcacta aggaatttag aaaagttttg aactgagtaa gaatataaca caatttatcc 74760
aaacttagga gatgcagtga atgtctttag gcttttacat aatttagat gctcttaggg 74820
aaaaacagaa gcatgtaata atcaagattt caaactgcaa ttctcaaagt gtagtctaga 74880
gaaacctgag gacctttgag taccttcaga gacagtccat gaggttaaag gactttgcta 74940
cgtgaaaagt aagatgctat tggccctttt tactttcatt ttccaacaag agaagagggg 75000
agttttccag cagttacata atatgtaatg gcatcatgtc tctgatggct aagaaaatgg 75060
gcaattgttg actttgtgtg ttaaaaaaat tctcagtgtt ggtttcttat actataaata 75120
ttcatcttgt gttttgaaaa agaaaagctc tttggaatcc cctatgaaca aagactttga 75180
cagttgttga tctaagacca cagcttaaat atctacacaa gaaaaaaaaa aaaagcaaat 75240
aagagccaag gaaagcagat ggaaggaagt agtccaaacc agtgacattc agtgaacaag 75300
aaaagagacc aacaagggag taaactcttg aaacagaaag ttgattcttt gaaaagatcc 75360
atatgattga acacagtctg gctaaacaaa tgacagacca atgagggtgc acaaccatca 75420
ccatctggag taacagagga gaggtgccat tactatagca tcttccagtt ctgaaagctg 75480
aaaagaagat tttgagaaca attgtatgtg aataaattca ggaatgttaa tcatgtgggc 75540
caattcctga ggaagacaac aaatcagcaa accagatgct gaatagttag tgtagtcctg 75600
tagagagaca tacagagagg ctgacagaga aatatttgta tgtgcataaa acaatctaca 75660
agacacactt caaaatcaat ctcagttaat ctggaggaac atatttcaca gaaggtggaa 75720
ggagggtatt ctgatcctct tgtacattgt acaacattgt acaatgtaca gagtataatt 75780
gtacaagtac aattgaagtt gtacaagtac aagtgcaact tgcacaatgt acagagtaaa 75840
cattgatgtt tactctcaat tttcttatgg agcacagatg actttggatg tgttacaata 75900
tgaatgataa tttgtctttg agatgttcgc agttgtttga aagttgagga ccatttgtgc 75960
atattatggg acctttagtg aaaatatttc aaagtctctt tttacacttt gttacagcaa 76020
aatgtagagg gcgctaagtg cccttgaatc ttctcccatc tctggtgacc tgtgttgttt 76080
tgaaatttgc agtggcctga ccaggaacta ctgcaggaat ccagatgctg agattcgccc 76140
ttggtgttac accatggatc ccagtgtcag gtgggagtac tgcaacctga cacaatgcct 76200
ggtgacagaa tcaagtgtcc ttgcaactct cacggtggtc ccagatccaa gcacagaggc 76260
ttcttctgaa gaaggtagga agtctatggc cagacaacca cacccctagga cgttgggatg 76320
aaaagagttg caaaatctta gtgatataga agccttccat gctcacacaa ttccaagtag 76380
aatgtggact cagggtcagc cactgggaag gaacactcaa cgccttctct gggagaagaa 76440
gagctgtgat gtttggtacc ctgtgaaagg gtggtatcta taggaagggt gcagaccctc 76500
tagggcactg gacttaccac tccccctggtt attcaaagga tcatttttagt gtcttagcca 76560
gaagaatatt ctaacatttt gccaaatttg tgaagattta ccaagctcat gataagcctt 76620
tcatggtatt tcttcaagta gtcagtgttc attgcatctt tggctttgcg gtttcggagg 76680
aatgcggttt ttgagtctgt catccttgag aaacctaata tgacttttct tagttccata 76740
tacttctggg tccaggtagc agtacatagc caacaaatgc tccatcgttc tggcctatct 76800
ccatcttaag ccagtcctgc acaactaggc tttgatggga gggatctctc agtgttcttg 76860
cccctccttc tcatgaaaca tatatctgtg ttggtctctg agaagaagag tagtggatat 76920
ctactttgtt gcaatgcaga atcctgggcc aaagatacca gccatccctc caagggaata 76980
aaattttggc cagtagccct ctctgagaga caatttgtct ttgcctacga gtcctagatg 77040
caggaccgct tcctgcccca tcttcaagaa gctgaaggct ttggctttgg aggatcagca 77100
gtctagggaa atgtgtgacg gtttcatgtc tgtccccact gacagtcaat caccacctac 77160
aacctgcaca gcctgatgca tagcagtcta gtttcctgcc ttattctcag gaacacccag 77220
aagatgtcta tattaaagag catgcacatg agtgcaattt tgactgatag gcactctgat 77280
cttttccttttg gtgcctgtgt tttaaaggaa atctttctaa gaactcgtta aagttctaga 77340
atgctatgaa tctttgggtt ttattattgg tatgtccatc tgcctgctag tacagaacag 77400
agcatggtag tcttttctcag agacaatgat cctgtttcag tcacagattt cttctgatgc 77460
ttctgtgttc tagaaattac tcagcttgat ttctcctctt tgaatttcag caccaacgga 77520
gcaaagcccc ggggtccagg attgctacca tggtgatgga cagagttatc gaggctcatt 77580
ctctaccact gtcacaggaa ggacatgtca gtcttggtcc tctatgacac cacactggca 77640
tcagaggaca acagaatatt atccaaatgg gtacaacctt gagttttcct caaagacaga 77700
cagcagcccc cttacatttc tcttggaagg gccatgcttc caactaactt cttatgacaa 77760
atttatctca gatctggaat gttgggtaga atgtctcagg cttcttttctt caggcacagt 77820
gtctgaaagg agagaaatgt caggccagct ctctttctc atagttgaca gaagcaggag 77880
gatatttgaa ggtggtgagt tctcatgaat agaaagctca ggacacatgg ccacgtgctt 77940
agaaatagca ccattccaca atgcccacta aagaccaatg caatagttca accagggatt 78000
tctgtcattc taatctccaa gtcctgaagt gaaggttgta ttagccatgt tcatcttggg 78060
caacaaataa aggatatcta tgttgacatc cagatcttcc aatcactttc tcctctaacc 78120
tgtacctggg ttctgagaac aaggtatctg aagagctatg tgttgccagc acatgagggg 78180
caaaagtagg aaggcagctg agagtcagga agtataaaga ttacactgaa 78240
aggaagatgg acagaaccc agttcagacc acgtcagcgt ttctgccatg aaggactatc 78300
aatacatag gaaagtgtt ttcataggtt ggacaacaga catgacaggc ctgagaaaat 78360
tcagaaaggg aatcaaagga gatcaacctt atcatgtccc tggcatcctt ccttgagacc 78420
cttcaagggc aagcagatgg agcccagctg accacagaca tcttgcttaa ctgaggagag 78480
agactggagt ttgtgatgcc tcaggcatct gacgtattct aggctggcta agatgagag 78540
gggatttgtg gaggaaagga gctccaagaa tacacaccga agtcttctca aggctttggc 78600
taaatacaaa gctgcgtatg cacaaggaga gttttcacaa agaaagaaca ataaagaaaa 78660
gctactgggg aaagaacaac tgcaagggaa cagtgagctc aatggagatg ctagagctca 78720
catagcactg ggggatattt gagttctgac cactcagagg agagacacct cactgaacat 78780
cagccatt cttgggcatt cagtagaggt caaagaaagc cataatttgg gagtaggatc ttcggattcc 78840
tagaaataag gtgactccag aaacactcca gcaaccttc ttccaagcca gtctaaaagg 78900
atccaaatga tttccaagta aattaactgc cttccagaaa aaagtaaact caaccctcct 78960
tagaggtaag gaacgaatac aagtttctca gttatatgac atccccagag tgcaacttgc 79020
atttaaaaat ttactagaca caaaagaagt tttcactgtg atccataact gggagaaaaa 79080
tcactcaaca caaataggcc cagaaataat agaaattatg gcattggcaa gaacatttaa 79140
```

```
aatgcacctc tgagaactgt gtttcaggaa aatgtcagca aaagctgacc atgagagaaa   79200
tgaatgcata atatcagaaa agaaaagaat tgaagagcca aatggaaatt taaaaactga   79260
gaaaagttat atctgtaatg aggaattcac tggatggcct tataaccagt ttagatatta   79320
tggtaggaaa aggtgaacga gaaaatgatt caattaaagc tagacaaacc acaagacaga   79380
cagacagaca caaatacaca tacacacaat gactgaacca attaatcaac agagcctcaa   79440
ggacatctag gaaaacatcc acacatttaa tatatgtgtt aggcaagtca cagaaagaga   79500
ggaaaaagat aatgtgacag aagttatact tgaagccatg acggctgaca aatttccaaa   79560
catacagaaa atgagaaatt catagtcatg aagctcaatg actcaggtat agattttttaa  79620
agagcaaaac tctgatttac tggggtacat catagttaaa ttgtctgatt tcaaagctaa   79680
gaagaaaaaa aggggggttcc tatgaacaaa cattttgaca gttgatctaa gaccacagct   79740
taaatatcta ggcaaggaaa agcaaataag acacaaggaa aggggatgga tggaaatagt   79800
ccaaaccaat gacattcagt gaacaagaaa atagaccaac aaaggagtaa atccatgaaa   79860
cagaaagttg gttcttgaa aagattcatg tgattgacca cagtctggct gaacagatga   79920
cagaccaagg agggagtaca accatcacca tttgaagtaa caggggagag gagccattgc   79980
tataccatac tccaggtctg aaagctgaca agaagatatc aagaaaaact gtatgtgaat   80040
aaattcatga atgtagatca tgtggatcaa ttccttaggt aaacaacaaa tcagcaaacc   80100
agatactgaa tagattgggt actcctatag aaagacatac agatagccag acagagaaac   80160
atttgtacgt gcataaaaca atctacaaga ctcacttcaa aatctctcag ttaatccaaa   80220
gtaacatatt tggcagaagg tggaaggagg gtattctgat cctttcttgt acacattgat   80280
gtttttctctc ggttttctta tggagtatag acgagtttgg atgtgttaca ataagaatga   80340
taatctgtct ttgaaatgtt cacagttgtt tagaagttga ggacgatttg tgattgttac   80400
aggaccttta gtgagaatat ttcaaagtca cttttttacca cttgttaca acaaaatgta   80460
gaggatgtct ggtgcccttg tatcttctcc catctctggt gaactgtatt gttttgtaat   80520
ttgcagtggc ctgaccagga actactgcag gaatccagat gctgagatta gtccttggtg   80580
ttataccatg gatcccaatg tcagatggga gtactgcaac ctgacacaat gtccagtgac   80640
agaatcaagt gtccttgcga cgtccacggc tgtttctgaa caaggtaaga agtctctggc   80700
cagacaacca cacccttgga cgttgggata aaaagagttg caaaatctta gtgatacaga   80760
agccttccat gctgcacggg aatctgaatg tggactcagg gtcagccaat gggaaggaag   80820
cctcagcgcc ttctctgggg gaaccagggc tgagattttt ggcaccccgt gacagggtgg   80880
tgtctttagg aagcgtgcag accttctagg gcactggatt taccactccc ctggttattc   80940
aatagattat ttcagtgtcc tagtgaaaat ggatattcta acatcctgcc aaatttgtga   81000
tgatttacca agctcatcat gagcctttcc tggtatttct tcaagtagac agtactcatt   81060
gcaaacttca gctttacagt ttcagaggaa tgtggttttt gagtctgtca tccttgaaa   81120
acctgatatg acttttactta gttccatatc ctcctgggtc taggtaacag tacatagcca   81180
gcaaatgctc tatctccctg tctaccttaa tcttaggcag gtgctgcaca cctaggcttt   81240
gatgcaaggg atttcttagt gttcttgccc ctccttctca tggaacacgt atctgtgttg   81300
ctgtttgtga agaagagtag tggatgtcta ctttgttgca atgcaggatc ctgggcccaa   81360
gatttcccgc cgtccctcca agggaataaa attttggcca gtaccctct ctgagagaca   81420
atgtgctttt gcctggaagt cctagatgga ggaccacttc ctgccccatc ttccagaaac   81480
ttaaggcttt ggcttggag gatcagtgct ctggagaaat gtgtgacggt ttcatgtctg   81540
ccccccactga caaccaccac ctacagcctg caccgcctga tgcatggcac tctggtctcc   81600
tgccttgttc tcaggaacac ccaaaagaga tctttgccaa agaacaggca catgagtgca   81660
attttgactg ataggcactc tgatctgtcc tttggtgccc aggttttaaa gaaaatcttt   81720
ctaaaaactc attgaagttc cagaatgcta tgaatctttg agctttgtta ttggcatgtc   81780
catctgccta ctaatgtaga acagagcatg gtcgtcattt tcagagatga tgtcctgttt   81840
ctatcatgga tttttttttct catgcttctg tgttctggaa attactcagt ttgttttctc   81900
ctctttgaat ttcagcacca acggagcaaa gccccacagt ccagtctgc taccatggtg   81960
atggacagag ttatcgaggc tcattctcca ccactgttac aggaaggaca tgtcagtctt   82020
ggtcctctat gacaccacac tggcatcaga gaaccacaga atactaccca aatgggtatg   82080
tctttgagtt ttctcccaag agaaacagcc acccacttaa atttctcctg gaagagccat   82140
gcttccagct aacttcttat gacccaattt ctctcagacc cgaatgttg gacagaatgt   82200
ctcaggcttc ttgctttggg cacagggtct gagaggagag aaatgtcagg ccagctctct   82260
tttctcatag ttgatagaag taggaggata cttggaggtg gtgaggtctc atgaatagaa   82320
agctcagaag aacatatgac catgtgctta gaaatagcac cattccacaa tgcccactaa   82380
agaccagtga aatagttcaa ccagggaatt ctgtcattct aatctccaaa ccctggagtg   82440
aaggttgtgt ttgccatgtt tgtcttggg aacaagtgaa ggatatctat attgacttcg   82500
agatcttccg atcactttct cctctaacct gtataaacac attgggttct gagaacaagg   82560
tgtctgaaaa gctatgtgtt gccagcccat gagggggcaaa aggaggaagg cagctgagag   82620
tcaggaagta tagagatgct gaagagttac acattcagga agatggacag aaacccatgt   82680
ctggctatgc cagcctttct gccatgaagg actatcaaat acatgagaaa acagttttca   82740
caggttggac aacagatatg gtaggcttga gagaactgag aaagggaatc aaaggagatc   82800
aacttcatca ttaacctgtc ttccttcctg gacacagtgt tggattgaag gacaagcaga   82860
tggagcccag ctgaccacag cagtcttgct taactgagga gagagactgg agtctgcgat   82920
gcctcaggca gctgatgtgt tctaggctgg ctaagaatga gaaggggattt gtggaagaag   82980
ggagctccag gaatacacac agaagtctcc tcaaggcttt ggctaaatac aaagctgcgt   83040
atgcacaggg agagttttca taagaaaaga acaacaaaga aaagctactt gggaaagaac   83100
aactgcaggg gaacagtaag ctcaatggag atgccagagc tcacatagca ctgggggata   83160
tttgaattct gaccactcag aggagaaaca cctcactaca ttttgggcat tcagtagaga   83220
ccaaagaaag ctgtatttg ggattgggat catcttattc ctagaatcaa ggtgactcca   83280
gaaaaactcc aacaacccctt cttccaagcc agtctaaaag gatccaaatg atctccaagt   83340
aaattaactg cattccacaa gaaaaaaaaa actcaacccc ccttagaggc aagggacaaa   83400
tacaagttgc tcagttatat ggcattccta ttgcgttact tctatttaaa aatttaatag   83460
agacacaaga agctttcact gtgatacata actgggagaa aaaatcactc aacacaaaca   83520
ggcccagaaa ttatagaatt gatgacattg gtgagaacat ttaaaatgca cctctgagaa   83580
ctgtgtttca ggaaaatgtc agcaaaagct gaccatgaga gaaacaaaag cagaatagca   83640
agagaaaaga aaagaaccgg agagccaaat gaaaattaaa gaactgagaa aaggtacatc   83700
tctaatgaag aactcactgg atggcttat catcactta gacattacgg taggaaaggt   83760
gacctagaaa ataattcaat aggagctaca caaatcacag gacagacaga cagaccaaca   83820
gacagaaaca cacacacaca cacacacaca cacacacaca cacacacaca cacacaaaga   83880
```

```
ctgaacctat taatcaacag agcctcaagg gcatctagga aaaatccaca catttaatat   83940
atgtgttagg caagtcacag aaggagaaga aaaagatatc atgacagaca ttatacttga   84000
agcgatgatg gctcgcaaca cgccaaatat acagaaaaca agaaactcat agtcaagaag   84060
ctaaatgact caggtataga attttaaaga gcaaaactct atgatttact gggatatatc   84120
atagttaagt tgcctcaatt caaagctaaa aagaaaaaaa gggggttcct atgaacaaca   84180
gctttgacag ctgttgatct aagaccacag cttaaatatc taggcaagga aaagcaaata   84240
aggcacaagg aaagaggatg gaaggaaata gtccaaacca atgacattca gtggaaaaga   84300
aaatagacca acaaaggagt aaatccatga aacagaaagt taggttcttt gaaaagtcta   84360
tatgattggc caaagtctgg ctaaacagat gacagaccaa ggagggagca tatccatcac   84420
catcatgagt aacaggagag agatgccatt gctatagcat cctccaggtg tgaaagctga   84480
gaagtagata ttgagatcaa ctgtatgtaa ataaattcat gaatgtagat catgtggatg   84540
gattgcttag gtaaataaca aatcagcaaa tcaaacactg aatagatcat gcagttttat   84600
agagacttac agacagcctg acagataaac atttgtatgt acgtgaaaca atctccaaga   84660
cacacttcaa aatccctctc ggttaatcca aaggaatgta tttggcagaa ggtagaagga   84720
gggtattctg atcctttctg gtacacattg atgttttctc tcagtttttct tataaagcat   84780
agattacttt gaatgtgtta caataagaat cataagctgt ctttgaaatg ttgacagttg   84840
tttagaagtt gaggaccatt tgtgagtgtt atgggactt agtgagaata tttcaaattt   84900
gcttgtttac actttgttac aagaaaacat agagggtgcc aggtggtgct gtatctctc    84960
caatctctgg tgacctgtat tgttttggaa tttgcagtgg cctgaccagg aactactgca   85020
ggaatccaga tgctgagatt cgcccttggt gttataccat ggatcccagt gtcagatggg   85080
agtactgcaa cctgacgcaa tgtccagtga tggaatcaac tctcctcaca actcccacgg   85140
tggtcccagt tccaagcaca gagcttcctt ctgaagaagg taagaagcct gcagtcagac   85200
aaccataccc tcggacattg ggataaaaag atttgcaaaa tctttgtgat gcagaaaact   85260
tccatgctgc acaggaagtc gaaggtgaag tcatggacag ccaatgggaa ggaagcttca   85320
gtgccttctc tgggggggacc agagctggga tgttgagtgc cttgtgaggg atggtgtctt   85380
taaaagggc acagaccctc taggacactg gatttatcac ttccctgtta tcaaacgaat   85440
catattagtg tcctagccaa gatggatatt ctaacatcct gccaaacttg tgaagatata   85500
ccaagctcct aagcctgtcc agcccttttct tcaagtaggc agtgtttatt gcagtcttca   85560
gctttaccat tttgaaggaa tgccattttt gaggctgttg ttcttgagaa acctaacatg   85620
tcttcattag atccgtattg tcctgagact ttgaagcagt acatagccac caaattgttt   85680
atctccccag cctaccttca tcttgggcat gccttccaca cctaggattt gagggaaggg   85740
atttctcagt gttctcatcc ctgcttctca tggaacattt atctccgttg ttttttgaga   85800
agaagagtag tggatgtcag ctttcttgta atgagggatc ctgggcccaa gattccctgt   85860
ctccccctcct aggctataaa attttggcct gtactccttc tccctgagag gcaatgtgtc   85920
tttacctaca agtcctagat gcaagatcct tttctgcccc acaccccaga atctgaaggc   85980
ttttgctttg gaggagcagt ggtctagtgt gcagggtttt catgtatacc ccccactaac   86040
agccaatcac cacctatagc ctgaacagct tgatgcatgg cacccctggtc tcctgccttg   86100
ttctcatgaa cacccagaag aggtgtaagc aaaagaccat tcacatgagt gtaattttga   86160
agtataggca ctctgatctg ttttttgttt gtttcttttgt ttgtttgtt tccagggttg   86220
aattaaaata tttatgacta cttattaaat ttctagaatc ctataagtct atttgtattt   86280
ttattctaca tttcaatttg catgctaata tagaagagtg taaattgtta atcctcagat   86340
tattccactt tgtgtgtcat aattttttttc acatttccct tttctaggca atactgagct   86400
tgattttctc ttttaattc agcaccaact gaaaacgaca ctggggtcca ggactgctaa   86460
cgaggtgatg gacagagtta tcgaggcaca ctctccacca ctatcacagg aagaacatgt   86520
cagtcttggt cgtctatgac accacattgg catcggagga tcccattata ctatccaaat   86580
gcgtatgtct atcatgttag ccataaaagg aacaatagtc aactaaaatt tctcttagct   86640
ggcccatgct acaagctcac ttcctaggtc caaatttctc atagactcag agtttgtagc   86700
aaaatgtctc aggaaactta cttttgagca aaaggtctga atgaagagaa gttttaggat   86760
tgctatcttt cataacaatt tgatggaagc agcaggatat atggaggtgg tgaagtctca   86820
ttaatgtaaa gctaaggaga tcaaatgacc aaatgctgag acaaagtatc attccacaat   86880
gcccactaaa ggtccatgca gtcttttcaac catgcaattc tatcattcta tcctccattc   86940
cctgaagtga aattttgtgtt tgccattttt gacacgaatc agaagtaaca aattcaggct   87000
gggtgcagtg gctcaggcct gtgatcccaa cactttggga ggacaagacg ggcagatcac   87060
cagaggtcag gagttcaaga ccagcctggc taacatggca aaaccccatc tctacgaaaa   87120
attaaaaaat tagccggtca tggtggtggg tacctgtaat tccaactact gggaggctga   87180
aggcaggaga aacacttgag cctgggattc agagtttgct gtgagccgag aacatgccac   87240
tgcactccag cctgggtgac agagcaagac tcaatctcaa aaaaaaaaaa aaagaagaag   87300
aagaagaaaa gaagaagagg aagaagaaga agaggaagaa gaagaagaag aagaagagga   87360
agaggaagag gaggaggagg aggaggagga agaagaagga agaagaagaa aagaagaaga   87420
agaagaagaa gaagaagaag aagaagaaat agaaatgagt gcatatatt    87480
atatatgagt actagcctgt atgaacacac tgggttctaa gcaccagttt tctgaaggga   87540
tatgggttgt caggcagagt aaaagcagga atgcagatga gagtcaggaa gtaaacagat   87600
gtggtgatta aaatgggcag gtacatggac aaaaaaatgc atgtctgaca aaaactggcc   87660
tcttgccata agtgagtatg aatatatgg aaaactgtt tgcacatgtt gaacagcaga   87720
cagtacaacc tgagatagtt tagaaaggga aacaaataag atcaaccccca taattaccct   87780
tcctagactt aagggcaaag agttttaacc aaagcattcc acagcagtct tgctaaactg   87840
gggagagaga ctggagtttt gtttactaat aaaaccgaga ttttctaggt taggtaataa   87900
tgagaaagta tttgtggaga aaaggagctc caggaataca cacagaagtc tcttcaagtc   87960
tctggctgaa cagaaagctg tgtatgcaca gaaagagttt ccagagagaa aggagaacaa   88020
agaacagcta ctggggaaag aacaactgct ggggaacagt gagctcaatg aagatgccag   88080
agctcacata gcactgggag gtatttgagc tctgaccagc ctgaggagag acacttcatt   88140
gaacatcttg ggcattcagc aaagaccca aaaaccata cttcaggagt agaattaatg   88200
cattcctaga ataaagtcta ctccagaaac accctagaaa agcttagaaa ccaagtcaa   88260
aaacaacaa atgatctcca agtaaattaa ttgcctgtca gaagaaaaca acctcttcag   88320
aggtaaacaa caaaattaaa ttgctcaatt atatagtatg cacaatgtgt ggcatacatt   88380
taaaaatttg ctaaacatac aaaaagcatt tagtgtgacc cataaccagg agaaaaatca   88440
gtcaatacaa atagacccaa aaatgataaa aataacagaa ttgcaaagga gatttaaaat   88500
gtatgtatca taattgtgtt caaggattta aagaagcgt ggacaagaaa taaataaatg   88560
gataaatatca acagaaagaa aaattgtaaa aaggaccaaat ggagagtcaa gaactgaaaa   88620
```

-continued

```
aaaagacatc tctttaatga gaaaatcact acatggcctt ataatcatat tagatagtac   88680
agatgataaa gctaactaga aaatattagg gtggtgcaaa ccatagcacg cttatacaaa   88740
gcctgagaag ataaacagag cctcaaggac atctatgaaa atatcaaaat atttaatatt   88800
tgtttaaagc aagtcacaga ggaagggaaa gagatattgg aacagaaaaa atacttgaag   88860
cagtgatggc tgatgacttt ctaaatatgg aaaaaatgat aaactcacat agtcaagaag   88920
ctcaatggat cagatatagg attttaaaaa gtaaagctgt atgatttatt tggacacatc   88980
ataattaaat tgtccataat caaagataga aagtaaaatc ttatttgaag cccaagggaa   89040
aaaacatacc tttacataga gtaacagtga cacaaatgac tgatgccttc tcatcagaaa   89100
caacacaaat cagaaacaat agaataacac ctttagagtg gtaagaagaa aaaaagatca   89160
aatcagaaac aacaaaataa cacgtttaga gtggtaagga ggaaaacaag atcatcaatcag   89220
aaacaatgga ataacacctt tagagtgtaa gaaagaaaaa aagatcaaat caggaacaac   89280
agaataacgc cttcagagtg gtaagaagga aaacaagata aaatcagaaa caatgaaata   89340
acacctttag agtagtaaga agaagaaaag atcaggtcag aaaaaatgga ataatatgct   89400
aagaagaaaa aaaaagatca agtcagaaac aatggaatat caccttttaga gtgaaaagaa   89460
ggaaaaaaac ccagcaagct taaacgctat gcacagcaaa caattccact gaaaatgaat   89520
gttacgtaag tacatattct gtcctcctaa aaacaaagaa caaataaaag aatgtttcat   89580
cagcaggatt atgtaataaa agatgtgaaa gaatgctatg taagtagaag aaaaataata   89640
ccatatggga attggcatca aaaccacaaa atactatcaa aacaaaaaaa ctttattgat   89700
aaatttaaca caatatgcaa aagaactata ccatgtatac tacataacat tggtgagaag   89760
aaaattagaa gatctaaata aagacacatc atgcttatag attaaaaaat ccaatgtcac   89820
ttttcacaaa actgatcttt agtttcaacc cacacccaag cagaattcct gcagtctttt   89880
cttgaaaacc taacagaatg tatatgctag aatcaccaag acaatcttta aaaagaataa   89940
aaaacttgga ataaaatcac aagtttgtgg gatagatgca tatggtaata tggaaattct   90000
cataaagaca cagtaatcaa gacatgtggt attggctggg acgcttggct gtaatcctaa   90060
cactttggga ggcaagatgg agaggattgc ctgagatgag gagttgcaga caagcctggg   90120
caacatagca agaccctcat ctctacaaat atttaaaaaa attagccagg tttggtgcca   90180
tgtgcctgta gtcccagcta ttcaggaagc tgaggtggga ggatcactgg agcccatgag   90240
gtggaggctg aaatgagcca tgattgtgct actgaacttt agcctgggag acagattaaa   90300
accttccctc tctctctcaa acaaacaaac aaaaaataca tagtattggg caaaacatat   90360
gcaaacaaaa acagaaaagg gtcagcataa atttacatat atggtcaatt tattttcaat   90420
acaggtagca aagcaattta atgaggaaat tttttttccaa aattggtctg aaacaactgg   90480
atagccatag aaaaaaacta taacaaatgt gacgcttgaa tcctactgta tgactcaaat   90540
taaattaatt tgagatagct cttagaccctc aatgtaacag ctaattctga ggctgaaata   90600
taagactgct atgaaaaagt atagtatctt ataaccttgg agaaggaaaa attttttgag   90660
ggaagaacca gaaaacacta actgtaaaag aaaacaaatg ataatgtgga cattcattga   90720
ataaaaactt atgctcacca aatatgactg ttaagaaaat aaaataagtaa gtaacacact   90780
ggaagaaaaa cactctcatc catatatctg acaaatggcc tgtatccaga gtatagaaac   90840
atttctccca ctcactaatc agaggacaaa caacctaatc aaaatgggca acaggcttga   90900
atagtcattt cttaggagaa gatgcacaca gagccaacaa tcacctgaaa aagtgcacaa   90960
catcttagcc atcaaaaatc aagagttata accctcataa gatgacactg aacatccagt   91020
gtacatggat atcattaaga agacacaata ataagtggtg tcaccgattt ggagctagaa   91080
tgtgccactc tctcatatgc tggtggaagt tcaaaatcat acaacaaatt aaaaaatcag   91140
tctgatgctt tcttataaag ttcgataaat atgcatctat cctacaaacc tgtaattcta   91200
ttcttgaata tttaccccccc aaaatgaaaa cataagtcca caaaaatcta tataaatatt   91260
catagcagct ttatgtttta taaactcaaa ataaaaacta tttcaatgtt ttcatcaaaa   91320
gaaaatgaaa actatttaaa tggtttcatc aaaagaaaat gaaaaaagaa tttccagtat   91380
atttatacaa aggaatacta ttcatcaaca aggaacagtt tactgatagt ctcagaagca   91440
tgaacaaacc tcaaaaatat attaaggaaa gaagccagac gtcaaagtgt atagtctgta   91500
tgagtccatt catgtgagtt tatagaaaac acaatttatg gtgaaagaaa ccaatagcat   91560
ttgacactgg ccgtgggaag agggtagcag agattgattg agcagccaca caagggagtt   91620
tctgggtgg tgaaaatgtt ctgcattgtg agggcagtgt gggctacaga agtatatgta   91680
tttatcaaat ctcatccagc tacatttaag atctgtgcat ctcactctat gtgaaaatat   91740
actcaactga aaaacagagc aggtatctgt ttcaggtgct acatcacttg atacgtccag   91800
ttgtgttaaa aaccactgcc taacatcctc aaatgggggga tctgggcttg agactaggtc   91860
acatgtgtag agtctctaca gagaccgtgt tggattccca tgctccataa tacgttccaa   91920
gttttctcag acagccacag gtcatgaatg tgaggattct gagagggttgg agcaacgttc   91980
ttgggaggca taatgggaa ggcattctcc aagattcctc cagcctgggg tcttcacctg   92040
ctgtgcctct tactgcattg ttttctgact catccatagc cacttgaccc cttcagatcc   92100
catagtctac ctagccgtct cccttttatgc cttgggtccc gctgttcttt caactcatca   92160
cccattcctt cagtcccaga gtggctgcag ccagcagagg atggactgag agcaggagag   92220
gaggtcgtgc ccatgaaccc atcctagaga agcagcatcc tgcctgggag ctagttttcc   92280
agggaagctt ttataagtcc tgtagaccca accccacttg ctctaccaga tacagtattt   92340
atagtaatac tattttcatg attatttat attgcaaatg tagagcattt atgctacact   92400
atgagtaaat agagtaaggg ggctggcatg ggaattatat aatcttggat gccacttctt   92460
ccttggggaa atgtatttga gttccaactt acatattact atatagtctt atagagagag   92520
agacaaagag ctagacagac agagatatct ttgtatgtgc attaaaaaat ctaagataca   92580
tatttcaaaa tctgtgtcat ttattctgga ggaaagtatt tggcagaagg tgaaggaag   92640
atattctgat cctttcttgt acagacatgt attatctcag ttttcataga gagcatatac   92700
tacttttgat gttttaaaac aaaaattata atctgtagtg tgtccacagt tgtttaaaag   92760
ttgaagctga agaccatttg tgcttgtggc aatattattg tggtataatg ggaatatttc   92820
aaaggcactt gttaacactt tgttacagca aaatgtagag ggcgctaagt gcccttgaat   92880
attctcccat ctctggtgac ctgtgttgtt ttgaaatttg cagtggcctg accaggaact   92940
actgcaggaa tccagatgct gagattcgcc cttggtgtta caccatggat cccagtgtca   93000
ggtgggagta ctgcaacctg acacgactga cagtgacaga gggtagtgtc ctcacaactc   93060
ccacagtggc cccggttcca agcacagagg ctccttctga acaaggtaag aaatttgtgg   93120
ttagacatct atatactggg atgaaaaacc atggaaaatc ttactgatgc agaagccttc   93180
agtggtacac tggaggggttg gttgagggtc tgcaatgtgg aggaaagcct cagcgccctc   93240
tctgggggat ccagaactgt gatttttggc acgctgtgag gaggcagtgt ctttaggaag   93300
ggcacggtgt ctttaggaag ggcacagacc cgccagggca ctgactttac cactcccctg   93360
```

-continued

```
gttattaaat gggtcatttc agtgtcctag ccaaaatgga tattctaaca gcctgccaaa    93420
tatgtgaaga tttccaagcc aataagcctt tccagtgatt taaagtagac ttttttcatt    93480
gcaatctaca gtttgcagtt tcttaagaac atggcctttg agtatgatat cctagagaaa    93540
cctaaggaga ctgcattatt tttctattgt cctggggctg catagcagga ggtaaccaac    93600
gaatgctgtc tctccctggc ctatctcagt ctttcacagg ctctgttcac ctcagctttg    93660
aagttagaaa tttctaggtg ttcttgcctc ttcttctcat gaaacctgca ttggcagtga    93720
gtctacagaa gaagaggaag agaattctgc tttgttacaa ttcaggactc tgggcactag    93780
aagattccct atctctcctc caagggaata agttgtttgt ctctaaccct ccttgagaaa    93840
caatgagtct ttgcctgcac tcctaaatgt aggatgattt cctgcccaaa ttttcaaaag    93900
attaagcctt ttgccttggt atgagcaatg gtctagggaa atgcgcaagg gtcttgtgtc    93960
ggcccctgac tgaccaccag tcacctccta cagcctgcac caaggaatgc attgcattct    94020
ggtcttctgc cctgtggttc tcatgaaaac cagcagagat tcatatgatg gagctgcaca    94080
tgaatgtaat ttccaaatgt ccagcattct ctctgttctt tatctttaga tttaaaaata    94140
atgtttctat gaacttatta aaattctaga atactataga tctactgggt cttttcacat    94200
ccttttgcta ctagtagaaa aaagaatagt aataattttc agaggctact gtccagtatg    94260
tgacataaat tgtctcccat gtttctctgc tcatgcaatt actgagtatg atttatttta    94320
ttttaatttc agcaccacct gagaaaagcc ctgtggtcca ggattgctac catggtgatg    94380
gacggagtta tcgaggcata tcctccacca ctgtcacagg aaggacctgt caatcttggt    94440
catctatgat accacactgg catcagagga ccccagaaaa ctacccaaat gcgtatgtat    94500
ttgattaaaa ccataagagg agcaacagcc aactcaaata ttggttagaa gacccatgct    94560
ttaagctcac ttcctaggga caaatttctc ttagactcac attttggcaa aatgtctcag    94620
gacctttgct tttgagcaaa gagtctaaga gaagagaaat tttaggcctg ctatttttcc    94680
taatagtttt atggaaggag tagaatatac ggaagtggcg aagtcatatt aatgtaaagc    94740
tcagaagata aatgaccaaa gcttaaacac agcaccattc cacaatgccc actaaaaatc    94800
aatgtcatct ttcactcgtg caattctgtc attctaaatt tcaattcccg aaggtttgtt    94860
tgccattttt gtcatgggta ataagtaaaa aaaaaaaaat taagatgtgt atatatatat    94920
atatatatat atatatacac acacacacac acacacaaac atctgaatat ttatatatat    94980
gtctgaatat ttatatactt gtgtataaaa cttatattta aatttttgca taaatttata    95040
tatttttaat atttcattaa aaattatatt gtttcactat gtatgtctga gtattttat    95100
atattttaat ataacatttt atatatttat atataaatat tcaggtatgt aactgaatat    95160
tcatttacac acacaaatat atgtgtgcat gtgtgtatat atatatatac ccatatatat    95220
atatatatat atatatacat atatatatat atatatatat gtatatatat atatatatat    95280
atatatacac acacacacac acacatac atacaggtat aaacacactg ggcctgaagc    95340
accagtggtc tgaaaggaca tgtgttgcca ggacttgaag agcaaaagca ggaaggcgga    95400
tgagagtcag gaggtacaca aacgctgaaa agtaaaatgg acaagtacat ggacaaaaag    95460
caggtataag cataacagcc ttttggaagt aaatgactat aaaatatatg aaaatactgt    95520
tttcacaagt tgcacaacag atagtagtgt attgagataa tttagaacag aaaacaaatg    95580
tgatcaaccc cataagtgtg ctgtatttca tcatggattg aaggaaaaag agatggagcc    95640
caagaagacc acagcagtct tgatgaactg agagcaccca gagtttggga ttacaaaggc    95700
agctgggatt ttctcacactt ggtaataatg agaaagaatt tgtggagata aagagctaca    95760
gtcatgtacc tagaagtcac ctcagtgtaa tataaatctg catatgcaca gggagtgatt    95820
ccacaatgaa agtaggacaa agaacagcta ctggggaaag aataactaca agggaacaat    95880
gagttcaatg gagatggcag agctcacaaa gcactggagt atatttgagt tcttaccagc    95940
tagaaaagag acctcattgc aaatcttggg cattcagtag agaccccaga aaagccactc    96000
tttgaaaaca gagttgatgt attttaagag caaaatctac tccacaaaaa tcctagcaaa    96060
attgaaaagc aagtcagaaa gaccaaaatc ctctcaacat aaattagttg cccatcagaa    96120
gaaagcttaa cctcttcata ggtaaacaat aaaatcaaat tgctcagtta tctggcatcc    96180
acaatatgtg acataaattt aaaaattac tagacataca agaagcattt agtgtgatcc    96240
ataaccagga gaaaaatcat tcaatacaaa tagacccaga aatgacagaa atgatagaat    96300
tagcaaaaac atttaaaata tacatatgat catttgatct tgtgatcaga tatcacaaga    96360
gaagaaagag atacttgaac agaaaaaatg cctgaagcaa tgatggctga aaactttcca    96420
aatatgaaga aaaaaagct cacagattca agaaaactaa tcaatcagaa atatgatttt    96480
gaaaagtaaa aatgtatgat ttactttggc aaatcttctt ggttaaattg tctaaaatca    96540
aagaaagcta ggaaaatttt ataagccaga ggaaaaaaga ttgtttatat aaaggaacag    96600
ttacacaaat gactgatgcc ttctcatcag aaacaatgaa agtcagaaac aataaagtaa    96660
catcttttaaa gtaatagaag aaaaacccaa gaggtgaggg atcgtggcag acaggaggca    96720
ggactagatt gcagctctgg acagagcagc atgcagaggc tcatattgtg aattttagcc    96780
ccatattgac tgcaagaaca gaccagcaat cctgagagga cccacagacc gtgtgaagga    96840
agcagactgc tcctgcagga taaggagac accccaaata ctgtgagttc cccaactgca    96900
gaagtggaaa agggaggcct tactccctca aacacacccc acaactggag aagctgaaag    96960
tctgtttgca ggagaagttc caacttact ctgggcctca gtaaatttag agagctgagc    97020
caagcaaaat ataggggtag aggaagcagc agagaagacc tcagagcttg ctggatcccc    97080
aagcagctca ttcctgcctg gcaccacaga gatccatcag aagtgtggcc aaaggaacag    97140
agggtaaaac tccacatgga ggactgctct acctgaactt tctaacaatt tgaacaggg    97200
gagaagcctc ctggccagaa cttggggag gcatgaatc tggtttgcag acttcacagg    97260
tgggggaagg actaaagccc ttttcttttca cagctgggag gtgaaagcc tcaggcaagt    97320
tttcaagcct gactttcccc ccacctgaa acagacttgg agctgttgcg gggttggggg    97380
catggtggga gtaagaccag ccccttcagtt tgcatgggtc ctgggtgagg cctgactg    97440
acagcttccc tccacttccc cgacaactca gataggcagc cataatcctc                97500
ctaggtacac aactccagtg acctgggaac ttcacccca caccatacag aagcttcagt    97560
aagacgtgcc caaggaaagt ctgagctcag acacgcctag tcccaccccc aactgatggt    97620
ccttccctac ccaccctggt agcagaagac aaagagcata taatctttgg agttctaggg    97680
cccacccacc tctagtccct ctccacacta gtatagctga tgcaggaggc caaccagcac    97740
aaaaatgag cattaaacca caaagctag gaaccctcct ggagtccatt gcaccctcct    97800
ccacctccac cagaacaggc actggtatcc acagctgaga gacccataga tggttcacat    97860
cacaggactc tgtacagaca gtcccagta ccagcccaga gctgggtaga cttgctaggt    97920
ggcaagaccc agaagacagg caataatcac tgcagttcag ctcacaggaa gccacatcca    97980
tagaaaagag gggagagtac tacatcaagg gaacacccca tgggataaaa acatctgaac    98040
aacagccttc agccctacct tccctctgac acagtctacc caaatgagaa ggaaccagaa    98100
```

```
aaccaaccct ggtaatatga caaaacaagg ctcatcacac tcccagttca ccagcaatgg  98160
atccaaacca agaagaaatc cctgatttac ctgaaagaga attcaggagg ttagttatta  98220
agctaatcag ggagggacca gagaaaggca agcccaatg  caaggaaatc caaaaaaaaa  98280
aaggtataag aagtaaaagg tgaaatattc aacaaaatag atagcttaat aaaaaaacaa  98340
taaaaaattc agtagacttt ggacacacct ttggaaatgt gacatgctct ggaaagtctc  98400
agcaatagaa ctgaacaagt agaaaaaata aattcagagc tcaaagacaa ggacttcaaa  98460
ttaacccaat ccaacaaaga caaagaataa aggataagaa aatatgaaca aagccttcaa  98520
gatgtctggg attatgttaa atgaccaaat ataagaataa tcgtggctcc tgaggaaaaa  98580
gacaatacta aaagcttgga aaacatattt ggggaataa ctggggaaaa cttacctggc  98640
cttgctggac acctagacat gcaaatacaa gaaacacaaa gaacatgtaa atacaagcag  98700
cacaaagaac acctgggaaa ttcatcacaa aaagatctta gcctaggcac attctcatca  98760
ggttatgcaa agtaagacg  aaggcaagaa tcttaagagc tgtgagacag aagcaccagg  98820
taatgtataa aggaaaccct atcagattaa cagccagttt ttcagcagga actgtacaag  98880
ctataaagga ttggagccct atcatagcct cctcaaacaa aacaattatc agtcaagaat  98940
tttgtatcca gcgaaagtaa gcatcatata tgaaggaaag atacagtcgt ttttggacaa  99000
acaaatgcta agagaattca ccattaccaa gtcaccacta gaagaactgc taaaaggagc  99060
tctaaatctt gaaacaaatc ctagaaacac atgaaaacag aatctcttta aagcataaat  99120
cacacaggac ctataaaaca aaagtacaag ttaaaaaaca aaacaaaaa  acaaaaccaa  99180
agtacggagg caataaagaa tatgatgaat gcagtggcac ctcacatttc aatgctaaaa  99240
ttgaatctaa atggcctaaa tgctccactt aaaggataca aaaagagttg gtggctggca  99300
agatggctga ataggaacag ctccagtctg ccgctcccg  tgagatcaac acataggggtg  99360
ggtcatttct gcatttccaa ccaaggtacc cggctcatct cattggact  ggttagacag  99420
tgggtgcagc ccacagaggg tgacctgaag cagggtgggg tgtcacctca cctgggaagt  99480
ggaaggggtc agggaactcc ctcccctagc caaggaagc  cgtgagggac tgtgccgtga  99540
agaccagtgc attctggcac aaatactatg cttttcccac ggtctttgca acctgaagac  99600
caggagattc ccttgggtgc ctacaccacc agggccctgg atttcaagcc caaaactggg  99660
ctggcatttg ggcagacact aagctagctg caggagtttt ttttcatacc ccagtggtcc  99720
ctggaatgcc agcaagacag aaccattcac ccccgtgaag aaagggctga agccaggag   99780
ctaagtggtc tttctcagtg gatcccaccc ccatggagcc cagcaagcta agctccactg  99840
gcttgaaatt cttgctgcca gcacagcagt tgaagttgca cctgggacgc tcaagcttgg  99900
tgggaggagg ggtatccaca aatactgggg cttgagtagg aggttttccc ctcacagtgt  99960
aagcaaaacc gctaggaagt ttgaactggg cagggtgcac tgcagcttgg caaagccatt 100020
gtagcaagag tgcctctcta gattcctcct ctctgggcag ggcatctctg aaagaaaggc 100080
agcagcccca gtcagaagct tatagataaa actcccatct ccctgggaca gagcaactga 100140
aggaagggg  ggctgtgagt gcagctccag cagacttagt ttcctgcctg ccagctctga 100200
aaagagcacc agatccccca acacagcact agagctctga taagggacag actgcctcct 100260
caagtgggtc ctggtttcag aagataataa gaaactcctc tgagctaaag gagcatgttc 100320
taacacaatg caaggaagct aagaaccttg aaaaaggtca gaggaattgc taactacagt 100380
aagcagttta gagaagaaca taaatgacct tagggagctg aaaaacacag cacgagaact 100440
tcatgcacaca tacacaagta tcaatagcaa aatcgatcaa gtggaagaaa ggatatcaga 100500
gattgaaaat caacttaatg aagtaaagcg tgaaaacaag attaaggaat aaagaatgaa 100560
aagaatgaa  caaatcctcc aagtatggga ctatgtgaaa agattgaacc tacgtttgat 100620
tggtgtacct gaaagtgatg ggagaatgga accaagttgg aaaacactct tcaggatatt 100680
atccaggaga acttccccaa cctagcaaga caggccaaca ttcaaattaa ggaaatacag 100740
agaataccac attcaaattc aggaaatcaa gagaacacca caaagatact cctcaagaag 100800
agcaacctga agacacataa tcgtcagatt caccaaggtt gaaatgaagg aaaaaaatgt 100860
tgagggcagc cagagagaaa gtttgggtta cccacaaagg gaaccccatc agactaacag 100920
tggatcttcc tgcagaaact ctacaagcca gaagagagtg ggaggccaat attcaacatt 100980
ctttttttact attattatac tttaagttct agggtacatg tgcacaaggt gcaggtttgt 101040
tacatatgta tacatgtgcc atgttggtgt gctgcaccca ttaactcttc atttacatta 101100
ggtatatctc ctaatactat ccctccccac tccccccata ccatgacagg cccccggttg 101160
tgatgttccc cactctgtgt ccatgtactc tcattgttca attcccacct atgagtgaga 101220
acattcggtg tttggatttc tgtccttgtg atagtttgct gagaatgatg gtttccagct 101280
tcatccacat ccctacaaag gacatgaagt catccttctt tatggctgca tagtattcca 101340
tggtgtatat gtgccacatt ttcttaatcc agtctaccat tgatggagct tgtgttggt  101400
tccaagtctt tgctattgtg aatagtgccg caataaacat atgtgtgcat gtgtctttat 101460
agcagcatga tttataatcc tttagatata tatccagtaa ttgtatggct gtgtcaaatg 101520
gtatttctag ttctaaatcc ttgaggaatc accgcactgt cttccacaat ggttaaacta 101580
gtttacagtc ccaccaccag tgtaaaaatg ttcctatttc tccacatcct ctctagcatc 101640
tgttgtttcc tgacttttta atgatcacca ttctaactgg tatgagatgg tatctcattg 101700
tggttttgat ttgcatttct ctgatggcca tgatggtga  gcacttttttc atgtgtctct 101760
tgactgcata aaagttttct tttgagaatt gtctgttaat atcctttgcc aacttttga  101820
tggggttgtt tgattttttt tcttgtaaat tgttatgt   tctttgtaga ttctggatat 101880
tagcccttg tcagatgggt agattgtaaa aattttctcc cattctgatg cttgcctgtt 101940
cattctgagg gtagtttctt ttgctgtgca gaagctcttt agtttaatta gatcccattg 102000
gtcaattttg gcttttgttg ctattgcttt ggtgatttta gtcatgaagt ccttgcccat 102060
gcctatgtcc tgaatggtat tgcttaggtt ttcttctagg gttatatgg  ttttaggtct 102120
aacatttaag tcttttaatc atcttgaatt aattttata  taaggtgtaa ggaagggatc 102180
cagtttcagc tttctacata tggctaggca gttttcccag caccatgtat taaataggga 102240
aacctttccc tatttcttgt ttttgtcagg tttgtcatag ttcagatggt tgtagatgtg 102300
tggtattatt tctgagggct ctgttctgtt ccattggtct atatctctgt tttggtacca 102360
gtaccatgct gttttggtta ctgtagcctt gtaatgtagt ttgaagtcag gcagagtgat 102420
gcctccagct ttgcttttt  ggcttaggat tgtcttggca atgcatgctc ttttttgttc 102480
caaact ttaaagtagt tttttccaat tctgtgaaga agtcattgg tagcttgatg 102540
gggatggcat tgaatctata aattaccttaa ggcagtatgg ccattttcac aatattgatt 102600
cttcctatcc atgagcatgg aatgttcttc catttgtttg tgtcctcttt tatttcatta 102660
agcagtggtt tgtagttctc cttgaagagg tccttcccat cccttgtaag ttggattcct 102720
aggtatttta ttctctttga agcaattgtg aatgggagtt catccatgtc cctacaaagg 102780
acatgaagtc atgtatggga atgcttgtga ttttttgcaca ttgattttgt atcttgagac 102840
```

```
tttgctgaag ttgcttatca gcttaaggag attttggtct gagaagatgg ggttttctaa   102900
atatacaatc atgtcatctg caaacaggga caatttaact tcctcttttc ctaactgaat   102960
accctttatt tccttctcct gcctaattgc cctggccaga acttccaaca ctatgttgaa   103020
taggagtggt gagagagggc atccctgtct tgtgccagtt ttcaaaggga atgcttccag   103080
tttttgccca ttcagtatga tattggctat gggtttgtca taaatagctc ttattatttt   103140
gagatatgtc ccatcaatac atagtttatt gagagttcag catggagagc tgttgaattt   103200
tgtcaaaggc cttttctgca tctattgaga taatcatgtg gtttttgtct ttggttctgt   103260
ttatatgatg gattacattt attgatttgc atatgttgaa ccagccttgc atcccaggga   103320
taaagccaac ttgatcatgg tggataagct ttttgatcgt ctgctggatt cggttttgcca   103380
gtattttatt gaggattttt gcatcaatgt tcatcatgga tgttggtcta aaattctcat   103440
ttttgttgtg tctctgccag gatttggtat caggatgatg ctggcctcat aaaatgagtt   103500
agggaggatt ccctcttttt ctatgattgg aatagtttca gaagaattgg taccagctcc   103560
tctttgtatc tgtggtagaa ttcggctatg aatctctcct ggacttttt tggttggtag   103620
gctcttaatt attgcctcaa tttcagagcc tgttattggt ctattcaagg attcaatttc   103680
tttctggttt agtcttggta gggtgtatgt gtccaggaat ttttccattt cttctagatt   103740
ttctagttta tttgcacaga ggtgtttata atattctctg atggtagttt gtatttctgt   103800
gggattggta gtgatatccc ctttatcatt ttttattgca tctatttgat tcttctctct   103860
tttcttcttt attagtcttg ctagtgtct atcaattttg ttgatcttct caaaaaacca   103920
gctcctggat tcattgatgt tttgaaggtt ttttttgtgtc tctatctcct tcagttctgc   103980
tctggtctta gttatttctt gccttctgct agctttttaa tgtgtttgct cttgcttctc   104040
tagttctttt aatggtgatg ttagggtgtc aattttagat cttcctgct ttctcttgtg   104100
ggcatttagt gctgtaaatc tcccccctaca cactgcttta aatgtgtccc agagattctg   104160
gtatgttgtg tctttgttgt cattggttc aaagaatatc tttatttctg ccttcatttc   104220
gttacatacc cagtagtcac tcaggtgcag gttgttcagt ttccatatag ttgagcagtt   104280
tttaatgagt ttcttaatcc tgagtcctag tttgattgca ctgtggtctg agagacagtt   104340
tgttataatt tctgttcttt tacatttgct gaggaatgcc tcacttccaa ctatctgctg   104400
aatttcagaa taagtgcgat gtggtgctga gaagaatgta tattctgttg atttgggtg   104460
gagagttctg tagatgtcta ttaggtctgc ttggtgcaga gctgagttca attcctggat   104520
atccatgtta actttctgtc tcattgatct gtctaatgtt gacagtgggg tgttaaagtc   104580
tcccattatt attgtgtggg agtctaagtc tcttttgtagg tctctaagga cttgcttttat   104640
gaatctaggt gctcctgtat tgggtgcata tatattttagg atagttagct cttcttgtta   104700
aattggtccc tttaccatta tgtaatggcc ttctttgtct cttttgatct ttgttagttt   104760
aaagtctgtt ttatcagaga ctaggattgc aaccccctgct ttttttgttg tttccatttt   104820
gcttggtaga tcttcctcca tcccttattt ttgagcctgt gtgtgtctct gcacgtgaga   104880
tgtgtcttca gaatacagca cactgatgga tcttgactct ttatccaatt ttccagtctg   104940
tgtcttttaa ttggagcatt tagcccattt acatttaagg ttaatatttt tatgtgtgaa   105000
tttgatcctg tcatcatgat gttcgctggt tattttgctc attagttgat gcagtttctt   105060
cctagcatcg atggttttta caatttggca tgtttgtgca gtggctgata ccgattgttt   105120
ctttccatgt ttagtgcttc cttcaggagc tcttgtaagg caggcctggt ggtgacaaaa   105180
tctctcagca tttgcttgtc tgtaaaggat tttatttctc cttcacttat gaagcttagt   105240
ttggctggat atgatattct cagttgaaaa ttcttttctt taagaatgtt gaatattggc   105300
tgccactctc ttctggcttg tagagtttct gctgagagat ctgctgttag tctgatgggc   105360
ttccctttgt gggtaacccg acctttctgg tgaatctgac aattatgtgt cttggagtta   105420
ctcttctcga ggagtatttt tgtggcattc tctgtatttc ctgaatttga atgttggcct   105480
gcctttgtag gttggggaag ttctcctgga taatatcctg aagagtgttt tccaacttgg   105540
ttccattctc ctcgtcactt tcaggtacac caagcagatg tagatttggt cttttcacat   105600
agtcccatat ttattggagg cttttgtcat ttcttttttac tccttttttt ctctaaactt   105660
ctcttctcgc ttcatttcat tcatttgatc tttaatcact gatacccttt cttccacttg   105720
attgaatcaa ctactgaaac ttgttcatgt gtcacgtagt tctcgtgcca tggttttcag   105780
ctccattaga tcatttaagg tcttctctat gctgtttatt ttagtctgcc attcatctaa   105840
actttttcaa ggttttttagc ttctttgcaa tgggttcgaa catccttctt tagctcggag   105900
aaatttgtta ttacagatcg tctgaagcct tcttctctca actcatcaaa gtcattctct   105960
gtccagcttt gttctgttgc tcgtgaggag ctgcgttcct tcggaggaga agaggcaccc   106020
tgattttag aattttcagc tgttctgctc tggtttctcc ccatctttgt ggtttatcta   106080
cctttggttc ttgatgatgg tgatgtacag atgggggtttt ggtgtggatg tcttttctgt   106140
ttgttagttt tccttctaac agtcaggacc ctcagctgca ggtctgttgg agtttgctgg   106200
aggtccactc cagtccctgt ttgcctgggt attaccagtg gaggctgcag aacagcaaat   106260
attacagaac agcaaatgtt gctgcctgat tcttcctctg gaagcttcat ctcagagggg   106320
caccccagctg tatgaggtgt cagttggccc ctactgggag gtgtcccca gttaggctac   106380
tcggggtca cggacccact tgaggaggca gtctgtccat tctcagatct caaactctct   106440
gctgggagaa ccactactct cttcaaagct gtcagacagg gatgtttaag tctgcagaag   106500
tttctgctgc cttttgttca gctatgccct gcccccagag gtgagtctca cagaggcagg   106560
caggtctcct tgagctgtgg tgggctccac ccagtttgag cttcctggtc gctttgttta   106620
cctactcaag tctcagcaat ggcagacgcc cctccccccag ctttgctgcc gccttgcagt   106680
tcggtctcag actactgtgc tagcagttca atctccagact gctgtactag cagtgagcaa   106740
ggctctgtgg gcatgggacc ctctgagcca tgtgcaggat ataatctcct ggtgtgccgt   106800
ttgctaagac cattggaaaa gtgcaatatt agggtgggga tgtcccgatt ttccgggtac   106860
atctgtcatg gcttcccttg gctaggaaag ggaattccct gaccccttac acttccccggg   106920
tgaggcaata tcccgccttg cttcggctca ctctccgtgg gctgcaccca ctgtctgaca   106980
agccccggtg agatgaaccc agtacctcag ctgaaatgc agaaaccacc catcttctgc   107040
tttgctcatg ctgggaactg tggactggag ctgttcctat tcggccatct tgaaacctcc   107100
cctctctcac gatcacaagg tcccacaata ggccgtctgc aggctgagga gcaagaaaag   107160
ccagtctgaa ttcaaaaact gaagaaattg gagtctgatg ttcaagggca ggaaacatcc   107220
agtgccaaag aaagatgtag aatattcaac attcttaaag aaaataattt tcaacctaga   107280
atttcatatc cagccaaact aagctttata acaaaggaga agtaaaatcc tttacaaaca   107340
agcaaatgct gaggaatttt gtcaacacca ggcctgcctt acaagaggtc ctgaagaaaa   107400
cactaaatat ggaaaggaaa aaccagtaac agctactgca aaaacatacc aaattgtaaa   107460
caccatcaac actataaaga aactgcatca actaatgggc aaaatagcca gctagcatca   107520
taatgacagg atcaaattca cacataacaa tattaacctt aaatgtaaat gggctaaatg   107580
```

```
ccccaattaa aagacacaga ctgggaaatt gaataaagag tcaagaccca ttggtttgct   107640
gtgttcagaa gacccatctc agggtgaaaa gacatacatg ggctcaaaat aaagaaatga   107700
aggaatattt accaagcaaa tggaaagaaa aaaaaagcag cggttgcaat cttagtcttt   107760
gatgaaacag actttaaacc atcaaagatc aaaagagaca aaggagggca ttacctaatg   107820
gtaaaagtat caatgcaaca agaagatctg actgtcctac ttatatatgc acccaataca   107880
ggagcaccca gattaataaa gcaagttctt agagacctac aaagagactt agacttccac   107940
acaaaaatag tgggagactt taacacccca cagccaatat tagatcgacg tgacagaaaa   108000
ttaacaagga tattcaggac gtgaattcag ctctggacca agctgaccta atagacatct   108060
acagaactcg acaccacaaa tcaacagaat atacattctt ctcagcacca cattgcactt   108120
attctaaaat tgaccacata attggaagta aaacacttct cagcaaatgc cgtagaatgg   108180
aaatcataac aaacagtctc tcagaccaaa gtgcaatcaa actagaactc aggattaata   108240
aactcactca aaaccacaca actatatgga aactgaacaa cctgctcctg aattactact   108300
gggtaaataa caaaattaag gcagaagtag ataagttctt agaaaccaaa gagaacaaag   108360
acacaatgtg ccagaatctc tggtacacag ctaaagccat gtttagaggg aaatttatag   108420
cactaaatgc ccacaggaga aagcgggaaa gatctaaaat caacacccta acatcacaat   108480
tcaaagaacc agagaagcaa gagcaaacaa atacaaaagc tagcagaaga caagaaataa   108540
ctaagatcag agcagaactg aaggggataa agacacgaaa acccttttaaa aaattaataa   108600
atccaagagc tggttttttg aaaagattaa caaaatacat agaagcctag ccagactaat   108660
aaagaagaaa atagaagaga atcaaataga cacaataaag aataataaag gggatatcac   108720
caatgatgcc acagaaatac aaactaccat cagagaatac tttaaacacc tctatgcaaa   108780
taaaatagaa aatctaaaag aaatggataa attcctggac acatacaccc tcccaagact   108840
aaaccaggaa gaagtcaaat ccctgaatag accaataaca agttctgaaa tcgaggcagt   108900
aattaatagc ttaccaacca aaaaaagccc agaccagagg gattaacagt caaatcctaa   108960
cagaggtaca aagaagagct agtactattc cttctgaaac tattccacac aatagaaaaa   109020
gagggactcc tgcctaactc attttatgag gccagcatca ttctgatacc aaaacctggc   109080
agagacacaa caagaaaaga aaatttcagg ccaacatccc tgatgaacat cgatgtgaaa   109140
atcctcaata aaatactggc aaactgaatc cagcagcaca tcaaaaagct tatccaccat   109200
gatcaagttg gcttcatccc tgggatgcaa ggctggttca acatattcaa atcaataaac   109260
ataatccatc acataaacag aaccaatgac aaaaaccgta tgattatcgc aatagacgca   109320
gaaaaggcct ttgataaaat tcaatacccc atcatgctaa aaactcttaa taaactaggt   109380
attgatggaa catgtctcaa aataataaga gctacttatg acaaatgcat agccaatatc   109440
atactgaatg agcagaagct ggaagcattc cctttgaaaa ccagcacaag acaaggatgc   109500
cctctctcac cactcctatt caacatagta ttggaaattc tgtccagggc aatcaggcaa   109560
gagaaagaaa taaaggtatt caagtgggaa gagagggagt caaattattt ctctttgcag   109620
atgacatgat tgtatattta gaaaactcta tcatctcagc ccaaaatctc cttaagctga   109680
taagcaactt cagcaaagtc tcaggataca aaatcaatgt gcaaaaatca caagcattcc   109740
tatacaccaa taagagacac agagccaaat cctgagtgaa ttcccattca caattgctac   109800
aaagagaata aaatatacct aggaatccaa cttacaaggg atgtgaagga cctcttcaag   109860
gagaactaca aaccactgct caaggaaata agataggaca caaacaaatg gaaaacatt   109920
ccatgctaat ggattggaag aatcaatatt gtgaaaattg ccatactgcc caaagtgatt   109980
tatagattca atgttatccc catcaagcta ccattgattt cttcacataa ttagaaaaaa   110040
ctactttcaa tttcatatgg aatagaaaaa gggcctgtat atccaagaca acctaagcaa   110100
aaagaacaaa gctgaggca tcatgctatc tgacttcaaa atactacaa aggctacagt   110160
aacaaaaaca gcatggtatg gtactggtac caaaacagat atatagacca atagaacaga   110220
acagaggcct cagaaataac accacacatc tacaactatt ggatctttga caaactggac   110280
aaaaataagc aatggggaaa ggattcccta tttaataaat ggtgttggga aaactggcta   110340
gccatatgca gaaaactgaa actggatccc ttccttacac cttatacaca aattaactca   110400
agatagatta aagaattaaa tgtaagacct aaaaccataa aaccctaga agacactttg   110460
ggaggccgag gtggatggat cacgaggtca ggagatcgag accatcttgg ctaacacagt   110520
gaaagcccat ctctactaaa aatacaaaaa attagctggg tgtggtcgtg ggcacctgta   110580
gtcccagcta cttgggaggc tgaggcagga aatggcatg agctgaggag gttgagcttg   110640
cagcaagcca agattgtgcc actgcactcc agcctgggca acagagtgag actccatcaa   110700
aaaaacaaaa acaaaaacaa aaaatcaaac cctagaagaa aacataggca ataccattca   110760
ggacataggc atgggagaag acttcatgac taaaacagca aaaccaatgg caacaaaagc   110820
caaaatttac aaatcagatc taattaaaat aaagagcttc tgcacagcaa aaaactctca   110880
tcagagtgaa aaagcaacct atggagaaaa attctgtggt ctagccatct gacaaagggc   110940
taatgtttag aatgtacaag caacttaaac aaatgtacaa gaaaaaaaa caaccccat   111000
caaaaagtgg gcaaggata tgaacagaca cttctgacag gaagaccttt atgtggctga   111060
caaacatgaa aaaagctcat catcactgtt aattagagaa atgcaaatcg aaaccacaat   111120
gagataccat ctcatgcccg ttagaatggc gatcattaaa aagtcaggaa acaacagatg   111180
ctgaagagga tgtgtggaga aagaggaaca catttacact gttggtggga gtgtaaatta   111240
gttcaaccat tgtggaagac agtgcggtga ttcctcaagg atctagaacc agaagtacca   111300
tttgacccag caatcccatt actgggtata tacccaaagg attataaatc attctacaat   111360
aaagacacat gcacacgtat gtttattgta gcactattca caatagcaaa gacttggaac   111420
caactgaaat gcccatcaat gatagactgg ataagaaaaa tgtggcacat atacactgtg   111480
gaatactatg cagccataaa acaggatgag ttcatgtctt ttgcagggac atggatgaag   111540
ctggaaacca tcattctcag caaactaaca caagaacaga aaaccaaaca ccatatgttc   111600
tcactcataa gtgtgagttg aacaatgaga acacatggac acaggaaggg gaacatcaca   111660
cacaggggcc tgttgggag ttgaggctag gggagggatt ggattaggaa aaatacctaa   111720
tgtagatgat gggttgctgg gtgcagcaaa ccaccatgac acgtgtatac ctatgtaaca   111780
aacccacaca ttctacacat gtatctcaga acttaaagta taataataat aagatacaga   111840
actgcagaat gaataagaac tcaccaacca tctgctgcct tcaggagact catttaagac   111900
ataaggactc acataaactt aaagtaaatg ggtggaaata ataataagtg gtgtcactga   111960
tgtggaggta gattataaaa ctcttatcat atgctgggta aagatcaaaa tgataaaacg   112020
aattaaaaaa tcagtcagat ggttttctaa aaagttccat caatatgcct ctatcttaca   112080
aacctgcaat tctattcctg aatctttatc ccaaggaaat gaaaaagtaa gtccacaaag   112140
agttctatat gaatatttat aggagcttta tttattataa ttcaaactgt aaaaataatt   112200
tcaatgttca tcaataacaa aatgaaaaaa taatttgcaa cctactggta cacttgaata   112260
ctattcagca ctgagtatct taaatagcat ggatggagct caaaaatata ctcaggaaag   112320
```

```
aagccatgta tattctgtat gagttcattt acatgagatc atttacattt cctccaaaag  112380
aggaaaaact aatttctgtt gaaagaaacc aatgtatttg cctctggcag tggtaagggg  112440
gtagcacaga ttaattgggt agggactcaa gagagtttct ggggtcacag aaatgttccg  112500
tgtggtgatg ggagtttggg ctccacaggt ataggtgttg atccaaaatc atcaaaaaaa  112560
caacattgca gatctgtgca tctcactctg tgggaaagta tatctcaact gtaaaaaggg  112620
cagaaattgc ttttaaacgc tcagccttt agcacatcca gttgcttgga gaaccagctt  112680
actcaaatgg gggtctaggc tggagactag gtcacaggca tagagtctct aaactttccc  112740
atggcacata atacgtttca ggttttctca gagagctgca ggttagtaat ctgaggattc  112800
tgacaagttg ggtcaacgtt cctaggaggc atgaatggga gtgcattctc taagatccct  112860
ccaccccagg gtccttgctt tctgtgcctc ttactccatt gttttctgac tcctctgtag  112920
ccactcgacc tcttcagatc ccattgtcta cccagccatc gcccttatg acttgggtcc  112980
cactgttctt tcatctcatc ctccattccc tcagtttcgg agtggctgcc gctagcagag  113040
gatggactga gagcaggaga ggtggtcctg cccaggaacc catcctagag aaatggcatc  113100
ctgtctggga gctagttttt tagggcaggt tttataagtc ttgtaaagcc agacacactt  113160
gatctacctg gtatgttatt tacagtaata ctattttcat aattgctttt cactctaaaa  113220
gtagagcctt ttagctacac tgtgagtaaa taaagggggct ggcctgggaa tggtatcatg  113280
ttggatgttg ttttcttccct gaagtaatat atatcagtta caattacat gttactgcag  113340
agtcctagag agagacacag agaatgagac agataccaat acattttat gtgcattaaa  113400
aaaatctaag gccaggcgca gtggctcaca cctgtaatcc cagcactttg ggaggccgag  113460
gtgggtggat cacgaggtca ggagattgag accatcctgg ctaacacggt gaaaccctgt  113520
ctctactaaa aatacaaaaa attagccagg cgtggtggcg ggcgcctgta gtcccagcta  113580
ctcaggagac tgaggcagga gaatggcttg aacccaggag gcagaccttg cagtgagccg  113640
agattgcgcc actgcactcc agtctgggcg acagagcgag actccgtcac aaaaaaaaaa  113700
aaaaatctaa aatgcactct tcaaaatcta tgtcatttat tctggaggaa tgcagttggc  113760
agaaggagga agatattccg aattttctt gtatacattt atgtatgatc tcagtttttt  113820
tatggatcat agaccaattt tgatatttta aaataaaaat tataatctat cttggaaatt  113880
tacatggttc tttagaactt gaggaccgtt tttgcttttc ggaatattat tgtacctaaa  113940
atgggaatat tacaacgtca cttttaaca cttgtttata acaaagttta gacagcgctg  114000
ggtgcccctg aattttttcc cgcctcttgt gacctgtgtt gttttggaat ttgcagtggc  114060
ctgaccgaga actactgcag gaatccagat tctgggaaac aaccctggtg ttacacaacc  114120
gatccgtgtg tgaggtggga ggactgcaat ctgacacaat gctcagaaac agaatcaggt  114180
gtcctagaga ctcccactgt tgttccagtt ccaagcatgg aggctcattc tgaagcaggt  114240
aagaagtctg tggccagata tctacacatt tgaacattgg gatgaaaaga gatggaaaat  114300
ctgactgatg cagaagcctt ccatgctaca cagaaacttg agggtatgge aggtggaaag  114360
aagcctcagc actctctctg gtggagcaat ttttggcgca acgtgcgtgg gcggtgactt  114420
caggaatggt gcaaacccac ctgggcactt gacttaccac tcactttgtt atgaaagggg  114480
ttatctcggt gttccagaca aaattccaat tctaacatca ggccaaattt gtgccaaatt  114540
tcacactagt gagtgtttcc aggcattat taaaatggac agtgttcatt gcaatcttca  114600
gcattgcagt tgctgaggta tgtgccgct gagtttgtca tcctgggaa acctaatatg  114660
atgatattta ttccatctaa tcctgggggct atttggcagt aaataccaca gaatacacta  114720
tttctctggc ttatttcagt cttaggtagg ctctgcacac ctatgcttgg aaggcaggaa  114780
tttcttggtg ttccttgtgcc ttcttctcat ggaacgtgca tctttggtgt gtgttgagag  114840
gaagggtagt agacttctgc tttgttgcaa tgcaggatgc tggaacaaga ggattccctg  114900
tctctactgt aagggaataa gattttagcc tccatccttc tctaagaagc aatgtgtctt  114960
tgcctccaag tactagatgc aggaccatga actgccccgt ccaccagaag cttaaggctt  115020
tggcttttca ggagcaatca tctagggaac tgtgcagggt tttcatgtct gtcccctact  115080
gacagccaat caccatacag cctgcataac ctaatccatc atcgtctgtt ttcctgcctc  115140
attgttttca tgaacaacca gtagagagcc atacgaaaga gcttcacat gagtcttgt  115200
tccaattgta agagcactga taggtccttt tcccaccagg ttttgaatat aaaatttcta  115260
agaacttatt aaaatattag aatgttatta atctattgtt tttgcttcag catgtccttc  115320
tgcttgtgag tatactaaag agaacagtca taattctgaa actactgtcc tgttttgtc  115380
ataaattgct tcacatgttt ctgcatacta gtagttactc agcttgattt tgtctatttt  115440
cagcaccaac tgagcaaacc cctgtggtcc ggcagtgcta ccatggtaat ggccagagtt  115500
atcgaggcac attctccacc actgtcacag gaaggacatg tcaatcttgg tcatccatga  115560
caccacccg gcatcagagg accccagaaa actacccaaa tgagtatgtc tttgatgtta  115620
cttgtaagag gagcaacagc caacttaagt tcctcctaga agagccttgc ttcaagctaa  115680
cttgttagga caaatttccc ttagaccag aaggtgtgtc aaaatgtcca gacaactttg  115740
cttttgatca aagagtctga gagaataggt attttaggct tgctatcttt tctaatagtc  115800
tgatgagaagc agaaggctac atggagctga tgaggtcttt ttaatataaa gctcaagaga  115860
tcaaatgatc aaatacttag agtgccattc tacaaggctc ataaaagatc aatgcactct  115920
ttcacccatg caattctatc attctaacct cccttctctg aaatgaaggc tttttgccat  115980
ttttgtcatg ggtcacaagt aaataattca catgtatatg agtatatata taccaggtg  116040
tgtttattca gactagtatg tatatatata catatatatg ttcatataag ttagtattca  116100
tatatatgtt catatatata tgttcataca gactagtatt catatatata tacatatact  116160
tatacacaca catatatata tatatatata tgttctaggg aaacatgcaa ggtttttatg  116220
tctgtccctg actgatgacc aaatacccta tagcctgcac agctgcaagc tgtatagcca  116280
tacaatttgc aggacacaca cacatacaca cacacacaca cacacacaca cactaacata  116340
taataataa taatataata taatataata taatataata taatataata aatatatata  116400
aacctgtgtg aacacactgg gttctaagct ccagttttct gaagggatat gggttgccag  116460
gagaggaaga gcaaaagcaa gaatgtgagt gagaattagg aagtaaacag atatggagat  116520
taaaatgggc aggtacatgg acaaaaaacc aggtctgaca aaaactggct ttctgccata  116580
aatgactata aaagatatta aaaacacttt tccacatgtt ggacaagaga cagtacagga  116640
ctgagataat ttagaaaagg aaatgaatga gcgcaactcc gtaactatta tgactttctt  116700
cctggagaac cttcctggac tgaagggcaa ggaattggaa ccaaagccaa ccacagccaa  116760
cttgctgaac tgaggaaaga gactggagtt tgggatagct aagaaaatgt gtattttcta  116820
tgctaggtaa taatgagaaa gaatttgtgg tgaaaaggaa ctgaaggaat atgcatggaa  116880
gtctaatata aactgcatat gcacaggag aaattctaca aagtgggaca gagaaccact  116940
actggggaaa ggacaaattc agggaaacag tgagctcaat ggtgacgcca gagctcacgt  117000
agcactgggg gataccgggg ttctgatcag cccgaggaga gacacctcat tgaacatctc  117060
```

```
gggcattcag tagagacccc agaaaagtca tactttagga gtaggattta tgccttctta   117120
gaataaagac tacccagaa acaccctagt aaagcttaaa aaccaagtct aaaaggaccc   117180
aaatgatctc caagtaaatt aactgcctga cagaagaaaa ctcaaccatc actggaggta   117240
aataacatga ttacagtgct ctgtaatgtt gcattcacaa ggagtgacat catttaaaaa   117300
tttatgaggc aggaaaaagc aattagtgtg atccataact aggagaaaaa ccagtcaata   117360
caaatagacc aagaaatagt agaaacgatg gaattgacaa agaaattaaa actgtatata   117420
tgataattgt gttcaaagat ttaaagaaaa catgaacatg agggaaacaa atgcagaata   117480
taaaaaaaag caaatgcgta aaacaaccaa atggaaatta agaactaca aaaaagtata   117540
accttaataa aatactcact ggatggcctt aatattagtt tatacattac agaagaaaaa   117600
gtgaaccaga agataactca atgaaagcca tacaatctgt aagacacaca cacacgcaca   117660
cgcgcgcgcg cgcacacaca cacacacaca gagagagaga gagagagaaa gagagagaga   117720
gaaaggctga aaaaaataaa tagaaccttta aggatatcag tgaaaatagc aaaagattta   117780
atatatgggt aaagcaagtc acagaaggac gggaaggaga tattgggaca gaaaaaaata   117840
ctcaaagcaa tgatggctga agactttaca cgtatgaaga aaatgataaa ctcacagtca   117900
agaagctcaa tgaatcagaa atagtatttt taaaagcaaa actctatgat ttacttgggt   117960
acattatcga taaatcgtcc aacatcaaag ataacaagga taatcttata agccagagga   118020
aaacaatatc atttacatag agggacagta atgaaagtga ccgatgcctt ctccttgaa   118080
acaatggcat aacatcttta aagtgataaa gagaaataaa aacagatcaa cctaggacga   118140
catgtccagc caaacaaac aaataaacaa aaaaaccctt taaaataaac gtgatgtaaa   118200
tacgtattct gccacctcca gaggaaacaa gcaaaaaaac aaaagaatgt ttccaaggca   118260
ggcttctgta ttaaaagatt ttaaggaaag ttattcaggt agaagaaaaa taataccaga   118320
tgggaacttt aatccatact aagtaatgaa gagccctgaa aatggcaaat ggcaatgtca   118380
atataaaata ctcttattta tctaattttt aaatgtattt aaaggacaat ttgtgatatt   118440
aattaaaata ataggaatat attgttgttt caacgtatgt agtagtaaaa ttcataaaaa   118500
cagtagcaca aataatgcag atgataactg gaagtatact gttaatgagt tttttgcatt   118560
atccatgaag ttatataata ttaatagatg gttgaatgta atagttttaag gtgggatatt   118620
ataaatccta ggacaaccaa aaaaatttaa actgagagga atggatagta agaggaatag   118680
tccttttatg caaagaagg aagaaaaaga ggaataaaga atataaaaga tatggtgtaa   118740
acagaaaata catagcatta ttgtagacac aaactgaact accttatgag tatattaaat   118800
ataaaaggat taagcattac aaattaaaagg cagagattgt aaattgaata aaaaccacag   118860
ctaagtgtgt tctttttaga ataaatactc tttaagtgta aagatctact ttaaacacca   118920
aaatatgaaa aaggatatat accatgaaaa cctgaatcat aaataagctg gagtggtgat   118980
taatggatgc aggcactcct aaagactaat aagtgaatgt ggtcaaattg aagaaacaaa   119040
agtatatacg tgctcaatgt gcaaaaactt tttctgatga tcctatga tccttttgga   119100
aattaaagtt ttaaagcaat atcactgaca atagtatcaa aaccaaaaaa tatttagtga   119160
taaatttcac acactatgct caaggactat acaccttgca ctagaaaaca atgttgagga   119220
aagaattaaa agatctaaat atacaccatg cttatagatt aaaagactcc atatcagttc   119280
tcgtgaaatt gatctttgga tgaaaccacc acccaagcac tattgcaaca gtccttttt   119340
ggaaaaaaaa attggaggac ttatatacct taatataaga acttataaga gtacaggaat   119400
caagacatgt ggtattggcc tggccccttg gctcatgcct gttaccccaa catttttggga   119460
ggctgagtct ggaggatggc ttgagcccag atgttcaaga ccagccttag caacagagtg   119520
agaccctctc tctacaaaaa ataaacaatt agatcgatgt gatgacttgc acatgtagtt   119580
tcagctactc ggaatgctga ggtgagagga ttgcttgact caggaggtct agccatgagt   119640
gagcattgat catgcctctg cattccagcc tggatgatga aatgagacac tgtctcaaaa   119700
aaaaaaaaaa aaaaggatat gtgttattgg ccaaaaaagt atgcaaacct aaaaagggat   119760
ggcccaccac cagacccaca tacatatatg gtaaatggat tttccgtata gatggcaaag   119820
caattcaatg gagacaaaaa tgttttacaa aatcattctg aaccatttgg atatccatga   119880
tacaaaacaa aagcagaact tgacttttgc ttttcatctc aaattatttt gatatctctt   119940
ccacctaagt gtcagagcta aaactgaacc tgaaatatga aagttccatg aaaaaatata   120000
aaatcttcac aaccttggag aaggcaaact tttttgaggc aggagtctgt aaacactcac   120060
tataaaataa aacaaattat aatgtgggct ttcatgaaaa ctcatgctta ccaaagtca   120120
ttgttaagaa aataaatagg caagtaacac atgagaagaa aaatgctctc tgtccatata   120180
tctgacaaat ggcttgtgtc cagaatatag gaacatttct cccactcact aaacagagga   120240
caaacaacta atgggcaaca gattgaatag gcatttcttg gggatagata gatgtacaca   120300
tagccaataa gcacctgaaa aaatgtccag tatctcagcc atgaaaaata aagagttata   120360
atcatcatga gatgtcacca aacacccaat ggacatggat attattaaga agacaccaca   120420
gtaactgatg tcactgatgt agagcaagga tgtgaaactc tctcatatgc tggtgaaagt   120480
gcaaaatgat acaaccactt ttgaaatcag tctgatagtt tctccaaaag ttcaataaat   120540
gcacttttac cctacaaacc tgcaatcctg tttgtgaata ttaccccac agaaatggaa   120600
acataagtcc acgaagacat ctccaagaat attcatagca gctttatttt ttataacccc   120660
aaactgtaga caatttcaat gtcaatcaat aagaaaatga ataaataatt tgtgaactag   120720
tcatacaatg gcatactgtt cagcaataaa agggagcatg tttttgatac tctcaaatag   120780
tatggaagat gctcaaaaat attacattaa agaaagatgc cagataacaa aaatgaacat   120840
tatgtatgag tctattgatg taaggttcca gaaaggtaaa actaatttct ggtgaaagaa   120900
accaatatca tttgcctctg gccatggaa gagagtagca gagattgatt gagcagtaaa   120960
acgaagtttt tttctggggt gatgtaaatg tcctgtattg tgattgaagt gtgagttaca   121020
caagtgtaca tgttcatcag aagtcatcaa actacatcta agatctgtgc atttgactat   121080
acatgaaaat ataccttcagt tgaaaataga tcaataacct ccctcatata ctatacttgc   121140
taacacagcc agctgcttgg agaaccagct tgctggaatg gagaatctgg gcttcagact   121200
gggtcacatg tatagagtct ctacagagac aatgttgcat tcccacggta cataatacat   121260
ttcaaggttt ctcagacagc cacatgtcat gaatgtgagg attctgagag gttggagcaa   121320
cattcctggg aggaacgaag gggagcacat tctccaagat cccccaccac cggggtcctc   121380
accggctgtg ctttttttttt tttttttctt gacagagtct cgctctgtcg ccaggcagga   121440
gtgtaatggc ccaatctcgg ctgattgcag cctccaactc cagggttcaa gagattctcc   121500
tgcctcagct tcatgagtcg ctgggactac agatgtgcgc cactgcgccc agctaatttt   121560
tgtatttta gtagacacgg ggttttgcca tgttggccaa gatggtctcg ctctgttgac   121620
ctcgtgatcc acccgccttg gcttcccaaa gtgctgggat tacaggcgtg agccaaagca   121680
cccagcctgt gcctctcact tactcaattg ttttctgaa ccctccatag ctggtggacc   121740
ttttcagatc ccatagtcta gccagccctc tcactttatg ccttgggtcc cactgttcct   121800
```

```
tcatctcatc cccttctgt cagtcccgca gtggctgtgg ccagtagagg atggactgag   121860
agtaggagag gaggttctgc ccaggaaccc atcctagaga aacagcatcc tgcctgggac   121920
ctagtcttcc aggtcagctt ttataagtct tttagactca aactcacttg acccacctga   121980
agtggtattg acaataatgc tattttcatg gttgttttc actgtaaatg cagagccttt   122040
tagctacacg actagtacag agagtaaggg aggctggctg gggaatgata tcatcttgga   122100
tggcatttcc tccttggaga aatatatgtt agttccaact cacatgttac tatacagtcc   122160
tgtagaaaga gatacagaga gttagacagg tatagacgca tttgtatatg cataacaatc   122220
tataagcac acatcaaaat ccgtataccg gttcctctag gggtatgtgc ttggcagaag   122280
gtagaaggag ggtattctgg ttcctttctt ttgcacattt atgtatgatc tcagtttta   122340
tatggagcat tgatagggtt tggctatgtc cccacccaaa atctcatctt gacttgtaat   122400
ctctataatc ctgataatcc ccatgtgtca agggcaggac caggtggagg taactggatc   122460
atgggggcag tttctcccag gctgttctca tgacagtgag agagtctcct gagatctgat   122520
ggttttgtaa gtgtctggca tttccctac ttgcacttac tctgtcctgc cgcctgtgaa   122580
gaaggtgcct gtttctccct tgccttctgc catgactgta aatttccaga ggcctcccca   122640
gcaatgtgaa actgtgagtc aattaaaact cttttcttg taacttaccc agtctgtctc   122700
gggtatttcc tcatagcaat gtgagaacgg gctaatacaa gcatactca cttttgatat   122760
ttaaaataa aaattatcat ctatctttga aaggcatgca caaatgggaa gttgaggaac   122820
atttgttg tggcaattgt atgataccttt taatgggaat atttcaaaga cacttgttaa   122880
gactttgtta gaacaaaatg tagagggtgc tggatgtccc tgaatattct tccgcctcct   122940
gtaacttgta ttgctttgga atttccagtg gcctgacaat gaactactgc aggaatccag   123000
atgccgatac aggcccttgg tgttttacca tggaccccag catcaggtgg gagtactgca   123060
acctgacgcg atgctcagac acagaaggga ctgtggtcgc tcctccgact gtcatccagg   123120
ttccaagcct agggcctcct tctgaacaag gtaagaagtc tgtgtcttac cttgtctagc   123180
acataccttct ctatgtgctt ggacaacggg atgaaaagac atgaaaaacc acactgatgc   123240
agaagccttt agtgctacac gggagctcga gtgttggttg aggttctgcc atgaccaagg   123300
aagtctcagt gccgtccctg ggaaagccag agctgtgatt tttggcacaa cttgtgggag   123360
tagtgacttt aggactggcg caaaaccctcc agggtgtcta acttaaccac tcaccttatt   123420
ctaaaatggg ttatttcagt gtcccagtca aattcctatt ctaacatgct gtcaactgtg   123480
tgattatttc caagccaata agcatttcca gtaatttctt aaaatagtgt tcattgcagt   123540
cttcagcgtt gtggctcctg agggatgtgg cccctgattc tgtcgtccta gagaagcctg   123600
acatgactgc attgattctg tatcgtcctg ggtctatgtg gctgcctggc tgtctgtaat   123660
catctgtttt attttattt ttttctacag actgtatgtt tgggaatggg aaggataccc   123720
ggggcaagaa ggcaaccact gttactggga cgccatgcca ggaatgggct gcccaggagc   123780
cccatagaca cagcacgttc attccaggga caaataaatg ggcaggtctg gaaaaaaatg   123840
taagccactt tgatttggac tcttttctcc tttgctgaca aatcttttca aacagaagag   123900
gggcagagga aaatactgga aagacttcag gaggctaagc gtaattagcc ttagcatgga   123960
aagtgcaagc agcacaggcc agcaaagccc cacgcgtgtg ggggttctca ggcctcttct   124020
cttttgacat ttctttactg tttccattgt tgggtgctgt ttctcgtttc tagtgcttgt   124080
cctctaagcc agggtcccc actccagtac tggtactggt actggtactg gaactggtaa   124140
ttatctgtgg cctgttagga actgggctgc acagcaggag gtgagcttcg ggggagcaaa   124200
caaagcttca tctgtatttt ctgctgcttc ccatcactct catagctgcc tgagctctgc   124260
cagctgtcag atcagaggca gcattagatt atcatagcac aaaccctatt gtgaactgca   124320
catgtgagga atctagattg catgctcctt atgagaatct aatgcctgat gatctgtcat   124380
gcttccatca cccccagatg ggaccaccta cttgcaggaa aattagctca gggctcccac   124440
tgattttacc ttatggtgag atgcacattt atttcattat atattacaat gtaataataa   124500
ttgaaataaa gtgcacgata aatggaaggt acttgagtca tccttaacc atcgcccct   124560
caccccaggt gcacagaaaa attgccttt atgaaactgg tctctggtgc caaaaaagtt   124620
ggggaaccac actgctctgg gttctagtag tcagagatgc cctctatgag gcttaagtca   124680
gatttttcta gaaaagattt ggatgggcca tcaggtcacc atgagacttc ccttagcctc   124740
atgcattctc tgtgatggtt tactttgggg cctatgaata gggaagactg agatatagga   124800
aaaaccaaag tgtctgtgtt ccccccactct cacacccatg taacataaca cttctcacac   124860
cagatatggg gggatttctc ctcacacccc aagcgagtct ccagcagata ccagctgggt   124920
gtcctacaat gtaactcggt cctgacactc tatctggaga cagtgtcaga tcccacaagt   124980
taaggctcag tcctacaaga ctgccccact gcagatgcca atcccaagtt gcaggctgtg   125040
acctgtactt ctgcccagct ggataaagat ctgttttct atatgaccct ccatgggtt   125100
gattactttg ctagagtggc tcacagaact cagggaaaca cgttactttt atttacccat   125160
ttattataaa agatattaaa aaggatcctg tgaacagcc aggtggaaga gatgcacagg   125220
gcaaggcacg tgggaagggg ctcagagcct ctatgccctc tccagtgcac cagtcccag   125280
taccctaagt gttcagcaac caagaagctc tccaagtgca gtcttgttgg gttttttatgg   125340
aggcttcatt acagaggcac agttgattac atcattggcc atcggtgatc ggctcacctt   125400
cggcccctct tccctccctg gaggttggag ggtggggctg aacagttcca accctcaagt   125460
cacatggttg gttcccttgg caaccagccc ctggggctat ccaggaaccc accaagagtt   125520
gcttcattgc agctcccttc acccaggaaa atccaaggga tttaggagct ctgtgttaag   125580
aactggggg cagagaccca atatacattt cttattctat cacaatatca caggaagcta   125640
aggatgatac tgcctttgtg tgtcttggct gtggatggtg cataatgcat ggaagtaagc   125700
atttctgaat caacagcaaa caggctttat caggtagaag acccctcagc gccccaggga   125760
caaagctcat caatgatgtc ccactgtcct ctgaggctct agctctaaga cctccagtgg   125820
gtcaagctcc tggagaagtg gcacattctc caaagaccct tcagggtcac cacaccctgg   125880
ttaagggtgt tggcctcataa ctccttttga ctatgactga tggcttacag catgaaaaga   125940
aataactttg tcaaaaaata taataatgat agaaaggaag aaggaacgct cccttttgtc   126000
ttctaagaat agatgtgaaa tgtgtgtgcc ttagaatatc ttctccctct cctgctccac   126060
gtgagctgga gcttacatgc ctgcttgttt tcagtactgc cgtaacctg atggtgacat   126120
caatggtccc tggtgctaca caatgaatcc aagaaaactt tttgactact gtgatatccc   126180
tctctgtgtt aagttgcctt tcgttttggt aaggaaactg cttccttaat atggatttgg   126240
aaaaaaaaaa gcaaaaaaaa cagaaaatgg cttttgagct gagtgcttct ggggaggaga   126300
tggctgccct ctccaccaga gcctgctttt catcatggcc accttgaacc tgccctacta   126360
ttggcccat tgttaggaa acacccgcc cctcccacca cacacacata aataaaataa   126420
atgtcaaatt cccaaagggc aaactagag gtgatctaat cagcccggga tagtcccacc   126480
gaaccctctc ttgtctagcg tgggatgcat gaaaaacaaa tttagagtca ttatgatgaa   126540
```

```
aaactgtcct cttctgcagc tgagaagaaa aaaaaaatac gagcagcagg aaacagctaa    126600
gcatgtaatg cacattgtaa acctcagatg gccatcctag gaaatcaatg aagggtagtg    126660
cagctcttta gccccagatg gcctttctcg taagattact actcatgagt cccattagcg    126720
acattgctta gagactgctt gttaggttcc ttcctcattg ctctgagact cttattggga    126780
gtatgaggct tggatcaggg gaaggggaat tgacattaga tcttaaatga ttggggtaac    126840
aaatccatgg gggaaaaaaa gccacttgta cttgttccct attttcttcc tgctgaccaa    126900
tcaacttgtc tgtccgagtt acagaacacc accctggact tttctttttgt gtaatttggt    126960
tgcttgtggt tgggtctgcc atgtgaaggg accttgagct gggggaagaa ggttggcctc    127020
caagtccact gaagaccagc atcctgagat tgcctgggga ggtggtacag ggcagtgatg    127080
aagatcatgg gagccacact gcccatcgtc acatttgggc cactcctggg gagagcaaga    127140
gggaagaagg agaggttagg gtgataggaa agattctact tggccaatat tattataatg    127200
tggcattgtg gtctctggat ttagtgtgag ttgatagctg acttttttct cgagtgggtg    127260
cttttgttct attttgtcgg tgctattgca gaagcatctt ggtggttcct ctacctcaaa    127320
gtctcttgat ggggtcagtt ccagttctcc gcttctggcc ccatctagta cacgccactg    127380
cctctcactg cctgggctct ctatccttga caggctgcct gaatttaag cccagtctga    127440
cttacctgcc tcaaacaccc acagtagtgc ctgggactca tgcacctttg actcccatgg    127500
aagggaagtg cagtagcttc ccaggtgcaa ttctgctgtc ctcacccaca ttgaggatgt    127560
atgagaatca ggttcttaga gattggaaca agaaggaaga atgggaacaa gatttcttcc    127620
aatggactgt gaggttcccc accttacttt gatgtaagac aagtgaggtt aaccccaagc    127680
ctggtgagga gggttcccat cagacacttg gaaatcctga ggactgtttc ctgcagaagg    127740
atgtggttgg tgggatattc aggtttgact catgattgag aaagttagag cctctggttg    127800
gagaaagagt ttaataacta tttcatttcc accaacacat tcagtacgaa taataaataa    127860
gtaaaaataa atagaaacat tcagtttat tttgaatagt aggagtaggg tataatttct    127920
gtagttactc ttttagtaca atgatgcatg tttactgtat gtaaggcata ctagcagaaa    127980
ttgagctcag cactagaaaa gatgattgca ttccatgcca tgcttctttt ttacaaaaga    128040
cttctataga tagattctca aaacaaccca cagcaaatga aaagttattt ggaaaactca    128100
ggttccagat tcactggagt gtagaatctc tggttggttg gggaggaatt tcctcttgca    128160
gttgttatta ataattatat gaataattat taactatatt aatatttata gttttgaaga    128220
ccttgaaggg ctggagacaa cagagaagca ttttttgaaca ccctctgtag cccctgcact    128280
gttgtaggca ttgatgggtg gtaccaaaga tgggacactt tccctacctc cagagacctt    128340
gtgggcttgc tgcagagaga aggcagggag gaggaaaaga agaatagagg cacatgtgtg    128400
taaattaccc ccacagcagt cagttagtca tgggaggctc cccagaagaa ctgtcctgaa    128460
gctggctgag agaaggcaac atttcaacat aggacagtta tccttgctac ataaaatcac    128520
atacacacat gcacatatgt ccacacacag agactcacat gcaaaagaat cctttgtgcc    128580
tttcagtaaa ctttcatatgg tttagaaaga acttatattt ccttgaaagg agagtgtcct    128640
ttgttgttta ctaccacttt ttaaacttag aaagaaaaat ctaaagagtg tttatgatt    128700
taccatttaa ttttcacctt gagatgtgaa aaactagtgc ttggaattcg tcctgaatta    128760
aacgacacaa ttgctaactt ggactcaaat gcgacttctt ttcccacctt gtgccacagc    128820
ttcctcttca tttgattgtg ggaagcctca agtggagccg aagaaatgtc ctggaagcat    128880
tgtaggggg tgtgtggccc acccacattc ctgccctgg caagtcagtc tcagaacaag    128940
gtaagaacag gcccagaaac catctatact gtccttccat gtaagcccca caaaccctt    129000
ctacatttac acagaaccca cacagctgat gcatcaatac ctgcctctct gttttctgaa    129060
ggaggaaaaa atatagaaaa attaaaaaaa gttatattat tataggttct ctacttggaa    129120
aatagccaaa atacaaatct ttttcttgat ctgggcagtt ccatcaaaat ctgtaggcac    129180
agtgatttgc accaagttcc aatacttttg gaaaatattg aagatgctct gagggttct    129240
atggatatcc attgtctcac tgtcagatga aagaaaggg aagttttag aaatgtgaca    129300
ctttgcagtg agggaggaca agagcaaact tacctacagt ctatcacagg cacagatttt    129360
ttttttacact tttgtgaatc attgaattca atgccgagtc tattcatcta ttcacaaaca    129420
catgaacaaa ttatgggttg tgatccccat aaatgaagag taatcagtcc gaacccacag    129480
aacctggaca ttttgggtat cgtttcagtg gaacatgcaa ttcgtaagtt cagtttgctt    129540
gggtgtctct taggaagaac acataggaca cagacccatc tgcctgcatg ttttgcttcc    129600
tcatctcctt tctacaccag ggcacctgtg ctcaattgct gttctcctct aaagagactt    129660
ccttctgtaa gtttgtgaaa tgccatcgac aaacctgatc gcatcgcatt tcactctgct    129720
gttgagttga ttttttcttta ctttatcgtt tgtaacttct tgctctacag agctttcacc    129780
ttccacatat ttcagattca ttctttccta aactgtgtgt tggtctatgt cctcactgac    129840
tatcaacata ctgccatcat gcacttccta tctctattcc tcttcgttgc aatctggctc    129900
caagtggctc acaccattat tctgatctat caactgccta cacagtccta gaaagtaagt    129960
gagtcaagaa acatccccca aaagtaaact tttcaggtaa gatcagaaga ccctcatgag    130020
tcactgctgc tcaggatcgt atctggctcc ttgaagagtg accttgcata gatcttgtca    130080
taaaaatga aagagacctt gggaaggtct tgggcggtc acttttgtca gagtccaggg    130140
ctgtggggtg aaagccacag ctatagagct tcattctgga gtcacttagc tttgctctcc    130200
tggggacagg ctgtgcctat tcttgcctca ggcatcaaaa aaagtggcac agatgggccc    130260
ttctgaaaaa tctcactact ggagcacagc tcgaagtttc tactatcctg acgttgggcg    130320
gtagtccttt gctttgggaa tatgaacatg atcaaaactg agtgaacttg tcttcctggc    130380
tttctgtaca atgaagtaga acaaaccatc caatttgacc aaagccttgg catgttttct    130440
ttctaggttt ggaaagcact tctgtggagg cacttaata tccccagagt gggtgctgac    130500
tgctgctcac tgcttgaaga agtacgttta agggaaaact gacatgggt cttatcttca    130560
agacttttt cctccctctc ttcctccatc ccttctttct tcccaccctc cccttccttc    130620
ctccccacct ctcttccttt tctggaagga acactaggac ccaggaatg catgcagaat    130680
cctgaggcag aatttccagg gcaattggat gagagaggag ggaagtgttt ctagagggaa    130740
tctgcagagg gaagacccag tgcaagtgat tttttggacc tgtataaacc gcaggacaga    130800
gctgttcact accagaggca tcaatctgta ttgcattgct ctagagcaat atctgaggct    130860
gaataattta taaagaaaag agtttaattg gcacatgttt ctgcaggctt tacaggaagc    130920
aggatgctgt catctcctct gcttctgtgt gggcctaagg aagattacaa tcatggtgga    130980
gggcaaagtg ggagcaggca tgtcacatgg ccagagcagg agcaagagac agagagagat    131040
ggggtggggg tgctgcacaa taccaaatga ccagactttg caagaactaa gagtgagagc    131100
tcactgatca ccatgaagat gtgggccaag ccattcaaga gggatgcacc tctatgatcc    131160
aaaccccttt cacaggccat agctccatca ctggggacta cagttgaaca cgagatttag    131220
gtggggacaa atatacaaac tatatcacag tctctgatga aacagattga gaacagacct    131280
```

```
taactgtcag tttccagcaa attgtgaatt ttgtttcttg ccactcataa gtcactgatt    131340
ctgggtggcc gagggtgtca gagggacagc gccaagttca tggcacagag gatacctgaa    131400
ggggctggac catatttttc tcttgacatc ctcatctttt ctaggtcctc aaggccttca    131460
tcctacaagg tcatcctggg tgcacaccaa gaagtgaacc tcgaatctca tgttcaggaa    131520
atagaagtgt ctaggctgtt cttggagccc acacaagcag atattgcctt gctaaagcta    131580
agcaggtact cgctcacctg tggtcttcac cccacgctgg tgaagatatt tgctttatgt    131640
ctgggttttg tgggccatgg ccactgcatg gcagtgggga ggaactgtct atcacatgaa    131700
aggctcaagg gctttgggga cagcatcaat cttcaacccc agccctgcca catgttagtt    131760
gtgctcttta aaaaggcaga aggattcgtt tcctcacgtg gaaaaagaga taccctgtta    131820
cccgtaaaac ttacttaatg ttcaccagtt catccacatt catgatcagg gaaaggttgt    131880
tattccaggc taactattct cctttcataa taatatgctg gagagaatca aatgagattg    131940
catttcaaag cgcttgaaaa accaccatat cgagccatgc ttagtgtggg cgcctctaat    132000
cactgctatt caggaggctg acgaggaaga attgcttgag cccaggactt caaggctgta    132060
ggcagctatg attgtgccac tgcactccag gctgggtgac agatcaagac cctgtctcaa    132120
caaaagaaaa gaaaacaaaa caaatgaaca gaaatattcc acaatgtcaa aaaaaaaaaa    132180
aacccacaca acatacaatt tacaaatgca aataataata ttattgttgt cttctttgat    132240
tttctctttc ctggtgaaat tttgttttat taagcctgac aaagtgatac ctttgcttac    132300
atcacttaaa gttagtctat ttggacctag gtgacagtac aatcagctaa gaaacagtat    132360
ttgtaggaga ggcaggtttg ggacaggtga caaggcatgt ggggtgctcg ctgtgctggt    132420
ggctctggaa ggcagggtgt caatgcagac agggatgagc atggcctggt tgggaaggca    132480
tggggcaggc aggagcctga gctgctctcc tgggcctggt cacaagccca tggcagcttc    132540
tctgggtctg tgaactgagg ggtgatgtcc tggaatcctc tgacactcta ggaaggagag    132600
aagggccttt ctggctcagc ctttataaac agtagctgat ctccctcttg ctccccaggg    132660
tcctccccac catcccagca aatgtgcaaa tacaagatct ctgctcctca tggtcctcag    132720
agagctgggg tgttctgatg gcttgaacaa gtcacttagg aaatgtgggg ttttggaggc    132780
attctctgat aggctgatac gttttgagtt tagagttccc accgcacatc cccacacccc    132840
tagagtctag ggcatttagt gctccatgag ggaacctgta gagtgaggac atctgcatca    132900
caggctgggc cttctagtgt ccagaagcag aaagtgtgtc tgcttcaaag ttggtgctaa    132960
tgatgatttt tggtcagaat acggcatttc tcatttccat tccttatcc ccttgaactt    133020
actaaagtag aatcaggtct aaaaaccaga gttctaatct ttaagagtcc ctgggattct    133080
aaggtatatg aatgtccttg gaaaacaata ccatttagtt catgcaaggt gcttatttcc    133140
catcctcttt catttgatgt ctagcatttt actgcattct taccaccacg tttagtaac    133200
attcacgagg aggaagtgga ggatccagat ggagcaactt gctctgggca cacaaggcat    133260
ttgcaatttt ataccctctt gatgatgtct cagccagaca ttctgcccag tcatcaatgc    133320
cctcttcaat taatatgaaa ggacacactt ggcatgagat tccaatcgtg cacagaatat    133380
acatgagaag tgtgccttg tcatccctac tttcaaaggc taaggccacc ctcagtttct    133440
tgcatgcaac tgatgccttt caaatgaaac cttacatctg tgtagtccat aggcaaccac    133500
aggcaaatgt gagggtgaaa cgctgtgttc tacattgttc tgtgtcagtg aagcaaggca    133560
gtgccagctc agagggctct ggggcttcaa ggcagggatg cctggttgta ggtactgcca    133620
cttccagctg ggcagtgaaa cataactgct aatactttcc ttacaggcct gccgtcatca    133680
ctgacaaagt aatgccagct tgtctgccat ccccagacta catggtcacc gccaggactg    133740
aatgttacat cactggctgg ggagaaaccc aaggtgagat caattccatt gcccacgtaa    133800
caaattgttt ttgaccttca gtgcatgtta caaaatggac attttggaga tagttgtaca    133860
aattcctacc catgaatgtg gtctacccac tcctgacttt gcctggacac ctgtctatgt    133920
ctccataatc agtcttcaag ggacttgggc aaggggagcg gtgccatttc cttgagtctc    133980
tctctttttt gttttcagaa tcttttaatt ttttttgtaa tgattgtatg tttccttac    134040
aacaaaaaca aacaccagta gaggtctttg agtctcttaa tcataatttc agcattcata    134100
ttgcttcccc aggtaagtgg ggttttgacc cagccctcaa gttaagggtg ttagattatt    134160
tttcatgtga aattagacag actgcgtttc taaacatggt gcaaacagt aacgacaaaa    134220
gttgtaatta aactattctt cttcccaaat acccacatgt ctaatgtgtg tgtgagggtg    134280
ttaggcaggg gacctgaagc tggggagag gcagacagtt cccatggccc caagtctagg    134340
atggcatttg gtattggttg atgggtgaga gcaagagagg gaatatttt gtgcatgatg    134400
tggtatcagc acctgtacta cattttatgg attccttctt ctctttgcgg tatgccctga    134460
caataattat atccgtcagc cttacccct tggcagtagg aaaactgaaa ctgtcttaaa    134520
gtctcagctc tactttctca gaggtgcagg caagggcact gggagtctgg ggccctggaa    134580
aactgttctg actctgccac ttgccagata gacctgaact agacacgtta cctctttgta    134640
ccacttggct ctaatccctt atctgtaaaa ccagcatttt caaatggtgc tttgcacatc    134700
agccttttgc ataagctttg atttgataaa atgtttttg tgtttttaaa aagattaaaa    134760
accacaggtt tagataattt caaagtaggc ttccctttt ctgtcatttt cctattattt    134820
ttaaaacctc acctccttga ctccttgttc cctttttctg cactgctgag tctgggagca    134880
ctgaggccag gtaaaaggaa acttggcaaa tgaggggcac ctatgggtgt gggaggctgc    134940
tcctggtgtt tgcatatttt aaaatttaaa tgctacaaac cactgtgagt taggtattat    135000
tgttcctatt ttaccattga ggaagctggg gctcagaaaa ggtggagggt ggtacagaca    135060
aacctgaatt ggaacctgg ctcctgccta tgggctgtca gattaagaa aagtcgtgag    135120
ctctcgctga ttgtttcctc agctgatgtg ggctgcaggg ctgttatggg ggaaataata    135180
agaaagtgca tcaagtgctg agcacatcct aagcactcca tcatggcagc tcctactact    135240
aataaagaat agaattatat ctaacatgat tctttcttgc aagtgacaga aaatccaact    135300
caaattggat taagcaaaac aagggaaatt cttagtgagc tgcaaagttt tcaggctcac    135360
atgatggcc caaatcccag gtcctcccaa tcatgggtgt tgcactattt gggggcacaa    135420
aggtgacatt cccatggctg cagatgctgt ggtgctgtgg ctgtaccggg aaagaataag    135480
aaaggccact ctcccaatta tgtgaacaat agtctgccca ctctgagaag tcaaacttgg    135540
gtcacagtcc tgccctgaa cccatcactg actggtctg acctgcacca attgttccat    135600
gttggaggtg aaggcaagac cccactaata cccataaggg gcaaagtta gatagatcct    135660
tcaagagtag tatgggaggt agggcaaaaa gctgctgggc agccagaaag caaacagagc    135720
ctctatgata cctcaactga tgaaagcatg aagctaaaat cataaggatc tgggtgtgag    135780
ttctggctct cccatcttcc atgtgacatt ggcagttat ttaatctctt ttagcctccg    135840
ctttctcatc ttacatatga gataattgtg aggattaaga ttacacataa tcatcatcat    135900
caccgtccac cactaccacc atcatcccca tcaacatcat cgccaccact atcatcattc    135960
ttactggcac taccatcacc atcaccacca ttccaccacc atcaccaata tcatcactgt    136020
```

```
caacatcatt accaccatca ccatcaccac caccatcatc attactacca ctaccactac    136080
taccaccatc accatcacca ccattccacc accatcacca atatcatcac tctcaacatc    136140
atcaccatca ccatcaccac caccatcatc atcattacta ccactaccac tactaccacc    136200
atcaccatca ccactgtccc actactatca gcatgacatc accatcacca ccaccatcat    136260
cattaccacc gctactacca acatcaccat caccacaatt ctactgccat caccattaac    136320
attaccacca ccatcatcac tatcaccatc accaccatca tcaccactgc cattatcact    136380
gccaccatca tcactatcct ctatatttcc tcatctgtat tatcattact accaccatca    136440
ctatcaccac catcgtcacc atcataatca ccatcaacac catctccaat accaccatca    136500
ctgtaaccat catcaccacc accatgatca ctatcaccat catcacaatg atcactgtaa    136560
ccatcattac tacccaccac catcaccact actccaccac catcaccatt atcattacca    136620
tcaccattat caccaccatc atcatcacca gcaccaccat catcaccagc accaccatca    136680
ccatcaccat cattaacacc atcactatca ccattggttt aatcatcacc accatcatca    136740
taaataaaca tcacataacc agggtgtagc tgggtgttga ccccagagcc cactcactgt    136800
ttcctctctc ccaccccat ccacacattt ctaaccacca tcctgcactg ggctcccagt    136860
ctcctctggt ctcacccaca tgtccactga gaaaaggatt ttcagaacac caactagacc    136920
aggaggagcc acatacataa ctcaggcctg cttatcaact ttctacatgt taataatgac    136980
atcagatcaa tgggtgttct cagcttctca gaaggaggtc aaaattctcc ccctctcccc    137040
ttcatgtgtc cagaccttcc cggatttgga tgtaccaagt gcagagtggt gttgaggcca    137100
agggctcat ccatgtaagt ctcatctgca atcactgggc tgatcccgtg gccctgtctc    137160
cagggcgcca tcagagaggg cttcaatcct caggttacct gtggcccacc ctgccctcag    137220
aggtgccatc tctacattgg ccacgagatg gcagcacata ctcatagact gcattaattt    137280
cccagcaact cctggtgggt tttccctctt atcaggatgt ttgcctttgct cagagagcaa    137340
atctgagagc agtgacacct aacttaactt tcagcaaaat attttgagaa gggtgcccct    137400
ttacacatct gtgcagtcca ggtgatgcat cccatgccca atgctcggta gtcaggagga    137460
gcttcctcca tgcagctctg cggaagagac tcttccacgc tgctcatgta aactccagat    137520
tcggtgtcag ttttctgaca ccgaagacaa tgatctaagt gcagtcaagg gctttgggga    137580
aagcaggaga gagtgcctca gttctagcct gtgccatgct tgcaaagttt tgcaaaattc    137640
taatgagagc tgggcttgca acattggaaa cttggattat ttgtgagagc actgagaaat    137700
ccctgggcat gtccatctgg aaaaacagca tttcctctgg cactttagca gaggttctgt    137760
ttcaatttgg cgaaggaaat taagcagttt ttcacaaaag aagaactaca acgaggagaa    137820
ttgtccctag tatttcttct ccctaattgt caaggaagtg taaattagaa aatgaatcag    137880
gacaatttcc acctactatg ttagctaata ttttaaaaat tgaatatcac aagggtgagg    137940
caaagtaatt gttttccagt gacatttttcc actgtcacac cctttagag aataatttgg    138000
caatgttact gtgagataga aatatgtcta tataattatg ggactgagat cttcagaaag    138060
taataaggaa taagaatgaa atttatgaac aaacatgtgg aaggttggaa gcaagagtgt    138120
ggccaacacg catggggagg aagcatttgg gcagcgactc cgcagaccca gactcaagct    138180
gagctataca acctccttac gcctcagttt cctcaactga agaacaggaa tgacaagtgc    138240
ctgtttcata ggaccgttgt gaggattaag tgagatatac cacattatga gcttgtgcct    138300
ggaaaggttg attcttagta aatgatgact attcttttt attgcaataa aatttataca    138360
acatagagtt actatttttaa ccatttttgc aggtaccact gagtggcatt cagtacattc    138420
acaatggtgt gcaaccgtca ccatatttcc aggacatttt tctcatcccc aaaggaaacc    138480
tcatgcccat taagcagtca ctcctcatta aaatattagt tatgaagact gtagcatttt    138540
tttaaaaact catgatataa cattgattga aaaaatcaagt ataggaaatt gtgcattatg    138600
atgtaatagt aaaagaagca tataaaaatc tgaaaaaagt atataaaaag aatagcaatt    138660
gtatttctca gactctcttt acattgtaaa aatcattttg atagcttcaa aagaaaagca    138720
aaagtacac aaacaacaac caaccccaaa gcagcatgac aaagcccaga ttgttgaatc    138780
caggtcttgg gaacataaaa tcttatatga catttgcact ttaatgggtc agagagtcca    138840
gtggcattgg gagctgcctt gtgttctgca gcctcacgga cagacaggag gtccagctcc    138900
actgctctgt tcttctggaa tttcctcgtg aacaagcttt ggcctcagta accatttctt    138960
tcatcttttt aaacacaggt acctttggga ctggccttct caaggaagcc cagctccttg    139020
ttattgagaa tgaagtgtgc aatcactata agtatatttg tgctgacgat ttggccagga    139080
gcactgacag ttgccaggta agaaaagatc aatagatcaa agtcttgtgc tctcccgtct    139140
cagtctcagt cccttagacg tcagtcccaa agtggcaaat tcaggaaggt tttgtcagtg    139200
gaagacccca gtcaagtgt tgctcagaaa ctccccagat ctgtccctga atgcatattc    139260
agatcatcta aggagacgtc ttggggcttg agttccagat ccatagcaag ggagccgtaa    139320
gtgccataac tacctcaggc cactcaccttt cctggtgtgt gctggtcacc agtgactgaa    139380
gtggtggctt ttcagtagaa gaggaaggta gagggtacag gaccgagaca aattacacac    139440
acttaacaat gatgtccagg ctagcccagt ctaaaggaaa caccaagtta ggaagcaatg    139500
catgcaggat tcacaaggga ttatttttt tcccaggaaa aaactaagtg atgtggtttt    139560
gttgaataga ctttgctaag tacttaagca ctgcagatgc ttgagtaata tgctcataag    139620
ttcctttctg atttgaatta ctgggaaaat gtacatatgg ataagagaag gatggcatcc    139680
catattaaaa ggttggcagc ttaaagctca catgaatttt cccctacctc tgtttagggt    139740
gacagtggag ggcctctggt ttgcttcgag aaggacaaat acattttaca aggagtcact    139800
tcttgggtc ttggctgtgc acgccccaat aagcctggtg tctatgctcg tgtttcaagg    139860
tttgttactt ggattgaggg aatgatgaga ataattaat tggacgggag acagagtgaa    139920
gcatcaacct acttagaagc tgaaacgtgg gtaaggattt agcatgctgg aaataataga    139980
cagcaatcaa acgaagacac tgttcccagc taccagctat gccaaacctt ggcatttttg    140040
gtattttgt gtataagctt ttaaggtctg actgacaaat tctgtattaa ggtgtcatag    140100
ctatgacatt tgttaaaaat aaactctgca cttattttga tttgaattaa ttttggtttt    140160
ggtcttcaaa attttcatgc tcttttcatc ccatctattt ttatttttat ttttttagact    140220
ttacgtcctg gggtacatgt gcagaatgtg caggtttgtt acatagatgt acacgtgcca    140280
tggtagtttg ctgcacccat caacctgtca tctaattcgg tatttctttt agttctatcc    140340
ctcccctagc cctccacccc ttgacaggcc caggtgtgtg atgttgccct ccctgtgtcc    140400
atgtgttctc attgttcaac tcacacttat gagtgagaac atgcggtgtt tgtttttctg    140460
ttcttgtgtt agtttgctga gaatgatagt ttccagcttc atccatgtcc ctgcaaagga    140520
catgaactca tccttttta tggctgcata gaattccatg gtgtatatgt gccacatttt    140580
atccaatcta acattgatgg gcaattgggt tggttccaac tctttgctat tgtgaatagt    140640
gccacaataa acatacgtgt gcatgtgttt tcatagcaga atgatttata atcctctggg    140700
tatataccca gtaatgggat tgcagggtca aatggtgttt ctggtgctag atctttgagg    140760
```

```
aatcaccaca ctgtcttcca caatggttga actaatttat gctcccacca acaatatcaa    140820
ggcattccta tttctccaca tcctctccaa catctgttgt ttcctgactt tttaatgatc    140880
gccattctaa ctggcatgag atggtatctc attgtggttt tgatttgcat ttctctaatg    140940
atcagtgatg atgagctttt ctcatatgtt tgttggctgc ataaatgcct tttttggaga    141000
agcatctgtt catatccttt gcccactttt tgatggtgtt gttttttttct ggtaaatttg    141060
tttaagttct ttgtagattc tggatattag ccttttgtca gatggataga tggcaaaaat    141120
tttatcctat tatgtaggtt gcctgttcac tccgatgata gtttcttttg ctgtgcagaa    141180
gctctttggt ttaattagat ctcatttgtc tattttggct tttgttacca ttgcttttag    141240
tgttttagtc atgaagtctt ctcccatgct atgtcctgaa tggtattgcc taagttttct    141300
tccagggttt ttatggtttt aggttttgca tttaagtctt taatccatct tgagttaatt    141360
tttgtataag taatgccctt cttgtctct tttgatcttt gttggcttaa agtatatttt    141420
atcagagact agaattgcaa tccctgcttt tttttttctt tttgctttcc ttttgcttgg    141480
taaatattct tccatccctt tattttgagc ctatgtatgt ctgcacatga gataggtttc    141540
ctgaatacag cacaccaatg ggtcttgact cttattcaa tttgccagtc tgtgtctttt    141600
aattggggc atttagtcca tttacattta aggttaatat tgttatgtgt gaatttgatc    141660
ctgtcattat gatgctagcg ggttattttg cccattagtt gatgcagttt cttcatagtg    141720
tggatggcct ttacaatttg gtagttttg cagtggctgg taccaattgt tccttttccat    141780
gtttagtgct tcgttcagga gctcttgtga ggcaggcctt ggtggtgacaa aatctttcag    141840
catttgcttg tctgtaaagg attttatttc tcctttgctt atgaagctta gtttcgctgg    141900
gtatgaaatt ctgggttgaa aatttattttc ttttagaatg ttgaatattg gcccccactc    141960
tcttcgggct tgttgggttt ctgcagagag atccactgtt agtctgattg gcttcccttt    142020
ccgggtaacc caacctttct ctctggctgc ccttagaaat ttttccttca tttcaacctt    142080
ggtgaatctg acgattatgt cttgaggtgg ctcttctcga ggagtatctt tgtggtgttc    142140
tctgtatttc ctgaatttga atgttggtct gtcttgctag gttggggaag ctctccttga    142200
taatatcctg aagagtgttt tccaacttgg ttctattctc cccatcactt tcaggtacat    142260
caatcaaatg tagatttggt cttttcacat agtcccatat ttcttggagc tttgtttat    142320
tccttttcat tctttatcct ctattcttgt cttcttgctt tatttcatta agttgatctt    142380
caatctctga tatcctttct tttgcttgat cgatttggct attgatactt gtatatgctt    142440
cacaaagttc ttatgctgtg ttttttcagtc agatcaggtc atttatgttc ttctctaaac    142500
tggttattct acttagcaat tcatgtaacc tttttcaag gttcttagct tctttgcatt    142560
gggttagaac atgctgcttt agctcggagg attttgttat tatacaccttt atataatagc    142620
ctgtatataac tataagattt ttttgtaagc accatcgtaa ccacaaagca aaacctaaa    142680
gtagatatac aaaagataaa aaggaatcaa agcataccac tagagaaaat cacttaatca    142740
caaataaaga tacgaaggagt ggaataaagg aacgaagggt ctacaaaaca accagaaagc    142800
aattaacaaa atggtgatag cagatcttac ctataaataa ttatcttgaa tggaaatgga    142860
ttaaattttc caataaaaag acatacagtg gccaaataga ttaaaaaata agatccaact    142920
atatgatgcc tataacacac tcacttcacc tgtaaggact caaacagact gaaagtaaag    142980
ggatggaaaa aatattctat gcaaatgaaa acaagaagat agaggggtag ttatacagat    143040
tgagtatcac taatccaaac atctgaaatc tgaaatactc caaaattaaa aatgtttaag    143100
tgccaacatg atgttcaaag gaaatgttct tcggagcatt ttggatttttt gtgtttaggg    143160
atgcaaaac agtaaatata aattttgtat tagtccattc tcacactgct ataaagaata    143220
ctacaaagag actgagtaat tataaaggaa agatgtttaa ttaactcaga gttccacagg    143280
cttaacagga agcatggcta aggaggccaa aggaaactta taatcatggc ggaagatgaa    143340
ggagaagcag gcaccttctt cacaaggtgg caggacggag tgtgagtgtg tgaaggagga    143400
actgtcaaac acttataaaa ccatcagatc ttgtgggaac tcactcactc tcacaagaac    143460
agcataggga aaaccgcccc catgatccaa tcccctccca ctgggctcct cccttgacac    143520
atgggggatca tgagggttac aattcacgat gagatttggg tgggacacag ccaaaccata    143580
tcataatgca aacattgcaa aaacaattca aaattcaaaa catttctggt ttcaggcatt    143640
ttggataagg gaaactcaac tcaacatgag gtaaagcaga ctttaagtca aaaactgtaa    143700
aaagagacga agaagaatgt aataataagg agatcagttc attacaaata tatagcaatt    143760
ataaatatat attaatatat atacccaaaa ttgtagtacc tacatatagt aactaaaaca    143820
aacattaata gatctcacag gagagctaca ctgtaatata atcatagtag cacacttgaa    143880
tagctccact ttcactaatg gacagatcat ccagacagag aatcaatatg gaaacacgag    143940
acttaaaacta cactttagcc aagtagacct aacagaaata tatagaacat tccatccaac    144000
agcagtagaa tacacattat tctcaagtgc acagggaata ttctccagaa tagatcatat    144060
gttaggtcac aaaactagtc aaaaaatgta agaagattga aatcatatca ggtttttttt    144120
ttagatcata atcgtatgaa actagaaatc aataatgggg gaatattgga aaatccacaa    144180
atagatagaa attaatcaat atgctcctga acaatcaatg agtcgaagaa gatattaaaa    144240
gaggaaattt taaaaaatca agacatgagt tcatgtcctt tgcagggaca tgaatgaagc    144300
tggaaaccat cattctcagc aaactatcat aaggacagaa atccaaacac cgcatgttct    144360
cactcatagg taggaattga acaatgagaa cacttggcca cagggcgggg aacatcacac    144420
accagggctt gtcaggggt gggaagctgg tgaaggata gcattaggag aaatatctaa    144480
tgtaaatgac gagttgatgg gtgcagcaaa ccaaacgcc acatgtatac ctatgtaaca    144540
aacctgcacg ttgtgcacat gtaccccaga acttaaagta taataataaa aaaagaaata    144600
tttgttttg atttatatgc caatcagaca aaatgtgaaa agccctactg aaattaagta    144660
tcaccatgaa agataaaattc tggataattt tttcaagttt taacaatgta gctttaattg    144720
gagaaagcta tcatttggaa tgagttaatc tatcctatac taaaataagt cacttgcttt    144780
aaaacataat aaatatgatt ttgaattgaa aacaaaaaca actcaagaca aaggaaaatg    144840
gacacactaa cataccaata atttatagta tgcagcaaaa gtggttttaa gagggaagct    144900
tttaccaata aacacttcca ttaaaaaaga agatctcaaa taagcaacct aagattacac    144960
ctcaacaaac tagacaaaga actaactaac ccaaaagtta gtagaaggaa agaaataata    145020
aagatcacat cagaaatagt aaagactaaa aaactgatac caaaagaaa taaaactact    145080
agttggtttt caataaaata acaaaattga ccaactttta gctagattaa gaaaacaga    145140
gaatactcaa ataaaaccag aaagaggaga cattacaata agtacaag aagtacaaag    145200
gatcataaga gactactatg aataattaca tgccaacaaa ttggataact tagaagaaat    145260
ggatgaattc ctagagcaaa aaacctacaa agactgactc agaagaaat agaaaatctg    145320
aacagaccaa taatgtgtac atgattgtat cagtaataac aagtctccca tcaatgaaaa    145380
ggccaggacc taatggcttc actgctgaag cataccaaac attacaaaga ctaatatcaa    145440
ccctcctcaa actcttctta aaaactaaaa agaaggaatg ctttcacatt cattttatga    145500
```

```
ggatagcatt acactgatac taaacacaga aaaataatac gctaataaaa gaacattaca  145560
ggcaatatcc ctgataaaca tatgtgcaaa aatccgcaac aaaatactag aaaactgaat  145620
ccagtagcac tttaaaaaga tcattcacca tgatcaagtg cgatttgttt cacgaatgca  145680
agaatagttc aacttacaca aataaataaa tgaaaggatg gatgataaaa atgtgtatct  145740
atatatatat gttttataca cacacacaca cacacacaca cacacacaca cagaggaata  145800
ttattcagcc ttaatgaaga agaaaatcct gcctttgcat caacctggag gacattataa  145860
taagtgaaat aagccagaca cagaaaggca aatactgtgt gatctcgctt acatatggaa  145920
tctaagaaag tcaaattcct agaaatagag agtagcttag tgattgccag agccgtggaa  145980
gggggaaatg gagagatgtt gatcaaagga tacaactgta tagctttgca agataaatag  146040
gttctggaga tctaatgtgc agaatggtga ctagagttaa taatactgta ttgcatactt  146100
gaaatttgct aaaagagttg atcttaagtg tcctcaccat atacacaaaa gtattatgtg  146160
aggtggtgaa tattttaatt agcttatgat aataatttca cagtgtacat ctatattaag  146220
gcattacatt gtacatctta aatatatata attttttattt gtgaagtgta cctcaataaa  146280
actgaaaaaa ataattgaaa agtaatgaaa aaaattaaaa gctattatgt gtcaaatgac  146340
attatcaaga aagtgaaaag caacctactg atgaagcaaa cctattgaca aaggcctggt  146400
gtccagaata tattaagatc tctaggctgg gagcagtggc tcacacctgt aatcccagca  146460
cttggggagg ccaaggtggg aggatcactt gagcctggga gttcgacact gcagtgagct  146520
atgattgggc cactgccctc caggctgcgt gacagagtga gactgccatc tcttaaccca  146580
cttcttattt agaaaagaa aatatgtagc ttgctgcctg catagtattc ttggggcaaa  146640
tgggaaatga gttaaaaaaa aaaaaagaa ctcttacaac tcaacaataa aaagaaaaac  146700
aagaacgtga atagacattt tttccaaaaa agatatacaa ataggcaata agtacatgaa  146760
atgatggtca acatcattag tcattaagaa aatgccaata aaatcacaat gaataagac  146820
ttcatatcca ttaaaatgtc tataatttaa aaaatgaaaa ataacaagca tttgtgagga  146880
tgtggagaaa ttagaatcct gtatattgct ggtgggaatg tacagggaaa atggtttggc  146940
cactgtggaa aacaatttga cagttcctta aaatgctaaa catagaatta ccatgtgatc  147000
taacaatttt actcttaggt gtatatatac aagaattgaa aacaagtgcc caaacagata  147060
ccttgcatga gaatgttcat agcagcactg ttcaacagc cacacccaaa tgtcaatcaa  147120
tagatgaggg gataaacaaa ttgtggttta tacagctaca aaaaggaatg aagtactggt  147180
atccgctaca tggctgaaac ttgaaagcaa gggctgggat ggggtcatgg aaagtaccag  147240
cttattgggt actgcattgt gctttggggt catgaaaatg ttttggaact ggatggaggt  147300
ggtggttgcc aatgtgaaca tactaaatac aacgcattgt tcactataag actgctactt  147360
ttcttatgag aatttcactt caattaaaaa ataccttcca tgtatccttt ctaaggatga  147420
tactagaata tttgctttgg caaaatgagg aagtaacttt ttttaaaaag gaagatgtgg  147480
gatccatgaa acgggatcaa atatcagaga ggaaaggggg tcttctggat gacagtccat  147540
ggagatccca caactgcaca gcaggccggc tgtgcaccca ggccacacca gagcagagcc  147600
ggtggttccc gaggagctct ctggaagaaa aacgctagat ggcctgattg gtttgggggc  147660
atattgaaaa ggtatataac tgagaatttg gagtggaatt aggaaacaga cataaaagct  147720
tacagaaaag aaaataatga aattctaggga gaaaatataaa aggatactac aggcctcagt  147780
tacataaaca ctgaatattt acttaaccaa aattacaata taattacata attattttag  147840
gtacatatgg caaaggatg tgtgggtgta tgtagtatgt acggtgtgtg aagtgtatgt  147900
gtgtggtatg tggacggtat gtgtatgctg tgtatgccaa taaatcaca atgaaataag  147960
acttcatatc cattaaaatg tctataattt aaatgtctat aattttaaaa atggaaaaca  148020
cttctcatat ggcaggagca ggagcaaggg tgggggaggt accacacaca cttaaacaac  148080
cagatctcct gagaactcac tatcaggaga acagcacctg gagaaggtgc taaaccattc  148140
atgagttact gccctatgag ccaatcacct cccatcagac cccgcctcca cactaaggat  148200
tacaatttga cttgaaattt gggcatgaac acagatcgaa accatatcaa taggtaatga  148260
ctaaaactga aaaaagaagt accacagtca gaaagttatt tagagagctg aaggtaaatg  148320
ccaataggat cagttgaaag aattggaggt ggccgggtgc ggtggctcag gcctgtaatc  148380
ccagcacttt gggaggcgga ggtgggtgga tcgccctgag gtcaggagtt tgagaccagc  148440
ctggccaaca tggtgaaacc cagtctctac taaaaataca aaaattagcc aggcctggtg  148500
gtgacgccg tagtcccagc tactcaagag gctgaggcag gagaatcgct tgaaccaggg  148560
aggtgaaggt tgcagtgaac cgagatcgtg ccactgcact ccagcctggg tgacagagca  148620
aaactccatc tcaaaaataa atgaaataaa gaattgaaag tgtttgcctc tggagagaag  148680
gaaacgcagt aattctgtaa aaacagaact ttttacttt tttctttttt ttttttttt  148740
tgagacagag tctccttctg tcacccaggc tggagtgcag tggtgcagtc ttggctcacc  148800
gcaacctctg cctcttgggt tcaagcaatt cccgtgcctc agcctcccaa gtagctagga  148860
ttacagatat gggctgctat atccagctaa ttttttttta ttttttattag agatgaagtt  148920
tcaccatgtt ggccaatctg gtctcaagct cctggactca tgatcctcct gcctcggcct  148980
tccaaattgc tatgattaca ggtgtgagcc accatgcctg gacagaactt tttgactctt  149040
taaactatgt gcatatataa agctgattta aaaaaaacca agtaaaataa ttttaaaatg  149100
ttccaaaaca gattggatgg gtacacactt catcatgagt ggttgaggga gactgggtta  149160
gagatgagga aattccaggg actggggaaa agttaaaatg acaaactgtt cacaattgtt  149220
aactgcaggt tgtgggaaag ttggtaagtt gctacagtgt ttgttccctc tgtaggtttg  149280
catatattta acatttctta aattagcata ataatgaact gtgtaatcag ctgtaagttt  149340
gagggtgtgg agctggcaca ggacagctga gctactggtt taaaataaat gacatttaaa  149400
aaaatggcta tttgtagaat taacagatat aagcaccct gatcaaggga tgataagaaa  149460
ggactccagg gctctgtctc agctgtcttg gcaacacctg gaagacatgg gcctctgcaa  149520
ggtctcatac tttcaggagg tgttgatgaa ggatatggac agatctgaag ctctgggcac  149580
tgcatggtct gagaagagaa gctccggaaa cgcgggagct gagtgcagt gcagaagggc  149640
tgtcatccag cagagggta ggtgacaact ggcctagcga gtgacccta tcatggctac  149700
atttgttgat cacttttcttt gtatgaggca ctgctgtgat tgcattaaat ttccacttac  149760
ctaaatccaa cgttgtgcac ttgtgaattt ctactcttac aaaaaacaca acggcaacaa  149820
cctcaaacca gtaatctagt caaaaaagca attcccaagg catgacattc agattcatca  149880
gcactcacag agactacagt gattgctgat aacgccaact taatacctgg ccaacagcat  149940
ggatcctgac ctcactttt cttgtgtgtt tacagaacca caaaaggtg cagtgttttc  150000
a                                                                  150001
```

SEQ ID NO: 3        moltype = DNA  length = 138001
FEATURE               Location/Qualifiers

| source | 1..138001 |
| | mol_type = genomic DNA |
| | organism = Homo sapiens |

SEQUENCE: 3

```
ctctcccaaa ttgtcaaaga agtataaatt agaaaatgaa tcaggacaat ttcaacctgt    60
tagattagct aatatttaaa aattgaacac tcatacaagt gtggtgaagt gattgttttc   120
tagtgacatt ttacactgtc ataaccttct agaaaataaa ttggcagtgt tattgggaga   180
cagaaatatg tctatataat ttatgggaac ttaggctcag aaaatattaa ggaataagaa   240
tgaactttat gaacaaagat gtggagggtt ggaagcaaga gggggggccaa cgcgcacggg   300
gaggaagcat ttgggcagtg actccgcaga cccaggctca ggttgaacta gacaacctcc   360
ttacacctca gtttccttaa ctgtagagca ggagtgatgg aactgcctgt ttcataggac   420
tgttgtgagg atgaagtgag atacaccaca ttataagctt gtgcctggaa aggataatgc   480
ttagtaaatg atgactattc ttttttattg caataaaatg tacacagcgt aagagttact   540
attttaacca ttttttgcagg gtaccaccaa gtggcattta gtacattcac agtggtgtgc   600
aaccatcatc atatttccag aatatttcc tcatccccaa aggaaacctc atgctcatta   660
atcagtagct ctcctttaaa atattagtta tgaagatcat agcactatac aaaactcatt   720
atgtaatgtt gagtgaaaaa atcagggtgt gaaattttgt gatatgatgt aattagtgaa   780
agaagcatac aaaaagtctg aaaatataaa aacaatagca attgcatttc tcagactcta   840
catttaaaca ttattccttta tggttttaaa agcaaagaaa aaggtaaaga aacaacaacc   900
aaccgcaaag caccatgaca aagctcagat tgttaaatcc aggttttttgg aacatagact   960
cttatatgac gtttacactc tccagggttc agagagtctg gcagcattgg gagctgcctt  1020
gtgttctaca gcctcacgga cagacaggag gtccatcacc actgctctgt tcttctggag  1080
tttccttgtg aacatgttgt ggacgtagtt accattctt tcatctttt aaacacaggt  1140
acctttgggg ctggctttct caaggaagcc cagctccctg tgattgagaa tgaagtgtgc  1200
aatcgctatg agtttctgaa tggaagagtc aaatccactg agctctgtgc tgggcatttg  1260
gctgaggca ttgacagttg caaggtaaga aaagatcaag agaccaaagt tagtcttgtg  1320
ctctcctgtc tcagtctcag tcccttagac ttgagtccca aagtagcgaa ttcaagtagg  1380
atttaatcaa tggaagaccc cagtctaagt gttgctcaga aactccctag atctgtccca  1440
aatgtatatt cagatcatcc aaggggactt cttgggggctt gagttccaga tcagcagcaa  1500
gggagccata agtgccataa ctacctcaga ccactccaga tcctggggtg tcccggttgg  1560
cagggactaa agtggtgatt tttctggtag ggaaggaggt agagggtaca ggacagagac  1620
taactgcaca caatatctga gactggagct cagatattgc tgatgatcag agttggcgtg  1680
tctcccccaat tgatttacaa ctggggcttg gatactgttt taaacgggag gagcctccta  1740
accatcttga cacaaccact gacgtgacta cactagagat agactctttc cacttaattc  1800
taccactctt gctttacttc atgagaacga aaatgtaaga ttgcaccatg aattcatttg  1860
cggaaagatt gatactatgc ttttatttta ttttatttta ttttatttta ttttatttta  1920
ttttattgag actctcaccc cggttgaagt gcactgacgt gattttggct cactgcaact  1980
tccacctcct gggttcaagt gaatactcca gcctcctag tagctgggat tacaggtgcc  2040
caccaccacg cctggctaat ttttgtattt ttagtagaga tgggggttttca ccacattgcc  2100
ctggctggtc tcaaactcct gaccttgtga tccacctgtc ttggcctccc aaagtgctgg  2160
gattacagag ttgagccacc gcactcgacc ctatgtttta ttttttaaaaa tatttattta  2220
tttatttaag ccacaactac tagaatagga aggattgata ttttattaat tttatttggt  2280
attattatt ttttttcttt tcctgagaca ttcttgctct gtcacccagg ctggagtgca  2340
gtggcacatt cttggctcac tgcaacctcc atctcctgtg ttcaagcaat tctagtgcct  2400
cagcctactt agtagctggg atgactggca tgtgcctcca cacccagcta atttttgtat  2460
ttttttgtaga cacaggtttt tggcatgttg cccaggcttg tctcaaactc ctggcctcag  2520
gtgatccatc tgccgtggcc tcccaaaatg ctgggattat aggcatgagc caccaccccc  2580
tcctggaagg attgatatct tataacataa tttataatta cagaaaacat gtgagttcac  2640
taggaataaa taaattttga agataataaa agatttcac ttatgttgtc atttcggcac  2700
agtttggtat aggatgtgga gatgttaaca tttataccta gcttgctcgt aaactaagac  2760
ctgaaagggt tgtgtctatc agctgcaccc ctgggtagcg acacaacctc gggaaggcct  2820
cagcccctc ctcgtacagc actgcctgtt ggaaagcttg agggaggcta tggatgtgca  2880
gcacttggca gagggtctgg tcatggaagt taccagcaaa tatgagctac ttttatgatt  2940
ttatttatc caaagaaag agaatgaaag aagaggggag gaaacaagac taatcaggaa  3000
agataaaggt ctaggggtga gggaaggagt aaggagacat aaaggcaatg tggagcagct  3060
gaggggggaa atggctttca ccacttccca gcatctattg acattgcact ctcaaatatt  3120
ttataagact ctatattcaa ggtaatgttt gaacctgct gagccagtgg catgggtctc  3180
tgagagaatc attaacttaa tttgactatc tggtttgtgg gtgcgtttac tctcatgtaa  3240
gtcaacaatg tcctgggatt gggacacact ttctggccac tgctggccag tcccaaaatg  3300
gaacataagg aagtggttct tctacttctt ttatttctga aatcaggtaa gacatagttt  3360
ttttaaatta taagaattat ttttttctccc acaatgtagt aaaaatacat atgccatggc  3420
tttatgtgca attcatttaa ttttttgattc atgaaattcc cagttcaaaa tcttgtatat  3480
gattgaaaaa ttcttaaaaa aataagttta atttccccgt gaagactgtc acggtgctgg  3540
aatgaatggg cagaaaaaat catggttgat ttttctaatc taaaagagtg tgcctacatg  3600
atggccagtc tggctgaaaa ataaatagcc attgtagcta actatgcaaa ggatgcgtaa  3660
gctcttcgct tggttctcag tttcattaat ttatatcatc tctgttcagg tgccatgctc  3720
ccctcactag caagttgaaa caatgaaata actctttgaa tatgtttggt tccttgacct  3780
gttcatggag tgggactcag catttctctc tttgttatgg cctgagtaag gcttttccatc  3840
ggtatacatt tgcttcttat ccctggagaa attatacaca tccctgc agatgatata  3900
cgcatataat gattcaacaa atactcaggg tatttgttga gtgggttagg tccccacatt  3960
tttatacata catacacaca tacacaccgt gtgtgattgt gaatgtaagt gtgtgtcctt  4020
tacaaatact agcttattta gctcatggta taggtagggt agcatagtca tccccatttt  4080
ataaacaaag aaatctagac ttaggaaaat catgttattt gtctcgtgac caaattccca  4140
aatgagaaa ataaagaaac ctggatttaa gccagattaa tctagggctg  4200
ttctcacttt ttcatcttttg tccaacatt tgaaaaata aatctaaaca cattccaatg  4260
taactgaaga gcaggttaat tgtttgccac ttgcagaatc caattaagaa gagagaagtc  4320
tggtataaaa aaagtgatttt gcttccaaag ctagcttagg ggaagaaatg cagcagtcct  4380
gccgtactac ttcactttag gagcagaaag tggcactttt aaaggcaac agaggaggcg  4440
agcaaggatt caggggtcca tgctagcttg ggcaccttat ccaccaggta gttgagcagt  4500
```

```
tgcctgctgg tgcctttgtg agcagggtgt tgtcccttga ggcaaatctc tggagggtga   4560
gagttttgta gtgggcatgc tttggtttat aaatcacctg tgaactcagg agttccatct   4620
tgaagcacat acatagttag atgaacttgc cctgcaggga gagtctgatg aaagggaggt   4680
agatgcttgc aatttaatct ataaattacc agataaaatt ttacaagttg actttaaagt   4740
caaacacatt tgaatttagt ggaagccatt caagaaaata tcaaagaaaa tacagagcag   4800
gagaagatta agcaaagagt tttttgggga aattggtgtc tatgtctgtg tgtgtaggga   4860
gtgcagggga tatgaatatt ctatttcagc ccatggaaac taggatgtag atcactgtga   4920
acttattcag caggctacac ccaaaggcta gaacaaactt ctctgccaca ggattaacat   4980
atgttttaat cgacctgggg ggcacattct ctgataagct cttttggaaa gccaggcttt   5040
ctgtggacgt gttatctttc caatgtgtgc tggaatgccc ggggagagga aaaagtttct   5100
tttacagcca tgctcagtga gaagcggaga aacatcttct attcacaaat tgctaagtct   5160
tttacacatg caaatatgca tacacattca cacaccacag tgaggaagaa attctcacac   5220
cattaataaa atacatttac ttcagtagca atatacatct acattttgcc tataatataa   5280
aagtatttt cctattaaaa gatttgttta atgtttcttc accaacaaat aaacccta   5340
aaatccccat tgccatatga gccctggagg tgaatcagag aaacaaaagg attgtggaaa   5400
aatcatcagg ttaaaaaaag aaaaattgat tctgttttgg gatatttcct agcaacatga   5460
gctgggagg ggatctcagc agtgatgctc tatgaagcat aataaaatga cacagttaca   5520
ggtaacttag ttaaaggggg aaataaatgg aagtttcctc tttttgaata tcaattgtag   5580
cctgctctgc tacatttcaa aaacactctt caaaatgttt aactgaactc actgtaggaa   5640
gcaccttatt aatttattgt gtgttttgaa gtcacactgt gagctataga atttacccaa   5700
gcacaactct tcctggaaaa gagagttcaa atgagaaaca gtgcggggtg aagacatgga   5760
tatgggccta aaatatctat ttctcaatga tattttgata tatctatcaa gtgctttta   5820
gtggattagg ttcagaatgc atcagccaat gcctgttcaa taatccagtt ttccagcata   5880
gagcatatta aattgaggaa ggacaaagtc acagaggtgg ggagcaggtg gactgtggcc   5940
aaggactttg catgaaacag tgagcgtgca tcctcctcct tgccctgccc tcatggtctg   6000
tgtactctca ggaggtcagg acaggccttt ctgagaatga gaatctgttc atctgccttt   6060
ctactggata cttgtcatcg gcatacaaac acatgttctc tgcagtgtgt catctttcag   6120
aacctcccct gaccctgtat tccctagaag tctcgctgct ttcagagcca ggcttctctc   6180
ctgctgccac ccccactgct cttctagtca ctctttaacc cactccatct gcatgtggcc   6240
cccaccacac ccctcaaagt ggtcaaggtt gtcctgttgc ttaattccat ggaagcttgg   6300
ctatcttcat tttattagcc tcttttggcc tctcaccctg tgaaaatcac tacatttgt   6360
gccagagatg gagctggcat ctccaggctt ggaagagggc tgctgaagct cagccaggtg   6420
tcctaaggag cctcaggaca ggggatgctc agtagcttg caatgggaac acagctgagc   6480
cccacttggc caccctttgc cacaaccagg cagaaagcag cttttgaaca gatttgttgc   6540
ctcagatttg atctcaaaga aaaatcgtgg gcagtattgg tcccaggttc tgcttttta   6600
caatttcctc tgaaatctgg atgcctatca acaccttgga aaaactgaat tctccccaac   6660
taatagtggt gtgtcactgt agtaagccta gtacaaaaat ggccttcttt gtggaggagc   6720
ttcatatcct ccattttttt tttgcttaat ttttgcccaa gatgagaaca taatttagtt   6780
cactttttat ttattcccaa catcatccat gcaccaacat ttttgtaact aaaggaggga   6840
ccattcagaa gatgcttatc aactgtcaaa gtgacagtgt tacaaccaat gcacatattg   6900
taagaaatca aacaatggcc tccaaggttc atttctacac agggattagc agatcaacat   6960
caatcttggc aacacagttg ccactgatgg tgtcttattt ttttatcat gacatggcaa   7020
tcaagagcaa acatgattta ttcttattta agattttatg gttagactag gcagatagct   7080
agatatgagc aggaggtgga agcccctgag agaatggagg tctggagaat ctgaaaccc    7140
agagattacc caagtcctgc atgctagaca tgagtggagg aggggaata cctaggataga   7200
aaagaatgcc ccttaagatg cccagcagtc gctcactgtg cagttaactt ttcagaatgc   7260
tgctagatac atgctgatag ggagggaaga gggcaaagga gaaattccta agagatacac   7320
ggttgcagtt agtatacatc tgagtgctat acaaccttct ttgggtggtg gcaaagagca   7380
atgcagccat tacgtagaat tcatatcaaa cacctgtatc acaggtgtta aagaaacaag   7440
aaacattgta cttcttgtat tcttaataat gatttgcaat attgtcttta gtatcactgc   7500
aaacctctat aaatatgatt tttaaaaagt atttcttttag gttggaatta cttctacgca   7560
ttgacttatc ttcctgggtt tcattagccg taccgttgt actttcttcc ttaccactgt   7620
ttatctcaaa ctcttgagat taagtatgg gctcaggagg gagcgaggag cttcaggact   7680
ctcacgacc tccagcacag tgtagctgcc ttatggaaaa gtggcacac tgttttctgc    7740
actggtccct gccccctacta ttcctcactg ggcagagcaa agccaccctg gccctgcctg   7800
aacattttag tcagtgttgg ctctgtgctt ctctggggag gaaatccaag agcaaccca    7860
cagcccctct gccatttcag ctgcagcagt accaccgtta atgcccttgg gcttgagaaa   7920
gaagggacct ggccacttcc ctgacacctc agcacacag cagggaaaga attccagttt    7980
ctctttcttg tgagctttca cctgctactc ttcaccaggc aaggctcctg gcttgggccc   8040
acagtgcagg cacctcgaac tcagttgaac atttccactg gctgcactct gtgttttgt    8100
ggggtgaagc tcccagaggt gactgaaagt ccttctgcca ctaacactgc agtcatactg   8160
cccttgctgt acttggacta gggaaggaaa aaagatcctg agtgctttac tcacacccca   8220
gtgtgccca gccaccctat ggaaaagagg ccagtgtgtc atccctgcaa gcaccctgag    8280
gcccctgccc ctgctgcccc caagctgtag agccagaata taaagctggc agaaaaatgt   8340
aaaaaggcta gactggctta gcctcccagc ctacatcttt ctcctgtgct ggatccttcc   8400
tgctcttgaa catcggactc caagttcttc agctgtggga cttggactgt cttccttgct   8460
cctcagattg caggtggcct attatgggac cttgaatcct tgtgagttaa taccacttaa   8520
taagctcccc tttgtgtgag tatatctata tctatagata gatataggta tactcactat   8580
atatacacat atatctctctc tctctctctc atatatatat atatataatc   8640
tcctattagt tctgtccctc tagagaaccc cgactaatac agattttcat accagaagtg   8700
gttcttgagg aacagaatat taaggatgga attctttcat tggttttggg acttctggtg   8760
ttggctgatt aatatgatta gaccaaaaaa tgctaaggac tctacttcta atagtatgga   8820
gaacactgat agtacttggc ctgaattgtt tagagagtta tgcaaaataa atgcatttga   8880
cactactctt tcatcactta tgagaggcaa ggagtttagt gactctatac ataataccttt   8940
tgactatatg tggagaacca aggaacataa tgaagttgat tgattgctcc taagttctct   9000
ggagaaaagag atgaaagaaa atgatgatct caggggatct gtctcccacc ttcagaagca   9060
gatactgagc cacaaatctg ctaagattgc cctgaatgag agttttaact cctgtagaga   9120
aagagttgaa attgtgaaaa aacagagaca agctgttatc atgcgagtag ctgatctgca   9180
acaagaggtg catgcacagc cttgccaggt gtttactgtt aaagtgaggg cattgactgg   9240
```

```
aaaaaaatgg gaccctggaa cttggagtgg ggatgtgtgg gagaaccctg atgaagctga  9300
ggacactgag tttgtgaact ctgatgaaac ttttttgcca gaagaaacag tttccccatc  9360
cccagtagtg gtaacatccc ctccctgacc cgtgctgcca ttagcctttc caccctttgtc  9420
tgaggatgta aaccctgcac tgcttgaggc aacagtgatg gccttccctg aggcagctgc  9480
caggcaagat aatgttgatt ctcctcaaga ggcacccctta atgcccctga atgcttctag  9540
acctataact aggctaaatt ccttgcgggc cccagaggtg aggttcagag tgtgacccat  9600
gaggaggtgc attatactct aaaagaactg cttaagcttt ctaatttata ttggcagaaa  9660
tctggagaac aggcatggga atggatatta agggtaaggg ataatggtgg aagggacata  9720
gagttggatc aagctgaatt tattggtttg gccctactaa gtagggattc tgcatttaat  9780
gttgcagctc ggggacttag aaaaggttct gataggggcg ggagcagtgg ctcacgcctg  9840
taatcccagc accttgggag gcggggggcgg gcagatcacg agatcaggag attgagacaa  9900
ttctggctaa aatggtgaaa ccccatctct gctaaaaata caaaaattag ctgggcatgg  9960
tgatgcgtaa ctgtaatctc atctacttgg gaggctgagg caagagaact gcttgaacct 10020
gtgaggcaga gattgcagtg agccaagatc gccccactgc attccagcct ggtaacagag 10080
caagactcca tttccaaaaa aaaaaaaaaa aaagttataa tagtttattt gcttggttag 10140
ctgaaatatg gattaaaaga tggtccaatg ttagtgagct ggaaatgcct tggtttaatg 10200
tagaggaagt gatccaaagg cttagggaga ttaggatggt ggagtggatt agtcacttta 10260
gacctactca tcccagctgg gagggtccaa aagatacacc cttggccgaa gcttttgtgaa 10320
atagatttgt gagagcagca cctgtatttt tgaagagccc gtaattgctc ttctctgtat 10380
gtcagatcta acagtaggaa ccacagtcac tcaactacaa aatttaaata caatgggaat 10440
aattggatcc tgaggtggca ggggccaagt gttggcactg aaccatcaaa ggcaaggtgg 10500
gcataactac cataatagac agcagaggca aagcagccat cagaatagtc tgactcatgt 10560
agagctctgg cattggctaa ttaatcatgg tgttcctaga agtgaaattg atgggaaacc 10620
tactgtattc ctacttgatt tatataaaca aaaaactgcc aggtagaatg gactaaagac 10680
taatctgaat tataaaaaca gagaatcatg ggccctcaat caatttccag actcgaacct 10740
gttacagttc cagaacccac tgaatgaagg ggaggctgga tccccttgag gaaggacacc 10800
actaggctac tgacaactta tgctgttact cttctctccca tccttcccta aggagacctc 10860
tggcctttta ccagggtaac tgtgtgtact ggagaaaggg aagtaatgag acatttcaga 10920
aagtactgga cactggctct gagctgacgt tgattccagg gtaccaaaa cgttattgtg 10980
gttccccagt taaagtaggg gcttatggag gttaggtaat taatgaagtt ttagctcatt 11040
tctgacttac agtggttcca gtgggtccct ggacttatcc tctggtcatt ttcccagtgc 11100
caaaatgcat aatttgtata gacatactta ttagctggca gaaatgccac attggctccc 11160
tgactggtag gatgagggct attatggtgg gaaaggccaa acagaagcca ttagagctgt 11220
ctctacctag aaaaataaaa aaatcaaaaa caatatccca tccctggagg gactgaagtg 11280
attagtgtca ccatcaagga cttgaaagac gcagggtgg tgattcccac cacatccctg 11340
ttcaactctc ccatttgacc tgtgcagagg acagatggat cttggaaaat gatggtggat 11400
tatttttaagc ttaaccaagt ggtgactcca attgcagctg ctctaccagt tgtggttttg 11460
ttgcttgagc aaattaacac atctcctggt gcctggtatg cagccattgg cttggcaagt 11520
ggcttttttct ccattcctgt ccataagacc caccagaagc aatttgcctt cagctgacaa 11580
ggccagcatt ataccttac cacccctacct caggggtgta tcaactctcc agctttgtgt 11640
cataatctta tttggagaga ccttgctcgc tttcacttc cacgagatat aacactggtc 11700
cattacattc atgacattat gatgattgga tacagtgagc aagaagtagc aaacacactg 11760
aacttattgg tgagacattt gtatgccaga ggatgggaaa taaatccagc taaaatttag 11820
ggactttcta cctcggtaaa atttctaggg ttccagtggc atgagaccta tggagatatt 11880
ccttctaagg tgaagcataa cttgctgcgt ttggcccctc ttacaaccaa gaaagaggca 11940
caatgcctgg tgggcctatt tggattttgg aggcaacaca ttcctcgttt gggtgtgtta 12000
ctctgcccca tttatcgagt gacctgaaag gctgccagat ttaagtgcag tctagaacaa 12060
aagaaggctc tgaaacaggt ccaggctgct gtgaaagctg ctctgccatt tgggccacat 12120
gaccccgcag atccaatggt gcttgaggtg tcagtggcag ataggggatgc tgtttggagc 12180
cttttggcagg ccccccatagg tgaatcacag tggagaccctc taggattttg gagcaaggcc 12240
ctgccacttc tgcagataac tactctcctt ttgagagaca gctattggtc tgtttattgg 12300
ctttggtggt aactgaacgt ttgactgtgg gtcataaagt caccatgcta cctgaacctg 12360
cctatcatga actggttgct ttcgaccca tctagccatg aagtgggtca gcacagcggc 12420
atttcatcat caaattgaag tggtgtgtat gtgatcgggc ttgagcaggt cctgaaggca 12480
caagtaagtt acataaggaa gtggctcaaa tgcccatgtt ctccactcat gccaccctgc 12540
cttccctccc ccagcctgca ccaatgggcct catggggagt tcccctatgat cagttgacag 12600
aggaagggaa gactaaggac tggttcatag atggttctgc acgatatgca ggcaccaccc 12660
gaaagtggac agctgcagca ctatatccac tttctaaatg catgtgtaca cttgtgctaa 12720
gaaaatatct ttatttttat tcctttattt ttccttttatc actgtgacctt agatttatgg 12780
acttcacatc agcatttaag catttaagtg ttgttcatat cagcatttaa atattgttaa 12840
ccttatgtaa taactttttgg tttgggggatt ggtgcgtttc tggttgtatg aggatagttg 12900
tattatatta ggcataatta tgaccttatt attgtcttta tttgaagatt atgtatgatt 12960
tcaggatgtg tgtatgggtt caagttgaca aggagttgga cttgtgatgg ttaatactgt 13020
caacttgatt ggattgaaag atgcaaagta ttaatctgt gagggtgtgg 13080
caaaaggaga ttaacatttg agtcagtggg ctgggaaggc agaccccacc ttaatctggg 13140
tacacaccat ctaatcaagt tccagtgtgg ccagattgta aagcagggag aaaaatgtga 13200
aaagactaga ctgaattagc ttcccagcct acatctttct cctgtgccaa atgcttcctg 13260
ctcttgaaca tcggactcca agttcttcag cgttgggagt tggactggct ttcttgctcc 13320
tcagcttgca gagggcctgt tgtggaacct tgtgatccgc tggttaata ctacttaata 13380
agatccccctt tatatacata taatatatta tattatatat aatatatata atatatatta 13440
tatataaattat atataatata ttatatatta tatataattat atattatata ttatatatat 13500
tatatattat atataatata tattatatat tatataatt atataatata ttatatatat 13560
aatatatata aaatatatat atatcctatt agttctgtcc ctcagagaa ccctgactaa 13620
taattt gtcattaatc tatttattg attgtatat attgaaccaa cctatatcc 13680
caggaataaa acctacttga ttgttggtgga ttagcttttt gatgtactct tggattcaat 13740
tgctggtatt ttattgagaa ttttttgcatc tgtgttcatc aaggatattg gcttgaagtt 13800
ttctttttttt gttgttccat atcagaatga tgacgacctc atagaatgag ttagtctgtc 13860
ctcttttatc ttttgggaatt gtttcaggag gcttgatatc agctcttctt tatatgactg 13920
gtatactttg gctaggaatc tctctggtcc aggggttttt ctggtgtagg tttttaatta 13980
```

```
ctgattcaac ttcagaactc attactcatt attgagttct aaaactcact ttcatgtact   14040
cttcaaaaga ctgtcttctt ctgttgttga gcggggtgtt ctctcaaggt cgtttaggtg   14100
aaggtggttg ctggtgttct tctgtatcct tactgcttgt cttctctctt ttttattgac   14160
tactgaggat taatggtgat gtgtccaact ttaactctag attagtctat ttctctttta   14220
gattgtaact ctgttttata tattttgaag ctctgttgtt aggcatgtgt atttggattg   14280
ttaggtcttc ttgatgatga cctttatcat tatgtaatgt ttcttcttat ctctggaagt   14340
attcgttgtt ctgaagtcta tttgtgctga tatgaataca gccttcacag ctctattttc   14400
actagtattt gtatatcttt ttctcagctt ttaaattgag atgttcagac catttgcatt   14460
aaagtagttg ttaataggat taaatttaaa tctaccatta agttggttat ttctctttgt   14520
cccatttaaa ctttgttcct tttttcatat ttttctgcct tcatttatat tgagtttatc   14580
tccacgactt acttattaaa ttaattttta atggttttag tattttccac aatgtttata   14640
atatatactt tgatttttc acattccacc ttcaaatgac agaattatac tggatatata    14700
gaaatcttac atcattgcac ttctccttcc tccctctcaa aatgttgtgc tattgctctt   14760
tgtaatagag gcttacttct attatgttat agctctcata atacattgac actattttta   14820
ccctgaataa tcagttgttt tttaaagtga ttatgactac aaatattttg aataatttct   14880
ttattttacc atttctggtg ctccttatct tttacagtag atcccaattt ccatctggag   14940
tcacattctt tctgtgaaaa acaaccttta gcatttctta tagcacggga ctgctgttgc   15000
tgttgtcttt cagcttttct ctgtctgaag aagtctttat tttgccttca gtttttaaaa   15060
gtgattttgc tgagtataga tactgggttg agagtttcat tccttgtatc attttaacaa   15120
tgatgttcca ttatattccg ttttgaatag tttctgacta gaaatctgat ctttgtttct   15180
ttgtattcaa tagttccttt ttctctgact gcctttaaga tattctcatc tttgtttttc   15240
aacagtttga ctataatttg tttattatta acttttttga ttattctgc ttgaggtttc    15300
ctgagctcct tggatttgca gattgttgat ttttattgtt tttgtaaaat tcatagccat   15360
tatctattct actgttttgt tttttttttc acttctctct ctctgtattc ttcttttttgg  15420
actgtaagta ttcaaatgtt agatcattca tattgcttca taaaccttat atgcttcttc   15480
tgcttttttt tttttgtcag gaactctttt tttgtatctg tgttggtttg gataagttct   15540
agtagactat gttcaagttt atggattatt ttgttagttg tgtctaattg actcctcagt   15600
gcattcagag aattcttcat ctctgatatt ataaatctct tcctagcatt ttcatgttac   15660
tcttttctat agtttccatc tctttgctga aattctcccc ctatccatgg atattgtcca   15720
cctttaccac aagattcttt aacatattaa cataggtatc atacaaaccc aaactgatag   15780
tttccagatg gtgtctttc tgagtctgtc tgtcttgatt gctttattat ttaacagtga   15840
cttatcttcc ctcttcagct tttggtgtgt cttgtaattg tttaatcaaa cactgggtat   15900
cataaatgga ggaacagtag agattgcagt aaatattatt tatgctttga aatgggcacc   15960
catcttctgt tgaaaatatg tttttggtc aattgagtca acctagtaac tggttgaact    16020
gaatttggca tttgtgcttg ttgcttttat cttaaatgca ccacaggttt aaattcctcc   16080
agtgatgggt tgctgctatc ttttgcttag agtggggcct ggggtgtgga agaattttct   16140
cagtgttcct atctattatt agattttagc agtcactgca tgcctgcact acagagggga   16200
tatcttcata cacataatct aaccccattg aaactgctgt ttcttcttaa tgaatgctca   16260
atctttggtg gaaataaaca atgctgtat ctcctggagc cacttcagtc ttagtcaggt    16320
tctgcagggc tttgaaggga atgcattctc agtattcttg tgccttattt ggatggaact   16380
tgaacctgtg gtgggtttgg agagaaagag tagcagacgt ctgctatgtt gcaatgcagg   16440
atgctgggca caagaaaatt tccagtctct cctccaagga aataagattt gatcatctac   16500
ctatccctga gaagtgaagg gctttgcctg cggtgctaga tgcaaaacca tttttctccc   16560
cccattgccc agaaacttaa ggctttggct tttctgagca gtggtctagg gaattgtgca   16620
aggttttcat atttgaccct gacagcccat caccacctac agcttgcagt gccaaatgta   16680
tctccctctg atctctcctg tcctgtggtc ctcatgaaca ttaagaagag atttctaaaa   16740
aagagcttgc acatgagcat agtttctggt gagaagaatt ctgatatgtt aacttcctct   16800
aaactttaa ataaaatatt tctaagaatt aaataaagtt ctagaatgat atgaatctat    16860
tccttttggtt ttttgcacgt ctgtctgcct gctaatcaag agaagagaat ggtcgtaatt   16920
ctcagagact ttttcctgtt tgtgtcataa atgacttcac atttttttct gttctaagaa   16980
ctattcagct tgatttcttc tgttttaatt ttagcagcac ctgagcaaag ccatgtgtgt   17040
caggattgct accatggtga tggacagagt tatcgaggca cgtactccac cactgtcaca   17100
ggaaggacct gccaagcttg gtcatctatg acaccacatc aacataatag gaccacagaa   17160
aactacccaa atgcgtatgt cattaatctt acagtaagca aaacaaggtc caagtaaaat   17220
ttgtcttaga aaaggtgtgc gtcaagctaa cttcttatga ttaaattttt ctcacacata   17280
gaatgcatgg caaaatgtct gagaaacatt actttgagca aagagtatga tagaagagaa   17340
atgttaagct ggctctcttt cctgagagtt tgataaaatc aggagaatat ctggcggtgg   17400
tgaggccaca ataatggaaa atcagaatgt ttagacagag tcagcttcaa caacactcac   17460
taaaggtcaa tgtgatcttt acccctttgaa atttctataat tctaatctcc aattcctgaa  17520
gtgaaggttg tgttggcctt ttctgtcttg gctcacaagt aaatgatatg tgcatatcta   17580
tggaaggcg aatctatctt tttctatatc tatgtctatt ccaacgggta gaaacaccct    17640
gggtcctgag caccagtggt ctgaaggaat acgggttgcc aggaagagag aagcaaaggc   17700
aggaaggcag atgaaagtaa gaaatgagac agatgctaaa caataaaaag tgcgggaaga   17760
tagacagaag ctgggtctg accacaccat ggccagtctt tcacacataa gtgactacta    17820
aagcaagaa aaaatgattt ccgcttgttg gacaatagat ggtagaggac caagggaatt    17880
gcgagagaga gaacaatgag atcaactcaa cagatgcact ggttttcttc ctggagaccc   17940
ttcctgcact gaagggcagg agatggagcc caaaaaaaac tgtagccatc ttgctgaaca   18000
gaggagggac attggagttt gggattattc aggtggctag gatttttctag gcctgctaac   18060
aatgaaaca gatttgtgga ggaaaggagt tctagaaata tgcatagaaa tctcctcgaa    18120
tcattggcta aacatgaagc tgcatgtaca cagaaaatag atccacaaga aagtagggca   18180
aagaacatct acggaaagagc agcaactaca atggaacagt gagctcaata acatgcacag  18240
agctcaaata gcactaaggg atattggagt ttggaccaca cagaggagag agacttcact   18300
gaacatcttg ggcattcagt agagacccag gaaaagccat actttaggag tagaattagt   18360
attcttag aataaaggca gctccacaca aacaatagca aaagaaa ggaagtctcc          18420
aagcatcaga atgatgtcca agtcaatgaa ctgcctctga gaggaaaact caaccatctt   18480
tagaggtaaa catcaaagtc aagtggctca gctatgcagt atccacagtg tgaggcctaa   18540
atataaaact tgactacaca tagaaaacctt ttagtgtgac ccacaagcag gaggaaaatc   18600
agccaataca aacagaccca gaagagacag aaatgattag aatggcataa aaatttgaca   18660
tatcactata taataattga gttctaggat ttaagaaaac atgaatatag aatgcaacag   18720
```

```
acaccttatc cagagacagt aagagtataa agagccaaat cgaagaacta ctaagagata  18780
tgtcttaaat gaaaaaatta ctagatggcc tccccatcta gttagacatt tcagaagaaa  18840
ataccaaatg aaaaataatt gcatagaacc tacagaacca gatacacaca tacaaaacac  18900
acgcatgcat acacacacac tcaaacatgt ataagcttac aaacacacac acacatccac  18960
aaatgctgaa aaatgaaatc aaccgagcca cacagacata aaggaaaaca taaaaagatt  19020
tcctacatgt gggaagcaag tcacagaaag ggggaaggag attggaacag aaatatatac  19080
tgaaagcaag gatggctgaa aattttccaa atataaagaa gattaaaaaa tcacggactc  19140
aagaagctca atggatcaga aaaataattt ctaaaatgac aattataggg tgccactggg  19200
tacatagcag ttcaactgtc agagggcaaa gacataatac acagaaaaat ctcgtaagga  19260
acgggaaaaa caaaaagctg tgtcttgcta gaggaacagt gatacaagtg actaatgtgt  19320
tcccatcaga aacactgcaa cctgacacaa aagaataac attaaagtaa taaacgtaag  19380
aaagaagagc tcaactgaga aggctacatc cagcaataaa atgccttgaa gttcatccat  19440
gttggaggaa tgcacattgt gcactcccct aaacaaagaa accggaaact gtaagacttt  19500
ggaatcagca ggcttatgta acaaaagagg tgaccctaag gaattaagga gaagaagaat  19560
agaacaagaa gggaactttc tgcagcctat ataatgaaga acctagcaat ggcaaatgt  19620
agatgaaaat gctacatgtt ttcttgatca aacgtttata tctttttaaa tgagagttga  19680
cgagttgaag caaaatgata ccaatatatt taactttacc atatgtagaa gtaaaaattt  19740
gaacatgtag cataaatcat gtagggatta attggaagtg taccactgta agtttcttac  19800
ctcatgcacg atagtatgta atactaataa aaggttaatg tgtgggttca aagggatatt  19860
gcaaatccta gagcaatcac aaagttttta actctgaggt ttgttgtata ataacaatat  19920
tttatgtatt caaaagaggg aagccaagga agaaaaaaaa gtctttaaag agctctggct  19980
cttagtacat ccagttgctc attgaatgag cttcctggaa tggagggtct gggactgaga  20040
ctaggccaca tgtgtagagc cactagagac acaatgttgg atccccatgg cccataatac  20100
atttcccatt ttctcaggca gccacaggtc atgaatgtga ggatactgag aggttggagc  20160
aacgttcttg ggaggcataa ggaagagcga atgcttcaag atccccgcag cccaaactcc  20220
tcagctgctt tgcctcctaa ttcattgttt tttgctcctc catagctgtc cgacctcttc  20280
agatctctta gtcttcctgc catcttcctt tatgccatgg gacccactgt tctttcaact  20340
catcccccag ttctggagtg gctgtggaca gcagaggata gactgagagc aggagagaag  20400
gtcctgccca ggaacccatt ctagagatac tgcattctgc ctgggagcaa gttttccagg  20460
gcagctttga gaagtcttgc agaaacaaac ctacttgacc gacatgatat gggaatgaca  20520
gacagtaata ctatttgcac aatgcttttc catgggaaag gtagagcctt ttcactaggt  20580
tttgagtaca tggagtgtga gagttgacct ggaaaggtta tcctccttga tgccatgttt  20640
tctctgaaga actacatgtt cgttgcaact cccacattag aatatgaagt cctaccgaga  20700
gagatacgga gactacacag atacagatgc atttgcatgt gaatacacaa tcccacaata  20760
cagacgtcaa aacccatacc agttattcca gagagatgga ttgggcagaa ggcagaaggga  20820
gaatactctg atcgtttttc ggccacgtgt gtgtgttatc tcagtgtttc taagaagcgt  20880
ttgctacttt agattttta tttaaaaaaa atagtaataa tctattaagt atgagagatg  20940
tgcagagagg attagtgatc gagagccatt tttgctggtg gcaatcatat ggtactttta  21000
atgggaatat tagaaaggca ccggtaatga ccttgttgca gacaaaggag agagtgttgg  21060
ggtgcccctg catgttgtcc cacctcttgt gacgtgtatc gttttggaat ttccagtggc  21120
ttgatcatga actactgcag gaatccagat gctgtggcag ctccttattg ttatacgagg  21180
gatcccggtg tcaggtggga gtactgcaac ctgacgcaat gctcagacgc agaagggact  21240
gccgtcgcgc ctccgactgt taccccggtt ccaagcctag aggctccttc cgaacaaggt  21300
aaggagtctg tggccagaca tctacacgct tcgatgctgg gatgaaagc catggaaatt  21360
cccactgatg cagccgcctt caatggtaaa cggatgctcg agtgttgcct gagttctacc  21420
atgtaggagg aagcctccgt gcactctctg ggggagccag cggagtgatt tctggtgcaa  21480
cgtggttggg ctttgtcttt aggatgggca caaaccctcc agggggatcg acttcaaaat  21540
tcaccttgtt gtaaaacggg ctacctcagt gtcccagcca aaattttat tgtaacatgc  21600
tgtcaggtgt gtcactcttt ccaagccagt aagctttttcc ggggatttct tcaagtagcc  21660
agcattcaga gcaatcttca gcattgcaga ttctgagaaa tgtggctctg gagcctgtca  21720
ccctcgagaa acctaagagg gctgcattga ttccatgtgg ccctgggtct atggagcagt  21780
acatgagctc ccagtgctct aaggctcttc agcctaggg tttgaaggga gtgatttctc  21840
agtattctta aacctctttc tgatgacact tgtacctgtg aggggtctag agagaaagag  21900
tagtagactc ctactttact acaattcagg atgcagggca tgagaggatt ccctctctcc  21960
tccaagggaa gaagcttttg gcgtgcacac atccctgaga agcaaagtgt cttttgtcttc  22020
agtcagatac ataggaccgt tttctgcccc atggcccgga agccaaaggc cttggctttc  22080
atgatcaacg gtctagggaa acatgcaaaa tttccatgtc tgtcccaaac tctgcccccg  22140
acagccaatt accacctgca gcccgcattg ccaaatgcgg tgccgtttgc atgaagattc  22200
agtagagttt cctagaaagg tgctacctcg tgagctcact ttccaatgag gaatctgact  22260
tgttgtgttt ctctcaaggtg tcaggtgaaa tatttccaag aacttactac agttcctagaa  22320
tgggaggaat ctgttgcttt ggtgtttgtt tgttggtcgg ttttctcaca tccatctgcc  22380
tatggataag gaaaagagaa cggtcgtaat tctcatagac tcctttctgg ttgtgtcaca  22440
aatggcttca catgtttctc tatgctcaga gatactcagc ttgatttccc gtgttttcat  22500
ttcagcaccg actgagcaaa ggcctggggt gcaggagtgc catggta atggacaggt  22560
ttatcgaggc acatactcca ccactgtcac aggaagaacc tgccaagctt ggtcatctat  22620
gacaccacac tcgcatagtc ggaccccaga atactaccca aatgcgtatg tctttgttct  22680
ttaccataag agaagaaagg gccaagtgaa gtttctgtta caagagatgt gtctcaagct  22740
gagttctccg aactcaactt gtgacagatg cagatggcgt agcaaaatgt ctcaggatga  22800
ttgccttgga gctaagggtc tgagagaagg gaaatgttaa gctccctctc cttcctccta  22860
gttctattga gcagaaggga aatctggagg tgaggagatc acattatgaa gaaagtcaga  22920
atgcaaaagg accagacact tagattaccc ttccacaaca ccaactaaac gtcaatggag  22980
actttccagt tggaattccg ttattctggc ttccacttcc tgaagggaag gttgcgtttg  23040
ccttttctct ctgggttcaa gaggaaagaa taggtgctta tttatggaca ggtgaattga  23100
tctgtttcta tatctacgta tattccgatt gtcagaaaaa cactcgttcc taagtaccag  23160
tggcctgaag ggatacaggt tcccagcaag agaagatcca aggaaggaag gcagatgaga  23220
gtcagcacag agaggggatgc tgaaagtaa aagggatggg tggatggaga gaagcccggg  23280
tctgaccacc caatgccaa tattttggcc acaagcgact accagagaca tggaaaaatg  23340
gtttctacat gtgggacaac agatggtaga ggacctagag aattgagaga ggggcaatga  23400
tgggctccac tccgcagatg ccttggcttt cttcctggat acccttcctg cactgaatag  23460
```

```
caaggagatg gagcccaagc agactgtagc catcttgctg aatggaggag agggattgga   23520
gtttgggatg actgtggtag ctgaaatttt tctaggtctg ctagaaataa gaactggttt   23580
gtgtggagga aaagagctct acaaatacgc atagaagtct cctccagtcg ttggcctgac   23640
atgacgctgc ctgtgcacag gaaatggttc cacgagaaag tgtggcaaag aacatttact   23700
gagaaacagc aagtacaaga gcacggaag ctcaataaag aagagagaga tcacatagca    23760
ctctgggata ctggagttct tcccagctag accagagagt cctcacggag cacattgcca   23820
attcagtgga gaccccagaa cagccgtaat ttaaaggtac acttagtata ttactagaat   23880
aaagtcagct gcagacaacc ccttgcacag ctggaaagca agtgtccaag catcaaatcg   23940
gtttccaatc aatgaagtgc ctgtgagagg aaatctcaac tctctttaga agtaaacaat   24000
aaagtcgatt gcctcagcta tgcggtatcc gcagagtgag tcctaaattt aaaatctgac   24060
tacatgtaga aaagcgtttc gtgtgaccca tgaccaggaa ataaatcggg taatacaaac   24120
aggctcagga atgagagaaa tgattagaat tgcgtgaaaa tttgacatat cagtatgata   24180
actgatttca aatatttaaa aaaacaacat gcaagaaagc agatatcata tcaagagaaa   24240
ttaacagtac agaatagcca aattaaatta aagaggtagt ataaaaaaag tatgtcttaa   24300
ttgaaaaaaa ttactgtatg gccggctgat caatttagac gtttcagagg aaaacattac   24360
ccaacacaca attctagaga acctacgaaa tgagctacac acacacacac acacacacac   24420
acacacactg aaaacacacc catactcaca cacacgcaga aactcacaag ttctaacaca   24480
cacagacaca cgcaccccctg aagaaacagt gaaatataaa attaagcgag cctcacagac   24540
atgtaggaaa atatgaaaag atttcctgca tgtgggaagc aagtcacagt aaagagcaag   24600
ggagtttata atagaaacaa ataccagaat caaggatggc tgataacttt tcaattacga   24660
agaacattaa aaaaaatcac agaatcgtga aactcaaggg atcatatagg gaatttcgga   24720
aaaaaaaccc aacctgtatg atgtactttt gtacatcaca gttcgaaggt aacaaggcaa   24780
agatgtaata agaagaaacc tgtcacgaga aactggagga aaaagagctg tgtcttccta   24840
caagtacact gatacaaatt gccaatgtgt tcacctcaga aacactggaa gccagatacc   24900
agggaatatt gttaaaatga taatcaggaa caaaaagaga tcaaccggga atgctgaatc   24960
cagcaataaa atgccttgaa ggtcatccat gtcggataaa tgcatattgt gcactgcccc   25020
aaagaaagaa accggaaact gtaagaattg gaaatcagca ggcttatgta acaagagagg   25080
tgacccgaag gaattaggta gaagaagaat tgaacaagaa aggaactttc tgcagcccac   25140
gtaatgaaga atccagcaat tggcaaatgt agatagatgt aaatgcaaaa tattttcttg   25200
atcaaatttc tatatctttg taaatgagag ttgactactt gaaacaaaat gatagcaaga   25260
tatttaactt cagcatatgt agaggtaaga atttgaaatg gtagcataaa tcacgaaggg   25320
attaattcga agtgtaccgt tgtaagtttc tttacctcat gcacgatggt gtgtcatatt   25380
aataaaaggg tactgtgcgg gttcgaaggg atattgcaaa tcctagagca atcacaaagg   25440
tttgaactct gaggtttttg gtataataag aatagtccat gcattcaaaa gagggaagcc   25500
aaggaagaac tagaagtctt tcaagagctc aggctcttat acatccagtt gctcattgaa   25560
ccagcttcct ggaatggagg gtctgggggtt gagactaggc cacaagtcta gagtctctag   25620
agagacagtg ttggaacccc atgggcccata atacatttcc cattttctca ggcagccaga   25680
ggtcatgaat gtgaggatac tgggaggttg gagcaacgtt cttgggaggc ataaggaaga   25740
gcgaatgctt caagatcccc gcagcccaaa ctactcgcct gcttttgccc ctaatgcatt   25800
tttctctgct gctccgtagc tgtccgacct cttcagatct cttagtccac cctgccgtct   25860
tcctttatgc catgggtccc actgttcttt caactcatcc cccttccct cagtcccgga    25920
gtagctgcgg ccagcagagg gtagactgag agcaggagag aaggacctgc ctaggaaccc   25980
cttctagaga tactgcatcc tgcctggag caagttttcc agggcagctt tgagaagtct    26040
tggagaaaca aacctactaa acctgacaga cagtaatact atttgcacaa tgcttttctg   26100
tgggaaaggt agagccttt cactacgtat tgagtacata gagtgtgagg gttgacctgg    26160
aacggctatc ctcctggatg acgtgtgttt tctgaagaac tacatgttcg ttgcaactcc   26220
cacattagaa tatgaagtcc taccgagaga gatacggaga ctagacagat acagatgcat   26280
ttgcatgtga atacacaatc ccacaataca gacgtcaaaa cccataccag ttattccaga   26340
gagatggatt gggcagaagg cagaaggaga atactctgat cgttttttcgg ccacgtgtgt   26400
gtgttatctc agtgttccta agaagcgttt gctactttag attttttatt taaaaaaata   26460
gtaataatct attaagtatg agagatgtgc agagaggatt agtgatcgag agccattttn   26520
gctggtggca atcatatggt acttttaatg ggaatattag aaaggcaccg gtaatgaccct   26580
tgttgcagca caaggagag agtgtggggt gcccctgcat gttgtccac ctcttgtgac    26640
gtgtatcgtt ttggaatttc cagtggcttg atcatgaact actgcaggaa tccagatgct   26700
gtggcagctc cttattgtta tacgagggat cccggtgtca ggtgggagta ctgcaacctg   26760
acgcaatgct cagacgcaga agggactgcc gtcgcgcctc cgactgttac cccggttcca   26820
agcctagagg ctccttccga acaaggtaag gagtctgtgg ccagacatct acacgcttcg   26880
atgctgggat gaaaagccat ggaaattccc actgatgcag ccgccttcaa tggtaaacgg   26940
atgctcgagt gttgcctgag ttctaccatg taggaggaag cctccgtgca ctctctgggg   27000
gagccagcga agtgatttct ggtgcaacgt ggttggtctt tgtcttagg atgggcacaa    27060
accctccagg gggatcgact tcaaaattca ccttgttgta aaacgggcta cctcagtgtc   27120
ccagccaaaa ttttttattgt aacatgctgt caggtgtgtc actctttcca agccagtaag    27180
ctttttccggg gatttcttca agtagccagc attcagagca atcttcagca ttgcagattc   27240
tgagaaatgt ggctctggag cctgtcaccc tcgagaaacc taagagggct gcattgattc   27300
catgtggccc tgggtctatg gagcagtaca tgagctccca gtgctctaag gctcttcagc   27360
cctaggcttt gaagggagtg atttctcagt attcttaaac ctctttctga tgacacttgt   27420
acctgtgagg ggtctagaga gaaagagtag tagactccta ctttactaca attcaggatg   27480
cagggcatga gaggattccc tctctcctcc aagggaagaa gcttttggcg tgcacacatc   27540
cctgagaagc aaagtgtctt tgtcttcagt cagatacata ggaccgtttt ctgccccatg   27600
gcccggaagc caaaggcctt ggctttcatg atcaacggtc tagggaaaca tgcaaaattt   27660
ccatgtctgt cccaaactct gcccccgaca gccaattacc acctgcagcc cgcattgcca   27720
aatgcggtgc cgtttgcatg aagattcagt agagtttcct agaaaggtgc tacctcgtga   27780
gctcactttc caatgaggaa tctgatctgt tgtgtttctc taaggtgtca ggtgaaatat   27840
ttccaagaac ttactacagt tctagaatgg gaggaatctg ttgcttttggt gtttgtttgt   27900
tggtcggttt tctcacatcc atctgcctat ggataaggaa aagagaacgg tcgtaattct   27960
catagactcc tttctggttg tgtcacaaat ggcttcacat gtttctctat gctcagagat   28020
actcagcttg atttcccgtg ttttcatttc agcaccgact gagcaaaggc ctgggggtgca   28080
ggagtgctac catggtaatg gacagagtta tcgaggcaca tactccacca ctgtcacagg   28140
aagaacctgc caagcttggt catctatgac accacactcg catagtcgga ccccagaata   28200
```

```
ctacccaaat gcgtatgtct ttgttcttta ccataagaga agaaagggcc aagtgaagtt   28260
tctgttacaa gagatgtgtc tcaagctgag ttctccgaac tcaacttgtg acagatgcag   28320
atggcgtagc aaaatgtctc aggatgattg ccttggagct aagggtctga gagaagggaa   28380
atgttaagct ccctctcctt cctcctagtt ctattgagca aagggaaat ctggaggtga    28440
ggagatcaca ttatgaagaa agtcagaatg acaaaggacc agacacttag attaccctc    28500
cacaacacca actaaacgtc aatggagact ttccagttgg aattccgtta ttctggcttc   28560
cacttcctga agggaaggtt gcgtttgcct tttctctctg ggttcaagag gaaagaatag   28620
gtgcttattt atggacaggt gaattgatct gtttctatat ctacgtatat tccgattgtc   28680
agaaaaacac tcgttcctaa gtaccagtgg cctgaaggga tacaggttcc cagcaagaga   28740
agatccaagg aaggaaggca gatgagagtc agcacagaga gggatgctga aaagtaaaag   28800
ggatgggtgg atggagagaa gcccgggtct gaccacccaa tggccaatat tttggccaca   28860
agcgactacc agagacatgg aaaaatggtt tctacatgtg ggacaacaga tggtagagga   28920
cctagagaat tgagagaggg gcaatgatgg gctccactcc gcagatgcct tggcttctt    28980
cctggatacc cttcctgcac tgaatagcaa ggagatggag cccaagcaga ctgtagccat   29040
cttgctgaat ggaggagagg gattggagtt tgggatgact gtggtagctg aaattttct    29100
aggtctgcta gaaataagaa ctggtttgtg gaggaaagaa gctctacaaa tacgcataga   29160
agtctcctcc agtcgttggc ctgacatgac gctgcctgtg cacaggaaat ggttccacga   29220
gaaagtgtgg caaagaacat ttactgagaa acagcaagta caagacaca ggaagctcaa    29280
taaagaagag agagatcaca tagcactctg ggatactgga gttcttccca gctagaccga   29340
agagtcctca cggagcacat tgccaattca gtggagaccc cagaacagcc gtaatttaaa   29400
ggtacactta gtatattact agaataaagt cagctgcaga caacccttg cacagctgga    29460
aagcaagtgt ccaagcatca aatcggtttc caatcaatga agtgcctgtg agaggaaatc   29520
tcaactctct ttagaagtaa acaacaaagt cgattgcctc agctatgcgg tatccgcaga   29580
gtgagtccta aatttaaaat ctgactacat gtagaaaagc gtttcgtgtg acccatgacc   29640
aggaaataaa tcgggtaata caaacaggct caggaatgag agaaatgatt agaattgcgt   29700
gaaaatttga catatcagta tgataactga tttcaaatat ttaaaaaaac aacatgcaag   29760
aaagcagata tcatatcaag agaaattaac agtacagaat agccaaatta aattaaaagag  29820
ctagtataaa aaaagtatgt cttaattgaa aaaaattact gtatggccgg ctgatcaatt   29880
tagacgtttc agaggaaaac attacccaac acacaattct agagaaccta cagaatgagc   29940
tacacacaca cacacacaca cacacacaaa ctgaaaacac acccatactc acacacacgc   30000
agaaactcac aagttctaac acacacagac acgcgcaccc ctgaagaaac agtgaaatat   30060
aaaattaagc gagcctcaca gacatgtagg aaaaatgaa aagatttcct gcatgtggga    30120
agcaagtcac agtaaagagc aagggagttt ggaatagaaa caaataccgg aatcaaggat   30180
ggctgataac ttttcaatta cgaagaacat taaaaaaaat cacagaatcg tgaaactcaa   30240
gggatcacat agggaatttc ggaaaaaaaa cccaacctgt atgatgtact tttgtacatc   30300
acagttcgaa ggtaacaagg caaagatata ataagaagaa acctgtcacg agaaactgga   30360
ggaaaaagag ctgtgtcttc ctacaagtac actgatacaa attgccaatg tgttcacctc   30420
agaaacactg gaagccagat accagggaat attgttaaaa tgataatcag gaacaaaaag   30480
agatcaaccg ggaatgctga atccagcaat aaaatgcctt gaagatcatc catgtcggat   30540
aaatgcatat tgtgcactgc cccaaagaaa gaaaccggaa actgtaagaa ttggaaatca   30600
gcaggcttat gtaacaagag aggtgacccg aaggaattag gtagaagaag aattgaacaa   30660
gaaaggaact ttctgcagcc cacgtaatga agaatccagc aattggcaaa tgtagataga   30720
tgtaaatgca aaatattttc ttgatcaaat ttctatatct tgtaaatga gagttgacta    30780
cttgaaacaa aatgatagca agatatttaa cttcagcata tgtagaggta agaatttgaa   30840
atggtagcat aaaatcacgaa gggattaatt cgaagtgtac cgttgtaagt ttctttacct   30900
catgcacgat ggtgtgtcat attaataaaa gggtactgtg cgggttcgaa gggatattgc   30960
aaatcctaga gcaatcacaa aggtttgaac tctgaggttt ttggtataat aagaatagtc   31020
catgcattca aaagagggaa gccaaggaag aactagaagt cttttcaagag ctcaggctct   31080
tatacatcca gttgctcatt gaaccagctt cctggaatgg agggtctggg gttgagacta   31140
ggccacaagt ctagagtctc tagagagaca gtgttggaac cccatggccc ataatacatt   31200
tcccatttc tcaggcagcc agaggtcatg aatgtgagga tactgggagg ttggagcaac    31260
gttcttggga ggcataagga agagcgaatg cttcaagatc cccgcagccc aaactactcg   31320
cctgctttgc cccctaatgc attttttctct gctgctccgt agctgtccga cctcttcaga   31380
tctcttagtc caccctgccg tcttccttta tgccatgggt cccactgttc tttcaactca   31440
tccccctttc cctcagtccc gggtagctg cggccaagca agggtagact gagagcagga    31500
gagaaggacc tgcctaggaa ccccttctag agatactgca tcctgcctgg gagcaagttt   31560
tccagggcag ctttgagaag tcttggagaa acaaacctac taaacctgac agacagtaat   31620
actatttgca caatgctttt ctgtgggaaa ggtagagcct tttcactacg tattgagtac   31680
atagagtgtg agggttgacc tggaacggct atcctcctgg atgacgtgtg ttttctgaag   31740
aactacatgt tcgttgcaac tcccacatta gaatatgaa tcctaccgag agatacgag    31800
agactagaca gatacagatg catttgcatg tgaatacaca atcccacaat acagacgtca   31860
aaacccatac cagttattcc agagagatgg attgggtagg aggcagaagg agaatactct   31920
gatcgttttt cggccacgtg tgtgtgttat ctcagtgttt ctaagaagcg tttgctactt   31980
tagatttttt atttaaaaaa aatagtaata atctattaag ttgagagat gtgcagagag    32040
gattagtgat cgagagccat ttttgctggt ggcaatcata tggtacttt aatgggaata    32100
ttagaaaggc accggtaatg accttgttgc agcacaaagg agagagtgtg gggtgcccct   32160
gcatgttgtc ccacctcttg tgacgtgtat cgttttggaa tttccagtgg cttgatcatg   32220
aactactgca ggaatccaga tgctgtggca gctccttatt gttatacgag ggatcccggt   32280
gtcaggtggg agtactgcaa cctgacgcaa tgctcagacg cagaagggac tgccgtccga   32340
cctccgactg ttaccccggt tccaagccta gaggctcctt ccgaacaagg taaggagtct   32400
gtggccagac atctacacgc ttcgatgctg ggatgaaaag ccatgaaaat tcccactgat   32460
gcagccgcct tcaatggtaa acggatgctc gagtgttgcc ggagttctgc catgttgggg   32520
gaagcctccg tgtactctct gggggagcca gcggagtgat ttctggtgca acttgggtgg   32580
gcttttgtctt tagaatgggc acaaaccttc cagggtgatg ggcttcacaa ctcacctcct   32640
tctaaaatgg gctatctcag tgtcttagcc aaaattttta ttgtaacgtg ctgtcaggtg   32700
tgtgattctt tctgtcgcag taagcttttt tggggatttc ttcaagtagc cagcagtcag   32760
tgcaatcttc agcattgcag atttcaaaaa atgtggctct ggagcctgtc atcctcgaga   32820
aacctaacag ggctgcatta attccatatg gtcctgggtc tatggagcag tatatgagct   32880
cccaatgctc taaggctctt cagtcctagg ctttgaaggg agtgatttct cagtgttctt   32940
```

```
aaacctctttt ctgatggcac ttgtacctgt gaggggtcta gagagaaagg ttagtagact    33000
tctcctttac tgcaattcag gatgcagggc atgagaagat tccctccctc ctccaaggga    33060
agaaggtttt ggcgtgcaca catccttgag aagcaaagtg tctttgcctt cagtcagata    33120
tataggatcg ttttctgccc catggcctgg aagccagagg ccttggcttt catgatcaac    33180
gatctaggga aacatgcaaa atttccatgt ctttcccctc ctctgccctc gacagccaat    33240
taccacctgc atcctgcatt gccaaatgca gtgcccttg tatgaacatt cagtagagtt    33300
tcatagaaag gtgctacttc gtgagcgcac tttgcagtga gaaggagtct gttctgttct    33360
gttttctaa ggatttcagg tgaaatattt cctagaactt actacagttc tagattggta    33420
ggaatctgta ggtttgctgt atgttttttg gttggttttc tcccatccat ctgcctacag    33480
gtaagggaaa gataacgttc gtaattctca tagactcctt tctggttgtg tcataaatgg    33540
cttcacatat ttcgttattc tcagagatac tcagtttatt tcttgtgttt tcatttcagc    33600
accgactgag cagaggcctg gggtgcagga gtgctaccac ggtaatggac agagttatcg    33660
aggcacatac tccaccactg tcactggaag aacctgccaa gcttggtcat ctatgacacc    33720
acactcgcat agtcggaccc cagaatacta cccaaatgcg tatgtctttg ttcttttacca    33780
taagagaaga aagggccaag tgaagtttct gttacaagag atgtgtctca agctgagttc    33840
tccgaactca acttgtgaca gatgcagatg gcgtagcaaa atgtctcagg atgattgcct    33900
tggagctaag ggtctgagag aagggaaatg ttaagctccc tctccttcct cctagttcta    33960
ttgagcagaa gggaaatctg gaggtgagga gatcacatta tgaagaaagt cagaatgaca    34020
aaggaccaga cacttagatt acccttccac aacaccaact aaacgtcaat ggagactttc    34080
cagttggaat tccgttattc tggcttccac ttcctgaagg gaaggttgcg tttgcctttt    34140
ctctctgggt tcaagaggaa agaataggtg cttatttatg gacaggtgaa ttgatctgtt    34200
tctatatcta cgtatattcc gattgtcaga aaaacactcg ttcctaagta ccagtggcct    34260
gaagggatac aggttcccag caagagaaga tccaaggaag gaaggcagat gagagccagc    34320
acagagaggg atgctgaaaa gtaaaaggga tgggtggatg gagagaagcc cgggtctgac    34380
cacccaatgg ccaatatttt ggccacaagc gactaccaga gacatggaaa aatgtttct    34440
acatgtggga caacagatgg tagagggacct agagaattga gagggggca atgatgggct    34500
ccactccgca gatgccttgg ctttcttcct ggatacccct cctgcactga atagcaagga    34560
gatggagccc aagcagactg tagccatctt gctgaatgga ggagagggat tggagttgg    34620
gatgactgtg gtagctgaaa ttttctagg tctgctagaa ataagaactg gtttgtggag    34680
gaaaagagct ctacaaatac gcatagaagt ctcctccact cgttggcctg acatgacgct    34740
gcctgtgcac aggaaatggt tccacgagaa agtgtggcaa agaacattta ctgagaaaca    34800
gcaagtacaa gagcacagga agctcaataa agaagagaga gatcacatag cactctggga    34860
tactggagtt cttcccagct agaccagaga gtcctcacgg agcacattgc caattcagtg    34920
gagacccag aacagccgta atttaaaggt acacttagta tattactaga ataaagtcag    34980
ctgcagacaa ccccttgcac agctggaaag caagtgtcca agcatcaaat cggttttccaa    35040
tcaatgaagt gcctgtggga ggaaatctca actctcttta gaagtaaaca acaaagtcga    35100
ttgcctcagc tatgcggtat ccgcagagtc agtcctaaat ttaaaatctg actacatgta    35160
gaaaagcgtt tcgtgtgacc catgaccagg aaataaatcg ggtaatacaa acaggctcag    35220
gaatgagaga aatgattaga attgcgtgaa aatttgacat atcagtatga taactgattt    35280
caaatattta aaaaaacaac atgcaagaaa gcagatatca tatcaagaga aattaacagt    35340
acagaatagc caaattaaat taagagcta gtataaaaa agtatgtctt aattgaaaaa    35400
aattactgta tggccggctg atcaaattag acgtttcaga ggaaaacatt acccaacaca    35460
caattctaga gaacctacag aatgagctac acacacac acacacacac acacacacac    35520
tgaaaacaca cccatactca cacacacgca gaaactcaca agttctaaca cacacagaca    35580
cgcgcacccc tgaagaaaca gtgaaatata aaattaagcg agcctcacag acatgtagga    35640
aaatatgaaa agatttcctg catgtgggaa gcaagtcaca gtaaagagca agggagttg    35700
gaataagaaac aaataccgga tcaaggatg gctgataact tttcaattac gaagaacatt    35760
aaaaaaaatc acagaatcgt gaaactcaag ggatcatata gggaatttcg gaaaaaaaac    35820
ccaacctgta tgatgtactt ttgtacatca cagttcgaag gtaacaaggc aaagatataa    35880
taagaagaaa cctgtcacga gaaactggag gaaaagagc tgtgtcttcc tacaagtaca    35940
ctgatacaaa ttgccaatgt gttcacctca gaaacactgg aagccagata ccagggaata    36000
ttgttaaaat gataatcagg aacaaaaaga gatcaaccgg gaatgctgaa tccagcaata    36060
aaatgccttg aagatcatcc atgtcggata aatgcatatt gtgcactgcc ccaaagaaag    36120
aaaccggaaa ctgtcagaat tggaaatcag caggcttatg taacaagaga ggtgacccga    36180
aggaattagg tagaagaaga attgaacaag aaaggaactt tctgcagccc acgtaatgaa    36240
gaatccagca attggcaaat gtagatagat gtaaatgcaa aatatttcct tgatcaaatt    36300
tctatatctt tgtaaatgag agttgactac ttgaaacaaa atgatagcaa gatatttaac    36360
ttcagcatat gtagaggtaa gaatttgaaa tggtagcata aatcacgaag ggattaattc    36420
gaagtgtacc gttgtaagtt tctttacctc atgcacgtga gtgtgtcata ttaataaaag    36480
ggtactgtgc gggttcgaag ggatattgca aatcctagag caatcacaaa ggtttgaact    36540
ctgaggtttt tggtataata agaatagtcc atgcattcaa aagagggaag ccaaggaaga    36600
actagaagtc tttcaagagc tcaggctctt atacatccag ttgctcattg aaccagcttc    36660
ctggaatgga gggtctgggg ttgagactag gccacaagtc tagagtctct agagagacag    36720
tgttgaacc ccatggccca taatacattt cccattttct gacccagcca gagtcatga    36780
atgtgaggat actgggaggt tggagcaacg ttcttgggag gcataaggaa gagcgaatgc    36840
ttcaagatcc ccgcagccca aactactcgc ctgctttgcc ccctaatgca ttttttctctg    36900
ctgctccgta gctgtccgac tcttcagat tcttagtcc accctgccgt cttcctttat    36960
gccatgggtc ccattgttct ttcaactcat cccccttttcc ctcagtcccg gagtagctgc    37020
ggccagcaga gggtagactg agagcaggag agaaggacct gcctaggaac ccccttctaga    37080
gatactgcat cctgcctggg agcaagtttt ccagggcagc tttgagaagt cttggagaaa    37140
caaacctact aaacctgaca gacagtaata ctatttgcac aatgctttc tgtgggaaag    37200
gtagagcctt tcactacgt attgagtaca tagagtgtga gggttgacct ggaacggcta    37260
tcctcctgga tgacgtgcgt tttctgaaga actacatgtt cgttgcaact cccacattag    37320
aatatgaagt cctaccgaga gagatacgga gactagacga ataacgatgc atttgcatgt    37380
gaatacacaa tcccacaata cagacgtcaa aacccatacc agttattcca gagagatgga    37440
ttgggcagaa ggcagaagga gaatactctg atcgttttc ggccacgtgt gtgtgtatc    37500
tcagtgtttc taagaagcgt ttgctacttt agatttttta ttaaaaaaa atagtaataa    37560
tctattaagt atgagagatg tgcagagagg attagtgatc gagagccatt tttgctggtg    37620
gcaatcatat ggtactttta atgggaatat tagaaaggca ccggtaatga ccttgttgca    37680
```

```
gcacaaagga gagagtgtgg ggtgccctg catgttgtcc cacctcttgt gacgtgtatc  37740
gttttggaat ttccagtggc ttgatcatga actactgcag gaatccagat gctgtggcag  37800
ctccttattg ttatacgagg gatcccggtg tcaggtggga gtactgcaac ctgacgcaat  37860
gctcagacgc agaagggact gccgtcgcgc ctccgactgt tacccccggtt ccaagcctag  37920
aggctccttc cgaacaaggt aaggagtctg tggccagaca tctacacgct tcgatgctgg  37980
gatgaaaagc catggaaatt cccactgatg cagccgcctt caatggtaaa cggatgctca  38040
agtgttgcct gagttctacc atgtaggagg aagcctccgt gcactctctg ggggagccag  38100
cggagtgatt tctggtgcaa cgtggttggg cttttgtcttt aggatgggca caaaccctcc  38160
aggggggatcg acttcaaaat tcaccttgtt gtaaaacggg ctacctcagt gtcccagcca  38220
aaatttttat tgtaacatgc tgtcaggtgt gtcactcttt ccaagccagt aagcttttcc  38280
ggggatttct tcaagtagcc agcattcaga gcaatcttca gcattgcaga ttctgagaaa  38340
tgtggctctg gagcctgtca ccctcgagaa acctaagagg gctgcattga ttccatgtgg  38400
ccctgggtct atggagcagt acatgagctc ccagtgtctc aaggtctctc agccctaggc  38460
tttgaaggga gtgatttctc agtattctta aacctcttc tgatgacact tgtacctgtg  38520
aggggtctag agagaaagag tagtagactc ctactttact acaattcagg atgcagggca  38580
tgagaggatt ccctctctcc tccaagggaa gaagcttttg gcgtgcacac atccctgaga  38640
agcaaagtgt ctttgtcttc agtcagatac ataggaccgt tttctgcccc atggcccgga  38700
agccaaaggc cttggctttc atgatcaacg gtctagggaa acatgcaaaa tttccatgtc  38760
tgtcccaaac tctgccccccg acagccaatt accacctgca gcccgcattg ccaaatgcgg  38820
tgccgtttgc atgaagattc agtagagttt cctagaaagg tgctacctcg tgagctcact  38880
ttccaatgag aatctgatc tgttgtgttt ctctaaggtg tcaggtgaaa tatttccaag  38940
aacttactac agttctagaa tgggaggaat ctgttgcttt ggtgttttgtt tgttggtcgg  39000
ttttctcaca tccatctgcc tatgggataag gaaaagagaa cggtcgtaat tctcatagac  39060
tccttctgg ttgtgtcaca aatggcttca catgtttctc tatgctcaga gatactcagc  39120
ttgatttccc gtgttttcat ttcagcaccg actgagcaaa ggcctggggt gcaggagtgc  39180
taccatggta atggacaggta ttatcgaggc acatactcca ccactgtcac aggaagaacc  39240
tgccaagctt ggtcatctat gacaccacac tcgcatagtc ggaccccaga atactcccca  39300
aatgcgtatg tctttgttct ttaccataag agaagaaagg gccaagtgaa gtttctgtta  39360
caagagatgt gtctcaagct gagttctccg aactcaactt gtgacagatg cagatggcgt  39420
agcaaaatgt ctcaggatga ttgccttgga gctaaggtc tgagagaagg gaaatgttaa  39480
gctccctctc cttcctccta gttctattga gcagaaggga aatctggagg tgaggaatc  39540
acattatgaa gaaagtcaga atgacaaagg accagacact tagattaccc ttccacaaca  39600
ccaactaaac gtcaatggag actttccagt tggaattccg ttattctggc ttccacttcc  39660
tgaagggaga gttgcgtttg ccttttctct ctgggttcaa gaggaaagaa taggtgctta  39720
tttatggaca ggtgaattga tctgtttcta tatctacgta tattccgatt gtcagaaaaa  39780
cactcgttcc taagtaccag tggcctgaag ggatacaggt tcccagcaag agaagatcca  39840
aggaaggaag gcagatgaga gtcagcacag agagggatgc tgaaaagtaa aagggatggg  39900
tggatggaga gaagcccggg tctgaccacc caatggccaa tattttggcc acaagcgact  39960
accagagaca tggaaaaatg gttttactact gtgggacaac agatggtaga ggacctagag  40020
aattgagaga ggggcaatga tgggctccac tccgcagatg ccttggcttt cttcctggat  40080
acccttcctg cactgaatag caaggagatg gagcccaagc agactgtagc catcttgctg  40140
aatggaggag agggattgga gtttgggatg actgtgtag ctgaaatttt tctaggtctg  40200
ctagaaaataa gaactggttt gtggaggaaa agagctctac agaagtctac  40260
tccagtcgtt ggcctgacat gacgctgcct gtgcacagga aatggttcca cgagaaagtg  40320
tggcaaagaa catttactga gaaacagcaa gtacaagagc acaggaagct caataaagaa  40380
gagagagatc acatagcact ctgggatact ggagttcttc ccagctagac cagagagtcc  40440
tcacgagaca cattgccaat tcagtggaga ccccagaaca gccgtaattt aaaggtacac  40500
ttagtatatt actagaataa agtcagctgc agacaacccc ttgcacagct ggaaagcaag  40560
tgtccaagca tcaaatcggt ttccaatcaa tgaagtgcct gtgagaggaa atctcaactc  40620
tctttagaag taaacaacaa agtcgattgc ctcagctatg cggtatccgc agagtgagtc  40680
ctaaatttaa aatctgacta catgtagaaa agcgtttcgt gtgacccatg accaggaaat  40740
aaatcgggta atacaaacag gctcaggaat gagagaaatt attagaattg cgtgaaaatt  40800
tgaaatatca gtatgataac tgatttcaaa tatttaaaaa aacaacatgc aagaaagcag  40860
atatcatatc aagagaaatt aacagtacag aatagccaaa ttaaattaaa gagctagtat  40920
aaaaaaagta tgtcttaatt gaaaaaaatt actgtatgcc cggctgatca atttagacgt  40980
ttcagaggaa aacattaccc aacacacaat tctagagaac ctacagaatg agctacacac  41040
acacacacac acacacacac aaactgaaaa cacacccata ctcacacaca cgcagaaact  41100
cacagttct aacacacaca gacacgcgca ccccctgaaga aacagtgaaa tataaaatta  41160
agcgagcctc acagacatgt aggaaaatat gaaaagattt cctgcatgtg ggaagcaagt  41220
cacagtaaag agcaagggag tttggaatag aaacaaatac cagaatcaag gatggctgat  41280
aacttttcaa ttacgaagaa cattaaaaaa aatcacagaa tcgtgaaact caagggatca  41340
catagggaat ttcggaaaaa aaacccaacc tgtatgatgt acttttgtac atcacagttc  41400
gaaggtaaca aggcaaagat ataataagaa gaaacctgtc acgagaaact ggaggaaaaa  41460
gagctgtgtc ttcctacaag tacactgata caattgcca tgttgttcac ctcagaaaca  41520
ctggaagcca gataccaggg aatattgtta aaatgataat caggaacaaa aagagatcaa  41580
ccgggaatgc tgaatccagc aataaaatgc cttgaagatc atccatgtcg gataaatgca  41640
tattgtcac tgcccaaag aaagaaaccg gaaactgtaa gaattggaaa tcagcaggct  41700
tatgtaacaa gagaggtgac ccgaaggaat taggtagaag aagaattgaa caagaaagga  41760
actttctgca gcccacgtaa tgaagaatcc agcaattggc aaatgtagat agatgtaaat  41820
gcaaaatatt ttcttgatca aatttctata tcttttgtaaa tgagagttga ctacttgaaa  41880
caaaatgata gcaagatatt taacttcagc atatgtagag gtaagaattt gaaatggtag  41940
cataaatcac gaagggatta attcgaagtg taccgttgta agtttcttta cctcatgcac  42000
gatggtgtgt catattaata aaagggtact gtgcgggttc gaagggatat tgcaaatcct  42060
agagcatca caaaggtttg aactctgagg tttttggtat aataagaata gtccatgcat  42120
tcaaaagagg gaagccaagg aagaactaga agtctttcaa gagctcaggc tcttatacat  42180
ccagttgctc attgaaccag cttcctggaa tggagggtct ggggttgaga ctaggccaca  42240
agtctagagt ctctagagag acagtgttgg aaccccatgg cccataatac atttcccatt  42300
ttctcaggca gccagaggtc atgaatgtga ggatactggg aggttggagc aacgttcttg  42360
ggaggcataa ggaagagcga atgcttcaag atccccgcag cccaaactac tcgcctgctt  42420
```

```
tgcccctaa tgcattttc tctgctgctc cgtagctgtc cgacctcttc agatctctta 42480
gtccaccctg ccgtcttcct ttatgccatg ggtcccactg ttctttcaac tcatccccct 42540
ttccctcagt cccggagtag ctgcggccag cagagggtag actgagagca ggagagaagg 42600
acctgcctag gaaccccttc tagagatact gcatcctgcc tgggagcaag ttttccaggg 42660
cagctttgag aagtcttgga gaaacaaacc tactaaacct gacagacagt aatactattt 42720
gcacaatgct tttctgtggg aaaggtagag cctttcact acgtattgag tacatagagt 42780
gtgagggttg acctggaacg gctatcctcc tggatgacgt gtgttttctg aagaactaca 42840
tgttcgttgc aactcccaca ttagaatatg aagtcctacc gagagagata cggagactag 42900
acagatacag atgcatttgc atgtgaatac acaatcccac aatacagacg tcaaaaccca 42960
taccagttat tccagagaga tggattgggc agaaggcaga aggagaatac tctgatcgtt 43020
tttcggccac gtgtgtgtgt tatctcagtg tttctaagaa gcgtttgcta ctttagattt 43080
tttatttaaa aaaatagta ataatctatt aagtatgaga gatgtgcaga gaggattagt 43140
gatcgagagc cattttgct ggtggcaatc atatggtact tttaatggga atattagaaa 43200
ggcaccggta atgaccttgt tgcagcacaa aggagagagt gtgggtgcc cctgcatgtt 43260
gtcccacctc ttgtgacgtg tatcgttttg gaatttccag tggcttgatc atgaactact 43320
gcaggaatcc agatgctgtg gcagctcctt attgttatac gagggatccc ggtgtcaggt 43380
gggagtactg caacctgacg caatgctcag acgcagaagg gactgccgtc gcgcctccga 43440
ctgttacccc ggttccaagc ctagaggctc cttccgaaca aggtaaggag tctgtggcca 43500
gacatctaca cgcttcgatg ctgggatgaa aagccatgga aattcccact gatgcagccg 43560
ccttcaatgg taaacggatg ctcgagtgtt gcctgagttc taccatgtag gaggaagcct 43620
ccgtgcactc tctgggggag ccagcggagt gatttctggt gcaacgtggt tgggctttgt 43680
ctttaggatg ggcacaaacc ctccagggg atcgacttca aaattcacct tgttgtaaaa 43740
cgggctacct cagtgtccca gccaaaattt ttattgtaac atgctgtcag gtgtgtcact 43800
cttttccaagc cagtaagctt ttccggggat tccttcaagt agccagcatt cagagcaatc 43860
ttcagcattg cagattctga gaaatgtggc tctggagcct gtcaccctcg agaaacctaa 43920
gagggctgca ttgattccat gtggccctgg tctatggag cagtacatga gctcccagtg 43980
ctctaaggct cttcagccct aggctttgaa gggagtgatt tctcagtatt cttaaacctc 44040
tttctgatga cacttgtacc tgtgaggggt ctagagagaa agagtagtag actcctactt 44100
tactacaatt caggatgcag ggcatgagag gattccctct ctcctccaag ggaagaagct 44160
tttggcgtgc acacatccct gagaagcaaa gtgtctttgt cttcagtcag atacatagga 44220
ccgttttctg ccccatggcc cggaagccaa aggccttggc tttcatgatc aacggtctag 44280
ggaaacatgc aaaatttcca tgtctgtccc aaactcttcc cccgacagcc aattaccacc 44340
tgcagcccgc attgccaaat gcggtgccgt ttgcatgaag attcagtaga gtttcctaga 44400
aaggtgctac ctcgtgagct cactttcaa tgaggaatct gatctgttgt gtttctctaa 44460
ggtgtcaggt gaaatatttc caagaactta ctacagttct agaatgggag gaatctgttg 44520
ctttggtgtt tgtttgttgg tcggttttct cacatccatc tgcctatgga taaggaaaag 44580
agaacggtcg taattctcat agactccttt ctggttgtgt cacaaatggc ttcacatgtt 44640
tctctatgct cagagatact cagcttgatt tcccgtgttt tcatttcagc accgactgag 44700
caaaggcctg gggtgcagga gtgctaccat ggtaatgac agagttatcg aggcacatac 44760
tccaccactg tcacaggaag aacctgccaa gcttggtcat ctatgacacc acactcgcat 44820
agtcggaccc cagaatacta cccaaatgcg tatgtctttg ttctttacca taagagaaga 44880
aagggccaag tgaagtttct gttacaagag atgtgtctca agctgagttc tccgaactca 44940
acttgtgaca gatgcagatg gcgtagcaaa atgtctcagg atgattgcct tggagctaag 45000
ggtctgagag aagggaaatg ttaagctccc tctccttcct cctagttcta ttgagcagaa 45060
gggaaatctg gaggtgagaa gatcacatta tgaagaaagt cagatgaca aaggaccaga 45120
cacttagatt accccttccac aacaccaact aaacgtcaat ggagctttc cagttggaat 45180
tccgttattc tggcttccac ttcctgaagg aaggttgcg tttgccttt ctctctgggt 45240
tcaagaggaa agaataggtg cttatttatg gacaggtgaa ttgatctgtt tctatatcta 45300
cgtatattcc gattgtcaga aaacactcg ttcctaagta ccagtggcct gaagggatac 45360
aggttcccag caagagaaga tccaaggaag gaaggcagat gagagtcagc acagagaggg 45420
atgctgaaaa gtaaaaggga tgggtggatg gagagaagcc cgggtctgac cacccaatgg 45480
ccaatatttt ggccacaagc gactaccaga gacatgaaaa aatggtttct acatgtggga 45540
caacagatgg tagaggacct agagaattga gagaggggca atgatgggct ccactccgca 45600
gatgccttgc ctttcttcct ggatacccttt cctgcactga atagcaagga gatggagccc 45660
aagcagactg tagccatctt gctgaatgga ggagagggat tggagtttgg gatgactgtg 45720
gtagctgaaa tttttctagg tctgctagaa ataagaactg gtttgtgtgg aggaaagag 45780
ctctacaaat acgcatagaa gtctcctcca gtcgttggcc tgacatgacg ctgcctgtgc 45840
acaggaaatg gttccacgag aaagtgtggc aagaacatt tactgagaaa cagcaagtac 45900
aagagcacag gaagctcaat aaagaagaga gagatccaat agcactctgg gatactggag 45960
ttcttcccag ctagaccaga gagtcctcac ggagcacatt gccaattcag tggagaccc 46020
agaacagccg taatttaaag gtacacttag tatattacta gaataaagtc agctgcagac 46080
aacccttgc acagctggaa agcaagtgtc caagcatcaa atcggttcc aatcaatgaa 46140
gtgcctgtga gaggaaatct caactctctt tagaagtaaa caacaaagtc gattgcctca 46200
gctatgcggt atccgcagag tgagtcctaa atttaaaatc tgactacttg tagaaaagcg 46260
tttcgtgtga cccatgacca ggaaataaat cgggtaatac aaacaggctc aggaatgaga 46320
gaaatgatta gaattgcgtg aaatttgac atatcagtat gataactgat ttcaaatatt 46380
taaaaaaaca acatgcaaga aagcagatat catatcaaga gaaattaaca gtacagaata 46440
gccaaattaa attaaagagg tagtataaaa aagtatgtc ttaattgaaa aaaattactg 46500
tatggccggc tgatcaattt agacgtttca gaggaaaaca ttacccaaca cacaattcta 46560
gagaacctac agaatgagct acacacacac acacacacac acacacaaac tgaaaacaca 46620
cccatactca cacacacgca gaaactcaca agttctaaca cacacagaca cgcgcacccc 46680
tgaagaaaca gtgaaatata aaattaagcg agcctcacag acatgtagga aaatatgaaa 46740
agatttcctg catgtgggaa gcaagtcaca gtaaagcca agggagtttg aatagaaac 46800
aaataccgga atcaaggatg gctgataact ttcaattac gaagaacatt aaaaaaaatc 46860
acagaatcgt gaaactcaag ggatcacata gggaatttcg gaaaaaaaac ccaacctgta 46920
tgatgtactt tgtacatca cagttcgaag gtaacaaggc aaagatataa taagaagaaa 46980
cctgtcacga gaaactggag gaaaaagagc tgtgtcttcc tacaagtaca ctgatacaaa 47040
ttgccaatgt gttcacctca gaaacactgg aagccagata ccaggaata ttgttaaaat 47100
gataatcagg aacaaaaaga gatcaaccgg gaatgctgaa tccagcaata aaatgccttg 47160
```

```
aaggtcatcc atgtcggata aatgcatatt gtgcactgcc ccaaagaaag aaaccggaaa   47220
ctgtaagaat tggaaatcag caggcttatg taacaagaga ggtgacccga aggaattagg   47280
tagaagaaga attgaacaag aaaggaactt tctgcagccc acgtaatgaa gaatccagca   47340
attggcaaat gtagatagat gtaaatgcaa aatattttct tgatcaaatt tctatatctt   47400
tgtaaatgag agttgactac ttgaaacaaa atgatagcaa gatatttaac ttcagcatat   47460
gtagaggtaa gaatttgaaa tggtagcata aatcacgaag ggattaattc gaagtgtacc   47520
gttgtaagtt tctttacctc atgcacgatg gtgtgtcata ttaataaaag ggtactgtgc   47580
gggttcgaag ggatattgca aatcctagag caatcacaaa ggtttgaact ctgaggtttt   47640
tggtataata agaatagtcc atgcattcaa aagagggaag ccaaggaaga actagaaagtc  47700
tttcaagagc tcaggctctt atacatccag ttgctcattg aaccagcttc ctggaatgaa   47760
gggtctgggg ttgagactag gccacaagtc tagagtctct agagagacag tgttggaacc   47820
ccatggccca taatacattt cccattttct caggcagcca gaggtcatga atgtgaggat   47880
actgggaggt tggagcaacg ttcttgggag gcataaggaa gagcgaatgc ttcaagatcc   47940
ccgcagccca aactactcgc ctgctttgcc ccctaatgca tttttctctg ctgctccgta   48000
gctgtccgac ctcttcagat ctcttagtcc accctgccgt cttcctttat gccatgggtc   48060
ccactgttct ttcaactcat cccccttttcc ctcagtcccg gagtagctgc ggccagcaga  48120
gggtagactg agagcaggag agaaggacct gcctaggaac cccttctaga gatactgcat   48180
cctgcctggg agcaagtttt ccagggcagc tttgagaagt cttgggagaaa caaacctact  48240
aaacctgaca gacagtaata ctatttgcac aatgcttttc tgtgggaaag gtagagcctt   48300
ttcactacgt attgagtaca tagagtgtga gggttgacct ggaacggcta tcctcctgga   48360
tgacgtgcgt tttctgaaga actacatgtt cgttgcaact cccacattag aatatgaagt   48420
cctaccgaga gagatacgga gactagacag atacagatgc atttgcatgt gaatacacaa   48480
tcccacaata cagacgtcaa aacccatacc agttattcca gagagatgga ttgggcagaa   48540
ggcagaagga gaatactctg atcgtttttc ggccacgtgt gtgtgttatc tcagtgtttc   48600
taagaagcgt ttgctacttt agattttta tttaaaaaa atagtaataa tctattaagt    48660
atgagagatg tgcagagagg attagtgatc gagagccatt tttgctgatg gcaatcatat   48720
ggtactttta atgggaatat tagaaaggca ccgtaatga ccttgttgca gcacaaagga    48780
gagagtgtgg ggtgcccctg catgttgtcc cacctcttgt gacgtgtatc gtttggaat    48840
ttccagtggc ttgatcatga actactgcag gaatccagat gctgtggcag ctccttattg   48900
ttatacgagg gatcccggtg tcaggtggga gtactgcaac ctgacgcaat gctcagacgc   48960
agaagggact gccgtcgcgc ctccgactgt taccccggtt ccaagcctag aggctccttc   49020
cgaacaaggt aaggagtctg tggccagaca tctacacgct tcgatgctgg gatgaaaagc   49080
catgaaaatt cccactgatg cagccgcctt caatggtaaa cggatgctcg agtgttgcct   49140
gagttctacc atgtaggagg aagcctccgt gcactcctg ggggagccag cggagtgatt    49200
tctggtgcaa cgtggttggg ctttgtcttt aggatgggca caaaccctcc aggggatcg    49260
acttcaaaat tcaccttgtt gtaaaacggg ctacctcagt gtcccagcca aaatttttat   49320
tgtaacatgc tgtcaggtgt gtcactcttt ccaagccagt aagcttttcc ggggatttct   49380
tcaagtagcc agcattcaga gcaatcttca gcattgacaga ttctgagaaa tgtggctctg  49440
gagcctgtca ccctcgagaa acctaagagg gctgcattga ttccatgtgg ccctgggtgt   49500
atggagcagt acatgagctc ccagtgctct aaggctcttc agccctaggc tttgaaggga   49560
gtgatttctc agtattctta aacctctttc tgatgacact tgtacctgtg aggggtctag   49620
agagaaagag tagtagactc ctactttact acaattcagg atgcagggca tgagaggatt   49680
ccctctctcc tccaagggaa gaagcttttg gcgtgcacac atccctgaga agcaaagtgt   49740
cttttgtcttc agtcagatac ataggaccgt tttctgcccc atggcccgga agccaaaggc  49800
cttggctttc atgatcaacg gtctaggaa acatgcaaaa tttccatgtc tgtcccaaac    49860
tctgcccccg acagccaatt accacctgca gcccgcattg ccaaatgcgg tgccgtttgc   49920
atgaagattc agtagagttt cctagaaagg tgctacctcg tgagctcact ttccaatgag   49980
gaatctgatc tgttgtgttt ctctaagtg tcaggtgaaa tatttccaag aacttactac    50040
agttctagaa tgggaggaat ctgttgcttt ggtgtttgtt tgttggtcgg ttttctcaca   50100
tccatctgcc tatggataag gaaaagaaa cggtcgtaat tctcatagac tccttttctgg   50160
ttgtgtcaca aatggcttca catgtttctc tatgctcaga gatactcagc ttgatttctc   50220
gtgtttcat ttcagcaccg actgagcaaa ggcctgggt gcaggagtgc taccatggta     50280
atggacagag ttatcgaggc acatactcca ccactgtcac aggaagaacc tgccaagctt   50340
ggtcatctat gacaccacac tcgcatagtc ggaccccaga atactaccca aatgcgtatg   50400
tctttgttct ttaccataag agaagaaagg gccaagtgaa gtttctgtta caagagatgt   50460
gtctcaagct gagttctccg aactcaactt gtgacagatg cagatggcgt agcaaaatgt   50520
ctcaggatga ttgccttgga gctaagggtc tgagagaagg gaaatgttaa gctccctctc   50580
cttcctccta gttctattga gcagaaggga aatctggagg tgaggagatc acattatgaa   50640
gaaagtcaga atgacaaagg accagacact tagattaccc ttccacaaca ccaactaaac   50700
gtcaatggag actttccagt tggaattccg ttattctggc ttccacttcc tgaagggaag   50760
gttgcgtttg ccttttctct ctgggttcaa gaggaaagaa taggtgctta tttatgggaca 50820
ggtgaattga tctgtttcta tatctacgta tattccgatt gtcagaaaaa cactcgttcc   50880
taagtaccag tggcctgaag ggatacaggt tcccagcaag agaagatcca aggaaggaag   50940
gcagatggaa gtcagcacag agagggatgc tgaaaagtaa aagggatggg tggatgggaa   51000
gaagcccggg tctgaccacc caatggccaa tatttttggcc acaagcgact accagagaca  51060
tggaaaaatg gtttctacat gtgggacaac agatggtaga ggacctagag aattgagaga   51120
ggggcaatga tgggctccac tccgcagatg ccttggcttt cttcctggat acccttcctg   51180
cactgaatag caaggagatg gagcccaagc agactgtagc catcttgctg aatgaggag    51240
agggattgga gtttgggatg actgtggtag ctgaaatttt tctaggtctg ctagaaataa   51300
gaactggttt gtgtggagga aaagagctct acaaatacgc atagaagtct cctccagtcg   51360
ttggcctgac atgacgctgc ctgtgcacag gaaatggttc cacagaaaag tgtggcaaag   51420
aacatttact gagaaacagc aagtacaaga gcacaggaag ctcaataaag aagagagaga   51480
tcacatagca ctctgggata ctggagttct tcccagctag accagagagt cctcacggag   51540
cacattgcta attcagtgga gaccccagaa cagccgtaat ttaaaggtac acttagaata   51600
ttactagaat aaaagtcagct gcagacaacc ccttgcacag ctggaaagca agtgtccaag  51660
catcaaatcg gttccaatc aatgaagtgc ctgtgagagg aaatctcaac tctcttagaa    51720
agtaaacaac aaagtcgatt gcctcagcta tgcggtatcc gcagagtgag tcctaaattt   51780
aaaatctgac tacatgtaga aaagcgtttc gtgtgaccca tgaccaggaa ataaatcggg   51840
taatacaaac aggctcagga atgagagaaa tgattagaat tgcgtgaaaa tttgacatat   51900
```

```
cagtatgata actgatttca aatatttaaa aaaacaacat gcaagaaagc agatatcata  51960
tcaagagaaa ttaacagtac agaatagcca aattaaatta aagagctagt ataaaaaaag  52020
tatgtcttaa ttgaaaaaaa ttactgtatg gccggctgat caaattagac gtttcagagg  52080
aaaacattac ccaacacaca attttagaga acctacagaa tgagctacac acacacacac  52140
acacacacac acacacacaa actgaaaaca cacccatact cacacacacg cagaaactca  52200
caagttctaa cacacacaga cacgcgcacc cctgaagaaa cagtgaaata taaaattaag  52260
cgagcctcac agacatgtag gaaaatatga aaagatttcc tgcatgtggg aagcaagtca  52320
cagtaaagag caagggagtt tataatagaa acaaatacca gaatcaagga tggctgataa  52380
cttttcaatt acgaagaaca ttaaaaaaaa tcacagaatc gtgaaactca agggatcata  52440
tagggaattt cggaaaaaaa acccaacctg tatgatgtac ttttgtacat cacagttcga  52500
aggtaacaag gcaaagatgt aataagaaga aacctgtcac gagaaactgg aggaaaaaga  52560
gctgtgtctt cctacaagta cactgataca aattgccaat gtgttcacct cagaaacact  52620
ggaagccaga taccagggaa tattgttaaa atgataatca ggaacaaaaa gagatcaacc  52680
gggaatgctg aatccagcaa taaaatgcct tgaaggtcat ccatgtcgga taatgcata  52740
ttgtgcactg ccccaaagaa agaaaccgga aactgtaaga attggaaatc agcaggctta  52800
tgtaacaaga gaggtgaccc gaaggaatta ggtagaagaa gaattgaaca agaaaggaac  52860
tttctgcagc ccacgtaatg aagaatccag caattggcaa atgtagatag atgtaaatgc  52920
aaaatatttt cttgatcaaa tttctatatc tttgtaaatg agagttgact acttgaaaca  52980
aaatgatagc aagatatttta acttcagcat atgtagaggt aagaatttga aatggtagca  53040
taaatcacga agggattaat tcgaagtgta ccgttgtaag tttctttacc tcatgcacga  53100
tggtgtgtca tattaataaa aggtactgt gcgggttcga agggatattg caaatcctag  53160
agcaatcaca aagtttgaa ctctgaggtt tttggtataa taagaatagt ccatgcattc  53220
aaaagaggga agccaaggaa gaactagaag tctttcaaga gctcaggctc ttatacatcc  53280
agttgctcat tgaaccagct tcctggaatg gagggtctgg ggttgagact aggccacaag  53340
tctagagtct ctagagagac agtgttgaa ccccatggcc cataatacat ttcccatttt  53400
ctcaggcagc cagaggtcat gaatgtgagg atactgggga gttggagcaa cgttcttggg  53460
aggcataagg aagagcgaat gcttcaagat ccccgcagcc caaactactc gcctgctttg  53520
cccctaatg catttttctc tgctgctccg tagctgtccg acctcttcag atctcttagt  53580
ccaccctgcc gtcttccttt atgccatggg tcccactgtt ctttcaactc atcccccttt  53640
ccctcagtcc cggagtagct gcggccagca gagggtagac tgagagcagg agagaaggac  53700
ctgcctagga acccttcta gagatactgc atcctgcctg ggagcaagtt ttccagggca  53760
gctttgagaa gtcttggaga aacaaaccta ctaaacctga cagacagtaa tactatttgc  53820
acaatgcttt tctgtgggaa aggtagagcc ttttcactac gtattgagta catagagtgt  53880
gagggttgac ctggaacggc tatcctcctg gatgacgtgc gttttctgaa gaactacatg  53940
ttcgttgcaa ctcccacatt agaatatgaa gtcctaccga gagagatacg gagactagac  54000
agatacagat gcatttgcat gtgaatacac aatcccacaa tacagacgtc aaaacccata  54060
ccagttattc cagagagatg gattgggcag aaggcagaag gagaatactc tgatcgtttt  54120
tcggccacgt gtgtgtgtta tctcagtgtt tctaagaagc gtttgctact ttagatttt  54180
tatttaaaaa aaatagtaat aatctattaa gtatgagaga tgtgcagaga cgattagtga  54240
tcgagagcca ttttttgctgg tggcaatcat atggtacttt taatgggaat attagaaagg  54300
caccggtaat gaccttgttg cagcacaaag gagagagtgt ggggtgcccc tgcatgttgt  54360
cccacctctt gtgacgtgta tcgttttgga atttccagtg gcttgatcat gaactactgc  54420
aggaatccag atgctgtggc agctccttat tgttatacga gggatcccgg tgtcaggtgg  54480
gagtactgca acctgacgca atgctcagac gcagaaggga ctgccgtcgc gcctccgact  54540
gttaccccgg ttccaagcct agaggctcct tccgaacaag gtaaggagtc tgtgccaga  54600
catctacacg cttcgatgct gggatgaaaa gccatggaaa ttcccactga tgcagccgcc  54660
ttcaattggta aacggatgct cgagtgttgc ctgagttcta ccatgtagga ggaagcctcc  54720
gtgcactctc tgggggagcc agcggagtga tttctggtgc aacgtggttg ggctttgtct  54780
ttaggatggg cacaaaccct ccaggggat cgacttcaaa attcaccttg ttgtaaaacg  54840
ggctacctca gtgtcccagc caaaattttt attgtaacat gctgtcaggt gtgtcactct  54900
ttccaagcca gtaagctttt ccggggatt cttcaagtag ccagcattca gagcaatctt  54960
cagcattgca gattctgaga aatgtggctc tggagcctgt catcctcgag aaacctaaca  55020
gggctgcatt aattccatat ggtcctgggt ctatggagca gtatatgagc tcccaatgct  55080
ctaaggctct tcagtcctag gctttgaagg gagtgatttc tcagtgttct taaacctctt  55140
tctgatggca cttgtacctg tgaggggtct agagagaaag gttagtagac ttctcccttta  55200
ctgcaattca ggatgcaggg catgagaaga ttccctccct cctccaaggg aagaaggttt  55260
tggcgtgcac acatccttga gaagcaaagt gtctttgcct tcagtcagat atataggatc  55320
gttttctgcc ccatggcctg gaagccgag gccttggctt tcatgatcaa cgatctaggg  55380
aaacatgcaa aatttccatg tcttttcccct cctctgccct cgacagccaa ttaccacctg  55440
catcctgcat tgccaaatgc agtgccctt gtatgaacat tcagtagagt ttcatgaaa  55500
ggtgctactt cgtgagcgca ctttgcagtg agaaggagtc tgttctgttc tgttttcta  55560
aggatttcag gtgaaatatt tcctagaact tactacagtt ctagattggt aggaatctgt  55620
aggtttgctg tatgttttt ggttggtttt ctcccatcca tctgcctaca ggtaagggaa  55680
agataacgtt cataattctc atagactcct ttctggttgt gtcataaatg gcttcacata  55740
tttcgttatt ctcagagata ctcagtttat ttcttgtgtt tcatttcag caccgactga  55800
gcagaggcct ggggtgcagg agtgctacca cggtaatgga cagagttatc gaggcacata  55860
ctccaccact gtcactggaa gaacctgcca agcttggtca tctatgacac cacactcgca  55920
tagtcggacc ccagaaatact acccaaatgc gtatgtcttt gttctttact ataagagaat  55980
aaagggccaa ctgaagtttc tgtgacaaga gacatgcttc aagctggagtt ctccgaactc  56040
aacttgtgtc agattcagat ggtgtagcaa aatgtctcag gatgatttcc ttggagctaa  56100
gggtctgaga gaagagaaat gttaagctgc ctcaccttcc tcctagttt gtggagcaga  56160
agggaaatga ggaggcgagg agatcacctt atgaagaaag tcagaatgac gaaccaccaa  56220
acacttgat taccccttgcc caacacccac taagcgtcaa tgaagactt ccagttggaa  56280
ttccgttatt ctgacttcca attcctgagg ggaagattgg gtttgcctt tctgtctggg  56340
ctcatgagga aagttatgt gcttacttat ggacaggtga attgatctgt ttctatttct  56400
acctgtattc caatagggag aaaatctctt ggtcctaagt accagtggcc tgaaggata  56460
gaggttccca gcaagagaag atccaaggaa ggaaggcaga tgagagtcag cacagagagg  56520
gatgctgaaa agtaaaaggg atgggtagat ggatagaagc cctggtctga ccaccccatg  56580
gccaatcatt tggccataat caacaaccaa agacatggaa aaatgtttc tacatgtggg  56640
```

-continued

```
acaacagatg gtagaggacc tagagaattg agagagggcc aatgatgagc tcaactccat   56700
agatgccttg gctttcttcc tggatacccct tcctgcactg aatagcaagg agatggagct   56760
caagcagcct gtagccatct agctgagcag aggagaggga ttggagtttg ggatgactct   56820
ggtatttttct aggtccgcta caaataagaa ctggtttgtg gaggaaagga gctctacaaa  56880
tacgcataga agtctcctcc agtagttggc ctcacatgac actgcatgtg cacagaaaat   56940
ggttctacag aaagtgtggc aaagaacatt tactgagaaa cagcaactac aagagaacag   57000
caagctcaat taagaagata gagatcacat agcactctgt gttattggag ttcttaccag   57060
ctagatgaga gagtgctcac ggaacacatt gccaattcag tggagacccc agaacagcca   57120
taatttcaaa gtacaattag tatattacta gaataaaggc agctgcagac aaccccttgc   57180
acagctgaaa agcaagtgtc caagcatcaa atgggtttcc aatcaatgaa gtgcctgtga   57240
gaggaaatct caactctctt cagaagtaaa caacaaagtc aattgcctca gctatgcggt   57300
atccccagag tgagtcctaa attaaaaatt tgactacgtg tagaaaagaa tttcgtgtga   57360
tccatgacca gaaatataat caggcaatac aaacaggctc agaaatgaca tcgataatta   57420
gaattgcatg aaaatttgac atatcagtat gataactgat ttcagatatt taaaaaaagt   57480
gcaacaaagc aggtatcata tcaagacaaa ttaatagtat agaatagcca aatcaaatta   57540
aagaactatt atacaaaaag tatgtcttaa atgaagaaat tactgtatgt ccgcctgaaa   57600
aatttagatg tttcagaaga aaaaattaac caaaaacaat tctgcagaac ctacagaatg   57660
agccacacac acacacattc aaaacacacc catcacacaa cacatgcaaa aactcacaag   57720
ttctaacaca cacacaaaca cacacacaca tgcacatccc taaagaaata gggaaatata   57780
aaattaaccg accctcagag acatgcagga aaatataaga agatttcctg catgtgggaa   57840
gcaagtcaca gtaaagagca agggagtttg gagtagatac aaataccgga atcacggatg   57900
gctgataact tttcaattat gaagaacgtt agaaaaatca cagattcatg aaactaaagg   57960
gatcaaatag gaaatttcga gaaaaaaaac tacatgatgc acttctctac atcacagttc   58020
aaaggtaaca aggcaaggat ataagaagaa gaaacatctc acgagaaact ggagaaaaaa   58080
gagctgtgtc ttcctagagt acagtgatac aaattgctaa tgcgttcacc tcagaaacac   58140
tggaagccag ataccaggga atattattaa aatgataatg aggaacaaga agagatcaac   58200
cgagaatgct gaatccagca ataaaatgcc ttgaagatca tccatgttgg ataaatgcat   58260
attgtgcact gcccaaaaca aagaaactgg aaagtgtaag actttggaat cagcaggctt   58320
atgtagcaac agaggtgacc cgaaagaatt aggtataaga agaatagaag aattgcatga   58380
aaatttgaca tatgactaag ataactattt caaatattta aaaaaagatg aatatgtaat   58440
aaaacagata aaatatcaaa agaaagtaac agtattgact agccaaatca aattaaagac   58500
ttagtgtaaa aagctatgtc ttaaaagaaa aaattactgg atggctgcct gatcaattta   58560
gacatttctg aataggaaac taaccaaaaa tcaattctac agaaccaact acacacatat   58620
atacacatac aacacaccca tacacaccca cgcaaaaact cacaagttca cacacacaca   58680
cacacacaca caaccctcaa gaaatagtga aatagaaaac caaccgaacc tcacagacat   58740
gttgcaaaat aggaaaagat ttcctgcata tgggaagcaa gtcacagaaa agagaacggg   58800
agattggaaa cagaaacaaa taccggaatc aaggatggcc gaaaactttt cattgatcaa   58860
gaatattaac aaaatcgcaa aaacacgaaa ttcaatgcat caaataggcg tttcgaaaaa   58920
aagaaaaaat ctggtatgat gcactttttgt acttcacatt ttcacggtaa gaagacaaag   58980
atataataac aagaaacttc ttatgagaaa ctggggaaaa acaagctgtt tcttgctaga   59040
agaacagtga tacaaattgc taatgcattc tcgtcaaaaa cactgaaagc cagataccgg   59100
gaatgttatt aatgtggtaa acaggaacaa gaagagatca accaagaatg ctaaatccag   59160
caataaaatg ccttgaagat catccatgct gcataaatgt atgttgtgca ctgccccaaa   59220
caaagaaacc ggaaactgta agaatttgga atcagcaggc tgatgtaaca agagaggtga   59280
cccaaaggaa ttaggtagaa gaagaatagt acaagaaggg aactttctgc agcccatgta   59340
atgaagaacc cagcaattgg caaatgtaga tgtaaatgca aaatatttc ttgaccaaat   59400
ttctatatat ttttaaatga gcgttgacta ctggaaacaa aatgatagca atatatttaa   59460
ttttagcata tgtagaggta agaatttgaa caagtagcgt aaatcatgta gggaataatt   59520
agaagtgtac cattgtaagt ttcttaccctc atgcacaatg gtatgtaata ttaataaaat   59580
gttactgtgt gggttcaagg agatattgca aatcctagag caatcacaaa gttttgaact   59640
ctgaggtata ttgtataata agaatattcc atgtattcaa aagagagaag tcaaggaaga   59700
aagaaatttg tcacgagttt gggctcttag tacatcctgt agctcattga accagcttcc   59760
tggaatggag ggtctgggat tgacactagg ccacatgtat agagtctcta gagagacagt   59820
gtttcatccc catggcccgt aatacatttc ccatttctc aggcagccac aggtcatgaa   59880
tgtgaggata gagagaggtt ggagcaacgt tcttgggagg cataaggaag agcaaatgct   59940
tcaagatccc cgcagcccaa actcctacct gctttgcccc ctaatgcagt gttcctccgt   60000
agctgtccga cctcttcaga tctcttagtc taccctgcca tcttccttta tgccatgggt   60060
cccactgttc tttcaactca tccccctttc cctcagtgca gagtagctgc ggccagcaga   60120
gggtagactg agagcaggag agaaggtcct gcccaggaac ccattctaga gatgctgcat   60180
tctgcctggg agcaagtttt ccagggcagc tttgagaagt cttgcagaaa caaacctatt   60240
tgacccacat gatatgggaa tgacagaaag taatacaatt tgcacagtgc ttttccatgg   60300
gaaaagtaga gccttttcgc gaggttttga gtacatagag agtgaaggtt gacctggaaa   60360
ggttatcctc ctggatccca tgtttttcct gaagaactac ctgttagttg caacttgcac   60420
attagaatat gaagtcctac cgagagagat acggagaat agatacttt gtatgtgaat   60480
aaacgattcc acaatacaca catcaaaatc cataccagtt attccagaga   60540
gatggattgg gcagaaggca gaaggagaat actctgatcg ttttttgccc acgtgtatgt   60600
attatctcag tgtttctaag aagcgtttgc tactttgat tttttttat aataataatc   60660
ttttaagtat gagaaatgtg cagacaggat tagtgattga gagccatttg tgcttgtggc   60720
aatcatatgg tacttttatg ggaatattag aaaggcactg gtaatgacct tgttgcacca   60780
caaaggagag ggtgtggggt gcccctgcat attgtcccac ctcttgtgac gtgtatcgtt   60840
ttggaatttc cagtggcttg atcatgaact actgcaggaa tccagatcct gtggcagccc   60900
cttattgtta tacgagggat cccagtgtca ggtgggagta ctgcaacctg acacaatgct   60960
cagacgcaga agggactgcc gtcgcgcctc caactattac cccgattcca agcctagagg   61020
ctccttctga acaaggtaag agcctgtgtg ccagaaacct acagttttcg atgctgggat   61080
gaaaagccat ggaaattccc actgatgcag cagcctccaa tggtaaacgg atgctcgagt   61140
gttgactgag ttctgtcatg taggaggaag cctccgtgca ctctctgggg gagccagcgg   61200
attgattttct ggtacaacgt tgggtgggct gtgtctttag aattggcaca aaccctccag   61260
ggtgatcgac ttcacaactc acctcgtgta aaaatggggct atctcagtgt cttagccaaa   61320
attttttattg taacatgctg tcagatgtgt gactctttcc aagccagtaa gcttttcctg   61380
```

```
ggacttcttc aattagccag cattcagtgc aatcttcagc attgcagatt cagagaaatg  61440
tggctctgga gcctgtcacc cttgagaaac agggctaaca gggttgcatt aattccaaat  61500
caccctggtt ctatggagca gtacatgaac tcccaatgat ctatgtttca ggacttcctc  61560
agtcataggt gggctctgca gccctaggtt tttaagtgag tgactgcccc gtgttctggt  61620
ggcagttgta cctgtgagcg gtctggatag aaagagtcgg agacttctgt attattgcaa  61680
ctcaggatgt gggtcatgag aggatttcat ctctcctgca ggggagtaag ctgttcgcct  61740
ccacccatcc ctgataactg aagtgtcttt gtctgcagtc ctagacgaag gactgttgtc  61800
tctcccatgg cccagaagct gaagaccttg ccttttgtta tgaaacgttc attgttttca  61860
tgtctgtccg tttctctgcc cctaacaccc aatcaccatg tatggcctgt acccccaaat  61920
gcatcgtgct ttgctgtttg ctgcccccata gtcctcatga acattcagta gaaattccca  61980
taaatgtgct tgcacgtgag cacagtttcc attgagaagc cctctcattt gtccttttt  62040
tctaagcttt tatgtgaaat atttctaaga acttactaca gttctaaagt gttaggaatt  62100
tgtttctttg gtgtttttgt ttgttggttg gttgttgctt ttctcaagtc catctgccta  62160
caaataaaga aacaagaatg ttacttgtca tattctcctg aggtcataat tctcagagac  62220
ttttttctgg tttgtgccat aagtggcttc acatgtttgt ctcttcttgg aaacactcag  62280
tttgatttct tttcttttca tttcagcacc aactgagcaa aggcctgggg tgcaggagtg  62340
ctaccacgga aatggacaga gttatcaagg cacatacttc attactgtca caggaagaac  62400
ctgccaagct tggtcatcta tgacaccaca ctcgcatagt cggacccccag cactactaccc  62460
aaatgcgtat gtctatttttc tttaccataa gtgaaggaag ggtcagtgga aatttctgtt  62520
agtagagtca tgcttcaagc tgagtgttca ggactcaagt tgtctcagat gaacagtgca  62580
tagcaaaatg tctcaggaac attgtctttg agcaaagagt ctaagagaag acaaatgtta  62640
atctgctct ccttcctcct agtttaatgg agcagaaagg tatctggagg caaggatatc  62700
acattaagaa acaagtcaag atgacaaatg atgaaactct tagagtaccc ttccacaaca  62760
cccactaagg ttcaatgcag ccttttctcc ttgaattct attaaactaa actccaattc  62820
ctgaagtgaa ggttctgttg gggttttctg ttttggctta caaggaaagt atatatgtat  62880
atctatggag aggcaaatct ttatctctttct atatctacgt ctattccaat atgtagaaac  62940
acagtcggtt ctgaccacca atggtctgaa gggatactgg ttgttagaa ataaaaatgg  63000
caggaaggca gatgagagtc agcaaagaga gagatcctgt aaagtaaaag ggtggataga  63060
tggacagaag cccaggtctg accagcccat ggccaggctt taggccataa gtgacaccaa  63120
agacatggaa aaatggttc tacatgttgg acaacagaca gtagtggacc aaaagaatag  63180
tgacaggggg aacaatgaga tcaactccaa agatacacttg gcttttcttc tggaggccct  63240
tcttgcactg aagagcaagg tgatggagcc cagatggact gtagccatct tcctgaatgc  63300
aggagagaga ttgaatttg ggactactgt ggtagctagg attttatagg cctgctgaga  63360
atgaagatga atttgtggat gaaaggagct ccaggggcac gcatagtgat ctcctcgaga  63420
ctttggctaa acatgacgtt gcatgtgccc agaaaaaggt tccacaagaa agtagagaaa  63480
agaatatatc ctgaggaata gcaactgcga ttgaacagtg agctcaataa agaggacaga  63540
gccctcatag cattctggga tactggagtt ctgaccagct ggaggagaga cctcactgaa  63600
cctcttggga atacagtaga gactccgaaa aagtcatact ttaggagtag aattagtaaa  63660
tttctagaaa aaaaggcagc tctagacaaa ccctggcaaa actgaaaagc aagtctccaa  63720
gcattaaaat catttccaag tcaattaact gcctgggaga ggaaaacccct ctttagaggt  63780
aaacaacaaa gtcaagtggc tcagctatgt ggtgttcaca gtgtgagttc taaatttaaa  63840
acttgactac acatagagaa gctttttagta tgaaccatga ccaggtgaaa aatcagtcaa  63900
tacaaataga cctagaaatg acagaaatga ttagaatgcc aaaaaattg acatatcaat  63960
atgtcaactg agttttaggt tttaagaaaa catgaatacg gaatgaagca gataccatat  64020
caagagacag taacagtata gaagagccaa attaaattaa agaactagta taagaaggta  64080
tgtcttaaat gaaaaaatta ctggatgtat tcccaatgga gtgagatgtt tcagaagtaa  64140
aaactaactg aaaaacaatt ttataccacc tacagaacca gctacacata cacaaaatgac  64200
acacacatat acacacatac tcacacatgc acaggcttag aaacatgcac gcacacacac  64260
acacacacac acacacacct ccacaaaatac taaaaaatga aatccactga tcctcacaga  64320
caggcgggaa aatataaaaa gatttcctgc atgtgggtag gaagtcacag aaggagagga  64380
aggagagatt gctacaggaa caaatactgg aagcaaggat agctaaaaac ttttcaaata  64440
agaagaatat taaaaaccac agattcaaga agctgaatga atcagacagg gaatttccaa  64500
aaaaaaaaaa aaaaaaactg tatgattcac ttttgtacat caccgttcaa cagtcagaag  64560
gcaaagatat aataacaaga aacatctcat gagaaactgg aggaaaaaga gctgtgtctt  64620
gctagaagaa cagtgataca aattgctaat gcattctcat cagaaaacact ggaacccagt  64680
taacaggga tatcattaaa atgataaact agaaaaaaaa gagatcaaat gagaatgcta  64740
catccagcaa taaatgcct tgaagatcat ccatgttgga taaatgcata ttgtgcactg  64800
ccccaaataa ataaaccaaa aactaataat ttggaatcag caggcttgtg taacaagaga  64860
tgttgcccaa agaaaattag ctagaagaag aatagttcaa gaggagaact ttctgcagcc  64920
cacgtaatga agaacccagc aaatggcaaa tgtagatgta aatgcaaaat attttcttga  64980
tcaaatttct atatcttttt aaatgagagt tgactacttg aagcaaaatg atagcaatat  65040
atttaacttt agcatatgta gaggtaaaaa tttgaacata tagactaaat catgtgggga  65100
ataattggaa gtgtaccatt gtaagtttct taccttatcc acgatggtat gtaatattaa  65160
tgaaagttg aatttgtggg tccaaaggga tattgtaaat cctaaagcaa tcataaaatt  65220
ttgaattctg agggatatta tataataaga attttccatg tatccaaaag agggaagcca  65280
aggaagaaaa agaagtcttt caagtactca agctctgagc acatccagtt gctcattgaa  65340
ccagcttcct ggaatggagg gtctgggctt gagactaggt cacatgtgta gagtctctag  65400
agagacagtg ttggatcccc atggcccata atacatttcc cgttttccca ggcagccaca  65460
ggtcacgaat gggaggattc ttgagaggtg gagcaatgtt cttaggaggc ataaggagga  65520
gtgaatgctc tgagatttcc ccagcctgag gtcctccata gctgcccgac tcttcagac  65580
ctcatagtct gcccagctgt ctcccttat gccatgagtg ccactgttct ttcaactcat  65640
cccccattcc ctcagtcccg gaattgctgt ggccagcaga ggatggactg agagcaggag  65700
aggaagtcct gaccaggaac ccatcctaga gatactgcat cctgcctgaa agctaggttt  65760
ccagggcagc tttgagaagt cttgcagaaa gaaacccact tgacccacct gatacggtat  65820
cgacagacag gaatactttt tgtgcaatgg ttttacatgc tgaacataga gcctttggc  65880
tacattttga gtcattgaa tgagactgct ggcctgggaa ggatatcatg ctggatgcca  65940
ttttttttctc tggagaacta tgtgttagtt ccaactcgca cattactata tgaagtccta  66000
cacagagaga tacggagagc tagacagata gagatacttt tgtatgtgca taaccaattc  66060
cacaatacac acgtcaaaat ccataccagt tattccagag agatggattg ggcagaaggc  66120
```

```
agaaggagga tattctgatc cctttttggc cacatgtatg tataatctca gtgtttctag 66180
gaagtgtgtg ctgcattaga ttttttttct ttaaaaaaag tgataatata ttaagtatga 66240
gaaatgtgca gagaggatta gagattgaga gccatttgtc attgtggcaa ttgtatggta 66300
tctcttttgg gaatatttca aaggcaccag taatgacctt gttgtagcaa aatatacagt 66360
gttcctgcat atgtacccat tttttgtgat gtgtattctt ttggaatttc cagtggcttg 66420
atcaagaact actgccgaaa tccagatcct gtggcagccc cttggtgtta tacaacagat 66480
cccagtgtca ggtgggagta ctgcaacctg acacgatgct cagatgcaga atggactgcc 66540
ttcgtccctc cgaatgttat tctggctcca agcctagagg cttttttga acaaggtaag 66600
aagttgtgcc agacatttac ctgcttggat gctgggatga aaagccatgg ataccccac 66660
tgacgcacaa cccttcagtg ctacactggt tctcgtgtgt tggttctggg tctgccatgt 66720
gggaggaagc cttagcgcac tctctggggg agccagaggt gtgattttg gtgcaacctg 66780
tgcgagctgt gtctttagga tgggcggaaa ccattctggg tgctcgactt caccactccc 66840
ctcattgtaa aaggggctat ctcattgtcc tagacaaaat tcttattgta atatgctgtc 66900
agatgtgtgt gtcttttccaa gccagtaaac ttttccaggg atttcttcaa gtagacagca 66960
ttcagtgcaa tcttcagcat tgcagattcc gagaaatgtg gctctagatc ctgttatcct 67020
tgagaaacct aactgggttg cattaattcc atatctccct gggtctgtgg agtagtacat 67080
gagctcccga agctctatct ctcaggtctt tttcagtccg aggcaggttg tgcagttctt 67140
agctttgaag ggagtgattt tttcgtgtgc ttttgcctct ttctgatgga acttgtacct 67200
gcggggggtc tggagaaaaa gagtagtaga cttttgcttt attgcaatgc attatgctgg 67260
gcacgagagg attcccctatc ttattgtagg tgataagctt ttggcctcca ctcatccctg 67320
agaagtgaag tgttgttgcc tacagtttta gctgcaggac tgttgtctgc cccatcacca 67380
ggagttttaat gcttctttt ttgagcaatc atctagtagc acatgcaagg tttttatatg 67440
tccttgcctc ctccccaaaa aaccatttta atgcttggag acttgctttt cagctttgcc 67500
aaaatgcatca cccttttcttc tatgctgttc catgtcgtca tgaacactct gtagagattc 67560
ctagaaatga gcttccatgt tagtggagtt tccgatgaga agcaatctga tattctcttt 67620
ccactaagtt ttacatgaaa tatttctaag aacttactac agttctagaa tggtaggcat 67680
ctcttacttt cgtgtttgtt tgtgtgtttt ctcatgtcca tttgcctatt aataaagaat 67740
agagaatggt tgtaaatctc agtgactctt ttttggttta tgtcataaat ggcttcctgt 67800
attttctgt tctaggaaat aataagcttg atgtcttctg ttttaatttc agcactgact 67860
gaggaaaccc ccggggtaca ggactgctac taccattatg gacagagtta ccgaggcaca 67920
tactccacca ctgtcacagg aagaacttgc caagcttggt catctatgac accacaccag 67980
catagtcgga ccccagaaaa ctacccaaat gcgtacgtct ttgttcttta ccataagcga 68040
aggaagggcc aatggaagtt tctgttagaa gagtcatgct tcaaggtgac tgctcaggac 68100
tcaacttggc tcagatgcag aggaacattt cctgtgagca aaagttctta gagaagactt 68160
tgttttttg agacagagtc ttgctttgtt gcccaggctg gagtgcagtg gcatgatctc 68220
ggctcactgc aagctccgcc tcccgggttc acaccattct cctgcttcag cctctctagc 68280
agctgggact acaggcaccc accaccacac ccggctaatt ttttgtattt ttagtagaga 68340
cagggtttca ctgttctagc caggatggtc ttggtctctt gacctcgtga tccgcctgcc 68400
tcagcctccc aaagtgctgg gattacaggc gtgagccacc gtgcctggct gagaagacat 68460
ttttaagct ggctctcctt cctcctagtt ttatggaagc agaaggatat atggagttga 68520
gaagatctta ttaataaaac agccgggatg acaaatgacc aaagagttag agtatccttc 68580
tacaacatcg gctgagggtt aatacaacct tttcaccttg gaattctatc attctaagct 68640
ctagtccctg aagtgaatgt tgtgttggcc ttttgcatct tgggtcacag ggaattgata 68700
cttgcacatc tatggagagg caaatctttt tctatctact tctttttcaa tgggtacaaa 68760
cacacttggt cctgagcacc agtggtctga agagatacgg tctgcccaga ggagaagaac 68820
aaaggcagga aagcagatga gagtcagcaa aggggcgatg ctgaaaagta aaggggcgg 68880
gtagatggac agaagccatg atctggccat tctatgcca gtctttcggc cataagtgac 68940
taccaaagac acgcaaac ggtttccaca tgttgaacaa cagatgctag aggaccaaga 69000
gtattgcaag agggagaaaa tgagatcaac ccatcaatgc cttggctttc ttcaaggaga 69060
cccttcctgc actgaagagc aaggagatgg agcccaagct gactgtagcc atgttgctga 69120
acagaggaga gtgattggac tttgggatta ccaggtagt taggattttc tagccatgct 69180
aagagtaaga atggacttgt ggaggatagg agctccaggc atagaagtct cctcaagtgt 69240
tagtctaaac ataaagcagc acttgcatag aagatttttcc acaagaaaat atggcaaaaa 69300
aacaccatat attgaggaac aacaactaca agggaacagt gagcttaata aaggtgacag 69360
agctcacata gtgctctgga atattggagt tttgaccagc tagagagaag agacctcatt 69420
gaaaatcttg ggcattcagt agagacctca gaaaagtcag actttatgag tagactttgt 69480
atattcctag aataaaggca gctccagaaa aaacctagca aagctgaaaa gcaaatctcc 69540
aagcattaaa atggtgtcct agtcaattaa ctgccttcta gaagaaaact caacactctt 69600
tacaggtgaa caacaaagtt aagttgctga gctatgcaat atccacagtg tgagtcctaa 69660
atttataact ttactacaca taaaaagca tttagtgtga accataacca ggaaaataat 69720
cagtcaataa aaatagaacc aggaatgata gaaatgattt aaatggcatg agaatttgac 69780
atattagtat cataactgca ttgctggatt taagaaaaca taaacatgga acgtaacaga 69840
tatcatatca agggaaagta aaaggataaa agagtcaaat caaattaagg gactattaaa 69900
aggtatatct taaatgaaaa attcactgga tggtctccca atcaggttag ttgtttccag 69960
ggaaaaaatt aactgaaaaa taattcaata gaatctacag aaatagctgc acatatatac 70020
acacaatggc acacgtgcac acacccacac ccacacaggt gtgaatccta gagccacacg 70080
agcattgaaa catagagaag taaaaattgt tcattgagga atatgtagca atgctcaatg 70140
tgttttaccc taataagagc ttttgtgatg tatgattgaa aaactgacac aactgaagag 70200
agaaatagat aagcccacac tctgagttag agatttcctt gattctctca ctatggttat 70260
aaatcttttcc caaacacaac aggctagaac aaatatgcag aaaattagac atagtatctt 70320
tgttctcaat aaaaacgtcg acctatttaa cattataccg aactaccgag tacacattaa 70380
agtgtgcatg gagcattcac tgaggtgtac tctacacatg accttccagc aagtctccat 70440
agatttaaaa gaattaaagt catacagagt gtgtcacttt attctcccag aataaagtga 70500
gatatgaata atgaagtt tgccagcttc tcaaatattt gggtgcata cggtgcattt 70560
caaaatactc tttgggacaa agaaaacatc actaaggaat ttagaaaagt tttgaactga 70620
gtaagaatat aacacaattt atccaaactt aggagatgca gtgaatgtct ttaggctttt 70680
acataatttt agatgctctt agggaaaaac agaagcatgt aataatcaag atttcaaact 70740
gcaattctca agtgtagtc tagagaaacc tgaggacctt tgagtacctt cagagacagt 70800
ccatgaggtt aaaggacttt gctacgtgaa aagtaagatg ctattggccc ttttactttt 70860
```

```
cattttccaa caagagaaga ggggagtttt ccagcagtta cataatatgt aatggcatca 70920
tgtctctgat ggctaagaaa atgggcaatt gttgactttg tgtgttaaaa aaattctcag 70980
tgttggtttc ttatactata aatattcatc ttgtgttttg aaaaagaaaa gctctttgga 71040
atccccctatg aacaaagact ttgacagttg ttgatctaag accacagctt aaatatctac 71100
acaagaaaaa aaaaaaaagc aaataagagc caaggaagc agatggaagg aagtagtcca 71160
aaccagtgac attcagtgaa caagaaaaga gaccaacaag ggagtaaact cttgaaacag 71220
aaagttgatt ctttgaaaag atccatatga ttgaacacag tctggctaaa caaatgacag 71280
accaatgagg gtgcacaacc atcaccatct ggagtaacag aggagaggtg ccattactat 71340
agcatcttcc agttctgaaa gctgaaaaga agatttttgag aacaattgta tgtgaataaa 71400
ttcaggaatg ttaatcatgt gggccaattc ctgaggaaga caacaaatca gcaaaccaga 71460
tgctgaatag ttagtgtagt cctgtagaga gacatacaga gaggctgaca gagaaatatt 71520
tgtatgtgca taaacaatc tacaagacac acttcaaaat caatctcagt taatctggag 71580
gaacatattt cacagaaggt ggaaggaggg tattctgatc ctcttgtaca ttgtacaaca 71640
ttgtacaatg tacagagtat aattgtacaa gtacaattga agttgtacaa gtacaagtgc 71700
aacttgcaca atgtacagag taaacattga tgtttactct caattttctt atggagcaca 71760
gatgactttg gatgtgttac aatatgaatg ataattgtc tttgagatgt tcgcagttgt 71820
ttagaagttg aggaccattt gtgcatatta tgggacctt agtgaaaata tttcaaagtc 71880
tcttttaca ctttgttaca gcaaaatgta gagggcgcta agtgccctttg aatcttctcc 71940
catctctggt gacctgtgtt gttttgaaat ttgcagtggc ctgaccagga actactgcag 72000
gaatccagat gctgagattc gcccttggtg ttacaccatg gatcccagtg tcaggtggga 72060
gtactgcaac ctgacacaat gcctggtgac agaatcaagt gtccttgcaa ctctcacggt 72120
ggtcccagat ccaagcacag aggcttcttc tgaagaagagt aggaagtca tggccagaca 72180
accacaccct aggacgttgg gatgaaaaga gttgcaaaat cttagtgata tagaagcctt 72240
ccatgctcac acaattccaa gtagaatgtg gactcagggt cagccactgg gaaggaacac 72300
tcagcgcctt ctctgggaga accagagctg tgatgtttgg taccctgtga aagggtggta 72360
tctataggaa gggtgcagac cctctagggc actggactta ccactcccct ggttattcaa 72420
aggatcattt tagtgtctta gccagaagaa tattctaaca ttttgccaaa tttgtgaaga 72480
tttaccaagc tcatgataag cctttcatgg tatttcttca agtagtcagt gttcattgca 72540
tctttggctt tgcggtttcg gaggaatgcg gttttttgagt ctgtcatcct tgagaaacct 72600
aatatgactt ttcttagttc catatacttc tgggtccagg tagcagtaca tagccaacaa 72660
atgctccatc gttctggcct atctccatct taagccagtc ctgcacaact aggctttgat 72720
ggggaggatc tctcagtgtt cttgcccctc cttctcatgg aacatatatc tgtgttggtc 72780
tctgagaaga agagtagtgg atatctactt tgttgcaatg cagaatcctg ggccaaagat 72840
accagccatc cctccaaggg aataaaattt tggccagtag ccctctctga gagacaattt 72900
gtctttgcct acgagtccta gatgcaggac cgcttcctgc cccatcttca agaagctgaa 72960
ggctttggct ttgaggatc agcagtctag ggaaatgtgt gacggtttca tgtctgtccc 73020
cactgacagt caatcaccac ctacaacctg cacagcctga tgcatagcag tctagttttcc 73080
tgccttattc tcaggaacac ccagaagatg tctatattaa agagcatgca catgagtgca 73140
attttgactg ataggcactc tgatctttcc tttggtgcct gtgttttaaa ggaaatcttt 73200
ctaagaactc gttaaagttc tagaatgcta tgaatctttg ggttttatta ttggtatgtc 73260
catctgcctg ctagtacaga acagagcatg gtagtctttc tcagagacaa tgatcctgtt 73320
tcagtcacag atttcttctg atgcttctgt gttctagaaa ttactcagct tgatttctcc 73380
tctttgaatt tcagcaccaa cggagcaaag ccccgggggtc aggattgct accatggtga 73440
tggacagagt tatcgaggct cattctctac cactgtcaca ggaaggacat gtcagtcttg 73500
gtcctctatg acaccacact ggcatcagag gacaacagaa tattatccaa atgggtacaa 73560
ccttgagttt tcttcaaaga cagacagcag cccccttaca tttctcttgg aagggccatg 73620
cttccaacta acttcttatg acaaatttat ctcagatctg gaatgttggg tagaatgtct 73680
caggcttctt tcttcaggca cagtgtctga aaggagagaa atgtcaggcc agctctcttt 73740
tctcatagtt gacagaagca ggaggatatt tgaaggtggt gagttctcat gaatagaaag 73800
ctcaggacac atggccacgt gcttagaaat agcaccattc cacaatgccc actaaagacc 73860
aatgcaatag ttcaaccagg gatttctgtc atttctaatct ccaagtcctg aagtgaaggt 73920
tgtattagcc atgttcatct tgggcaacaa ataaaggata tctatgttga catccagatc 73980
ttccaatcac tttctcctct aacctgtacc tgggttctga gaacaaggta tctgaagagc 74040
tatgtgttgc cagcacatga ggggcaaaag taggaaggca gctgagagtc aggaagtata 74100
aagattctga agagttacac atgcaggaag atggacagaa acccagttca gaccacgtca 74160
gcgtttctgc catgaaggac tatcaaatac ataggaaaag tgttttcata ggttggacaa 74220
cagacatgac aggcctgaga aaattcagaa agggaatcaa aggagatcaa ccttatcatg 74280
tccctggcat ccttccttga gacccttgaa gggcaagcag atggagccca gctgaccaca 74340
gcagtcttgc ttaactgagg agagaagctg gagtttgtga tgcctcaggc atctgacgta 74400
ttctaggctg gctaagaatg gaggggatt tgtggaggaa aggagctcca agaatacaca 74460
ccgaagtctt ctcaaggctt tggctaaata caaagctgcg tatgcacaag gagagttttc 74520
acaaagaaag aacaataaag aaaagctact ggggaagaa caactgcaag ggaacagtga 74580
gctcaatgga gatgctagag ctcacatagc actgggggat atttgagttc tgaccactga 74640
gaggagagac acctcactga acatcttggg cattcagtag ggtcaaaga aagccataat 74700
ttgggagtag gatcttcgga ttcctagaaa taaggtgact ccagaaacac tccagcaacc 74760
cttcttccaa gccagtctaa aaggatccaa atgatttcca agtaaattaa ctgccttcca 74820
gaaaaaagta aactcaaccc tccttagagg taaggaacga atacaagttt ctcagttata 74880
tgcatcccc agagtgcaac ttgcatttaa aaatttacta gacacaaaag aagttttcac 74940
tgtgatccat aactgggaga aaaatcactc aacacaaata ggcccagaaa taatagaaat 75000
tatggcattg gcaagaacat ttaaaatgca cctctgagaa ctgtgtttca ggaaaatgtc 75060
agcaaaagct gaccatgaga gaaatgaatg cataatatca gaaaagaaaa gaattgaaga 75120
gccaaatgga aatttaaaaa ctgagaaaag ttatatctgt aatgaggaat tcactggatg 75180
gccttataac cagtttagat attatggtag gaaaaggtga acgagaaaat gattcaatta 75240
aagctagaca aaccacaaga cagacagaca gacacaaata cagacacaca caatgactga 75300
accaattaat caacagagcc tcaaggacat ctaggaaaac atccacacat ttaatatatg 75360
tgttaggcaa gtcacagaaa gagaggaaaa agataatgtg acagaagtta tacttgaagc 75420
catgacggct gacaaatttc caaacataca gaaaatgaga aattcatagt catgaagctc 75480
aatgactcag gtatagattt ttaaagagca aaactctgat ttactgggt acatcatagt 75540
taaattgtct gatttcaaag ctaagaagaa aaaaaggggg ttcctatgaa caaacatttt 75600
```

```
gacagttgat ctaagaccac agcttaaata tctaggcaag gaaaagcaaa taagacacaa   75660
ggaaagggga tggatggaaa tagtccaaac caatgacatt cagtgaacaa gaaaatagac   75720
caacaaagga gtaaatccat gaaacagaaa gttggttctt tgaaaagatt catgtgattg   75780
accacagtct ggctgaacag atgacagacc aaggagggag tacaaccatc accatttgaa   75840
gtaacagggg agaggagcca ttgctatacc atactccagg tctgaaagct gacaagaaga   75900
tatcaagaaa aactgtatgt gaataaaattc atgaatgtag atcatgtgga tcaattcctt   75960
aggtaaacaa caaatcagca aaccagatac tgaatagatt gggtactcct atagaaagac   76020
atacagatag ccagacagag aaacatttgt acgtgcataa aacaatctac aagactcact   76080
tcaaaatctc tcagttaatc caaagtaaca tatttggcag aagtgggaag gagggtattc   76140
tgatcctttc ttgtacacat tgatgttttc tctcggtttt cttatggagt atagacgagt   76200
ttggatgtgt tacaataaga atgataatct gtctttgaaa tgttcacagt tgtttagaag   76260
ttgaggacga tttgtgattg ttacaggacc tttagtgaga atatttcaaa gtcacttttt   76320
accactttgt tacaacaaaa tgtagaggat gtctggtgcc cttgtatctt ctcccatctc   76380
tggtgaactg tattgttttg taatttgcag tggcctgacc aggaactact gcaggaatcc   76440
agatgctgag attagtcctt ggtgttatac catggatccc aatgtcagat gggagtactg   76500
caacctgaca caatgtccag tgacagaatc aagtgtcctt gcgacgtcca cggctgtttc   76560
tgaacaaggt aagaagtctc tggccagaca accacacccc tggacgttgg gataaaaaga   76620
gttgcaaaat cttagtgata cagaagcctt ccatgctgca cgggaatctg aatgtggact   76680
cagggtcagc caatgggaag gaagcctcag cgccttctct gggggaacca gggctgagat   76740
ttttggcacc ccgtgacagg gtggtgtctt taggaagcgt gcagaccttc tagggcactg   76800
gatttaccac tcccctggtt attcaataga ttatttcagt gtcctagtga aaatggatat   76860
tctaacatcc tgccaaattt gtgatgattt accaagctca tcatgagcct ttcctggtat   76920
ttcttcaagt agacagtact cattgcaaac ttcagcttta cagtttcaga ggaatgtggt   76980
ttttgagtct gtcatccttg agaaacctga tatgacttta cttagttcca tatcctcctg   77040
ggtctaggta acagtacata gccagcaaat gctctatctc cctgtctacc ttaatcttag   77100
gcaggtgctg cacacctagg cctttgatgga agggatttct tagtgttctt gccccctcctt   77160
ctcatggaac acgtatctgt gttgctgttt gtgaagaaga gtagtggatg tctactttgt   77220
tgcaatgcag gatcctgggc ccaagatttc ccgccgtccc tccaagggaa taaaattttg   77280
gccagtaccc ctctctgaga gacaatgtgt ctttgcctgg aagtcctaga tggaggacca   77340
cttcctgccc catcttccag aaacttaagg cttttggcttt ggaggatcag tgctctggag   77400
aaatgtgtga cggtttcatg tctgccccca ctgacaacca ccacctacag cctgcaccgc   77460
ctgatgcatg gcactctggt ctcctgcctt gttctcagga acacccaaaa gagatctttg   77520
ccaaagaaca ggcacatgag tgcaattttg actgataggc actctgatct gtcctttggt   77580
gcccaggttt taaagaaaat cttttctaaaa actcattgaa gttccagaat gctatgaatc   77640
tttgagcttt gttattgcca tgtccatctg cctactaatg tagaacagag catggtcgtc   77700
attttcagag atgatgtcct gttctatcca tggattttt ttctcatgct tctgtgttct   77760
ggaaattact cagtttgttt tctcctcttt gaatttcagc accaacggag caaagcccca   77820
cagtccagga ctgctaccat ggtgatggac agagttatcg aggctcattc tccaccactg   77880
ttacaggaag tgcatgtcag tcttggtcct ctatgacacc acactggcat cagagaacca   77940
cagaatacta cccaaatggg tatgtctttg agttttctcc caagagaaac agccaccac   78000
ttaaatttct cctggaagag ccatgcttcc agctaacttc ttatgaccca atttctctca   78060
gacccagaat gttggacaga atgtctcagg cttcttgctt tgggcacagg gtctgagagg   78120
agagaaatgt caggccagct ctcttttctc atagttgata gaagtaggag gatacttgga   78180
ggtggtgagg tctcatgaat agaaagctca gaagaacata tgaccatgtg cttagaaata   78240
gcaccattcc acaatgccca ctaaagacca gtgaaatagt tcaaccaggg aattctgtca   78300
ttctaatctc caagccctgg agtgaaggtt gtgtttgcca tgtttgtctt gggtaacaag   78360
tgaaggatat ctatattgac ttcgaagatct tccgatcact ttctcctcta acctgtataa   78420
acacattggg ttctgagaac aaggtgtctg aaaagctatg tgttgccagc ccatgagggg   78480
caaaaggagg aaggcagctg agagtcagga agtatagaga tgctgaagag ttacacattc   78540
aggaagatga acagaaaccc atgtctggct atgccagcct ttctgccatg aaggactatc   78600
aaatacatga gaaaacagtt ttcacaggtt ggacaacaga tatggtaggc ttgagagaac   78660
tgagaaaggg aatcaaagga gatcaacttc atcattaacc tgtcttcctt cctggacaca   78720
gtgttggatt gaaggacaag cagatggagc ccagctgacc acagcagtct tgcttaactg   78780
aggagagaga ctggagtctg cgatgcctca ggcagctgat gtgttctagg ctggctaaga   78840
atgagaaggg attttgtggaa gaaaggagct ccaggaatac acacagaagt ctcctcaagg   78900
ctttggctaa atacaaagct gcgtatgcac agggagagtt ttcataaaga aagaacaaca   78960
aagaaaagct acttgggaaa gaacaactgc aggggaacag taagctcaat ggagatgcca   79020
gagctcacat agcactgggg gatatttgaa ttctgaccac tcagaggaga aacacctcac   79080
tacattttgg gcattcagta gagaccaaag aaagctgtat tttggggattg ggatcatctt   79140
attcctagaa tcaaggtgac tccagaaaaa ctccaacaac ccttcttcca agccagtcta   79200
aaaggatcca aatgatctcc aagtaaatta actgcattcc acaagaaaaa aaaaactcaa   79260
ccccccttag aggcaaggga caaatacaag ttgctcagtt atatggcatt cctattgcgt   79320
tacttctatt taaaaattta atagagacac aagaagcttt cactgtgata cataactggg   79380
agaaaaaatc actcaacaca aacaggccca gaaattatag aattgatgac attggtgaga   79440
acatttaaaa tgcacctctg agaactgtgt ttcaggaaaa tgtcagcaaa agctgaccat   79500
gagagaaaca aaagcagaat agcaagagaa aagaaaagaa ccggagagcc aaatgaaaat   79560
taaagaactg agaaaggta catctctaat gaagaactca ctggatgcc ttatcatcac   79620
tttagacatt acggtaggaa aggtgaccta gaaaataatt caataggagc tacacaaatc   79680
acaggacaga cagacagacc aacacacaca cacacacaca cacacacaca cacacacaca   79740
cacacacaca cacacacaca aagactgaac ctattaatca acagagcctc aagggcatct   79800
aggaaaaatc cacacatttta atatatgtgt taggcaagtc acagaaggag aagaaaaaga   79860
tatcatgaca gacattatac ttgaagcgat gatggctcgc aacacgccaa atatacgaaa   79920
aacaagaaac tcatagtcaa gaagctaaat gactcaggta tagaatttta aagagcaaaa   79980
ctctatgatt tactgggata tatcatagtt aagttgcctc aattcaaagc taaaagaaaa   80040
aaaagggggt tccatgaac aacagctttg acagctgttg atctaagacc acagcttaaa   80100
tatctaggca aggaaaagca aataaggcac aaggaaagag gatggaagga aatagtccaa   80160
accaatgaca ttcagtggaa aagaaaatag accaacaaag gagtaaatcc atgaaacaga   80220
aagttaggtt ctttgaaaag tctatatgat tggccaaagt ctggctaaac agatgacaga   80280
ccaaggaggg agcatatcca tcaccatcat gagtaacagg agagagatgc cattgctata   80340
```

```
gcatcctcca ggtgtgaaag ctgagaagta gatattgaga tcaactgtat gtaaataaat   80400
tcatgaatgt agatcatgtg gatggattgc ttaggtaaat aacaaatcag caaatcaaac   80460
actgaataga tcatgcagtt ttatagagac ttacagacag cctgacagat aaacatttgt   80520
atgtacgtga aacaatctcc aagcacact  tcaaatccc  tctcggttaa tccaaaggaa   80580
tgtatttggc agaaggtaga aggaggtat  tctgatcctt tctggtacac attgatgttt   80640
tctctcagtt ttcttataaa gcatagatta ctttgaatgt gttacaataa gaatcataag   80700
ctgtctttga aatgttgaca gttgtttaga agttgaggac catttgtgag tgttatggga   80760
ctttagtgag aatatttcaa atttgcttgt ttacactttg ttacaagaaa acatagaggg   80820
tgccaggtgg tgctgtatct tctccaatct ctggtgacct gtattgtttt ggaatttgca   80880
gtggcctgac caggaactac tgcaggaatc cagatgctga gattcgccct tggtgttata   80940
ccatggatcc cagtgtcaga tgggagtact gcaacctgac gcaatgtcca gtgatggaat   81000
caactctcct cacaactccc acggtggtcc cagttccaag cacagagctt ccttctgaag   81060
aaggtaagaa gcctgcagtc agacaaccat accctcggac attgggataa aaagatttgt   81120
aaaatctttg tgatgcagaa aacttccatg ctgcacagga agtcgaaggt gaagtcatgg   81180
acagccaatg ggaaggaagc ttcagtgcct tctctgggg  gaccagagct gggatgttga   81240
gtgccttgtg agggatggtg tctttaaaag gggcacagac cctctaggac actggattta   81300
tcacttccct gttatcaaac gaatcatatt agtgtcctag ccaagatgga tattctaaca   81360
tcctgccaaa cttgtgaaga tataccaagc tcctaagcct gtccagccct ttcttcaagt   81420
aggcagtgtt tattgcagtc ttcagcttta ccattttgaa ggaatgccat tttgaggct    81480
gttgttcttg agaaacctaa catgtcttca ttagatccgt attgtcctga gacttttgaag 81540
cagtacatag ccaccaaatt gtttatctcc ccagcctacc ttcatcttgg gcatgccttc   81600
cacacctagg atttgaggga agggatttct cagtgttctc ctccctgctt ctcatggaac   81660
atttatctcc gttgttttt  gagaagaaga gtagtggatg tcagctttct tgtaatgagg   81720
gatcctgggc ccaagattcc ctgtctcccc tcctaggcta taaaattttg gcctgtactc   81780
cttctccctg agaggcaatg tgtctttacc tacaagtcct agatgcaaga tccttttctg   81840
ccccacaccc cagaatctga aggcttttgc tttggaggga cagtggtcta gtgtgcaagg   81900
gtttcatgta tacccccccac taacagccaa tcaccaccta tagcctgaac agcttgatgc   81960
atggcaccct ggtctcctgc cttgttctca tgaacaccca gaagaggtgt aagcaaaaga   82020
ccattcacat gagtgtaatt ttgaagtata ggcactctga tctgttttt  gtttgtttct   82080
ttgttttgttt gttttccagg gttgaattaa aatatttatg actacttatt aaatttctag   82140
aatcctataa gtctatttgt atttttattc tacatttcaa tttgcatgct aatatagaag   82200
agtgtaaatt gttaatcctc agattattcc actttgtgtg tcataatttt tttcacattt   82260
ccctttttcta ggcaatactg agcttgattt tctcttttaa tttcagcacc aactgaaaac   82320
agcactgggg tccaggactg ctaccgaggt gatggacaga gttatcgagg cacactctcc   82380
accactatca caggaagaac atgtcagtct tggtcgtcta tgacaccaca ttggcatcgg   82440
aggatcccat tatactatcc aaatgcgtat gtctatcatg ttagccataa aaggaacaat   82500
agtcaactaa aatttctctt agctggccca tgctacaagc tcacttccta ggtccaaatt   82560
tctcatagac tcagagtttg tagcaaaatg tctcaggaaa cttactttg  agcaaaaggt   82620
ctgaatgaag agaagtttta ggattgctat cttcataac aatttgatgg aagcagcagg    82680
atatatggag gtggtgaagt ctcattaatg taaagctaag gagatcaaat gaccaaatgc   82740
tgagacaaag tatcattcca caatgcccac taaaggtcca tgcagtcttt caaccatgca   82800
attctatcat tctatcctcc attccctgaa gtgaaatttg tgtttgccat ttttgacacg   82860
aatcagaagt aacaaattca ggctgggtgc agtggctcag gcctgtgatc ccaacacttt   82920
gggaggacaa gacgggcaga tcaccagagg tcaggagttc aagaccagcc tggctaacat   82980
ggcaaaaccc catctctacg aaaaattaaa aaattagccg gtcatggtgg tgggtacctg   83040
taattccaac tacttgggag gctgaggcag gagaaacact tgagcctggg attcagagtt   83100
tgctgtgagc cgagacatg  ccactgcact ccagcctgg  tgacagagca agactcaatc   83160
tcaaaaaaaa aaaaaagaa  gaagaagaag aaaagaagaa gaggaagaag aagaaggga    83220
agaagaagaa gaagaagaag aggaagagga agagaggagg gaggagagg  aaggaagaa    83280
agaagaagaa gaagaagaag aagaagaaga agaagaagaa gaagaagaag aagaagaaga   83340
aaatagaaat gagtgcatat atttatatat gagtactagc ctgtatgaac acactgggtt   83400
ctaagcacca gttttctgaa gggatatggg ttgtcaggca gagtaaaagc aggaatgcag   83460
atgagagtca ggaagtaaac agatgtggtg attaaaatgg gcaggtacat ggacaaaaaa   83520
atgcatgtct gacaaaaact ggcctcttgc cataagtgag tatgaataat atggaaaaac   83580
tgtttgcaca tgttgaacag cagacagtac aacctggcat agtttagaaa gggaaacaaa   83640
taagatcaac cccataatta cccttcctag acttaagggc aaaagagttt  aaccaaagca  83700
ttccacagca gtccttgctaa actggggaga gagactggag ttttgtttac taataaaacc   83760
gagattttct aggttaggta ataatgagaa agtatttgtg gagaaaagga gctccaggaa   83820
tacacacaga agtctcttca agtctctggc tgaacagaaa gctgtgtatg cacagaaaga   83880
gtttccagag agaaggaga acaaagaaca gctactggg  aaagaacaac tgctgggaa     83940
cagtgagctc aatgaagatg ccagagctca catagcactg ggaggtattt gagctctgac   84000
cagcctgagg agagacactt cattgaacat cttgggcatt cagcaaagac cccaaaaaac   84060
catacttcag gagtagaatt aatgcattcc tagaataaag tctactccag aaacacccta   84120
gaaaagctta gaaaccaagt ctaaaaagat ccaaatgatc tccaagtaaa ttaattgcct   84180
gtcagaagaa aacaacctct tcagaggtaa acaacaaaat taaattgctc aattatatag   84240
tatgcacaat gtgtggcata catttaaaaa tttgctaaac atacaaaaag catttagtgt   84300
gacccataac caggagaaaa atcagtcaat acaaatagac ccaaaaatga taaaaataac   84360
agaattggca aggagattta aaatgtatgt atcataattg tgttcaagga tttaaagaaa   84420
gcgtggacaa gaaataaata aatgataat atcaacagaa gaaaaatttg taaaaggacc   84480
aaatggagag tcaagaactg aaaaaaaaga catctctta atgagaaaat cactacatgg   84540
ccttataatc atattagata gtacagatga taaagctaac tagaaaatat tagggtggtg   84600
caaaccatag cacgcttata caaagcctga aagataaac  agagcctcaa ggacatctat   84660
gaaaatatca aatatttaa  tatttgttta aagcaagtca cagaggaagg gaaagagata   84720
ttggaacaga aaaatactt  gaagcagtga tggctgatga ctttctaaat atggaaaaaa   84780
tgataaactc acatagtcaa gaagctcaat ggatcagata taggatttta aaaagtaaag   84840
ctgtatgatt tatttggaca catcataatt aaattgtcca taatcaaaga tagaaagtaa   84900
aatcttattt gaagcccaag ggaaaaaaca tacctttaca tagagtaaca gtgacacaaa   84960
tgactgatgc cttctcatca gaaacaacac aaatcagaaa caatagaata acacctttag   85020
agtggtaaga agaaaaaaag atcaaatcag aaacaacaaa ataacacgtt tagagtggta   85080
```

```
aggaggaaaa caagatcaaa tcagaaacaa tggaataaca cctttagagt gtaagaaaga   85140
aaaaaagatc aaatcaggaa caacagaata acgccttcag agtggtaaga aggaaaacaa   85200
gataaaatca gaaacaatga aataacacct ttagagtagt aagaagaaga aaagatcagg   85260
tcagaaaaaa tggaataata tgctaagaag aaaaaaaaag atcaagtcag aaacaatgga   85320
ataacacctt tagagtgaaa agaaggaaaa aaacccagca agcttaaacg ctatgcacag   85380
caaacaattc cactgaaaat gaatgttacg taagtacata ttctgtcctc ctaaaaacaa   85440
agaacaaata aaagaatgtt tcatcagcag gattatgtaa taaagatgt gaaagaatgc    85500
tatgtaagta aagaaaaat aataccatat gggaattggc atcaaaacca caaaatacta    85560
tcaaaacaaa aaaactttat tgataaattt aacacaatat gcaaaagaac tataccatgt   85620
atactacata acattggtga gaagaaaatt agaagatcta aataaagaca catccatgctt  85680
atagattaaa aaatccaatg tcacttttca caaaactgat ctttagtttc aacccacacc   85740
caagcagaat tcctgcagtc ttttcttgaa aacctaacag aatgtatatg ctagaatcac   85800
caagacaatc tttaaaaaga ataaaaaact tggaataaca tcacaagttt gtgggaataa   85860
tgcatatggt aatatggaaa ttctcataaa gacacagtaa tcaagacatg tggtattggc   85920
tgggacgctt ggctgtaatc ctaacacttt ggaggccaa gatgagagga ttgcctgaga    85980
tgaggagttg cagacaagcc tgggcaacat agcaagaccc tcatctctac aaatatttaa   86040
aaaaattagc caggtttggt gccatgtgcc tgtagtccca gctattcagg aagctgaggt   86100
gggaggatca ctggagccca tgaggtggag gctgaaatga gccatgattg tgctactgaa   86160
ctttagcctg ggagacagat taaaaccttc cctctctctc tcaaacaaac aaacaaaaaa   86220
tacatagtat tgggcaaaac atatgcaaac aaaaacagaa aagggtcagc ataaatttac   86280
atatatggtc aatttatttt caatacaggt agcaaagcaa tttaatgagg aaattttttt   86340
ccaaaattgg tctgaaacaa ctggatagcc atagaaaaaa actataacaa atgtgacgct   86400
tgaatcctac tgtatgactc aaattaaatt aatttgagat agctcttaga cctcaatgta   86460
acagctaatt ctgaggctga aattaagac tgctatgaaa aagtatagta tcttataacc     86520
ttggagaagg aaaaatttt tgagggaaga accagaaaac actaactgta aagaaaaca     86580
aatgataatg tggacattca ttgaataaaa acttatgctc accaaatatg actgttaaga   86640
aaataaataa gtaagtaaca cactggaaga aaaacactct catccatata tctgacaaat   86700
ggcctgtatc cagagtatag aaacatttct cccactcact aatcagagga caaacaacct   86760
aatcaaaatg ggcaacaggc ttgaatagtc atttcttagg agaagatgca cacagagcca   86820
acaatcacct gaaaaagtgc acaacatctt agccatcaaa actcaagagt tataaccctc   86880
ataagatgac actgaacatc cagtgtacat ggatatcatt aagaagacac aataataagt   86940
ggtgtcaccg atttggagct agaatgtgcc actctctcat atgctggtgg aagttcaaaa   87000
tcatacaaca aattaaaaaa tcagtctgat gctttcttat aaagttcgat aaatatgcat   87060
ctatcctaca aacctgtaat tctattcttg aatatttacc cccaaaatg aaaacataag     87120
tccacaaaaa tctatataaa tattcatagc agctttatgt tttataaact caaaataaaa   87180
actatttcaa tgttttcatc aaaagaaaat gaaaactatt taaatggttt catcaaaaga   87240
aaatgaaaaa agaatttcca gtatatttat acaaaggaat actattcatc aacaaggaac   87300
aagttactga tagtctcaga agcatgaaca aacctcaaaa atatattaag gaaagaagcc   87360
agacgtcaaa gtgtatagtc tgtatgagtc cattcatgtg agtttataga aaacacaatt   87420
tatggtgaaa gaaaccaata gcatttgaca ctggccgtgg gaagagggta gcagagattg   87480
attgagcagc cacacaaggg agttctgggg gtggtgaaaa tgttctgcat tgtgagggca   87540
gtgtgggcta cacaagtata tgtatttatc aaatctcatc cagctacatt taagatctgt   87600
gcatctcact ctatgtgaaa atatactcaa ctgaaaaaca gagcaggtat ctgtttcagg   87660
tgctacatca cttgatacgt ccagttgtgt taaaaaccac tgcctaacat cctcaaatgg   87720
gggatctggg cttgagacta ggtcacacgt gtagagtctc tacagagacc gtgttggatt   87780
cccatgctcc ataatacgtt ccaagtttc tcagacagcc acaggtcatg aatgtgagga    87840
ttctgagagg ttggagcaac gttcttggga ggcataatgg gaaaggcatt ctccaagatt   87900
cctccagcct ggggtcttca cctgctgtgc ctcttactgc attgttttct gactcatcca   87960
tagccacttg ccccttcag atcccatagt ctacctagcc gtctcccttt atgccttggg     88020
tcccgctgtt ctttcaactc atcacccatt ccttcagtcc cagagtggct gcagccagca   88080
gaggatggac tgagagcagg agaggaggtc gtgcccatga acccatccta gagaagcagc   88140
atcctgcctg ggagctagtt ttccaggaa gcttttataa gtcctgtaga cccaaaccca     88200
cttgctctac cagatacagt atttatagta atactatttt catgattatt ttatattgca   88260
aatgtagagc atttatgcta cactatgagt aaatagagta aggggctgg catgggaatt     88320
atataatctt ggatgccact tcttccttgg ggaaatgtat ttgagttcca acttacatat   88380
tactatatag tcttatagag agagacaa agagctagac agacagagat atctttgtat      88440
gtgcattaaa aaatctaaga tacatatttc aaaatctgtg tcatttattc tggaggaaag   88500
tatttggcag aaggtgaaag gaagatattc tgatcctttc ttgtacagac atgtattatc   88560
tcagttttca tagagagcat atactacttt tgatgtttta aaacaaaaat tataatctgt   88620
gatgtgtcca cagttgttta aaagttgaag ctgaagacca tttgtgcttg tggcaatatt   88680
attgtggtat aatgggaata tttcaaaggc acttgttaac acttttgttac agcaaaatgt   88740
agagggcgct aagtgccctt gaatattctc ccatctctgg tgacctgtgt tgttttgaaa   88800
tttgcagtgg cctgaccagg aactactgca ggaatccaga tgctgagatt cgcccttggt   88860
gttacaccat ggatcccagt gtcaggtggg agtactgcaa cctgacacga tgtccagtga   88920
cagaatcgag tgtcctcaca actcccacag tggcccggt tccaagcaca gaggctcctt     88980
ctgaacaagg taagaaattt gtggttagac atctatatac tgggatgaaa aaccatggaa   89040
aatcttactg atgcagaagc cttcagtggt acactggagg gttggttgag ggtctgcaat   89100
gtggaggaaa gcctcagcgc cctctctggg ggatccagaa ctgtgattt tggcacgctg     89160
tgaggagca gtgtcttag gaagggcacg gtgtctttga gaagggcaca gacccgccag     89220
ggcactggac ttaccactcc cctggttatt aaatgggtca tttcagtgtc ctagccaaaa   89280
tggatattct aacagcctgc caaatatgtg aagatttcca agccaataag cctttccagt   89340
gatttaaagt agactttttt cattgcaatc tacagtttgc agtttcttaa gaacatggcc   89400
tttgagtatg atatcctaga gaaacctaag gagactgcat tattttttcta ttgtcctggg  89460
gctgcatagc aggaggtaac caacgaatgc tgtccttccc tggcctatct cagtcttttca  89520
caggctctgt tcacctcagc tttgaagtta gaaatttcta ggtgttcttg cctcttcttc   89580
tcatgaaacc tgcattggca gtgagtctac agaagaagag gaagagaatt ctgctttgtt   89640
acaattcagg actctgggca ctagaagatt ccctatctct cctccaaggg aataagttgt   89700
ttgtctctaa ccctccttga gaaacaatga gtctttgcct gcactcctaa atgtaggatg   89760
atttcctgcc caaattttca aaagattaag ccttttgcct tggtatgagc aatggtctag   89820
```

```
ggaaatgcgc aagggtcttg tgtcggcccc tgactgacca ccagtcacct cctacagcct 89880
gcaccaagga atgcattgca ttctggtctt ctgccctgtg ttctcatga aaaccagcag 89940
agattcatat gatggagctg cacatgaatg taatttccaa tgtccagcat tctcctctgt 90000
tctttatctt tagatttaaa aataatgttt ctatgaactt attaaaattc tagaatacta 90060
tgaatctact gggtcttttc acatccttt gctactagta gaaaaaagaa tagtaataat 90120
tttcagaggc tactgtccag tatgtgacat aaattgtctc ccatgtttct ctgctcatgc 90180
aattactgag tatgatttat tttattttaa tttcagcacc acctgagaaa agccctgtgg 90240
tccaggattg ctaccatggt gatggacgga gttatcgagg catatcctcc accactgtca 90300
cagggaggac ctgtcaatct tggtcatcta tgataccaca ctggcatcag aggacccccag 90360
aaaactaccc aaatgcgtat gtatttgatt aaaaccataa gaggagcaac agccaactca 90420
aatattggtt agaagaccca tgctttaagc tcacttccta gggacaaatt tctcttagac 90480
tcacatttg gcaaaatgtc tcaggacctt tgcttttgag caaagagtct aagagaagag 90540
aaattttagg cctgctattt ttcctaatag ttttatggaa ggagtagaat atacggaagt 90600
ggcgaagtca tattaatgta aagctcagaa gataaatgac caaagcttaa acacagcacc 90660
attccacaat gcccactaaa aatcaatgtc atctttcact cgtgcaattc tgtcattcta 90720
aatttcaatt cccgactggt tgtttgccat tttgtcatg ggtaataagt aaaaaaaaaa 90780
aaattaagat gtgtatatat atatatatat atatatatat acacacacac acacacacac 90840
aaacatctga atatttatat atatgtctga atatttatat acttgtgtat aaaacttata 90900
tttaaatttt tgcataaatt tatatatttt taatatttca ttaaaaatta tattgtttca 90960
ctatgtatgt ctgagtattt ttatataltttt taatataaca ttttaaatat ttatataaa 91020
atattcaggt atgtaactga atattcattt acacacacaa atatatgtgt gcatgtgtgt 91080
atatatatat atcccatat atatatatat atatatatat acatatatat atatatatat 91140
atatgtatat atatatatat atatatatat acacacacac acacacacac atacatacag 91200
gtataaacac actgggcctg aagcaccagt ggtctgaaag gacatgtgtt gccaggactt 91260
gaagagcaaa agcaggaagg cggatgagag tcaggaggta cacaaacgct gaaaagtaaa 91320
atggacaagt acatggacaa aaagcaggta taagcataac agccttttgg aagtaaatga 91380
ctataaaata tatgaaaata ctgttttcac aagttgcaca acagatagta gtgtattgag 91440
ataatttaga acagaaaaca aatgtgatca acccctaaag tgtgctgtat ttcatcatgg 91500
attgaaggaa aaagagatgg agcccaagaa gaccacagca gtcttgatga actgagagac 91560
accagagttt gggattacaa aggcagctgg gattttctac acttggtaat aatgagaaag 91620
aatttgtgga gataaagagc tacagtcatg tacctagaag tcacctcagt gtaatataaa 91680
tctgcatatg cacagggagt gattccacaa tgaaagtagg acaaagaaca gctactgggg 91740
aaagaataac tacaagggaa caatgagttc aatggagatg gcagagctca caaagcactg 91800
ggggatatttt gagttcttac cagctagaaa agagacctca ttgcaaatct tggcattca 91860
gtagagaccc cagaaaagcc actctttgga aacagagttg atgtattta agagcaaat 91920
ctactccaca aaaatcctag caaaattgaa aagcaagtca gaaagaccaa aatcctctca 91980
acataaatta gttgcccatc agaagaaagc ttaacctctt cataggtaaa caataaaatc 92040
aaattgctca gttatcgtggc atccacaata tgtgacataa atttaaaaat ttactagaca 92100
tacaagaagc atttagtgtg atccataacc aggagaaaca tcattcaata caaatagacc 92160
cagaaatgac agaaatgata gaattagcaa aaacattaa aatatacata tgatcatttg 92220
atcttgtgat cagatatcac aagagaagaa agagatactt gaacagaaaa aatgcctgaa 92280
gcaatgatgg ctgaaaactt tccaaatatg aagaaaaaaa agctcacaga ttcaagaaaa 92340
ctaatcaatc agaaatatga tttttgaaaag taaaaatgta tgatttactt tgccaaatct 92400
tcttggttaa attgtctaaa atcaaagaaa gctaggaaaa ttttataagc cagaggaaaa 92460
aagattgttt atataaagga acagttacac aaatgactga tgccttctca tcagaaacaa 92520
tgaaagtcag aaacaataaa gtaacatctt taagtaata gaagaaaaac ccaagaggtg 92580
agggatcgtg gcagacagga ggcaggacta gattgcaggt ctggacagag cagcatgcag 92640
aggctcatat tgtgaatttt agccccatat tgactgcaag aacagaccag caatcctgag 92700
aggacccaca gaccgtgtga aggaagcaga ctgctcctgc aggataaggg agacaccca 92760
aatactgtga gttccccaac tgcagaagtg gaaaagggag gccttactcc ctcaaacaca 92820
ccccacacct ggagaagctg aaagtctgtt gcaggagaga gttcccaact ttacctggga 92880
ctcagtaaat ttagagagct gagccaagca aaatataggg gtagaggaag cagcagagaa 92940
gacctcagag cttgctggat ccccaagcag ctcattcctg cctggcacca cagagatcca 93000
tcagaagtgt ggcaaagga acagagggta aaactccaca tggaggactg ctctacctga 93060
actttctaac aatttgaaca gggggagaag cctcctggcc agaacttggg ggagggcatg 93120
aatctggttt gcagacttca caggtggggg aaggactaaa gcccttttct ttcacactg 93180
ggaggtggaa agcctcaggc aagttttcaa gcctgacttt ccccccacct ggaaacagac 93240
ttggagctgt tgcgggttg ggggcatggt gggagtaaga ccagcccttc agtttgcatg 93300
ggtgctgggt gaggcctgtg actgacagct tccctccact tccccgacaa ctcagatgac 93360
tcagcagagg cagccataat cctcctaggt acacaactcc agtgacctgg gaacttcacc 93420
cccacaccat acagaagctt cagtaagacg tgcccaagga aagtctgagc tcagacacgc 93480
ctagtcccac cccaactga tggtccttcc ctacccaccc tggtagcaga agacaaagag 93540
catataatct ttgagttct agggcccacc cacctctagt ccctctccac actagtatag 93600
ctgatgcagg aggccaacca gcacaaaaat agagcattaa accaccaaag ctaggaaccc 93660
ctatggagtc cattgcaccc tcctccacct ccaccagaac aggcactggt atccacagct 93720
gagagaccca tagatggttc acatcacagg actctgtaca gacagtcccc agtaccagcc 93780
cagagctggg tagacttgct aggtggcaag acccagaaga caggcaataa tcactgcagt 93840
tcagctcaca ggaagccaca tccataggaa aagagggaga gtactacatc aagggaacac 93900
cccatgggat aaaaacatct gaacaacagc cttcagccct accttccctc tgacacagtc 93960
tacccaaatg agaaggaacc agaaaaccaa ccctggtaat atgacaaaac aaggctcatc 94020
acactcccag ttcaccagca atggatccaa accaagaaga aatccctgat ttacctgaaa 94080
gagaattcag gaggttagtt attaagctaa tcagggaggg accagagaaa ggcaaagccc 94140
aatgcaagga aatccaaaaa aaaaaggta taagaagtaa aaggtgaaat attcaacaaa 94200
agtaataagc taataaaaaa acaataaaaa attcagtaca ctttggacac accttggaa 94260
atgtgacatg ctctggaaag tctcagcaat agaactgaac aagtagaaaa aataaattca 94320
gagctcaaag acaaggactt caaattaacc caatccaaca aagacaaaga ataaggata 94380
agaaaatatg aacaaagcct tcaagatgtc tgggattatg ttaaatgacc aaatataaga 94440
ataatcgtgt ctcctgagga aaaagacaat actaaaagct tggaaaacat atttggggga 94500
ataactgggg aaaacttacc tggccttgct ggacaccta acatgcaaat acaagaaaca 94560
```

```
caaagaacat gtaaatacaa gcagcacaaa gaacacctgg gaaattcatc acaaaaagat   94620
cttagcctag gcacattctc atcaggttat gcaaagttaa gacgaaggca agaatcttaa   94680
gagctgtgag acagaagcac caggtaatgt ataaaggaaa ccctatcaga ttaacagcca   94740
gttttcagc aggaactgta caagctataa aggattggag ccctatcata gcctcctcaa   94800
acaaaacaat tatcagtcaa gaattttgta tccagcagaa gtaagcatca tatatgaagg   94860
aaagatacag tcgtttttgg acaaacaaat gctaagagaa ttcaccatta ccaagtcacc   94920
actagaagaa ctgctaaaag gagctctaaa tcttgaaaca aatcctagaa acacatgaaa   94980
acagaatctc tttaaagcat aaatcacaca ggacctataa aacaaagta caagttaaaa   95040
aacaaaaaca aaaaacaaaa ccaaagtacg gaggcaataa agaatatgat gaatgcagtg   95100
gcacctcaca tttcaatgct aaaattgaat ctaaatggcc taaatgctcc acttaaagga   95160
tacaaaaaga gttggtggct ggcaagatgg ctgaatagga acagctccag tctgccgctc   95220
cccgtgagat caacacatag ggtgggtcat ttctgcattt ccaaccaagg tacccggctc   95280
atctcattgg gactggttag acagtgggtg cagcccacag agggtgacct gaagcagggt   95340
ggggtgtcac ctcacctggg aagtggaagg ggtcagggaa ctccctcccc tagccaaagg   95400
aagccgtgag ggactgtgcc gtgaagacca gtgcattctg gcacaaatac tatgcttttc   95460
ccacggtctt tgcaacctga agaccaggag attcccttgg gtgcctacac caccagggcc   95520
ctggatttca agcccaaaac tgggctggca tttgggcaga cactaagcta gctgcaggag   95580
tttttttca taccccagtg gtccctggaa tgccagcaag acagaaccat tcacccccgt   95640
gaagaaaggg ctgaagccag ggagctaagt ggtcttctc agtggatccc accccatgg   95700
agcccagcaa gctaagctcc actggcttga aattcttgct gccagcacag cagtctgaag   95760
ttgacctggg acgctcaagc ttggtgggag gaggggtatc cacaaatact ggggcttgag   95820
taggaggttt tcccctcaca gtgtaagcaa aaccgctaag aagtttgaac tgggcagggt   95880
gcactgcagc ttggcaaagc cattgtagca agagtgcctc tctagattcc tcctctctgg   95940
gcagggcatc tctgaaagaa aggcagcagc cccagtcaga agcttataga taaaactccc   96000
atctccctgg gacagagcaa ctggaggaag gggtggctgt gagtgcagct ccagcagact   96060
tagtttcctg cctgccagct ctgaaaagag caccagatcc ccaacacag cactagagct   96120
ctgataaggg acagactgcc tcctcaagtg ggtcctggtt tcagaagata ataagaaact   96180
cctctgagct aaaggagcat gttctaacac aatgcaagga agctaagaac cttgaaaaag   96240
gtcagaggaa ttgctaacta cagtaagcag tttagaaag aacataaatg accttaggga   96300
gctgaaaaac acagcacgag aacttcatga cacatacaca agtatcaata gcaaaatcga   96360
tcaagtggaa gaaaggatat cagagattga aaatcaactt aatgaagtaa agcgtgaaaa   96420
caagattaag gaataaagaa tgaaaggaa tgaacaaatc ctccaagtat gggactatgt   96480
gaaaagattg aacctacgtt tgattggtgt acctgaaagt gatgggagaa tggaaccaag   96540
ttggaaaaca ctcttcagga tattatccag gagaacttcc ccaacctagc aagacaggcc   96600
aacattcaaa ttaaggaaat acagagaata ccacattcaa attcaggaaa tacagagaac   96660
accacaaaga tactcctcaa gaagagcaac ctgaagacac ataatcgtca gattcaccaa   96720
ggttgaaatg aaggaaaaaa atgttgaggg cagccagaga gaaagtttgg gttacccaca   96780
aagggaaccc catcagacta acagtggatc ttcctgcaga aactctacaa gccagaaagag   96840
agtgggaggc caatattcaa cattcttttt tactattatt atacttaag ttctaggta   96900
catgtgcaca aggtgcaggt tgttacata tgtatacatg tgccatgttg gtgtgctgca   96960
cccattaact cttcatttac attaggtata tctcctaata ctatccctcc ccactcccc   97020
catcccatga caggccccgg tgtgtgatgt tccccactct gtgtccatgt actctcattg   97080
ttcaattccc acctatgagt gagaacattc ggtgttttga tttctgtcct tgtgatagtt   97140
tgctgagaat gatggtttcc agcttcatcc acatccctac aaaggacatg aagtcatcct   97200
tctttatggc tgcatagtat tccatggtgt atatgtgcca catttcta atccagtcta   97260
ccattgatgg acgtttgtgt tggttccaag tctttgctat tgtgaatagt gccgcaataa   97320
acatatgtgt gcatgtgtct ttatagcagc atgatttata atccttttaga tatatatcca   97380
gtaattgtat ggctgtgtca aatggtattt ctagttctaa atccttgagg aatcaccgca   97440
ctgtcttcca caatggttga actagtttac agtcccacca ccagtgtaaa aatgttccta   97500
tttctccaca tcctctctag catctgttgt ttcctgactt tttaatgatc accattctaa   97560
ctggtatgag atggtatctc attgtggttt tgatttgcat ttctctgatg gccagtgatg   97620
gtgagcactt tttcatgtgt ctcttgactg cataaaagtt ttcttttgag aattgtctgt   97680
taatatcctt tgccaacttt ttgatgggt tgtttgattt ttttcttgt aaatttgttt   97740
atgttcttg tagattctgg atattagccc tttgtcagat gggtagattg taaaattttt   97800
ctcccattct gtagcttgcc tgttcattct gagggtagtt tcttttgctg tgcagaagct   97860
ctttagttta attagatccc attggtcaat tttggctttt gttgctattg cttttggtga   97920
tttagtcatg aagtccttgc ccatgcctat gtcctgaatg gtattgctta ggtttcttc   97980
tagggtttat atggttttag gtctaacatt taagtcttta atccatcttg aattaatttt   98040
tatataaggt gtaaggaagg gatccagttt cagctttcta catatggcta gccagtttc   98100
ccagcaccat gtattaaata gggaaaccctt tcccctatttc ttgttttttgt caggtttgtc   98160
atagatcaga tggttgtaga tgtgtggtat tatttctgag ggctctgttc tgttccattg   98220
gtctatatct ctgttttggt accagtacca tgctgttttg gttactgtag ccttgtaatg   98280
tagtttgaag tcaggcagag tgatgcctcc agctttgctt ttttggctta ggattgtctt   98340
ggcaatgcat gctcttttt gttccatatg tagttttttc caattctgtg   98400
aagaaagtca ttggtagctt gatgggatg gcattgaatc tataaattac cttaggcagt   98460
atggccattt tcacaatatt gattcttcct atccatgagc atgaatgtt cttccatttg   98520
tttgtgtcct cttttatttc attaagcagt ggtttgtagt tctccttgaa gaggtccttc   98580
ccatcccttg taagttggat tcctaggtat tttattctct ttgaagcaat tgtgaatggg   98640
agttcatcca tgtccctaca aaggacatga agtcatgat ggaatgctt gtgattttt   98700
cacattgatt ttgtatcttg agactttgct gaagttgctt atcagcttaa ggagattttg   98760
gtctgagaag atgggttttt ctaaatatac aatcatgtca tctgcaaaca gggacaattt   98820
aacttcctct tttcctaact gaatacccttt tatttccttc tcctgcctaa ttgccctggc   98880
cagaacttcc aacactatgt tgaataggag tggtgagaga gggcatccct gtcttgtgcc   98940
agttttcaaa gggaatgctt ccagtttttg ccattcagt atgatattgg ctatgggttt   99000
gtcataaaata gctcttatta ttttgagata tgtcccatca atacatagtt tattgagagt   99060
tcagcatgga gagctgttga attttgtcaa aggccttttc tgcatctatt gagataatca   99120
tgtggttttt gtctttggtt ctgttatat gatggattac atttattgat ttgcatatgt   99180
tgaaccagcc ttgcatccca gggataaagc caacttgatc atggtggata agcttttga   99240
tgtgctgctg gattcggttt gccagtattt tattgaggat ttttgcatca atgttcatca   99300
```

```
tggatgttgg tctaaaattc tcattttgt tgtgtctctg ccaggatttg gtatcaggat    99360
gatgctggcc tcataaaatg agttaggag gattccctct ttttctatga ttggaatagt    99420
ttcagaagaa ttggtaccag ctcctctttg tatctgtggt agaattcggc tatgaatctc    99480
tcctggactt ttttttggttg gtaggctctt aattattgcc tcaatttcag agcctgttat    99540
tggtctattc aaggattcaa tttctttctg gtttagtctt ggtagggtgt atgtgtccag    99600
gaattttttcc atttcttcta gattttctag tttatttgca cagaggtgtt tataatattc    99660
tctgatggta gtttgtattt ctgtgggatt ggtagtgata tcccctttat catttttat    99720
tgcatctatt tgattcttct ctcttttctt ctttattagt cttgctagtg gtctatcaat    99780
tttgttgatc ttttcaaaaa accagctcct ggattcattg atgttttgaa ggtttttttg    99840
tgtctctatc tccttcagtt ctgctctggt cttagttatt tcttgccttc tgctagcttt    99900
ttaatgtgtt tgctcttgct tctcagttc ttttaatggt gatgttaggg tgtcaatttt    99960
agatctttcc tgctttctct tgtgggcatt tagtgctgta aatctcccc tacacactgc   100020
ttaaatgtg tcccagagat tctggtatgt tgtgtctttg ttgtcattgg tttcaaagaa   100080
tatctttatt tctgccttca tttcgttaca tacccagtag tcactcaggt gcaggttgtt   100140
cagtttccat atagttgagc agttttaat gagtttctta atcctgagtc ctagtttgat   100200
tgcactgtgg tctgagagac agtttgttat aatttctgtt cttttacatt tgctgaggaa   100260
tgcctcactt ccaactatct ggtcaatttc agaataagtg cgatgtggtg ctgagaagaa   100320
tgtatattct gttgatttgg ggtggagagt tctgtagatg tctattaggt ctgcttggtg   100380
cagagctgag ttcaattcct ggatatccat gttaactttc tgtctcattg atctgtctaa   100440
tgttgacagt ggggtgttaa agtctcccat tattattgtg tgggagtcta agtctctttg   100500
taggtctcta aggacttgct ttatgaatct aggtgctcct gtattgggtg catatatatt   100560
taggatagtt agctcttctt gttaaattgg tcccttaac attatgtaat ggcctttctt   100620
gtctctttg atctttgtta gtttaaagtc tgttttatca gagactagga ttgcaacccc   100680
tgctttttt gttgttttcc atttgcttgg tagatcttcc tccatccctt tattttgagc   100740
ctatgtgtgt ctctgcacgt gagatgtgtc ttcagaatac agcacactga tggatcttga   100800
ctcttatcc aattttccag tctgtgtctt ttaattggag catttagccc atttacattt   100860
aaggttaata tttttatgtg tgaatttgat cctgtcatca tgatgttcgc tggttattt   100920
gctcattagt tgatgcagtt tcttcctagc atcgatggtt tttacaattt ggcatgtttg   100980
tgcagtggct gataccgatt gtttcttttcc atgtttagtg cttccttcag gagctcttgt   101040
aaggcaggcc tggtggtgac aaaatctctc agcatttgct tgtctgtaaa ggatttttt   101100
tctccttcac ttatgaagct tagtttggct ggatatgata ttctcagttg aaaattcttt   101160
tctttaagaa tgttgaatat tggctgccac tctcttctgg cttgtagagt ttctgctgag   101220
agatctgctg ttagtctgat gggcttccct ttgtgggtaa cccgaccttt ctggtgaatc   101280
tgacaattat gtgtcttga gttactcttc tcgaggagta tttttgtggc attctctgta   101340
tttcctgaat ttgaatgttg gcctgccttt gtaggttggg gaagttctcc tggataatat   101400
cctgaagagt gtttttccaac ttggttccat tctcctcgtc actttcaggt acaccaagca   101460
gatgtagatt tggtctttc acatagtccc atatttattg gaggctttgt tcattctttt   101520
ttactccttt ttttctctaa acttctcttc tcgcttcatt tcattcattt gatctttaat   101580
cactgatacc ctttcttcca cttgattgaa tcaactacttg ttc aaacttgttc atgtgtcacg   101640
tagttctcgt gccatggttt tcagctccat tagatcattt aaggtcttct ctatgctgtt   101700
tattttagtc tgccattcat ctaaactttt tcaaggtttt tagcttcttt gcaatgggtt   101760
cgaacatcct tctttagctc ggagaaattt gttattacag atcgtctgaa gccttcttct   101820
ctcaactcat caaagtcatt ctctgtccag cttttgttctg ttgctcgtga ggagctgcgt   101880
tccttcggag gagaagaggc accctgattt ttagaatttt cagctgttct gctctggttt   101940
ctccccatct ttgtggttta tctacccttt g gttcttgatg atggtgatgt acagatgggg   102000
ttttggtgtg gatgtctttt ctgtttgtta gttttccttc taacagtcag gaccctcagc   102060
tgcaggtctg ttggagtttg ctggaggtcc actccagtcc ctgtttgcct gggtattacc   102120
agtggaggct gcagaacagc aaatattaca gaacagcaaa tgttgctgcc tgattcttcc   102180
tctgaagct tcatctcaga ggggcaccca gctgtatgag gtgtcagttg gcccctactg   102240
ggaggtgtcc cccagttagg ctactcgggg gtcacggacc cacttgagga ggcagtctgt   102300
ccattctcag atctcaaact ctctgctggg agaaccacta ctctcttcaa agctgtcaga   102360
cagggatgtt taagtctgca gaagtttctg ctgcctttttg ttcagctatg ccctgcccc   102420
agaggtggag tctacagagg caggcaggtc tccttgagct gtggtgggct ccacccagtt   102480
tgagcttcct ggtcgctttg tttacctact caagtctcag caatggcaga cgcccctccc   102540
ccagctttgc tgccgccttg cagttcggtc tcagactact gtgctagcag ttcaatctca   102600
gactgctgta ctagcagtga gcaaggctct gtgggcatgg gaccctctga gccatgtgca   102660
ggatataatc tcctggtgtg ccgtttgcta agaccattgg aaaagtgcaa tattagggtg   102720
ggagtgtccc gattttccgg gtacatctgt catggcttcc cttggctagg aaagggaatt   102780
ccctgacccc ttacacttcc cgggtgaggc aatatcccgc cttgcttcgg ctcactctcc   102840
gtgggctgca cccactgtct gacaagcccc ggtgagatga acccagtacc tcagctggaa   102900
atgcagaaac cacccatctt ctgctttgct catgctggga actgtggact ggagctgttc   102960
ctattcggcc atcttgaaac ctcccctctc tcacgatcac aaggtccac aataggccgt   103020
ctgcaggctg aggagcaaga aaagccagtc tgaattccaa aactgaagaa attggagtct   103080
gatgttcaag ggcaggaaac atccagtgcc aaagaaagat gtagaatatt caacattctt   103140
aaagaaaata atttcaacc tagaatttca tatccagcca aactaagctt tataacaaag   103200
gagaagtaaa atcctttaca aacaagcaaa tgctgaggaa ttttgtcaac accaggcctg   103260
ccttacaaga ggtcctgaag aaaacactaa atatggaaag gaaaaccag taacagctac   103320
tgcaaaaaca taccaaattg taaacaccat aacactata aagaaactgc atcaactaat   103380
gggcaaaata gccagctagc atcataatga caggatcaaa ttcacacata acaatattaa   103440
ccttaaatgt aaatgggcta aatgcccaa ttaaaagaca cagactggga aattgaataa   103500
agagtcaaga cccattggtt tgctgtgttc agaagaccca tctcagggtg aaaagacata   103560
catgggctca aaataaagaa atgaaggaat atttaccaag caaatggaaa gaaaaaaaaa   103620
gcagcggttg caatcttagt ctttgatgaa acagacttta aaccatcaaa gatcaaaaga   103680
gacaaaggag ggcattacct aatggtaaaa ggatcaatgc aacaagaatc tgactgtc    103740
ctacttatat atgcacccaa tacaggagca cccagattaa taaagcaagt tcttagagac   103800
ctacaaagag acttagactt ccacacaaaa atagtgggag actttaacac cccacagcca   103860
atattagatc gacgtgacag aaaattaaca aggatattca ggacgtgaat tcagctctgg   103920
accaagctga cctaatagac atctacagaa ctcgacacca caaatcaaca gaatatacat   103980
tcttctcagc accacattgc acttattcta aaattgacca cataattgga agtaaaacac   104040
```

```
ttctcagcaa atgccgtaga atggaaatca taacaaacag tctctcgac caaagtgcaa   104100
tcaaactaga actcaggatt aataaactca ctcaaaacca cacaactata tggaaactga   104160
acaacctgct cctgaattac tactgggtaa ataacaaaat taaggcagaa gtagataagt   104220
tcttagaaac caaagagaac aaagacacaa tgtgccagaa tctctggtac acagctaaag   104280
ccatgtttag agggaaattt atagcactaa atgcccacag gagaaagcgg gaaagatcta   104340
aaatcaacac cctaacatca caattcaaag aaccagagaa gcaagagcaa acaaatacaa   104400
aagctagcag aagacaagaa ataactaaga tcagagcaga actgaagggg ataaagacac   104460
gaaaacccctt taaaaaatta ataaatccaa gagctggttt tttgaaaaga ttaacaaaat   104520
acatagaagc ctagccagac taataaagaa gaaaataaga aagaatcaaa tagacacaat   104580
aaagaataat aaaggggata tcaccaatga tgccacagaa atacaaacta ccatcagaga   104640
atactttaaa cacctctatg caaataaaat agaaaatcta aaagaaatgg ataaattcct   104700
ggacacatac accctcccaa gactaaacca ggaagaagtc aaatccctga atagaccaat   104760
aacaagttct gaaatcgagg cagtaattaa tagcttacca accaaaaaaa gcccagacca   104820
gagggattaa cagtcaaatc ctaacagagg tacaaagaag agctagtact attccctctg   104880
aaactattcc acacaataga aaaagaggga ctcctgccta actcattta tgaggccagc   104940
atcattctga taccaaaacc tggcagagac acaacaagaa aagaaaattt caggccaaca   105000
tccctgatga acatcaatgt gaaaatcctc aataaaatac tggcaaactg aatccagcag   105060
cacatcaaaa agcttatcca ccatgatcaa gttggcttca tccctgggat gcaaggctgg   105120
ttcaacatat tcaaatcaat aaacataatc catcacataa acagaaccaa tgacaaaaac   105180
cgtatgatta tcgcaataga cgcagaaaag gcctttgata aaattcaata cccaatcatg   105240
ctaaaaactc ttaataaact aggtattgat ggagcatgtc tcaaaataat aagagctact   105300
tatgacaaat gcatagccaa tatcatactg aatgagcaga gctgaagc attcccttg    105360
aaaaccagca caagaaaagg atgccctctc tcaccactcc tattcaacat agtattggaa   105420
attctgtcca gggcaatcag gcaagagaaa gaaataagg tattcaagtg gaagagagg    105480
gagtcaaatt atttctcttt gcagatgaca tgattgtata tttagaaaac tctatcatct   105540
cagcccaaaa tctccttaag tctgataagca acttcagcaa agtctcagga tacaaaatca   105600
atgtgcaaaa atcacaagca ttcctataca ccaataagag acacagagcc aaatcctgag   105660
tgaattccca ttcacaattg ctacaaagag aataaaatat acctaggaat ccaacttaca   105720
agggatgtga aggacctctt caaggagaac tacaaaccac tgctcaagga aataagatag   105780
gacacaaaca aatggaaaaa cattccatgc taatggattg gaagaatcaa tattgtgaaa   105840
attgccatac tgcccaaagt gatttataga ttcaatgtta tccccatcaa gctaccattg   105900
atttcttcac ataattagaa aaaactactt tcaatttcat atggaataga aaagggcct    105960
gtatatccaa gacaacctaa gcaaaagaa caaagctgga ggcatcatgc tatctgactt    106020
caaaatatac tacaaggcta cagtaacaaa aacagcatgg tatggtactg gtaccaaaac   106080
agatatatag accaagatgaa cagaacagag gcctcagaa taacaccaca catctcaac    106140
tattggatct ttgacaaact ggacaaaaat aagcaatggg gaaaggattc cctatttaat   106200
aaatggtgtt gggaaaactg gctagccata tgcagaaaac tgaaactgga tcccttcctt   106260
acaccttata cacaaattaa ctcaagatag attaaagaat taaatgtaag acctaaaacc   106320
ataaaaaccc tagaagacac tttgggaggc cgaggtggat ggatcacgag gtcaggagat   106380
cgagaccatc ttggctaaca cagtgaaagc ccatctctac taaaaataca aaaaattagc   106440
tgggtgtggt cgtgggcacc tgtagtccca gctacttggg aggctgaggc aggagaatgg   106500
catgagctga ggaggttgag cttgcagcaa gccaagattg tgccactgca ctccagcctg   106560
ggcaacagag tgagactcca tcaaaaaaac aaaaacaaaa acaaaaaatc aaaaccctaga  106620
agaaaacata ggcaatacca ttcaggacat aggcatggga gaagacttca tgactaaaac   106680
agcaaaacca atggcaacaa aagccaaaat ttacaaatca gatctaatta aaataaagag   106740
cttctgcaca gcaaaaaact ctcatcagag tgaaaaagca acctatggag aaaaattctg   106800
tggtctagcc atctgacaaa gggctaatgt ttagaatgta caagcaactt aaacaaatgt   106860
acaagaaaaa aaaaacaacc ccatcaaaaa gtgggcaaag gatatgaaca gacacttctg   106920
acaggaagac ctttatgtgg ctgacaaaca tgaaaaaagc tcatcatcac tgttaattag   106980
agaaatgcaa atcgaaacca caatgagata ccatctcatg cccgttagaa tggcgatcat   107040
taaaaagtca ggaaacaaca gatgctgaag aggatgtgg gagaaagagg aacacattta   107100
cactgttggt gggagtgtaa attagttcaa ccattgtgga agacagtgcg gtgattcctc   107160
aaggatctag aaccagaagt accatttgac ccagcaatcc cattactggg tatataccca   107220
aaggattata aatcattcta caataaagac acatgcacac gtatgtttat tgtagcacta   107280
ttcacaatag caaagacttg gaaccaactg aaatgcccat caatgataga ctggataaag   107340
aaaatgtggc acatacacac tgtggaatac tatgcagcca taaaacagga tgagttcatg   107400
tcttttgcag gacatggat gaagctggaa accatcattc tcagcaaact aacacaagaa   107460
cagaaaacca aacaccatat gttctcactc ataagtgtga gttgaacaat gagaacacat   107520
ggacacagga aggggaacat cacacacagg ggcctgttgg ggagttgagg ctaggggagg   107580
gattggatta ggagaaatac ctaatgtaga tgatgggttg ctgggtgcag caaccacca   107640
tgacacgtgt ataccatgt aacaaaccca cacattctac acatgtatct cagaacttaa    107700
agtataataa taataagata cagaactgca gaatgaataa gaactcacca accatctgct   107760
gccttcagga gactcattta agacataagg actcacataa acttaaagta aatgggtgga   107820
aataataata agtggtgtca ctgatgtgga ttagattat aaaactctta tcatatgctg    107880
gtggaagatc aaaatgataa aacgaattaa aaaatcagtc agatggtttc ttaaaaagtt   107940
ccatcaatat gcctctatct tacaaacctg caattctatt cctgaatctt tatcccaagg   108000
aaatgaaaaa gtaagtccac aaagagttct atatgaatat ttataggagc tttatttatt   108060
ataattcaaa ctgtaaaaat aatttcaatg ttcatcaata acaaaatgaa aaataattt    108120
gcaacctact ggtacacttg aatactattc agcactgagt atcttaaata gcatggatgg   108180
agctcaaaaa tatactcagg aaagaagcca tgtatattct gtatgagttc atttacatga   108240
gatcatttac atttcctcca aaagaggaaa aactaatttc tgttgaaaga aaccaatgta   108300
tttgcctctg gcagtggtaa gggggtagca cagattaatt gggtagggac tcaagagagt   108360
ttctgggtc acagaaatgt tccgtgtggt gatgggagt tgggctccac aggtatagg     108420
gttgatccaa aatcatccaa aaaacaacat tgcatcctcac tctgtgggaa               108480
agtatatctc aactgtaaaa agggcagaaa ttgcttttaa acgctcagcc ttttagcaca    108540
tccagttgct tggagaacca gcttactcaa atgggggtct aggctggaga ctaggtcaca   108600
ggcatagagt ctctaaactt tcccatggca cataatacgt ttcaggtttt ctcagagagc   108660
tgcaggttag taatctgagg attctgacaa gttgggtcaa cgttcctagg aggcatgaat   108720
gggagtgcat tctctaagat ccctccaccc cagggtcctt gctttctgtg cctcttactc   108780
```

```
cattgttttc tgactcctct gtagccactc gacctcttca gatcccattg tctacccagc 108840
catcgccctt tatgacttgg gtcccactgt tctttcatct catcctccat tccctcagtt 108900
tcggagtggc tgccgctagc agaggatgga ctgagagcag gagaggtggt cctgcccagg 108960
aacccatcct agagaaatgg catcctgtct gggagctagt tttttagggc aggttttata 109020
agtcttgtaa agccagacac acttgatcta cctggtagtt tatttacagt aatactattt 109080
tcataattgc ttttcactct aaaagtagag ccttttagct acactgtgag taaataaagg 109140
ggctggcctg ggaatggtat catgttggat gttgtttctt ccctgaagta atatatatca 109200
gttacaattt acatgttact gcagagtcct agagagagac acagagaatg agacagatac 109260
caatacattt ttatgtgcat taaaaaaatc taaggccagg cgcagtggct cacacctgta 109320
atcccagcac tttgggaggc cgaggtgggt ggatcacgag gtcaggagat tgagaccatc 109380
ctggctaaca cggtgaaacc ctgtctctac taaaaataca aaaaattagc caggcgtggt 109440
ggcgggcgcc tgtagtccca gctactcagg agactgaggc aggagaatgg cttgaaccca 109500
ggaggcagac cttgcagtga gccgagattg cgccactgca ctccagtctg ggcgacagag 109560
cgagactccg tcacaaaaaa aaaaaaaaat ctaaaatgca ctcttcaaaa tctatgtcat 109620
ttattctgga ggaatgcagt tggcagaagg aggaagatat tccgaatttt tcttgtatac 109680
atttatgtat gatctcagtt tttttatgga tcatagacca attttgatat tttaaaataa 109740
aaattataat ctatcttgga aatttacatg gttcttttaga acttgaggac cgttttttgct 109800
tttcggaata ttattgtacc taaaatggga atattacaac gtcacttttt aacacttttgt 109860
tataacaaag tttagacagc gctgggtgcc cctgaattttt ttcccgcctc ttgtgacctg 109920
tgttgttttg gaatttgcag tggcctgacc gagaactact gcaggaatcc agattctggg 109980
aaacaaccct ggtgttacac aaccgatccg tgtgtgaggt gggagtactg caatctgaca 110040
caatgctcag aaacagaatc aggtgtccta gagactccca ctgttgttcc agttccaagc 110100
atggaggctc attctgaagc aggtaagaag tctgtggcca gatatctaca catttgaaca 110160
ttgggatgaa aagagatgga aaatctgact gatgcagaag ccttccatgc tacacagaaa 110220
cttgagggta tggcaggtgg aaagaagcct cagcactctc tctggtggag caattttttgg 110280
cgcaacgtgc gtgggcggtg acttcaggaa tggtgcaaaa cccacctggg acttgactta 110340
ccactcactt tgttatgaaa ggggttatct cggtgttcca gacaaaattc caattctaac 110400
atcaggccaa atttgtgcca aatttcacac tagtgagtgt ttccaggcat ttattaaaat 110460
ggacagtgtt cattgcaatc ttcagcattg cagttgctga ggtatgtggc cgctgagttt 110520
gtcatcctgg ggaaacctaa tatgatgata tttattccat ctaatcctgg ggctatttgg 110580
cagtaaatac cacagaatac actatttctc tggcttattt cagtcttagg taggctctgc 110640
acacctatgc ttggaaggca ggaatttctt ggtgttcttg tgccttcttc tcatggaacg 110700
tgcatctttg gtgtgtgttg agaggaaggg tagtagactt ctgctttgtt gcaatgcagg 110760
atgctggaac agaggattc cctgtctcta ctgtaaggga ataagatttt agcctccatc 110820
cttctctaag aagcaatgtg tctttgcctc caagtactag atgcaggacc atgaactgcc 110880
ccgtccacca gaagcttaag gctttggctt tcaggagca atcatctagg gaactgtgca 110940
gggttttcat gtctgtcccc tactgacagc caatcaccat acagcctgca taacctaatc 111000
catcatcgtc tggtttcctg cctcattgtt ttcatgaaca accagtagag agccatacga 111060
aagagcttgc acatgagtct ttgttccaat tgtaagagca ctgataggtc cttttcccac 111120
caggttttga atataaaatt tctaagaact tattaaaata ttagaatgtt attaatctat 111180
tgttttttgct tcagcatgtc cttctgcttg tgagtatact aaagagaaca gtcataattc 111240
tgaaactact gtcctgtttg tgtcataaat tgcttcacat gtttctgcat actagtagtt 111300
actcagcttg attttgtcta ttttcagcac caactgagca aaccccctgtg gtccggcagt 111360
gctaccatgg taatgccag agttatcgag gcacattctc caccactgtc acaggaagga 111420
catgtcaatc ttggtcatcc atgacaccac accggcatca gaggaccccca gaaaactacc 111480
caaatgagta tgtctttgat gttacttgta agaggagcaa cagccaactt aagttcctcc 111540
tagaagacc ttgcttcaag ctaacttgtt aggacaaatt tcccttagac ccagaaggtg 111600
tgtcaaaatg tccagacaac tttgcttttg atcaaagagt ctgagagaat aggtatttta 111660
ggcttgctat ctttttctaat agtctgatgg aagcagaagg ctacatggag ctgatgaggt 111720
cttttttaata taaagctcaa gagatcaaat gatcaaatac ttagagtgcc attctacaag 111780
gctcataaaa gatcaatgca ctcttttcacc catgcaattc tatcattcta acctccctc 111840
tctgaaatga aggcttttttg ccattttttgt catgggtcac aagtaaataa ttcacatgta 111900
tatgagtata tatataacca ggtgtgttta ttcagactag tatgtatata tatacatata 111960
tatgttcata taagttagta ttcatatata tgttcatata tatatgttca tacagactag 112020
tattcatata tatatacata tatatataca cacacatata tatatatata tatatgttct 112080
agggaaacat gcaaggtttt tatgtctgtc cctgactgat gaccaaatac cctatagcct 112140
gcacagctgc aagctgtata gccatacaat ttgcaggaca cacacacata cacacacaca 112200
cacacacaca cacacactaa catataatat aatataatat aatataatat aatataatat 112260
aatataatat aattaatata tataaaacctg tgtgaacaca ctgggttcta agctccagtt 112320
ttctgaaggg atatgggttg ccaggagagg aagagcaaaa gcaagaatgt agatgagaat 112380
taggaagtaa acagatatgg agattaaaat gggcaggtac atggacaaaa aaccaggtct 112440
gacaaaaact ggctttctgc cataaatgac tataaaagat attaaaaaac actttccaca 112500
tgttggacaa gagacagtac aggactgaga taatttagaa aaggaaatga atgagcgcaa 112560
ctccgtaact attatgactt tcttcctgga gaaccttcct ggctgaaagg gcaaggaatt 112620
ggagccaaag ccaaccacag cagtcttgct gaactgagga aagagactgg agtttgggat 112680
agctaagaaa atgtgtattt tctatgctag gtaataatga gaaagaattt gtggtgaaaa 112740
ggagctgaag gaatatgcat ggaagtctaa tataaactgc atatgcacag ggagaaattc 112800
tacaaagtgg gacagagaac cactctgggg gaaaggacaa attcagggaa acagtgagct 112860
caatggtgac gccagagctc acgtagcact ggggggatacc gggttgctga tcagcccgag 112920
gagagacacc tcattgaaca tctcgggcat tcagtagaga ccccagaaaa gtcatacttt 112980
aggagtagga tttatgcctt cttagaataa agactacccc agaaacaccc tagtaaagct 113040
taaaaaccaa gtcaaaaggg acccaaatga tctccaagta aattaactgc ctgacagaag 113100
aaaactcaac catcactgga ggtaaataac atgattacag tgctctgtaa tgttgcattc 113160
acaaggagtg acatcattta aaaatttatg aggcaggaaa aagcaattag tgtgatccat 113220
aactaggaga aaaaccagtc aatacaaata gaccaagaaa tagtagaaac gatggaattg 113280
acaaagaaat taaaactgta tatatgataa ttgtgttcaa agatttaaag aaaacatgaa 113340
catgagggaa acaaatgcag aatataaaaa aagcaaatg cgtaaaacaa ccaaatggaa 113400
attaaagaac tacaaaaaag tataaaccttta ataaaatact cactgatgg ccttaatatt 113460
agtttataca ttacagaaga aaaagtgaac cagaagataa ctcaatgaaa gccatacaat 113520
```

```
ctgtaagaca cacacacacg cacacgcgcg cgcgcgcaca cacacacaca cacagagaga    113580
gagagagaga gaaagagaga gagagaaagg ctgaaaaaaa taaatagaac cttaaggata    113640
tcagtgaaaa tagcaaaaga tttaatatat gggtaaagca agtcacagaa ggacgggaag    113700
gagatattgg gacagaaaaa aatactcaaa gcaatgatgg ctgaagactt tacacgtatg    113760
aagaaaatga taaactcaca gtcaagaagc tcaatgaatc agaaatagta tttttaaaag    113820
caaaactcta tgatttactt gggtacatta tagataaatc gtccaacatc aaagataaca    113880
aggataatct tataagccag aggaaaacaa tatcatttac atagagggac agtaatgaaa    113940
gtgaccgatg ccttctcctt ggaaacaatg gcataacatc tttaaagtga taaagagaaa    114000
taaaaacaga tcaacctagg acgacatgtc cagccaaaac aaacaaataa acaaaaaaac    114060
cctttaaaat aaacgtgatg taaatacgta ttctgccacc tccagaggaa acaagcaaaa    114120
aaacaaaaga atgtttccaa ggcaggcttc tgtattaaaa gattttaagg aaagttattc    114180
aggtagaaga aaaataatac cagatgggaa ctttaatcca tactaagtaa tgaagagccc    114240
tggaaatggc aaatggcaat gtcaaatataa aatactctta tttatctaat tttttaaatgt   114300
atttaaagga caatttgtga tattaattaa aataatagga atatattgtt gtttcaacgt    114360
atgtagtagt aaaattcata aaaacagtag cacaaataat gcagatgata actgaagta    114420
tactgttaat gagtttttg cattatccat gaagttatat aatattaata gatggttgaa     114480
tgtgatagtt taaggtggga tattataaat cctaggacaa ccaaaaaaat ttaaactgag    114540
aggaatggat agtaagagga atagtccttt tatgcaaaag aaggaagaaa aagaggaata    114600
aagaatataa aagatatggt gtaaacagaa aatacatagc attattgtag acacaaactg    114660
aactaccta tgagtatatt aaatataaaa ggattaagca ttacaaataa aaggcagaga    114720
ttgtaaattg aataaaaacc acagctaagt gtgttctttt tagaataaat actctttaag    114780
tgtaaagatc tactttaaac accaaaatat gaaaaaggat atataccatg aaacctgaa    114840
tcataaaataa gctggagtgg tgattaatgg atgcaggcac tcctaaagac taataagtga    114900
atgtggtcaa attgaagaaa caaaagtata tacgtgctca atgtgcaaaa acttttctg    114960
tatacatgct atgatccttt ggaaaattaa agttttaaag caatatcact gacaatagta    115020
tcaaaaccaa aaaatattta gtgataaatt tcacacacta tgctcaagga ctatacacct    115080
tgcactagaa aacaatgttg aggaaagaat taaaagatct aaatatacac catgcttata    115140
gattaaaaga ctccatatca gttctcgtga aattgatctt tggatgaaac ccacacccaa    115200
gcactattgc aacagtcctt ttttggaaaa aaaaattgga ggacttatat accttaatat    115260
aaaagacttat aaaagtacag gaatcaagac atgtggtatt ggctggccc cttggctcat    115320
gcctgttacc ccaacatttt gggaggctga gtctggagga tggcttgagc ccagatgttc    115380
aagaccagcc ttagcaacag agtgagaccc tctctctaca aaaaataaac aattagatcg    115440
atgtgatgac ttgcacatgt agtttcagct actcggaatg ctgaggtgag aggattgctt    115500
gactcaggag gtctagccat gagtgagcat tgatcatgcc tctgcattcc agcctggatg    115560
atggaatgag acactgtctc aaaaaaaaaa aaaaaaaagg atatgtgtta ttggccaaaa    115620
aagtatgcaa acctaaaaag ggatggccca ccaccagacc cacatacata tatggtaaat    115680
ggatttccg tatagatggc aaagcaattc aatggagaca aaaatgtttt acaaaatcat    115740
tctgaaccat ttggatatcc atgatacaaa acaaaagcag aacttgactt ttgcttttca    115800
tctcaaatta ttttgatatc tcttccacct aagtgtcaga gctaaaactg aacctgaaat    115860
atgaaagttc catgaaaaaa tataaaatct tcaaccctt ggagaaggca aactttttg     115920
aggcaggagt ctgtaaacac tcactataaa ataaaacaaa ttataatgtg ggctttcatg    115980
aaaactcatg cttaccaaaa gtcattgtta agaaaataaa taggcaagta acacatgaga    116040
agaaaaatgc tctctgtcca tatatctgac aaatggcttg tgtccagaat ataggaacat    116100
ttctcccact cactaaacag aggacaaaca actaatgggc aacagattga ataggcatttt   116160
cttggggata gatagatgta cacatagcca ataagcacct gaaaaaatgt ccagtatctc    116220
agccatgaaa aataaagagt tataatcatc atgagatgtc accaaacacc caatggacat    116280
ggatattatt aagaagacac cacagtaact gatgtcactg atgtagagca aggatgtgaa    116340
actctctcat atgctggtga aagtgcaaaa tgatacaacc acttttgaaa tcagtctgat    116400
agtttctcca aaagttcaat aaatgcactt ttacccctaca aacctgcaat cctgtttgtg    116460
aatatttacc ccacagaaat ggaaacataa gtccacgaag acatcccaa gaatattcat     116520
agcagcttta ttttttataa cccccaaactg tagacaattt caatgtcaat caataagaaa    116580
atgaataaat aatttgtgaa ctagtcatac aatggcatac tgttcagcaa taaaagggag    116640
catgttttttg atactctcaa atagtatgga agatgctcaa aaatattaca ttaaagaaag    116700
atgccagata acaaaaatga acattatgta tgagtctatt gatgtaaggt tccagaaagg    116760
taaaactaat ttctggtgaa agaaaccaat atcatttgcc tctggccatg ggaagagagt    116820
agcagagatt gattgagcag taaaacgaag ttttttttctg gggtgatgta aatgtcctgt    116880
attgtgattg aagtgtgagt tacacaagtg tacatgttca tcagaagtca tcaaactaca    116940
tctaagatct gtgcatttga ctatacatga aaatatacct cagttgaaaa tagatcaata    117000
acctccctca tatactatac ttgctaacac agccagctgc ttggagaacc agcttgctgg    117060
aatggagaat ctgggcttga gactgggtca catgtataga gtctctacag agacaatgtt    117120
gcattcccac ggtacataat acatttcaag gttctcaga cagccacatg tcatgaatgt      117180
gaggattctg agaggttgga gcaacattcc tgggaggaac gaaggggagc acattctcca    117240
agatccccca ccacgggt cctcaccggc tgtgctttt tttttttttt tcttgacaga       117300
gtctcgctct gtcgccaggc aggagtgtaa tggcccaatc tcggctgatt gcagcctcca    117360
actccagggt tcaagagatt ctcctgcctc agcttcatga gtagctggga ctacagatgt    117420
gcgccactgc gcccagctaa ttttttgtatt tttagtagag acgggggttt gccatgttgg    117480
ccaagatggt ctcgctctgt tgacctcgtg atccaccgc cttggcttcc caaagtgctg      117540
ggattacagg cgtgagccaa agcacccagc ctgtgcctcc cacttactca attgtttttc     117600
tgaaccctcc atagctggtg gacctttca gatcccatag tctagccagc cctctcactt      117660
tatgccttgg gtcccactgt tccttcatct catcccccctt ctgtcagtcc cgcagtggct    117720
gtggccagta gaggatggac tgagagtagg agaggaggtt ctgcccagga acccatccta    117780
gagaaacagc atcctgcctg ggaccagtc ttccaggtca gcttttataa gtcttttaga      117840
ctcaaactca cttgacccac ctgaagtggt attgacaata atgctatttt catggttgtt     117900
aagaatgagc cttttagcta cacgactagt acagagagta agggagagctg                117960
gcctgggaat gatatcatct tggatgcat ttcctccttg gagaaatata tgttagttcc      118020
aactcacatg ttactataca gtcctgtaga aagagataca gagagttaga caggtataga    118080
cgcatttgta tatgcataac aatctataag acacacatca aaatccgtat accggttcct    118140
ctaggggtat gtgcttggca gaaggtagaa ggagggtatt ctggttcctt tctttttgcac   118200
atttatgtat gatctcagtt tttatatgga gcattgatag ggtttggcta tgtccccacc    118260
```

```
caaaatctca tcttgacttg taatctctat aatcctgata atccccatgt gtcaagggca  118320
ggaccaggtg gaggtaactg gatcatgggg gcagtttctc ccaggctgtt ctcatgacag  118380
tgagagagtc tcctgagatc tgatggtttt gtaagtgtct ggcatttccc ctacttgcac  118440
ttactctgtc ctgccgcctg tgaagaaggt gcctgtttct cccttgcctt ctgccatgac  118500
tgtaaatttc cagagggcctc cccagcaatg tggaactgtg agtcaattaa aactcttttc  118560
tttgtaactt acccagtctg tctcgggtat ttcctcatag caatgtgaga acgggctaat  118620
acaagcatat actactttg atattttaaa ataaaaatta tcatctatct ttgaaaggca  118680
tgcacaaatg ggaagttgag gaacatttgt gttgtggcaa ttgtatgata cctttaatgg  118740
gaatatttca aagacacttg ttaagacttt gttagaacaa aatgtagagg gtgctggatg  118800
tccctgaata ttcttccgcc tcctgtaact tgtattgctt tggaatttcc agtggcctga  118860
caatgaacta ctgcaggaat ccagatgccg atacaggccc ttggtgtttt accatggacc  118920
ccagcatcag gtgggagtac tgcaacctga cgcgatgctc agacacagaa gggactgtgg  118980
tcgctcctcc gactgtcatc caggttccaa gcctagggcc tccttctgaa caaggtaaga  119040
gtctgtgtc ttaccttgtc tagcacatac ctctctatgt gcttggacaa cgggatgaaa  119100
agacatgaaa aaccacactg atgcagaagc ctttagtgct acacgggagc tcgagtgttg  119160
gttgaggttc tgccatgacc aaggaagtct cagtgccgtc cctgggaaag ccagagctgt  119220
gattttggc acaacttgtg ggagtagtga ctttaggact ggcgcaaaac ctccaggatg  119280
ctcaacttaa ccactcacct tattctaaaa tgggttattt cagtgtccca gtcaaattcc  119340
tattctaaca tgctgtcaac tgtgtgatta tttccaagcc aataagcatt tccagtaatt  119400
tcttaaaata gtgttcattg cagtcttcag cgttgtggct cctgagggat gtggcccctg  119460
attctgtcgt cctagagaag cctgacatga ctgcattgat tctgtatcgt cctgggtcta  119520
tgtggctgcc tggctgtctg taatcatctg tttatttt attttttct acagactgta  119580
tgtttgggaa tgggaaagga taccgggca agaaggcaac cactgttact gggacgccat  119640
gccaggaatg ggctgcccag gagcccccata gacacagcac gttcattcca gggacaaata  119700
aatgggcagg tctggaaaaa aatgtaagcc actttgattt ggactctttt tcccttgct  119760
gacaaatctt ttcaaacaga agaggggcag aggaaaatac tggaaagact tcaggaggct  119820
aagcgtaatt agccttagca tggaaagtgc aagcagcaca ggccagcaaa gcccacgcg  119880
tgtggggtt ctcaggcctc ttctcttttg acatttcttt actgttccca ttgtttgggtg  119940
ctgtttctcg tttctagtgc ttgtcctcta agccaggggt ccccactcca gtactggtac  120000
tggtactggt actgaaactg gtaattatct gtggcctgtt aggaactggg ctgcacagca  120060
ggaggtgagc ttcggggag caaacaaagc ttcatctgta ttttctgctg cttcccatca  120120
ctctcatagc tgcctgagct ctgccagctg tcagatcaga ggcagcatta gattatcata  120180
gcacaaaccc tattgtgaac tgcacatgtg aggaatctag attgcatgct ccttatgaga  120240
atctaatgcc tgatgatctg tcatgcttcc atcaccccca gatgggacca cctacttgca  120300
ggaaaattag ctcagggctc ccactgattt taccttatgg tgagatgcac atttatttca  120360
ttatatatta caatgtaata ataattgaaa taaagtgcac gataaatgga aggtacttga  120420
gtcatccttt aaccatcgcc ccctcacccc aggtgcacag aaaaattgcc ttttatgaaa  120480
ctggtctctg gtgccaaaaa agttggggaa ccacactgct ctgggttcta gtagtcagag  120540
atgcctcta tgaggcttaa gtcagatttt tctagaaaag atttggatgg gccatcaggt  120600
caccatgaga cttcccttag cctcatgcat tctctgtgat ggtttacttt ggggcctatg  120660
aataggaag actgagatat aggaaaaacc aaagtgtctg tgttcccca ctctcacacc  120720
catgtaacat aacacttctc acaccagata tggggggatt tctcctcaca ccccaagcga  120780
gtctccagca gataccagct gggtgtccta caatgtaact cggtcctgac actctatctg  120840
gagacagtgt cagatcccac aagttaaggc tcagtcctac aagactgccc cactgcagat  120900
gccaatccca agttgcaggc tgtgaccgt acttctgccc agctggataa agatctgttt  120960
ttctatatga cccctccatgg gtttgattac tttgctagag tggctcacag aactcaggga  121020
aacacgttac ttttatttac ccatttatta taaaagatat taaaaaggat cctggtgaac  121080
agccaggtgg aagagatgca caggggcaagg cacgtgggaa ggggctcaga gcctctatgc  121140
cctctccagt gcaccagtcc ccagtaccct aagtgttcag caaccagaa gctctccaag  121200
tgcagtcttg ttgggttttt atggaggctt cattacagag gcacagttga ttacatcatt  121260
ggccatcggt gatcggctca ccttcggccc ctcttccctc cctggaggtt ggagggtggg  121320
gctgaacagt tccaaccctc aagtcacatg gttggttccc ttggcaacca gcccctgggg  121380
ctatccagga acccaccaag agttgcttca ttgcagctcc cttcacccag gaaactccaa  121440
gggatttagg agctctgtgt taagaactgg ggggcagaga cccaatatac atttcttatt  121500
ctatcacaat atcacaggaa gctaaggatg atactgcctt tgtgtgtctt ggctgttgat  121560
ggtgcataat gcatggaagt aagcatttct gaatcaacag caaacaggct ttatcaggta  121620
gaagacccct cagcgcccca gggacaaagc tcatcaatga tgtcccactg tcctctgagg  121680
ctctagctct aagacctcca gtgggtcaag ctcctggaga agtggcacat tctccaaaga  121740
cccttcaggg tcaccacacc ctggttaagg gtgtggcctc ataactcctt ttgactatga  121800
ctgatggctt acagcataga aagaaataac tttgtcaaaa aatataataa tgatagaaag  121860
gaagaaggaa cgctcccttt tgtcttctaa gaatagatgt gaaatgtgtg tgccttagaa  121920
tatcttctcc ctctcctgct ccacgtgagc tggagcttac atgcctgctt gttttcagta  121980
ctgccgtaac cctgatggtg acatcaatgg tcccctggtgc tacacaatga atccaagaaa  122040
acttttgac tactgtgata tccctctctg tggtaagttg ccttctgttt tggtaaggaa  122100
actgcttcct taatatggat ttggaaaaaaa aaagcaaaa aaacagaaa atggcttttg  122160
agctgagtgc ttctggggag gagatggctg ccctctccac cagagcctgc ttttcatcat  122220
ggccaccttg aacctgccct actattggcc ccatttgtta ggaaaacacc cgcccctccc  122280
accacacaca cataaataaa ataaatgtca aattcccaaa gggcaaactt agaggtgatc  122340
taatcagccc gggatagtcc caccgaaccc ttctttgtct agcgtgggat tgcatgaaaa  122400
caaatttaga gtcattatga tgaaaaactg tcctctcttg cagctgagaa gaaaaaaaa  122460
atacgagcag caggaaacag ctaagcatgt aatgcacatt gtaaacctca gatgccatc  122520
ctaggaaatc aatgaagggt agtgcagctc tttagcccca gatggccttt tcgtaagat  122580
tactactcat gagtcccatt agcgacattg cttagagact gcttgttagg ttccttcctc  122640
attgctctga gactcttatt ggggatgatga ggcttgggaggg gaattgcat  122700
tagatcttaa atgattgggg taacaaatcc atggggggaaa aaagccact tgtacttgtt  122760
ccctattttc ttcctgctga ccaatcaact tgtctgtccg agttacagaa caccacctg  122820
gacttttctt ttgtgtaatt tggttgcttg tggttgggtc tgccatgtga agggaccttg  122880
agctggggga agaaggttgg cctccaagtc cactgaagac cagcatcctg agattgcctg  122940
gggaggtggt acagggcagt gatgaagatc atgggagcca cactgcccat cgtcactttt  123000
```

```
gggccactcc tggggagagc aagagggaag aaggagaggt tagggtgata ggaaagattc  123060
tacttggcca atattattat aatgtggcat tgtggtctct ggatttagtg tgagttgata  123120
gctgactttt ttctcgagtg ggtgcttttg ttcatttttg tcggtgctat tgcagaagca  123180
tcttggtggt tcctctacct caaagtctct tgatggggtc agttccagtt ctccgcttct  123240
ggcccatct agtacacgcc actgcctctc actgcctggg ctctctatcc ttgacaggct  123300
gccttgaatt taagcccagt ctgacttacc tgcctcaaac acccacagta gtgcctggga  123360
ctcatgccac tttgactccc atggaaggga agtgcagtag cttcccaggt gcaattctgc  123420
tgtcctcacc cacattgagg atgtatgaga atcaggttct tagagattgg agaaagaagg  123480
aagaatggga acaagatttc ttccaatgga ctgtgaggtt ccccacctta ctttgatgta  123540
agacaagtga ggttaacccc aagcctggtg aggagggttc ccatcagaca cttggaaatc  123600
ctgaggactg tttcctgcag aaggatgtgg ttggtgggat attcaggttt gactcatgat  123660
tgagaaagtt agagcctctg gttggagaaa gagtttaata actatttcat ttccaccaac  123720
acattcagta cgaataataa ataagtaaaa ataaatagaa acattcagtt ttattttgaa  123780
tagtaggagt agggtataat ttctgtagtt actctttag tacaatgatg catgtttact  123840
gtatgtaagg catactagca gaaattgagc tcagcactag aaaagatgat tgcattccat  123900
gccatgcttc tttttttacaa aagacttcta tagatagatt ctcaaaacaa cccacagcaa  123960
atgaaaagtt atttggaaaa ctcaggttcc agattcactg gagtgtagaa tctctggttg  124020
gttggggagg aatttcctct tgcagttgtt attaataatt atatgaataa ttattaacta  124080
tattaatatt tatagttttg aagaccttga agggctggag acaacagaga agcatttttg  124140
aacaccctct gtagccctg cactgttgta ggcattgatg ggtggtacca aagatgggac  124200
actttcccta cctccagaga ccttgtgggc ttgctgcaga gagaaggcag ggaggaggaa  124260
aagaagaata gaggcacatg tgtgtaaatt acccccacag cagtcagtta gtcatgggga  124320
gctcccagda agaactgtcc tgaagctggc tgagagaagc caacatttca acataggaca  124380
gttatccttg ctacataaaa tcacatacac acatgcacat atgtccacac acagagactc  124440
acatgcaaaa gaatcctttg tgcctttcag taaactttac atggtttaga aagaacttat  124500
atttccttga aaggagagtg tcctttgttg tttactacca ctttttaaac ttagaaagaa  124560
aaatctaaag agtgtttatg attttaccat ttaatttcac ctttgagatg tgaaaaacta  124620
gtgcttggaa ttcgtcctga attaaacgac acaattgcta acttggactc aaatgcgact  124680
tcttttccca ccttgtgcca cagcatcctc ttcatttgat tgtgggaagc ctcaagtgga  124740
gccgaagaaa tgtcctggaa gcattgtagg ggggtgtgtg gcccacccac attcctgccc  124800
ctggcaagtc agtctcagaa caaggtaaga acaggcccag aaaccatcta tactgtcctt  124860
ccatgtaagc cccacaaaac cctcctacat ttacacagaa cccacacagc tgatgcatca  124920
atacctgcct ctctgtttc tgaaggagga aaaaatatag aaaaattaaa aaagttata  124980
ttattatagg ttctctactt ggaaaatagc caaaatacaa atcttttttct tgatctgggc  125040
agttccatca aaatctgtag gcacagtgat ttgcaccaag ttccaatact tttggaaaat  125100
attgaagatg ctctgagggt ttctatggat atccattgtc tcactgtcag atgaaaagaa  125160
agggaagttt ttagaaatgt gacactttgc agtgagggag gacaagagca aacttaccta  125220
cagtctatca caggcacaga ttttttttta cacttttgtg aatcattgaa ttcaatgccg  125280
aggctattca tctattcaca aacacatgaa caaattatgg gttgtgatcc ccataaatga  125340
agagtaatca gtccgaaccc acagaacctg gacattttgg gtatcgtttc agtggaacat  125400
gcaattcgta agttcagttt gcttgggtgt ctcttaggaa gaacacatag gacacagacc  125460
catctgcctg catgtttttgc ttcctcatct ccttctaca ccagggcacc tgtgctcaat  125520
tgctgttctc ctctaaagag acttccttct gtaagttttgt gaaatgccat cgacaaacct  125580
gatcgcatcg catttcactc tgctgttgag ttgattttttc tttacttat cgtttgtaac  125640
ttcttgctct acagagcttt caccttccac atatttcaga ttcattcttt cctaaactgt  125700
gtggtggtct atgtcctcac tgactatcaa catactgcca tcatgcactt cctatctcta  125760
ttcctcttcg ttgcaatctg gctccaagtg gctcacacca ttattctgat ctatcaactg  125820
cctacacagt cctagaaagt aagtgagtca agaaacatcc cccaaaagta aacttttcag  125880
gtaagatcag aagaccctca tgagtcactg ctgctcagga tcgtatctgg ctccttgaag  125940
agtgaccttg catagatctt gtcataaaaa atgaaagaga ccttgggaag gtcttgggct  126000
ggtcacttttt gtcagagtcc agggctgtgg ggtgaaagcc acagctatag agcttcattc  126060
tggagtcact tagctttgct ctcctgggga caggctgtgc ctattcttgc ctcaggcatc  126120
aaaaaaagtg gcacagatgg gcccttctga aaaatctcac tactggagca cagctcgaag  126180
tttctactat cctgacgttg ggcggtagtc ctttgctttg ggaatatgaa catgatcaaa  126240
actgagtgaa cttgtcttcc tggctttctg tacaatgaag tagaacaaac catccaattt  126300
gaccaaagcc ttggcatgtt ttcttttctag gtttggaaag cacttctgtg gaggcacctt  126360
aatatcccca gagtgggtgc tgactgctgc tcactgcttg aagaagtacg tttaagggaa  126420
aactgacatg gggtcttatc ttcaagactt ttttcctccc tctcttcctc catcccttct  126480
ttcttcccac ctcccctttc cttcctcccc acctctcttc cttttctgga aggaacacta  126540
ggaaccaggg aatgcatgca gaatcctgag gcagaatttc cagggcaatt ggatgagaga  126600
ggagggaagt gtttctagag ggaatctgca gagggaagac ccagtgcaag tgatttttttg  126660
gacctgtata aaccgcagga cagagctgtt cactaccaga ggcatcaatc tgtattgcat  126720
tgctctagag caatatctga ggctgaataa tttataaaga aaagagttta attggcacat  126780
gtttctgcag gctttacagg aagcaggatg ctgtcatctc ctctgcttct ggtgggcct  126840
aaggaagatt acaatcatgg tggagggcaa agtgggagca ggcatgtcac atggccagag  126900
caggagcaag agacagagag agtgggtgtg ggggtgctgc acaataccaa atgaccagac  126960
tttgcaagaa ctaagagtga gagctcactg atcaccatga agatgtggcc caagccattc  127020
aagagggatg cacctctatg atccaaaccc ctttcacagg ccatagctcc atcactgggg  127080
actacagttg aacacgagat ttaggtgggg acaaatataa aaactatatc acagtctctg  127140
atgaaacaga ttgagaacag accttaactg tcagtttcca gcaaattgtg aattttgttt  127200
cttgccactc ataagtcact gattctgggt ggccgagggt gtcagaggga cagcgccaag  127260
tcatgccac agaggatacc tgaagggggct ggaccatatt tttctcttga catcctcatc  127320
ttttctaggt cctcaaggcc ttcatcctac aaggtcatcc tgggtgcaca ccaagaagtg  127380
aacctcgaat tcatgttca ggaaatagaa gtgtctggc tgttcttgga gccacacaa  127440
gcagatattg ccttgctaaa gctaagcagg tactcgctca cctgtggtct tcaccccacg  127500
ctggtgaaga tatttgcttt atgtctgggt tttatgggcc atggccactg catggccagtg  127560
gggaggaact gtctatcaca tgaaaggctc aagggctttg gggacagcat caatcttcaa  127620
ccccagccct gccacatgtt agttgtgctc tttaaaagg cagaaggatt cgtttcctca  127680
cgtggaaaaa gagatacct gttacccgta aaacttactt aatgttcacc agttcatcca  127740
```

```
cattcatgat caggggaaagg ttgttattcc aggctaacta ttctcctttc ataataatat   127800
gctggagaga atcaaatgag attgcatttc aaagcgcttg aaaaaccacc atatcgagcc   127860
atgcttagtg tgggcgcctc taatcactgc tattcaggag gctgacgagg aagaattgct   127920
tgagcccagg acttcaaggc tgtaggcagc tatgattgtg ccactgcact ccaggctggg   127980
tgacagatca agaccctgtc tcaacaaaag aaaagaaaac aaaacaaatg aacagaaata   128040
ttccacaatg tcaaaaaaaa aaaaaaccca cacaacatac aatttacaaa tgcaaataat   128100
aatattattg ttgtcttctt tgattttctc tttcctggtg aaatttttgtt ttattaagcc   128160
tgacaaagtg ataccttttgc ttacatcact taaagttagt ctatttggac ctaggtgaca   128220
gtacaatcag ctaagaaaca gtatttgtag gagaggcagg tttgggacag gtgacaaggc   128280
atgtgggtg ctcgctgtgc tggtggctct ggaaggcagg gtgtcaatgc agacagggat   128340
gagcatggcc tggttgggaa ggcatggggc aggcaggagc ctgagctgct ctcctgggcc   128400
tggtcacaag cccatggcag cttctctggg tctgtgaact gaggggtgat gtcctggaat   128460
cctctgacac tctaggaagg agagaaggc ctttctggct cagcctttat aaacagtagc   128520
tgatctccct cttgctcccc agggtcctcc ccaccatcc agcaaatgtg caaatacaag   128580
atctctgctc ctcatggtcc tcagagagct ggggtgttct gatggcttga acaagtcact   128640
taggaaaatgt ggggttttgg aggcattctc tgataggctg atacgttttg agtttagagt   128700
tcccaccgca catccccaca ccctagagt ctagggcatt tagtgctcca tgagggaacc   128760
tgtagagtga ggacatctgc atcacaggct gggccttcta gtgtccagaa gcagaaagtg   128820
tgtctgcttc aaagttggtg ctaatgatga ttttttggtca gaatacggca tttctcattt   128880
ccattccttt atcccttga acttactaaa gtagaatcag gtctaaaaac cagagttcta   128940
atctttaaga gtccctggga ttctaaggta tatgaatgtc cttggaaaac aataccattt   129000
agttcatgca aggtgcttat ttcccatcct ctttcatttg atgtctagca ttttactgca   129060
ttcttaccac cacggtttag taacattcac gaggaggaag tggaggatcc agatggagca   129120
acttgctctg ggcacacaag gcatttgcaa ttttataccc tcttgatgat gtctcagcca   129180
gacattctgc ccagtcatca atgccctctt caattaatat gaaaggacac acttggcatg   129240
agattccaat cgtgcacaga atatacatga gaagtgtgcc tttgtcatcc ctactttcaa   129300
aggctaaggc caccctcagt ttcttgcatg caactgatgc ctttcaaatg aaaccttaca   129360
tctgtgtagt ccataggcaa ccacaggcaa atgtgagggt gaaacgctgt gttctacatt   129420
gttctgtgtc agtgaagcaa ggcagtgcca gctcagaggg ctctgggggct tcaaggcagg   129480
gatgcctggt tgtaggtact gccacttcca gctgggcagt gaaacataac tgctaatact   129540
ttccttacag gcctgccgtc atcactgaca aagtaatgcc agcttgtctg ccatccccag   129600
actacatggt caccgccagg actgaatgtt acatcactgg ctggggagaa acccaaggtg   129660
agatcaattc cattgcccac gtaacaaatt gttttgacc ttcagtgcat gttacaaaat   129720
gagcattttg gagatagttg tacaaattcc tacccatgaa tgtggtctac ccactctgca   129780
ctttgcctgg acacctgtct atgtctccat aatcagtctt caagggactt gggcaagggg   129840
agcggtgcca tttccttgag tctctctctt tttttgtttc agaatctttt aatttttttt   129900
gtaatgattg tatgtttccc ttacaacaaa acaaacacc agtagaggtc tttgagtctc   129960
ttaatcataa tttcagcatt catattgctt ccccaggtaa gtgggggtttt gacccagccc   130020
tcaagttaag ggtgttagat tattttttcat gtgaaattag acagactgcg tttctaaaca   130080
tggtgcaaaa cagtaacgac aaaagttgta attaaactat tcttcttccc aaatacccac   130140
atgtctaatg tgtgtgtgag ggtgttaggc aggggacctg aagctggggg agaggcagac   130200
agttcccatg gccccaagtc taggatggca tttggtattg gttgatgggt gagagcaaga   130260
gagggaatat ttttgtgcat gatgtggtat cagcacctgt actacattt atggattcct   130320
tcttctctttt gcggtatgcc ctgacaataa ttatatccgt cagccttacc cccttggcag   130380
taggaaaaact gaaactgtct taaagtctca gctctacttt ctcagaggtg caggcaaggg   130440
cactgggagt ctggggccct ggaaaactgt tctgactctg ccacttgcca gatagacctg   130500
aactagacac cttacctctt tgtaccactt ggctctaatc ccttatctgt aaaaccagca   130560
ttttcaaatg gtgctttgca catcagcctt ttgcataagc tttgatttga taaaatgttt   130620
tttgtgtttt taaaagatt aaaaaccaca ggtttagata atttcaaagt aggcttccct   130680
ttttctgtca ttttccttatt attttttaaaa cctcacctcc ttgactcctt gttccctttt   130740
tctgcactgc tgagtctggg agcactgagg ccaggtaaaa ggaaacttgg caaatgaggg   130800
gcacctatgg gtgtgggagg ctgctcctgg tgtttgcata tttttaaaatt taaatgctac   130860
aaaccactgt gagttaggta ttattgttcc tatttttacca ttgaggaagc tggggctcag   130920
agaaggtgga ggtggtaca gacaaacctg aattggaacc ctggctcctg cctatgggct   130980
gtcaggactt agaaaagtcg tgagctctcg ctgattgttt cctcagctga tgtgggctgc   131040
agggctgtta tgggggaaat aataagaaag tgcatcaagt gctgagcaca tcctaagcac   131100
tccatcatgg cagctcctac tactaataaa gaatagaatt atatctaaca tgattctttc   131160
ttgcaagtga cagaaaatcc aactcaaatt ggattaagca aaacaaggga aattcttagt   131220
gagctgcaaa gttttcaggc tcacatgatg gccccaaatc ccaggtcctc ccaatcatgg   131280
agtaggcact atttggggc acaaggtga cattcccatg gctgcagatg ctgtggtctg   131340
gtggctgtac cgggaaagaa taagaaaggc cactctccca attatgtgaa caatagtctg   131400
cccactctga gaagtcaaac ttgggtcaca gtcctgcccc tgaacccatc actgactggc   131460
tctgacctgc accaattgtt ccatgttgga ggtgaaggca agacccccact aatacccata   131520
aggggcaaaa gttagataga tccttcaaga ggattatggg aggtagggca aaaagctgct   131580
gggcagccag aaagcaaaca gagcctctat gatacctcaa ctgatgaaag catgaagcta   131640
aaatcataag gatctgggtg tgagttcgg ctctcccatc ttccatgtga cattgggcag   131700
ttatttaatc tcttttagcc tccgctttct catcttacat atgagataat tgtgaggatt   131760
aagattacac ataatcatca tcatcaccgt ccaccactac caccatcac cccatcaaca   131820
tcatcgccac cactatcatc attcttactg gcactaccat caccatcacc accattccac   131880
caccatcacc aatatcatca ctgtcaacat cattaccacc atcaccatca ccaccaccat   131940
catcattact accactacca ctaccaccac catcaccatc accaccattc caccaccatc   132000
accaatatca tcactctcaa catcatcacc atcaccatca ccaccaccat catcatcatt   132060
actaccacta ccactactac caccatcacc atcaccactg tcccactact atcagcatga   132120
catcaccatc accaccacca caccaccacc accatcattac caccgtcact accaccaccac   132180
aattctactg ccatcaccat taacattacc accaccatca tcactatcac catcaccacc   132240
atcatcacca ctgccattat cactgccacc atcatcacta tcctctatat ttcctcatct   132300
gtattatcat tactaccacc atcactatca ccaccatcgt caccatcata atcaccatca   132360
acaccatctc caataccacc atcactgtaa ccatcatcac caccaccatg atcactatca   132420
ccatcatcac aatgatcact gtaaccatca ttactaccca ccaccatcac cactactcca   132480
```

```
ccaccatcac cattatcatt accatcacca ttatcaccac catcatcatc accagcacca    132540
ccatcatcac cagcaccacc atcaccatca ccatcattaa caccatcact atcaccattg    132600
gtttaatcat caccaccatc atcataaata aacatcacat aaccagggtg tagctgggtg    132660
ttgaccccga agcccactca ctgtttcctc tctcccaccc ccatccacac atttctaacc    132720
accatcctgc actgggctcc cagtctcctc tggtctcacc cacatgtcca ctgagaaaag    132780
gattttcaga acaccaacta gaccaggagg agccacatac ataactcagg cctgcttatc    132840
aactttctac atgttaataa tgacatcaga tcaatgggtg ttctcagctt ctcagaagga    132900
ggtcaaaatt ctccccctct ccccttcatg tgtccagacc ttcccggatt tggatgtacc    132960
aagtgcagag tggtgttgag gccaagggc tcatccatct aagtctcatc tgcaatcact     133020
gggctgatcc cgtggccctg tctccagggc gccatcagag agggcttcaa tcctcaggtt    133080
acctgtggcc caccctgccc tcagaggtgc catctctaca ttggccacga gatggcagca    133140
catactcata gactgcatta atttcccagc aactcctggt gggttttccc tcttatcagg    133200
atgtttgcct tgctcagaga gcaaatctga gagcagtgac acctaactta actttcagca    133260
aaatattttg agaagggtgc cccttacac atctgtgcag tccaggtgat gcatccatg      133320
cccaatgctc ggtagtcagg aggagcttcc tccatgcagc tctgcggaag agactcttcc    133380
acgctgctca tgtaaactcc agattcggtg tcagttttct gacaccgaag acaatgatct    133440
aagtgcagtc aagggctttg gggaaagcag gagagagtgc ctcagttcta gcctgtgcca    133500
tgcttgcaaa gttttgcaaa attctaatga gagctgggct tgcaacattg gaaacttgga    133560
ttatttgtga gagcactgag aaatccctgg gcatgtccat ctggaaaaac agcatttcct    133620
ctggcacttt agcagaggtt ctgtttcaat ttggcgaagg aaattaagca gttttttcaca   133680
aaagaagaac tacaacgagg agaattgtcc ctagtatttc ttctccctaa ttgtcaagga    133740
agtgtaaatt agaaaatgaa tcaggacaat ttccacctac tatgttagct aatattttaa    133800
aaattgaata tcacaagggt gaggcaaagt aattgttttc cagtgacatt ttccactgtc    133860
acacccttt agagaataat ttggcaatgt tactgtgaga tagaaatatg tctatataat     133920
tatgggaact gagacttcag aaagtaataa ggaataagaa tgaaatttat gaacaaacat    133980
gtggaaggtt ggaagcaaga gtggggccaa cacgcatggg gaggaagcat ttgggcaggt    134040
actccgcaga cccagactca agctgagcta tacaacctcc ttacgcctca gtttcctcaa    134100
ctgaagaaca ggaatgacaa gtgcctgttt cataggaccg ttgtgaggat taagtgagat    134160
ataccacatt atgagcttgt gcctggaaag gttgattctt agtaaatgat gactattctt    134220
ttttattgca ataaaattta tacaacatag agttactatt ttaaccattt ttgcaggtac    134280
cactgagtgg cattcagtac attcacaatg gtgtgcaacc gtcaccatat ttccaggaca    134340
ttttttctcat ccccaaagga aacctcatgc ccattaagca gtcactcctc attaaaatat   134400
tagttatgaa gactgtagca ttttttaaa aactcatgat ataacattga ttgaaaaaat     134460
cagtatagga aattgtgcat tatgatgtaa tagtaaaaga agcatataaa aatctgaaaa    134520
aagtatataa aaagaatagc aattgtattt ctcagactct ctttacattg taaaaatcat    134580
tttgatagct tcaaaagaaa agcaaaaagt acacaaacaa caaccaaccc caaagcagca    134640
tgacaaagcc cagattgttg aatccaggtc ttgggaacat aaaaatcttat atgacatttg   134700
cactttaatg ggtcagagag tccagtggca ttgggagctg ccttgtgttc tgcagcctca    134760
cggacagaca ggaggtccag ctccactgct ctgttcttct ggaatttcct cgtgaacaag    134820
cttttggcctc agtaaccatt tcttttcatct ttttaaacac aggtaccttt gggactggcc   134880
ttctcaagga agcccagctc cttgttattg agaatgaagt gtgcaatcac tataagtata    134940
tttgtgctga gcatttggcc agaggcactg acagttgcca ggtaagaaaa gatcaataga    135000
tcaaagtctt gtgctctccc gtctcagtct cagtcccta gacgtcagtc ccaaagtggc     135060
aaattcagga aggttttgtc agtggaagac cccagtctaa gtgttgctca gaaactcccc    135120
agatctgtcc ctgaatgcat attcagatca tctaaggaga cgtcttgggg cttgagttcc    135180
agatccatag caagggagcc gtaagtgcca taactacctc aggccactca ccttcctggt    135240
gtgtgctggt caccagtgac tgaagtggtg gcttttccag tagagaggaa ggtagagggt    135300
acaggaccga gacaaattac acacacttaa caatgatgtc caggctagcc cagtctaaag    135360
gaaacaccaa gttaggaagc aatgcatgca ggattcacaa gggattattt ttttttcccag   135420
gaaaaaacta agtgatgtgg ttttgttgaa tagactttgc taagtactta agcactgcag    135480
atgcttgagt aatatgctca taagttcctt tctgatttga attactggga aaatgtacat    135540
atggataaga gaaggatggc atcccatatt aaaaaggttgg cagcttaaag ctcacatgaa   135600
ttttcccccta cctctgttta gggtgacagt ggagggcctc tggtttgctt cgagaaggac    135660
aaatacattt tacaaggagt cacttcttgg ggtcttggct gtgcacgccc caataagcct    135720
ggtgtctatg ctcgtgtttc aaggtttgtt acttggattg agggaatgat gagaaaataat   135780
taattggacg ggagacagag tgaagcatca acctacttag aagctgaaac gtgggtaagg    135840
atttagcatg ctggaaataa tagacagcaa tcaaacgaag acactgttcc cagctaccag    135900
ctatgccaaa ccttggcatt tttggtattt ttgtgtataa gcttttaagg tctgactgac    135960
aaattctgta ttaaggtgtc atagctatga catttgttaa aaataaactc tgcacttatt    136020
ttgatttgaa ttaattttgg ttttggtctt caaaattttc atgctctttt catcccatct    136080
atttttattt ttattttta gactttacgt cctggggtac atgtgcagaa tgtgcaggtt     136140
tgttacatag atgtacacgt gccatggtag tttgctgcac ccatcaacct gtcatctaat    136200
tcggtatttc ttttagttct atccctcccc tagccctcca cccctgaca ggcccaggtg     136260
tgtgatgttg ccctccctgt gtccatgtgt tctcattgtt caactcacac ttatgagtga    136320
gaacatgccg tgtttgtttt tctgttcttg tgttagtttg ctgagaatga tagtttccag    136380
cttcatccat gtccctgcaa aggacatgaa ctcatccttt tttatggctg catagaattc    136440
catggtgtat atgtgccaca ttttatccaa tctaacattg atgggcaatt gggttggttc    136500
caactctttg ctattgtgaa tagtgccaca ataaacatac gtgtgcatgt gttttcatag    136560
cagaatgatt tataatcctc tgggtatata cccagtaatg ggattgcagg gtcaaatgat    136620
gtttctggtg ctagatcttt gaggaatcac cacactgtct tccacaatgg ttgaactaat    136680
ttatgctccc accaacaata tcaaggcatt cctattctc cacatcctct ccagcatctg     136740
ttgtttcctg acttttaat gatcgccatt ctaactggca tgagatggta tctcattgtg     136800
gttttgattt gcatttctct aatgatcagt gatgatgagc ttttctcata tgtttgttgg    136860
ctgcataaat gccttttttg gagaagcatc ttcatatc ttttttgatgg                 136920
tgttgttttt ttctggtaaa tttgtttaag ttctttgtag attctggata ttagcctttt    136980
gtcagatgga tagatggcaa aaattttatc ctattatgta ggttgcctgt tcactccgat    137040
gatagtttct tttgctgtgc agaagctctt tggtttaatt agatctcatt tgtctatttt    137100
ggcttttgtt accattgctt ttagtgtttt agtcatgaag tcttctccca tgctatgtcc    137160
tgaatggtat tgcctaagtt ttcttccagg gttttttatgg ttttaggttt tgcatttaag   137220
```

```
tctttaatcc atcttgagtt aatttttgta taagtaatgc ccttcttgt ctcttttgat    137280
ctttgttggc ttaaagtata ttttatcaga gactagaatt gcaatccctg cttttttttt    137340
tcttttgct ttccttttgc ttggtaaata ttcttccatc cctttatttt gagcctatgt    137400
atgtctgcac atgagatagg tttcctgaat acagcacacc aatgggtctt gactcttat    137460
tcaatttgcc agtctgtgtc tttaattgg gggcatttaa tccatttaca tttaaggtta    137520
atattgttat gtgtgaattt gatcctgtca ttatgatgct agcgggttat tttgcccatt    137580
agttgatgca gtttcttcat agtgtggatg gcctttacaa tttggtagtt tttgcagtgg    137640
ctggtaccaa ttgttccttt ccatgtttag tgcttcgttc aggagctctt gtgaggcagg    137700
ccttgtggtg acaaaatctt tcagcatttg ctttgtctgta aaggatttta tttctccttt    137760
gcttatgaag cttagtttcg ctgggtatga aattctgggt tgaaaattat tttcttttag    137820
aatgttgaat attggccccc actctcttcg ggcttgttgg gtttctgcag agagatccac    137880
tgttagtctg attggcttcc cttccgggt aacccaacct ttctctctgg ctgccctag    137940
aaattttcc ttcatttcaa ccttggtgaa tctgacgatt atgtcttgag gtggctcttc    138000
t                                                                   138001

SEQ ID NO: 4         moltype = DNA  length = 13938
FEATURE              Location/Qualifiers
source               1..13938
                     mol_type = genomic DNA
                     organism = Homo sapiens
SEQUENCE: 4
ctgggattgg gacacacttt ctggacactg ctggccagtc ccaaaatgga acataaggaa    60
gtggttcttc tacttctttt atttctgaaa tcagcagcac ctgagcaaag ccatgtggtc    120
caggattgct accatggtga tggacagagt tatcgaggca cgtactccac cactgtcaca    180
ggaaggacct gccaagcttg gtcatctatg acaccacatc aacataatag gaccacagaa    240
aactacccaa atgctggctt gatcatgaac tactgcagga atccagatgc tgtggcagct    300
ccttattgtt atacgaggga tcccggtgtc aggtgggagt actgcaacct gacgcaatgc    360
tcagacgcag aagggactgc cgtcgcgcct ccgactgtta ccccggttcc aagcctagag    420
gctccttccg aacaagcacc gactgagcaa aggcctgggg tgcaggagtg ctaccatggt    480
aatggacaga gttatcgagg cacatactcc accactgtca caggaagaac ctgccaagct    540
tggtcatcta tgacaccaca ctcgcatagt cggaccccag aatactaccc aaatgctggc    600
ttgatcatga actactgcag gaatccagat gctgtggcag ctccttattg ttatacgagg    660
gatcccggtg tcaggtggga gtactgcaac ctgacgcaat gctcagacgc agaagggact    720
gccgtcgcgc ctccgactgt taccccggtt ccaagcctag aggctccttc cgaacaagca    780
ccgactgagc aaaggcctgg ggtgcaggag tgctaccatg gtaatggaca gagttatcga    840
ggcacatact ccaccactgt cacaggaaga acctgccaag cttggtcatc tatgacacca    900
cactcgcata gtcggacccc agaatactac ccaaatgctg gcttgatcat gaactactgc    960
aggaatccag atgctgtggc agctccttat tgttatacga gggatcccgg tgtcaggtgg    1020
gagtactgca acctgacgca atgctcagac gcagaaggga ctgccgtcgc gcctccgact    1080
gttaccccgg ttccaagcct agaggctcct tccgaacaag caccgactga gcaaaggcct    1140
ggggtgcagg agtgctacca tggtaatgga cagagttatc gaggcacata ctccaccact    1200
gtcacaggaa gaacctgcca agcttggtca tctatgacac cacactcgca tagtcggacc    1260
ccagaatact acccaaatgc tggcttgatc atgaactact gcaggaatcc agatgctgtg    1320
gcagctcctt attgttatac gagggatccc ggtgtcaggt gggagtactg caacctgacg    1380
caatgctcag acgcagaagg gactgccgtc gcgcctccga ctgttacccc ggttccaagc    1440
ctagaggctc cttccgaaca agcaccgact gagcaaaggc ctggggtgca ggagtgctac    1500
catggtaatg gacagagtta tcgaggcaca tactccacca ctgtcacagg aagaacctgc    1560
caagcttggt catctatgac accacactcg catagtcgga ccccagaata ctacccaaat    1620
gctggcttga tcatgaacta ctgcaggaat ccagatgctg tggcagctcc ttattgttat    1680
acgagggatc ccggtgtcag gtgggagtac tgcaacctga cgcaatgctc agacgcagaa    1740
gggactgccg tcgcgcctcc gactgttacc ccggttccaa gcctagaggc tccttccgaa    1800
caagcaccga ctgagcaaag gcctggggtg caggagtgct accatggtaa tggacagagt    1860
tatcgaggca catactccac cactgtcaca ggaagaacct gccaagcttg gtcatctatg    1920
acaccacact cgcatagtcg gaccccagaa tactacccaa atgctggctt gatcatgaac    1980
tactgcagga atccagatgc tgtggcagct ccttattgtt atacgaggga tcccggtgtc    2040
aggtgggagt actgcaacct gacgcaatgc tcagacgcag aagggactgc cgtcgcgcct    2100
ccgactgtta ccccggttcc aagcctagag gctccttccg aacaagcacc gactgagcaa    2160
aggcctgggg tgcaggagtg ctaccatggt aatggacaga gttatcgagg cacatactcc    2220
accactgtca caggaagaac ctgccaagct tggtcatcta tgacaccaca ctcgcatagt    2280
cggaccccag aatactaccc aaatgctggc ttgatcatga actactgcag gaatccagat    2340
gctgtggcag ctccttattg ttatacgagg gatcccggtg tcaggtggga gtactgcaac    2400
ctgacgcaat gctcagacgc agaagggact gccgtcgcgc ctccgactgt taccccggtt    2460
ccaagcctag aggctccttc cgaacaagca ccgactgagc aaaggcctgg ggtgcaggag    2520
tgctaccatg gtaatggaca gagttatcga ggcacatact ccaccactgt cacaggaaga    2580
acctgccaag cttggtcatc tatgacacca cactcgcata gtcggacccc agaatactac    2640
ccaaatgctg gcttgatcat gaactactgc aggaatccag atgctgtggc agctccttat    2700
tgttatacga gggatcccgg tgtcaggtgg gagtactgca acctgacgca atgctcagac    2760
gcagaaggga ctgccgtcgc gcctccgact gttaccccgg ttccaagcct agaggctcct    2820
tccgaacaag caccgactga gcaaaggcct ggggtgcagg agtgctacca tggtaatgga    2880
cagagttatc gaggcacata ctccaccact gtcacaggaa gaacctgcca agcttggtca    2940
tctatgacac cacactcgca tagtcggacc ccagaatact acccaaatgc tggcttgatc    3000
atgaactact gcaggaatcc agatgctgtg gcagctcctt attgttatac gagggatccc    3060
ggtgtcaggt gggagtactg caacctgacg caatgctcag acgcagaagg gactgccgtc    3120
gcgcctccga ctgttacccc ggttccaagc ctagaggctc cttccgaaca agcaccgact    3180
gagcaaaggc ctggggtgca ggagtgctac catggtaatg gacagagtta tcgaggcaca    3240
tactccacca ctgtcacagg aagaacctgc caagcttggt catctatgac accacactcg    3300
catagtcgga ccccagaata ctacccaaat gctggcttga tcatgaacta ctgcaggaat    3360
ccagatgctg tggcagctcc ttattgttat acgagggatc ccggtgtcag gtgggagtac    3420
tgcaacctga cgcaatgctc agacgcagaa gggactgccg tcgcgcctcc gactgttacc    3480
```

```
ccggttccaa gcctagaggc tccttccgaa caagcaccga ctgagcaaag gcctggggtg   3540
caggagtgct accatggtaa tggacagagt tatcgaggca catactccac cactgtcaca   3600
ggaagaacct gccaagcttg gtcatctatg acaccacact cgcatagtcg gaccccagaa   3660
tactacccaa atgctggctt gatcatgaac tactgcagga atccagatgc tgtggcagct   3720
ccttattgtt atacgaggga tcccggtgtc aggtgggagt actgcaacct gacgcaatgc   3780
tcagacgcag aagggactgc cgtcgcgcct ccgactgtta ccccggttcc aagcctagag   3840
gctccttccg aacaagcacc gactgagcaa aggcctgggg tgcaggagtg ctaccatggt   3900
aatggacaga gttatcgagg cacatactcc accactgtca caggaagaac ctgccaagct   3960
tggtcatcta tgacaccaca ctcgcatagt cggaccccag aatactaccc aaatgctggc   4020
ttgatcatga actactgcag gaatccagat gctgtggcag ctccttattg ttatacgagg   4080
gatcccggtg tcaggtggga gtactgcaac ctgacgcaat gctcagacgc agaagggact   4140
gccgtcgcgc ctccgactgt taccccggtt ccaagcctag aggctccttc cgaacaagca   4200
ccgactgagc aaaggcctgg ggtgcaggag tgctaccatg gtaatggaca gagttatcga   4260
ggcacatact ccaccactgt cacaggaaga acctgccaag cttggtcatc tatgacacca   4320
cactcgcata gtcggacccc agaatactac ccaaatgctg gcttgatcat gaactactgc   4380
aggaatccag atgctgtggc agctccttat tgttatacga gggatcccgg tgtcaggtgg   4440
gagtactgca acctgacgca atgctcagac gcagaaggga ctgccgtcgc gcctccgact   4500
gttaccccgg ttccaagcct agaggctcct tccgaacaag caccgactga gcaaaggcct   4560
ggggtgcagg agtgctacca tggtaatgga cagagttatc gaggcacata ctccaccact   4620
gtcacaggaa gaacctgcca agcttggtca tctatgacac cacactcgca tagtcggacc   4680
ccagaatact acccaaatgc tggcttgatc atgaactact gcaggaatcc agatgctgtg   4740
gcagctcctt attgttatac gagggatccc ggtgtcaggt gggagtactg caacctgacg   4800
caatgctcag acgcagaagg gactgccgtc gcgcctccga ctgttacccc ggttccaagc   4860
ctagaggctc cttccgaaca agcaccgact gagcaaaggc tggggtgca ggagtgctac   4920
catggtaatg gacagagtta tcgaggcaca tactccacca ctgtcacagg aagaacctgc   4980
caagcttggt catctatgac accacactcg catagtcgga ccccagaata ctacccaaat   5040
gctggcttga tcatgaacta ctgcaggaat ccagatgctg tggcagctcc ttattgttat   5100
acgagggatc ccggtgtcag gtgggagtac tgcaacctga cgcaatgctc agacgcagaa   5160
gggactgccg tcgcgcctcc gactgttacc ccggttccaa gcctagaggc tccttccgaa   5220
caagcaccga ctgagcaaag gcctggggtg caggagtgct accatggtaa tggacagagt   5280
tatcgaggca catactccac cactgtcaca ggaagaacct gccaagcttg gtcatctatg   5340
acaccacact cgcatagtcg gaccccagaa tactacccaa atgctggctt gatcatgaac   5400
tactgcagga atccagatgc tgtggcagct ccttattgtt atacgaggga tcccggtgtc   5460
aggtgggagt actgcaacct gacgcaatgc tcagacgcag aagggactgc cgtcgcgcct   5520
ccgactgtta ccccggttcc aagcctagag gctccttccg aacaagcacc gactgagcaa   5580
aggcctgggg tgcaggagtg ctaccatggt aatggacaga gttatcgagg cacatactcc   5640
accactgtca caggaagaac ctgccaagct tggtcatcta tgacaccaca ctcgcatagt   5700
cggaccccag aatactaccc aaatgctggc ttgatcatga actactgcag gaatccagat   5760
gctgtggcag ctccttattg ttatacgagg gatcccggtg tcaggtggga gtactgcaac   5820
ctgacgcaat gctcagacgc agaagggact gccgtcgcgc ctccgactgt taccccggtt   5880
ccaagcctag aggctccttc cgaacaagca ccgactgagc aaaggcctgg ggtgcaggag   5940
tgctaccatg gtaatggaca gagttatcga ggcacatact ccaccactgt cacaggaaga   6000
acctgccaag cttggtcatc tatgacacca cactcgcata gtcggacccc agaatactac   6060
ccaaatgctg gcttgatcat gaactactgc aggaatccag atgctgtggc agctccttat   6120
tgttatacga gggatcccgg tgtcaggtgg gagtactgca acctgacgca atgctcagac   6180
gcagaaggga ctgccgtcgc gcctccgact gttaccccgg ttccaagcct agaggctcct   6240
tccgaacaag caccgactga gcaaaggcct ggggtgcagg agtgctacca tggtaatgga   6300
cagagttatc gaggcacata ctccaccact gtcacaggaa gaacctgcca agcttggtca   6360
tctatgacac cacactcgca tagtcggacc ccagaatact acccaaatgc tggcttgatc   6420
atgaactact gcaggaatcc agatgctgtg gcagctcctt attgttatac gagggatccc   6480
ggtgtcaggt gggagtactg caacctgacg caatgctcag acgcagaagg gactgccgtc   6540
gcgcctccga ctgttacccc ggttccaagc ctagaggctc cttccgaaca agcaccgact   6600
gagcaaaggc tggggtgca ggagtgctac catggtaatg gacagagtta tcgaggcaca   6660
tactccacca ctgtcacagg aagaacctgc caagcttggt catctatgac accacactcg   6720
catagtcgga ccccagaata ctacccaaat gctggcttga tcatgaacta ctgcaggaat   6780
ccagatgctg tggcagctcc ttattgttat acgagggatc ccggtgtcag gtgggagtac   6840
tgcaacctga cgcaatgctc agacgcagaa gggactgccg tcgcgcctcc gactgttacc   6900
ccggttccaa gcctagaggc tccttccgaa caagcaccga ctgagcaaag gcctggggtg   6960
caggagtgct accatggtaa tggacagagt tatcgaggca catactccac cactgtcaca   7020
ggaagaacct gccaagcttg gtcatctatg acaccacact cgcatagtcg gaccccagaa   7080
tactacccaa atgctggctt gatcatgaac tactgcagga atccagatgc tgtggcagct   7140
ccttattgtt atacgaggga tcccggtgtc aggtgggagt actgcaacct gacgcaatgc   7200
tcagacgcag aagggactgc cgtcgcgcct ccgactgtta ccccggttcc aagcctagag   7260
gctccttccg aacaagcacc gactgagcaa aggcctgggg tgcaggagtg ctaccatggt   7320
aatggacaga gttatcgagg cacatactcc accactgtca caggaagaac ctgccaagct   7380
tggtcatcta tgacaccaca ctcgcatagt cggaccccag aatactaccc aaatgctggc   7440
ttgatcatga actactgcag gaatccagat gctgtggcag ctccttattg ttatacgagg   7500
gatcccggtg tcaggtggga gtactgcaac ctgacgcaat gctcagacgc agaagggact   7560
gccgtcgcgc ctccgactgt taccccggtt ccaagcctag aggctccttc cgaacaagca   7620
ccgactgagc aaaggcctgg ggtgcaggag tgctaccatg gtaatggaca gagttatcga   7680
ggcacatact ccaccactgt cacaggaaga acctgccaag cttggtcatc tatgacacca   7740
cactcgcata gtcggacccc agaatactac ccaaatgctg gcttgatcat gaactactgc   7800
aggaatccag atgctgtggc agctccttat tgttatacga gggatcccgg tgtcaggtgg   7860
gagtactgca acctgacgca atgctcagac gcagaaggga ctgccgtcgc gcctccgact   7920
gttaccccgg ttccaagcct agaggctcct tccgaacaag caccgactga gcagaggcct   7980
ggggtgcagg agtgctacca cggtaatgga cagagttatc gaggcacata ctccaccact   8040
gtcactggaa gaacctgcca agcttggtca tctatgacac cacactcgca tagtcggacc   8100
ccagaatact acccaaatgc tggcttgatc atgaactact gcaggaatcc agatgctgtg   8160
gcagctcctt attgttatac gagggatccc ggtgtcaggt gggagtactg caacctgacg   8220
```

```
caatgctcag acgcagaagg gactgccgtc gcgcctccga ctgttacccc ggttccaagc  8280
ctagaggctc cttccgaaca agcaccgact gagcaaaggc ctggggtgca ggagtgctac  8340
catggtaatg gacagagtta tcgaggcaca tactccacca ctgtcacagg aagaacctgc  8400
caagcttggt catctatgac accacactcg catagtcgga ccccagaata ctacccaaat  8460
gctggcttga tcatgaacta ctgcaggaat ccagatgctg tggcagctcc ttattgttat  8520
acgagggatc ccggtgtcag gtgggagtac tgcaacctga cgcaatgctc agacgcagaa  8580
gggactgccg tcgcgcctcc gactgttacc ccggttccaa gcctagaggc tccttccgaa  8640
caagcaccga ctgagcaaag gcctggggtg caggagtgct accatggtaa tggacagagt  8700
tatcgaggca catactccac cactgtcaca ggaagaacct gccaagcttg gtcatctatg  8760
acaccacact cgcatagtcg gaccccagaa tactacccaa atgctggctt gatcatgaac  8820
tactgcagga atccagatgc tgtggcagct ccttattgtt atacgaggga tcccggtgtc  8880
aggtgggagt actgcaacct gacgcaatgc tcagacgcag aagggactgc cgtcgcgcct  8940
ccgactgtta ccccggttcc aagcctagag gctccttccg aacaagcacc gactgagcag  9000
aggcctgggg tgcaggagtg ctaccacggt aatggacaga gttatcgagg cacatactcc  9060
accactgtca ctggaagaac ctgccaagct tggtcatcta tgacaccaca ctcgcatagt  9120
cggaccccag aatactaccc aaatgctggc ttgatcatga actactgcag gaatccagat  9180
gctgtggcag ctccttattg ttatacgagg gatcccggtg tcaggtggga gtactgcaac  9240
ctgacgcaat gctcagacgc agaagggact gccgtcgcgc ctccgactgt tacccccggtt  9300
ccaagcctag aggctccttc cgaacaagca ccgactgagc agaggcctgg ggtgcaggag  9360
tgctaccacg gtaatggaca gagttatcga ggcacatact ccaccactgt cactggaaga  9420
acctgccaag cttggtcatc tatgacacca cactcgcata gtcggacccc agaatactac  9480
ccaaatgctg gcttgatcat gaactactgc aggaatccag atgctgtgc agctccttat  9540
tgttatacga gggatcccgg tgtcaggtgg gagtactgca acctgacgca atgctcagac  9600
gcagaaggga ctgccgtcgc gcctccgact gttaccccgg ttccaagcct agaggctcct  9660
tccgaacaag caccgactga gcagaggcct ggggtgcagg agtgctacca cggtaatgga  9720
cagagttatc gaggcacata ctccaccact gtcactggaa gaacctgcca agcttggtca  9780
tctatgacac cacactcgca tagtcggacc ccagaatact acccaaatgc tggcttgatc  9840
atgaactact gcaggaatcc agatgctgtg gcagctcctt attgttatac gagggatccc  9900
ggtgtcaggt gggagtactg caacctgacg caatgctcag acgcagaagg gactgccgtc  9960
gcgcctccga ctgttacccc ggttccaagc ctagaggctc cttccgaaca agcaccgact 10020
gagcagaggc ctggggtgca ggagtgctac cacggtaatg gacagagtta tcgaggcaca 10080
tactccacca ctgtcactgg aagaacctgc caagcttggt catctatgac accacactcg 10140
catagtcgga ccccagaata ctacccaaat gctggcttga tcatgaacta ctgcaggaat 10200
ccagatcctg tggcagcccc ttattgttat acgagggatc ccagtgtcag gtgggagtac 10260
tgcaacctga cacaatgctc agacgcagaa gggactgccg tcgcgcctcc aactattacc 10320
ccgattccaa gcctagaggc tccttctgaa caagcaccaa ctgagcaaag gcctggggtg 10380
caggagtgct accacggaaa tggacagagt tatcaaggca catacttcat tactgtcaca 10440
ggaagaacct gccaagcttg gtcatctatg acaccacact cgcatagtcg gacccccagca 10500
tactacccaa atgctggctt gatcaagaac tactgccgaa atccagatcc tgtggcagcc 10560
ccttggtgtt atacaacaga tcccagtgtc aggtgggagt actgcaacct gacacgatgc 10620
tcagatgcag aatggactgc cttcgtccct ccgaatgtta ttctggctcc aagcctagag 10680
gcttttttg aacaagcact gactgaggaa accccgggg tacaggactg ctactaccat 10740
tatggcagga gttaccgagg cacatactcc accactgtca caggaagaac ttgccaagct 10800
tggtcatcta tgacaccaca ccagcatagt cggaccccag aaaactaccc aaatgctggc 10860
ctgaccagga actactgcag gaatccagat gctgagattc gcccttggtg ttacaccatg 10920
gatcccagtg tcaggtggga gtactgcaac ctgacacaat gcctggtgac agaatcaagt 10980
gtccttgcaa ctctcacggt ggtcccagtt ccaagcacag agcttccttc tgaagaagca 11040
ccaacggagc aaagcccgg ggtccaggat tgctaccatg gtgatggaca gagttatcga 11100
ggctcattct ctaccactgt cacaggaagg acatgtcagt cttggtcctc tatgacacca 11160
cactggcatc agaggacaac agaatattat ccaaatggtg gcctgaccag gaactactgc 11220
aggaatccag atgctgagat tagtccttgg tgttatacca tggatcccaa tgtcagatgg 11280
gagtactgca acctgacaca atgtccagtc acagaatcaa gtgtccttgc gacgtccacg 11340
gctgttttctg aacaagcacc aacggagcaa agcccacag tccaggactg ctaccatggt 11400
gatggacaga gttatcgagg ctcattctcc accactgtta caggaaggac atgtcagtct 11460
tggtcctcta tgacaccaca ctggcatcag agaaccacaa aatactaccc aaatggtggc 11520
ctgaccagga actactgcag gaatccagat gctgagattc gcccttggtg ttataccatg 11580
gatcccagtg tcagatggga gtactgcaac ctgacgcaat gtccagtgat ggaatcaact 11640
ctcctcacaa ctcccacggt ggtcccagtt ccaagcacag agcttccttc tgaagaagca 11700
ccaactgaaa acagcactgg ggtccaggac tgctaccatg gtgatggaca gagttatcga 11760
ggcacactct ccaccactat cacaggaaga acatgtcagt cttggtcgtc tatgacacca 11820
cattggcatc ggaggatccc attatactat ccaaatgctg gcctgaccag gaactactgc 11880
aggaatccag atgctgagat tcgcccttgg tgttacacca tggatcccag tgtcaggtgg 11940
gagtactgca acctgacacg atgtccagtc acagaatcga gtgtcctcac aactcccaca 12000
gtggcccccgg ttccaagcac agaggctcct tctgaacaag caccacctga gaaaagccct 12060
gtggtccagg attgctacca tggtgatgga cggagttatc gaggcatatc ctccaccact 12120
gtcacaggaa ggacctgtca atcttggtca tctatgatac cacactggca tcagaggacc 12180
ccagaaaact acccaaatgc tggcctgacc gagaactact gcaggaatcc agattctggg 12240
aaacaaccct ggtgttacac aaccgatccg tgtgtgaggt gggagtactg caatctgaca 12300
caatgctcag aaacagaatc aggtgtccta gagctcccca tgtcttgttc cagttccaagc 12360
atggaggctc attctgaagc agcaccaact gagcaaaccc ctgtggtccg gcagtgctac 12420
catggtaatg gccagagtta tcgaggcaca ttctccacca ctgtcacagg aagacatgt 12480
caatcttggt catccatgac accacaccgg catcagagga ccccagaaaa ctacccaaat 12540
gatggcctga caatgaacta ctgcaggaat ccagatgccg ataccaggccc ttggtgtttt 12600
accatggacc ccagcatcag gtgggagtac tgcaacctga ccgcatgctc agacacagaa 12660
gggactgtgg tcgctcctcc gactgtcatc caggttccaa gcctagggcc tcttctgaa 12720
caagactgta tgtttgggaa tgggaaagga taccggggca agaggcaaca cactgttact 12780
gggacgccat gccaggaatg ggctgcccag gagcccatag acacagcac gttcattcca 12840
gggacaaata aatgggcagg tctggaaaaa aattactgcc gtaaccctga tggtgacatc 12900
aatggtccct ggtgctacac aatgaatcca agaaaacttt tgactactg tgatatccct 12960
```

```
ctctgtgcat cctcttcatt tgattgtggg aagcctcaag tggagccgaa gaaatgtcct   13020
ggaagcattg tagggggtg tgtgccccac ccacattcct ggccctggca agtcagtctc    13080
agaacaaggt ttggaaagca cttctgtgga ggcaccttaa tatccccaga gtgggtgctg   13140
actgctgctc actgcttgaa gaagtcctca aggccttcat cctacaaggt catcctgggt   13200
gcacaccaag aagtgaacct cgaatctcat gttcaggaaa tagaagtgtc taggctgttc   13260
ttggagccca cacaagcaga tattgccttg ctaaagctaa gcaggcctgc cgtcatcact   13320
gacaaagtaa tgccagcttg tctgccatcc ccagactaca tggtcaccgc caggactgaa   13380
tgttacatca ctggctgggg agaaacccaa ggtacctttg ggactggcct tctcaaggaa   13440
gcccagctcc ttgttattga gaatgaagtg tgcaatcact ataagtatat ttgtgctgag   13500
catttggcca gaggcactga cagttgccag ggtgacagtg gagggcctct ggtttgcttc   13560
gagaaggaca aatacatttt acaaggagtc acttctgggg gtcttggctg tgcacgcccc   13620
aataagcctg gtgtctatgc tcgtgtttca aggtttgtta cttggattga gggaatgatg   13680
agaaataatt aattggacgg gagacagagt gaagcatcaa cctacttaga agctgaaacg   13740
tgggtaagga tttagcatgc tggaaataat agacagcaat caaacgaaga cactgttcct   13800
agctaccagc tatgccaaac cttggcattt ttggtatttt tgtgtataag ctttttaaggt  13860
ctgactgaca aattctgtat taaggtgtca tagctatgac atttgttaaa aataaactct   13920
gcacttattt tgatttga                                                  13938

SEQ ID NO: 5              moltype = DNA   length = 23
FEATURE                   Location/Qualifiers
misc_feature              1..23
                          note = Primer
source                    1..23
                          mol_type = other DNA
                          organism = synthetic construct
SEQUENCE: 5
acagcaatca aacgaagaca ctg                                           23

SEQ ID NO: 6              moltype = DNA   length = 28
FEATURE                   Location/Qualifiers
misc_feature              1..28
                          note = Primer
source                    1..28
                          mol_type = other DNA
                          organism = synthetic construct
SEQUENCE: 6
agcttataca caaaaatacc aaaaatgc                                      28

SEQ ID NO: 7              moltype = DNA   length = 27
FEATURE                   Location/Qualifiers
misc_feature              1..27
                          note = Probe
source                    1..27
                          mol_type = other DNA
                          organism = synthetic construct
SEQUENCE: 7
tcccagctac cagctatgcc aaacctt                                       27

SEQ ID NO: 8              moltype = DNA   length = 16
FEATURE                   Location/Qualifiers
misc_feature              1..16
                          note = Primer
source                    1..16
                          mol_type = other DNA
                          organism = synthetic construct
SEQUENCE: 8
ccacagtggc cccggt                                                   16

SEQ ID NO: 9              moltype = DNA   length = 21
FEATURE                   Location/Qualifiers
misc_feature              1..21
                          note = Primer
source                    1..21
                          mol_type = other DNA
                          organism = synthetic construct
SEQUENCE: 9
acagggcttt tctcaggtgg t                                             21

SEQ ID NO: 10             moltype = DNA   length = 28
FEATURE                   Location/Qualifiers
misc_feature              1..28
                          note = Probe
source                    1..28
                          mol_type = other DNA
                          organism = synthetic construct
SEQUENCE: 10
ccaagcacag aggctccttc tgaacaag                                      28

SEQ ID NO: 11             moltype = DNA   length = 20
```

```
FEATURE                  Location/Qualifiers
misc_feature             1..20
                         note = Synthetic oligonucleotide
source                   1..20
                         mol_type = other DNA
                         organism = synthetic construct
SEQUENCE: 11
ggcaggtcct tcctgtgaca                                                   20

SEQ ID NO: 12            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 12
cctgtgacag tggtggagta                                                   20

SEQ ID NO: 13            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 13
tcctgtgaca gtggtggagt                                                   20

SEQ ID NO: 14            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 14
cttcctgtga cagtggtgga                                                   20

SEQ ID NO: 15            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 15
ccttcctgtg acagtggtgg                                                   20

SEQ ID NO: 16            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 16
tccttcctgt gacagtggtg                                                   20

SEQ ID NO: 17            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 17
gtccttcctg tgacagtggt                                                   20

SEQ ID NO: 18            moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 18
ggtccttcct gtgacagtgg                                                   20
```

```
SEQ ID NO: 19              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 19
aggtccttcc tgtgacagtg                                                       20

SEQ ID NO: 20              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 20
caggtccttc ctgtgacagt                                                       20

SEQ ID NO: 21              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 21
gcaggtcctt cctgtgacag                                                       20

SEQ ID NO: 22              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 22
tggcaggtcc ttcctgtgac                                                       20

SEQ ID NO: 23              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 23
ttggcaggtc cttcctgtga                                                       20

SEQ ID NO: 24              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 24
cttggcaggt ccttcctgtg                                                       20

SEQ ID NO: 25              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 25
gcttggcagg tccttcctgt                                                       20

SEQ ID NO: 26              moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 26
tcttcctgtg acagtggtgg                                                       20
```

```
SEQ ID NO: 27           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 27
ttcttcctgt gacagtggtg                                              20

SEQ ID NO: 28           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 28
gttcttcctg tgacagtggt                                              20

SEQ ID NO: 29           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 29
ggttcttcct gtgacagtgg                                              20

SEQ ID NO: 30           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 30
aggttcttcc tgtgacagtg                                              20

SEQ ID NO: 31           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 31
caggttcttc ctgtgacagt                                              20

SEQ ID NO: 32           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 32
tggcaggttc ttcctgtgac                                              20

SEQ ID NO: 33           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 33
ttggcaggtt cttcctgtga                                              20

SEQ ID NO: 34           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 34
```
cttggcaggt tcttcctgtg                                                     20

SEQ ID NO: 35         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 35
agcttggcag gttcttcctg                                                     20

SEQ ID NO: 36         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 36
actatgcgag tgtggtgtca                                                     20

SEQ ID NO: 37         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 37
gactatgcga gtgtggtgtc                                                     20

SEQ ID NO: 38         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 38
cgactatgcg agtgtggtgt                                                     20

SEQ ID NO: 39         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 39
ccgactatgc gagtgtggtg                                                     20

SEQ ID NO: 40         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 40
tccgactatg cgagtgtggt                                                     20

SEQ ID NO: 41         moltype = DNA  length = 20
FEATURE               Location/Qualifiers
misc_feature          1..20
                      note = Synthetic oligonucleotide
source                1..20
                      mol_type = other DNA
                      organism = synthetic construct
SEQUENCE: 41
gtccgactat gcgagtgtgg                                                     20

SEQ ID NO: 42         moltype = DNA  length = 20
FEATURE               Location/Qualifiers
misc_feature          1..20
                      note = Synthetic oligonucleotide
source                1..20
                      mol_type = other DNA
                      organism = synthetic construct

```
SEQUENCE: 42
ggtccgacta tgcgagtgtg                                                    20

SEQ ID NO: 43           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 43
gggtccgact atgcgagtgt                                                    20

SEQ ID NO: 44           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 44
ctgctcagtc ggtgcttgtt                                                    20

SEQ ID NO: 45           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 45
cctctgctca gtcggtgctt                                                    20

SEQ ID NO: 46           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 46
gcctctgctc agtcggtgct                                                    20

SEQ ID NO: 47           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 47
cttccagtga cagtggtgga                                                    20

SEQ ID NO: 48           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 48
ttcttccagt gacagtggtg                                                    20

SEQ ID NO: 49           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 49
gttcttccag tgacagtggt                                                    20

SEQ ID NO: 50           moltype = DNA  length = 20
FEATURE                 Location/Qualifiers
misc_feature            1..20
                        note = Synthetic oligonucleotide
source                  1..20
                        mol_type = other DNA
```

```
                            organism = synthetic construct
SEQUENCE: 50
ggttcttcca gtgacagtgg                                              20

SEQ ID NO: 51               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 51
gaccttaaaa gcttatacac                                              20

SEQ ID NO: 52               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 52
gtcagacctt aaaagcttat                                              20

SEQ ID NO: 53               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 53
tgtcagtcag accttaaaag                                              20

SEQ ID NO: 54               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 54
gaatttgtca gtcagacctt                                              20

SEQ ID NO: 55               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 55
agaatttgtc agtcagacct                                              20

SEQ ID NO: 56               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 56
ccttaataca gaatttgtca                                              20

SEQ ID NO: 57               moltype = DNA   length = 20
FEATURE                     Location/Qualifiers
misc_feature                1..20
                            note = Synthetic oligonucleotide
source                      1..20
                            mol_type = other DNA
                            organism = synthetic construct
SEQUENCE: 57
gctccgttgg tgcttgttca                                              20

SEQ ID NO: 58               moltype = DNA   length = 20
FEATURE                     Location/Qualifiers
misc_feature                1..20
                            note = Synthetic oligonucleotide
source                      1..20
```

```
                        mol_type = other DNA
                        organism = synthetic construct
modified_base           1
                        mod_base = OTHER
                        note = 2'-O-methoxyethyl-thymidine
modified_base           2
                        mod_base = OTHER
                        note = 2'-O-methoxyethyl-guanosine
modified_base           3
                        mod_base = OTHER
                        note = 2'-O-methoxyethyl-5-methylcytidine
modified_base           4
                        mod_base = OTHER
                        note = 2'-O-methoxyethyl-thymidine
modified_base           5
                        mod_base = OTHER
                        note = 2'-O-methoxyethyl-5-methylcytidine
modified_base           6
                        mod_base = m5c
modified_base           14
                        mod_base = m5c
modified_base           16
                        mod_base = OTHER
                        note = 2'-O-methoxyethyl-thymidine
modified_base           17
                        mod_base = OTHER
                        note = 2'-O-methoxyethyl-guanosine
modified_base           18..19
                        mod_base = OTHER
                        note = 2'-O-methoxyethyl-thymidine
modified_base           20
                        mod_base = OTHER
                        note = 2'-O-methoxyethyl-5-methylcytidine
SEQUENCE: 58
tgctccgttg gtgcttgttc                                                 20

SEQ ID NO: 59           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 59
ttgctccgtt ggtgcttgtt                                                 20

SEQ ID NO: 60           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 60
tttgctccgt tggtgcttgt                                                 20

SEQ ID NO: 61           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 61
ctttgctccg ttggtgcttg                                                 20

SEQ ID NO: 62           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 62
tcctgtaaca gtggtggaga                                                 20

SEQ ID NO: 63           moltype = DNA   length = 20
FEATURE                 Location/Qualifiers
misc_feature            1..20
```

```
                    note = Synthetic oligonucleotide
source              1..20
                    mol_type = other DNA
                    organism = synthetic construct
SEQUENCE: 63
ttcctgtaac agtggtggag                                                   20

SEQ ID NO: 64       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 64
cttcctgtaa cagtggtgga                                                   20

SEQ ID NO: 65       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 65
ccttcctgta acagtggtgg                                                   20

SEQ ID NO: 66       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 66
tccttcctgt aacagtggtg                                                   20

SEQ ID NO: 67       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 67
gtccttcctg taacagtggt                                                   20

SEQ ID NO: 68       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 68
tgtccttcct gtaacagtgg                                                   20

SEQ ID NO: 69       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 69
tggagccaga ataacattcg                                                   20

SEQ ID NO: 70       moltype = DNA  length = 20
FEATURE             Location/Qualifiers
misc_feature        1..20
                    note = Synthetic oligonucleotide
source              1..20
                    mol_type = other DNA
                    organism = synthetic construct
SEQUENCE: 70
cctctaggct tggagccaga                                                   20

SEQ ID NO: 71       moltype = DNA  length = 20
FEATURE             Location/Qualifiers
```

```
misc_feature              1..20
                          note = Synthetic oligonucleotide
source                    1..20
                          mol_type = other DNA
                          organism = synthetic construct
SEQUENCE: 71
agttcttcct gtgacagtgg                                                        20

SEQ ID NO: 72             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 72
gtccgactat gctggtgtgg                                                        20

SEQ ID NO: 73             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 73
ggtccgacta tgctggtgtg                                                        20

SEQ ID NO: 74             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 74
gggtccgact atgctggtgt                                                        20

SEQ ID NO: 75             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 75
cctctaggct tggaatcggg                                                        20

SEQ ID NO: 76             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 76
gttcagaagg agcctctagg                                                        20

SEQ ID NO: 77             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 77
tgttcagaag gagcctctag                                                        20

SEQ ID NO: 78             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 78
gcttgttcag aaggagcctc                                                        20

SEQ ID NO: 79             moltype = DNA  length = 20
```

```
FEATURE                      Location/Qualifiers
misc_feature                 1..20
                             note = Synthetic oligonucleotide
source                       1..20
                             mol_type = other DNA
                             organism = synthetic construct
SEQUENCE: 79
tgcttgttca gaaggagcct                                                   20

SEQ ID NO: 80                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 80
gtgcttgttc agaaggagcc                                                   20

SEQ ID NO: 81                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 81
ggtgcttgtt cagaaggagc                                                   20

SEQ ID NO: 82                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 82
tggtgcttgt tcagaaggag                                                   20

SEQ ID NO: 83                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 83
gctcagttgg tgcttgttca                                                   20

SEQ ID NO: 84                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 84
tgctcagttg gtgcttgttc                                                   20

SEQ ID NO: 85                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 85
gcttggatct gggaccaccg                                                   20

SEQ ID NO: 86                moltype = DNA   length = 20
FEATURE                      Location/Qualifiers
misc_feature                 1..20
                             note = Synthetic oligonucleotide
source                       1..20
                             mol_type = other DNA
                             organism = synthetic construct
SEQUENCE: 86
gcctccatgc ttggaactgg                                                   20
```

```
SEQ ID NO: 87            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 87
gctcagttgg tgctgcttca                                                   20

SEQ ID NO: 88            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 88
cctcgataac tctggccatt                                                   20

SEQ ID NO: 89            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 89
tcctgtgaca gtggtggaga                                                   20

SEQ ID NO: 90            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 90
gtaggttgat gcttcactct                                                   20

SEQ ID NO: 91            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 91
cgtttgattg ctgtctatta                                                   20

SEQ ID NO: 92            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 92
ctctgtgctt ggatctggga                                                   20

SEQ ID NO: 93            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 93
cctctgtgct tggatctggg                                                   20

SEQ ID NO: 94            moltype = DNA   length = 20
FEATURE                  Location/Qualifiers
misc_feature             1..20
                         note = Synthetic oligonucleotide
source                   1..20
                         mol_type = other DNA
                         organism = synthetic construct
SEQUENCE: 94
gcctctgtgc ttggatctgg                                                   20
```

```
SEQ ID NO: 95           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 95
agaagcctct gtgcttggat                                                   20

SEQ ID NO: 96           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 96
ttcagaagaa gcctctgtgc                                                   20

SEQ ID NO: 97           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 97
gctccgttgg tgcttcttca                                                   20

SEQ ID NO: 98           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 98
tttgctccgt tggtgcttct                                                   20

SEQ ID NO: 99           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 99
gctttgctcc gttggtgctt                                                   20

SEQ ID NO: 100          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 100
ggctttgctc cgttggtgct                                                   20

SEQ ID NO: 101          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 101
gggctttgct ccgttggtgc                                                   20

SEQ ID NO: 102          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 102
```

```
ccttcctgtg acagtggtag                                                       20

SEQ ID NO: 103          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 103
tccttcctgt gacagtggta                                                       20

SEQ ID NO: 104          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 104
tgtccttcct gtgacagtgg                                                       20

SEQ ID NO: 105          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 105
cctctaggct tggaaccggg                                                       20

SEQ ID NO: 106          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 106
tgcttgttcg gaaggagcct                                                       20

SEQ ID NO: 107          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 107
gtgcttgttc ggaaggagcc                                                       20

SEQ ID NO: 108          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 108
gcttggaact gggaccaccg                                                       20

SEQ ID NO: 109          moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 109
ctgtgcttgg aactgggacc                                                       20

SEQ ID NO: 110          moltype = DNA   length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 110
ctctgtgctt ggaactggga                                                    20

SEQ ID NO: 111          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 111
cctgtgacag tggtgga                                                       17

SEQ ID NO: 112          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 112
tcctgtgaca gtggtgg                                                       17

SEQ ID NO: 113          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 113
ttcctgtgac agtggtg                                                       17

SEQ ID NO: 114          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 114
cttcctgtga cagtggt                                                       17

SEQ ID NO: 115          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 115
ccttcctgtg acagtgg                                                       17

SEQ ID NO: 116          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 116
tccttcctgt gacagtg                                                       17

SEQ ID NO: 117          moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 117
gtccttcctg tgacagt                                                       17

SEQ ID NO: 118          moltype = DNA  length = 17
FEATURE                 Location/Qualifiers
misc_feature            1..17
                        note = Synthetic oligonucleotide
source                  1..17
                        mol_type = other DNA
```

```
SEQUENCE: 118
ggtccttcct gtgacag                                                    17

SEQ ID NO: 119         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 119
ccgactatgc gagtgtg                                                    17

SEQ ID NO: 120         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 120
gtccgactat gcgagtg                                                    17

SEQ ID NO: 121         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 121
ggtccgacta tgcgagt                                                    17

SEQ ID NO: 122         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 122
gtcagacctt aaaagct                                                    17

SEQ ID NO: 123         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 123
aagcctctgt gcttgga                                                    17

SEQ ID NO: 124         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 124
agcctctgtg cttggat                                                    17

SEQ ID NO: 125         moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 125
gcctctgtgc ttggatc                                                    17

SEQ ID NO: 126         moltype = DNA  length = 17
FEATURE                Location/Qualifiers
misc_feature           1..17
                       note = Synthetic oligonucleotide
source                 1..17
```

| | |
|---|---|
| | mol_type = other DNA |
| | organism = synthetic construct |
| SEQUENCE: 126 | | gctccgttgg tgcttct                                                          17

| | |
|---|---|
| SEQ ID NO: 127 | moltype = DNA   length = 17 |
| FEATURE | Location/Qualifiers |
| misc_feature | 1..17 |
| | note = Synthetic oligonucleotide |
| source | 1..17 |
| | mol_type = other DNA |
| | organism = synthetic construct |
| SEQUENCE: 127 | | ctctgtgctt ggaactg                                                          17

| | |
|---|---|
| SEQ ID NO: 128 | moltype = DNA   length = 17 |
| FEATURE | Location/Qualifiers |
| misc_feature | 1..17 |
| | note = Synthetic oligonucleotide |
| source | 1..17 |
| | mol_type = other DNA |
| | organism = synthetic construct |
| SEQUENCE: 128 | | tgcctcgata actctgt                                                          17

| | |
|---|---|
| SEQ ID NO: 129 | moltype = DNA   length = 17 |
| FEATURE | Location/Qualifiers |
| misc_feature | 1..17 |
| | note = Synthetic oligonucleotide |
| source | 1..17 |
| | mol_type = other DNA |
| | organism = synthetic construct |
| SEQUENCE: 129 | | tgtgcctcga taactct                                                          17

| | |
|---|---|
| SEQ ID NO: 130 | moltype = DNA   length = 17 |
| FEATURE | Location/Qualifiers |
| misc_feature | 1..17 |
| | note = Synthetic oligonucleotide |
| source | 1..17 |
| | mol_type = other DNA |
| | organism = synthetic construct |
| SEQUENCE: 130 | | gctcagttgg tgctgct                                                          17

| | |
|---|---|
| SEQ ID NO: 131 | moltype = DNA   length = 27 |
| FEATURE | Location/Qualifiers |
| misc_feature | 1..27 |
| | note = Synthetic oligonucleotide |
| source | 1..27 |
| | mol_type = other DNA |
| | organism = synthetic construct |
| SEQUENCE: 131 | | gcgtttgctc ttcttcttgc gtttttt                                               27

| | |
|---|---|
| SEQ ID NO: 132 | moltype = DNA   length = 3987 |
| FEATURE | Location/Qualifiers |
| source | 1..3987 |
| | mol_type = genomic DNA |
| | organism = Macaca mulatta |
| SEQUENCE: 132 | |

```
atgtatcgtt ttggaatttc cagtggcttg atcaggaact actgcaggaa tccagatcct   60
gtggcagccc cttattgtta tacgatggat cccaatgtca ggtgggagta ctgcaacctg  120
acacaatgct cagatgcaga agggactgcc gtcgcacctc cgaatgtcac cctggttcca  180
agcctagagg ctccttccga acaatccaccg actgagcaaa ggcctggggt gcaggagtgc  240
taccacggta atggacagag ttatcgaggc acatacttca ccactgtgac aggaagaacc  300
tgccaagctt ggtcatctat gacaccgcac tctcatagtc ggaccccgga aaactaccca  360
aatggtggct tgatcaggaa ctactgcagg aatccgatc ctgtggcagc cccttattgt  420
tataccatgg atcccaatgt caggtgggag tactgcaacg taacacaatg ctcagacgca  480
gaagggattg ccgtcacacc tctgactgtt acccgggttc caagcctaga ggctccttcc  540
aagcaagcac caactgagca aaggcctggt gtccaggagt gctaccatgg taatggacag  600
agttatcgag gcacatactt caccactgtg acaggaagaa cctgccaagc ttggtcatct  660
atgacaccac attctcatag tcgtacccca gaaaactacc caaatggcag tccgacctct  720
tcagatctct tagtctaccc tgccgtcttc cttgatgcca tgggtcccac tgttctttca  780
actcatccgc tttccctcag tcccggagtg gctgcgacca gcaggaggata tattgagagc  840
aagagagaag caccgactga gcaaaggcct ggggtgcagg agtgctacca cggtaatgga  900
cagagttatc gaggcacata cttcaccact gtgacaggaa gaacctgcca agcttggtca 960
tctatgacac cgcactctca tagtcggacc ccggaaaact acccaaatgg tggcttgatc 1020
aggaactact gcaggaatcc agatcctgtg gcagccccct attgttatac catggatccc 1080
```

```
agtgtcaggt gggagtactg caacctgaca caatgctcag acgcagaagg gactgccgtc  1140
gcacctccga atgtcacccc ggttccaagc ctagaggctc cttctgagca agcaccaact  1200
gagcaaaggc ttggggtgca ggagtgctac cacagtaatg gacagagtta tcgaggcaca  1260
tacttcacca ctgtgacagg aagaacctgc caagcttggt catctatgac accacactct  1320
catagtcgga ccccagaaaa ctacccaaat gctggcttca tcaagaacta ctgccgaaat  1380
ccagatcctg tggcagcccc ttggtgttat acaacggatc ccagtgtcag gtgggagtac  1440
tgcaacctga cacgatgctc agatgcagaa gggactgctg tcgtgcctcc aaatattatt  1500
ccggttccaa gcctagaggc ttttcttgaa caagaaccga ctgaggaaac ccccggggta  1560
caggagtgct actaccatta tggacagagt tatagaggca catactccac cactgttaca  1620
ggaagaactt gccaagcttg gtcatctatg acaccacacc agcatagtcg gaccccaaaa  1680
aactatccaa atgctggcct gaccaggaac tactgcagga atccagatgc tgagattcgc  1740
ccttggtgtt ataccatgga tcccagtgtc aggtgggagt actgcaacct gacacaatgt  1800
ctggtgacag aatcaagtgt ccttgaaact ctcacagtgg tcccagatcc aagcacacag  1860
gcttcttctg aagaagcacc aacggacaa agtcccgagg tccagactg ctaccaagt   1920
gatggacaga gttatcgagg ctcattctcc accactgtca caggaaggac atgtcagtct  1980
tggtcctcta tgacaccaca ctggcatcag aggacaacag aatattatcc agatggtggc  2040
ctgaccagga actactgcag gaatccagat gctgagattc gcccttggtg ttataccatg  2100
gatcccagtg tcaggtggga gtactgcaac ctgacacaat gtccagtgac agaatcaagt  2160
gtcctcgcaa cgtccatggc tgtttctgaa caagcaccaa tggagcaaag ccccggggtc  2220
caggactgct accatggtga tggacagagt tatcgaggtt cattctccac cactgtcaca  2280
ggaaggacat gtcagtcttg gtcctctatg acaccacact ggcatcagag gaccatagaa  2340
tacccccaa atggtggcct gaccaagaac tactgcagga atccagatgc tgagattcgc  2400
ccttggtgtt ataccatgga tcccagagtc agatgggagt actgcaacct gacacaatgt  2460
gtggtgatgg aatcaagtgt ccttgcaact cccatggtgg tcccagttcc aagcagagag  2520
gttccttctg aagaagcacc aactgaaaac agccctgggg tccaggactg ctaccaaggt  2580
gatggacaga gttatcgagg cacattctcc accactatca caggaagaac atgtcagtct  2640
tggttgtcta tgacaccaca tcggcatcgg aggatcccat tacgctatcc aaatgctggc  2700
ctgaccagga actattgcag aaatccagat gctgagattc gcccttggtg ttataccatg  2760
gatcccagtg tcaggtggga gtactgcaac ctgacacaat gtccagtgac agaatcaagt  2820
gtcctcaacaa ctcccacggt ggtcccggtt ccaagcacag aggctccttc tgaacaagca  2880
ccacctgaga aaagccctgt ggtccaggat tgctaccatg gtgatggaca gagttatcga  2940
ggcacatcct ccaccactgt cacaggaagg aactgtcagt cttggtcatc tatgatacca  3000
cactggcatc agaggacccc agaaaactac ccaaatgctg gcctgaccag gaactactgc  3060
aggaatccag attctgggaa acaacccgtc tgttacacga ctgatccatg tgtgaggtgg  3120
gagtactgca acctgacaca atgtcagaaa acagaatcag gtgtcctaga gactcccact  3180
gttgttccgg ttccaagcat ggaagctcat tctgaagcag caccaactga gcaaacccct  3240
gtggtccagc agtgctacca tggtaatgga cagagttatc gaggcacatt ctccaccact  3300
gtcacaggaa ggacatgtca atcttggtca tccatgacac cacaccagca taagaggacc  3360
ccggaaaaacc acccaaatga tggcttgaca atgaactact gcaggaatcc agatgctgac  3420
acaggcccctt ggtgttttac catggacccc agcgtcaggc gggagtactg caacctgacg  3480
cgatgctcag acacagaagg gactgtggtc acacctccga ctgttatccc ggttccaagc  3540
ctagaggctc cttctgaaca agtgcttgga attcatcctg aattaaacga cacaattgct  3600
aacttggact caaaggtgaa ttcttcccca ccttgtgcca cagcatcctc ttcattgat   3660
tgtgggaagc tcaagtgga gccaaagaaa tgtcctggaa gcattgtagg tgggtgtgtg  3720
gcccaccccac attcctggcc ctggcaagtc agtcttagaa caaggtttgg aaagcacttc  3780
tgtggaggca ccttaatatc cccagagtgg gtgctgactg ctgcttgctg cttggagacg  3840
ttctcaaggc cttccttcta caaggtcatc ctgggtgcac accaagaagt gaatctcgaa  3900
tctcatgttc aagaaataga agtgtctagg ttgttcttgg agcccatagg agcagatatt  3960
gccttgctaa agctaagcag gtactaa                                      3987

SEQ ID NO: 133           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 133
ggttcttcca gtgacagtgg                                               20

SEQ ID NO: 134           moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 134
atgcctcgat aactccgtcc                                               20

SEQ ID NO: 135           moltype = DNA  length = 20
FEATURE                  Location/Qualifiers
misc_feature             1..20
                         note = Synthetic oligonucleotide
source                   1..20
                         mol_type = other DNA
                         organism = synthetic construct
modified_base            1
                         mod_base = OTHER
```

```
                         note = 2'-O-methoxyethyl-adenosine
modified_base            2
                         mod_base = OTHER
                         note = 2'-O-methoxyethyl-guanosine
modified_base            3
                         mod_base = OTHER
                         note = 2'-O-methoxyethyl-5-methylcytidine
modified_base            4..5
                         mod_base = OTHER
                         note = 2'-O-methoxyethyl-thymidine
modified_base            6
                         mod_base = m5c
modified_base            11
                         mod_base = m5c
modified_base            12
                         mod_base = m5c
modified_base            15
                         mod_base = m5c
modified_base            16..18
                         mod_base = OTHER
                         note = 2'-O-methoxyethyl-thymidine
modified_base            19
                         mod_base = OTHER
                         note = 2'-O-methoxyethyl-adenosine
modified_base            20
                         mod_base = OTHER
                         note = 2'-O-methoxyethyl-thymidine
SEQUENCE: 135
agcttcttgt ccagctttat                                                   20

SEQ ID NO: 136           moltype = DNA   length = 21
FEATURE                  Location/Qualifiers
misc_feature             1..21
                         note = Synthetic oligonucleotide
source                   1..21
                         mol_type = other DNA
                         organism = synthetic construct
modified_base            1
                         mod_base = OTHER
                         note = 2'-O-methoxyethyl-adenosine
modified_base            2
                         mod_base = OTHER
                         note = 2'-O-methoxyethyl-guanosine
modified_base            3
                         mod_base = OTHER
                         note = 2'-O-methoxyethyl-5-methylcytidine
modified_base            4..5
                         mod_base = OTHER
                         note = 2'-O-methoxyethyl-thymidine
modified_base            6
                         mod_base = m5c
modified_base            11..12
                         mod_base = m5c
modified_base            15
                         mod_base = m5c
modified_base            16..18
                         mod_base = OTHER
                         note = 2'-O-methoxyethyl-thymidine
modified_base            19
                         mod_base = OTHER
                         note = 2'-O-methoxyethyl-adenosine
modified_base            20
                         mod_base = OTHER
                         note = 2'-O-methoxyethyl-thymidine
SEQUENCE: 136
agcttcttgt ccagctttat a                                                 21

SEQ ID NO: 137           moltype = DNA   length = 14
FEATURE                  Location/Qualifiers
misc_feature             1..14
                         note = Synthetic oligonucleotide
source                   1..14
                         mol_type = other DNA
                         organism = synthetic construct
modified_base            1
                         mod_base = OTHER
                         note = 6'-(S)-methyl-thymidine
modified_base            2
                         mod_base = OTHER
```

|                | |
|---|---|
| | note = 6'-(S)-methyl-5-methylcytidine |
| modified_base | 6 |
| | mod_base = m5c |
| modified_base | 11 |
| | mod_base = m5c |
| modified_base | 13 |
| | mod_base = OTHER |
| | note = 6'-(S)-methyl-thymidine |
| modified_base | 14 |
| | mod_base = OTHER |
| | note = 6'-(S)-methyl-5-methylcytidine |

SEQUENCE: 137
tcagtcatga cttc                                                    14

| | |
|---|---|
| SEQ ID NO: 138 | moltype = DNA  length = 15 |
| FEATURE | Location/Qualifiers |
| misc_feature | 1..15 |
| | note = Synthetic oligonucleotide |
| source | 1..15 |
| | mol_type = other DNA |
| | organism = synthetic construct |
| modified_base | 1 |
| | mod_base = OTHER |
| | note = 6'-(S)-methyl-thymidine |
| modified_base | 2 |
| | mod_base = OTHER |
| | note = 6'-(S)-methyl-5-methylcytidine |
| modified_base | 6 |
| | mod_base = m5c |
| modified_base | 11 |
| | mod_base = m5c |
| modified_base | 13 |
| | mod_base = OTHER |
| | note = 6'-(S)-methyl-thymidine |
| modified_base | 14 |
| | mod_base = OTHER |
| | note = 6'-(S)-methyl-5-methylcytidine |

SEQUENCE: 138
tcagtcatga cttca                                                   15

| | |
|---|---|
| SEQ ID NO: 139 | moltype = DNA  length = 20 |
| FEATURE | Location/Qualifiers |
| misc_feature | 1..20 |
| | note = Synthetic oligonucleotide |
| source | 1..20 |
| | mol_type = other DNA |
| | organism = synthetic construct |
| modified_base | 1 |
| | mod_base = OTHER |
| | note = 2'-O-methoxyethyl-guanosine |
| modified_base | 2 |
| | mod_base = OTHER |
| | note = 2'-O-methoxyethyl-5-methylcytidine |
| modified_base | 3 |
| | mod_base = OTHER |
| | note = 2'-O-methoxyethyl-thymidine |
| modified_base | 4 |
| | mod_base = OTHER |
| | note = 2'-O-methoxyethyl-guanosine |
| modified_base | 5 |
| | mod_base = OTHER |
| | note = 2'-O-methoxyethyl-adenosine |
| modified_base | 16 |
| | mod_base = OTHER |
| | note = 2'-O-methoxyethyl-guanosine |
| modified_base | 17 |
| | mod_base = OTHER |
| | note = 2'-O-methoxyethyl-thymidine |
| modified_base | 18..19 |
| | mod_base = OTHER |
| | note = 2'-O-methoxyethyl-5-methylcytidine |
| modified_base | 20 |
| | mod_base = OTHER |
| | note = 2'-O-methoxyethyl-5-methylcytidine |

SEQUENCE: 139
gctgattaga gagaggtccc                                              20

| | |
|---|---|
| SEQ ID NO: 140 | moltype = DNA  length = 20 |
| FEATURE | Location/Qualifiers |

```
misc_feature              1..20
                          note = Synthetic oligonucleotide
source                    1..20
                          mol_type = other DNA
                          organism = synthetic construct
modified_base             1
                          mod_base = OTHER
                          note = 2'-O-methoxyethyl-thymidine
modified_base             2..3
                          mod_base = OTHER
                          note = 2'-O-methoxyethyl-5-methylcytidine
modified_base             4
                          mod_base = m5c
modified_base             9
                          mod_base = m5c
modified_base             16..17
                          mod_base = m5c
modified_base             18
                          mod_base = OTHER
                          note = 2'-O-methoxyethyl-thymidine
modified_base             19
                          mod_base = OTHER
                          note = 2'-O-methoxyethyl-guanosine
modified_base             20
                          mod_base = OTHER
                          note = 2'-O-methoxyethyl-guanosine
SEQUENCE: 140
tcccatttca ggagacctgg                                                    20

SEQ ID NO: 141            moltype = DNA  length = 15
FEATURE                   Location/Qualifiers
misc_feature              1..15
                          note = Synthetic oligonucleotide
source                    1..15
                          mol_type = other DNA
                          organism = synthetic construct
modified_base             2
                          mod_base = OTHER
                          note = 6'-(S)-methyl-thymidine
modified_base             3
                          mod_base = OTHER
                          note = 6'-(S)-methyl-5-methylcytidine
modified_base             7
                          mod_base = m5c
modified_base             12
                          mod_base = m5c
modified_base             14
                          mod_base = OTHER
                          note = 6'-(S)-methyl-thymidine
modified_base             15
                          mod_base = OTHER
                          note = 6'-(S)-methyl-5-methylcytidine
SEQUENCE: 141
atcagtcatg acttc                                                         15

SEQ ID NO: 142            moltype = DNA  length = 20
FEATURE                   Location/Qualifiers
misc_feature              1..20
                          note = Synthetic oligonucleotide
source                    1..20
                          mol_type = other DNA
                          organism = synthetic construct
modified_base             1
                          mod_base = OTHER
                          note = 2'-O-methoxyethyl-5-methylcytidine
modified_base             2..3
                          mod_base = OTHER
                          note = 2'-O-methoxyethyl-guanosine
modified_base             4
                          mod_base = OTHER
                          note = 2'-O-methoxyethyl-thymidine
modified_base             5
                          mod_base = OTHER
                          note = 2'-O-methoxyethyl-guanosine
modified_base             6
                          mod_base = m5c
modified_base             11
                          mod_base = m5c
modified_base             16
```

```
                        mod_base = OTHER
                        note = 2'-O-methoxyethyl-guanosine
modified_base           17..18
                        mod_base = OTHER
                        note = 2'-O-methoxyethyl-adenosine
modified_base           19
                        mod_base = OTHER
                        note = 2'-O-methoxyethyl-thymidine
modified_base           20
                        mod_base = OTHER
                        note = 2'-O-methoxyethyl-thymidine
SEQUENCE: 142
cggtgcaagg cttaggaatt                                              20

SEQ ID NO: 143          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-guanosine
modified_base           2
                        mod_base = OTHER
                        note = 2'-O-methoxyethyl-5-methylcytidine
modified_base           3..4
                        mod_base = OTHER
                        note = 2'-O-methoxyethyl-thymidine
modified_base           5
                        mod_base = OTHER
                        note = 2'-O-methoxyethyl-5-methylcytidine
modified_base           9
                        mod_base = m5c
modified_base           14
                        mod_base = m5c
modified_base           16
                        mod_base = OTHER
                        note = 2'-O-methoxyethyl-thymidine
modified_base           17..18
                        mod_base = OTHER
                        note = 2'-O-methoxyethyl-5-methylcytidine
modified_base           19
                        mod_base = OTHER
                        note = 2'-O-methoxyethyl-thymidine
modified_base           20
                        mod_base = OTHER
                        note = 2'-O-methoxyethyl-thymidine
SEQUENCE: 143
gcttcagtca tgacttcctt                                              20

SEQ ID NO: 144          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           1
                        mod_base = OTHER
                        note = 2'-O-methoxyethyl-guanosine
modified_base           2
                        mod_base = OTHER
                        note = 2'-O-methoxyethyl-5-methylcytidine
modified_base           3..4
                        mod_base = OTHER
                        note = 2'-O-methoxyethyl-thymidine
modified_base           5
                        mod_base = OTHER
                        note = 2'-O-methoxyethyl-5-methylcytidine
modified_base           9
                        mod_base = m5c
modified_base           14
                        mod_base = m5c
modified_base           16
                        mod_base = OTHER
                        note = 2'-O-methoxyethyl-thymidine
modified_base           17..18
```

```
                        mod_base = OTHER
                        note = 2'-O-methoxyethyl-5-methylcytidine
modified_base           19
                        mod_base = OTHER
                        note = 2'-O-methoxyethyl-thymidine
modified_base           20
                        mod_base = OTHER
                        note = 2'-O-methoxyethyl-thymidine
SEQUENCE: 144
gcttcagtca tgacttcctt a                                                21

SEQ ID NO: 145          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           2
                        mod_base = OTHER
                        note = 2'-O-methoxyethyl-guanosine
modified_base           3
                        mod_base = OTHER
                        note = 2'-O-methoxyethyl-5-methylcytidine
modified_base           4..5
                        mod_base = OTHER
                        note = 2'-O-methoxyethyl-thymidine
modified_base           6
                        mod_base = OTHER
                        note = 2'-O-methoxyethyl-5-methylcytidine
modified_base           10
                        mod_base = m5c
modified_base           15
                        mod_base = m5c
modified_base           17
                        mod_base = OTHER
                        note = 2'-O-methoxyethyl-thymidine
modified_base           18..19
                        mod_base = OTHER
                        note = 2'-O-methoxyethyl-5-methylcytidine
modified_base           20
                        mod_base = OTHER
                        note = 2'-O-methoxyethyl-thymidine
modified_base           21
                        mod_base = OTHER
                        note = 2'-O-methoxyethyl-thymidine
SEQUENCE: 145
agcttcagtc atgacttcct t                                                21

SEQ ID NO: 146          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-thymidine
modified_base           2..3
                        mod_base = OTHER
                        note = 2'-O-methoxyethyl-guanosine
modified_base           4
                        mod_base = OTHER
                        note = 2'-O-methoxyethyl-thymidine
modified_base           5
                        mod_base = OTHER
                        note = 2'-O-methoxyethyl-adenosine
modified_base           8..9
                        mod_base = m5c
modified_base           11
                        mod_base = m5c
modified_base           15
                        mod_base = m5c
modified_base           16
                        mod_base = OTHER
                        note = 2'-O-methoxyethyl-adenosine
modified_base           17
                        mod_base = OTHER
```

```
                    note = 2'-O-methoxyethyl-guanosine
modified_base       18
                    mod_base = OTHER
                    note = 2'-O-methoxyethyl-adenosine
modified_base       19
                    mod_base = OTHER
                    note = 2'-O-methoxyethyl-guanosine
modified_base       20
                    mod_base = OTHER
                    note = 2'-O-methoxyethyl-guanosine
SEQUENCE: 146
tggtaatcca ctttcagagg                                                   20

SEQ ID NO: 147      moltype = DNA  length = 21
FEATURE             Location/Qualifiers
misc_feature        1..21
                    note = Synthetic oligonucleotide
source              1..21
                    mol_type = other DNA
                    organism = synthetic construct
modified_base       1
                    mod_base = OTHER
                    note = 2'-O-methoxyethyl-thymidine
modified_base       2..3
                    mod_base = OTHER
                    note = 2'-O-methoxyethyl-guanosine
modified_base       4
                    mod_base = OTHER
                    note = 2'-O-methoxyethyl-thymidine
modified_base       5
                    mod_base = OTHER
                    note = 2'-O-methoxyethyl-adenosine
modified_base       8..9
                    mod_base = m5c
modified_base       11
                    mod_base = m5c
modified_base       15
                    mod_base = m5c
modified_base       16
                    mod_base = OTHER
                    note = 2'-O-methoxyethyl-adenosine
modified_base       17
                    mod_base = OTHER
                    note = 2'-O-methoxyethyl-guanosine
modified_base       18
                    mod_base = OTHER
                    note = 2'-O-methoxyethyl-adenosine
modified_base       19
                    mod_base = OTHER
                    note = 2'-O-methoxyethyl-guanosine
modified_base       20
                    mod_base = OTHER
                    note = 2'-O-methoxyethyl-guanosine
SEQUENCE: 147
tggtaatcca ctttcagagg a                                                 21

SEQ ID NO: 148      moltype = DNA  length = 21
FEATURE             Location/Qualifiers
misc_feature        1..21
                    note = Synthetic oligonucleotide
source              1..21
                    mol_type = other DNA
                    organism = synthetic construct
modified_base       2
                    mod_base = OTHER
                    note = 2'-O-methoxyethyl-guanosine
modified_base       3
                    mod_base = OTHER
                    note = 2'-O-methoxyethyl-5-methylcytidine
modified_base       4..5
                    mod_base = OTHER
                    note = 2'-O-methoxyethyl-thymidine
modified_base       6
                    mod_base = OTHER
                    note = 2'-O-methoxyethyl-5-methylcytidine
modified_base       10
                    mod_base = m5c
modified_base       15
                    mod_base = m5c
```

| | | |
|---|---|---|
| modified_base | 17 | |
| | mod_base = OTHER | |
| | note = 2'-O-methoxyethyl-thymidine | |
| modified_base | 18 | |
| | mod_base = OTHER | |
| | note = 2'-O-methoxyethyl-5-methylcytidine | |
| modified_base | 19 | |
| | mod_base = OTHER | |
| | note = 2'-O-methoxyethyl-5-methylcytidine | |
| modified_base | 20 | |
| | mod_base = OTHER | |
| | note = 2'-O-methoxyethyl-thymidine | |
| modified_base | 21 | |
| | mod_base = OTHER | |
| | note = 2'-O-methoxyethyl-thymidine | |
| SEQUENCE: 148 | | |
| tgcttcagtc atgacttcct t | | 21 |
| | | |
| SEQ ID NO: 149 | moltype = DNA  length = 20 | |
| FEATURE | Location/Qualifiers | |
| misc_feature | 1..20 | |
| | note = Synthetic oligonucleotide | |
| source | 1..20 | |
| | mol_type = other DNA | |
| | organism = synthetic construct | |
| modified_base | 1 | |
| | mod_base = OTHER | |
| | note = 2'-O-methoxyethyl-5-methylcytidine | |
| modified_base | 2 | |
| | mod_base = OTHER | |
| | note = 2'-O-methoxyethyl-adenosine | |
| modified_base | 3 | |
| | mod_base = OTHER | |
| | note = 2'-O-methoxyethyl-5-methylcytidine | |
| modified_base | 4 | |
| | mod_base = OTHER | |
| | note = 2'-O-methoxyethyl-thymidine | |
| modified_base | 5 | |
| | mod_base = OTHER | |
| | note = 2'-O-methoxyethyl-guanosine | |
| modified_base | 13..15 | |
| | mod_base = m5c | |
| modified_base | 16 | |
| | mod_base = OTHER | |
| | note = 2'-O-methoxyethyl-adenosine | |
| modified_base | 17..18 | |
| | mod_base = OTHER | |
| | note = 2'-O-methoxyethyl-guanosine | |
| modified_base | 19 | |
| | mod_base = OTHER | |
| | note = 2'-O-methoxyethyl-adenosine | |
| modified_base | 20 | |
| | mod_base = OTHER | |
| | note = 2'-O-methoxyethyl-thymidine | |
| SEQUENCE: 149 | | |
| cactgatttt tgcccaggat | | 20 |
| | | |
| SEQ ID NO: 150 | moltype = DNA  length = 21 | |
| FEATURE | Location/Qualifiers | |
| misc_feature | 1..21 | |
| | note = Synthetic oligonucleotide | |
| source | 1..21 | |
| | mol_type = other DNA | |
| | organism = synthetic construct | |
| modified_base | 1 | |
| | mod_base = OTHER | |
| | note = 2'-O-methoxyethyl-5-methylcytidine | |
| modified_base | 2 | |
| | mod_base = OTHER | |
| | note = 2'-O-methoxyethyl-adenosine | |
| modified_base | 3 | |
| | mod_base = OTHER | |
| | note = 2'-O-methoxyethyl-5-methylcytidine | |
| modified_base | 4 | |
| | mod_base = OTHER | |
| | note = 2'-O-methoxyethyl-thymidine | |
| modified_base | 5 | |
| | mod_base = OTHER | |
| | note = 2'-O-methoxyethyl-guanosine | |

```
modified_base          13..15
                       mod_base = m5c
modified_base          16
                       mod_base = OTHER
                       note = 2'-O-methoxyethyl-adenosine
modified_base          17..18
                       mod_base = OTHER
                       note = 2'-O-methoxyethyl-guanosine
modified_base          19
                       mod_base = OTHER
                       note = 2'-O-methoxyethyl-adenosine
modified_base          20
                       mod_base = OTHER
                       note = 2'-O-methoxyethyl-thymidine
SEQUENCE: 150
cactgatttt tgcccaggat a                                              21

SEQ ID NO: 151         moltype = DNA  length = 21
FEATURE                Location/Qualifiers
misc_feature           1..21
                       note = Synthetic oligonucleotide
source                 1..21
                       mol_type = other DNA
                       organism = synthetic construct
modified_base          2
                       mod_base = OTHER
                       note = 2'-O-methoxyethyl-adenosine
modified_base          3
                       mod_base = OTHER
                       note = 2'-O-methoxyethyl-guanosine
modified_base          4
                       mod_base = OTHER
                       note = 2'-O-methoxyethyl-5-methylcytidine
modified_base          5..6
                       mod_base = OTHER
                       note = 2'-O-methoxyethyl-thymidine
modified_base          7
                       mod_base = m5c
modified_base          12..13
                       mod_base = m5c
modified_base          16
                       mod_base = m5c
modified_base          17..19
                       mod_base = OTHER
                       note = 2'-O-methoxyethyl-thymidine
modified_base          20
                       mod_base = OTHER
                       note = 2'-O-methoxyethyl-adenosine
modified_base          21
                       mod_base = OTHER
                       note = 2'-O-methoxyethyl-thymidine
SEQUENCE: 151
aagcttcttg tccagcttta t                                              21

SEQ ID NO: 152         moltype = DNA  length = 20
FEATURE                Location/Qualifiers
misc_feature           1..20
                       note = Synthetic oligonucleotide
source                 1..20
                       mol_type = other DNA
                       organism = synthetic construct
modified_base          1
                       mod_base = OTHER
                       note = 2'-O-methoxyethyl-adenosine
modified_base          2..4
                       mod_base = OTHER
                       note = 2'-O-methoxyethyl-5-methylcytidine
modified_base          5
                       mod_base = OTHER
                       note = 2'-O-methoxyethyl-adenosine
modified_base          9
                       mod_base = m5c
modified_base          16..17
                       mod_base = OTHER
                       note = 2'-O-methoxyethyl-adenosine
modified_base          18..19
                       mod_base = OTHER
                       note = 2'-O-methoxyethyl-guanosine
modified_base          20
```

```
                        mod_base = OTHER
                        note = 2'-O-methoxyethyl-adenosine
SEQUENCE: 152
acccaattca gaaggaagga                                           20

SEQ ID NO: 153          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           1
                        mod_base = OTHER
                        note = 2'-O-methoxyethyl-adenosine
modified_base           2..4
                        mod_base = OTHER
                        note = 2'-O-methoxyethyl-5-methylcytidine
modified_base           5
                        mod_base = OTHER
                        note = 2'-O-methoxyethyl-adenosine
modified_base           9
                        mod_base = m5c
modified_base           16..17
                        mod_base = OTHER
                        note = 2'-O-methoxyethyl-adenosine
modified_base           18..19
                        mod_base = OTHER
                        note = 2'-O-methoxyethyl-guanosine
modified_base           20
                        mod_base = OTHER
                        note = 2'-O-methoxyethyl-adenosine
SEQUENCE: 153
acccaattca gaaggaagga a                                         21

SEQ ID NO: 154          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           2
                        mod_base = OTHER
                        note = 2'-O-methoxyethyl-adenosine
modified_base           3..5
                        mod_base = OTHER
                        note = 2'-O-methoxyethyl-5-methylcytidine
modified_base           6
                        mod_base = OTHER
                        note = 2'-O-methoxyethyl-adenosine
modified_base           10
                        mod_base = m5c
modified_base           17..18
                        mod_base = OTHER
                        note = 2'-O-methoxyethyl-adenosine
modified_base           19..20
                        mod_base = OTHER
                        note = 2'-O-methoxyethyl-guanosine
modified_base           21
                        mod_base = OTHER
                        note = 2'-O-methoxyethyl-adenosine
SEQUENCE: 154
aacccaattc agaaggaagg a                                         21

SEQ ID NO: 155          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           2
                        mod_base = OTHER
                        note = 2'-O-methoxyethyl-thymidine
modified_base           3..4
                        mod_base = OTHER
                        note = 2'-O-methoxyethyl-guanosine
modified_base           5
```

```
                        mod_base = OTHER
                        note = 2'-O-methoxyethyl-thymidine
modified_base           6
                        mod_base = OTHER
                        note = 2'-O-methoxyethyl-adenosine
modified_base           9..10
                        mod_base = m5c
modified_base           12
                        mod_base = m5c
modified_base           16
                        mod_base = m5c
modified_base           17
                        mod_base = OTHER
                        note = 2'-O-methoxyethyl-adenosine
modified_base           18
                        mod_base = OTHER
                        note = 2'-O-methoxyethyl-guanosine
modified_base           19
                        mod_base = OTHER
                        note = 2'-O-methoxyethyl-adenosine
modified_base           20
                        mod_base = OTHER
                        note = 2'-O-methoxyethyl-guanosine
modified_base           21
                        mod_base = OTHER
                        note = 2'-O-methoxyethyl-guanosine
SEQUENCE: 155
atggtaatcc actttcagag g                                                    21

SEQ ID NO: 156          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-thymidine
modified_base           2
                        mod_base = OTHER
                        note = 2'-O-methoxyethyl-5-methylcytidine
modified_base           3..4
                        mod_base = OTHER
                        note = 2'-O-methoxyethyl-thymidine
modified_base           5
                        mod_base = OTHER
                        note = 2'-O-methoxyethyl-guanosine
modified_base           10
                        mod_base = m5c
modified_base           16
                        mod_base = OTHER
                        note = 2'-O-methoxyethyl-adenosine
modified_base           17
                        mod_base = OTHER
                        note = 2'-O-methoxyethyl-thymidine
modified_base           18..19
                        mod_base = OTHER
                        note = 2'-O-methoxyethyl-5-methylcytidine
modified_base           20
                        mod_base = OTHER
                        note = 2'-O-methoxyethyl-5-methylcytidine
SEQUENCE: 156
tcttggttac atgaaatccc                                                      20

SEQ ID NO: 157          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           1
                        mod_base = OTHER
                        note = 2'-O-methoxyethyl-thymidine
modified_base           2
                        mod_base = OTHER
                        note = 2'-O-methoxyethyl-5-methylcytidine
modified_base           3..4
```

```
                        mod_base = OTHER
                        note = 2'-O-methoxyethyl-thymidine
modified_base           5
                        mod_base = OTHER
                        note = 2'-O-methoxyethyl-guanosine
modified_base           10
                        mod_base = m5c
modified_base           16
                        mod_base = OTHER
                        note = 2'-O-methoxyethyl-adenosine
modified_base           17
                        mod_base = OTHER
                        note = 2'-O-methoxyethyl-thymidine
modified_base           18..19
                        mod_base = OTHER
                        note = 2'-O-methoxyethyl-5-methylcytidine
modified_base           20
                        mod_base = OTHER
                        note = 2'-O-methoxyethyl-5-methylcytidine
SEQUENCE: 157
tcttggttac atgaaatccc a                                           21

SEQ ID NO: 158          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-adenosine
modified_base           2..3
                        mod_base = OTHER
                        note = 2'-O-methoxyethyl-thymidine
modified_base           4
                        mod_base = OTHER
                        note = 2'-O-methoxyethyl-5-methylcytidine
modified_base           5
                        mod_base = OTHER
                        note = 2'-O-methoxyethyl-adenosine
modified_base           6
                        mod_base = OTHER
                        note = 2'-O-methoxyethyl-5-methylcytidine
modified_base           7..9
                        mod_base = OTHER
                        note = 2'-O-methoxyethyl-thymidine
modified_base           10
                        mod_base = OTHER
                        note = 2'-O-methoxyethyl-5-methylcytidine
modified_base           11
                        mod_base = OTHER
                        note = 2'-O-methoxyethyl-adenosine
modified_base           12
                        mod_base = OTHER
                        note = 2'-O-methoxyethyl-thymidine
modified_base           13..14
                        mod_base = OTHER
                        note = 2'-O-methoxyethyl-adenosine
modified_base           15
                        mod_base = OTHER
                        note = 2'-O-methoxyethyl-thymidine
modified_base           16
                        mod_base = OTHER
                        note = 2'-O-methoxyethyl-guanosine
modified_base           17
                        mod_base = OTHER
                        note = 2'-O-methoxyethyl-5-methylcytidine
modified_base           18
                        mod_base = OTHER
                        note = 2'-O-methoxyethyl-thymidine
modified_base           19
                        mod_base = OTHER
                        note = 2'-O-methoxyethyl-guanosine
modified_base           20
                        mod_base = OTHER
                        note = 2'-O-methoxyethyl-guanosine
SEQUENCE: 158
attcactttc ataatgctgg                                             20
```

-continued

```
SEQ ID NO: 159          moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 159
attcactttc ataatgctgg a                                                 21

SEQ ID NO: 160          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           2
                        mod_base = OTHER
                        note = 2'-O-methoxyethyl-thymidine
modified_base           3
                        mod_base = OTHER
                        note = 2'-O-methoxyethyl-5-methylcytidine
modified_base           4..5
                        mod_base = OTHER
                        note = 2'-O-methoxyethyl-thymidine
modified_base           6
                        mod_base = OTHER
                        note = 2'-O-methoxyethyl-guanosine
modified_base           11
                        mod_base = m5c
modified_base           17
                        mod_base = OTHER
                        note = 2'-O-methoxyethyl-adenosine
modified_base           18
                        mod_base = OTHER
                        note = 2'-O-methoxyethyl-thymidine
modified_base           19..20
                        mod_base = OTHER
                        note = 2'-O-methoxyethyl-5-methylcytidine
modified_base           21
                        mod_base = OTHER
                        note = 2'-O-methoxyethyl-5-methylcytidine
SEQUENCE: 160
atcttggtta catgaaatcc c                                                 21

SEQ ID NO: 161          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-adenosine
modified_base           2
                        mod_base = OTHER
                        note = 2'-O-methoxyethyl-thymidine
modified_base           3
                        mod_base = OTHER
                        note = 2'-O-methoxyethyl-guanosine
modified_base           4
                        mod_base = OTHER
                        note = 2'-O-methoxyethyl-5-methylcytidine
modified_base           5
                        mod_base = OTHER
                        note = 2'-O-methoxyethyl-adenosine
modified_base           14
                        mod_base = m5c
modified_base           16
                        mod_base = OTHER
                        note = 2'-O-methoxyethyl-thymidine
modified_base           17
                        mod_base = OTHER
                        note = 2'-O-methoxyethyl-5-methylcytidine
modified_base           18
                        mod_base = OTHER
```

```
                        note = 2'-O-methoxyethyl-thymidine
modified_base           19
                        mod_base = OTHER
                        note = 2'-O-methoxyethyl-guanosine
modified_base           20
                        mod_base = OTHER
                        note = 2'-O-methoxyethyl-adenosine
SEQUENCE: 161
atgcatggtg atgcttctga                                                          20

SEQ ID NO: 162          moltype = DNA   length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = OTHER
                        note = 2'-O-methoxyethyl-5-methylcytidine
modified_base           2
                        mod_base = OTHER
                        note = 2'-O-methoxyethyl-adenosine
modified_base           3
                        mod_base = OTHER
                        note = 2'-O-methoxyethyl-guanosine
modified_base           4
                        mod_base = OTHER
                        note = 2'-O-methoxyethyl-5-methylcytidine
modified_base           5
                        mod_base = OTHER
                        note = 2'-O-methoxyethyl-thymidine
modified_base           16
                        mod_base = OTHER
                        note = 2'-O-methoxyethyl-5-methylcytidine
modified_base           17
                        mod_base = OTHER
                        note = 2'-O-methoxyethyl-adenosine
modified_base           18
                        mod_base = OTHER
                        note = 2'-O-methoxyethyl-guanosine
modified_base           19
                        mod_base = OTHER
                        note = 2'-O-methoxyethyl-5-methylcytidine
modified_base           20
                        mod_base = OTHER
                        note = 2'-O-methoxyethyl-adenosine
SEQUENCE: 162
cagctttatt agggacagca                                                          20

SEQ ID NO: 163          moltype = DNA   length = 21
FEATURE                 Location/Qualifiers
misc_feature            1..21
                        note = Synthetic oligonucleotide
source                  1..21
                        mol_type = other DNA
                        organism = synthetic construct
modified_base           1
                        mod_base = OTHER
                        note = 2'-O-methoxyethyl-5-methylcytidine
modified_base           2
                        mod_base = OTHER
                        note = 2'-O-methoxyethyl-adenosine
modified_base           3
                        mod_base = OTHER
                        note = 2'-O-methoxyethyl-guanosine
modified_base           4
                        mod_base = OTHER
                        note = 2'-O-methoxyethyl-5-methylcytidine
modified_base           5
                        mod_base = OTHER
                        note = 2'-O-methoxyethyl-thymidine
modified_base           16
                        mod_base = OTHER
                        note = 2'-O-methoxyethyl-5-methylcytidine
modified_base           17
                        mod_base = OTHER
                        note = 2'-O-methoxyethyl-adenosine
modified_base           18
```

```
                            mod_base = OTHER
                            note = 2'-O-methoxyethyl-guanosine
modified_base               19
                            mod_base = OTHER
                            note = 2'-O-methoxyethyl-5-methylcytidine
modified_base               20
                            mod_base = OTHER
                            note = 2'-O-methoxyethyl-adenosine
SEQUENCE: 163
cagctttatt agggacagca a                                              21

SEQ ID NO: 164              moltype = DNA  length = 21
FEATURE                     Location/Qualifiers
misc_feature                1..21
                            note = Synthetic oligonucleotide
source                      1..21
                            mol_type = other DNA
                            organism = synthetic construct
modified_base               2
                            mod_base = OTHER
                            note = 2'-O-methoxyethyl-5-methylcytidine
modified_base               4
                            mod_base = OTHER
                            note = 2'-O-methoxyethyl-guanosine
modified_base               5
                            mod_base = OTHER
                            note = 2'-O-methoxyethyl-5-methylcytidine
modified_base               3
                            mod_base = OTHER
                            note = 2'-O-methoxyethyl-adenosine
modified_base               6
                            mod_base = OTHER
                            note = 2'-O-methoxyethyl-thymidine
modified_base               17
                            mod_base = OTHER
                            note = 2'-O-methoxyethyl-5-methylcytidine
modified_base               18
                            mod_base = OTHER
                            note = 2'-O-methoxyethyl-adenosine
modified_base               19
                            mod_base = OTHER
                            note = 2'-O-methoxyethyl-guanosine
modified_base               20
                            mod_base = OTHER
                            note = 2'-O-methoxyethyl-5-methylcytidine
modified_base               21
                            mod_base = OTHER
                            note = 2'-O-methoxyethyl-adenosine
SEQUENCE: 164
acagctttat tagggacagc a                                              21

SEQ ID NO: 165              moltype = DNA  length = 16
FEATURE                     Location/Qualifiers
misc_feature                1..16
                            note = Synthetic oligonucleotide
source                      1..16
                            mol_type = other DNA
                            organism = synthetic construct
modified_base               1..2
                            mod_base = OTHER
                            note = 6'-(S)-methyl-thymidine
modified_base               3
                            mod_base = OTHER
                            note = 6'-(S)-methyl-5-methylcytidine
modified_base               7
                            mod_base = m5c
modified_base               12
                            mod_base = m5c
modified_base               14
                            mod_base = OTHER
                            note = 6'-(S)-methyl-thymidine
modified_base               15
                            mod_base = OTHER
                            note = 6'-(S)-methyl-5-methylcytidine
modified_base               16
                            mod_base = OTHER
                            note = 6'-(S)-methyl-5-methylcytidine
SEQUENCE: 165
ttcagtcatg acttcc                                                    16
```

```
SEQ ID NO: 166          moltype = DNA  length = 20
FEATURE                 Location/Qualifiers
misc_feature            1..20
                        note = Synthetic oligonucleotide
source                  1..20
                        mol_type = other DNA
                        organism = synthetic construct
modified_base           1
                        mod_base = gm
modified_base           2
                        mod_base = cm
modified_base           5
                        mod_base = cm
modified_base           3..4
                        mod_base = um
modified_base           16
                        mod_base = um
modified_base           9
                        mod_base = cm
modified_base           14
                        mod_base = m5c
modified_base           17..18
                        mod_base = cm
modified_base           19..20
                        mod_base = um
misc_feature            1..5
                        note = bases at these poistions are RNA
misc_feature            16..20
                        note = bases at these poistions are RNA
misc_feature            6..15
                        note = bases at these positions are DNA
SEQUENCE: 166
gcttcagtca tgacttcctt                                                   20

SEQ ID NO: 167          moltype = DNA  length = 21
FEATURE                 Location/Qualifiers
misc_feature            1..21
                        note = Synthetic oligonucleotide
source                  1..21
                        mol_type = other DNA
                        organism = synthetic construct
modified_base           1
                        mod_base = OTHER
                        note = 2'-O-methoxyethyl-thymidine
modified_base           2
                        mod_base = OTHER
                        note = 2'-O-methoxyethyl-guanosine
modified_base           3
                        mod_base = OTHER
                        note = 2'-O-methoxyethyl-5-methylcytidine
modified_base           4
                        mod_base = OTHER
                        note = 2'-O-methoxyethyl-thymidine
modified_base           5
                        mod_base = OTHER
                        note = 2'-O-methoxyethyl-5-methylcytidine
modified_base           6
                        mod_base = m5c
modified_base           14
                        mod_base = m5c
modified_base           16
                        mod_base = OTHER
                        note = 2'-O-methoxyethyl-thymidine
modified_base           17
                        mod_base = OTHER
                        note = 2'-O-methoxyethyl-guanosine
modified_base           18..19
                        mod_base = OTHER
                        note = 2'-O-methoxyethyl-thymidine
modified_base           20
                        mod_base = OTHER
                        note = 2'-O-methoxyethyl-5-methylcytidine
SEQUENCE: 167
tgctccgttg gtgcttgttc a                                                 21
```

COMPOSITIONS AND METHODS FOR MODULATING APOLIPOPROTEIN (a) EXPRESSION

RELATED APPLICATIONS

This application is a continuation of U.S. application Ser. No. 17/060,440, filed on Oct. 1, 2020, which a continuation of U.S. application Ser. No. 15/891,156, filed on Feb. 7, 2018, now U.S. Pat. No. 10,883,104, which is a continuation of U.S. application Ser. No. 14/839,580, filed on Aug. 28, 2015, now U.S. Pat. No. 9,957,504, which is a continuation of U.S. application Ser. No. 14/588,061, filed on Dec. 31, 2014, now U.S. Pat. No. 9,181,550, which is a continuation of International Application No. PCT/US2014/036460 with an international filing date of May 1, 2014, which claims the benefit of and priority to U.S. Provisional Application Nos: 61/818,442, filed on May 1, 2013; 61/823,826, filed May 15, 2013; 61/843,887, filed Jul. 8, 2013; 61/871,673, filed Aug. 29, 2013; 61/880,790, filed Sep. 20, 2013; 61/976,991, filed Apr. 8, 2014; 61/986,867, filed Apr. 30, 2014; the entire contents of each of which are incorporated herein by reference in their entireties.

SEQUENCE LISTING

The present application is being filed along with a Sequence Listing in electronic format. The Sequence Listing is provided as a file entitled "PAT058755-US-CNT05 Sequence listing.xml", created on Jun. 14, 2024, which is 674 Kb in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, CA) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Ergou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009)361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; WO2013/177468; US20040242516; U.S. Pat. Nos. 8,138,328, 8,673,632 and 7,259,150; Merki et al., J Am Coll Cardiol 2011; 57:1611-1621; each publication incorporated by reference in its entirely) have been developed but none have been approved for commercial use.

Thus, there remains a clear unmet medical need for novel agents which can potently and selectively reduce apo(a) levels in patients at enhanced risk for cardiovascular events due to chronically elevated plasma Lp(a) levels.

SUMMARY OF THE INVENTION

Provided herein are compositions and methods for modulating expression of apo(a) mRNA and protein. In certain embodiments, the apo(a) specific inhibitor decreases expression of apo(a) mRNA and protein. Provided herein are compositions and methods for modulating expression of Lp(a) levels.

In certain embodiments, the composition is an apo(a) specific inhibitor. In certain embodiments, the apo(a) specific inhibitor is a nucleic acid, protein, or small molecule. In certain embodiments, the apo(a) specific inhibitor is an antisense oligonucleotide targeting apo(a) with a conjugate. In certain embodiments, the apo(a) specific inhibitor is a modified oligonucleotide and a conjugate, wherein the modified oligonucleotide consists of 12 to 30 linked nucleosides and comprises a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide and a conjugate, wherein the modified oligonucleotide consists of 12 to 30 linked nucleosides and has a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 1-130, 133, 134. In certain embodiments, the apo(a) specific inhibitor is a modified oligonucleotide and a conjugate, wherein the modified oligonucleotide consists of 20 linked nucleosides and has a nucleobase sequence comprising at least 8 contiguous nucleobases of any of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a composition comprising a conjugated antisense compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

Certain embodiments provide conjugated antisense compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide. In certain embodiments, the antisense compound is a modified oligonucleotide with a conjugate.

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., PNAS vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022. Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc3-10 in Example 46 and GalNAc3-7 in Example 48 are much simpler than previously described conjugates such as those described in U.S. Pat. No. 8,106,022 or U.S. Pat. No. 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

$$A-B-C-D-(E-F)_q$$

wherein
A is the antisense oligonucleotide;
B is the cleavable moiety
C is the conjugate linker
D is the branching group
each E is a tether;
each F is a ligand; and
q is an integer between 1 and 5.

In the above diagram and in similar diagrams herein, the branching group "D" branches as many times as is necessary to accommodate the number of (E-F) groups as indicated by "q". Thus, where q=1, the formula is:

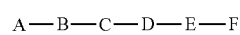

where q=2, the formula is:

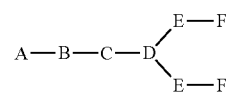

where q=3, the formula is:

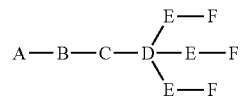

where q=4, the formula is:

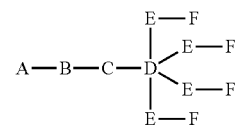

where q=5, the formula is:

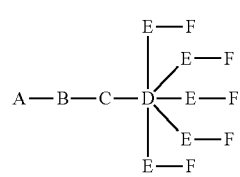

In certain embodiments, conjugated antisense compounds are provided having the structure:

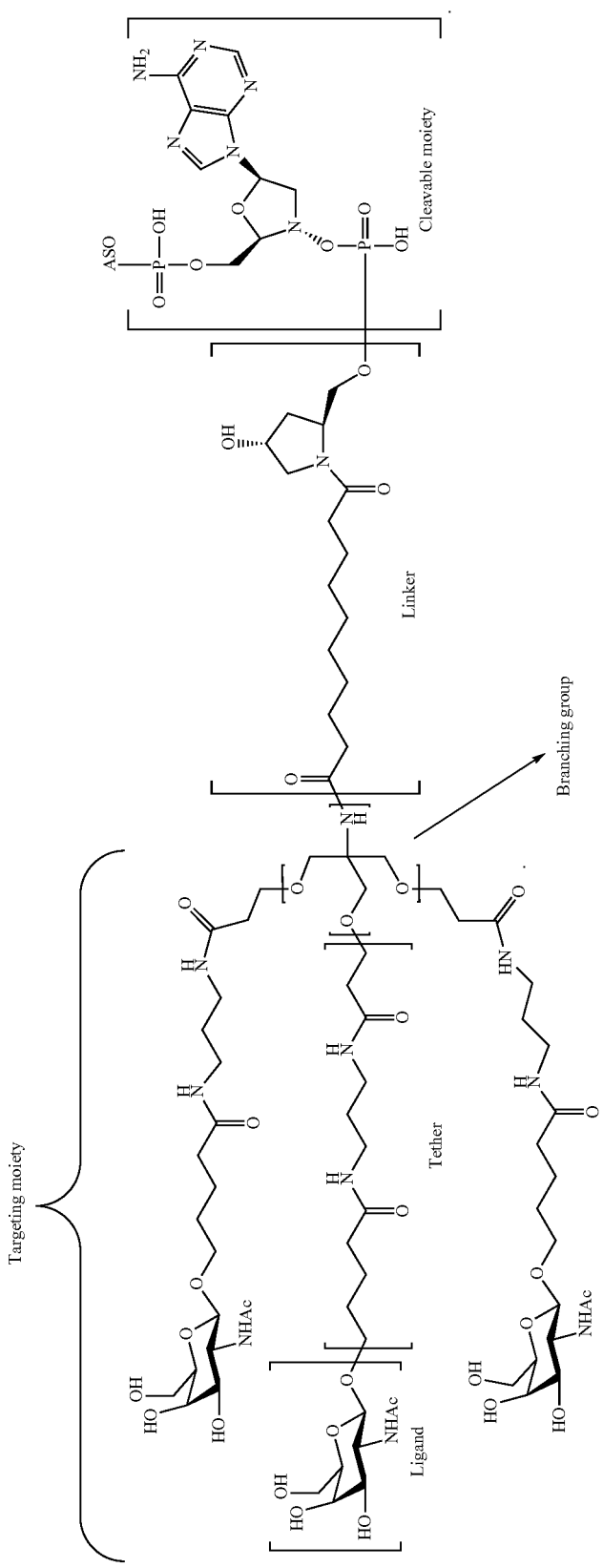

In certain embodiments, conjugated antisense compounds are provided having the structure:
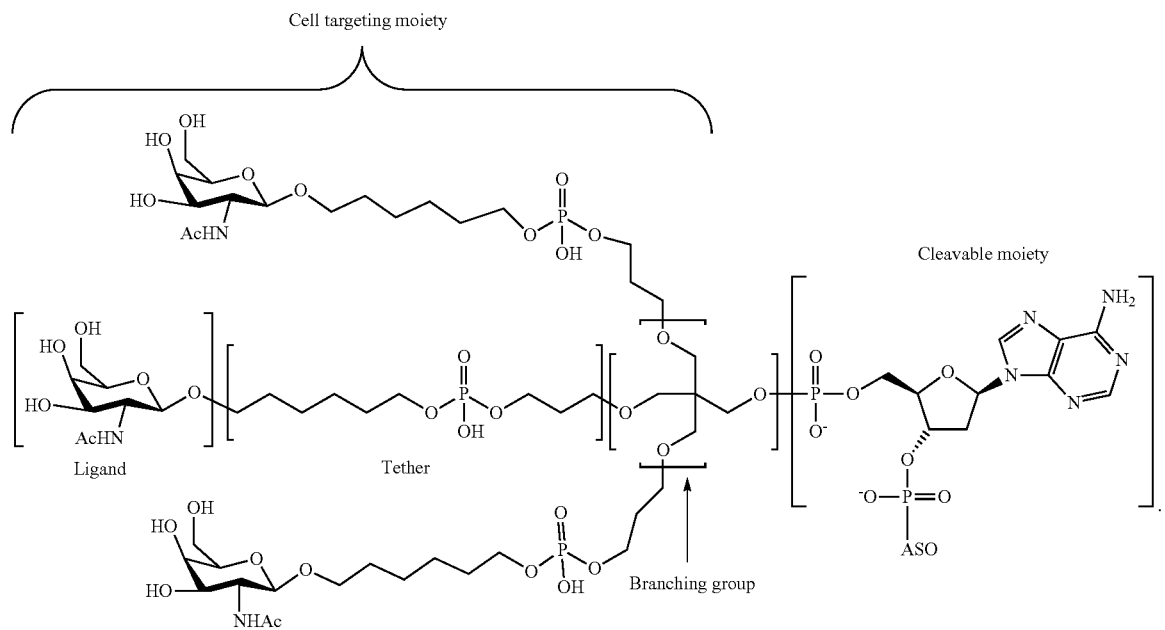
In certain embodiments, conjugated antisense compounds are provided having the structure:
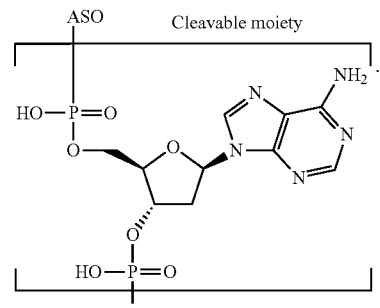

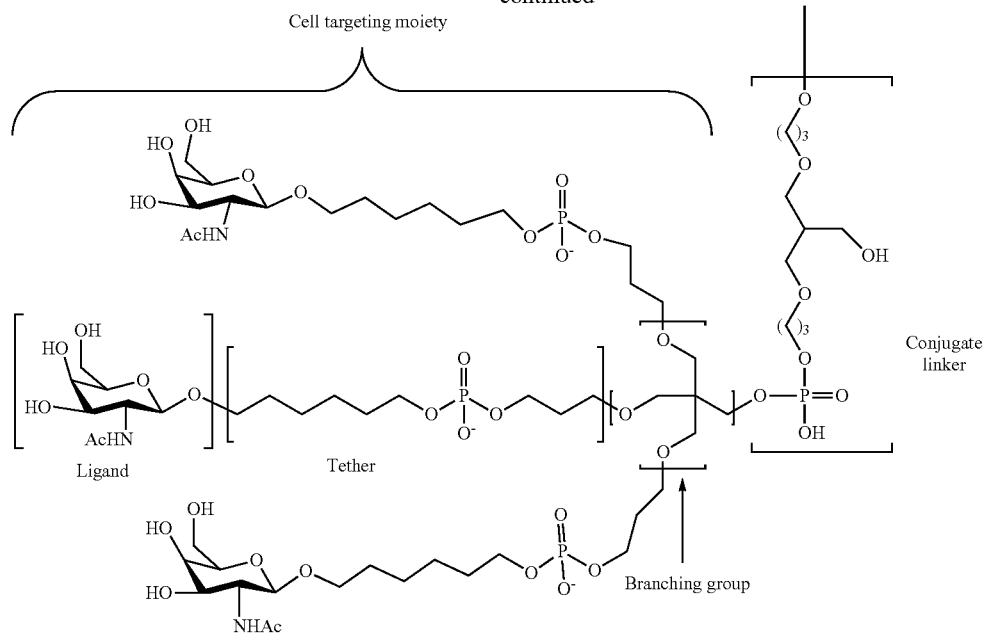

In certain embodiments, conjugated antisense compounds are provided having the structure:

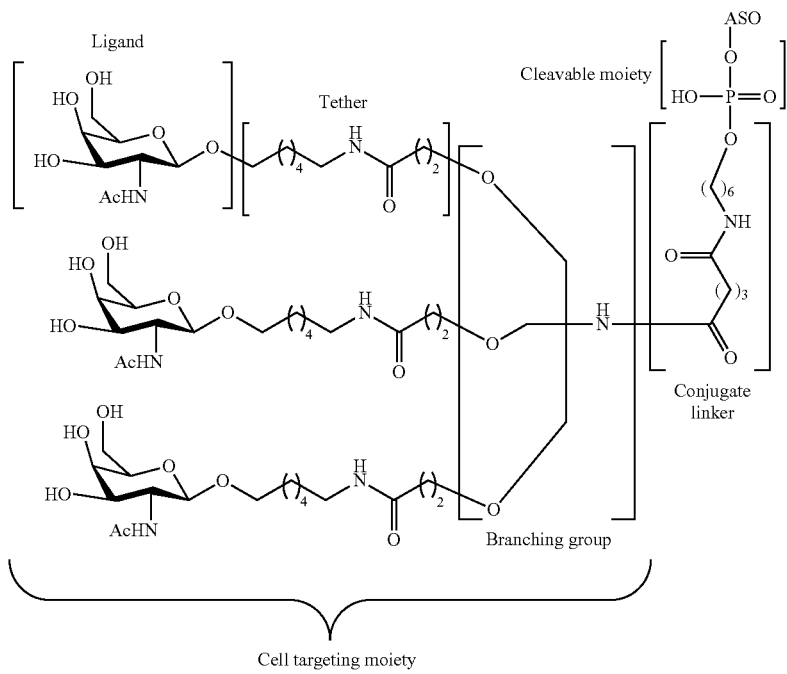

The present disclosure provides the following non-limiting numbered embodiments:

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

In certain embodiments, the present disclosure provides conjugated antisense compounds represented by the following structure. In certain embodiments, the antisense compound comprises modified oligonucleotide ISIS 494372 with a 5'-X, wherein X is a conjugate group comprising GalNAc. In certain embodiments, the antisense compound consists of modified oligonucleotide ISIS 494372 with a 5'-X, wherein X is a conjugate group comprising GalNAc.

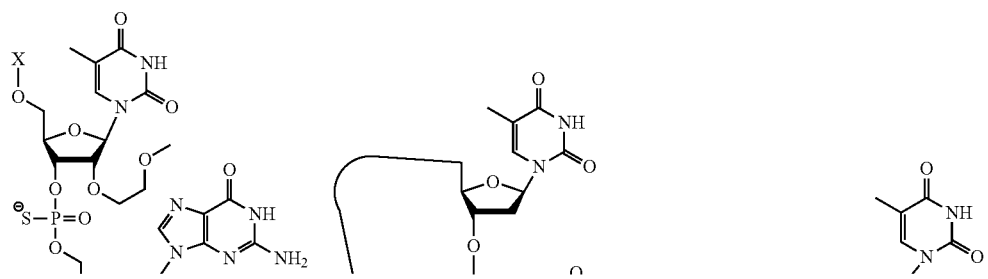
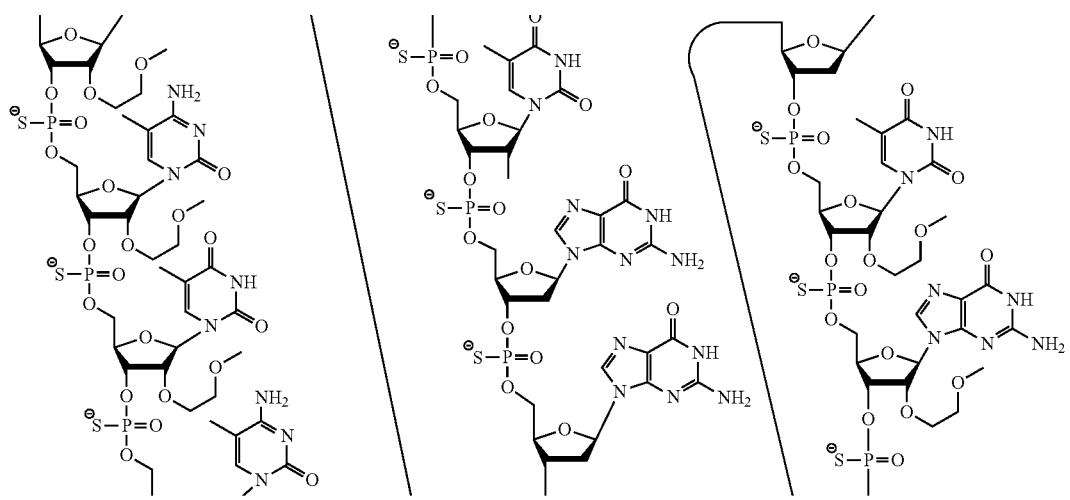
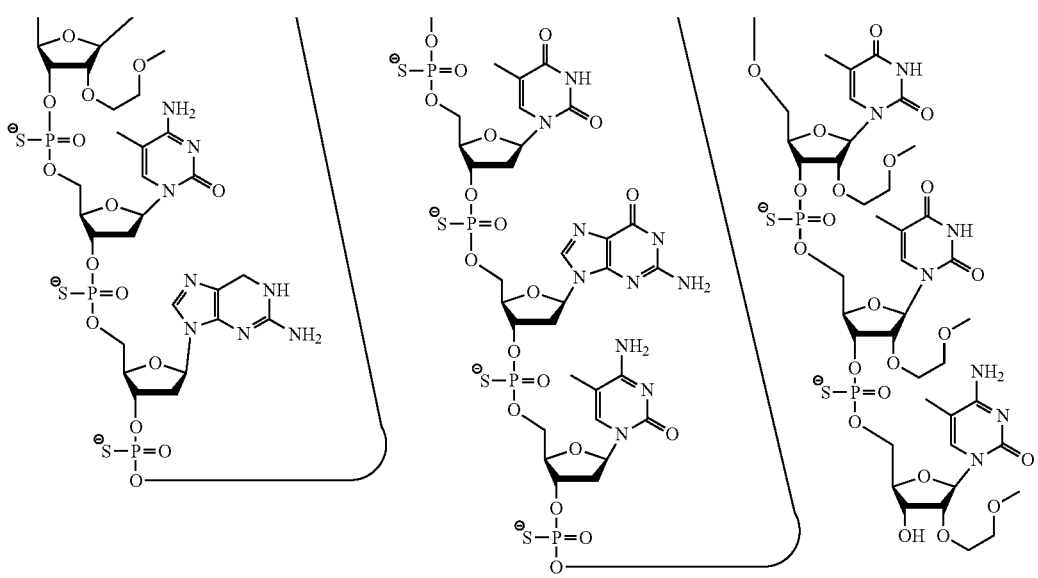
In certain embodiments, the present disclosure provides conjugated antisense compounds represented by the following structure. In certain embodiments, the antisense compound comprises the conjugated modified oligonucleotide ISIS 681251. In certain embodiments, the antisense compound consists of the conjugated modified oligonucleotide ISIS 681251.

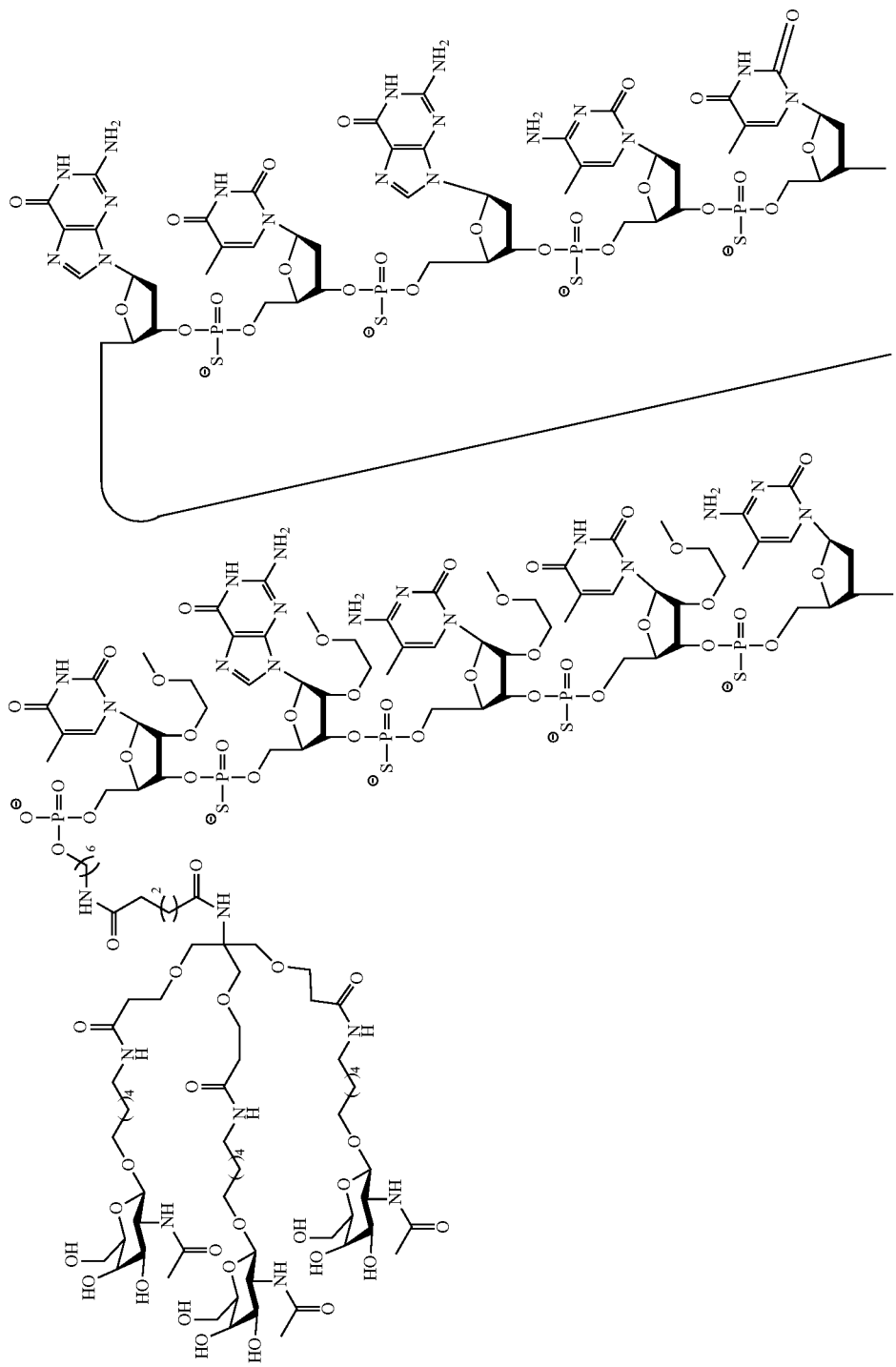

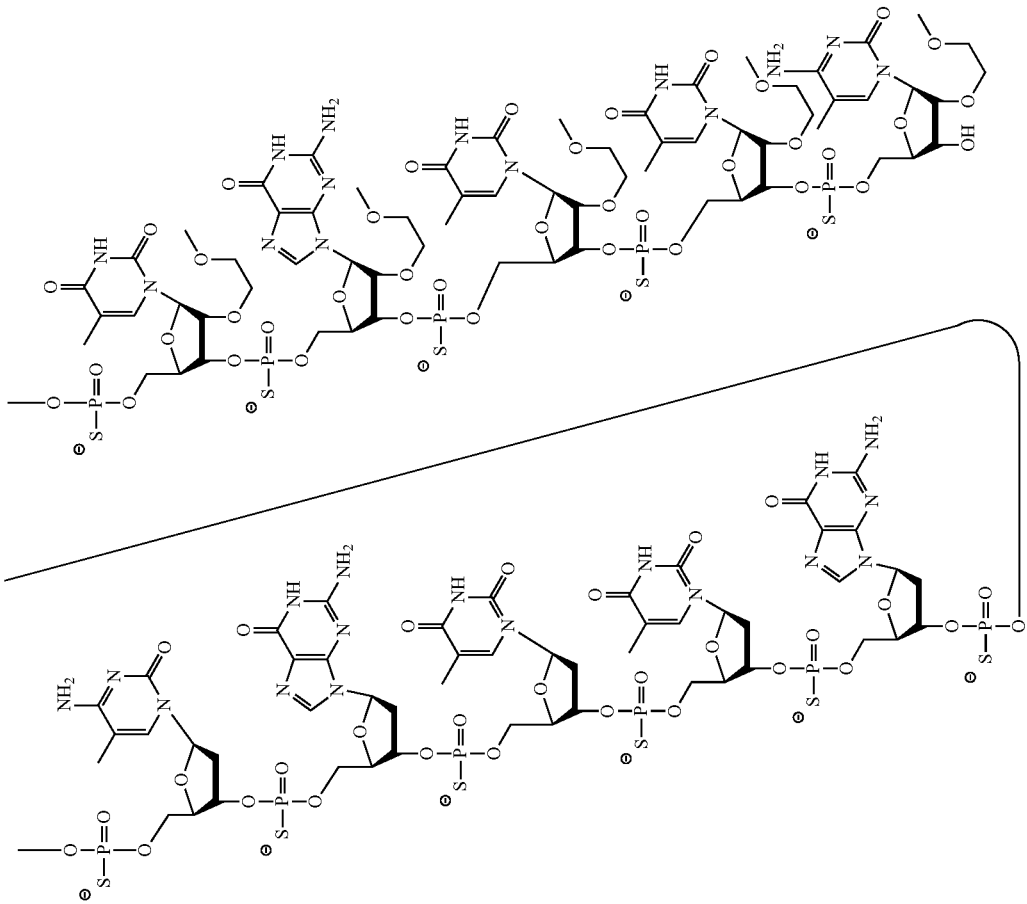

In certain embodiments, the present disclosure provides conjugated antisense compounds represented by the following structure. In certain embodiments, the antisense compound comprises the conjugated modified oligonucleotide ISIS 681257. In certain embodiments, the antisense compound consists of the conjugated modified oligonucleotide ISIS 681257.

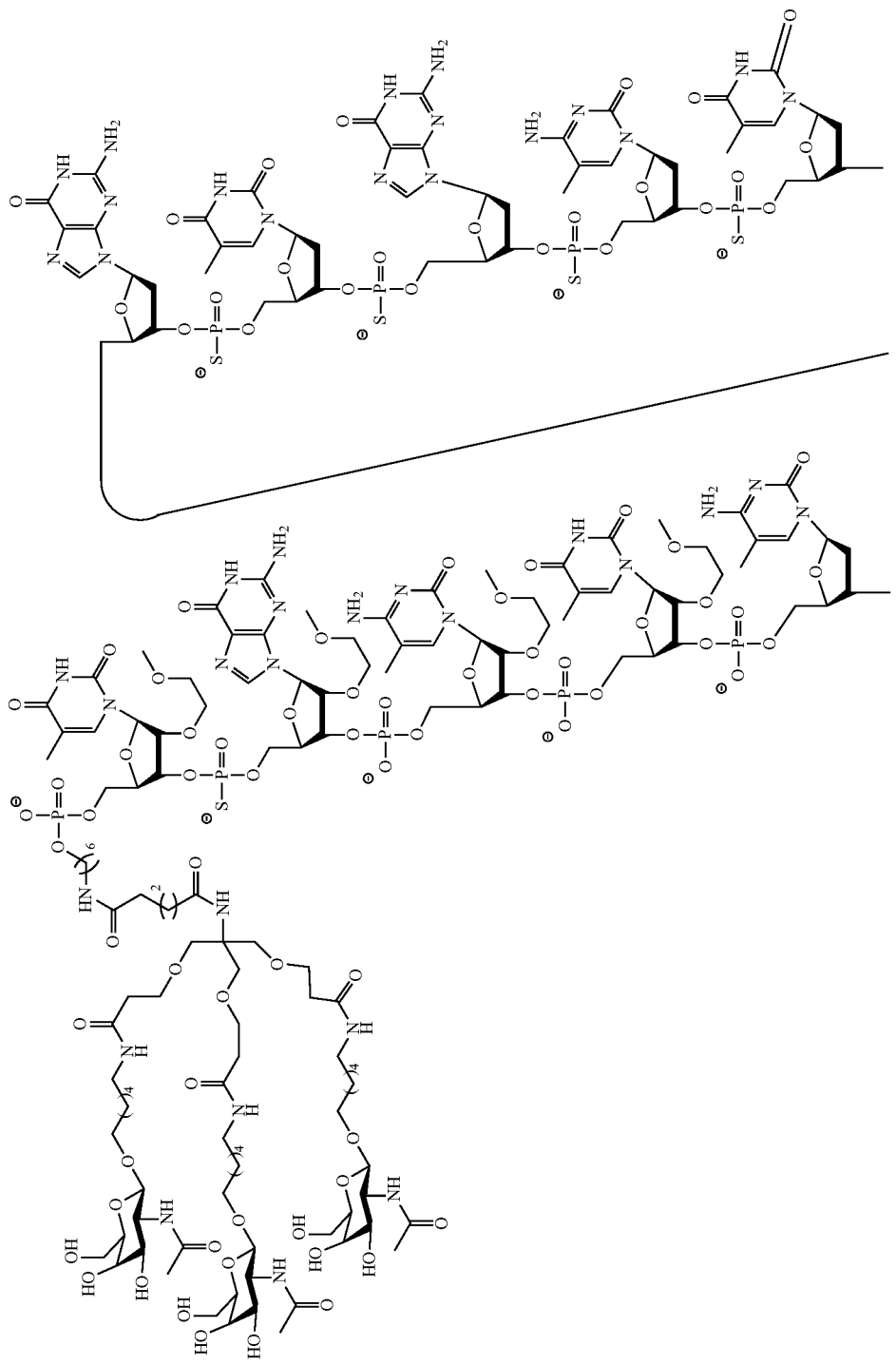

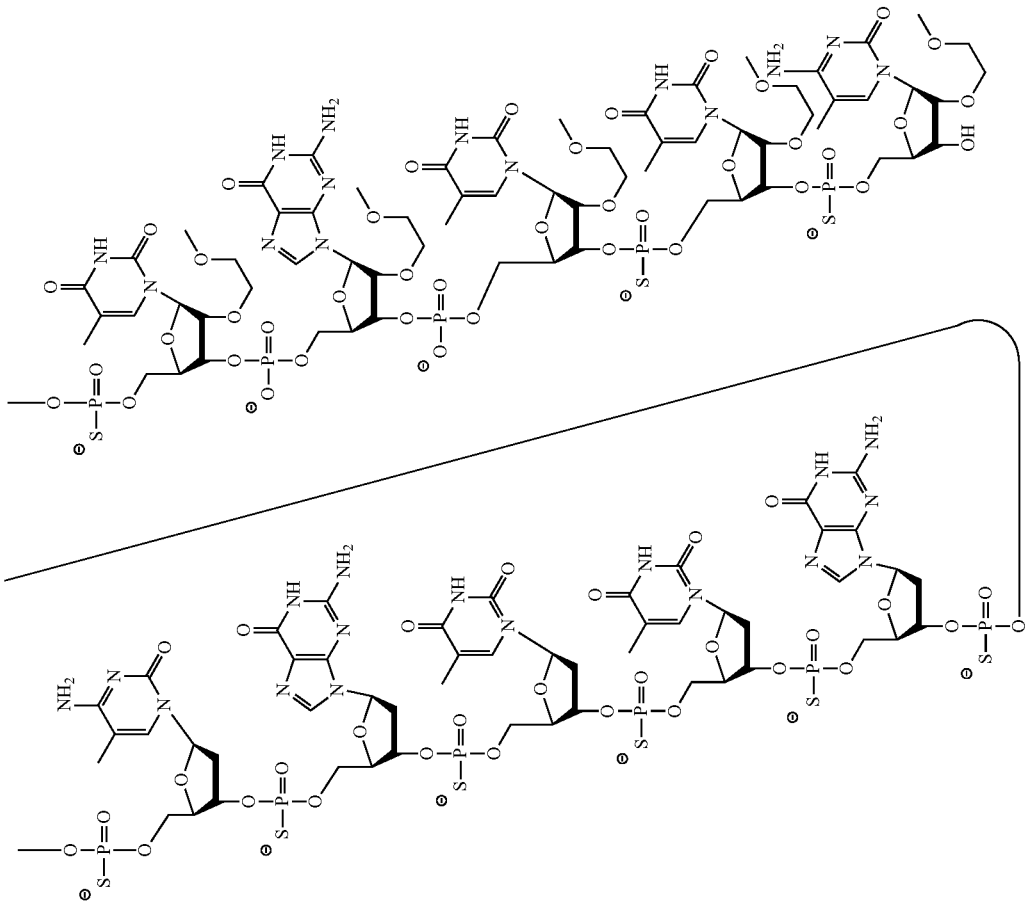

In certain embodiments, the present disclosure provides conjugated antisense compounds represented by the following structure. In certain embodiments, the antisense compound comprises a modified oligonucleotide with SEQ ID NO: 58 with a 5'-GalNAc with variability in the sugar mods of the wings. In certain embodiments, the antisense compound consists of a modified oligonucleotide with SEQ ID NO: 58 with a 5'-GalNAc with variability in the sugar mods of the wings.

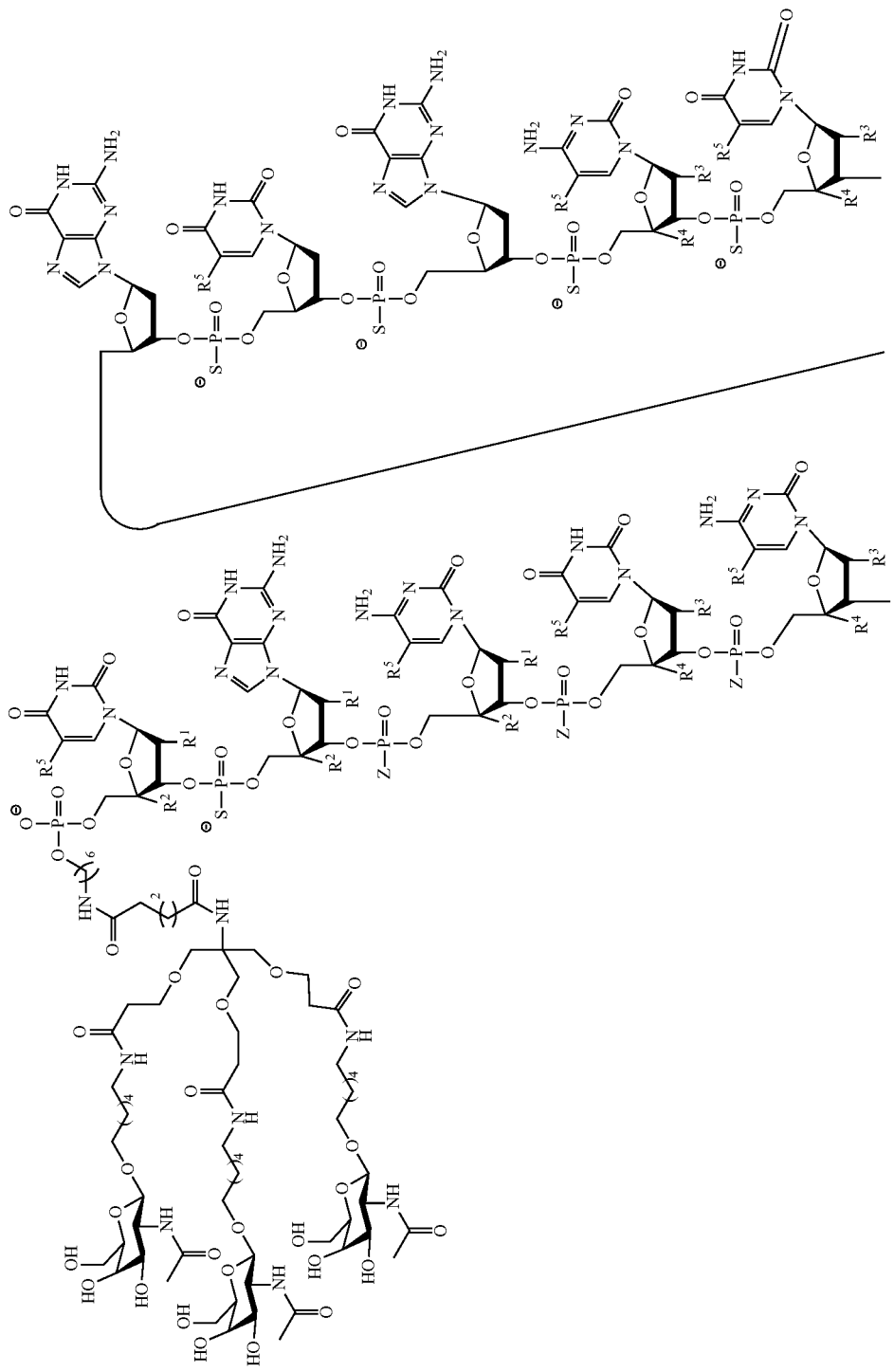

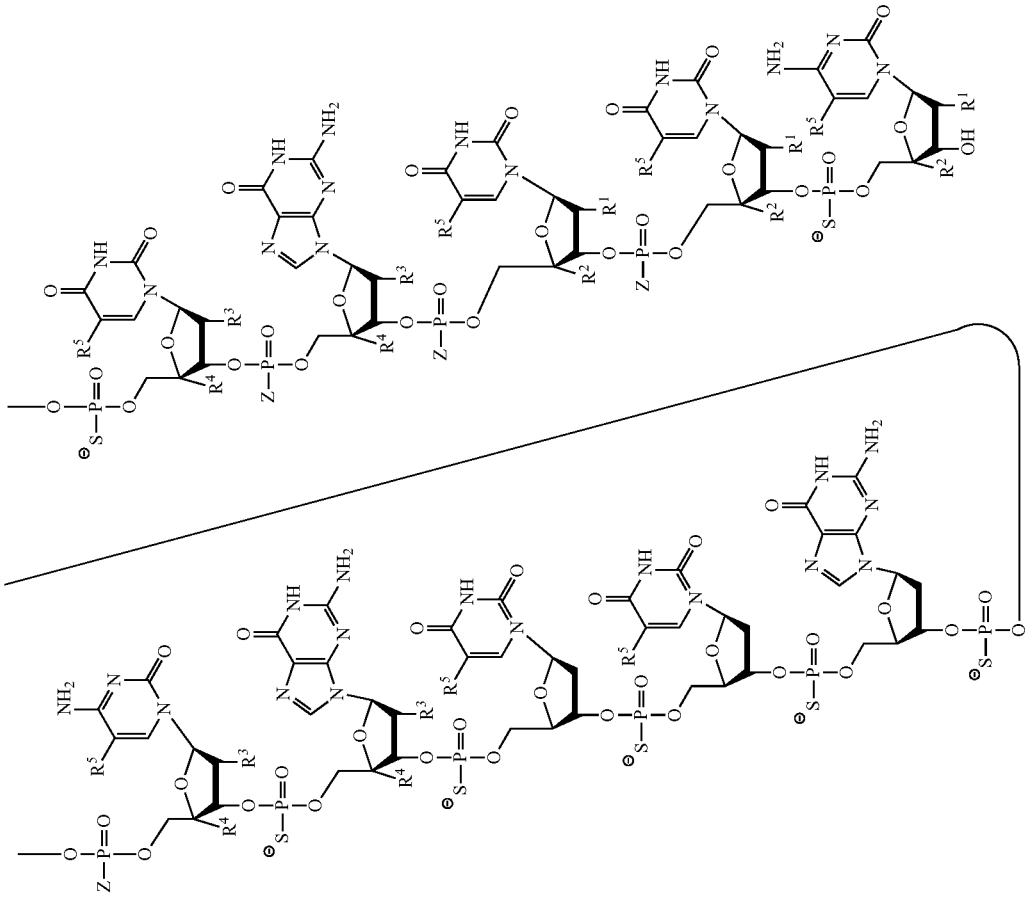

Wherein either $R^1$ is —OCH$_2$CH$_2$OCH$_3$ (MOE) and $R^2$ is H; or $R^1$ and R2 together form a bridge, wherein $R^1$ is —O— and $R^2$ is —CH$_2$—, —CH(CH$_3$)—, or —CH$_2$CH$_2$—, and $R^1$ and $R^2$ are directly connected such that the resulting bridge is selected from: —O—CH$_2$—, —O—CH(CH$_3$)—, and —O—CH$_2$CH$_2$—;

And for each pair of $R^3$ and $R^4$ on the same ring, independently for each ring: either $R^3$ is selected from H and —OCH$_2$CH$_2$OCH$_3$ and $R^4$ is H; or $R^3$ and $R^4$ together form a bridge, wherein $R^3$ is —O—, and $R^4$ is —CH$_2$—, —CH(CH$_3$)—, or —CH$_2$CH$_2$— and $R^3$ and $R^4$ are directly connected such that the resulting bridge is selected from: —O—CH$_2$—, —O—CH(CH$_3$)—, and —O—CH$_2$CH$_2$—;

And $R^5$ is selected from H and —CH$_3$;

And Z is selected from S$^-$ and O$^-$.

The present disclosure provides the following non-limiting numbered embodiments:

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Florida; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified. As used herein, "nucleobase sequence" means the order of contiguous nucleobases independent of any sugar, linkage, or nucleobase modification.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

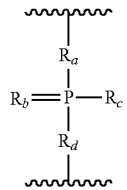

wherein:
R$_a$ and R$_d$ are each, independently, O, S, CH$_2$, NH, or NJ$_1$ wherein J$_1$ is C$_1$-C$_6$ alkyl or substituted C$_1$-C$_6$ alkyl;
R$_b$ is O or S;
R$_c$ is OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino; and
J$_1$ is R$_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI (—CH$_2$—N(CH$_3$)—O—), amide-3 (—CH$_2$—C(=O)—N(H)—), amide-4 (—CH$_2$—N(H)—C(=O)—), formacetal (—O—CH$_2$—O—), and thioformacetal (—S—CH$_2$—O—). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3-hydroxyl group of the 3' terminal nucleoside of the oligomeric compound. In certain embodiments the point of attachment on the oligomeric compound is the 5'-oxygen atom of the 5-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "$GalNAc_3$". In certain embodiments, the carbohydrate cluster portion comprises 4 GalNAc groups and is designated "$GalNAc_4$". Specific carbohydrate cluster portions (having specific tether, branching and conjugate linker groups) are described herein and designated by Roman numeral followed by subscript "a". Accordingly "$GalNac3-1_a$" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, "cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "double stranded" means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "RISC based antisense compound" means an antisense compound wherein at least some of the antisense activity of the antisense compound is attributable to the RNA Induced Silencing Complex (RISC).

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "prodrug" means an inactive or less active form of a compound which, when administered to a subject, is metabolized to form the active, or more active, compound (e.g., drug).

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N—($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, "5' target site" refers to the nucleotide of a target nucleic acid which is complementary to the 5'-most nucleotide of a particular antisense compound.

As used herein, "About" means within +10% of a value. For example, if it is stated, "a marker may be increased by about 50%", it is implied that the marker may be increased between 45%-55%.

As used herein, "administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

As used herein, "agent" means an active substance that can provide a therapeutic benefit when administered to an animal. "First agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo(a) therapeutic compound.

As used herein, "amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

As used herein, "animal" refers to a human or non-human animal, including, but not limited to, mice, rats, rabbits, dogs, cats, pigs, and non-human primates, including, but not limited to, monkeys and chimpanzees.

As used herein, "apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

As used herein, "apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

As used herein, "apo(a) mRNA" means a mRNA encoding an apo(a) protein.

As used herein, "apo(a) protein" means any protein sequence encoding Apo(a).

As used herein, "apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

As used herein, "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

As used herein, "coronary heart disease (CHD)" means a narrowing of the small blood vessels that supply blood and oxygen to the heart, which is often a result of atherosclerosis.

As used herein, "diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

As used herein, "diabetic dyslipidemia" or "type 2 diabetes with dyslipidemia" means a condition characterized by Type 2 diabetes, reduced HDL-C, elevated triglycerides (TG), and elevated small, dense LDL particles.

As used herein, "diluent" means an ingredient in a composition that lacks pharmacological activity, but is pharmaceutically necessary or desirable. For example, the diluent in an injected composition can be a liquid, e.g. saline solution.

As used herein, "dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

As used herein, "dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

As used herein, "dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

As used herein, "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

As used herein, "glucose" is a monosaccharide used by cells as a source of energy and inflammatory intermediate. "Plasma glucose" refers to glucose present in the plasma.

As used herein, "high density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

As used herein, "HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

As used herein, "hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

As used herein, "hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

As used herein, "hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120).

As used herein, "identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

As used herein, "improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

As used herein, "immediately adjacent" means there are no intervening elements between the immediately adjacent elements, for example, between regions, segments, nucleotides and/or nucleosides.

As used herein, "increasing HDL" or "raising HDL" means increasing the level of HDL in an animal after administration of at least one compound of the invention, compared to the HDL level in an animal not administered any compound.

As used herein, "individual" or "subject" or "animal" means a human or non-human animal selected for treatment or therapy.

As used herein, "individual in need thereof" refers to a human or non-human animal selected for treatment or therapy that is in need of such treatment or therapy.

As used herein, "induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

As used herein, "inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

As used herein, "inhibiting the expression or activity" refers to a reduction or blockade of the expression or activity of a RNA or protein and does not necessarily indicate a total elimination of expression or activity.

As used herein, "insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose.

High plasma levels of insulin and glucose due to insulin resistance often leads to metabolic syndrome and type 2 diabetes.

As used herein, "insulin sensitivity" is a measure of how effectively an individual processes glucose. An individual having high insulin sensitivity effectively processes glucose whereas an individual with low insulin sensitivity does not effectively process glucose.

As used herein, "lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

As used herein, "lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

As used herein, "lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

As used herein, "Lp(a)" comprises apo(a) and a LDL like particle containing apoB. The apo(a) is linked to the apoB by a disulfide bond.

As used herein, "low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

As used herein, "major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

As used herein, "metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

As used herein, "metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

As used herein, "peptide" means a molecule formed by linking at least two amino acids by amide bonds. Peptide refers to polypeptides and proteins.

As used herein, "pharmaceutical agent" means a substance that provides a therapeutic benefit when administered to an individual. For example, in certain embodiments, an antisense oligonucleotide targeted to apo(a) is a pharmaceutical agent.

As used herein, "pharmaceutical composition" or "composition" means a mixture of substances suitable for administering to an individual. For example, a pharmaceutical composition can comprise one or more active agents and a pharmaceutical carrier e.g., a sterile aqueous solution.

As used herein, "pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

As used herein, "pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

As used herein, "portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

As used herein, "prevent" or "preventing" refers to delaying or forestalling the onset or development of a disease, disorder, or condition for a period of time from minutes to indefinitely. Prevent also means reducing risk of developing a disease, disorder, or condition.

As used herein, "raise" means to increase in amount. For example, to raise plasma HDL levels means to increase the amount of HDL in the plasma.

As used herein, "reduce" means to bring down to a smaller extent, size, amount, or number. For example, to reduce plasma triglyceride levels means to bring down the amount of triglyceride in the plasma.

As used herein, "region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

As used herein, "second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

As used herein, "segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

As used herein, "statin" means an agent that inhibits the activity of HMG-CoA reductase.

As used herein, "subcutaneous administration" means administration just below the skin.

As used herein, "subject" means a human or non-human animal selected for treatment or therapy.

As used herein, "symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

As used herein, "targeting" or "targeted" means the process of design and selection of an antisense compound that will specifically hybridize to a target nucleic acid and induce a desired effect.

As used herein, "therapeutically effective amount" means an amount of a pharmaceutical agent that provides a therapeutic benefit to an individual.

As used herein, "therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

As used herein, "treat" or "treating" refers to administering a compound described herein to effect an alteration or improvement of a disease, disorder, or condition.

As used herein, "triglyceride" or "TG" means a lipid or neutral fat consisting of glycerol combined with three fatty acid molecules.

As used herein, "type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

CERTAIN EMBODIMENTS

In certain embodiments, a compound comprises a siRNA or antisense oligonucleotide targeted to apolipoprotein(a) (apo(a)) known in the art and a conjugate group described herein. Examples of antisense oligonucleotides targeted to apo(a) suitable for conjugation include but are not limited to those disclosed in WO 2013/177468; U.S. Pat. Nos. 8,673,632; 7,259,150; and US Patent Application Publication No. US 2004/0242516; which are incorporated by reference in their entireties herein. In certain embodiments, a compound comprises an antisense oligonucleotide having a nucleobase sequence of any of SEQ ID NOs 12-130, 133, 134 disclosed in WO 2013/177468 and a conjugate group described herein. In certain embodiments, a compound comprises an antisense oligonucleotide having a nucleobase sequence of any of SEQ ID NOs 11-45 and 85-96 disclosed in U.S. Pat. No. 8,673,632 and a conjugate group described herein. In certain embodiments, a compound comprises an antisense oligonucleotide having a nucleobase sequence of any of SEQ ID NOs 11-45 disclosed in U.S. Pat. No. 7,259,150 and a conjugate group described herein. In certain embodiments, a compound comprises an antisense oligonucleotide having a nucleobase sequence of any of SEQ ID NOs 7-41 disclosed in US Patent Application Publication No. US 2004/0242516 and a conjugate group described herein. The nucleobase sequences of all of the aforementioned referenced SEQ ID NOs are incorporated by reference herein.

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a). In certain embodiments, the compound is an antisense oligonucleotide targeting apo(a) and a conjugate group.

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a). In certain embodiments, the compound is an antisense oligonucleotide targeting apo(a) and a conjugate group.

Certain embodiments provide a compound comprising a modified oligonucleotide targeting apo(a) and a conjugate group, wherein the modified oligonucleotide consists of 12 to 30 linked nucleosides. In certain embodiments, the modified oligonucleotide with the conjugate group consists of 15 to 30, 18 to 24, 19 to 22, 13 to 25, 14 to 25, 15 to 25 linked nucleosides. In certain embodiments, the modified oligonucleotide with the conjugate group comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide with the conjugate group consists of 20 linked nucleosides.

Certain embodiments provide a compound comprising a modified oligonucleotide targeting apo(a) and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4.

Certain embodiments provide a compound comprising a modified oligonucleotide targeting an apo(a) segment and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in, for example, Examples 114 and 117. In the tables, the "Start Site" refers to the 5'-most nucleotide of a target segment and "Stop Site" refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 125, a target segment can range from 3901-3920, the start site to the stop site of SEQ ID NO: 58. In another example, as shown in Table 125, a target segment can range from 3900-3923, the start site of SEQ ID NO: 57 to the stop site of SEQ ID NO: 61.

Certain embodiments provide a compound comprising a modified oligonucleotide targeting apo(a) and a conjugate group, wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a) and a conjugate group, wherein the nucleobase sequence of the modified oligonucleotide is at least 80%, at least 85%, at least 90%, at least 95%, or 100% complementary to any of the target segments shown in, for example, Examples 114 and 117.

Certain embodiments provide a compound comprising a modified oligonucleotide targeting apo(a) and a conjugate group, wherein the modified oligonucleotide consists of 12 to 30 linked nucleosides and comprises a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) and a conjugate group, wherein the modified oligonucleotide consists of 12 to 30 linked nucleosides and comprises a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134. In certain embodiments, the compound consists of any one of SEQ ID NOs: 12-130, 133, 134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134. In certain embodiments, the compound consists of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110. In certain embodiments, the compound consists of any of the nucleobase sequences of SEQ ID NOs: 12-19, 26-30, 32, 35, 38-44, 46-47, 50, 57-58, 61, 64-66, 68, 72-74, 76-77, 92-94, 103-110 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 111, 114-121, 123-129. In certain embodiments, the compound consists of any of the nucleobase sequences of SEQ ID NOs: 111, 114-121, 123-129 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 17, 18, 26-28, 39, 71, 106-107. In certain embodiments, the compound consists of any of the nucleobase sequences of SEQ ID NOs: 14, 17, 18, 26-28, 39, 71, 106-107 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 26-29, 39-40, 82. In certain embodiments, the compound consists of any of the nucleobase sequences of SEQ ID NOs: 14, 26-29, 39-40, 82 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 14, 16-18. In certain embodiments, the compound consists of any of the nucleobase sequences of SEQ ID NOs: 14, 16-18 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 26-27, 107. In certain embodiments, the compound consists of any of the nucleobase sequences of SEQ ID NOs: 26-27, 107 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 28-29, 39-40, 47. In certain embodiments, the compound consists of any of the nucleobase sequences of SEQ ID NOs: 28-29, 39-40, 47 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 28, 93, 104, 134. In certain embodiments, the compound consists of any of the nucleobase sequences of SEQ ID NOs: 28, 93, 104, 134 and a conjugate group.

Certain embodiments provide a compound comprising a modified oligonucleotide targeting apo(a) and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of the nucleobase sequence of SEQ ID NO: 58. In certain embodiments, the modified oligonucleotide with the conjugate group has a nucleobase sequence comprising at least 8 contiguous nucleobases of the nucleobase sequence of SEQ ID NO: 58. In certain embodiments, the compound consists of SEQ ID NO: 58 and a conjugate group.

In certain embodiments, the present disclosure provides conjugated antisense compounds represented by the following structure. In certain embodiments, the antisense compound comprises the modified oligonucleotide ISIS 494372 with a 5'-X, wherein X is a conjugate group comprising GalNAc. In certain embodiments, the antisense compound consists of the modified oligonucleotide ISIS 494372 with a 5'-X, wherein X is a conjugate group comprising GalNAc.

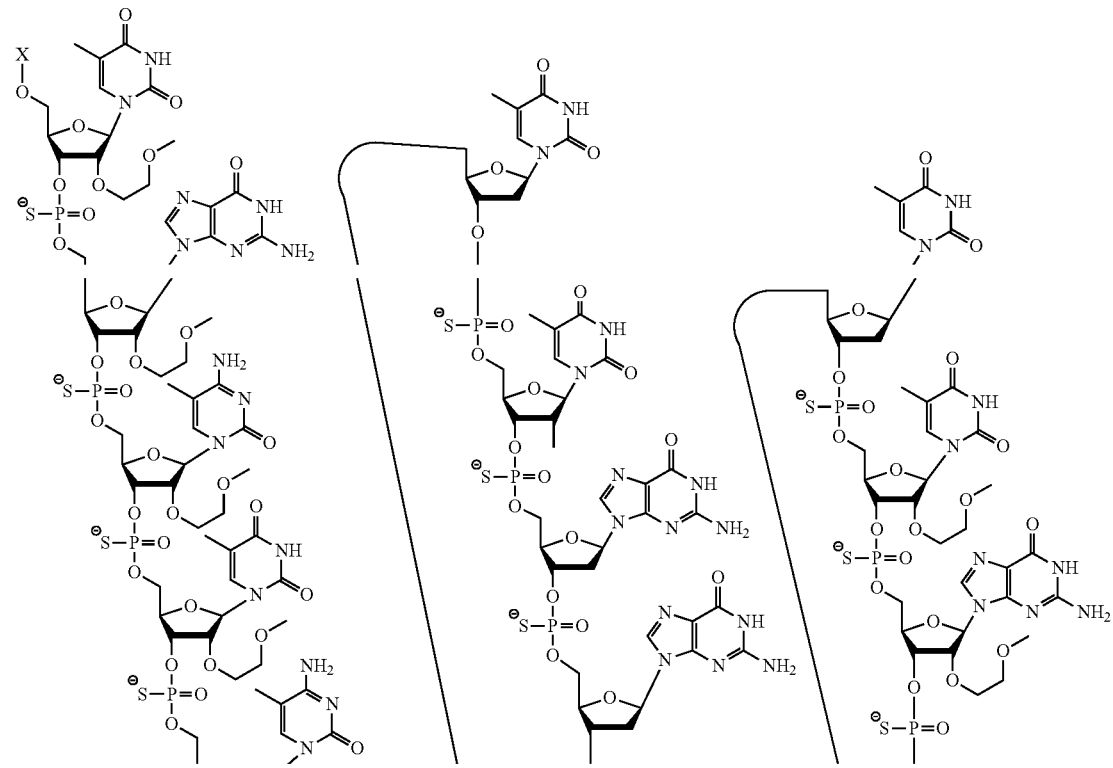

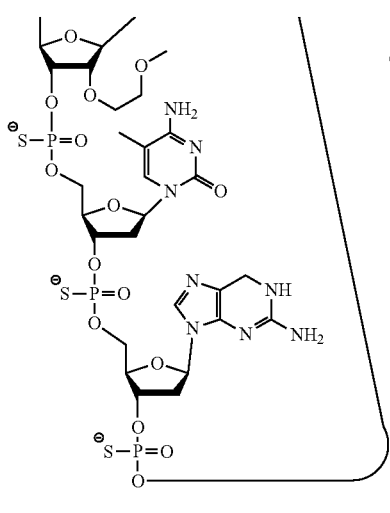
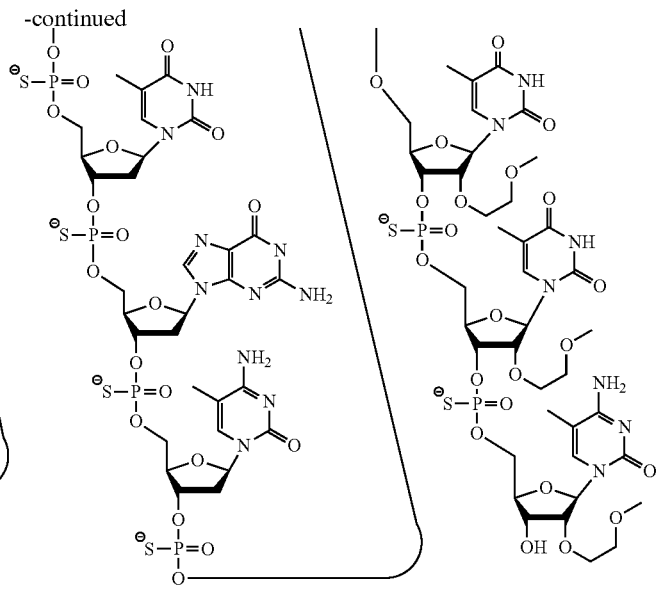
In certain embodiments, the present disclosure provides conjugated antisense compounds represented by the following structure. In certain embodiments, the antisense compound comprises the conjugated modified oligonucleotide ISIS 681251. In certain embodiments, the antisense compound consists of the conjugated modified oligonucleotide ISIS 681251.
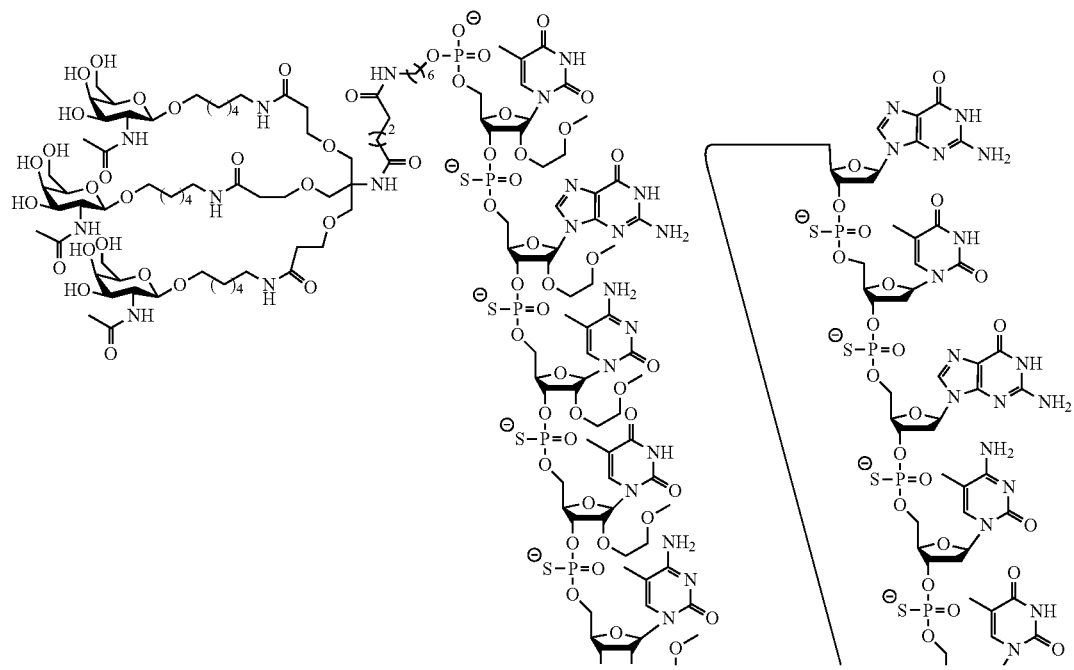

-continued
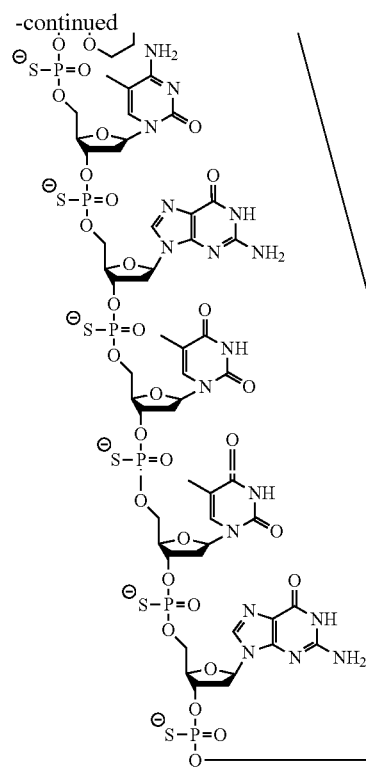
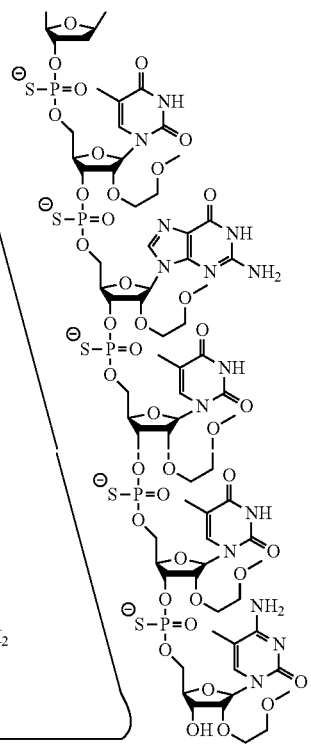
In certain embodiments, the present disclosure provides conjugated antisense compounds represented by the following structure. In certain embodiments, the antisense compound comprises the conjugated modified oligonucleotide ISIS 681257. In certain embodiments, the antisense compound consists of the conjugated modified oligonucleotide ISIS 681257.
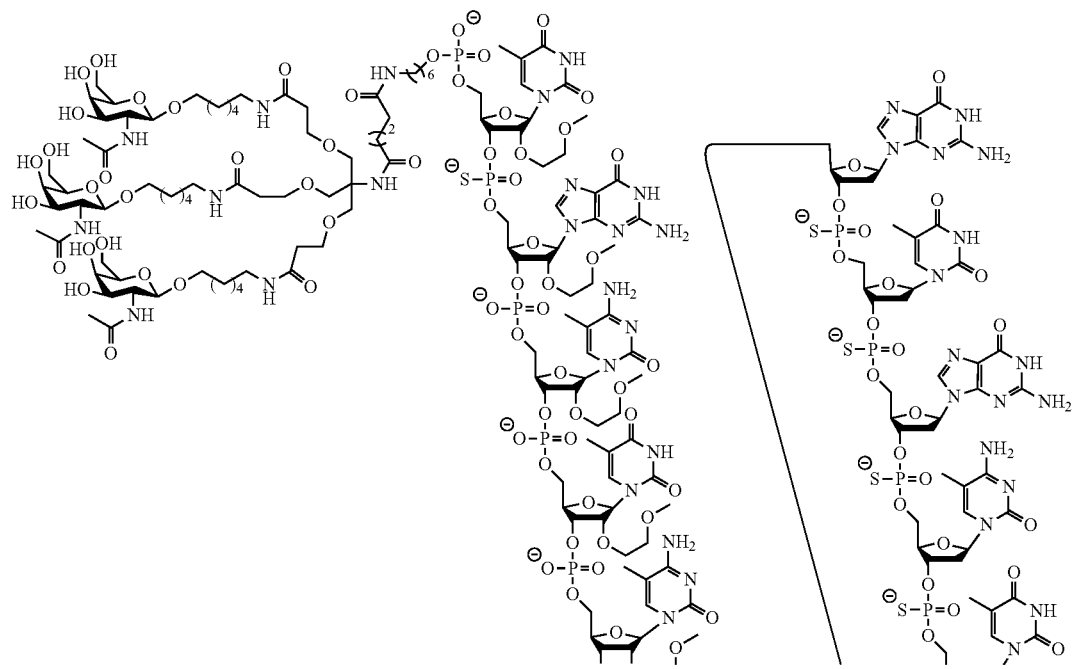

-continued

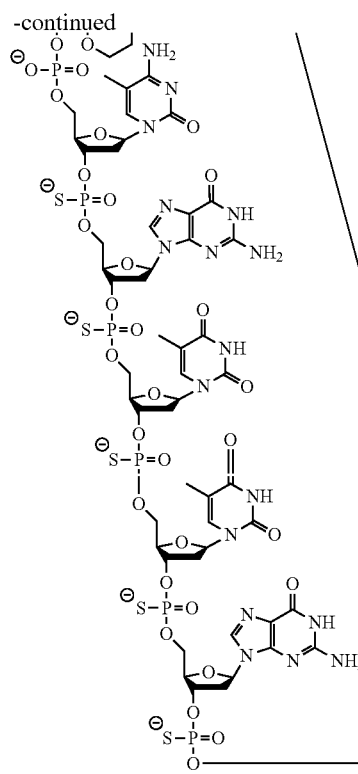
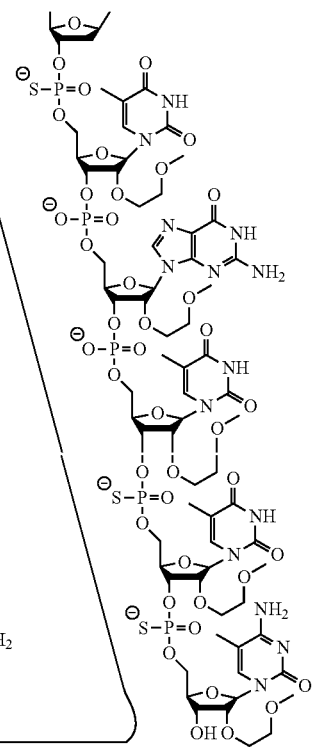

In certain embodiments, the present disclosure provides conjugated antisense compounds represented by the following structure. In certain embodiments, the antisense compound comprises a modified oligonucleotide with the nucleobase sequence of SEQ ID NO: 58 with a 5'-GalNAc with variability in the sugar mods of the wings. In certain embodiments, the antisense compound consists of a modified oligonucleotide with the nucleobase sequence of SEQ ID NO: 58 with a 5'-GalNAc with variability in the sugar mods of the wings.

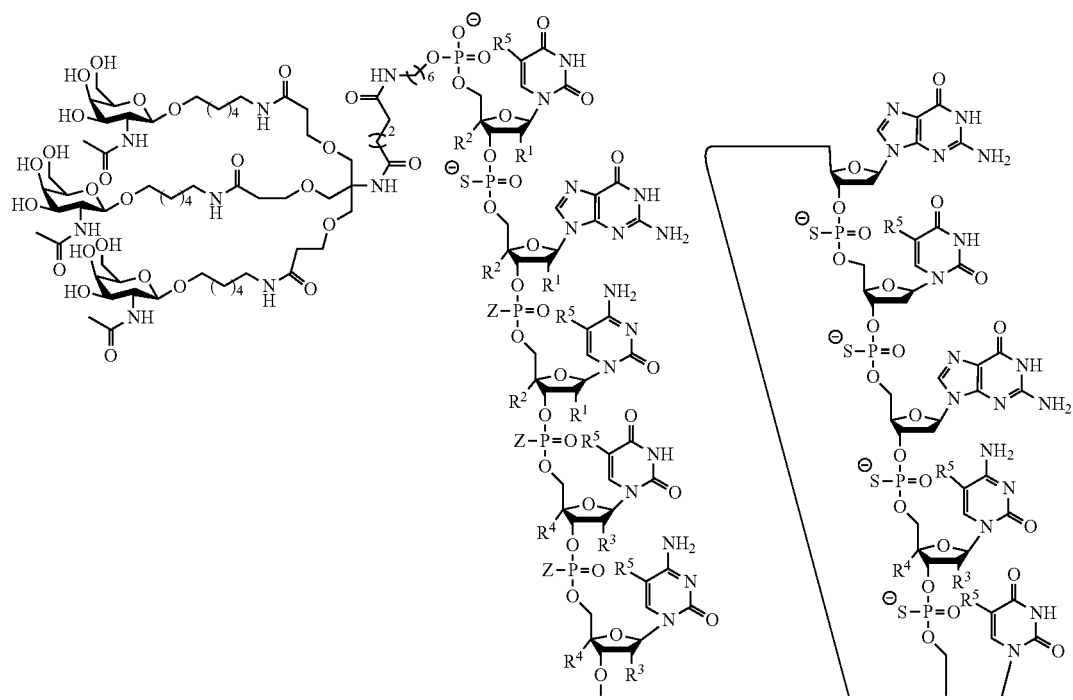

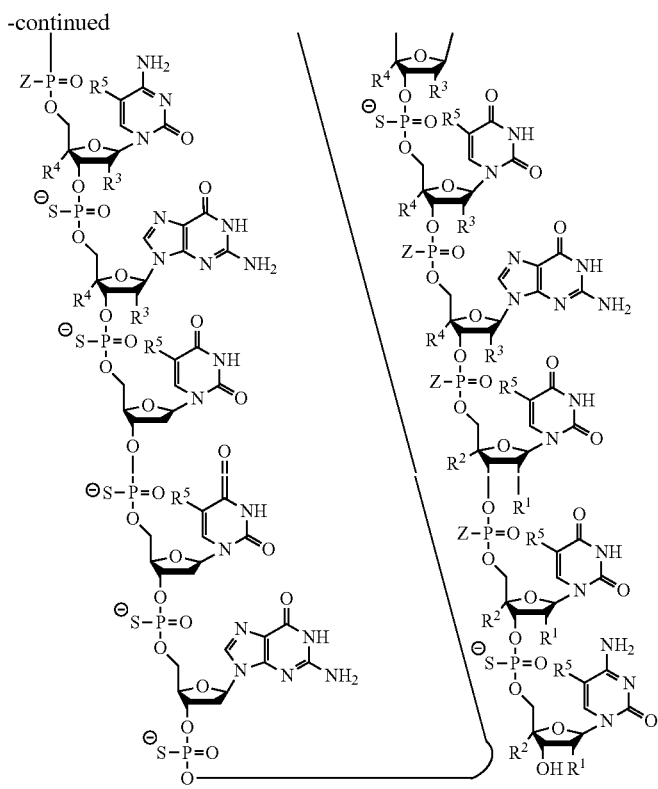

Wherein either R¹ is —OCH₂CH₂OCH₃ (MOE) and R² is H; or R¹ and R² together form a bridge, wherein R¹ is —O— and R² is —CH₂—, —CH(CH₃)—, or —CH₂CH₂—, and R¹ and R² are directly connected such that the resulting bridge is selected from: —O—CH₂—, —O—CH(CH₃)—, and —O—CH₂CH₂—;

And for each pair of R³ and R⁴ on the same ring, independently for each ring: either R³ is selected from H and —OCH₂CH₂OCH₃ and R⁴ is H; or R³ and R⁴ together form a bridge, wherein R³ is —O—, and R⁴ is —CH₂—, —CH(CH₃)—, or —CH₂CH₂— and R³ and R⁴ are directly connected such that the resulting bridge is selected from: —O—CH₂—, —O—CH(CH₃)—, and —O—CH₂CH₂—;

And R⁵ is selected from H and —CH₃;

And Z is selected from S⁻ and O⁻.

Certain embodiments provide a compound comprising a modified oligonucleotide targeting apo(a) and a conjugate group, wherein the modified oligonucleotide is single-stranded.

Certain embodiments provide a compound comprising a modified oligonucleotide targeting apo(a) and a conjugate group, wherein at least one internucleoside linkage is a modified internucleoside linkage. In certain embodiments, the modified internucleoside linkage is a phosphorothioate internucleoside linkage. In certain embodiments, at least 1, at least 2, at least 3, at least 4, at least 5, at least 6, at least 7, at least 8, at least 9 or at least 10 internucleoside linkages of said modified oligonucleotide are phosphorothioate internucleoside linkages. In certain embodiments, each internucleoside linkage is a phosphorothioate internucleoside linkage. In certain embodiments, the modified oligonucleotide comprises at least 1, at least 2, at least 3, at least 4, at least 5, at least 6, at least 7, at least 8, at least 9 or at least 10 phosphodiester internucleoside linkages. In certain embodiments, each internucleoside linkage of the modified oligonucleotide is selected from a phosphodiester internucleoside linkage and a phosphorothioate internucleoside linkage.

Certain embodiments provide a compound comprising a modified oligonucleotide targeting apo(a) and a conjugate group, wherein at least one nucleoside comprises a modified nucleobase. In certain embodiments, the modified nucleobase is a 5-methylcytosine.

Certain embodiments provide a compound comprising a modified oligonucleotide targeting apo(a) and a conjugate group, wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-(CH₂)ₙ—O-2' bridge, wherein n is 1 or 2.

Certain embodiments provide a compound comprising a modified oligonucleotide targeting apo(a) and a conjugate group, wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a) and a conjugate group, wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting apo(a) and a conjugate group, wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting apo(a) and a conjugate group, wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a modified oligonucleotide targeting apo(a) and a conjugate group, wherein the modified oligonucleotide consists of 20 linked nucleosides with the nucleobase sequence of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide.

In certain embodiments, the conjugate group comprises one or more ligands. In certain embodiments, the conjugate group comprises two or more ligands. In certain embodiments, the conjugate group comprises three or more ligands. In certain embodiments, the conjugate group comprises three ligands. In certain embodiments, each ligand is selected from among: a polysaccharide, modified polysaccharide, mannose, galactose, a mannose derivative, a galactose derivative, D-mannopyranose, L-Mannopyranose, D-Arabinose, L-Galactose, D-xylofuranose, L-xylofuranose, D-glucose, L-glucose, D-Galactose, L-Galactose, α-D-Mannofuranose, β-D-Mannofuranose, α-D-Mannopyranose, β-D-Mannopyranose, α-D-Glucopyranose, β-D-Glucopyranose, α-D-Glucofuranose, β-D-Glucofuranose, α-D-fructofuranose, α-D-fructopyranose, α-D-Galactopyranose, β-D-Galactopyranose, α-D-Galactofuranose, β-D-Galactofuranose, glucosamine, sialic acid, α-D-galactosamine, N-Acetylgalactosamine, 2-Amino-3-O—[(R)-1-carboxyethyl]-2-deoxy-β-D-glucopyranose, 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose, N-Glycoloyl-α-neuraminic acid, 5-thio-β-D-glucopyranose, methyl 2,3,4-tri-O-acetyl-1-thio-6-O-trityl-α-D-glucopyranoside, 4-Thio-β-D-galactopyranose, ethyl 3,4,6,7-tetra-O-acetyl-2-deoxy-1,5-dithio-α-D-glucoheptopyranoside, 2,5-Anhydro-D-allononitrile, ribose, D-ribose, D-4-thioribose, L-ribose, L-4-thioribose. In certain embodiments, each ligand is N-acetyl galactosamine.

In certain embodiments, each ligand is N-acetyl galactosamine.

In certain embodiments, the conjugate group comprises:

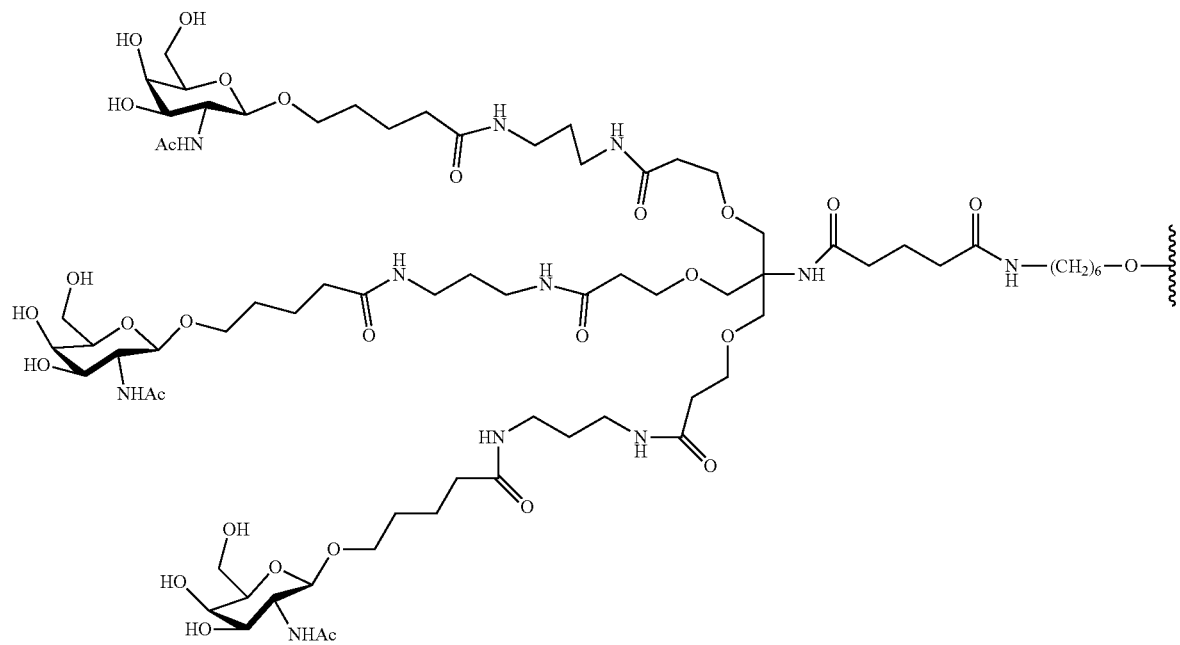

In certain embodiments, the conjugate group comprises:
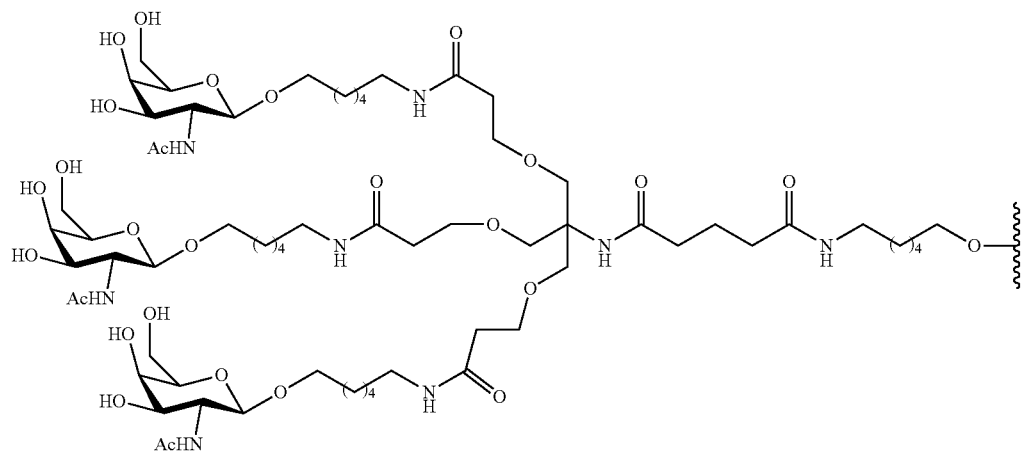
In certain embodiments, the conjugate group comprises:
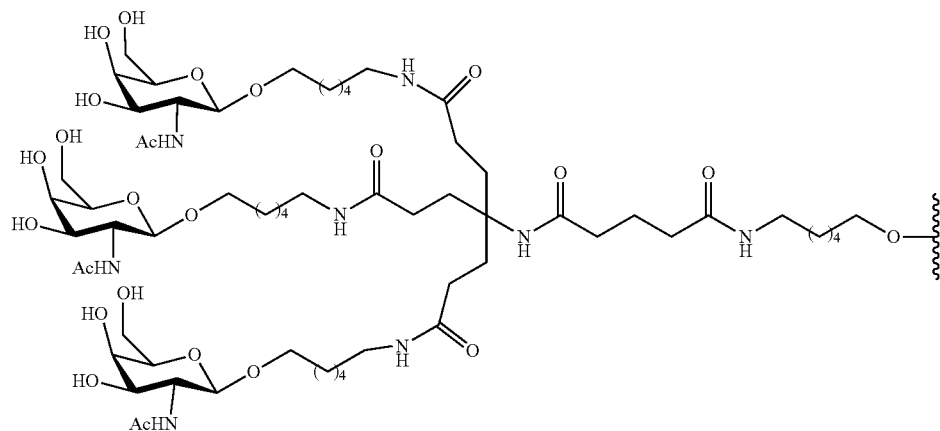
In certain embodiments, the conjugate group comprises:
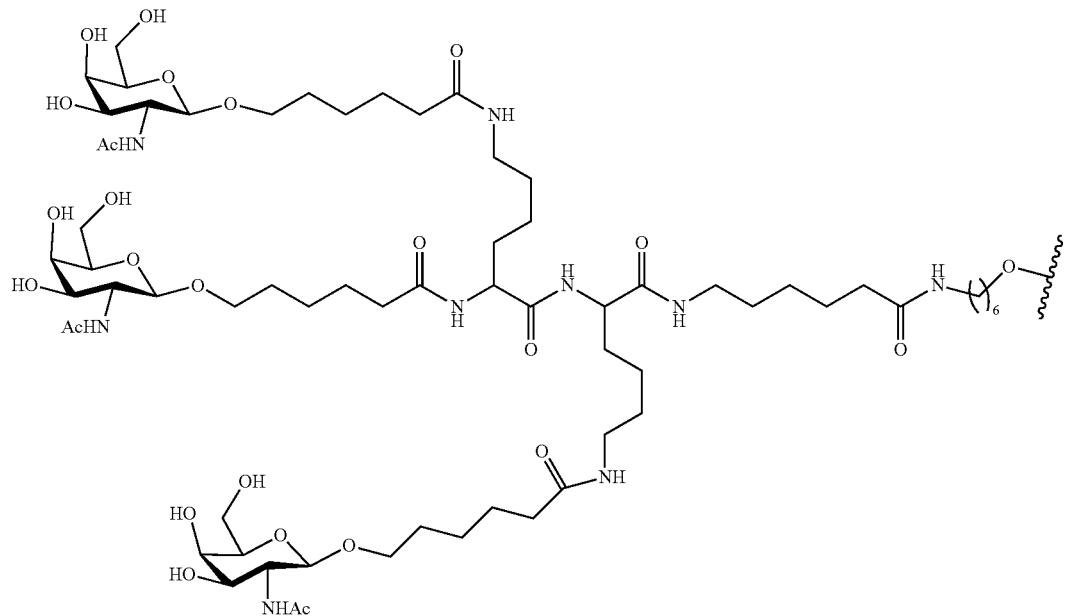

In certain embodiments, the conjugate group comprises:

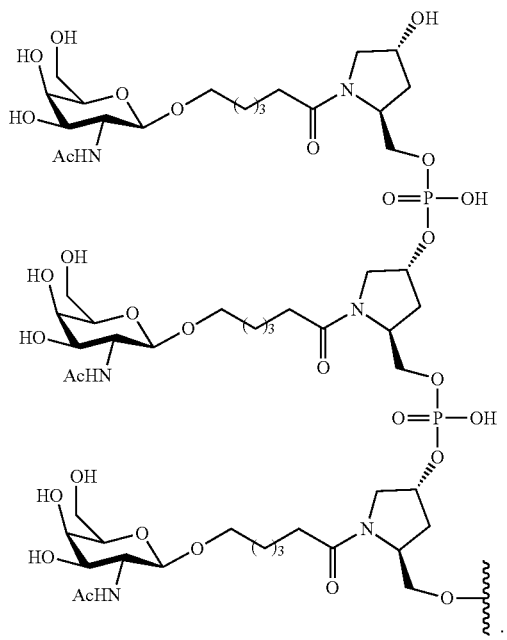

In certain embodiments, the conjugate group comprises at least one phosphorus linking group or neutral linking group.

In certain embodiments, the conjugate group comprises a structure selected from among:

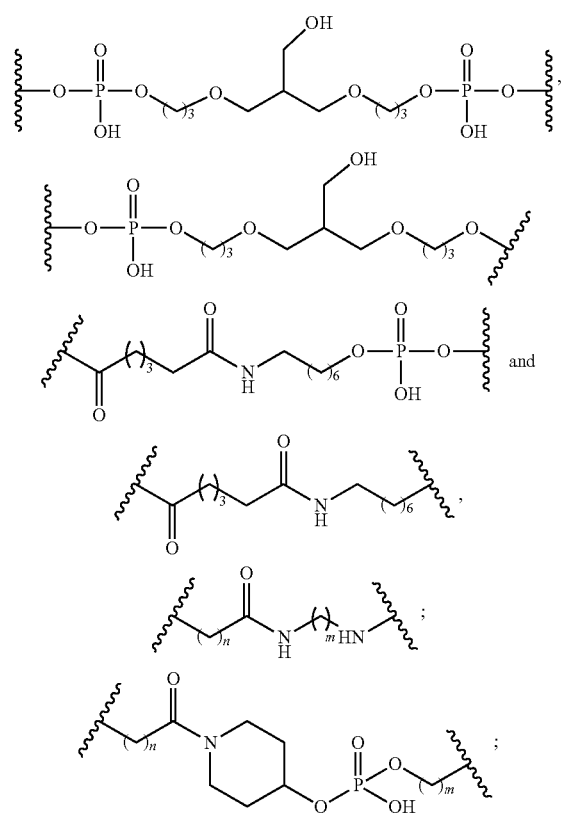

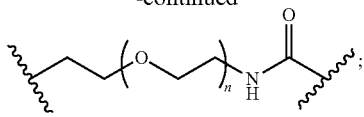

wherein n is from 1 to 12; and
wherein m is from 1 to 12.

In certain embodiments, the conjugate group has a tether having a structure selected from among:

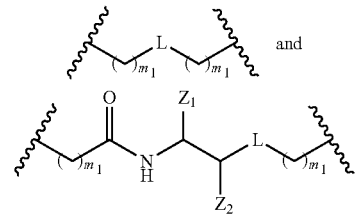

wherein L is either a phosphorus linking group or a neutral linking group;
Z1 is C(=O)O—R2;
Z2 is H, C1-C6 alkyl or substituted C1-C6 alky;
R2 is H, C1-C6 alkyl or substituted C1-C6 alky; and
each m1 is, independently, from 0 to 20 wherein at least one m1 is greater than 0 for each tether.

In certain embodiments, conjugate group has a tether having a structure selected from among:

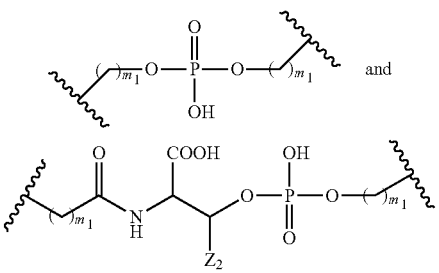

wherein Z2 is H or CH3; and
each m1 is, independently, from 0 to 20 wherein at least one m1 is greater than 0 for each tether.

In certain embodiments, the conjugate group has tether having a structure selected from among:

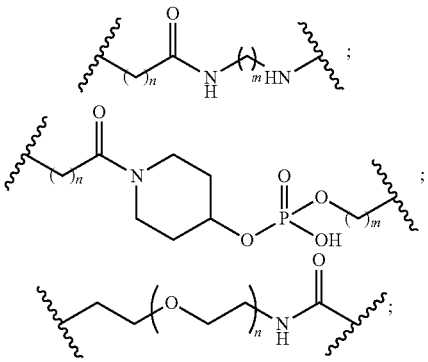

wherein n is from 1 to 12; and
wherein m is from 1 to 12.

In certain embodiments, the conjugate group is covalently attached to the modified oligonucleotide.

In certain embodiments, the compound has a structure represented by the formula:

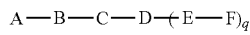

wherein
A is the modified oligonucleotide;
B is the cleavable moiety
C is the conjugate linker
D is the branching group
each E is a tether;
each F is a ligand; and
q is an integer between 1 and 5.

In certain embodiments, the compound has a structure represented by the formula:

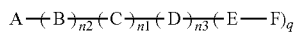

wherein:
A is the modified oligonucleotide;
B is the cleavable moiety
C is the conjugate linker
D is the branching group
each E is a tether;
each F is a ligand;
each n is independently 0 or 1; and
q is an integer between 1 and 5.

In certain embodiments, the compound has a structure represented by the formula:

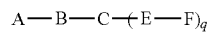

wherein
A is the modified oligonucleotide;
B is the cleavable moiety;
C is the conjugate linker;
each E is a tether;
each F is a ligand; and
q is an integer between 1 and 5.

In certain embodiments, the compound has a structure represented by the formula:

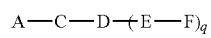

wherein
A is the modified oligonucleotide;
C is the conjugate linker;
D is the branching group;
each E is a tether;
each F is a ligand; and
q is an integer between 1 and 5.

In certain embodiments, the compound has a structure represented by the formula:

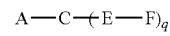

wherein
A is the modified oligonucleotide;
C is the conjugate linker;
each E is a tether;
each F is a ligand; and
q is an integer between 1 and 5.

In certain embodiments, the compound has a structure represented by the formula:

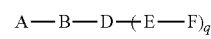

wherein
A is the modified oligonucleotide;
B is the cleavable moiety;
D is the branching group;
each E is a tether;
each F is a ligand; and
q is an integer between 1 and 5.

In certain embodiments, the compound has a structure represented by the formula:

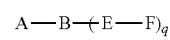

wherein
A is the modified oligonucleotide;
B is the cleavable moiety;
each E is a tether;
each F is a ligand; and
q is an integer between 1 and 5.

In certain embodiments, the compound has a structure represented by the formula:

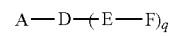

wherein
A is the modified oligonucleotide;
D is the branching group;
each E is a tether;
each F is a ligand; and
q is an integer between 1 and 5.

In certain embodiments, the conjugate linker has a structure selected from among:

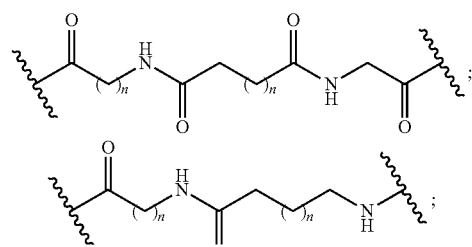

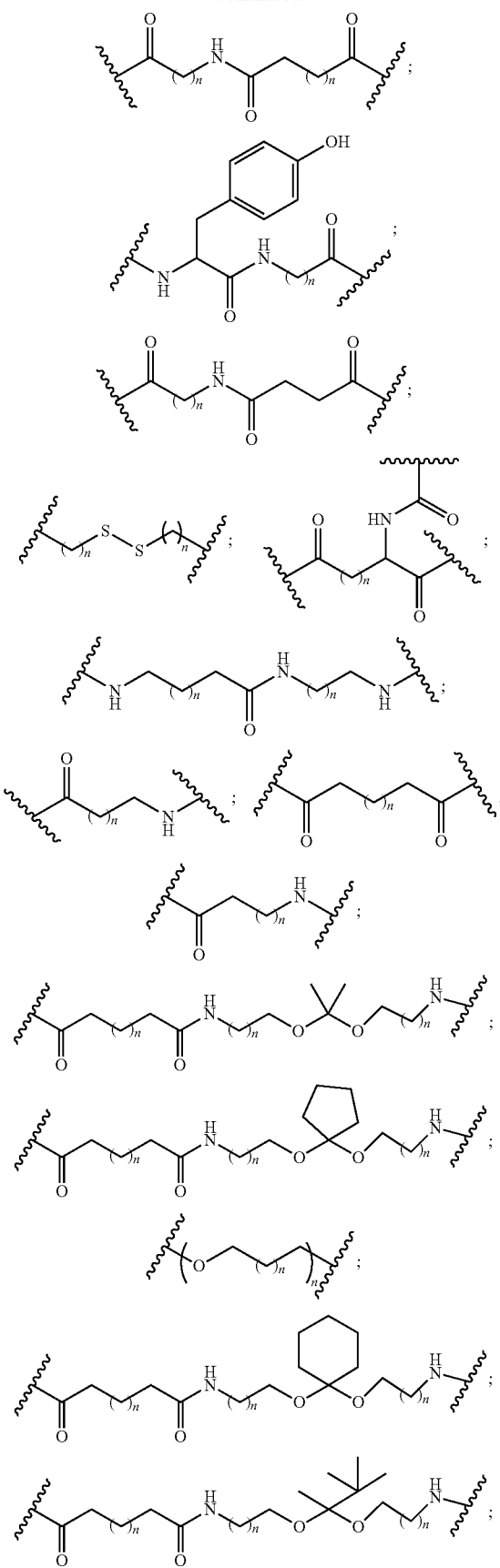
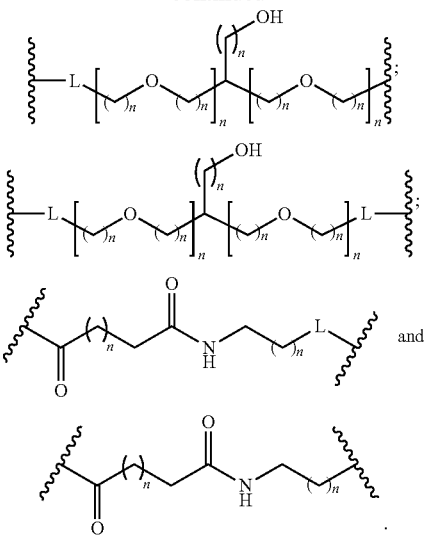
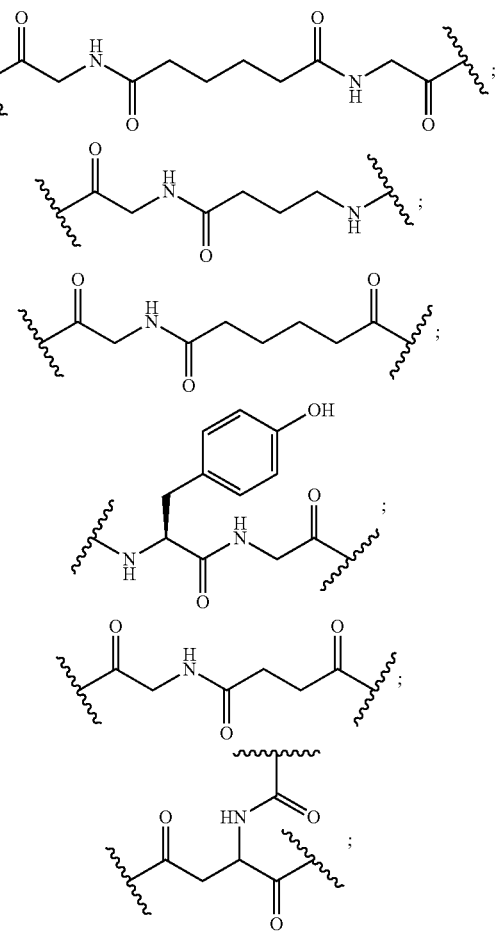
wherein each L is, independently, a phosphorus linking group or a neutral linking group; and
each n is, independently, from 1 to 20.
In certain embodiments, the conjugate linker has a structure selected from among:

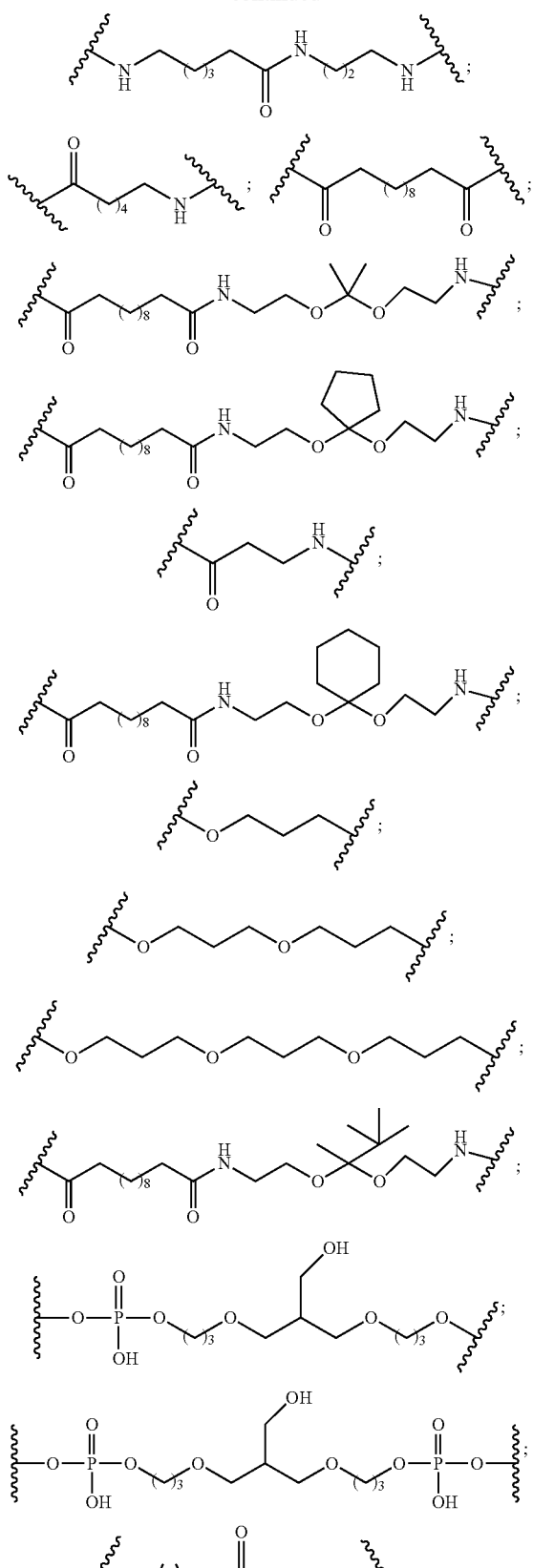
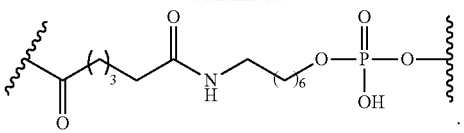
In certain embodiments, the conjugate linker has the following structure:
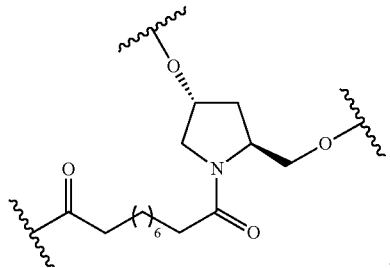
In certain embodiments, the conjugate linker has a structure selected from among:
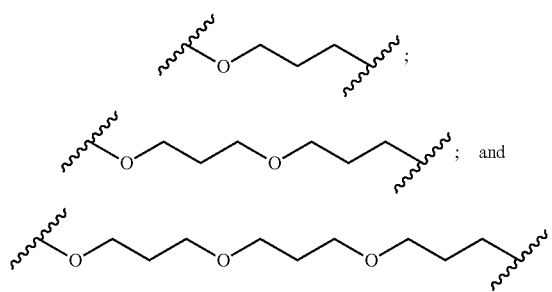
In certain embodiments, the conjugate linker has a structure selected from among:
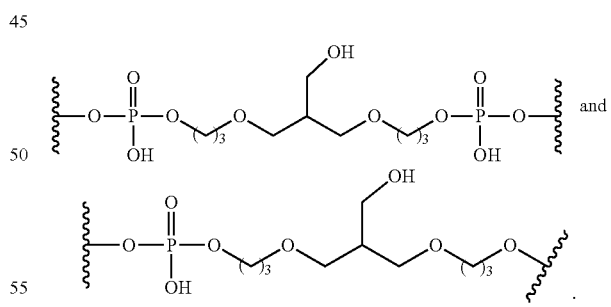
In certain embodiments, the conjugate linker has a structure selected from among:
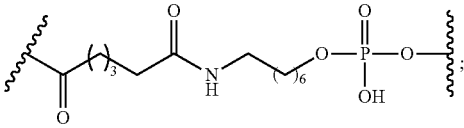

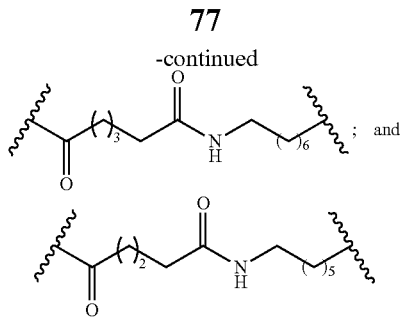

In certain embodiments, the conjugate linker comprises a pyrrolidine. In certain embodiments, the conjugate linker does not comprise a pyrrolidine. In certain embodiments, the conjugate linker comprises PEG. In certain embodiments, the conjugate linker comprises an amide. In certain embodiments, the conjugate linker comprises at least two amides. In certain embodiments, the conjugate linker does not comprise an amide. In certain embodiments, the conjugate linker comprises a polyamide. In certain embodiments, the conjugate linker comprises an amine. In certain embodiments, the conjugate linker comprises one or more disulfide bonds. In certain embodiments, the conjugate linker comprises a protein binding moiety. In certain embodiments, the protein binding moiety comprises a lipid.

In certain embodiments, the protein binding moiety is selected from among: cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid.

In certain embodiments, the protein binding moiety is selected from among: a C16 to C22 long chain saturated or unsaturated fatty acid, cholesterol, cholic acid, vitamin E, adamantane or 1-pentafluoropropyl.

In certain embodiments, the conjugate linker has a structure selected from among:

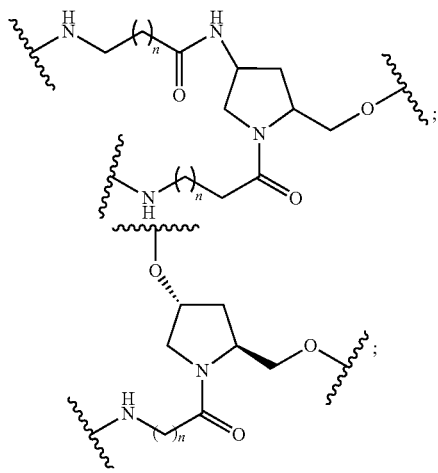

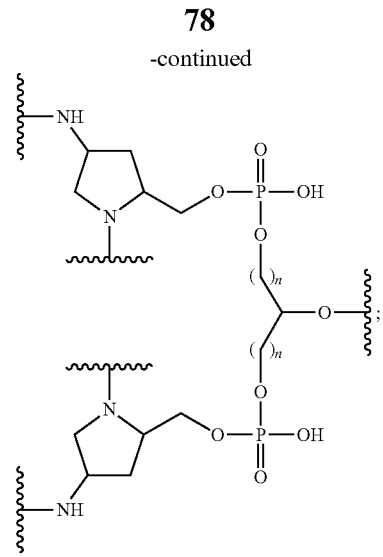

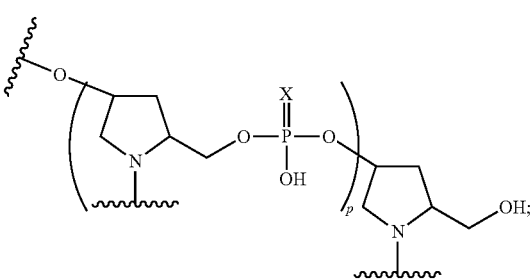

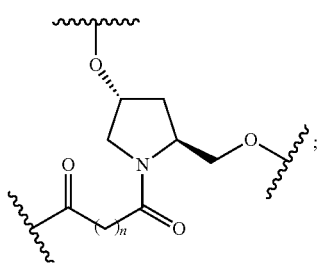

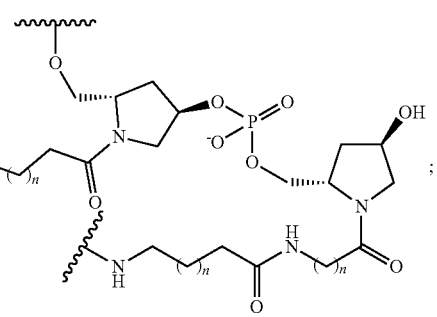

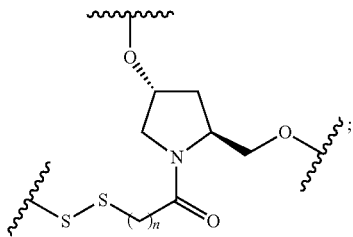

-continued
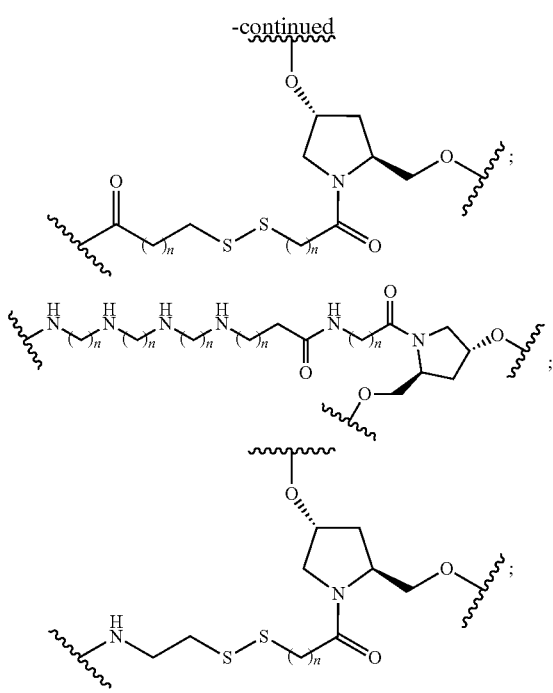
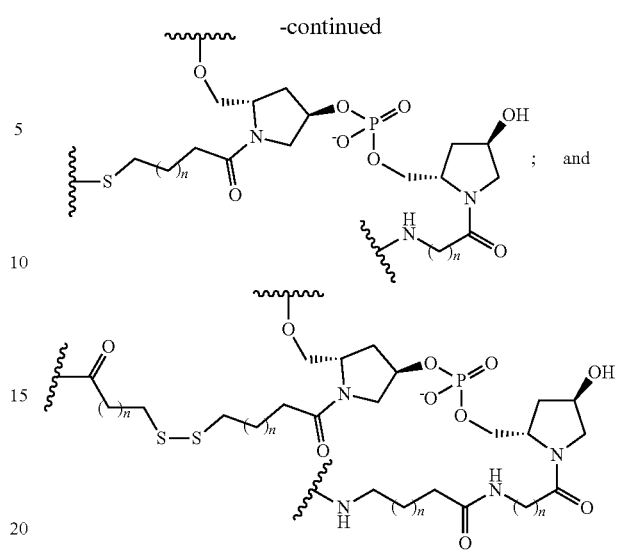
wherein each n is, independently, is from 1 to 20; and p is from 1 to 6.
In certain embodiments, the conjugate linker has a structure selected from among:
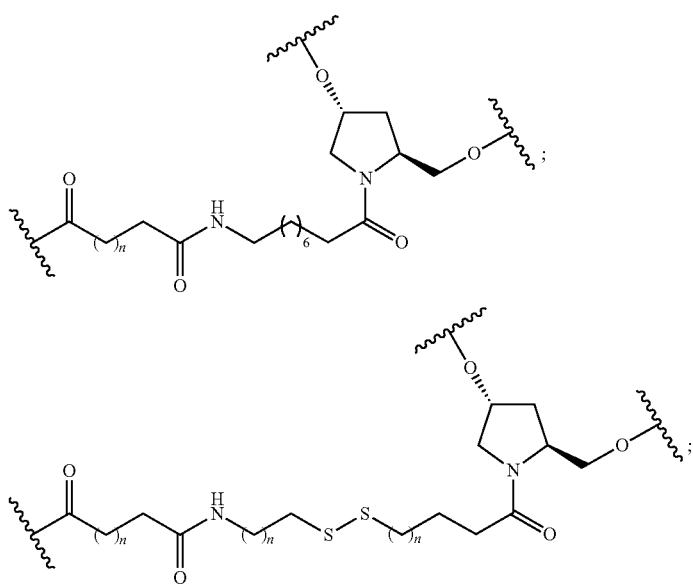
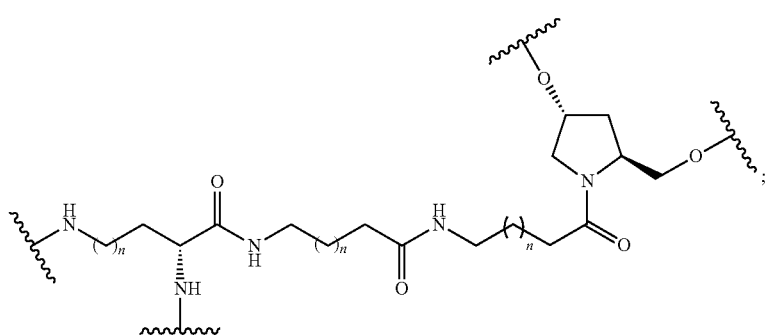

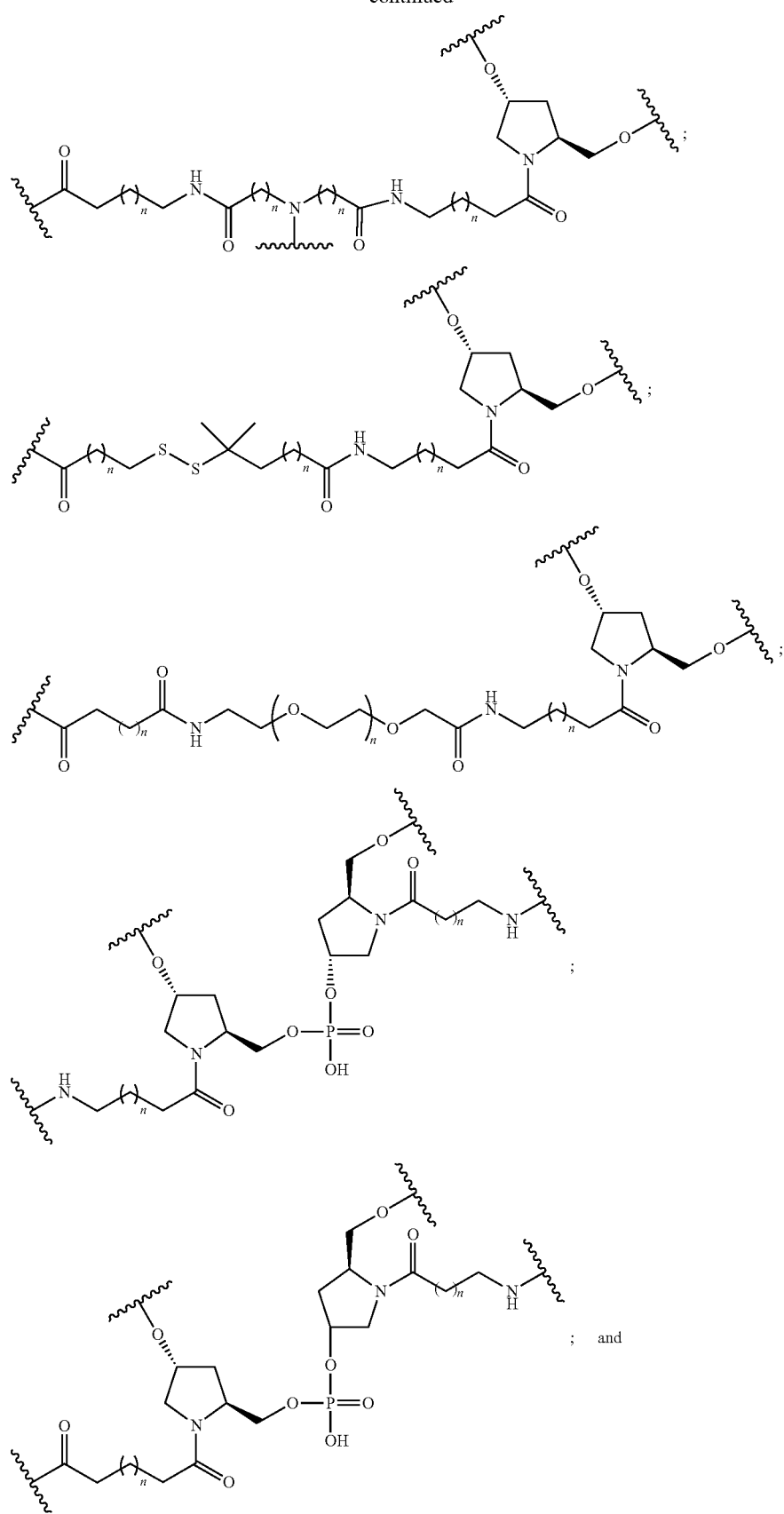

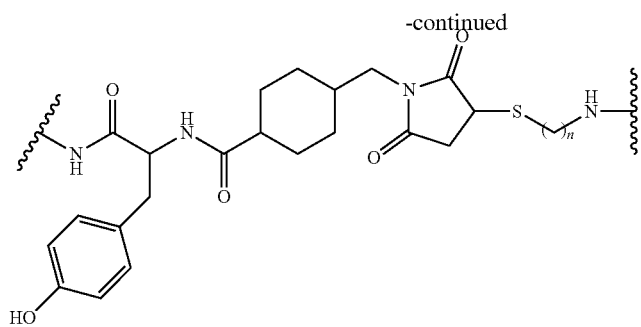
wherein each n is, independently, from 1 to 20.
In certain embodiments, the conjugate linker has a structure selected from among:
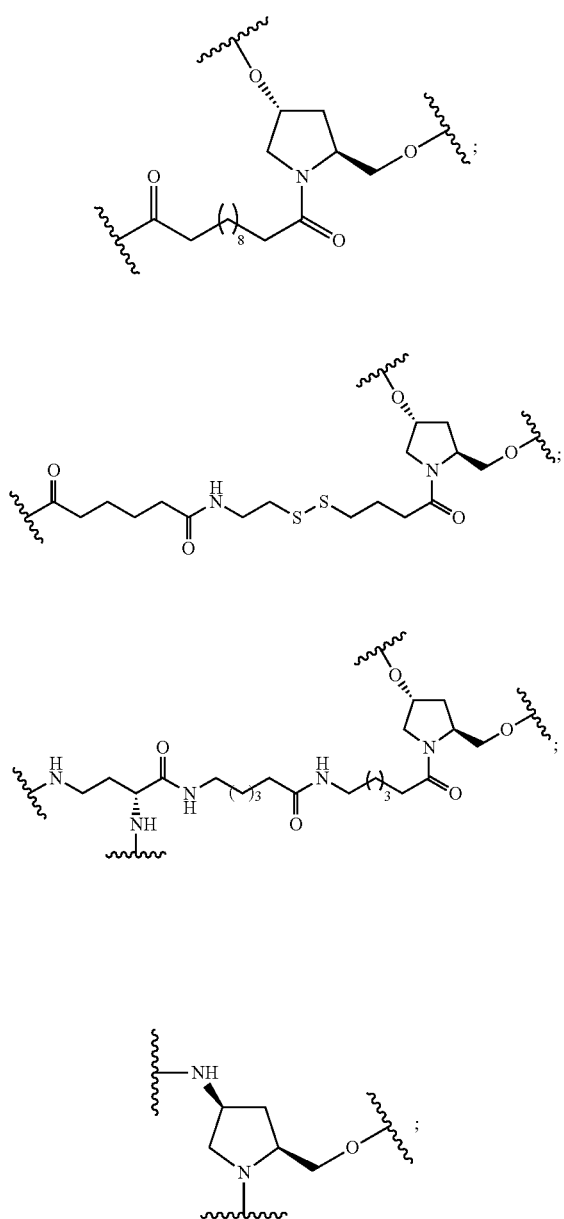
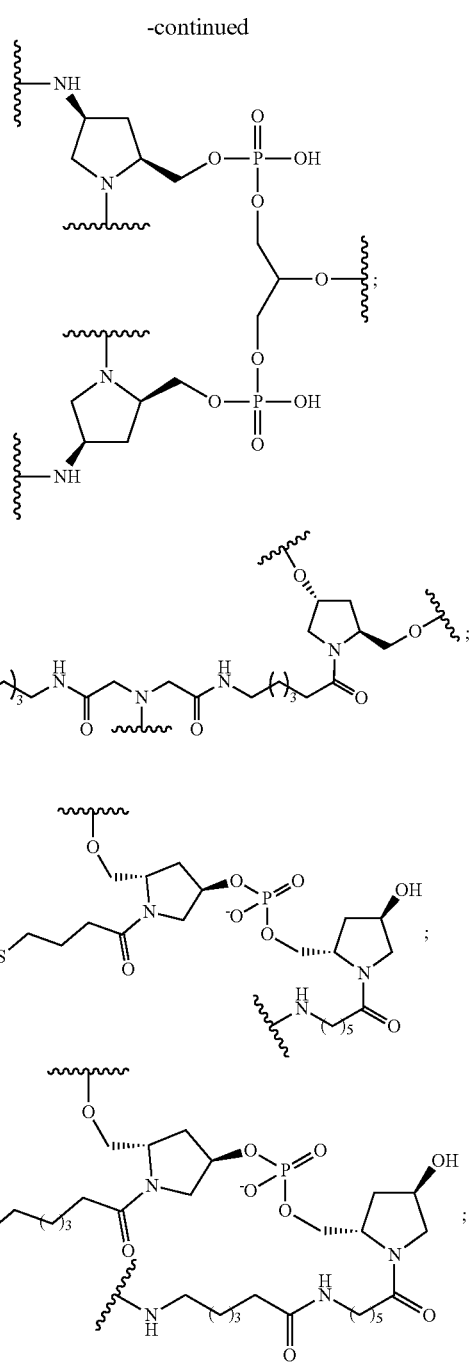

85

-continued

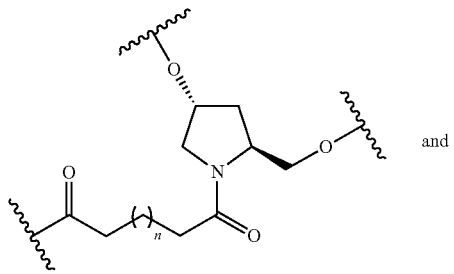

86

In certain embodiments, the conjugate linker has a structure selected from among:

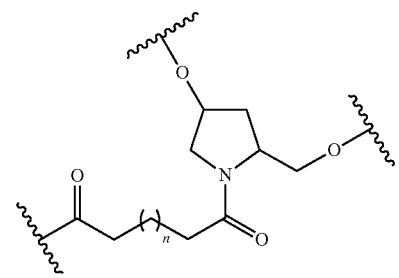

and wherein n is from 1 to 20.

In certain embodiments, the conjugate linker has a structure selected from among:

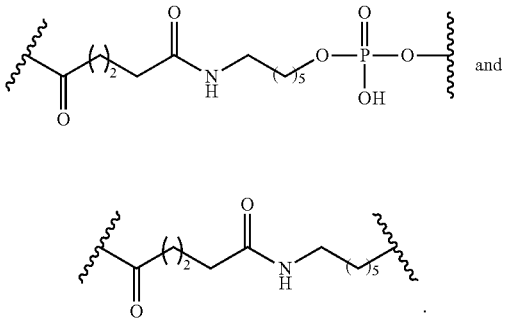

and

In certain embodiments, the conjugate linker has a structure selected from among:

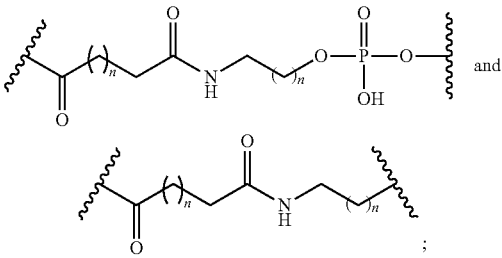

and

;

wherein each n is independently, 0, 1, 2, 3, 4, 5, 6, or 7.

In certain embodiments, the conjugate linker has the following structure:

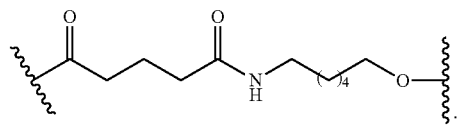

In certain embodiments, the branching group has one of the following structures:

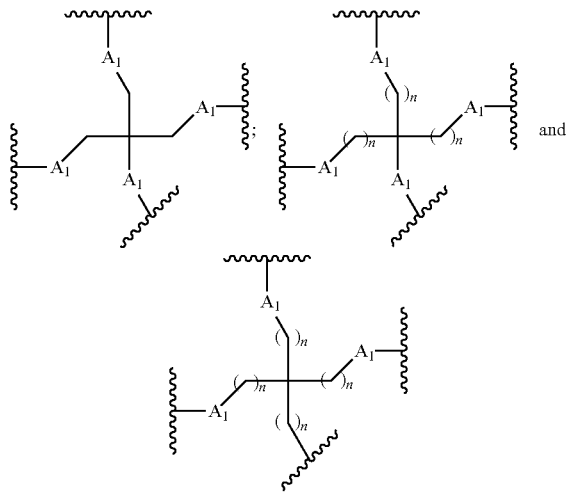

wherein each A1 is independently, O, S, C=O or NH; and each n is, independently, from 1 to 20.

In certain embodiments, the branching group has one of the following structures:

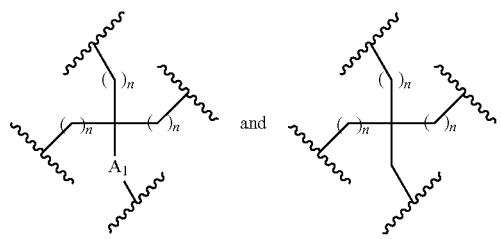

wherein each A1 is independently, O, S, C=O or NH; and each n is, independently, from 1 to 20.

In certain embodiments, the branching group has the following structure:

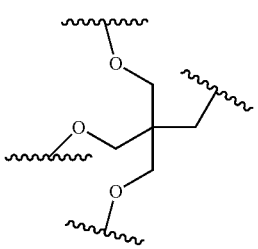

In certain embodiments, the branching group has the following structure:

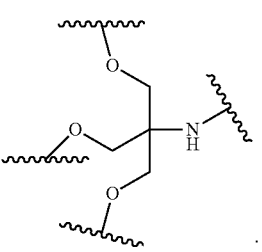

In certain embodiments, the branching group has the following structure:

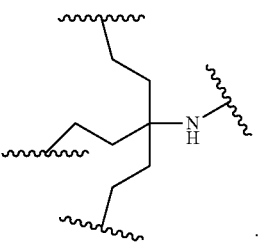 [SMILES: *CCC(CC*)(CC*)N*]

In certain embodiments, the branching group has the following structure:

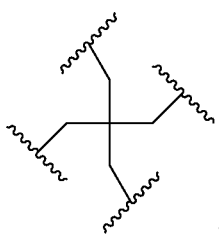

In certain embodiments, the branching group comprises an ether.

In certain embodiments, the branching group has the following structure:

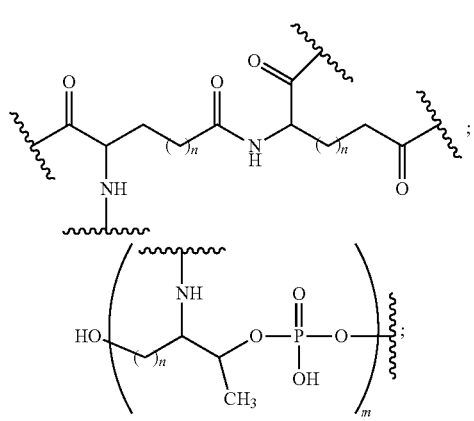

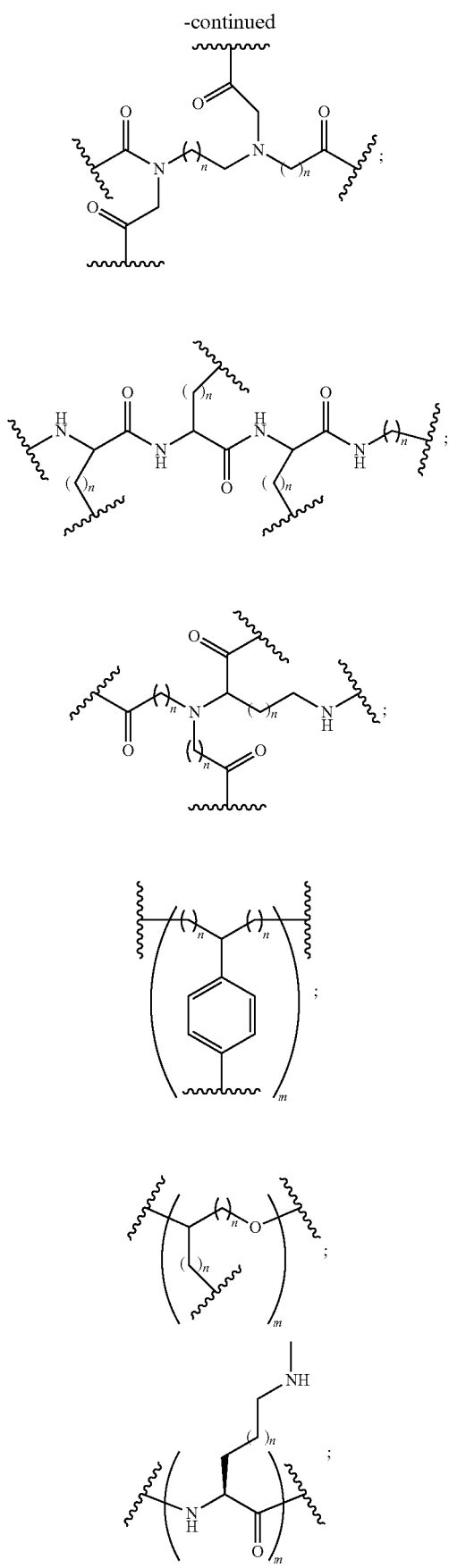
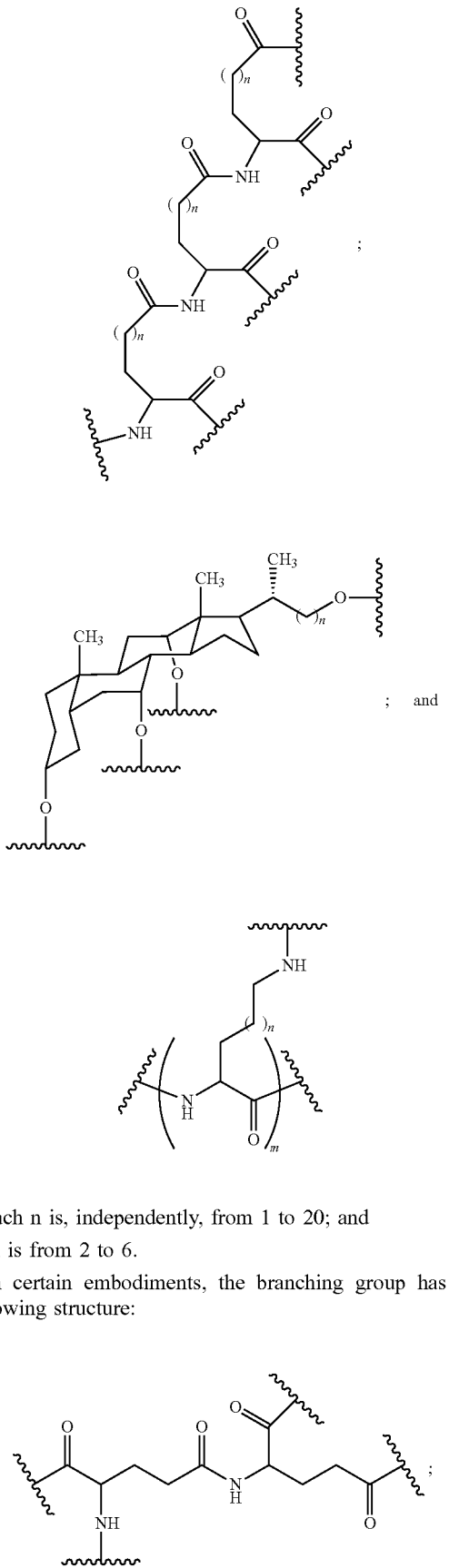
each n is, independently, from 1 to 20; and
m is from 2 to 6.
In certain embodiments, the branching group has the following structure:
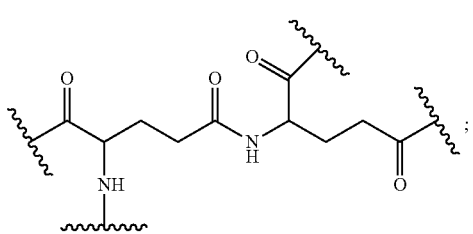

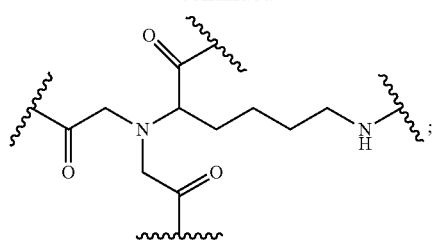
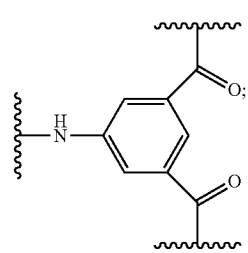
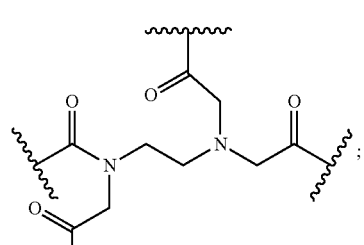
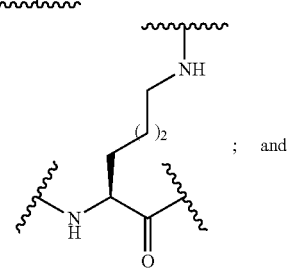
; and
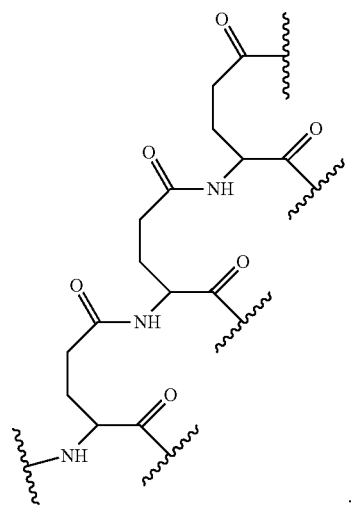
In certain embodiments, the branching group has the following structure:
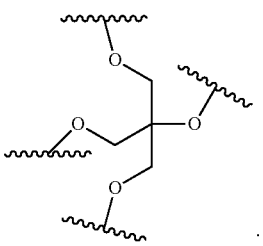
In certain embodiments, the branching group comprises:
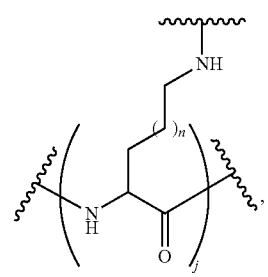
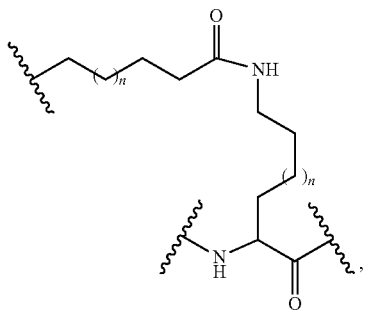
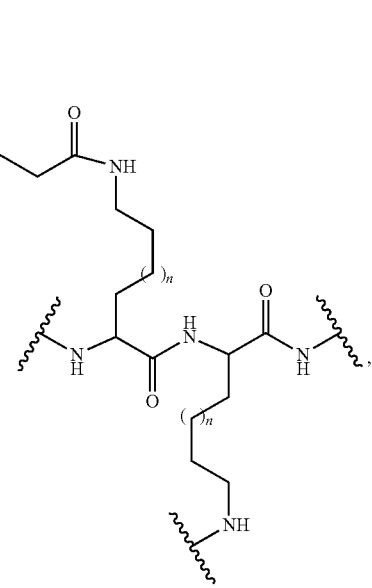

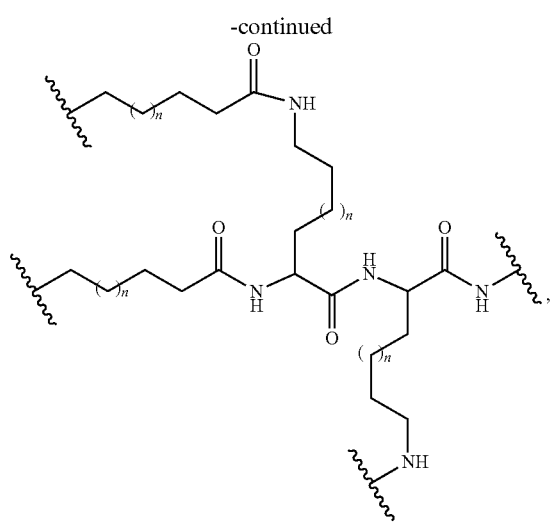
or
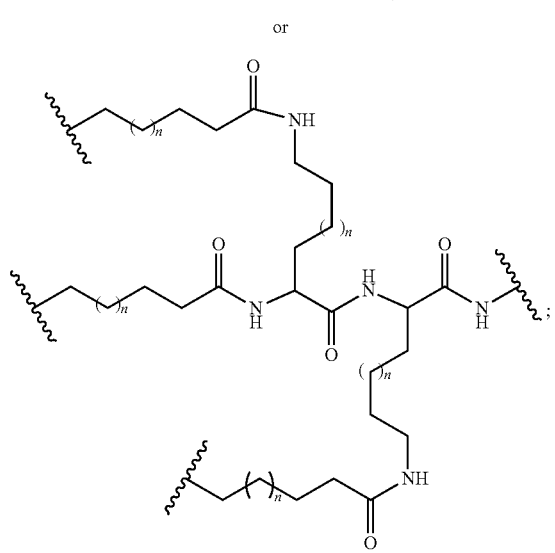
wherein each j is an integer from 1 to 3; and
wherein each n is an integer from 1 to 20.
In certain embodiments, the branching group comprises:
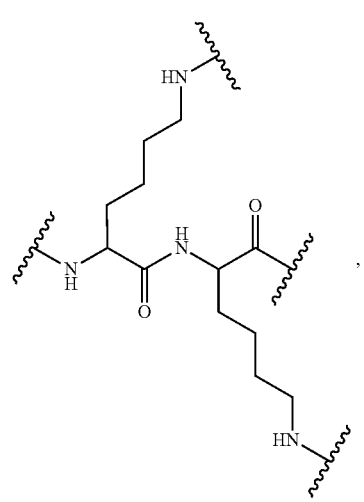
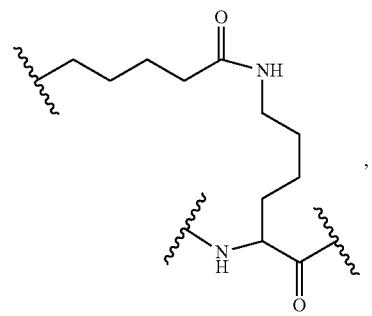
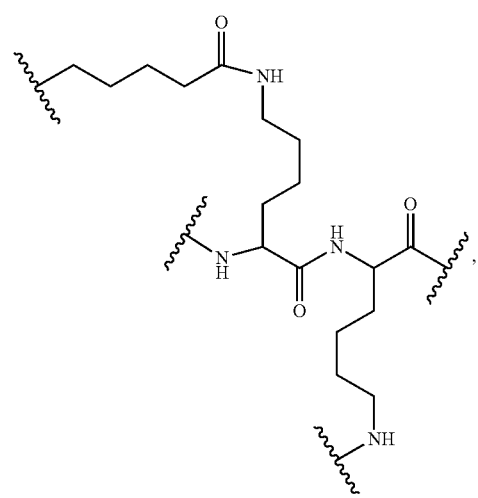
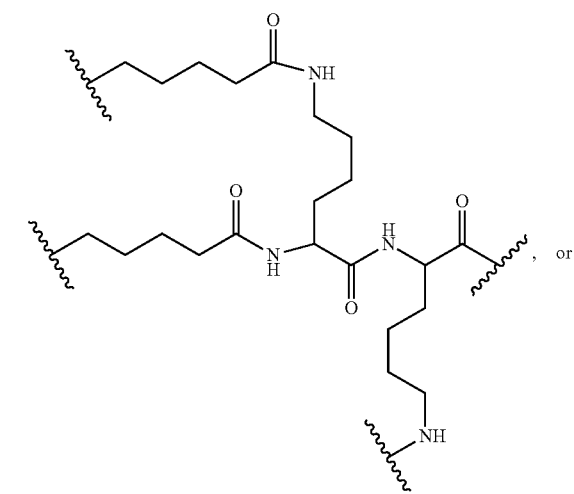, or

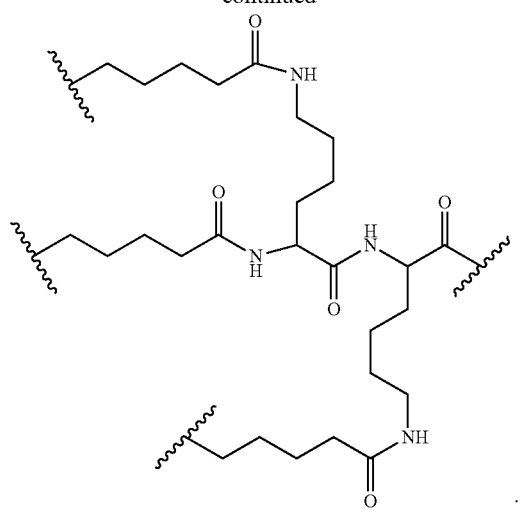

In certain embodiments, each tether is selected from among:

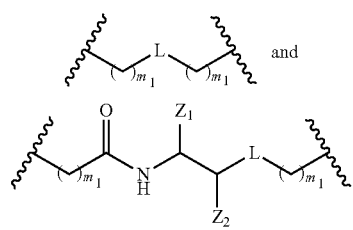

wherein L is selected from a phosphorus linking group and a neutral linking group;

Z1 is C(=O)O—R²;

Z2 is H, C1-C6 alkyl or substituted C1-C6 alky;

R2 is H, C1-C6 alkyl or substituted C1-C6 alky; and each m1 is, independently, from 0 to 20 wherein at least one m1 is greater than 0 for each tether.

In certain embodiments, each tether is selected from among:

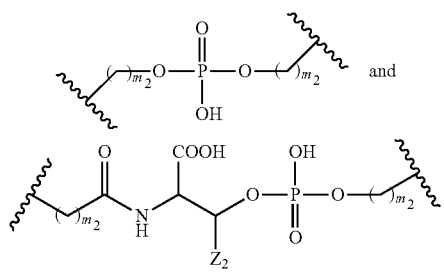

wherein Z2 is H or CH3; and each m2 is, independently, from 0 to 20 wherein at least one m2 is greater than 0 for each tether.

In certain embodiments, each tether is selected from among:

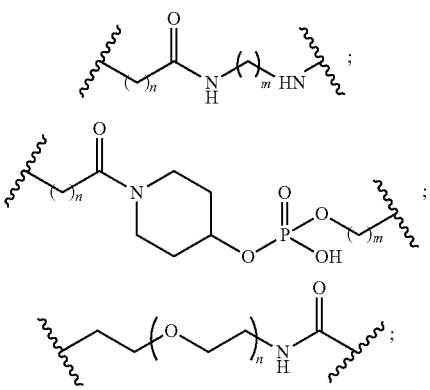

wherein n is from 1 to 12; and wherein m is from 1 to 12.

In certain embodiments, at least one tether comprises ethylene glycol. In certain embodiments, at least one tether comprises an amide. In certain embodiments, at least one tether comprises a polyamide. In certain embodiments, at least one tether comprises an amine. In certain embodiments, at least two tethers are different from one another. In certain embodiments, all of the tethers are the same as one another. In certain embodiments, each tether is selected from among:

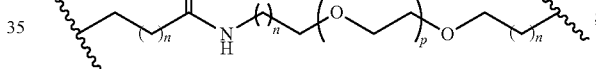

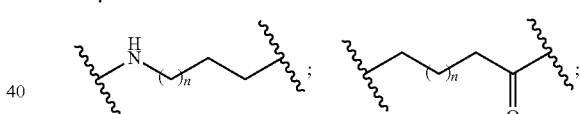

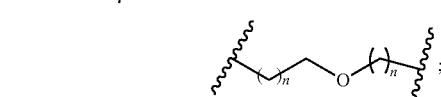

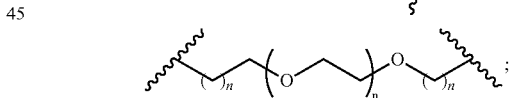

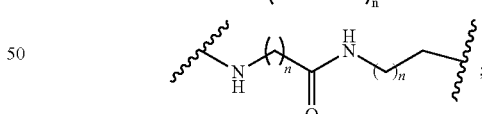

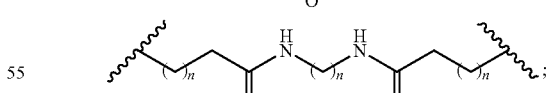

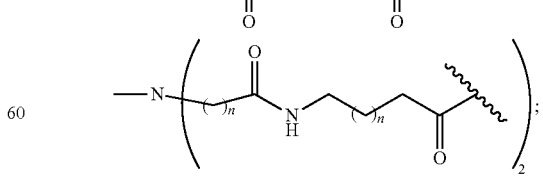

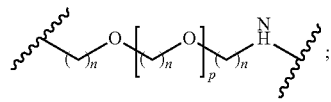

-continued

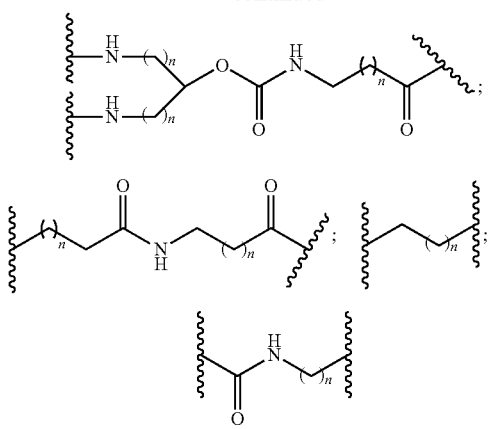

wherein each n is, independently, from 1 to 20; and each p is from 1 to about 6.

In certain embodiments, each tether is selected from among:

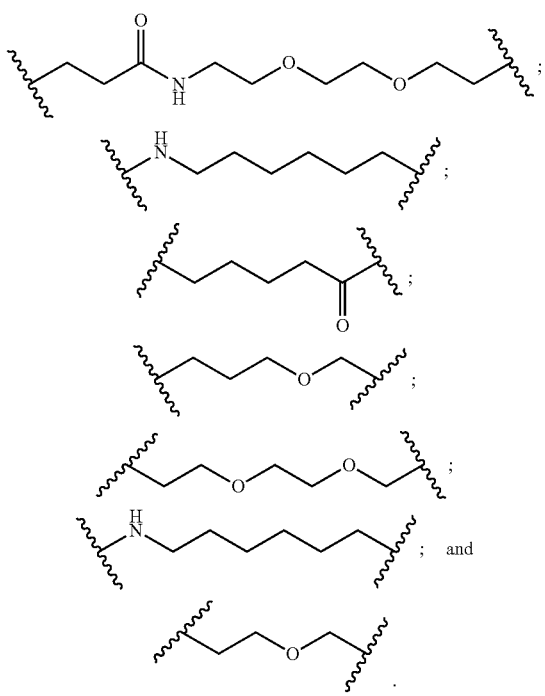

In certain embodiments, each tether has the following structure:

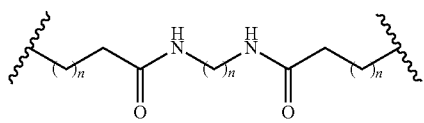

wherein each n is, independently, from 1 to 20.

In certain embodiments, each tether has the following structure:

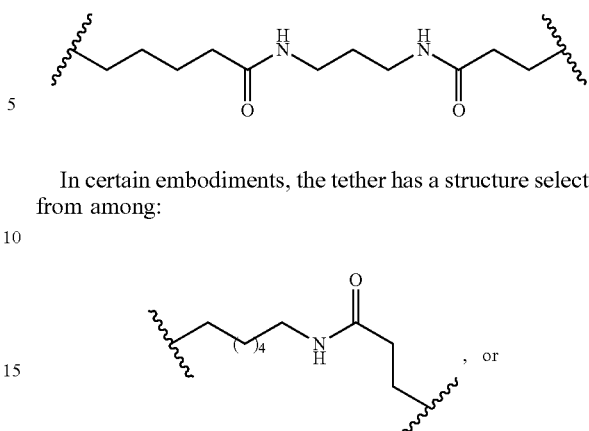

In certain embodiments, the tether has a structure selected from among:

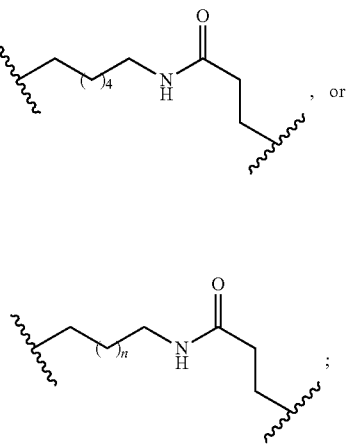

wherein each n is independently, 0, 1, 2, 3, 4, 5, 6, or 7.

In certain embodiments, the tether has a structure selected from among:

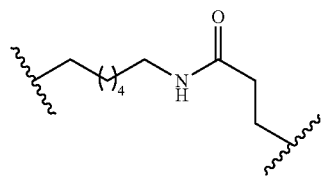

In certain embodiments, the ligand is galactose. In certain embodiments, the ligand is mannose-6-phosphate.

In certain embodiments, each ligand is selected from among:

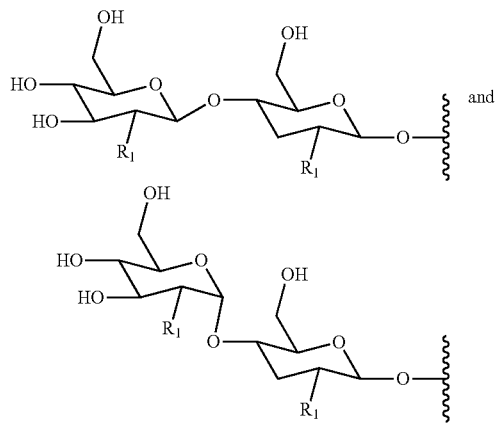

wherein each R1 is selected from OH and NHCOOH.

In certain embodiments, each ligand is selected from among:

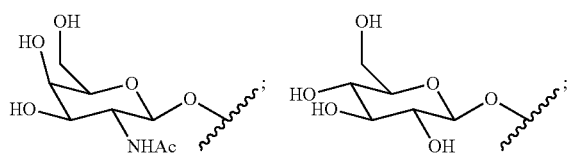

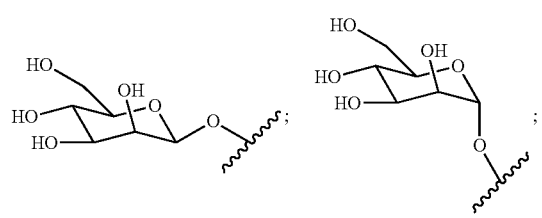

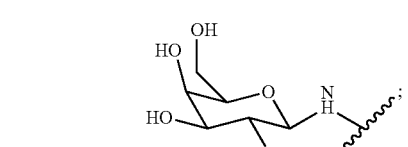

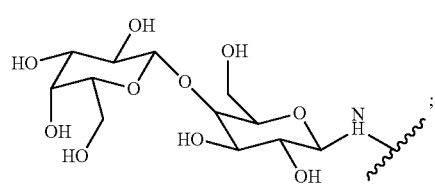

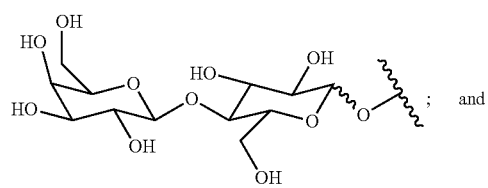 and

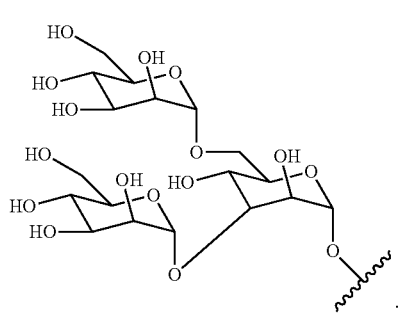

In certain embodiments each ligand has the following structure:

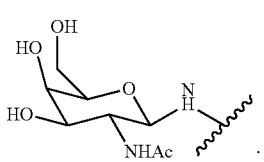 [SMILES: *NC1OC(CO)C(O)C(O)C1NC(C)=O]

In certain embodiments, each ligand has the following structure:

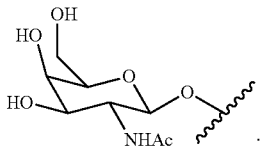 [SMILES: *OC1OC(CO)C(O)C(O)C1NC(C)=O]

In certain embodiments, the conjugate group comprises a cell-targeting moiety.

In certain embodiments, the conjugate group comprises a cell-targeting moiety having the following structure:

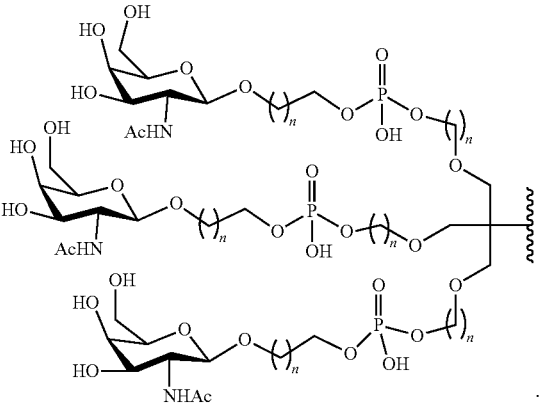

wherein each n is, independently, from 1 to 20.

In certain embodiments, the cell-targeting moiety has the following structure:
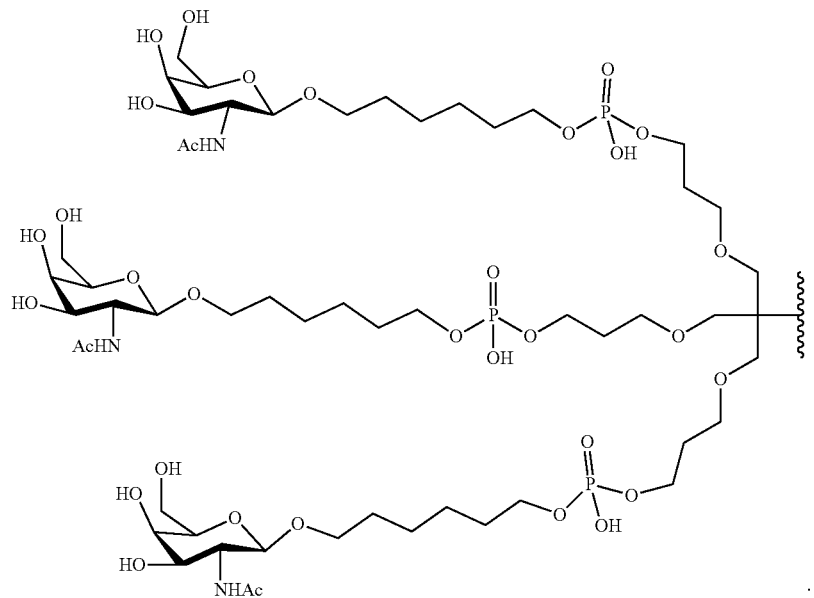
In certain embodiments, the cell-targeting moiety has the following structure:
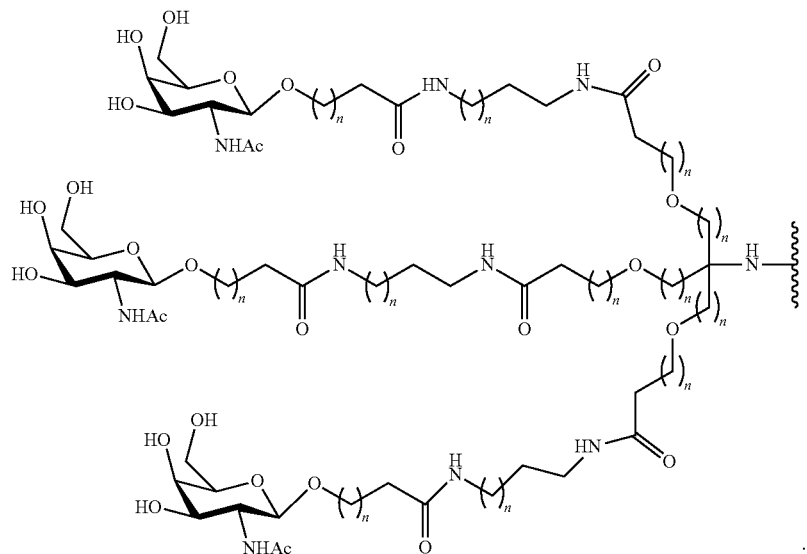
wherein each n is, independently, from 1 to 20.

In certain embodiments, the cell-targeting moiety has the following structure:
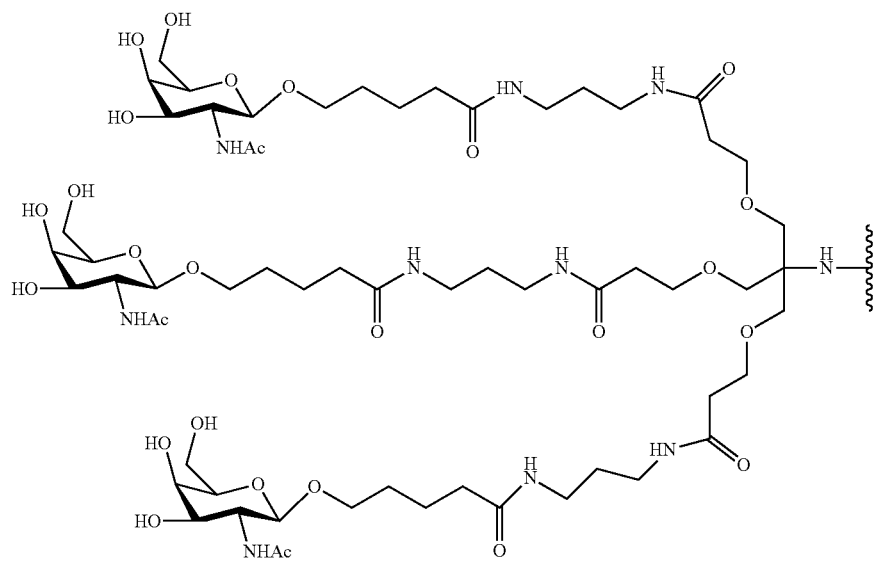
In certain embodiments, the cell-targeting moiety comprises:
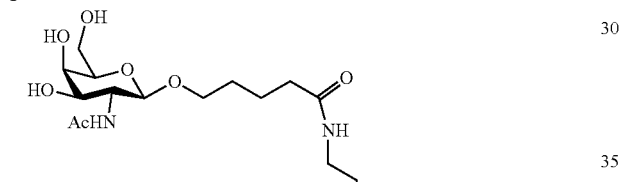
In certain embodiments, the cell-targeting moiety comprises:
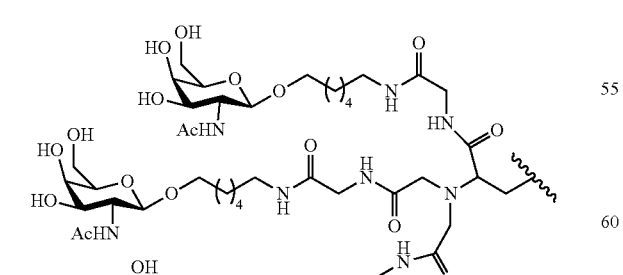
In certain embodiments, the cell-targeting moiety comprises:
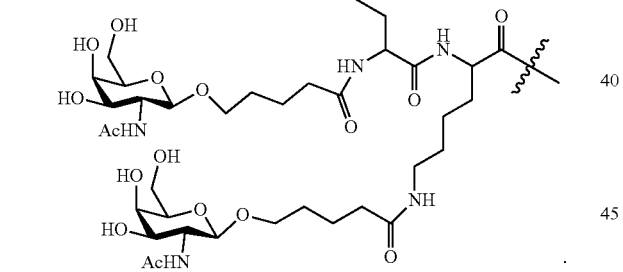
In certain embodiments, the cell-targeting moiety comprises:

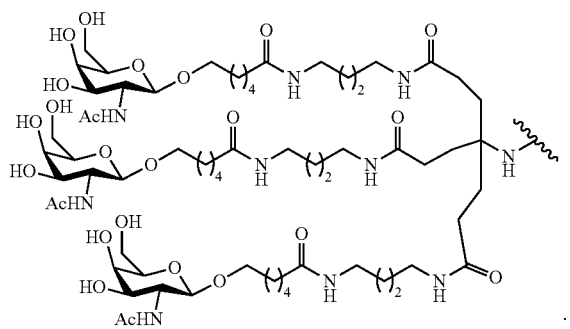
In certain embodiments, the cell-targeting moiety comprises:
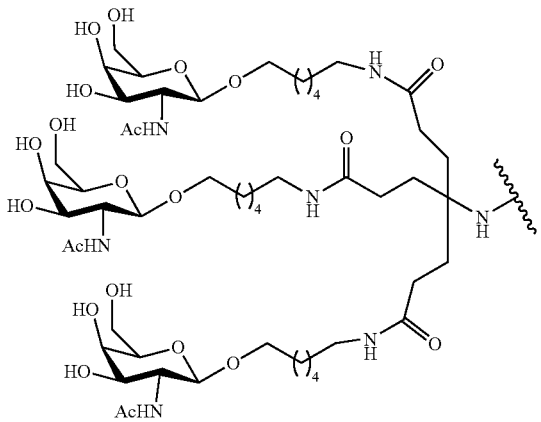
In certain embodiments, the cell-targeting moiety comprises:
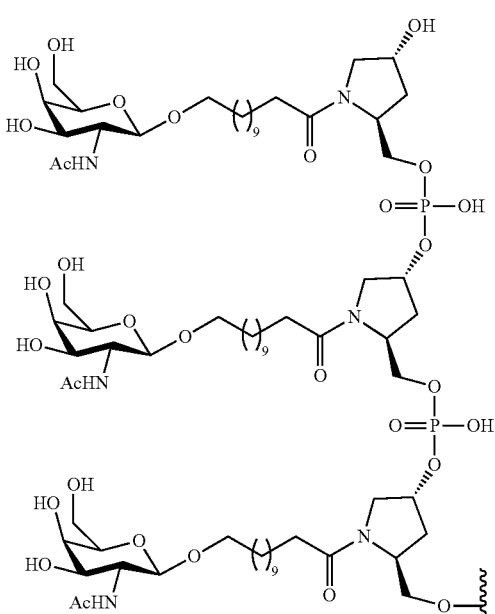
In certain embodiments, the cell-targeting moiety comprises:
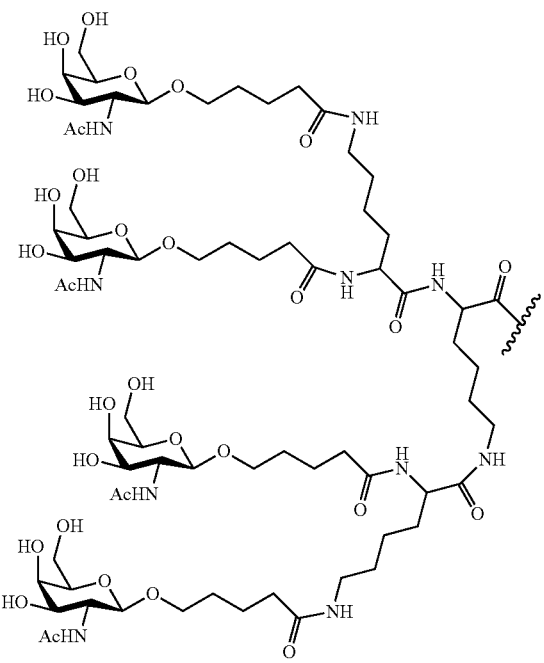

In certain embodiments, the cell-targeting moiety comprises:
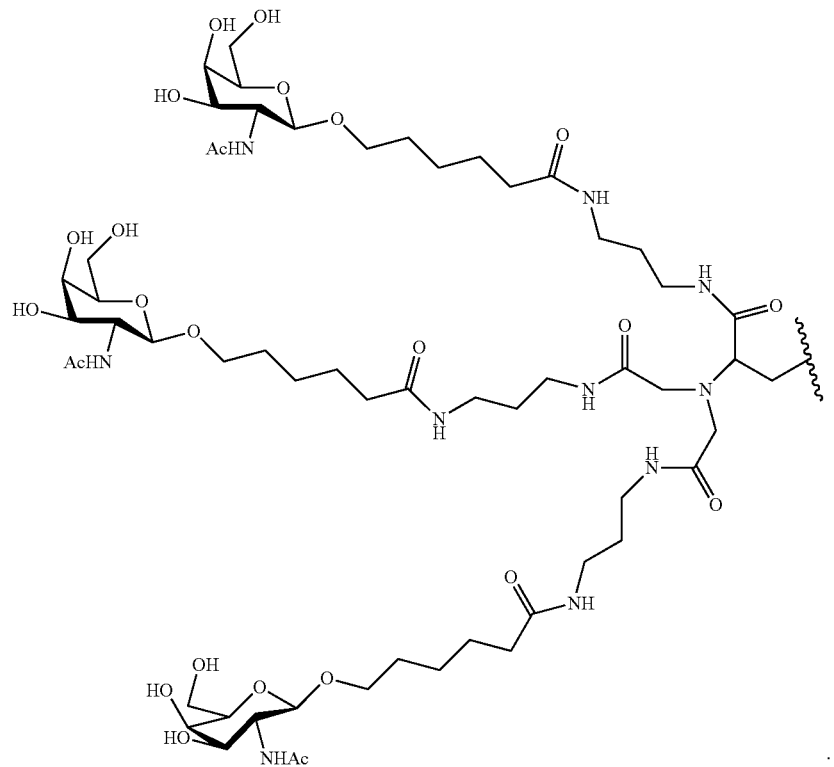
In certain embodiments the cell-targeting moiety comprises:
In certain embodiments, the cell-targeting moiety comprises:
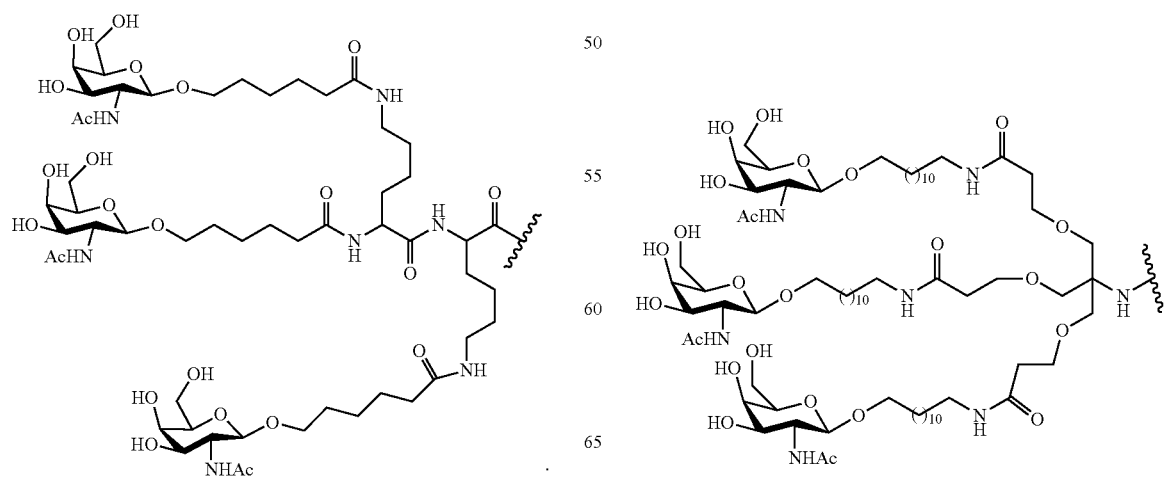

In certain embodiments, the cell-targeting moiety comprises:
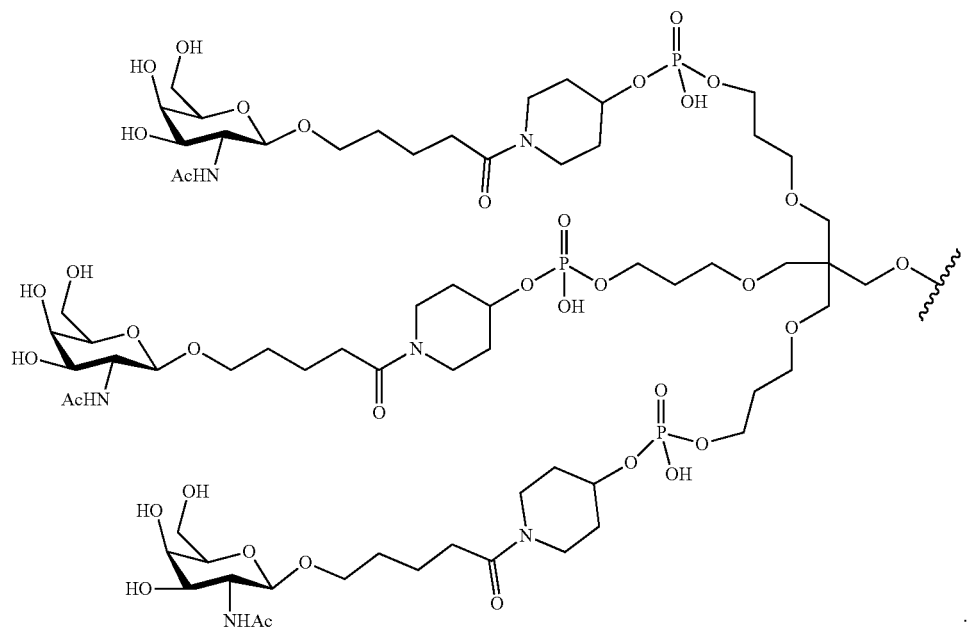
In certain embodiments, the cell-targeting moiety comprises:
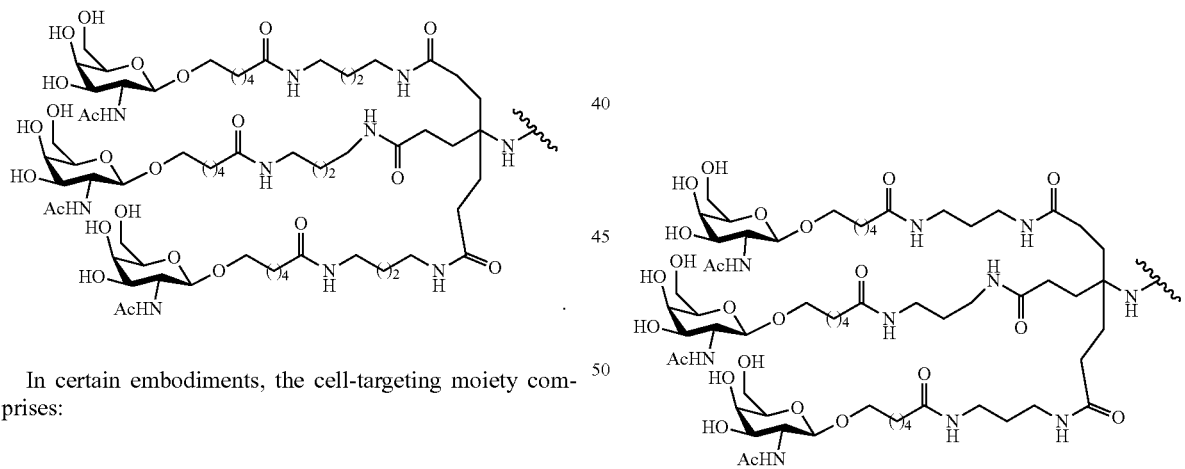
In certain embodiments, the cell-targeting moiety comprises:
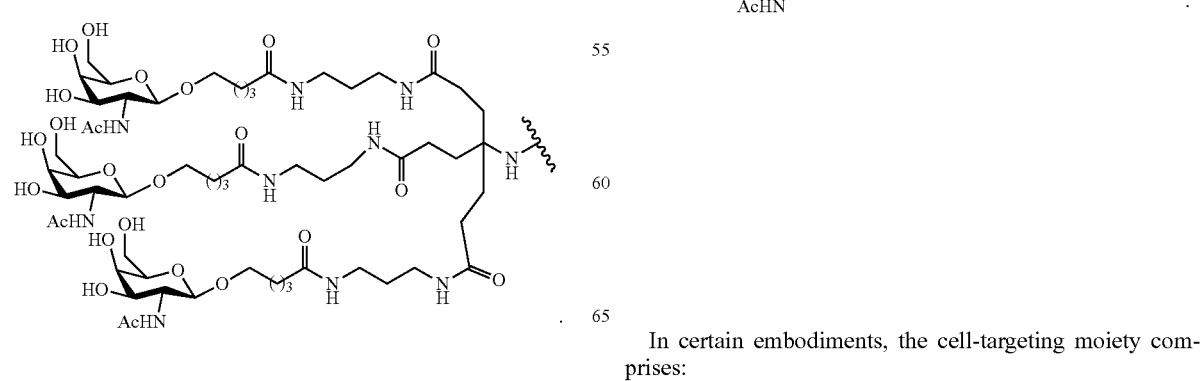
In certain embodiments, the cell-targeting moiety comprises:

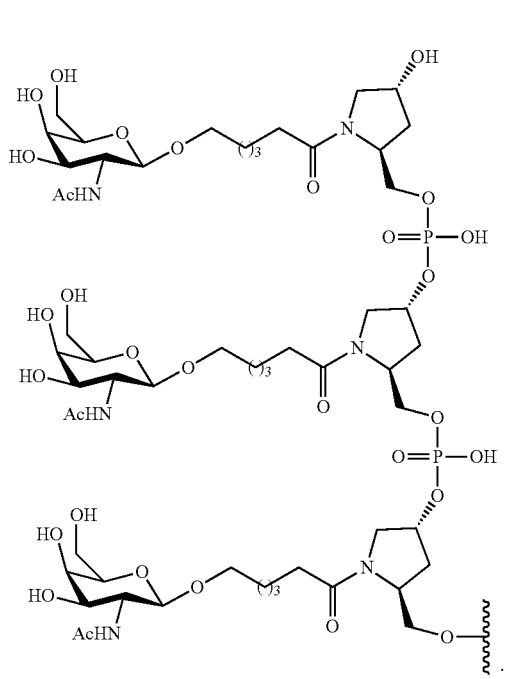
In certain embodiments, the cell-targeting moiety comprises:
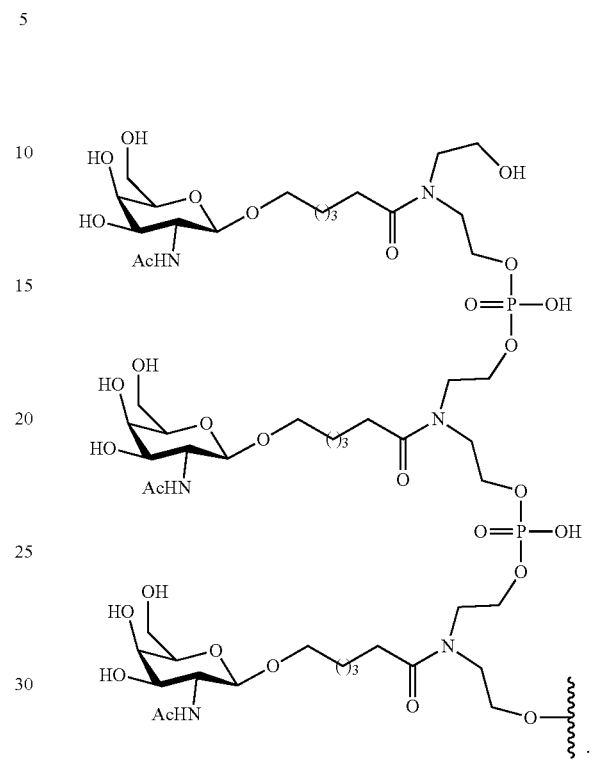
In certain embodiments, the cell-targeting moiety comprises:
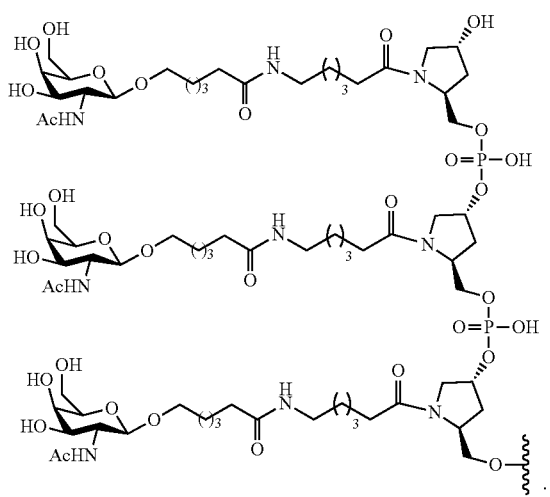

In certain embodiments, the cell-targeting moiety comprises:

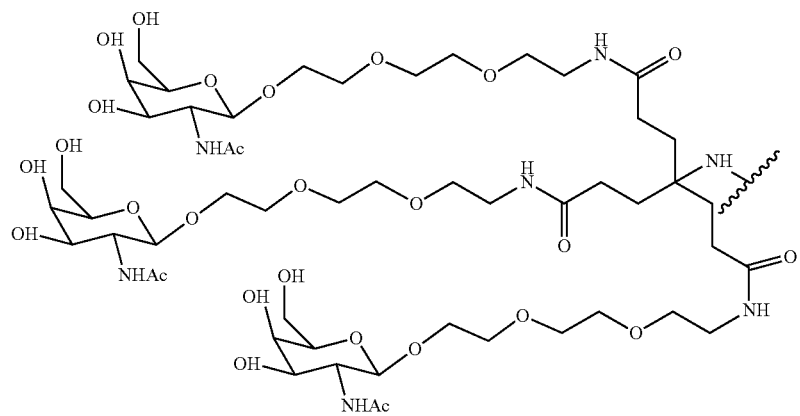 [SMILES: *NC(CCC(=O)NCCOCCOCCOC1OC(CO)C(O)C(O)C1NC(C)=O)(CCC(=O)NCCOCCOCCOC1OC(CO)C(O)C(O)C1NC(C)=O)CCC(=O)NCCOCCOCCOC1OC(CO)C(O)C(O)C1NC(C)=O]

In certain embodiments, the cell-targeting moiety comprises:

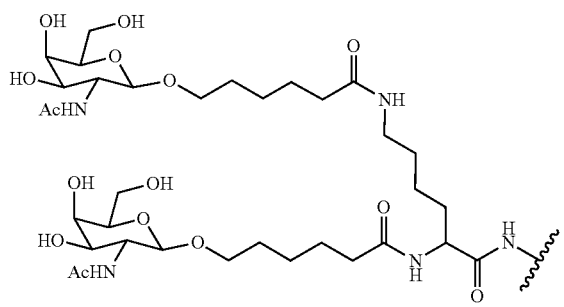 [SMILES: *NC(=O)C(CCCCNC(=O)CCCCCCOC1OC(CO)C(O)C(O)C1NC(C)=O)NC(=O)CCCCCOC1OC(CO)C(O)C(O)C1NC(C)=O]

In certain embodiments, the cell-targeting moiety comprises:

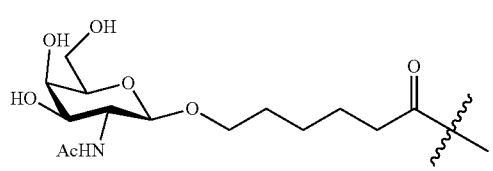

In certain embodiments, the cell-targeting moiety comprises:

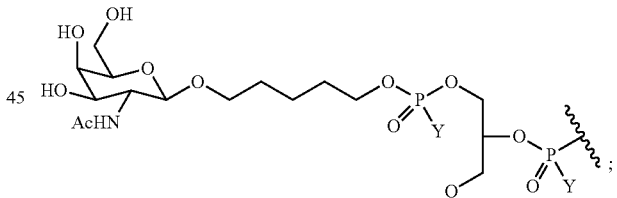

wherein each Y is selected from O, S, a substituted or unsubstituted C1-C10 alkyl, amino, substituted amino, azido, alkenyl or alkynyl.

In certain embodiments, the conjugate group comprises:

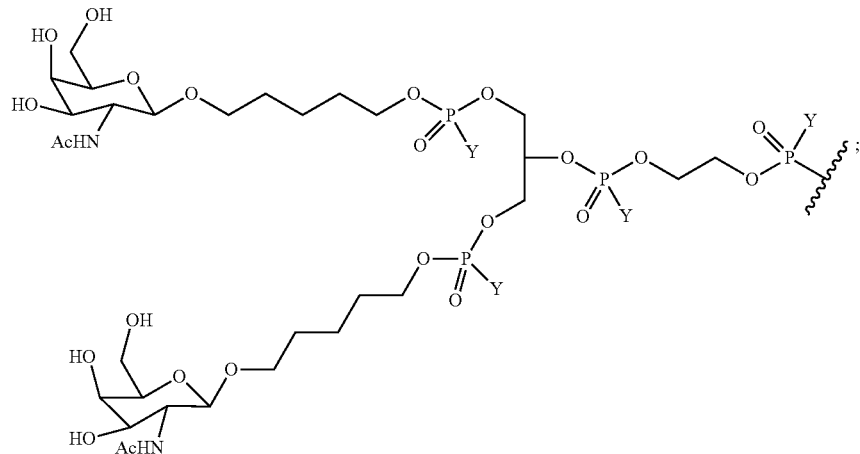

wherein each Y is selected from O, S, a substituted or unsubstituted C1-C10 alkyl, amino, substituted amino, azido, alkenyl or alkynyl.

In certain embodiments, the conjugate group comprises:

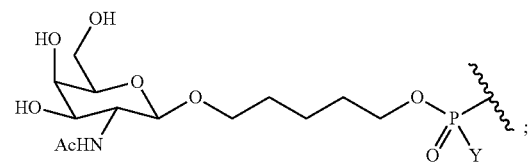

wherein each Y is selected from O, S, a substituted or unsubstituted C1-C10 alkyl, amino, substituted amino, azido, alkenyl or alkynyl.

In certain embodiments, the conjugate group comprises:

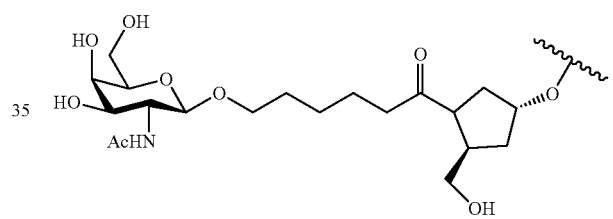

In certain embodiments, the conjugate group comprises:

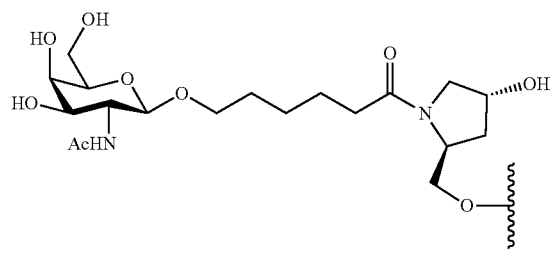

In certain embodiments, the conjugate group comprises:

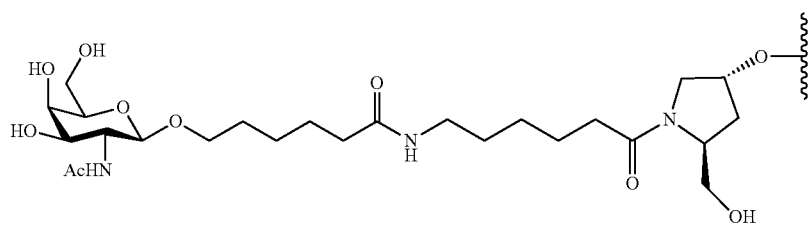

In certain embodiments, the conjugate group comprises:

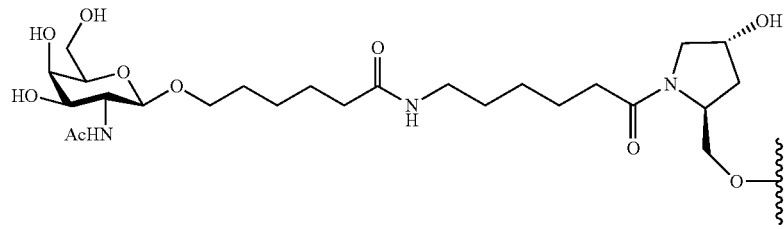

In certain embodiments, the conjugate group comprises a cleavable moiety selected from among: a phosphodiester, an amide, or an ester.

In certain embodiments, the conjugate group comprises a phosphodiester cleavable moiety.

In certain embodiments, the conjugate group does not comprise a cleavable moiety, and wherein the conjugate group comprises a phosphorothioate linkage between the conjugate group and the oligonucleotide.

In certain embodiments, the conjugate group comprises an amide cleavable moiety. In certain embodiments, the conjugate group comprises an ester cleavable moiety.

In certain embodiments, the compound has the following structure:

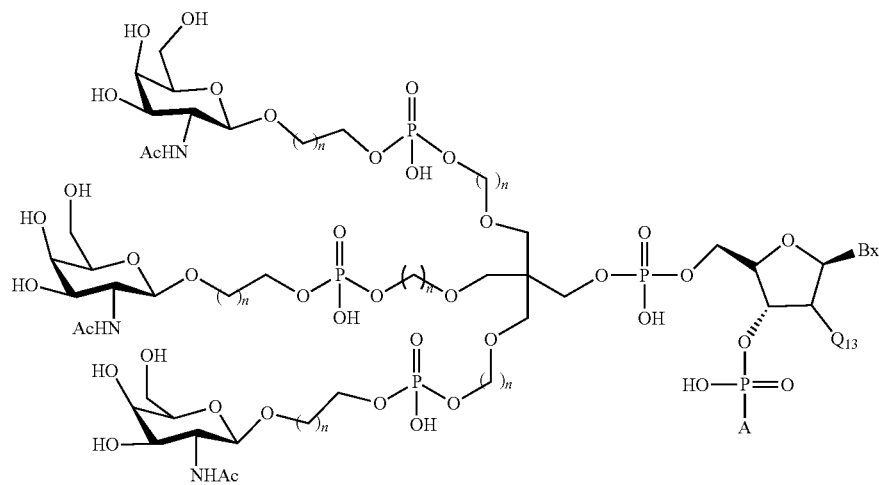

wherein each n is, independently, from 1 to 20;
Q13 is H or O(CH2)2-OCH3;
A is the modified oligonucleotide; and
Bx is a heterocyclic base moiety.

In certain embodiments, the compound has the following structure:
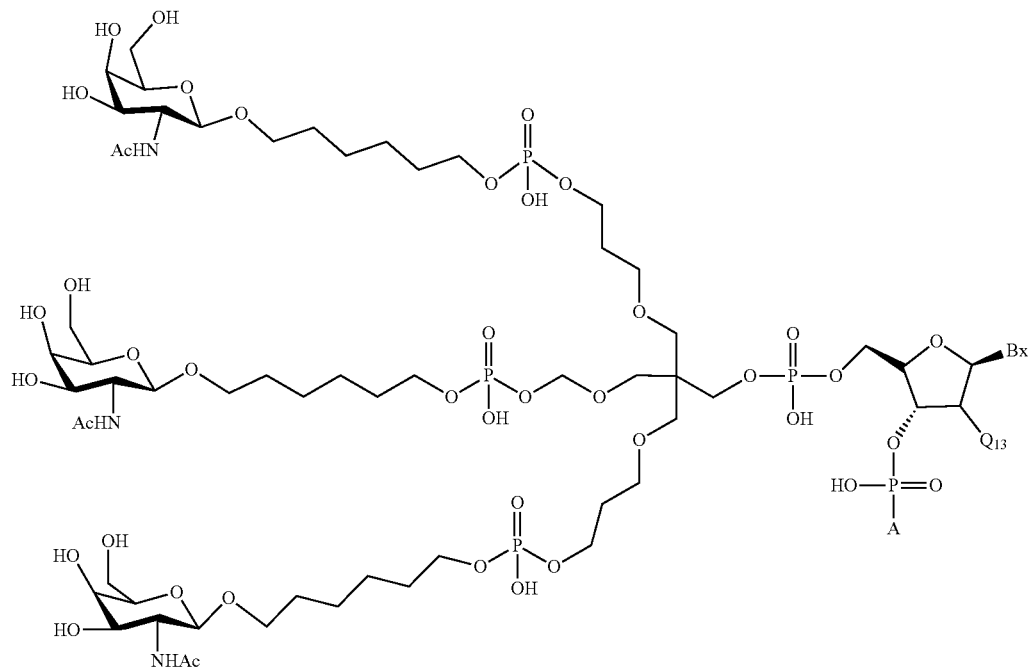
wherein each n is, independently, from 1 to 20;
Q13 is H or O(CH2)2-OCH3;
A is the modified oligonucleotide; and
Bx is a heterocyclic base moiety.
In certain embodiments, the compound has the following structure:
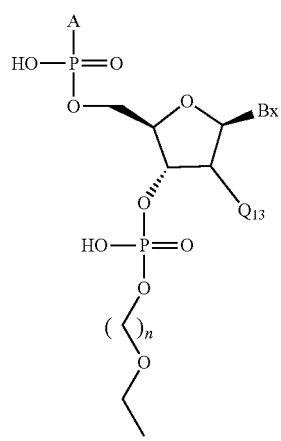

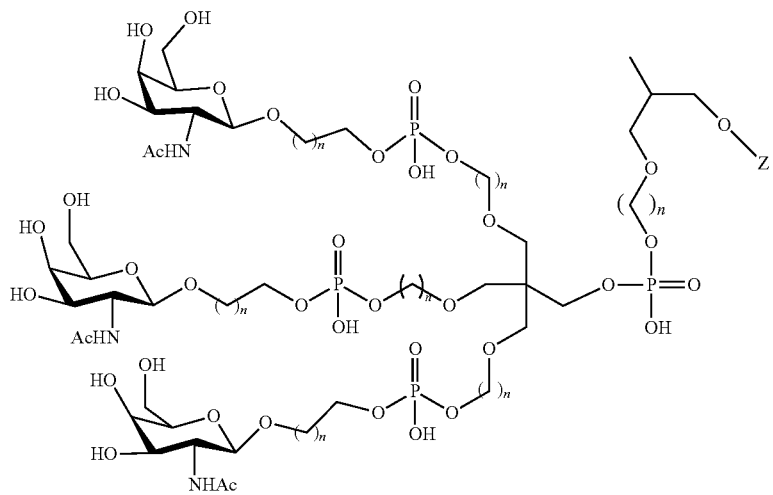
25
wherein each n is, independently, from 1 to 20;
Q13 is H or O(CH2)2-OCH3;
A is the modified oligonucleotide;
Z is H or a linked solid support; and
Bx is a heterocyclic base moiety.
In certain embodiments, the compound has the following structure:
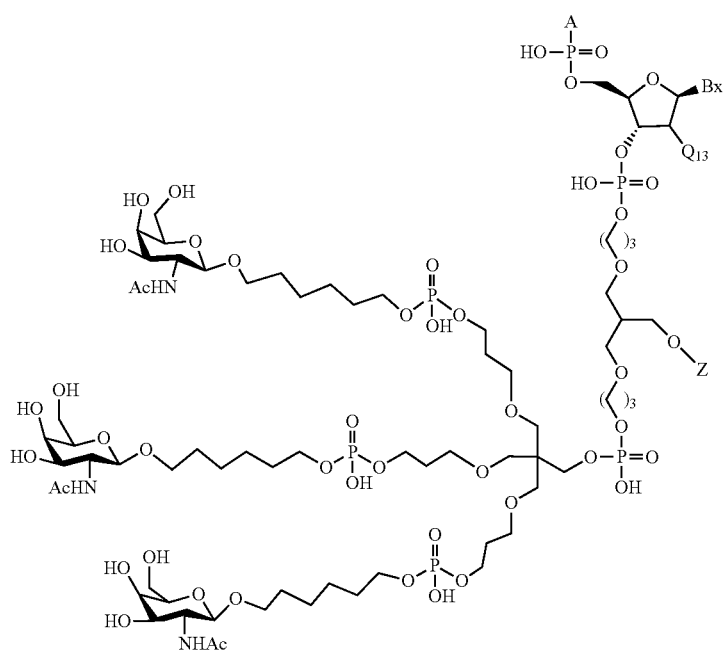

wherein each n is, independently, from 1 to 20;
Q13 is H or O(CH2)2-OCH3;
A is the modified oligonucleotide;
Z is H or a linked solid support; and

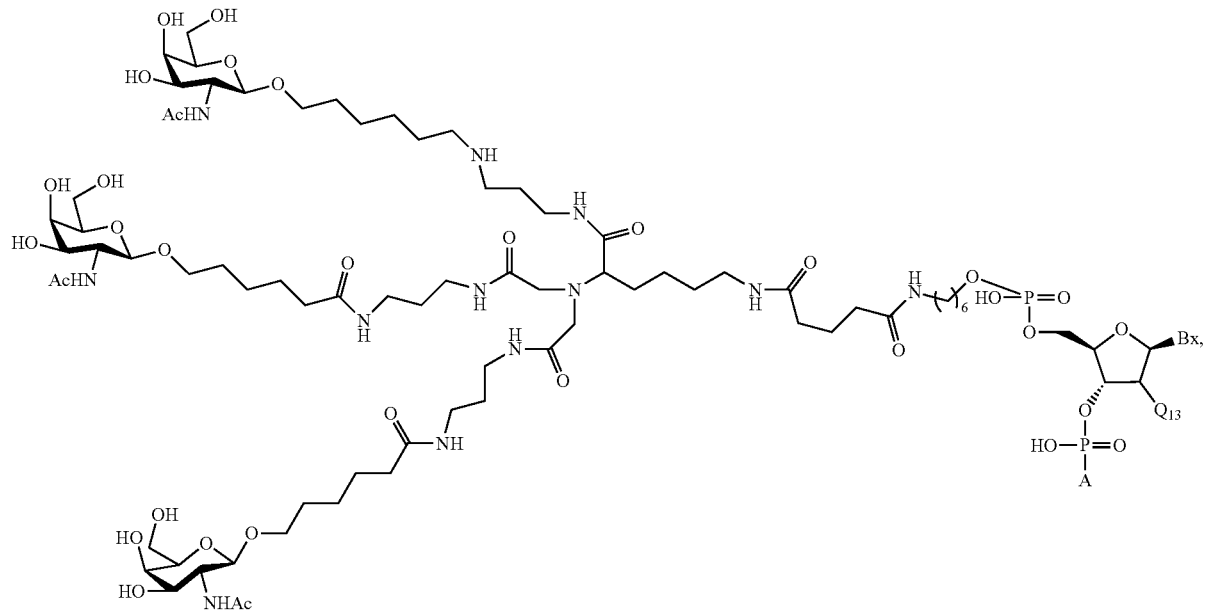

wherein Q13 is H or O(CH2)2-OCH3;
A is the modified oligonucleotide; and
Bx is a heterocyclic base moiety.

In certain embodiments, the compound has the following structure:

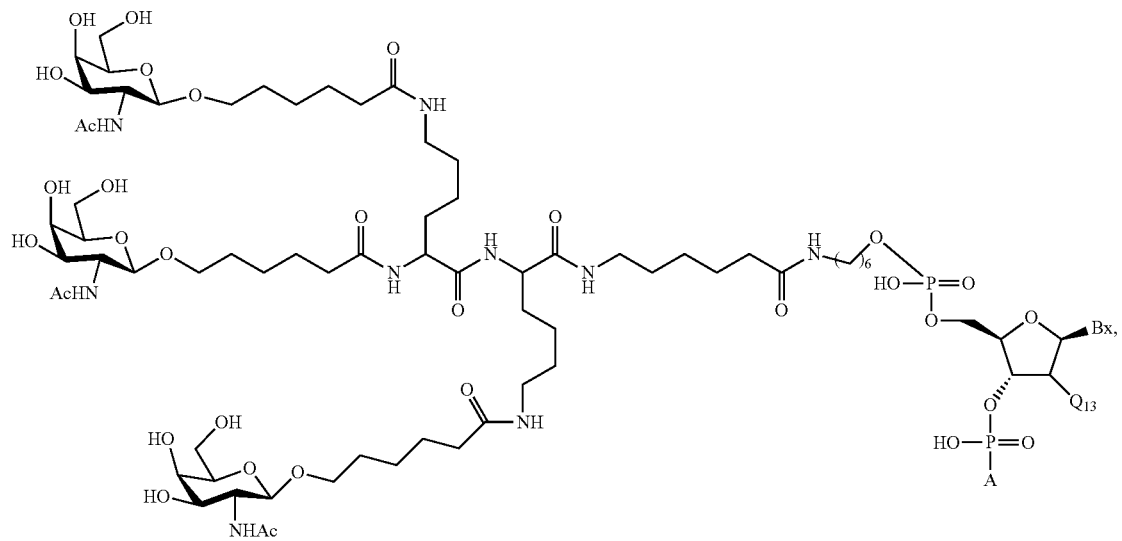

wherein Q13 is H or O(CH2)2-OCH3;
A is the modified oligonucleotide; and
Bx is a heterocyclic base moiety.

In certain embodiments, the compound has the following structure:

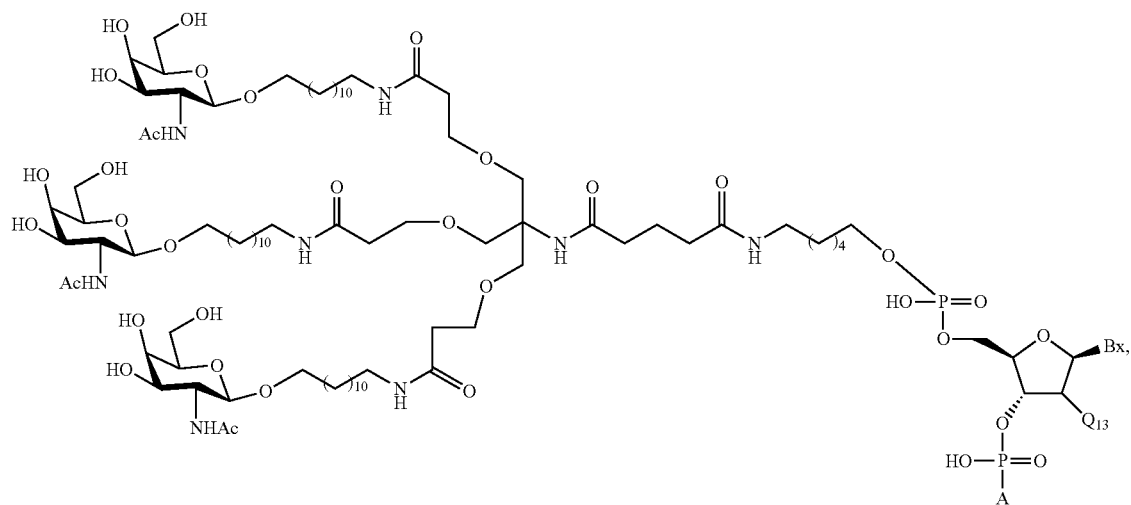
wherein Q13 is H or O(CH2)2-OCH3;
A is the modified oligonucleotide; and
Bx is a heterocyclic base moiety.
In certain embodiments, the compound has the following structure:
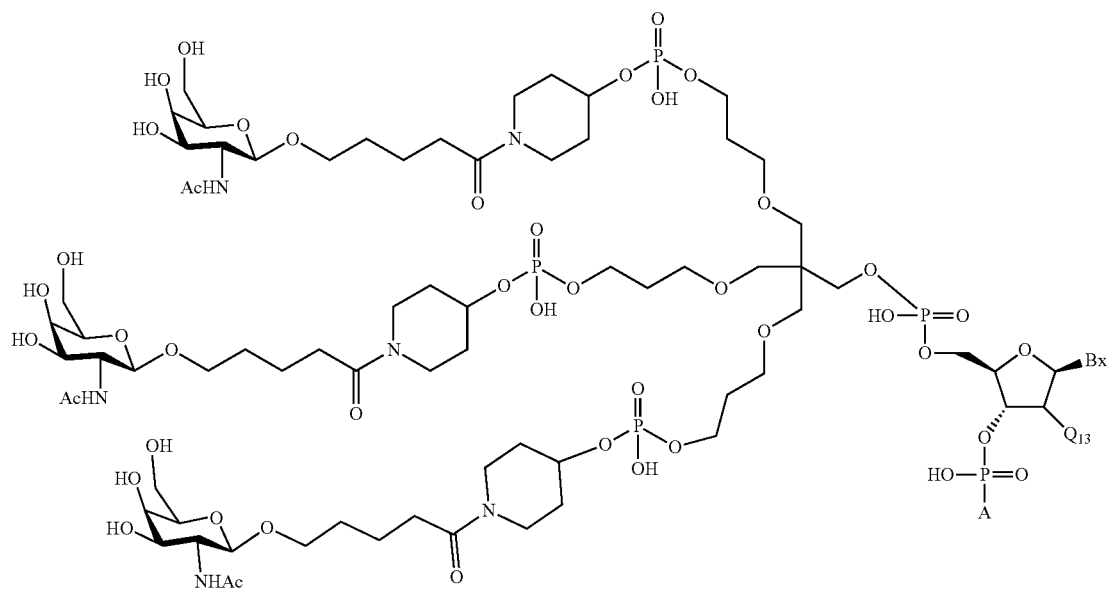
wherein Q13 is H or O(CH2)2-OCH3;
A is the modified oligonucleotide; and
Bx is a heterocyclic base moiety.
In certain embodiments, the compound has the following structure:

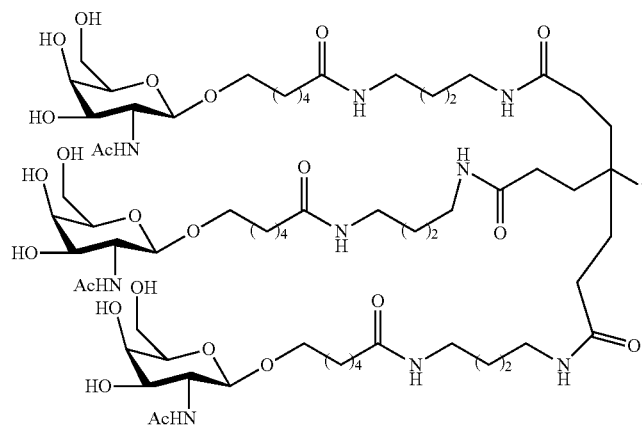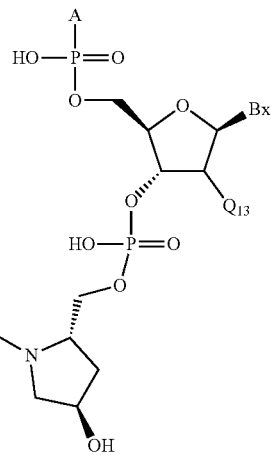
wherein Q13 is H or O(CH2)2-OCH3;
A is the modified oligonucleotide; and
Bx is a heterocyclic base moiety.
In certain embodiments, the compound has the following structure:
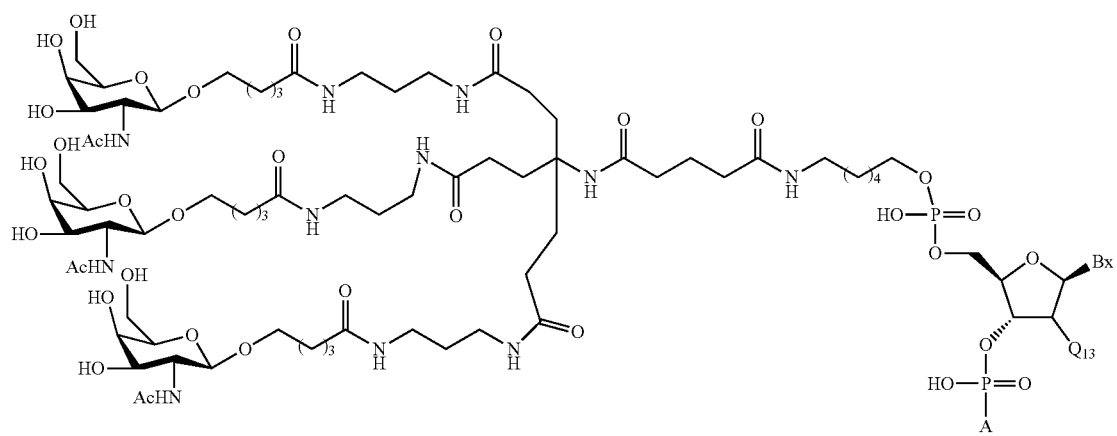
wherein Q13 is H or O(CH2)2-OCH3;
A is the modified oligonucleotide; and
Bx is a heterocyclic base moiety.
In certain embodiments, the compound has the following structure:

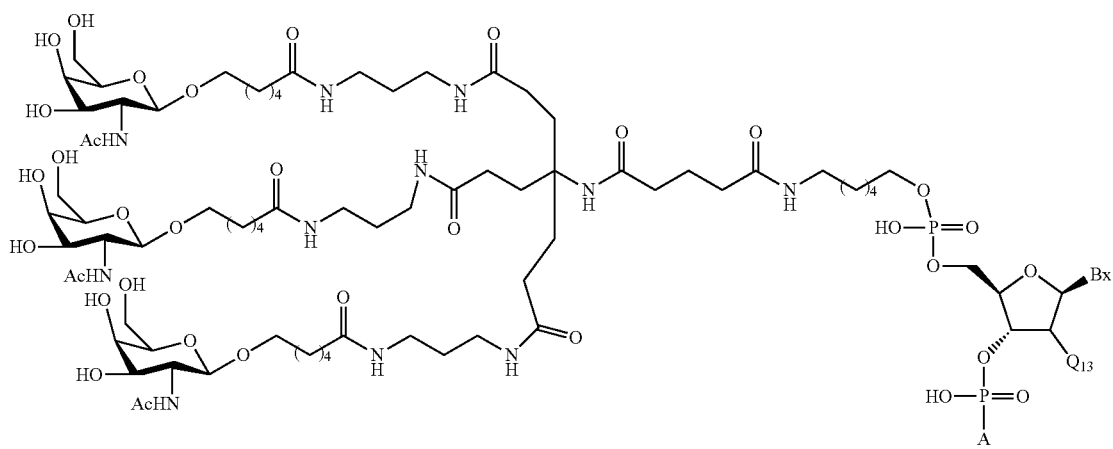
wherein Q13 is H or O(CH2)2-OCH3;
A is the modified oligonucleotide; and
Bx is a heterocyclic base moiety.
In certain embodiments, the compound has the following structure:
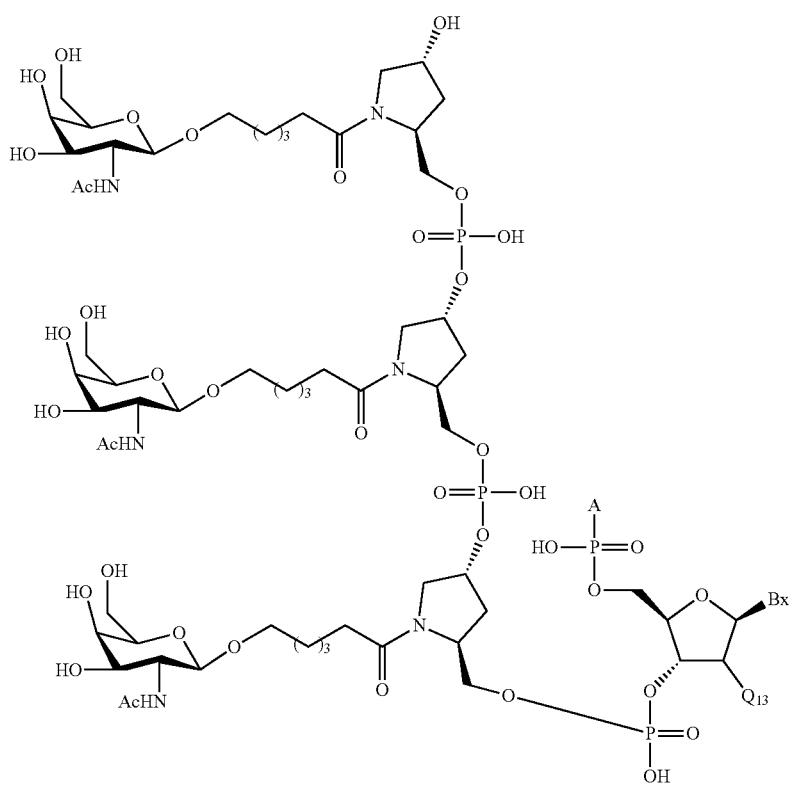
wherein Q13 is H or O(CH2)2-OCH3;
A is the modified oligonucleotide; and
Bx is a heterocyclic base moiety.
In certain embodiments, the compound has the following structure:

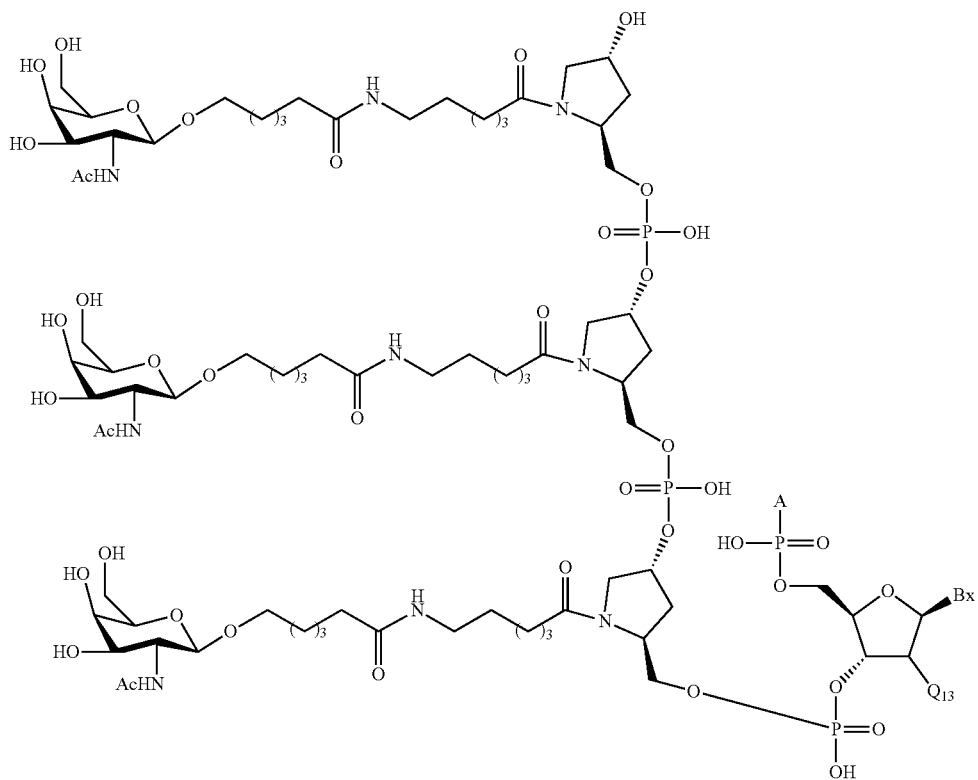
wherein Q13 is H or O(CH2)2-OCH3;
A is the modified oligonucleotide; and
Bx is a heterocyclic base moiety.
In certain embodiments, the compound has the following structure:
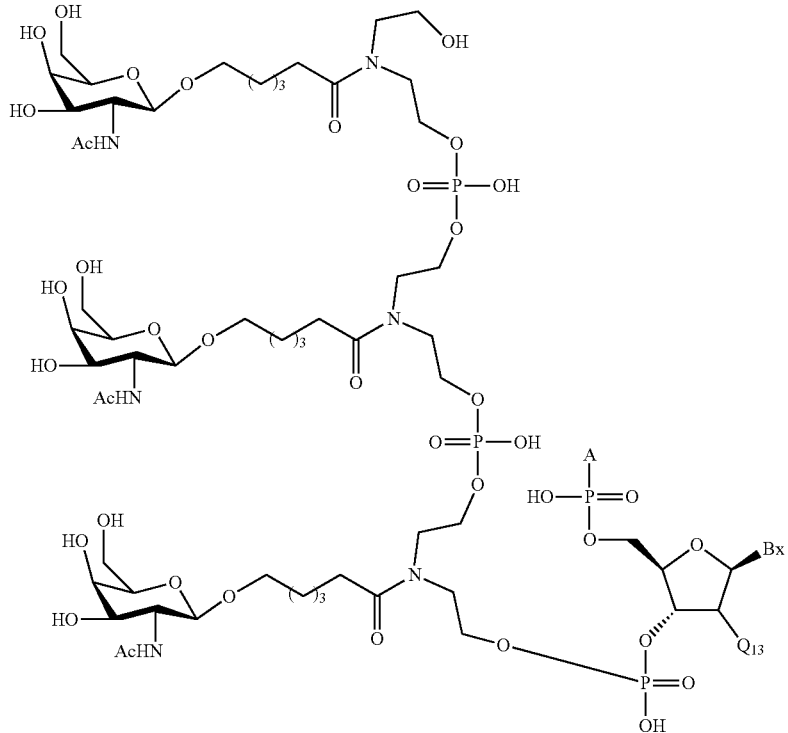

wherein Q13 is H or O(CH2)2-OCH3;
A is the modified oligonucleotide; and
Bx is a heterocyclic base moiety.
In certain embodiments, the compound has the following structure:
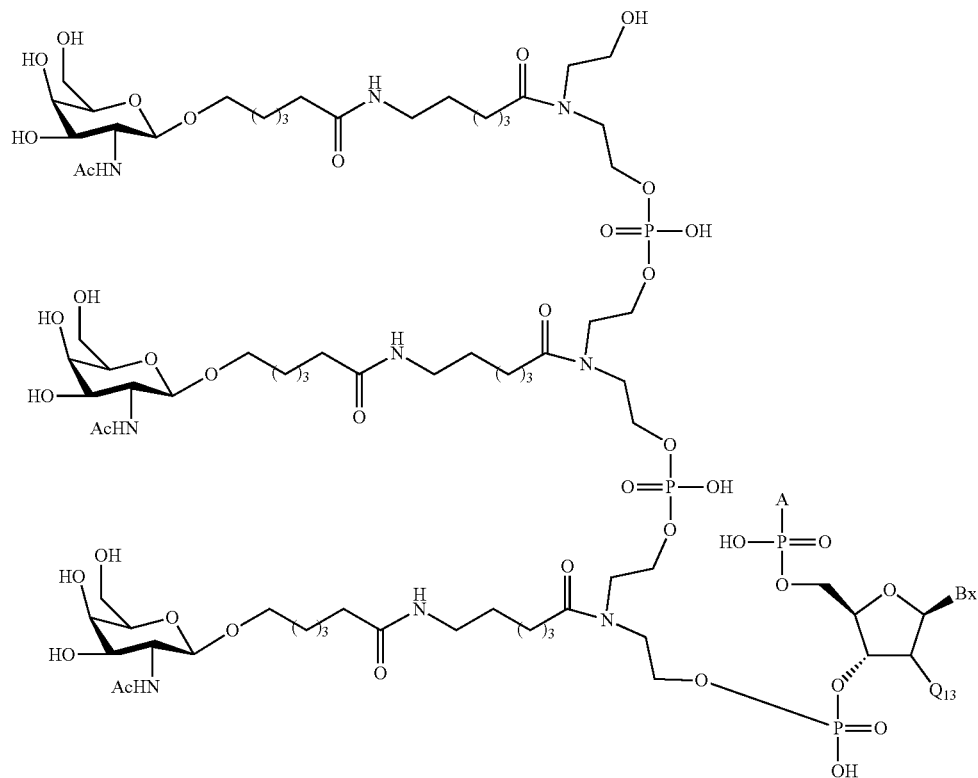
wherein Q13 is H or O(CH2)2-OCH3;
A is the modified oligonucleotide; and
Bx is a heterocyclic base moiety.
In certain embodiments, the conjugate group comprises:
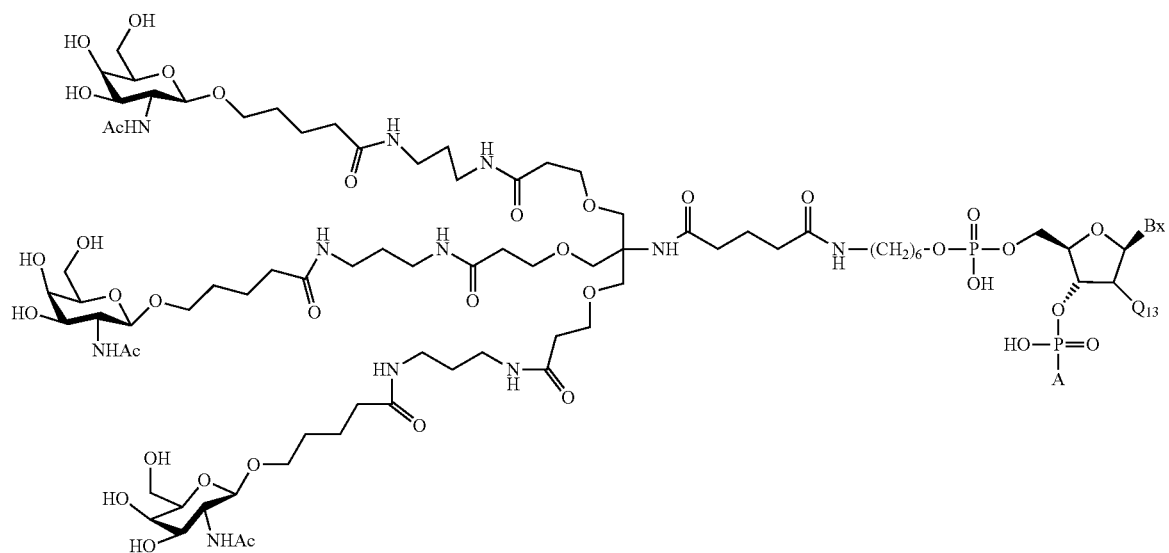

wherein Q13 is H or O(CH2)2-OCH3;
A is the modified oligonucleotide; and
Bx is a heterocyclic base moiety.
In certain embodiments, the conjugate group comprises:

virtue of having a viscosity of less than 40 cP, less than 35 cP, less than 30 cP, less than 25 cP, less than 20 cP or less than 15 cP when measured by the parameters as described in Example 125.

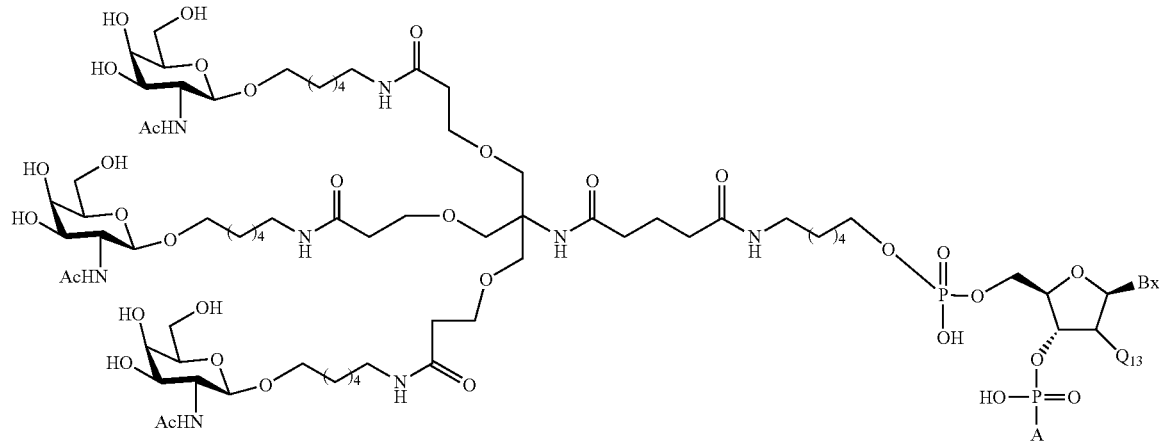

wherein Q13 is H or O(CH2)2-OCH3;
A is the modified oligonucleotide; and
Bx is a heterocyclic base moiety.
In certain embodiments, the conjugate group comprises:

Certain embodiments provide compositions and methods comprising administering to an animal a conjugated antisense compound or composition disclosed herein. In certain embodiments, administering the conjugated antisense com-

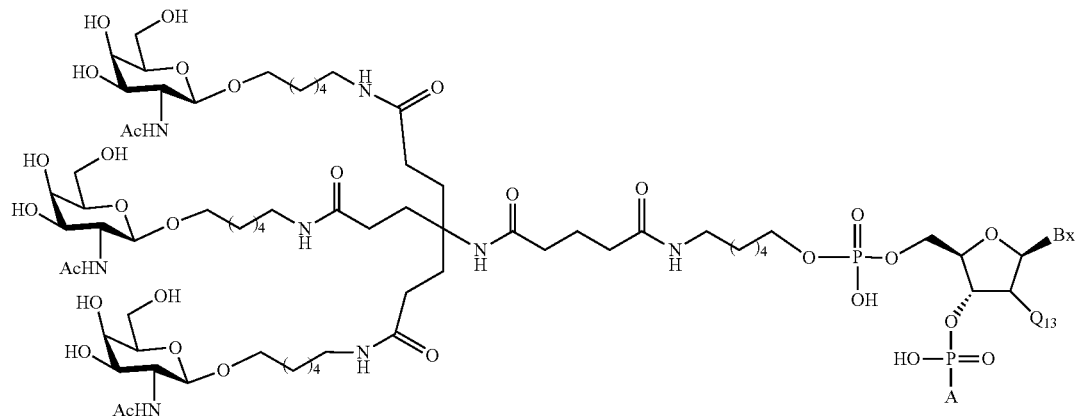

wherein Q13 is H or O(CH2)2-OCH3;
A is the modified oligonucleotide; and
Bx is a heterocyclic base moiety.
In certain embodiments, Bx is selected from among from adenine, guanine, thymine, uracil, or cytosine, or 5-methyl cytosine. In certain embodiments, Bx is adenine. In certain embodiments, Bx is thymine. In certain embodiments, Q13 is O(CH2)2-OCH3. In certain embodiments, Q13 is H.

In certain embodiments, the compound is in a salt form. In further embodiments, the compound further comprises of a pharmaceutically acceptable carrier or diluent. In certain embodiments, the compound comprises a modified oligonucleotide targeting apo(a) and a conjugate group, or a salt thereof, and a pharmaceutically acceptable carrier or diluent.

Certain embodiments provide a composition comprising a conjugated antisense compound as described herein, wherein the viscosity level of the compound is less than 40 centipoise (cP). In certain embodiments, the conjugated antisense compounds as described herein are efficacious by pound prevents, treats, ameliorates, or slows progression of a cardiovascular, metabolic and/or inflammatory disease Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, apo(a) and/or Lp(a) levels are elevated in an animal. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the antisense compound is a modified oligonucleotide targeting apo(a) and a conjugate group. In certain embodiments, the modified oligonucleotide targeting apo(a) with the conjugate group, is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL. Certain embodiments provide compositions and methods to reduce apo(a) mRNA or protein expression in an animal comprising administering to the animal a conjugated antisense compound or composition disclosed herein to reduce apo(a) mRNA or protein expression in the animal. Certain embodiments provide compositions and methods to reduce Lp(a) levels in an animal comprising administering to the animal a conjugated antisense compound or composition disclosed herein to reduce apo(a) mRNA or protein expression in the animal.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include inflammatory, cardiovascular and/or metabolic diseases, disorders, and conditions. Certain such cardiovascular diseases, disorders or conditions include, but are not limited to, aortic stenosis, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, aortic stenosis, coronary artery disease (CAD), Alzheimer's Disease and thromboembolic diseases, disorder or conditions. Certain thromboembolic diseases, disorders or conditions include, but are not limited to, stroke, thrombosis (e.g., venous thromboembolism), myocardial infarction and peripheral vascular disease. Certain embodiments provide compositions and methods for preventing, treating, delaying, slowing the progression and/or ameliorating aortic stenosis.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever. Certain embodiments provide a method of reducing at least one symptom of aortic stenosis.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the conjugated antisense compound is parenterally administered. In further embodiments, the parenteral administration is subcutaneous.

In certain embodiments, the conjugated antisense compound or composition is co-administered with a second agent or therapy. In certain embodiments, the conjugated antisense compound or composition and the second agent are administered concomitantly.

In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a conjugated antisense compound targeted to apo(a) for decreasing apo(a) levels in an animal. Certain embodiments provide use of a conjugated antisense compound targeted to apo(a) for decreasing Lp(a) levels in an animal. Certain embodiments provide use of a conjugated antisense compounds targeted to apo(a) for the treatment, prevention, or amelioration of a disease, disorder, or condition associated with apo(a). Certain embodiments provide use of a conjugated antisense compounds targeted to apo(a) for the treatment, prevention, or amelioration of a disease, disorder, or condition associated with Lp(a).

Certain embodiments provide use of a conjugated antisense compound targeted to apo(a) in the preparation of a medicament for decreasing apo(a) levels in an animal. Certain embodiments provide use of a conjugated antisense compound targeted to apo(a) in the preparation of a medicament for decreasing Lp(a) levels in an animal. Certain embodiments provide use of a conjugated antisense compound for the preparation of a medicament for the treatment, prevention, or amelioration of a disease, disorder, or condition associated with apo(a). Certain embodiments provide use of a conjugated antisense compound for the preparation of a medicament for the treatment, prevention, or amelioration of a disease, disorder, or condition associated with Lp(a).

Certain embodiments provide the use of a conjugated antisense compound as described herein in the manufacture of a medicament for treating, ameliorating, delaying or preventing one or more of a disease related to apo(a) and/or Lp(a).

Certain embodiments provide a kit for treating, preventing, or ameliorating a disease, disorder or condition as described herein wherein the kit comprises: (i) an apo(a) specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

B. Certain Compounds

In certain embodiments, the invention provides conjugated antisense compounds comprising antisense oligonucleoitdes and a conjugate.

a. Certain Antisense Oligonucleotides

In certain embodiments, the invention provides antisense oligonucleotides. Such antisense oligonucleotides comprise linked nucleosides, each nucleoside comprising a sugar moiety and a nucleobase. The structure of such antisense oligonucleotides may be considered in terms of chemical features (e.g., modifications and patterns of modifications) and nucleobase sequence (e.g., sequence of antisense oligonucleotide, identity and sequence of target nucleic acid).

i. Certain Chemistry Features

In certain embodiments, antisense oligonucleotide comprise one or more modification. In certain such embodiments, antisense oligonucleotides comprise one or more modified nucleosides and/or modified internucleoside linkages. In certain embodiments, modified nucleosides comprise a modified sugar moiety and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)2SCH$_3$, O—(CH$_2$)2-O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'—(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$-O-2' (ENA); 4'- CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$-N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

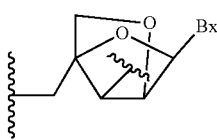
(A)

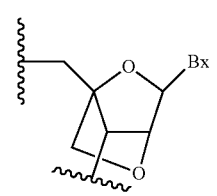
(B)

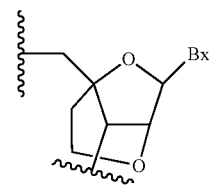
(C)

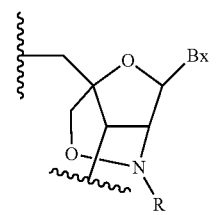
(D)

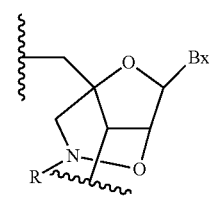
(E)

-continued

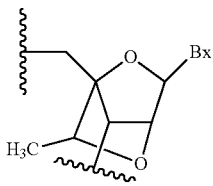
(F)

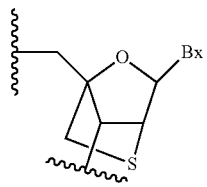
(G)

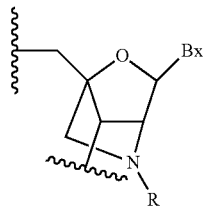
(H)

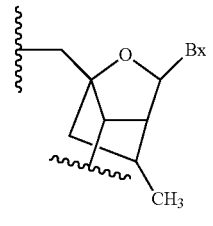
(I)

(J)

wherein Bx is a nucleobase moiety and R is, independently, H, a protecting group, or C$_1$-C$_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a morphlino. Morpholino compounds and their use in oligomeric compounds has been reported in numerous patents and published articles (see for example: Braasch et al., Biochemistry, 2002, 41, 4503-4510; and U.S. Pat. Nos. 5,698,685; 5,166,315; 5,185, 444; and 5,034,506). As used here, the term "morpholino" means a sugar surrogate having the following structure:

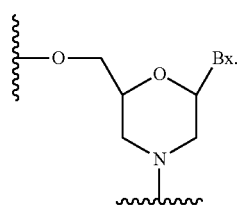

In certain embodiments, morpholinos may be modified, for example by adding or altering various substituent groups from the above morpholino structure. Such sugar surrogates are referred to herein as "modified morpholinos."

For another example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), fluoro HNA (F-HNA), and those compounds having Formula VI:

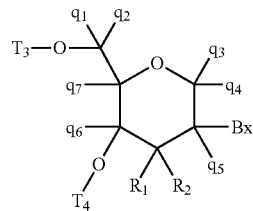

wherein independently for each of said at least one tetrahydropyran nucleoside analog of Formula VI:

Bx is a nucleobase moiety;

T$_3$ and T$_4$ are each, independently, an internucleoside linking group linking the tetrahydropyran nucleoside analog to the antisense compound or one of T$_3$ and T$_4$ is an internucleoside linking group linking the tetrahydropyran nucleoside analog to the antisense compound and the other of T$_3$ and T$_4$ is H, a hydroxyl protecting group, a linked conjugate group, or a 5' or 3'-terminal group; q$_1$, q$_2$, q$_3$, q$_4$, q$_5$, q$_6$ and q$_7$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl; and each of R$_1$ and R$_2$ is independently selected from among: hydrogen, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X)NJ$_1$J$_2$, and CN, wherein X is O, S or NJ$_1$, and each J$_1$, J$_2$, and J$_3$ is, independently, H or C$_1$-C$_6$ alkyl.

In certain embodiments, the modified THP nucleosides of Formula VI are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VI are provided wherein one of R$_1$ and R$_2$ is F. In certain embodiments, R$_1$ is fluoro and R$_2$ is H, R$_1$ is methoxy and R$_2$ is H, and R$_1$ is methoxyethoxy and R$_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379). In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cyto-sines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), a or b such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

4. Certain Motifs

In certain embodiments, antisense oligonucleotides comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified. In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Oligonucleotide Chemistry Motifs

In certain embodiments, the chemical structural features of antisense oligonucleotides are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

In certain embodiments, a conjugate group comprises a cleavable moiety. In certain embodiments, a conjugate group comprises one or more cleavable bond. In certain embodiments, a conjugate group comprises a linker. In certain embodiments, a linker comprises a protein binding moiety. In certain embodiments, a conjugate group comprises a cell-targeting moiety (also referred to as a cell-targeting group). In certain embodiments a cell-targeting moiety comprises a branching group. In certain embodiments, a cell-targeting moiety comprises one or more tethers. In certain embodiments, a cell-targeting moiety comprises a carbohydrate or carbohydrate cluster.

ii. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

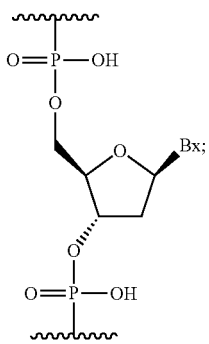
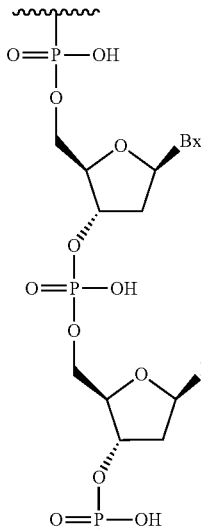

and

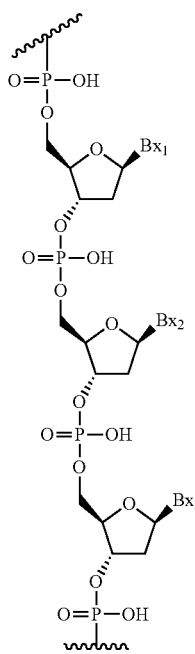

wherein each of Bx, Bx$_1$, Bx$_2$, and Bx$_3$ is independently a heterocyclic base moiety. In certain embodiments, the cleavable moiety has a structure selected from among the following:

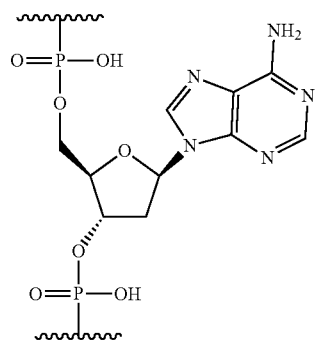 [SMILES: *P(=O)(O)OC[C@H]1O[C@@H](n2cnc3c(N)ncnc32)C[C@@H]1OP(*)(=O)O]

iii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a linker has a structure selected from among:

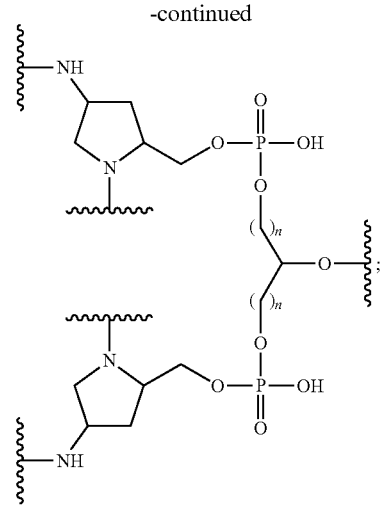

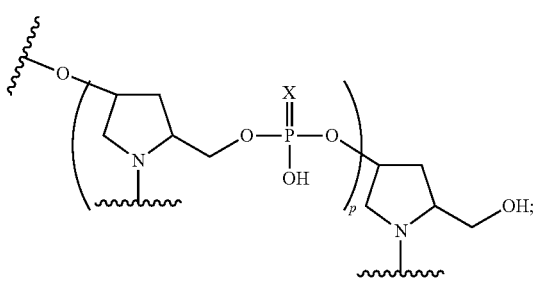

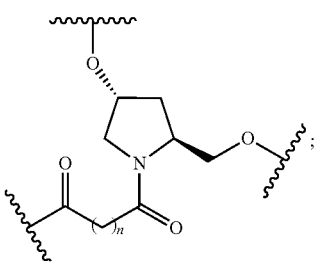

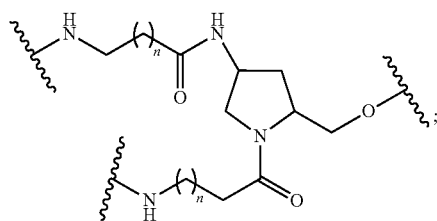

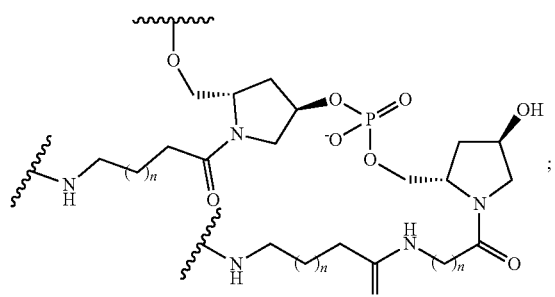

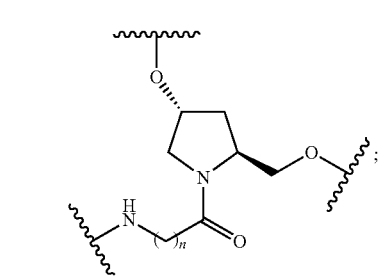

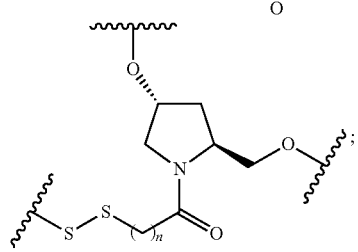

161
-continued
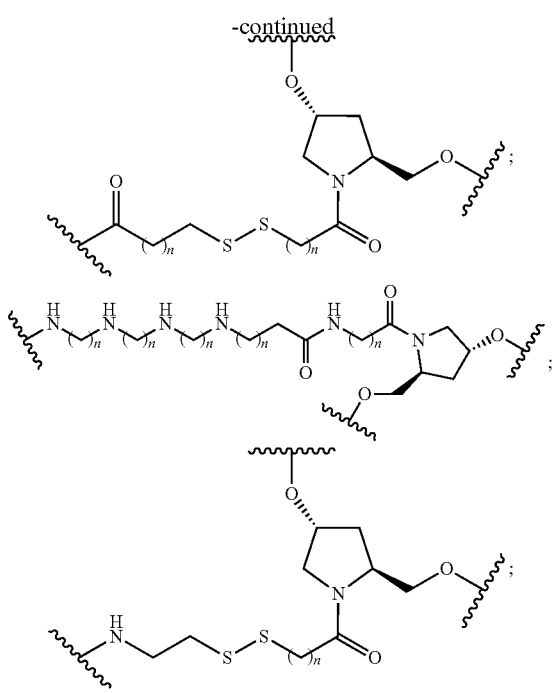
162
-continued
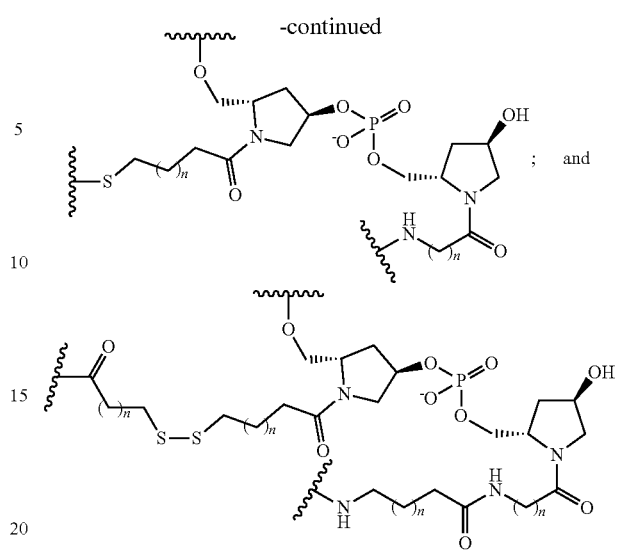
wherein each n is, independently, from 1 to 20; and p is from 1 to 6.
In certain embodiments, a linker has a structure selected from among:
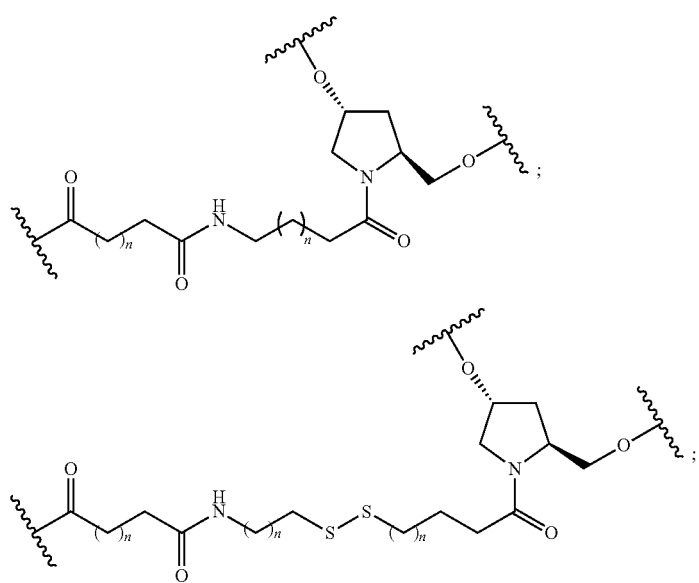
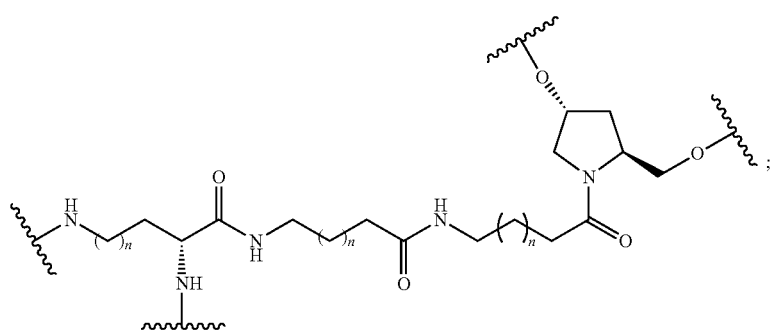

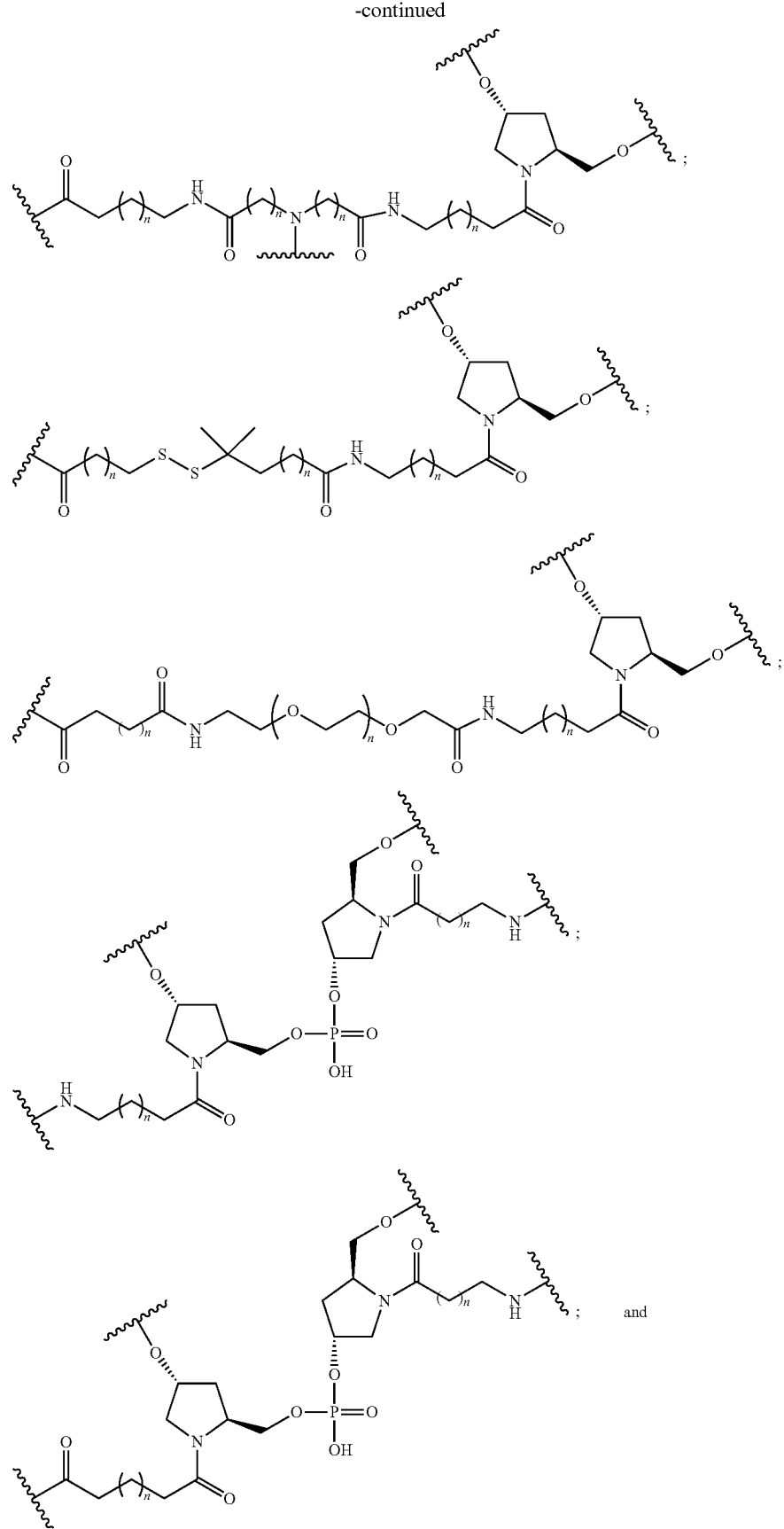

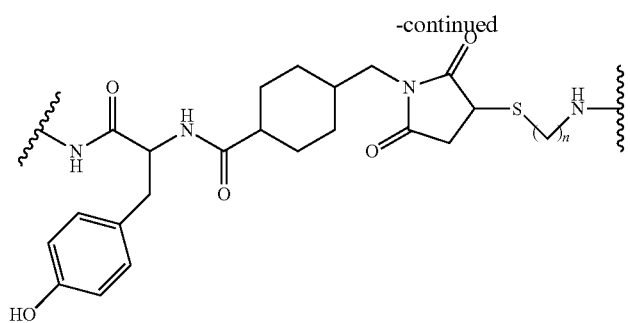
wherein each n is, independently, from 1 to 20.
In certain embodiments, a linker has a structure selected from among:
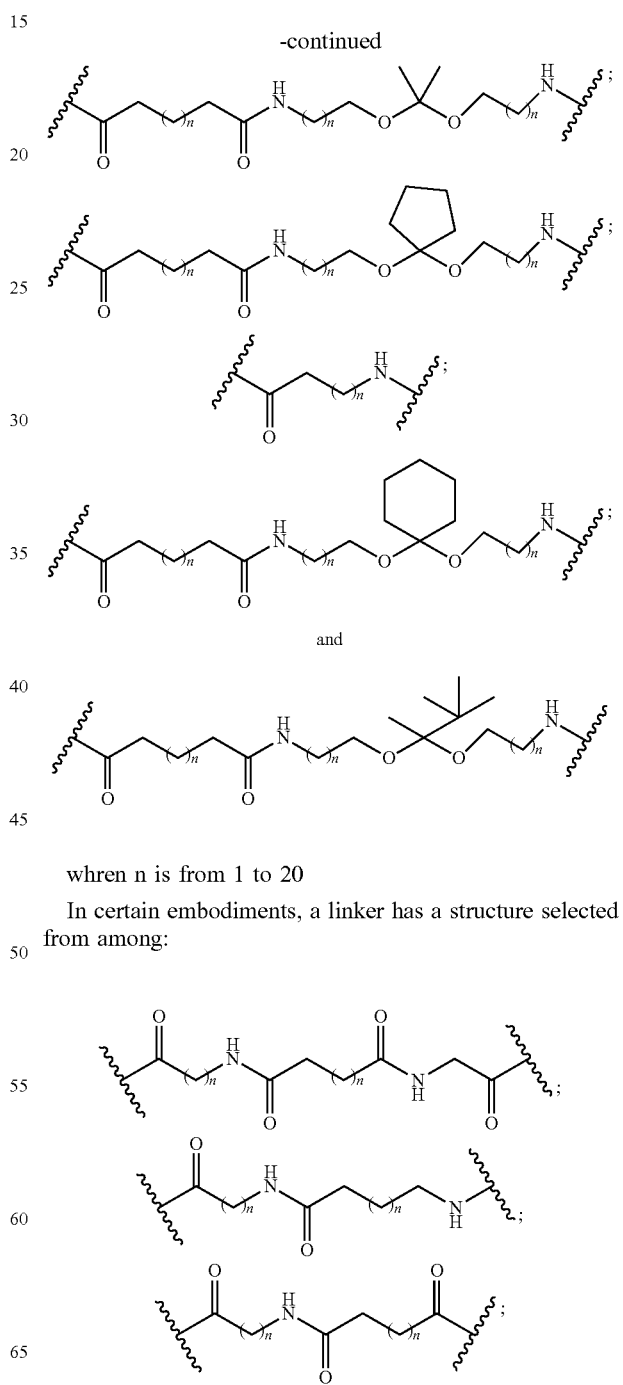
whren n is from 1 to 20
In certain embodiments, a linker has a structure selected from among:

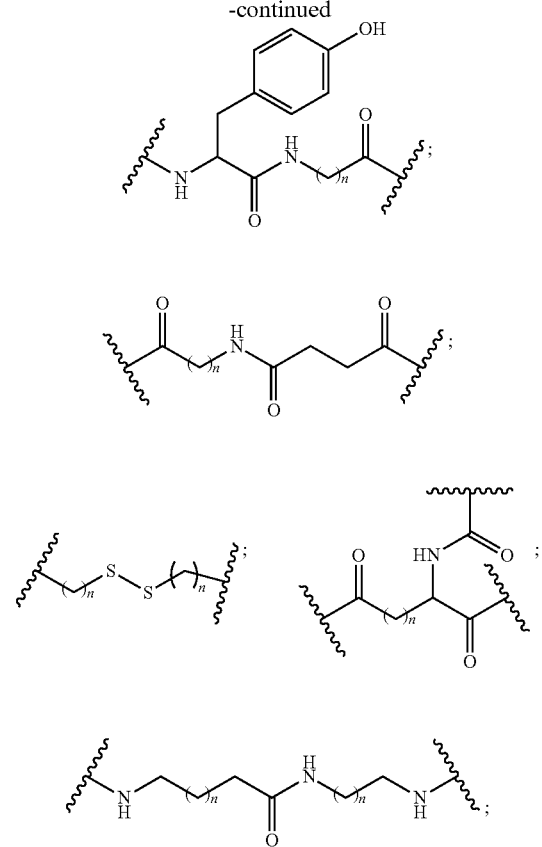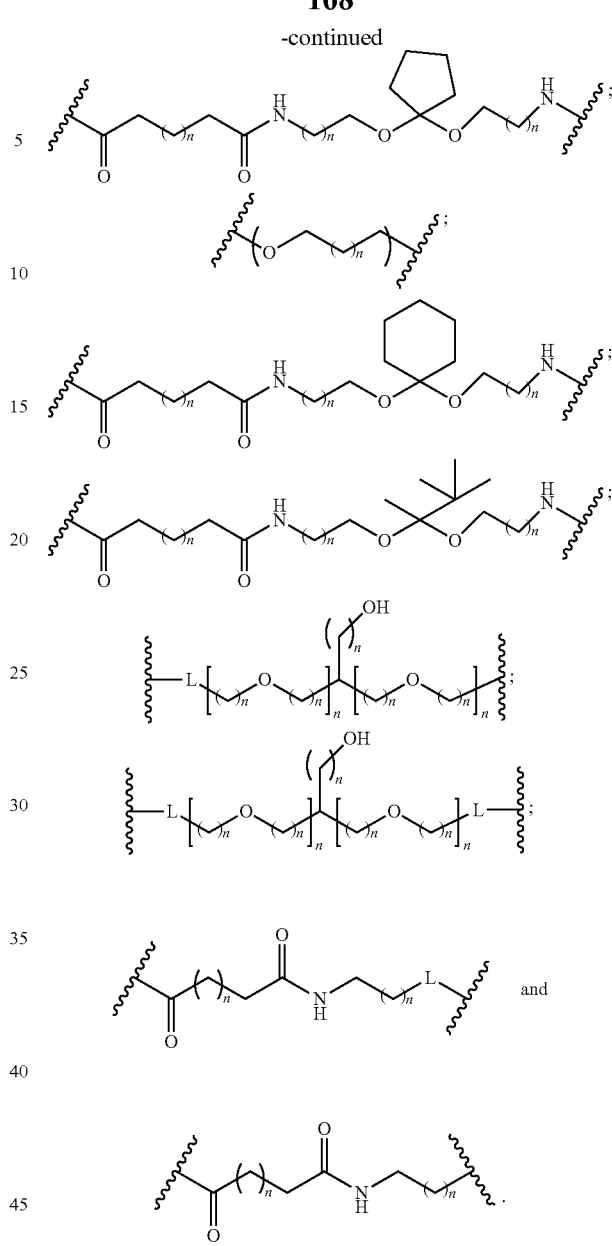
wherein each L is, independently, a phosphorus linking group or a neutral linking group; and each n is, independently, from 1 to 20.
In certain embodiments, a linker has a structure selected from among:
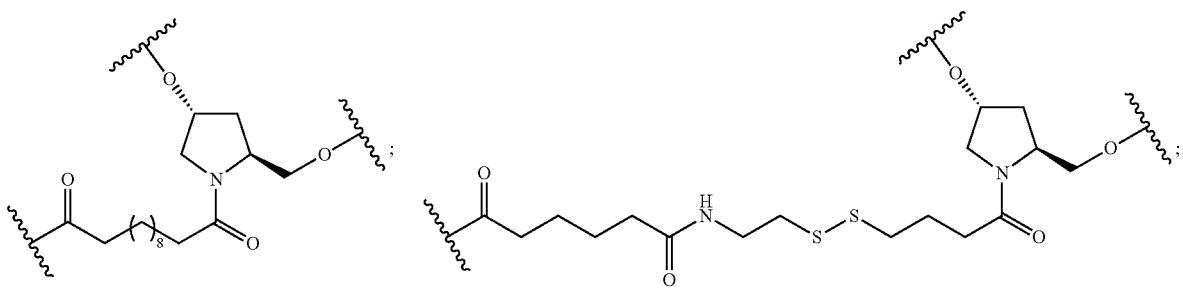

-continued
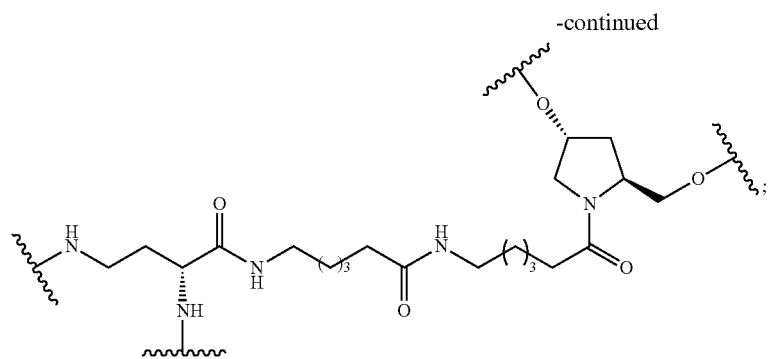
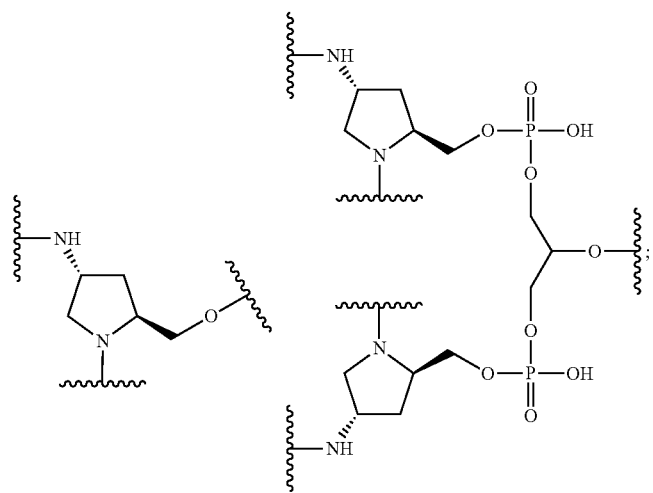
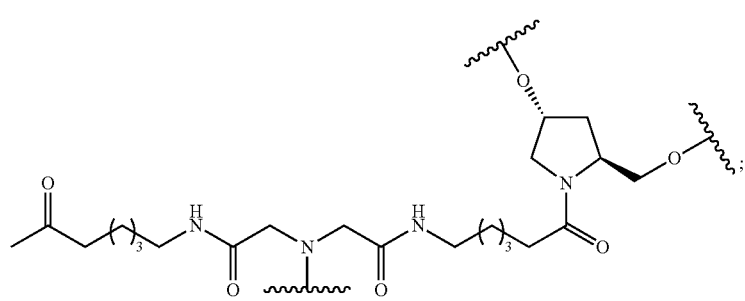
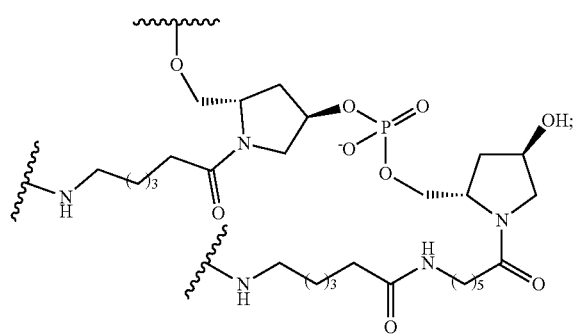

-continued
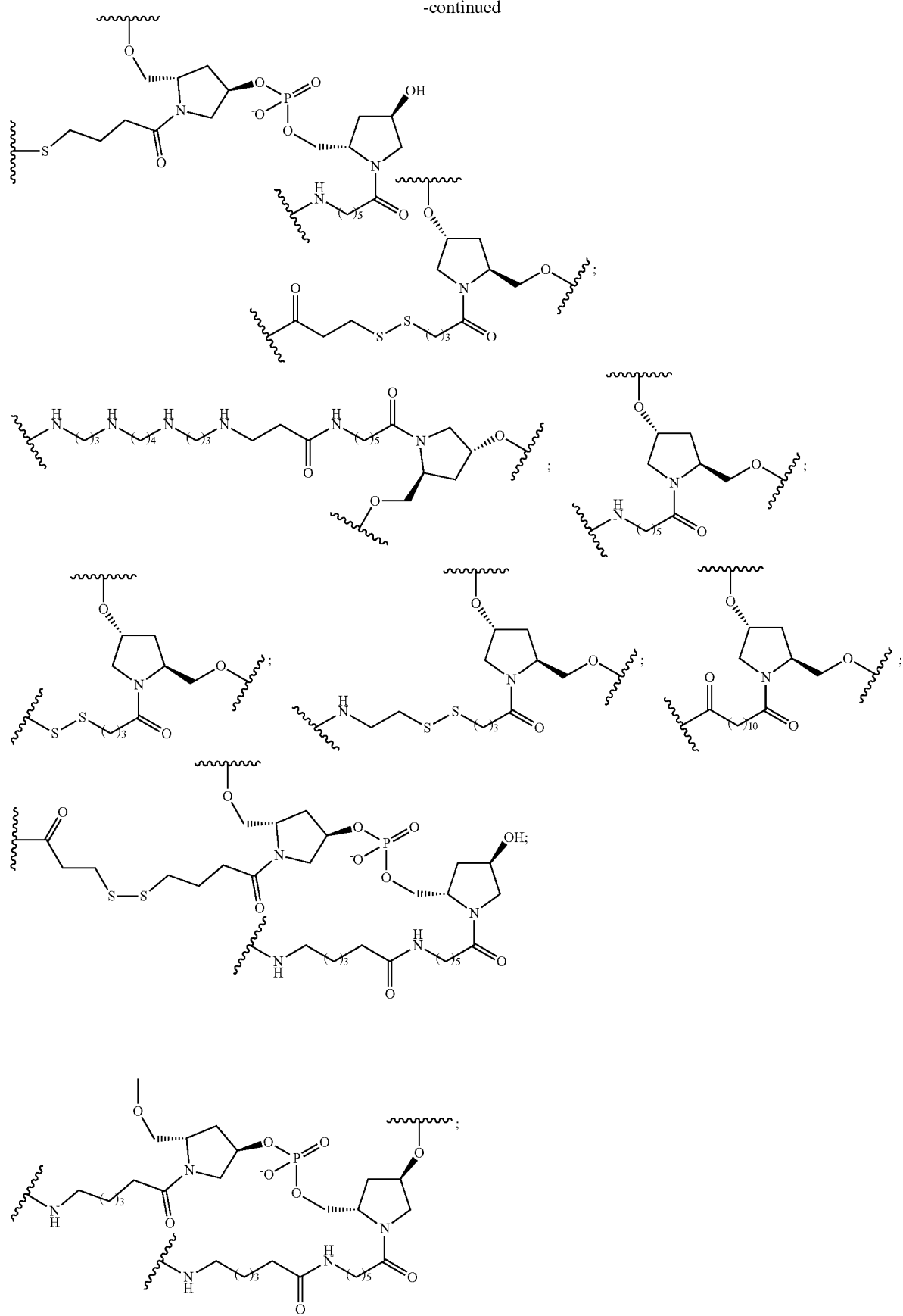

-continued
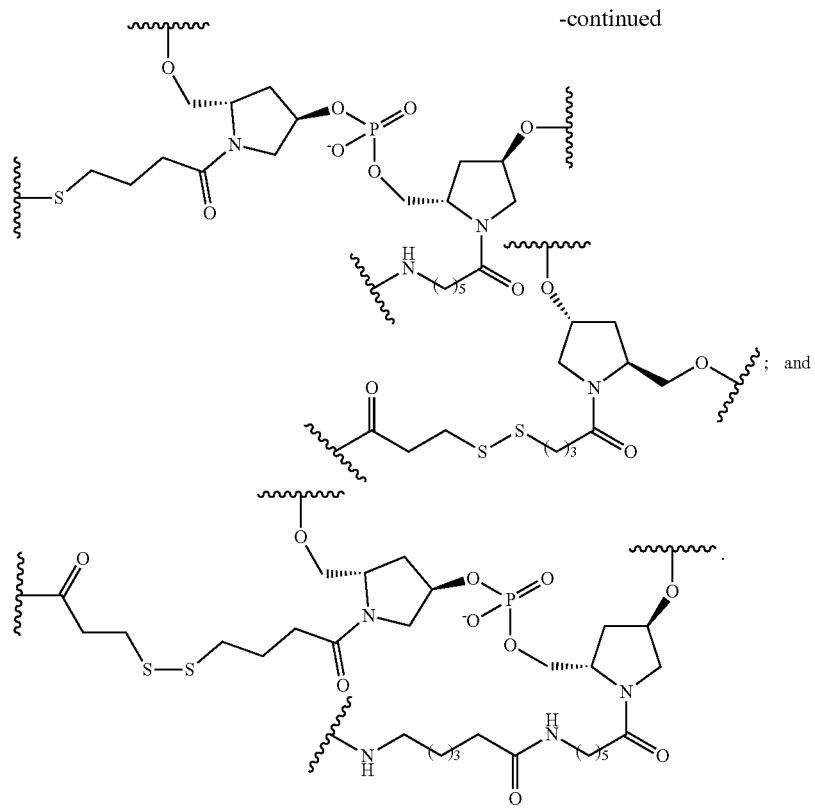
In certain embodiments, a linker has a structure selected from among:
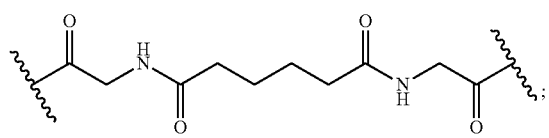
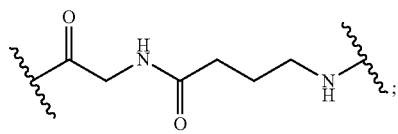
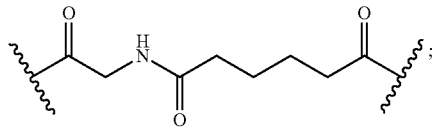
-continued
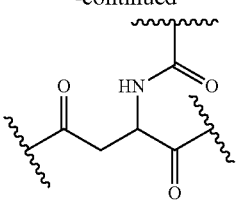
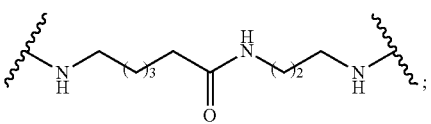
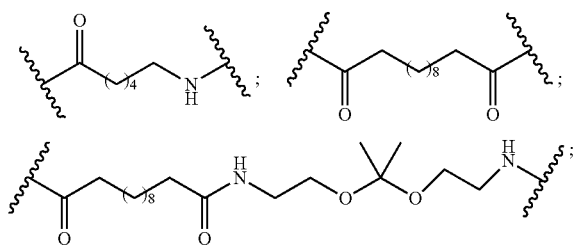
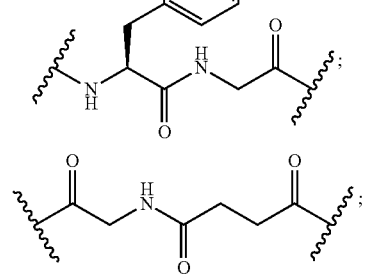
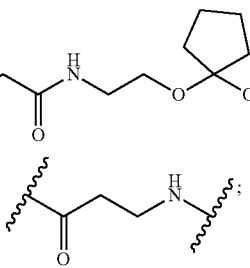

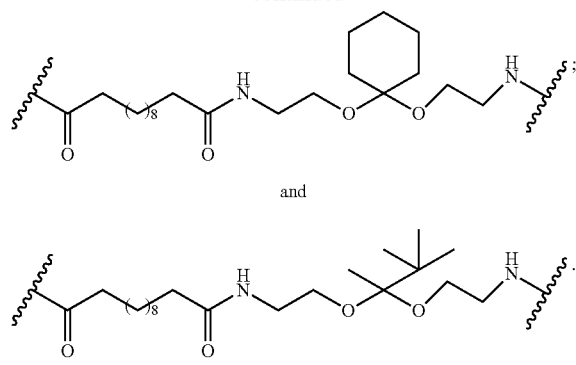
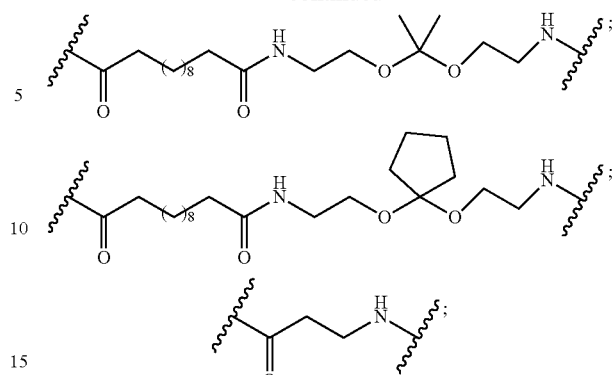
In certain embodiments, a linker has a structure selected from among:
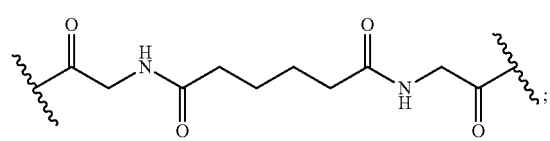
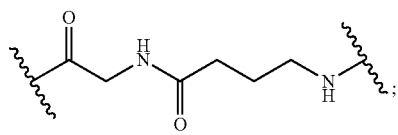
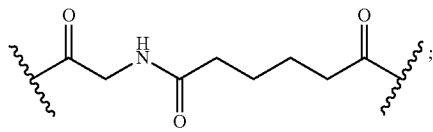
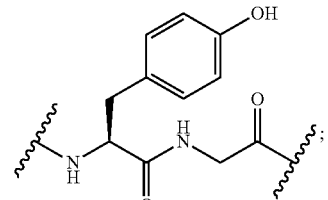
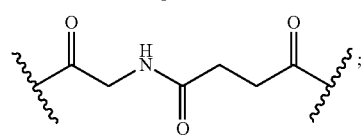
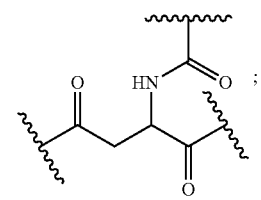
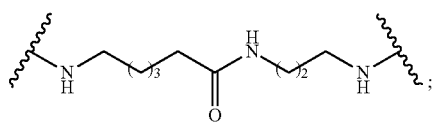
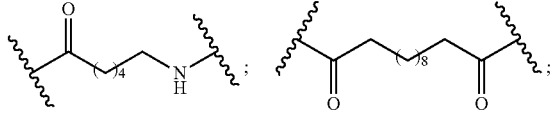
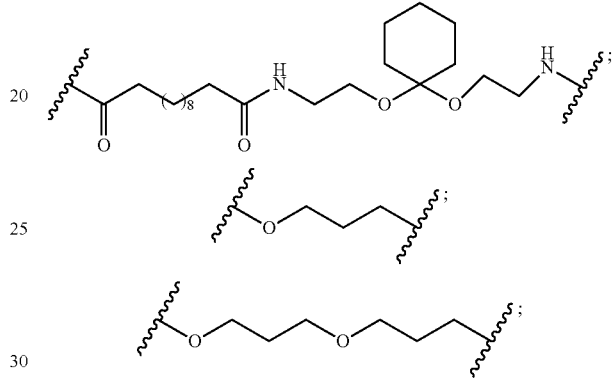
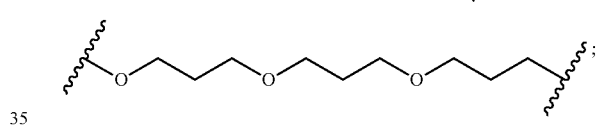
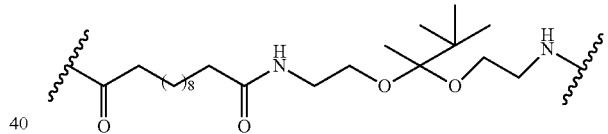
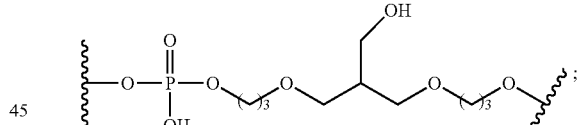
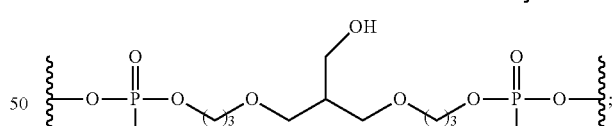
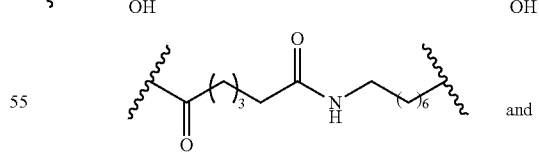
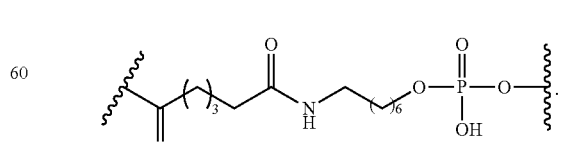
In certain embodiments, a linker has a structure selected from among:

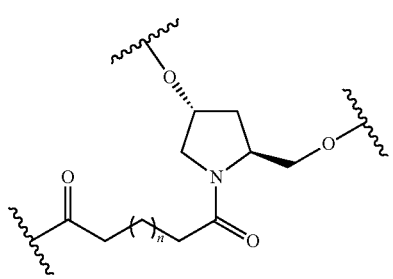

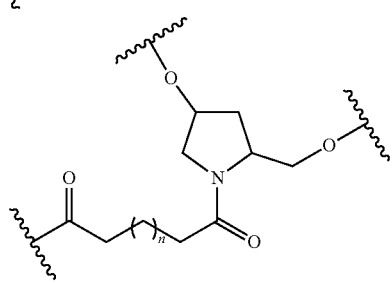
and wherein n is from 1 to 20.

In certain embodiments, a linker has a structure selected from among;

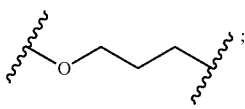

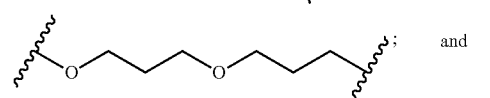
and

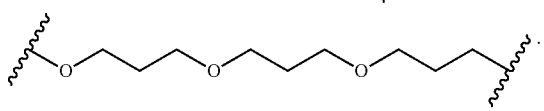

In certain embodiments, a linker has a structure selected from among:

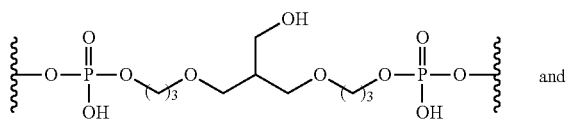
and

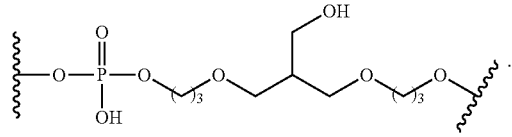

In certain embodiments, a linker has a structure selected from among:

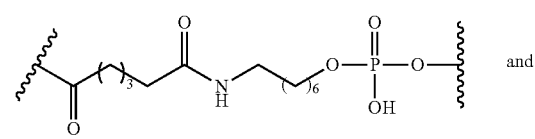
and

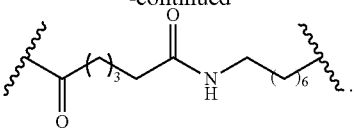

In certain embodiments, the conjugate linker has the structure:

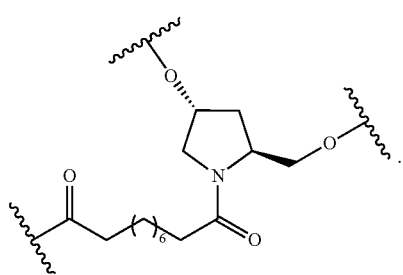

In certain embodiments, the conjugate linker has the structure:

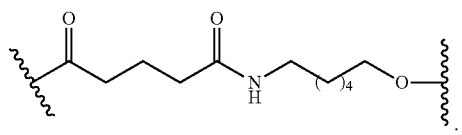

In certain embodiments, a linker has a structure selected from among:

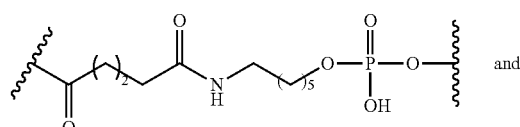
and

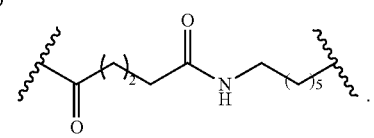

In certain embodiments, a linker has a structure selected from among:

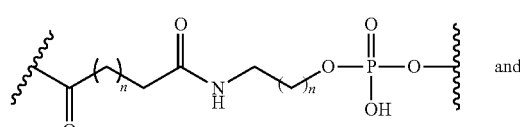
and

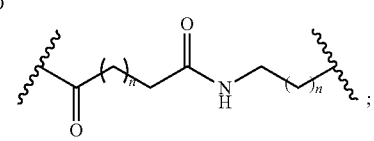

wherein each n is independently, 0, 1, 2, 3, 4, 5, 6, or 7.

iv. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

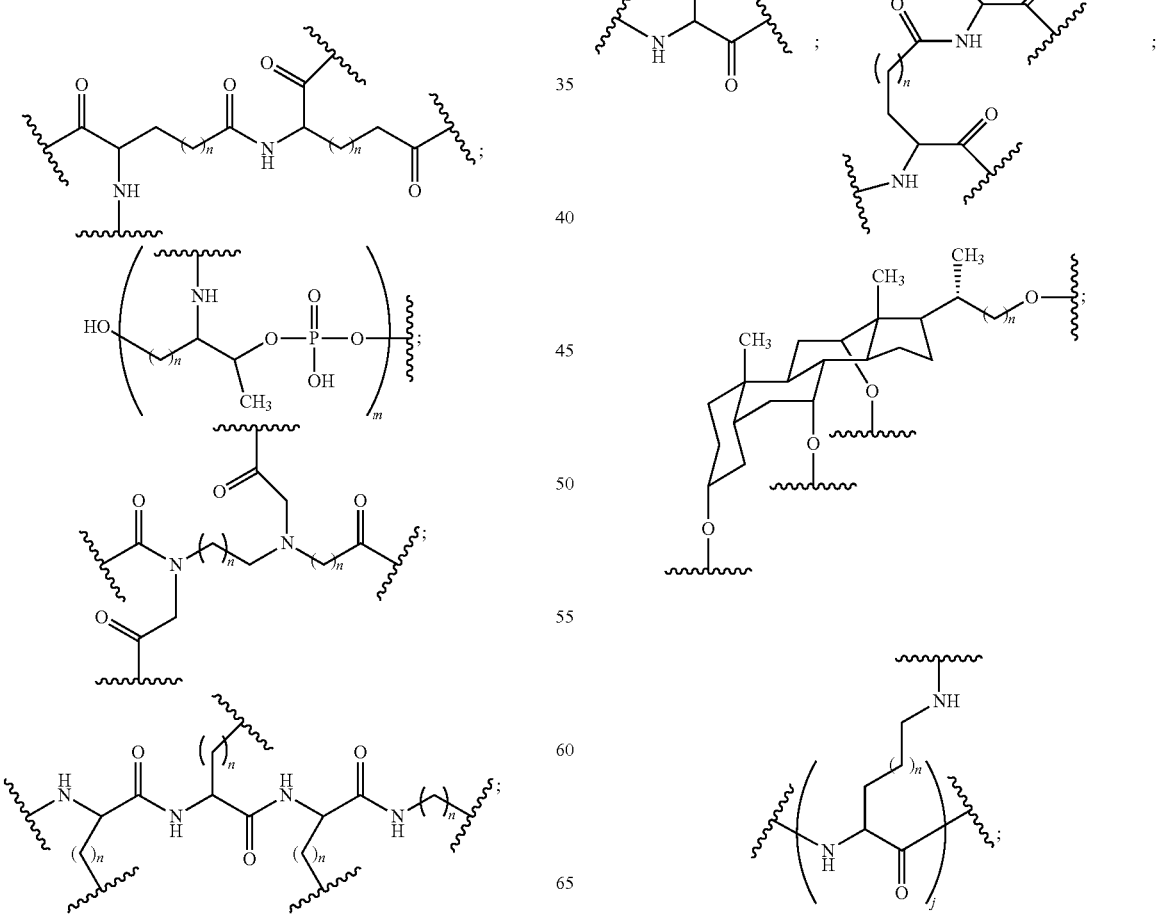

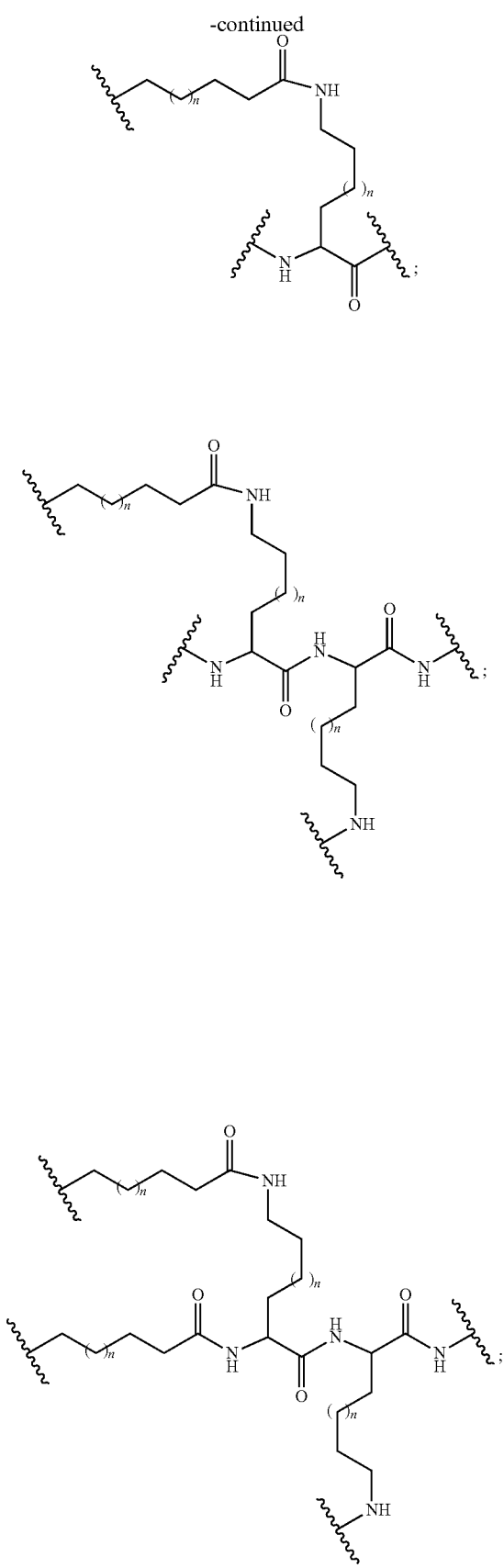
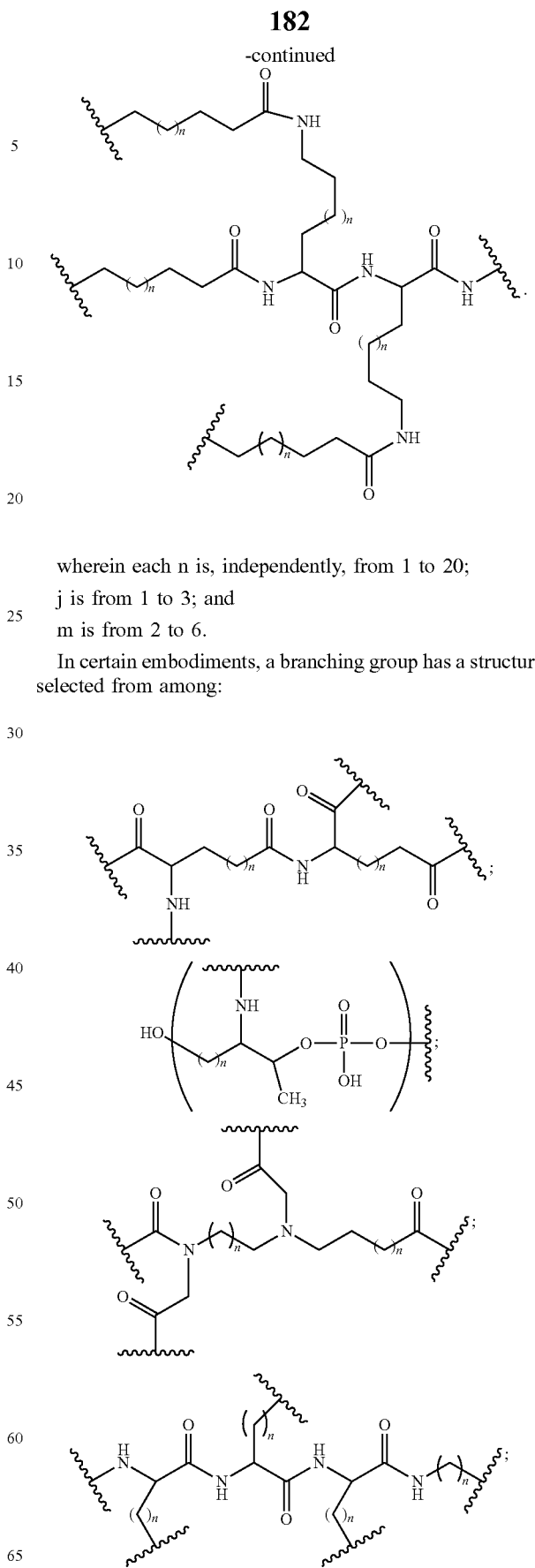
wherein each n is, independently, from 1 to 20;
j is from 1 to 3; and
m is from 2 to 6.
In certain embodiments, a branching group has a structure selected from among:

-continued
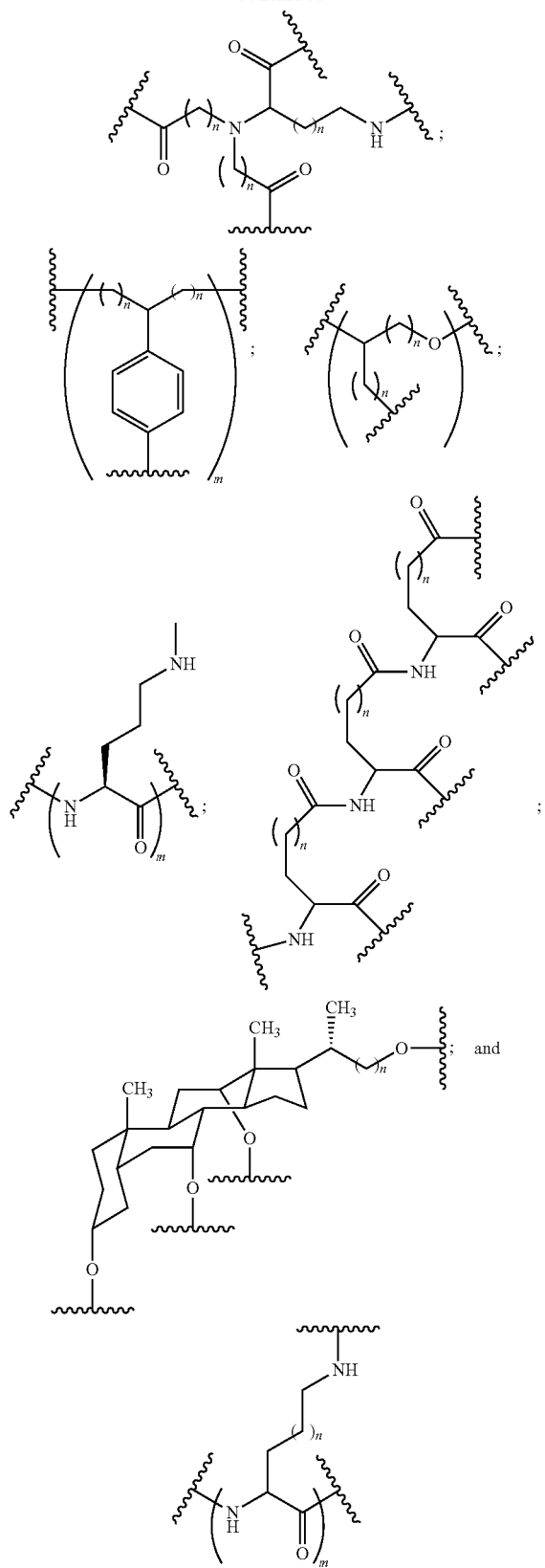
wherein each n is, independently, from 1 to 20; and m is from 2 to 6.
In certain embodiments, a branching group has a structure selected from among:
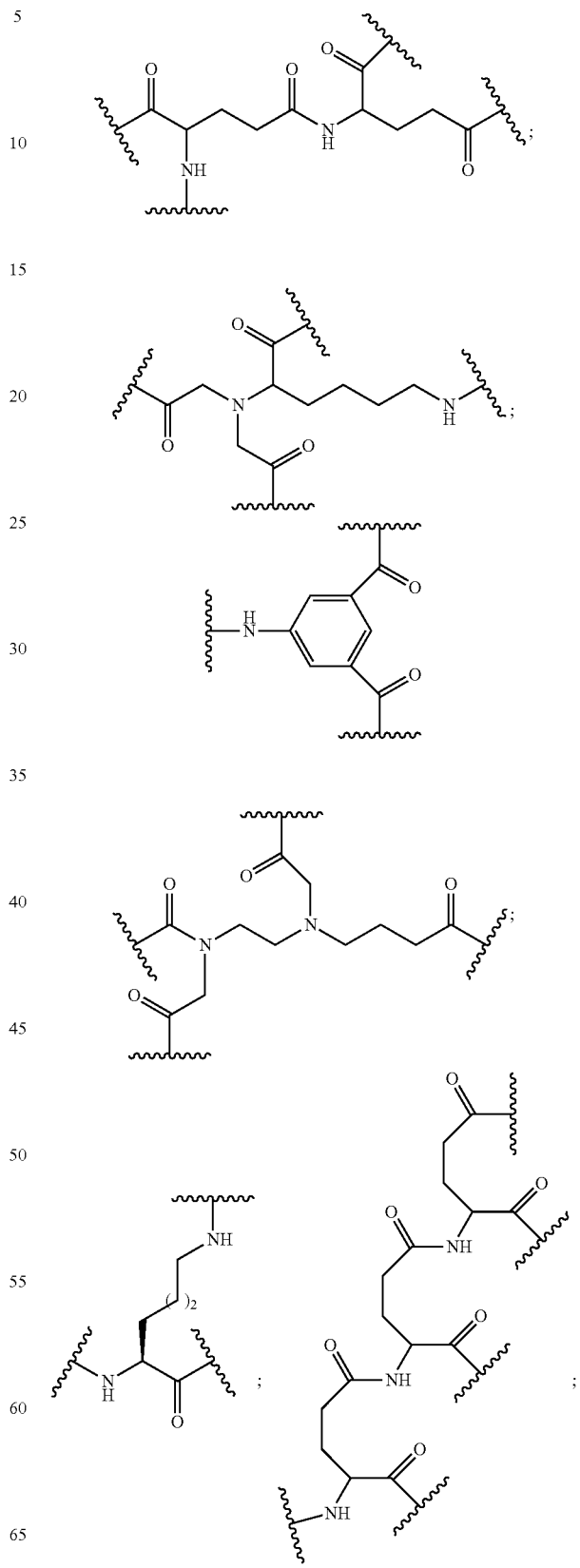

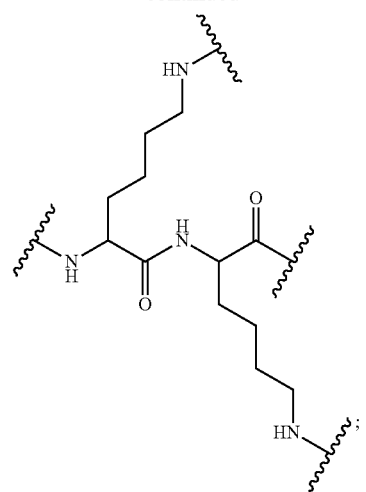
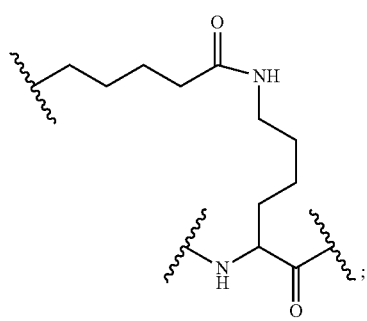
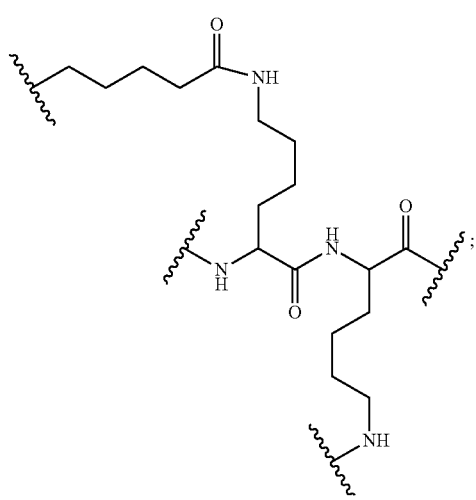
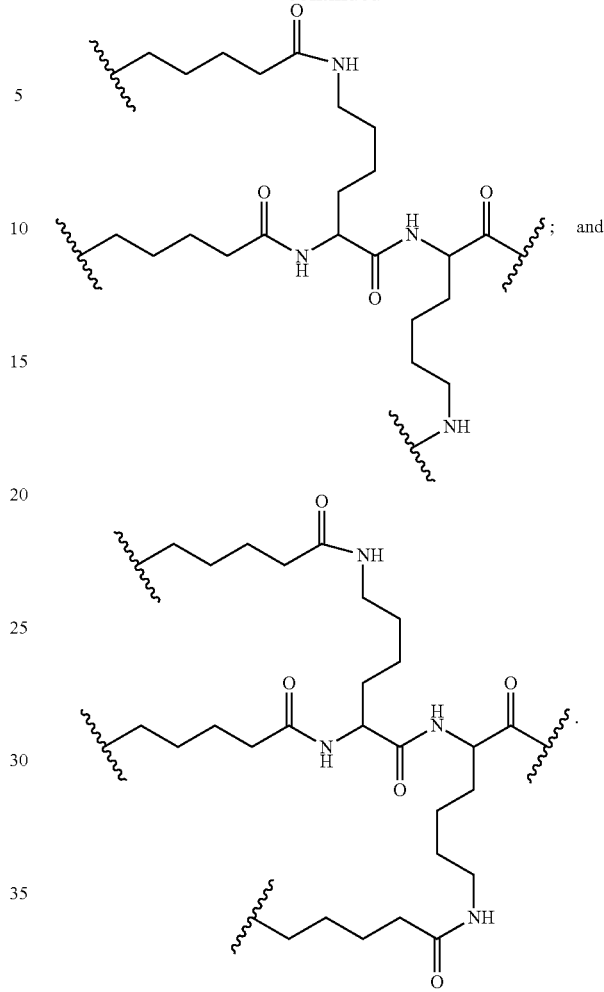
In certain embodiments, a branching group has a structure selected from among:
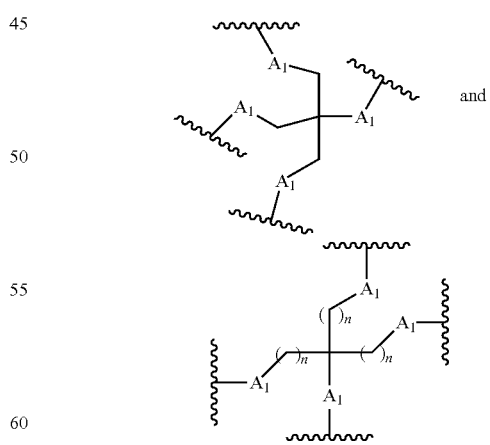
wherein each $A_1$ is independently, O, S, C=O or NH; and each n is, independently, from 1 to 20.
In certain embodiments, a branching group has a structure selected from among:

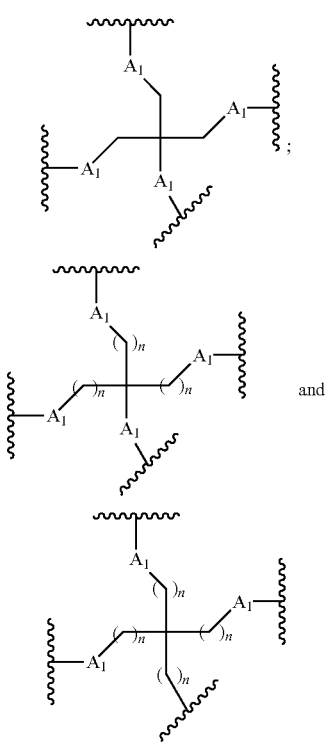

wherein each $A_1$ is independently, O, S, C=O or NH; and each n is, independently, from 1 to 20.

In certain embodiments, a branching group has a structure selected from among:

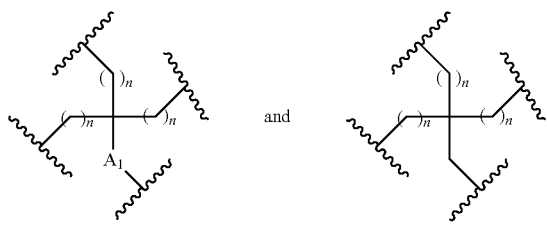

wherein $A_1$ is O, S, C=O or NH; and
each n is, independently, from 1 to 20.

In certain embodiments, a branching group has a structure selected from among:

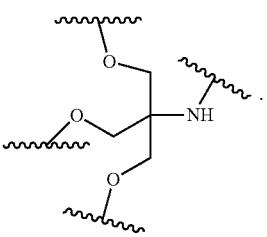 [SMILES: *NC(CO*)(CO*)CO*]

In certain embodiments, a branching group has a structure selected from among:

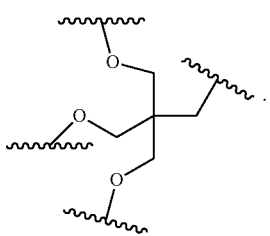 [SMILES: *CC(CO*)(CO*)CO*]

In certain embodiments, a branching group has a structure selected from among:

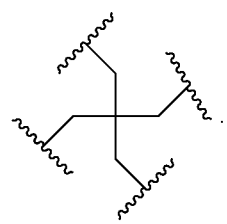 [SMILES: *CC(C*)(C*)C*]

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

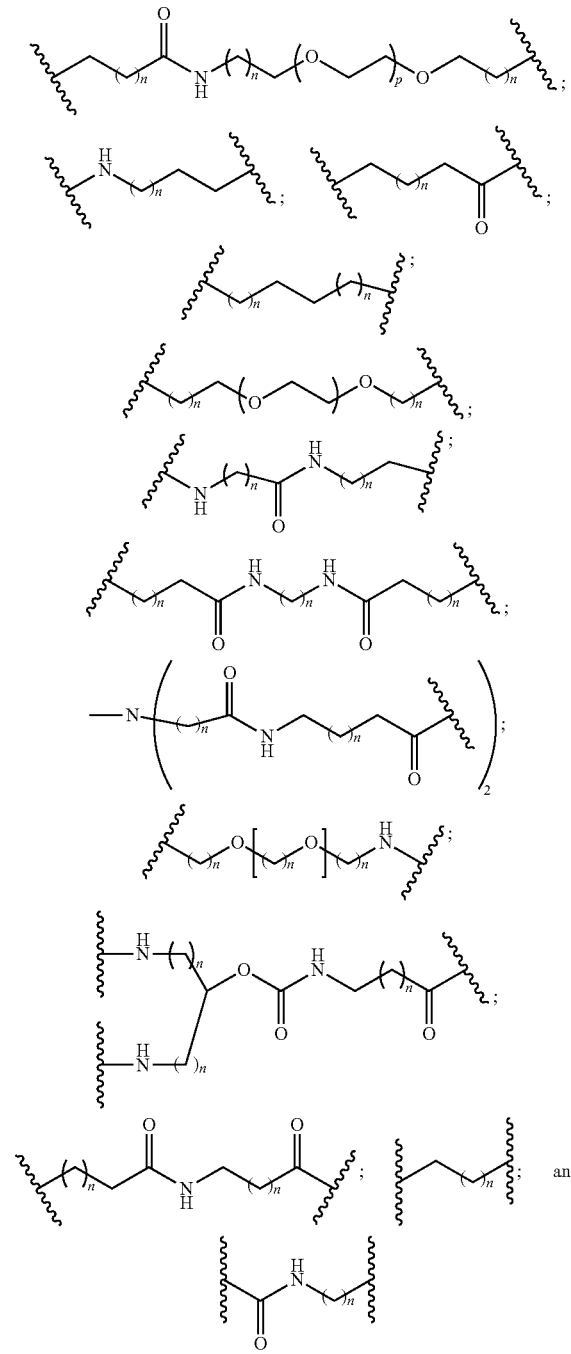

wherein each n is, independently, from 1 to 20; and each p is from 1 to about 6.

In certain embodiments, a tether has a structure selected from among:

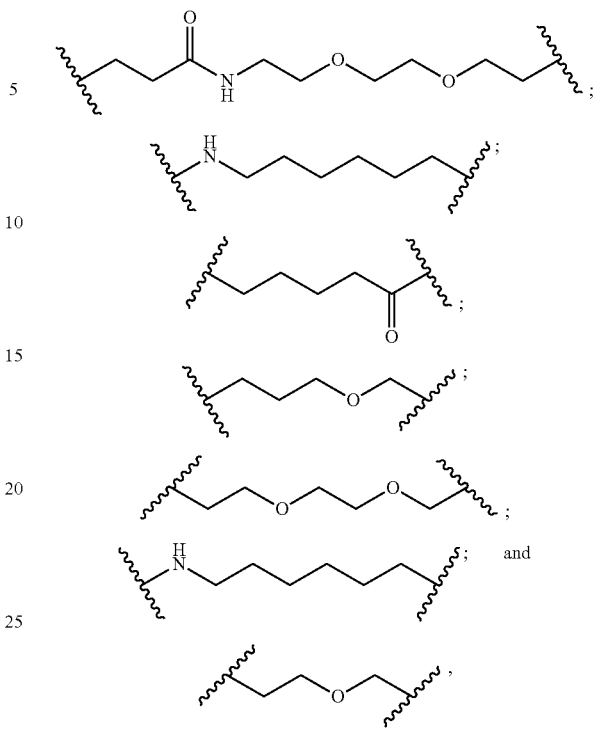

In certain embodiments, a tether has a structure selected from among:

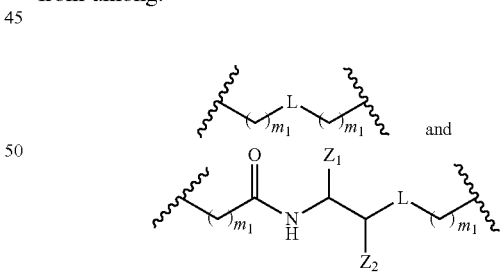

wherein each n is, independently, from 1 to 20.

In certain embodiments, a tether has a structure selected from among:

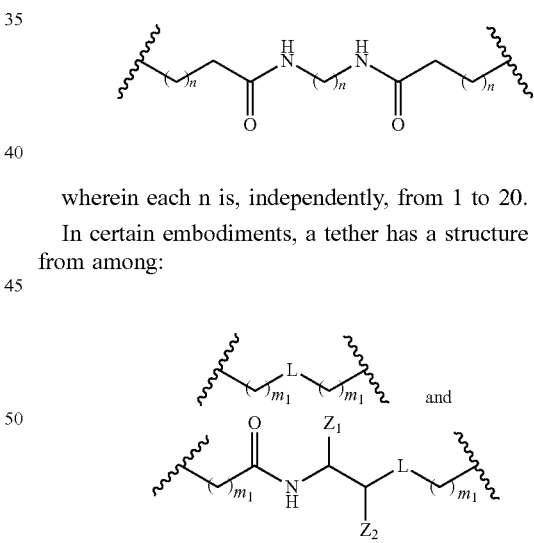

wherein L is either a phosphorus linking group or a neutral linking group;

$Z_1$ is $C(=O)O-R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

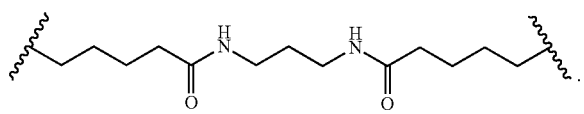 [SMILES: *CCCCC(=O)NCCCNC(=O)CCCC*]

In certain embodiments, a tether has a structure selected from among:

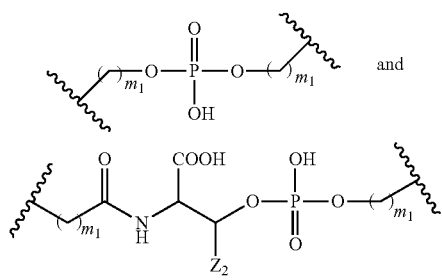

wherein $Z_2$ is H or $CH_3$; and each $m_1$ is, independently, from 0 to 20 wherein at least one $m_1$ is greater than 0 for each tether.

In certain embodiments, a tether has a structure selected from among:

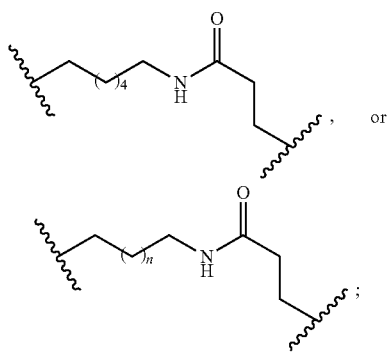

or; wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-2-deoxy-D-galactopyranose may be used interchangeably. Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

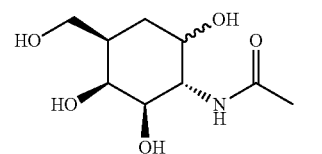

2-(Acetylamino)-2-deoxy-D-galactopyranose

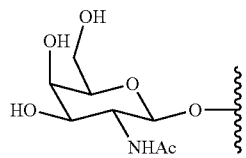

2-(Acetylamino)-2-deoxy-β-D-galactopyranose

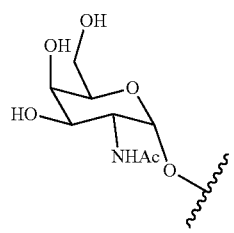

2-(Acetylamino)-2-deoxy-α-D-galactopyranose

In certain embodiments one or more ligand has a structure selected from among:

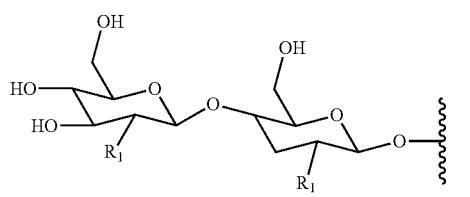

and

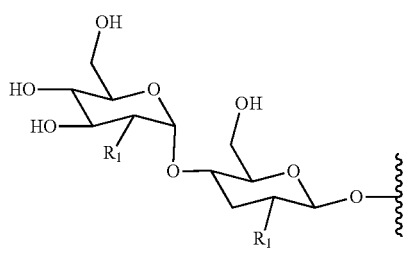

wherein each $R_1$ is selected from OH and NHCOOH.

In certain embodiments one or more ligand has a structure selected from among:

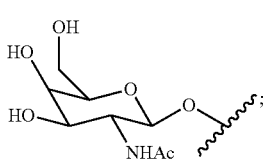

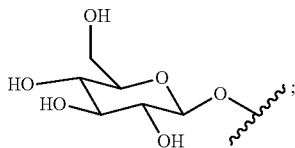

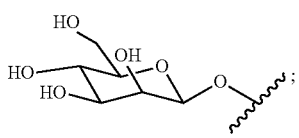

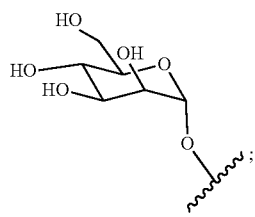
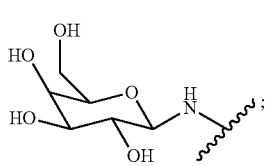

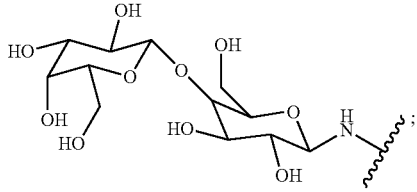

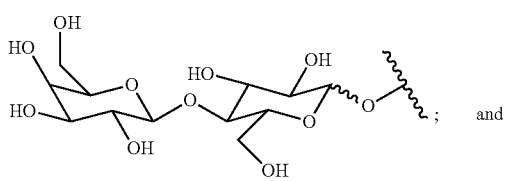

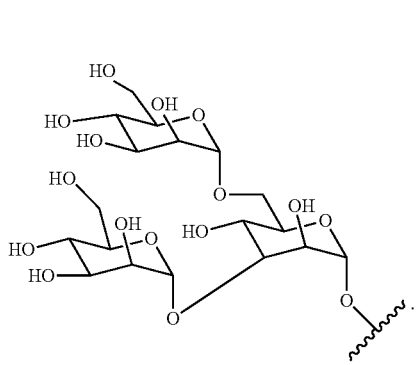

In certain embodiments one or more ligand has a structure selected from among:

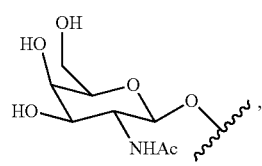 [SMILES: *OC1OC(CO)C(O)C(O)C1NC(C)=O]

In certain embodiments one or more ligand has a structure selected from among:

i. Certain Conjugates
In certain embodiments, conjugate groups comprise the structural features above. In certain such embodiments, conjugate groups have the following structure:
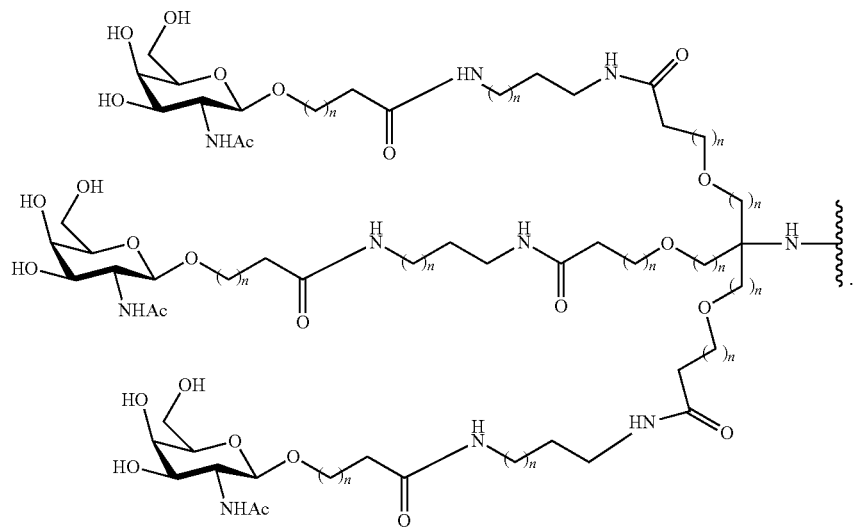
wherein each n is, independently, from 1 to 20.
In certain such embodiments, conjugate groups have the following structure:
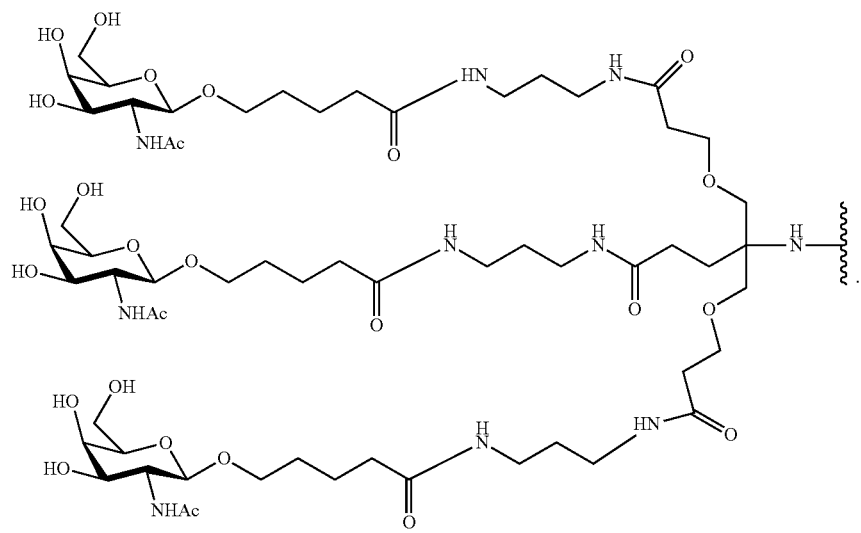

In certain such embodiments, conjugate groups have the following structure:
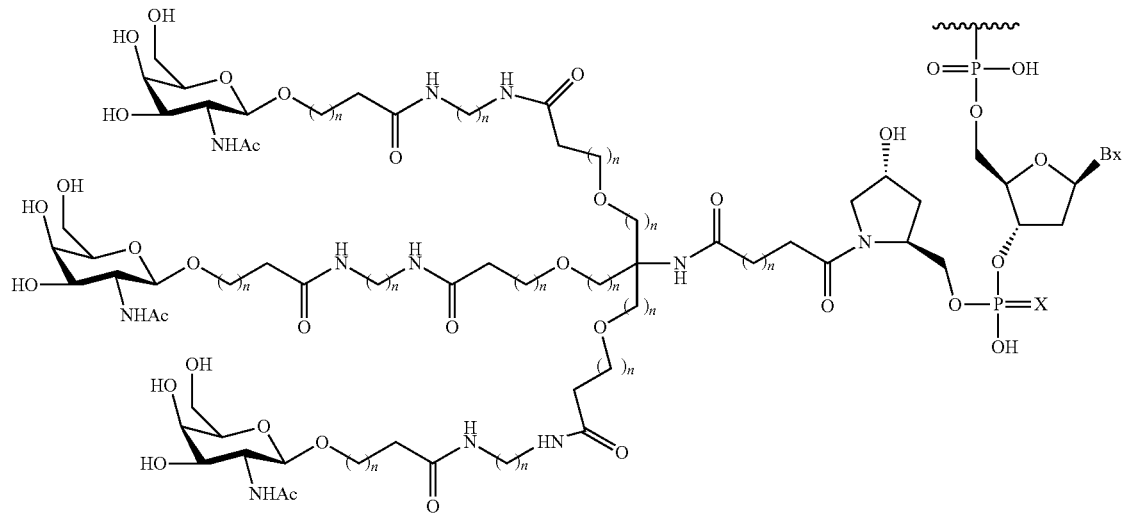
wherein each n is, independently, from 1 to 20;
Z is H or a linked solid support;
Q is an antisense compound;
X is O or S; and
Bx is a heterocyclic base moiety.
In certain such embodiments, conjugate groups have the following structure:
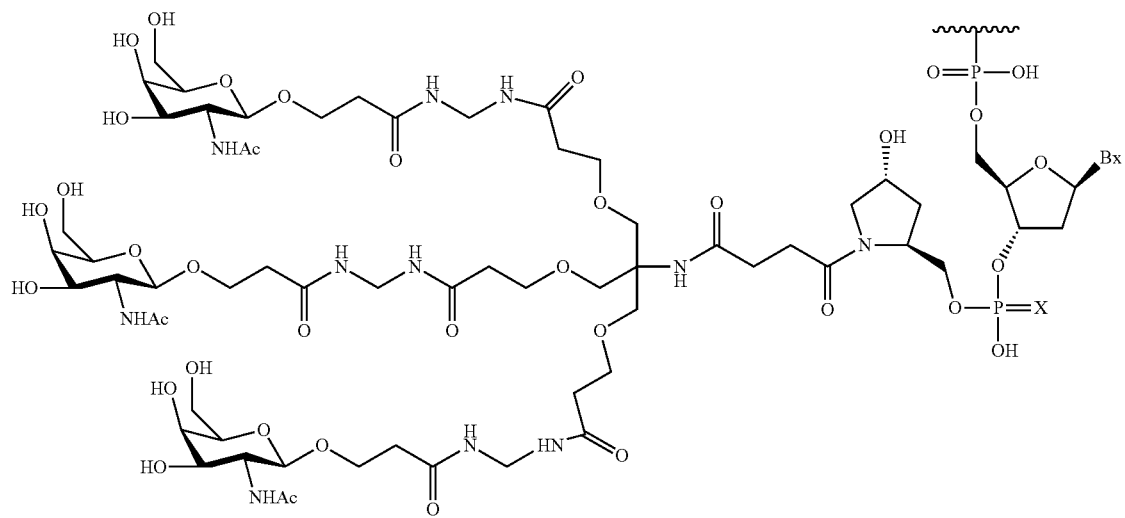

In certain such embodiments, conjugate groups have the following structure:
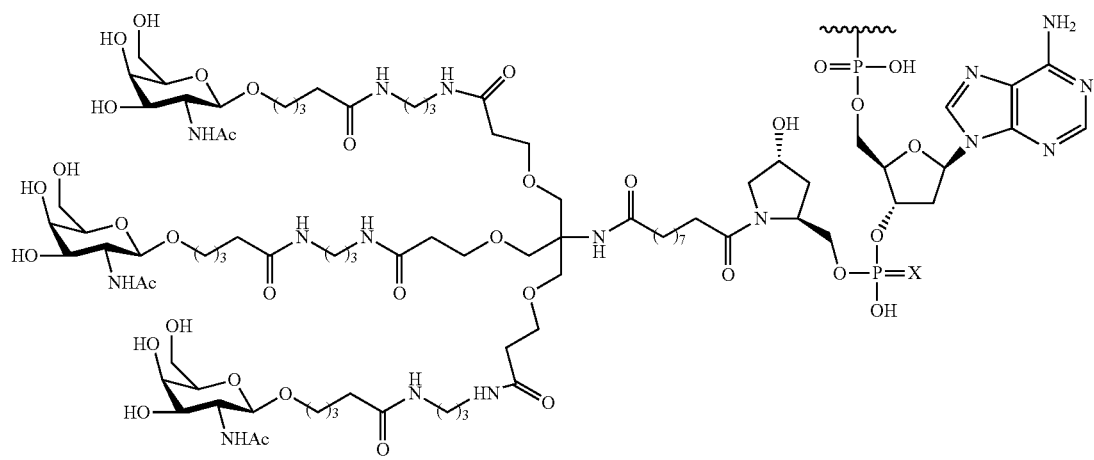
In certain such embodiments, conjugate groups have the following structure:
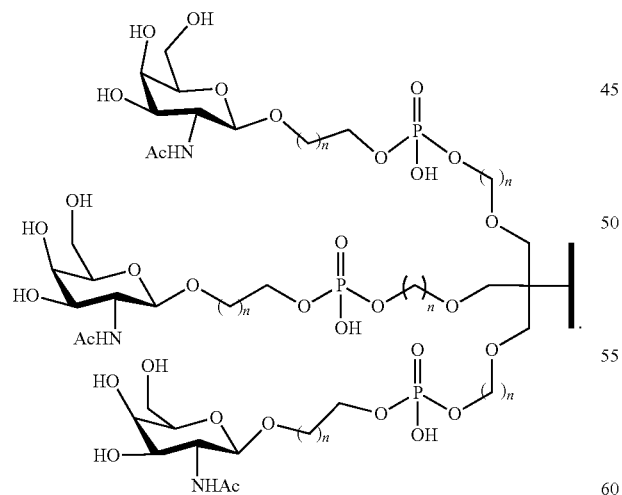
In certain such embodiments, conjugate groups have the following structure:

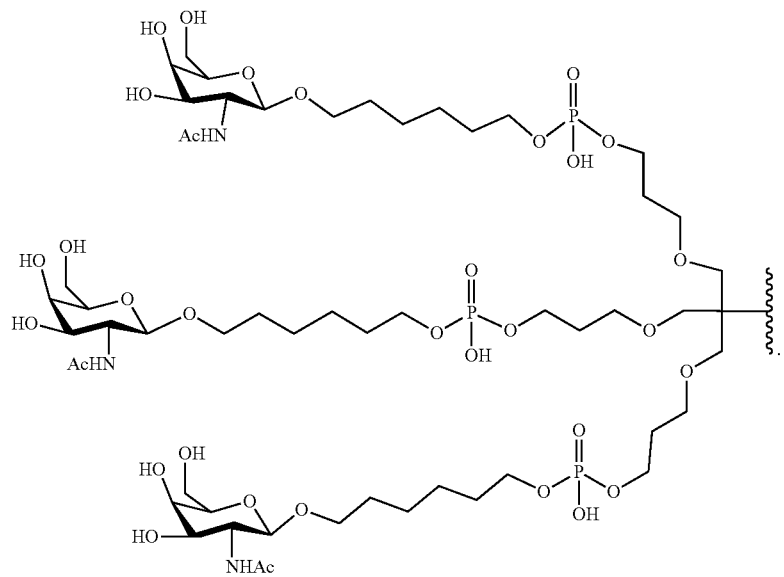
In certain such embodiments, conjugate groups have the following structure:
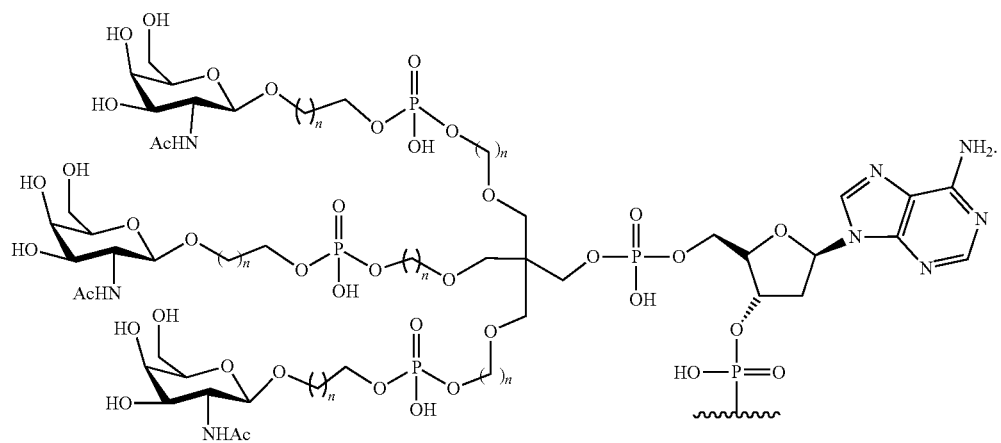
In certain such embodiments, conjugate groups have the following structure:

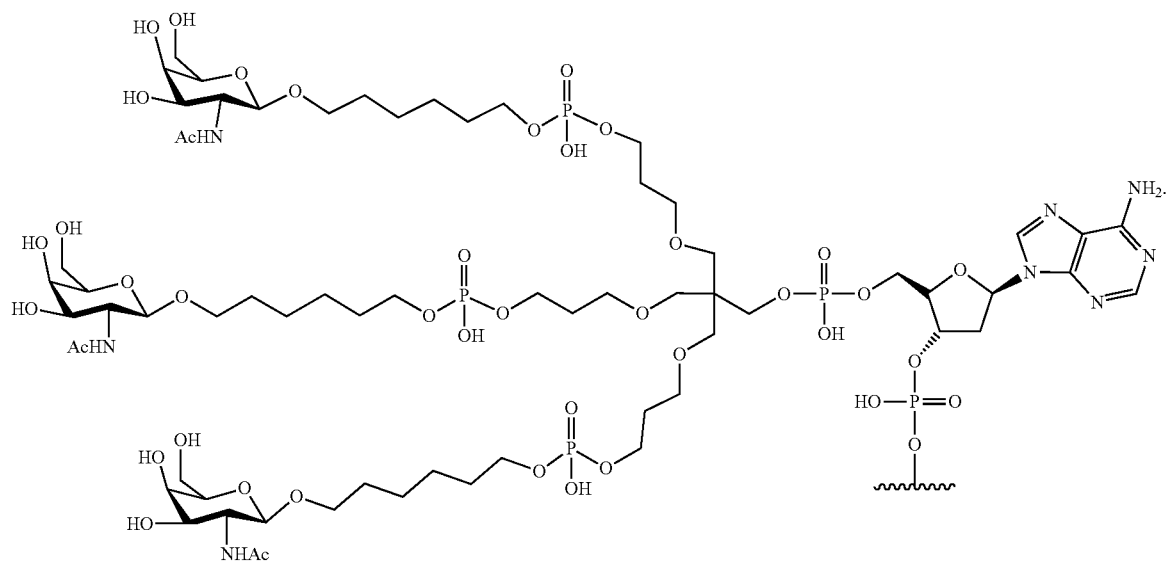
In certain such embodiments, conjugate groups have the following structure:
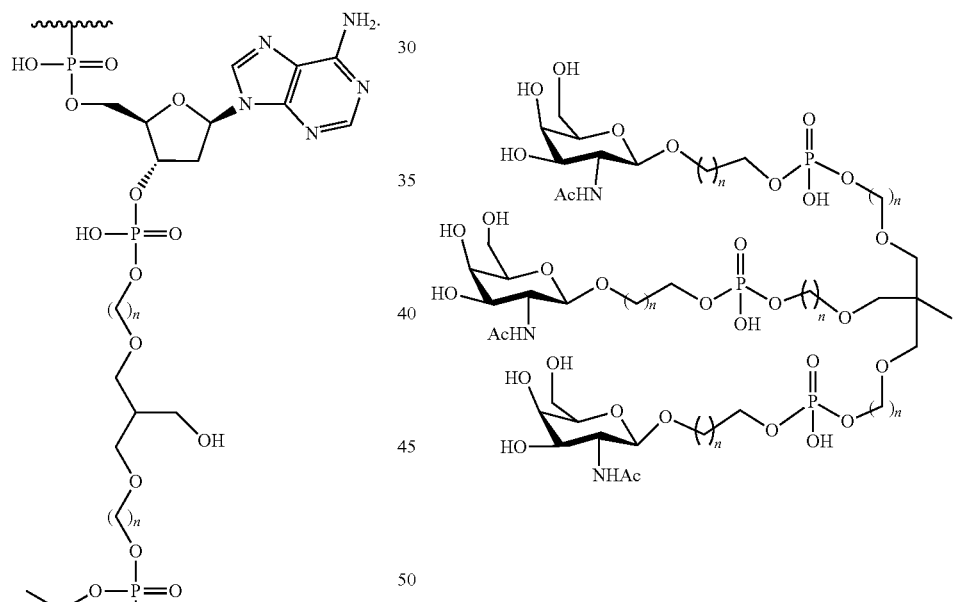
-continued
In certain such embodiments, conjugate groups have the following structure:
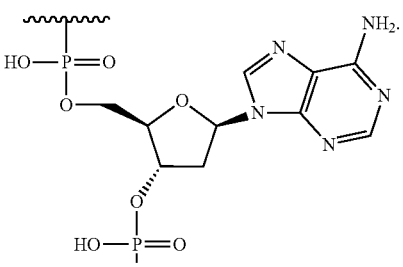

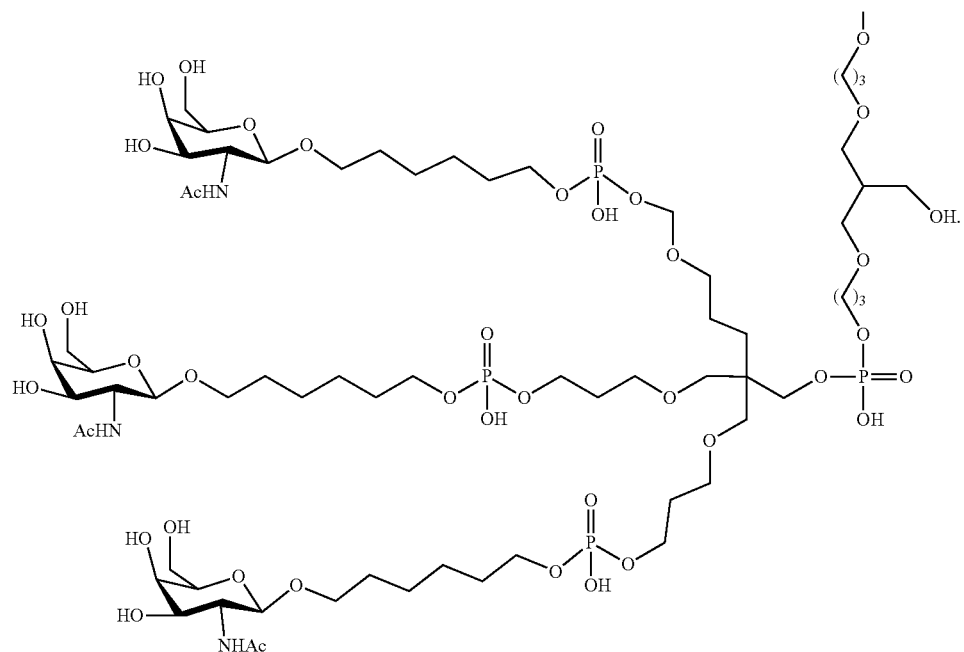
In certain embodiments, conjugates do not comprise a pyrrolidine.
In certain such embodiments, conjugate groups have the following structure:
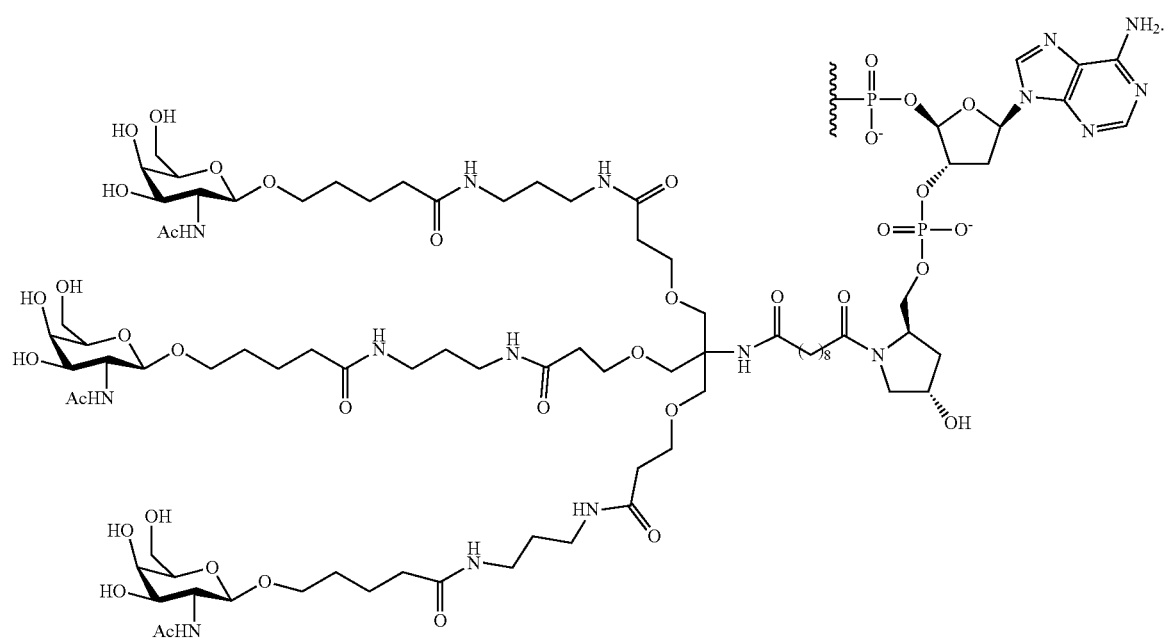

In certain such embodiments, conjugate groups have the following structure:
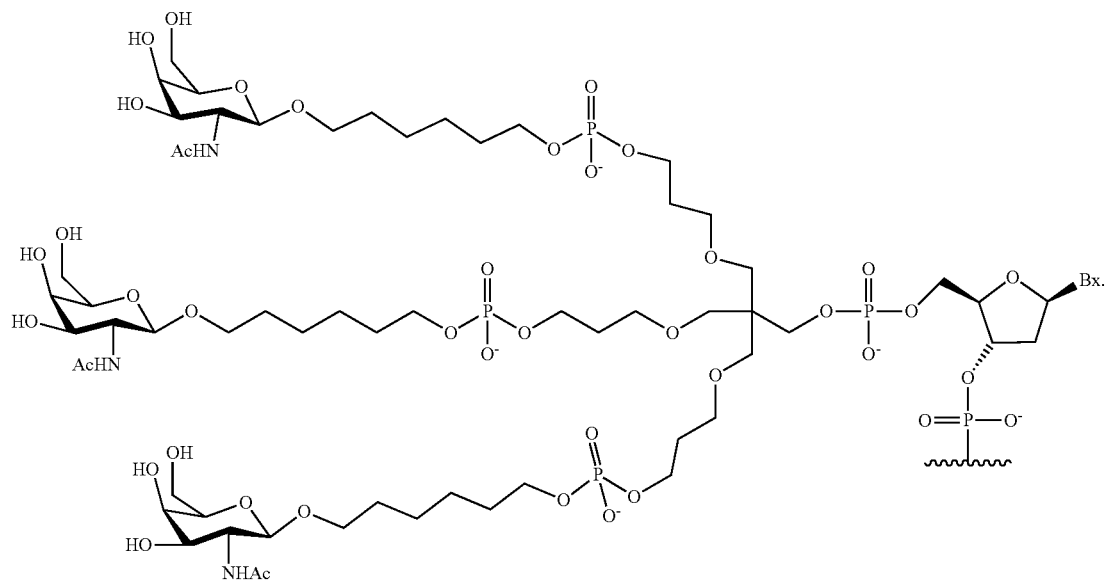
In certain such embodiments, conjugate groups have the following structure:
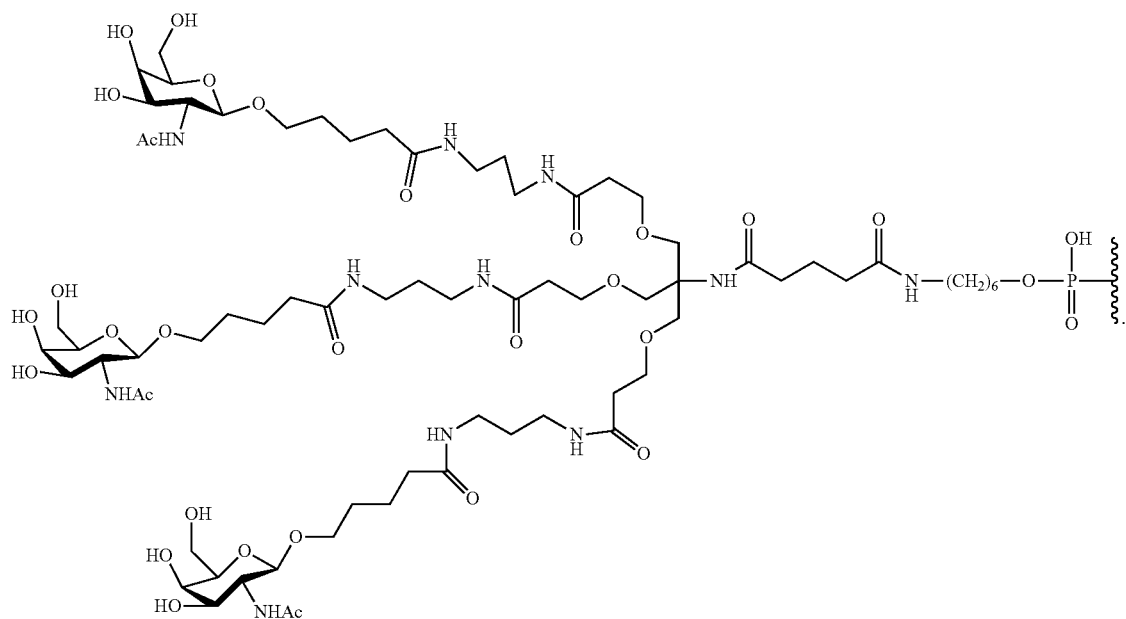
In certain such embodiments, conjugate groups have the following structure:

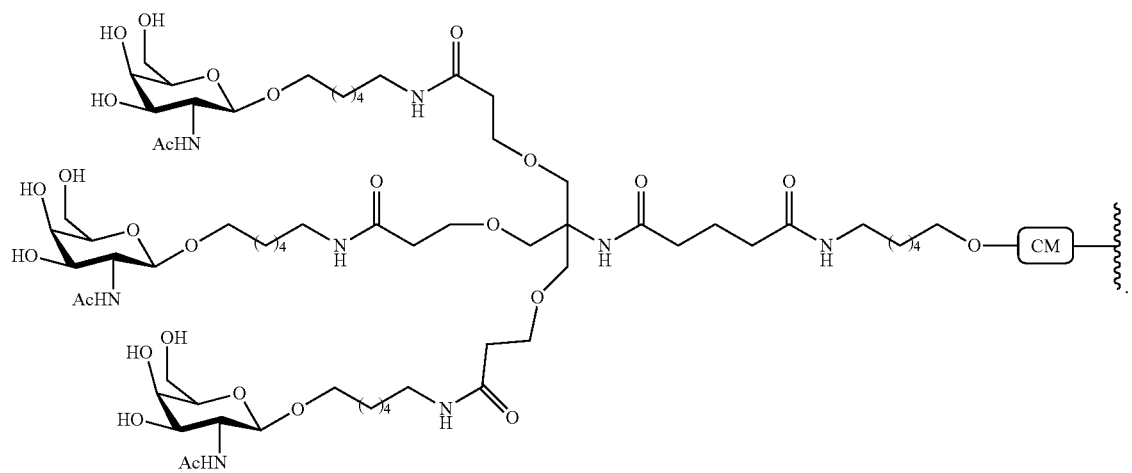
In certain such embodiments, conjugate groups have the following structure:
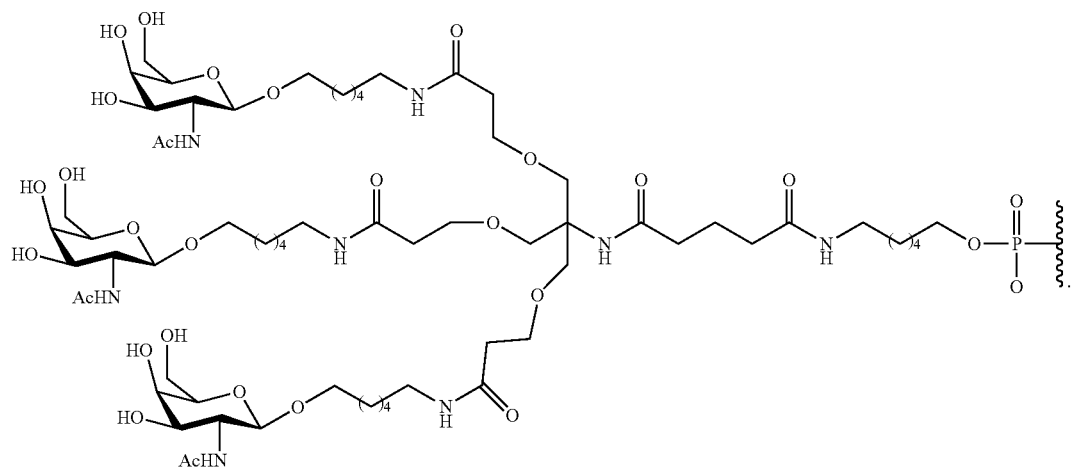
In certain such embodiments, conjugate groups have the following structure:
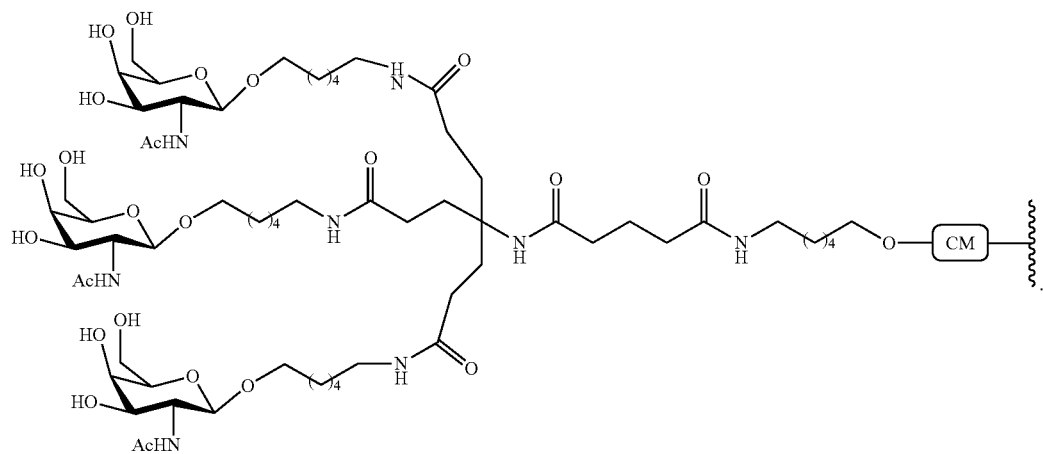

In certain such embodiments, conjugate groups have the following structure:
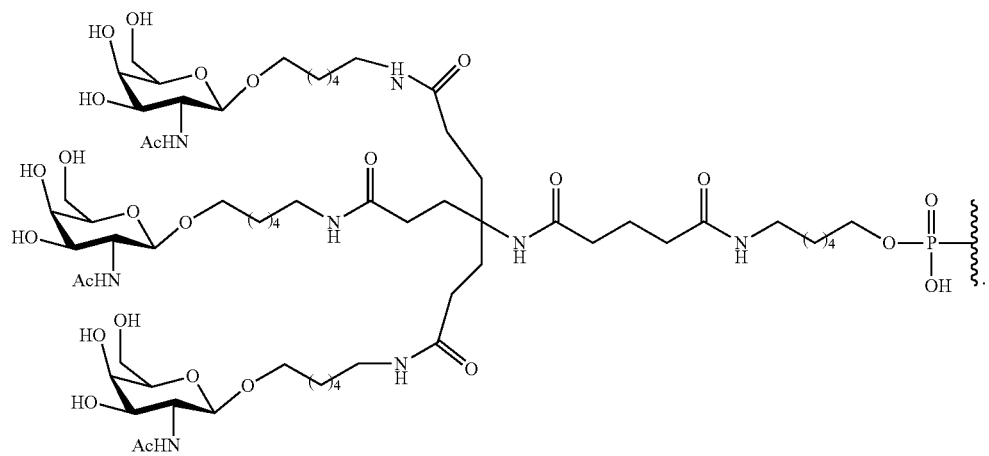
In certain such embodiments, conjugate groups have the following structure:
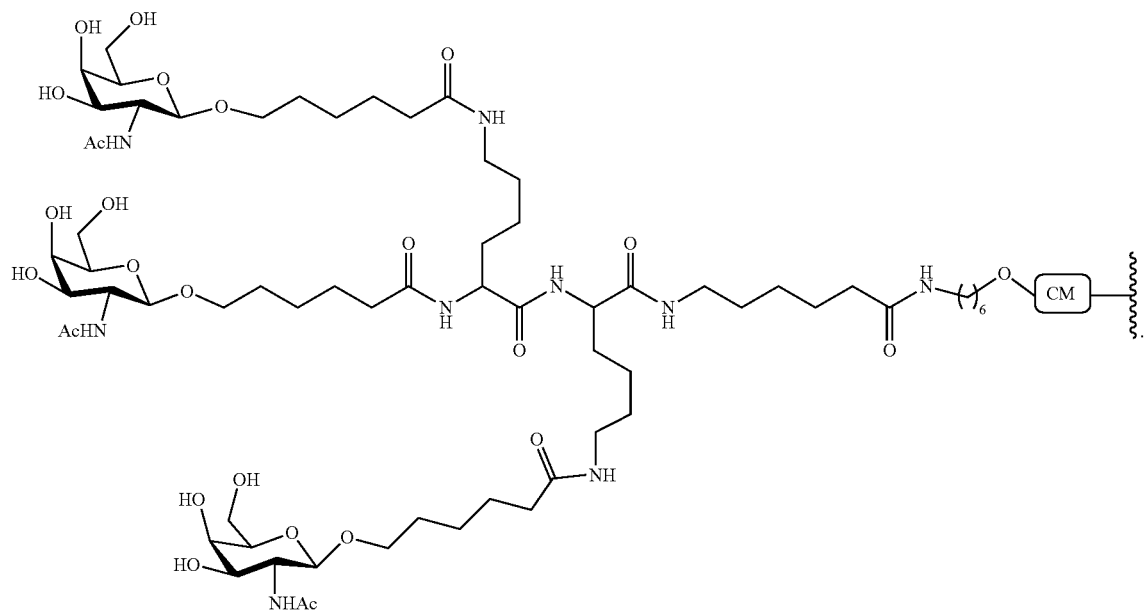
In certain such embodiments, conjugate groups have the following structure:

213
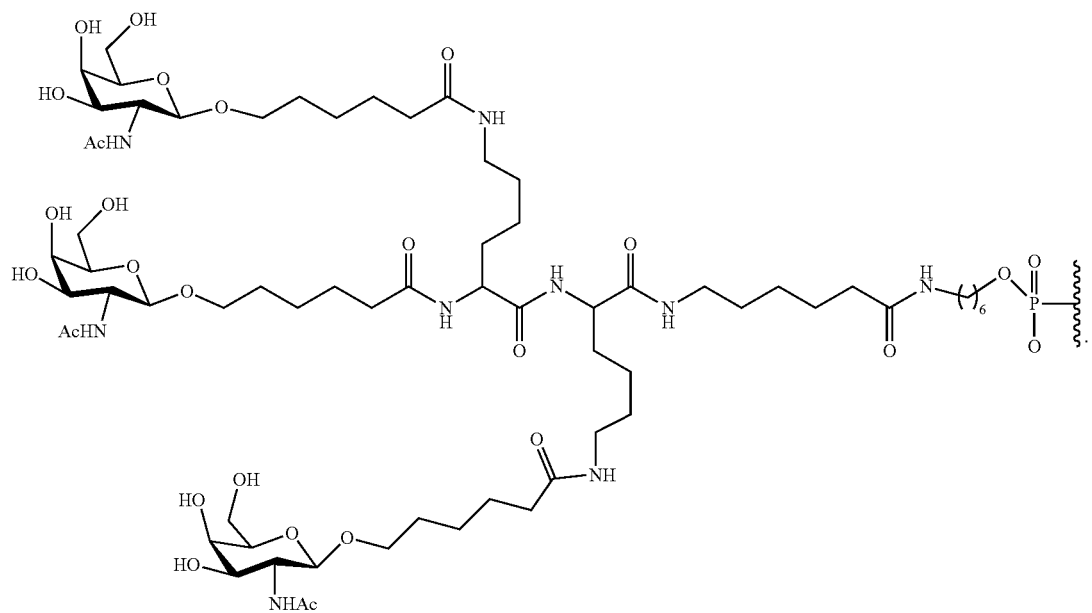
In certain such embodiments, conjugate groups have the following structure:
214
In certain such embodiments, conjugate groups have the following structure:
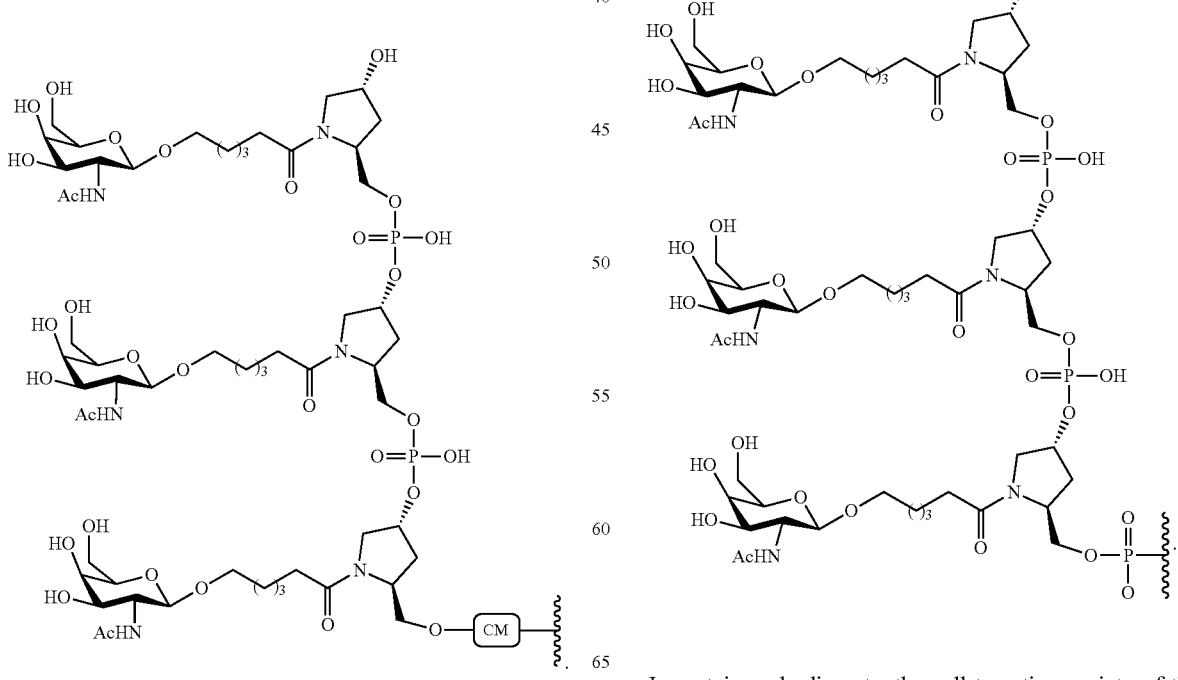
In certain embodiments, the cell-targeting moiety of the conjugate group has the following structure:

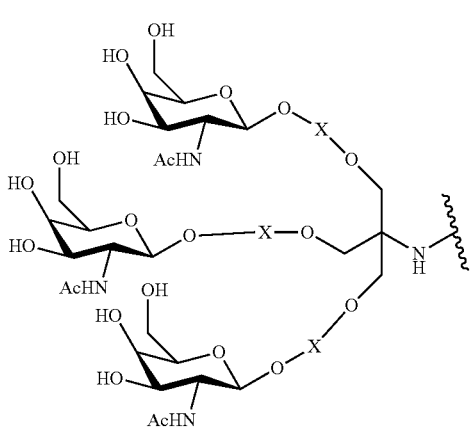

wherein X is a substituted or unsubstituted tether of six to eleven consecutively bonded atoms.

In certain embodiments, the cell-targeting moiety of the conjugate group has the following structure:

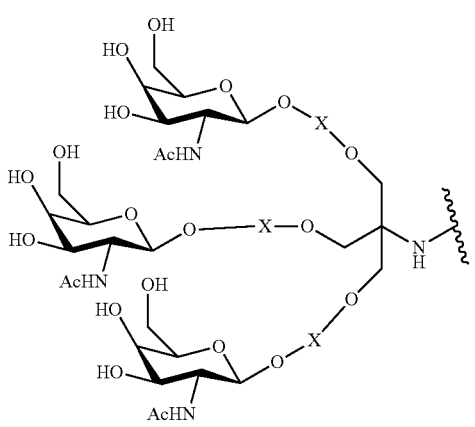

wherein X is a substituted or unsubstituted tether of ten consecutively bonded atoms.

In certain embodiments, the cell-targeting moiety of the conjugate group has the following structure:

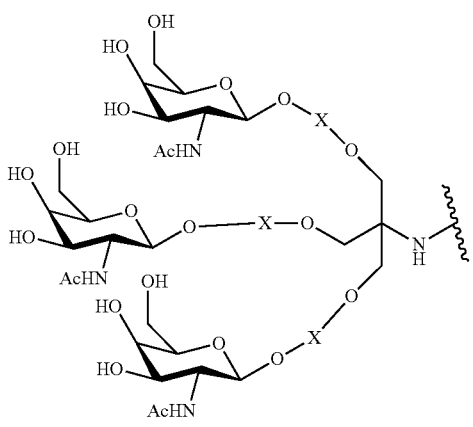

wherein X is a substituted or unsubstituted tether of four to eleven consecutively bonded atoms and wherein the tether comprises exactly one amide bond.

In certain embodiments, the cell-targeting moiety of the conjugate group has the following structure:

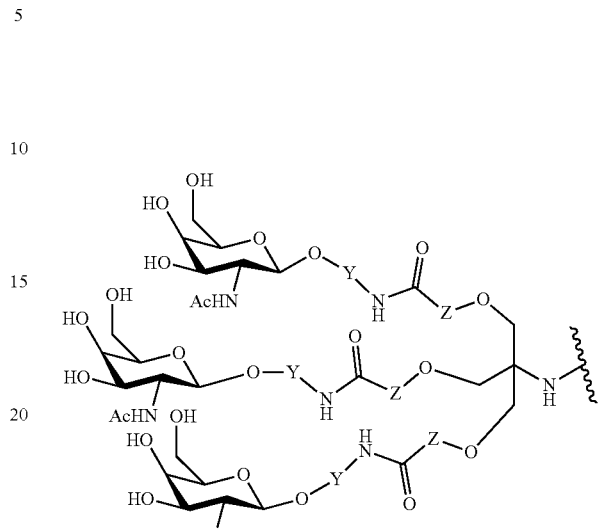

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

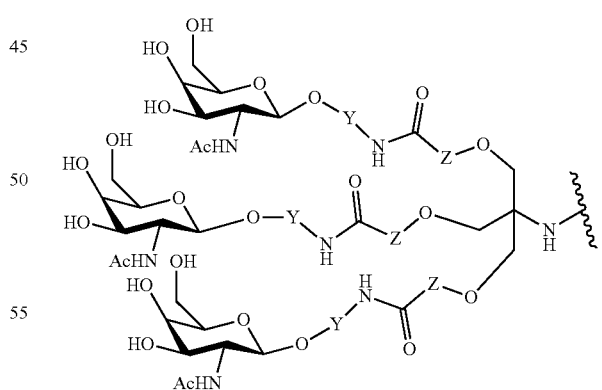

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

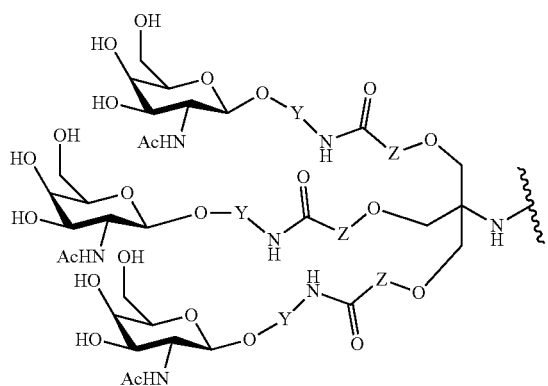

wherein Y and Z are independently selected from a $C_1$-$C_{12}$ substituted or unsubstituted alkyl group.

In certain such embodiments, the cell-targeting moiety of the conjugate group has the following structure:

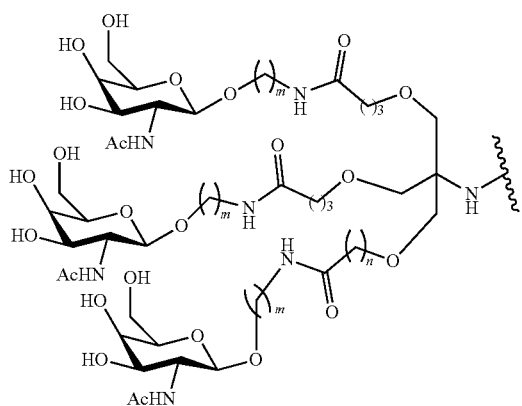

wherein m and n are independently selected from 1, 2, 3, 4, 5, 6, 7, 8, 9, 10, 11, and 12.

In certain such embodiments, the cell-targeting moiety of the conjugate group has the following structure:

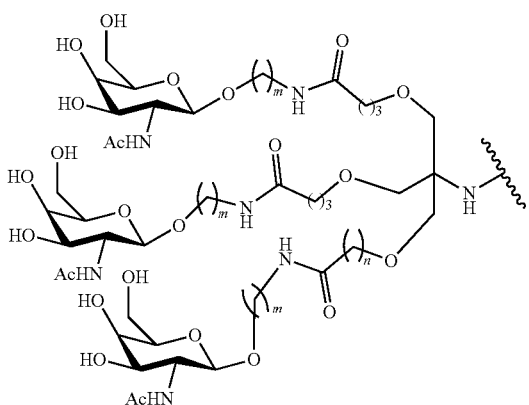

wherein m is 4, 5, 6, 7, or 8, and n is 1, 2, 3, or 4.

In certain embodiments, the cell-targeting moiety of the conjugate group has the following structure:

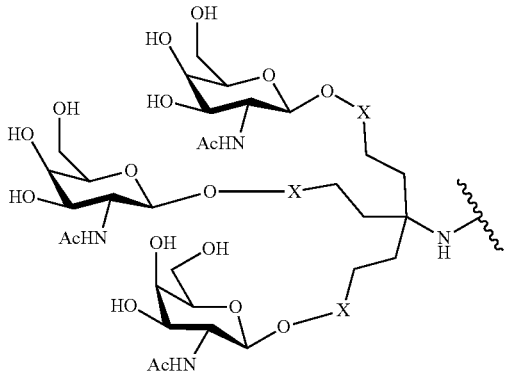

wherein X is a substituted or unsubstituted tether of four to thirteen consecutively bonded atoms, and wherein X does not comprise an ether group.

In certain embodiments, the cell-targeting moiety of the conjugate group has the following structure:

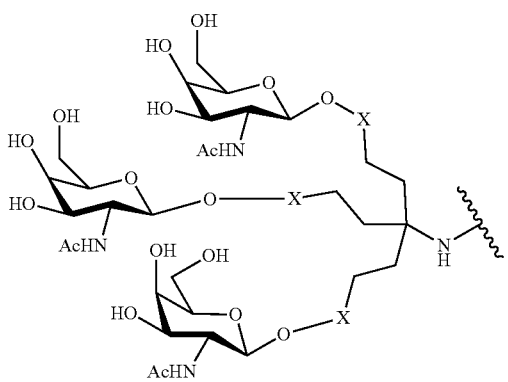

wherein X is a substituted or unsubstituted tether of eight consecutively bonded atoms, and wherein X does not comprise an ether group.

In certain embodiments, the cell-targeting moiety of the conjugate group has the following structure:

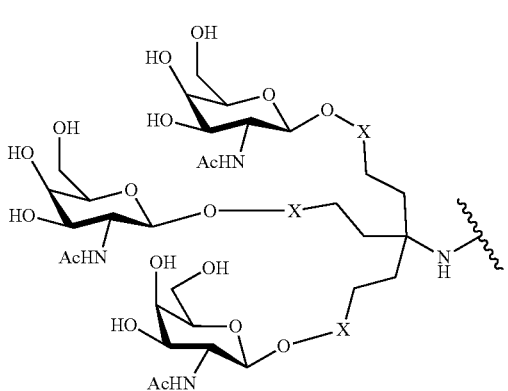

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

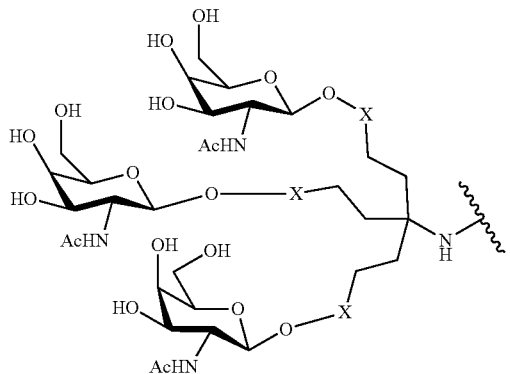

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

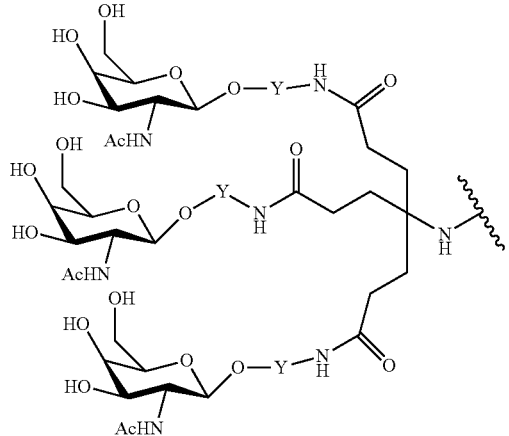

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

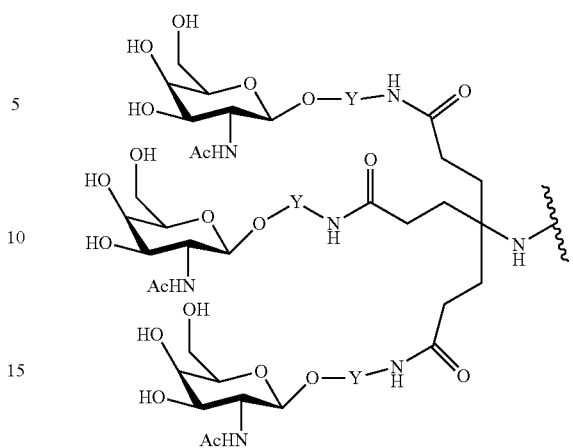

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

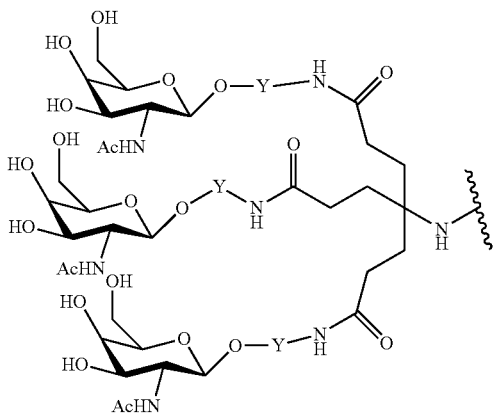

wherein Y is selected from a $C_1$-$C_{12}$ substituted or unsubstituted alkyl group.

In certain such embodiments, the cell-targeting moiety of the conjugate group has the following structure:

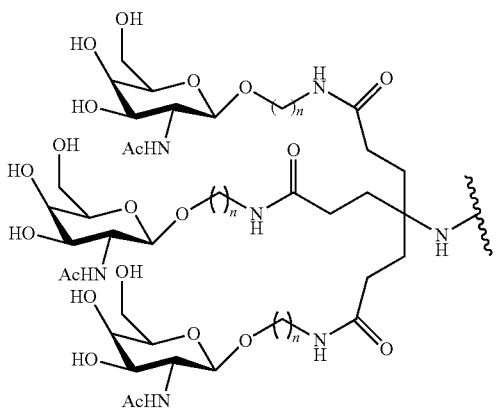

Wherein n is 1, 2, 3, 4, 5, 6, 7, 8, 9, 10, 11 or 12.

In certain such embodiments, the cell-targeting moiety of the conjugate group has the following structure:

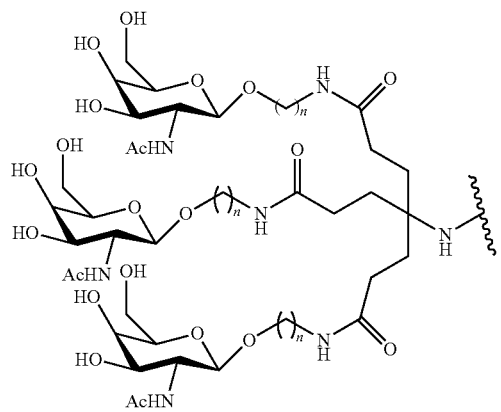

wherein n is 4, 5, 6, 7, or 8.

b. Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

wherein
A is the antisense oligonucleotide;
B is the cleavable moiety
C is the conjugate linker
D is the branching group
each E is a tether;
each F is a ligand; and
q is an integer between 1 and 5.

In certain embodiments, a conjugated antisense compound has the following structure:

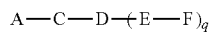

wherein
A is the antisense oligonucleotide;
C is the conjugate linker
D is the branching group
each E is a tether;
each F is a ligand; and
q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

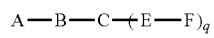

wherein
A is the antisense oligonucleotide;
B is the cleavable moiety
C is the conjugate linker
each E is a tether;
each F is a ligand; and
q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

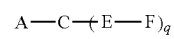

wherein
A is the antisense oligonucleotide;
C is the conjugate linker
each E is a tether;
each F is a ligand; and
q is an integer between 1 and 5.

In certain embodiments, a conjugated antisense compound has the following structure:

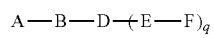

wherein
A is the antisense oligonucleotide;
B is the cleavable moiety
D is the branching group
each E is a tether;
each F is a ligand; and
q is an integer between 1 and 5.

In certain embodiments, a conjugated antisense compound has the following structure:

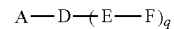

wherein
A is the antisense oligonucleotide;
D is the branching group
each E is a tether;
each F is a ligand; and
q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:
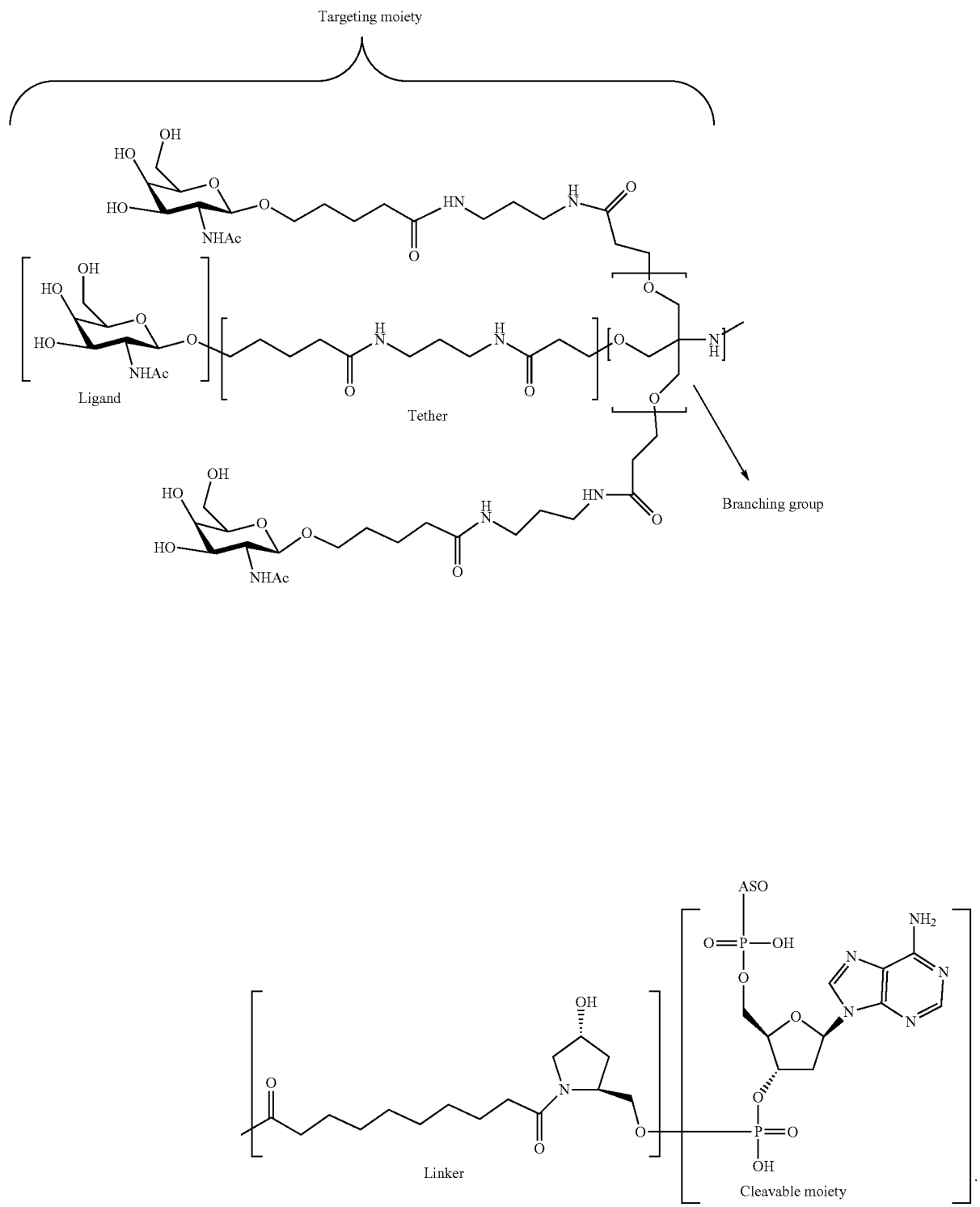

In certain embodiments, a conjugated antisense compound has a structure selected from among the following:
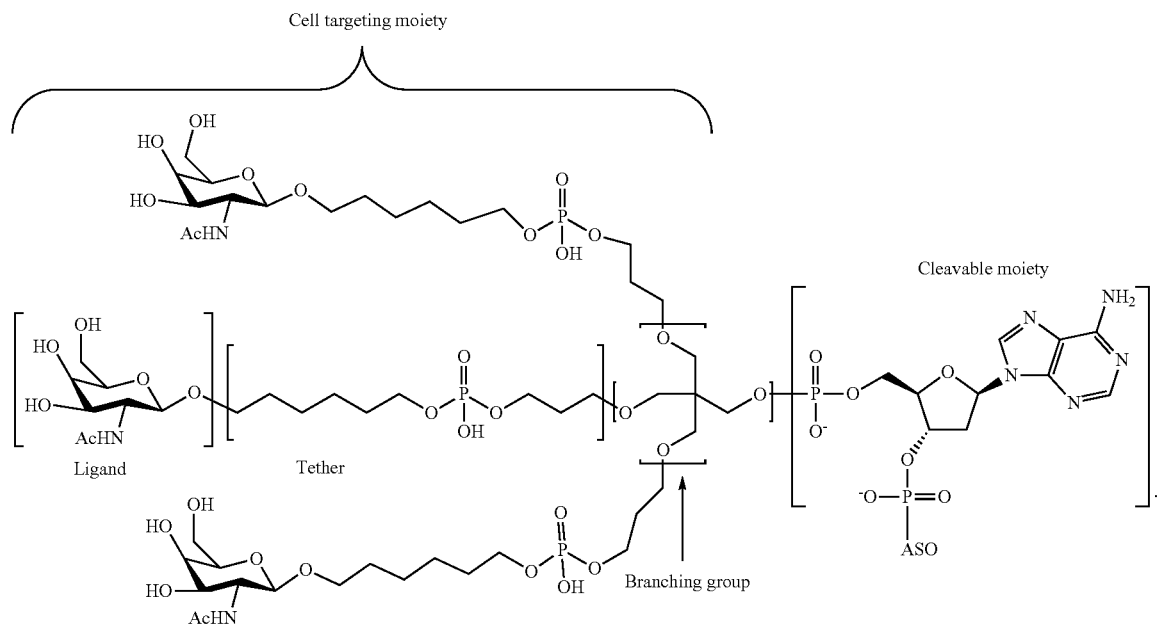
In certain embodiments, a conjugated antisense compound has a structure selected from among the following:
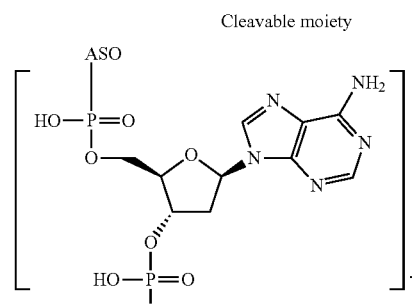

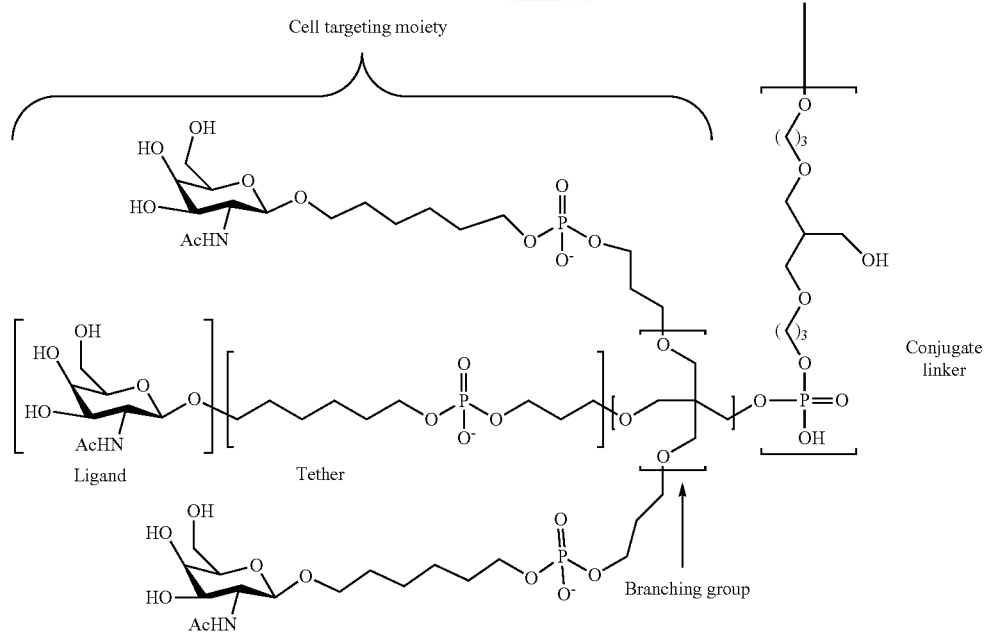
In certain embodiments, the conjugated antisense compound has the following structure:

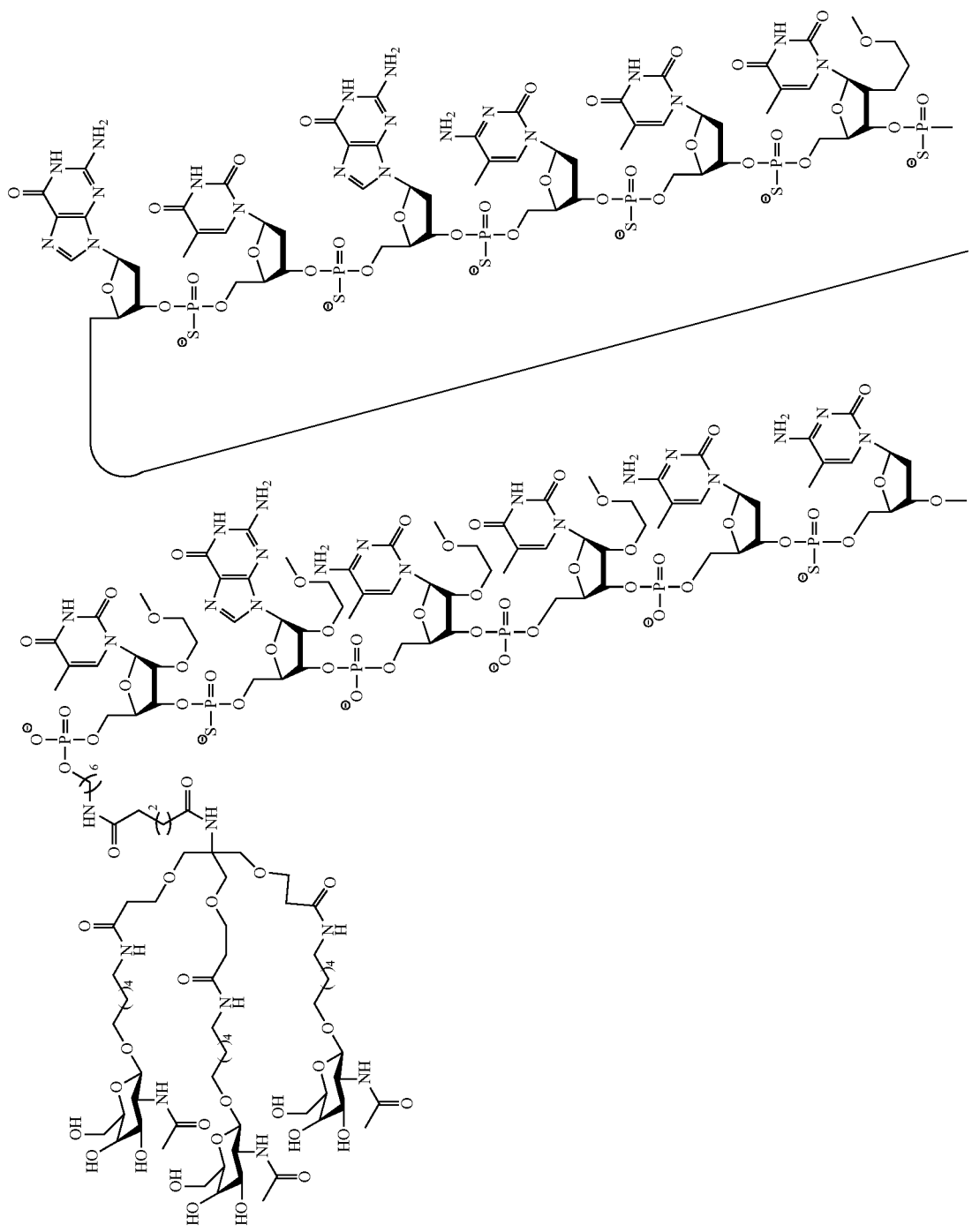

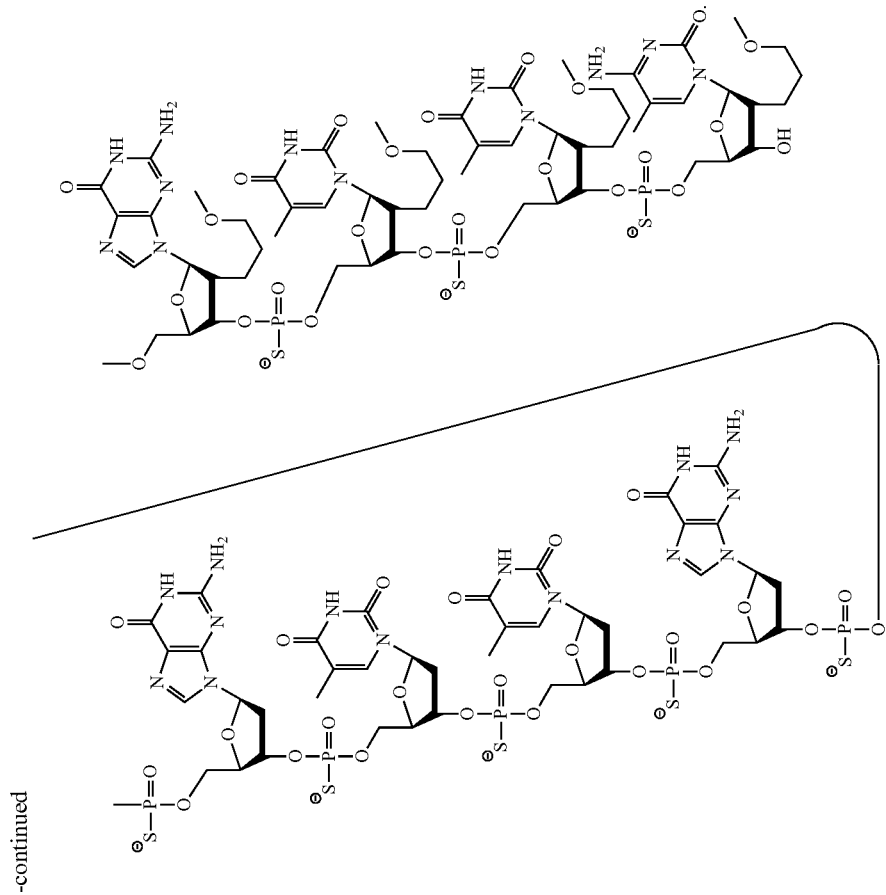

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn etal., "Solid-phase synthesis oflysine-based cluster galactosides with high affinity for the Asialoglycoprotein Receptor" Tetrahedron, 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

C. Certain Uses and Features

In certain embodiments, conjugated antisense compounds exhibit potent target RNA reduction in vivo. In certain embodiments, unconjugated antisense compounds accumulate in the kidney. In certain embodiments, conjugated antisense compounds accumulate in the liver. In certain embodiments, conjugated antisense compounds are well tolerated. Such properties render conjugated antisense compounds particularly useful for inhibition of many target RNAs, including, but not limited to those involved in metabolic, cardiovascular and other diseases, disorders or conditions. Thus, provided herein are methods of treating such diseases, disorders or conditions by contacting liver tissues with the conjugated antisense compounds targeted to RNAs associated with such diseases, disorders or conditions. Thus, also provided are methods for ameliorating any of a variety of metabolic, cardiovascular and other diseases, disorders or conditions with the conjugated antisense compounds of the present invention.

In certain embodiments, conjugated antisense compounds are more potent than unconjugated counterpart at a particular tissue concentration. Without wishing to be bound by any theory or mechanism, in certain embodiments, the conjugate may allow the conjugated antisense compound to enter the cell more efficiently or to enter the cell more productively.

For example, in certain embodiments conjugated antisense compounds may exhibit greater target reduction as compared to its unconjugated counterpart wherein both the conjugated antisense compound and its unconjugated counterpart are present in the tissue at the same concentrations. For example, in certain embodiments conjugated antisense compounds may exhibit greater target reduction as compared to its unconjugated counterpart wherein both the conjugated antisense compound and its unconjugated counterpart are present in the liver at the same concentrations.

Productive and non-productive uptake of oligonucleotides has been discussed previously (See e.g. Geary, R. S., E. Wancewicz, et al. (2009). "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. 78(3): 284-91; & Koller, E., T. M. Vincent, et al. (2011). "Mechanisms of single-stranded phosphorothioate modified antisense oligonucleotide accumulation in hepatocytes." Nucleic Acids Res. 39(11): 4795-807). Conjugate groups described herein may improve productive uptake.

In certain embodiments, the conjugate groups described herein may further improve potency by increasing the affinity of the conjugated antisense compound for a particular type of cell or tissue. In certain embodiments, the conjugate groups described herein may further improve potency by increasing recognition of the conjugated antisense compound by one or more cell-surface receptors. In certain embodiments, the conjugate groups described herein may further improve potency by facilitating endocytosis of the conjugated antisense compound.

In certain embodiments, the cleavable moiety may further improve potency by allowing the conjugate to be cleaved from the antisense oligonucleotide after the conjugated antisense compound has entered the cell. Accordingly, in certain embodiments, conjugated antisense compounds can be administered at doses lower than would be necessary for unconjugated antisense oligonucleotides.

Phosphorothioate linkages have been incorporated into antisense oligonucleotides previously. Such phosphorothioate linkages are resistant to nucleases and so improve stability of the oligonucleotide. Further, phosphorothioate linkages also bind certain proteins, which results in accumulation of antisense oligonucleotide in the liver. Oligonucleotides with fewer phosphorothioate linkages accumulate less in the liver and more in the kidney (see, for example, Geary, R., "Pharmacokinetic Properties of 2'-O-(2-Methoxyethyl)-Modified Oligonucleotide Analogs in Rats," *Journal of Pharmacology and Experimental Therapeutics*, Vol. 296, No. 3, 890-897; & Pharmacological Properties of 2'-O-Methoxyethyl Modified Oligonucleotides in Antisense a Drug Technology, Chapter 10, Crooke, S. T., ed., 2008) In certain embodiments, oligonucleotides with fewer phosphorothioate intemculeoside linkages and more phosphodiester internucleoside linkages accumulate less in the liver and more in the kidney. When treating diseases in the liver, this is undesibable for several reasons (1) less drug is getting to the site of desired action (liver); (2) drug is escaping into the urine; and (3) the kidney is exposed to relatively high concentration of drug which can result in toxicities in the kidney. Thus, for liver diseases, phosphorothioate linkages provide important benefits.

In certain embodiments, however, administration of oligonucleotides uniformly linked by phosphoro-thioate internucleoside linkages induces one or more proinflammatory reactions. (see for example: *J Lab Clin Med.* 1996 September; 128(3):329-38. "Amplification of antibody production by phosphorothioate oligodeoxynucleotides". Branda et al.; and see also for example: *Toxicologic Properties* in Antisense a Drug Technology, Chapter 12, pages 342-351, Crooke, S. T., ed., 2008). In certain embodiments, administration of oligonucleotides wherein most of the internucleoside linkages comprise phosphorothioate internucleoside linkages induces one or more proinflammatory reactions.

In certain embodiments, the degree of proinflammatory effect may depend on several variables (e.g. backbone modification, off-target effects, nucleobase modifications, and/or nucleoside modifications) see for example: *Toxicologic Properties* in Antisense a Drug Technology, Chapter 12, pages 342-351, Crooke, S. T., ed., 2008). In certain embodiments, the degree of proinflammatory effect may be mitigated by adjusting one or more variables. For example the degree of proinflammatory effect of a given oligonucleotide may be mitigated by replacing any number of phosphorothioate internucleoside linkages with phosphodiester internucleoside linkages and thereby reducing the total number of phosphorothioate internucleoside linkages.

In certain embodiments, it would be desirable to reduce the number of phosphorothioate linkages, if doing so could be done without losing stability and without shifting the distribution from liver to kidney. For example, in certain embodiments, the number of phosphorothioate linkages may be reduced by replacing phosphorothioate linkages with phosphodiester linkages. In such an embodiment, the antisense compound having fewer phosphorothioate linkages and more phosphodiester linkages may induce less proinflammatory reactions or no proinflammatory reaction. Although the antisense compound having fewer phosphorothioate linkages and more phosphodiester linkages may induce fewer proinflammatory reactions, the antisense compound having fewer phosphorothioate linkages and more phosphodiester linkages may not accumulate in the liver and may be less efficacious at the same or similar dose as compared to an antisense compound having more phosphorothioate linkages. In certain embodiments, it is therefore desirable to design an antisense compound that has a plurality of phosphodiester bonds and a plurality of phosphorothioate bonds but which also possesses stability and good distribution to the liver.

In certain embodiments, conjugated antisense compounds accumulate more in the liver and less in the kidney than unconjugated counterparts, even when some of the phosporothioate linkages are replaced with less proinflammatory phosphodiester intemucleoside linkages. In certain embodiments, conjugated antisense compounds accumulate more in the liver and are not excreted as much in the urine compared to its unconjugated counterparts, even when some of the phosporothioate linkages are replaced with less proinflammatory phosphodiester intemucleoside linkages. In certain embodiments, the use of a conjugate allows one to design more potent and better tolerated antisense drugs. Indeed, in certain embodiments, conjugated antisense compounds have larger therapeutic indexes than unconjugated counterparts. This allows the conjugated antisense compound to be administered at a higher absolute dose, because there is less risk of proinflammatory response and less risk of kidney toxicity. This higher dose, allows one to dose less frequently, since the clearance (metabolism) is expected to be similar. Further, because the compound is more potent, as described above, one can allow the concentration to go lower before the next dose without losing therapeutic activity, allowing for even longer periods between dosing.

In certain embodiments, the inclusion of some phosphorothioate linkages remains desirable. For example, the terminal linkages are vulnerable to exonucleases and so in certain embodiments, those linkages are phosphorothioate or other modified linkage. Internucleoside linkages linking two deoxynucleosides are vulnerable to endonucleases and so in certain embodiments those linkages are phosphorothioate or other modified linkage. Internucleoside linkages between a modified nucleoside and a deoxynucleoside where the deoxynucleoside is on the 5' side of the linkage deoxynucleosides are vulnerable to endonucleases and so in certain embodiments those linkages are phosphorothioate or other modified linkage. Internucleoside linkages between two modified nucleosides of certain types and between a deoxynucleoside and a modified nucleoside of certain type where the modified nucleoside is at the 5' side of the linkage are sufficiently resistant to nuclease digestion, that the linkage can be phosphodiester.

In certain embodiments, the antisense oligonucleotide of a conjugated antisense compound comprises fewer than 16 phosphorthioate linkages. In certain embodiments, the antisense oligonucleotide of a conjugated antisense compound comprises fewer than 15 phosphorthioate linkages. In certain embodiments, the antisense oligonucleotide of a conjugated antisense compound comprises fewer than 14 phosphorthioate linkages. In certain embodiments, the antisense oligonucleotide of a conjugated antisense compound comprises fewer than 13 phosphorthioate linkages. In certain embodiments, the antisense oligonucleotide of a conjugated antisense compound comprises fewer than 12 phosphorthioate linkages. In certain embodiments, the antisense oligonucleotide of a conjugated antisense compound comprises fewer than 11 phosphorthioate linkages. In certain embodiments, the antisense oligonucleotide of a conjugated antisense compound comprises fewer than 10 phosphorthioate linkages. In certain embodiments, the antisense oligonucleotide of a conjugated antisense compound comprises fewer than 9 phosphorthioate linkages. In certain embodiments, the antisense oligonucleotide of a conjugated antisense compound comprises fewer than 8 phosphorthioate linkages.

In certain embodiments, antisense compounds comprising one or more conjugate group described herein has increased activity and/or potency and/or tolerability compared to a parent antisense compound lacking such one or more conjugate group. Accordingly, in certain embodiments, attachment of such conjugate groups to an oligonucleotide is desirable. Such conjugate groups may be attached at the 5'-, and/or 3'-end of an oligonucleotide. In certain instances, attachment at the 5'-end is synthetically desireable. Typically, oligonucleieitdes are synthesized by attachment of the 3' terminal nucleoside to a solid support and sequential coupling of nucleosides from 3' to 5' using techniques that are well known in the art. Accordingly if a conjugate group is desired at the 3'-terminus, one may (1) attach the conjugate group to the 3'-terminal nucleoside and attach that conjugated nucleoside to the solid support for subsequent preparation of the oligonucleotide or (2) attach the conjugate group to the 3'-terminal nucleoside of a completed oligonucleotide after synthesis. Neither of these approaches is very efficient and thus both are costly. In particular, attachment of the conjugated nucleoside to the solid support, while demonstrated in the Examples herein, is an inefficient process. In certain embodiments, attaching a conjugate group to the 5'-terminal nucleoside is synthetically easier than attachment at the 3'-end. One may attach a non-conjugated 3' terminal nucleoside to the solid support and prepare the oligonucleotide using standard and well characterized reactions. One then needs only to attach a 5'nucleoside having a conjugate group at the final coupling step. In certain embodiments, this is more efficient than attaching a conjugated nucleoside directly to the solid support as is typically done to prepare a 3'-conjugated oligonucleotide. The Examples herein demonstrate attachment at the 5'-end. In addition, certain conjugate groups have synthetic advantages. For Example, certain conjugate groups comprising phosphorus linkage groups are synthetically simpler and more efficiently prepared than other conjugate groups, including conjugate groups reported previously (e.g., WO/2012/037254).

In certain embodiments, conjugated antisense compounds are administered to a subject. In such embodiments, antisense compounds comprising one or more conjugate group described herein has increased activity and/or potency and/or tolerability compared to a parent antisense compound lacking such one or more conjugate group. Without being bound by mechanism, it is believed that the conjugate group helps with distribution, delivery, and/or uptake into a target cell or tissue. In certain embodiments, once inside the target cell or tissue, it is desirable that all or part of the conjugate group to be cleaved to release the active oligonucleoitdes. In certain embodiments, it is not necessary that the entire conjugate group be cleaved from the oligonucleotide. For example, in Example 20 a conjugated oligonucleotide was administered to mice and a number of different chemical species, each comprising a different portion of the conjugate group remaining on the oligonucleotide, were detected (Table 23a). This conjugated antisense compound demonstrated good potency (Table 23). Thus, in certain embodiments, such metabolite profile of multiple partial cleavage of the conjugate group does not interfere with activity/potency. Nevertheless, in certain embodiments it is desirable that a prodrug (conjugated oligonucleotide) yield a single active compound. In certain instances, if multiple forms of the active compound are found, it may be necessary to determine relative amounts and activities for each one. In certain embodiments where regulatory review is required (e.g., USFDA or counterpart) it is desirable to have a single (or predominantly single) active species. In certain such embodiments, it is desirable that such single active species be the antisense oligonucleotide lacking any portion of the conjugate group. In certain embodiments, conjugate groups at the 5'-end are more likely to result in complete metabolism of the conjugate group. Without being bound by mechanism it may be that endogenous enzymes responsible for metabolism at the 5' end (e.g., 5' nucleases) are more active/efficient than the 3' counterparts. In certain embodiments, the specific conjugate groups are more amenable to metabolism to a single active species. In certain embodiments, certain conjugate groups are more amenable to metabolism to the oligonucleotide.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, oligonucleotides comprising conjugates described herein are RNAi compounds. In certain embodiments, oligomeric oligonucleotides comprising conjugates described herein are ssRNA compounds. In certain embodiments, oligonucleotides comprising conjugates described herein are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligonucleotides comprising conjugates described herein is the antisense strand in an siRNA compound. In certain embodiments, the oligonucleotides comprising conjugates described herein is the sense strand in an siRNA compound. In embodiments in which the conjugated oligomeric compound is double-stranded siRnA, the conjugate may be on the sense strand, the antisense strand or both the sense strand and the antisense strand.

C. Apolinorotein (a) (Apo(a))

In certain embodiments, conjugated antisense compounds target any apo(a) nucleic acid. In certain embodiments, the target nucleic acid encodes an apo(a) target protein that is clinically relevant. In such embodiments, modulation of the target nucleic acid results in clinical benefit.

The targeting process usually includes determination of at least one target region, segment, or site within the target nucleic acid for the antisense interaction to occur such that the desired effect will result.

In certain embodiments, a target region is a structurally defined region of the nucleic acid. For example, in certain such embodiments, a target region may encompass a 3' UTR, a 5' UTR, an exon, an intron, a coding region, a translation initiation region, translation termination region, or other defined nucleic acid region or target segment.

In certain embodiments, a target segment is at least about an 8-nucleobase portion of a target region to which a conjugated antisense compound is targeted. Target segments can include DNA or RNA sequences that comprise at least 8 consecutive nucleobases from the 5'-terminus of one of the target segments (the remaining nucleobases being a consecutive stretch of the same DNA or RNA beginning immediately upstream of the 5'-terminus of the target segment and continuing until the DNA or RNA comprises about 8 to about 30 nucleobases). Target segments are also represented by DNA or RNA sequences that comprise at least 8 consecutive nucleobases from the 3'-terminus of one of the target segments (the remaining nucleobases being a consecutive stretch of the same DNA or RNA beginning immediately downstream of the 3'-terminus of the target segment and continuing until the DNA or RNA comprises about 8 to about 30 nucleobases). Target segments can also be represented by DNA or RNA sequences that comprise at least 8 consecutive nucleobases from an internal portion of the sequence of a target segment, and may extend in either or both directions until the conjugated antisense compound comprises about 8 to about 30 nucleobases.

In certain embodiments, antisense compounds targeted to an apo(a) nucleic acid can be modified as described herein. In certain embodiments, the antisense compounds can have a modified sugar moiety, an unmodified sugar moiety or a mixture of modified and unmodified sugar moieties as described herein. In certain embodiments, the antisense compounds can have a modified internucleoside linkage, an unmodified internucleoside linkage or a mixture of modified and unmodified internucleoside linkages as described herein. In certain embodiments, the antisense compounds can have a modified nucleobase, an unmodified nucleobase or a mixture of modified and unmodified nucleobases as described herein. In certain embodiments, the antisense compounds can have a motif as described herein.

In certain embodiments, antisense compounds targeted to apo(a) nucleic acids can be conjugated as described herein.

One apo(a) protein is linked via a disulfide bond to a single apolipoprotein B (apoB) protein to form a lipoprotein (a) (Lp(a)) particle. The apo(a) protein shares a high degree of homology with plasminogen particularly within the kringle IV type 2 repetitive domain. It is thought that the kringle repeat domain in apo(a) may be responsible for its pro-thrombotic and anti-fibrinolytic properties, potentially enhancing atherosclerotic progression. Apo(a) is transcriptionally regulated by IL-6 and in studies in rheumatoid arthritis patients treated with an IL-6 inhibitor (tocilizumab), plasma levels were reduced by 30% after 3 month treatment. Apo(a) has been shown to preferentially bind oxidized phospholipids and potentiate vascular inflammation. Further, studies suggest that the Lp(a) particle may also stimulate endothelial permeability, induce plasminogen activator inhibitor type-1 expression and activate macrophage interleukin-8 secretion. Importantly, recent genetic association studies revealed that Lp(a) was an independent risk factor for myocardial infarction, stroke, peripheral vascular disease and abdominal aortic aneurysm. Further, in the Precocious Coronary Artery Disease (PROCARDIS) study, Clarke et al. described robust and independent associations between coronary heart disease and plasma Lp(a) concentrations. Additionally, Solfrizzi et al., suggested that increased serum Lp(a) may be linked to an increased risk for Alzheimer's Disease (AD). Antisense compounds targeting apo(a) have been previously disclosed in WO2005/000201 and US2010-0331390, herein incorporated by reference in its entirety. An antisense oligonucleobase targeting Apo(a), ISIS-APOA$_{Rx}$, was assessed in a Phase I clinical trial to study it's safety profile.

Certain Conjugated Antisense Compounds Targeted to an Apo(a) Nucleic Acid

In certain embodiments, conjugated antisense compounds are targeted to an Apo(a) nucleic acid having the sequence of GENBANK® Accession No. NM_005577.2, incorporated herein as SEQ ID NO: 1; GENBANK Accession No. NT_007422.12 truncated from nucleotides 3230000 to 3380000, incorporated herein as SEQ ID NO: 2; GENBANK Accession No. NT_025741.15 truncated from nucleotides 65120000 to 65/258,000, designated herein as SEQ ID NO: 3; and GENBANK Accession No. NM_005577.1, incorporated herein as SEQ ID NO: 4. In certain such embodiments, a conjugated antisense compound is at least 90%, at least 95%, or 100% complementary to any of the nucleobase sequences of SEQ ID NOs: 1-4.

In certain embodiments, a conjugated antisense compound targeted to any of the nucleobase sequences of SEQ ID NOs: 1-4 comprises an at least 8 consecutive nucleobase sequence selected from the nucleobase sequence of any of SEQ ID NOs: 12-130, 133, 134. In certain embodiments, a conjugated antisense compound targeted to any of SEQ ID NOs: 1-4 comprises a nucleobase sequence selected from the nucleobase sequence of any of SEQ ID NOs: 12-130, 133, 134.

TABLE A

Antisense Compounds targeted to Apo(a) SEQ ID NO: 1

| ISIS No | Target Start Site | Sequence (5'-3') | Motif | SEQ ID NO |
|---|---|---|---|---|
| 494372 | 3901 | TGCTCCGTTGGTGCTTGTTC | eeeeedddddddddeeeee | 58 |
| 494283 | 584<br>926<br>1610<br>1952<br>2294<br>3320 | TCTTCCTGTGACAGTGGTGG | eeeeedddddddddeeeee | 26 |
| 494284 | 585<br>927<br>1611<br>1953<br>2295<br>3321 | TTCTTCCTGTGACAGTGGTG | eeeeedddddddddeeeee | 27 |
| 494286 | 587<br>929<br>1613<br>1955<br>2297 | GGTTCTTCCTGTGACAGTGG | eeeeedddddddddeeeee | 29 |
| 494301 | 628<br>970<br>1312<
1654<br>1996<br>2338<br>2680<br>3022 | CGACTATGCGAGTGTGGTGT | eeeeedddddddddeeeee | 38 |
| 494302 | 629<br>971<br>1313<br>1655<br>1997<br>2339<br>2681<br>3023 | CCGACTATGCGAGTGTGGTG | eeeeedddddddddeeeee | 39 |

Apo(a) Therapeutic Indications

In certain embodiments, the invention provides methods for using a conjugated antisense compound targeted to an apo(a) nucleic acid for modulating the expression of apo(a) in a subject. In certain embodiments, the expression of apo(a) is reduced.

In certain embodiments, provided herein are methods of treating a subject comprising administering one or more pharmaceutical compositions as described herein. In certain embodiments, the invention provides methods for using a conjugated antisense compound targeted to an apo(a) nucleic acid in a pharmaceutical composition for treating a subject. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the subject has an inflammatory, cardiovascular and/or metabolic disease, disorder or condition.

In certain embodiments, the cardiovascular diseases, disorders or conditions include, but are not limited to, aortic stenosis, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administration of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, aortic stenosis, coronary artery disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by at least about 5%, 10%, 15%, 20%, 25%, 30%, 35%, 40%, 45%, 50%, 55%, 60%, 65%, 70%, 75%, 80%, 85%, 90%, 95% or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, apo(a) expression is reduced to at least ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, Lp(a) expression is reduced to at least ≤200 mg/dL, ≤190 mg/dL, ≤180 mg/dL, ≤175 mg/dL, ≤170 mg/dL, ≤160 mg/dL, ≤150 mg/dL, ≤140 mg/dL, ≤130 mg/dL, ≤120 mg/dL, ≤110 mg/dL, ≤100 mg/dL, ≤90 mg/dL, ≤80 mg/dL, ≤70 mg/dL, ≤60 mg/dL, ≤55 mg/dL, ≤50 mg/dL, ≤45 mg/dL, ≤40 mg/dL, ≤35 mg/dL, ≤30 mg/dL, ≤25 mg/dL, ≤20 mg/dL, ≤15 mg/dL, or ≤10 mg/dL.

In certain embodiments, the invention provides methods for using a conjugated antisense compound targeted to an apo(a) nucleic acid in the preparation of a medicament. In certain embodiments, pharmaceutical compositions comprising a conjugated antisense compound targeted to apo(a) are used for the preparation of a medicament for treating a patient suffering or susceptible to an inflammatory, cardiovascular and/or a metabolic disease, disorder or condition.

Apo(a) Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has apo(a) levels ≥10 mg/dL, ≥20 mg/dL, ≥30 mg/dL, ≥40 mg/dL, ≥50 mg/dL, ≥60 mg/dL, ≥70 mg/dL, ≥80 mg/dL, ≥90 mg/dL or ≥100 mg/dL. In certain embodiments, the human has Lp(a) levels ≥10 mg/dL, ≥15 mg/dL, ≥20 mg/dL, ≥25 mg/dL, ≥30 mg/dL, ≥35 mg/dL, ≥40 mg/dL, ≥50 mg/dL, ≥60 mg/dL, ≥70 mg/dL, ≥80 mg/dL, ≥90 mg/dL, ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥175 mg/dL, ≥180 mg/dL, ≥190 mg/dL, ≥200 mg/dL.

D. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: General Method for the Preparation of Phosphoramidites, Compounds 1, 1a and 2

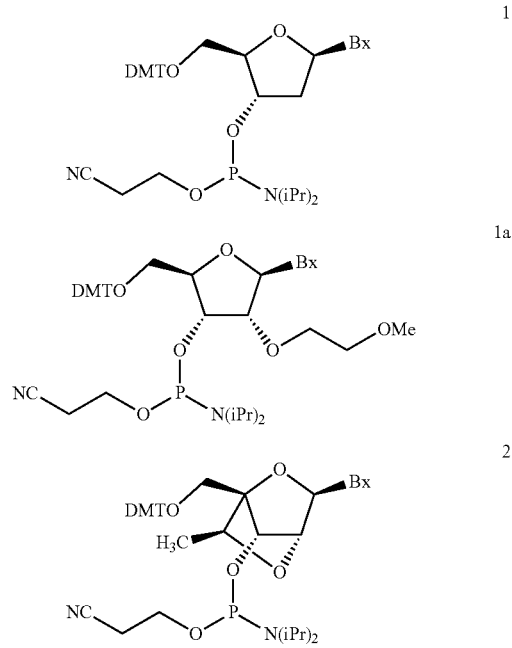

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7

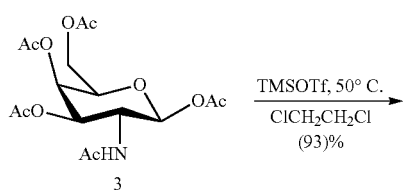

251
-continued
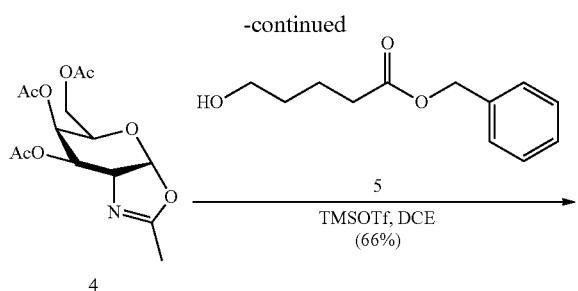
Compounds 3 (2-acetamido-1,3,4,6-tetra-O-acetyl-2-deoxy-β-galactopyranose or galactosamine pentaacetate) is commercially available. Compound 5 was prepared according to published procedures (Weber et al., *J Med. Chem.*, 1991, 34, 2692).
252
Example 3: Preparation of Compound 11
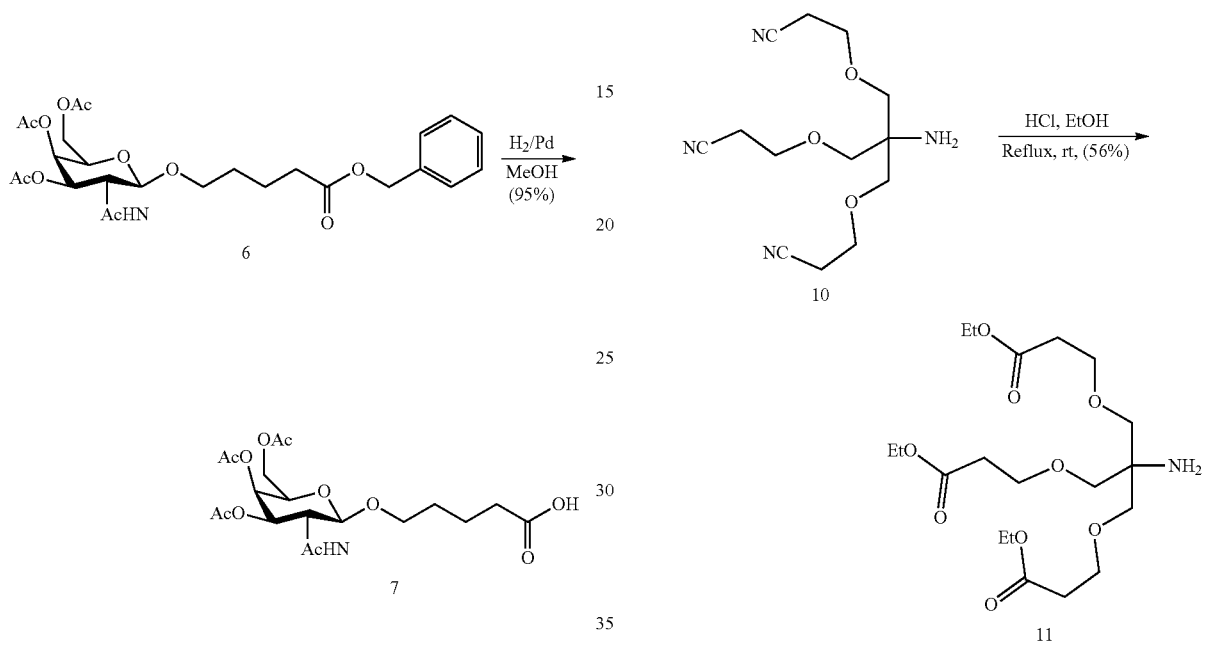
Compounds 8 and 9 are commercially available.
Example 4: Preparation of Compound 18
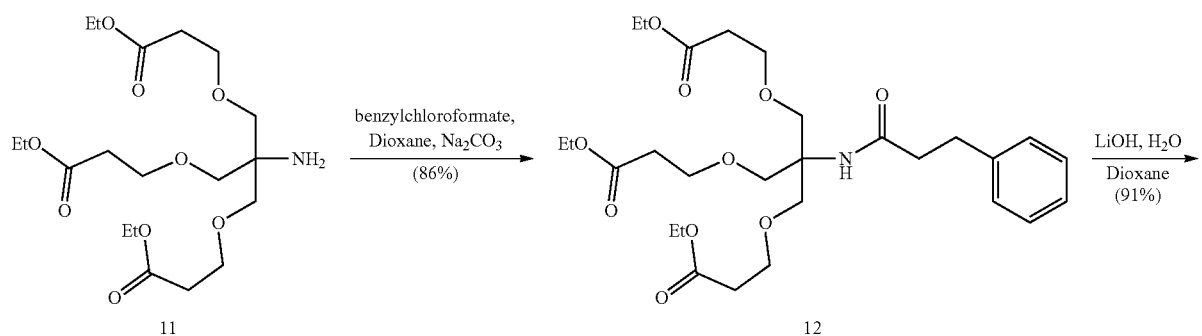

-continued
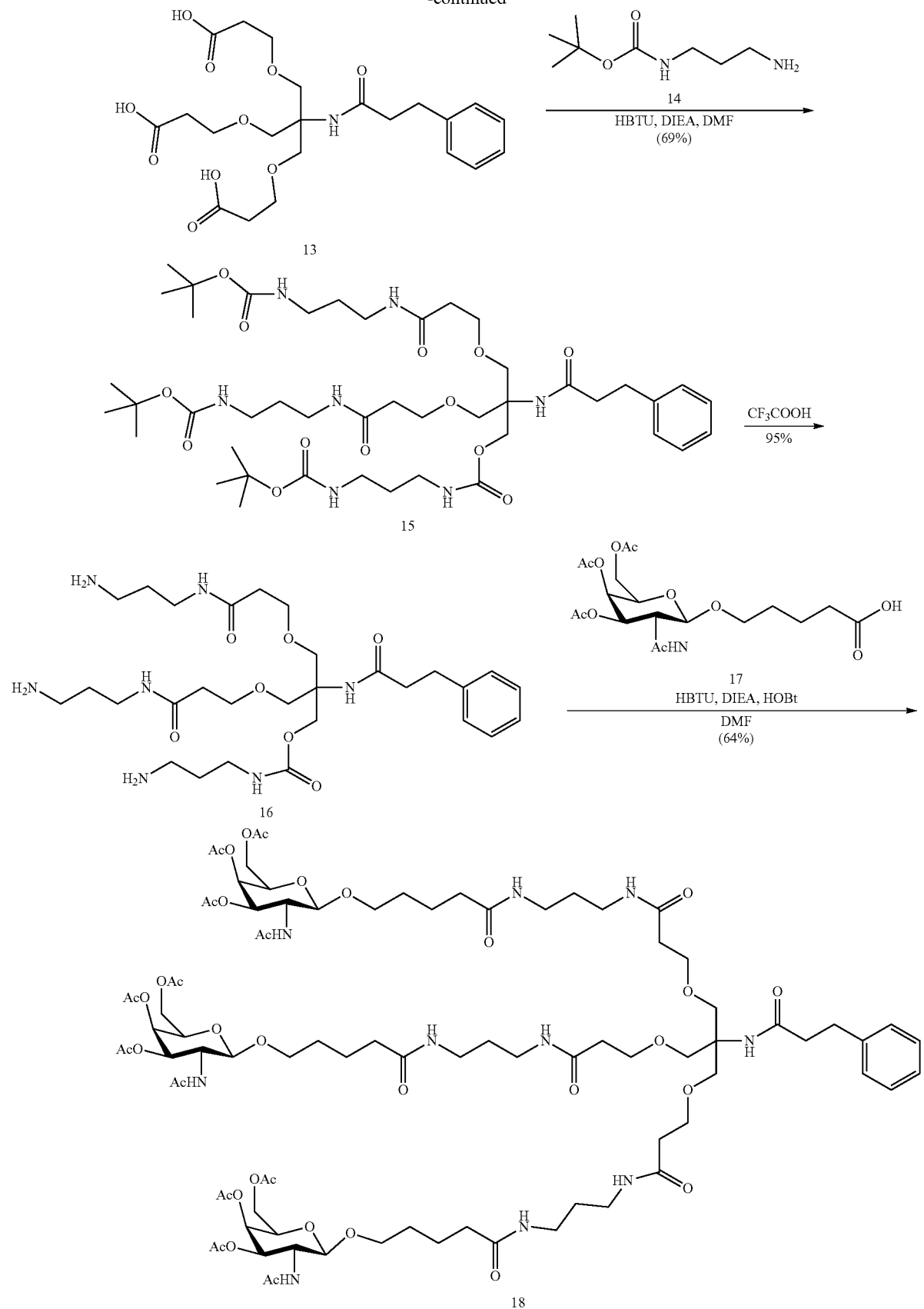

Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5: Preparation of Compound 23
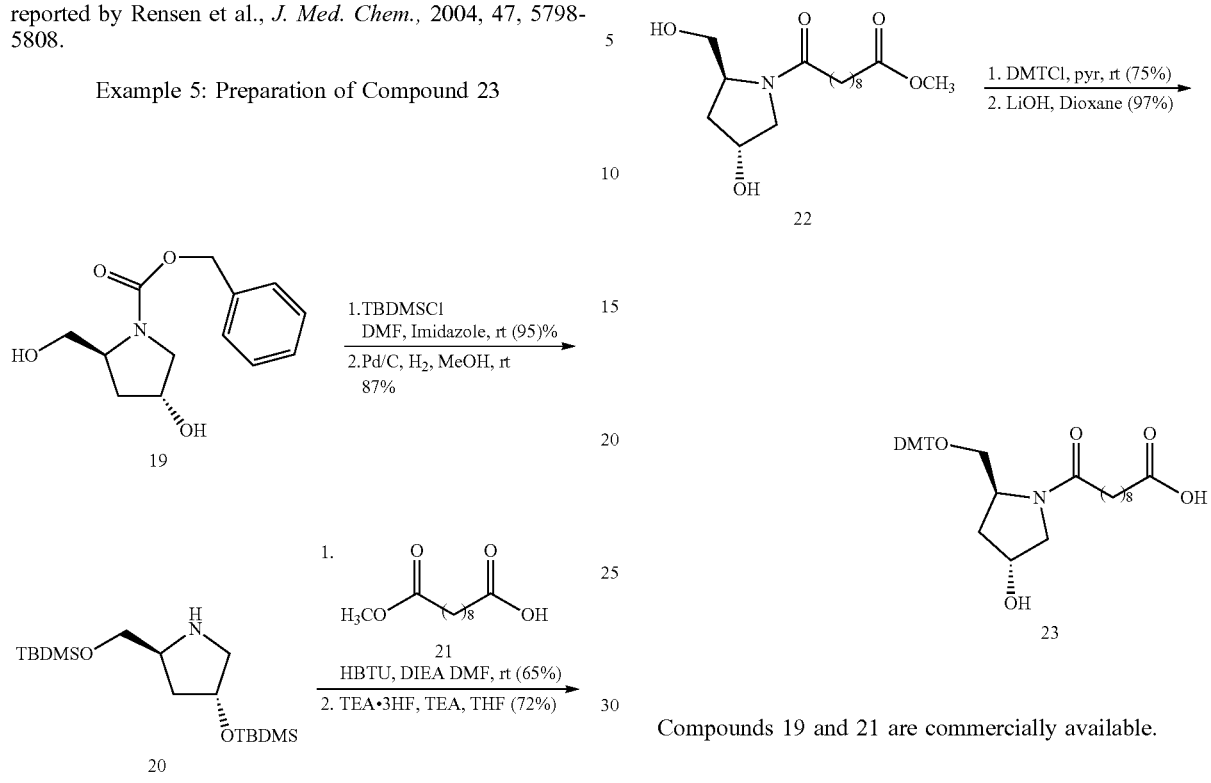
Compounds 19 and 21 are commercially available.
Example 6: Preparation of Compound 24
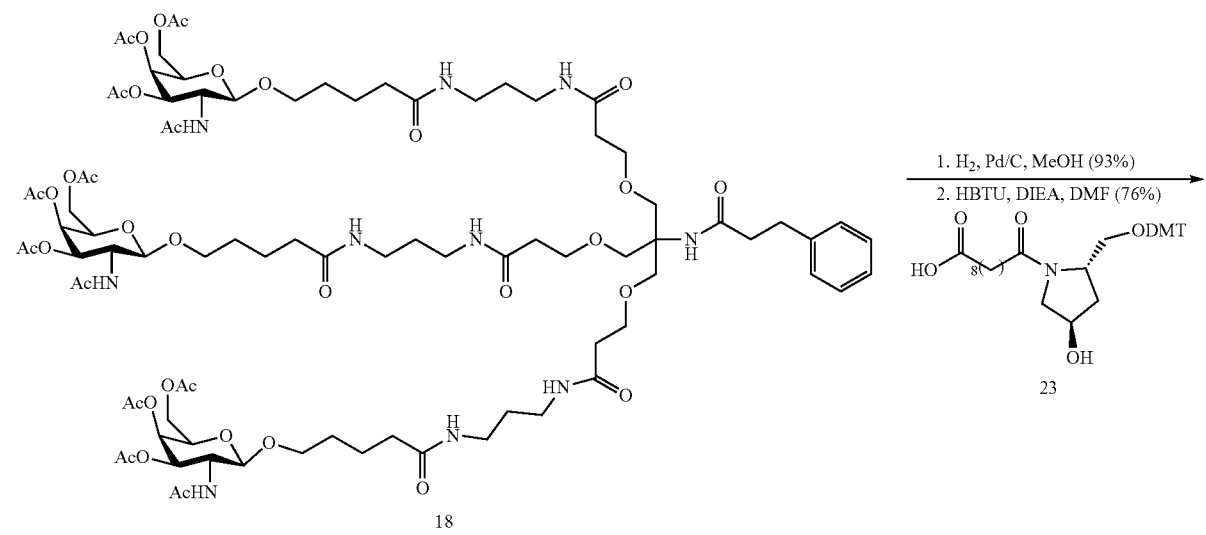

-continued
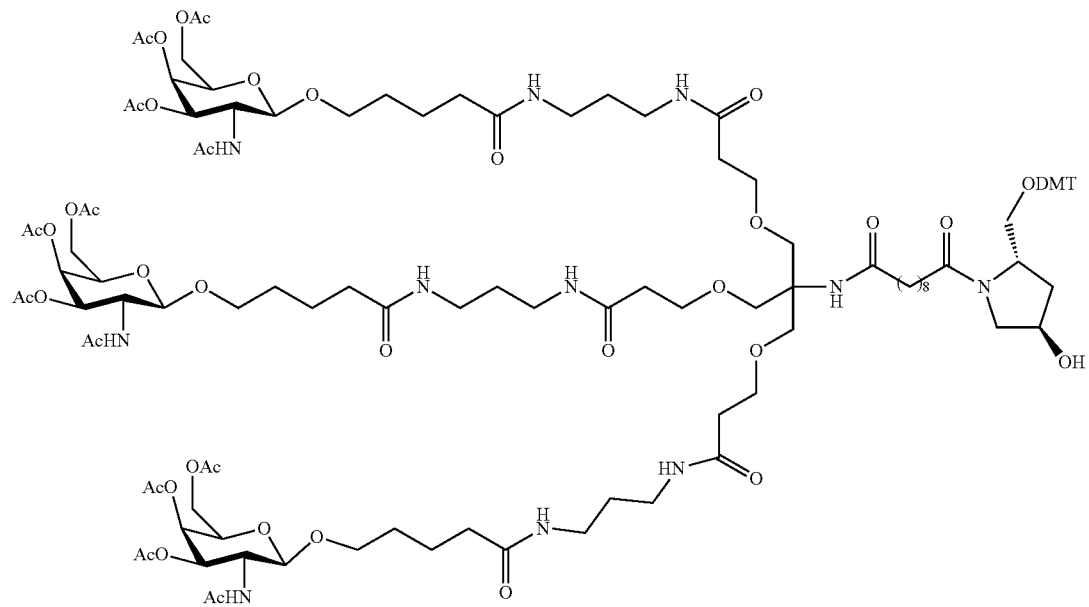
24
Compounds 18 and 23 were prepared as per the procedures illustrated in Examples 4 and 5.
Example 7: Preparation of Compound 25
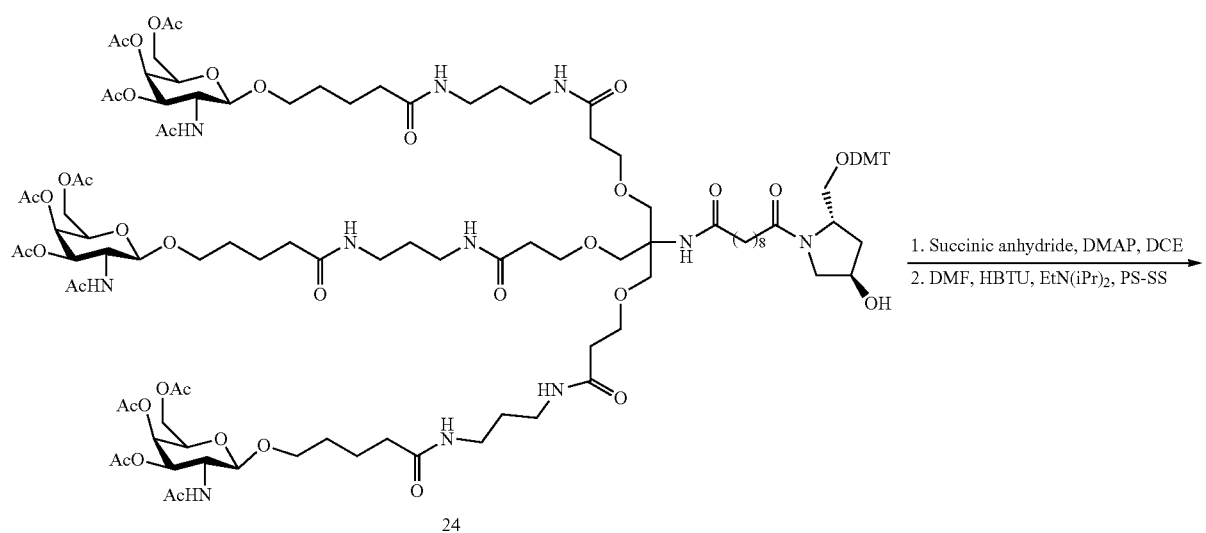
24

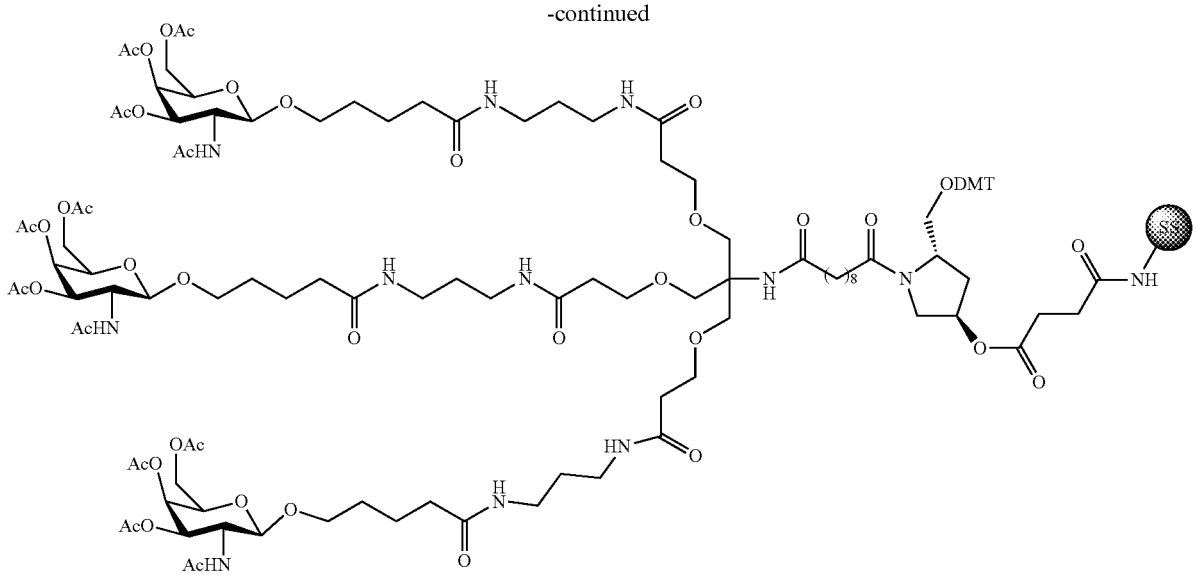
25
Compound 24 was prepared as per the procedures illustrated in Example 6.
Example 8: Preparation of Compound 26
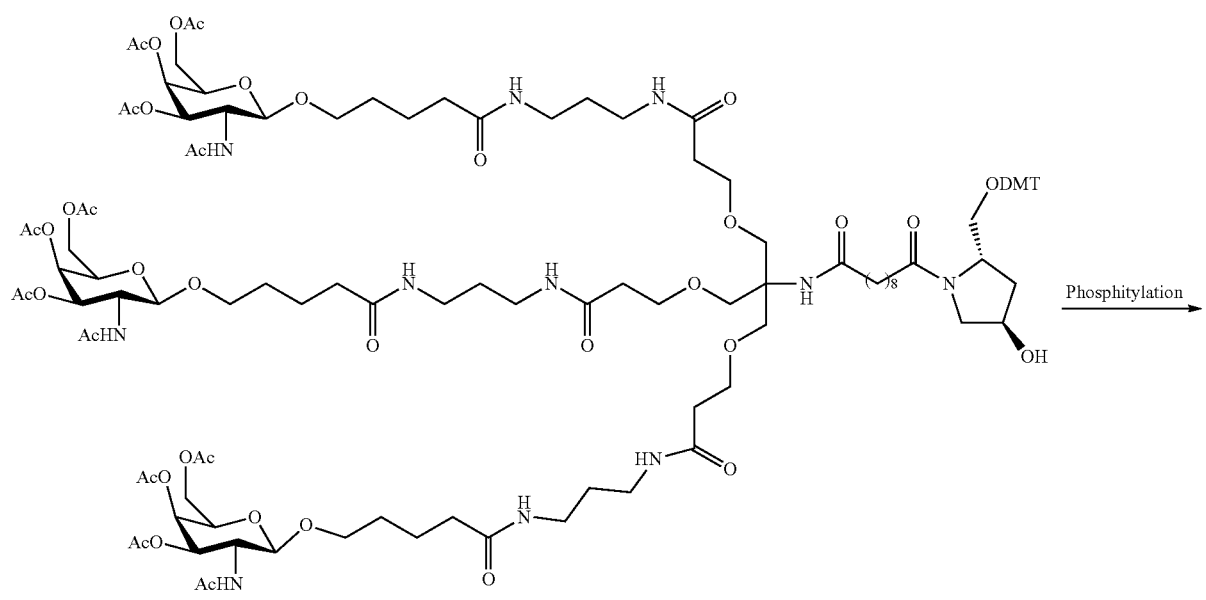

-continued
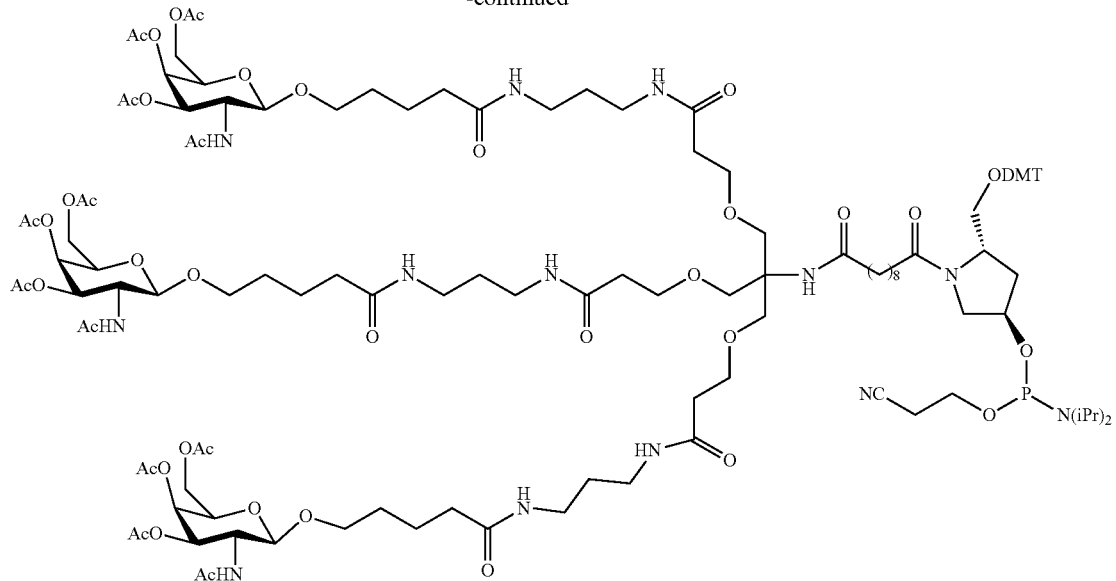
26
Compound 24 is prepared as per the procedures illustrated in Example 6.
Example 9: General Preparation of Conjugated ASOs Comprising GalNAc₃-1 at the 3' Terminus, Compound 29
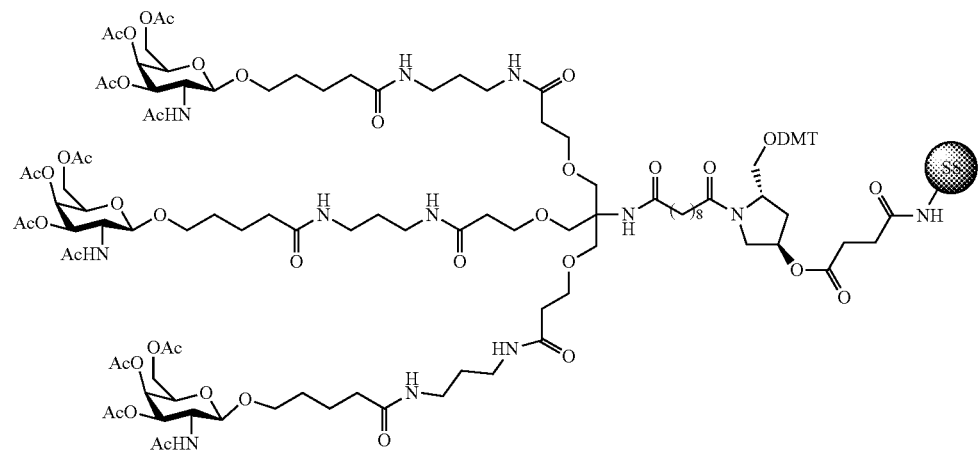
25
1. DCA, DCM
2. DCI, NMI, ACN
   Phosphoramidite
   building block 1 — DNA/RNA automated synthesizer
3. Capping
4. t-BuOOH

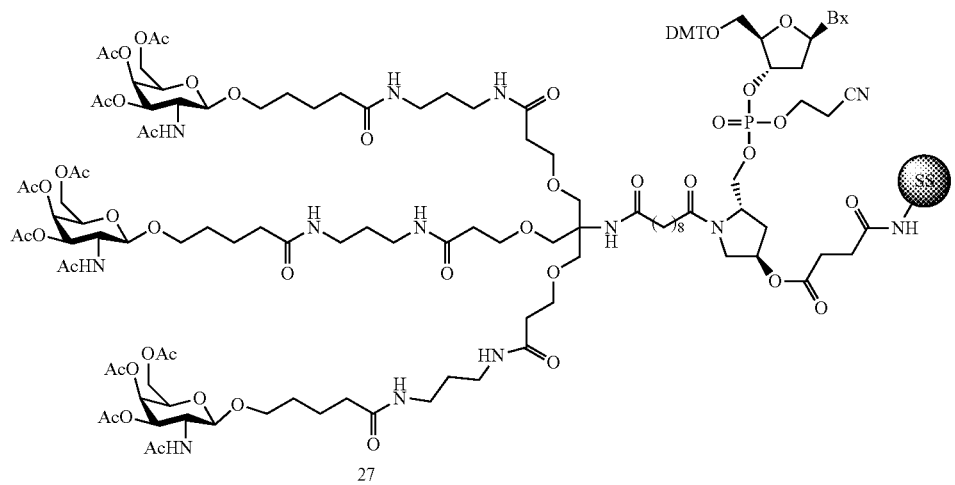
27
1. DCA, DCM
2. DCI, NMI, ACN
   Phosphoramidite
   building block 1a
3. Capping
4. t-BuOOH
DNA/RNA automated synthesizer
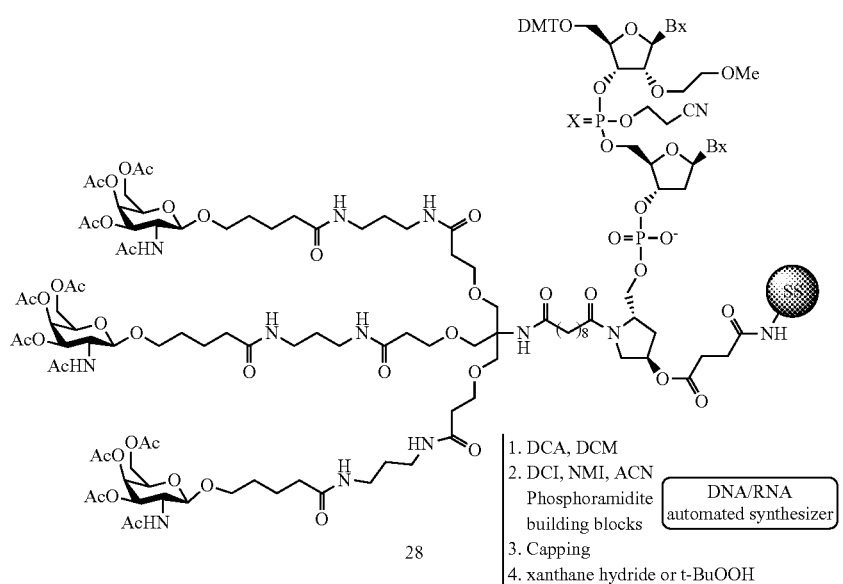
28
1. DCA, DCM
2. DCI, NMI, ACN
   Phosphoramidite
   building blocks
3. Capping
4. xanthane hydride or t-BuOOH
5. $Et_3N/CH_3CN$ (1:1)
6. Aqueous $NH_3$ (cleavage)
DNA/RNA automated synthesizer

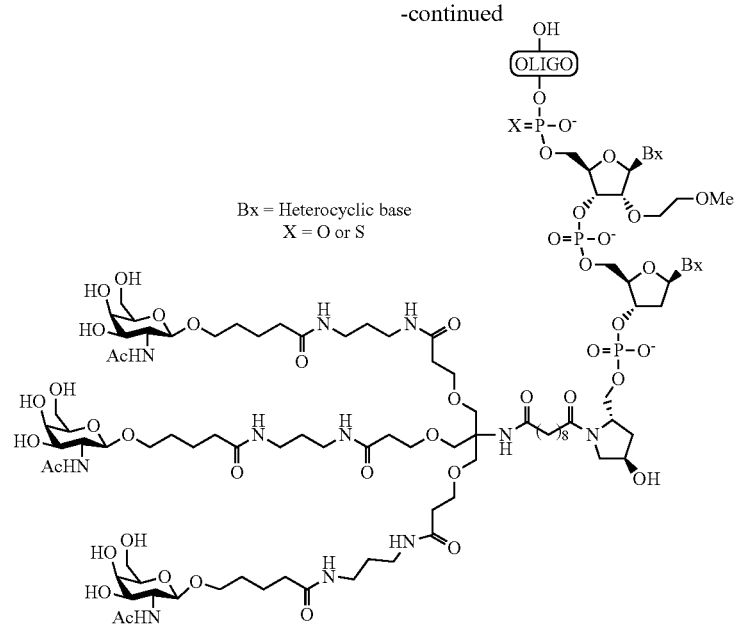
Wherein the protected GalNAc₃-1 has the structure:
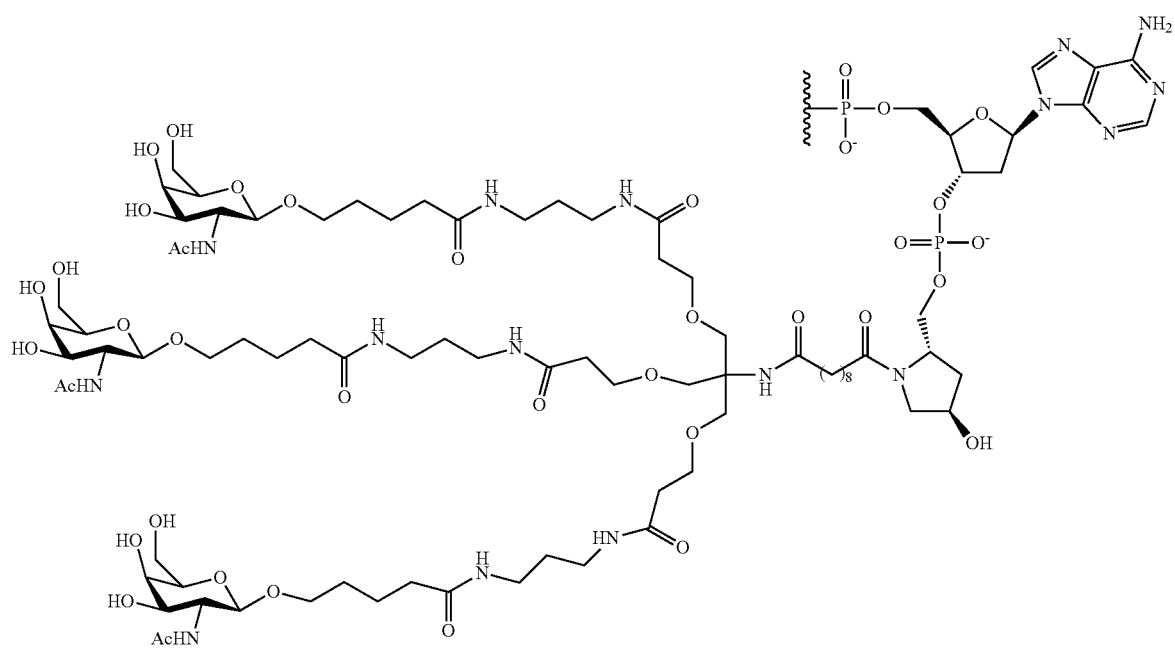

The GalNAc₃ cluster portion of the conjugate group GalNAc₃-1 (GalNAc₃-1$_a$) can be combined with any cleavable moiety to provide a variety of conjugate groups. Wherein GalNAc₃-1$_a$ has the formula:

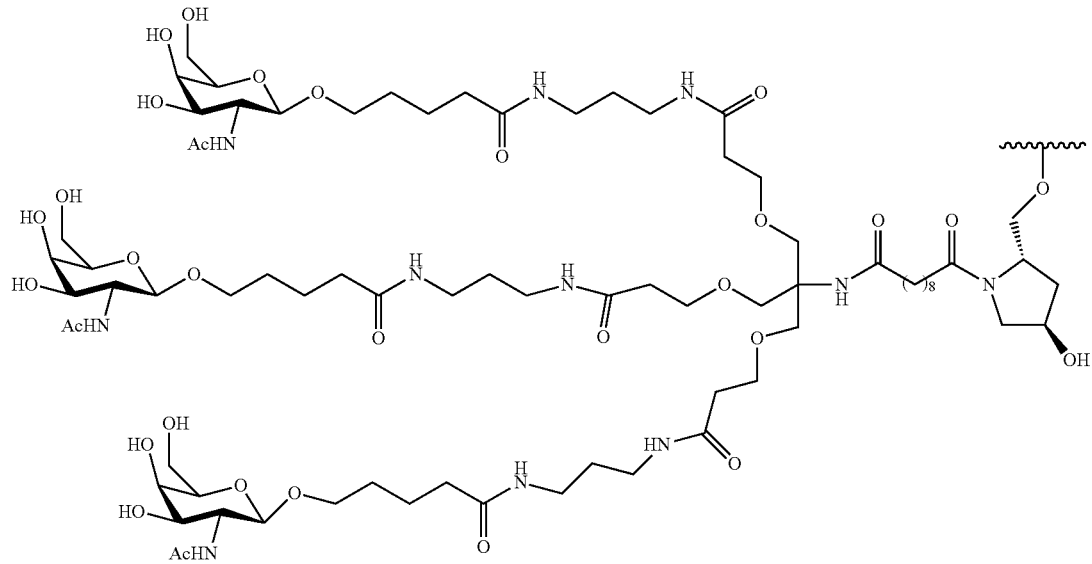

The solid support bound protected GalNAc₃-1, Compound 25, was prepared as per the procedures illustrated in Example 7. Oligomeric Compound 29 comprising GalNAc₃-1 at the 3' terminus was prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: General Preparation Conjugated ASOs Comprising GalNAc₃-1 at the 5' Terminus, Compound 34

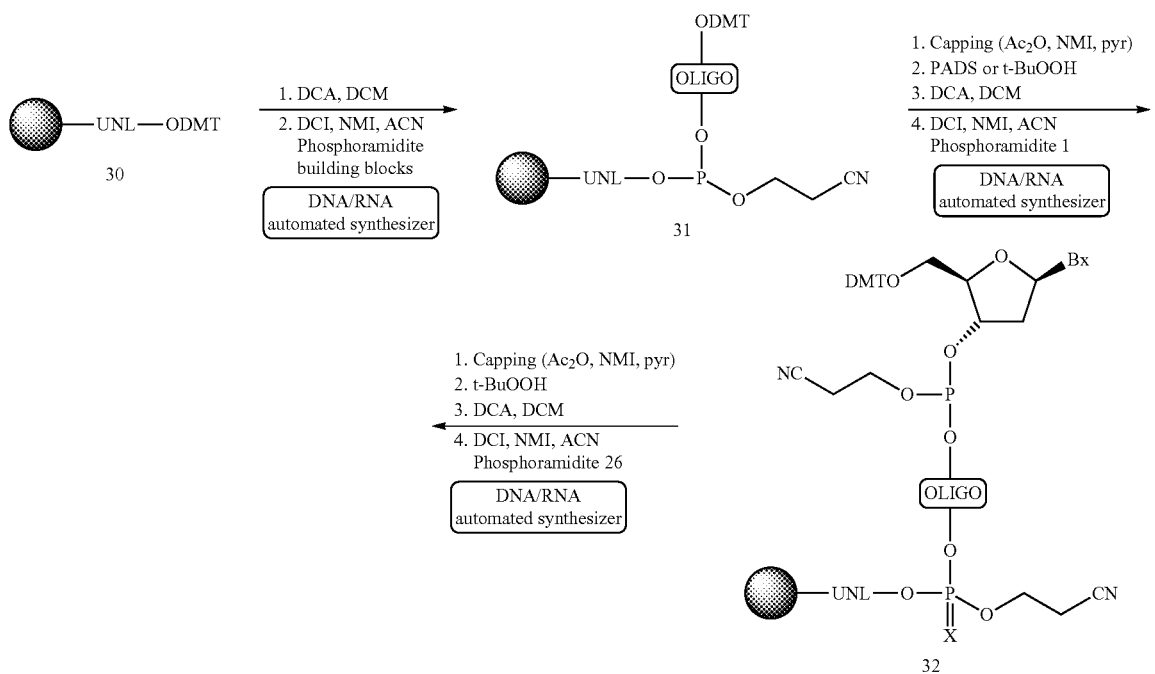

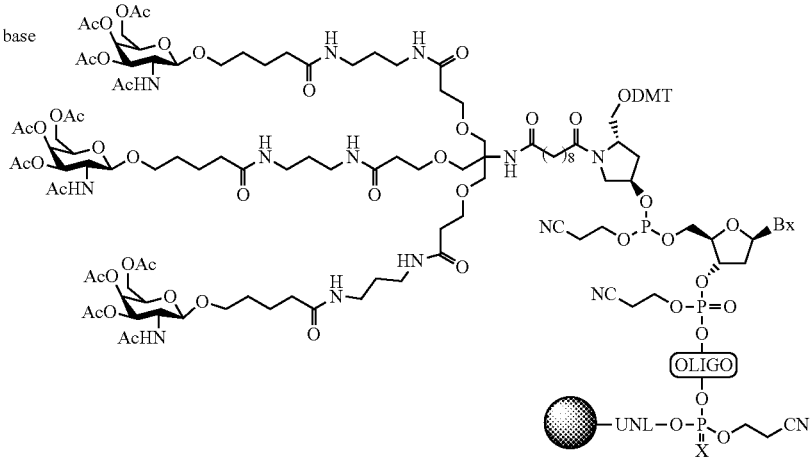

33

1. Capping (Ac₂O, NMI, pyr)
2. t-BuOOH
3. Et₃N:CH₃CN (1:1 v/v)
4. DCA, DCM
5. NH₄, rt (cleavage)

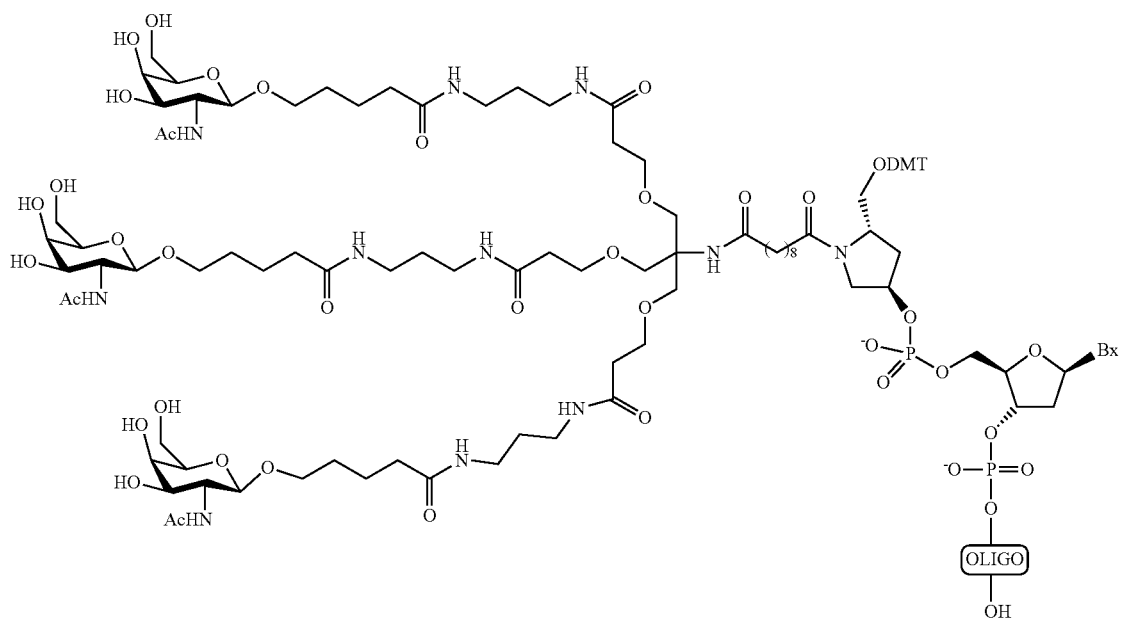

34

The Unylinker™ 30 is commercially available. Oligomeric Compound 34 comprising a GalNAc₃-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11: Preparation of Compound 39
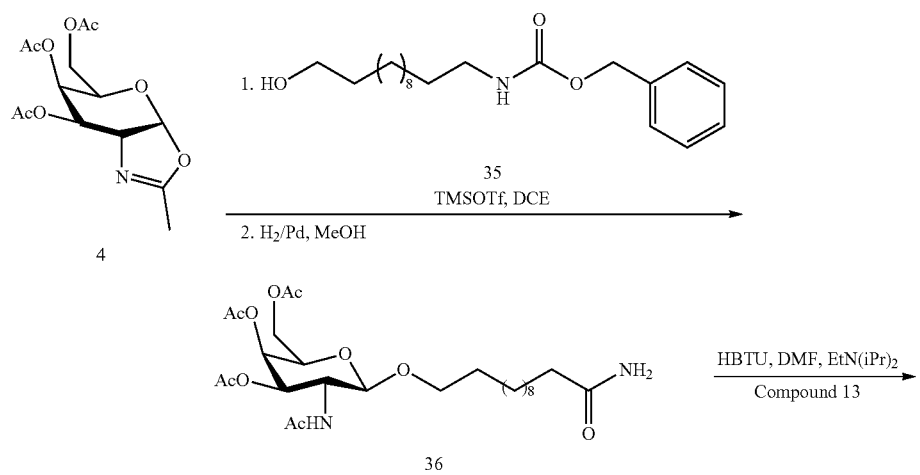
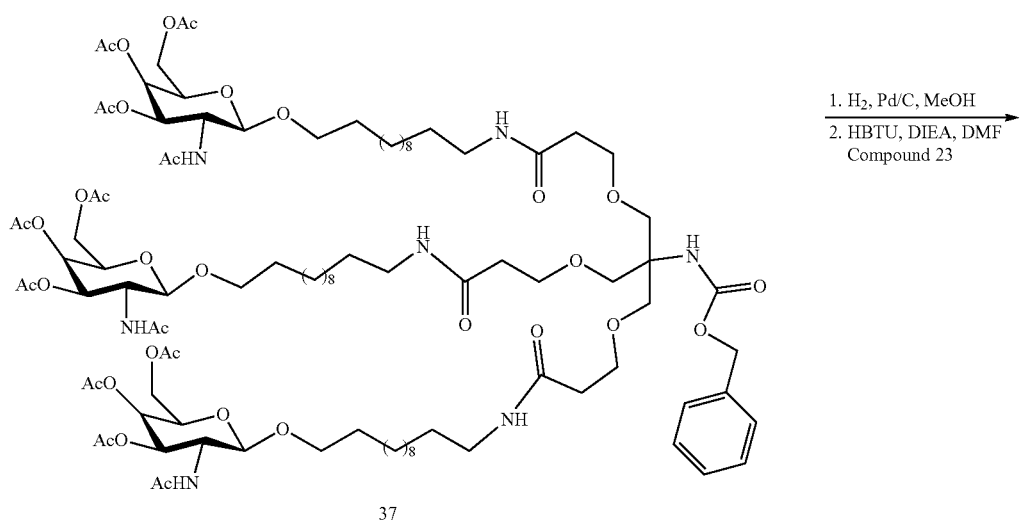
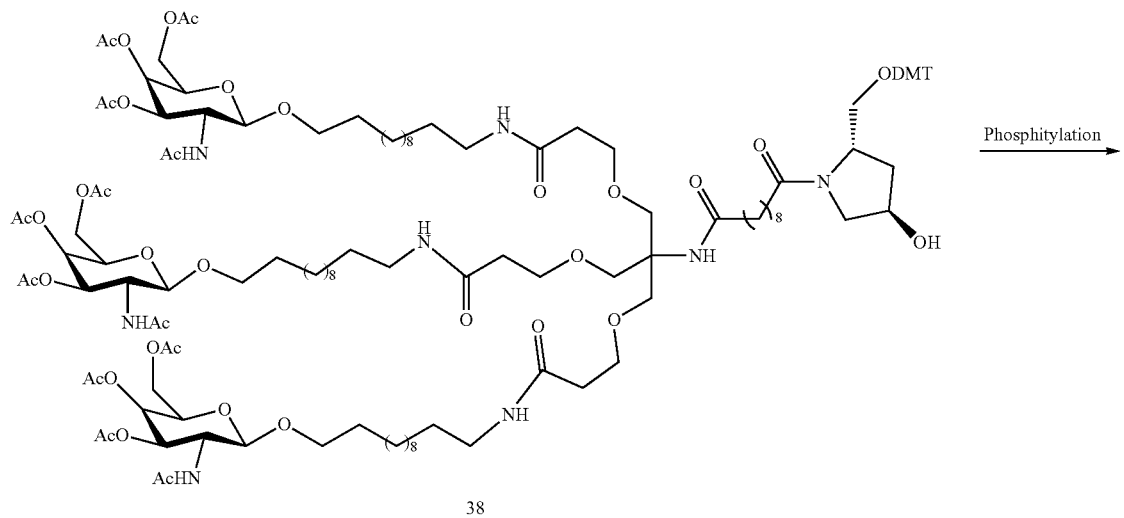

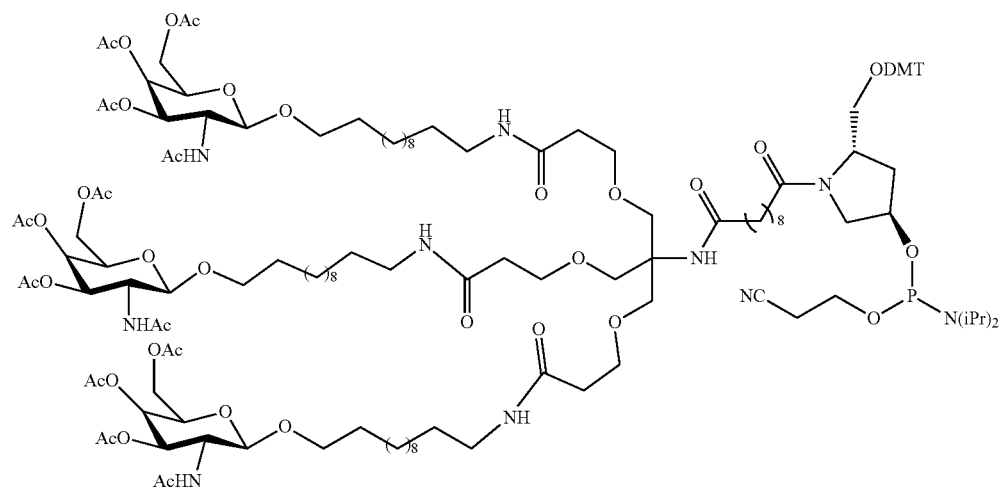
39
Compounds 4, 13 and 23 were prepared as per the procedures illustrated in Examples 2, 4, and 5. Compound 35 is prepared using similar procedures published in Rouchaud etal., *Eur. J. Org. Chem.*, 2011, 12, 2346-2353.
Example 12: Preparation of Compound 40
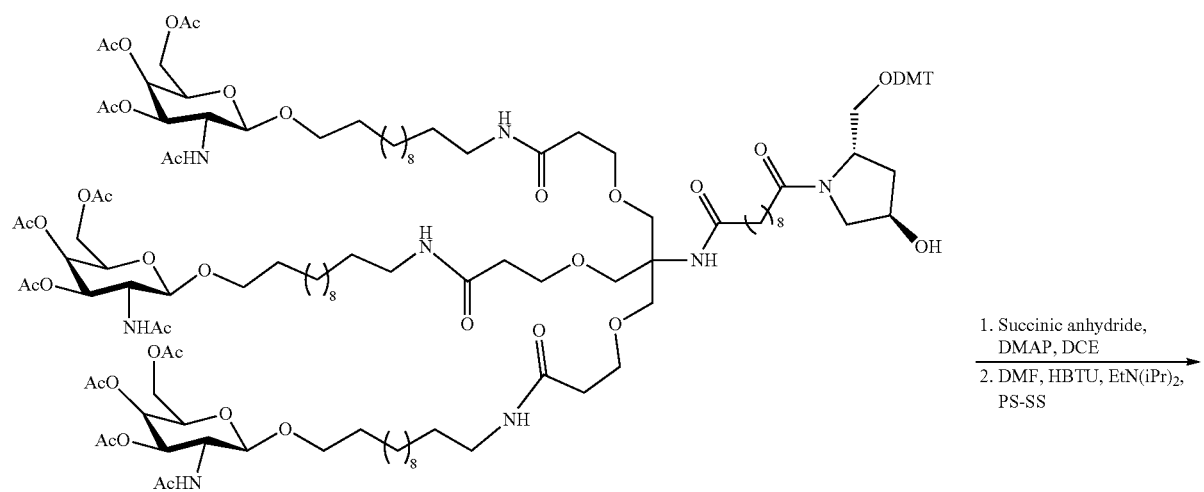
38
1. Succinic anhydride, DMAP, DCE
2. DMF, HBTU, EtN(iPr)$_2$, PS-SS

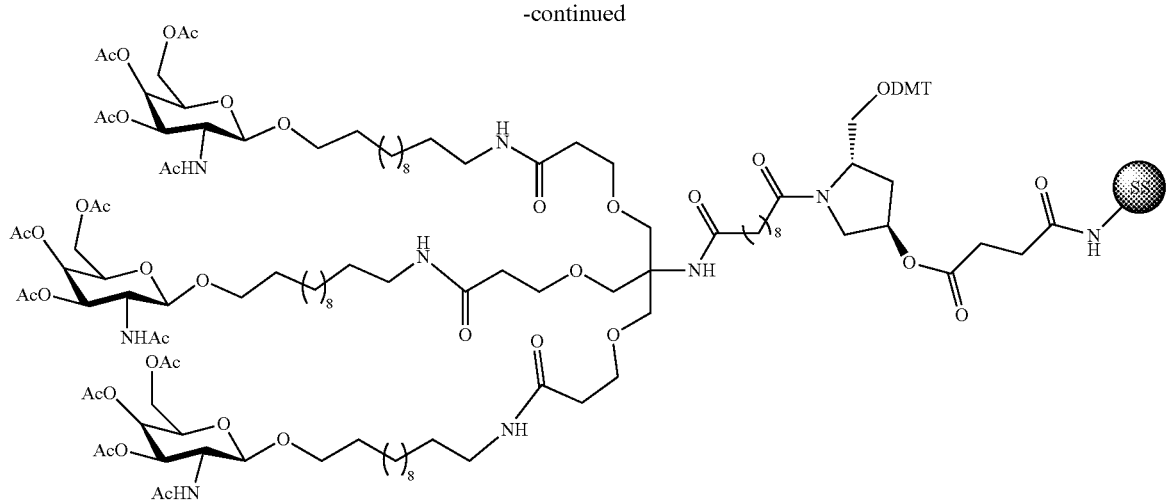
40
Compound 38 is prepared as per the procedures illustrated in Example 11.
Example 13: Preparation of Compound 44
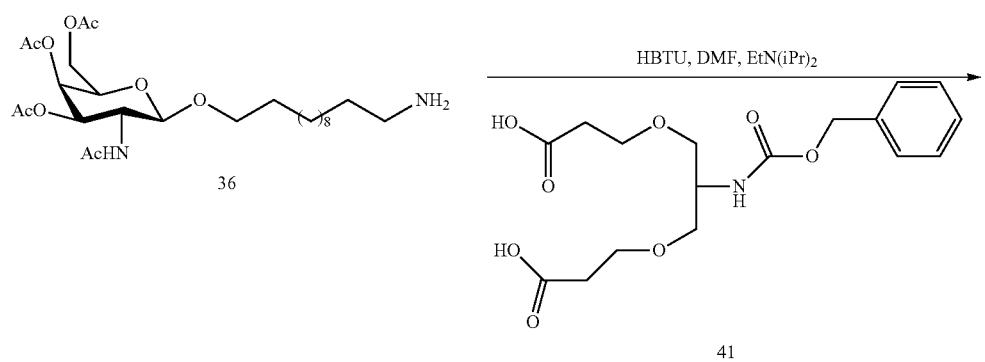
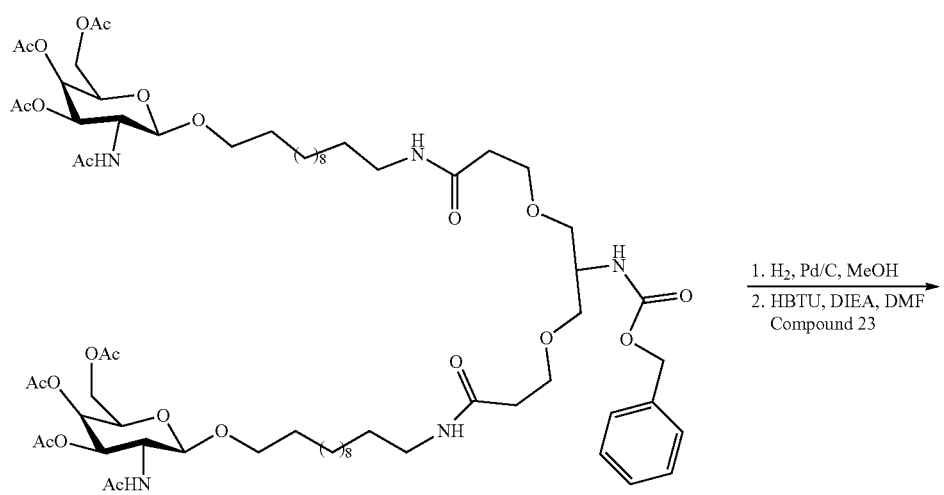

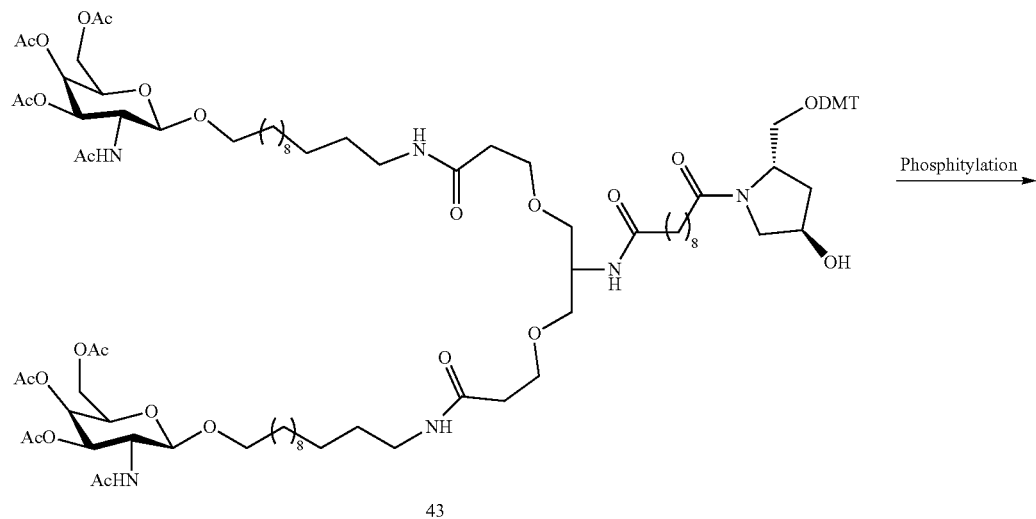
43
Phosphitylation →
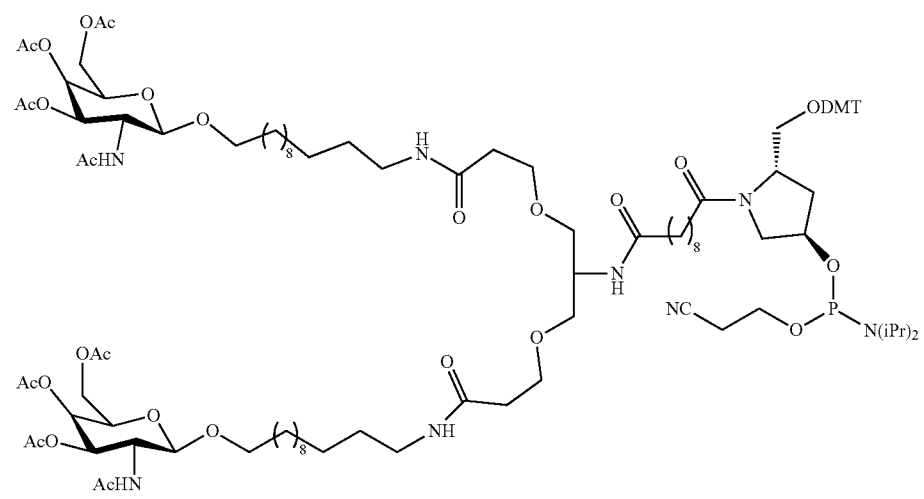
44

Compounds 23 and 36 are prepared as per the procedures illustrated in Examples 5 and 11. Compound 41 is prepared using similar procedures published in WO 2009082607.
Example 14: Preparation of Compound 45
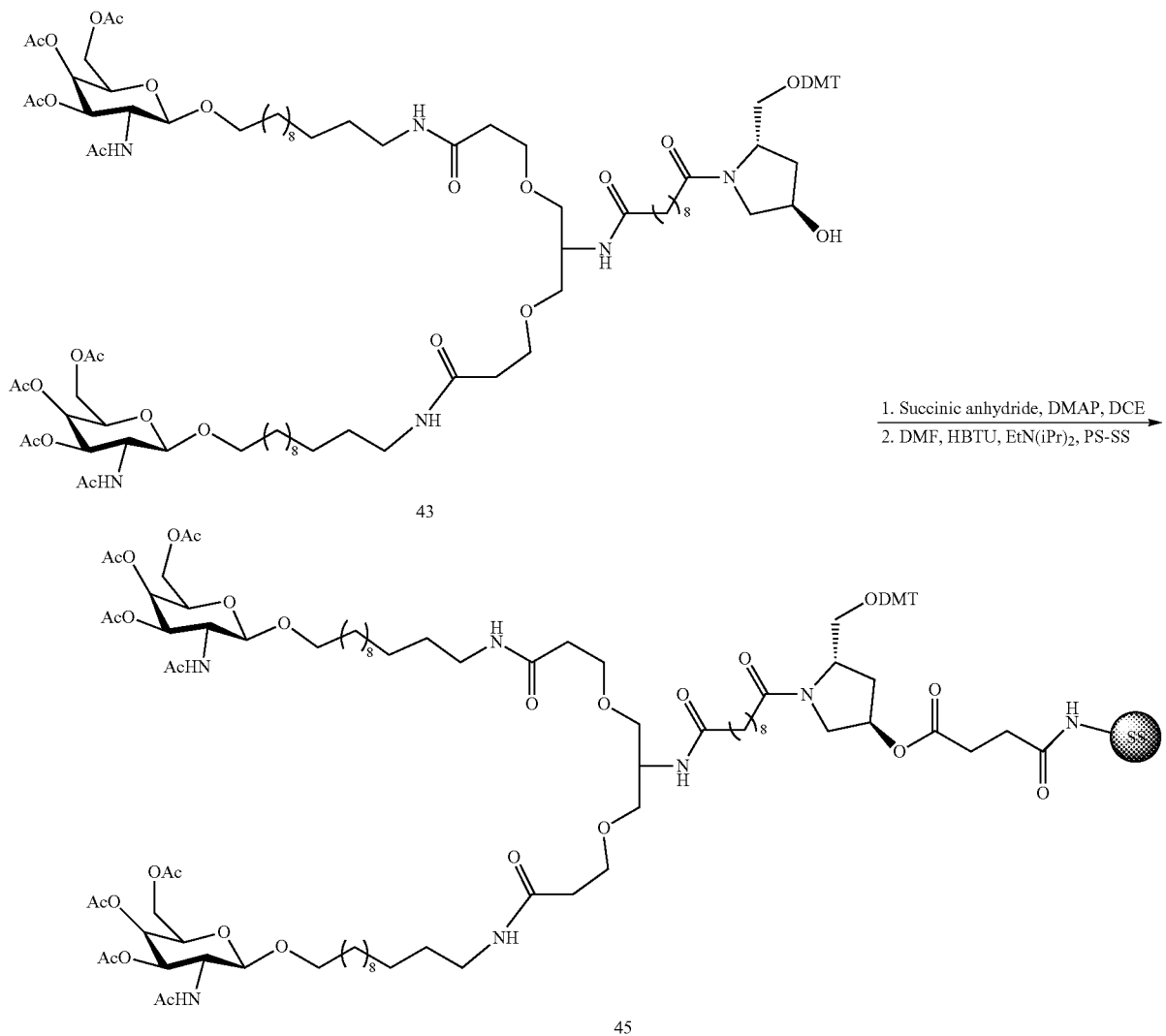
Compound 43 is prepared as per the procedures illustrated in Example 13.
Example 15: Preparation of Compound 47
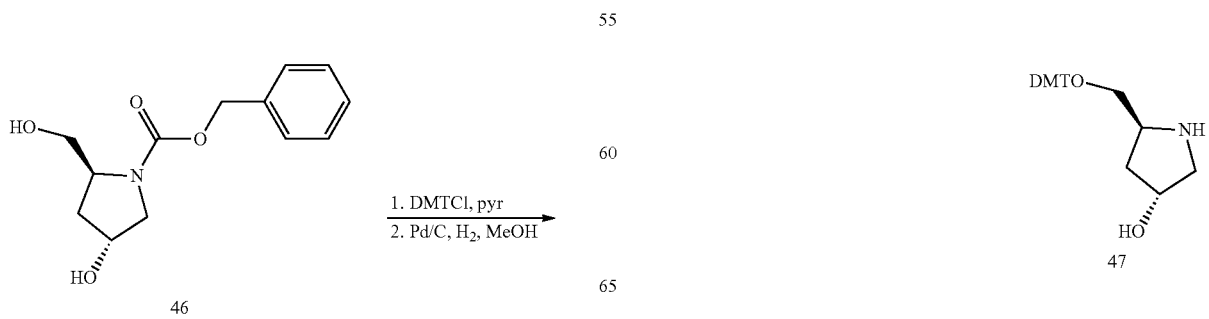
Compound 46 is commercially available.

Example 16: Preparation of Compound 53
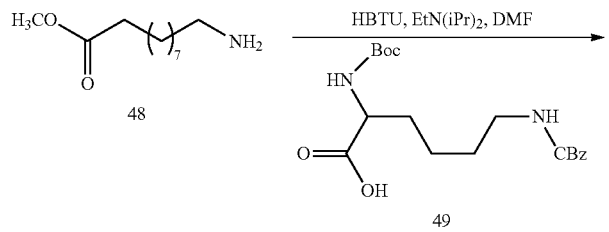
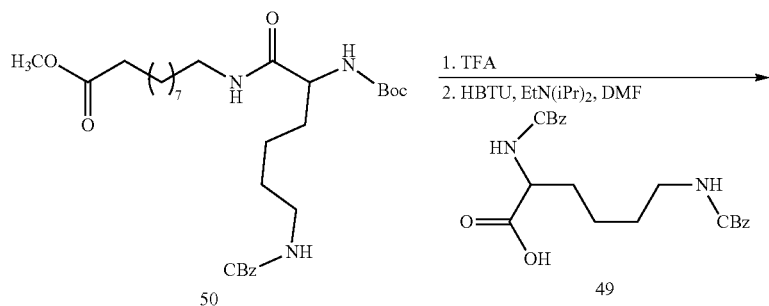
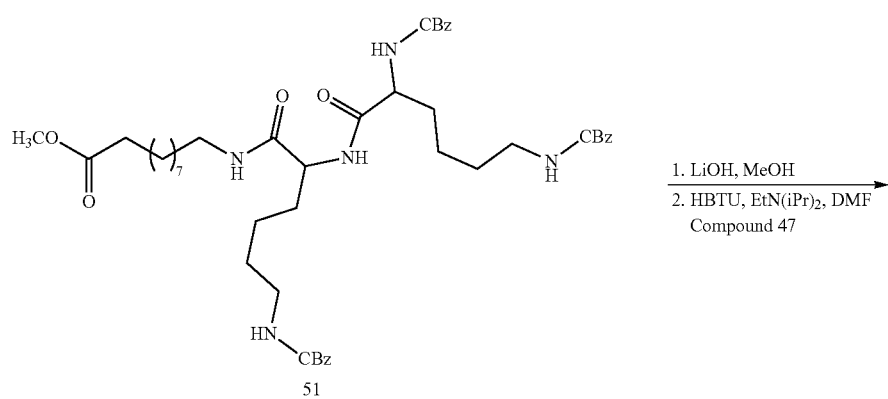
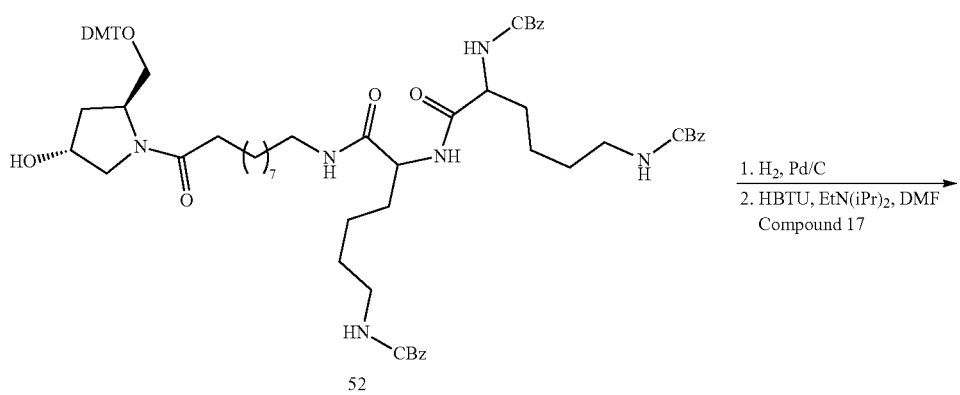

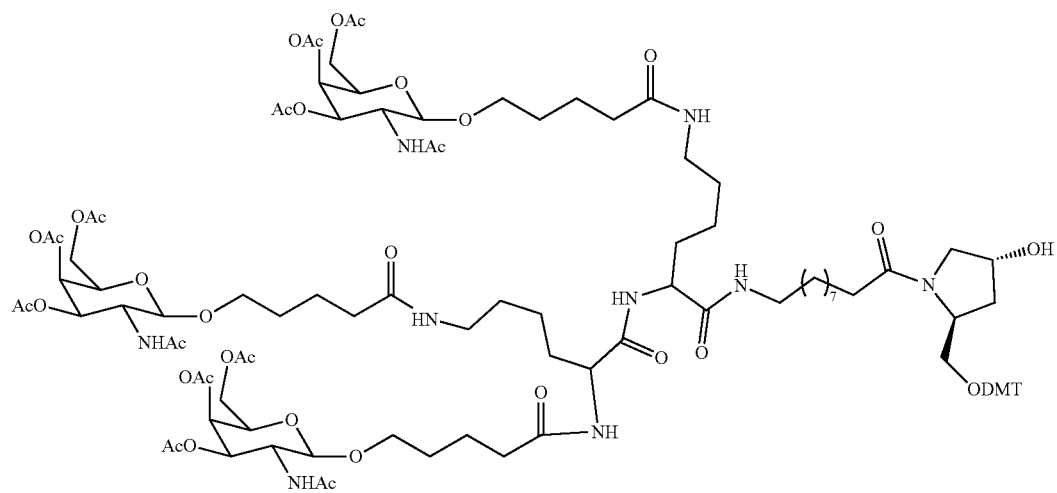
53
Compounds 48 and 49 are commercially available. Compounds 17 and 47 are prepared as per the procedures illustrated in Examples 4 and 15.
Example 17: Preparation of Compound 54
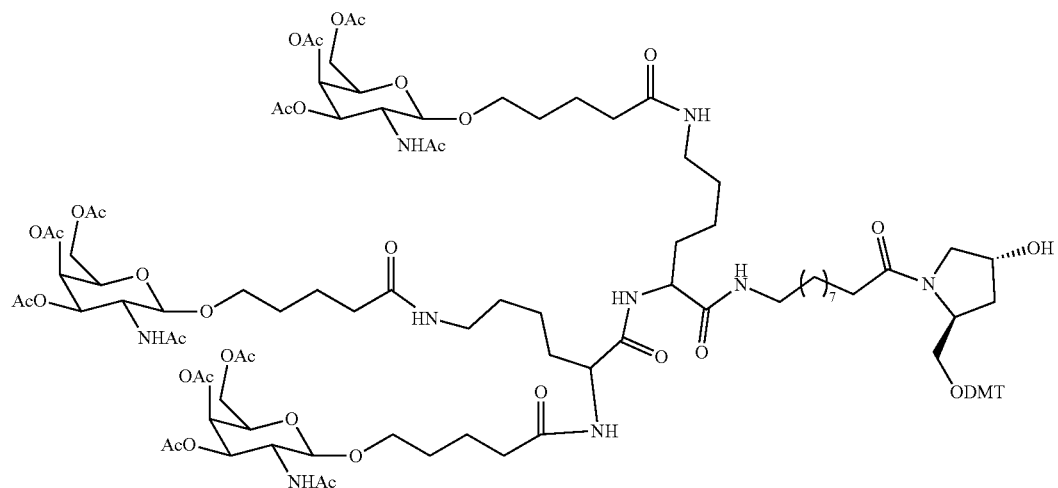
53
↓ Phosphitylation

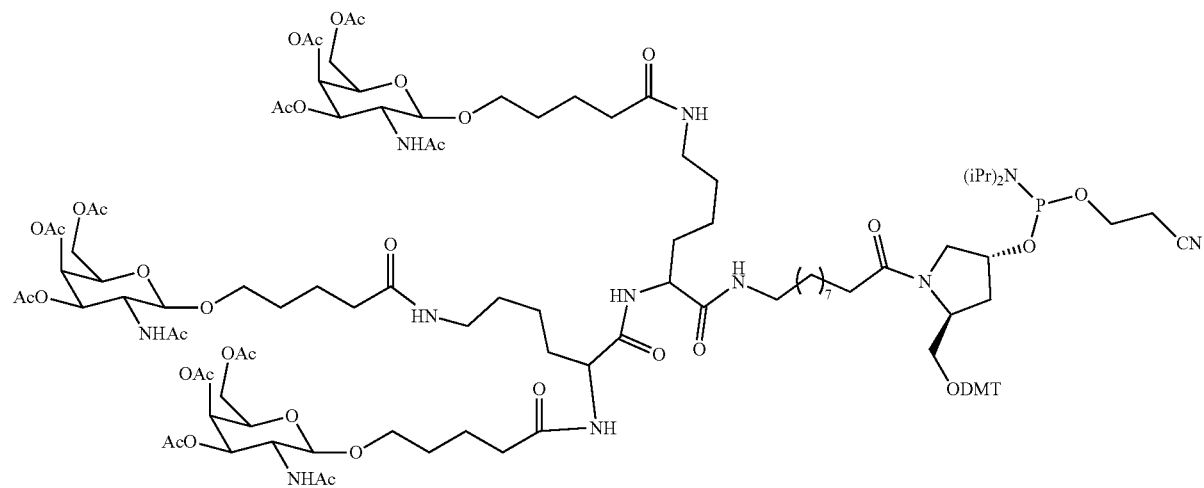
54
Compound 53 is prepared as per the procedures illustrated in Example 16.
Example 18: Preparation of Compound 55
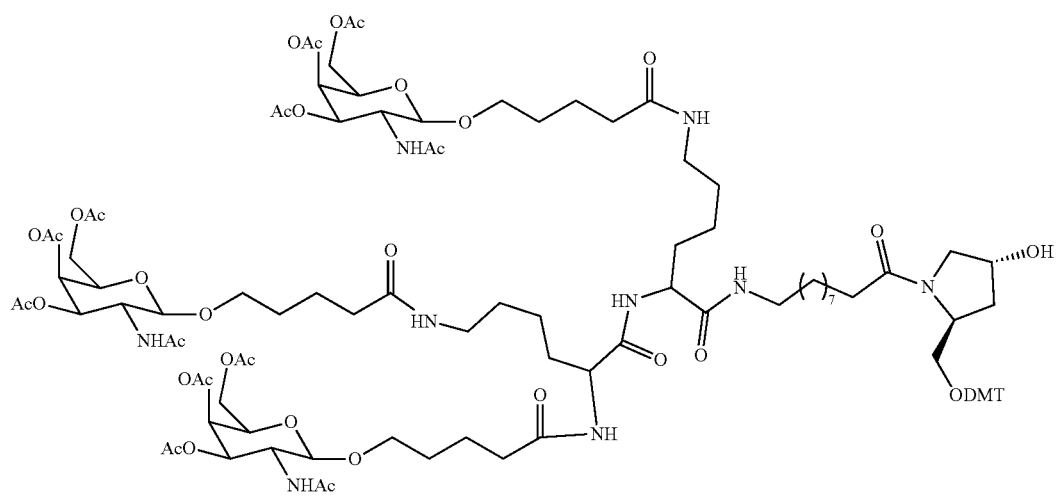
53
1. Succinic anhydride, DMAP, DCE
2. DMF, HBTU, EtN(iPr)$_2$, PS-SS -continued

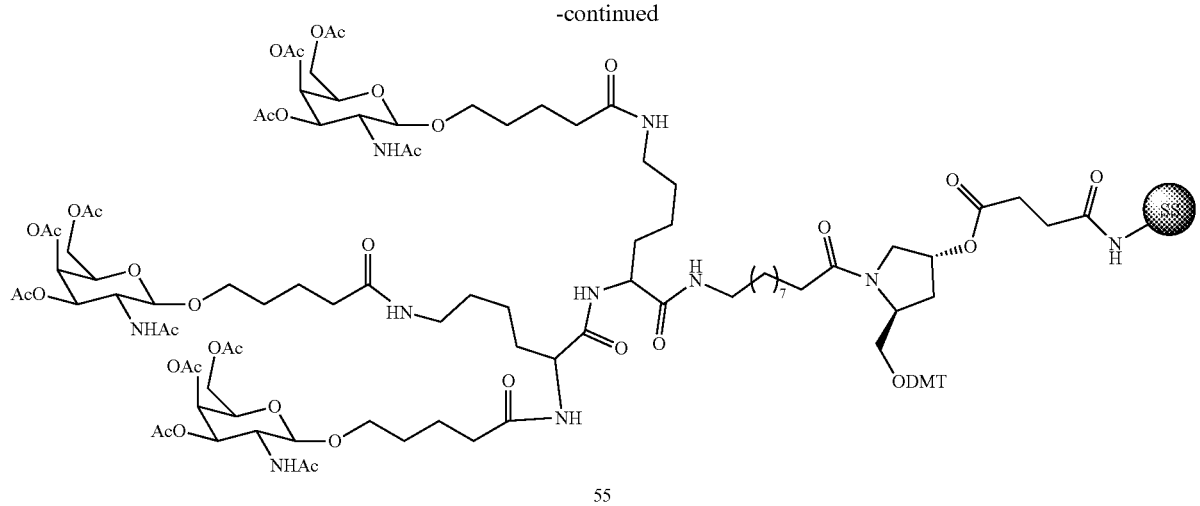

55

Compound 53 is prepared as per the procedures illustrated in Example 16.

Example 19: General Method for the Preparation of Conjugated ASOs Comprising GalNAc$_3$-1 at the 3' Position Via Solid Phase Techniques (Preparation of Isis 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 µmol scale) or on GE Healthcare Bioscience ÄKTA oligopilot synthesizer (40-200 µmol scale) by the phosphoramidite coupling method on an GalNAc$_3$-1 loaded VIMAD solid support (110 µmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous CH$_3$CN was used as activator during coupling step. Phosphorothioate linkages were introduced by sulfurization with 0.1 M solution of xanthane hydride in 1:1 pyridine/CH$_3$CN for a contact time of 3 minutes. A solution of 20% tert-butylhydroperoxide in CH$_3$CN containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 µm, 2.54×8 cm, A=100 mM ammonium acetate in 30% aqueous CH$_3$CN, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 17, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a GalNAc$_3$-1 conjugated at its 3'end; and ISIS 647536 is the same as ISIS 647535 except that certain internucleoside linkages of that compound are phosphodiester linkages. As further summarized in Table 17, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a GalNAc$_3$-1 at its 3'-end.

TABLE 17

Modified ASO targeting ApoC III and SRB-1

| ASO | Sequence (5' to 3') | Target | CalCd Mass | Observed Mass | SEQ ID No. |
|---|---|---|---|---|---|
| ISIS 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | ApoC III | 7165.4 | 7164.4 | 135 |

TABLE 17-continued

Modified ASO targeting ApoC III and SRB-1

| ASO | Sequence (5' to 3') | Target | CalCd Mass | Observed Mass | SEQ ID No. |
|---|---|---|---|---|---|
| ISIS 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}A_{do}$,-GalNAc$_3$-1$_a$ | ApoC III | 9239.5 | 9237.8 | 136 |
| ISIS 647536 | $A_{es}G_{eo}{}^mC_{eo}T_{eo}T_{eo}{}^mC_{ds}T_{ds}T_{ds}G_{ds}T_{ds}{}^mC_{ds}{}^mC_{ds}A_{ds}G_{ds}{}^mC_{ds}T_{eo}T_{eo}T_{es}A_{es}T_{eo}A_{do}$,-GalNAc$_3$-1$_a$ | ApoC III | 9142.9 | 9140.8 | 136 |
| ISIS 440762 | $T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_k$ | SRB-1 | 4647.0 | 4646.4 | 137 |
| ISIS 651900 | $T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ko}A_{do}$,-GalNAc$_3$-1$_a$ | SRB-1 | 6721.1 | 6719.4 | 138 |

Subscripts: "e" indicates 2'-MOE modified nucleoside; "d" indicates β-D-2'-deoxyribonucleoside; "k" indicates 6'-(S)—CH$_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. "GalNAc$_3$-1" indicates a conjugate group having the structure shown previously in Example 9. Note that GalNAc$_3$-1 comprises a cleavable adenosine which links the ASO to remainder of the conjugate, which is designated "GalNAc$_3$-1$_a$." This nomenclature is used in the above table to show the full nucleobase sequence, including the adenosine, which is part of the conjugate. Thus, in the above table, the sequences could also be listed as ending with "GalNAc$_3$-1" with the "$A_{do}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or "GalNAc$_3$ cluster." In certain instances it is convenient to describe a conjugate group by separately providing its cluster and its cleavable moiety.

Example 20: Dose-Dependent Antisense Inhibition of Human Apoc III in Huapoc III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 µmol/kg or with PBS as a control. Each treatment group consisted of 4 animals. Forty-eight hours after the administration of the last dose, blood was drawn from each mouse and the mice were sacrificed and tissues were collected.

ApoC III mRNA Analysis

ApoC III mRNA levels in the mice's livers were determined using real-time PCR and RIBOGREEN® RNA quantification reagent (Molecular Probes, Inc. Eugene, OR) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage (ED$_{50}$) of each ASO is also presented in Table 18, below.

As illustrated, both antisense compounds reduced ApoC III RNA relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 18

Effect of ASO treatment on ApoC III mRNA levels in human ApoC III transgenic mice

| ASO | Dose (µmol/kg) | % PBS | ED$_{50}$ (µmol/kg) | 3' Conjugate | Internucleoside linkage/Length | SEQ ID No. |
|---|---|---|---|---|---|---|
| PBS | 0 | 100 | — | — | — | |
| ISIS 304801 | 0.08 | 95 | 0.77 | None | PS/20 | 135 |
| | 0.75 | 42 | | | | |
| | 2.25 | 32 | | | | |
| | 6.75 | 19 | | | | |
| ISIS 647535 | 0.08 | 50 | 0.074 | GalNAc$_3$-1 | PS/20 | 136 |
| | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, Circulation Research, published online before print Mar. 29, 2013.

Approximately 100 µl of plasma isolated from mice was analyzed without dilution using an Olympus Clinical Analyzer and a commercially available turbidometric ApoC III assay (Kamiya, Cat #KAI-006, Kamiya Biomedical, Seattle, WA). The assay protocol was performed as described by the vendor.

As shown in the Table 19 below, both antisense compounds reduced ApoC III protein relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 19

Effect of ASO treatment on ApoC III plasma protein levels in human ApoC III transgenic mice

| ASO | Dose (μmol/ kg) | % PBS | ED$_{50}$ (μmol/ kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 86 | 0.73 | None | PS/20 | 135 |
| | 0.75 | 51 | | | | |
| | 2.25 | 23 | | | | |
| | 6.75 | 13 | | | | |
| ISIS 647535 | 0.08 | 72 | 0.19 | GalNAc$_3$-1 | PS/20 | 136 |
| | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. Can. J. Biochem. Physiol. 37: 911-917, 1959)(Bligh, E and Dyer, W, *Can J Biochem Physiol,* 37, 911-917, 1959)(Bligh, E and Dyer, W, *Can J Biochem Physiol,* 37, 911-917, 1959) and measured by using a Beckmann Coulter clinical analyzer and commercially available reagents.

The triglyceride levels were measured relative to PBS injected mice and are denoted as PBS". Results are presented in Table 20. As illustrated, both antisense compounds loweredtriglyceride levels. Further, the antisense compound conjugated to GalNAc$_3$-1 (ISIS 647535) was substantially more potent than the antisense compound lacking the GalNAc$_3$-1 Conjugate (ISIS 304801).

TABLE 20

Effect of ASO treatment on triglyceride levels in transgenic mice

| ASO | Dose (μmol/ kg) | % PBS | ED$_{50}$ (μmol/ kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 87 | 0.63 | None | PS/20 | 135 |
| | 0.75 | 46 | | | | |
| | 2.25 | 21 | | | | |
| | 6.75 | 12 | | | | |
| ISIS 647535 | 0.08 | 65 | 0.13 | GalNAc$_3$-1 | PS/20 | 136 |
| | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 21 and 22. As illustrated, both antisense compounds lowered total cholesterol levels; both lowered LDL; and both raised HDL. Further, the antisense compound conjugated to GalNAc$_3$-1 (ISIS 647535) was substantially more potent than the antisense compound lacking the GalNAC$_3$-1 Conjugate (ISIS 304801). An increase in HDL and a decrease in LDL levels is a cardiovascular beneficial effect of antisense inhibition of ApoC III.

TABLE 21

Effect of ASO treatment on total cholesterol levels in transgenic mice

| ASO | Dose (μmol/kg) | Total Cholesterol (mg/dL) | 3' Conjugate | Internucleoside Linkage/Length | SEQ ID No. |
|---|---|---|---|---|---|
| PBS | 0 | 257 | — | — | |
| ISIS 304801 | 0.08 | 226 | None | PS/20 | 135 |
| | 0.75 | 164 | | | |
| | 2.25 | 110 | | | |
| | 6.75 | 82 | | | |
| ISIS 647535 | 0.08 | 230 | GalNAc$_3$-1 | PS/20 | 136 |
| | 0.75 | 82 | | | |
| | 2.25 | 86 | | | |
| | 6.75 | 99 | | | |

TABLE 22

Effect of ASO treatment on HDL and LDL cholesterol levels in transgenic mice

| ASO | Dose (μmol/ kg) | HDL (mg/ dL) | LDL (mg/ dL) | 3' Conjugate | Internucleoside Linkage/Length | SEQ ID No. |
|---|---|---|---|---|---|---|
| PBS | 0 | 17 | 28 | — | — | |
| ISIS 304801 | 0.08 | 17 | 23 | None | PS/20 | 135 |
| | 0.75 | 27 | 12 | | | |
| | 2.25 | 50 | 4 | | | |
| | 6.75 | 45 | 2 | | | |
| ISIS 647535 | 0.08 | 21 | 21 | GalNAc$_3$-1 | PS/20 | 136 |
| | 0.75 | 44 | 2 | | | |
| | 2.25 | 50 | 2 | | | |
| | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (μg/g) of full-length ISIS 304801 and 647535 was measured and the results are provided in Table 23. As illustrated, liver concentrations of total full-length antisense compounds were similar for the two antisense compounds. Thus, even though the GalNAc$_3$-1-conjugated antisense compound is more active in the liver (as demonstrated by the RNA and protein data above), it is not present at substantially higher concentration in the liver. Indeed, the calculated EC$_{50}$ (provided in Table 23) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of GalNAc$_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that GalNAc$_3$-1 conjugation reduces kidney accumulation.

TABLE 23

PK analysis of ASO treatment in transgenic mice

| ASO | Dose (μmol/kg) | Liver (μg/g) | Kidney (μg/g) | Liver $EC_{50}$ (μg/g) | 3' Conjugate | Internucleoside Linkage/Length | SEQ ID No. |
|---|---|---|---|---|---|---|---|
| ISIS 304801 | 0.1 | 5.2 | 2.1 | 53 | None | PS/20 | 135 |
|  | 0.8 | 62.8 | 119.6 |  |  |  |  |
|  | 2.3 | 142.3 | 191.5 |  |  |  |  |
|  | 6.8 | 202.3 | 337.7 |  |  |  |  |
| ISIS 647535 | 0.1 | 3.8 | 0.7 | 3.8 | $GalNAc_3$-1 | PS/20 | 136 |
|  | 0.8 | 72.7 | 34.3 |  |  |  |  |
|  | 2.3 | 106.8 | 111.4 |  |  |  |  |
|  | 6.8 | 237.2 | 179.3 |  |  |  |  |

Metabolites of ISIS 647535 were also identified and their masses were confirmed by high resolution mass spectrometry analysis. The cleavage sites and structures of the observed metabolites are shown below. The relative % of full length ASO was calculated using standard procedures and the results are presented in Table 23a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleavable bonds such as esters, peptides, disulfides, phosphoramidates or acyl-hydrazones between the $GalNAc_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 23a

Observed full length metabolites of ISIS 647535

| Metabolite | ASO | Cleavage site | Relative % |
|---|---|---|---|
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxypentanoic acid tether] | D | 17.6 |
| 5 | ISIS 647535 minus [2 GalNAc + 2 5-hydroxypentanoic acid tether] | D | 9.9 |
| 6 | ISIS 647535 minus [3 GalNAc + 3 5-hydroxypentanoic acid tether] | D | 9.8 |

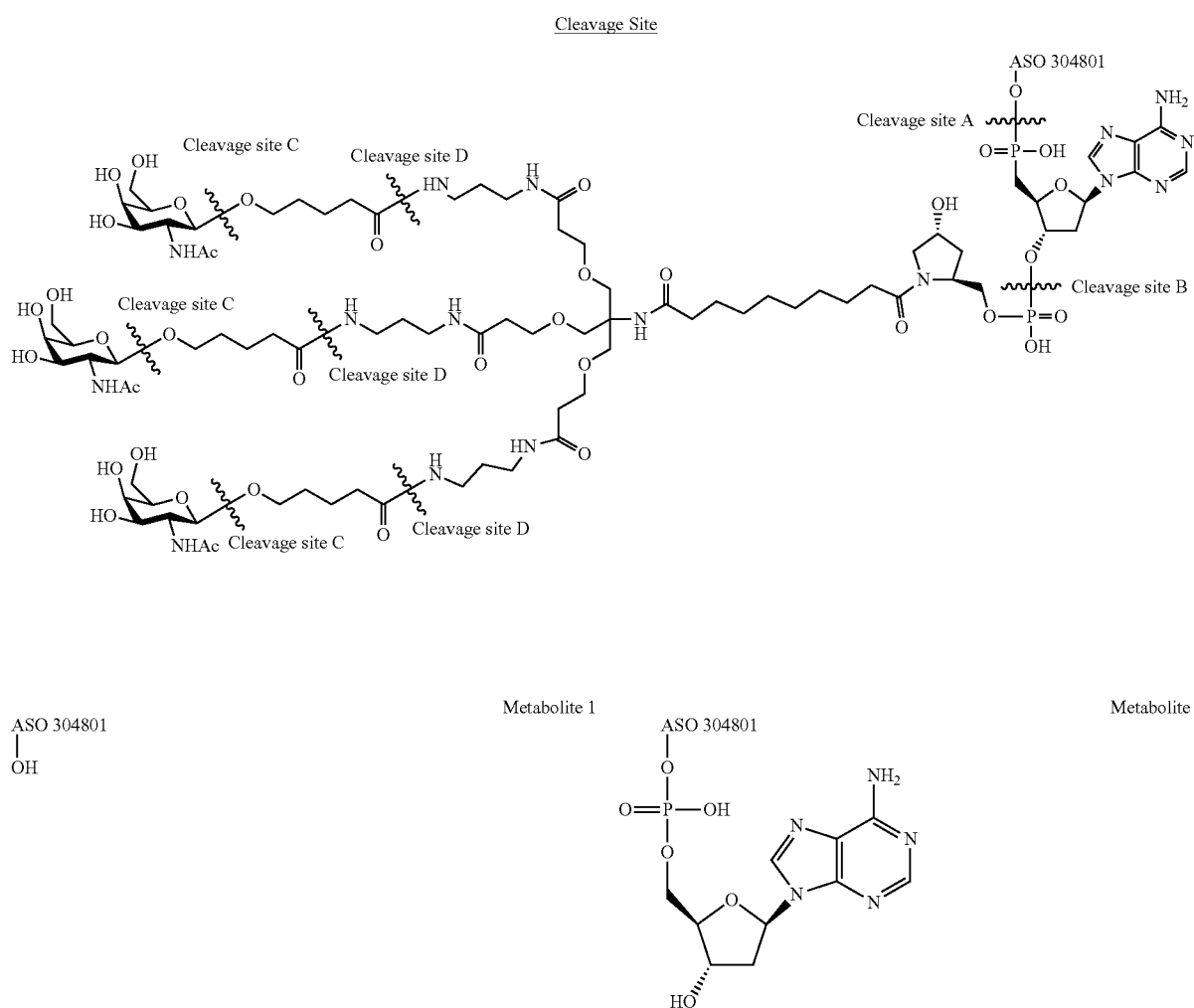

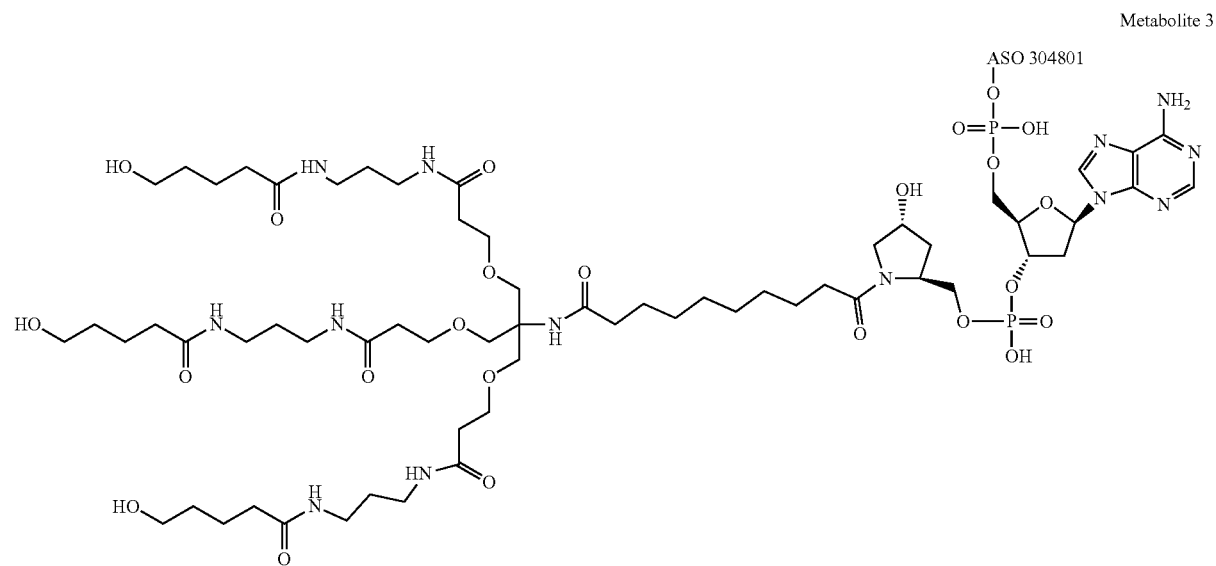
Metabolite 3
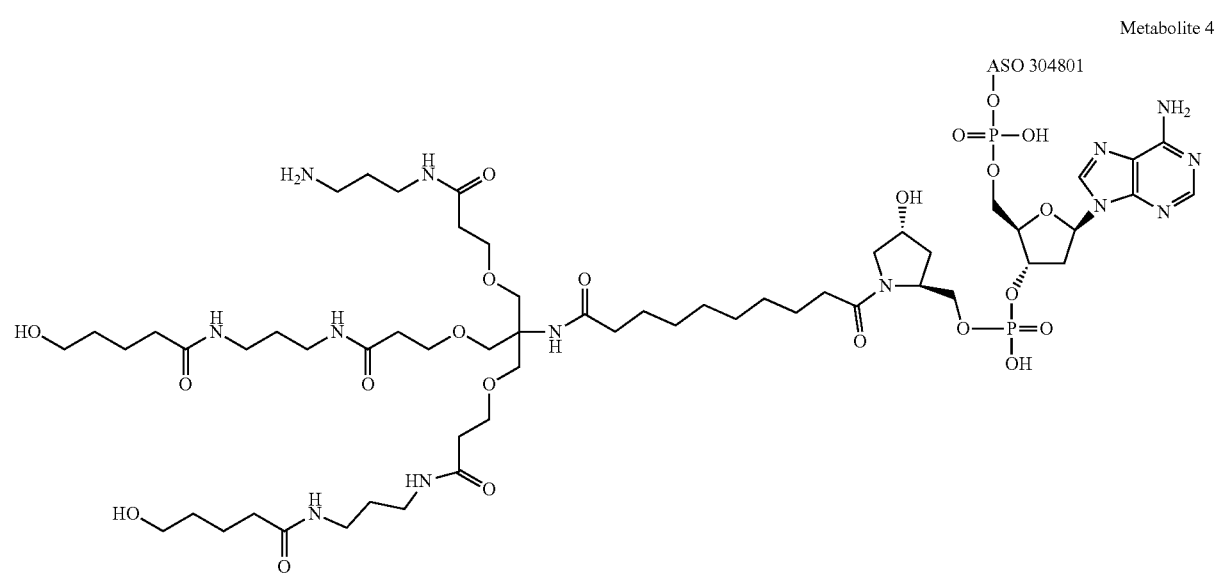
Metabolite 4

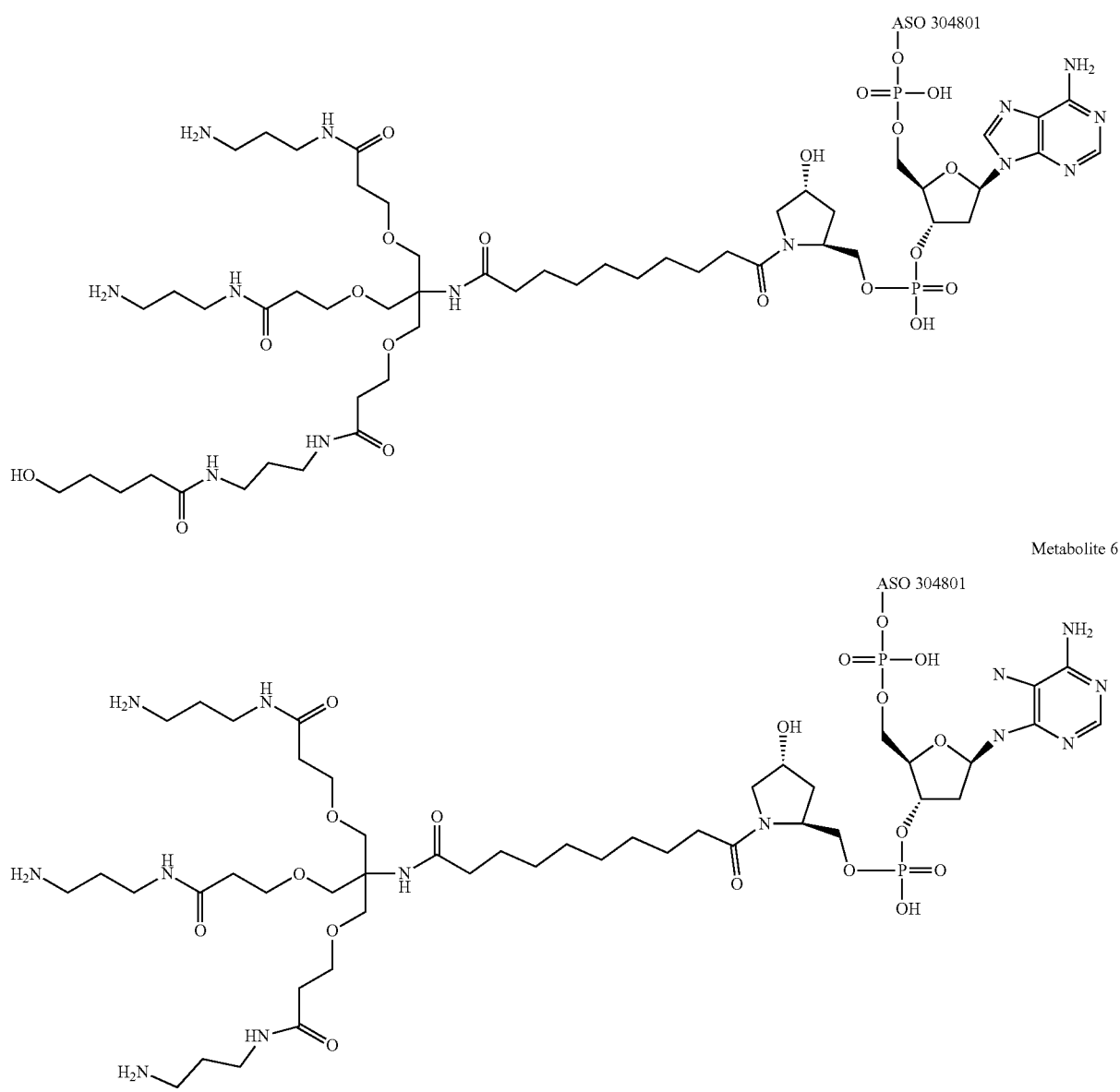

Example 21: Antisense Inhibition of Human Apoc III in Human Apoc III Transgenic Mice in Single Administration Study ISIS 304801, 647535 and 647536 each targeting human ApoC III and described in Table 17, were further evaluated in a single administration study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 24-28, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a GalNAc$_3$-1 conjugate at the 3' terminus (ISIS 647535 and 647536) compared to the antisense compound lacking a GalNAc$_3$-1 conjugate (ISIS 304801). Further, ISIS 647536, which comprises a GalNAc$_3$-1 conjugate and some phosphodiester linkages was as potent as ISIS 647535, which comprises the same conjugate and all internucleoside linkages within the ASO are phosphorothioate.

TABLE 24

Effect of ASO treatment on ApoC III mRNA levels in human ApoC III transgenic mice

| ASO | Dose (mg/kg) | % PBS | ED$_{50}$ (mg/kg) | 3' Conjugate | Internucleoside linkage/Length | SEQ ID No. |
|---|---|---|---|---|---|---|
| PBS | 0 | 99 | — | — | — | |
| ISIS 304801 | 1 | 104 | 13.2 | None | PS/20 | 135 |
| | 3 | 92 | | | | |
| | 10 | 71 | | | | |
| | 30 | 40 | | | | |
| ISIS 647535 | 0.3 | 98 | 1.9 | GalNAc$_3$-1 | PS/20 | 136 |
| | 1 | 70 | | | | |
| | 3 | 33 | | | | |
| | 10 | 20 | | | | |
| ISIS 647536 | 0.3 | 103 | 1.7 | GalNAc$_3$-1 | PS/PO/20 | 136 |
| | 1 | 60 | | | | |
| | 3 | 31 | | | | |
| | 10 | 21 | | | | |

TABLE 25

Effect of ASO treatment on ApoC III plasma protein levels in human ApoC III transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 99 | — | — | — | |
| ISIS 304801 | 1 | 104 | 23.2 | None | PS/20 | 135 |
| | 3 | 92 | | | | |
| | 10 | 71 | | | | |
| | 30 | 40 | | | | |
| ISIS 647535 | 0.3 | 98 | 2.1 | GalNAc$_3$-1 | PS/20 | 136 |
| | 1 | 70 | | | | |
| | 3 | 33 | | | | |
| | 10 | 20 | | | | |
| ISIS 647536 | 0.3 | 103 | 1.8 | GalNAc$_3$-1 | PS/PO/20 | 136 |
| | 1 | 60 | | | | |
| | 3 | 31 | | | | |
| | 10 | 21 | | | | |

TABLE 26

Effect of ASO treatment on triglyceride levels in transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 98 | — | — | — | |
| ISIS 304801 | 1 | 80 | 29.1 | None | PS/20 | 135 |
| | 3 | 92 | | | | |
| | 10 | 70 | | | | |
| | 30 | 47 | | | | |
| ISIS 647535 | 0.3 | 100 | 2.2 | GalNAc$_3$-1 | PS/20 | 136 |
| | 1 | 70 | | | | |
| | 3 | 34 | | | | |
| | 10 | 23 | | | | |
| ISIS 647536 | 0.3 | 95 | 1.9 | GalNAc$_3$-1 | PS/PO/20 | 136 |
| | 1 | 66 | | | | |
| | 3 | 31 | | | | |
| | 10 | 23 | | | | |

TABLE 27

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS 304801 | 1 | 104 | None | PS/20 | 135 |
| | 3 | 96 | | | |
| | 10 | 86 | | | |
| | 30 | 72 | | | |
| ISIS 647535 | 0.3 | 93 | GalNAc$_3$-1 | PS/20 | 136 |
| | 1 | 85 | | | |
| | 3 | 61 | | | |
| | 10 | 53 | | | |
| ISIS 647536 | 0.3 | 115 | GalNAc$_3$-1 | PS/PO/20 | 136 |
| | 1 | 79 | | | |
| | 3 | 51 | | | |
| | 10 | 54 | | | |

TABLE 28

Effect of ASO treatment on HDL and LDL cholesterol levels in transgenic mice

| ASO | Dose (mg/kg) | HDL % PBS | LDL % PBS | 3' Conjugate | Internucleoside Linkage/Length | SEQ ID No. |
|---|---|---|---|---|---|---|
| PBS | 0 | 131 | 90 | — | — | |
| ISIS 304801 | 1 | 130 | 72 | None | PS/20 | 135 |
| | 3 | 186 | 79 | | | |
| | 10 | 226 | 63 | | | |
| | 30 | 240 | 46 | | | |
| ISIS 647535 | 0.3 | 98 | 86 | GalNAc$_3$-1 | PS/20 | 136 |
| | 1 | 214 | 67 | | | |
| | 3 | 212 | 39 | | | |
| | 10 | 218 | 35 | | | |
| ISIS 647536 | 0.3 | 143 | 89 | GalNAc$_3$-1 | PS/PO/20 | 136 |
| | 1 | 187 | 56 | | | |
| | 3 | 213 | 33 | | | |
| | 10 | 221 | 34 | | | |

These results confirm that the GalNAc$_3$-1 Conjugate improves potency of an antisense compound. The results also show equal potency of a GalNAc$_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a GalNAc$_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22: Effect of GalNAc$_3$-1 Conjugated Modified Aso Targeting SRB-1 In Vivo ISIS 440762 and 651900, each targeting SRB-1 and described in Table 17, were evaluated in a dose-dependent study for their ability to inhibit SRB-1 in Balb/c mice.
Treatment Six week old male Balb/c mice (Jackson Laboratory, Bar Harbor, ME) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 29, both antisense compounds lowered SRB-1 mRNA levels. Further, the antisense compound comprising the GalNAc$_3$-1 conjugate (ISIS 651900) was substantially more potent than the antisense compound lacking the GalNAc$_3$-1 conjugate (ISIS 440762). These results demonstrate that the potency benefit of GalNAc$_3$-1 conjugates are observed using antisense oligonucleotides complementary to a different target and having different chemically modified nucleosides, in this instance modified nucleosides comprise constrained ethyl sugar moieties (a bicyclic sugar moiety).

TABLE 29

Effect of ASO treatment on SRB-1 mRNA levels in Balb/c mice

| ASO | Dose (mg/kg) | Liver % PBS | ED$_{50}$ (mg/kg) | 3' Conjugate | Internucleoside linkage/ Length | SEQ ID No. |
|---|---|---|---|---|---|---|
| PBS | 0 | 100 | — | — | | |
| ISIS 440762 | 0.7 | 85 | 2.2 | None | PS/14 | 137 |
| | 2 | 55 | | | | |
| | 7 | 12 | | | | |
| | 20 | 3 | | | | |
| ISIS 651900 | 0.07 | 98 | 0.3 | GalNAc$_3$-1 | PS/14 | 138 |
| | 0.2 | 63 | | | | |
| | 0.7 | 20 | | | | |
| | 2 | 6 | | | | |
| | 7 | 5 | | | | |

Example 23: Human Peripheral Blood Mononuclear Cells (Hpbmc) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS (Ca$^{++}$, Mg$^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 µl sample was pipette into a sample vial (Beckman Coulter) with 600 µl VersaLyse reagent (Beckman Coulter Cat #A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to 1×10$^7$ live PBMC/ml in RPMI+10% FBS+pen/strep.

The cells were plated at 5×10$^5$ in 50 µl/well of 96-well tissue culture plate (Falcon Microtest). 50 µl/well of 2× concentration oligos/controls diluted in RPMI+10% FBS+pen/strep. was added according to experiment template (100 µl/well total). Plates were placed on the shaker and allowed to mix for approx. 1 min. After being incubated for 24 hrs at 37° C.; 5% CO$_2$, the plates were centrifuged at 400×g for 10 minutes before removing the supernatant for MSD cytokine assay (i.e. human IL-6, IL-10, IL-8 and MCP-1).

Example 24: Evaluation of Proinflammatory Effects in Hpbmc Assay for GalNAca-1 Conjugated ASOs The antisense oligonucleotides (ASOs) listed in Table 30 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 µM concentrations. After a 24 hr treatment, the cytokine levels were measured.

The levels of IL-6 were used as the primary readout. The EC$_{50}$ and E$_{max}$ was calculated using standard procedures. Results are expressed as the average ratio of E$_{max}$/EC$_{50}$ from two donors and is denoted as "E$_{max}$/EC$_{50}$." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The GalNAcA-1 conjugated ASO, ISIS 647535 was slightly less proinflammatory than its non-conjugated counterpart ISIS 304801. These results indicate that incorporation of some PO linkages reduces proinflammatory reaction and addition of a GalNAcA-1 conjugate does not make a compound more proinflammatory and may reduce proinflammatory response. Accordingly, one would expect that an antisense compound comprising both mixed PS/PO linkages and a GalNAcA-1 conjugate would produce lower proinflammatory responses relative to full PS linked antisense compound with or without a GalNAcA-1 conjugate. These results show that GalNAc$_3$_1 conjugated antisense compounds, particularly those having reduced PS content are less proinflammatory.

Together, these results suggest that a GalNAc$_3$-1 conjugated compound, particularly one with reduced PS content, can be administered at a higher dose than a counterpart full PS antisense compound lacking a GalNAc$_3$-1 conjugate. Since half-life is not expected to be substantially different for these compounds, such higher administration would result in less frequent dosing. Indeed such administration could be even less frequent, because the GalNAcA-1 conjugated compounds are more potent (See Examples 20-22) and re-dosing is necessary once the concentration of a compound has dropped below a desired level, where such desired level is based on potency.

Example 25: Effect of GalNAc$_3$-1 Conjugated Modified Aso Targeting Human Apoc III In Vitro ISIS 304801 and 647535 described above were tested in vitro. Primary hepatocyte cells from transgenic mice at a density of 25,000 cells per well were treated with 0.03, 0.08, 0.24, 0.74, 2.22, 6.67 and 20 µM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The IC$_{50}$ was calculated using the standard methods and the results are presented in Table 32. As illustrated, comparable potency was observed in cells treated with ISIS 647535 as compared to the control, ISIS 304801.

TABLE 30

Modified ASOs

| ASO | Sequence (5' to 3') | Target | SEQ ID No. |
| --- | --- | --- | --- |
| ISIS 104838 | G$_{es}$$^m$C$_{es}$T$_{es}$G$_{es}$A$_{es}$T$_{ds}$T$_{ds}$A$_{ds}$G$_{ds}$A$_{ds}$G$_{ds}$A$_{ds}$G$_{ds}$A$_{ds}$G$_{ds}$G$_{es}$T$_{es}$$^m$C$_{es}$$^m$C$_{es}$$^m$C$_{e}$ | TNFα | 139 |
| ISIS 353512 | T$_{es}$$^m$C$_{es}$$^m$C$_{es}$$^m$C$_{ds}$A$_{ds}$T$_{ds}$T$_{ds}$T$_{ds}$$^m$C$_{ds}$A$_{ds}$G$_{ds}$G$_{ds}$A$_{ds}$G$_{ds}$A$_{ds}$$^m$C$_{ds}$$^m$C$_{ds}$T$_{es}$G$_{es}$G$_{e}$ | CRP | 140 |
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{e}$ | ApoC III | 135 |
| ISIS 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{e}$A$_{do}$,-GalNAc$_3$-1$_a$ | ApoC III | 136 |
| ISIS 616468 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{es}$A$_{es}$T$_{e}$ | ApoC III | 135 |

Subscripts: "e" indicates 2'-MOE modified nucleoside; "d" indicates β-D-2'-deoxyribonucleoside; "k" indicates 6'-(S)—CH$_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "in" indicates 5-methylcytosines. "A$_{do}$,-GalNAC$_3$-1$_a$" indicates a conjugate having the structure GalNAc$_3$-1 shown in Example 9 attached to the 3'-end of the antisense oligonucleotide, as indicated.

TABLE 31

Proinflammatory Effect of ASOs targeting ApoC III in hPBMC assay

| ASO | EC$_{50}$ (µM) | E$_{max}$ (µM) | E$_{max}$/EC$_{50}$ | 3' Conjugate | Internucleoside Linkage/Length | SEQ ID No. |
| --- | --- | --- | --- | --- | --- | --- |
| ISIS 353512 (high responder) | 0.01 | 265.9 | 26,590 | None | PS/20 | 140 |
| ISIS 304801 | 0.07 | 106.55 | 1,522 | None | PS/20 | 135 |
| ISIS 647535 | 0.12 | 138 | 1,150 | GalNAc$_3$-1 | PS/20 | 136 |
| ISIS 616468 | 0.32 | 71.52 | 224 | None | PS/PO/20 | 135 |

TABLE 32

Modified ASO targeting human ApoC III in primary hepatocytes

| ASO | IC50 (µM) | 3' Conjugate | Internucleoside linkage/Length | SEQ ID No. |
| --- | --- | --- | --- | --- |
| ISIS 304801 | 0.44 | None | PS/20 | 135 |
| ISIS 647535 | 0.31 | GalNAc3-1 | PS/20 | 136 |

In this experiment, the large potency benefits of GalNAc$_3$-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26: Effect of Po/Ps Linkages on Apoc III Aso Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 33, below.

These results show reduction in potency for antisense compounds with PO/PS (ISIS 616468) in the wings relative to full PS (ISIS 304801).

TABLE 33

Effect of ASO treatment on ApoC III protein levels in human ApoC III transgenic mice

| ASO | Dose (mg/kg) | % PBS | 3' Conjugate | Internucleoside linkage/Length | SEQ ID No. |
|---|---|---|---|---|---|
| PBS | 0 | 99 | — | — | |
| ISIS 304801 | 25 mg/kg/wk for 2 wks | 24 | None | Full PS | 135 |
| ISIS 616468 | 25 mg/kg/wk for 2 wks | 40 | None | 14 PS/6 PO | 135 |

Example 27: Compound 56

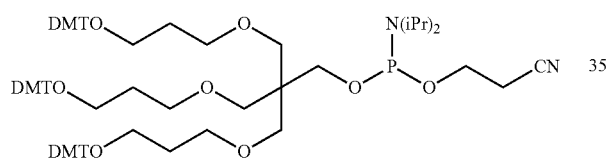

Compound 56 is commercially available from Glen Research or may be prepared according to published procedures reported by Shchepinov et al., *Nucleic Acids Research*, 1997, 25(22), 4447-4454.

Example 28: Preparation of Compound 60

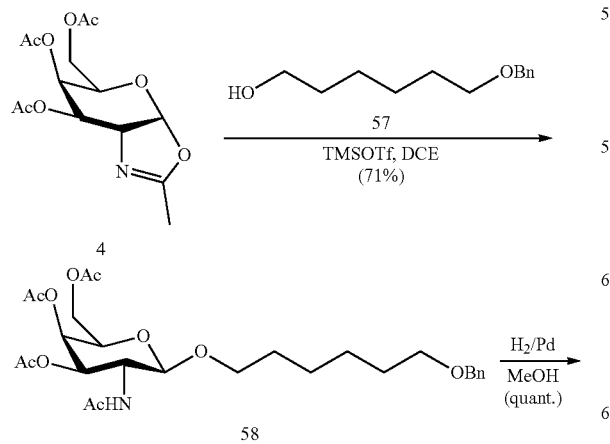

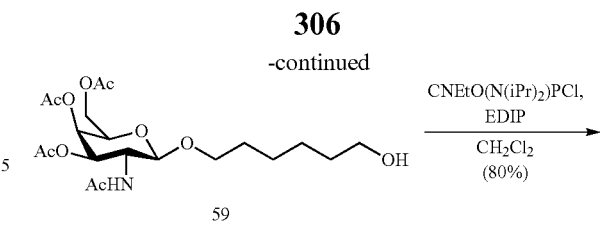

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 29: Preparation of Compound 63

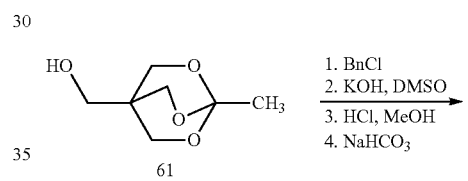

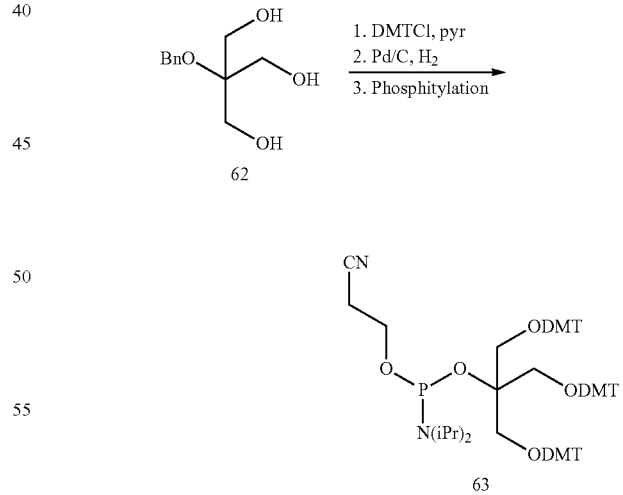

Compounds 61 and 62 are prepared using procedures similar to those reported by Tober et al., *Eur. J. Org. Chem.*, 2013, 3, 566-577; and Jiang et al., *Tetrahedron*, 2007, 63(19), 3982-3988. Alternatively, Compound 63 is prepared using procedures similar to those reported in scientific and patent literature by Kim et al., Synlett, 2003, 12, 1838-1840; and Kim et al., published PCT International Application, WO 2004063208.

Example 30: Preparation of Compound 63B
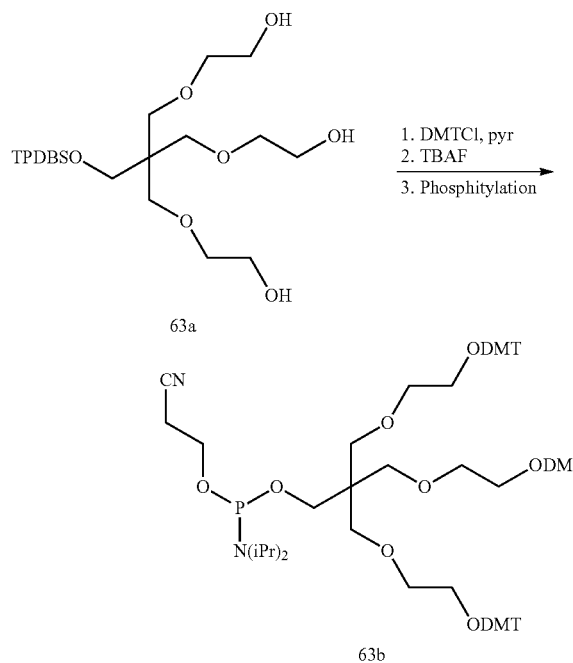
Compound 63a is prepared using procedures similar to those reported by Hanessian et al., *Canadian Journal of Chemistry*, 1996, 74(9), 1731-1737.
Example 31: Preparation of Compound 63D
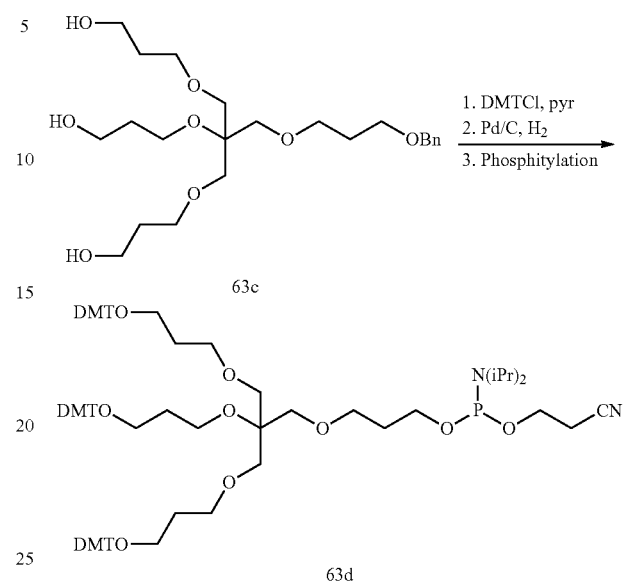
Compound 63c is prepared using procedures similar to those reported by Chen et al., *Chinese Chemical Letters*, 1998, 9(5), 451-453.
Example 32: Preparation of Compound 67
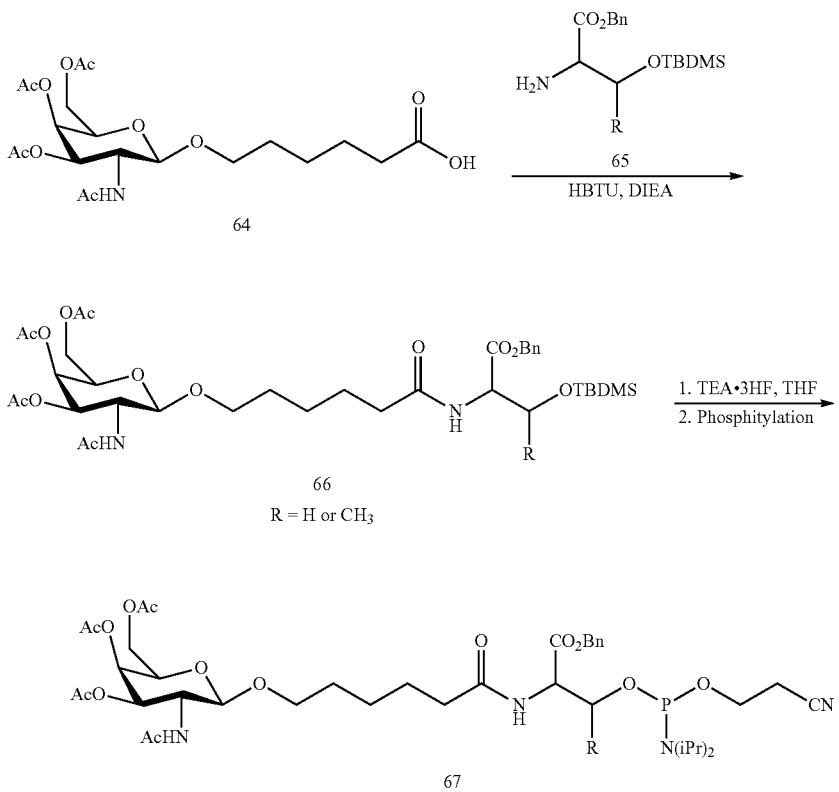
R = H or CH₃

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33: Preparation of Compound 70

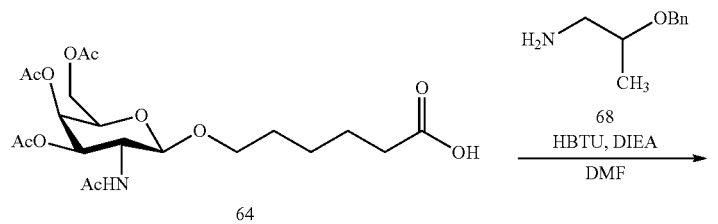

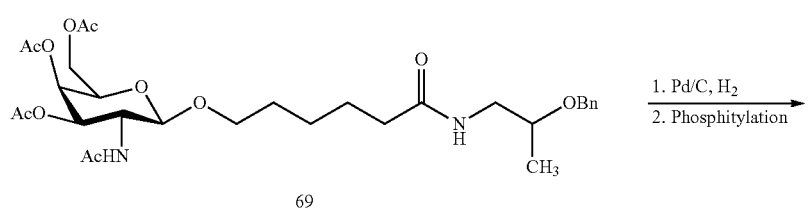

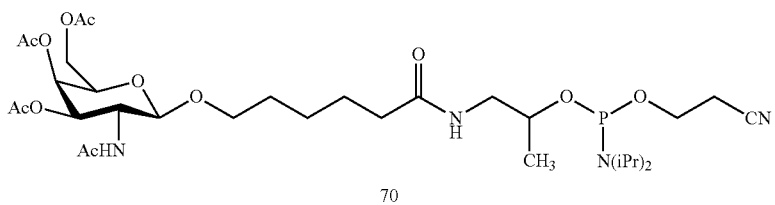

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34: Preparation of Compound 75a

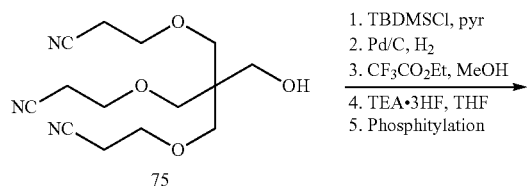

-continued

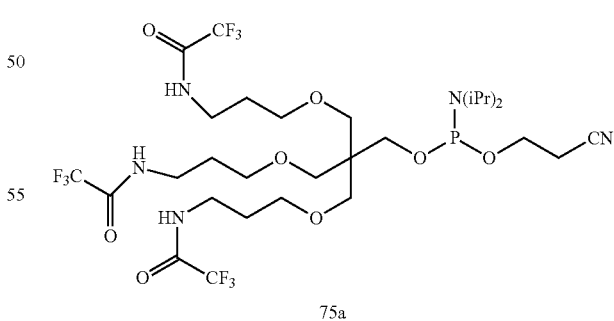

Compound 75 is prepared according to published procedures reported by Shchepinov et al., *Nucleic Acids Research*, 1997, 25(22), 4447-4454.

Example 35: Preparation of Compound 79
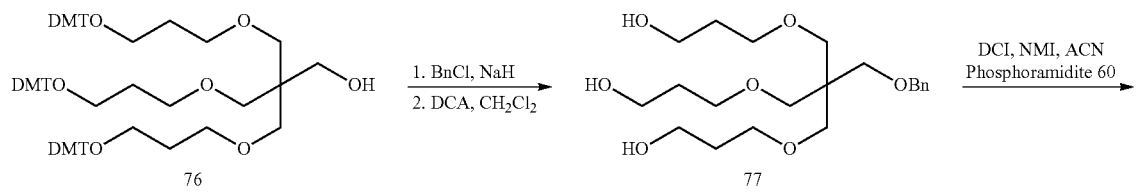
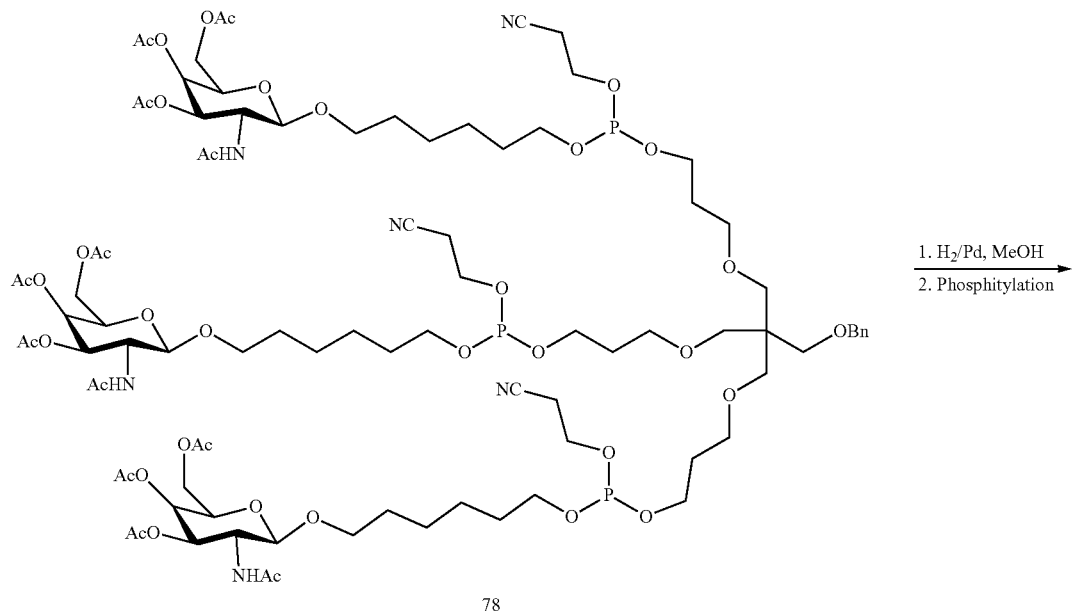
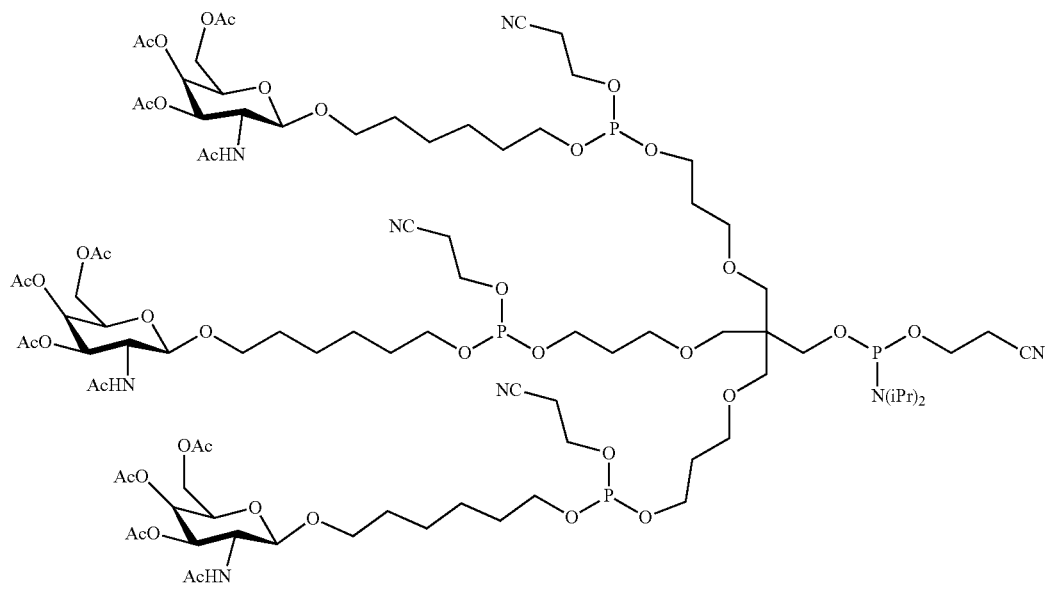
Compound 76 was prepared according to published procedures reported by Shchepinov et al., *Nucleic Acids Research*, 1997, 25(22), 4447-4454.

Example 36: Preparation of Compound 79a
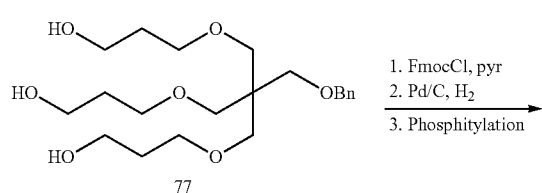
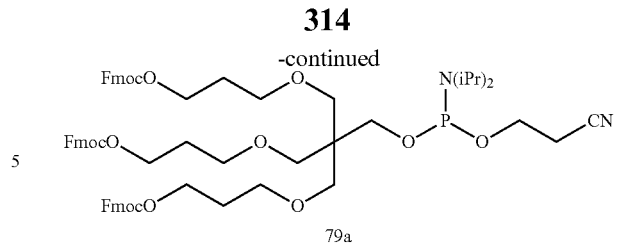
Compound 77 is prepared as per the procedures illustrated in Example 35.
Example 37: General Method for the Preparation of Conjugated Oligomeric Compound 82 Comprising A Phosphodiester Linked GalNAc₃-2 Conjugate at 5' Terminus Via Solid Support (Method I)
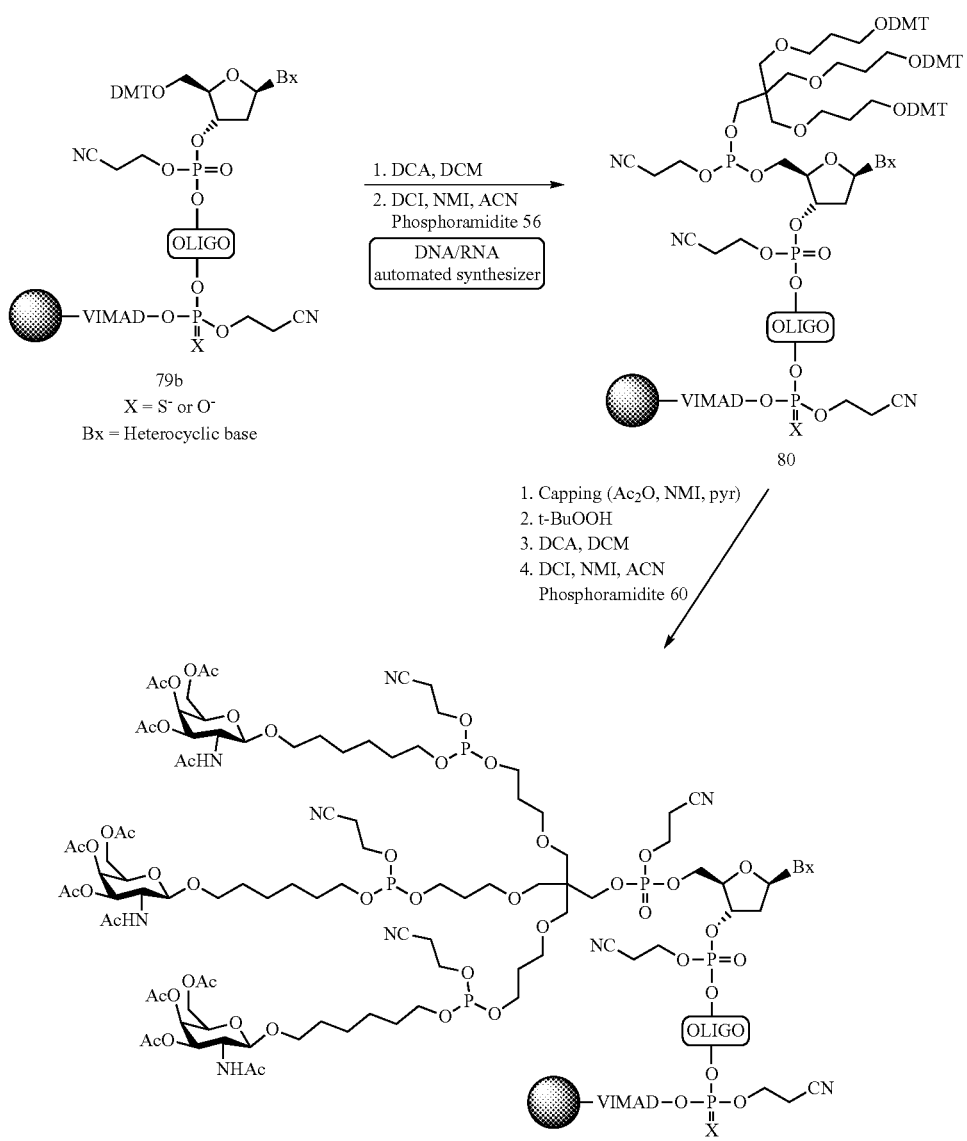

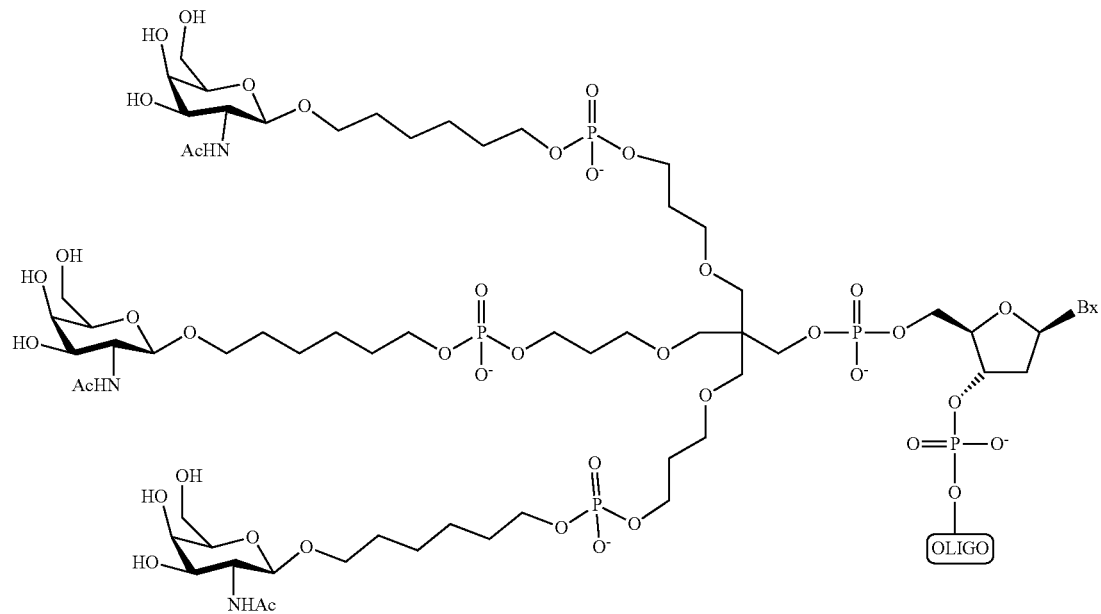
82
wherein GalNAc₃-2 has the structure:
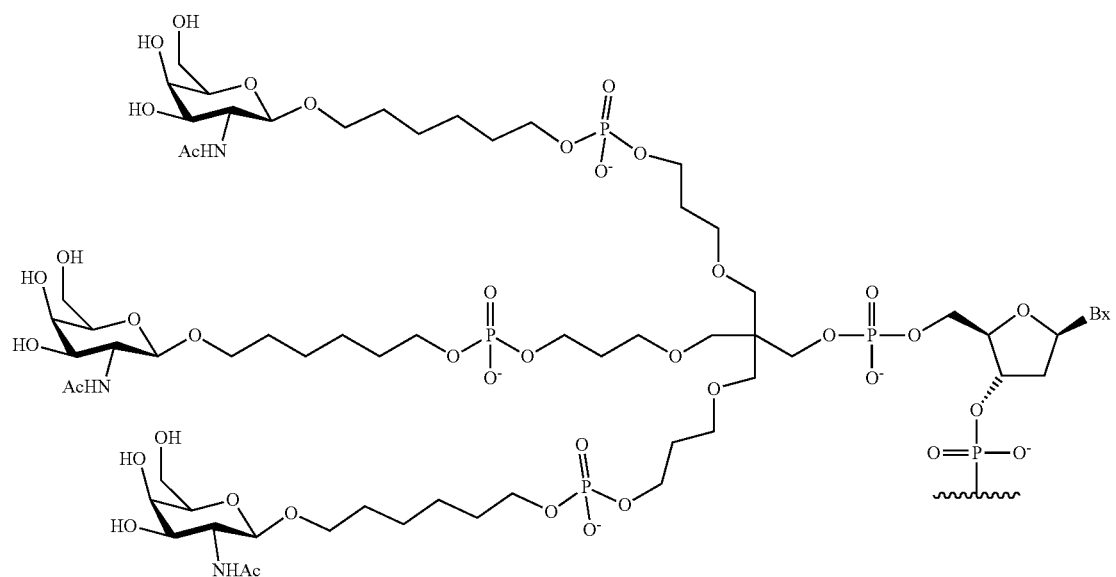

The GalNAc₃ cluster portion of the conjugate group GalNAc₃-2 (GalNAc₃-2$_a$) can be combined with any cleavable moiety to provide a variety of conjugate groups. Wherein GalNAc₃-2$_a$ has the formula:

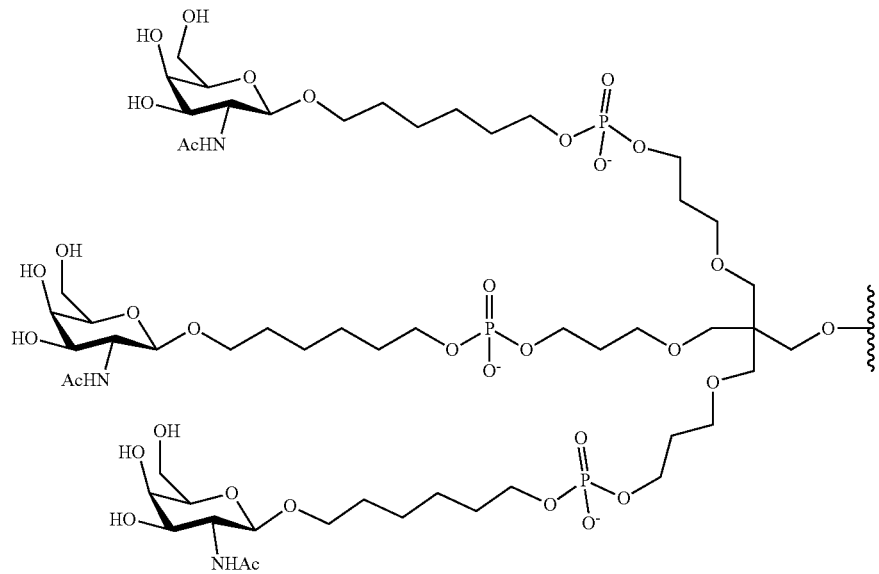

The VIMAD-bound oligomeric compound 79b was prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus.

The order and quantity of phosphoramidites added to the solid support can be adjusted to prepare the oligomeric compounds as described herein having any predetermined sequence and composition.

Example 38: Alternative Method for the Preparation of Oligomeric Compound 82 Comprising a Phosphodiester Linked GalNAc₃-2 Conjugate at 5' Terminus (Method II)

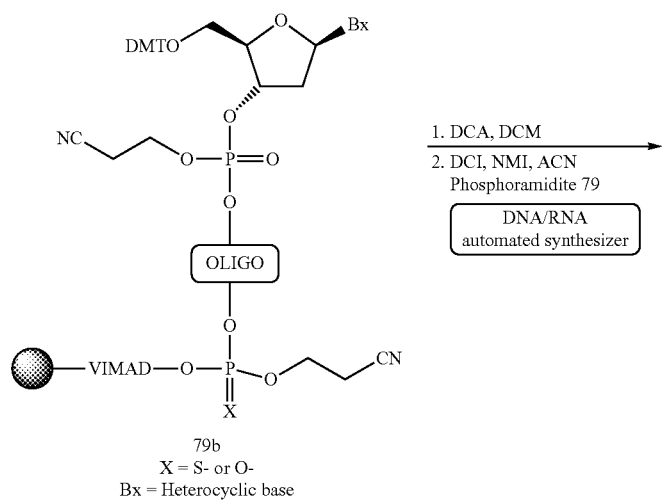

79b
X = S- or O-
Bx = Heterocyclic base

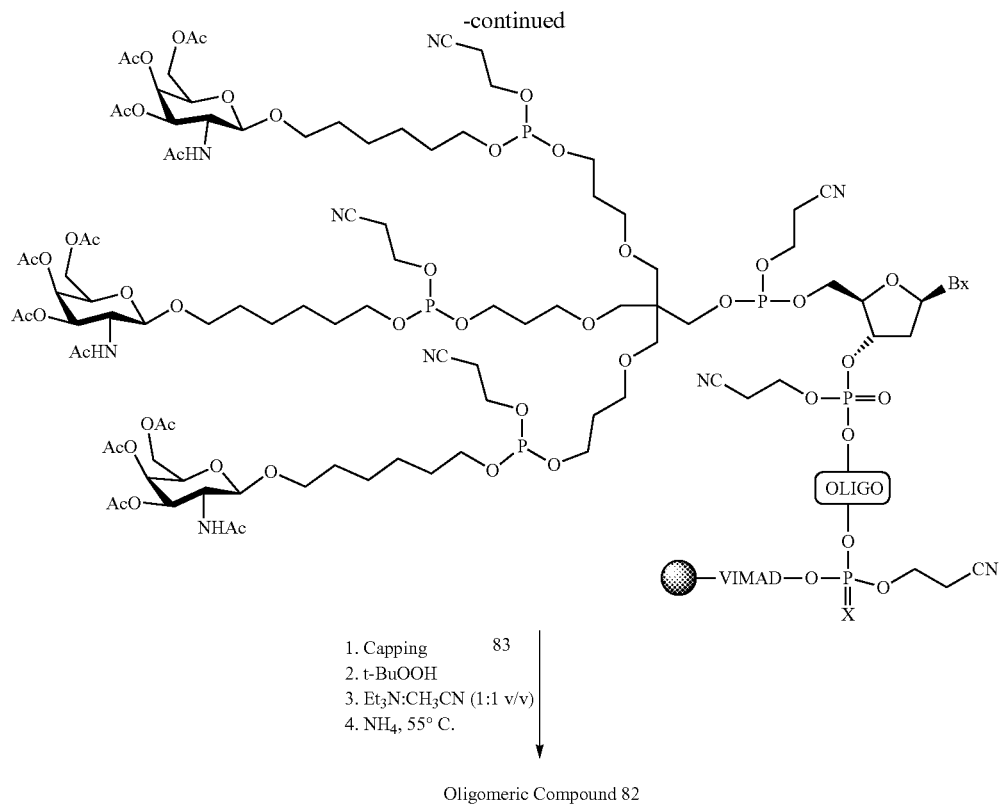

1. Capping   83
2. t-BuOOH
3. Et$_3$N:CH$_3$CN (1:1 v/v)
4. NH$_4$, 55° C.

Oligomeric Compound 82

The VIMAD-bound oligomeric compound 79b was prepared using standard procedures for automated DNA/RNA synthesis (see Dupouy et al., *Angew. Chem. Int. Ed.,* 2006, 45, 3623-3627). The GalNAc$_3$-2 cluster phosphoramidite, Compound 79 was prepared as per the procedures illustrated in Example 35. This alternative method allows a one-step installation of the phosphodiester linked GalNAc$_3$-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39: General Method for the Preparation of Oligomeric Compound 83H Comprising a GalNAc$_3$-3 Conjugate at the 5' Terminus (GalNAc$_3$-1 Modified for 5' End Attachment) Via Solid Support

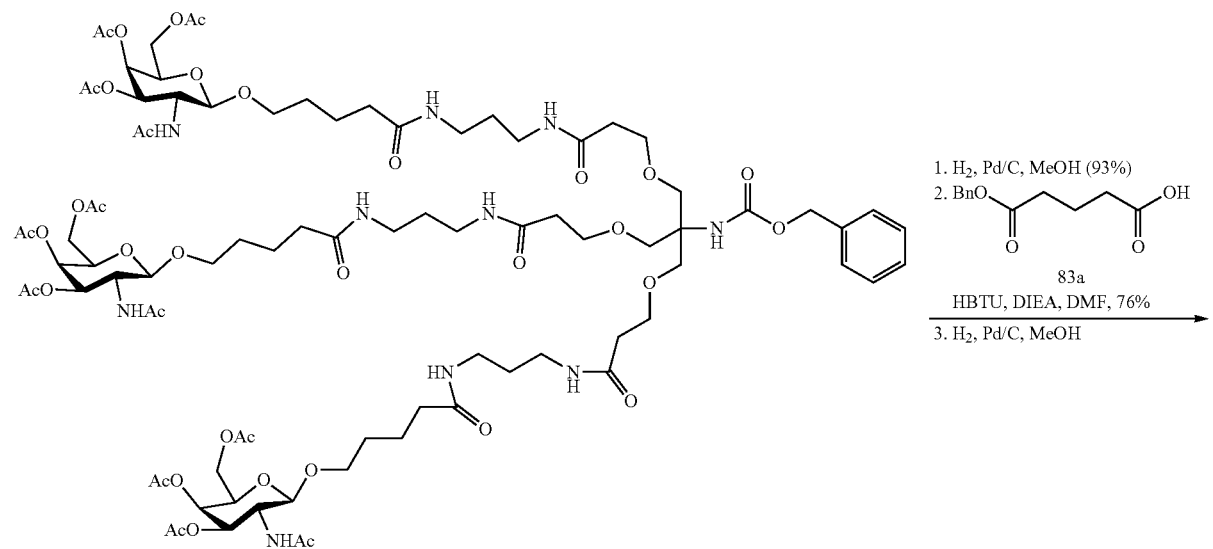

-continued
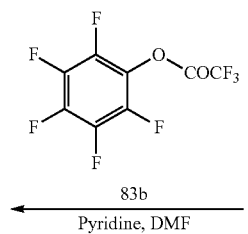 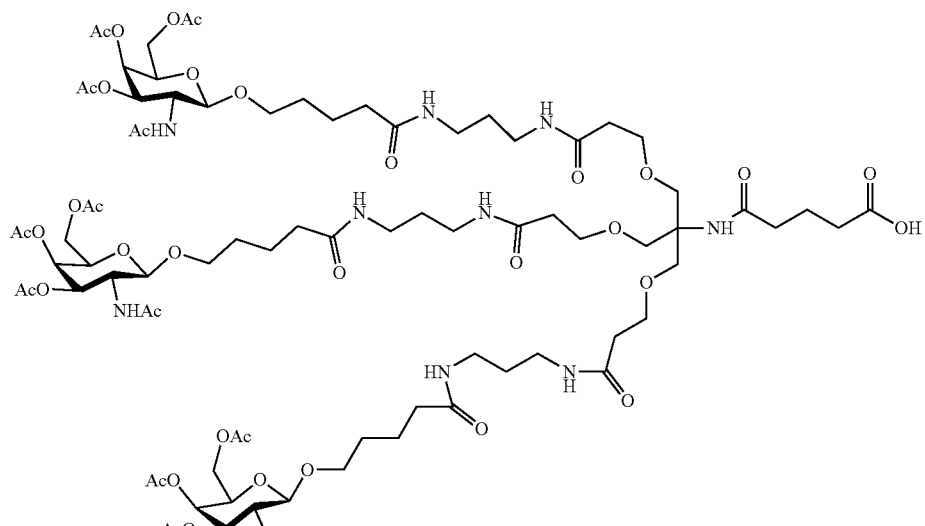
83b
Pyridine, DMF
83c
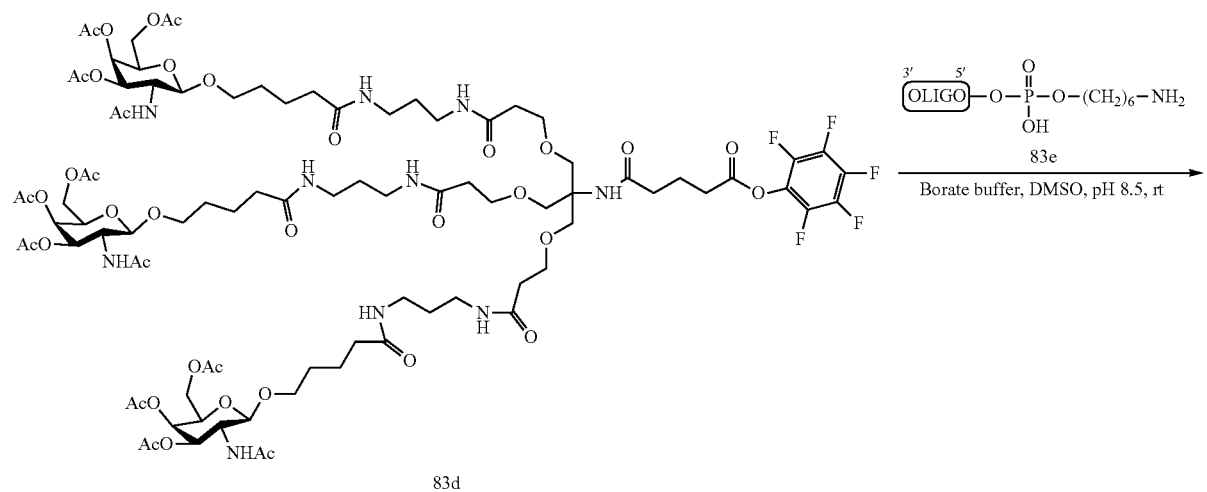
83e
Borate buffer, DMSO, pH 8.5, rt
83d
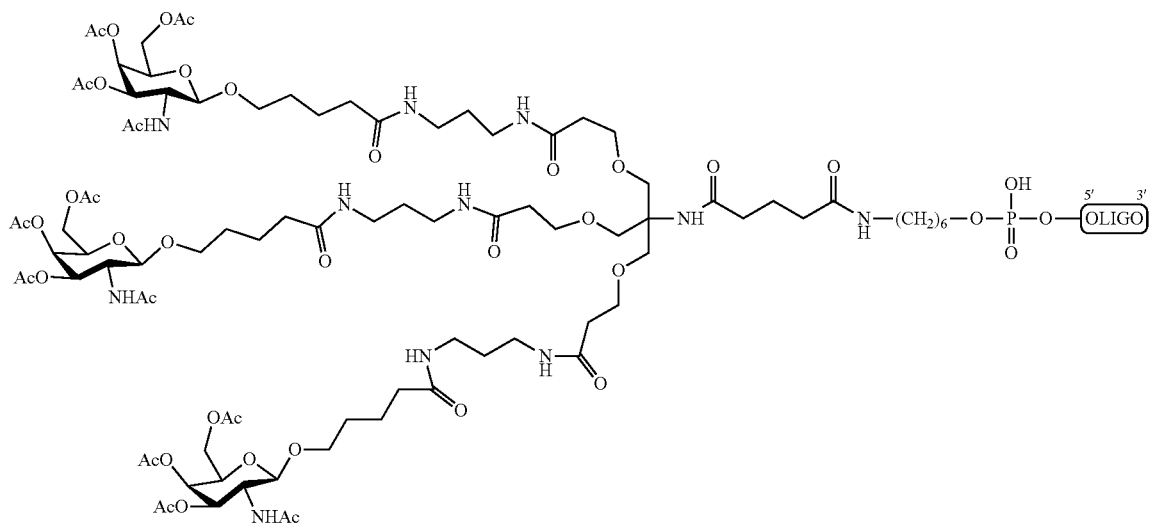
83f
Aqueous ammonia

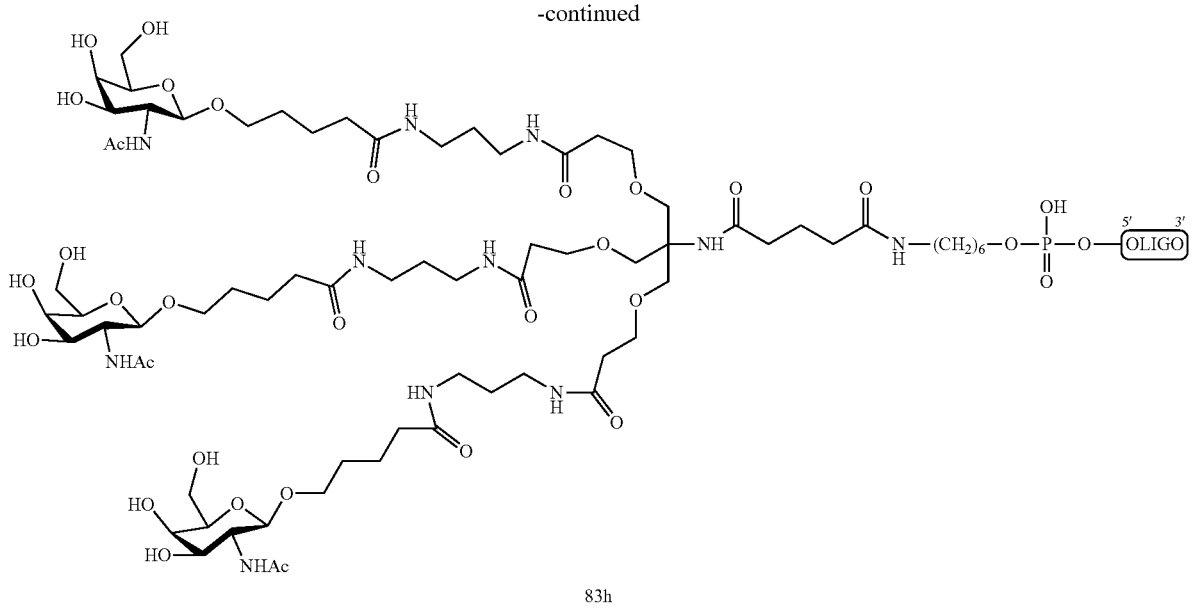

83h

Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83h).

Wherein GalNAc$_3$-3 has the structure:

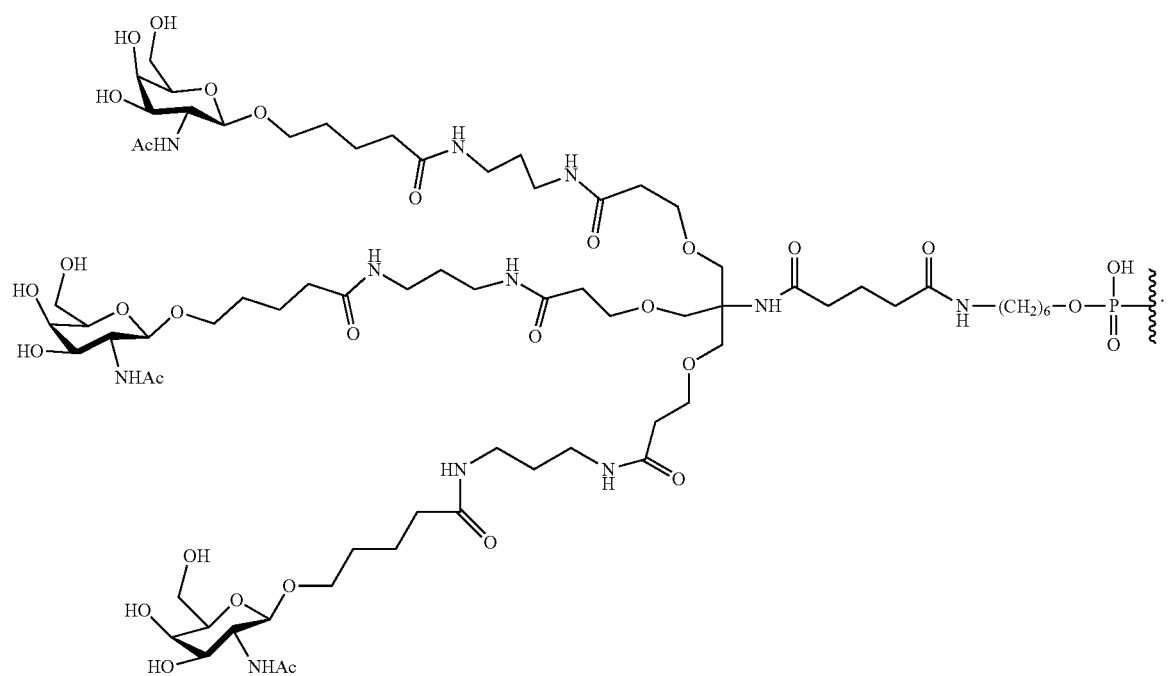

The GalNAc₃ cluster portion of the conjugate group GalNAc₃-3 (GalNAc₃-3$_a$) can be combined with any cleavable moiety to provide a variety of conjugate groups. Wherein GalNAc₃-3$_a$ has the formula:
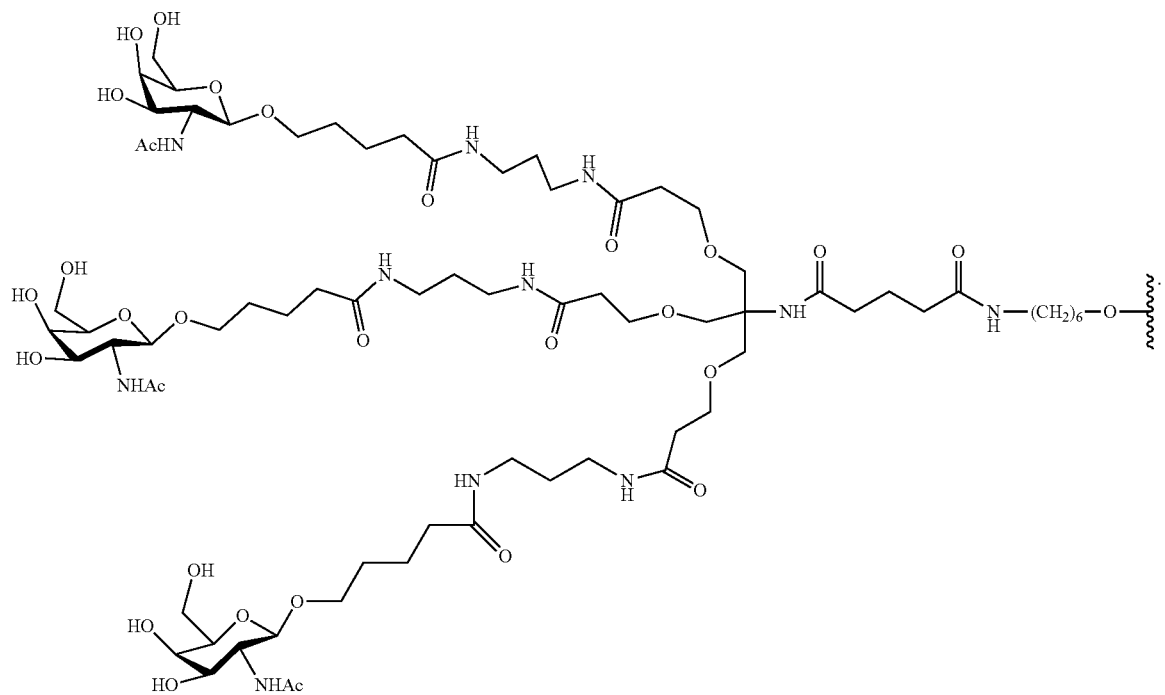
35
Example 40: General Method for the Preparation of Oligomeric Compound 89 Comprising A Phosphodiester Linked GalNAc₃-4 Conjugate at the 3' Terminus Via Solid Support
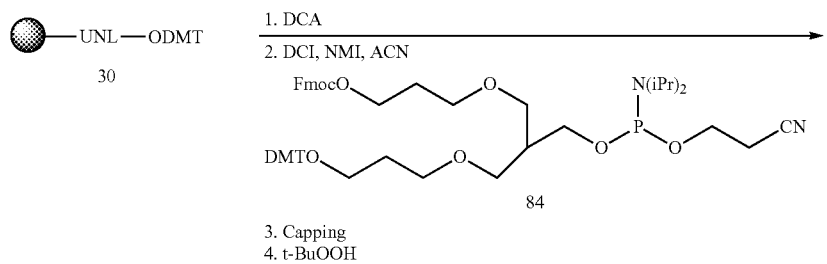
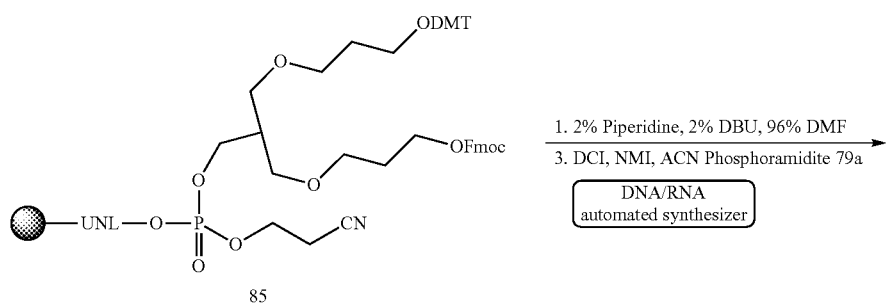

-continued
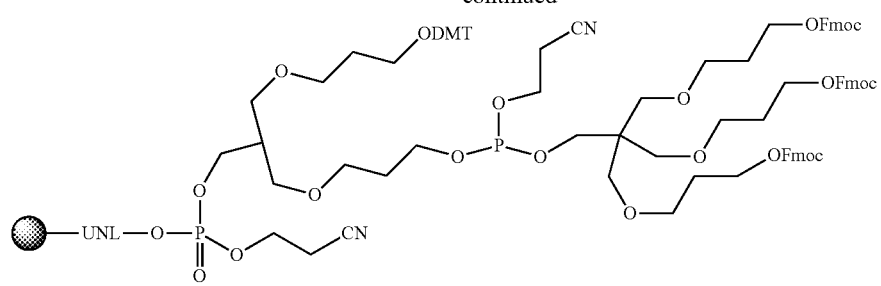
86
1. Capping
2. t-BuOOH
3. 2% Piperidine, 2% DBU, 96% DMF
4. DCI, NMI, ACN, Phosphoramidite 60
DNA/RNA automated synthesizer
5. Capping
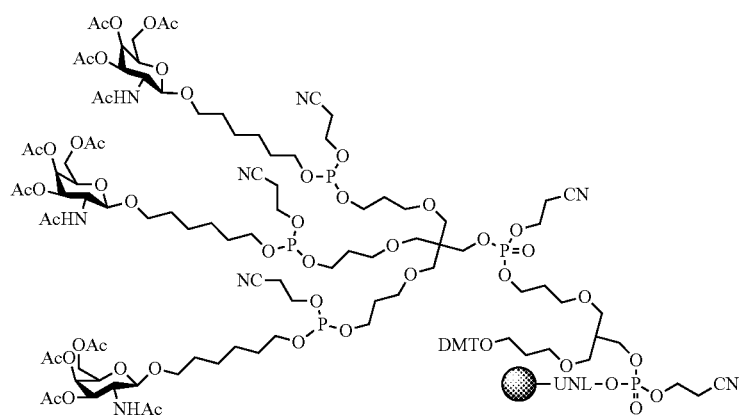
87
1. t-BuOOH
2. DCA
3. Oligo synthesis (DNA/RNA automated synthesizer)
4. Capping
5. Oxidation
6. Et₃N:CH₃CN (1:1, v/v)

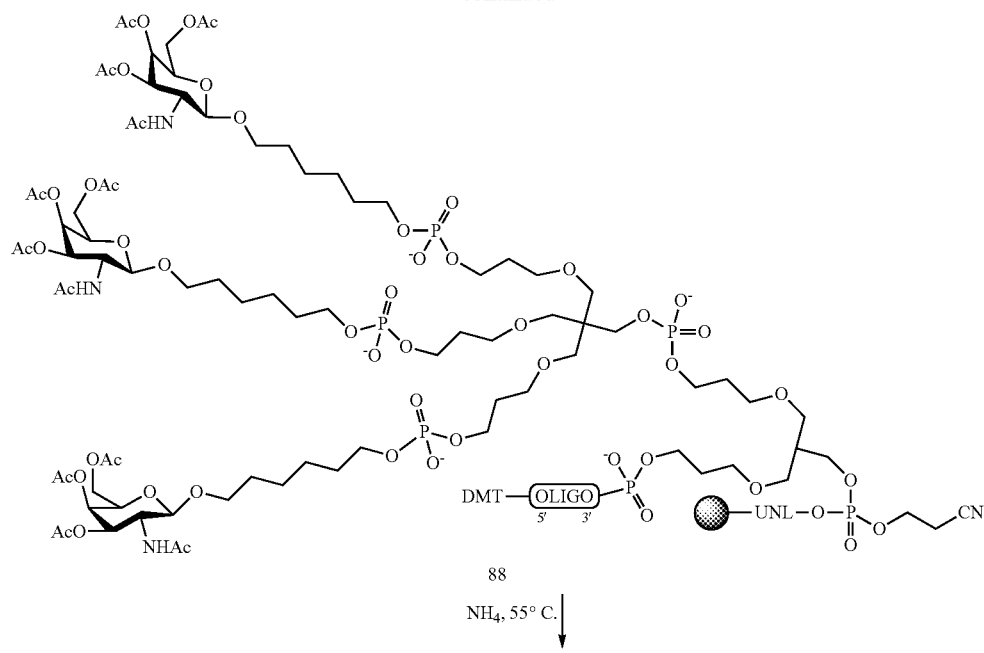
88
NH₄, 55° C.
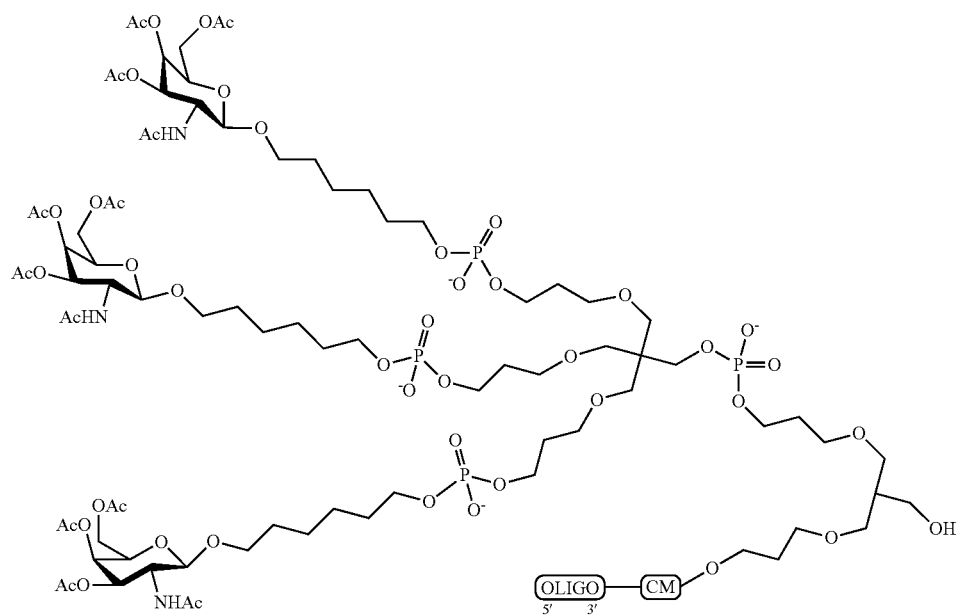
89

Wherein GalNAc$_3$-4 has the structure:
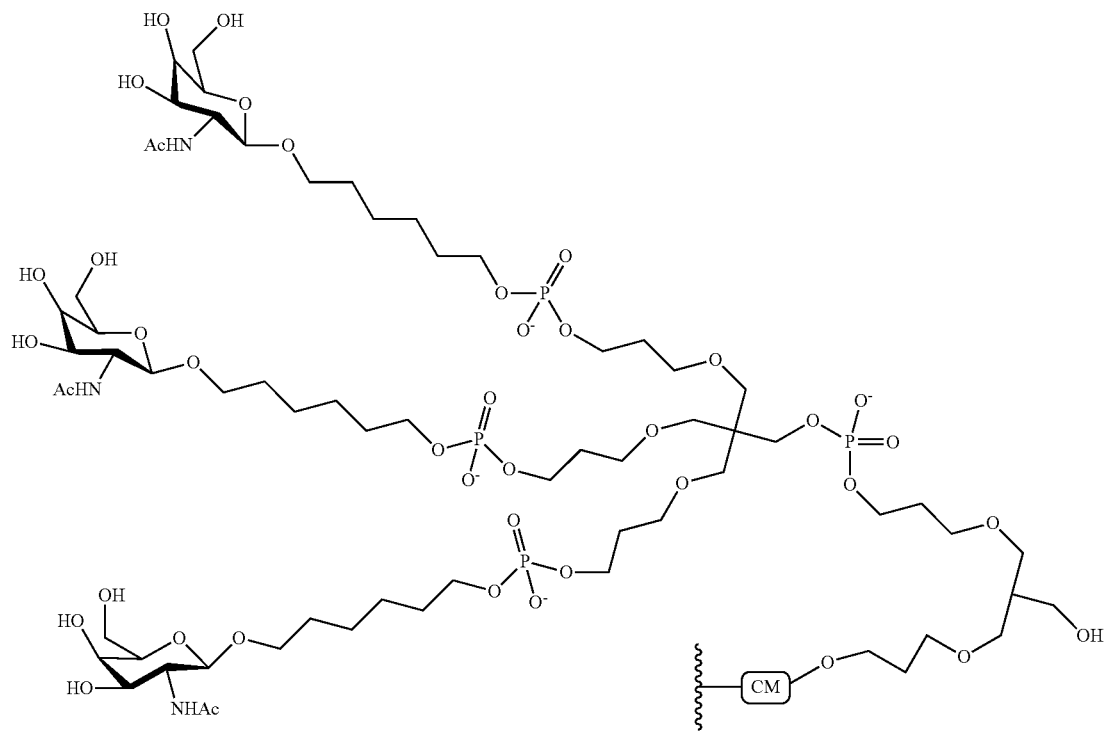
Wherein CM is a cleavable moiety. In certain embodiments, cleavable moiety is:
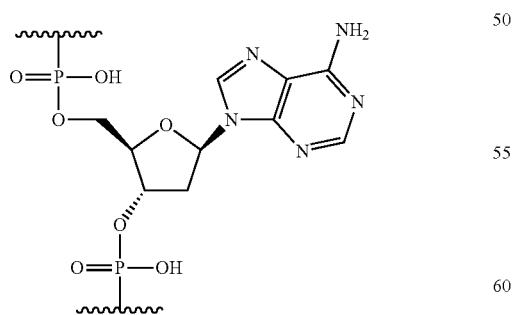
The GalNAc$_3$ cluster portion of the conjugate group GalNAc$_3$-4 (GalNAc$_3$-4$_a$) can be combined with any cleavable moiety to provide a variety of conjugate groups. Wherein GalNAc$_3$-4$_a$ has the formula:

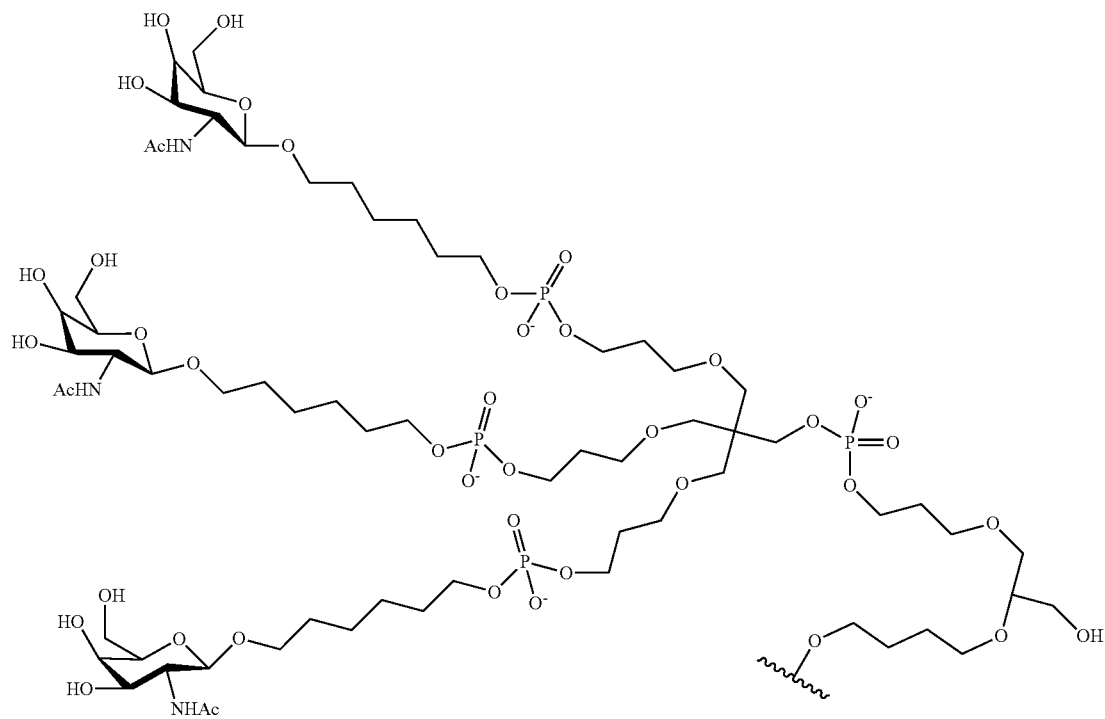

The protected Unylinker functionalized solid support Compound 30 is commercially available. Compound 84 is prepared using procedures similar to those reported in the literature (see Shchepinov et al., *Nucleic Acids Research*, 1997, 25(22), 4447-4454; Shchepinov etal., *Nucleic Acids Research*, 1999, 27, 3035-3041; and Hornet et al., *Nucleic Acids Research*, 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41: General Method for the Preparation of ASOs Comprising a Phosphodiester Linked GalNAc$_3$-2 (See Example 37, Bx is Adenine) Conjugate at the 5' Position Via Solid Phase Techniques (Preparation of Isis 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. Phosphoramidite compounds 56 and 60 were used to synthesize the phosphodiester linked GalNAc$_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience AKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous CH$_3$CN was used as activator during the coupling step. Phosphorothioate linkages were introduced by sulfurization with 0.1 M solution of xanthane hydride in 1:1 pyridine/CH$_3$CN for a contact time of 3 minutes. A solution of 20% tert-butylhydroperoxide in CH$_3$CN containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h. The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous CH$_3$CN, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 34

ASO comprising a phosphodiester linked GalNAc$_3$-2 conjugate at the 5' position targeting SRB-1

| ISIS No. | Sequence (5' to 3') | CalCd Mass | Observed Mass | SEQ ID No. |
|---|---|---|---|---|
| 661134 | GalNAc$_3$-2$_a$-$_o$,A$_{do}$T$_{ks}{}^m$C$_{ks}$A$_{ds}$G$_{ds}$T$_{ds}{}^m$C$_{ds}$A$_{ds}$T$_{ds}$G$_{ds}$A$_{ds}{}^m$C$_{ds}$T$_{ds}$T$_{ks}{}^m$C$_k$ | 6482.2 | 6481.6 | 141 |

Subscripts: "e" indicates 2'-MOE modified nucleoside; "d" indicates β-D-2'-deoxyribonucleoside; "k" indicates 6'-(S)—CH$_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of GalNAc$_3$-2$_a$ is shown in Example 37.

Example 42: General Method for the Preparation of ASOs Comprising a GalNAc$_3$-3 Conjugate at the 5' Position Via Solid Phase Techniques (Preparation of Isis 661166)

The synthesis for ISIS 661166 was performed using similar procedures as illustrated in Examples 39 and 41.

ISIS 661166 is a 5-10-5 MOE gapmer, wherein the 5' position comprises a GalNAc$_3$-3 conjugate. The ASO was characterized by ion-pair-HPLC coupled MS analysis with Agilent 1100 MSD system.

TABLE 34a

ASO comprising a GalNAc$_3$-3 conjugate at the 5' position via a hexylamino phosphodiester linkage targeting Malat-1

| ISIS No. | Sequence (5' to 3') | Conjugate | Calcd Mass | Observed Mass | SEQ ID No. |
|---|---|---|---|---|---|
| 661166 | 5'-GalNAc$_3$-3$_{a-o'}${}^m$C$_{es}$G$_{es}$G$_{es}$T$_{es}$G$_{es}$ ${}^m$C$_{ds}$A$_{ds}$A$_{ds}$G$_{ds}$G$_{ds}{}^m$C$_{ds}$T$_{ds}$T$_{ds}$A$_{ds}$G$_{ds}$ G$_{es}$A$_{es}$A$_{es}$T$_{es}$T$_e$ | 5'-GalNAc$_3$-3 | 8992.16 | 8990.51 | 142 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "5'-GalNAc$_3$-3a" is shown in Example 39.

Example 43: Dose-Dependent Study of Phosphodiester Linked GalNAc$_3$-2 (See Examples 37 and 41, Bx is Adenine) at the 5' Terminus Targeting SRB-1 In Vivo ISIS 661134 (see Example 41) comprising a phosphodiester linked GalNAc$_3$-2 conjugate at the 5' terminus was tested in a dose-dependent study for antisense inhibition of SRB-1 in mice. Unconjugated ISIS 440762 and 651900 (GalNAc$_3$-1 conjugate at 3' terminus, see Example 9) were included in the study for comparison and are described previously in Table 17.

Treatment

Six week old male Balb/c mice (Jackson Laboratory, Bar Harbor, ME) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are presented below.

As illustrated in Table 35, treatment with antisense oligonucleotides lowered SRB-1 mRNA levels in a dose-dependent manner. Indeed, the antisense oligonucleotides comprising the phosphodiester linked GalNAc$_3$-2 conjugate at the 5' terminus (ISIS 661134) or the GalNAc$_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked GalNAc$_3$-2 conjugate at the 5' terminus was equipotent compared to ISIS 651900, which comprises the GalNAc$_3$-1 conjugate at the 3' terminus.

TABLE 35

ASOs containing GalNAc$_3$-1 or GalNAc$_3$-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| PBS | 0 | 100 | — | — | |
| 440762 | 0.2 | 116 | 2.58 | No conjugate | 137 |
| | 0.7 | 91 | | | |
| | 2 | 69 | | | |
| | 7 | 22 | | | |
| | 20 | 5 | | | |
| 651900 | 0.07 | 95 | 0.26 | 3' GalNAc$_3$-1 | 138 |
| | 0.2 | 77 | | | |
| | 0.7 | 28 | | | |
| | 2 | 11 | | | |
| | 7 | 8 | | | |
| 661134 | 0.07 | 107 | 0.25 | 5' GalNAc$_3$-2 | 141 |
| | 0.2 | 86 | | | |

TABLE 35-continued

ASOs containing GalNAc$_3$-1 or GalNAc$_3$-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| | 0.7 | 28 | | | |
| | 2 | 10 | | | |
| | 7 | 6 | | | |

Structures for 3' GalNAc$_3$-1 and 5' GalNAc$_3$-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' GalNAc$_3$-2) and ISIS 651900 (3' GalNAc$_3$-1) were identified and their masses were confirmed by high resolution mass spectrometry analysis. The results showed that the major metabolite detected for the ASO comprising a phosphodiester linked GalNAc$_3$-2 conjugate at the 5' terminus (ISIS 661134) was ISIS 440762 (data not shown). No additional metabolites, at a detectable level, were observed. Unlike its counterpart, additional metabolites similar to those reported previously in Table 23a were observed for the ASO having the GalNAc$_3$-1 conjugate at the 3' terminus (ISIS 651900). These results suggest that having the phosphodiester linked GalNAc$_3$-1 or GalNAc$_3$-2 conjugate may improve the PK profile of ASOs without compromising their potency.

Example 44: Effect of Po/Ps Linkages on Antisense Inhibition of ASOs Comprising GalNAc$_3$-1 Conjugate (See Example 9) at the 3' Terminus Targeting SRB-1

ISIS 655861 and 655862 comprising a GalNAc$_3$-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table 36, below.

TABLE 36

Modified ASOs comprising GalNAc$_3$-1 conjugate at the 3' terminus targeting SRB-I

| ISIS No. | Sequence (5' to 3') | Chemistry | SEQ ID No. |
|---|---|---|---|
| 353382 (parent) | G$_{es}$$^m$C$_{es}$T$_{es}$T$_{es}$ $^m$C$_{es}$A$_{ds}$G$_{ds}$T$_{ds}$ $^m$C$_{ds}$A$_{ds}$T$_{ds}$G$_{ds}$ A$_{ds}$$^m$C$_{ds}$T$_{ds}$T$_{es}$ $^m$C$_{es}$T$_{es}$T$_e$ | Full PS no conjugate | 143 |
| 655861 | G$_{es}$$^m$C$_{es}$T$_{es}$T$_{es}$ $^m$C$_{es}$A$_{ds}$G$_{ds}$T$_{ds}$ $^m$C$_{ds}$A$_{ds}$T$_{ds}$G$_{ds}$ A$_{ds}$$^m$C$_{ds}$T$_{ds}$T$_{es}$ $^m$C$_{es}$T$_{es}$T$_e$o Ado'-GalNAc3-1a | Full PS with GalNAc3-1 conjugate | 144 |

TABLE 36-continued

Modified ASOs comprising GalNAc$_3$-1 conjugate at the 3' terminus targeting SRB-I

| ISIS No. | Sequence (5' to 3') | Chemistry | SEQ ID No. |
|---|---|---|---|
| 655862 | G$_{es}$$^m$C$_{es}$T$_{eo}$T$_{eo}$ $^m$C$_{eo}$A$_{ds}$G$_{ds}$T$_{ds}$ $^m$C$_{ds}$A$_{ds}$T$_{ds}$G$_{ds}$ A$_{ds}$$^m$C$_{ds}$T$_{ds}$T$_{eo}$ $^m$C$_{eo}$T$_{eo}$T$_e$o Ado'-GalNAc3-1a | Mixed PS/PO with GalNAc3-1 conjugate | 144 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "GalNAc$_3$-1" is shown in Example 9.

Treatment

Six week old male Balb/c mice (Jackson Laboratory, Bar Harbor, ME) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are reported below.

As illustrated in Table 37, treatment with antisense oligonucleotides lowered SRB-1 mRNA levels in a dose-dependent manner compared to PBS treated control. Indeed, the antisense oligonucleotides comprising the GalNAc$_3$-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 37

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | ED$_{50}$ (mg/kg) | Chemistry | SEQ ID No. |
|---|---|---|---|---|---|
| PBS | 0 | 100 | — | — | |
| 353382 (parent) | 3 | 76.65 | 10.4 | Full PS without conjugate | 143 |
| | 10 | 52.40 | | | |
| | 30 | 24.95 | | | |
| 655861 | 0.5 | 81.22 | 2.2 | Full PS with GalNAc$_3$-1 conjugate | 144 |
| | 1.5 | 63.51 | | | |
| | 5 | 24.61 | | | |
| | 15 | 14.80 | | | |

TABLE 37-continued

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | ED$_{50}$ (mg/kg) | Chemistry | SEQ ID No. |
|---|---|---|---|---|---|
| 655862 | 0.5 | 69.57 | 1.3 | Mixed PS/PO with GalNAc$_3$-1 conjugate | 144 |
| | 1.5 | 45.78 | | | |
| | 5 | 19.70 | | | |
| | 15 | 12.90 | | | |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 38) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 38

Effect of PO/PS linkages on transaminase levels of ASOs comprising GalNAc$_3$-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — | |
| 353382 (parent) | 3 | 50.25 | 89 | Full PS without conjugate | 143 |
| | 10 | 27.5 | 79.3 | | |
| | 30 | 27.3 | 97 | | |
| 655861 | 0.5 | 28 | 55.7 | Full PS with GalNAc$_3$-1 | 144 |
| | 1.5 | 30 | 78 | | |
| | 5 | 29 | 63.5 | | |
| | 15 | 28.8 | 67.8 | | |
| 655862 | 0.5 | 50 | 75.5 | Mixed PS/PO with GalNAc$_3$-1 | 144 |
| | 1.5 | 21.7 | 58.5 | | |
| | 5 | 29.3 | 69 | | |
| | 15 | 22 | 61 | | |

Example 45: Preparation of Pfp Ester, Compound 110a

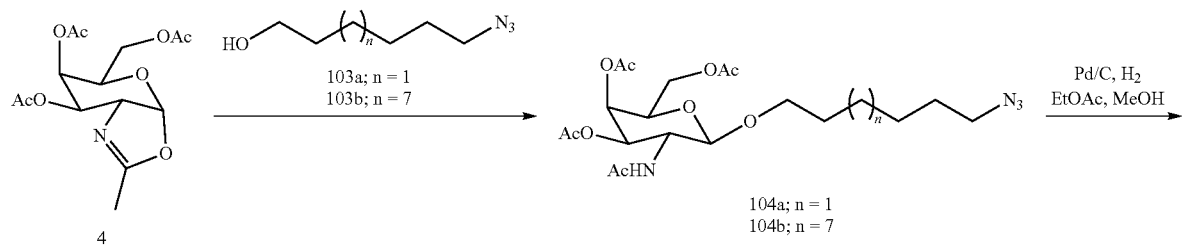

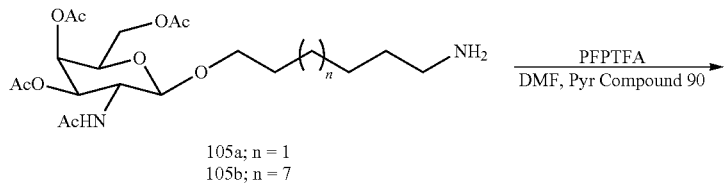

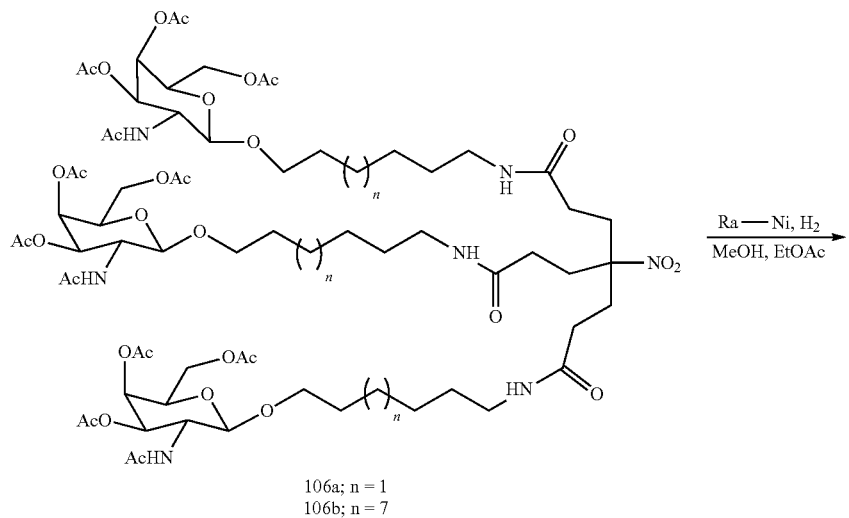

-continued
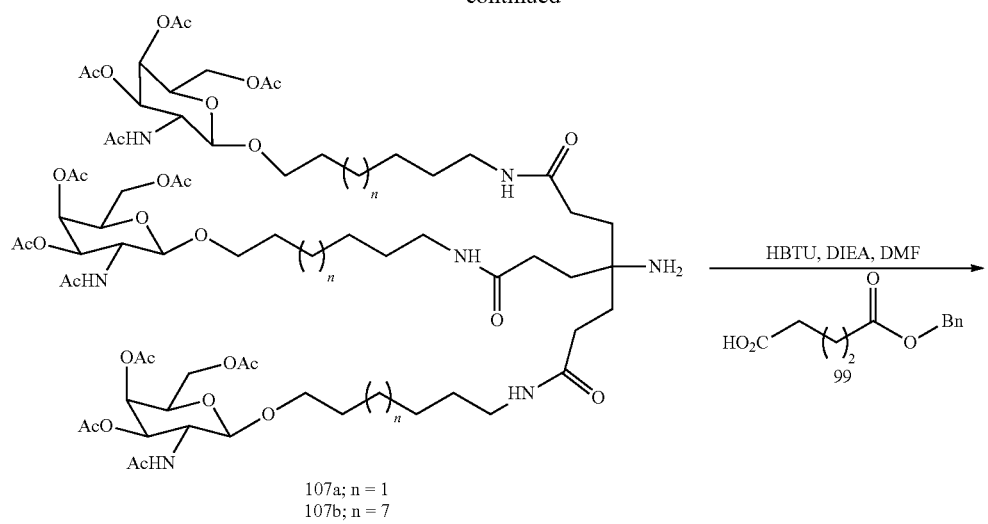
107a; n = 1
107b; n = 7
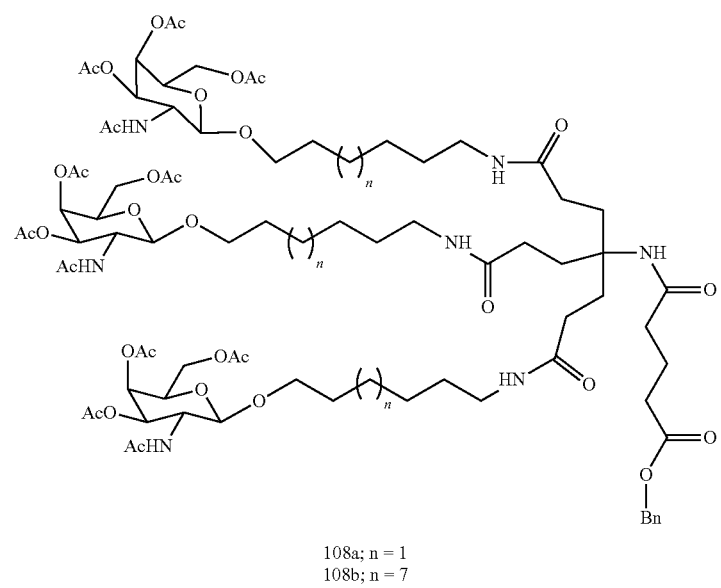
108a; n = 1
108b; n = 7
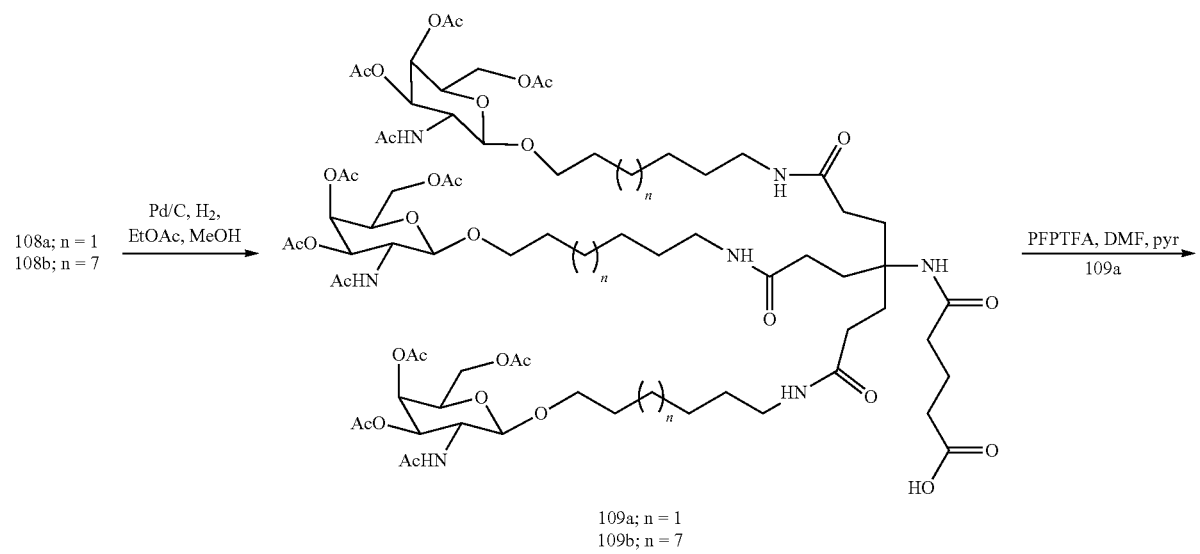
109a; n = 1
109b; n = 7

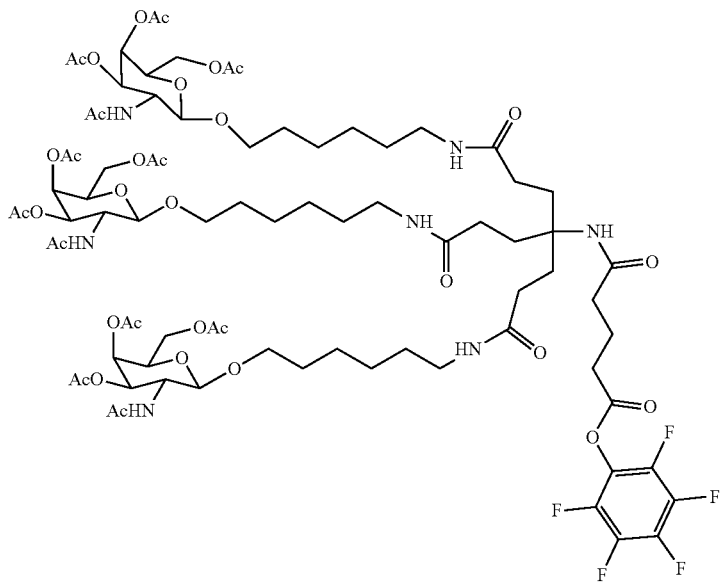

110a

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%-->10% methanol/dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100a-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46: General Procedure for Conjugation with Pfp Esters (Oligonucleotide 111); Preparation of Isis 666881 (GalNAc$_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5 (200 μL) and 3 equivalents of a selected PFP esterified GalNAc$_3$ cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the GalNAc$_3$ conjugated oligonucleotide.

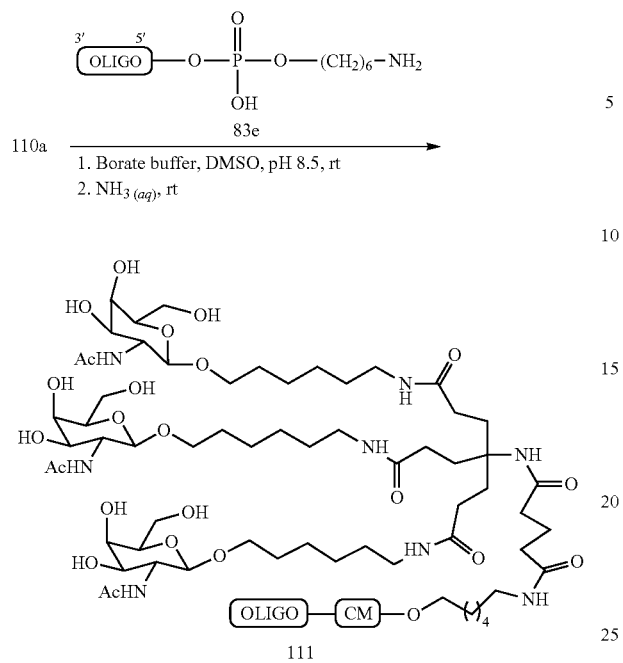

Oligonucleotide 111 is conjugated with GalNAc$_3$-10. The GalNAc$_3$ cluster portion of the conjugate group GalNAc$_3$-10 (GalNAc$_3$-10$_a$) can be combined with any cleavable moiety to provide a variety of conjugate groups. In certain embodiments, the cleavable moiety is —P(=O)(OH)-A$_d$-P(=O)(OH)— as shown in the oligonucleotide (ISIS 666881) synthesized with GalNAc$_3$-10 below. The structure of GalNAc$_3$-10 (GalNAc$_3$-10$_a$-CM-) is shown below:

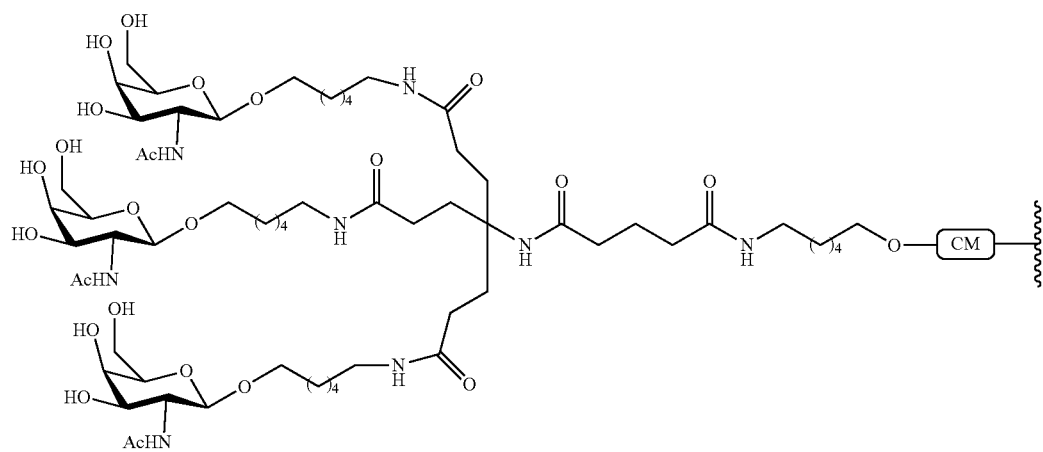

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 μmol) was dissolved in 0.1 M sodium tetraborate, pH 8.5 (200 μL) and 3 equivalents PFP ester (Compound 110a) dissolved in DMSO (50 μL) was added. The PFP ester precipitated upon addition to the ASO solution requiring additional DMSO (600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 μmol).

| GalNAc₃-10 conjugated oligonucleotide | | | |
|---|---|---|---|
| ASO | Sequence (5' to 3') | 5' group | SEQ ID No. |
| ISIS 660254 | NH₂(CH₂)₆-₀A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | Hexylamine | 145 |
| ISIS 666881 | GalNAc3-10a-o'AdoG$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc3-10 | 145 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Example 47: Preparation of Oligonucleotide 102 Comprising GalNAc₃-8

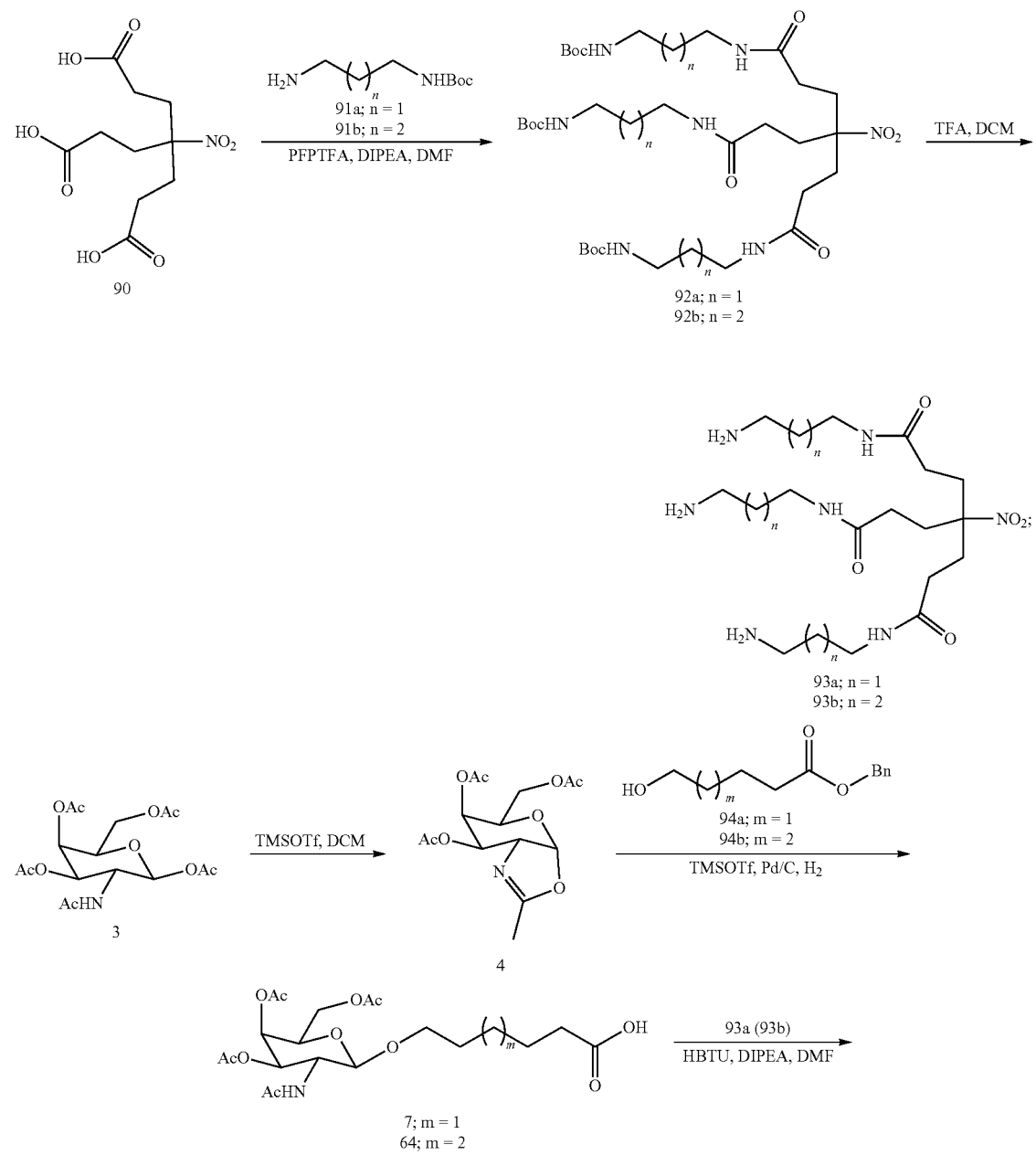

-continued
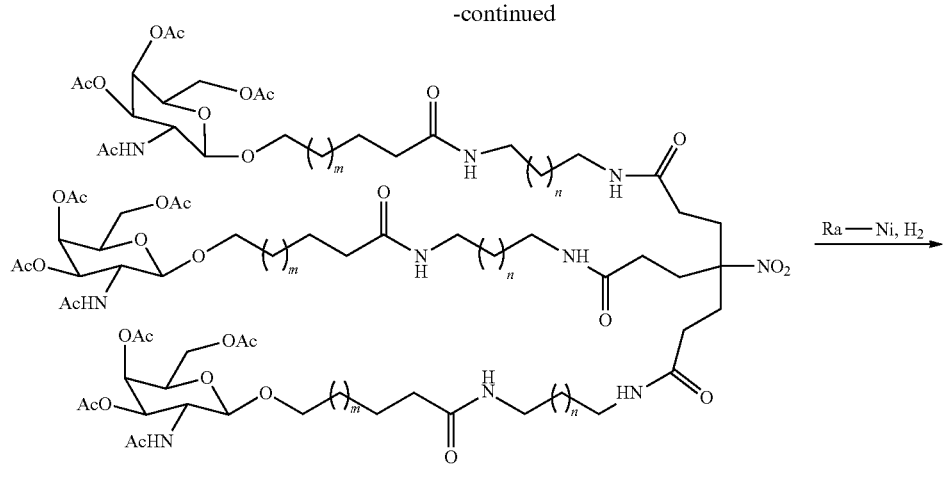
96a; n = 1, m = 1
96b; n = 1, m = 2
96c; n = 2, m = 1
96d; n = 2, m = 2
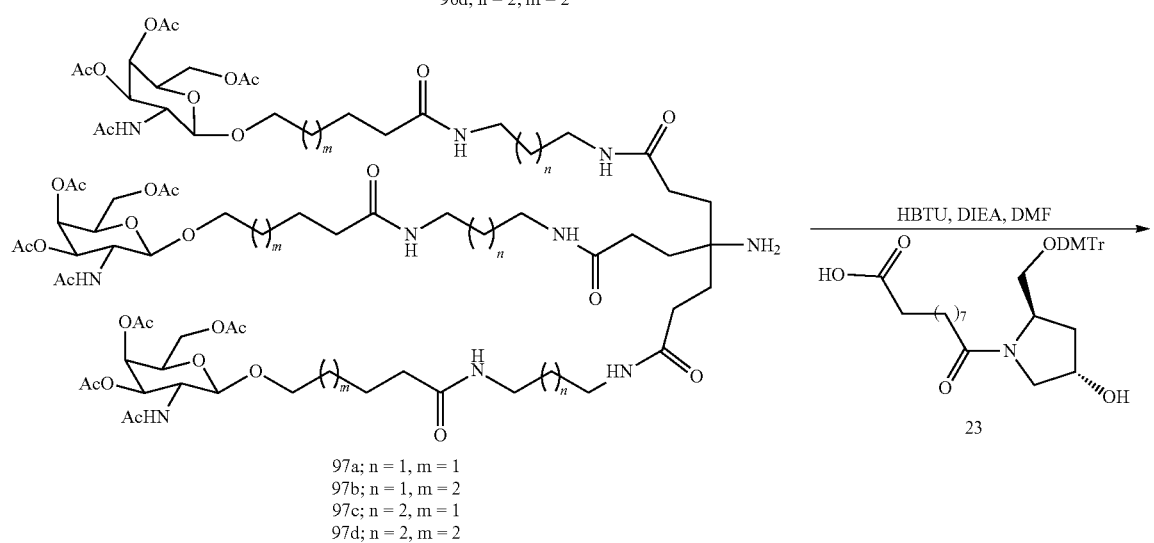
97a; n = 1, m = 1
97b; n = 1, m = 2
97c; n = 2, m = 1
97d; n = 2, m = 2
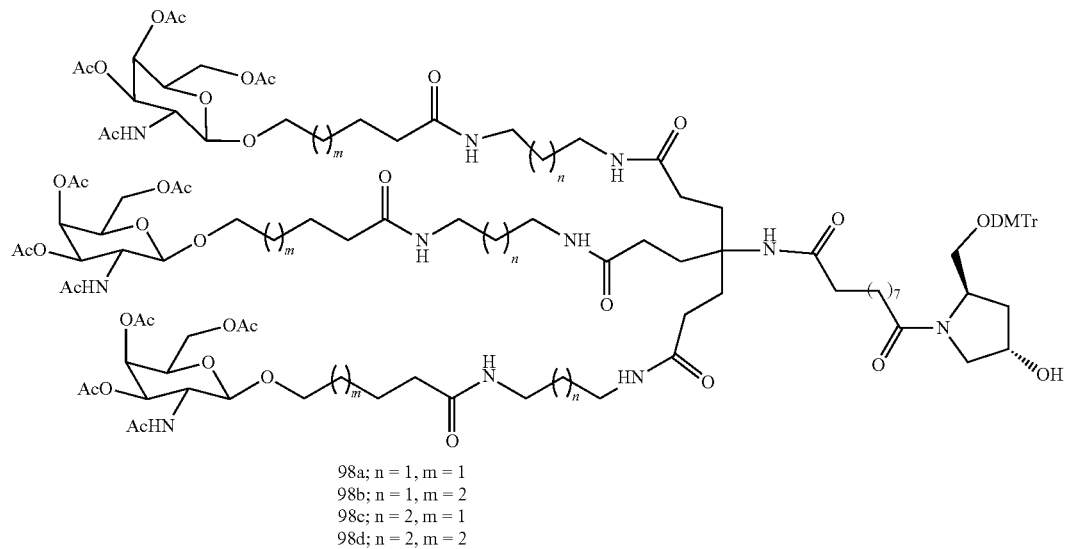
98a; n = 1, m = 1
98b; n = 1, m = 2
98c; n = 2, m = 1
98d; n = 2, m = 2

-continued
97a; n = 1, m = 1
97b; n = 1, m = 2
97c; n = 2, m = 1
97d; n = 2, m = 2
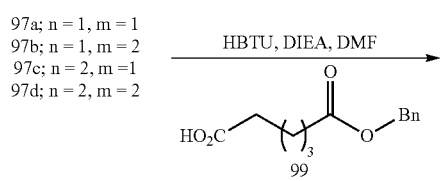
HBTU, DIEA, DMF
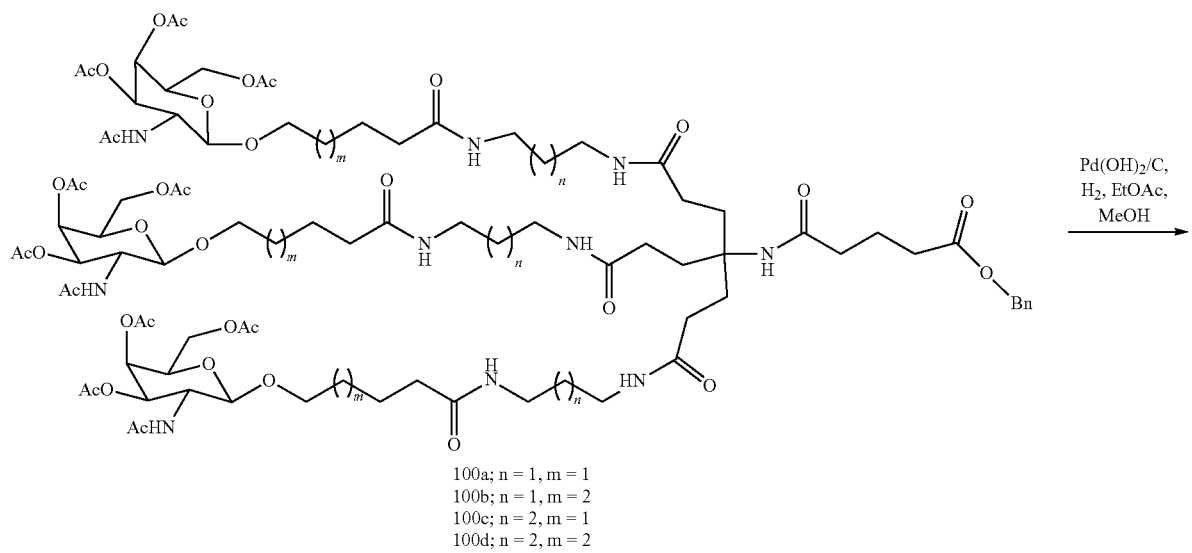
100a; n = 1, m = 1
100b; n = 1, m = 2
100c; n = 2, m = 1
100d; n = 2, m = 2
Pd(OH)₂/C, H₂, EtOAc, MeOH
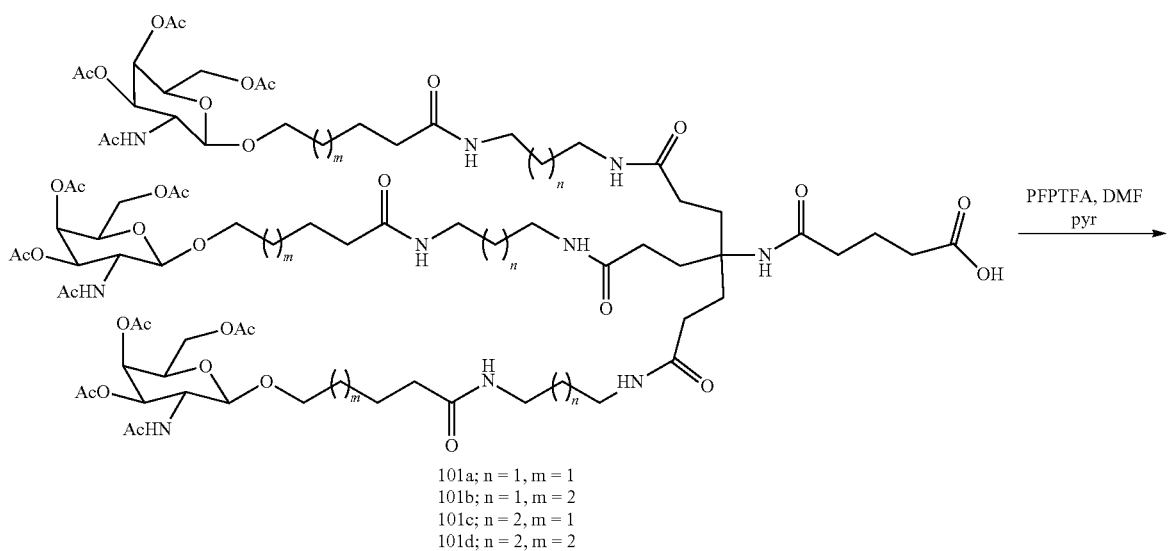
101a; n = 1, m = 1
101b; n = 1, m = 2
101c; n = 2, m = 1
101d; n = 2, m = 2
PFPTFA, DMF pyr

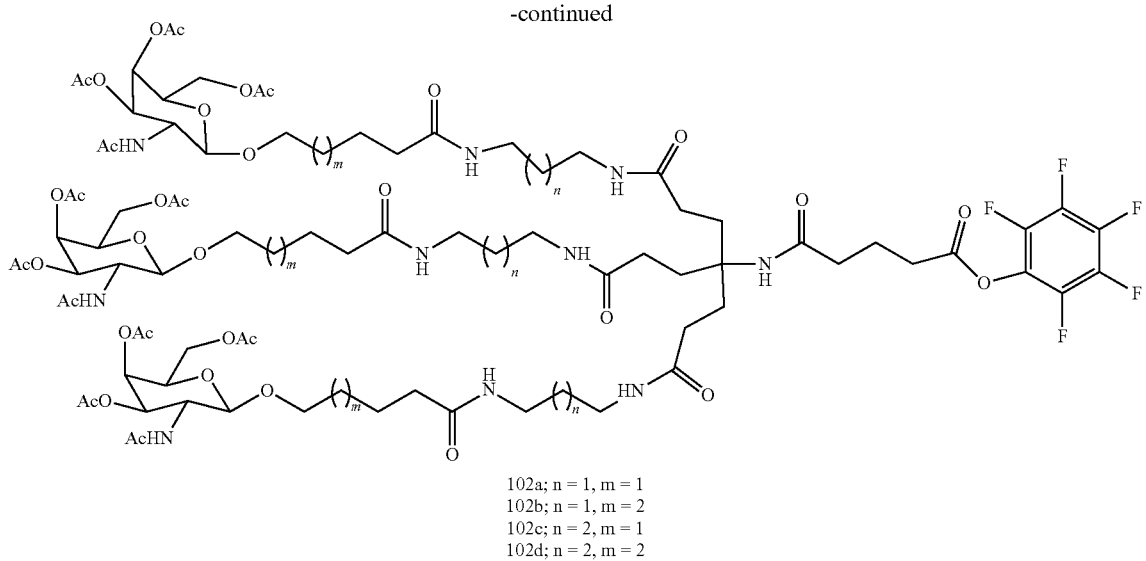

102a; n = 1, m = 1
102b; n = 1, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%-->10% methanol/dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%-->20% methanol/dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%-->20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%-->20% methanol/dichloromethane) to give compounds 100a-d in 40-60% yield. LCMS and proton NMR was consistent with the structure.

Compounds 100a-d (0.16 mmoles), individually, were hydrogenated over 10% Pd(OH)$_2$/C for 3 hours in methanol/ethyl acetate (1.1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%-->50% methanol/dichloromethane) to give compounds 102a-d in an approximate 80% yield. LCMS and proton NMR were consistent with the structure.

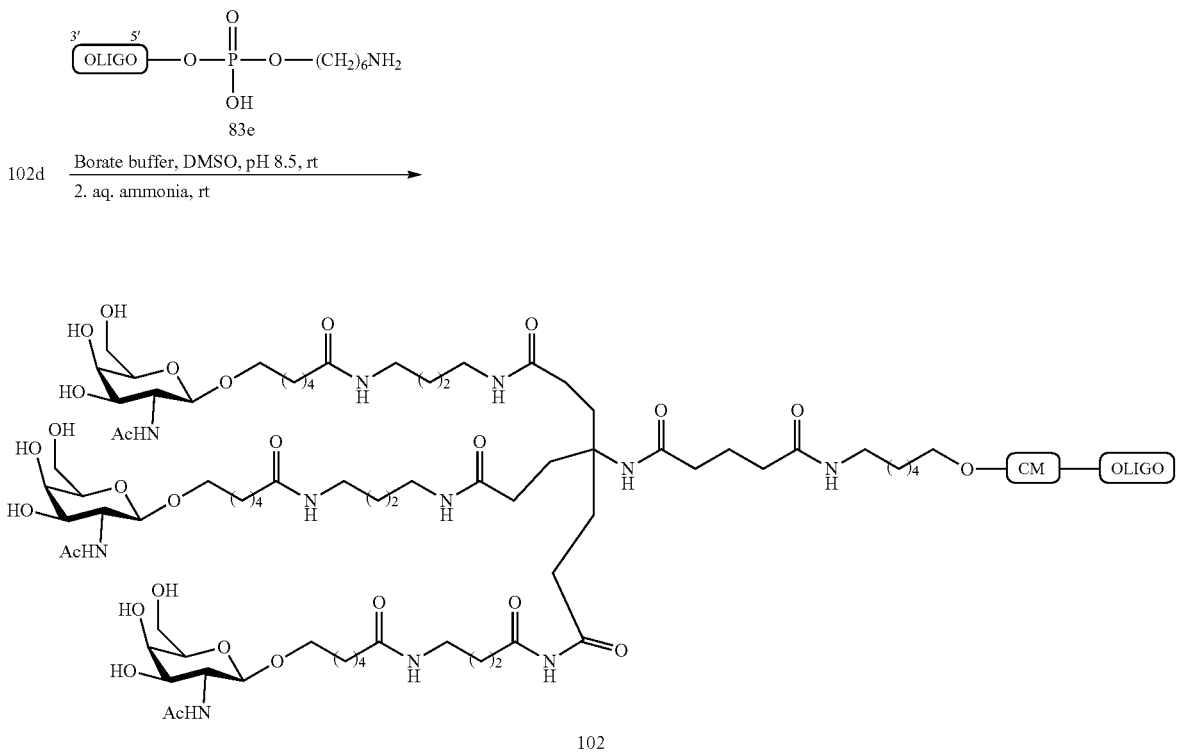

Oligomeric Compound 102, comprising a GalNAc$_3$-8 conjugate group, was prepared using the general procedures illustrated in Example 46. The GalNAc$_3$ cluster portion of the conjugate group GalNAc$_3$-8 (GalNAc$_3$-8$_a$) can be combined with any cleavable moiety to provide a variety of conjugate groups. In a preferred embodiment, the cleavable moiety is —P(=O)(OH)-A$_d$-P(=O)(OH)—.

The structure of GalNAc$_3$-8 (GalNAc$_3$-8$_a$-CM-) is shown below:

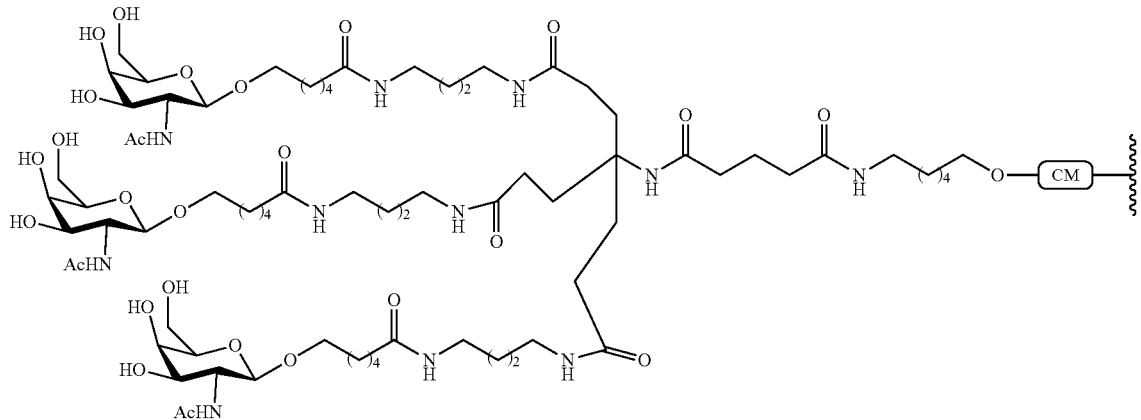

Example 48: Preparation of Oligonucleotide 119 Comprising GalNAc$_3$-7
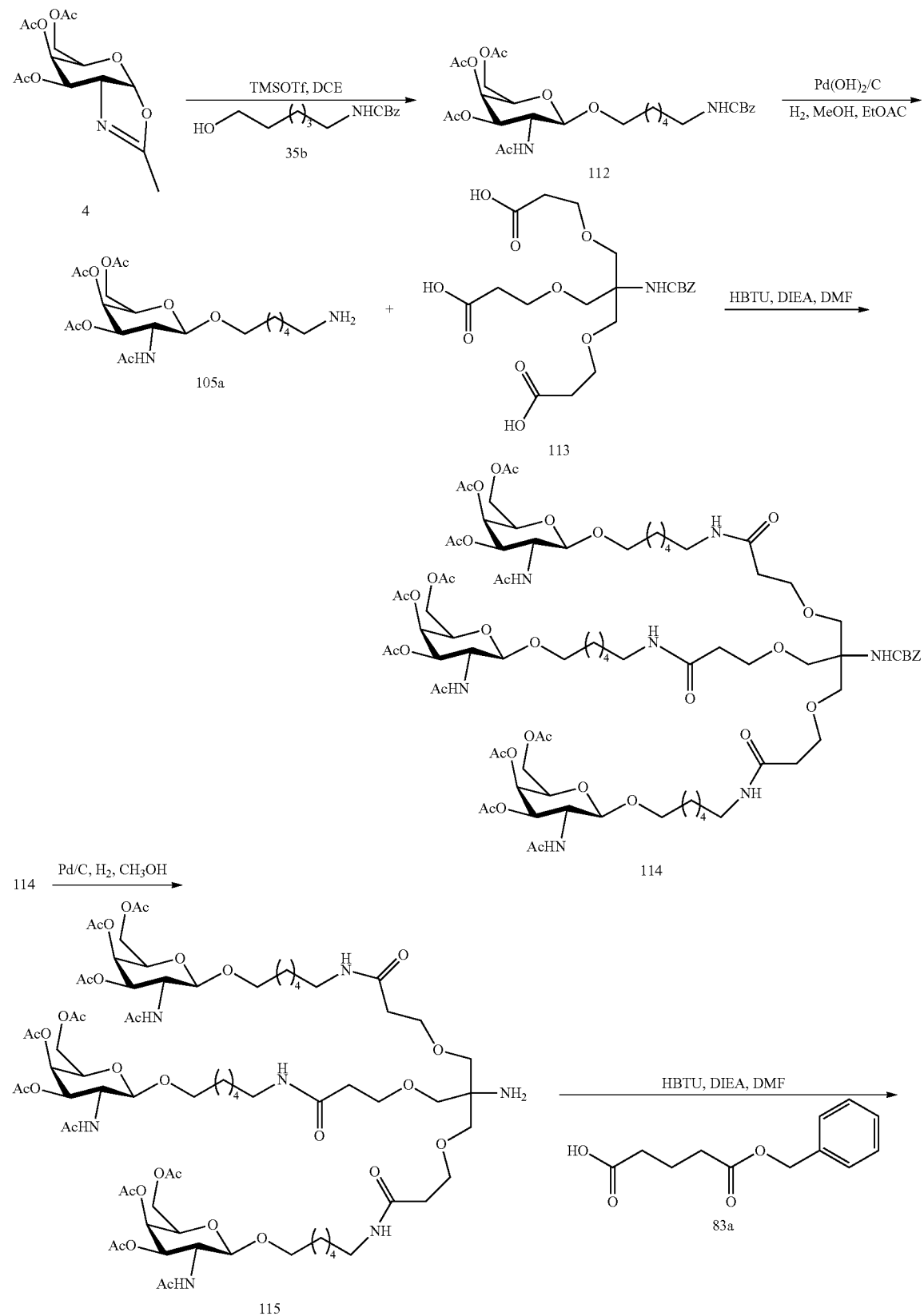

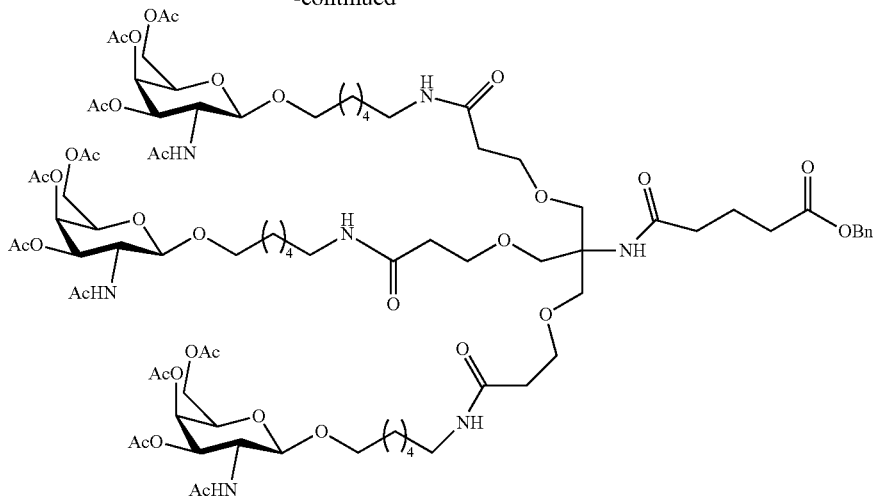

116

Compound 112 was synthesized following the procedure described in the literature (J. Med. Chem. 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in CH$_2$Cl$_2$ (100 mL) and washed with aqueous saturated NaHCO$_3$ solution (100 mL) and brine (100 mL). The organic phase was separated, dried (Na$_2$SO$_4$), filtered and evaporated. The residue was purified by silica gel column chromatography and eluted with 10 to 20% MeOH in dichloromethane to yield Compound 114 (1.45 g, 30%). The structure was confirmed by LCMS and $^1$H NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1$H NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in CH$_2$Cl$_2$. The organic layer was washed aqueous saturated NaHCO$_3$ solution and brine and dried over anhydrous Na$_2$SO$_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1$H NMR analysis.

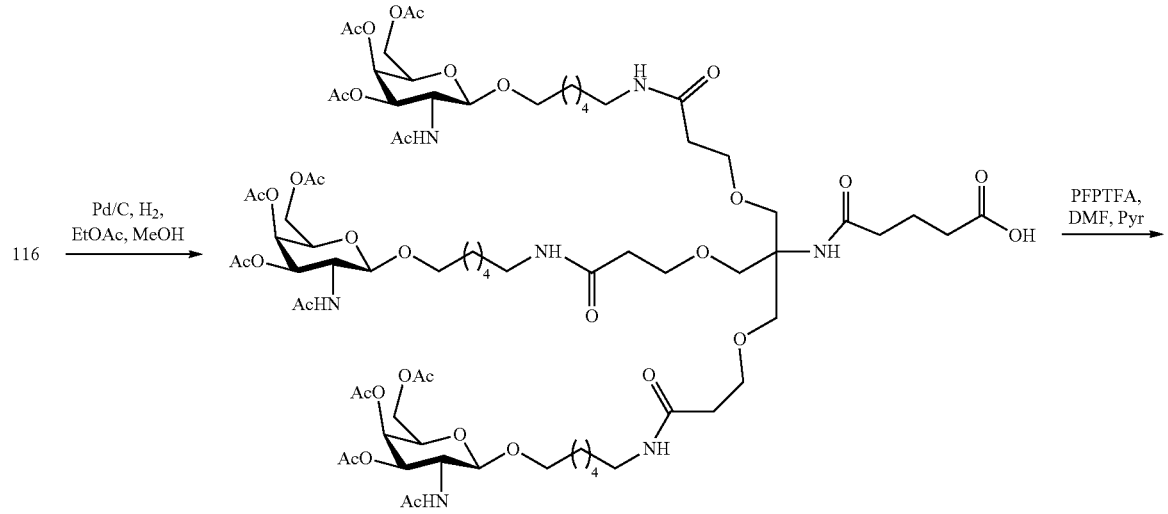

117

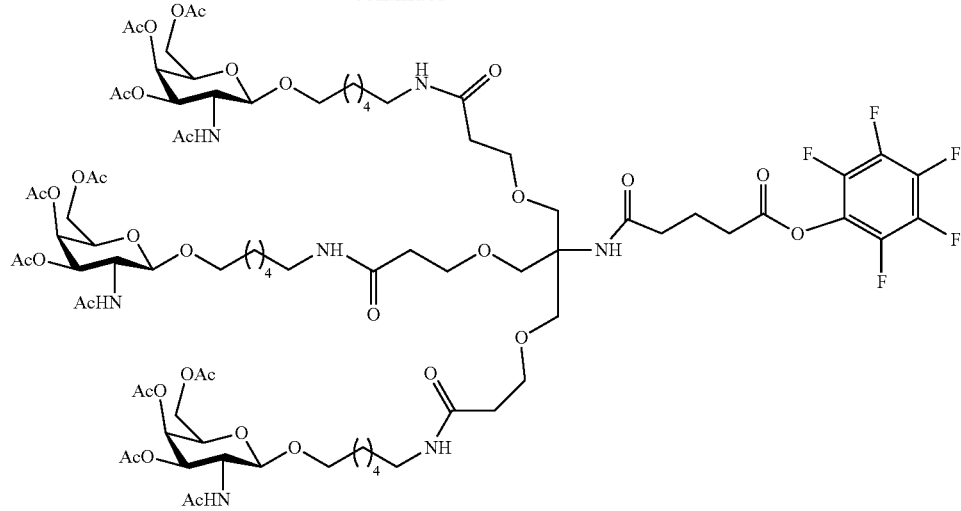

118

Compound 116 (0.74 g, 0.4 mmol) was dissolved in 1:1 methanol/ethyl acetate (5 mL/5 mL). Pall added. The reaction (we was added mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and hH NMR analysis.

Compound 117 (0.63 g, 0.36 mmol) was dissolved in anhydrous DMF (3 mL). To this solution N,N-Diisopropylethylamnine (70 μL, 0.4 mmol) and pentafluorophenyl trifluoroacetate (72 μL, 0.42 mmol) were added. The reaction mixture was stirred at room temperature for 12 h and poured into a aqueous saturated $NaHCO_3$ solution. The mixture was extracted with dichloromethane, washed with brine and dried over anhydrous $Na_2SO_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1H$ and $^1H$ and $^{19}F$ NMR.

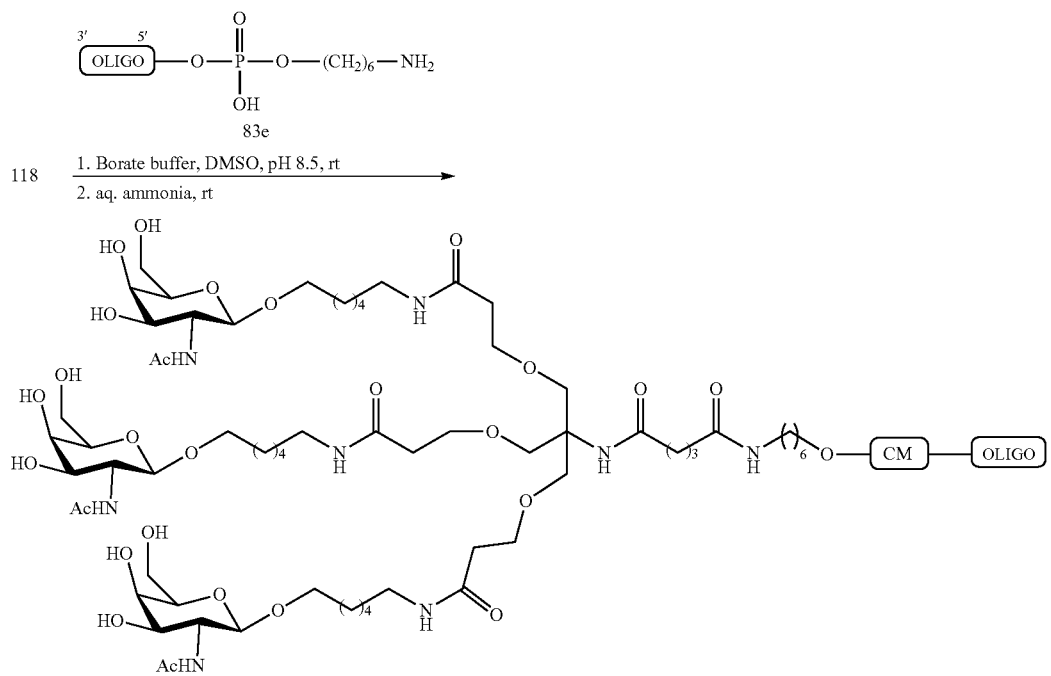

119

Oligomeric Compound 119, comprising a GalNAc₃-7 conjugate group, was prepared using the general procedures illustrated in Example 46. The GalNAc₃ cluster portion of the conjugate group GalNAc₃-7 (GalNAc₃-7$_a$) can be combined with any cleavable moiety to provide a variety of conjugate groups. In certain embodiments, the cleavable moiety is —P(=O)(OH)-A$_d$-P(=O)(OH)—.

The structure of GalNAc₃-7 (GalNAc₃-7$_a$-CM-) is shown below:

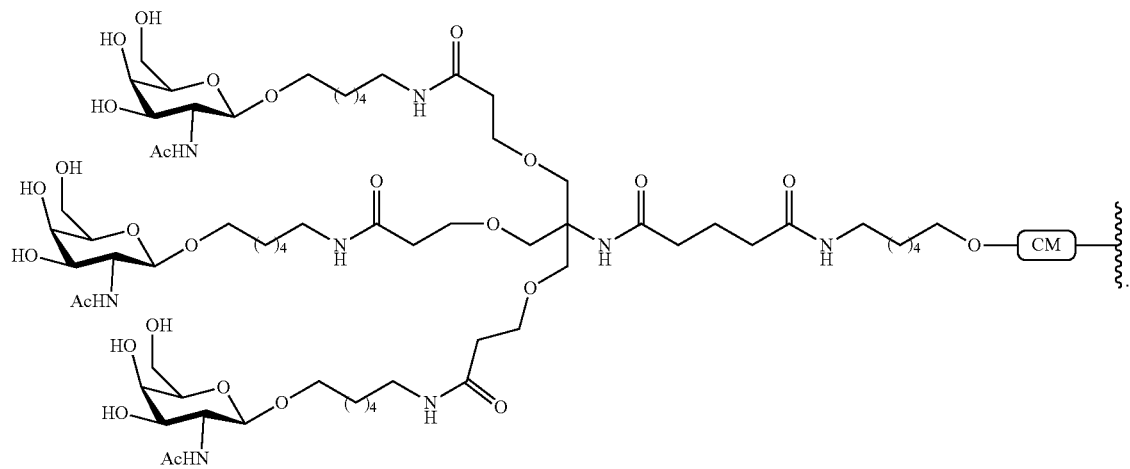

Example 49: Preparation of Oligonucleotide 132 Comprising GalNAc₃-5

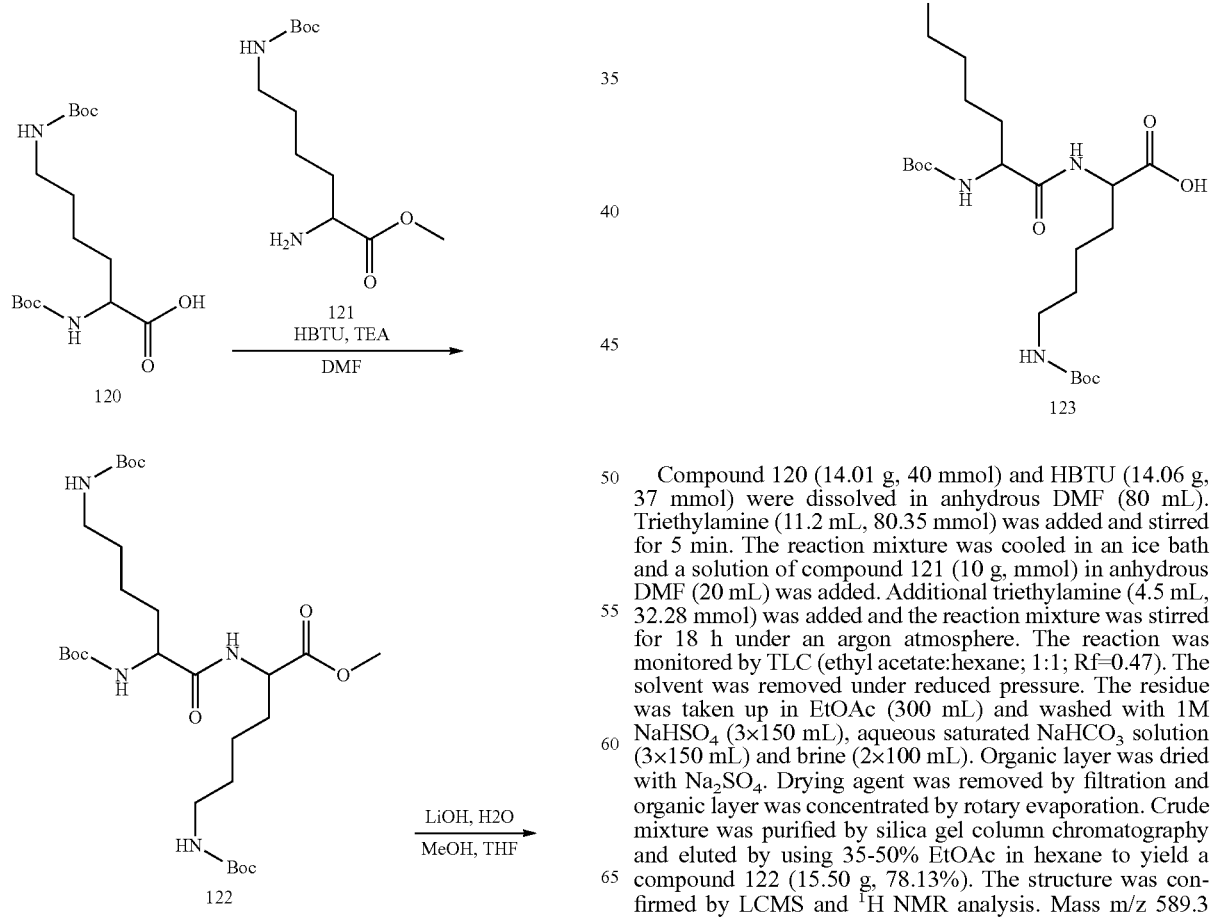

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M NaHSO₄ (3×150 mL), aqueous saturated NaHCO₃ solution (3×150 mL) and brine (2×100 mL). Organic layer was dried with Na₂SO₄. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and ¹H NMR analysis. Mass m/z 589.3 [M+H]⁺.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried (Na$_2$SO$_4$), filtered and evaporated to yield Compound 123 (8.42 g). Residual salt is the likely cause of excess mass. LCMS is consistent with structure. Product was used without any further purification. M. W.cal:574.36; M.W.fd:575.3 [M+H]$^+$.

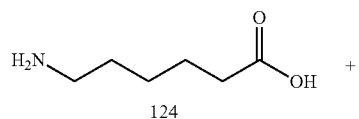

124

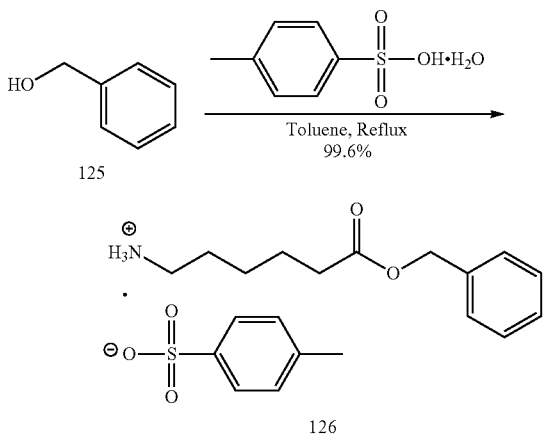

Compound 126 was synthesized following the procedure described in the literature (*J. Am. Chem. Soc.* 2011, 133, 958-963).

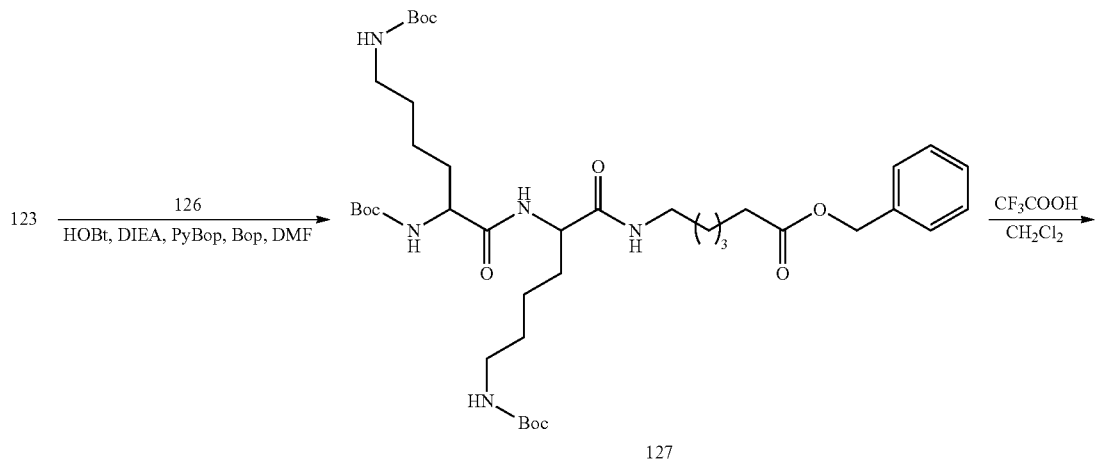

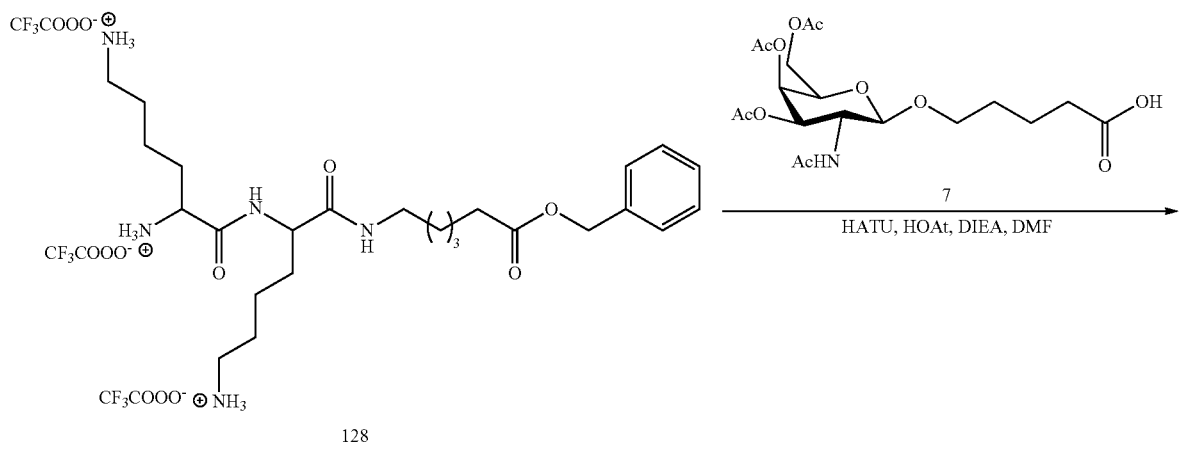

-continued
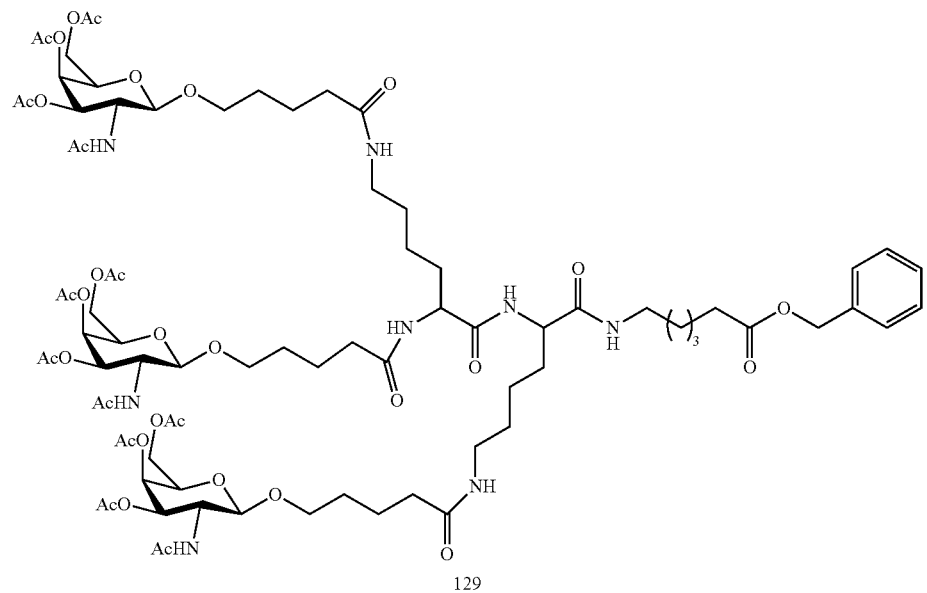
129
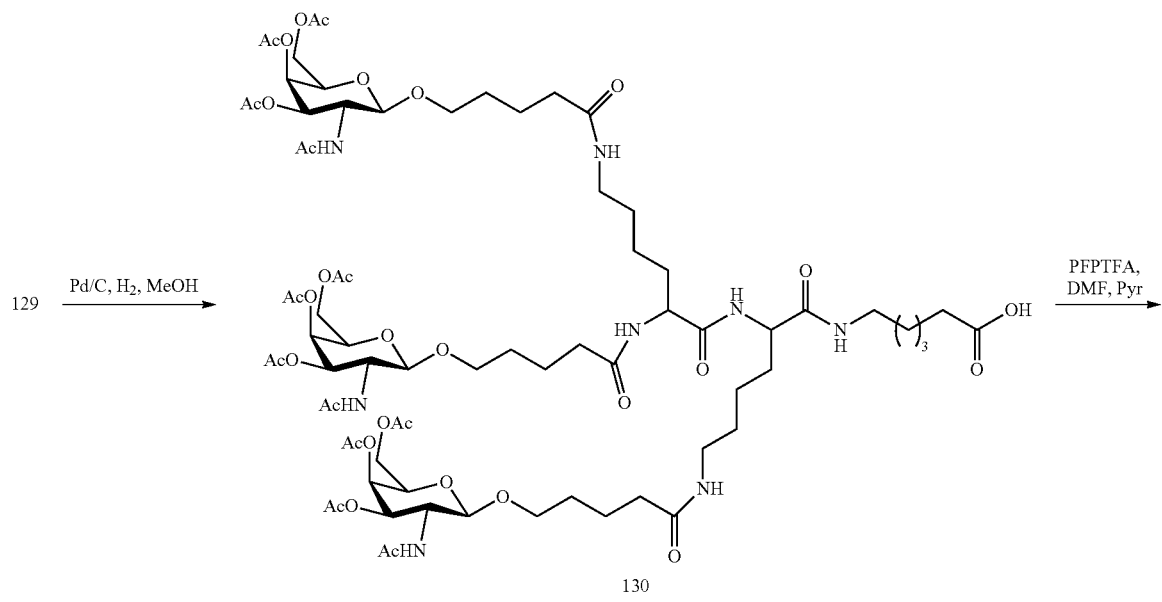
130

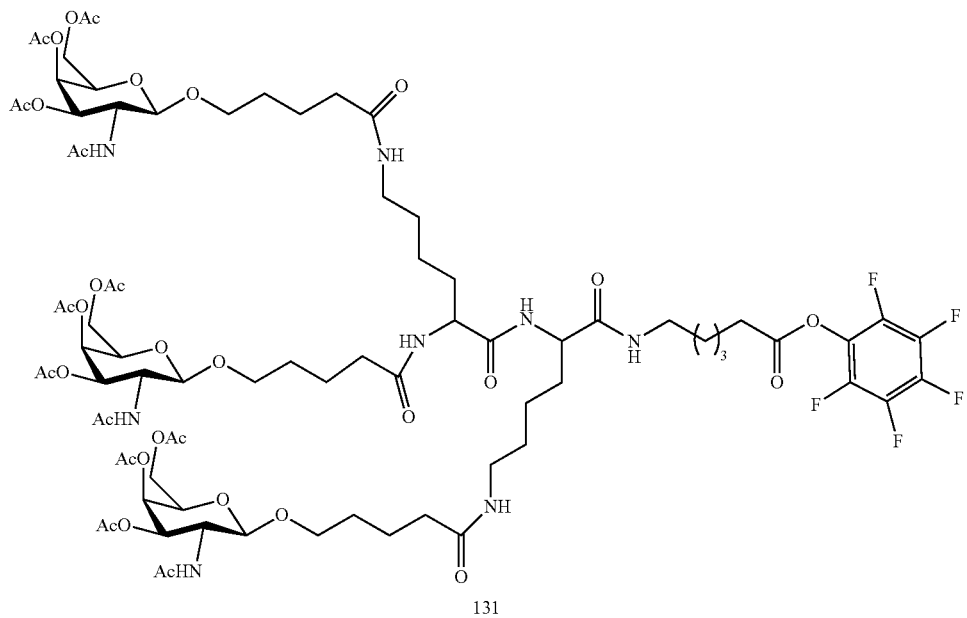

131

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M $NaHSO_4$ (3×100 mL), aqueous saturated $NaHCO_3$ (3×100 mL) and brine (2×100 mL). The organic phase separated dried ($Na_2SO_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m/z 778.4 $[M+H]^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m/z 478.2 $[M+H]^+$.

Compound 7 (0.43 g, 0.963 mmol), HATU (0.35 g, 0.91 mmol), and HOAt (0.035 g, 0.26 mmol) were combined together and dried for 4 h over $P_2O_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M $NaHSO_4$ (3×20 mL), aqueous saturated $NaHCO_3$ (3×20 mL) and brine (3×20 mL). The organic phase was separated, dried over $Na_2SO_4$, filtered and concentrated. The residue was purified by silica gel column chromatography using 5-15% MeOH in dichloromethane to yield Compound 129 (96.6 mg). LC MS and $^1$H NMR are consistent with structure. Mass m/z 883.4 $[M+2H]^+$.

Compound 129 (0.09 g, 0.051 mmol) was dissolved in methanol (5 mL) in 20 mL scintillation vial. To this was added a small amount of 10% Pd/C (0.015 mg) and the reaction vessel was flushed with $H_2$ gas. The reaction mixture was stirred at room temperature under $H_2$ atmosphere for 18 h. The reaction mixture was filtered through a pad of Celite and the Celite pad was washed with methanol. The filtrate washings were pooled together and concentrated under reduced pressure to yield Compound 130 (0.08 g). LCMS and $^1$H NMR were consistent with structure. The product was used without further purification. Mass m/z 838.3 $[M+2H]^+$.

To a 10 mL pointed round bottom flask were added compound 130 (75.8 mg, 0.046 mmol), 0.37 M pyridine/ DMF (200 µL) and a stir bar. To this solution was added 0.7 M pentafluorophenyl trifluoroacetate/DMF (100 µL) drop wise with stirring. The reaction was completed after 1 h as determined by LC MS. The solvent was removed under reduced pressure and the residue was dissolved in $CHCl_3$ (~10 mL). The organic layer was partitioned against $NaHSO_4$ (1 M, 10 mL), aqueous saturated $NaHCO_3$ (10 mL) and brine (10 mL) three times each. The organic phase separated and dried over$Na_2SO_4$, filtered and concentrated to yield Compound 131 (77.7 mg). LCMS is consistent with structure. Used without further purification. Mass m/z 921.3 $[M+2H]^+$.

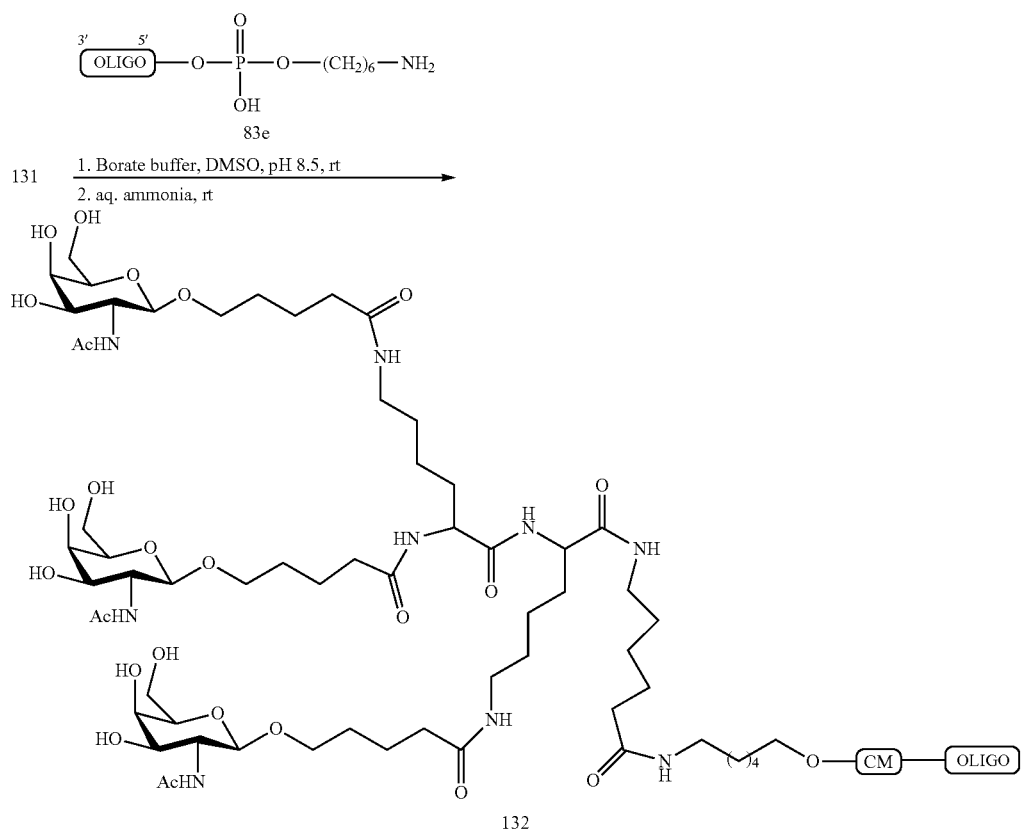

Oligomeric Compound 132, comprising a GalNAc$_3$-5 conjugate group, was prepared using the general procedures illustrated in Example 46. The GalNAc$_3$ cluster portion of the conjugate group GalNAc$_3$-5 (GalNAc$_3$-5$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-5 (GalNAc$_3$-5$_a$-CM-) is shown below:

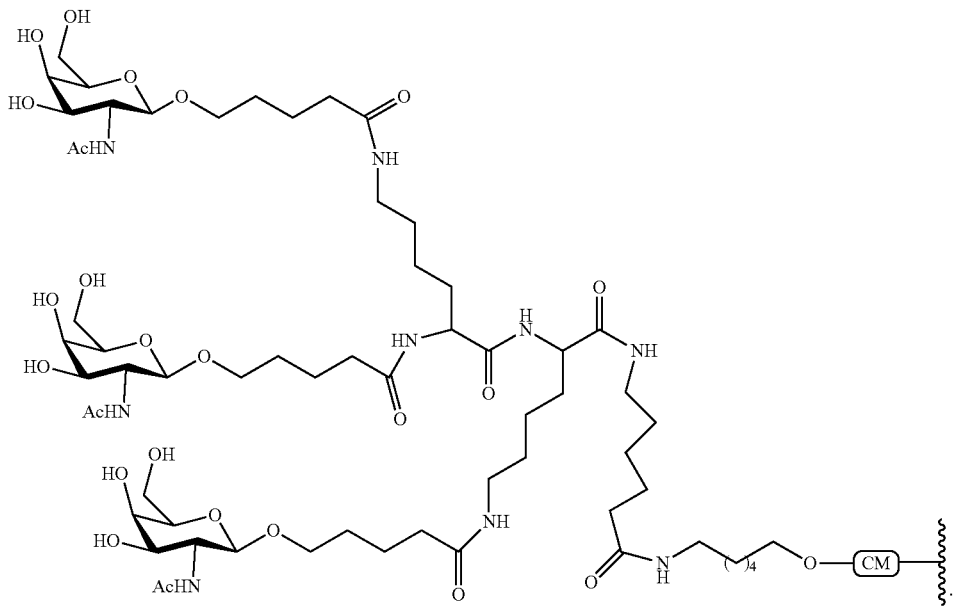

Example 50: Preparation of Oligonucleotide 144 Comprising GalNAc₄-11
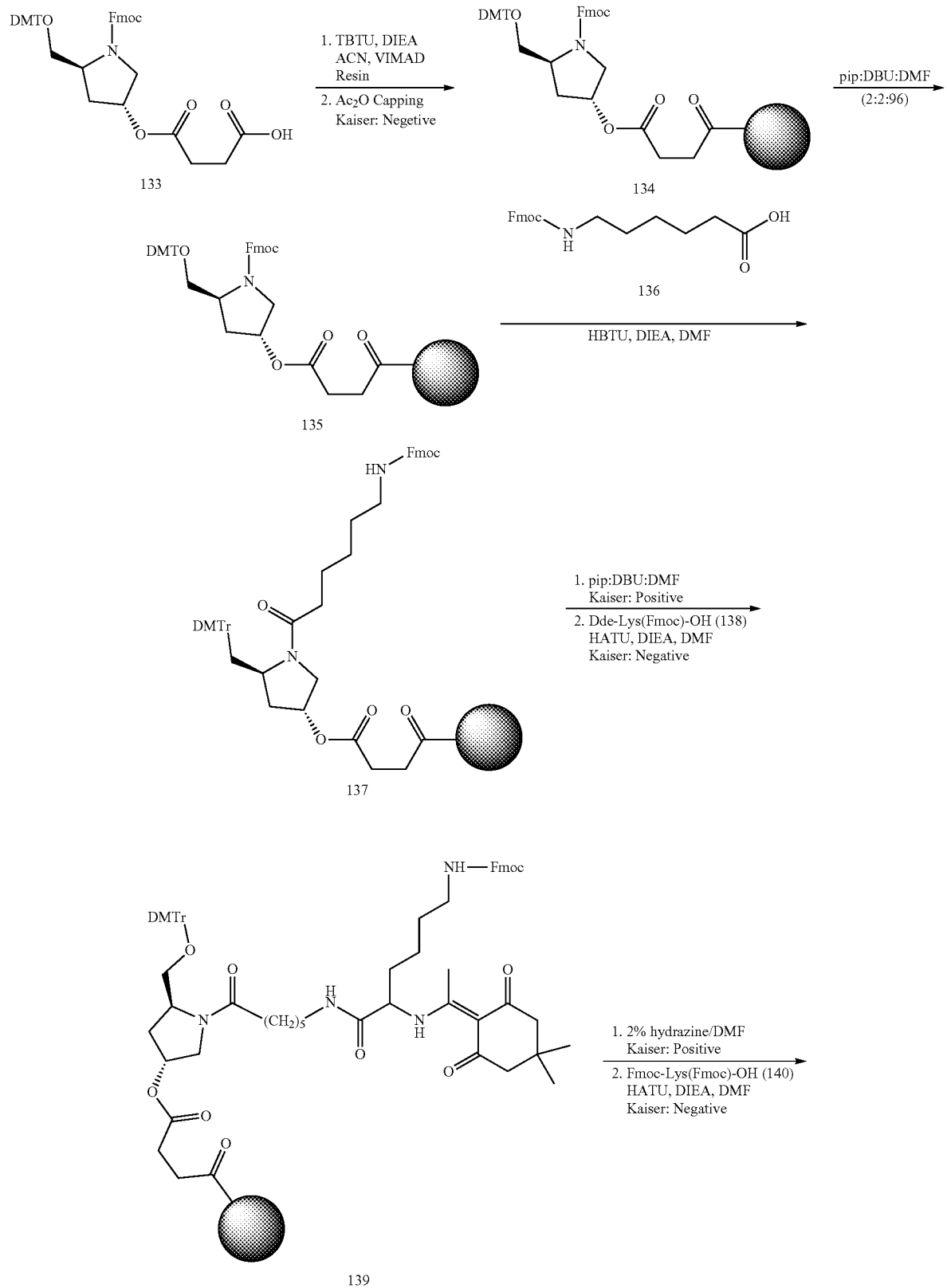

-continued

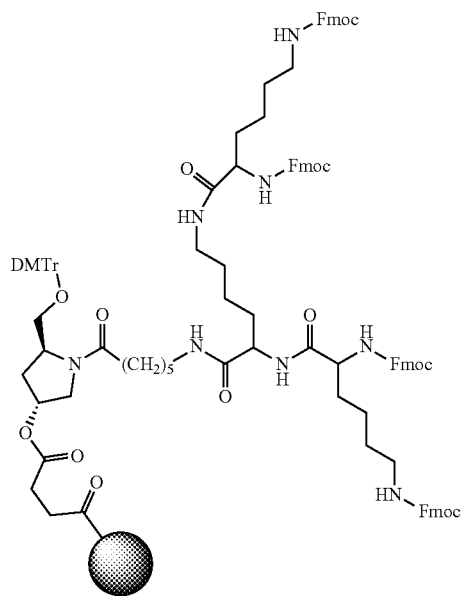

141

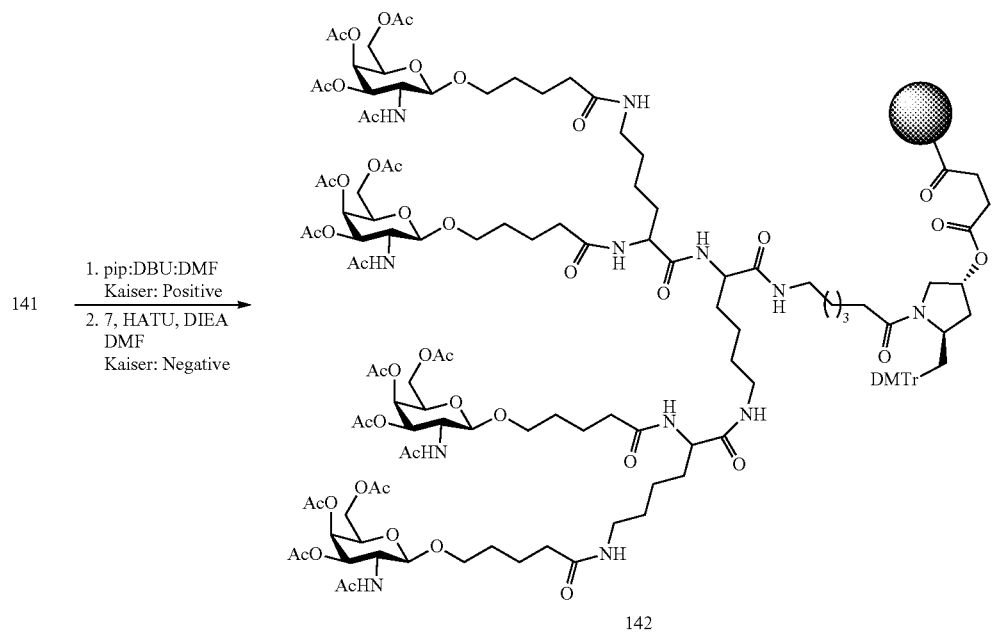

142

Synthesis of Compound 134. To a Merrifield flask was added aminomethyl VIMAD resin (2.5 g, 450 μmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 μmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 [M+2H]$^+$.

The solid support bound compound 142 was synthesized using solid phase peptide synthesis methods.

142 →DNA syntesizer→ 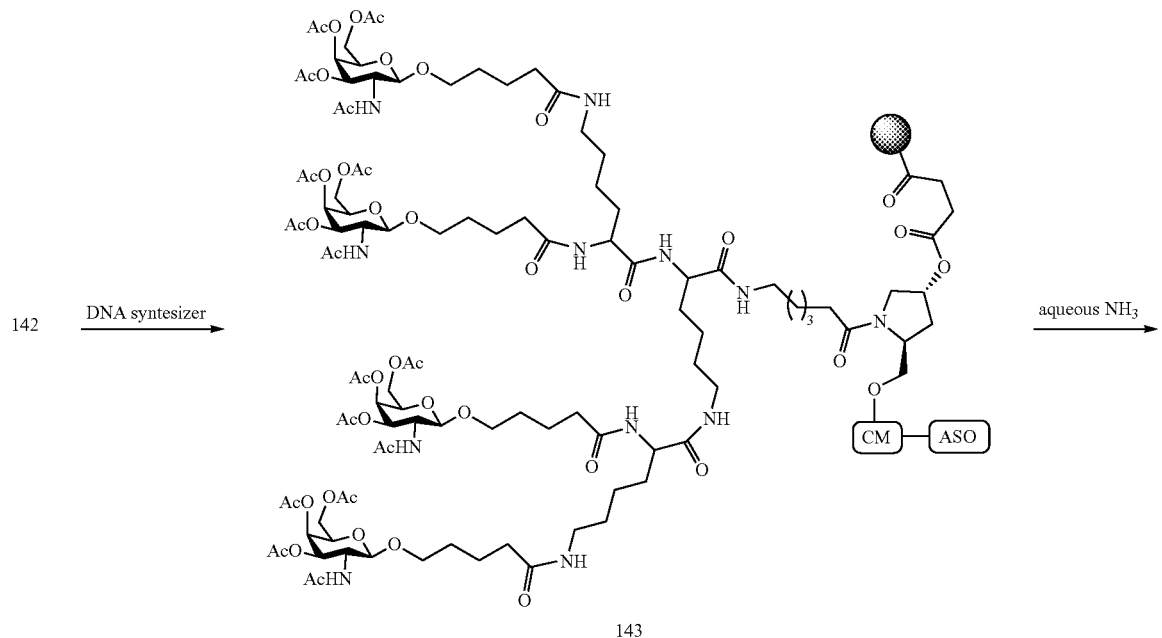 143 →aqueous NH₃→

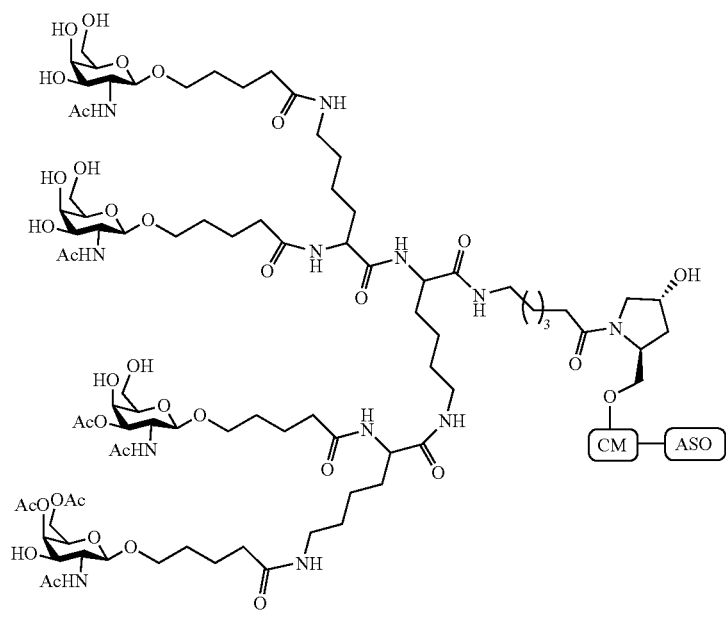 144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting GalNAc₄-11 conjugated oligomeric compound was analyzed by LC-MS and the observed mass was consistent with structure.

The GalNAc₄ cluster portion of the conjugate group GalNAc₄-11 (GalNAc₄-11$_a$) can be combined with any cleavable moiety to provide a variety of conjugate groups. In certain embodiments, the cleavable moiety is —P(=O)(OH)-A$_d$-P(=O)(OH)—.

The structure of GalNAc₄-11 (GalNAc₄-11$_a$-CM) is shown below:

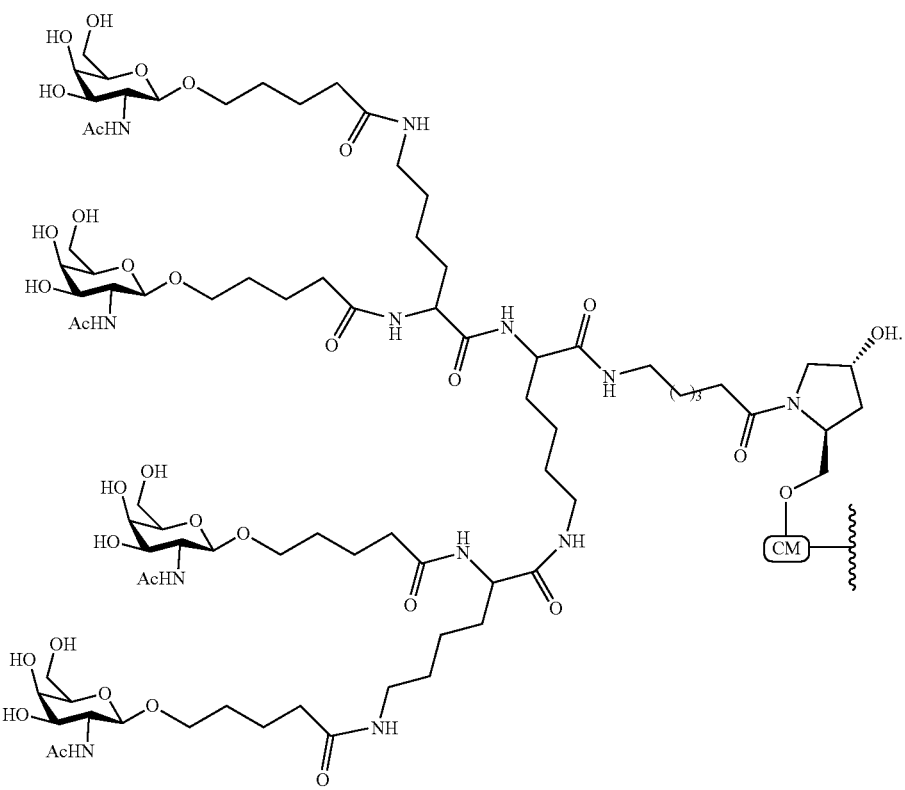
Example 51: Preparation of Oligonucleotide 155 Comprising GalNAc₃-6
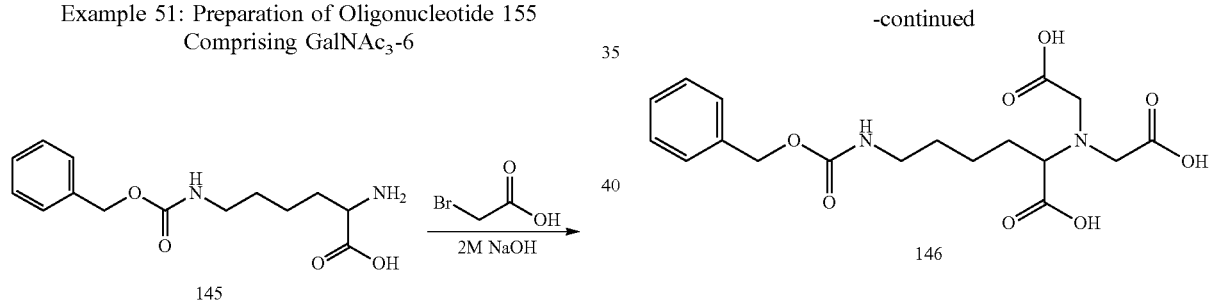
Compound 146 was synthesized as described in the literature (Analytical Biochemistry 1995, 229, 54-60).
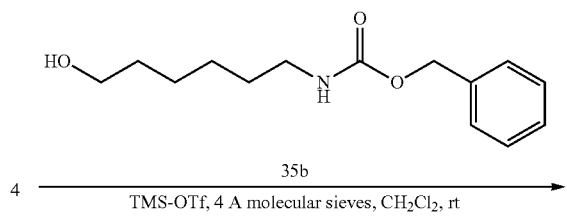
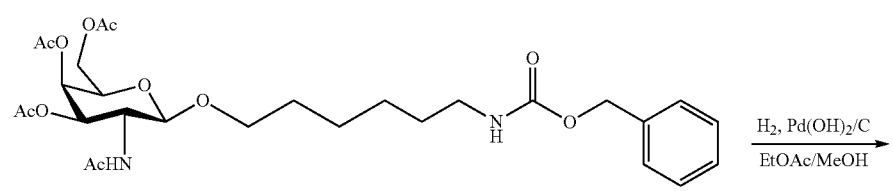

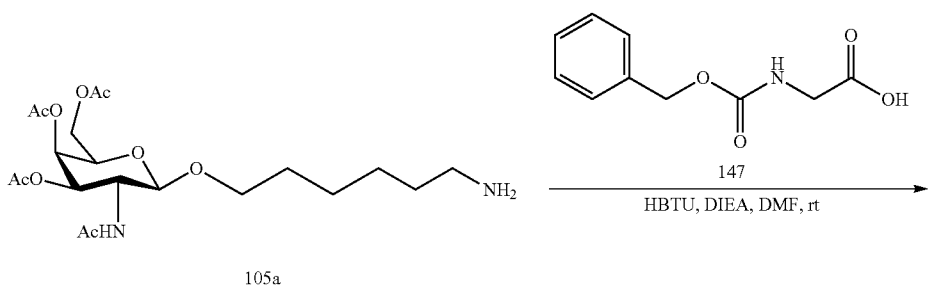

105a

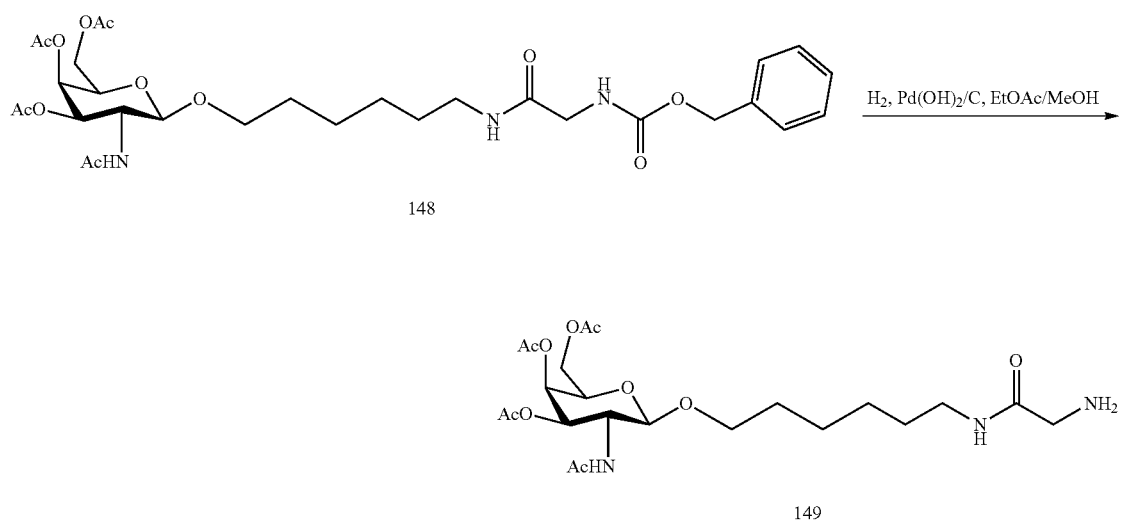

148

149

Compound 4 (15 g, 45.55 mmol) and compound 35b (14.3 grams, 57 mmol) were dissolved in CH$_2$Cl$_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous NaHCO$_3$ (500 ml) and crushed ice (~150 g). The organic layer was separated, washed with brine, dried over MgSO$_4$, filtered, and was concentrated to an orange oil under reduced pressure. The crude material was purified by silica gel column chromatography and eluted with 2-10% MeOH in CH$_2$Cl$_2$ to yield Compound 112 (16.53 g, 63%). LCMS and $^1$H NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in CH$_2$Cl$_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous NaHCO$_3$ and brine. The organics phase was separated, dried (MgSO$_4$), filtered, and concentrated to an orange syrup. The crude material was purified by column chromatography 2-5% MeOH in CH$_2$Cl$_2$ to yield Compound 148 (3.44 g, 73%). LCMS and $^1$H NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

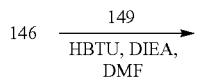

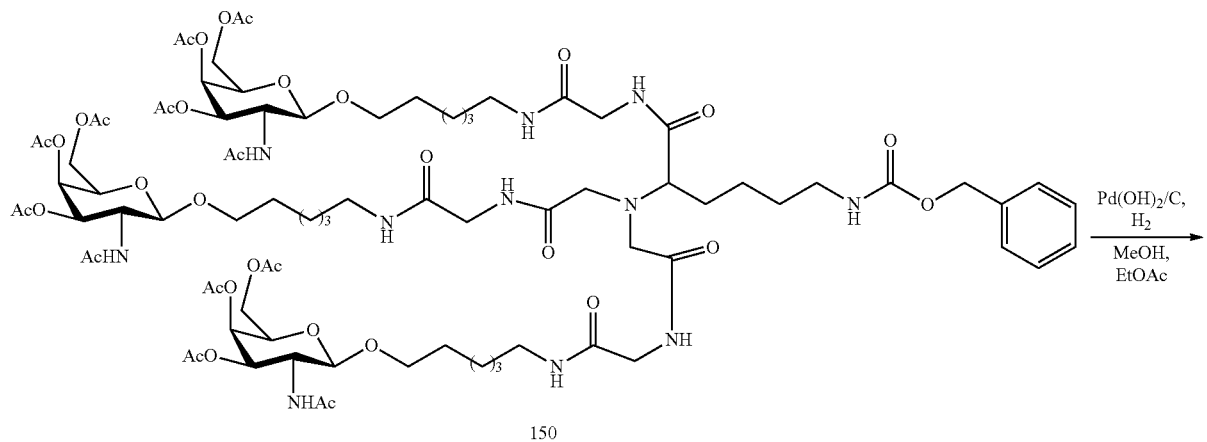

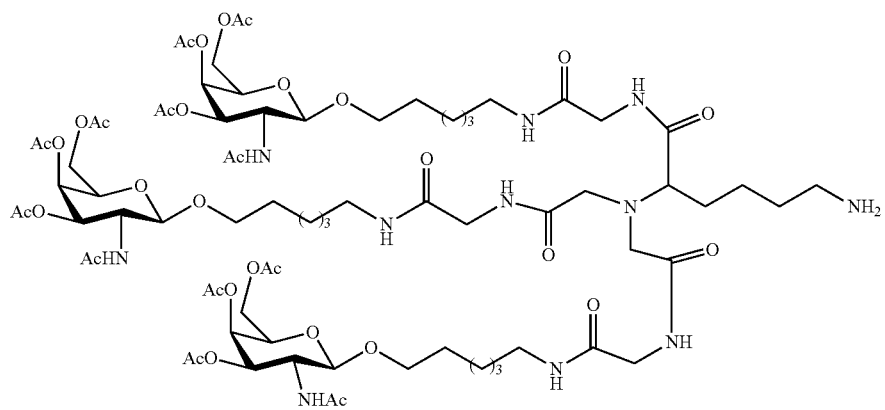

Compound 146 (0.68 g, 1.73 mmol) was dissolved in dry DMF (20 ml). To this DIEA (450 µL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous NaHCO$_3$, followed by brine. The organic phase was separated, dried over MgSO$_4$, filtered, and concentrated. The residue was purified by silica gel column chromatography and eluted with 2-10% MeOH in CH$_2$Cl$_2$ to yield Compound 150 (0.62 g, 20%). LCMS and $^1$H NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

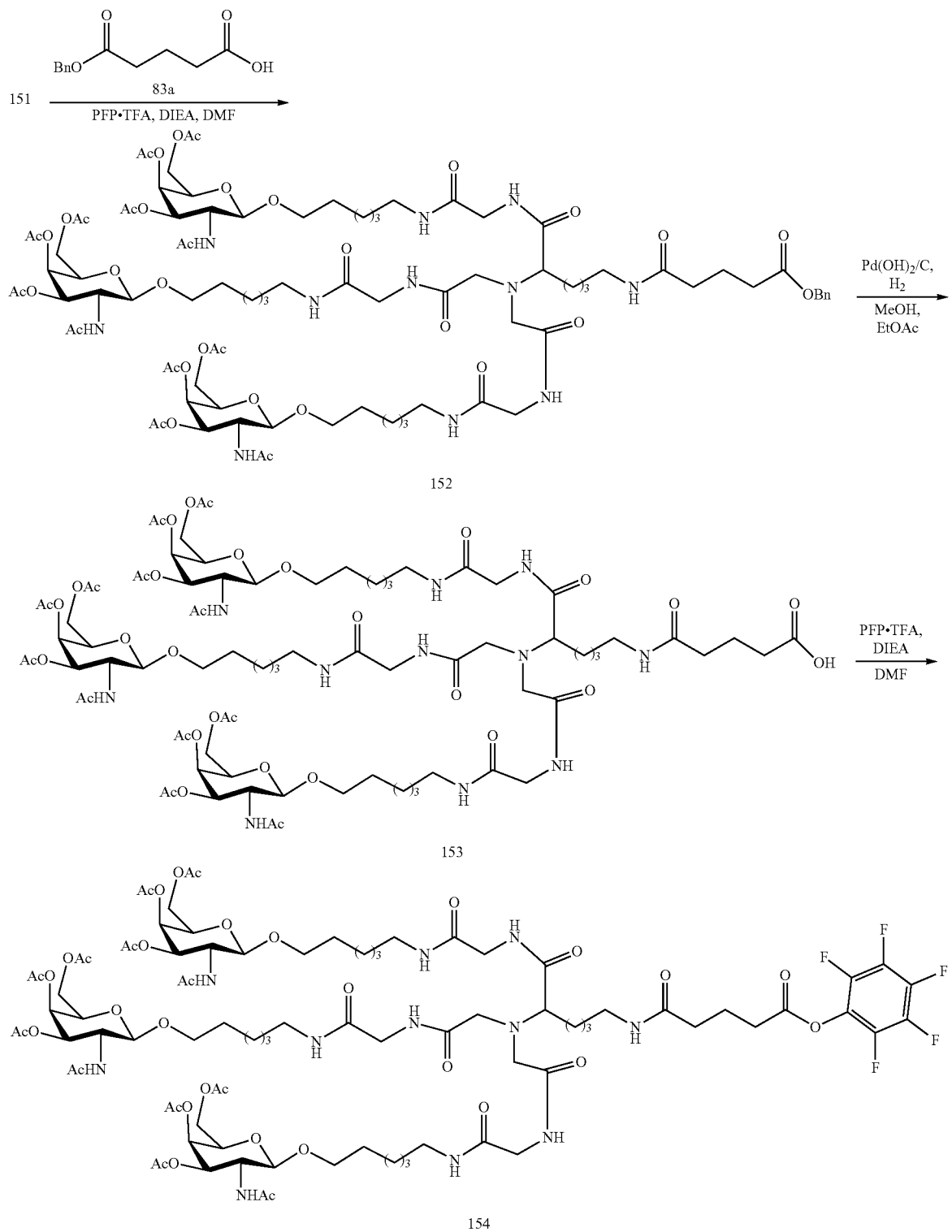

Compound 83a (0.11 g, 0.33 mmol) was dissolved in anhydrous DMF (5 mL) and N,N-Diisopropylethylamine (75 μL, 1 mmol) and PFP-TFA (90 μL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min. Upon completion, the majority of the solvent was removed under reduced pressure. The residue was diluted with CH$_2$Cl$_2$ and washed with aqueous saturated NaHCO$_3$, followed by brine. The organic phase separated, dried over MgSO$_4$, filtered, and concentrated to an orange syrup. The residue was purified by silica gel column chromatography (2-10% MeOH in CH$_2$Cl$_2$) to yield Compound 152 (0.35 g, 55%). LCMS and H NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 µL, 0.37 mmol) and PFP-TFA (35 µL, 0.28 mmol) were added. The reaction mixture was stirred under nitrogen for ~ 30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with CH$_2$Cl$_2$ (50 mL), and washed with saturated aqueous NaHCO$_3$, followed by brine. The organic layer was dried over MgSO$_4$, filtered, and concentrated to an orange syrup. The residue was purified by column chromatography and eluted with 2-10% MeOH in CH$_2$Cl$_2$ to yield Compound 154 (0.29 g, 79%). LCMS and $^1$H NMR were consistent with the desired product.

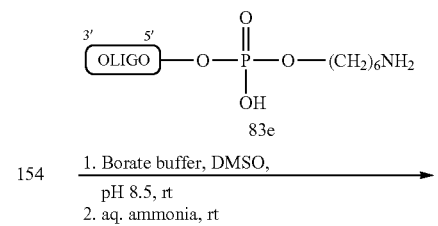

154

1. Borate buffer, DMSO, pH 8.5, rt
2. aq. ammonia, rt

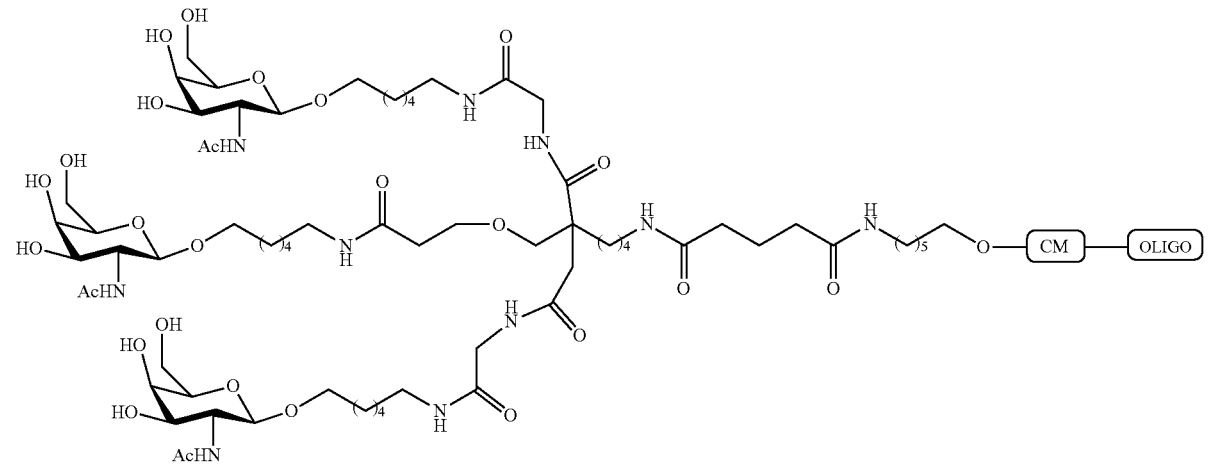

155

Oligomeric Compound 155, comprising a GalNAc$_3$-6 conjugate group, was prepared using the general procedures illustrated in Example 46. The GalNAc$_3$ cluster portion of the conjugate group GalNAc$_3$-6 (GalNAc$_3$-6$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-6 (GalNAc$_3$-6$_a$-CM-) is shown below:

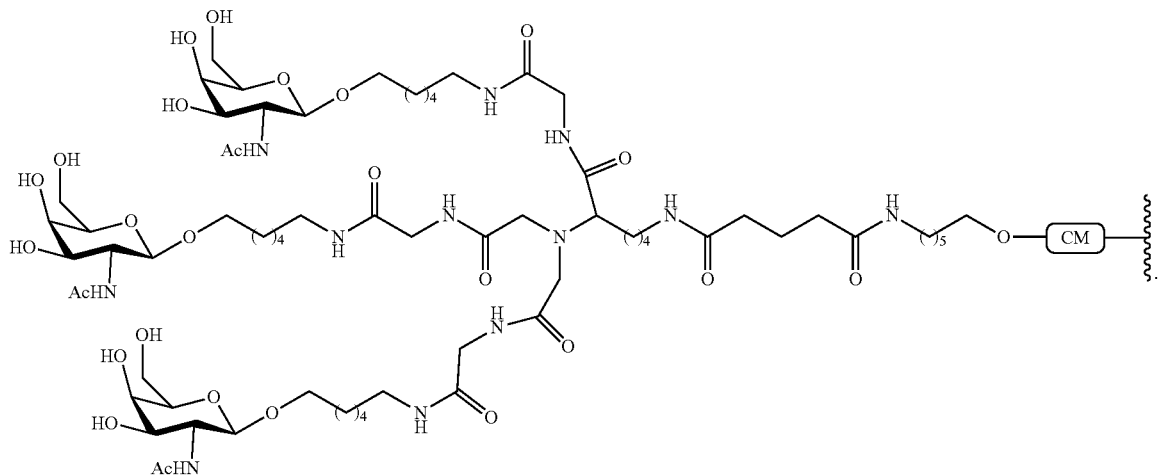

Example 52: Preparation of Oligonucleotide 160 Comprising GalNAc$_3$-9

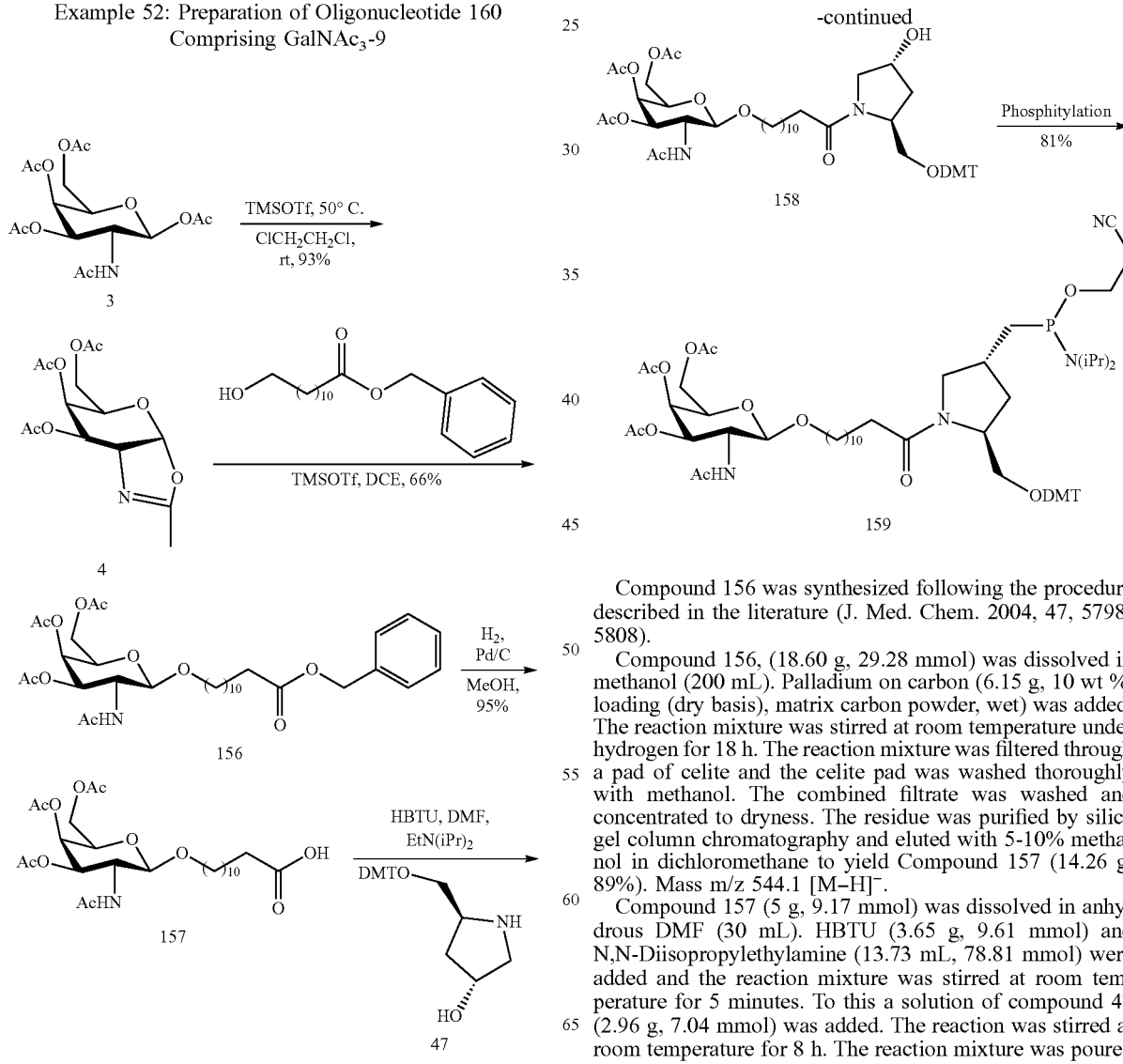

Compound 156 was synthesized following the procedure described in the literature (J. Med. Chem. 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 [M−H]$^−$.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated NaHCO$_3$ aqueous solution. The mixture was extracted with ethyl acetate and the organic layer was washed with brine and dried (Na$_2$SO$_4$), filtered and evaporated. The residue obtained was purified by silica gel column chromatography and eluted with 50% ethyl acetate in hexane to yield compound 158 (8.25 g, 73.3%). The structure was confirmed by MS and $^1$H NMR analysis.

Compound 158 (7.2 g, 7.61 mmol) was dried over P$_2$O$_5$ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated NaHCO$_3$ and brine. The organic phase was separated, dried (Na$_2$SO$_4$), filtered and evaporated. The residue was purified by silica gel column chromatography and eluted with 50-90% ethyl acetate in hexane to yield Compound 159 (7.82 g, 80.5%). The structure was confirmed by LCMS and $^{31}$P NMR analysis.

Oligomeric Compound 160, comprising a GalNAc$_3$-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160. The GalNAc$_3$ cluster portion of the conjugate group Gal-NAc$_3$-9 (GalNAc$_3$-9$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-9 (GalNAc$_3$-9$_a$-CM) is shown below:

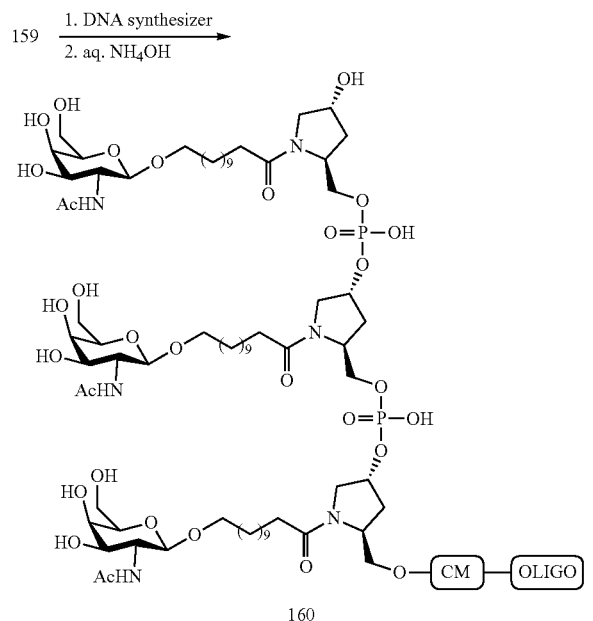

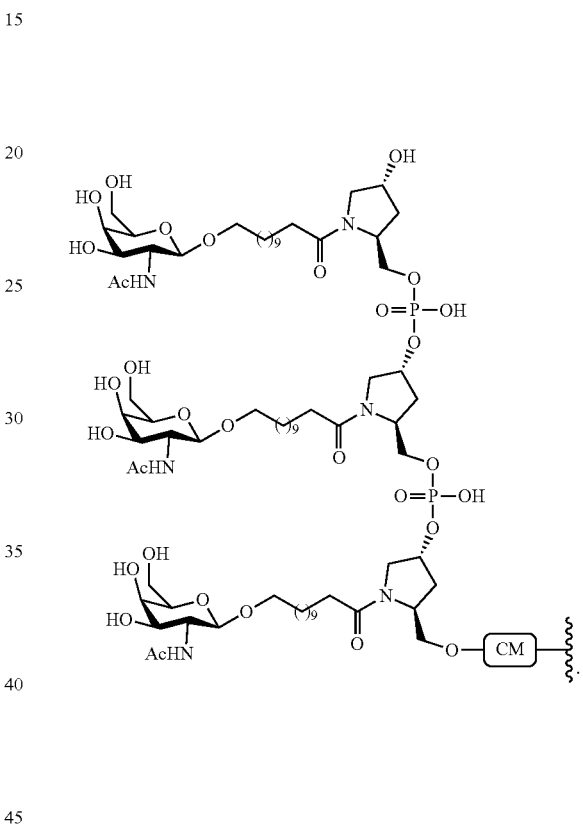

Example 53: Alternate Procedure for Preparation of Compound 18 (GalNAc$_3$-1a and GalNAc$_3$-3a)

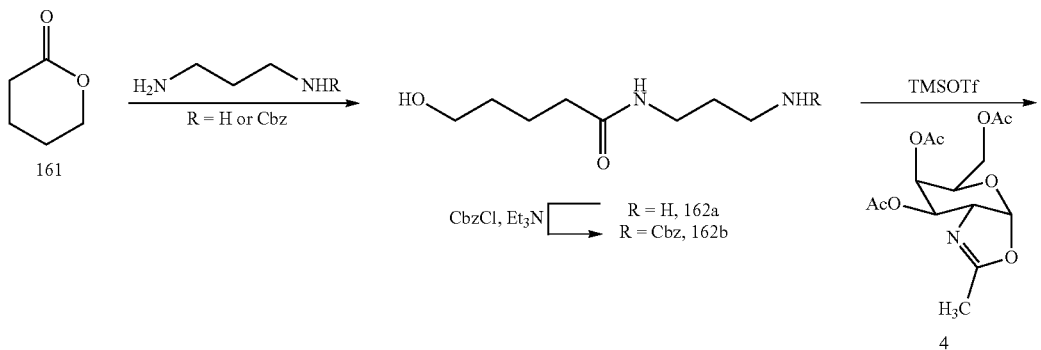

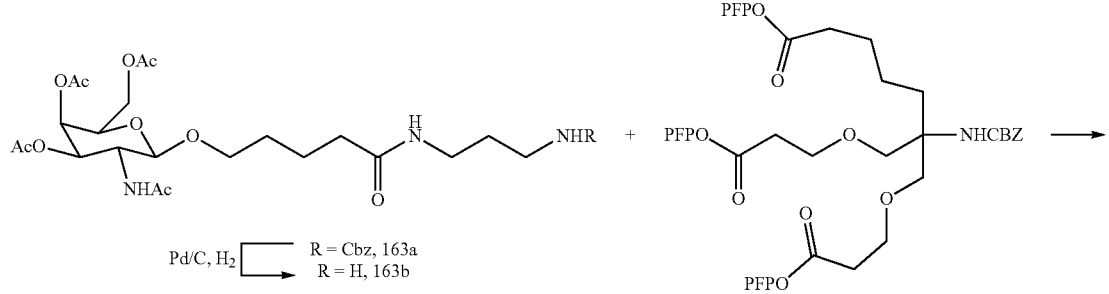

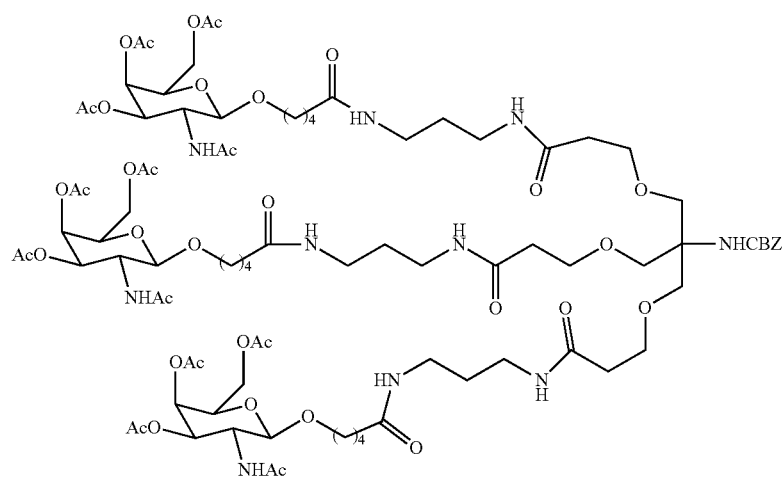

18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b was further reacted with compound 4 in the presence of TMSOTf to provide 163a which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54: Alternate Procedure for Preparation of Compound 18 (GalNAc$_3$-1a and GalNAc$_3$-3a)

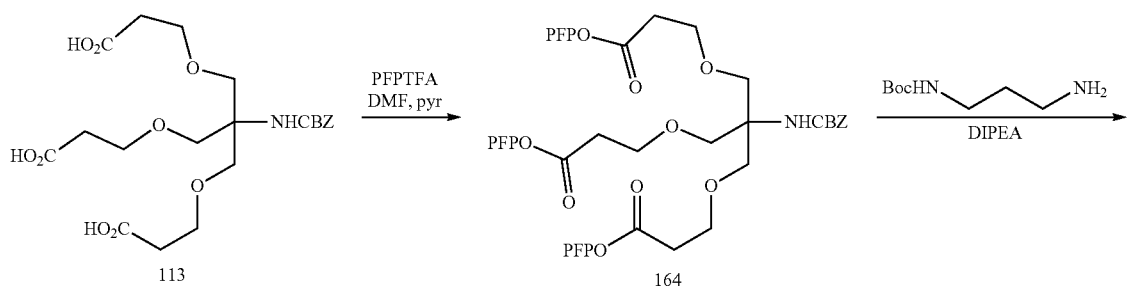

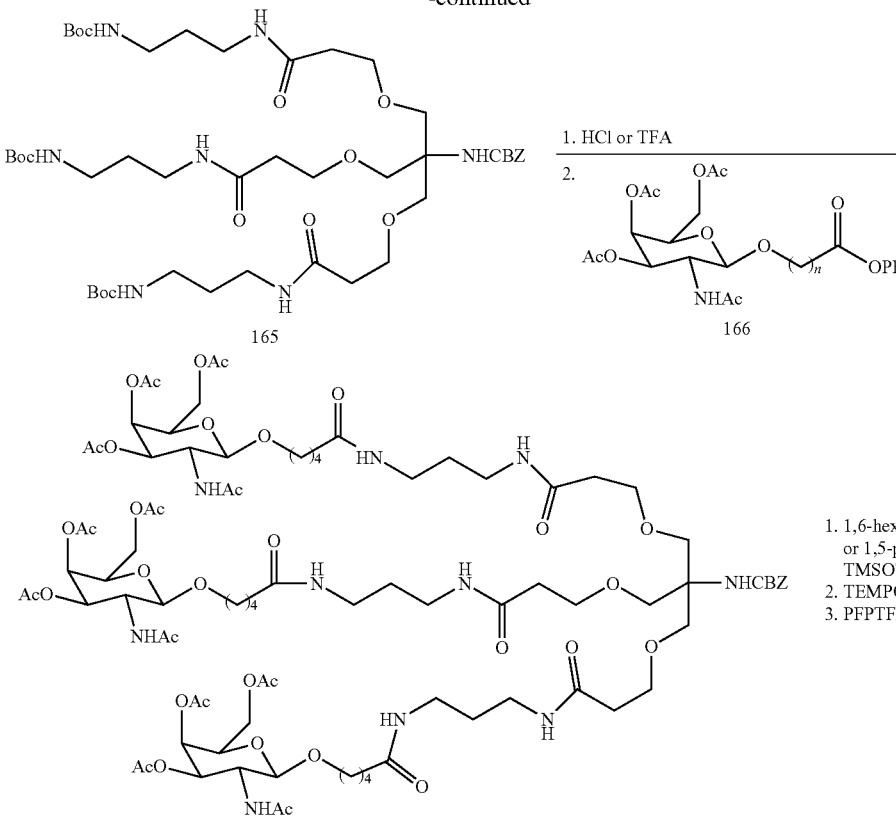

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using conditions described previously in example 47.

Example 55: Dose-Dependent Study of Oligonucleotides Comprising Either a 3' or 5'-Conjugate Group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at either the 3' or 5' terminus of the respective oligonucleotide by a phosphodiester linked 2'-deoxyadenosine nucleoside (cleavable moiety).

TABLE 39

| | Modified ASO targeting SRB-1 | | | |
|---|---|---|---|---|
| ASO | Sequence (5' to 3') | Motif | Conjugate | SEQ ID No. |
| ISIS 353382 (parent) | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$ | 5/10/5 | none | 143 |
| ISIS 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$oAdo'-GalNAc3-1a | 5/10/5 | GalNAc3-1 | 144 |
| ISIS 664078 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$Ado'-GalNAc3-9a | 5/10/5 | GalNAc3-9 | 144 |

TABLE 39-continued

Modified ASO targeting SRB-1

| ASO | Sequence (5' to 3') | Motif | Conjugate | SEQ ID No. |
|---|---|---|---|---|
| ISIS 661161 | GalNAC3-3a-o'Ado $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_e$ | 5/10/5 | GalNAc3-3 | 145 |
| ISIS 665001 | GalNAc3-8a-o'Ado $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_e$ | 5/10/5 | GalNAc3-8 | 145 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P (=O)(OH)—. Conjugate groups are in bold. The structure of GalNAc$_3$-1$_a$ was shown previously in Example 9. The structure of GalNAc$_3$-9 was shown previously in Example 52. The structure of GalNAc$_3$-3 was shown previously in Example 39. The structure of GalNAc$_3$-8 was shown previously in Example 47.

Treatment

Six week old male Balb/c mice (Jackson Laboratory, Bar Harbor, ME) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 40, treatment with antisense oligonucleotides lowered SRB-1 mRNA levels in a dose-dependent manner. Indeed, the antisense oligonucleotides comprising the phosphodiester linked GalNAc$_3$-1 and GalNAc$_3$-9 conjugates at the 3' terminus (ISIS 655861 and ISIS 664078) and the GalNAc$_3$-3 and GalNAc$_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a GalNAc$_3$-9 conjugate at the 3' terminus was essentially equipotent compared to ISIS 655861, which comprises a GalNAc$_3$-1 conjugate at the 3' terminus. The 5' conjugated antisense oligonucleotides, ISIS 661161 and ISIS 665001, comprising a GalNAc$_3$-3 or GalNAc$_3$-9, respectively, had increased potency compared to the 3' conjugated antisense oligonucleotides (ISIS 655861 and ISIS 664078).

TABLE 40

ASOs containing GalNAc$_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
|  | 10 | 68 |  |
|  | 30 | 36 |  |
| 655861 | 0.5 | 98 | GalNac$_3$-1 (3') |
|  | 1.5 | 76 |  |
|  | 5 | 31 |  |
|  | 15 | 20 |  |
| 664078 | 0.5 | 88 | GalNac$_3$-9 (3') |
|  | 1.5 | 85 |  |
|  | 5 | 46 |  |
|  | 15 | 20 |  |
| 661161 | 0.5 | 92 | GalNac$_3$-3 (5') |
|  | 1.5 | 59 |  |
|  | 5 | 19 |  |
|  | 15 | 11 |  |
| 665001 | 0.5 | 100 | GalNac$_3$-8 (5') |
|  | 1.5 | 73 |  |
|  | 5 | 29 |  |
|  | 15 | 13 |  |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 41

| ISIS No. | Dosage mg/kg | ALT | AST | Total Bilirubin | BUN | Conjugate |
|---|---|---|---|---|---|---|
| Saline |  | 24 | 59 | 0.1 | 37.52 |  |
| 353382 | 3 | 21 | 66 | 0.2 | 34.65 | none |
|  | 10 | 22 | 54 | 0.2 | 34.2 |  |
|  | 30 | 22 | 49 | 0.2 | 33.72 |  |
| 655861 | 0.5 | 25 | 62 | 0.2 | 30.65 | GalNac$_3$-1 (3') |
|  | 1.5 | 23 | 48 | 0.2 | 30.97 |  |
|  | 5 | 28 | 49 | 0.1 | 32.92 |  |
|  | 15 | 40 | 97 | 0.1 | 31.62 |  |
| 664078 | 0.5 | 40 | 74 | 0.1 | 35.3 | GalNac$_3$-9 (3') |
|  | 1.5 | 47 | 104 | 0.1 | 32.75 |  |
|  | 5 | 20 | 43 | 0.1 | 30.62 |  |
|  | 15 | 38 | 92 | 0.1 | 26.2 |  |
| 661161 | 0.5 | 101 | 162 | 0.1 | 34.17 | GalNac$_3$-3 (5') |
|  | 1.5 g | 42 | 100 | 0.1 | 33.37 |  |
|  | 5 g | 23 | 99 | 0.1 | 34.97 |  |
|  | 15 | 53 | 83 | 0.1 | 34.8 |  |
| 665001 | 0.5 | 28 | 54 | 0.1 | 31.32 | GalNac$_3$-8 (5') |
|  | 1.5 | 42 | 75 | 0.1 | 32.32 |  |
|  | 5 | 24 | 42 | 0.1 | 31.85 |  |
|  | 15 | 32 | 67 | 0.1 | 31. |  |

Example 56: Dose-Dependent Study of Oligonucleotides Comprising Either a 3' or 5'-Conjugate Group (Comparison of GalNAc$_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various GalNAC$_3$ Conjugate groups was attached at the 5' terminus of the respective oligonucleotide by a phosphodiester linked 2'-deoxyadenosine nucleoside (cleavable moiety) except for ISIS 655861 which had the GaNAc$_3$ Conjugate group attached at the 3' terminus.

protocols. The results below are presented as the average percent of SRB-1 mRNA levels for each treatment group, normalized to the saline control.

As illustrated in Table 43, treatment with antisense oligonucleotides lowered SRB-1 mRNA levels in a dose-dependent manner. Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 42

Modified ASO targeting SRB-1

| ASO | Sequence (5' to 3') | Motif Conjugate | SEQ ID No. |
|---|---|---|---|
| ISIS 353382 (parent) | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$ | 5/10/5 no conjugate | 143 |
| ISIS 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$A$_{do}$,-GalNAc$_3$-1$_a$ | 5/10/5 GalNAc$_3$-1 | 144 |
| ISIS 664507 | GalNAc$_3$-2$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 GalNAc$_3$-2 | 145 |
| ISIS 661161 | GalNAc$_3$-3$_a$-$_o$,A$_{do}$ G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_e$ | 5/10/5 GalNAc$_3$-3 | 145 |
| ISIS 666224 | GalNAc$_3$-5$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 GalNAc$_3$-5 | 145 |
| ISIS 666961 | GalNAc$_3$-6$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 GalNAc$_3$-6 | 145 |
| ISIS 666981 | GalNAc$_3$-7$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 GalNAc$_3$-7 | 145 |
| ISIS 666881 | GalNAc$_3$-10$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | 5/10/5 GalNAc$_3$-10 | 145 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, ME) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard

TABLE 43

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNac$_3$-2 (5') |
| | 1.5 | 73.2 | |
| | 5 | 31.3 | |
| | 15 | 10.8 | |
| 661161 | 0.5 | 90.7 | GalNac$_3$-3 (5') |
| | 1.5 | 67.6 | |
| | 5 | 24.3 | |
| | 15 | 11.5 | |
| 666224 | 0.5 | 96.1 | GalNac$_3$-5 (5') |
| | 1.5 | 61.6 | |
| | 5 | 25.6 | |
| | 15 | 11.7 | |
| 666961 | 0.5 | 85.5 | GalNAc$_3$-6 (5') |
| | 1.5 | 56.3 | |
| | 5 | 34.2 | |
| | 15 | 13.1 | |

TABLE 43-continued

| ISIS No. | Dosage (mg/kg) | SRB-1 mRNA (% Saline) | Conjugate |
|---|---|---|---|
| 666981 | 0.5 | 84.7 | GalNAc$_3$-7 (5') |
|  | 1.5 | 59.9 |  |
|  | 5 | 24.9 |  |
|  | 15 | 8.5 |  |
| 666881 | 0.5 | 100.0 | GalNAc$_3$-10 (5') |
|  | 1.5 | 65.8 |  |
|  | 5 | 26.0 |  |
|  | 15 | 13.0 |  |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 44 below.

TABLE 44

| ISIS No. | Dosage mg/kg | ALT | AST | Total Bilirubin | BUN | Conjugate |
|---|---|---|---|---|---|---|
| Saline |  | 26 | 57 | 0.2 | 27 |  |
| 353382 | 3 | 25 | 92 | 0.2 | 27 | none |
|  | 10 | 23 | 40 | 0.2 | 25 |  |
|  | 30 | 29 | 54 | 0.1 | 28 |  |
| 655861 | 0.5 | 25 | 71 | 0.2 | 34 | GalNac$_3$-1 (3') |
|  | 1.5 | 28 | 60 | 0.2 | 26 |  |
|  | 5 | 26 | 63 | 0.2 | 28 |  |
|  | 15 | 25 | 61 | 0.2 | 28 |  |
| 664507 | 0.5 | 25 | 62 | 0.2 | 25 | GalNac$_3$-2 (5') |
|  | 1.5 | 24 | 49 | 0.2 | 26 |  |
|  | 5 | 21 | 50 | 0.2 | 26 |  |
|  | 15 | 59 | 84 | 0.1 | 22 |  |
| 661161 | 0.5 | 20 | 42 | 0.2 | 29 | GalNac$_3$-3 (5') |
|  | 1.5 g | 37 | 74 | 0.2 | 25 |  |
|  | 5 g | 28 | 61 | 0.2 | 29 |  |
|  | 15 | 21 | 41 | 0.2 | 25 |  |
| 666224 | 0.5 | 34 | 48 | 0.2 | 21 | GalNac$_3$-5 (5') |
|  | 1.5 | 23 | 46 | 0.2 | 26 |  |
|  | 5 | 24 | 47 | 0.2 | 23 |  |
|  | 15 | 32 | 49 | 0.1 | 26 |  |
| 666961 | 0.5 | 17 | 63 | 0.2 | 26 | GalNAc$_3$-6 (5') |
|  | 1.5 | 23 | 68 | 0.2 | 26 |  |
|  | 5 | 25 | 66 | 0.2 | 26 |  |
|  | 15 | 29 | 107 | 0.2 | 28 |  |
| 666981 | 0.5 | 24 | 48 | 0.2 | 26 | GalNAc$_3$-7 (5') |
|  | 1.5 | 30 | 55 | 0.2 | 24 |  |
|  | 5 | 46 | 74 | 0.1 | 24 |  |
|  | 15 | 29 | 58 | 0.1 | 26 |  |
| 666881 | 0.5 | 20 | 65 | 0.2 | 27 | GalNAc$_3$-10 (5') |
|  | 1.5 | 23 | 59 | 0.2 | 24 |  |
|  | 5 | 45 | 70 | 0.2 | 26 |  |
|  | 15 | 21 | 57 | 0.2 | 24 |  |

Example 57: Duration of Action Study of Oligonucleotides Comprising a 3'-Conjugate Group Targeting Apoc III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 45

Modified ASO targeting ApoC III

| ASO | Sequence (5' to 3') | Linkages | SEQ ID No. |
|---|---|---|---|
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$ $^m$C$_{ds}$$^m$C$_{ds}$A$_{ds}$G$_{ds}$$^m$C$_{ds}$T$_{es}$T$_{es}$T$_{es}$A$_{es}$T$_{e}$ | PS | 135 |
| ISIS 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$ A$_{ds}$G$_{ds}$$^m$C$_{ds}$T$_{es}$T$_{es}$T$_{es}$A$_{es}$T$_{eo}$A$_{do}$,-GalNAc$_3$-1$_a$ | PS | 136 |
| ISIS 647536 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$ A$_{ds}$G$_{ds}$$^m$C$_{ds}$T$_{eo}$T$_{eo}$T$_{es}$A$_{es}$T$_{eo}$A$_{do}$,-GalNAc$_3$-1$_a$ | PO/PS | 136 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9.

TABLE 46

ApoC III mRNA (% Saline on Day 1) and Plasma TG Levels (% Saline on Day 1)

| ASO | Dose | Target | Day 3 | Day 7 | Day 14 | Day 35 | Day 42 |
|---|---|---|---|---|---|---|---|
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58: Dose-Dependent Study of Oligonucleotides Comprising a 3'-Conjugate Group (Comparison of GalNAc$_3$-1 and GalNAc$_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of GalNAc$_3$-1$_a$ was shown previously in Example 9. The structure of GalNAc$_3$-11$_a$ was shown previously in Example 50.

Treatment

Six week old male Balb/c mice (Jackson Laboratory, Bar Harbor, ME) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 47, treatment with antisense oligonucleotides lowered SRB-1 mRNA levels in a dose-dependent manner. The antisense oligonucleotides comprising the phosphodiester linked GalNAc$_3$-1 and GalNAc$_4$-11 conjugates at the 3' terminus (ISIS 651900 and ISIS 663748) showed substantial improvement in potency compared to the unconjugated antisense oligonucleotide (ISIS 440762). The two conjugated oligonucleotides, GalNAc$_3$-1 and GalNAc$_4$-11, were equipotent.

TABLE 47

Modified ASO targeting SRB-1

| ASO | Sequence (5' to 3') | Dose mg/kg | % Saline control | SEQ ID No. |
|---|---|---|---|---|
| Saline | | | 100 | |
| ISIS 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{ks}$$^m$C$_k$ | 0.6 | 73.45 | 137 |
| | | 2 | 59.66 | |
| | | 6 | 23.50 | |
| ISIS 651900 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{ks}$$^m$C$_{ko}$A$_{do'}$-GalNAc$_3$-1$_a$ | 0.2 | 62.75 | 138 |
| | | 0.6 | 29.14 | |
| | | 2 | 8.61 | |
| | | 6 | 5.62 | |
| ISIS 663748 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{ks}$$^m$C$_{ko}$A$_{do'}$-GalNAc$_4$-11$_a$ | 0.2 | 63.99 | 138 |
| | | 0.6 | 33.53 | |
| | | 2 | 7.58 | |
| | | 6 | 5.52 | |

Capital letters indicate the nucleobase for each nucleoside and $^m$C indicates a 5-methyl cytosine. Subscripts: "e" indicates a 2'-MOE modified nucleoside; "k" indicates 6'-(S)—CH$_3$ bicyclic nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 48 below.

TABLE 48

| ISIS No. | Dosage mg/kg | ALT | AST | Total Bilirubin | BUN | Conjugate |
|---|---|---|---|---|---|---|
| Saline | | 30 | 76 | 0.2 | 40 | |
| 440762 | 0.60 | 32 | 70 | 0.1 | 35 | none |
| | 2 | 26 | 57 | 0.1 | 35 | |
| | 6 | 31 | 48 | 0.1 | 39 | |
| 651900 | 0.2 | 32 | 115 | 0.2 | 39 | GalNac$_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | GalNac$_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59: Effects of GalNAc$_3$-1 Conjugated ASOs Targeting Fxi In Vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 49

Modified ASOs targeting FXI

| ASO | Sequence (5' to 3') | Linkages | SEQ ID No. |
|---|---|---|---|
| ISIS 404071 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$ T$_{ds}$T$_{ds}$T$_{ds}$$^m$C$_{ds}$A$_{es}$G$_{es}$A$_{es}$G$_{es}$G$_{e}$ | PS | 146 |
| ISIS 656172 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$ T$_{ds}$T$_{ds}$T$_{ds}$$^m$C$_{ds}$A$_{es}$G$_{es}$A$_{es}$G$_{es}$G$_{eo}$A$_{do'}$-GalNAc$_3$-1$_a$ | PS | 147 |
| ISIS 656173 | T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$ T$_{ds}$T$_{ds}$T$_{ds}$$^m$C$_{ds}$A$_{eo}$G$_{eo}$A$_{es}$G$_{es}$G$_{eo}$A$_{do'}$-GalNAc$_3$-1$_a$ | PO/PS | 147 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAC$_3$-1$_a$ was shown previously in Example 9.

Treatment

Six week old male Balb/c mice (Jackson Laboratory, Bar Harbor, ME) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, OR) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The ED$_{50}$s were measured using similar methods as described previously and are presented below.

As illustrated in Table 50, treatment with antisense oligonucleotides lowered FXI mRNA levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

As illustrated in Table 50a, treatment with antisense oligonucleotides lowered FXI protein levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

TABLE 50

Factor XI mRNA (% Saline)

| ASO | Dose mg/kg | % Control | Conjugate | Linkages |
|---|---|---|---|---|
| Saline |  | 100 | none |  |
| ISIS 404071 | 3 | 92 | none | PS |
|  | 10 | 40 |  |  |
|  | 30 | 15 |  |  |
| ISIS 656172 | 0.7 | 74 | GalNAc$_3$-1 | PS |
|  | 2 | 33 |  |  |
|  | 6 | 9 |  |  |
| ISIS 656173 | 0.7 | 49 | GalNAc$_3$-1 | PO/PS |
|  | 2 | 22 |  |  |
|  | 6 | 1 |  |  |

TABLE 50a

Factor XI protein (% Saline)

| ASO | Dose mg/kg | Protein (% Control) | Conjugate | Linkages |
|---|---|---|---|---|
| Saline |  | 100 | none |  |
| ISIS 404071 | 3 | 127 | none | PS |
|  | 10 | 32 |  |  |
|  | 30 | 3 |  |  |
| ISIS 656172 | 0.7 | 70 | GalNAc$_3$-1 | PS |
|  | 2 | 23 |  |  |
|  | 6 | 1 |  |  |
| ISIS 656173 | 0.7 | 45 | GalNAc$_3$-1 | PO/PS |
|  | 2 | 6 |  |  |
|  | 6 | 0 |  |  |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 51

| ISIS No. | Dosage mg/kg | ALT | AST | Total Albumin | Total Bilirubin | CRE | BUN | Conjugate |
|---|---|---|---|---|---|---|---|---|
| Saline |  | 71.8 | 84.0 | 3.1 | 0.2 | 0.2 | 22.9 |  |
| 404071 | 3 | 152.8 | 176.0 | 3.1 | 0.3 | 0.2 | 23.0 | none |
|  | 10 | 73.3 | 121.5 | 3.0 | 0.2 | 0.2 | 21.4 |  |
|  | 30 | 82.5 | 92.3 | 3.0 | 0.2 | 0.2 | 23.0 |  |
| 656172 | 0.7 | 62.5 | 111.5 | 3.1 | 0.2 | 0.2 | 23.8 | GalNac$_3$-1 (3') |
|  | 2 | 33.0 | 51.8 | 2.9 | 0.2 | 0.2 | 22.0 |  |
|  | 6 | 65.0 | 71.5 | 3.2 | 0.2 | 0.2 | 23.9 |  |
| 656173 | 0.7 | 54.8 | 90.5 | 3.0 | 0.2 | 0.2 | 24.9 | GalNac$_3$-1 (3') |
|  | 2 | 85.8 | 71.5 | 3.2 | 0.2 | 0.2 | 21.0 |  |
|  | 6 | 114.0 | 101.8 | 3.3 | 0.2 | 0.2 | 22.7 |  |

Example 60: Effects of Conjugated ASOs Targeting SRB-1 In Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

TABLE 52
Modified ASO targeting SRB-1

| ASO | Sequence (5' to 3') | Motif Conjugate | SEQ ID No. |
|---|---|---|---|
| ISIS 353382 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_{e}$ | 5/10/5 none | 143 |
| ISIS 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_{eo}A_{do}$,-GalNAc$_3$-1$_a$ | 5/10/5 GalNAc$_3$-1 | 144 |
| ISIS 655862 | $G_{es}{}^mC_{eo}T_{eo}T_{eo}{}^mC_{eo}A_{ds}G_{ds}T_{ds}{}^mC_{ds}A_{ds}T_{ds}G_{ds}A_{ds}$ ${}^mC_{ds}T_{ds}T_{eo}{}^mC_{eo}{}^mC_{es}T_{es}T_{eo}A_{do}$,-GalNAc$_3$-1$_a$ | 5/10/5 GalNAc$_3$-1 | 144 |
| ISIS 661161 | GalNAc$_3$-3$_{a-o}$,$A_{do}G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-3 | 145 |
| ISIS 665001 | GalNAc$_3$-8$_{a-o}$,$A_{do}G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-8 | 145 |
| ISIS 664078 | $G_{es}{}^mC_{es}T_{es}T_{es}{}^mC_{es}A_{ds}G_{ds}T_{ds}{}^mC_{ds}A_{ds}T_{ds}G_{ds}A_{ds}$ ${}^mC_{ds}T_{ds}T_{es}{}^mC_{es}{}^mC_{es}T_{es}T_{eo}A_{do}$,-GalNAc$_3$-9$_a$ | 5/10/5 GalNAc$_3$-9 | 144 |
| ISIS 666961 | GalNAc$_3$-6$_{a-o}$,$A_{do}G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-6 | 145 |
| ISIS 664507 | GalNAc$_3$-2$_{a-o}$,$A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-2 | 145 |
| ISIS 666881 | GalNAc$_3$-10$_{a-o}$,$A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-10 | 145 |
| ISIS 666224 | GalNAc$_3$-5$_{a-o}$,$A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-5 | 145 |
| ISIS 666981 | GalNAc$_3$-7$_{a-o}$,$A_{do}G_{es}{}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}T_{es}{}^mC_{es}{}^mC_{es}T_{es}T_{e}$ | 5/10/5 GalNAc$_3$-7 | 145 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAC$_3$-1$_a$ was shown previously in Example 9. The structure of GalNAC$_3$-3a was shown previously in Example 39. The structure of GalNAC$_3$-8a was shown previously in Example 47. The structure of GalNAC$_3$-9a was shown previously in Example 52. The structure of GalNAC$_3$-6a was shown previously in Example 51. The structure of GalNAC$_3$-2a was shown previously in Example 37. The structure of GalNAC$_3$-10$_a$ was shown previously in Example 46. The structure of GalNAC$_3$-5a was shown previously in Example 49. The structure of GalNAC$_3$-7a was shown previously in Example 48.

Treatment

The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The IC$_{50}$ was calculated using standard methods and the results are presented in Table 53. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 53

| ASO | IC$_{50}$ (nM) | Internucleoside linkages | Conjugate | SEQ ID No. |
|---|---|---|---|---|
| ISIS 353382 | 190[a] | PS | none | 143 |
| ISIS 655861 | 11[a] | PS | GalNAc$_3$-1 | 144 |
| ISIS 655862 | 3 | PO/PS | GalNAc$_3$-1 | 144 |
| ISIS 661161 | 15[a] | PS | GalNAc$_3$-3 | 145 |
| ISIS 665001 | 20 | PS | GalNAc$_3$-8 | 145 |
| ISIS 664078 | 55 | PS | GalNAc$_3$-9 | 144 |
| ISIS 666961 | 22[a] | PS | GalNAc$_3$-6 | 145 |
| ISIS 664507 | 30 | PS | GalNAc$_3$-2 | 145 |
| ISIS 666881 | 30 | PS | GalNAc$_3$-10 | 145 |
| ISIS 666224 | 30[a] | PS | GalNAc$_3$-5 | 145 |
| ISIS 666981 | 40 | PS | GalNAc$_3$-7 | 145 |

[a]Average of multiple runs.

Example 61: Preparation of Oligomeric Compound 175 Comprising GalNAc₃-12
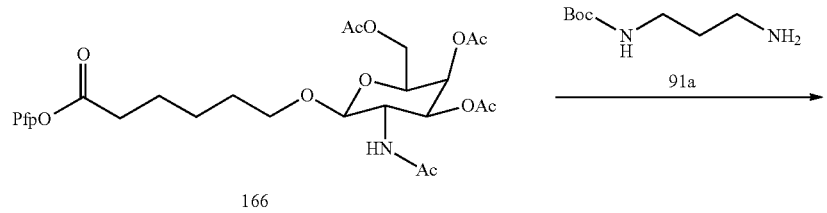
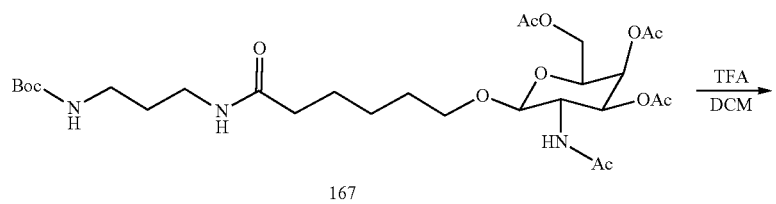
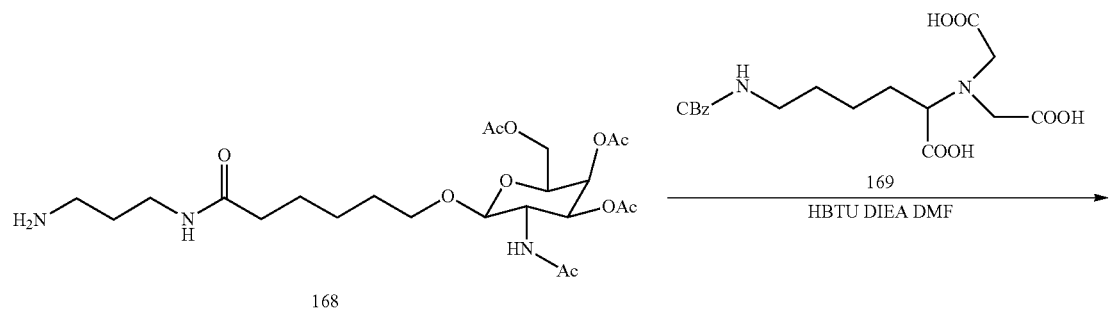
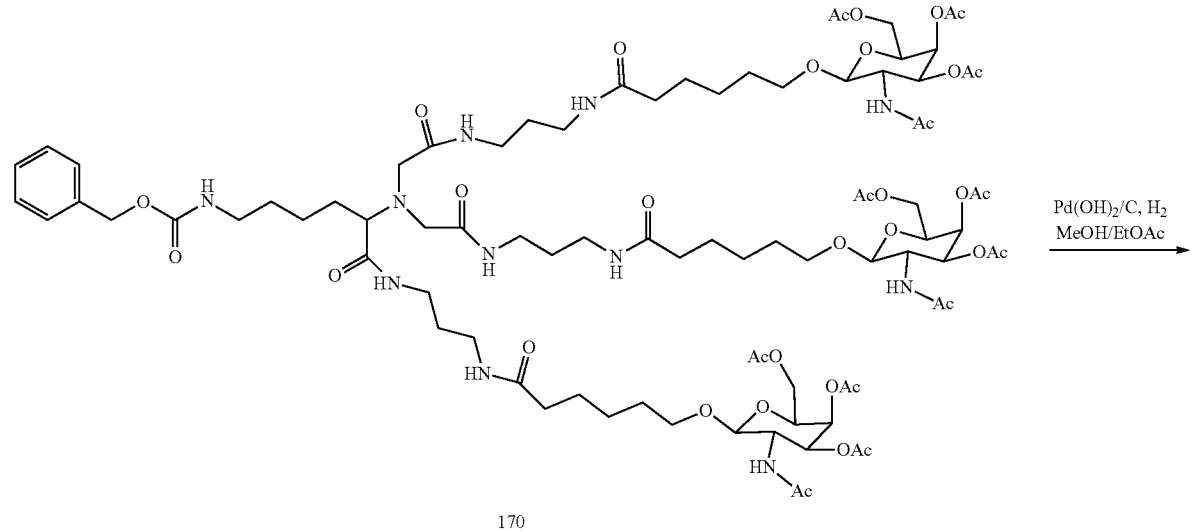

411
412
-continued
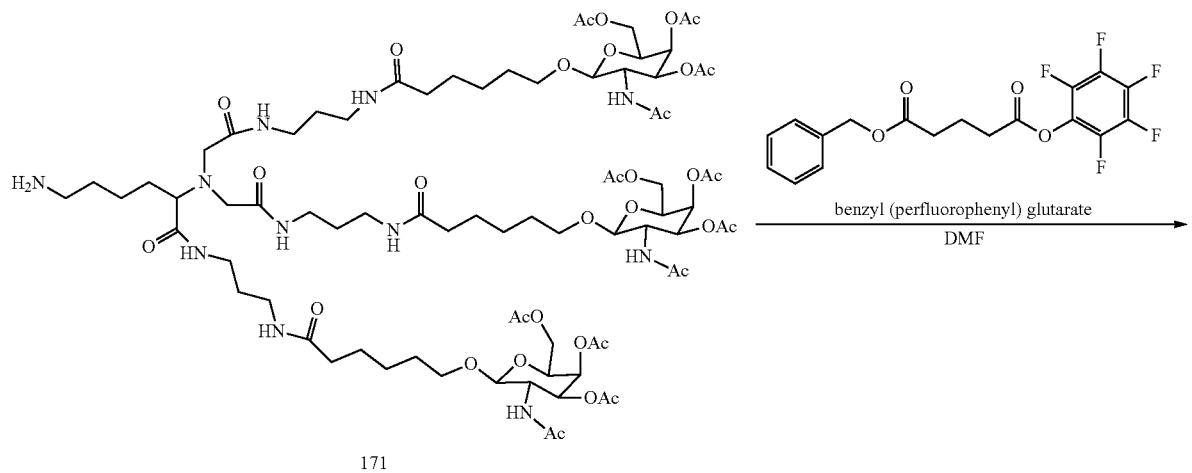
171
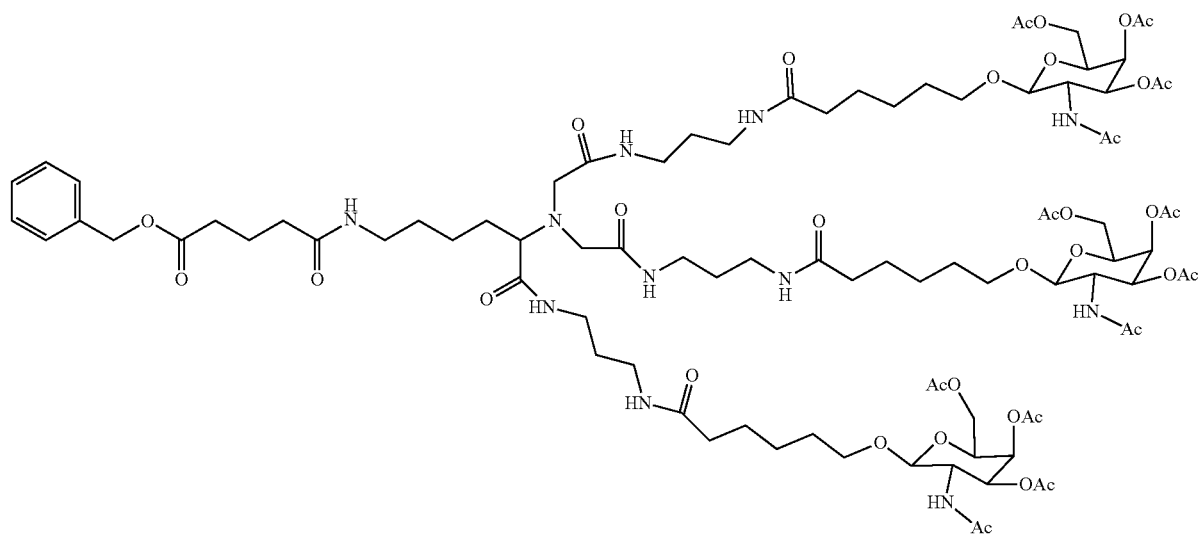
172
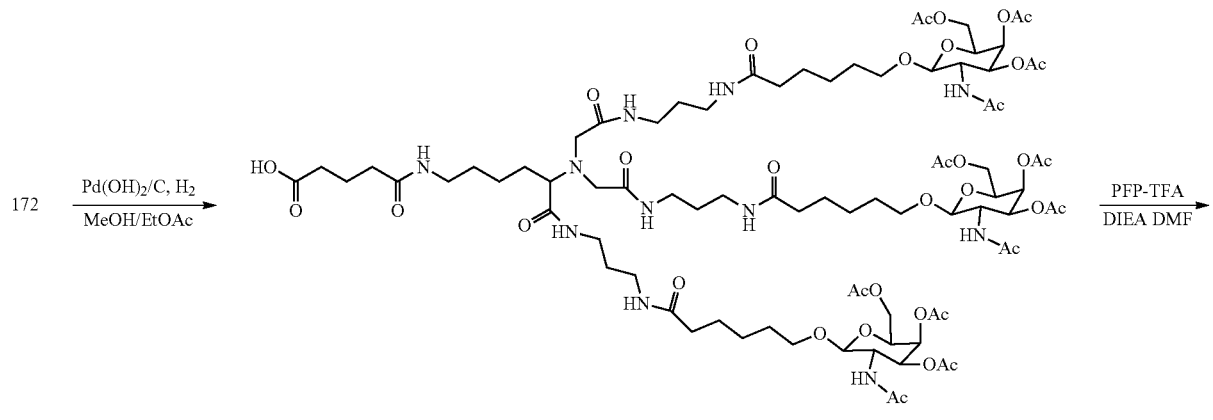
173

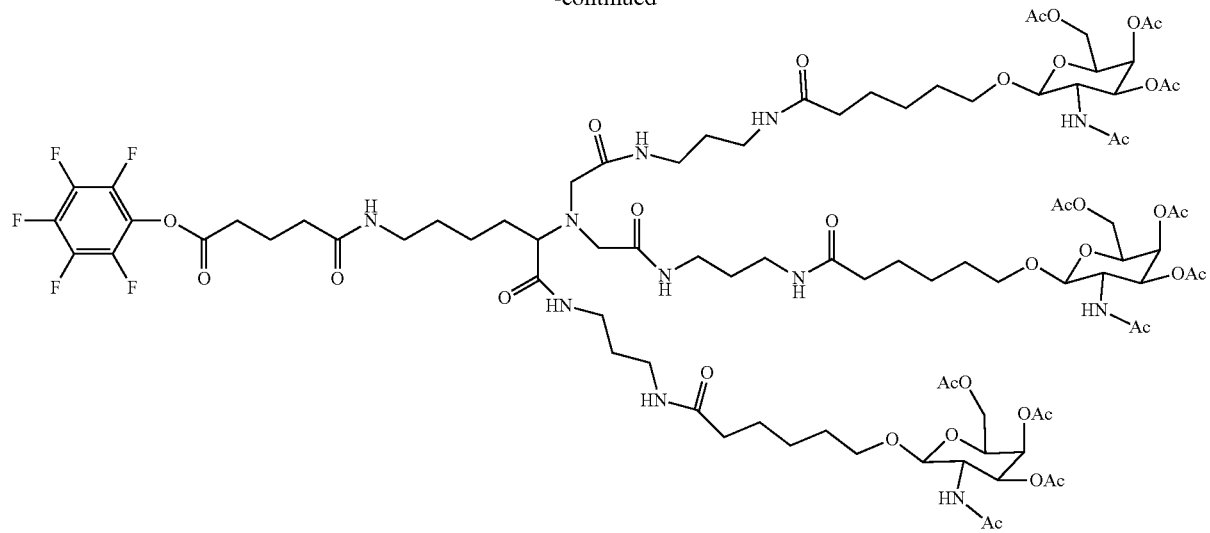

174

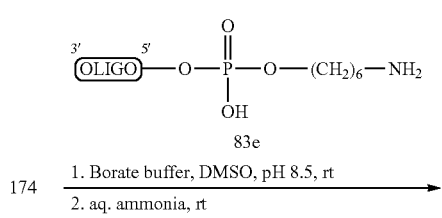

83e

174 → 1. Borate buffer, DMSO, pH 8.5, rt
2. aq. ammonia, rt

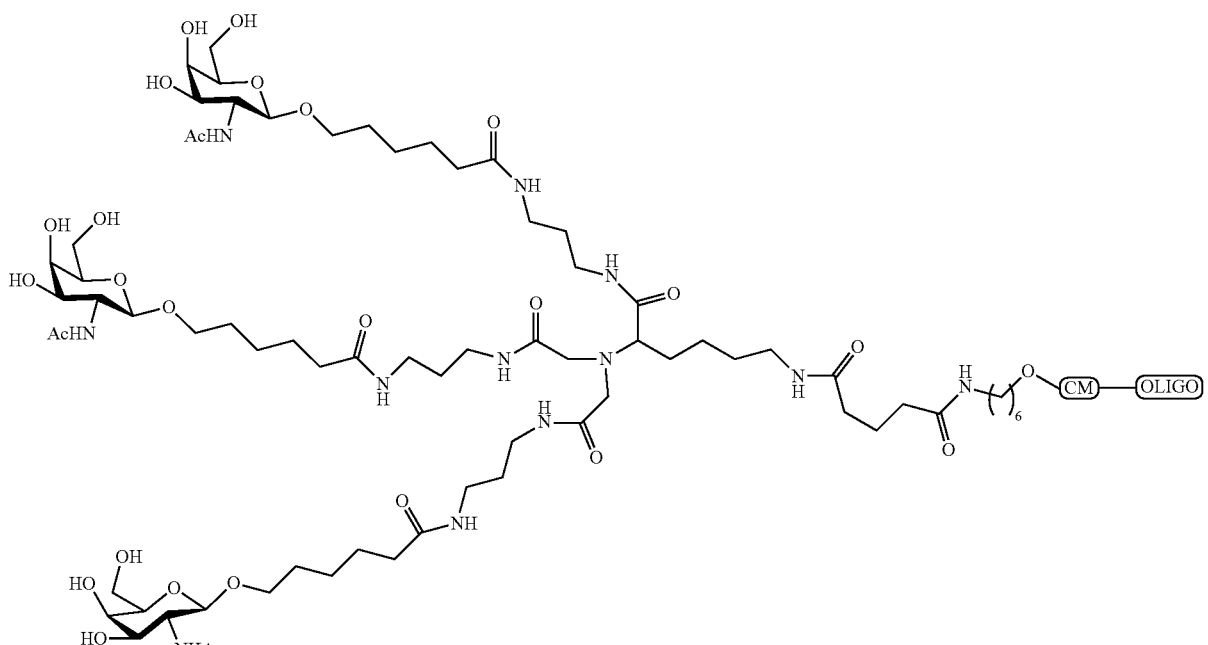

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-12 (GalNAc$_3$-12$_a$-CM-) is shown below:

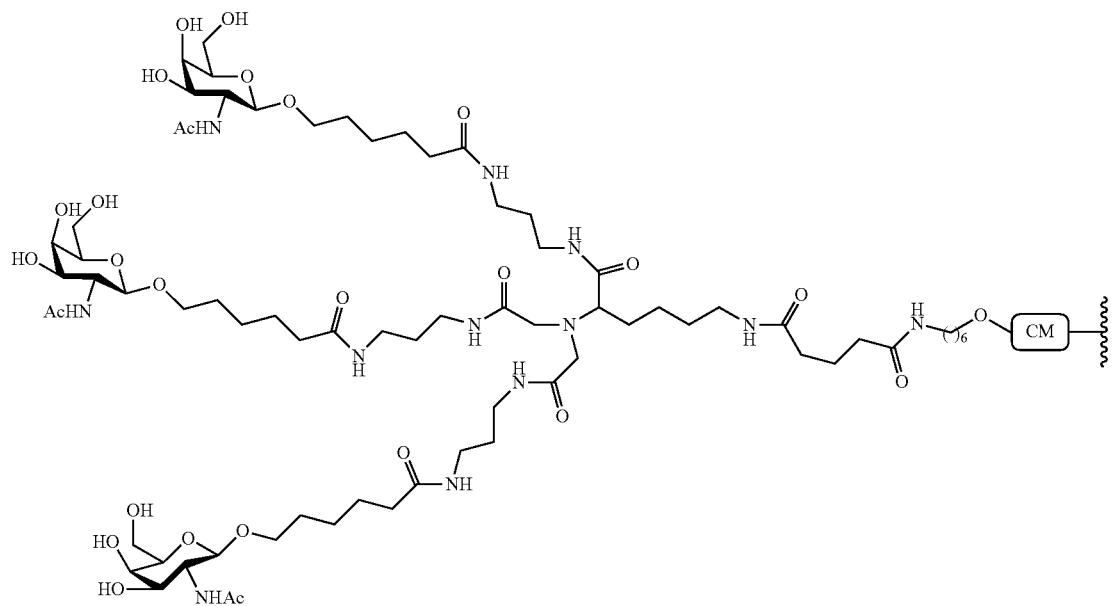
Example 62: Preparation of Oligomeric Compound 180 Comprising GalNAc$_3$-13
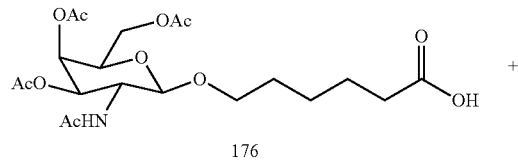
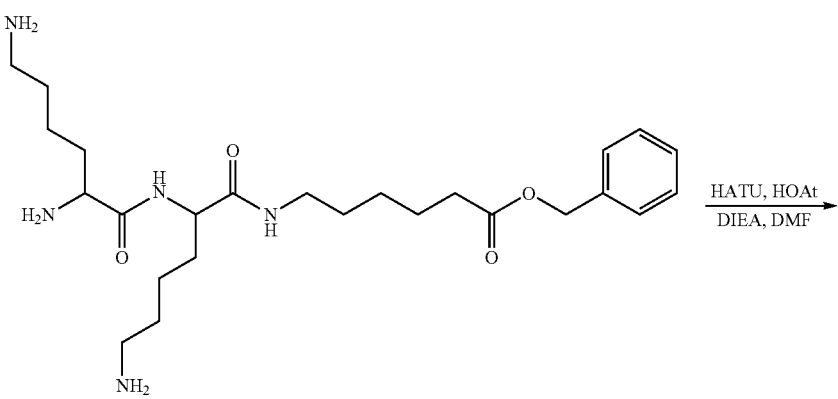

-continued
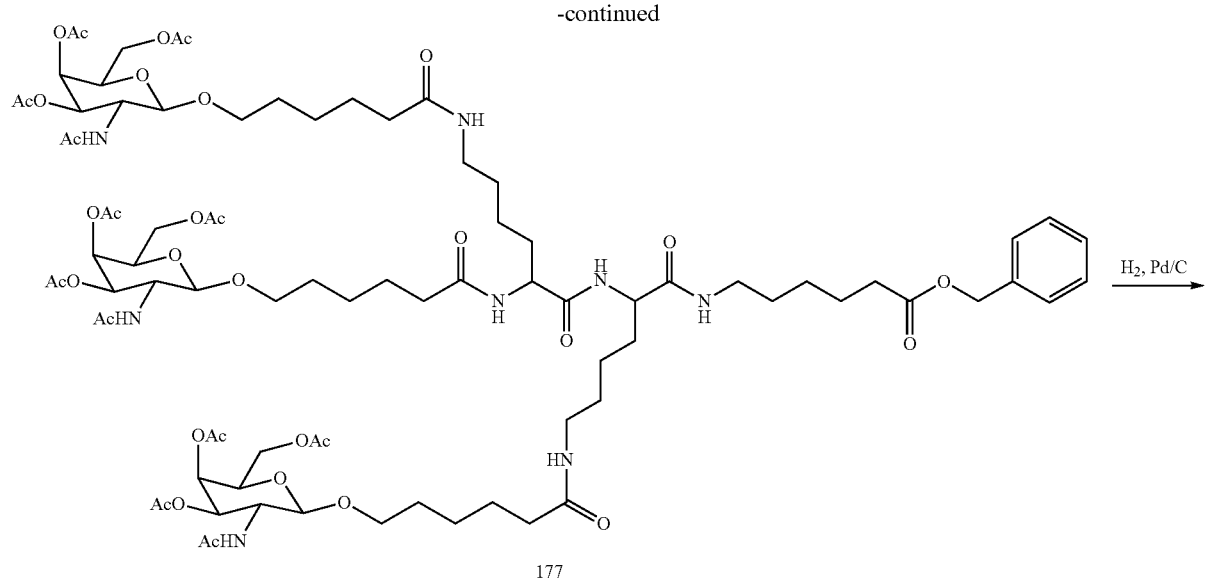
177
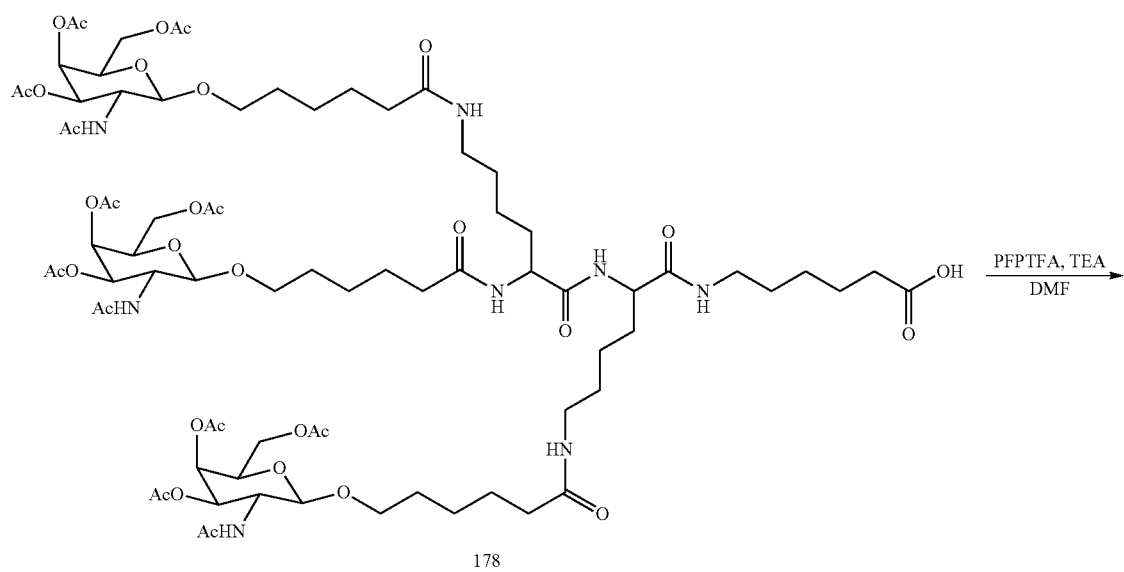
178
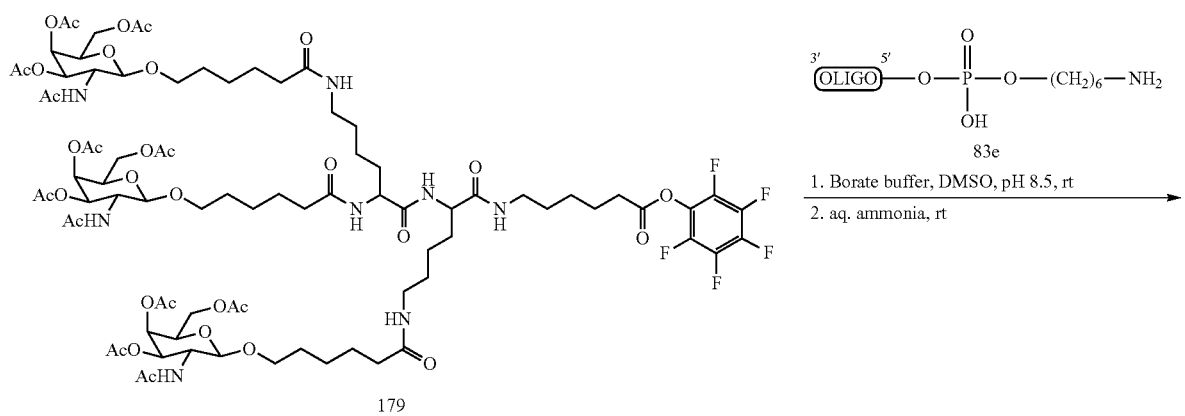
179

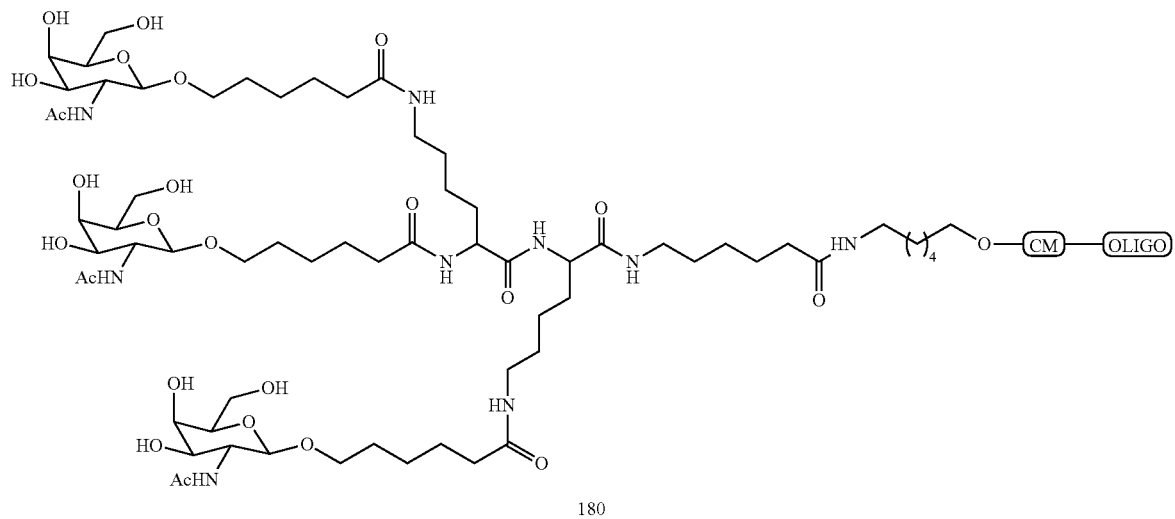

180

Compound 176 was prepared using the general procedure shown in Example 2. Oligomeric compound 180, comprising a GalNAc$_3$-13 conjugate group, was prepared from compound 177 using the general procedures illustrated in Example 49. The GalNAc$_3$ cluster portion of the conjugate group GalNAc$_3$-13 (GalNAc$_3$-13$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-13 (GalNAc$_3$-13$_a$-CM-) is shown below:

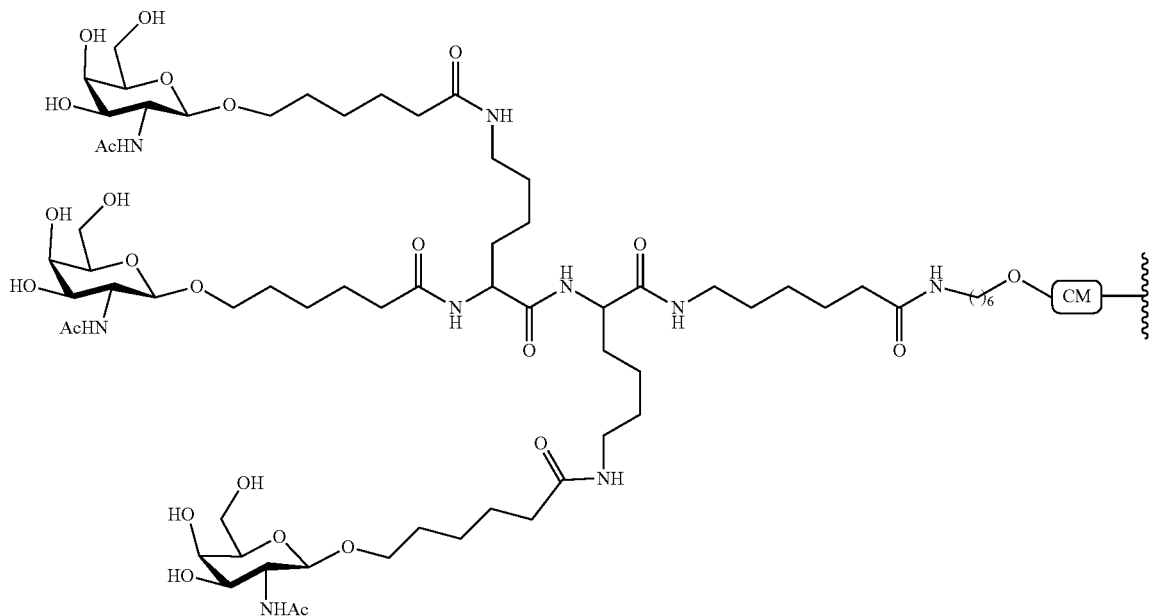

Example 63: Preparation of Oligomeric Compound 188 Comprising GalNAc$_3$-14
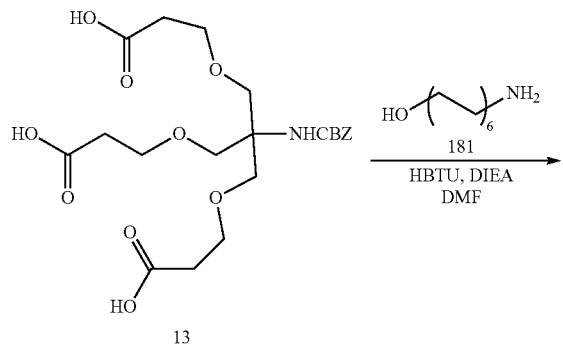
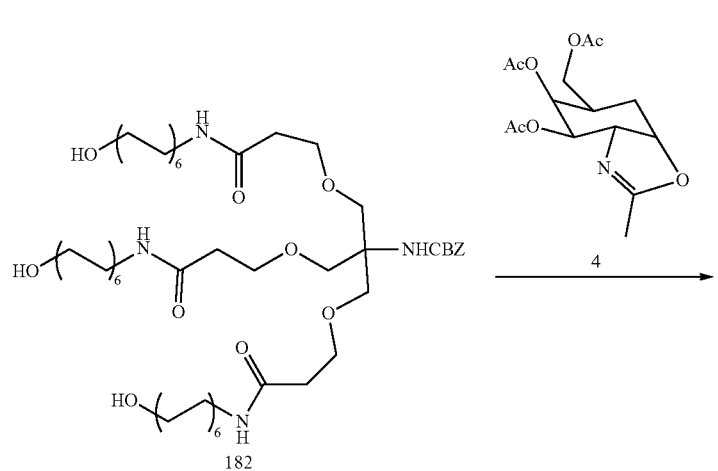
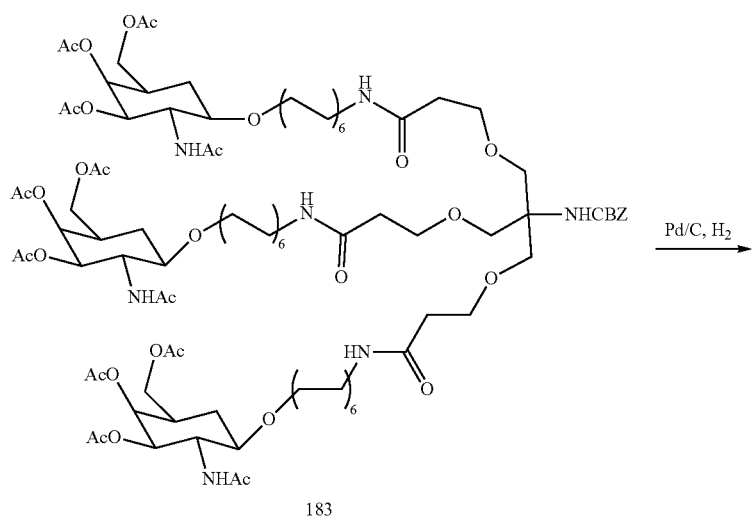

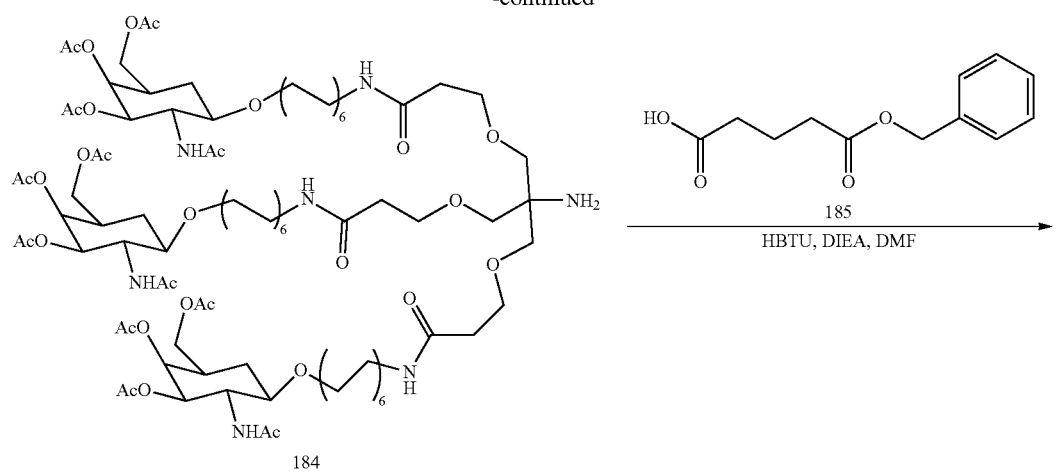
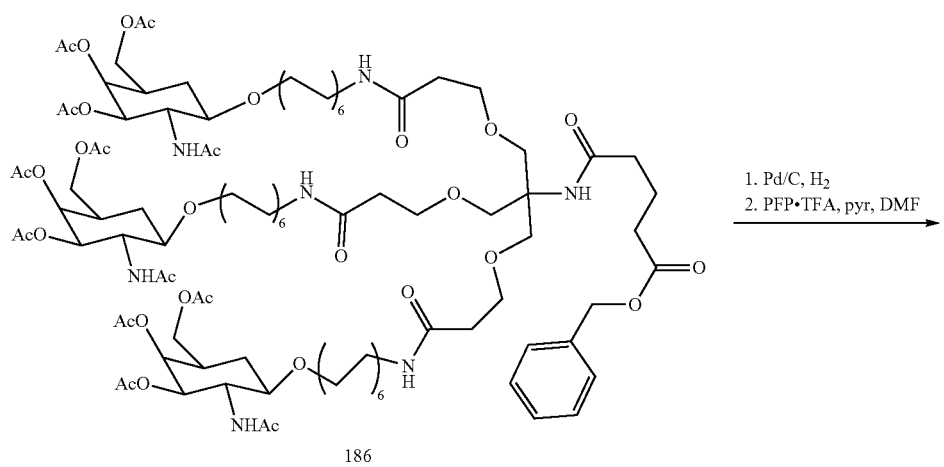
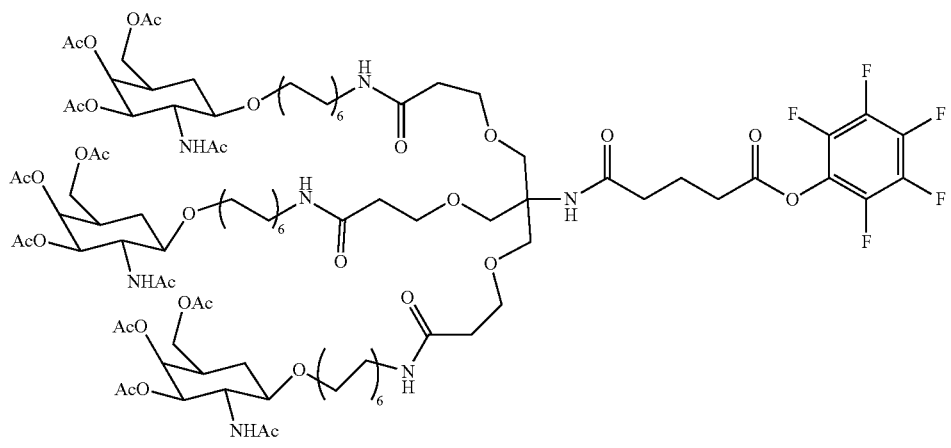
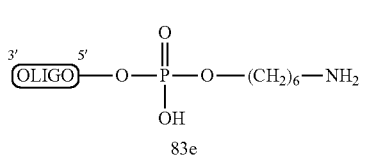
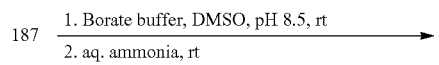

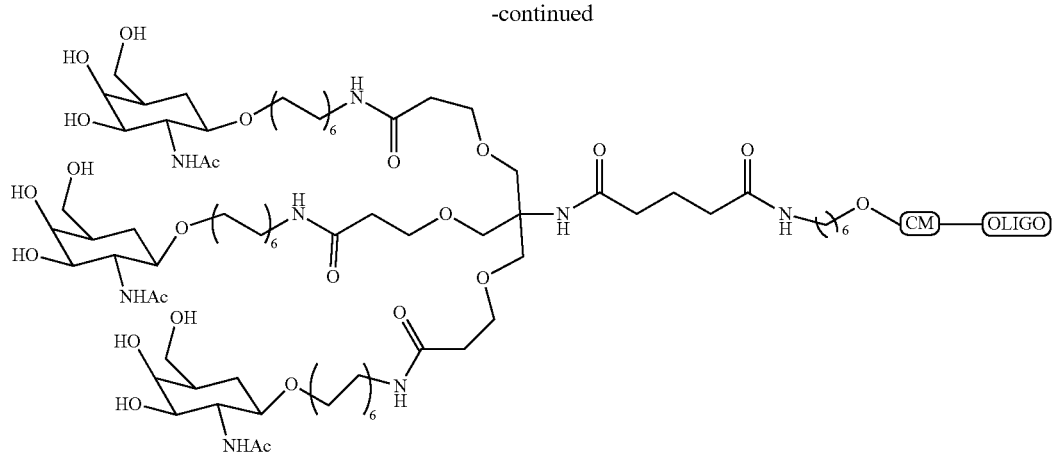

188

Compounds 181 and 185 are commercially available. Oligomeric compound 188, comprising a GalNAc$_3$-14 conjugate group, was prepared from compound 187 using the general procedures illustrated in Example 46. The GalNAc$_3$ cluster portion of the conjugate group GalNAc$_3$-14 (GalNAc$_3$-14$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-14 (GalNAc$_3$-14$_a$-CM-) is shown below:

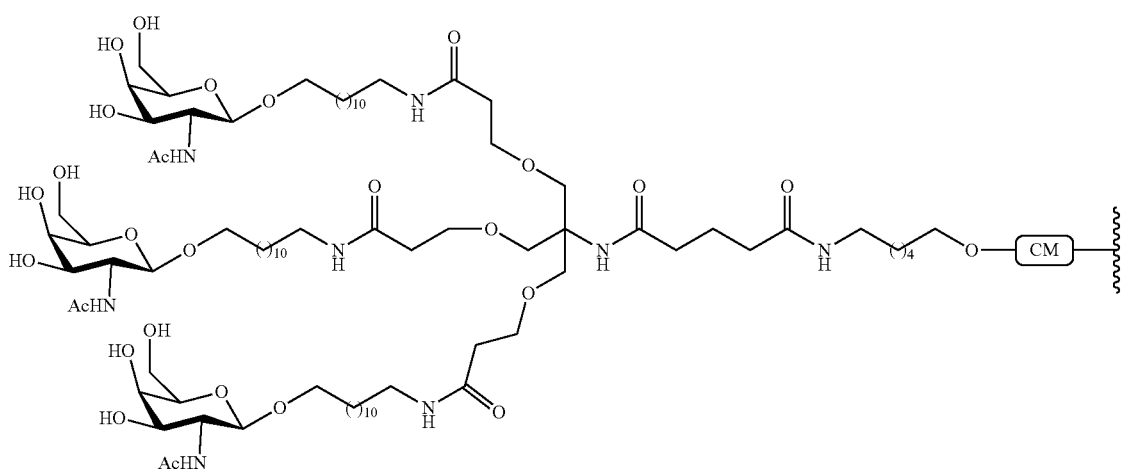

Example 64: Preparation of Oligomeric Compound 197 Comprising GalNAc$_3$-15

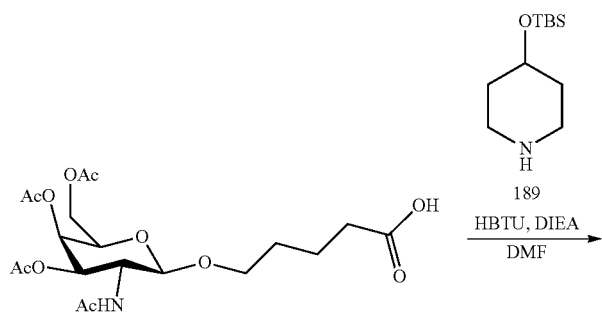

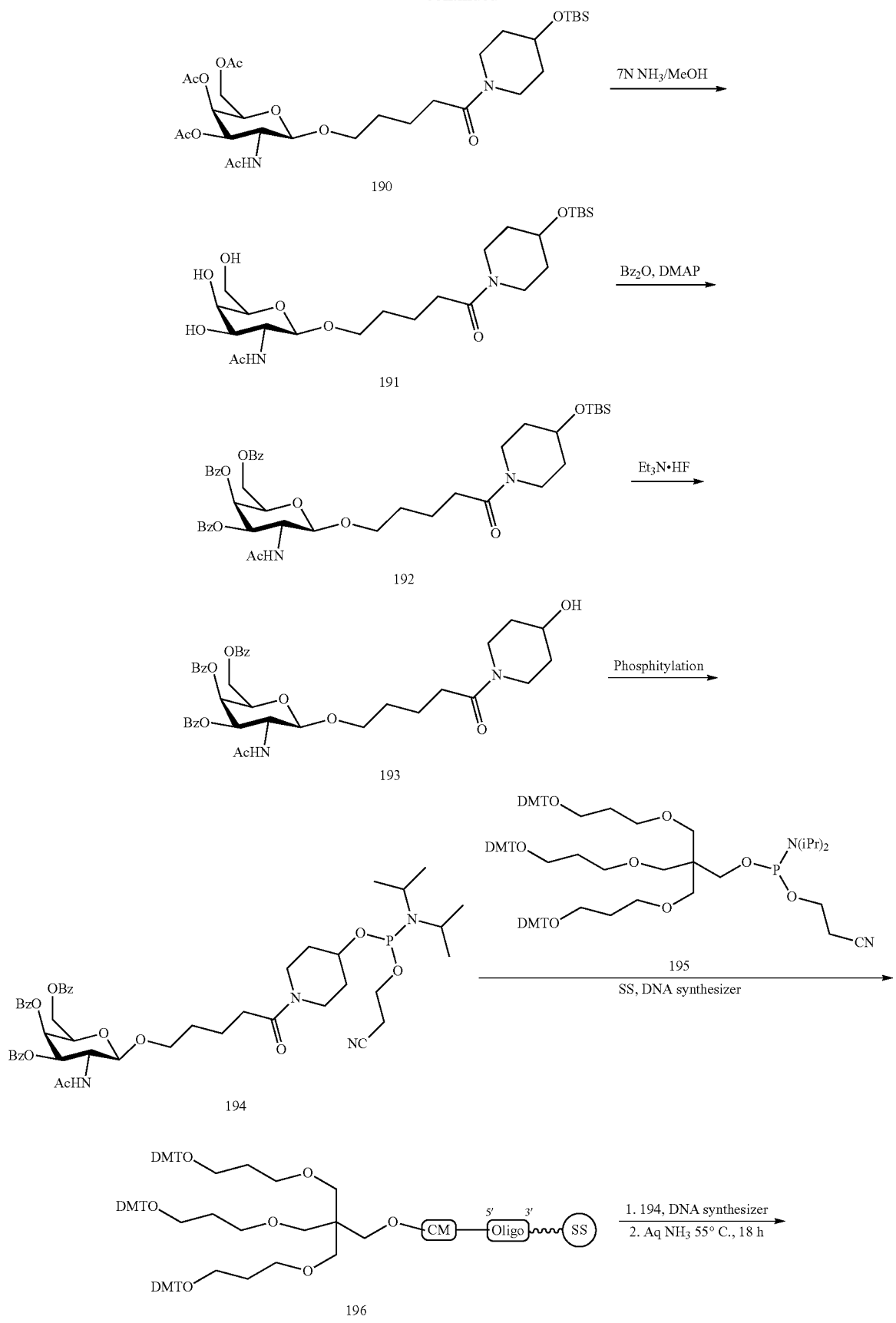

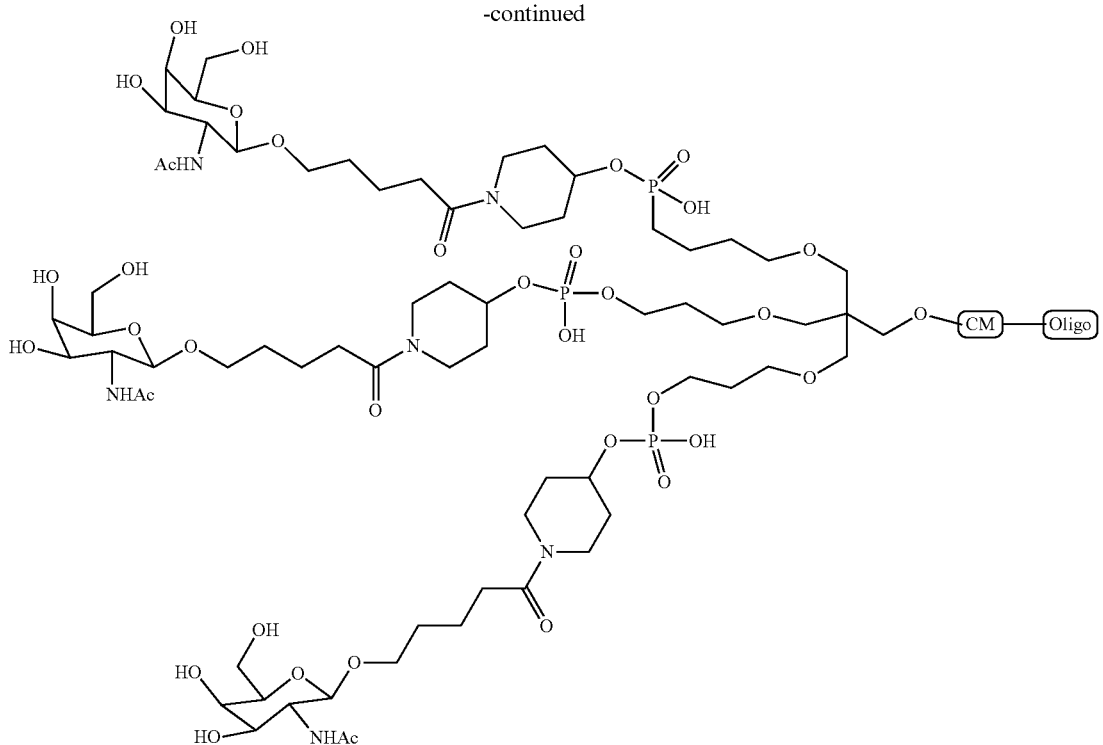

197

Compound 189 is commercially available. Compound 195 was prepared using the general procedure shown in Example 31. Oligomeric compound 197, comprising a GalNAc₃-15 conjugate group, was prepared from compounds 194 and 195 using standard oligonucleotide synthesis procedures. The GalNAc₃ cluster portion of the conjugate group GalNAc₃-15 (GalNAc₃-15$_a$) can be combined with any cleavable moiety to provide a variety of conjugate groups. In certain embodiments, the cleavable moiety is —P(=O)(OH)-A$_d$-P(=O)(OH)—. The structure of GalNAc₃-15 (GalNAc₃-15$_a$-CM-) is shown below:

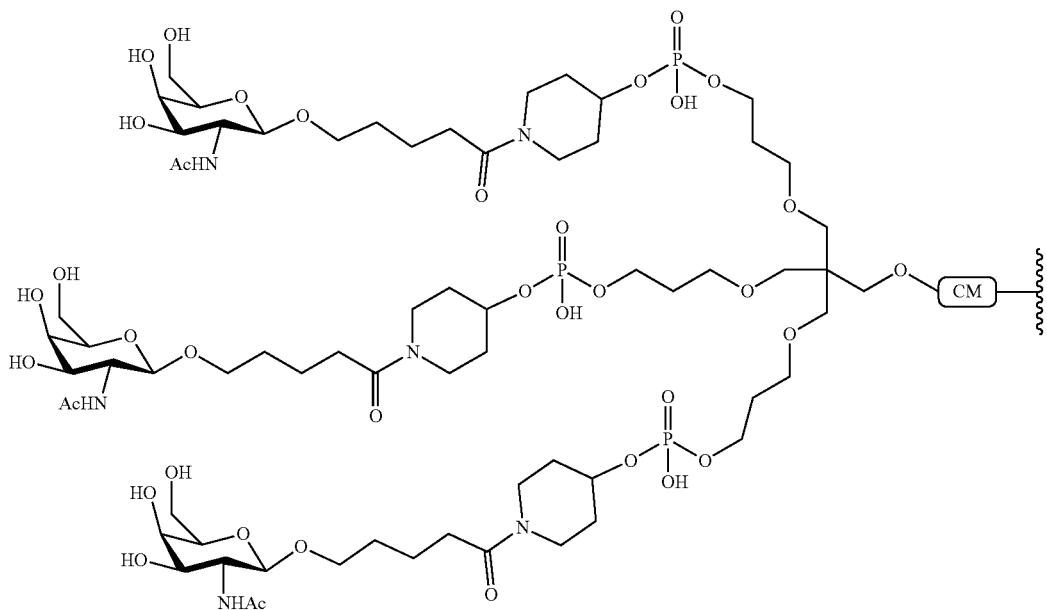

Example 65: Dose-Dependent Study of Oligonucleotides Comprising a 5'-Conjugate Group (Comparison of GalNAc$_3$-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the GalNAc$_3$ conjugate groups was attached at the 5' terminus of the respective oligonucleotide by a phosphodiester linked 2'-deoxyadenosine nucleoside (cleavable moiety).

As illustrated in Table 55, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked GalNAc$_3$-3, 12, 13, 14, and 15 conjugates showed substantial improvement in potency compared to the unconjugated antisense oligonucleotide (ISIS 335382).

TABLE 54

Modified ASOs targeting SRB-1

| ISIS No. | Sequences (5' to 3') | Conjugate | SEQ ID NO. |
|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | none | 143 |
| 661161 | GalNAc$_3$-3$_{a}$-$_{o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_3$-3 | 145 |
| 671144 | GalNAc$_3$-12$_{a}$-$_{o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_3$-12 | 145 |
| 670061 | GalNAc$_3$-13$_{a}$-$_{o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_3$-13 | 145 |
| 671261 | GalNAc$_3$-14$_{a}$-$_{o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_3$-14 | 145 |
| 671262 | GalNAc$_3$-15$_{a}$-$_{o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_3$-15 | 145 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-12a was shown previously in Example 61. The structure of GalNAc$_3$-13a was shown previously in Example 62. The structure of GalNAc$_3$-14a was shown previously in Example 63. The structure of GalNAc$_3$-15a was shown previously in Example 64.

Treatment

Six to eight week old C57b16 mice (Jackson Laboratory, Bar Harbor, ME) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

TABLE 55

SRB-1 mRNA (% Saline)

| ISIS No. | Dosage (mg/kg) | SRB-1 mRNA (% Saline) | ED$_{50}$ (mg/kg) | Conjugate |
|---|---|---|---|---|
| Saline | n/a | 100.0 | n/a | n/a |
| 353382 | 3 | 85.0 | 22.4 | none |
|  | 10 | 69.2 |  |  |
|  | 30 | 34.2 |  |  |
|  | 2 × 15 | 36.0 |  |  |
| 661161 | 0.5 | 87.4 | 2.2 | GalNAc$_3$-3 |
|  | 1.5 | 59.0 |  |  |
|  | 5 | 25.6 |  |  |
|  | 2 × 2.5 | 27.5 |  |  |
|  | 15 | 17.4 |  |  |
| 671144 | 0.5 | 101.2 | 3.4 | GalNAc$_3$-12 |
|  | 1.5 | 76.1 |  |  |
|  | 5 | 32.0 |  |  |
|  | 15 | 17.6 |  |  |
| 670061 | 0.5 | 94.8 | 2.1 | GalNAc$_3$-13 |
|  | 1.5 | 57.8 |  |  |
|  | 5 | 20.7 |  |  |
|  | 15 | 13.3 |  |  |
| 671261 | 0.5 | 110.7 | 4.1 | GalNAc$_3$-14 |
|  | 1.5 | 81.9 |  |  |
|  | 5 | 39.8 |  |  |
|  | 15 | 14.1 |  |  |
| 671262 | 0.5 | 109.4 | 9.8 | GalNAc$_3$-15 |
|  | 1.5 | 99.5 |  |  |
|  | 5 | 69.2 |  |  |
|  | 15 | 36.1 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 56

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
|  | 10 | 25 | 78 | 0.2 | 36 |  |
|  | 30 | 28 | 62 | 0.2 | 35 |  |
|  | 2 × 15 | 22 | 59 | 0.2 | 33 |  |
| 661161 | 0.5 | 39 | 72 | 0.2 | 34 | GalNAc$_3$-3 |
|  | 1.5 | 26 | 50 | 0.2 | 33 |  |
|  | 5 | 41 | 80 | 0.2 | 32 |  |
|  | 2 × 2.5 | 24 | 72 | 0.2 | 28 |  |
|  | 15 | 32 | 69 | 0.2 | 36 |  |
| 671144 | 0.5 | 25 | 39 | 0.2 | 34 | GalNAc$_3$-12 |
|  | 1.5 | 26 | 55 | 0.2 | 28 |  |
|  | 5 | 48 | 82 | 0.2 | 34 |  |
|  | 15 | 23 | 46 | 0.2 | 32 |  |
| 670061 | 0.5 | 27 | 53 | 0.2 | 33 | GalNAc$_3$-13 |
|  | 1.5 | 24 | 45 | 0.2 | 35 |  |
|  | 5 | 23 | 58 | 0.1 | 34 |  |
|  | 15 | 24 | 72 | 0.1 | 31 |  |
| 671261 | 0.5 | 69 | 99 | 0.1 | 33 | GalNAc$_3$-14 |
|  | 1.5 | 34 | 62 | 0.1 | 33 |  |
|  | 5 | 43 | 73 | 0.1 | 32 |  |
|  | 15 | 32 | 53 | 0.2 | 30 |  |
| 671262 | 0.5 | 24 | 51 | 0.2 | 29 | GalNAc$_3$-15 |
|  | 1.5 | 32 | 62 | 0.1 | 31 |  |
|  | 5 | 30 | 76 | 0.2 | 32 |  |
|  | 15 | 31 | 64 | 0.1 | 32 |  |

Example 66: Effect of Various Cleavable Moieties on Antisense Inhibition In Vivo by Oligonucleotides Targeting SRB-1 Comprising a 5'-GalNAc$_3$ Cluster The oligonucleotides listed below were tested in a dose-dependent study for antisense inhibition of SRB-1 in mice. Each of the GalNAc$_3$ conjugate groups was attached at the 5' terminus of the respective oligonucleotide by a phosphodiester linked nucleoside (cleavable moiety (CM)).

TABLE 57

Modified ASOs targeting SRB-1

| ISIS No. | Sequences (5' to 3') | GalNAc$_3$ Cluster | CM | SEQ ID No. |
|---|---|---|---|---|
| 661161 | GalNAc$_3$-3$_{a-o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | A$_d$ | 145 |
| 670699 | GalNAc$_3$-3$_{a-o}$,T$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | T$_d$ | 148 |
| 670700 | GalNAc$_3$-3$_{a-o}$,A$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | A$_e$ | 145 |
| 670701 | GalNAc$_3$-3$_{a-o}$,T$_{eo}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-3a | T$_e$ | 148 |
| 671165 | GalNAc$_3$-13$_{a-o}$,A$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_e$ | GalNAc$_3$-13a | A$_d$ | 145 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester intemucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-13a was shown previously in Example 62.

Treatment

Six to eight week old C57b16 mice (Jackson Laboratory, Bar Harbor, ME) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 58, treatment with antisense oligonucleotides lowered SRB-1 mRNA levels in a dose-dependent manner. The antisense oligonucleotides comprising various cleavable moieties all showed similar potencies.

TABLE 58

| | | SRB-1 mRNA (% Saline) | | |
|---|---|---|---|---|
| ISIS No. | Dosage (mg/kg) | SRB-1 mRNA (% Saline) | GalNAc$_3$ Cluster | CM |
| Saline | n/a | 100.0 | n/a | n/a |
| 661161 | 0.5 | 87.8 | GalNAc$_3$-3a | A$_d$ |
|  | 1.5 | 61.3 |  |  |
|  | 5 | 33.8 |  |  |
|  | 15 | 14.0 |  |  |
| 670699 | 0.5 | 89.4 | GalNAc$_3$-3a | T$_d$ |
|  | 1.5 | 59.4 |  |  |
|  | 5 | 31.3 |  |  |
|  | 15 | 17.1 |  |  |
| 670700 | 0.5 | 79.0 | GalNAc$_3$-3a | A$_e$ |
|  | 1.5 | 63.3 |  |  |
|  | 5 | 32.8 |  |  |
|  | 15 | 17.9 |  |  |
| 670701 | 0.5 | 79.1 | GalNAc$_3$-3a | T$_e$ |
|  | 1.5 | 59.2 |  |  |

TABLE 58-continued

SRB-1 mRNA (% Saline)

| ISIS No. | Dosage (mg/kg) | SRB-1 mRNA (% Saline) | GalNAc$_3$ Cluster | CM |
|---|---|---|---|---|
|  | 5 | 35.8 |  |  |
|  | 15 | 17.7 |  |  |
| 671165 | 0.5 | 76.4 | GalNAc$_3$-13a | $A_d$ |
|  | 1.5 | 43.2 |  |  |
|  | 5 | 22.6 |  |  |
|  | 15 | 10.0 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 59

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | GalNAc$_3$-3a | $A_d$ |
|  | 1.5 | 24 | 50 | 0.2 | 32 |  |  |
|  | 5 | 26 | 55 | 0.2 | 28 |  |  |
|  | 15 | 27 | 52 | 0.2 | 31 |  |  |

TABLE 59-continued

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| 670699 | 0.5 | 42 | 83 | 0.2 | 31 | GalNAc$_3$-3a | $T_d$ |
|  | 1.5 | 33 | 58 | 0.2 | 32 |  |  |
|  | 5 | 26 | 70 | 0.2 | 29 |  |  |
|  | 15 | 25 | 67 | 0.2 | 29 |  |  |
| 670700 | 0.5 | 40 | 74 | 0.2 | 27 | GalNAc$_3$-3a | $A_e$ |
|  | 1.5 | 23 | 62 | 0.2 | 27 |  |  |
|  | 5 | 24 | 49 | 0.2 | 29 |  |  |
|  | 15 | 25 | 87 | 0.1 | 25 |  |  |
| 670701 | 0.5 | 30 | 77 | 0.2 | 27 | GalNAc$_3$-3a | $T_e$ |
|  | 1.5 | 22 | 55 | 0.2 | 30 |  |  |
|  | 5 | 81 | 101 | 0.2 | 25 |  |  |
|  | 15 | 31 | 82 | 0.2 | 24 |  |  |
| 671165 | 0.5 | 44 | 84 | 0.2 | 26 | GalNAc$_3$-13a | $A_d$ |
|  | 1.5 | 47 | 71 | 0.1 | 24 |  |  |
|  | 5 | 33 | 91 | 0.2 | 26 |  |  |
|  | 15 | 33 | 56 | 0.2 | 29 |  |  |

Example 67: Preparation of Oligomeric Compound 199 Comprising GalNAc$_3$-16

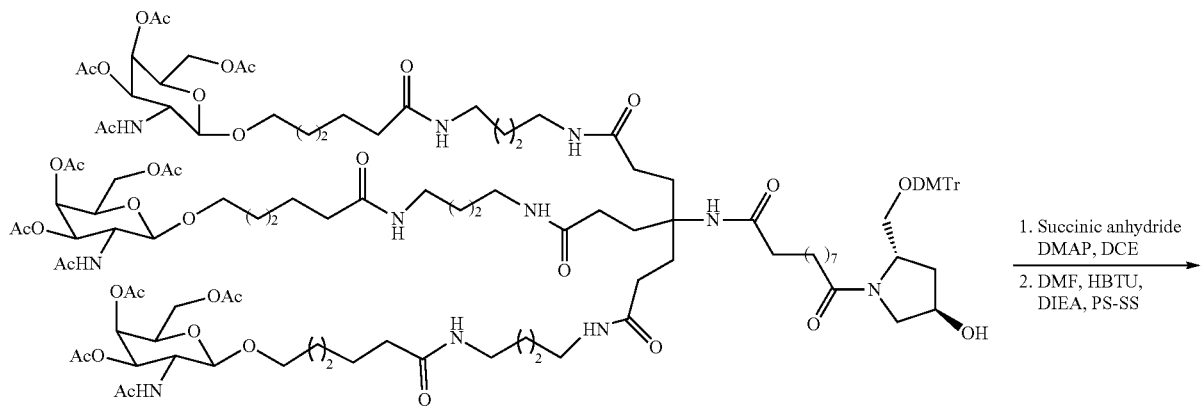

98d

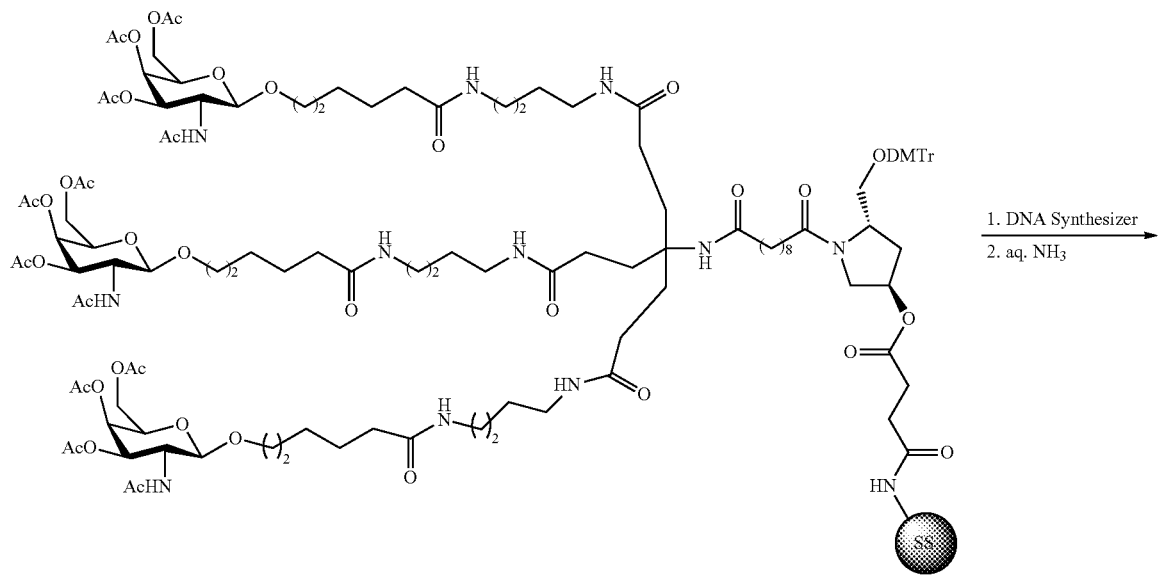

198

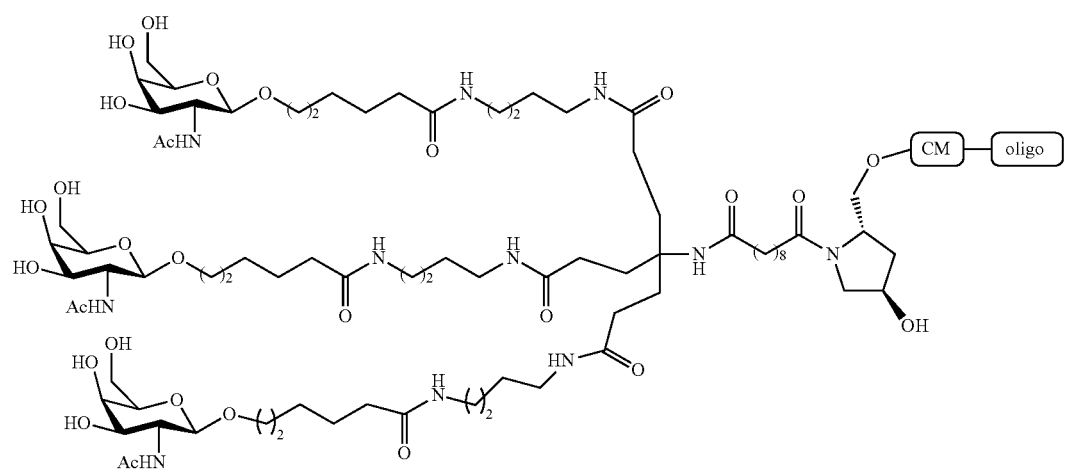

199

Oligomeric compound 199, comprising a GalNAc$_3$-16 conjugate group, is prepared using the general procedures illustrated in Examples 7 and 9. The GalNAc$_3$ cluster portion of the conjugate group GalNAc$_3$-16 (GalNAc$_3$-16$_a$) can be combined with any cleavable moiety to provide a variety of conjugate groups. In certain embodiments, the cleavable moiety is —P(=O)(OH)-A$_d$-P(=O)(OH)-. The structure of GalNAc$_3$-16 (GalNAc$_3$-16$_a$-CM-) is shown below:

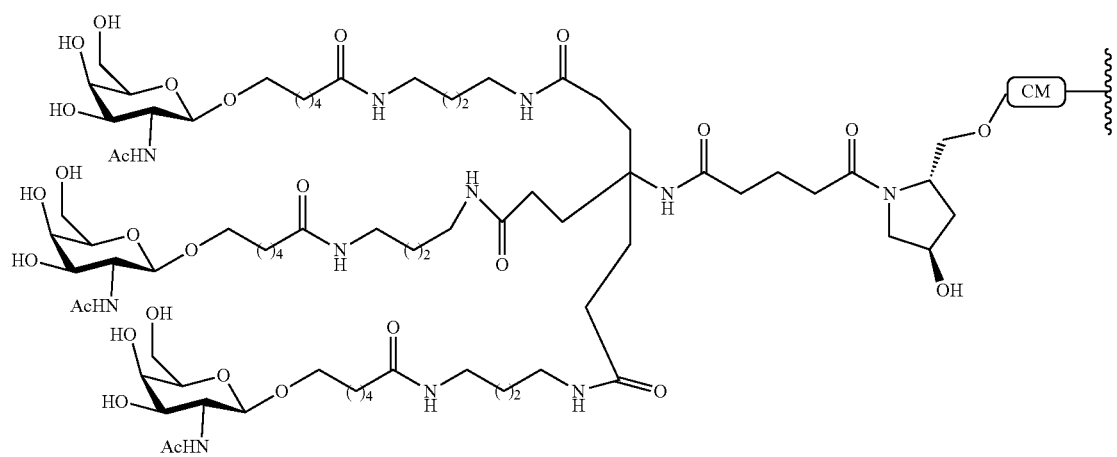

20

Example 68: Preparation of Oligomeric Compound 200 Comprising GalNAc₃-17

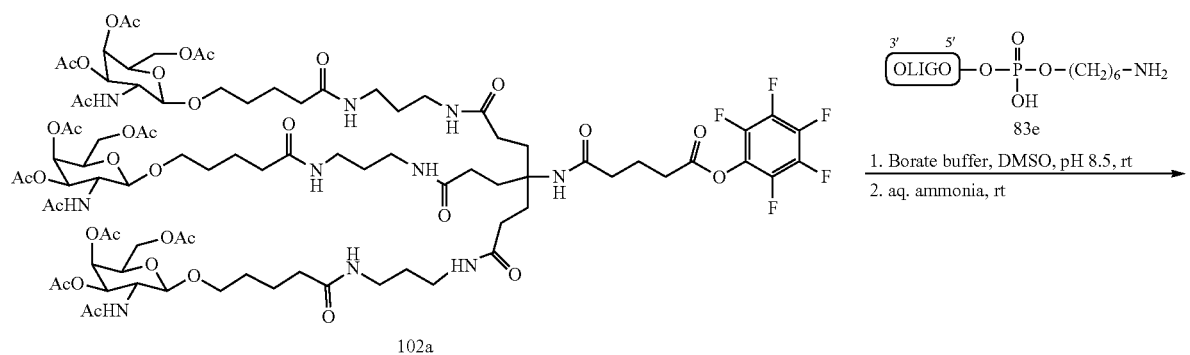

102a

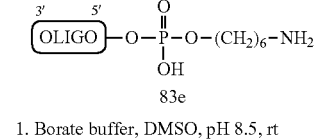

83e

1. Borate buffer, DMSO, pH 8.5, rt
2. aq. ammonia, rt

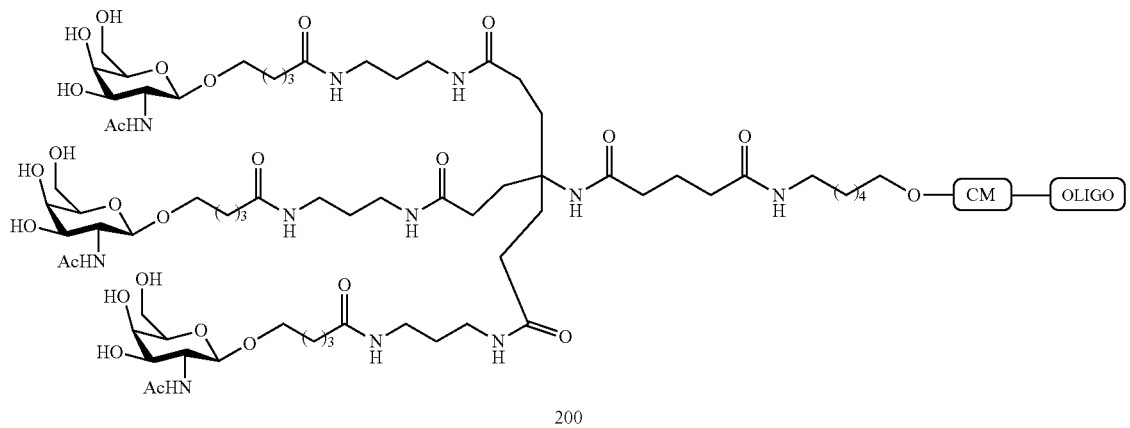

200

Oligomeric compound 200, comprising a GalNAc₃-17 conjugate group, was prepared using the general procedures illustrated in Example 46. The GalNAc₃ cluster portion of the conjugate group GalNAc₃-17 (GalNAc₃-17$_a$) can be combined with any cleavable moiety to provide a variety of conjugate groups. In certain embodiments, the cleavable moiety is —P(=O)(OH)-A$_d$-P(=O)(OH)—. The structure of GalNAc₃-17 (GalNAc₃-17$_a$-CM-) is shown below:

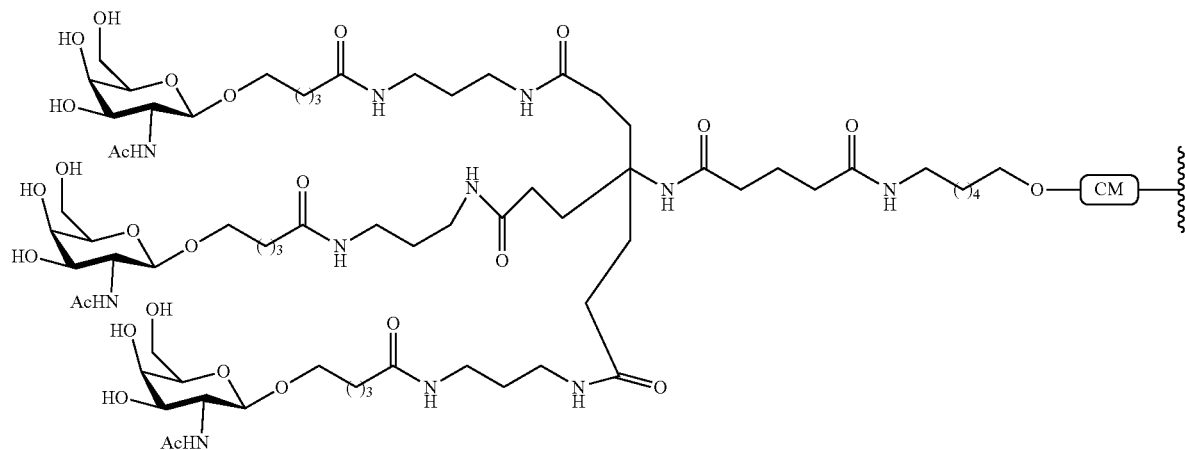

Example 69: Preparation of Oligomeric Compound 201 Comprising GalNAc$_3$-18

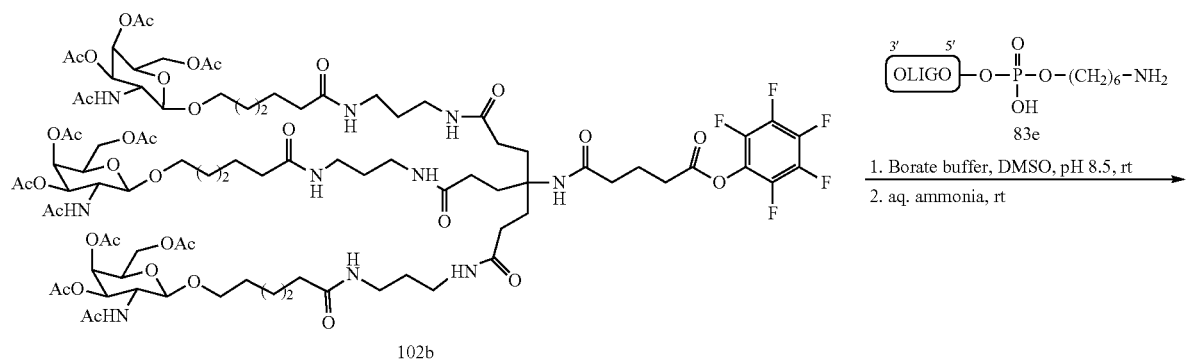

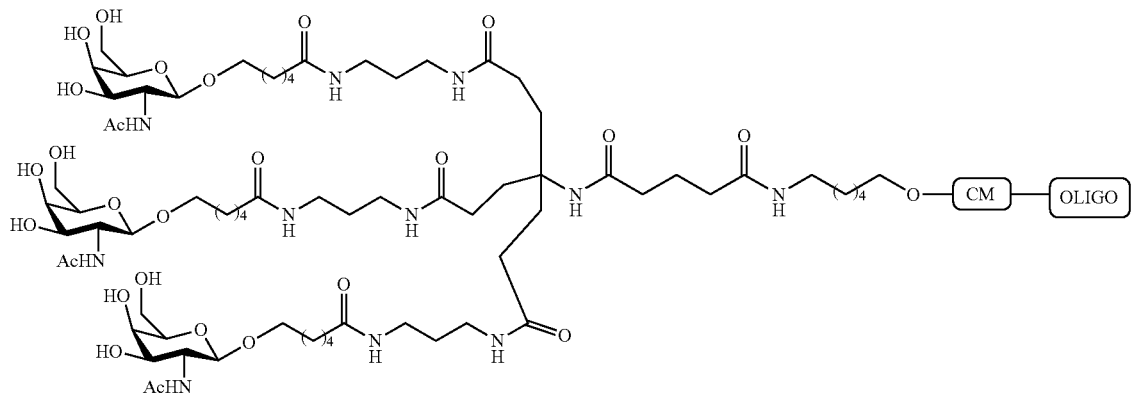

Oligomeric compound 201, comprising a GalNAc$_3$-18 conjugate group, was prepared using the general procedures illustrated in Example 46. The GalNAc$_3$ cluster portion of the conjugate group GalNAc$_3$-18 (GalNAc$_3$-18$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-18 (GalNAc$_3$-18$_a$-CM-) is shown below:

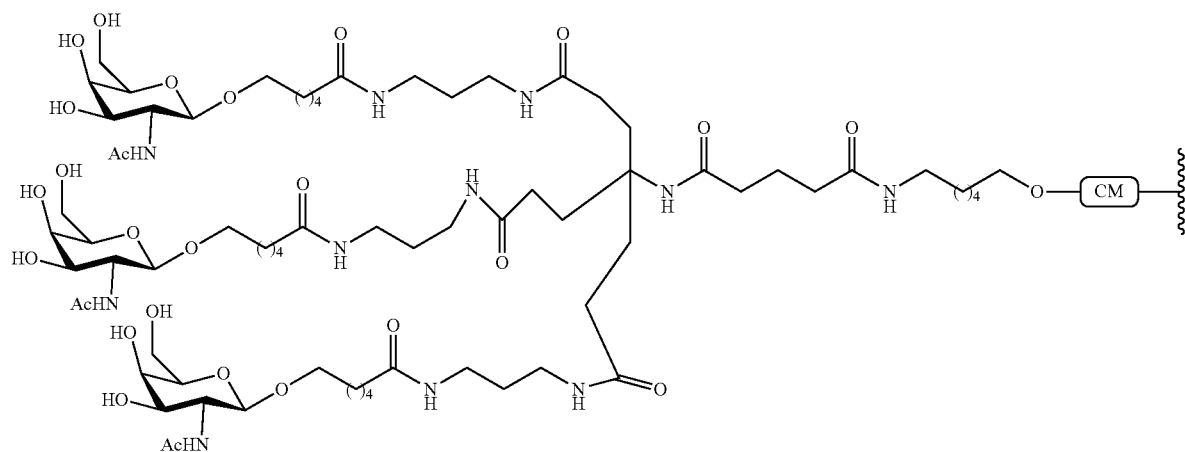
20
Example 70: Preparation of Oligomeric Compound 204 Comprising GalNAc₃-19
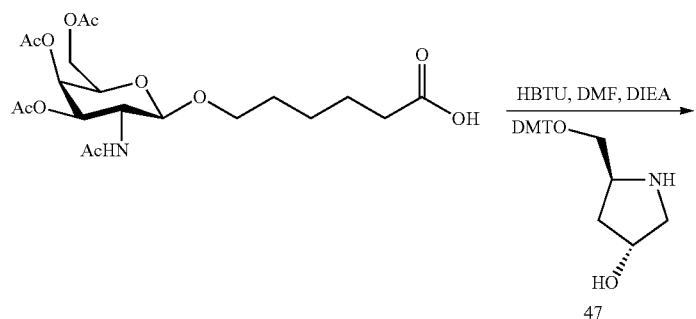
47
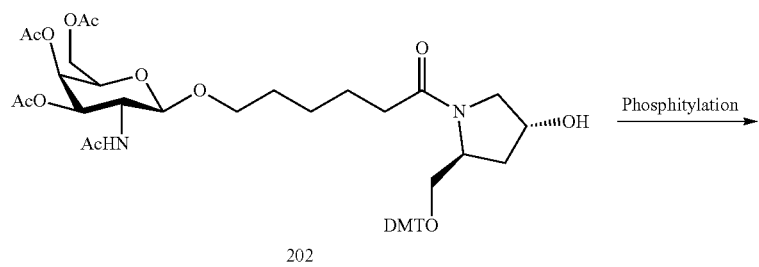
202
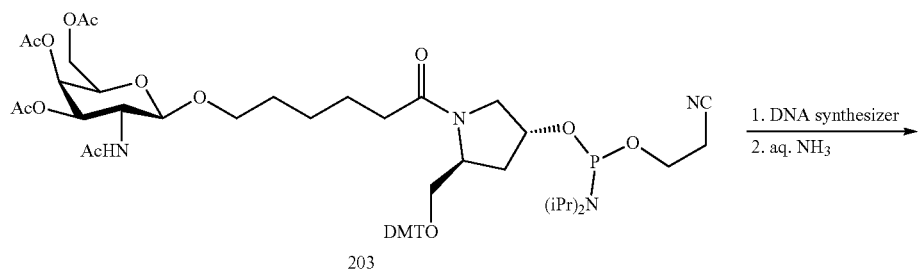
203

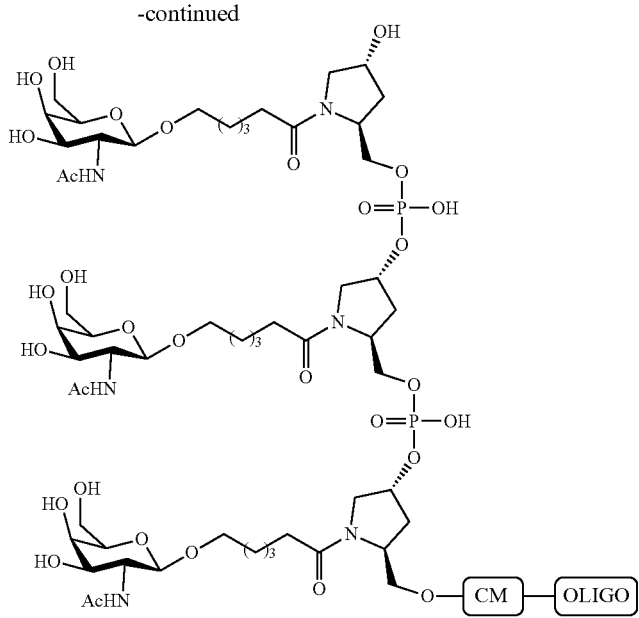

204

Oligomeric compound 204, comprising a GalNAc$_3$-19 conjugate group, was prepared from compound 64 using the general procedures illustrated in Example 52. The GalNAc$_3$ cluster portion of the conjugate group GalNAc$_3$-19 (GalNAc$_3$-19$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-19 (GalNAc$_3$-19$_a$-CM-) is shown below:

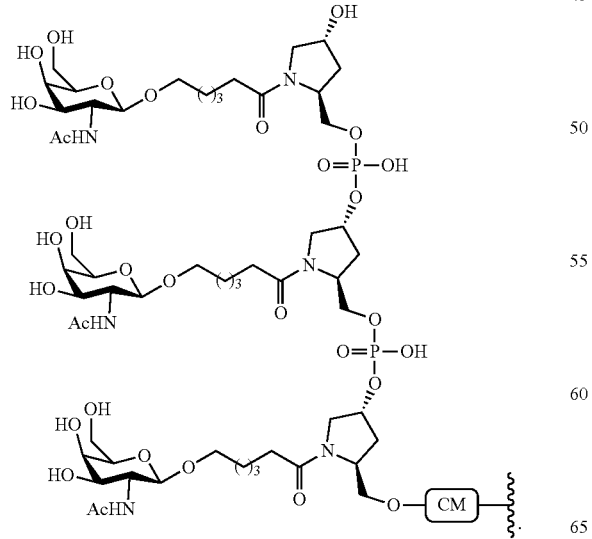

Example 71: Preparation of Oligomeric Compound 210 Comprising GalNAc₃-20
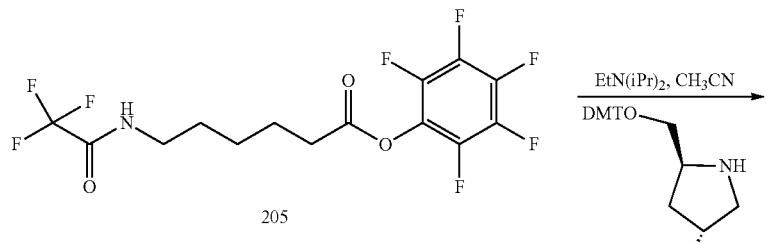
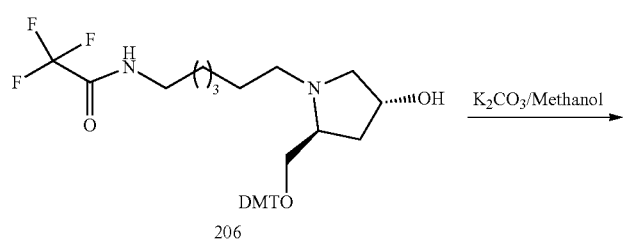
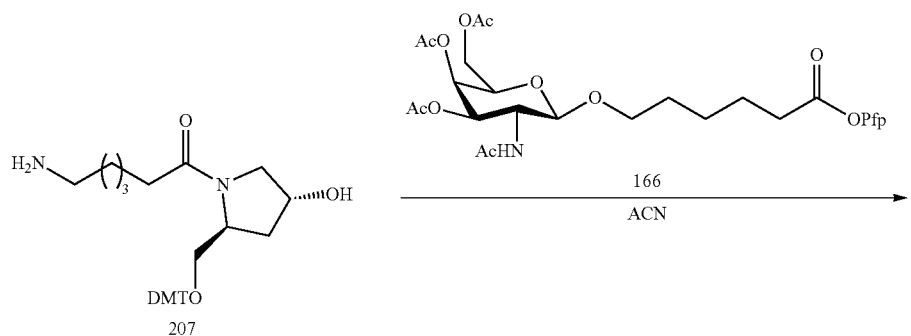
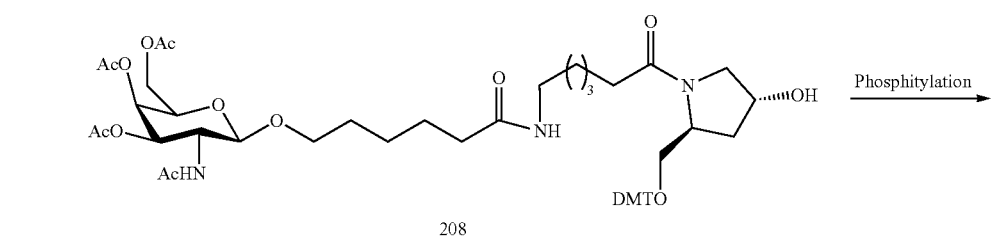
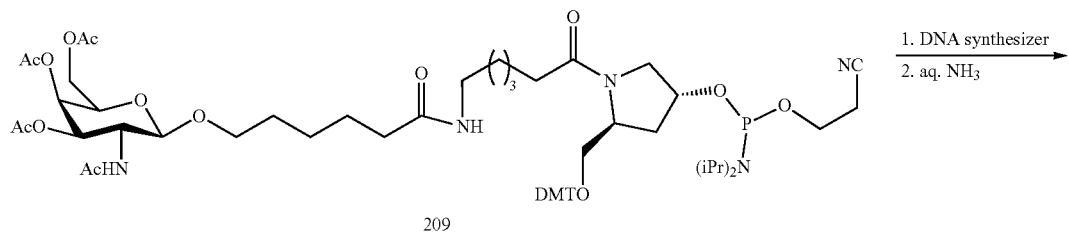

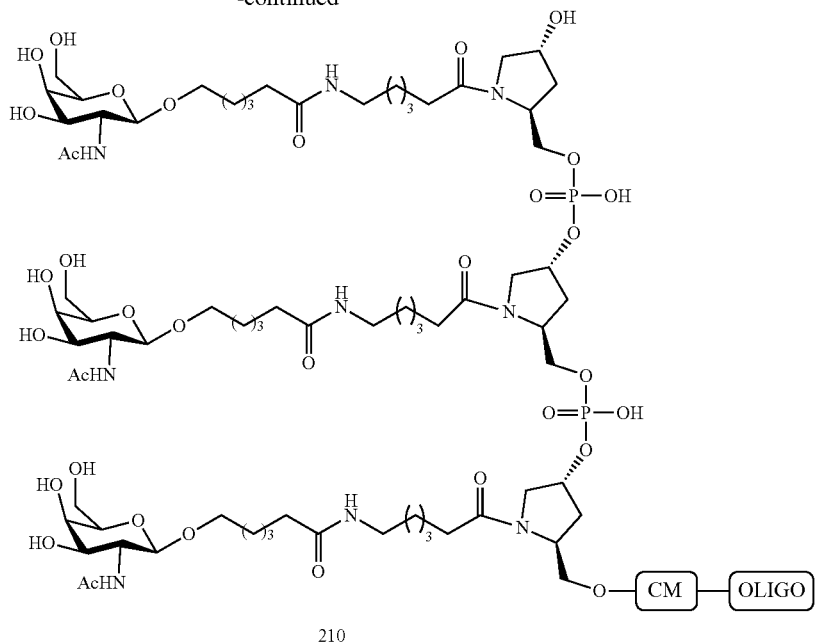

210

Compound 205 was prepared by adding PFP-TFA and DIEA to 6-(2,2,2-trifluoroacetamido)hexanoic acid in acetonitrile, which was prepared by adding triflic anhydride to 6-aminohexanoic acid. The reaction mixture was heated to 80° C., then lowered to rt. Oligomeric compound 210, comprising a GalNAc$_3$-20 conjugate group, was prepared from compound 208 using the general procedures illustrated in Example 52.

The GalNAc$_3$ cluster portion of the conjugate group GalNAc$_3$-20 (GalNAc$_3$-20$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-20 (GalNAc$_3$-20$_a$-CM-) is shown below:

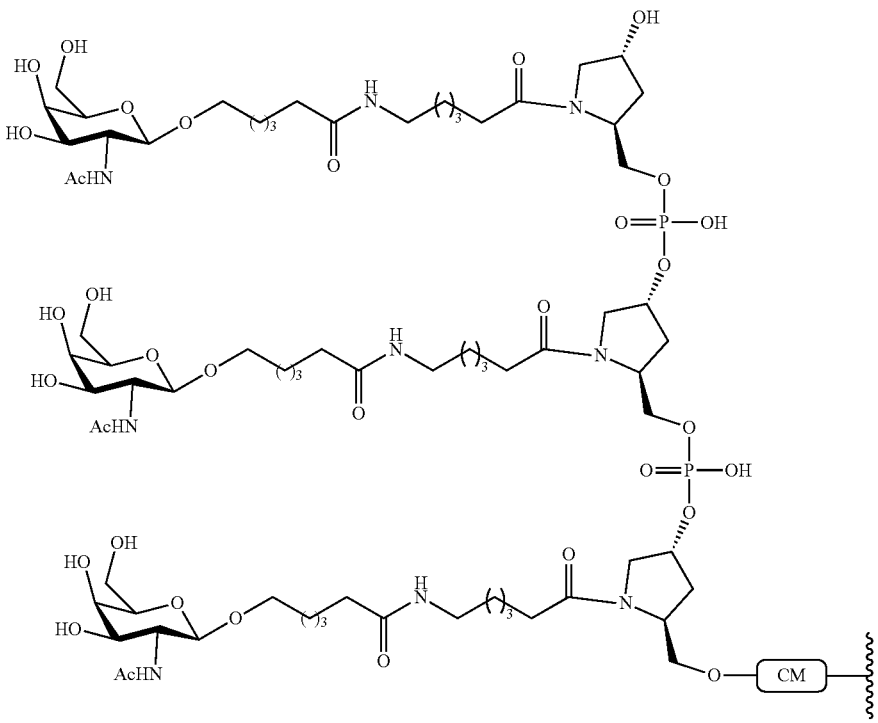

Example 72: Preparation of Oligomeric Compound 215 Comprising GalNAc$_3$-21
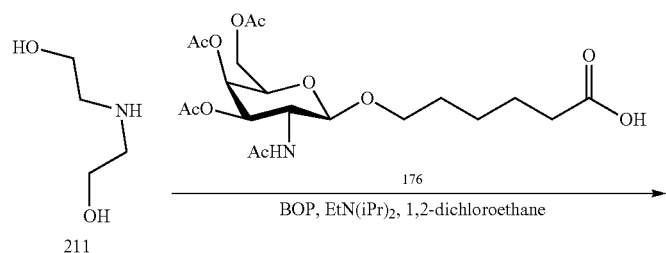
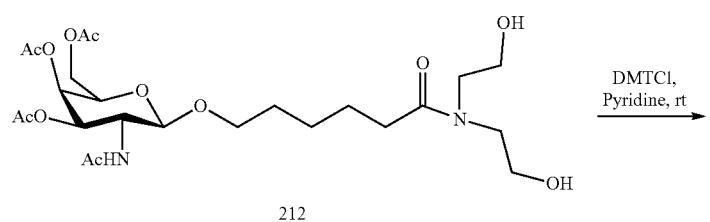
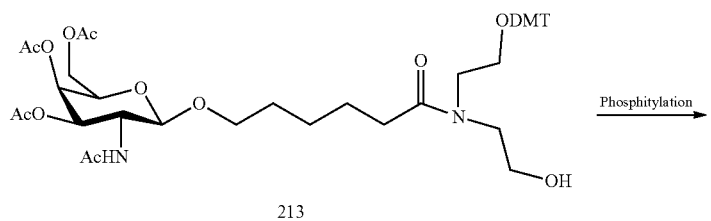
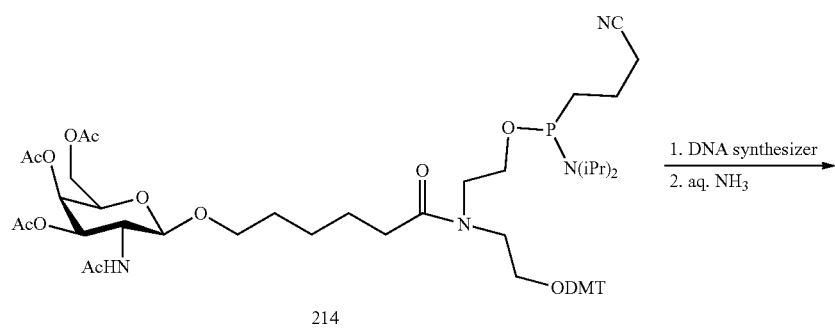

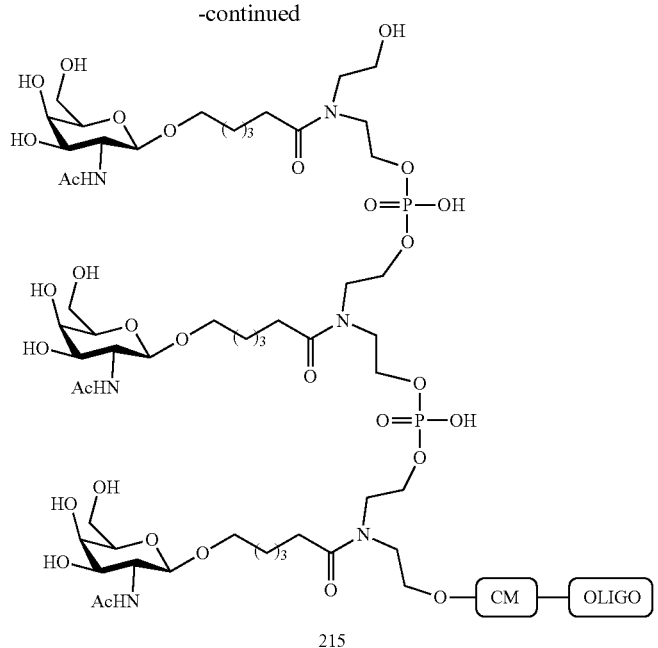

215

Compound 211 is commercially available. Oligomeric compound 215, comprising a GalNAc$_3$-21 conjugate group, was prepared from compound 213 using the general procedures illustrated in Example 52. The GalNAc$_3$ cluster portion of the conjugate group GalNAc$_3$-21 (GalNAc$_3$-21$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-21 (GalNAc$_3$-21$_a$-CM-) is shown below:

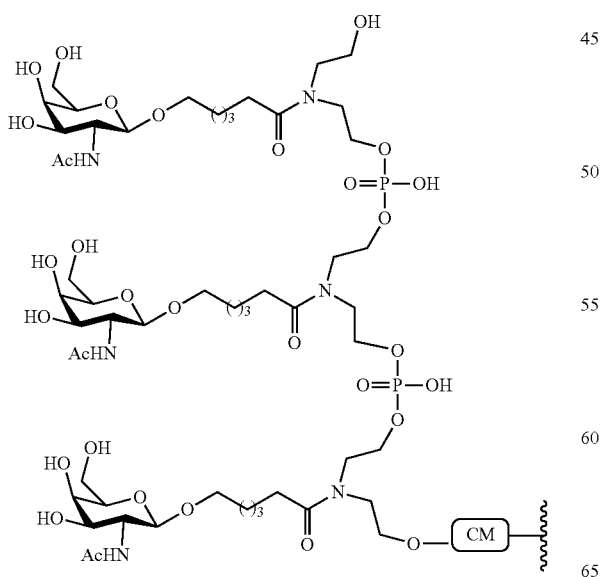

Example 73: Preparation of Oligomeric Compound 221 Comprising GalNAc$_3$-22
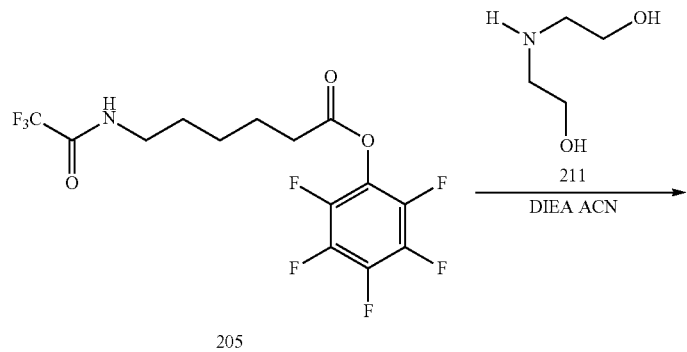
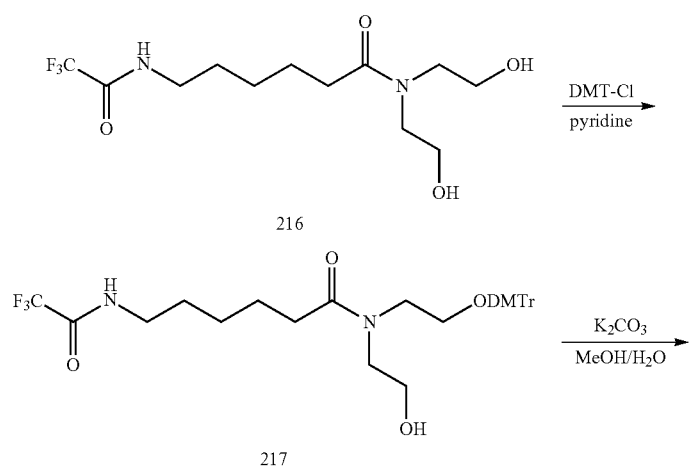
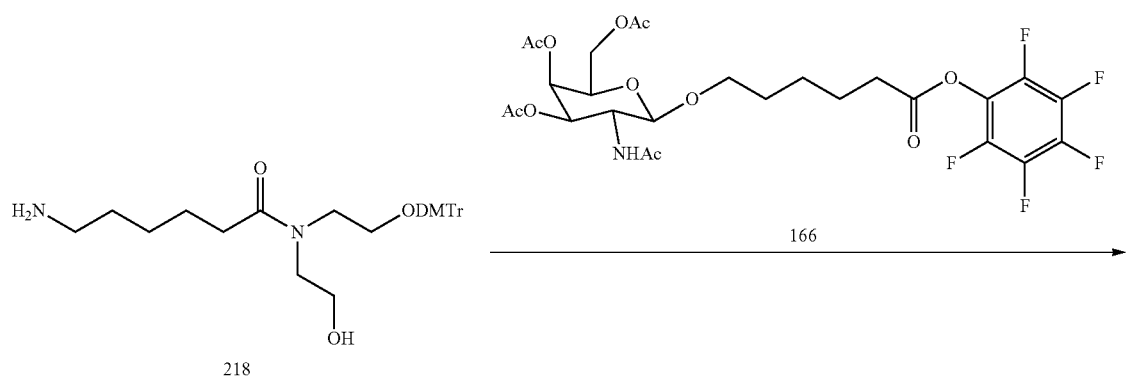
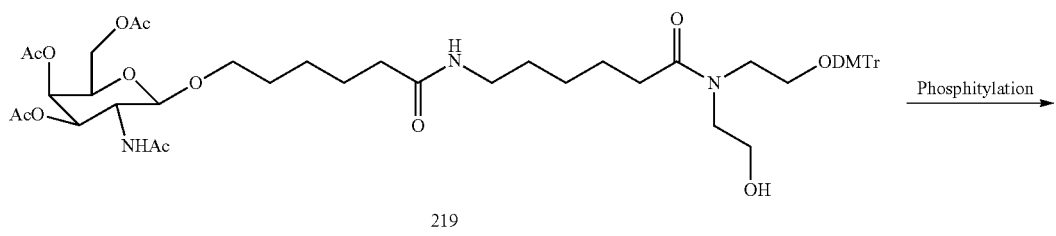

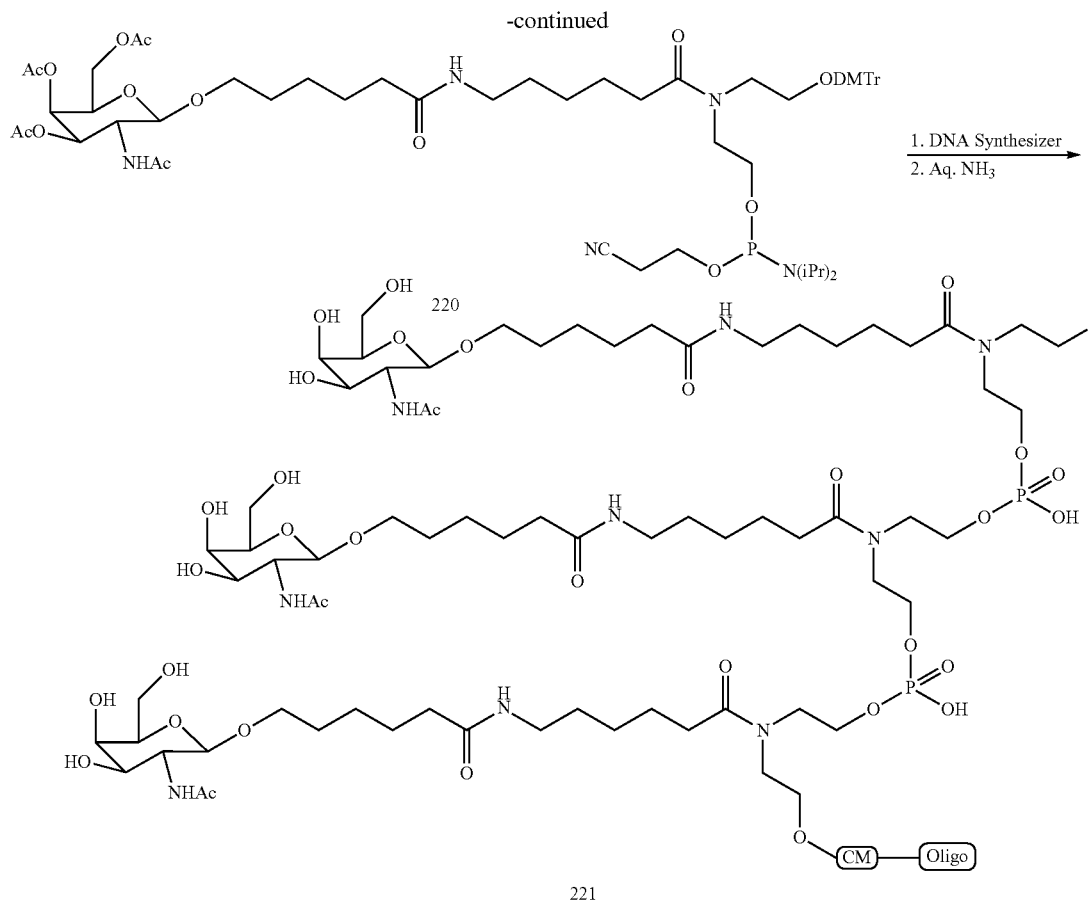

Compound 220 was prepared from compound 219 using diisopropylammonium tetrazolide. Oligomeric compound 221, comprising a GalNAc$_3$-21 conjugate group, is prepared from compound 220 using the general procedure illustrated in Example 52. The GalNAc$_3$ cluster portion of the conjugate group GalNAc$_3$-22 (GalNAc$_3$-22$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-22 (GalNAc$_3$-22$_a$-CM-) is shown below:

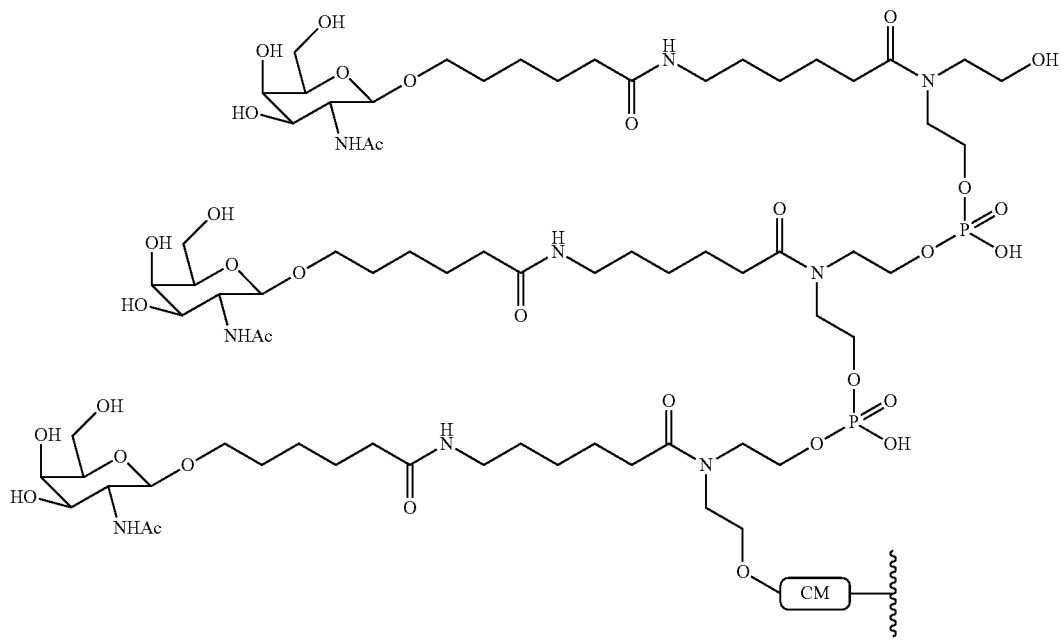

Example 74: Effect of Various Cleavable Moieties on Antisense Inhibition In Vivo by Oligonucleotides Targeting SRB-1 Comprising a 5'-GalNAc$_3$ Conjugate The oligonucleotides listed below were tested in a dose-dependent study for antisense inhibition of SRB-1 in mice. Each of the GalNAc$_3$ conjugate groups was attached at the 5' terminus of the respective oligonucleotide.

TABLE 60

Modified ASOs targeting SRB-1

| ISIS No. | Sequences (5' to 3') | GalNAc$_3$ Cluster | CM | SEQ ID No. |
|---|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | n/a | n/a | 143 |
| 661161 | GalNAc$_3$-3$_{a\text{-}o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | A$_d$ | 145 |
| 666904 | GalNAc$_3$-3$_{a\text{-}o}$,G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | PO | 143 |
| 675441 | GalNAc$_3$-17$_{a\text{-}o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-17a | A$_d$ | 145 |
| 675442 | GalNAc$_3$-18$_{a\text{-}o}$,A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-18a | A$_d$ | 145 |

In all tables, capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-17a was shown previously in Example 68, and the structure of GalNAc$_3$-18a was shown in Example 69.

Treatment

Six to eight week old C57BL/6 mice (Jackson Laboratory, Bar Harbor, ME) were injected subcutaneously once at the dosage shown below with an oligonucleotide listed in Table 60 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 61, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNAc conjugate.

TABLE 61

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 353382 | 3 | 79.38 | n/a | n/a |
|  | 10 | 68.67 |  |  |
|  | 30 | 40.70 |  |  |
| 661161 | 0.5 | 79.18 | GalNAc$_3$-3a | A$_d$ |
|  | 1.5 | 75.96 |  |  |
|  | 5 | 30.53 |  |  |
|  | 15 | 12.52 |  |  |
| 666904 | 0.5 | 91.30 | GalNAc$_3$-3a | PO |
|  | 1.5 | 57.88 |  |  |
|  | 5 | 21.22 |  |  |
|  | 15 | 16.49 |  |  |
| 675441 | 0.5 | 76.71 | GalNAc$_3$-17a | A$_d$ |
|  | 1.5 | 63.63 |  |  |
|  | 5 | 29.57 |  |  |
|  | 15 | 13.49 |  |  |
| 675442 | 0.5 | 95.03 | GalNAc$_3$-18a | A$_d$ |
|  | 1.5 | 60.06 |  |  |
|  | 5 | 31.04 |  |  |
|  | 15 | 19.40 |  |  |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 62 below.

TABLE 62

| ISIS No. | Dosage (mg/kg) | ALT (U/L) | AST (U/L) | Total Bilirubin (mg/dL) | BUN (mg/dL) | GalNAc₃ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
|  | 10 | 28 | 58 | 0.16 | 43 |  |  |
|  | 30 | 20 | 48 | 0.12 | 34 |  |  |
| 661161 | 0.5 | 30 | 47 | 0.13 | 35 | GalNAc₃-3a | $A_d$ |
|  | 1.5 | 23 | 53 | 0.14 | 37 |  |  |
|  | 5 | 26 | 48 | 0.15 | 39 |  |  |
|  | 15 | 32 | 57 | 0.15 | 42 |  |  |
| 666904 | 0.5 | 24 | 73 | 0.13 | 36 | GalNAc₃-3a | PO |
|  | 1.5 | 21 | 48 | 0.12 | 32 |  |  |
|  | 5 | 19 | 49 | 0.14 | 33 |  |  |
|  | 15 | 20 | 52 | 0.15 | 26 |  |  |
| 675441 | 0.5 | 42 | 148 | 0.21 | 36 | GalNAc₃-17a | $A_d$ |
|  | 1.5 | 60 | 95 | 0.16 | 34 |  |  |
|  | 5 | 27 | 75 | 0.14 | 37 |  |  |
|  | 15 | 24 | 61 | 0.14 | 36 |  |  |
| 675442 | 0.5 | 26 | 65 | 0.15 | 37 | GalNAc₃-18a | $A_d$ |
|  | 1.5 | 25 | 64 | 0.15 | 43 |  |  |
|  | 5 | 27 | 69 | 0.15 | 37 |  |  |
|  | 15 | 30 | 84 | 0.14 | 37 |  |  |

TABLE 63

| | PK Analysis in Liver | | | |
|---|---|---|---|---|
| ISIS No. | Dosage (mg/kg) | Total Tissue Level by UV (μg/g) | Parent ASO Tissue Level by EIC (μg/g) | GalNAC₃ Cluster | CM |
| 353382 | 3 | 8.9 | 8.6 | n/a | n/a |
|  | 10 | 22.4 | 21.0 |  |  |
|  | 30 | 54.2 | 44.2 |  |  |
| 661161 | 5 | 32.4 | 20.7 | GalNAc₃-3a | $A_d$ |
|  | 15 | 63.2 | 44.1 |  |  |
| 671144 | 5 | 20.5 | 19.2 | GalNAc₃-12a | $A_d$ |
|  | 15 | 48.6 | 41.5 |  |  |
| 670061 | 5 | 31.6 | 28.0 | GalNAc₃-13a | $A_d$ |
|  | 15 | 67.6 | 55.5 |  |  |
| 671261 | 5 | 19.8 | 16.8 | GalNAc₃-14a | $A_d$ |
|  | 15 | 64.7 | 49.1 |  |  |
| 671262 | 5 | 18.5 | 7.4 | GalNAc₃-15a | $A_d$ |
|  | 15 | 52.3 | 24.2 |  |  |
| 670699 | 5 | 16.4 | 10.4 | GalNAc₃-3a | $T_d$ |
|  | 15 | 31.5 | 22.5 |  |  |
| 670700 | 5 | 19.3 | 10.9 | GalNAc₃-3a | $A_e$ |
|  | 15 | 38.1 | 20.0 |  |  |
| 670701 | 5 | 21.8 | 8.8 | GalNAc₃-3a | $T_e$ |
|  | 15 | 35.2 | 16.1 |  |  |
| 671165 | 5 | 27.1 | 26.5 | GalNAc₃-13a | $A_d$ |
|  | 15 | 48.3 | 44.3 |  |  |
| 666904 | 5 | 30.8 | 24.0 | GalNAc₃-3a | PO |
|  | 15 | 52.6 | 37.6 |  |  |
| 675441 | 5 | 25.4 | 19.0 | GalNAc₃-17a | $A_d$ |
|  | 15 | 54.2 | 42.1 |  |  |
| 675442 | 5 | 22.2 | 20.7 | GalNAc₃-18a | $A_d$ |
|  | 15 | 39.6 | 29.0 |  |  |

Example 75: Pharmacokinetic Analysis of Oligonucleotides Comprising a 5'-Conjugate Group The PK of the ASOs in Tables 54, 57 and 60 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (μg/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

The results in Table 63 above show that there were greater liver tissue levels of the oligonucleotides comprising a GalNAc₃ conjugate group than of the parent oligonucleotide that does not comprise a GalNAc₃ conjugate group (ISIS 353382) 72 hours following oligonucleotide administration, particularly when taking into consideration the differences in dosing between the oligonucleotides with and without a GalNAc₃ conjugate group. Furthermore, by 72 hours, 40-98% of each oligonucleotide comprising a GalNAc₃ conjugate group was metabolized to the parent compound, indicating that the GalNAc₃ conjugate groups were cleaved from the oligonucleotides.

Example 76: Preparation of Oligomeric Compound 230 Comprising GalNAc₃-23

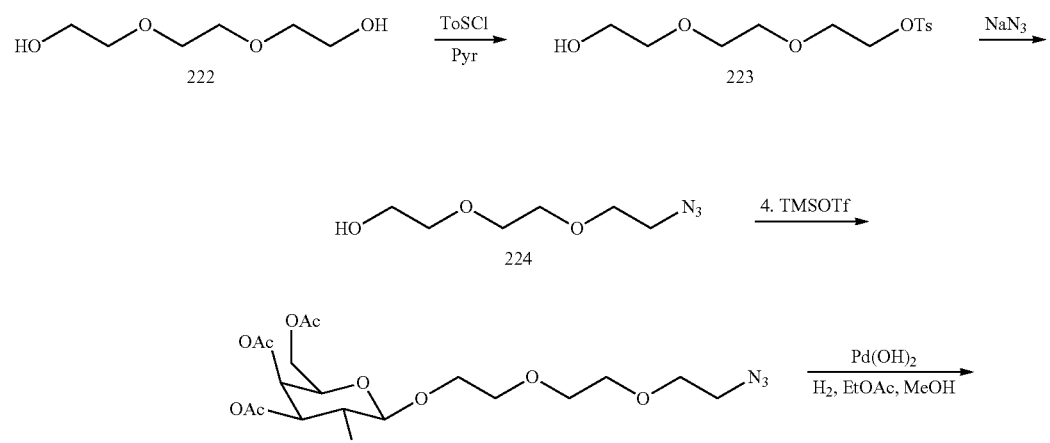

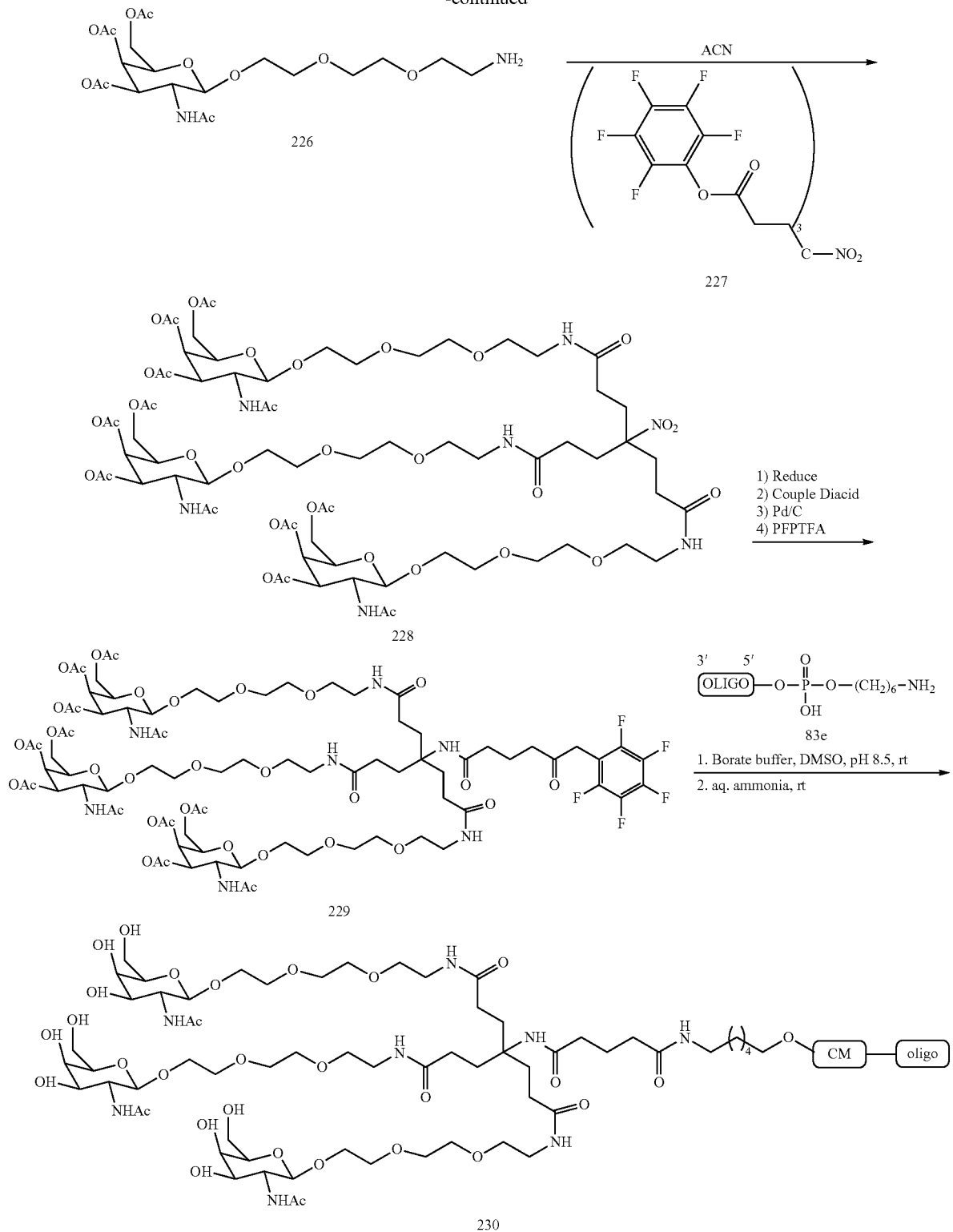

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. NaHCO₃, brine, and dried over Na₂SO₄. The ethyl acetate was concentrated to dryness and purified by column chromatography, eluted with EtOAc/hexanes (1:1) followed by 10% methanol in CH₂Cl₂ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over $Na_2SO_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. $NaHCO_3$, water, brine, and dried over $Na_2SO_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over $Na_2SO_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 µl, 1.6 mmol) in DMF (5 mL). After 16 hours, the DMF was removed under reduced pressure at 65° C. to an oil, and the oil was dissolved in dichloromethane. The organic layer was washed with sat. $NaHCO_3$, brine, and dried over $Na_2SO_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 µl, 0.66 mmol) was added and the reaction was purged with argon. Pentaflourotriflouro acetate (46.39 µl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N $NaHSO_4$, brine, saturated sodium bicarbonate and brine again. The organics were dried over $Na_2SO_4$, filtered, and were concentrated to dryness to give 225 mg of compound 229 as a brittle yellow foam. LCMS and NMR were consistent with the structure.

Oligomeric compound 230, comprising a $GalNAc_3$-23 conjugate group, was prepared from compound 229 using the general procedure illustrated in Example 46. The $GalNAc_3$ cluster portion of the $GalNAc_3$-23 conjugate group ($GalNAc_3$-23$_a$) can be combined with any cleavable moiety to provide a variety of conjugate groups. The structure of $GalNAC_3$-23 ($GalNAC_3$-23$_a$-CM) is shown below:

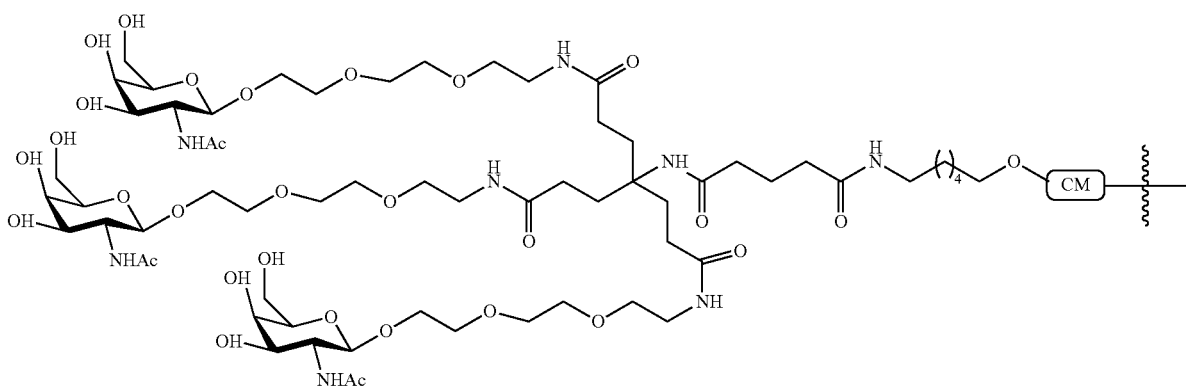

Example 77: Antisense Inhibition In Vivo by Oligonucleotides Targeting SRB-1 Comprising a GalNAc₃ Conjugate The oligonucleotides listed below were tested in a dose-dependent study for antisense inhibition of SRB-1 in mice.

TABLE 64

Modified ASOs targeting SRB-1

| ISIS No. | Sequences (5' to 3') | GalNAc₃ Cluster | CM | SEQ ID No. |
|---|---|---|---|---|
| 661161 | GalNAc₃-3$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc₃-3a | A$_d$ | 145 |
| 666904 | GalNAc₃-3$_{a-o'}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc₃-3a | PO | 143 |
| 673502 | GalNAc₃-10$_{a-o'}$A$_{do}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_{e}$ | GalNAc₃-10a | A$_d$ | 145 |
| 677844 | GalNAc₃-9$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc₃-9a | A$_d$ | 145 |
| 677843 | GalNAc₃-23$_{a-o'}$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc₃-23a | A$_d$ | 145 |
| 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$ $^m$C$_{es}$T$_{es}$T$_{eo}$A$_{do'}$-GalNAc₃-1$_a$ | GalNAc₃-1a | A$_d$ | 144 |
| 677841 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$ $^m$C$_{es}$T$_{es}$T$_{eo}$A$_{do'}$-GalNAc₃-19$_a$ | GalNAc₃-19a | A$_d$ | 144 |
| 677842 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$ $^m$C$_{es}$T$_{es}$T$_{eo}$A$_{do'}$-GalNAc₃-20$_a$ | GalNAc₃-20a | A$_d$ | 144 |

The structure of GalNAc₃-1$_a$ was shown previously in Example 9, GalNAc₃-3$_a$ was shown in Example 39, GalNAc₃-9a was shown in Example 52, GalNAc₃—10a was shown in Example 46, GalNAc₃-19$_a$ was shown in Example 70, GalNAc₃-20$_a$ was shown in Example 71, and GalNAc₃-23$_a$ was shown in Example 76.

Treatment

Six to eight week old C57BL/6 mice (Jackson Laboratory, Bar Harbor, ME) were each injected subcutaneously once at a dosage shown below with an oligonucleotide listed in Table 64 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 65, treatment with antisense oligonucleotides lowered SRB-1 mRNA levels in a dose-dependent manner.

TABLE 65

SRB-1 mRNA (% Saline)

| ISIS No. | Dosage (mg/kg) | SRB-1 mRNA (% Saline) | GalNAc₃ Cluster | CM |
|---|---|---|---|---|
| Saline | n/a | 100.0 | n/a | n/a |
| 661161 | 0.5 | 89.18 | GalNAc₃-3a | A$_d$ |
|  | 1.5 | 77.02 |  |  |
|  | 5 | 29.10 |  |  |
|  | 15 | 12.64 |  |  |

TABLE 65-continued

SRB-1 mRNA (% Saline)

| ISIS No. | Dosage (mg/kg) | SRB-1 mRNA (% Saline) | GalNAc₃ Cluster | CM |
|---|---|---|---|---|
| 666904 | 0.5 | 93.11 | GalNAc₃-3a | PO |
|  | 1.5 | 55.85 |  |  |
|  | 5 | 21.29 |  |  |
|  | 15 | 13.43 |  |  |
| 673502 | 0.5 | 77.75 | GalNAc₃-10a | A$_d$ |
|  | 1.5 | 41.05 |  |  |
|  | 5 | 19.27 |  |  |
|  | 15 | 14.41 |  |  |
| 677844 | 0.5 | 87.65 | GalNAc₃-9a | A$_d$ |
|  | 1.5 | 93.04 |  |  |
|  | 5 | 40.77 |  |  |
|  | 15 | 16.95 |  |  |
| 677843 | 0.5 | 102.28 | GalNAc₃-23a | A$_d$ |
|  | 1.5 | 70.51 |  |  |
|  | 5 | 30.68 |  |  |
|  | 15 | 13.26 |  |  |
| 655861 | 0.5 | 79.72 | GalNAc₃-1a | A$_d$ |
|  | 1.5 | 55.48 |  |  |
|  | 5 | 26.99 |  |  |
|  | 15 | 17.58 |  |  |
| 677841 | 0.5 | 67.43 | GalNAc₃-19a | A$_d$ |
|  | 1.5 | 45.13 |  |  |
|  | 5 | 27.02 |  |  |
|  | 15 | 12.41 |  |  |
| 677842 | 0.5 | 64.13 | GalNAc₃-20a | A$_d$ |
|  | 1.5 | 53.56 |  |  |
|  | 5 | 20.47 |  |  |
|  | 15 | 10.23 |  |  |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 66 below.

TABLE 66

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | GalNAc$_3$-3a | A$_d$ |
|  | 1.5 | 23 | 42 | 0.13 | 39 |  |  |
|  | 5 | 22 | 59 | 0.13 | 37 |  |  |
|  | 15 | 21 | 56 | 0.15 | 35 |  |  |
| 666904 | 0.5 | 24 | 56 | 0.14 | 37 | GalNAc$_3$-3a | PO |
|  | 1.5 | 26 | 68 | 0.15 | 35 |  |  |
|  | 5 | 23 | 77 | 0.14 | 34 |  |  |
|  | 15 | 24 | 60 | 0.13 | 35 |  |  |
| 673502 | 0.5 | 24 | 59 | 0.16 | 34 | GalNAc$_3$-10a | A$_d$ |
|  | 1.5 | 20 | 46 | 0.17 | 32 |  |  |
|  | 5 | 24 | 45 | 0.12 | 31 |  |  |
|  | 15 | 24 | 47 | 0.13 | 34 |  |  |
| 677844 | 0.5 | 25 | 61 | 0.14 | 37 | GalNAc$_3$-9a | A$_d$ |
|  | 1.5 | 23 | 64 | 0.17 | 33 |  |  |
|  | 5 | 25 | 58 | 0.13 | 35 |  |  |
|  | 15 | 22 | 65 | 0.14 | 34 |  |  |
| 677843 | 0.5 | 53 | 53 | 0.13 | 35 | GalNAc$_3$-23a | A$_d$ |
|  | 1.5 | 25 | 54 | 0.13 | 34 |  |  |
|  | 5 | 21 | 60 | 0.15 | 34 |  |  |
|  | 15 | 22 | 43 | 0.12 | 38 |  |  |
| 655861 | 0.5 | 21 | 48 | 0.15 | 33 | GalNAc$_3$-1a | A$_d$ |
|  | 1.5 | 28 | 54 | 0.12 | 35 |  |  |
|  | 5 | 22 | 60 | 0.13 | 36 |  |  |
|  | 15 | 21 | 55 | 0.17 | 30 |  |  |
| 677841 | 0.5 | 32 | 54 | 0.13 | 34 | GalNAc$_3$-19a | A$_d$ |
|  | 1.5 | 24 | 56 | 0.14 | 34 |  |  |
|  | 5 | 23 | 92 | 0.18 | 31 |  |  |
|  | 15 | 24 | 58 | 0.15 | 31 |  |  |
| 677842 | 0.5 | 23 | 61 | 0.15 | 35 | GalNAc$_3$-20a | A$_d$ |
|  | 1.5 | 24 | 57 | 0.14 | 34 |  |  |
|  | 5 | 41 | 62 | 0.15 | 35 |  |  |
|  | 15 | 24 | 37 | 0.14 | 32 |  |  |

Example 78: Antisense Inhibition In Vivo by Oligonucleotides Targeting Angiotensinogen Comprising a GalNAc$_3$ Conjugate The oligonucleotides listed below were tested in a dose-dependent study for antisense inhibition of Angiotensinogen (AGT) in normotensive Sprague Dawley rats.

TABLE 67

Modified ASOs targeting AGT

| ISIS No. | Sequences (5' to 3') | GalNAc$_3$ Cluster | CM | SEQ ID No. |
|---|---|---|---|---|
| 552668 | $^mC_{es}A_{es}{}^mC_{es}T_{es}G_{es}A_{ds}T_{ds}T_{ds}T_{ds}T_{ds}T_{ds}G_{ds}{}^mC_{ds}{}^mC_{ds}{}^mC_{ds}A_{es}G_{es}G_{es}A_{es}T_e$ | n/a | n/a | 149 |
| 669509 | $^mC_{es}A_{es}{}^mC_{es}T_{es}G_{es}A_{ds}T_{ds}T_{ds}T_{ds}T_{ds}T_{ds}G_{ds}{}^mC_{ds}{}^mC_{ds}{}^mC_{ds}A_{es}G_{es}G_{es}A_{es}T_{eo}A_{do}$,-GalNAc$_3$-1$_a$ | GalNAc$_3$-1$_a$ | A$_d$ | 150 |

The structure of GalNAc$_3$-1$_a$ was shown previously in Example 9.

Treatment

Six week old, male Sprague Dawley rats were each injected subcutaneously once per week at a dosage shown below, for a total of three doses, with an oligonucleotide listed in Table 67 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, OR) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 68, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 68

AGT liver mRNA and plasma protein levels

| ISIS No. | Dosage (mg/kg) | AGT liver mRNA (% PBS) | AGT plasma protein (% PBS) | GalNAc$_3$ Cluster | CM |
|---|---|---|---|---|---|
| PBS | n/a | 100 | 100 | n/a | n/a |
| 552668 | 3 | 95 | 122 | n/a | n/a |
|  | 10 | 85 | 97 |  |  |
|  | 30 | 46 | 79 |  |  |
|  | 90 | 8 | 11 |  |  |
| 669509 | 0.3 | 95 | 70 | GalNAc$_3$-1a | A$_d$ |
|  | 1 | 95 | 129 |  |  |
|  | 3 | 62 | 97 |  |  |
|  | 10 | 9 | 23 |  |  |

Liver transaminase levels, alanine aminotransferase (ALT) and aspartate aminotransferase (AST), in plasma and body weights were also measured at time of sacrifice using standard protocols. The results are shown in Table 69 below.

TABLE 69

Liver transaminase levels and rat body weights

| ISIS No. | Dosage (mg/kg) | ALT (U/L) | AST (U/L) | Body Weight (% of baseline) | GalNAc$_3$ Cluster | CM |
|---|---|---|---|---|---|---|
| PBS | n/a | 51 | 81 | 186 | n/a | n/a |
| 552668 | 3 | 54 | 93 | 183 | n/a | n/a |

TABLE 69-continued

Liver transaminase levels and rat body weights

| ISIS No. | Dosage (mg/kg) | ALT (U/L) | AST (U/L) | Body Weight (% of baseline) | GalNAc$_3$ Cluster | CM |
|---|---|---|---|---|---|---|
|  | 10 | 51 | 93 | 194 |  |  |
|  | 30 | 59 | 99 | 182 |  |  |
|  | 90 | 56 | 78 | 170 |  |  |

TABLE 69-continued

Liver transaminase levels and rat body weights

| ISIS No. | Dosage (mg/kg) | ALT (U/L) | AST (U/L) | Body Weight (% of baseline) | GalNAc$_3$ Cluster | CM |
|---|---|---|---|---|---|---|
| 669509 | 0.3 | 53 | 90 | 190 | GalNAc$_3$-1a | A$_d$ |
|  | 1 | 51 | 93 | 192 |  |  |
|  | 3 | 48 | 85 | 189 |  |  |
|  | 10 | 56 | 95 | 189 |  |  |

Example 79: Duration of Action In Vivo of Oligonucleotides Targeting Apoc-III Comprising a GalNAc$_3$ Conjugate The oligonucleotides listed in Table 70 below were tested in a single dose study for duration of action in mice.

TABLE 70

Modified ASOs targeting APOC-III

| ISIS No. | Sequences (5' to 3') | GalNAc$_3$ Cluster | CM | SEQ ID No. |
|---|---|---|---|---|
| 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | n/a | n/a | 135 |
| 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{eo}$A$_{do}$,-GalNAc$_3$-1$_a$ | GalNAc$_3$-1a | A$_d$ | 136 |
| 663083 | GalNAc$_3$-3$_{a\text{-}o}$,A$_{do}$A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | GalNAc$_3$-3a | A$_d$ | 151 |
| 674449 | GalNAc$_3$-7$_{a\text{-}o}$,A$_{do}$A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | GalNAc$_3$-7a | A$_d$ | 151 |
| 674450 | GalNAc$_3$-10$_{a\text{-}o}$,A$_{do}$A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | GalNAc$_3$-10a | A$_d$ | 151 |
| 674451 | GalNAc$_3$-13$_{a\text{-}o}$,A$_{do}$A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | GalNAc$_3$-13a | A$_d$ | 151 |

The structure of GalNAC$_3$-1$_a$ was shown previously in Example 9, GalNAc$_3$-3$_a$ was shown in Example 39, GalNAC$_3$-7$_a$ was shown in Example 48, GalNAC$_3$-10$_a$ was shown in Example 46, and GalNAC$_3$-13$_a$ was shown in Example 62.

Treatment

Six to eight week old transgenic mice that express human APOC-III were each injected subcutaneously once with an oligonucleotide listed in Table 70 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-III levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 71

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| PBS | n/a | 3 | 97 | 102 | n/a | n/a |
|  |  | 7 | 101 | 98 |  |  |
|  |  | 14 | 108 | 98 |  |  |
|  |  | 21 | 107 | 107 |  |  |
|  |  | 28 | 94 | 91 |  |  |
|  |  | 35 | 88 | 90 |  |  |
|  |  | 42 | 91 | 105 |  |  |
| 304801 | 30 | 3 | 40 | 34 | n/a | n/a |
|  |  | 7 | 41 | 37 |  |  |
|  |  | 14 | 50 | 57 |  |  |
|  |  | 21 | 50 | 50 |  |  |
|  |  | 28 | 57 | 73 |  |  |
|  |  | 35 | 68 | 70 |  |  |
|  |  | 42 | 75 | 93 |  |  |
| 647535 | 10 | 3 | 36 | 37 | GalNAc$_3$-1a | A$_d$ |
|  |  | 7 | 39 | 47 |  |  |
|  |  | 14 | 40 | 45 |  |  |
|  |  | 21 | 41 | 41 |  |  |
|  |  | 28 | 42 | 62 |  |  |
|  |  | 35 | 69 | 69 |  |  |
|  |  | 42 | 85 | 102 |  |  |
| 663083 | 10 | 3 | 24 | 18 | GalNAc$_3$-3a | A$_d$ |
|  |  | 7 | 28 | 23 |  |  |
|  |  | 14 | 25 | 27 |  |  |
|  |  | 21 | 28 | 28 |  |  |
|  |  | 28 | 37 | 44 |  |  |
|  |  | 35 | 55 | 57 |  |  |
|  |  | 42 | 60 | 78 |  |  |
| 674449 | 10 | 3 | 29 | 26 | GalNAc$_3$-7a | A$_d$ |
|  |  | 7 | 32 | 31 |  |  |
|  |  | 14 | 38 | 41 |  |  |
|  |  | 21 | 44 | 44 |  |  |
|  |  | 28 | 53 | 63 |  |  |
|  |  | 35 | 69 | 77 |  |  |
|  |  | 42 | 78 | 99 |  |  |

TABLE 71-continued

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| 674450 | 10 | 3 | 33 | 30 | | |
| | | 7 | 35 | 34 | | |
| | | 14 | 31 | 34 | | |
| | | 21 | 44 | 44 | GalNAc$_3$-10a | A$_d$ |
| | | 28 | 56 | 61 | | |
| | | 35 | 68 | 70 | | |
| | | 42 | 83 | 95 | | |
| 674451 | 10 | 3 | 35 | 33 | | |
| | | 7 | 24 | 32 | | |
| | | 14 | 40 | 34 | | |
| | | 21 | 48 | 48 | GalNAc$_3$-13a | A$_d$ |
| | | 28 | 54 | 67 | | |
| | | 35 | 65 | 75 | | |
| | | 42 | 74 | 97 | | |

Example 80: Antisense Inhibition In Vivo by Oligonucleotides Targeting Alpha-1 Antitrypsin (A1AT) Comprising a GalNAc$_3$ Conjugate The oligonucleotides listed in Table 72 below were tested in a study for dose-dependent inhibition of A1AT in mice.

TABLE 72

Modified ASOs targeting A1AT

| ISIS No. | Sequences (5' to 3') | GalNAc$_3$ Cluster | CM | SEQ ID No. |
|---|---|---|---|---|
| 476366 | A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | n/a | n/a | 152 |
| 656326 | A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_{eo}$A$_{do}$,-GalNAc$_3$-1$_a$ | GalNAc$_3$-1a | A$_d$ | 153 |
| 678381 | GalNAc$_3$-3$_{a^-o}$,A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-3a | A$_d$ | 154 |
| 678382 | GalNAc$_3$-7$_{a^-o}$,A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-7a | A$_d$ | 154 |
| 678383 | GalNAc$_3$-10$_{a^-o}$,A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-10a | A$_d$ | 154 |
| 678384 | GalNAc$_3$-13$_{a^-o}$,A$_{do}$A$_{es}$$^m$C$_{es}$$^m$C$_{es}$$^m$C$_{es}$A$_{es}$A$_{ds}$T$_{ds}$T$_{ds}$$^m$C$_{ds}$A$_{ds}$G$_{ds}$A$_{ds}$A$_{ds}$G$_{ds}$G$_{ds}$A$_{es}$A$_{es}$G$_{es}$G$_{es}$A$_e$ | GalNAc$_3$-13a | A$_d$ | 154 |

The structure of GaNAc$_3$-1$_a$ was shown previously in Example 9, GalNAc$_3$-3$_a$ was shown in Example 39, GalNAc$_3$-7$_a$ was shown in Example 48, GaNAc$_3$-10$_a$ was shown in Example 46, and GaNAc$_3$-13$_a$ was shown in Example 62.

Treatment

Six week old, male C57BL/6 mice (Jackson Laboratory, Bar Harbor, ME) were each injected subcutaneously once per week at a dosage shown below, for a total of three doses, with an oligonucleotide listed in Table 72 or with PBS. Each treatment group consisted of 4 animals. The mice were sacrificed 72 hours following the final administration. A1AT liver mRNA levels were determined using real-time PCR and RIBOGREEN® RNA quantification reagent (Molecular Probes, Inc. Eugene, OR) according to standard protocols. A1AT plasma protein levels were determined using the Mouse Alpha 1-Antitrypsin ELISA (catalog ∩41-A1AMS-EO1, Alpco, Salem, NH). The results below are presented as the average percent of A1AT liver mRNA and plasma protein levels for each treatment group, normalized to the PBS control.

As illustrated in Table 73, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 73

A1AT liver mRNA and plasma protein levels

| ISIS No. | Dosage (mg/kg) | A1AT liver mRNA (% PBS) | A1AT plasma protein (% PBS) | GalNAc$_3$ Cluster | CM |
|---|---|---|---|---|---|
| PBS | n/a | 100 | 100 | n/a | n/a |
| 476366 | 5 | 86 | 78 | n/a | n/a |
| | 15 | 73 | 61 | | |
| | 45 | 30 | 38 | | |
| 656326 | 0.6 | 99 | 90 | GalNAc$_3$-1a | A$_d$ |
| | 2 | 61 | 70 | | |
| | 6 | 15 | 30 | | |
| | 18 | 6 | 10 | | |
| 678381 | 0.6 | 105 | 90 | GalNAc$_3$-3a | A$_d$ |
| | 2 | 53 | 60 | | |
| | 6 | 16 | 20 | | |
| | 18 | 7 | 13 | | |

TABLE 73-continued

A1AT liver mRNA and plasma protein levels

| ISIS No. | Dosage (mg/kg) | A1AT liver mRNA (% PBS) | A1AT plasma protein (% PBS) | GalNAc$_3$ Cluster | CM |
|---|---|---|---|---|---|
| 678382 | 0.6 | 90 | 79 | GalNAc$_3$-7a | A$_d$ |
| | 2 | 49 | 57 | | |
| | 6 | 21 | 27 | | |
| | 18 | 8 | 11 | | |
| 678383 | 0.6 | 94 | 84 | GalNAc$_3$-10a | A$_d$ |
| | 2 | 44 | 53 | | |
| | 6 | 13 | 24 | | |
| | 18 | 6 | 10 | | |
| 678384 | 0.6 | 106 | 91 | GalNAc$_3$-13a | A$_d$ |
| | 2 | 65 | 59 | | |
| | 6 | 26 | 31 | | |
| | 18 | 11 | 15 | | |

Liver transaminase and BUN levels in plasma were measured at time of sacrifice using standard protocols. Body weights and organ weights were also measured. The results are shown in Table 74 below. Body weight is shown as % relative to baseline. Organ weights are shown as % of body weight relative to the PBS control group.

TABLE 74

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
|  | 15 | 37 | 74 | 30 | 122 | 92 | 101 | 128 |
|  | 45 | 30 | 47 | 31 | 118 | 99 | 108 | 123 |
| 656326 | 0.6 | 29 | 57 | 40 | 123 | 100 | 103 | 119 |
|  | 2 | 36 | 75 | 39 | 114 | 98 | 111 | 106 |
|  | 6 | 32 | 67 | 39 | 125 | 99 | 97 | 122 |
|  | 18 | 46 | 77 | 36 | 116 | 102 | 109 | 101 |
| 678381 | 0.6 | 26 | 57 | 32 | 117 | 93 | 109 | 110 |
|  | 2 | 26 | 52 | 33 | 121 | 96 | 106 | 125 |
|  | 6 | 40 | 78 | 32 | 124 | 92 | 106 | 126 |
|  | 18 | 31 | 54 | 28 | 118 | 94 | 103 | 120 |
| 678382 | 0.6 | 26 | 42 | 35 | 114 | 100 | 103 | 103 |
|  | 2 | 25 | 50 | 31 | 117 | 91 | 104 | 117 |
|  | 6 | 30 | 79 | 29 | 117 | 89 | 102 | 107 |
|  | 18 | 65 | 112 | 31 | 120 | 89 | 104 | 113 |
| 678383 | 0.6 | 30 | 67 | 38 | 121 | 91 | 100 | 123 |
|  | 2 | 33 | 53 | 33 | 118 | 98 | 102 | 121 |
|  | 6 | 32 | 63 | 32 | 117 | 97 | 105 | 105 |
|  | 18 | 36 | 68 | 31 | 118 | 99 | 103 | 108 |
| 678384 | 0.6 | 36 | 63 | 31 | 118 | 98 | 103 | 98 |
|  | 2 | 32 | 61 | 32 | 119 | 93 | 102 | 114 |
|  | 6 | 34 | 69 | 34 | 122 | 100 | 100 | 96 |
|  | 18 | 28 | 54 | 30 | 117 | 98 | 101 | 104 |

Example 81: Duration of Action In Vivo of Oligonucleotides Targeting A1AT Comprising a Ganac₃ Cluster The oligonucleotides listed in Table 72 were tested in a single dose study for duration of action in mice.

Treatment

Six week old, male C57BL/6 mice were each injected subcutaneously once with an oligonucleotide listed in Table 72 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 75

Plasma A1AT protein levels in mice

| ISIS No. | Dosage (mg/kg) | Time point (days post-dose) | A1AT (% baseline) | GalNAC₃ Cluster | CM |
|---|---|---|---|---|---|
| PBS | n/a | 5 | 93 | n/a | n/a |
|  |  | 12 | 93 |  |  |

TABLE 75-continued

Plasma A1AT protein levels in mice

| ISIS No. | Dosage (mg/kg) | Time point (days post-dose) | A1AT (% baseline) | GalNAC₃ Cluster | CM |
|---|---|---|---|---|---|
|  |  | 19 | 90 |  |  |
|  |  | 25 | 97 |  |  |
| 476366 | 100 | 5 | 38 | n/a | n/a |
|  |  | 12 | 46 |  |  |
|  |  | 19 | 62 |  |  |
|  |  | 25 | 77 |  |  |
| 656326 | 18 | 5 | 33 | GalNAc₃-1a | $A_d$ |
|  |  | 12 | 36 |  |  |
|  |  | 19 | 51 |  |  |
|  |  | 25 | 72 |  |  |
| 678381 | 18 | 5 | 21 | GalNAc₃-3a | $A_d$ |
|  |  | 12 | 21 |  |  |
|  |  | 19 | 35 |  |  |
|  |  | 25 | 48 |  |  |
| 678382 | 18 | 5 | 21 | GalNAc₃-7a | $A_d$ |
|  |  | 12 | 21 |  |  |
|  |  | 19 | 39 |  |  |
|  |  | 25 | 60 |  |  |
| 678383 | 18 | 5 | 24 | GalNAc₃-10a | $A_d$ |
|  |  | 12 | 21 |  |  |
|  |  | 19 | 45 |  |  |
|  |  | 25 | 73 |  |  |
| 678384 | 18 | 5 | 29 | GalNAc₃-13a | $A_d$ |
|  |  | 12 | 34 |  |  |
|  |  | 19 | 57 |  |  |
|  |  | 25 | 76 |  |  |

Example 82: Antisense Inhibition In Vitro by Oligonucleotides Targeting SRB-1 Comprising a GalNAc₃ Conjugate Primary mouse liver hepatocytes were seeded in 96 well plates at 15,000 cells/well 2 hours prior to treatment. The oligonucleotides listed in Table 76 were added at 2, 10, 50, or 250 nM in Williams E medium and cells were incubated overnight at 37° C. in 500 $CO_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, OR) according to standard protocols. $IC_{50}$ values were determined using Prism 4 software (Graph-Pad). The results show that oligonucleotides comprising variety of different GalNAc conjugate groups and variety of different cleavable moieties are significantly more potent in an in vitro free uptake experiment than the parent oligonucleotides lacking a GalNAc conjugate group (ISIS 353382 and 666841).

TABLE 76

Inhibition of SRB-1 expression in vitro

| ISIS No. | Sequence (5' to 3') | Linkages | GalNAc cluster | CM | $IC_{50}$ (nM) | SEQ ID No. |
|---|---|---|---|---|---|---|
| 353382 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | n/a | n/a | 250 | 143 |
| 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}A_{do}$,-GalNAc₃-1$_a$ | PS | GalNAc₃-1$_a$ | $A_d$ | 40 | 144 |
| 661161 | GalNAc₃-3$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-3$_a$ | $A_d$ | 40 | 145 |
| 661162 | GalNAc₃-3$_{a-o}$,$A_{do}G_{es}{}^mC_{eo}T_{eo}T_{eo}{}^mC_{eo}A_{ds}G_{ds}T_{ds}{}^mC_{ds}A_{ds}G_{ds}A_{ds}{}^mC_{ds}T_{ds}T_{eo}{}^mC_{eo}{}^mC_{es}T_{es}T_e$ | PO/PS | GalNAc₃-3$_a$ | $A_d$ | 8 | 145 |
| 664078 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}A_{do}$,-GalNAc₃-9$_a$ | PS | GalNAc₃-9$_a$ | $A_d$ | 20 | 144 |
| 665001 | GalNAc₃-8$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-8$_a$ | $A_d$ | 70 | 145 |
| 666224 | GalNAc₃-5$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-5$_a$ | $A_d$ | 80 | 145 |
| 666841 | $G_{es}{}^mC_{eo}T_{eo}T_{eo}{}^mC_{es}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | n/a | n/a | >250 | 143 |
| 666881 | GalNAc₃-10$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-10$_a$ | $A_d$ | 30 | 145 |
| 666904 | GalNAc₃-3$_{a-o}$,$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-3$_a$ | PO | 9 | 143 |
| 666924 | GalNAc₃-3$_{a-o}$,$T_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-3$_a$ | $T_d$ | 15 | 148 |
| 666961 | GalNAc₃-6$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-6$_a$ | $A_d$ | 150 | 145 |
| 666981 | GalNAc₃-7$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-7$_a$ | $A_d$ | 20 | 145 |
| 670061 | GalNAc₃-13$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-13$_a$ | $A_d$ | 30 | 145 |
| 670699 | GalNAc₃-3$_{a-o}$,$T_{do}G_{es}{}^mC_{es}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{es}{}^mC_{eo}{}^mC_{es}T_{es}T_e$ | PO/PS | GalNAc₃-3$_a$ | $T_d$ | 15 | 148 |
| 670700 | GalNAc₃-3$_{a-o}$,$A_{eo}G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{es}{}^mC_{eo}{}^mC_{es}T_{es}T$ | PO/PS | GalNAc₃-3$_a$ | $A_e$ | 30 | 145 |
| 670701 | GalNAc₃-3$_{a-o}$,$T_{eo}G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | PO/PS | GalNAc₃-3$_a$ | $T_e$ | 25 | 148 |
| 671144 | GalNAc₃-12$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-12$_a$ | $A_d$ | 40 | 145 |
| 671165 | GalNAc₃-13$_{a-o}$,$A_{do}G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{es}{}^mC_{eo}{}^mC_{es}T_{es}T$ | PO/PS | GalNAc₃-13$_a$ | $A_d$ | 8 | 145 |
| 671261 | GalNAc₃-14$_{a-o}$,$A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc₃-14$_a$ | $A_d$ | >250 | 145 |

TABLE 76-continued

Inhibition of SRB-1 expression in vitro

| ISIS No. | Sequence (5' to 3') | Linkages | GalNAc cluster | CM | IC$_{50}$ (nM) | SEQ ID No. |
|---|---|---|---|---|---|---|
| 671262 | GalNAc$_3$-15$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-15$_a$ | A$_d$ | >250 | 145 |
| 673501 | GalNAc$_3$-7$_a$-$_o$,A$_{do}$G$_{es}$$^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-7$_a$ | A$_d$ | 30 | 145 |
| 673502 | GalNAc$_3$-10$_a$-$_o$,A$_{do}$G$_{es}$$^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_e$ | PO/PS | GalNAc$_3$-10$_a$ | A$_d$ | 8 | 145 |
| 675441 | GalNAc$_3$-17$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-17$_a$ | A$_d$ | 30 | 145 |
| 675442 | GalNAc$_3$-18$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-18$_a$ | A$_d$ | 20 | 145 |
| 677841 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$A$_{do}$,-GalNAc$_3$-19$_a$ | PS | GalNAc$_3$-19$_a$ | A$_d$ | 40 | 144 |
| 677842 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$ $^m$C$_{ds}$T$_{ds}$T$_{es}$$^m$C$_{es}$$^m$C$_{es}$T$_{es}$T$_{eo}$A$_{do}$,-GalNAc$_3$-20$_a$ | PS | GalNAc$_3$-20$_a$ | A$_d$ | 30 | 144 |
| 677843 | GalNAc$_3$-23$_a$-$_o$,A$_{do}$G$_{es}$$^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | PS | GalNAc$_3$-23$_a$ | A$_d$ | 40 | 145 |

The structure of GalNAc$_3$-1$_a$ was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-7$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17a was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83: Antisense Inhibition In Vivo by Oligonucleotides Targeting Factor XI Comprising a GalNAc$_3$ Cluster The oligonucleotides listed in Table 77 below were tested in a study for dose-dependent inhibition of Factor XI in mice.

TABLE 77

Modified oligonucleotides targeting Factor XI

| ISIS No. | Sequence (5' to 3') | GalNAc cluster | CM | SEQ ID No. |
|---|---|---|---|---|
| 404071 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{es}$G$_{es}$A$_{es}$G$_{es}$G$_e$ | n/a | n/a | 146 |
| 656173 | T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{eo}$G$_{eo}$ A$_{es}$G$_{es}$G$_{eo}$A$_{do}$,-GalNAc$_3$-1$_a$ | GalNAc$_3$-1$_a$ | A$_d$ | 147 |
| 663086 | GalNAc$_3$-3$_a$-$_o$,A$_{do}$T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$T$_{ds}$ T$_{ds}$T$_{ds}$$^m$C$_{ds}$A$_{eo}$G$_{eo}$A$_{es}$G$_{es}$G$_e$ | GalNAc$_3$-3$_a$ | A$_d$ | 155 |
| 678347 | GalNAc$_3$-7$_a$-$_o$,A$_{do}$T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$T$_{ds}$ T$_{ds}$T$_{ds}$$^m$C$_{ds}$A$_{eo}$G$_{eo}$A$_{es}$G$_{es}$G$_e$ | GalNAc$_3$-7$_a$ | A$_d$ | 155 |
| 678348 | GalNAc$_3$-10$_a$-$_o$,A$_{do}$T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$ T$_{ds}$T$_{ds}$T$_{ds}$$^m$C$_{ds}$A$_{eo}$G$_{eo}$A$_{es}$G$_{es}$G$_e$ | GalNAc$_3$-10$_a$ | A$_d$ | 155 |
| 678349 | GalNAc$_3$-13$_a$-$_o$,A$_{do}$T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$ T$_{ds}$T$_{ds}$T$_{ds}$$^m$C$_{ds}$A$_{eo}$G$_{eo}$A$_{es}$G$_{es}$G$_e$ | GalNAc$_3$-13$_a$ | A$_d$ | 155 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 78, treatment with antisense oligonucleotides lowered Factor XI liver mRNA in a dose-dependent manner. The results show that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even more potent with an even longer duration of action than the oligonucleotide comprising a 3'-GalNAc conjugate (ISIS 656173).

TABLE 79

Plasma Factor XI protein levels in mice

| ISIS No. | Dosage (mg/kg) | Time point (days post-dose) | Factor XI (% baseline) | GalNAc$_3$ Cluster | CM | SEQ ID No. |
|---|---|---|---|---|---|---|
| PBS | n/a | 3 | 123 | n/a | n/a | n/a |
|  |  | 10 | 56 |  |  |  |
|  |  | 17 | 100 |  |  |  |
| 404071 | 30 | 3 | 11 | n/a | n/a | 146 |
|  |  | 10 | 47 |  |  |  |
|  |  | 17 | 52 |  |  |  |

TABLE 78

Factor XI liver mRNA, liver transaminase, BUN, and bilirubin levels

| ISIS No. | Dosage (mg/kg) | Factor XI mRNA (% PBS) | ALT (U/L) | AST (U/L) | BUN (mg/dL) | Bilirubin (mg/dL) | GalNAc$_3$ Cluster | SEQ ID No. |
|---|---|---|---|---|---|---|---|---|
| PBS | n/a | 100 | 63 | 70 | 21 | 0.18 | n/a | n/a |
| 404071 | 3 | 65 | 41 | 58 | 21 | 0.15 | n/a | 146 |
|  | 10 | 33 | 49 | 53 | 23 | 0.15 |  |  |
|  | 30 | 17 | 43 | 57 | 22 | 0.14 |  |  |
| 656173 | 0.7 | 43 | 90 | 89 | 21 | 0.16 | GalNAc$_3$-1a | 147 |
|  | 2 | 9 | 36 | 58 | 26 | 0.17 |  |  |
|  | 6 | 3 | 50 | 63 | 25 | 0.15 |  |  |
| 663086 | 0.7 | 33 | 91 | 169 | 25 | 0.16 | GalNAc$_3$-3a | 155 |
|  | 2 | 7 | 38 | 55 | 21 | 0.16 |  |  |
|  | 6 | 1 | 34 | 40 | 23 | 0.14 |  |  |
| 678347 | 0.7 | 35 | 28 | 49 | 20 | 0.14 | GalNAc$_3$-7a | 155 |
|  | 2 | 10 | 180 | 149 | 21 | 0.18 |  |  |
|  | 6 | 1 | 44 | 76 | 19 | 0.15 |  |  |
| 678348 | 0.7 | 39 | 43 | 54 | 21 | 0.16 | GalNAc$_3$-10a | 155 |
|  | 2 | 5 | 38 | 55 | 22 | 0.17 |  |  |
|  | 6 | 2 | 25 | 38 | 20 | 0.14 |  |  |
| 678349 | 0.7 | 34 | 39 | 46 | 20 | 0.16 | GalNAc$_3$-13a | 155 |
|  | 2 | 8 | 43 | 63 | 21 | 0.14 |  |  |
|  | 6 | 2 | 28 | 41 | 20 | 0.14 |  |  |

Example 84: Duration of Action In Vivo of Oligonucleotides Targeting Factor XI Comprising a GalNAc$_3$ Conjugate The oligonucleotides listed in Table 77 were tested in a single dose study for duration of action in mice.

Treatment

Six to eight week old mice were each injected subcutaneously once with an oligonucleotide listed in Table 77 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, MN (catalog 4 AF2460 and 4 BAF2460, respectively) and the OptEIA Reagent Set B (Catalog #550534, BD Biosciences, San Jose, CA). The results below are presented as the average percent TABLE 79-continued Plasma Factor XI protein levels in mice

| ISIS No. | Dosage (mg/kg) | Time point (days post-dose) | Factor XI (% baseline) | GalNAc$_3$ Cluster | CM | SEQ ID No. |
|---|---|---|---|---|---|---|
| 656173 | 6 | 3 | 1 | GalNAc$_3$-1a | A$_d$ | 147 |
|  |  | 10 | 3 |  |  |  |
|  |  | 17 | 21 |  |  |  |
| 663086 | 6 | 3 | 1 | GalNAc$_3$-3a | A$_d$ | 155 |
|  |  | 10 | 2 |  |  |  |
|  |  | 17 | 9 |  |  |  |
| 678347 | 6 | 3 | 1 | GalNAc$_3$-7a | A$_d$ | 155 |
|  |  | 10 | 1 |  |  |  |
|  |  | 17 | 8 |  |  |  |
| 678348 | 6 | 3 | 1 | GalNAc$_3$-10a | A$_d$ | 155 |
|  |  | 10 | 1 |  |  |  |
|  |  | 17 | 6 |  |  |  |

TABLE 79-continued

Plasma Factor XI protein levels in mice

| ISIS No. | Dosage (mg/kg) | Time point (days post-dose) | Factor XI (% baseline) | GalNAc$_3$ Cluster | CM | SEQ ID No. |
|---|---|---|---|---|---|---|
| 678349 | 6 | 3 | 1 | GalNAc$_3$-13a | A$_d$ | 155 |
|  |  | 10 | 1 |  |  |  |
|  |  | 17 | 5 |  |  |  |

Example 85: Antisense Inhibition In Vivo by Oligonucleotides Targeting SRB-1 Comprising a GalNAc$_3$ Conjugate Oligonucleotides listed in Table 76 were tested in a dose-dependent study for antisense inhibition of SRB-1 in mice.

Treatment

Six to eight week old C57B3L/6 mice were each injected subcutaneously once per week at a dosage shown below, for a total of three doses, with an oligonucleotide listed in Table 76 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of liver SRB-1 mRNA levels for each treatment group, normalized to the saline control.

As illustrated in Tables 80 and 81, treatment with antisense oligonucleotides lowered SRB-1 mRNA levels in a dose-dependent manner.

TABLE 80

SRB-1 mRNA in liver

| ISIS No. | Dosage (mg/kg) | SRB-1 mRNA (% Saline) | GalNAc$_3$ Cluster | CM |
|---|---|---|---|---|
| Saline | n/a | 100 | n/a | n/a |
| 655861 | 0.1 | 94 | GalNAc$_3$-1a | A$_d$ |
|  | 0.3 | 119 |  |  |
|  | 1 | 68 |  |  |
|  | 3 | 32 |  |  |
| 661161 | 0.1 | 120 | GalNAc$_3$-3a | A$_d$ |
|  | 0.3 | 107 |  |  |
|  | 1 | 68 |  |  |
|  | 3 | 26 |  |  |
| 666881 | 0.1 | 107 | GalNAc$_3$-10a | A$_d$ |
|  | 0.3 | 107 |  |  |
|  | 1 | 69 |  |  |
|  | 3 | 27 |  |  |
| 666981 | 0.1 | 120 | GalNAc$_3$-7a | A$_d$ |
|  | 0.3 | 103 |  |  |
|  | 1 | 54 |  |  |
|  | 3 | 21 |  |  |
| 670061 | 0.1 | 118 | GalNAc$_3$-13a | A$_d$ |
|  | 0.3 | 89 |  |  |
|  | 1 | 52 |  |  |
|  | 3 | 18 |  |  |
| 677842 | 0.1 | 119 | GalNAc$_3$-20a | A$_d$ |
|  | 0.3 | 96 |  |  |
|  | 1 | 65 |  |  |
|  | 3 | 23 |  |  |

TABLE 81

SRB-1 mRNA in liver

| ISIS No. | Dosage (mg/kg) | SRB-1 mRNA (% Saline) | GalNAc$_3$ Cluster | CM |
|---|---|---|---|---|
| 661161 | 0.1 | 107 | GalNAc$_3$-3a | A$_d$ |
|  | 0.3 | 95 |  |  |
|  | 1 | 53 |  |  |
|  | 3 | 18 |  |  |
| 677841 | 0.1 | 110 | GalNAc$_3$-19a | A$_d$ |
|  | 0.3 | 88 |  |  |
|  | 1 | 52 |  |  |
|  | 3 | 25 |  |  |

Liver transaminase levels, total bilirubin, BUN, and body weights were also measured using standard protocols. Average values for each treatment group are shown in Table 82 below.

TABLE 82

| ISIS No. | Dosage (mg/kg) | ALT (U/L) | AST (U/L) | Bilirubin (mg/dL) | BUN (mg/dL) | Body Weight (% baseline) | GalNAc$_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | GalNAc$_3$-1a | A$_d$ |
|  | 0.3 | 29 | 56 | 0.15 | 27 | 118 |  |  |
|  | 1 | 20 | 32 | 0.14 | 24 | 112 |  |  |
|  | 3 | 27 | 54 | 0.14 | 24 | 115 |  |  |
| 661161 | 0.1 | 35 | 83 | 0.13 | 24 | 113 | GalNAc$_3$-3a | A$_d$ |
|  | 0.3 | 42 | 61 | 0.15 | 23 | 117 |  |  |
|  | 1 | 34 | 60 | 0.18 | 22 | 116 |  |  |
|  | 3 | 29 | 52 | 0.13 | 25 | 117 |  |  |
| 666881 | 0.1 | 30 | 51 | 0.15 | 23 | 118 | GalNAc$_3$-10a | A$_d$ |
|  | 0.3 | 49 | 82 | 0.16 | 25 | 119 |  |  |
|  | 1 | 23 | 45 | 0.14 | 24 | 117 |  |  |
|  | 3 | 20 | 38 | 0.15 | 21 | 112 |  |  |
| 666981 | 0.1 | 21 | 41 | 0.14 | 22 | 113 | GalNAc$_3$-7a | A$_d$ |
|  | 0.3 | 29 | 49 | 0.16 | 24 | 112 |  |  |
|  | 1 | 19 | 34 | 0.15 | 22 | 111 |  |  |
|  | 3 | 77 | 78 | 0.18 | 25 | 115 |  |  |
| 670061 | 0.1 | 20 | 63 | 0.18 | 24 | 111 | GalNAc$_3$-13a | A$_d$ |
|  | 0.3 | 20 | 57 | 0.15 | 21 | 115 |  |  |
|  | 1 | 20 | 35 | 0.14 | 20 | 115 |  |  |
|  | 3 | 27 | 42 | 0.12 | 20 | 116 |  |  |

TABLE 82-continued

| ISIS No. | Dosage (mg/kg) | ALT (U/L) | AST (U/L) | Bilirubin (mg/dL) | BUN (mg/dL) | Body Weight (% baseline) | GalNAc$_3$ Cluster | CM |
|---|---|---|---|---|---|---|---|---|
| 677842 | 0.1 | 20 | 38 | 0.17 | 24 | 114 | GalNAc$_3$-20a | A$_d$ |
|  | 0.3 | 31 | 46 | 0.17 | 21 | 117 |  |  |
|  | 1 | 22 | 34 | 0.15 | 21 | 119 |  |  |
|  | 3 | 41 | 57 | 0.14 | 23 | 118 |  |  |

Example 86: Antisense Inhibition In Vivo by Oligonucleotides Targeting Ttr Comprising a GalNAc$_3$ Cluster Oligonucleotides listed in Table 83 below were tested in a dose-dependent study for antisense inhibition of human transthyretin (TTR) in transgenic mice that express the human TTR gene.

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 85-87. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Tables 84-87 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

In Tables 84-87, "BL" indicates baseline, measurements that were taken just prior to the first dose. As illustrated in Tables 84 and 85, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PO internucleoside linkages were even more potent than the oligonucleotide Comprising a GalNAc conjugate and full PS linkages.

TABLE 83

Oligonucleotides targeting human TTR

| Isis No. | Sequence 5' to 3' | Linkages | GalNAc cluster | CM | SEQ ID No. |
|---|---|---|---|---|---|
| 420915 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | PS | n/a | n/a | 156 |
| 660261 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_{eo}$A$_{do}$,-GalNAc$_3$-1$_a$ | PS | GalNAc$_3$-1a | A$_d$ | 157 |
| 682883 | GalNAc$_3$-3$_{a-o}$,T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_e$ | PS/PO | GalNAc$_3$-3a | PO | 156 |
| 682884 | GalNAc$_3$-7$_{a-o}$,T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_e$ | PS/PO | GalNAc$_3$-7a | PO | 156 |
| 682885 | GalNAc$_3$-10$_{a-o}$,T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_e$ | PS/PO | GalNAc$_3$-10a | PO | 156 |
| 682886 | GalNAc$_3$-13$_{a-o}$,T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_e$ | PS/PO | GalNAc$_3$-13a | PO | 156 |
| 684057 | T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{eo}$A$_{do}$,-GalNAc$_3$-19$_a$ | PS/PO | GalNAc$_3$-19a | A$_d$ | 157 |

The legend for Table 85 can be found in Example 74. The structure of GalNAC$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

TABLE 84

Antisense inhibition of human TTR in vivo

| Isis No. | Dosage (mg/kg) | TTR mRNA (% PBS) | Plasma TTR protein (% PBS) | GalNAc cluster | CM | SEQ ID No. |
|---|---|---|---|---|---|---|
| PBS | n/a | 100 | 100 | n/a | n/a | |
| 420915 | 6 | 99 | 95 | n/a | n/a | 156 |
| | 20 | 48 | 65 | | | |
| | 60 | 18 | 28 | | | |
| 660261 | 0.6 | 113 | 87 | GalNAc$_3$-1a | A$_d$ | 157 |
| | 2 | 40 | 56 | | | |
| | 6 | 20 | 27 | | | |
| | 20 | 9 | 11 | | | |

TABLE 85

Antisense inhibition of human TTR in vivo

Plasma TTR protein (% PBS at BL)

| Isis No. | Dosage (mg/kg) | TTR mRNA (% PBS) | BL | Day 3 | Day 10 | Day 17 (After sac) | GalNAc cluster | CM | SEQ ID No. |
|---|---|---|---|---|---|---|---|---|---|
| PBS | n/a | 100 | 100 | 96 | 90 | 114 | n/a | n/a | |
| 420915 | 6 | 74 | 106 | 86 | 76 | 83 | n/a | n/a | 156 |
| | 20 | 43 | 102 | 66 | 61 | 58 | | | |
| | 60 | 24 | 92 | 43 | 29 | 32 | | | |
| 682883 | 0.6 | 60 | 88 | 73 | 63 | 68 | GalNAc$_3$-3a | PO | 156 |
| | 2 | 18 | 75 | 38 | 23 | 23 | | | |
| | 6 | 10 | 80 | 35 | 11 | 9 | | | |
| 682884 | 0.6 | 56 | 88 | 78 | 63 | 67 | GalNAc$_3$-7a | PO | 156 |
| | 2 | 19 | 76 | 44 | 25 | 23 | | | |
| | 6 | 15 | 82 | 35 | 21 | 24 | | | |
| 682885 | 0.6 | 60 | 92 | 77 | 68 | 76 | GalNAc$_3$-10a | PO | 156 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | GalNAc$_3$-13a | PO | 156 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | GalNAc$_3$-19a | A$_d$ | 157 |
| | 2 | 21 | 92 | 55 | 34 | 30 | | | |
| | 6 | 11 | 82 | 50 | 18 | 13 | | | |

TABLE 86

Transaminase levels, body weight changes, and relative organ weights

| | | ALT (U/L) | | | | AST (U/L) | | | | | | | |
|---|---|---|---|---|---|---|---|---|---|---|---|---|---|
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 156 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 157 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 87

Transaminase levels, body weight changes, and relative organ weights

| | | ALT (U/L) | | | | AST (U/L) | | | | | | | |
|---|---|---|---|---|---|---|---|---|---|---|---|---|---|
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 156 |

TABLE 87-continued

Transaminase levels, body weight changes, and relative organ weights

| | | ALT (U/L) | | | AST (U/L) | | | | | | | |
|---|---|---|---|---|---|---|---|---|---|---|---|---|
| Isis No. | Dosage (mg/kg) | BL | Day 3 | Day 10 | Day 17 | BL | Day 3 | Day 10 | Day 17 | Body (% BL) | Liver (% PBS) | Spleen (% PBS) | Kidney (% PBS) | SEQ ID No. |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |
| 682883 | 0.6 | 32 | 35 | 38 | 40 | 53 | 81 | 74 | 76 | 104 | 101 | 112 | 95 | 156 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 156 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 156 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 156 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |
| 684057 | 0.6 | 35 | 26 | 33 | 39 | 56 | 51 | 51 | 69 | 104 | 99 | 110 | 102 | 157 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87: Duration of Action In Vivo by Single Doses of Oligonucleotides Targeting Ttr Comprising a GalNAc$_3$ Cluster ISIS numbers 420915 and 660261 (see Table 83) were tested in a single dose study for duration of action in mice. ISIS numbers 420915, 682883, and 682885 (see Table 83) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 88

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 30 | n/a | n/a | 156 |
| | | 7 | 23 | | | |
| | | 10 | 35 | | | |
| | | 17 | 53 | | | |
| | | 24 | 75 | | | |
| | | 39 | 100 | | | |
| 660261 | 13.5 | 3 | 27 | GalNAc$_3$-1a | A$_d$ | 157 |
| | | 7 | 21 | | | |
| | | 10 | 22 | | | |
| | | 17 | 36 | | | |
| | | 24 | 48 | | | |
| | | 39 | 69 | | | |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 89

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 48 | n/a | n/a | 156 |
| | | 7 | 48 | | | |
| | | 10 | 48 | | | |
| | | 17 | 66 | | | |
| | | 31 | 80 | | | |
| 682883 | 10.0 | 3 | 45 | GalNAc$_3$-3a | PO | 156 |
| | | 7 | 37 | | | |
| | | 10 | 38 | | | |
| | | 17 | 42 | | | |
| | | 31 | 65 | | | |
| 682885 | 10.0 | 3 | 40 | GalNAc$_3$-10a | PO | 156 |
| | | 7 | 33 | | | |
| | | 10 | 34 | | | |
| | | 17 | 40 | | | |
| | | 31 | 64 | | | |

The results in Tables 88 and 89 show that the oligonucleotides comprising a GalNAc conjugate are more potent with a longer duration of action than the parent oligonucleotide lacking a conjugate (ISIS 420915).

Example 88: Splicing Modulation In Vivo by Oligonucleotides Targeting Smn Comprising a GalNAc$_3$ Conjugate The oligonucleotides listed in Table 90 were tested for splicing modulation of human survival of motor neuron (SMN) in mice.

TABLE 90

Modified ASOs targeting SMN

| ISIS No. | Sequences (5' to 3') | GalNAc$_3$ Cluster | CM | SEQ ID No. |
|---|---|---|---|---|
| 387954 | A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$T$_{es}$G$_{es}$$^m$C$_{es}$T$_{es}$G$_{es}$G$_e$ | n/a | n/a | 158 |
| 699819 | GalNAc$_3$-7$_{a-o'}$A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$T$_{es}$G$_{es}$$^m$C$_{es}$T$_{es}$G$_{es}$G$_e$ | GalNAc$_3$-7a | PO | 158 |
| 699821 | GalNAc$_3$-7$_{a-o'}$A$_{es}$T$_{eo}$T$_{eo}$$^m$C$_{eo}$A$_{eo}$$^m$C$_{eo}$T$_{eo}$T$_{eo}$T$_{eo}$$^m$C$_{eo}$A$_{eo}$T$_{eo}$A$_{eo}$A$_{eo}$T$_{eo}$G$_{eo}$$^m$C$_{eo}$T$_{es}$G$_{es}$G$_e$ | GalNAc$_3$-7a | PO | 158 |
| 700000 | A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$T$_{es}$G$_{es}$$^m$C$_{es}$T$_{es}$G$_{es}$G$_{eo}$A$_{do'}$-GalNAc$_3$-1$_a$ | GalNAc$_3$-1a | A$_d$ | 157 |
| 703421 | X-ATT$^m$CA$^m$CTTT$^m$CATAATG$^m$CTGG | n/a | n/a | 158 |
| 703422 | GalNAc$_3$-7$_b$-X-ATT$^m$CA$^m$CTTT$^m$CATAATG$^m$CTGG | GalNAc$_3$-7b | n/a | 158 |

The structure of GalNAc$_3$-7$_a$ was shown previously in Example 48. "X" indicates a 5' primary amine generated by Gene Tools (Philomath, OR), and GalNAc$_3$-7$_b$ indicates the structure of GalNAc$_3$-7$_a$ lacking the —NH—C$_6$—O portion of the linker as shown below:

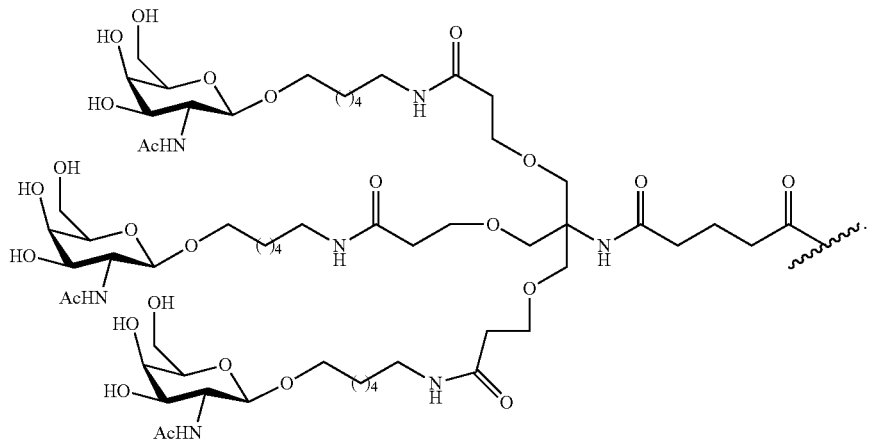

ISIS numbers 703421 and 703422 are morphlino oligonucleotides, wherein each nucleotide of the two oligonucleotides is a morpholino nucleotide.

Treatment

Six week old transgenic mice that express human SMN were injected subcutaneously once with an oligonucleotide listed in Table 91 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 91. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 91

Effect of oligonucleotides targeting human SMN in vivo

| ISIS No. | Dose (mg/kg) | +Exon 7/ −Exon 7 | GalNAc$_3$ Cluster | CM | SEQ ID No. |
|---|---|---|---|---|---|
| Saline | n/a | 1.00 | n/a | n/a | n/a |
| 387954 | 32 | 1.65 | n/a | n/a | 158 |
| 387954 | 288 | 5.00 | n/a | n/a | 158 |
| 699819 | 32 | 7.84 | GalNAc$_3$-7a | PO | 158 |
| 699821 | 32 | 7.22 | GalNAc$_3$-7a | PO | 158 |
| 700000 | 32 | 6.91 | GalNAc$_3$-1a | A$_d$ | 159 |
| 703421 | 32 | 1.27 | n/a | n/a | 158 |
| 703422 | 32 | 4.12 | GalNAc$_3$-7b | n/a | 158 |

Example 89: Antisense Inhibition In Vivo by Oligonucleotides Targeting Apolipoprotein a (Apo(a)) Comprising a GalNAc$_3$ Conjugate The oligonucleotides listed in Table 92 below were tested in a study for dose-dependent inhibition of Apo(a) in transgenic mice.

TABLE 92

Modified ASOs targeting Apo(a)

| ISIS No. | Sequences (5' to 3') | GalNAc3 Cluster | CM | SEQ ID No. |
|---|---|---|---|---|
| 494372 | $T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}$ $T_{ds}T_{es}G_{es}T_{es}T_{es}{}^mC_e$ | n/a | n/a | 58 |
| 681257 | GalNAc3-7a-o'$T_{es}G_{eo}{}^mC_{eo}T_{eo}{}^mC_{eo}{}^mC_{ds}G_{ds}T_{ds}T_{ds}G_{ds}G_{ds}$GalNAc3-7a $T_{ds}G_{ds}{}^mC_{ds}T_{ds}T_{eo}G_{eo}T_{es}T_{es}{}^mC_e$ | PO | 58 |

The structure of GalNAc$_3$-7$_a$ was shown in Example 48.

Treatment

Eight week old, female C57BL/6 mice (Jackson Laboratory, Bar Harbor, ME) were each injected subcutaneously once per week at a dosage shown below, for a total of six doses, with an oligonucleotide listed in Table 92 or with PBS. Each treatment group consisted of 3-4 animals. Tail bleeds were performed the day before the first dose and weekly following each dose to determine plasma Apo(a) protein levels. The mice were sacrificed two days following the final administration. Apo(a) liver mRNA levels were determined using real-time PCR and RIBOGREEN® RNA quantification reagent (Molecular Probes, Inc. Eugene, OR) according to standard protocols. Apo(a) plasma protein levels were determined using ELISA, and liver transaminase levels were determined. The mRNA and plasma protein results in Table 93 are presented as the treatment group average percent relative to the PBS treated group. Plasma protein levels were further normalized to the baseline (BL) value for the PBS group. Average absolute transaminase levels and body weights (% relative to baseline averages) are reported in Table 94.

As illustrated in Table 93, treatment with the oligonucleotides lowered Apo(a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 94, transaminase levels and body weights were unaffected by the oligonucleotides, indicating that the oligonucleotides were well tolerated.

TABLE 93

Apo(a) liver mRNA and plasma protein levels

| ISIS No. | Dosage (mg/kg) | Apo(a) mRNA (% PBS) | Apo(a) plasma protein (% PBS) |  |  |  |  |  |
|---|---|---|---|---|---|---|---|---|
|  |  |  | BL | Week 1 | Week 2 | Week 3 | Week 4 | Week 5 | Week 6 |

| ISIS No. | Dosage (mg/kg) | mRNA (% PBS) | BL | Week 1 | Week 2 | Week 3 | Week 4 | Week 5 | Week 6 |
|---|---|---|---|---|---|---|---|---|---|
| PBS | n/a | 100 | 100 | 120 | 119 | 113 | 88 | 121 | 97 |
| 494372 | 3 | 80 | 84 | 89 | 91 | 98 | 87 | 87 | 79 |
|  | 10 | 30 | 87 | 72 | 76 | 71 | 57 | 59 | 46 |
|  | 30 | 5 | 92 | 54 | 28 | 10 | 7 | 9 | 7 |
| 681257 | 0.3 | 75 | 79 | 76 | 89 | 98 | 71 | 94 | 78 |
|  | 1 | 19 | 79 | 88 | 66 | 60 | 54 | 32 | 24 |
|  | 3 | 2 | 82 | 52 | 17 | 7 | 4 | 6 | 5 |
|  | 10 | 2 | 79 | 17 | 6 | 3 | 2 | 4 | 5 |

TABLE 94

| ISIS No. | Dosage (mg/kg) | ALT (U/L) | AST (U/L) | Body weight (% baseline) |
|---|---|---|---|---|
| PBS | n/a | 37 | 54 | 103 |

TABLE 94-continued

| ISIS No. | Dosage (mg/kg) | ALT (U/L) | AST (U/L) | Body weight (% baseline) |
|---|---|---|---|---|
| 494372 | 3 | 28 | 68 | 106 |
|  | 10 | 22 | 55 | 102 |
|  | 30 | 19 | 48 | 103 |
| 681257 | 0.3 | 30 | 80 | 104 |
|  | 1 | 26 | 47 | 105 |
|  | 3 | 29 | 62 | 102 |
|  | 10 | 21 | 52 | 107 |

Example 90: Antisense Inhibition In Vivo by Oligonucleotides Targeting Ttr Comprising a GalNAc$_3$ Cluster Oligonucleotides listed in Table 95 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 96 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Table 96 are the average values for each treatment group. The mRNA levels are the average values relative to the average for the PBS group. Plasma protein levels are the average values relative to the average value for the PBS group at baseline. "BL" indicates baseline, measurements that were taken just prior to the first dose. As illustrated in Table 96, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 95

Oligonucleotides targeting human TTR

| Isis No. | Sequence 5' to 3' | Linkages | GalNAc cluster | CM | SEQ ID No. |
|---|---|---|---|---|---|
| 420915 | $T_{es}{}^mC_{es}T_{es}T_{es}G_{es}G_{ds}T_{ds}T_{ds}A_{ds}{}^mC_{ds}A_{ds}T_{ds}G_{ds}A_{ds}A_{ds}A_{es}T_{es}{}^mC_{es}{}^mC_{es}{}^mC_e$ | PS | n/a | n/a | 156 |
| 682883 | GalNAc3-3a-o'$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-3a | PO | 156 |
| 666943 | GalNAc3-3a-o'Ado$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-3a | $A_d$ | 160 |
| 682887 | GalNAc3-7a-o'Ado$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-7a | $A_d$ | 160 |
| 682888 | GalNAc3-10a-o'Ado$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-10a | $A_d$ | 160 |
| 682889 | GalNAc3-13a-o'Ado$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-13a | $A_d$ | 160 |

The legend for Table 95 can be found in Example 74. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62.

TABLE 96

Antisense inhibition of human TTR in vivo

| Isis No. | Dosage (mg/kg) | TTR mRNA (% PBS) | TTR protein (% BL) | GalNAc cluster | CM |
|---|---|---|---|---|---|
| PBS | n/a | 100 | 124 | n/a | n/a |
| 420915 | 6 | 69 | 114 | n/a | n/a |
|  | 20 | 71 | 86 |  |  |
|  | 60 | 21 | 36 |  |  |
| 682883 | 0.6 | 61 | 73 | GalNAc$_3$-3a | PO |
|  | 2 | 23 | 36 |  |  |
|  | 6 | 18 | 23 |  |  |
| 666943 | 0.6 | 74 | 93 | GalNAc$_3$-3a | $A_d$ |
|  | 2 | 33 | 57 |  |  |
|  | 6 | 17 | 22 |  |  |
| 682887 | 0.6 | 60 | 97 | GalNAc$_3$-7a | $A_d$ |
|  | 2 | 36 | 49 |  |  |
|  | 6 | 12 | 19 |  |  |
| 682888 | 0.6 | 65 | 92 | GalNAc$_3$-10a | $A_d$ |
|  | 2 | 32 | 46 |  |  |
|  | 6 | 17 | 22 |  |  |
| 682889 | 0.6 | 72 | 74 | GalNAc$_3$-13a | $A_d$ |
|  | 2 | 38 | 45 |  |  |
|  | 6 | 16 | 18 |  |  |

Example 91: Antisense Inhibition In Vivo by Oligonucleotides Targeting Factor VII Comprising a GalNAc$_3$ Conjugate in Non-Human Primates Oligonucleotides listed in Table 97 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 97 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 98 are the average values for each treatment group relative to the average value for the PBS group at baseline (BL), the measurements taken just prior to the first dose. As illustrated in Table 98, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 97

Oligonucleotides targeting Factor VII

| Isis No. | Sequence 5' to 3' | Linkages | GalNAc cluster | CM | SEQ ID No. |
|---|---|---|---|---|---|
| 407935 | $A_{es}T_{es}G_{es}{}^mC_{es}A_{es}T_{ds}G_{ds}G_{ds}T_{ds}G_{ds}A_{ds}T_{ds}G_{ds}{}^mC_{ds}T_{ds}T_{es}{}^mC_{es}T_{es}G_{es}A_e$ | PS | n/a | n/a | 161 |
| 686892 | GalNAc3-10a-o'$A_{es}T_{es}G_{es}{}^mC_{es}A_{es}T_{ds}G_{ds}G_{ds}T_{ds}G_{ds}A_{ds}T_{ds}G_{ds}{}^mC_{ds}T_{ds}T_{es}{}^mC_{es}T_{es}G_{es}A_e$ | PS | GalNAc$_3$-10a | PO | 161 |

The legend for Table 97 can be found in Example 74. The structure of GalNAc$_3$-10$_a$ was shown in Example 46.

TABLE 98

| Factor VII plasma protein levels | | | |
|---|---|---|---|
| ISIS No. | Day | Dose (mg/kg) | Factor VII (% BL) |
| 407935 | 0 | n/a | 100 |
| | 15 | 10 | 87 |
| | 22 | n/a | 92 |
| | 29 | 30 | 77 |
| | 36 | n/a | 46 |
| | 43 | n/a | 43 |
| 686892 | 0 | 3 | 100 |
| | 15 | 10 | 56 |
| | 22 | n/a | 29 |
| | 29 | 30 | 19 |
| | 36 | n/a | 15 |
| | 43 | n/a | 11 |

Example 92: Antisense Inhibition in Primary Hepatocytes by Antisense Oligonucleotides Targeting Apo-Ciii Comprising a GalNAc$_3$ Conjugate Primary mouse hepatocytes were seeded in 96-well plates at 15,000 cells per well, and the oligonucleotides listed in Table 99, targeting mouse ApoC-III, were added at 0.46, 1.37, 4.12, or 12.35, 37.04, 111.11, or 333.33 nM or 1.00 µM. After incubation with the oligonucleotides for 24 hours, the cells were lysed and total RNA was purified using RNeasy (Qiagen). ApoC-III mRNA levels were determined using real-time PCR and RIBOGREEN RNA quantification reagent (MolecularProbes, Inc.) according to standard protocols. IC$_{50}$ values were determined using Prism 4 software (GraphPad). The results show that regardless of whether the cleavable moiety was a phosphodiester or a phosphodiester-linked deoxyadensoine, the oligonucleotides comprising a GalNAc conjugate were significantly more potent than the parent oligonucleotide lacking a conjugate.

TABLE 99

Inhibition of mouse APOC-III expression in mouse primary hepatocytes

| ISIS No. | Sequence (5' to 3') | CM | IC$_{50}$ (nM) | SEQ ID No. |
|---|---|---|---|---|
| 440670 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | n/a | 13.20 | 162 |
| 661180 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_{eo}$Ado'-GalNAc3-1a | A$_d$ | 1.40 | 163 |
| 680771 | GalNAc3-3a-o'$^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 0.70 | 162 |
| 680772 | GalNAC3-7a-o'$^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 1.70 | 162 |
| 680773 | GalNAc3-10a-o'$^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 2.00 | 162 |
| 680774 | GalNAc3-13a-o'$^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 1.50 | 162 |
| 681272 | GalNAc3-3a-o'$^mC_{es}A_{eo}G_{eo}{}^mC_{eo}T_{eo}T_{ds}T_{ds}A_{ds}T_{ds}T_{ds}A_{ds}G_{ds}G_{ds}G_{ds}A_{ds}{}^mC_{eo}A_{eo}G_{es}{}^mC_{es}A_e$ | PO | <0.46 | 162 |
| 681273 | GalNAc3-3a-o,A$_{do}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | A$_d$ | 1.10 | 164 |
| 683733 | $^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_{eo}$Ado'-GalNAc3-19a | A$_d$ | 2.50 | 163 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, GalNAc$_3$-13$_a$ was shown in Example 62, and GalNAc$_3$-19$_a$ was shown in Example 70.

Example 93: Antisense Inhibition In Vivo by Oligonucleotides Targeting SRB-1 Comprising Mixed Wings and a 5'-GalNAc$_3$ Conjugate The oligonucleotides listed in Table 100 were tested in a dose-dependent study for antisense inhibition of SRB-1 in mice.

TABLE 100

Modified ASOs targeting SRB-1

| ISIS No. | Sequences (5' to 3') | GalNAc$_3$ Cluster | CM | SEQ ID No. |
|---|---|---|---|---|
| 449093 | T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_{k}$ | n/a | n/a | 165 |
| 699806 | GalNAc3-3a-o'T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_{k}$ | GalNAc$_3$-3a | PO | 165 |
| 699807 | GalNAc3-7a-o'T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_{k}$ | GalNAc$_3$-7a | PO | 165 |
| 699809 | GalNAc3-7a-o'T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{e}$ | GalNAc$_3$-7a | PO | 165 |
| 699811 | GalNAc3-7a-o'T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_{k}$ | GalNAc$_3$-7a | PO | 165 |
| 699813 | GalNAc3-7a-o'T$_{ks}$T$_{ds}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ds}$$^m$C$_{k}$ | GalNAc$_3$-7a | PO | 165 |
| 699815 | GalNAc3-7a-o'T$_{es}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_{e}$ | GalNAc$_3$-7a | PO | 165 |

The structure of GalNAc$_3$-3a was shown previously in Example 39, and the structure of GalNAc$_3$-7a was shown previously in Example 48. Subscripts: "e" indicates 2'-MOE modified nucleoside; "d" indicates β-D-2'-deoxyribonucleoside; "k" indicates 6'-(S)—CH$_3$ bicyclic nucleoside (cEt); "s" indicates phosphorothioate internucleoside linkages (PS); "o" indicates phosphodiester internucleoside linkages (PO). Superscript "m" indicates 5-methylcytosines. Treatment Six to eight week old C57BL/6 mice (Jackson Laboratory, Bar Harbor, ME) were injected subcutaneously once at the dosage shown below with an oligonucleotide listed in Table 100 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 101, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 101. Body weight is shown as the average percent body weight relative to the baseline body weight (% BL) measured just prior to the oligonucleotide dose.

TABLE 101

SRB-1 mRNA, ALT, AST, BUN, and total bilirubin levels and body weights

| ISIS No. | Dosage (mg/kg) | SRB-1 mRNA (% PBS) | ALT (U/L) | AST (U/L) | Bil | BUN | Body weight (% BL) |
|---|---|---|---|---|---|---|---|
| PBS | n/a | 100 | 31 | 84 | 0.15 | 28 | 102 |
| 449093 | 1 | 111 | 18 | 48 | 0.17 | 31 | 104 |
|  | 3 | 94 | 20 | 43 | 0.15 | 26 | 103 |
|  | 10 | 36 | 19 | 50 | 0.12 | 29 | 104 |
| 699806 | 0.1 | 114 | 23 | 58 | 0.13 | 26 | 107 |
|  | 0.3 | 59 | 21 | 45 | 0.12 | 27 | 108 |
|  | 1 | 25 | 30 | 61 | 0.12 | 30 | 104 |
| 699807 | 0.1 | 121 | 19 | 41 | 0.14 | 25 | 100 |
|  | 0.3 | 73 | 23 | 56 | 0.13 | 26 | 105 |
|  | 1 | 24 | 22 | 69 | 0.14 | 25 | 102 |
| 699809 | 0.1 | 125 | 23 | 57 | 0.14 | 26 | 104 |
|  | 0.3 | 70 | 20 | 49 | 0.10 | 25 | 105 |
|  | 1 | 33 | 34 | 62 | 0.17 | 25 | 107 |
| 699811 | 0.1 | 123 | 48 | 77 | 0.14 | 24 | 106 |
|  | 0.3 | 94 | 20 | 45 | 0.13 | 25 | 101 |
|  | 1 | 66 | 57 | 104 | 0.14 | 24 | 107 |
| 699813 | 0.1 | 95 | 20 | 58 | 0.13 | 28 | 104 |
|  | 0.3 | 98 | 22 | 61 | 0.17 | 28 | 105 |
|  | 1 | 49 | 19 | 47 | 0.11 | 27 | 106 |
| 699815 | 0.1 | 93 | 30 | 79 | 0.17 | 25 | 105 |
|  | 0.3 | 64 | 30 | 61 | 0.12 | 26 | 105 |
|  | 1 | 24 | 18 | 41 | 0.14 | 25 | 106 |

Example 94: Antisense Inhibition In Vivo by Oligonucleotides Targeting SRB-1 Comprising 2'-Sugar Modifications and a 5'-GalNAc$_3$ Conjugate The oligonucleotides listed in Table 102 were tested in a dose-dependent study for antisense inhibition of SRB-1 in mice.

TABLE 102

Modified ASOs targeting SRB-1

| ISIS No. | Sequences (5' to 3') | GalNAc$_3$ Cluster | CM | SEQ ID No. |
|---|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | n/a | n/a | 143 |
| 700989 | G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$U$_{ms}$C$_{ms}$C$_{ms}$U$_{ms}$U$_m$ | n/a | n/a | 166 |
| 666904 | GalNAc3-3a-o'G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | PO | 143 |
| 700991 | GalNAc3-7a-o'G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$U$_{ms}$C$_{ms}$C$_{ms}$U$_{ms}$U$_m$ | GalNAc$_3$-7a | PO | 166 |

Subscript "m" indicates a 2'-O-methyl modified nucleoside. See Example 74 for complete table legend. The structure of GalNAc$_3$-3$_a$ was shown previously in Example 39, and the structure of GalNAc$_3$-7a was shown previously in Example 48.

Treatment

The study was completed using the protocol described in Example 93. Results are shown in Table 103 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 103

| ISIS No. | Dosage (mg/kg) | SRB-1 mRNA (% PBS) |
|---|---|---|
| PBS | n/a | 100 |
| 353382 | 5 | 116 |
| | 15 | 58 |
| | 45 | 27 |
| 700989 | 5 | 120 |
| | 15 | 92 |
| | 45 | 46 |
| 666904 | 1 | 98 |
| | 3 | 45 |
| | 10 | 17 |
| 700991 | 1 | 118 |
| | 3 | 63 |
| | 10 | 14 |

Example 95: Antisense Inhibition In Vivo by Oligonucleotides Targeting SRB-1 Comprising Bicyclic Nucleosides and a 5'-GalNAc$_3$ Conjugate The oligonucleotides listed in Table 104 were tested in a dose-dependent study for antisense inhibition of SRB-1 in mice.

TABLE 104

Modified ASOs targeting SRB-1

| ISIS No. | Sequences (5' to 3') | GalNAc$_3$ Cluster | CM | SEQ ID No. |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | n/a | 137 |
| 666905 | GalNAc3-3a-o'T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-3$_a$ | PO | 137 |
| 699782 | GalNAc3-7a-o'T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-7$_a$ | PO | 137 |
| 699783 | GalNAc3-3a-o'T$_{ls}$$^m$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ls}$$^m$C$_l$ | GalNAc$_3$-3$_a$ | PO | 137 |
| 653621 | T$_{ls}$$^m$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ls}$$^m$C$_l$Ado'-GalNAc3-1a | GalNAc$_3$-1$_a$ | A$_d$ | 138 |
| 439879 | T$_{gs}$$^m$C$_{gs}$A$_{ds}$G$_{ds}$T$_{ds}$$^m$C$_{ds}$A$_{ds}$T$_d$G$_{ds}$A$_{ds}$$^m$C$_{ds}$T$_{ds}$T$_{gs}$$^m$C$_g$ | n/a | n/a | 137 |
| 699789 | GalNAc3-3a-o'T$_{gs}$$^m$C$_{gs}$A$_{ds}$G$_{ds}$T$_{ds}$$^m$C$_{ds}$A$_{ds}$T$_d$G$_{ds}$A$_{ds}$$^m$C$_{ds}$T$_{ds}$T$_{gs}$$^m$C$_g$ | GalNAc$_3$-3$_a$ | PO | 137 |

Subscript "g" indicates a fluoro-HNA nucleoside, subscript "l" indicates a locked nucleoside comprising a 2'-O-CH$_2$-4' bridge. See the Example 74 table legend for other abbreviations. The structure of GalNAc$_3$-1$_a$ was shown previously in Example 9, the structure of GalNAc$_3$-3$_a$ was shown previously in Example 39, and the structure of GalNAc$_3$-7a was shown previously in Example 48.

Treatment

The study was completed using the protocol described in Example 93. Results are shown in Table 105 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 105

SRB-1 mRNA, ALT, AST, BUN, and total bilirubin levels and body weights

| ISIS No. | Dosage (mg/kg) | SRB-1 mRNA (% PBS) |
|---|---|---|
| PBS | n/a | 100 |
| 440762 | 1 | 104 |
|  | 3 | 65 |
|  | 10 | 35 |
| 666905 | 0.1 | 105 |
|  | 0.3 | 56 |
|  | 1 | 18 |
| 699782 | 0.1 | 93 |
|  | 0.3 | 63 |
|  | 1 | 15 |
| 699783 | 0.1 | 105 |
|  | 0.3 | 53 |
|  | 1 | 12 |
| 653621 | 0.1 | 109 |
|  | 0.3 | 82 |
|  | 1 | 27 |
| 439879 | 1 | 96 |
|  | 3 | 77 |
|  | 10 | 37 |
| 699789 | 0.1 | 82 |
|  | 0.3 | 69 |
|  | 1 | 26 |

Example 96: Plasma Protein Binding of Antisense Oligonucleotides Comprising a GalNAc$_3$ Conjugate Group Oligonucleotides listed in Table 70 targeting ApoCIII and oligonucleotides in Table 106 targeting Apo(a) were tested in an ultra-filtration assay in order to assess plasma protein binding.

TABLE 106

Modified oligonucleotides targeting Apo(a)

| ISIS No. | Sequences (5' to 3') | GalNAc$_3$ Cluster | CM | SEQ ID No. |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | n/a | n/a | 58 |
| 693401 | T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | n/a | n/a | 58 |
| 681251 | GalNAc3-7a-o'T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | GalNAc$_3$-7$_a$ | PO | 58 |
| 681257 | GalNAc3-7a-o'T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | GalNAc$_3$-7$_a$ | PO | 58 |

See the Example 74 for table legend. The structure of GalNAc$_3$-7a was shown previously in Example 48.

Ultrafree-MC ultrafiltration units (30,000 NMWL, low-binding regenerated cellulose membrane, Millipore, Bedford, MA) were pre-conditioned with 300 µL of 0.5% Tween 80 and centrifuged at 2000 g for 10 minutes, then with 300 µL of a 300 µg/mL solution of a control oligonucleotide in H$_2$O and centrifuged at 2000 g for 16 minutes. In order to assess non-specific binding to the filters of each test oligonucleotide from Tables 70 and 106 to be used in the studies, 300 µL of a 250 ng/mL solution of oligonucleotide in H$_2$O at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC (Westbury, NY). The test oligonucleotides were added to 1.2 mL aliquots of plasma at two concentrations (5 and 150 µg/mL). An aliquot (300 µL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 107 for the two concentrations of oligonucleotide tested (5 and 150 µg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 107

Percent of modified oligonucleotide bound to plasma proteins

| ISIS No. | Human plasma | | Monkey plasma | | Mouse plasma | |
|---|---|---|---|---|---|---|
|  | 5 µg/mL | 150 µg/mL | 5 µg/mL | 150 µg/mL | 5 µg/mL | 150 µg/mL |
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |

TABLE 107-continued

Percent of modified oligonucleotide bound to plasma proteins

| ISIS No. | Human plasma | | Monkey plasma | | Mouse plasma | |
|---|---|---|---|---|---|---|
| | 5 µg/mL | 150 µg/mL | 5 µg/mL | 150 µg/mL | 5 µg/mL | 150 µg/mL |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97: Modified Oligonucleotides Targeting Ttr Comprising a GalNAc₃ Conjugate Group The oligonucleotides shown in Table 108 comprising a GalNAc conjugate were designed to target TTR.

TABLE 108

Modified oligonucleotides targeting TTR

| ISIS No. | Sequences (5' to 3') | GalNAc₃ Cluster | CM | SEQ ID No. |
|---|---|---|---|---|
| 666941 | GalNAc3-3a-o'AdoT$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-3 | A$_d$ | 160 |
| 666942 | T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{eo}$Ado'-GalNAc3-3a | GalNAc₃-1 | A$_d$ | 157 |
| 682876 | GalNAc3-3a-o'T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc3-3 | PO | 156 |
| 682877 | GalNAc3-7a-o'T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-7 | PO | 156 |
| 682878 | GalNAc3-10a-o'T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-10 | PO | 156 |
| 682879 | GalNAc3-13a-o'T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-13 | PO | 156 |
| 682880 | GalNAc3-7a-o'AdoT$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-7 | A$_d$ | 160 |
| 682881 | GalNAc3-10a-o'AdoT$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-10 | A$_d$ | 160 |
| 682882 | GalNAc3-13a-o'AdoT$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_e$ | GalNAc₃-13 | A$_d$ | 160 |
| 684056 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$C$_{es}$$^m$C$_{eo}$Ado'-GalNAc3-19a | GalNAc₃-19 | A$_d$ | 157 |

The legend for Table 108 can be found in Example 74. The structure of GalNAc₃-1 was shown in Example 9. The structure of GalNAc₃-3$_a$ was shown in Example 39. The structure of GalNAc₃-7$_a$ was shown in Example 48. The structure of GaNAc₃-1$_a$ was shown in Example 46. The structure of GaNAc₃-13$_a$ was shown in Example 62. The structure of GalNAc₃-19$_a$ was shown in Example 70.

Example 98: Evaluation of Pro-Inflammatory Effects of Oligonucleotides Comprising a GalNAc Conjugate in Hpmbc Assay The oligonucleotides listed in Table 109 and were tested for pro-inflammatory effects in an hPMBC assay as described in Examples 23 and 24. (See Tables 30, 83, 95, and 108 for descriptions of the oligonucleotides.) ISIS 353512 is a high responder used as a positive control, and the other oligonucleotides are described in Tables 83, 95, and 108. The results shown in Table 109 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 109

| ISIS No. | $E_{max}/EC_{50}$ | GalNAc₃ cluster | Linkages | CM |
|---|---|---|---|---|
| 353512 | 3630 | n/a | PS | n/a |
| 420915 | 802 | n/a | PS | n/a |
| 682881 | 1311 | GalNAc₃-10 | PS | A$_d$ |

TABLE 109-continued

| ISIS No. | $E_{max}/EC_{50}$ | GalNAc₃ cluster | Linkages | CM |
|---|---|---|---|---|
| 682888 | 0.26 | GalNAc₃-10 | PO/PS | A$_d$ |
| 684057 | 1.03 | GalNAc₃-19 | PO/PS | A$_d$ |

Example 99: Binding Affinities of Oligonucleotides Comprising a GalNAc Conjugate for the Asialoglycoprotein Receptor The binding affinities of the oligonucleotides listed in Table 110 (see Table 76 for descriptions of the oligonucleotides) for the asialoglycoprotein receptor were tested in a competitive receptor binding assay. The competitor ligand, α1-acid glycoprotein (AGP), was incubated in 50 mM sodium acetate buffer (pH 5) with 1 U neuraminidaseagarose for 16 hours at 37° C., and >90% desialylation was confirmed by either sialic acid assay or size exclusion chromatography (SEC). Iodine monochloride was used to iodinate the AGP according to the procedure by Atsma et al. (see J Lipid Res. 1991 January; 32(1):173-81.) In this method, desialylated α1-acid glycoprotein (de-AGP) was added to 10 mM iodine chloride, Na$^{125}$I, and 1 M glycine in 0.25 M NaOH. After incubation for 10 minutes at room temperature, $^{125}$I-labeled de-AGP was separated from free $^{125}$I by concentrating the mixture twice utilizing a 3 KDMWCO spin column. The protein was tested for labeling efficiency and purity on a HPLC system equipped with an Agilent SEC-3 column (7.8×300 mm) and a ß-RAM counter. Competition experiments utilizing $^{125}$I-labeled de-AGP and various GalNAc-cluster containing ASOs were performed as follows. Human HepG2 cells (10$^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 37° C. with 5% and 10% CO$_2$ respectively. Cells were washed with media without FBS prior to the experiment. Cells were incubated for 30 min @37° C. with 1 ml competition mix containing appropriate growth media with 2% FBS, 10$^{-8}$ M $^{125}$I-labeled de-AGP and GalNAc-cluster containing ASOs at concentrations ranging from 10$^{-11}$ to 10$^{-5}$ M. Non-specific binding was determined in the presence of 10$^{-2}$ M GalNAc sugar. Cells were washed twice with media without FBS to remove unbound $^{125}$I-labeled de-AGP and competitor GalNAc ASO. Cells were lysed using Qiagen's RLT buffer containing 1% ß-mercaptoethanol. Lysates were transferred to round bottom assay tubes after a brief 10 min freeze/thaw cycle and assayed on a γ-counter. Non-specific binding was subtracted before dividing $^{125}$I protein counts by the value of the lowest GalNAc-ASO concentration counts. The inhibition curves were fitted according to a single site competition binding equation using a nonlinear regression algorithm to calculate the binding affinities (K$_D$'s).

The results in Table 110 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 110

Asialoglycoprotein receptor binding assay results

| ISIS No. | GalNAc conjugate | Oligonucleotide end to which GalNAc conjugate is attached | K$_D$ (nM) |
|---|---|---|---|
| 661161[a] | GalNAc$_3$-3 | 5' | 3.7 |
| 666881[a] | GalNAc$_3$-10 | 5' | 7.6 |
| 666981 | GalNAc$_3$-7 | 5' | 6.0 |
| 670061 | GalNAc$_3$-13 | 5' | 7.4 |
| 655861[a] | GalNAc$_3$-1 | 3' | 11.6 |
| 677841[a] | GalNAc$_3$-19 | 3' | 60.8 |

Example 100: Antisense Inhibition In Vivo by Oligonucleotides Comprising a GalNAc Conjugate Group Targeting Apo(a) In Vivo The oligonucleotides listed in Table 111a below were tested in a single dose study for duration of action in mice.

TABLE 111a

Modified ASOs targeting APO(a)

| ISIS No. | Sequences (5' to 3') | GalNAc$_3$ Cluster | CM | SEQ ID No. |
|---|---|---|---|---|
| 681251 | GalNAc3-7a-o'T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_e$ | GalNAc$_3$-7a | PO | 58 |
| 681257 | GalNAc3-7a-o'T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_e$ | GalNAc$_3$-7a | PO | 58 |

The structure of GalNAc$_3$-7$_a$ was shown in Example 48.

Treatment

Female transgenic mice that express human Apo(a) were each injected subcutaneously once per week, for a total of 6 doses, with an oligonucleotide and dosage listed in Table 111b or with PBS. Each treatment group consisted of 3 animals. Blood was drawn the day before dosing to determine baseline levels of Apo(a) protein in plasma and at 72 hours, 1 week, and 2 weeks following the first dose. Additional blood draws will occur at 3 weeks, 4 weeks, 5 weeks, and 6 weeks following the first dose. Plasma Apo(a) protein levels were measured using an ELISA. The results in Table 111b are presented as the average percent of plasma Apo(a) protein levels for each treatment group, normalized to baseline levels (% BL), The results show that the oligonucleotides comprising a GalNAc conjugate group exhibited potent reduction in Apo(a) expression. This potent effect was observed for the oligonucleotide that comprises full PS internucleoside linkages and the oligonucleotide that comprises mixed PO and PS linkages.

TABLE 111b

Apo(a) plasma protein levels

| ISIS No. | Dosage (mg/kg) | Apo(a) at 72 hours (% BL) | Apo(a) at 1 week (% BL) | Apo(a) at 3 weeks (% BL) |
|---|---|---|---|---|
| PBS | n/a | 116 | 104 | 107 |
| 681251 | 0.3 | 97 | 108 | 93 |
|  | 1.0 | 85 | 77 | 57 |
|  | 3.0 | 54 | 49 | 11 |
|  | 10.0 | 23 | 15 | 4 |
| 681257 | 0.3 | 114 | 138 | 104 |
|  | 1.0 | 91 | 98 | 54 |
|  | 3.0 | 69 | 40 | 6 |
|  | 10.0 | 30 | 21 | 4 |

Example 101: Antisense Inhibition by Oligonucleotides Comprising a GalNAc Cluster Linked Via a Stable Moiety The oligonucleotides listed in Table 112 were tested for inhibition of mouse APOC-III expression in vivo. C571B1/6 mice were each injected subcutaneously once with an oligonucleotide listed in Table 112 or with PBS. Each treatment group consisted of 4 animals. Each mouse treated with ISIS 440670 received a dose of 2, 6, 20S or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-III mRNA levels were measured using real-time PCR. APOC-III mRNA levels were normalized to cyclophilin mRNA levels according to standard protocols. The results are presented in Table 112 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 113 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 112

Modified oligonucleotides targeting mouse APOC-III

| ISIS No. | Sequences (5' to 3') | CM | Dosage (mg/kg) | APOC-III mRNA (% PBS) | SEQ ID No. |
|---|---|---|---|---|---|
| 440670 | $^mC_{es}A_{es}G_{es}{}^mC_{es}T_{es}T_{ds}T_{ds}A_{ds}T_{ds}T_{ds}A_{ds}$ $G_{ds}G_{ds}G_{ds}A_{ds}{}^mC_{es}A_{es}G_{es}{}^mC_{es}A_{e}$ | n/a | 2<br>6<br>20<br>60 | 92<br>86<br>59<br>37 | 162 |
| 680772 | GalNAc3-7a-o'$^mC_{es}A_{es}G_{es}{}^mC_{es}T_{es}T_{ds}T_{ds}A_{ds}$ $T_{ds}T_{ds}A_{ds}G_{ds}G_{ds}G_{ds}A_{ds}{}^mC_{es}A_{es}G_{es}{}^mC_{es}A_{e}$ | PO | 0.6<br>2<br>6<br>20 | 79<br>58<br>31<br>13 | 162 |
| 696847 | GalNAc3-7$_{a-s}$,$^mC_{es}A_{es}G_{es}{}^mC_{es}T_{es}T_{ds}T_{ds}A_{ds}T_{ds}$ $T_{ds}A_{ds}G_{ds}G_{ds}G_{ds}A_{ds}{}^mC_{es}A_{es}G_{es}{}^mC_{es}A_{e}$ | n/a (PS) | 0.6<br>2<br>6<br>20 | 83<br>73<br>40<br>28 | 162 |

The structure of GalNAc$_3$-7$_a$ was shown in Example 48.

Example 102: Distribution in Liver of Antisense Oligonucleotides Comprising a GalNAc Conjugate The liver distribution of ISIS 353382 (see Table 36) that does not comprise a GalNAc conjugate and ISIS 655861 (see Table 36) that does comprise a GalNAc conjugate was evaluated. Male balb/c mice were subcutaneously injected once with ISIS 353382 or 655861 at a dosage listed in Table 113. Each treatment group consisted of 3 animals except for the 18 mg/kg group for ISIS 655861, which consisted of 2 animals. The animals were sacrificed 48 hours following the

TABLE 113

| ISIS No. | Dosage (mg/kg) | Concentration in whole liver (molecules* 10^6 per cell) | Concentration in hepatocytes (molecules* 10^6 per cell) | Concentration in non-parenchymal liver cells (molecules* 10^6 per cell) |
|---|---|---|---|---|
| 353382 | 3 | 9.7 | 1.2 | 37.2 |
|  | 10 | 17.3 | 4.5 | 34.0 |
|  | 20 | 23.6 | 6.6 | 65.6 |
|  | 30 | 29.1 | 11.7 | 80.0 |
|  | 60 | 73.4 | 14.8 | 98.0 |
|  | 90 | 89.6 | 18.5 | 119.9 |
| 655861 | 0.5 | 2.6 | 2.9 | 3.2 |
|  | 1 | 6.2 | 7.0 | 8.8 |
|  | 3 | 19.1 | 25.1 | 28.5 |

TABLE 113-continued

| ISIS No. | Dosage (mg/kg) | Concentration in whole liver (molecules* 10^6 per cell) | Concentration in hepatocytes (molecules* 10^6 per cell) | Concentration in non-parenchymal liver cells (molecules* 10^6 per cell) |
|---|---|---|---|---|
| | 6 | 44.1 | 48.7 | 55.0 |
| | 18 | 76.6 | 82.3 | 77.1 |

Example 103: Duration of Action In Vivo of Oligonucleotides Targeting Apoc-III Comprising a GalNAc$_3$ Conjugate The oligonucleotides listed in Table 114 below were tested in a single dose study for duration of action in mice.

TABLE 114

Modified ASOs targeting APOC-III

| ISIS No. | Sequences (5' to 3') | GalNAc$_3$ Cluster | CM | SEQ ID No. |
|---|---|---|---|---|
| 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_e$ | n/a | n/a | 135 |
| 663084 | GalNAc3-3a-o'AdoA$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{es}$A$_{es}$T$_e$ | GalNAc$_3$-3a | A$_d$ | 151 |
| 679241 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{es}$A$_{es}$T$_{eo}$Ado'-GalNAc3-19a | GalNAc$_3$-19a | A$_d$ | 136 |

The structure of GalNAc$_3$-3$_a$ was shown in Example 39, and GalNAc$_3$-19$_a$ was shown in Example 70.

Treatment

Female transgenic mice that express human APOC-III were each injected subcutaneously once with an oligonucleotide listed in Table 114 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 115 are presented as the average percent of plasma triglyceride and APOC-III levels for each treatment group, normalized to baseline levels. A comparison of the results in Table 71 of example 79 with the results in Table 115 below show that oligonucleotides comprising a mixture of phosphodiester and phosphorothioate internucleoside linkages exhibited increased duration of action than equivalent oligonucleotides comprising only phosphorothioate internucleoside linkages.

TABLE 115

Plasma triglyceride and APOC-III protein levels in transgenic mice

| ISIS No. | Dosage (mg/kg) | Time point (days post-dose) | Tri-glycerides (% baseline) | APOC-III protein (% baseline) | GalNAc$_3$ Cluster | CM |
|---|---|---|---|---|---|---|
| PBS | n/a | 3 | 96 | 101 | n/a | n/a |
| | | 7 | 88 | 98 | | |
| | | 14 | 91 | 103 | | |
| | | 21 | 69 | 92 | | |
| | | 28 | 83 | 81 | | |
| | | 35 | 65 | 86 | | |
| | | 42 | 72 | 88 | | |
| 304801 | 30 | 3 | 42 | 46 | n/a | n/a |
| | | 7 | 42 | 51 | | |
| | | 14 | 59 | 69 | | |
| | | 21 | 67 | 81 | | |
| | | 28 | 79 | 76 | | |
| | | 35 | 72 | 95 | | |
| | | 42 | 82 | 92 | | |
| 663084 | 10 | 3 | 35 | 28 | GalNAc$_3$-3a | A$_d$ |
| | | 7 | 23 | 24 | | |
| | | 14 | 23 | 26 | | |
| | | 21 | 23 | 29 | | |
| | | 28 | 30 | 22 | | |
| | | 35 | 32 | 36 | | |
| | | 42 | 37 | 47 | | |
| 679241 | 10 | 3 | 38 | 30 | GalNAc$_3$-19a | A$_d$ |
| | | 7 | 31 | 28 | | |
| | | 14 | 30 | 22 | | |
| | | 21 | 36 | 34 | | |
| | | 28 | 48 | 34 | | |
| | | 35 | 50 | 45 | | |
| | | 42 | 72 | 64 | | |

Example 104: Synthesis of Oligonucleotides Comprising a 5'-GalNAc₂ Conjugate
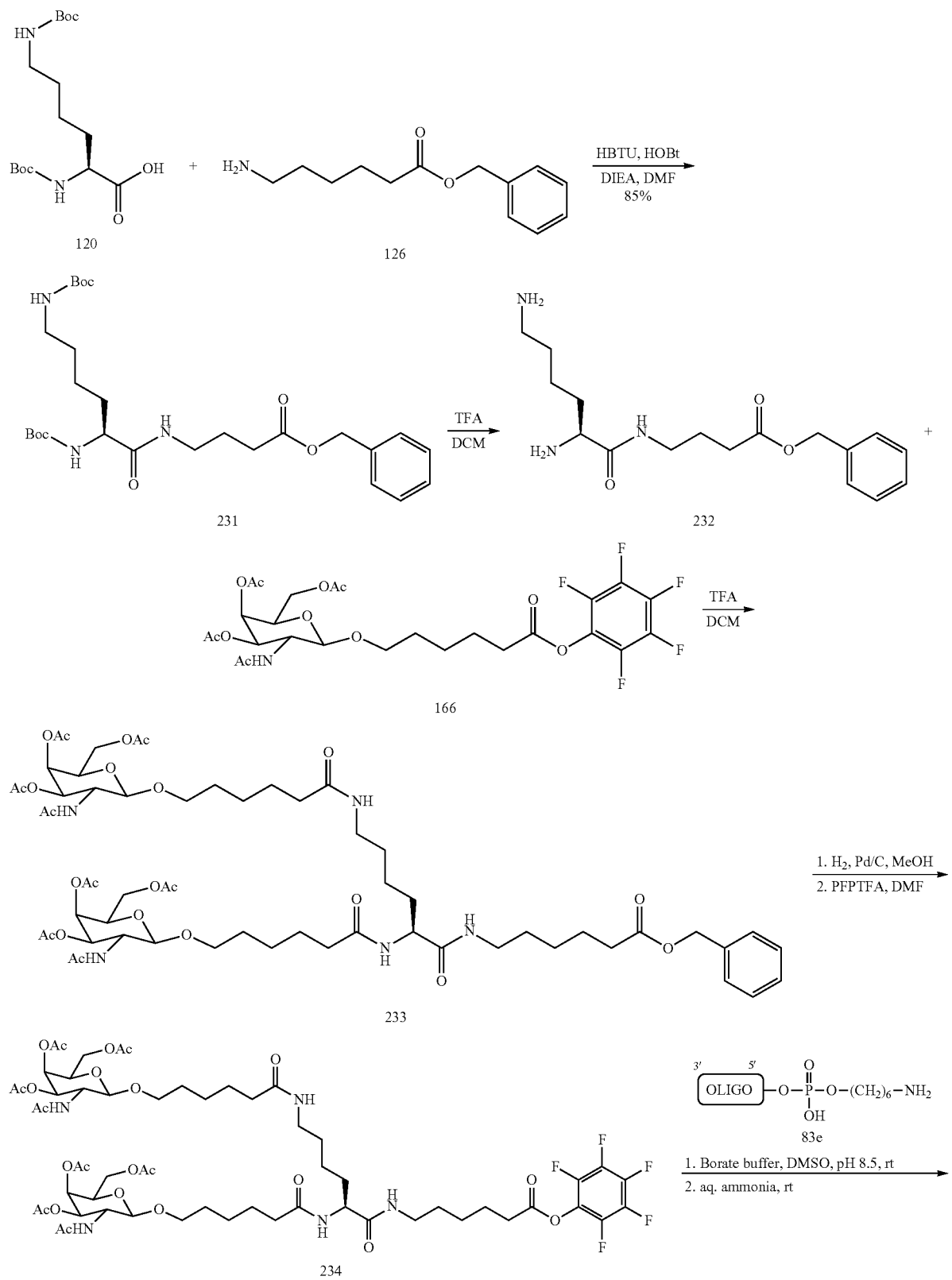

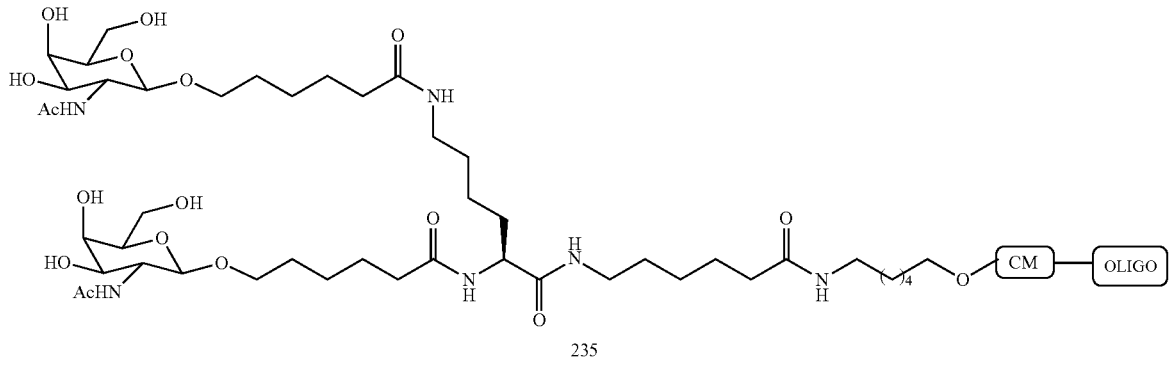

235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL. and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO4 and extracted with 2×50 mL ethyl acetate. Organic layers were combined and washed with 3×40 mL sat NaHCO$_3$ and 2×brine, dried with Na$_2$SO$_4$, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifuloracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat. aqueous NaHCO$_3$ (3×80 mL), 1 M NaHSO$_4$ (3×80 mL) and brine (2×80 mL), then dried (Na$_2$SO$_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylehtylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The GalNAc$_2$ cluster portion (GalNAc$_2$-24$_a$) of the conjugate group GalNAc$_2$-24 can be combined with any cleavable moiety present on the oligonucleotide to provide a variety of conjugate groups. The structure of GalNAc$_2$-24 (GalNAc$_2$-24$_a$-CM) is shown below:

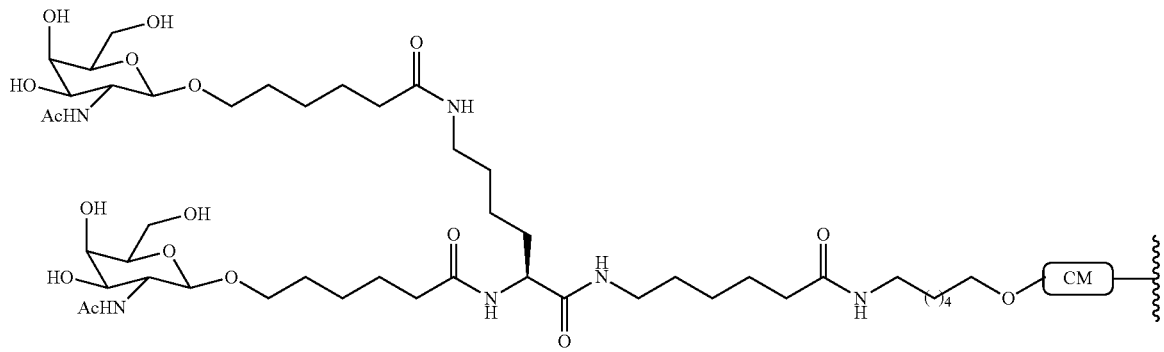

Example 105: Synthesis of Oligonucleotides Comprising a GalNAc$_1$-25 Conjugate

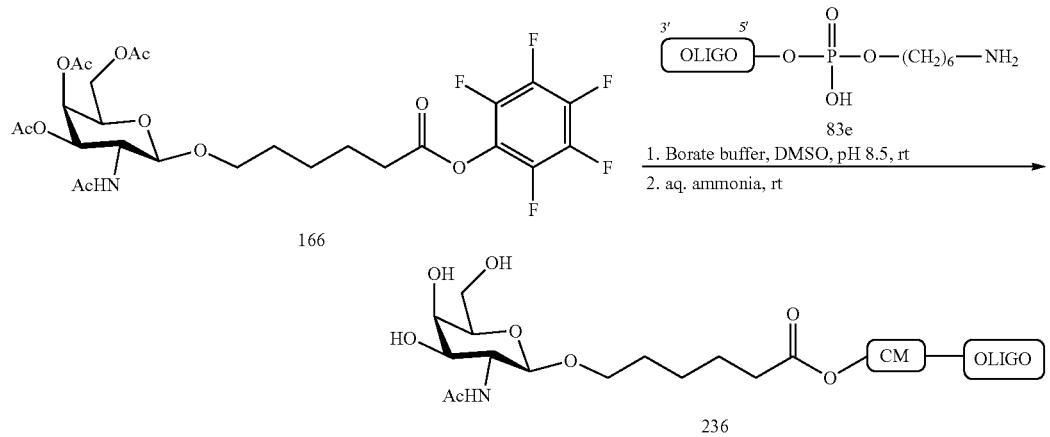

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

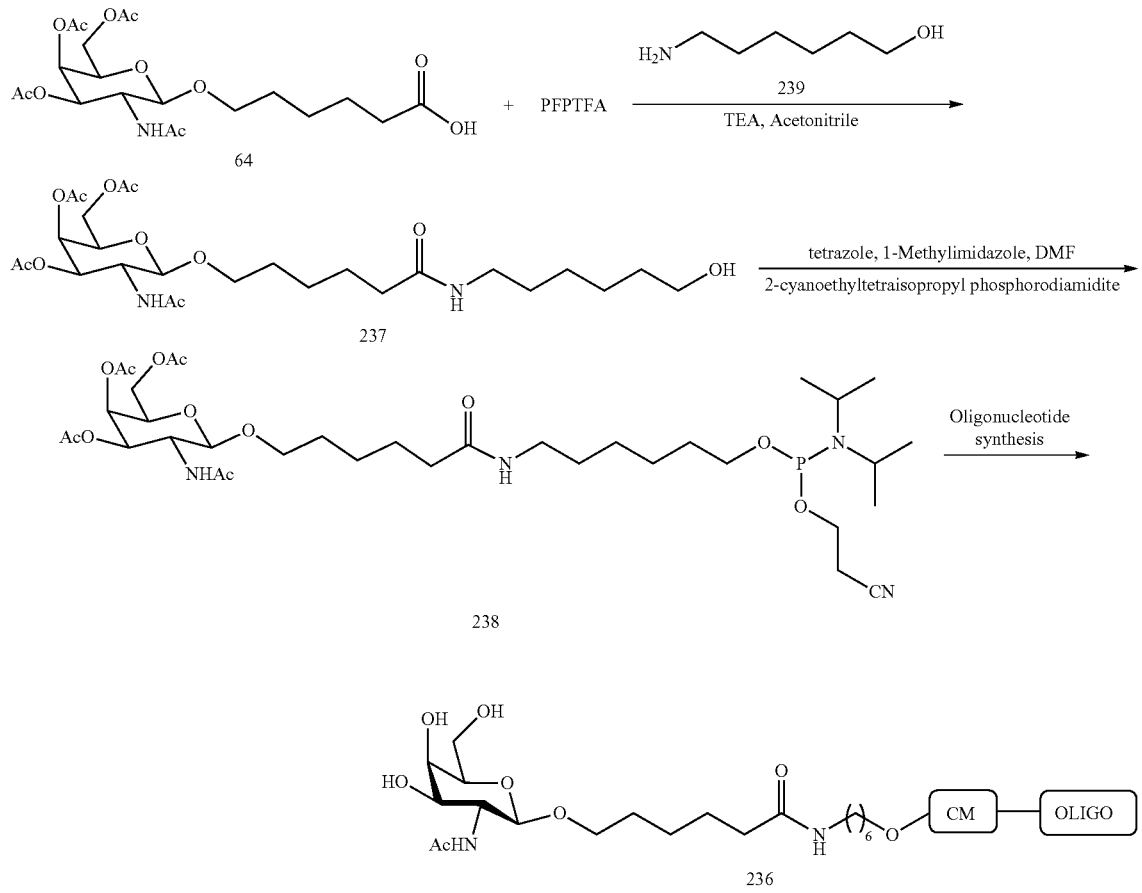

The GalNAc$_1$ cluster portion (GalNAc$_1$-25$_a$) of the conjugate group GalNAc$_1$-25 can be combined with any cleavable moiety present on the oligonucleotide to provide a variety of conjugate groups. The structure of GalNAc$_1$-25 (GalNAc$_1$-25$_a$-CM) is shown below:

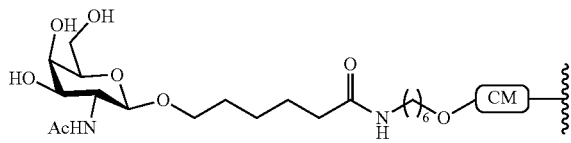

Example 106: Antisense Inhibition In Vivo by Oligonucleotides Targeting SRB-1 Comprising a 5'-GalNAc$_2$ or a 5'-GalNAc$_3$ Conjugate Oligonucleotides listed in Tables 116 and 117 were tested in dose-dependent studies for antisense inhibition of SRB-1 in mice.

Treatment

Six to week old, male C57BL/6 mice (Jackson Laboratory, Bar Harbor, ME) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the ED$_{50}$ results are presented in Tables 116 and 117. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., *Bioorg. & Med. Chem.*, Vol. 16, 5216-5231 (2008)), treatment with antisense oligonucleotides comprising monovalent, divalent, and trivalent GalNAc clusters lowered SRB-1 mRNA levels with similar potencies as shown in Tables 116 and 117.

TABLE 116

Modified oligonucleotides targeting SRB-1

| ISIS No. | Sequences (5' to 3') | GalNAc Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 4.7 | 137 |
| 686221 | GalNAc2-24a-o'AdoT$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_2$-24$_a$ | 0.39 | 141 |
| 686222 | GalNAc3-13a-o'AdoT$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-13$_a$ | 0.41 | 141 |

See Example 93 for table legend. The structure of GalNAc$_3$-13a was shown in Example 62, and the structure of GalNAc$_2$-24a was shown in Example 104.

TABLE 117

Modified oligonucleotides targeting SRB-1

| ISIS No. | Sequences (5' to 3') | GalNAc Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 5 | 137 |
| 708561 | GalNAc1-25a-o'T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_1$-25$_a$ | 0.4 | 137 |

See Example 93 for table legend. The structure of GalNAc$_1$-25a was shown in Example 105.

The concentrations of the oligonucleotides in Tables 116 and 117 in liver were also assessed, using procedures described in Example 75. The results shown in Tables 117a and 117b below are the average total antisense oligonucleotide tissues levels for each treatment group, as measured by UV in units of μg oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 116 and 117 above.

TABLE 117a

Liver concentrations of oligonucleotides comprising a GalNAc$_2$ or GalNAc$_3$ conjugate group

| ISIS No. | Dosage (mg/kg) | [Antisense oligonucleotide] (μg/g) | GalNAc cluster | CM |
|---|---|---|---|---|
| 440762 | 2 | 2.1 | n/a | n/a |
| | 7 | 13.1 | | |
| | 20 | 31.1 | | |
| 686221 | 0.2 | 0.9 | GalNAc$_2$-24$_a$ | A$_d$ |
| | 0.6 | 2.7 | | |
| | 2 | 12.0 | | |
| | 6 | 26.5 | | |
| 686222 | 0.2 | 0.5 | GalNAc$_3$-13$_a$ | A$_d$ |
| | 0.6 | 1.6 | | |
| | 2 | 11.6 | | |
| | 6 | 19.8 | | |

TABLE 117b

Liver concentrations of oligonucleotides comprising a GalNAc$_1$ conjugate group

| ISIS No. | Dosage (mg/kg) | [Antisense oligonucleotide] (μg/g) | GalNAc cluster | CM |
|---|---|---|---|---|
| 440762 | 2 | 2.3 | n/a | n/a |
| | 7 | 8.9 | | |
| | 20 | 23.7 | | |
| 708561 | 0.2 | 0.4 | GalNAc$_1$-25$_a$ | PO |
| | 0.6 | 1.1 | | |
| | 2 | 5.9 | | |
| | 6 | 23.7 | | |
| | 20 | 53.9 | | |

Example 107: Synthesis of Oligonucleotides Comprising a GalNAc$_1$-26 or GalNAc$_1$-27 Conjugate

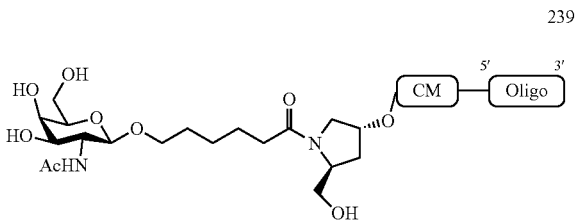

239

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc$_1$ cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

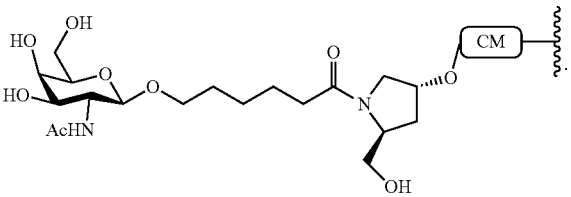

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

240

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

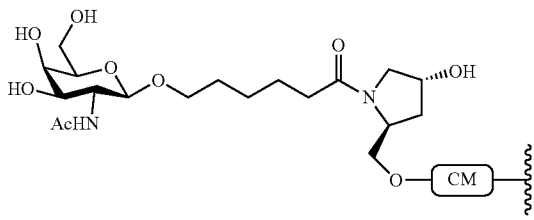

Example 108: Antisense Inhibition In Vivo by Oligonucleotides Comprising a GalNAc Conjugate Group Targeting Apo(a) In Vivo The oligonucleotides listed in Table 118 below were tested in a single dose study in mice.

TABLE 118

Modified ASOs targeting APO(a)

| ISIS No. | Sequences (5' to 3') | GalNAc$_3$ Cluster | CM | SEQ ID No. |
|---|---|---|---|---|
| 494372 | $T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}$ $T_{ds}T_{es}G_{es}T_{es}T_{es}{}^mC_e$ | n/a | n/a | 58 |
| 681251 | GalNAc3-7a-o'$T_{es}G_{es}{}^mC_{es}T_{es}{}^mC_{es}{}^mC_{ds}G_{ds}T_{ds}T_{ds}G_{ds}G_{ds}$ $T_{ds}G_{ds}{}^mC_{ds}T_{ds}T_{es}G_{es}T_{es}T_{es}{}^mC_e$ | GalNAc$_3$-7a | PO | 58 |
| 681255 | GalNAc3-3a-o'$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-3a | PO | 58 |
| 681256 | GalNAc3-10a-o'$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-10a | PO | 58 |
| 681257 | GalNAc3-7a-o'$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-7a | PO | 58 |
| 681258 | GalNAc3-13a-o'$T_{es}G_{eo}{}^mC_{eo}T_{eo}{}^mC_{eo}{}^mC_{ds}G_{ds}T_{ds}T_{ds}G_{ds}G_{ds}$ $T_{ds}G_{ds}{}^mC_{ds}T_{ds}T_{eo}G_{eo}T_{es}T_{es}{}^mC_e$ | GalNAc$_3$-13a | PO | 58 |
| 681260 | $T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}T_{ds}T_{eo}G_{eo}$ $T_{es}T_{es}{}^mC_{eo}$Ado'-GalNAc3-19 | GalNAc$_3$-19a | A$_d$ | 167 |

The structure of GalNAc$_3$-7$_a$ was shown in Example 48.

Treatment

Male transgenic mice that express human Apo(a) were each injected subcutaneously once with an oligonucleotide and dosage listed in Table 119 or with PBS. Each treatment group consisted of 4 animals. Blood was drawn the day before dosing to determine baseline levels of Apo(a) protein in plasma and at 1 week following the first dose. Additional blood draws will occur weekly for approximately 8 weeks. Plasma Apo(a) protein levels were measured using an ELISA. The results in Table 119 are presented as the average percent of plasma Apo(a) protein levels for each treatment group, normalized to baseline levels (% BL), The results show that the antisense oligonucleotides reduced Apo(a) protein expression. Furthermore, the oligonucleotides comprising a GalNAc conjugate group exhibited even more potent reduction in Apo(a) expression than the oligonucleotide that does not comprise a conjugate group.

TABLE 119

Apo(a) plasma protein levels

| ISIS No. | Dosage (mg/kg) | Apo(a) at 1 week (% BL) |
|---|---|---|
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

Example 109: Synthesis of Oligonucleotides Comprising a GalNAc$_1$-28 or GalNAc$_1$-29 Conjugate

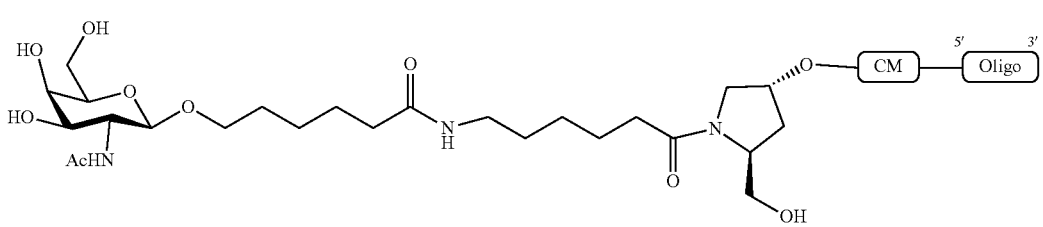

Oligonucleotide 241 is synthesized using procedures similar to those described in Example 71 to form the phosphoramidite intermediate, followed by procedures described in Example 10 to synthesize the oligonucleotide. The GalNAc$_1$ cluster portion (GalNAc$_1$-28$_a$) of the conjugate group GalNAc$_1$-28 can be combined with any cleavable moiety present on the oligonucleotide to provide a variety of conjugate groups. The structure of GalNAc$_1$-28 (GalNAc$_1$-28$_a$-CM) is shown below:

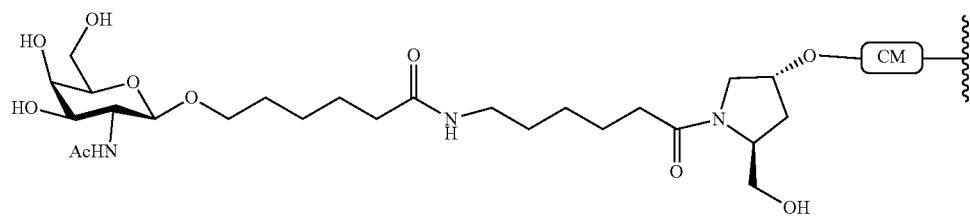

In order to add the GalNAc$_1$ conjugate group to the 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

lp;4p

242

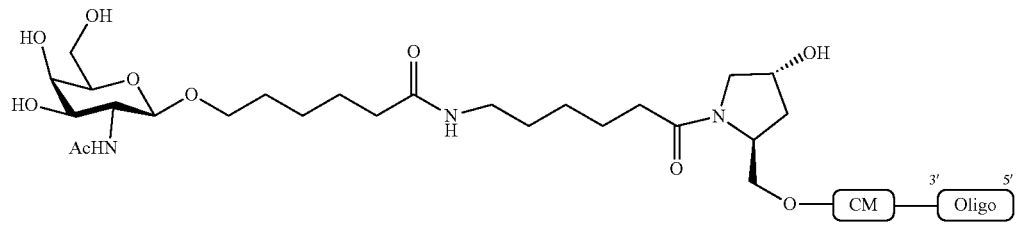

The GalNAc$_1$ cluster portion (GalNAc$_1$-29$_a$) of the conjugate group GalNAc$_1$-29 can be combined with any cleavable moiety present on the oligonucleotide to provide a variety of conjugate groups. The structure of GalNAc$_1$-29 (GalNAc$_1$-29$_a$-CM) is shown below:

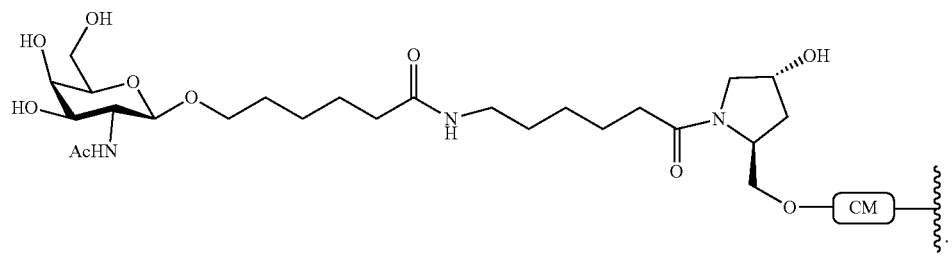

Example 110: Synthesis of Oligonucleotides Comprising a GalNAc$_1$-30 Conjugate

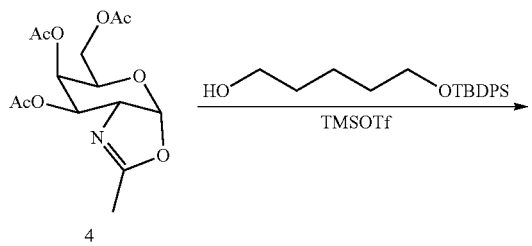

4

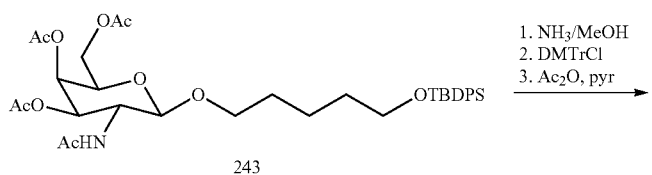

243

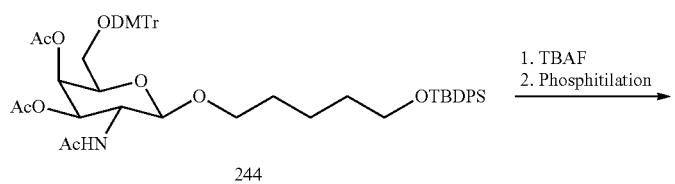

244

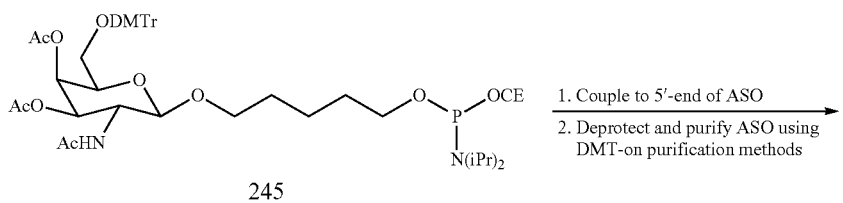

245

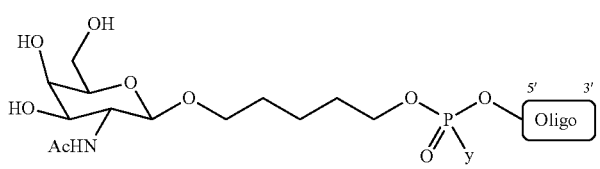

246

Oligonucleotide 246 comprising a GalNAc$_1$-30 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc$_1$ cluster portion (GalNAc$_1$-30$_a$) of the conjugate group GalNAc$_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of GalNAc$_1$-30$_a$ is shown below:

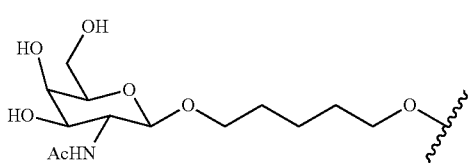 [SMILES: *OCCCCCOC1OC(CO)C(O)C(O)C1NC(C)=O]

Example 111: Synthesis of Oligonucleotides Comprising a GalNAc$_2$-31 or GalNAc$_2$-32 Conjugate

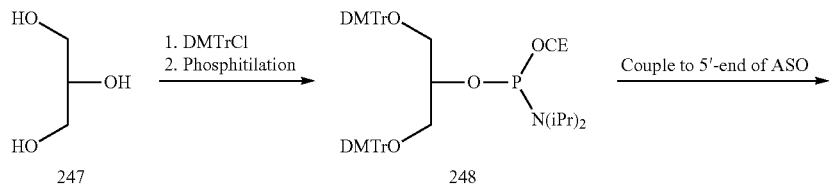

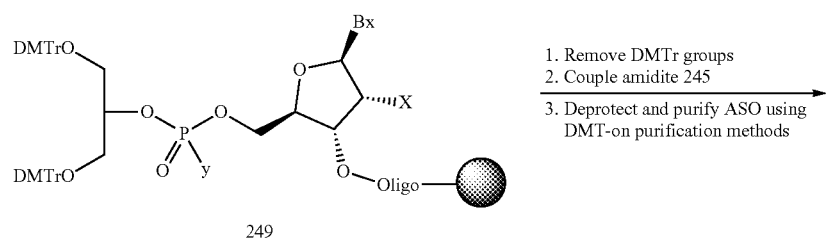

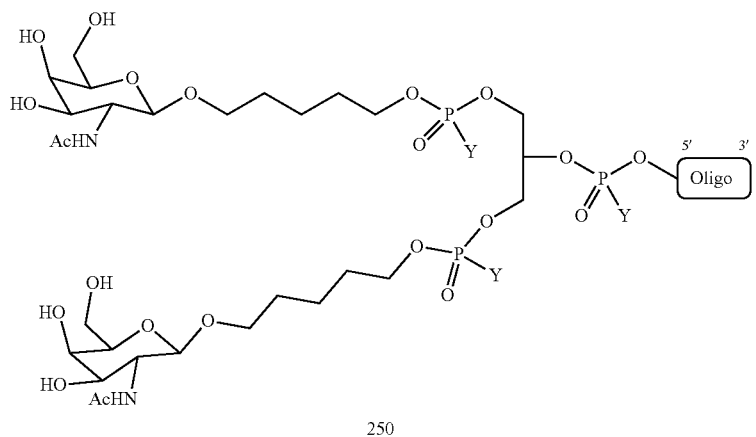

Oligonucleotide 250 comprising a GalNAc$_2$-31 conjugate group, wherein Y is selected from O, S, a substituted or unsubstituted C$_1$-C$_{10}$ alkyl, amino, substituted amino, azido, alkenyl or alkynyl, is synthesized as shown above. The GalNAc$_2$ cluster portion (GalNAc$_2$-31$_a$) of the conjugate group GalNAc$_2$-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc$_2$-31$_a$ is shown below:

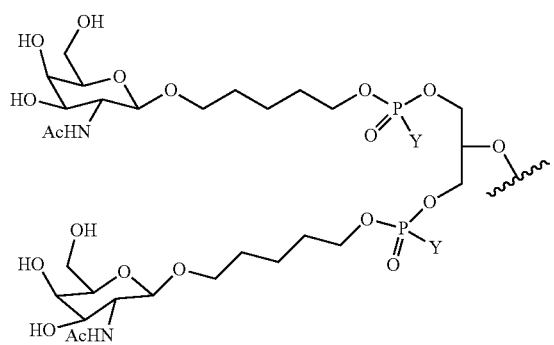

The synthesis of an oligonucleotide comprising a GalNAc₂-32 conjugate is shown below.

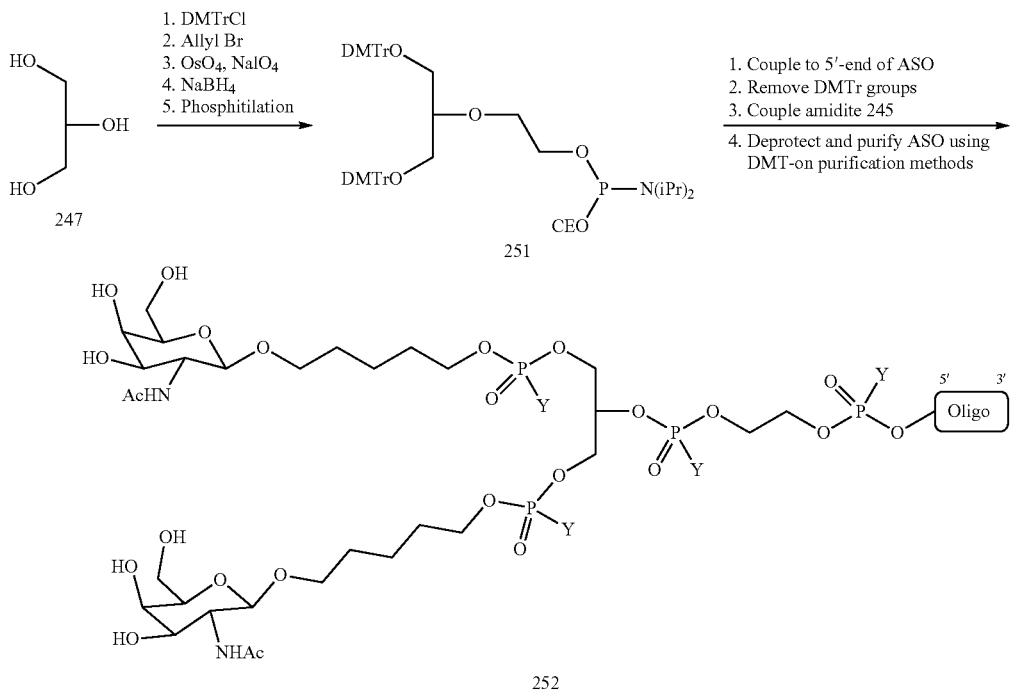

Oligonucleotide 252 comprising a GalNAc₂-32 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc₂ cluster portion (GalNAc₂-32$_a$) of the conjugate group GalNAc₂-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc₂-32a is shown below:

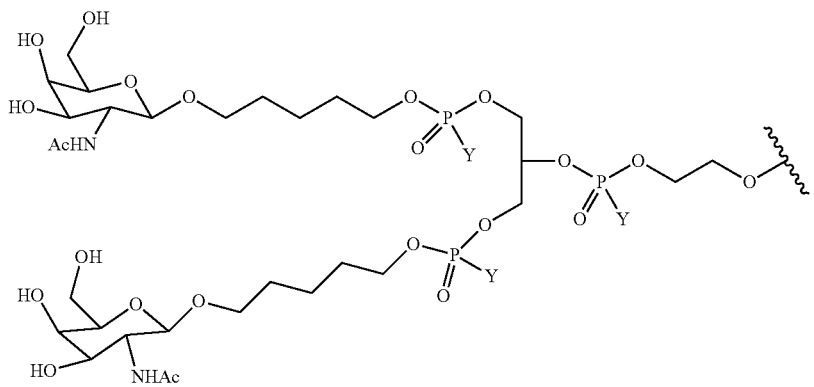

Example 112: Modified Oligonucleotides Comprising a GalNAc₁ Conjugate

The oligonucleotides in Table 120 targeting SRB-1 were synthesized with a GalNAc₁ conjugate group in order to further test the potency of oligonucleotides comprising conjugate groups that contain one GalNAc ligand.

TABLE 120

| ISIS No. | Sequences (5' to 3') | GalNAc Cluster | CM | SEQ ID NO. |
|---|---|---|---|---|
| 711461 | GalNAc1-25a-o'AdoG$_{es}$$^m$C$_{es}$T$_{es}$T$_{es}$$^m$C$_{es}$A$_{ds}$G$_{ds}$T$_{ds}$$^m$C$_{ds}$A$_{ds}$ T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-25$_a$ | A$_d$ | 145 |
| 711462 | GalNAc1-25a-o'G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-25$_a$ | PO | 143 |
| 711463 | GalNAc1-25a-o'G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_{e}$ | GalNAc$_1$-25$_a$ | PO | 143 |
| 711465 | GalNAc1-26a-o'AdoG$_{es}$$^m$C$_{es}$T$_{es}$T$_{es}$$^m$C$_{es}$A$_{ds}$G$_{ds}$T$_{ds}$$^m$C$_{ds}$A$_{ds}$ T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-26$_a$ | A$_d$ | 145 |
| 711466 | GalNAc1-26a-o'G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-26$_a$ | PO | 143 |
| 711467 | GalNAc1-26a-o'G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_{e}$ | GalNAc$_1$-26$_a$ | PO | 143 |
| 711468 | GalNAc1-28a-o'AdoG$_{es}$$^m$C$_{es}$T$_{es}$T$_{es}$$^m$C$_{es}$A$_{ds}$G$_{ds}$T$_{ds}$$^m$C$_{ds}$A$_{ds}$ T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-28$_a$ | A$_d$ | 145 |
| 711469 | GalNAc1-28a-o'G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-28$_a$ | PO | 143 |
| 711470 | GalNAc1-28a-o'G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{eo}$$^m$C$_{eo}$$^m$C$_{es}$T$_{es}$T$_{e}$ | GalNAc$_1$-28$_a$ | PO | 143 |
| 713844 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_{eo}$'-GalNAc1-27a | GalNAc$_1$-27$_a$ | PO | 143 |
| 713845 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_{eo}$'-GalNAc1-27a | GalNAc$_1$-27$_a$ | PO | 143 |
| 713846 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_{eo}$A$_{do}$'-GalNAc1-27a | GalNAc$_1$-27$_a$ | A$_d$ | 144 |
| 713847 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_{eo}$'-GalNAc1-29a | GalNAc$_1$-29$_a$ | PO | 143 |
| 713848 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_{eo}$'-GalNAc1-29a | GalNAc$_1$-29$_a$ | PO | 143 |
| 713849 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_{eo}$Ado'-GalNAc1-29a | GalNAc$_1$-29$_a$ | A$_d$ | 144 |
| 713850 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_{eo}$Ado'-GalNAc1-29a | GalNAc$_1$-29$_a$ | A$_d$ | 144 |

Example 113: Dose-Dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, NJ) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTACCAGCTATGCCAAACCTT, designated herein as SEQ ID NO: 7) was used to measure mRNA levels. Additionally, mRNA levels were also measured using human apo(a) primer probe set hAPO(a)12 kB (forward sequence CCACAGTGGCCCCGGT, designated herein as SEQ ID NO: 8; reverse sequence ACAGGGCTTTTCTCAGGTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in the table below as percent inhibition of apo(a), relative to untreated control cells.

TABLE 121

Antisense inhibition of human apo(a) in human primary hepatocytes

| ISIS No | % inhibition (hAPO(a)3' PPset) | % inhibition (hAPO(a)12kB PPset) |
|---|---|---|
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |

TABLE 121-continued

Antisense inhibition of human apo(a) in human primary hepatocytes

| ISIS No | % inhibition (hAPO(a)3' PPset) | % inhibition (hAPO(a)12kB PPset) |
|---|---|---|
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |
| 144383 | 63 | 79 |
| 144384 | 38 | 0 |
| 144385 | 40 | 94 |
| 144386 | 47 | 61 |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in the table below. After a treatment period of approximately 16 hours, RNA was isolated from the cells and apo(a) mRNA levels were measured by quantitative real-time PCR. Human apo(a) primer probe set hAPO(a)3' was used to measure mRNA levels. Apo(a) mRNA levels were normalized to GAPDH mRNA expression. Results are presented as percent inhibition of apo(a), relative to untreated control cells.

TABLE 122

Dose-dependent antisense inhibition of human apo(a) in human primary hepatocytes, as measured with hAPO(a)3'

| ISIS No | 25 nM | 50 nM | 150 nM | 300 nM |
|---|---|---|---|---|
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 114: Antisense Inhibition of Human Apo(a) in Transgenic Mouse Primary Hepatocytes Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)$_{12}$ kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the tables are targeted with 10000 complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 123

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 494157 | 238 | 257 | CCTGTGACAGTGGTGGAGTA | 95 | 21199 26690 32237 | 21218 26709 32256 | 12 |
|  | 580 | 599 |  |  |  |  |  |
|  | 922 | 941 |  |  |  |  |  |

TABLE 123-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1606 | 1625 | | | 43330 | 43349 | |
| | 1948 | 1967 | | | 48874 | 48893 | |
| | 2290 | 2309 | | | 54420 | 54439 | |
| | 3316 | 3335 | | | 72037 | 72056 | |
| 494158 | 239 | 258 | TCCTGTGA CAGTGGTG GAGT | 95 | 21200 | 21219 | 13 |
| | 581 | 600 | | | 26691 | 26710 | |
| | 923 | 942 | | | 32238 | 32257 | |
| | 1607 | 1626 | | | 43331 | 43350 | |
| | 1949 | 1968 | | | 48875 | 48894 | |
| | 2291 | 2310 | | | 54421 | 54440 | |
| | 3317 | 3336 | | | 72038 | 72057 | |
| 494159 | 241 | 260 | CTTCCTGT GACAGTGG TGGA | 97 | 21202 | 21221 | 14 |
| | 583 | 602 | | | 26693 | 26712 | |
| | 925 | 944 | | | 32240 | 32259 | |
| | 1609 | 1628 | | | 43333 | 43352 | |
| | 1951 | 1970 | | | 48877 | 48896 | |
| | 2293 | 2312 | | | 54423 | 54442 | |
| | 3319 | 3338 | | | 72040 | 72059 | |
| | 4663 | 4682 | | | 94404 | 94423 | |
| | 5005 | 5024 | | | 115515 | 115534 | |
| 494160 | 242 | 261 | CCTTCCTG TGACAGTG GTGG | 97 | 21203 | 21222 | 15 |
| | 4664 | 4683 | | | 94405 | 94424 | |
| | 5006 | 5025 | | | 115516 | 115535 | |
| 494161 | 243 | 262 | TCCTTCC TGTGACA GTGGTG | 96 | 21204 | 21223 | 16 |
| | 4665 | 4684 | | | 4406 | 94425 | |
| | 5007 | 5026 | | | 115517 | 115536 | |
| 494162 | 244 | 263 | GTCCTTCC TGTGACAG TGGT | 95 | 21205 | 21224 | 17 |
| | 3664 | 3683 | | | 77585 | 77604 | |
| | 4666 | 4685 | | | 94407 | 94426 | |
| | 5008 | 5027 | | | 115518 | 115537 | |
| 494163 | 245 | 264 | GGTCCTTC CTGTGACA GTGG | 96 | 21206 | 21225 | 18 |
| | 4667 | 4686 | | | 94408 | 94427 | |
| 494164 | 246 | 265 | AGGTCCTT CCTGTGAC AGTG | 93 | 21207 | 21226 | 19 |
| | 4668 | 4687 | | | 94409 | 94428 | |
| 494165 | 247 | 266 | CAGGTCCT TCCTGTGA CAGT | 91 | 21208 | 21227 | 20 |
| | 4669 | 4688 | | | 94410 | 94429 | |
| 494166 | 248 | 267 | GCAGGTCC TTCCTGTG ACAG | 89 | 21209 | 21228 | 21 |
| 494167 | 250 | 269 | TGGCAGGT CCTTCCTG TGAC | 92 | 21211 | 21230 | 22 |
| 494168 | 251 | 270 | TTGGCAGG TCCTTCCT GTGA | 89 | 21212 | 21231 | 23 |
| 494169 | 252 | 271 | CTTGGCAG GTCCTTCC TGTG | 92 | 21213 | 21232 | 24 |
| 494170 | 253 | 272 | GCTTGGCA GGTCCTTC CTGT | 88 | 21214 | 21233 | 25 |

TABLE 124

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTC CTTCCTGT GACA | 91 84 | 21210 | 21229 | 11 |
| 494283 | 584 | 603 | TCTTCCT GTGACAG TGGTGG | 93 | 26694 | 26713 | 26 |
| | 926 | 945 | | | 32241 | 32260 | |
| | 1610 | 1629 | | | 43334 | 43353 | |
| | 1952 | 1971 | | | 48878 | 48897 | |
| | 2294 | 2313 | | | 54424 | 54443 | |
| | 3320 | 3339 | | | 72041 | 72060 | |
| 494284 | 585 | 604 | TTCTTCC TGTGACA GTGGTG | 95 | 26695 | 26714 | 27 |
| | 927 | 946 | | | 32242 | 32261 | |
| | 1611 | 1630 | | | 43335 | 43354 | |
| | 1953 | 1972 | | | 48879 | 48898 | |
| | 2295 | 2314 | | | 54425 | 54444 | |
| | 3321 | 3340 | | | 72042 | 72061 | |
| 494285 | 586 | 605 | GTTCTTC CTGTGAC AGTGGT | 95 | 26696 | 26715 | 28 |
| | 928 | 947 | | | 32243 | 32262 | |
| | 1612 | 1631 | | | 43336 | 43355 | |
| | 1954 | 1973 | | | 48880 | 48899 | |
| | 2296 | 2315 | | | 54426 | 54445 | |
| | 3322 | 3341 | | | 72043 | 72062 | |
| 494286 | 587 | 606 | GGTTCTT CCTGTGA CAGTGG | 95 | 26697 | 26716 | 29 |
| | 929 | 948 | | | 32244 | 32263 | |
| | 1613 | 1632 | | | 43337 | 43356 | |
| | 1955 | 1974 | | | 48881 | 48900 | |
| | 2297 | 2316 | | | 54427 | 54446 | |
| 494287 | 588 | 607 | AGGTTCT TCCTGTG ACAGTG | 95 | 26698 | 26717 | 30 |
| | 930 | 949 | | | 32245 | 32264 | |
| | 1614 | 1633 | | | 43338 | 43357 | |
| | 1956 | 1975 | | | 48882 | 48901 | |
| | 2298 | 2317 | | | 54428 | 54447 | |
| 494288 | 589 | 608 | CAGGTTC TTCCTGT GACAGT | 91 | 26699 | 26718 | 31 |
| | 931 | 950 | | | 32246 | 32265 | |
| | 1615 | 1634 | | | 43339 | 43358 | |
| | 1957 | 1976 | | | 48883 | 48902 | |
| | 2299 | 2318 | | | 54429 | 54448 | |
| | 2983 | 3002 | | | 66500 | 66519 | |
| 494290 | 592 | 611 | TGGCAGG TTCTTCC TGTGAC | 90 | 26702 | 26721 | 32 |
| | 934 | 953 | | | 32249 | 32268 | |
| | 1618 | 1637 | | | 43342 | 43361 | |
| | I960 | 1979 | | | 48886 | 48905 | |
| | 2302 | 2321 | | | 54432 | 54451 | |
| | 2986 | 3005 | | | 66503 | 66522 | |
| 494291 | 593 | 612 | TTGGCAG GTTCTTC CTGTGA | 89 | 26703 | 26722 | 33 |
| | 935 | 954 | | | 32250 | 32269 | |
| | 1619 | 1638 | | | 43343 | 43362 | |
| | 1961 | 1980 | | | 48887 | 48906 | |
| | 2303 | 2322 | | | 54433 | 54452 | |
| | 2987 | 3006 | | | 66504 | 66523 | |
| 494292 | 594 | 613 | CTTGGCA GGTTCTT CCTGTG | 94 | 26704 | 26723 | 35 |
| | 936 | 955 | | | 32251 | 32270 | |
| | 1620 | 1639 | | | 43344 | 43363 | |
| | 1962 | 1981 | | | 48888 | 48907 | |
| | 2304 | 2323 | | | 54434 | 54453 | |
| | 2988 | 3007 | | | 66505 | 66524 | |
| 494294 | 596 | 615 | AGCTTGG CAGGTTC TTCCTG | 90 | 26706 | 26725 | 36 |
| | 938 | 957 | | | 32253 | 32272 | |
| | 1622 | 1641 | | | 43346 | 43365 | |
| | 1964 | 1983 | | | 48890 | 48909 | |
| | 2306 | 2325 | | | 54436 | 54455 | |
| | 2990 | 3009 | | | 66507 | 66526 | |

TABLE 124-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494299 | 626 | 645 | ACTATGCGAGTGTGGTGTCA | 91 | 26736 32283 37830 43376 48920 54466 60021 66537 | 26755 32302 37849 43395 48939 54485 60040 66556 | 37 |
| | 968 | 987 | | | | | |
| | 1310 | 1329 | | | | | |
| | 1652 | 1671 | | | | | |
| | 1994 | 2013 | | | | | |
| | 2336 | 2355 | | | | | |
| | 2678 | 2697 | | | | | |
| | 3020 | 3039 | | | | | |
| 494300 | 627 | 646 | GACTATGCGAGTGTGGTGTC | 93 | 26737 32284 37831 43377 48921 54467 60022 66538 | 26756 32303 37850 43396 48940 54486 60041 66557 | 38 |
| | 969 | 988 | | | | | |
| | 1311 | 1330 | | | | | |
| | 1653 | 1672 | | | | | |
| | 1995 | 2014 | | | | | |
| | 2337 | 2356 | | | | | |
| | 2679 | 2698 | | | | | |
| | 3021 | 3040 | | | | | |
| 494301 | 628 | 647 | CGACTATGCGAGTGTGGTGT | 93 | 26738 32285 37832 43378 48922 54468 60023 66539 | 26757 32304 37851 43397 48941 54487 60042 66558 | 39 |
| | 970 | 989 | | | | | |
| | 1312 | 1331 | | | | | |
| | 1654 | 1673 | | | | | |
| | 1996 | 2015 | | | | | |
| | 2338 | 2357 | | | | | |
| | 2680 | 2699 | | | | | |
| | 3022 | 3041 | | | | | |
| 494302 | 629 | 648 | CCGACTATGCGAGTGTGGTG | 94 | 26739 32286 37833 43379 48923 54469 60024 66540 | 26758 32305 37852 43398 48942 54488 60043 66559 | 40 |
| | 971 | 990 | | | | | |
| | 1313 | 1332 | | | | | |
| | 1655 | 1674 | | | | | |
| | 1997 | 2016 | | | | | |
| | 2339 | 2358 | | | | | |
| | 2681 | 2700 | | | | | |
| | 3023 | 3042 | | | | | |
| 494303 | 630 | 649 | TCCGACTATGCGAGTGTGGT | 93 | 26740 32287 37834 43380 48924 54470 60025 66541 | 26759 32306 37853 43399 48943 54489 60044 66560 | 41 |
| | 972 | 991 | | | | | |
| | 1314 | 1333 | | | | | |
| | 1656 | 1675 | | | | | |
| | 1998 | 2017 | | | | | |
| | 2340 | 2359 | | | | | |
| | 2682 | 2701 | | | | | |
| | 3024 | 3043 | | | | | |
| 494304 | 631 | 650 | GTCCGACTATGCGAGTGTGG | 94 | 26741 32288 37835 43381 48925 54471 60026 66542 | 26760 32307 37854 43400 48944 54490 60045 66561 | 42 |
| | 973 | 992 | | | | | |
| | 1315 | 1334 | | | | | |
| | 1657 | 1676 | | | | | |
| | 1999 | 2018 | | | | | |
| | 2341 | 2360 | | | | | |
| | 2683 | 2702 | | | | | |
| | 3025 | 3044 | | | | | |
| 494305 | 632 | 651 | GGTCCGACTATGCGAGTGTG | 93 | 26742 32289 37836 43382 48926 54472 60027 66543 | 26761 32308 37855 43401 48945 54491 60046 66562 | 43 |
| | 974 | 993 | | | | | |
| | 1316 | 1335 | | | | | |
| | 1658 | 1677 | | | | | |
| | 2000 | 2019 | | | | | |
| | 2342 | 2361 | | | | | |
| | 2684 | 2703 | | | | | |
| | 3026 | 3045 | | | | | |
| 494306 | 633 | 652 | GGGTCCGACTATGCGAGTGT | 92 | 26743 32290 37837 43383 48927 54473 60028 66544 | 26762 32309 37856 43402 48946 54492 60047 66563 | 44 |
| | 975 | 994 | | | | | |
| | 1317 | 1336 | | | | | |
| | 1659 | 1678 | | | | | |
| | 2001 | 2020 | | | | | |
| | 2343 | 2362 | | | | | |
| | 2685 | 2704 | | | | | |
| | 3027 | 3046 | | | | | |
| 494307 | 1190 | 1209 | CTGCTCAGTCGGTGCTTGTT | 91 | n/a | n/a | 45 |
| | 2558 | 2577 | | | | | |
| 494310 | 1193 | 1212 | CCTCTGCTCAGTCGGTGCTT | 90 | n/a | n/a | 46 |
| | 2561 | 2580 | | | | | |
| 494311 | 1194 | 1213 | GCCTCTGCTCAGTCGGTGCT | 88 | 37714 59905 | 37733 59924 | 47 |
| | 2562 | 2581 | | | | | |
| 494334 | 1267 | 1286 | CTTCCAGTGACAGTGGTGGA | 90 | 37787 59978 | 37806 59997 | 48 |
| | 2635 | 2654 | | | | | |
| 494336 | 1269 | 1288 | TTCTTCCAGTGACAGTGGTG | 90 | 37789 59980 | 37808 59999 | 49 |
| | 2637 | 2656 | | | | | |
| 494337 | 1270 | 1289 | GTTCTTCCAGTGACAGTGGT | 95 | 37790 59981 | 37809 60000 | 50 |
| | 2638 | 2657 | | | | | |
| 494338 | 1271 | 1290 | GGTTCTTCCAGTGACAGTGG | 91 | 37791 59982 | 37810 60001 | 133 |
| | 2639 | 2658 | | | | | |
| 494521 | 6393 | 6412 | GACCTTAAAAGCTTATACAC | 82 | 140049 | 140068 | 51 |
| 494525 | 6397 | 6416 | GTCAGACCTTAAAAGCTTAT | 84 | 140053 | 140072 | 52 |
| 494530 | 6402 | 6421 | TGTCAGTCAGACCTTAAAAG | 82 | 140058 | 140077 | 53 |
| 494535 | 6407 | 6426 | GAATTTGTCAGTCAGACCTT | 85 | 140063 | 140082 | 54 |
| 494536 | 6408 | 6427 | AGAATTTGTCAGTCAGACCT | 83 | 140064 | 140083 | 55 |
| 494544 | 6417 | 6436 | CCTTAATACAGAATTTGTCA | 82 | 140073 | 140092 | 56 |

TABLE 125

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |

TABLE 125-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 8198 | 582004 | 62 |
| 494387 | 3978 | 3997 | TTCCTGTAACAGTGGTGGAG | 82 | 8198 | 682005 | 63 |
| 494388 | 3979 | 3998 | CTTCCTGTAACAGTGGTGGA | 86 | 8198 | 782006 | 64 |
| 494389 | 3980 | 3999 | CCTTCCTGTAACAGTGGTGG | 92 | 8198 | 882007 | 65 |
| 494390 | 3981 | 4000 | TCCTTCCTGTAACAGTGGTG | 92 | 8198 | 982008 | 66 |
| 494391 | 3982 | 4001 | GTCCTTCCTGTAACAGTGGT | 84 | 8199 | 082009 | 67 |
| 494392 | 3983 | 4002 | TGTCCTTCCTGTAACAGTGG | 81 | 8199 | 182010 | 68 |

TABLE 126

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 2121 | 021229 | 11 |
| 498369 | 3203 | 3222 | TGGAGCCAGAATAACATTCG | 91 | 7066 | 770686 | 69 |
| 498379 | 3213 | 3232 | CCTCTAGGCTTGGAGCCAGA | 85 | 7067 | 770696 | 70 |
| 498408 | 3323 | 3342 | AGTTCTTCCTGTGACAGTGG | 86 | 7204 | 472063 | 71 |

TABLE 126-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 498433 | 3367 | 3386 | GTCCGACTATGCTGGTGTGG | 87 | 7208 | 872107 | 72 |
| 498434 | 3368 | 3387 | GGTCCGACTATGCTGGTGTG | 86 | 7208 | 972108 | 73 |
| 498435 | 3369 | 3388 | GGGTCCGACTATGCTGGTGT | 83 | 7209 | 072109 | 74 |

TABLE 127

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 2121 | 021229 | 11 |
| 498229 | 2871 | 2890 | CCTCTAGGCTTGGAATCGGG | 90 | 6511 | 765136 | 75 |
| 498238 | 2883 | 2902 | GTTCAGAAGGAGCCTCTAGG | 93 | 6512 | 965148 | 76 |
| 498239 | 2884 | 2903 | TGTTCAGAAGGAGCCTCTAG | 94 | 6513 | 065149 | 77 |
| 498240 | 2887 4573 | 2906 4592 | GCTTGTTCAGAAGGAGCCTC | 98 | n/a | n/a | 78 |
| 498241 | 2888 4574 | 2907 4593 | TGCTTGTTCAGAAGGAGCCT | 94 | n/a | n/a | 79 |
| 498242 | 2889 4575 | 2908 4594 | GTGCTTGTTCAGAAGGAGCC | 96 | n/a | n/a | 80 |
| 498243 | 2890 4576 | 2909 4595 | GGTGCTTGTTCAGAAGGAGC | 97 | n/a | n/a | 81 |
| 498244 | 2891 4577 | 2910 4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |
| 498252 | 2899 | 2918 | TGCTCAGTTGGTGCTTGTTC | 90 | n/a | n/a | 84 |

TABLE 128

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498517 | 3548 | 3567 | GCTTGGATCTGGGACCACCG | 89 | 76233 | 76252 | 85 |

TABLE 129

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 94 | 21210 | 21229 | 11 |
| 498833 | 4900 | 4919 | GCCTCCATGCTTGGAACTGG | 94 | 114205 | 114224 | 86 |
| 498859 | 4926 | 4945 | GCTCAGTTGGTGCTGCTTCA | 92 | n/a | n/a | 87 |
| 498868 | 4978 | 4997 | CCTCGATAACTCTGGCCATT | 94 | 115488 | 115507 | 88 |
| 498875 | 5003 | 5022 | TCCTGTGACAGTGGTGGAGA | 94 | 115513 | 115532 | 89 |

TABLE 130

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 92 | 21210 | 21229 | 11 |
| 499020 | 6257 | 6276 | GTAGGTTGATGCTTCACTCT | 91 | 139913 | 139932 | 90 |
| 499041 | 6318 | 6337 | CGTTTGATTGCTGTCTATTA | 90 | 139974 | 139993 | 91 |

TABLE 131

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498523 | 3554 | 3573 | CTCTGTGCTTGGATCTGGGA | 94 | 76239 | 76258 | 92 |
| 498524 | 3555 | 3574 | CCTCTGTGCTTGGATCTGGG | 96 | 76240 | 76259 | 93 |
| 498525 | 3556 | 3575 | GCCTCTGTGCTTGGATCTGG | 94 | 76241 | 76260 | 94 |
| 498529 | 3560 | 3579 | AGAAGCCTCTGTGCTTGGAT | 89 | 76245 | 76264 | 95 |
| 498535 | 3566 | 3585 | TTCAGAAGAAGCCTCTGTGC | 89 | 76251 | 76270 | 96 |
| 498550 | 3582 | 3601 | GCTCCGTTGGTGCTTCTTCA | 90 | n/a | n/a | 97 |
| 498553 | 3585 | 3604 | TTTGCTCCGTTGGTGCTTCT | 87 | n/a | n/a | 98 |
| 498555 | 3587 | 3606 | GCTTTGCTCCGTTGGTGCTT | 90 | n/a | n/a | 99 |
| 498556 | 3588 3906 | 3607 3925 | GGCTTTGCTCCGTTGGTGCT | 89 | 77509 81914 | 77528 81933 | 100 |
| 498557 | 3589 3907 | 3608 3926 | GGGCTTTGCTCCGTTGGTGC | 89 | 77510 81915 | 77529 81934 | 101 |
| 498579 | 3662 | 3681 | CCTTCCTGTGACAGTGGTAG | 87 | 77583 | 77602 | 102 |
| 498580 | 3663 | 3682 | TCCTTCCTGTGACAGTGGTA | 92 | 77584 | 77603 | 103 |
| 498581 | 3665 5009 | 3684 5028 | TGTCCTTCCTGTGACAGTGG | 94 | 77586 115519 | 77605 115538 | 104 |

TABLE 132

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 100 | 21210 | 21229 | 11 |
| 494230 | 477 819 1161 1503 1845 2187 2529 | 496 838 1180 1522 1864 2206 2548 | CCTCTAGGCTTGGAACCGGG | 95 | 25380 30927 36471 42020 47564 53110 58662 | 25399 30946 36490 42039 47583 53129 58681 | 105 |

TABLE 132-continued

| ISIS NO | SEQ ID NO: 1 Start Site | SEQ ID NO: 1 Stop Site | Sequence | % inhi- bi- tion | SEQ ID NO: 2 Start Site | SEQ ID NO: 2 Stop Site | SEQ ID NO |
|---|---|---|---|---|---|---|---|
| 494243 | 494 836 1178 1520 1862 2204 2546 | 513 855 1197 1539 1881 2223 2565 | TGCTTGTTC GGAAGGAGC CT | 93 | n/a | n/a | 106 |
| 494244 | 495 837 1179 1521 1863 2205 2547 | 514 856 1198 1540 1882 2224 2566 | GTGCTTGTT CGGAAGGAG CC | 95 | n/a | n/a | 107 |

TABLE 133

| ISIS NO | SEQ ID NO: 1 Start Site | SEQ ID NO: 1 Stop Site | Sequence | % inhi- bi- tion | SEQ ID NO: 2 Start Site | SEQ ID NO: 2 Stop Site | SEQ ID NO |
|---|---|---|---|---|---|---|---|
| 144367 | 249 | 268 | GGCAGGTCCT TCCTGTGACA | 96 | 21210 | 21229 | 11 |
| 494466 | 4208 | 4227 | GCTTGGAACT GGGACCACCG | 95 | 85138 | 85157 | 108 |
| 494470 | 4212 | 4231 | CTGTGCTTGG AACTGGGACC | 94 | 85142 | 85161 | 109 |
| 494472 | 4214 | 4233 | CTCTGTGCTT GGAACTGGGA | 92 | 85144 | 85163 | 110 |

Example 115: Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 µM, 0.125 µM, 0.25 µM, 0.500 µM, or 1.000 µM concentrations of antisense oligonucleotide. After a treatment period of approximately 16 hours, RNA was isolated from the cells and apo(a) mRNA levels were measured by quantitative real-time PCR. Apo(a) primer probe set hAPO(a) 12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each table representing a separate experiment. The half maximal inhibitory concentration ($IC_{50}$) of each oligonucleotide is also presented in the tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 134

| ISIS No | 0.0625 µM | 0.125 µM | 0.250 µM | 0.500 µM | 1.000 µM | $IC_{50}$ (µM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 135

| ISIS No | 0.0625 µM | 0.125 µM | 0.250 µM | 0.500 µM | 1.000 µM | $IC_{50}$ (µM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 136

| ISIS No | 0.0625 µM | 0.125 µM | 0.250 µM | 0.500 µM | 1.000 µM | $IC_{50}$ (µM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 137

| ISIS No | 0.0625 µM | 0.125 µM | 0.250 µM | 0.500 µM | 1.000 µM | $IC_{50}$ (µM) |
|---|---|---|---|---|---|---|
| 144367 | 0 | 29 | 45 | 73 | 92 | 0.27 |
| 494311 | 28 | 53 | 65 | 85 | 95 | 0.13 |
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |

TABLE 137-continued

| ISIS No | 0.0625 μM | 0.125 μM | 0.250 μM | 0.500 μM | 1.000 μM | IC$_{50}$ (μM) |
|---|---|---|---|---|---|---|
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 138

| ISIS No | 0.0625 μM | 0.125 μM | 0.250 μM | 0.500 μM | 1.000 μM | IC$_{50}$ (μM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 139

| ISIS No | 0.0625 μM | 0.125 μM | 0.250 μM | 0.500 μM | 1.000 μM | IC$_{50}$ (μM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 140

| ISIS No | 0.0625 μM | 0.125 μM | 0.250 μM | 0.500 μM | 1.000 μM | IC$_{50}$ (μM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |
| 498580 | 36 | 57 | 81 | 91 | 96 | 0.10 |
| 498581 | 34 | 64 | 75 | 93 | 97 | 0.05 |

TABLE 141

| ISIS No | 0.0625 μM | 0.125 μM | 0.250 μM | 0.500 μM | 1.000 μM | IC$_{50}$ (μM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 142

| ISIS No | 0.0625 μM | 0.125 μM | 0.250 μM | 0.500 μM | 1.000 μM | IC$_{50}$ (μM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the tables above, ISIS 494157 (SEQ ID NO: 12), ISIS 494158 (SEQ ID NO: 13), ISIS 494159 (SEQ ID NO: 14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO:43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO: 60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO: 85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGATAACTCCGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 116: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 µM, 0.148 µM, 0.444 µM, 1.333 µM, or 4.000 µM concentrations of antisense oligonucleotide, as specified in tables below. After a treatment period of approximately 16 hours, RNA was isolated from the cells and apo(a) mRNA levels were measured by quantitative real-time PCR. Apo(a) primer probe set hAPO(a)$_{12}$ kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each table representing a separate experiment. The half maximal inhibitory concentration (IC$_{50}$) of each oligonucleotide is also presented in the tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the tables below, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 143

| ISIS No | 0.049 µM | 0.148 µM | 0.444 µM | 1.333 µM | 4.000 µM | IC$_{50}$ (µM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |
| 494283 | 18 | 45 | 80 | 93 | 91 | 0.18 |
| 494284 | 9 | 53 | 80 | 95 | 94 | 0.18 |

TABLE 144

| ISIS No | 0.049 µM | 0.148 µM | 0.444 µM | 1.333 µM | 4.000 µM | IC$_{50}$ (µM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 145

| ISIS No | 0.049 µM | 0.148 µM | 0.444 µM | 1.333 µM | 4.000 µM | IC$_{50}$ (µM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 146

| ISIS No | 0.049 µM | 0.148 µM | 0.444 µM | 1.333 µM | 4.000 µM | IC$_{50}$ (µM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |

TABLE 146-continued

| ISIS No | 0.049 μM | 0.148 μM | 0.444 μM | 1.333 μM | 4.000 μM | IC$_{50}$ (μM) |
|---|---|---|---|---|---|---|
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |
| 498408 | 1 | 38 | 63 | 79 | 80 | 0.32 |
| 498433 | 23 | 43 | 70 | 77 | 79 | 0.21 |

TABLE 147

| ISIS No | 0.049 μM | 0.148 μM | 0.444 μM | 1.333 μM | 4.000 μM | IC$_{50}$ (μM) |
|---|---|---|---|---|---|---|
| 144367 | 0 | 40 | 76 | 90 | 93 | 0.26 |
| 498434 | 32 | 44 | 64 | 78 | 84 | 0.20 |
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 117: Antisense Inhibition of Human Apo(a) in Transgenic Mouse Primary Hepatocytes Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12 kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises of ten 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 148

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO: |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
|  | 583 | 599 | CCTGTGACAGTGGTGGA |  | 26693 | 26709 |  |
|  | 925 | 941 | CCTGTGACAGTGGTGGA |  | 32240 | 32256 |  |
|  | 1609 | 1625 | CCTGTGACAGTGGTGGA |  | 43333 | 43349 |  |
|  | 1951 | 1967 | CCTGTGACAGTGGTGGA |  | 48877 | 48893 |  |
|  | 2293 | 2309 | CCTGTGACAGTGGTGGA |  | 54423 | 54439 |  |
|  | 3319 | 3335 | CCTGTGACAGTGGTGGA |  | 72040 | 72056 |  |
|  | 4663 | 4679 | CCTGTGACAGTGGTGGA |  | 94404 | 94420 |  |
|  | 5005 | 5021 | CCTGTGACAGTGGTGGA |  | 115515 | 115531 |  |
| 510543 | 242 | 258 | TCCTGTGACAGTGGTGG | 75 | 21203 | 21219 | 112 |
|  | 584 | 600 | TCCTGTGACAGTGGTGG |  | 26694 | 26710 |  |
|  | 926 | 942 | TCCTGTGACAGTGGTGG |  | 32241 | 32257 |  |
|  | 1610 | 1626 | TCCTGTGACAGTGGTGG |  | 43334 | 43350 |  |
|  | 1952 | 1968 | TCCTGTGACAGTGGTGG |  | 48878 | 48894 |  |
|  | 2294 | 2310 | TCCTGTGACAGTGGTGG |  | 54424 | 54440 |  |
|  | 3320 | 3336 | TCCTGTGACAGTGGTGG |  | 72041 | 72057 |  |
|  | 4664 | 4680 | TCCTGTGACAGTGGTGG |  | 94405 | 94421 |  |
|  | 5006 | 5022 | TCCTGTGACAGTGGTGG |  | 115516 | 115532 |  |

TABLE 148-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO: |
|---|---|---|---|---|---|---|---|
| 510544 | 243 | 259 | TTCCTGTGACAGTGGTG | 73 | 21204 | 21220 | 113 |
|  | 585 | 601 | TTCCTGTGACAGTGGTG |  | 26695 | 26711 |  |
|  | 927 | 943 | TTCCTGTGACAGTGGTG |  | 32242 | 32258 |  |
|  | 1611 | 1627 | TTCCTGTGACAGTGGTG |  | 43335 | 43351 |  |
|  | 1953 | 1969 | TTCCTGTGACAGTGGTG |  | 48879 | 48895 |  |
|  | 2295 | 2311 | TTCCTGTGACAGTGGTG |  | 54425 | 54441 |  |
|  | 3321 | 3337 | TTCCTGTGACAGTGGTG |  | 72042 | 72058 |  |
|  | 4665 | 4681 | TTCCTGTGACAGTGGTG |  | 94406 | 94422 |  |
|  | 5007 | 5023 | TTCCTGTGACAGTGGTG |  | 115517 | 115533 |  |
| 510545 | 244 | 260 | CTTCCTGTGACAGTGGT | 65 | 21205 | 21221 | 114 |
|  | 586 | 602 | CTTCCTGTGACAGTGGT |  | 26696 | 26712 |  |
|  | 928 | 944 | CTTCCTGTGACAGTGGT |  | 32243 | 32259 |  |
|  | 1612 | 1628 | CTTCCTGTGACAGTGGT |  | 43336 | 43352 |  |
|  | 1954 | 1970 | CTTCCTGTGACAGTGGT |  | 48880 | 48896 |  |
|  | 2296 | 2312 | CTTCCTGTGACAGTGGT |  | 54426 | 54442 |  |
|  | 3322 | 3338 | CTTCCTGTGACAGTGGT |  | 72043 | 72059 |  |
|  | 3664 | 3680 | CTTCCTGTGACAGTGGT |  | 77585 | 77601 |  |
|  | 4666 | 4682 | CTTCCTGTGACAGTGGT |  | 94407 | 94423 |  |
|  | 5008 | 5024 | CTTCCTGTGACAGTGGT |  | 115518 | 115534 |  |
| 510546 | 245 | 261 | CCTTCCTGTGACAGTGG | 74 | 21206 | 21222 | 115 |
|  | 3665 | 3681 | CCTTCCTGTGACAGTGG |  | 77586 | 77602 |  |
|  | 4667 | 4683 | CCTTCCTGTGACAGTGG |  | 94408 | 94424 |  |
|  | 5009 | 5025 | CCTTCCTGTGACAGTGG |  | 115519 | 115535 |  |
| 510547 | 246 | 262 | TCCTTCCTGTGACAGTG | 77 | 21207 | 21223 | 116 |
|  | 3666 | 3682 | TCCTTCCTGTGACAGTG |  | 77587 | 77603 |  |
|  | 4668 | 4684 | TCCTTCCTGTGACAGTG |  | 94409 | 94425 |  |
|  | 5010 | 5026 | TCCTTCCTGTGACAGTG |  | 115520 | 115536 |  |
| 510548 | 247 | 263 | GTCCTTCCTGTGACAGT | 73 | 21208 | 21224 | 117 |
|  | 3667 | 3683 | GTCCTTCCTGTGACAGT |  | 77588 | 77604 |  |
|  | 4669 | 4685 | GTCCTTCCTGTGACAGT |  | 94410 | 94426 |  |
|  | 5011 | 5027 | GTCCTTCCTGTGACAGT |  | 115521 | 115537 |  |
| 510549 | 248 | 264 | GGTCCTTCCTGTGACAG | 67 | 21209 | 21225 | 118 |
|  | 4670 | 4686 | GGTCCTTCCTGTGACAG |  | 94411 | 94427 |  |
| 510595 | 632 | 648 | CCGACTATGCGAGTGTG | 76 | 26742 | 26758 | 119 |
|  | 974 | 990 | CCGACTATGCGAGTGTG |  | 32289 | 32305 |  |
|  | 1316 | 1332 | CCGACTATGCGAGTGTG |  | 37836 | 37852 |  |
|  | 1658 | 1674 | CCGACTATGCGAGTGTG |  | 43382 | 43398 |  |
|  | 2000 | 2016 | CCGACTATGCGAGTGTG |  | 48926 | 48942 |  |
|  | 2342 | 2358 | CCGACTATGCGAGTGTG |  | 54472 | 54488 |  |
|  | 2684 | 2700 | CCGACTATGCGAGTGTG |  | 60027 | 60043 |  |
|  | 3026 | 3042 | CCGACTATGCGAGTGTG |  | 66543 | 66559 |  |
| 510597 | 634 | 650 | GTCCGACTATGCGAGTG | 70 | 26744 | 26760 | 120 |
|  | 976 | 992 | GTCCGACTATGCGAGTG |  | 32291 | 32307 |  |
|  | 1318 | 1334 | GTCCGACTATGCGAGTG |  | 37838 | 37854 |  |
|  | 1660 | 1676 | GTCCGACTATGCGAGTG |  | 43384 | 43400 |  |
|  | 2002 | 2018 | GTCCGACTATGCGAGTG |  | 48928 | 48944 |  |
|  | 2344 | 2360 | GTCCGACTATGCGAGTG |  | 54474 | 54490 |  |
|  | 2686 | 2702 | GTCCGACTATGCGAGTG |  | 60029 | 60045 |  |
|  | 3028 | 3044 | GTCCGACTATGCGAGTG |  | 66545 | 66561 |  |
| 510598 | 635 | 651 | GGTCCGACTATGCGAGT | 70 | 26745 | 26761 | 121 |
|  | 977 | 993 | GGTCCGACTATGCGAGT |  | 32292 | 32308 |  |
|  | 1319 | 1335 | GGTCCGACTATGCGAGT |  | 37839 | 37855 |  |
|  | 1661 | 1677 | GGTCCGACTATGCGAGT |  | 43385 | 43401 |  |
|  | 2003 | 2019 | GGTCCGACTATGCGAGT |  | 48929 | 48945 |  |
|  | 2345 | 2361 | GGTCCGACTATGCGAGT |  | 54475 | 54491 |  |
|  | 2687 | 2703 | GGTCCGACTATGCGAGT |  | 60030 | 60046 |  |
|  | 3029 | 3045 | GGTCCGACTATGCGAGT |  | 66546 | 66562 |  |

TABLE 149

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 83 | 21210 | 21229 | 11 |
| 510783 | 6400 | 6416 | GTCAGACCTTAAAAGCT | 75 | 140056 | 140072 | 122 |
| 512944 | 3561 | 3577 | AAGCCTCTGTGCTTGGA | 81 | 76246 | 76262 | 123 |
| 512947 | 3560 | 3576 | AGCCTCTGTGCTTGGAT | 85 | 76245 | 76261 | 124 |
| 512958 | 3559 | 3575 | GCCTCTGTGCTTGGATC | 82 | 76244 | 76260 | 125 |
| 512959 | 3585 | 3601 | GCTCCGTTGGTGCTTCT | 77 | n/a | n/a | 126 |

TABLE 150

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 76 | 21210 | 21229 | 11 |
| 510701 | 4217 | 4233 | CTCTGTGCTTGGAACTG | 78 | 85147 | 85163 | 127 |
| 510702 | 219 | 235 | TGCCTCGATAACTCTGT | 79 | 21180 | 21196 | 128 |
|  | 561 | 577 |  |  | 26671 | 26687 |  |
|  | 903 | 919 |  |  | 32218 | 32234 |  |
|  | 1245 | 1261 |  |  | 37765 | 37781 |  |
|  | 1587 | 1603 |  |  | 43311 | 43327 |  |
|  | 1929 | 1945 |  |  | 48855 | 48871 |  |
|  | 2271 | 2287 |  |  | 54401 | 54417 |  |
|  | 2613 | 2629 |  |  | 59956 | 59972 |  |
|  | 4299 | 4315 |  |  | 86472 | 86488 |  |
| 510704 | 563 | 579 | TGTGCCTCGATAACTCT | 80 | 26673 | 26689 | 129 |
|  | 905 | 921 |  |  | 32220 | 32236 |  |
|  | 1247 | 1263 |  |  | 37767 | 37783 |  |
|  | 1589 | 1605 |  |  | 43313 | 43329 |  |
|  | 1931 | 1947 |  |  | 48857 | 48873 |  |
|  | 2273 | 2289 |  |  | 54403 | 54419 |  |
|  | 2615 | 2631 |  |  | 59958 | 59974 |  |
|  | 4301 | 4317 |  |  | 86474 | 86490 |  |
|  | 4985 | 5001 |  |  | 115495 | 115511 |  |
| 510757 | 4929 | 4945 | GCTCAGTTGGTGCTGCT | 74 | n/a | n/a | 130 |

Example 118: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 µM, 0.313 µM, 0.625 µM, 1.250 µM, 2.500 µM, or 5.000 µM concentrations of antisense oligonucleotide, as specified in the tables below. After a treatment period of approximately 16 hours, RNA was isolated from the cells and apo(a) mRNA levels were measured by quantitative real-time PCR. Apo(a) primer probe set hAPO(a) 12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the tables presented below with each study represented in a separate table. The half maximal inhibitory concentration ($IC_{50}$) of each oligonucleotide is also presented in the tables.

TABLE 151

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 152

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 153

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 154

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |
| 510704 | 54 | 61 | 77 | 84 | 89 | 80 | 0.12 |

TABLE 154-continued

| ISIS No | 0.156 µM | 0.312 µM | 0.625 µM | 1.250 µM | 2.500 µM | 5.000 µM | IC$_{50}$ (µM) |
|---|---|---|---|---|---|---|---|
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the tables above, ISIS 510542 (SEQ ID NO: 111), ISIS 510545 (SEQ ID NO: 114). ISIS 510546 (SEQ ID NO: 115). ISIS 510547 (SEQ ID NO: 116). ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 119: Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS494311, ISIS494337, ISIS 494372, ISIS 498238, ISIS 498523, ISIS498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in the table below, expressed as percent inhibition of apo(a) mRNA compared to the PBS control.

TABLE 155

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in the table below, expressed as percent inhibition of apo(a) mRNA compared to the PBS control.

TABLE 156

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |

TABLE 156-continued

Percent inhibition of human apo(a) protein in transgenic mice

| ISIS No | % inhibition |
|---|---|
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control.

TABLE 157

Dose-dependent inhibition of human apo(a) mRNA in transgenic mice

| ISIS No | Dose (mg/kg/wk) | % inhibition | $ED_{50}$ |
|---|---|---|---|
| 144367 | 100 | 71 | 31 |
|  | 30 | 42 |  |
|  | 10 | 0 |  |
|  | 3 | 5 |  |
| 494159 | 100 | 91 | 5 |
|  | 30 | 67 |  |
|  | 10 | 48 |  |
|  | 3 | 39 |  |
| 494161 | 100 | 82 | 6 |
|  | 30 | 49 |  |
|  | 10 | 61 |  |
|  | 3 | 30 |  |
| 494162 | 100 | 90 | 5 |
|  | 30 | 67 |  |
|  | 10 | 58 |  |
|  | 3 | 25 |  |
| 494163 | 100 | 83 | 5 |
|  | 30 | 66 |  |
|  | 10 | 58 |  |
|  | 3 | 21 |  |
| 494243 | 100 | 80 | 32 |
|  | 30 | 26 |  |
|  | 10 | 0 |  |
|  | 3 | 6 |  |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO: 17), and ISIS 94163 (SEQ ID NO: 18) were more efficacious than the benchmark ISIS 144367 (SEQ ID NO: 11).

Reduction of human apo(a) protein levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control.

TABLE 158

Dose-dependent inhibition of human apo(a) protein in transgenic mice

| ISIS No | Dose (mg/kg/wk) | % inhibition | $ED_{50}$ |
|---|---|---|---|
| 144367 | 100 | 73 | 71 |
|  | 30 | 0 |  |
|  | 10 | 6 |  |
|  | 3 | 69 |  |
| 494159 | 100 | 88 | 2 |
|  | 30 | 88 |  |
|  | 10 | 85 |  |
|  | 3 | 36 |  |
| 494161 | 100 | 90 | 2 |
|  | 30 | 85 |  |
|  | 10 | 73 |  |
|  | 3 | 44 |  |
| 494162 | 100 | 89 | 3 |
|  | 30 | 78 |  |
|  | 10 | 76 |  |
|  | 3 | 24 |  |
| 494163 | 100 | 90 | 3 |
|  | 30 | 86 |  |
|  | 10 | 60 |  |
|  | 3 | 37 |  |
| 494243 | 100 | 61 | 174 |
|  | 30 | 0 |  |
|  | 10 | 0 |  |
|  | 3 | 0 |  |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control.

TABLE 159

Dose-dependent inhibition of human apo(a) mRNA in transgenic mice

| ISIS No | Dose (mg/kg/wk) | % inhibition | $ED_{50}$ |
|---|---|---|---|
| 144367 | 50 | 75 | 22 |
|  | 15 | 60 |  |
|  | 5 | 0 |  |
|  | 1.5 | 0 |  |
| 494244 | 50 | 73 | 18 |
|  | 15 | 41 |  |
|  | 5 | 34 |  |
|  | 1.5 | 0 |  |
| 494283 | 50 | 74 | 16 |
|  | 15 | 52 |  |
|  | 5 | 24 |  |
|  | 1.5 | 0 |  |
| 494284 | 50 | 73 | 16 |
|  | 15 | 58 |  |
|  | 5 | 17 |  |
|  | 1.5 | 2 |  |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control.

TABLE 160

Dose-dependent inhibition of human apo(a) plasma protein in transgenic mice

| ISIS No | Dose (mg/kg/wk) | % inhibition | $ED_{50}$ |
|---|---|---|---|
| 144367 | 50 | 64 | 16 |
|  | 15 | 14 |  |
|  | 5 | 0 |  |
|  | 1.5 | 0 |  |
| 494244 | 50 | 67 | 2 |
|  | 15 | 60 |  |
|  | 5 | 58 |  |
|  | 1.5 | 0 |  |
| 494283 | 50 | 64 | 4 |
|  | 15 | 65 |  |
|  | 5 | 64 |  |
|  | 1.5 | 69 |  |
| 494284 | 50 | 66 | 4 |
|  | 15 | 63 |  |
|  | 5 | 51 |  |
|  | 1.5 | 54 |  |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 161

Dose-dependent inhibition of human Apo(a) mRNA in transgenic mice

| ISIS No | Dose (mg/kg/wk) | % inhibition | $ED_{50}$ |
|---|---|---|---|
| 494285 | 50 | 98 | 1 |
|  | 15 | 97 |  |
|  | 5 | 79 |  |
| 494286 | 50 | 97 | 1 |
|  | 15 | 91 |  |
|  | 5 | 80 |  |
| 494301 | 50 | 98 | 3 |
|  | 15 | 96 |  |
|  | 5 | 59 |  |
| 494302 | 50 | 98 | 2 |
|  | 15 | 88 |  |
|  | 5 | 72 |  |
| 494311 | 50 | 99 | 1 |
|  | 15 | 96 |  |
|  | 5 | 87 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control. The data demonstrates significant reduction of apo (a) plasma protein levels by ISIS 494285, ISIS 494286, ISIS 494301, ISIS 494302 and ISIS 494311.

TABLE 162

Dose-dependent inhibition of human apo(a) protein in transgenic mice

| ISIS No | Dose (mg/kg/wk) | % inhibition | $ED_{50}$ |
|---|---|---|---|
| 494285 | 50 | 88 | 2 |
|  | 15 | 88 |  |
|  | 5 | 72 |  |
| 494286 | 50 | 90 | 2 |
|  | 15 | 85 |  |
|  | 5 | 75 |  |

TABLE 162-continued

Dose-dependent inhibition of human apo(a) protein in transgenic mice

| ISIS No | Dose (mg/kg/wk) | % inhibition | ED$_{50}$ |
|---|---|---|---|
| 494301 | 50 | 89 | 5 |
|  | 15 | 86 |  |
|  | 5 | 38 |  |
| 494302 | 50 | 90 | 3 |
|  | 15 | 82 |  |
|  | 5 | 61 |  |
| 494311 | 50 | 90 | 3 |
|  | 15 | 82 |  |
|  | 5 | 69 |  |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in the table below, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 163

Dose-dependent inhibition of human Apo(a) mRNA in transgenic mice

| ISIS No | Dose (mg/kg/wk) | % inhibition | ED$_{50}$ |
|---|---|---|---|
| 494372 | 50 | 88 | 18 |
|  | 15 | 49 |  |
|  | 5 | 0 |  |
| 498524 | 50 | 83 | 8 |
|  | 15 | 74 |  |
|  | 5 | 34 |  |
| 498581 | 50 | 98 | 7 |
|  | 15 | 58 |  |
|  | 5 | 48 |  |
| 498721 | 50 | 97 | 14 |
|  | 15 | 68 |  |
|  | 5 | 0 |  |
| 498833 | 50 | 61 | 155 |
|  | 15 | 0 |  |
|  | 5 | 17 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in the table below, expressed as percent reduction of apo(a) protein levels compared to the PBS control. The data demonstrates significant reduction of apo(a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 164

Dose-dependent inhibition of human apo(a) protein in transgenic mice

| ISIS No | Dose (mg/kg/wk) | % inhibition | ED$_{50}$ |
|---|---|---|---|
| 494372 | 50 | 68 | 32 |
|  | 15 | 25 |  |
|  | 5 | 12 |  |
| 498524 | 50 | 38 | 118 |
|  | 15 | 0 |  |
|  | 5 | 0 |  |
| 498581 | 50 | 79 | 9 |
|  | 15 | 52 |  |
|  | 5 | 49 |  |
| 498721 | 50 | 81 | 10 |
|  | 15 | 63 |  |
|  | 5 | 29 |  |
| 498833 | 50 | 15 | 738 |
|  | 15 | 0 |  |
|  | 5 | 67 |  |

Example 120: Tolerability of Antisense Oligonucleotides Targeting Human Apo(a) in Rodent Models Gapmer antisense oligonucleotides targeting human apo(a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 Mice: Study 1

CD1® mice (Charles River, MA) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, NY). The results are presented in the table below. ISIS oligonucleotides that caused changes in the levels of any of the liver or kidney function markers outside the expected range for antisense oligonucleotides were excluded in further studies.

TABLE 165

Plasma chemistry markers of CD1 mice

|  | ALT (IU/L) | AST (IU/L) | Albumin (g/dL) | BUN (mg/dL) | Creatinine (mg/dL) | Bilirubin (mg/dL) |
|---|---|---|---|---|---|---|
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in the table below. ISIS oligonucleotides that caused any changes in organ weights outside the expected range for antisense oligonucleotides were excluded from further studies.

TABLE 166

Organ weights of CDI mice (g)

|  | Kidney | Liver | Spleen |
|---|---|---|---|
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |
| ISIS 494337 | 0.56 | 2.3 | 0.17 |
| ISIS 494372 | 0.60 | 2.5 | 0.27 |
| ISIS 510548 | 0.55 | 3.7 | 0.20 |

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, NY). The results are presented in the table below. ISIS oligonucleotides that caused changes in the levels of any of the liver or kidney function markers outside the expected range for antisense oligonucleotides were excluded in further studies.

TABLE 167

Plasma chemistry markers of Sprague Dawley rats

|  | ALT (IU/L) | AST (IU/L) | Bilirubin (mg/dL) | Albumin (mg/dL) | BUN (mg/dL) | Creatinine (mg/dL) |
|---|---|---|---|---|---|---|
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function

To evaluate the effect of ISIS oligonucleotides on kidney function, urine levels of total protein and creatinine were measured using an automated clinical chemistry analyzer (Hitachi Olympus AU400e, Melville, NY). Results are presented in the table below, expressed in mg/dL.

TABLE 168

Kidney function markers (mg/dL) in Sprague-Dawley rats

|  | Creatinine | Total protein |
|---|---|---|
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in the table below. ISIS oligonucleotides that caused any changes in organ weights outside the expected range for antisense oligonucleotides were excluded from further studies.

TABLE 169

Organ weights of Sprague Dawley rats (g)

|  | Kidney | liver | Spleen |
|---|---|---|---|
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |

TABLE 169-continued

Organ weights of Sprague Dawley rats (g)

|  | Kidney | liver | Spleen |
|---|---|---|---|
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 121: Pharmacokinetics of Antisense Oligonucleotide in Cd1 Mice

CD1 mice were treated with ISIS oligonucleotides and the oligonucleotide concentrations in the liver and kidney were evaluated.

Treatment

Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in the table below, expressed as µg/g liver or kidney tissue. The data indicates that ISIS 494372 was at an acceptable concentration in the liver and kidneys.

TABLE 170

Oligonucleotide concentration (µg/g tissue) of ISIS oligonucleotides in CD1 mice

| ISIS No | Liver | Kidney |
|---|---|---|
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 122: Pharmacokinetics of Antisense Oligonucleotide in Sprague Dawley Rats Male Sprague Dawley rats were treated with ISIS oligonucleotides and the oligonucleotide concentrations in the liver and kidney were evaluated.

Treatment

Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in the table below, expressed as µg/g liver or kidney tissue. The data indicates that ISIS 494372 was at an acceptable concentration in the liver and kidneys.

TABLE 171

Oligonucleotide concentration (µg/g tissue) of ISIS oligonucleotides in Sprague Dawley rats

| ISIS No | Liver | Kidney |
|---|---|---|
| 494283 | 220 | 434 |
| 494284 | 178 | 573 |
| 494286 | 234 | 448 |
| 494301 | 279 | 540 |
| 494302 | 205 | 387 |
| 494372 | 288 | 663 |

Example 123: Effect of Isis Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in the table below. Each antisense oligonucleotide targets more than one region in SEQ ID NO:132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 172

Antisense oligonucleotides complementary to SEQ ID NO: 132

| ISIS No | Start Site | Mismatches |
|---------|------------|------------|
| 494283  | 278        | 2          |
|         | 620        | 2          |
|         | 923        | 2          |
|         | 1265       | 2          |
|         | 1607       | 1          |
|         | 1949       | 1          |
|         | 2267       | 1          |
|         | 2609       | 1          |
|         | 2951       | 1          |
|         | 3293       | 1          |
| 494284  | 279        | 1          |
|         | 621        | 1          |
|         | 924        | 1          |
|         | 1266       | 1          |
|         | 1608       | 1          |
|         | 1950       | 1          |
|         | 2268       | 1          |
|         | 2610       | 1          |
|         | 2952       | 1          |
|         | 3294       | 1          |
| 494286  | 281        | 1          |
|         | 623        | 1          |
|         | 926        | 1          |
|         | 1268       | 1          |
|         | 1610       | 2          |
|         | 1952       | 2          |
|         | 2270       | 2          |
|         | 2612       | 2          |
|         | 2954       | 2          |
|         | 3296       | 2          |
| 494301  | 322        | 2          |
|         | 664        | 2          |
|         | 967        | 2          |
|         | 1309       | 1          |
|         | 1651       | 2          |
| 494302  | 323        | 2          |
|         | 968        | 2          |
|         | 1310       | 1          |
|         | 1652       | 2          |
| 494372  | 1186       | 2          |
|         | 1870       | 1          |
|         | 2188       | 1          |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized. Scheduled euthanasia of the animals was conducted on days 86 and 87 by exsanguination under deep anesthesia. The protocols described in the Example were approved by the Institutional Animal Care and Use Committee (IACUC).

Target Reduction

RNA Analysis

On day 86, RNA was extracted from liver tissue for real-time PCR analysis of apo(a) using human primer probe set ABI Hs00916691_m1 (Applied Biosystems, Carlsbad CA). Results are presented as percent inhibition of apo(a) mRNA, relative to PBS control. As shown in the table below, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 173

Percent Inhibition of apo(a) mRNA in the cynomolgus monkey liver relative to the PBS control

| ISIS No | % inhibition |
|---------|--------------|
| 494283  | 91           |
| 494284  | 99           |
| 494286  | 96           |
| 494301  | 88           |
| 494302  | 89           |
| 494372  | 93           |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in the table below, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 174

Apo(a) plasma protein levels (% inhibition over baseline values) in the cynomolgus monkey

|             | Day 16 | Day 30 | Day 44 | Day 56 | Day 72 | Day 86 |
|-------------|--------|--------|--------|--------|--------|--------|
| PBS         | 0      | 0      | 10     | 0      | 0      | 0      |
| ISIS 494283 | 78     | 79     | 81     | 66     | 66     | 70     |
| ISIS 494284 | 92     | 95     | 95     | 93     | 93     | 94     |
| ISIS 494286 | 92     | 95     | 96     | 94     | 94     | 94     |

TABLE 174-continued

Apo(a) plasma protein levels (% inhibition over baseline values) in the cynomolgus monkey

|  | Day 16 | Day 30 | Day 44 | Day 56 | Day 72 | Day 86 |
|---|---|---|---|---|---|---|
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies

Body and Organ Weight Measurements

To evaluate the effect of ISIS oligonucleotides on the overall health of the animals, body and organ weights were measured at day 86. Body weights were measured and are presented in the table below. Organ weights were measured and the data is presented in the table below. The results indicate that treatment with ISIS 494372 was well tolerated in terms of the body and organ weights of the monkeys.

TABLE 175

Body weights (g) in the cynomolgus monkey

|  | Day 14 | Day 35 | Day 49 | Day 56 | Day 70 | Day 84 |
|---|---|---|---|---|---|---|
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 176

Organ weights (% body weight) in the cynomolgus monkey

|  | Spleen | Kidneys | Liver | Heart | Lungs |
|---|---|---|---|---|---|
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in the table below, expressed in IU/L. Bilirubin, a liver function marker, was similarly measured and is presented in the table below, expressed in mg/dL. The results indicate that treatment with ISIS 494372 was well tolerated in terms of the liver function in monkeys.

TABLE 177

Liver function markers in cynomolgus monkey plasma

|  | ALT (IU/L) | AST (IU/L) | Bilirubin (mg/dL) |
|---|---|---|---|
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-Reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 178

C-reactive protein levels (mg/L) in cynomolgus monkey plasma

|  | CRP |
|---|---|
| PBS | 1.4 |
| ISIS 494283 | 14.7 |
| ISIS 494284 | 7.7 |
| ISIS 494286 | 4.4 |
| ISIS 494301 | 3.5 |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 179

Complement C3 levels (mg/dL) in cynomolgus monkey plasma

|  | Pre-dose | Post-dose |
|---|---|---|
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |

TABLE 179-continued

Complement C3 levels (mg/dL) in cynomolgus monkey plasma

|  | Pre-dose | Post-dose |
|---|---|---|
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing $K_2$-EDTA. Samples were analyzed for red blood cell (RBC) count, white blood cells (WBC) count, as well as for platelet count, using an ADVIA120 hematology analyzer (Bayer, USA). The data is presented in the table below.

The data indicate that treatment with ISIS 494372 was well tolerated in terms of the hematologic parameters of the monkeys.

TABLE 180

Blood cell counts in cynomolgus monkeys

|  | WBC ($\times 10^3$/uL) | RBC ($\times 10^6$/uL) | Platelet ($\times 10^3$/uL) |
|---|---|---|---|
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 124: Characterization of the Pharmacological Activity of Isis 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 181

Dosing groups in cynomolgus monkeys

| Group | Test Article | Dose | Number of animals for necropsy | | |
|---|---|---|---|---|---|
| | | | Interim | Terminal | Recovery |
| 1 | PBS | — | 4 | 6 | 4 |
| 2 | ISIS | 4 | — | 6 | — |
| 3 | 494372 | 8 | — | 6 | — |
| 4 | | 12 | 4 | 6 | 4 |
| 5 | | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns. After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_ml, Applied Biosystems, Carlsbad CA) targeting position 1512 of the rhesus monkey apo(a) mRNA transcript GENBANK Accession No XM_001098061.2 (SEQ ID NO: 132) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in the table below, treatment with ISIS 494372 resulted in a dose-dependent reduction of apo(a) mRNA in comparison to the PBS control. At day 30, hepatic apo(a) mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, P<0.05).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 182

Percent inhibition levels of liver apo(a) mRNA in the dosing phase in cynomolgus monkeys treated with ISIS 494372

| Day | Dose (mg/kg/wk) | % inhibition |
|---|---|---|
| 30 | 12 | 73 |
|  | 40 | 99 |
| 93 | 4 | 44 |
|  | 8 | 43 |
|  | 12 | 53 |
|  | 40 | 93 |

Protein Analysis

Approximately 20 μl of plasma was analyzed using a commercially available apo(a) ELISA kit (Mercodia 10-1106-01, Uppsala, Sweden). The assay protocol was performed as described by the manufacturer. The results are presented in the tables below as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 183

Apo(a) plasma protein levels as a percent of Day 1 levels in the dosing phase in cynomolgus monkeys treatedwith ISIS 494372

| Day | Dose (mg/kg/wk) | % |
|---|---|---|
| 30 | 4 | 93 |
|  | 8 | 70 |
|  | 12 | 49 |
|  | 40 | 15* |
| 93 | 4 | 73 |
|  | 8 | 56 |
|  | 12 | 32* |
|  | 40 | 11* |

TABLE 184

Apo(a) plasma protein levels as a percent of Day 1 levels in the recovery phase in cynomolgus monkeys treated with ISIS 494372

| Day | Dose (mg/kg/wk) | % |
|---|---|---|
| 121 | 12 | 38* |
|  | 40 | 22* |
| 182 | 12 | 84 |
|  | 40 | 93 |

Example 125: Measurement of Viscosity of Isis Antisense Oligonucleotides Targeting Human Apo(a)

The viscosity of select antisense oligonucleotides from the studies described above was measured with the aim of screening out antisense oligonucleotides which have a viscosity more than 40 centipoise (cP). Oligonucleotides having a viscosity greater than 40 cP would have less than optimal viscosity.

ISIS oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in the table below and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 185

Viscosity and concentration of ISIS antisense oligonucleotides targeting human Apo(a)

| ISIS No | Motif | Viscosity (cP) | Concentration (mg/mL) |
|---|---|---|---|
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A method for treating a disease related to elevated Lp(a) comprising administering to a human in need a compound, wherein the compound has the formula:

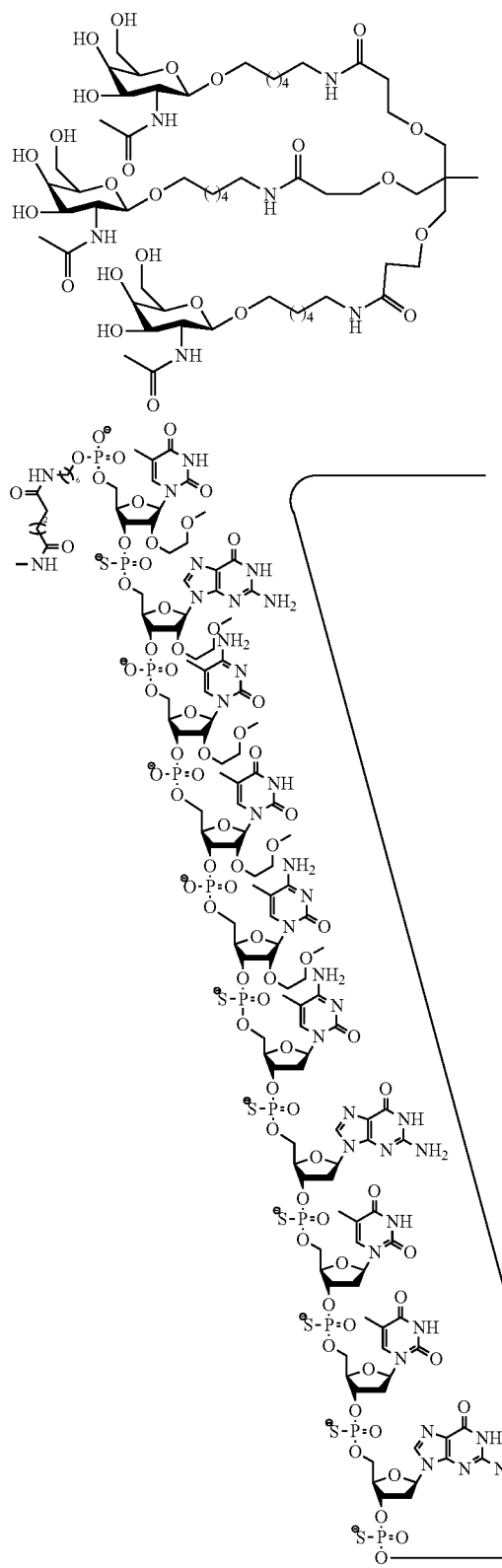
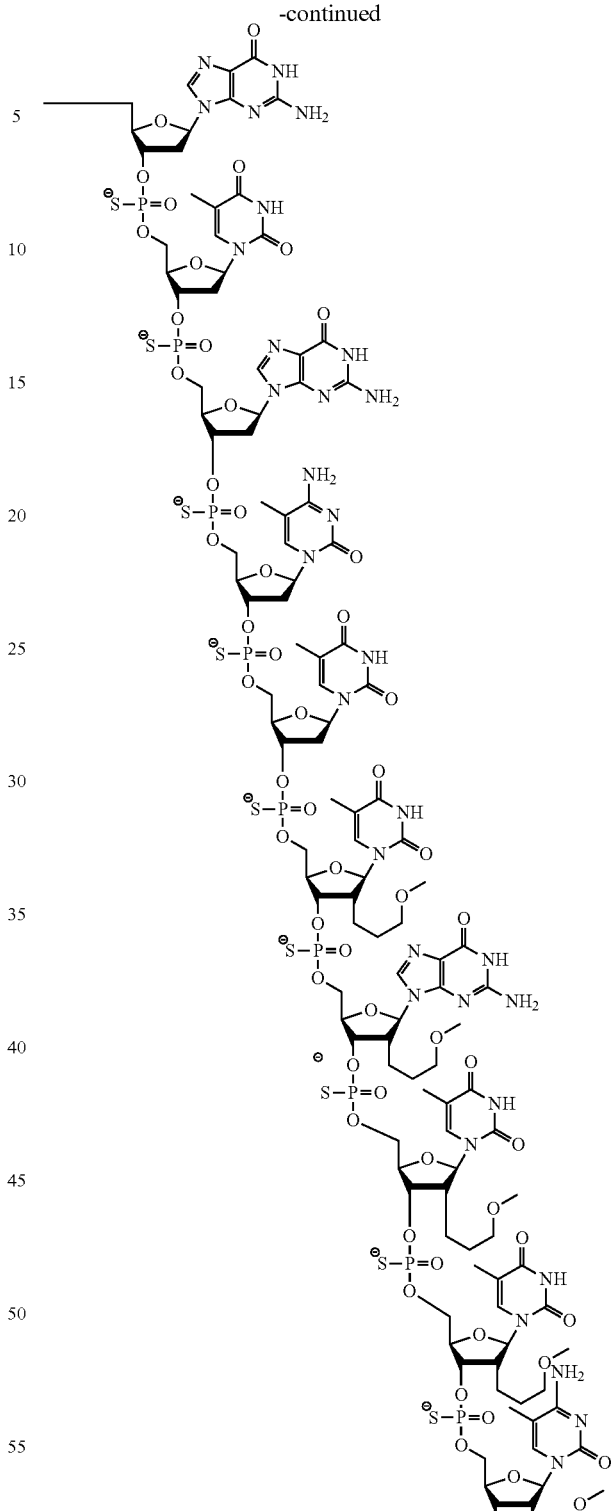

or a pharmaceutically acceptable salt thereof.

2. The method of claim 1, wherein the pharmaceutically acceptable salt is the sodium salt.

3. The method of claim 1, wherein the disease is a cardiovascular, metabolic and/or inflammatory disease, disorder or condition.

4. The method of claim 1, wherein the disease is a cardiovascular disease.

5. The method of claim 1, wherein the disease is hyperlipidemia.

6. The method of claim 3, wherein the disease is aneurysm, angina, arrhythmia, atherosclerosis, cerebrovascular disease, coronary artery disease, coronary heart disease myocardial infarction, peripheral vascular disease, peripheral artery disease, peripheral artery occlusive disease, retinal vascular occlusion, or stroke.

7. The method of claim 2, wherein the disease is a cardiovascular disease.

8. A method for preventing a disease related to elevated Lp (a) comprising administering to a human in need a compound or pharmaceutically acceptable salt thereof, wherein the compound has the formula:

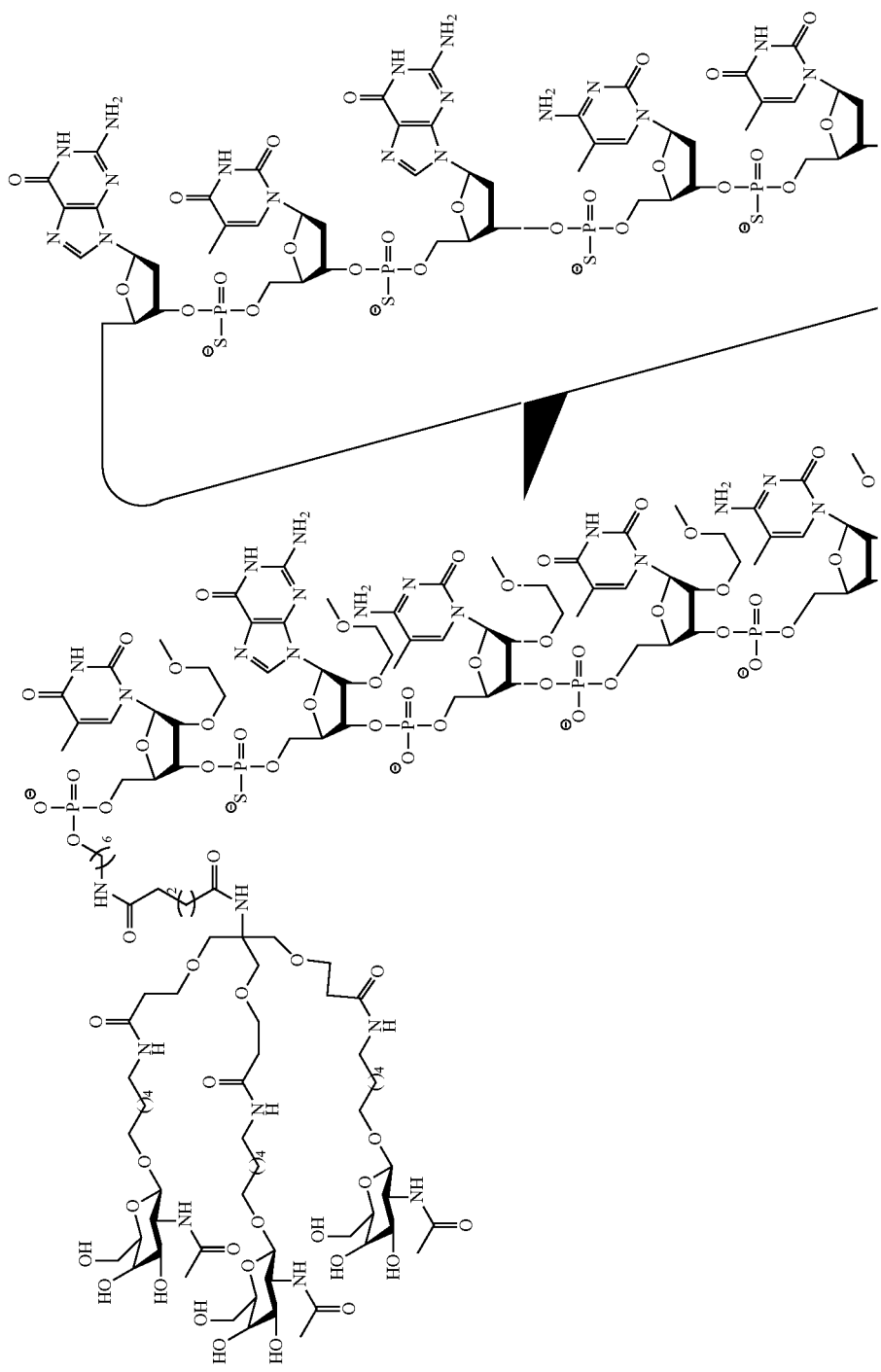

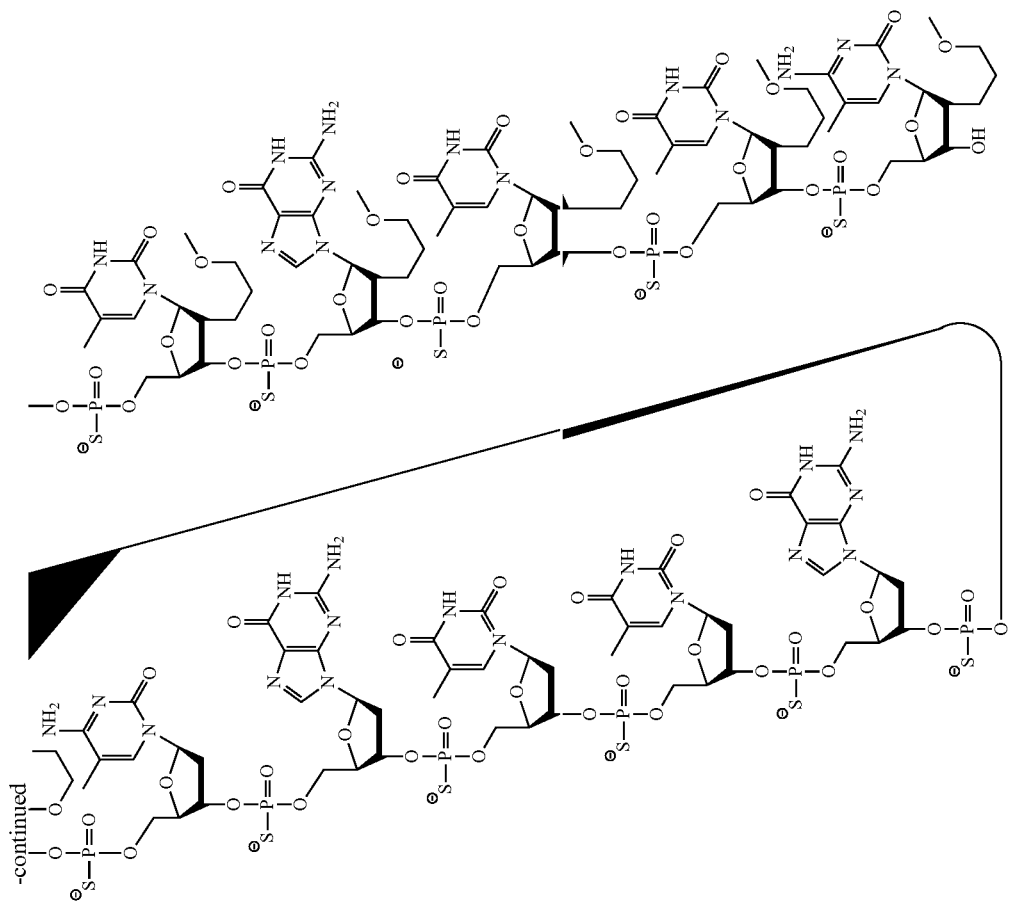

or a pharmaceutically acceptable salt thereof.

9. The method of claim 8, wherein the pharmaceutically acceptable salt is the sodium salt.

10. The method of claim 8, wherein the disease is a cardiovascular, metabolic and/or inflammatory disease, disorder or condition.

11. The method of claim 8, wherein the disease is a cardiovascular disease.

12. The method of claim 11, wherein the disease is hyperlipidemia.

13. The method of claim 11, wherein the disease is aneurysm, angina, arrhythmia, atherosclerosis, cerebrovascular disease, coronary artery disease, coronary heart disease myocardial infarction, peripheral vascular disease, peripheral artery disease, peripheral artery occlusive disease, retinal vascular occlusion, or stroke.

14. The method of claim 9, wherein the disease is a cardiovascular disease.

15. A pharmaceutically acceptable salt of a compound having the formula:

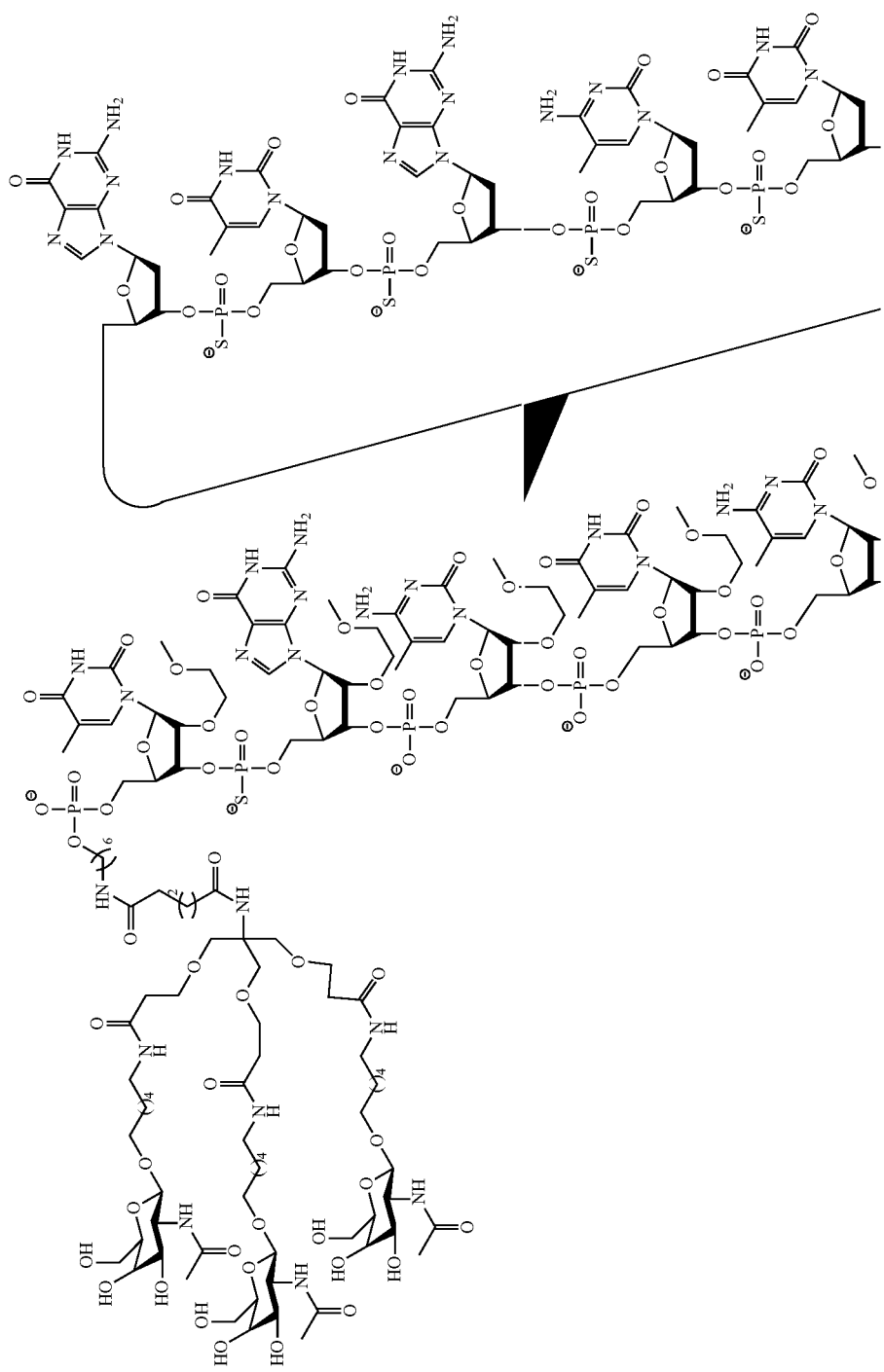

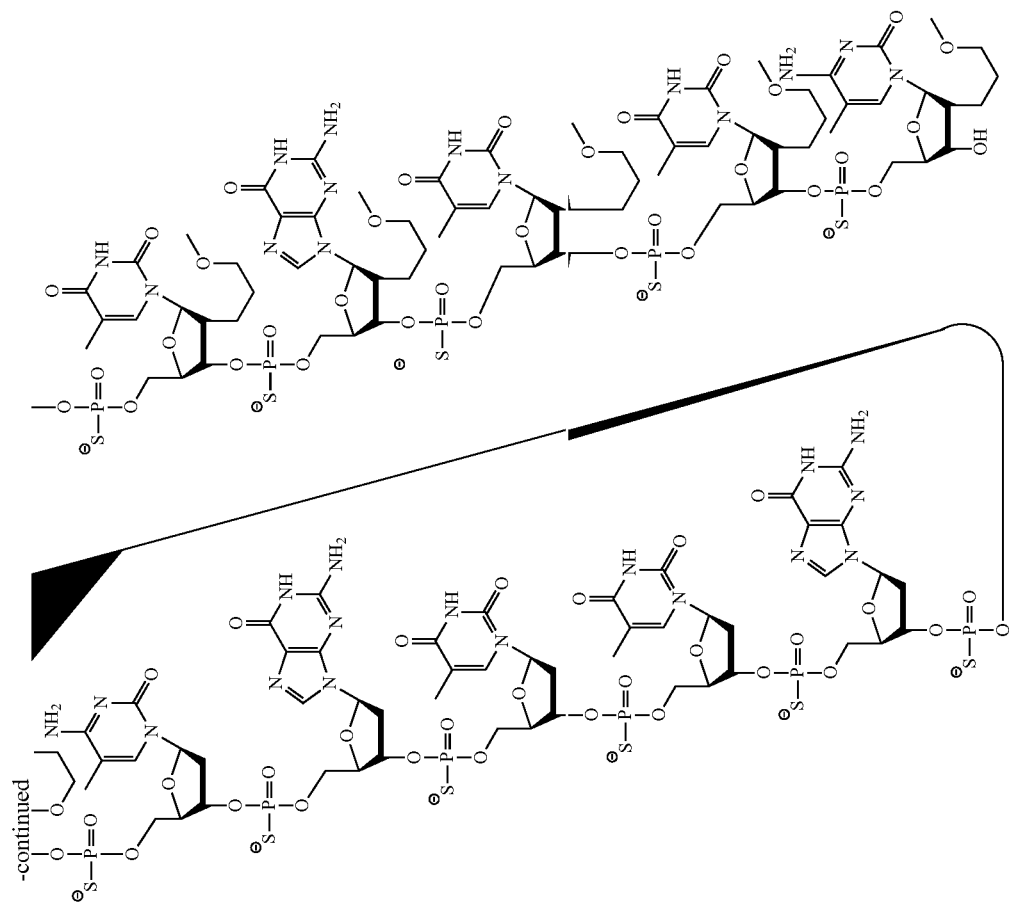

16. The pharmaceutically acceptable salt of claim 15, wherein the pharmaceutically acceptable salt is the sodium salt.

* * * * *